(12) United States Patent
Balan et al.

(10) Patent No.: US 11,203,591 B2
(45) Date of Patent: Dec. 21, 2021

(54) SUBSTITUTED 6-AZABENZIMIDAZOLE COMPOUNDS

(71) Applicant: Gilead Sciences, Inc., Foster City, CA (US)

(72) Inventors: Gayatri Balan, Bellevue, WA (US); Mark J. Bartlett, Castro Valley, CA (US); Jayaraman Chandrasekhar, Redmond, WA (US); Julian A. Codelli, Seattle, WA (US); John H. Conway, Seattle, WA (US); Jennifer L. Cosman, Foster City, CA (US); Rao V. Kalla, Cupertino, CA (US); Zachary A. Kasun, Seattle, WA (US); Musong Kim, Bellevue, WA (US); Seung H. Lee, Sammamish, WA (US); Jennifer R. Lo, Seattle, WA (US); Jennifer A. Loyer-Drew, Seattle, WA (US); Scott A. Mitchell, Kenmore, WA (US); Thao D. Perry, San Jose, CA (US); Gary B. Phillips, Issaquah, WA (US); Patrick J. Salvo, Burien, WA (US); Sundaramoorthi Swaminathan, Burlingame, CA (US); Joshua J. Van Veldhuizen, Seattle, WA (US); Suet C. Yeung, Redmond, WA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 93 days.

(21) Appl. No.: 16/669,346

(22) Filed: Oct. 30, 2019

(65) Prior Publication Data

US 2021/0115037 A1    Apr. 22, 2021

Related U.S. Application Data

(60) Provisional application No. 62/868,550, filed on Jun. 28, 2019, provisional application No. 62/753,339, filed on Oct. 31, 2018.

(51) Int. Cl.
*C07D 471/04*   (2006.01)
*A61K 31/437*   (2006.01)
*C07D 519/00*   (2006.01)

(52) U.S. Cl.
CPC ......... *C07D 471/04* (2013.01); *C07D 519/00* (2013.01)

(58) Field of Classification Search
CPC ...... C07D 471/04; A61K 31/437; A61P 35/00
USPC .......................................... 546/118; 514/303
See application file for complete search history.

(56) References Cited

U.S. PATENT DOCUMENTS

| | | | |
|---|---|---|---|
| 7,713,973 B2 | 5/2010 | Dong et al. | |
| 8,288,536 B2 | 10/2012 | Dong et al. | |
| 9,725,769 B1 | 8/2017 | Knudsen | |
| 10,722,495 B2 | 7/2020 | Vechorkin et al. | |
| 10,745,388 B2 | 8/2020 | Vechorkin et al. | |
| 11,034,694 B2 | 6/2021 | Kaila et al. | |
| 2014/0275033 A1 | 9/2014 | Li et al. | |
| 2017/0298443 A1 | 10/2017 | Dai | |
| 2017/0306303 A1 | 10/2017 | Taunton et al. | |
| 2019/0315717 A1 | 10/2019 | Hummel et al. | |
| 2020/0048241 A1 | 2/2020 | Hummel et al. | |
| 2020/0087301 A1 | 3/2020 | Vechorkin et al. | |
| 2020/0140456 A1 | 5/2020 | Phillips et al. | |
| 2020/0171020 A1* | 6/2020 | Balan et al. ....... | A61K 31/4545 514/303 |
| 2020/0291076 A1 | 9/2020 | Dalton et al. | |
| 2020/0299279 A1 | 9/2020 | Burkart et al. | |
| 2021/0078996 A1 | 3/2021 | Kaila et al. | |
| 2021/0078997 A1 | 3/2021 | Kaila et al. | |
| 2021/0078998 A1 | 3/2021 | Kaila et al. | |
| 2021/0139484 A1 | 5/2021 | Aicher et al. | |
| 2021/0163417 A1 | 6/2021 | Chan et al. | |
| 2021/0171518 A1 | 6/2021 | Hummel et al. | |

FOREIGN PATENT DOCUMENTS

| | | |
|---|---|---|
| CN | 103110932 A | 5/2013 |
| CN | 103114087 B | 5/2015 |
| CN | 104878084 B | 1/2018 |
| CN | 109721620 A | 5/2019 |
| CN | 108823307 B | 10/2020 |
| CN | 112239473 A | 1/2021 |
| DK | 3322711 T3 | 4/2021 |
| EP | 3042903 A1 | 7/2016 |
| WO | WO-200055153 A1 | 9/2000 |
| WO | WO-200183485 A1 | 11/2001 |
| WO | WO-2005035520 A1 | 4/2005 |
| WO | WO-2005063766 A2 | 7/2005 |
| WO | WO-2005120510 A1 | 12/2005 |
| WO | WO-2006004702 A1 | 1/2006 |
| WO | WO-2007032371 A1 | 3/2007 |
| WO | WO-2007041511 A2 | 4/2007 |
| WO | WO-2007058850 A2 | 5/2007 |
| WO | WO-2008046083 A2 | 4/2008 |
| WO | WO-2008077550 A1 | 7/2008 |
| WO | WO-2008077552 A1 | 7/2008 |
| WO | WO-2008078091 A1 | 7/2008 |
| WO | WO-2008113469 A2 | 9/2008 |
| WO | WO-2008124323 A1 | 10/2008 |
| WO | WO-2008131859 A2 | 11/2008 |

(Continued)

OTHER PUBLICATIONS

Alzabin, S. (2007) "Hematopoietic Progenitor Kinase is a negative regulator of the immune system" Dissertation, NYU, 278 pages.

(Continued)

*Primary Examiner* — Charanjit Aulakh

(57) ABSTRACT

The present disclosure relates generally to certain 6-azabenzimidazole compounds, pharmaceutical compositions comprising said compounds, and methods of making and using said compounds and pharmaceutical compositions. The compounds and compositions disclosed herein may be used for the treatment or prevention of diseases, disorders, or infections modifiable by hematopoietic progenitor kinase 1 (HPK1) inhibitors, such as HBV, HIV, cancer, and/or a hyper-proliferative disease.

45 Claims, No Drawings

(56) References Cited

FOREIGN PATENT DOCUMENTS

| | | |
|---|---|---|
| WO | WO-2009010299 A1 | 1/2009 |
| WO | WO-2009015867 A1 | 2/2009 |
| WO | WO-2009099801 A1 | 8/2009 |
| WO | WO-2010020675 A1 | 2/2010 |
| WO | WO-2010059393 A1 | 5/2010 |
| WO | WO-2011014795 A2 | 2/2011 |
| WO | WO-2011090738 A2 | 7/2011 |
| WO | WO-2011119777 A2 | 9/2011 |
| WO | WO-2011130146 A1 | 10/2011 |
| WO | WO-2011134971 A1 | 11/2011 |
| WO | WO-2012020813 A1 | 2/2012 |
| WO | WO-2012097479 A1 | 7/2012 |
| WO | WO-2012101064 A1 | 8/2012 |
| WO | WO-2012123312 A1 | 9/2012 |
| WO | WO-2013020062 A1 | 2/2013 |
| WO | WO-2013055645 A1 | 4/2013 |
| WO | WO-2013117285 A1 | 8/2013 |
| WO | WO-2013130660 A1 | 9/2013 |
| WO | WO-2014100065 A1 | 6/2014 |
| WO | WO-2014202493 A1 | 12/2014 |
| WO | WO-2015017610 A1 | 2/2015 |
| WO | WO-2015082887 A2 | 6/2015 |
| WO | WO-2015089479 A1 | 6/2015 |
| WO | WO-2015089481 A2 | 6/2015 |
| WO | WO-2015140051 A1 | 9/2015 |
| WO | WO-2015140054 A1 | 9/2015 |
| WO | WO-2015140055 A1 | 9/2015 |
| WO | WO-2015144001 A1 | 10/2015 |
| WO | WO-2016004272 A1 | 1/2016 |
| WO | WO-2016057624 A1 | 4/2016 |
| WO | WO-2016067112 A1 | 5/2016 |
| WO | WO-2016073378 A1 | 5/2016 |
| WO | WO-2016073738 A2 | 5/2016 |
| WO | WO-2016090300 A1 | 6/2016 |
| WO | WO-2016097863 A1 | 6/2016 |
| WO | WO-2016097870 A1 | 6/2016 |
| WO | WO-2016100285 A1 | 6/2016 |
| WO | WO-2016100608 A1 | 6/2016 |
| WO | WO-2016100975 A1 | 6/2016 |
| WO | WO-2016106623 A1 | 7/2016 |
| WO | WO-2016106624 A1 | 7/2016 |
| WO | WO-2016106625 A1 | 7/2016 |
| WO | WO-2016106626 A1 | 7/2016 |
| WO | WO-2016106652 A1 | 7/2016 |
| WO | WO-2016108707 A1 | 7/2016 |
| WO | WO-2016109219 A1 | 7/2016 |
| WO | WO-2016109220 A1 | 7/2016 |
| WO | WO-2016109221 A1 | 7/2016 |
| WO | WO-2016109222 A1 | 7/2016 |
| WO | WO-2016109223 A1 | 7/2016 |
| WO | WO-2016109480 A1 | 7/2016 |
| WO | WO-2016120196 A1 | 8/2016 |
| WO | WO-2016145252 A1 | 9/2016 |
| WO | WO-2016146985 A1 | 9/2016 |
| WO | WO-2016149351 A1 | 9/2016 |
| WO | WO-2016149668 A1 | 9/2016 |
| WO | WO-2016161145 A1 | 10/2016 |
| WO | WO-2016161196 A1 | 10/2016 |
| WO | WO-2016161960 A1 | 10/2016 |
| WO | WO-2016162867 A1 | 10/2016 |
| WO | WO-2016164428 A1 | 10/2016 |
| WO | WO-2016164641 A1 | 10/2016 |
| WO | WO-2016172010 A1 | 10/2016 |
| WO | WO-2016176726 A1 | 11/2016 |
| WO | WO-2016201370 A1 | 12/2016 |
| WO | WO-2016205942 A1 | 12/2016 |
| WO | WO-2017002078 A1 | 1/2017 |
| WO | WO-2017021501 A1 | 2/2017 |
| WO | WO-2017055530 A1 | 4/2017 |
| WO | WO-2017055533 A1 | 4/2017 |
| WO | WO-2017087723 A1 | 5/2017 |
| WO | WO-2017103205 A1 | 6/2017 |
| WO | WO-2017151732 A1 | 9/2017 |
| WO | WO-2017181177 A1 | 10/2017 |
| WO | WO-2017222285 A1 | 12/2017 |
| WO | WO-2017222287 A1 | 12/2017 |
| WO | WO-2018004213 A1 | 1/2018 |
| WO | WO-2018049152 A1 | 3/2018 |
| WO | WO-2018049191 A1 | 3/2018 |
| WO | WO-2018049200 A1 | 3/2018 |
| WO | WO-2018049214 A1 | 3/2018 |
| WO | WO-2018081531 A2 | 5/2018 |
| WO | WO-2018102366 A1 | 6/2018 |
| WO | WO-2018148745 A1 | 8/2018 |
| WO | WO-2018152220 A1 | 8/2018 |
| WO | WO-2018167147 A1 | 9/2018 |
| WO | WO-2018183956 A1 | 10/2018 |
| WO | WO-2018183964 A1 | 10/2018 |
| WO | WO-2018215668 A1 | 11/2018 |
| WO | WO-2018228920 A1 | 12/2018 |
| WO | WO-2018228923 A1 | 12/2018 |
| WO | WO-2018228925 A1 | 12/2018 |
| WO | WO-2019057102 A1 | 3/2019 |
| WO | WO-2019089641 A1 | 5/2019 |
| WO | WO-2019090198 A1 | 5/2019 |
| WO | WO-2019141250 A1 | 7/2019 |
| WO | WO-2019164846 A1 | 8/2019 |
| WO | WO-2019164847 A1 | 8/2019 |
| WO | WO-2019200120 A1 | 10/2019 |
| WO | WO-2019206049 A1 | 10/2019 |
| WO | WO-2019238067 A1 | 12/2019 |
| WO | WO-2020023551 A1 | 1/2020 |
| WO | WO-2020023560 A1 | 1/2020 |
| WO | WO-2020061377 A1 | 3/2020 |
| WO | WO-2020069402 A1 | 4/2020 |
| WO | WO-2020070331 A1 | 4/2020 |
| WO | WO-2020070332 A1 | 4/2020 |
| WO | WO-2020072627 A1 | 4/2020 |
| WO | WO-2020072695 A1 | 4/2020 |
| WO | WO-2020089892 A1 | 5/2020 |
| WO | WO-2020092528 A1 | 5/2020 |
| WO | WO-2020100027 A1 | 5/2020 |
| WO | WO-2020103896 A1 | 5/2020 |
| WO | WO-2020113233 A1 | 6/2020 |
| WO | WO-2020120257 A1 | 6/2020 |
| WO | WO-2020163248 A1 | 8/2020 |
| WO | WO-2020163382 A1 | 8/2020 |
| WO | WO-2020163401 A1 | 8/2020 |
| WO | WO-2020163405 A1 | 8/2020 |
| WO | WO-2020163409 A1 | 8/2020 |
| WO | WO-2020163544 A1 | 8/2020 |
| WO | WO-2020188467 A1 | 9/2020 |
| WO | WO-2020193511 A1 | 10/2020 |
| WO | WO-2020193512 A1 | 10/2020 |
| WO | WO-2020210537 A1 | 10/2020 |
| WO | WO-2020219934 A1 | 10/2020 |
| WO | WO-2020227325 A1 | 11/2020 |
| WO | WO-2020235902 A1 | 11/2020 |
| WO | WO-2020237025 A1 | 11/2020 |
| WO | WO-2020255022 A1 | 12/2020 |
| WO | WO-2021000925 A1 | 1/2021 |
| WO | WO-2021000935 A1 | 1/2021 |
| WO | WO-2021004535 A1 | 1/2021 |
| WO | WO-2021004547 A1 | 1/2021 |
| WO | WO-2021013083 A1 | 1/2021 |
| WO | WO-2021026180 A1 | 2/2021 |
| WO | WO-2021029896 A1 | 2/2021 |
| WO | WO-2021030627 A1 | 2/2021 |
| WO | WO-2021032148 A1 | 2/2021 |
| WO | WO-2021046254 A1 | 3/2021 |
| WO | WO-2021050964 A1 | 3/2021 |
| WO | WO-2021057872 A1 | 4/2021 |
| WO | WO-2021074279 A1 | 4/2021 |

OTHER PUBLICATIONS

Alzabin, S. et al. (2009) "Hematopoietic Progenitor Kinase 1 is a Negative Regulator of Dendritic Cell Activation" The Journal of Immunology, 6187-6194.

(56) References Cited

OTHER PUBLICATIONS

Alzabin, S. et al. (2010) "Hematopoietic progenitor kinase 1 is a critical component of prostaglandin E2-mediated suppression of the anti-tumor immune response" Cancer Immunol Immunother, 59:419-429.

Arnold, R. et al. (2001) "Caspase-mediated Cleavage of Hematopoietic Progenitor Kinase 1 (HPK1) Converts an Activator of NFkB into an Inhibitor of NFkB*" The Journal of Biological Chemistry, 276(18):14675-14684.

Arnold, R. et al. (2005) "Activation of Hematopoietic Progenitor Kinase 1 Involves Relocation, Autophosphorylation, and Transphosphorylation by Protein Kinase D1" Molecular and Cellular Biology, 25(6):2364-2383.

Arnold, S. et al. (2007) "Sustained JNK signaling by proteolytically processed HPK1 mediates IL-3 independent survival during monocytic differentiation" Cell Death and Differentiation, 14:568-575.

Batcha, M. et al. (2019) "Identification of a new type of haematopoietic progenitor kinase-interacting protein (HIP-55) in Aedes aegypti mosquito haemocytes and its involvement in immunity-like functions in mosquito: a molecular study" Parasitology Research, 118:2509-2521.

Bhattarai, D. et al. (2017) "Design, synthesis, and biological evaluation of structurally modified isoindolinone and quinazolinone derivatives as hedgehog pathway inhibitors" European Journal of Medicinal Chemistry, 125:1036-1050.

Boomer, J. et al. (2005) "Functional Interactions of HPK1 With Adaptor Proteins" Journal of Cellular Biochemistry, 95:34-44.

Borgogno, A. et al. (2013) "The impact of either 4-R-hydroxyproline or 4-R-fluoroproline on the conformation and SH3m-cort binding of HPK1 proline-rich peptide" Amino Acids, 44:607,614.

Bos, P. et al. (2019) "Development of MAP4 Kinase Inhibitors as Motor Neuron-Protecting Agents" Cell Chemical Biology, 26:1703-1715.e37.

Brenner, D. et al. (2007) "Caspase-cleaved HPK1 induces CD95L-independent activation-induced cell death in T and B lymphocytes" Blood, 110(12):3968-3977.

Brenner, D. et al. (2009) "Phosphorylation of CARMA1 by HPK1 is critical for NF-B activation in T cells" PNAS, 106(34):14508-14513.

Burns, J. et al. (2011) "The SLP-76 Src Homology 2 Domain is Required for T Cell Development and Activation" The Journal of Immunology, 187:4459-4466.

Chen, Y. et al. (2020) "Abstract 4513: The role of HPK1 in the regulation of T cell function and anti-tumor immune activity" Cancer Research [downloaded from https://cancerres.aacrjournals.org/content/80/16_Supplement/4513] 4 pages.

Chen-Deutsch, X. et al. (2012) "Dual role of hematopoietic progenitor kinase 1 (HPK1) as a positive regulator of 1 ?,25-dihydroxyvitamin D-induced differentiation and cell cycle arrest of AML cells and as a mediator of vitamin D resistance" Cell Cycle, 11(7):1364-1373.

Chen-Deutsch, X. et al. (2012) "The pan-caspase inhibitor Q-VD-OPh has anti-leukemia effects and can interact with vitamin D analogs to increase HPK1 signaling in AML cells" Leukemia Research, 36:884-888.

Chmielewski, S. et al. (2020) "Abstract 1947: Development and characterization of small molecule HPK1 inhibitors" Cancer Research [downloaded from https://cancerres.aacrjournals.org/content/80/16_Supplement/1947] 5 pages.

Chuang, H. et al. (2016) "MAP4K Family Kinases in Immunity and Inflammation" Advances in Immunology, 129:277-314.

Chuang, H. et al. (2019) "MAP4K Family Kinases and DUSP Family Phosphatases in T-Cell Signaling and Systemic Lupus Erythematosus" Cells, 8:1-13.

Chuang, H. et al. (2019) "MAP4K3/GLK in autoimmune disease, cancer and aging" Journal of Biomedical Science, 26(82):1-8.

Ciccone, D. et al. (2020) "Abstract 942: HPK1, hematopoietic progenitor kinase 1 , is a promising therapeutic target for cancer immunotherapy" Cancer Research [downloaded from https://cancerres.aacrjournals.org/content/80/16_Supplement/942] 4 pages.

Ciccone, D. et al. (2020) Abstract for "A Highly Selective and Potent HPK1 Inhibitor Enhances Immune Cell Activation and Induces Robust Tumor Growth Inhibition in a Murine Syngeneic Tumor Model" Journal for ImmoTherapy of Cancer preprint, A724.

Cossa, G. et al. (2020) "Localized Inhibition of Protein Phosphatase 1 by NUAK1 Promotes Spliceosome Activity and Reveals a MYC-Sensitive Feedback Control of Transcription" Molecular Cell 77:1322-1339.

Deford-Watts, L. et al. (2007) "The Membrane-proximal Portion of CD3 Associates with the Serine/Threonine Kinase GRK2*" The Journal of Biological Chemistry, 282(22):16126-16134.

Deng, X. et al. (2010) "Broad spectrum alkynyl inhibitors of T315I Bcr-Abl" Bioorganic & Medicinal Chemistry Letters, 20:4196-4200.

Di Bartolo, V. et al. (2007) "A novel pathway down-modulating T cell activation involves HPK-1-dependent recruitment of 14-3-3 proteins on SLP-76" JEM, 204(3):681-691.

Ensenat, D. et al. (1999) "A Novel Src Homology 3 Domain-containing Adaptor Protein, HIP-55, That Interacts with Hematopoietic Progenitor Kinase 1*" The Journal of Biological Chemistry, 274(48):33945-33950.

Escobar-Hoyos, L. et al. (2020) "Altered RNA Splicing by Mutant p53 Activates Oncogenic RAS Signaling in Pancreatic Cancer" Cancer Cell, 38:198-211.e8.

Eymin, B. (2020) "Targeting the spliceosome machinery: A new therapeutic axis in cancer?" Biochemical Pharmacology, 1-11.

Fornvik, K. et al. (2016) "ITPP Treatment of RG2 Glioblastoma in a Rat Model" Anticancer Research, 36:5751-5756.

Fukuda, T. et al. (2020) "BMP signaling is a therapeutic target in ovarian cancer" Cell Death Discovery, 6(139):1-15.

Geisberger, R. et al. (2002) "Phage Display Based Cloning of Proteins Interacting with the Cytoplasmic Tail of Membrane Immunoglobulins*" Developmental Immunology, 9(3):127-134.

Gilardi, D. et al. (2020) "PK, PD, and interactions: the new scenario with JAK inhibitors and S1P receptor modulators, two classes of small molecule drugs, in IBD" Expert Review of Gastroenterology & Hepatology, 1-10.

Han, A. et al. (2003) "Bam32 Links the B Cell Receptor to ERK and JNK and Mediates B Cell Proliferation but Not Survival" Immunity, 19:621-632.

Han, J. et al. (2003) "The SH3 Domain-containing Adaptor HIP-55 Mediates c-Jun N-terminal Kinase Activation in T Cell Receptor Signaling*" The Journal of Biological Chemistry, 278(52):52195-52202.

Han, J. et al. (2005) "HIP-55 is Important for T-Cell Proliferation, Cytokine Production, and Immune Responses" Molecular and Cellular Biology, 25(16):6869-6878.

Hansen, S. (2016) "Tumor cell checkpoints" BioCentury on BioBusiness, 1-3.

Hehner, S. et al. (2000) "Tyrosine-phosphorylated Vav1 as a Point of Integration for T-cell Receptor- and CD28-mediated Activation of JNK, p38, and lnterleukin-2 Transcription*" The Journal of Biological Chemistry, 275(24):18160-18171.

Hellwig, S. et al. (2012) "Small-Molecule Inhibitors of the c-Fes Protein-Tyrosine Kinase" Chemistry & Biology, 19:529-540.

Hernandez, S. et al. (2018) "The Kinase Activity of Hematopoietic Progenitor Kinase 1 is Essential for the Regulation of T Cell Function" Cell Reports 25:80-94.

Hsieh, W. et al. (2009) "Pharmacodynamic Effects of Seliciclib, an OrallyAdministered Cell CycleModulator, in Undifferentiated Nasopharyngeal Cancer" Clin Cancer Res, 15(4):1435-1442.

Hu, M. et al. (1996) "Human HPK1, a novel human hematopoietic progenitor kinase that activates the JNK/SAPK kinase cascade" Genes & Development, 10:2251-2264.

Intl. Search Report and Written Opinion dated Jan. 20, 2020 for Intl. Appl. No. PCT/US2019/058932.

Iribarren, K. et al. (2016) "Trial Watch: Immunostimulation with Toll-like receptor agonists in cancer therapy" Oncolmmunology, 5(3):1-11.

Ishak, C. et al. (2021) "Spliceosome-Targeted Therapies Induce dsRNA Responses" Immunity, 54:11-13.

(56) References Cited

OTHER PUBLICATIONS

Ito, Y. et al. (2001) "Interaction of Hematopoietic Progenitor Kinase 1 and c-Abl Tyrosine Kinase in Response to Genotoxic Stress*" The Journal of Biological Chemistry, 276(21):18130-18138.
Jagtap, P. et al. (2020) "Identification of phenothiazine derivatives as UHMbinding inhibitors of early spliceosome assembly" Nature Communications, 1-11.
Jakob, S. et al. (2013) "Hematopoietic progenitor kinase 1 (HPK1) is required for LFA-1-mediated neutrophil recruitment during the acute inflammatory response" Blood, 121(20):4184-4194.
Jiang, Y. et al. (2020) "Multi-omic analysis reveals HIP-55-dependent regulation of cytokines release" Bioscience Reports, 40(3):1-22.
Karaosmanoglu, O. (2020) "P38-b/SAPK-inhibiting and apoptosisinducing activities of (E)-4-chloro-2-((3-ethoxy-2-hydroxybenzylidene)amino)phenol" Human and Experimental Toxicology, 1-16.
Keilhack, H. et al. (2001) "Negative Regulation of Ros Receptor Tyrosine Kinase Signaling: An Epithelial Function of the SH2 Domain Protein Tyrosine Phosphatase SHP-1" The Journal of Cell Biology, 152(2):325-334.
Kiefer, F. et al. (1996) "HPK1, a hematopoietic protein kinase activating the SAPK/JNK pathway" The EMBO Journal, 15(24):7013-7025.
Kiefer, F. et al. (2002) "Signal transduction and co-stimulatory pathways" Transplant Immunology, 9:69-82.
Konigsberger, S. et al. (2010) "HPK1 Associates with SKAP-HOM to Negatively Regulate Rap1-Mediated B-Lymphocyte Adhesion" Plos One, 5(9):1-9.
Krammer, P. et al. (2007) "Life and death in peripheral T cells" Nature, 7:532-542.
Kumar, S. et al. (2020) "Mitogen-Activated Protein Kinase Inhibitors and T-Cell-Dependent Immunotherapy in Cancer" Pharmaceuticals, 13(9):1-11.
Kwon, S. et al. (2020) "Global spliceosome activity regulates entry into cellular senescence" The Faseb Journal, 35:1-13.
Lacey, B. et al. (2020) "Development of High-Throughput Assays for Evaluation of Hematopoietic Progenitor Kinase 1 Inhibitors" SLAS Discovery, 1-12.
Lacey, B. et al. (2021) "Development of High-Throughput Assays for Evaluation of Hematopoietic Progenitor Kinase 1 Inhibitors" SLAS Discovery, 26(1):88-99.
Lai, B. et al. (2020) "Activation of c-Jun N-Terminal Kinase, a Potential Therapeutic Target in Autoimmune Arthritis" Cells, 9:1-17.
Larsen, N. (2020) "The SF3b Complex is an Integral Component of the Spliceosome and Targeted by Natural Product-Based Inhibitors" Macromolecular Protein Complexes III: Structure and Function, 409-432.
Lasserre, R. et al. (2011) "Release of serine/threonine-phosphorylated adaptors from signaling microclusters down-regulates T cell activation" JCB, 195(5):839-853.s6.
Lau, W. et al. (2021) "Using yeast surface display to engineer a soluble and crystallizable construct of hematopoietic progenitor kinase 1 (HPK1)" Acta Cryst, F77:22-28.
Le Bras, S. et al. (2004) "Recruitment of the Actin-binding Protein HIP-55 to the Immunological Synapse Regulates T Cell Receptor Signaling and Endocytosis*" The Journal of Biological Chemistry, 279(15):15550-15560.
Lee, J. et al. (2009) "Recruitment of Sprouty1 to Immune Synapse Regulates T Cell Receptor Signaling1" The Journal of Immunology, 183:7178-7186.
Lee, Y. et al. (2020) Abstract for "Inhibition of the Kinase Activity of Hematopoietic Progenitor Kinase 1 Enhances Anti-PD-1-Induced Reinvigoration of Human Tumor-Infiltrating CD8+ T Cells" Journal of ImmunoTherapy of Cancer preprint, A912.
Leung, I. et al. (2001) "The Kinase Activation Loop is the Key to Mixed Lineage Kinase-3 Activation via Both Autophosphorylation and Hematopoetic Progenitor Kinase 1 Phosphorylation*" The Journal of Biological Chemistry, 276(3):1961-1967.
Lewitzky, M. et al. (2004) "Mona/Gads SH3C Binding to Hematopoietic Progenitor Kinase 1 (HPK1) Combines an Atypical SH3 Binding Motif, R/KXXK, with a Classical P XXP Motif Embedded in a Polyproline Type II (PPII) Helix*" The Journal of Biological Chemistry, 279(27):28724-28732.
Lin, J. et al. (2008) "Critical role for Rsk2 in T-lymphocyte activation" Blood, 111(2):525-533.
Ling, P. et al. (1999) "Interaction of Hematopoietic Progenitor Kinase 1 with Adapter Proteins Crk and CrkL Leads to Synergistic Activation of c-Jun N-Terminal Kinase" Molecular and Cellular Biology, 19(2):1359-1368.
Ling, P. et al. (2001) "Involvement of Hematopoietic Progenitor Kinase 1 in T Cell Receptor Signaling*" The Journal of Biological Chemistry, 276(22):18908-18914.
Liu, J. et al. (2019) "Critical role of kinase activity of hematopoietic progenitor kinase 1 in anti-tumor immune surveillance" Plos One, 14(3):1-18.
Ma, W. et al. (2001) "Leukocyte-specific adaptor protein Grap2 interacts with hematopoietic progenitor kinase 1 (HPK1) to activate JNK signaling pathway in T lymphocytes" Oncogene, 20:1703-1714.
Mahlab-Aviv, S. et al. (2020) "Spliceosome-Associated microRNAs Signify Breast Cancer Cells and Portray Potential Novel Nuclear Targets" International Journal of Molecular Sciences, 21:1-23.
Mallory, K. et al. (2016) "Cyclic-di-GMP binding induces structural rearrangements in the PlzA and PlzC proteins of the Lyme disease and relapsing fever spirochetes: a possible switch mechanism for c-di-GMP-mediated effector functions" Pathogens and Disease, 74(8):1-8.
Mayya, V. et al. (2009) "Quantitative Phosphoproteomic Analysis of T Cell Receptor Signaling Reveals System-Wide Modulation of Protein-Protein Interactions" Science Signaling, 2(84):1-16.
Meng, D. et al. (2020) "S100A14 suppresses metastasis of nasopharyngeal carcinoma by inhibition of NF-kB signaling through degradation of IRAK1" Oncogene, (39)5307-5322.
Metwally, K. et al. (2007) "Synthesis and biological activity of 2,5-diaryl-3-methylpyrimido[4,5-c]quinolin-1(2H)-one derivatives" Bioorganic & Medicinal Chemistry, 15:2434-2440.
Metwally, K. et al. (2013) "Structure-activity relationship investigation of methoxy substitution on anticancer pyrimido[4,5-c]quinolin-1(2H)-ones" Med Chem Res, 22:4481-4491.
Morrissey, KM. et al. (2016) "Immunotherapy and Novel Combinations in Oncology: Current Landscape, Challenges, and Opportunities" Clin Transl Sci, 9:89-104.
Navas, V. et al. (2017) "Serine Phosphorylation of SLP76 is Dispensable for T Cell Development but Modulates Helper T Cell Function" Plos One, 1-17.
Nicolaou, K. et al. (2021) "Design, Synthesis, and Biological Investigation of Thailanstatin A and Spliceostatin D Analogues Containing Tetrahydropyran, Tetrahydrooxazine, and Fluorinated Structural Motifs" The Journal of Organic Chemistry, A-W.
Office Action dated Aug. 10, 2020 for Taiwan Appl. No. 108139340.
Palaga, T. et al. (2003) "TCR-Mediated Notch Signaling Regulates Proliferation and IFN-Production in Peripheral T Cells" 171:3019-3024.
Palakurthi, S. et al. (2007) "Screening of 14C-Polyamines in the AT3B-1 Rat Prostate Tumor Model: The Search for a New PET Prostate Imaging Agent" In Vivo, 21:823-828.
Pan, L. et al. (2020) "Expanding the Mitogen-Activated Protein Kinase (MARK) Universe: An Update on MAP4Ks" Frontiers in Plant Science, 11:1-7.
Patzak, I. et al. (2010) "HPK1 competes with ADAP for SLP-76 binding and via Rap1 negatively affects T-cell adhesion" European Journal of Immunology, 40:3220-3225.
Paul, S. et al. (2013) "A new look at T cell receptor signaling to nuclear factor-kB" Trends in Immunology, 34(6):269-281.
Petasny, M. et al. (2020) "Splicing to Keep Cycling: The Importance of Pre-mRNA Splicing during the Cell Cycle" Trends in Genetics, 1-13.
Rajasekaran, K. et al. (2013) "Signaling by Fyn-ADAP via the Carma1-Bcl-10-MAP3K7 signalosome exclusively regulates inflammatory cytokine production in NK cells" Nature Immunology, 14(11):1127-1139.

(56) References Cited

OTHER PUBLICATIONS

Rocha-Perugini, V. et al. (2017) "Role of Drebrin at the Immunological Synapse" Drebrin, Advances in Experimental Medicine and Biology 1006: 271-280.
Rogers, E. et al. (2009) "Rrp1, a cyclic-di-GMP-producing response regulator, is an important regulator of Borrelia burgdorferi core cellular functions" Molecular Microbiology, 71(6):1551-1573.
Sanchez-Gonzalez, P. et al. (2011) "Quercetin reduces cisplatin nephrotoxicity in rats without compromising its anti-tumour activity" Nephrol Dial Transplant, 26:3484-3495.
Sanlorenzo, M. et al. (2016) "Oncogenic KIT mutations in different exons lead to specific changes in melanocyte phospho-proteome" Journal of Proteomics, 144:140-147.
Sauer, K. et al. (2001) "Hematopoietic Progenitor Kinase 1 Associates Physically and Functionally with the Adaptor Proteins B Cell Linker Protein and SLP-76 in Lymphocytes*" The Journal of Biological Chemistry, 276(48):45207-45216.
Sawasdikosol, S. et al. (2003) "Hematopoietic progenitor kinase 1 (HPK1) negatively regulates prostaglandin E2-induced fos gene transcription" Blood, 101(9):3687-3689.
Sawasdikosol, S. et al. (2007) "Prostaglandin E2 Activates HPK1 Kinase Activity via a PKA-dependent Pathway" The Journal of Biological Chemistry, 282(48):34693-34699.
Sawasdikosol, S. et al. (2012) "HPK1 as a novel target for cancer immunotherapy" Immunology Institute at the Mount Sinai School of Medicine, 4 pages.
Sawasdikosol, S. et al. (2020) "A perspective on HPK1 as a novel immuno-oncology drug target" eLife, 1-15.
Sawasdikosol, S. et al. (2020) "HPK1 Influences Regulatory T Cell Functions" ImmunoHorizons, 4(7)382-391.
Schulze-Luehrmann, J. et al. (2002) "Hematopoietic progenitor kinase 1 supports apoptosis of T lymphocytes" Blood, 100(3):954-960.
Seo, G. et al. (2020) "MAP4K Interactome Reveals STRN4 as a Key STRIPAK Complex Component in Hippo Pathway Regulation" Cell Reports, 32:1-12.e5.
Shi, Y. et al. (2020) "An exon skipping screen identifies antitumor drugs that are potent modulators of premRNA splicing, suggesting new therapeutic applications" Plos One, 15(5):1-19.
Shui, J. et al. (2007) "Hematopoietic progenitor kinase 1 negatively regulates T cell receptor signaling and T cell-mediated immune responses" Nature Immunology, 8(1):84-91.
Si, J. et al. (2020) "Hematopoietic Progenitor Kinasei (HPK1) Mediates T Cell Dysfunction and is a Druggable Target for T Cell-Based Immunotherapies" Cancer Cell, 38:1-16.e11.
Siligardi, G. et al. (2012) "The SH3 domain of HS1 protein recognizes lysine-rich polyproline motifs" Amino Acids, 42:1361-1370.
Simon, S. (2013) "Gimme a brake: HPK1 regulates LFA-1 and neutrophil traction" Blood, 121(20):4017-4018.
Soini, L. et al. (2020) "A biophysical and structural analysis of the interaction of BLNK with 14-3-3 proteins" Journal of Structural Biology, 212:1-6.
Song, X. et al. (2020) "Hematopoietic progenitor kinase 1 down-regulates the oncogenic receptor tyrosine kinase AXL in pancreatic cancer" J. Biol. Chem., 295(8):2348-2358.
Tanaka, N. et al. (2006) "Choroidal Neovascularization in Transgenic Mice Expressing Prokineticin 1: An Animal Model for Age-Related Macular Degeneration" Molecular Therapy, 13(3):609-616.
Taniguchi-Ponciano, K. et al. (2020) "Proteomic and Transcriptomic Analysis Identify Spliceosome as a Significant Component of the Molecular Machinery in the Pituitary Tumors Derived from POU1F1- and NR5A1-Cell Lineages" Genes, 11: 1-14.
Tolba, M. (2020) "Revolutionizing the Landscape of Colorectal Cancer Treatment: The Potential Role of Immune Checkpoint Inhibitors" International Journal of Cancer, 1-29.
Townsend, C. et al. (2020) "Mechanism of protein-guided folding of the active site U2/U6 RNA during spliceosome activation" Science, 1-23.
Vanzyl, E. et al. (2020) "The spliceosome inhibitors isoginkgetin and pladienolide B induce ATF3-dependent cell death" Plos One, 15:1-12.
Verma, N. et al. (2020) "Editorial: Adaptor Protein Regulation in Immune Signalling" Frontiers in Immunology, 11:1-3.
Vivier, E. et al. (2013) "ADAPted secretion of cytokines in NK cells" Nature Immunology, 14(11):1108-1110.
Volovitz, I. et al. (2011) "Split Immunity: Immune Inhibition of Rat Gliomas by Subcutaneous Exposure to Unmodified Live Tumor Cells" The Journal of Immunology, 1-11.
Wang, H. et al. (2009) "Proteasome-Mediated Degradation and Functions of Hematopoietic Progenitor Kinase 1 in Pancreatic Cancer" Cancer Res, 69(3):1063-1070.
Wang, H. et al. (2014) "The CUL7/F-box and WD Repeat Domain ontaining 8 (CUL7/Fbxw8) Ubiquitin Ligase Promotes Degradation of Hematopoietic Progenitor Kinase 1" The Journal of Biological Chemistry, 289(7):4009-4017.
Wang, H. et al. (2016) "The emerging roles of F-box proteins in pancreatic tumorigenesis" Seminars in Cancer Biology, 36:88-94.
Wang, H. et al. (2019) "Discovery of (R)?8-(6-Methyl-4-oxo-1,4,5,6-tetrahydropyrrolo[3,4?b]pyrrol-2-yl)-3-(1-methylcyclopropyl)-2-((1-methylcyclopropyl)amino)quinazolin-4(3H)?one, a Potent and Selective Pim-1/2 Kinase Inhibitor for Hematological Malignancies" J. Med. Chem., 62:1523-1540.
Wang, H. et al. (2020) "Abstract 4711: Novel mechanism involved in the regulation ofoncogenic Axl receptor tyrosine kinase in cancer" [downloaded from https://cancerres.aacrjournals.org/content/80/16_Supplement/4711] 4 pages.
Wang, J. et al. (2017) "HPK1 positive expression associated with longer overall survival in patients with estrogen receptor-positive invasive ductal carcinoma—not otherwise specified" Molecular Medicine Reports, 1-9.
Wang, L. et al. (2018) "EMT- and stroma-related gene expression and resistance to PD-1 blockade in urothelial cancer" Nature Communications, 1-12.
Wang, Q. et al. (2012) "Pdcd4 knockdown up-regulates MAP4K1 expression and activation of AP-1 dependent transcription through c-Myc" Biochimica et Biophysica Acta, 1823:1807-1814.
Wang, S. et al. (2020) "Homeodomain-interacting protein kinase (Hipk) plays roles in nervous system and muscle structure and function" Plos One, 15(3):1-22.
Wang, W. et al. (1997) "Activation of the Hematopoietic Progenitor Kinase-1 (HPK1)-dependent, Stress-activated c-Jun N-terminal Kinase (JNK) Pathway by Transforming Growth Factor b (TGF-b)-activated Kinase (TAK1), a Kinase Mediator of TGF b Signal Transduction" The Journal of Biological Chemistry, 272(36):22771-22775.
Wang, X. et al. (2011) "MEKK3 Regulates IFN-g Production in T Cells through the Rac1/2-Dependent MAPK Cascades" The Journal of Immunology, 186:5791-5800.
Wang, X. et al. (2012) "Attenuation of T Cell Receptor Signaling by Serine Phosphorylation-mediated Lysine 30 Ubiquitination of SLP-76 Protein" The Journal of Biological Chemistry, 287(41): 34091-34100.
Wang, X. et al. (2012) "Down-regulation of B Cell Receptor Signaling by Hematopoietic Progenitor Kinase 1 (HPK1)-mediated Phosphorylation and Ubiquitination of Activated B Cell Linker Protein (BLNK)" The Journal of Biological Chemistry, 287(14):11037-11048.
Wang, Y. et al. (2020) "Pharmacological inhibition of hematopoietic progenitor kinase 1 positively regulates T-cell function" Plos One, 15(12):1-19.
Wen, S. et al. (2005) "Discovery of an MIT-like atracotoxin family: Spider venom peptides that share sequence homology but not pharmacological properties with AVIT family proteins" Peptides, 26:2412-2426.
Wood, K. et al. (2020) "Modelling the developmental spliceosomal craniofacial disorder Burn-McKeown syndrome using induced pluripotent stem cells" Plos One, 15(7):1-30.
Wu, G. et al. (2018) "Inhibition of SF3B1 by molecules targeting the spliceosome results in massive aberrant exon skipping" RNA, 24(8):1056-1066.

(56) References Cited

OTHER PUBLICATIONS

Wu, Q. et al. (2020) "DLX6-AS1 promotes cell proliferation, migration and EMT of gastric cancer through FUS-regulated MAP4K1" Cancer Biology & Therapy, 21(1):17-25.

Yablonski, D. (2019) "Bridging the Gap: Modulatory Roles of the Grb2-Family Adaptor, Gads, in Cellular and Allergic Immune Responses" Frontiers in Immunology, 10:1-19.

Yamamoto, J. et al. (2015) "5-Aminolevulinic acid-induced protoporphyrin IX with multi-dose ionizing irradiation enhances host antitumor response and strongly inhibits tumor growth in experimental glioma in vivo" Molecular Medicine Reports, 11:1813-1819.

Yang, H. et al. (2006) "Tumorigenesis Suppressor Pdcd4 Down-Regulates Mitogen-Activated Protein Kinase Kinase Kinase Kinase 1 Expression To Suppress Colon Carcinoma Cell Invasion" Molecular and Cellular Biology, 26(4):1297-1306.

Yankee, T. et al. (2003) "Expression of the Grb2-Related Protein of the Lymphoid System in B Cell Subsets Enhances B Cell Antigen Receptor Signaling Through Mitogen-Activated Protein Kinase Pathways" The Journal of Immunology, 170:349-355.

Yao, Z. et al. (1999) "A Novel Human STE20-related Protein Kinase, HGK, That Specifically Activates the c-Jun N-terminal Kinase Signaling Pathway" The Journal of Biological Chemistry, 274(4):2118-2125.

You, D. et al. (2017) "Critical Role of Hematopoietic Progenitor Kinase 1 in Anittumor Immune Responses" SITC Annual Meeting, Poster P339.

You, D. et al. (2021) "Enhanced antitumor immunity by a novel small molecule HPK1 inhibitor" Journal for ImmunoTherapy of Cancer, 9:1-12.

Yu, J. et al. (2001) "Synergistic Regulation of Immunoreceptor Signaling by SLP-76-Related Adaptor Clnk and Serine/Threonine Protein Kinase HPK-1" Molecular and Cellular Biology, 21(18):6102-6112.

Yurchenko, M. et al. (2010) "CD150 regulates JNK1/2 activation in normal and Hodgkin's lymphoma B cells" Immunology and Cell Biology, 88:565-574.

Zhang, D. et al. (2020) "Intron retention is a hallmark and spliceosome represents a therapeutic vulnerability in aggressive prostate cancer" Nature Communications, 1-19.

Zhang, Q. et al. (2011) "Inhibited expression of hematopoietic progenitor kinase 1 associated with loss of jumonji domain containing 3 promoter binding contributes to autoimmunity in systemic lupus erythematosus" Journal of Autoimmunity, 37:180-189.

Zhang, Q. et al. (2017) "Interactions between hematopoietic progenitor kinase 1and its adaptor proteins (Review)" Molecular Medicine Reports, 1-11.

Zheng, X. et al. (2020) "Serine/arginine-rich splicing factors: the bridge linking alternative splicing and cancer" International Journal of Biological Sciences, 16(13):2442-2453.

Zhou, G. et al. (1999) "Hematopoietic Progenitor Kinase 1 is a Component of Transforming Growth Factor b-induced c-Jun N-terminal Kinase Signaling Cascade" The Journal of Biological Chemistry, 274(19):13133-13138.

Zhou, G. et al. (2004) "Protein Phosphatase 4 is a Positive Regulator of Hematopoietic Progenitor Kinase 1" The Journal of Biological Chemistry, 279(47):49551-49561.

Doering, K. et al. (2021) "Nuclear Hormone Receptor NHR-49 controls a HIF-1-independent hypoxia adaptation pathway in *Caenorhabditis elegans*" bioRxiv, 71 pages.

Degnan, A. et al. (2021) "Discovery of Orally Active Isofuranones as Potent, Selective Inhibitors of Hematopoetic Progenitor Kinase 1Discovery of Orally Active Isofuranones as Potent, Selective Inhibitors of Hematopoetic Progenitor Kinase 1" ACS Medicinal Chemistry Letters, 12 (3), 443-450.

Tang, L. et al. (2021) "T Cell Exhaustion and CAR-T Immunotherapy in Hematological Malignancies" BioMed Research International, 8 pages.

Yu, E. et al. (2021) "Identification of Potent Reverse Indazole Inhibitors for HPK1" ACS Med. Chem. Lett. 12:459-466.

Vara, B. et al. (2021) "Discovery of Diaminopyrimidine Carboxamide HPK1 Inhibitors as Preclinical Immunotherapy Tool Compounds" ACS Med. Chem. Lett. 12:653-661.

Sabnis, R. (2021) "Novel Substituted Exomethylene-oxindoles as HPK1 Inhibitors" ACS Med. Chem. Lett. 12:681-682.

Linney, I. et al. (2021) "Inhibitors of immuno-oncology target HPK1—a patent review (2016 to 2020)" Expert Opinion on Therapeutic Patents, 33 pages.

Shi, Y. et al. (2021) "Aberrant splicing in neuroblastoma generates RNA-fusion transcripts and provides vulnerability to spliceosome inhibitors" Nucleic Acids Research, 1-13.

Ghosh, A. et al. (2021) "Design and synthesis of herboxidiene derivatives that potently inhibit in vitro splicing" Org. Biomol. Chem. 19:1365-1377.

Kaur, H. et al. (2021) "Network Theory Reveals Principles of Spliceosome Structure and Dynamics" bioRxiv, 1-39.

Tailor, D. et al. (2021) "Y box binding protein 1 inhibition as a targeted therapy for ovarian cancer" Cell Chemical Biology, 22 pages.

Chatrikhi, R. et al. (2021) "A synthetic small molecule stalls pre-mRNA splicing by promoting an early-stage U2AF2-RNA complex" Cell Chemical Biology, 20 pages.

Ghosh, A. et al. (2021) "Spliceostatins and Derivatives: Chemical Syntheses and Biological Properties of Potent Splicing Inhibitors" J. Nat. Prod. 84:1681-1706.

\* cited by examiner

SUBSTITUTED 6-AZABENZIMIDAZOLE COMPOUNDS

CROSS REFERENCE TO RELATED APPLICATIONS

This application claims priority to U.S. Provisional Application No. 62/753,339, filed Oct. 31, 2018 and U.S. Provisional Application No. 62/868,550, filed Jun. 28, 2019, each of which is incorporated herein in its entirety for all purposes.

FIELD

This disclosure relates generally to certain 6-azabenzimidazole compounds, pharmaceutical compositions comprising said compounds, and methods of making and using said compounds and pharmaceutical compositions.

BACKGROUND

Immuno-oncology is a burgeoning area of cancer research, highlighted by inhibitor antibodies against the immune checkpoint receptors CTLA4, PD-1 and PD-L1. Targeted disruption of these checkpoint pathways releases the immune cell from key regulatory pathways, allowing for a boost in the immune response against cancer cells. Current therapies utilizing these antibodies are highlighted by both significant and durable response to many different cancers but also by low overall response rates (<25%). Understanding and improving these response rates is a formidable goal, and the combination of checkpoint blockade with other immune activating agents or cell based therapies could provide an inroad to expand upon patient responses.

Hematopoietic progenitor kinase 1 (HPK1), a STE20 ser/thr kinase from the germinal center family of kinases, regulates the function of diverse immune populations including T cells, B cells, and dendritic cells (Hu et al., Gens Dev, 1996; Alzabin et al., J Immunol 2009). In T cells, HPK1 serves as a negative regulator of T cell receptor (TCR) signaling (Liou et al., Immunity 2000; Sauer et al., JBC 2001) by phosphorylating SLP76 on serine 376, which induces the association of SLP76 with 14-3-3 proteins, and leads to the disassociation of the signaling complex (Di Bartolo et al., JEM 2007). Further supporting the role of HPK1 as a negative regulator of TCR signaling, murine HPK1 deficient T cells or HPK1 kinase inactive mutant T cells have enhanced ERK 1/2 activation and effector cytokine secretion upon TCR activation compared to their wild-type counterparts (Shui et al., Nat Immunol 2007; Hernandez et al., Cell Reports 2018). Accordingly, a small molecule inhibitor of HPK1 could provide a novel way to enhance anti-tumor immunity and also provide a way to increase the response to checkpoint receptor blockade.

SUMMARY

In one aspect, provided herein is a compound of Formula I,

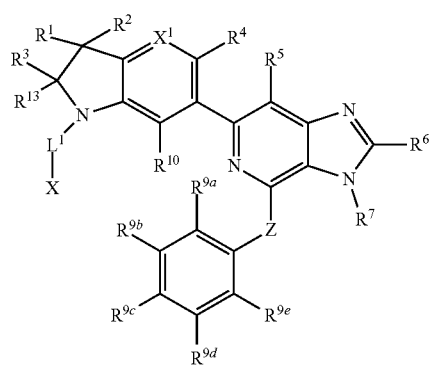

Formula I or a pharmaceutically acceptable salt thereof,
wherein:
one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or $R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or $R^1$ and $R^2$ together form =O;
$R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$C$_{1-6}$ alkyl,
  iii) —S(O)$_2$C$_{3-7}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)R$^{21}$;
$R^{21}$ is
  i) H,
  ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy, v) —$NH_2$, vi) —NH($C_{1-6}$ alkyl), wherein the $C_{1-6}$ alkyl is optionally substituted with 1-3 groups independently selected from —CN, —OH, halogen, and $C_{1-3}$ alkoxy, vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy, viii) $C_{1-6}$ alkoxy optionally substituted with 1-3 groups independently selected from —OH, halogen, $C_{1-3}$ alkyl, and $C_{3-7}$ monocyclic cycloalkyl, or ix) $C_{1-6}$ alkyl optionally substituted with 1-3 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —CN, —OH, halogen, $C_{1-3}$ alkyl, and $C_{1-3}$ alkoxy,
  f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
  g) —OC(O)$C_{1-6}$ alkyl optionally substituted with one —OH;

$R^3$ and $R^{13}$ are each H, or $R^3$ and $R^{13}$ together form =O;

$L^1$ is a cyclobutylene optionally substituted with 1-6 groups independently selected from —OH, halogen, $C_{1-3}$ alkyl, and $C_{1-3}$ alkoxy;

X is —$NR^{15}R^{16}$, wherein $R^{15}$ and $R^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —OH, halogen, $C_{1-3}$ alkyl, and $C_{1-3}$ alkoxy, and
  f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) —C(O)N($R^{22}$)$_2$, wherein each $R^{22}$ is independently H or $C_{1-6}$ alkyl;

$X^1$ is N or $CR^{17}$;

$R^4$, $R^5$, $R^6$, $R^{10}$ and $R^{17}$ are each independently H, halogen, $C_{1-3}$ alkyl, or $C_{1-3}$ alkoxy;

$R^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;

Z is —O—, —C($R^8$)$_2$—, or —$NR^8$—;

each $R^8$ is independently H or $C_{1-3}$ alkyl;

$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —$NH_2$,
v) —NH($C_{1-6}$ alkyl), wherein the $C_{1-6}$ alkyl is optionally substituted with 1-3 groups independently selected from —OH, halogen, and $C_{1-3}$ alkoxy,
vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —S(O)$_2$$C_{1-6}$ alkyl,
ix) —S(O)$_2$N($R^{23}$)$_2$, wherein each $R^{23}$ is independently H or $C_{1-6}$ alkyl,
x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and f) —$NR^{20}C(O)OC_{1-3}$ alkyl, wherein $R^{20}$ is H or $C_{1-3}$ alkyl, xi) $C_{3-7}$ monocyclic cycloalkyl optionally substituted with 1-3 groups independently selected from —OH, halogen, $C_{1-3}$ alkyl, and $C_{1-3}$ alkoxy, xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy, xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, xiv) —COOH, xv) —$C(O)N(R^{19})_2$, or xvi) —$C_{1-3}$ alkyl$C(O)N(R^{19})_2$, wherein one or more of $R^{9a}$, $R^{9b}$, $R^{9c}$, $R^{9d}$, and $R^{9e}$ is —$C(O)N(R^{19})_2$ or —$C_{1-3}$ alkyl$C(O)N(R^{19})_2$; and each $R^{19}$ is independently i) H, ii) —$S(O)_2C_{1-6}$ alkyl, iii) $C_{1-6}$ alkyl optionally substituted with 1-6 groups independently selected from —CN, —OH, halogen, $C_{1-3}$ alkoxy, and $C_{3-7}$ monocyclic cycloalkyl, iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

In one aspect, provided herein are pharmaceutical compositions comprising a compound provided herein, or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

In one aspect, the present disclosure provides methods of inhibiting HPK1 activity in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In one aspect, the present disclosure provides methods of treating a disease or disorder associated with increased HPK1 activity in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of increasing T-cell activation in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In one aspect, the present disclosure provides methods of treating cancer in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In one aspect, the present disclosure provides methods of inhibiting the growth or proliferation of cancer cells in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, $R^a$ in the below structure can be attached to any of the five carbon ring atoms or $R^a$ can replace the hydrogen attached to the nitrogen ring atom:

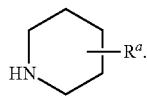

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I, II, IIa, IIb, III, IIIa, IV, IVa, IVb, IVc, V, Va, Vb, Vc, VI, VIa, VIb, VIc, VII, VIIa, VIIb, or VIIc. Also included are the specific compounds of Examples 1 to 297.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X".

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)$NR^YR^Z$ and an "N-amido" group which refers to the group —$NR^YC(=O)R^Z$, wherein $R^Y$ and $R^Z$ are independently selected from the group consisting of hydrogen, alkyl, aryl, haloalkyl, heteroaryl, cycloalkyl, or heterocyclyl; each of which may be optionally substituted.

"Amino" refers to the group —$NR^YR^Z$ wherein $R^Y$ and $R^Z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5] nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably. In some embodiments, a heterocyclyl is substituted with an oxo group.

"Hydroxy" or "hydroxyl" refers to the group —OH.

"Oxo" refers to the group (=O) or (O).

"Sulfonyl" refers to the group —$S(O)_2R^c$, where $R^c$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

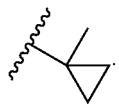

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^2$H, $^3$H, $^{13}$C and $^{14}$C are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, II, IIa, IIb, III, IIIa, IV, IVa, IVb, IVc, V, Va, Vb, Vc, VI, VIa, VIb, VIc, VII, VIIa, VIIb, or VIIc in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, II, IIa, IIb, III, IIIa, IV, IVa, IVb, IVc, V, Va, Vb, Vc, VI, VIa, VIb, VIc, VII, VIIa, VIIb, or VIIc, when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, II, IIa, IIb, III, IIIa, IV, IVa, IVb, IVc, V, Va, Vb, Vc, VI, VIa, VIb, VIc, VII, VIIa, VIIb, or VIIc.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of hematopoietic progenitor kinase 1 (HPK1) activity. The therapeutically effective amount may vary depending on the subject, and the disease or condition being treated, the weight and age of the subject, the severity of the disease or condition, and the manner of administering, which can readily be determined by one of ordinary skill in the art.

The term "inhibition" indicates a decrease in the baseline activity of a biological activity or process. "Inhibition of activity of HPK1" or variants thereof refers to a decrease in HPK1 activity as a direct or indirect response to the presence of a compound of the present disclosure relative to the HPK1 activity in the absence of the compound of the present disclosure. "Inhibition of HPK1" refers to a decrease in HPK1 activity as a direct or indirect response to the presence of a compound provided herein relative to the HPK1 activity in the absence of the compound provided herein. In some embodiments, the inhibition of HPK1 activity may be compared in the same subject prior to treatment, or other subjects not receiving the treatment.

II. Compounds

In one aspect, provided herein is a compound of Formula I,

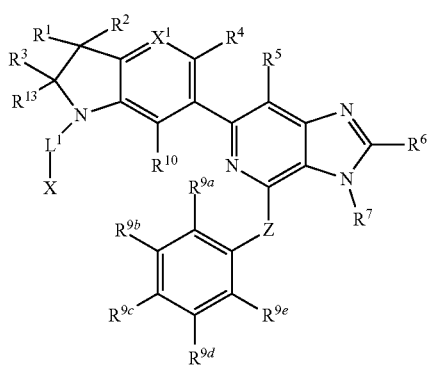

Formula I or a pharmaceutically acceptable salt thereof,
wherein:
one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or $R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or $R^1$ and $R^2$ together form =O;

$R^{11}$ is
i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
ii) —S(O)$_2$C$_{1-6}$ alkyl,
iii) —S(O)$_2$C$_{3-7}$ monocyclic cycloalkyl,
iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
v) —C(O)R$^{21}$;

$R^{21}$ is
i) H,
ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy,
v) —NH$_2$,
vi) —NH(C$_{1-6}$ alkyl), wherein the $C_{1-6}$ alkyl is optionally substituted with 1-3 groups independently selected from —CN, —OH, halogen, and $C_{1-3}$ alkoxy,
vii) —N(C$_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy,
viii) $C_{1-6}$ alkoxy optionally substituted with 1-3 groups independently selected from —OH, halogen, $C_{1-3}$ alkyl, and $C_{3-7}$ monocyclic cycloalkyl, or
ix) $C_{1-6}$ alkyl optionally substituted with 1-3 groups independently selected from
a) —CN,
b) —OH,
c) halogen,
d) $C_{1-3}$ alkoxy,
e) $C_{3-7}$ monocyclic cycloalkyl optionally substituted with 1-3 groups independently selected from —CN, —OH, halogen, $C_{1-3}$ alkyl, and $C_{1-3}$ alkoxy,
f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
g) —OC(O)C$_{1-6}$ alkyl optionally substituted with one —OH;

$R^3$ and $R^{13}$ are each H, or
$R^3$ and $R^{13}$ together form =O;

$L^1$ is a cyclobutylene optionally substituted with 1-6 groups independently selected from —OH, halogen, $C_{1-3}$ alkyl, and $C_{1-3}$ alkoxy;

X is —NR$^{15}$R$^{16}$, wherein R$^{15}$ and R$^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)C$_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
a) —CN,
b) —OH,
c) halogen,
d) $C_{1-3}$ alkoxy,
e) $C_{3-7}$ monocyclic cycloalkyl optionally substituted with 1-3 groups independently selected from —OH, halogen, $C_{1-3}$ alkyl, and $C_{1-3}$ alkoxy, and f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
- i) —CN,
- ii) a halogen,
- iii) —OH,
- iv) $C_{1-6}$ alkoxy optionally substituted with 1-3 groups independently selected from —OH, halogen, $C_1$-3 alkoxy, and $C_{3-7}$ monocyclic cycloalkyl,
- v) $C_{1-6}$ alkyl optionally substituted with 1-3 groups independently selected from —OH, halogen, $C_{1-3}$ alkoxy, and $C_{3-7}$ monocyclic cycloalkyl,
- vi) —COOH, or
- vii) —C(O)N($R^{22}$)$_2$, wherein each $R^{22}$ is independently H or $C_{1-6}$ alkyl;

$X^1$ is N or $CR^{17}$;

$R^4$, $R^5$, $R^6$, $R^{10}$ and $R^{17}$ are each independently H, halogen, $C_{1-3}$ alkyl, or $C_{1-3}$ alkoxy;

$R^7$ is
- i) H,
- ii) $C_{1-6}$ alkyl optionally substituted with 1-3 groups independently selected from —OH, halogen, $C_{1-3}$ alkoxy, and $C_{3-7}$ monocyclic cycloalkyl, or
- iii) $C_{3-7}$ monocyclic cycloalkyl optionally substituted with 1-3 groups independently selected from —OH, halogen, $C_1$-3 alkyl, and $C_{1-3}$ alkoxy;

Z is —O—, —C($R^8$)$_2$—, or —N$R^8$—;

each $R^8$ is independently H or $C_1$-3 alkyl;

$R^{9a}$, $R^{9b}$, $R^{9c}$, $R^{9d}$, and $R^{9e}$ are independently
- i) H,
- ii) halogen,
- iii) $C_{1-6}$ alkoxy optionally substituted with 1-3 groups independently selected from —OH, halogen, $C_{1-3}$ alkyl, and $C_{3-7}$ monocyclic cycloalkyl,
- iv) —NH$_2$,
- v) —NH($C_{1-6}$ alkyl), wherein the $C_{1-6}$ alkyl is optionally substituted with 1-3 groups independently selected from —OH, halogen, and $C_{1-3}$ alkoxy,
- vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
- vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
- viii) —S(O)$_2$$C_{1-6}$ alkyl,
- ix) —S(O)$_2$N($R^{23}$)$_2$, wherein each $R^{23}$ is independently H or $C_{1-6}$ alkyl,
- x) $C_{1-6}$ alkyl optionally substituted with 1-3 groups independently selected from
  - a) —OH,
  - b) halogen,
  - c) $C_{1-3}$ alkoxy,
  - d) $C_{3-7}$ monocyclic cycloalkyl,
  - e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  - f) —N$R^{20}$C(O)O$C_{1-3}$ alkyl, wherein $R^{20}$ is H or $C_{1-3}$ alkyl,
- xi) $C_{3-7}$ monocyclic cycloalkyl optionally substituted with 1-3 groups independently selected from —OH, halogen, $C_{1-3}$ alkyl, and $C_{1-3}$ alkoxy,
- xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
- xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
- xiv) —COOH,
- xv) —C(O)N($R^{19}$)$_2$, or
- xvi) —$C_{1-3}$ alkylC(O)N($R^{19}$)$_2$, wherein one or more of $R^{9a}$, $R^{9b}$, $R^{9c}$, $R^{9d}$, and $R^{9e}$ is —C(O)N($R^{19}$)$_2$ or —$C_{1-3}$ alkylC(O)N($R^{19}$)$_2$; and each $R^{19}$ is independently
- i) H,
- ii) —S(O)$_2$$C_{1-6}$ alkyl,
- iii) $C_{1-6}$ alkyl optionally substituted with 1-6 groups independently selected from —CN, —OH, halogen, $C_{1-3}$ alkoxy, and $C_{3-7}$ monocyclic cycloalkyl,
- iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or
- v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

In some embodiments, the compound of Formula I is of Formula II,

Formula II or a pharmaceutically acceptable salt thereof, wherein
each $R^{12}$ is independently —OH, halogen, $C_{1-3}$ alkyl, or $C_{1-3}$ alkoxy; and n is 0, 1, 2, 3, or 4;

and the remaining variables are as defined as in Formula I.

In some embodiments, the compound of Formula I or II is of Formula IIa,

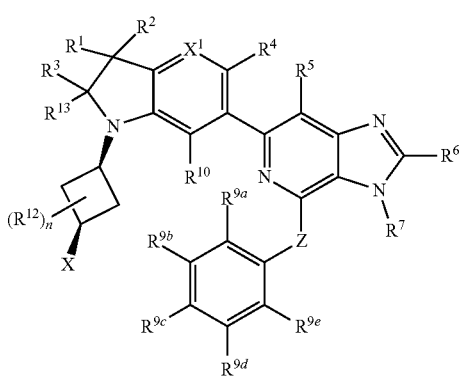

Formula IIa or a pharmaceutically acceptable salt thereof, wherein the variables are as defined as in Formula I.

In some embodiments, the compound of Formula I, II or IIa is of Formula IIb:

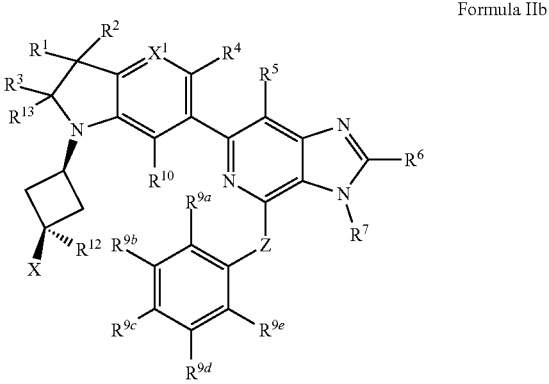

Formula IIb or a pharmaceutically acceptable salt thereof, wherein the variables are as defined as in Formula I.

In some embodiments of the compound of Formula I, or a pharmaceutically acceptable salt thereof, $L^1$ is a cyclobutylene optionally substituted with 1, 2, 3, 4, 5, or 6 groups independently selected from —OH, halogen, $C_{1-3}$ alkyl, and $C_{1-3}$ alkoxy. In some embodiments of the compound of Formula I, or a pharmaceutically acceptable salt thereof, $L^1$ is a cyclobutylene. In some embodiments of the compound of Formula I, or a pharmaceutically acceptable salt thereof, $L^1$ is a cyclobutylene substituted with one $C_{1-3}$ alkyl group. In some embodiments of the compound of Formula I, or a pharmaceutically acceptable salt thereof, $L^1$ is a cyclobutylene substituted with one methyl group.

In some embodiments of the compound of Formula II, IIa, or IIb, or a pharmaceutically acceptable salt thereof, $R^{12}$ is OH. In some embodiments of the compound of Formula II, IIa, or IIb, or a pharmaceutically acceptable salt thereof, $R^{12}$ is halogen. In some embodiments of the compound of Formula II, IIa, or IIb, or a pharmaceutically acceptable salt thereof, $R^{12}$ is $C_{1-3}$ alkyl. In some embodiments of the compound of Formula II, IIa, or IIb, or a pharmaceutically acceptable salt thereof, $R^{12}$ is $C_{1-3}$ alkoxy. In some embodiments of the compound of Formula II, IIa, or IIb, or a pharmaceutically acceptable salt thereof, $R^{12}$ is methyl.

In some embodiments of the compound of Formula II or IIa, or a pharmaceutically acceptable salt thereof, n is 0, 1, 2, 3, or 4. In some embodiments of the compound of Formula II or IIa, or a pharmaceutically acceptable salt thereof, n is 0, 1, 2, or 3. In some embodiments of the compound of Formula II or IIa, or a pharmaceutically acceptable salt thereof, n is 0, 1, or 2. In some embodiments of the compound of Formula II or IIa, or a pharmaceutically acceptable salt thereof, n is 0 or 1. In some embodiments of the compound of Formula II or IIa, or a pharmaceutically acceptable salt thereof, n is 0. In some embodiments of the compound of Formula II or IIa, or a pharmaceutically acceptable salt thereof, n is 1. In some embodiments of the compound of Formula II or IIa, or a pharmaceutically acceptable salt thereof, n is 2. In some embodiments of the compound of Formula II or IIa, or a pharmaceutically acceptable salt thereof, n is 3. In some embodiments of the compound of Formula II or IIa, or a pharmaceutically acceptable salt thereof, n is 4.

In some embodiments of the compound of Formula II, IIa, or IIb, or a pharmaceutically acceptable salt thereof, n is 1 and $R^{12}$ is $C_{1-3}$ alkyl. In some embodiments of the compound of Formula II, IIa, or IIb, or a pharmaceutically acceptable salt thereof, n is 1 and $R^{12}$ is methyl. In some embodiments of the compound of Formula II, IIa, or IIb, or a pharmaceutically acceptable salt thereof, n is 1 and $R^{12}$ is $C_{1-3}$ alkyl. In some embodiments of the compound of Formula II, IIa, or IIb, or a pharmaceutically acceptable salt thereof, n is 1 and $R^{12}$ is methyl.

In some embodiments of the compound of Formula I, II, IIa, or IIb, or a pharmaceutically acceptable salt thereof, $R^4$ is H. In some embodiments of the compound of Formula I, II, IIa, or IIb, or a pharmaceutically acceptable salt thereof, $R^4$ is halogen. In some embodiments of the compound of Formula I, II, IIa, or IIb, or a pharmaceutically acceptable salt thereof, $R^4$ is fluoro. In some embodiments of the compound of Formula I, II, IIa, or IIb, or a pharmaceutically acceptable salt thereof, $R^4$ is $C_{1-3}$ alkyl. In some embodiments of the compound of Formula I, II, IIa, or IIb, or a pharmaceutically acceptable salt thereof, $R^4$ is $C_{1-3}$ alkoxy.

In some embodiments of the compound of Formula I, II, IIa, or IIb, or a pharmaceutically acceptable salt thereof, $R^5$ is H. In some embodiments of the compound of Formula I, II, IIa, or IIb, or a pharmaceutically acceptable salt thereof, $R^5$ is halogen. In some embodiments of the compound of Formula I, II, IIa, or IIb, or a pharmaceutically acceptable salt thereof, $R^5$ is $C_{1-3}$ alkyl. In some embodiments of the compound of Formula I, II, IIa, or IIb, or a pharmaceutically acceptable salt thereof, $R^5$ is $C_{1-3}$ alkoxy.

In some embodiments of the compound of Formula I, II, IIa, or IIb, or a pharmaceutically acceptable salt thereof, $R^6$ is H. In some embodiments of the compound of Formula I, II, IIa, or IIb, or a pharmaceutically acceptable salt thereof, $R^6$ is halogen. In some embodiments of the compound of Formula I, II, IIa, or IIb, or a pharmaceutically acceptable salt thereof, $R^6$ is $C_{1-3}$ alkyl. In some embodiments of the compound of Formula I, II, IIa, or IIb, or a pharmaceutically acceptable salt thereof, $R^6$ is $C_{1-3}$ alkoxy.

In some embodiments of the compound of Formula I, II, IIa, or IIb, or a pharmaceutically acceptable salt thereof, $R^{10}$ is H. In some embodiments of the compound of Formula I, II, IIa, or IIb, or a pharmaceutically acceptable salt thereof, $R^{10}$ is halogen. In some embodiments of the compound of Formula I, II, IIa, or IIb, or a pharmaceutically acceptable salt thereof, $R^{10}$ is $C_{1-3}$ alkyl. In some embodiments of the compound of Formula I, II, IIa, or IIb, or a pharmaceutically acceptable salt thereof, $R^{10}$ is $C_{1-3}$ alkoxy.

In some embodiments of the compound of Formula I, II, IIa, or IIb, or a pharmaceutically acceptable salt thereof, $R^4$, $R^5$, $R^6$, and $R^{10}$ are H.

In some embodiments, the compound of Formula I, II, or IIa is of Formula III,

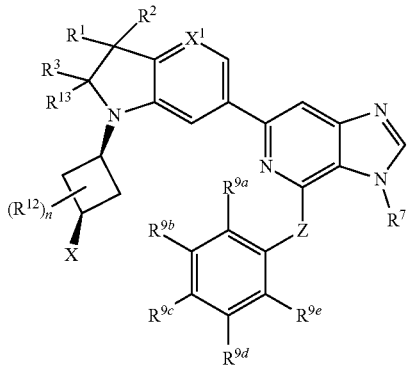

Formula III or a pharmaceutically acceptable salt thereof, wherein the variables are as defined as in Formula I.

In some embodiments, the compound of Formula I, II, IIa, IIb, and III is of Formula IIIa:

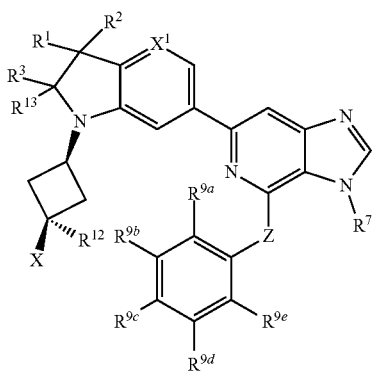

Formula IIIa or a pharmaceutically acceptable salt thereof, wherein the variables are as defined as in Formula I.

In some embodiments, the compound of Formula I, II, or IIa is of Formula III,

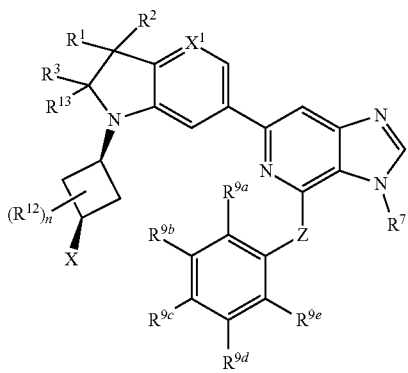

Formula III or a pharmaceutically acceptable salt thereof, wherein:
one of $R^1$ and $R^2$ is —OH, halogen or $C_{1-3}$ alkyl, and the other of $R^1$ and $R^2$ is halogen or $C_{1-3}$ alkyl, or $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;

$R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$C$_{1-3}$ alkyl,
  iii) —S(O)$_2$C$_{3-5}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)R$^{21}$;

$R^{21}$ is
  i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) $C_{1-6}$ alkoxy optionally substituted with 1-3 groups independently selected from —OH, halogen, $C_{1-3}$ alkyl, and $C_{3-7}$ monocyclic cycloalkyl, or
  iv) $C_{1-6}$ alkyl optionally substituted with 1-3 groups independently selected from
    a) —CN,
    b) —OH,
    c) halogen, and
    d) $C_{1-3}$ alkoxy, $R^3$ and $R^{13}$ are each H, or
$R^3$ and $R^{13}$ together form =O;
n is 0 or 1;
$R^{12}$ is $C_{1-3}$ alkyl;
X is —NR$^{15}$R$^{16}$, wherein $R^{15}$ and $R^{16}$ are independently
  i) H,
  ii) $C_{3-7}$ monocyclic cycloalkyl optionally substituted with 1-3 groups independently selected from —OH, halogen, $C_{1-3}$ alkyl, and $C_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
  iv) —C(O)C$_{1-6}$ alkyl, wherein the $C_{1-6}$ alkyl is optionally substituted with 1-3 groups independently selected from —CN, —OH, halogen, and $C_{1-3}$ alkoxy, or
  v) $C_{1-6}$ alkyl optionally substituted with 1-6 groups independently selected from
    g) —OH,
    h) halogen, and
    i) $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
  i) a halogen,
  ii) —OH, or
  iii) $C_{1-6}$ alkyl optionally substituted with 1-3 groups independently selected from —OH, halogen, $C_{1-3}$ alkoxy, and $C_{3-7}$ monocyclic cycloalkyl;

$X^1$ is N or CH;

$R^7$ is
  i) $C_{1-6}$ alkyl optionally substituted with 1-3 groups independently selected from —OH, halogen, $C_{1-3}$ alkoxy, and $C_{3-7}$ monocyclic cycloalkyl, or
  ii) $C_{3-7}$ monocyclic cycloalkyl optionally substituted with 1-3 groups independently selected from —OH, halogen, $C_{1-3}$ alkyl, and $C_{1-3}$ alkoxy;

Z is —O— or NH;

$R^{9a}$, $R^{9b}$, $R^{9c}$, $R^{9d}$, and $R^{9e}$ are independently
  i) H,
  ii) halogen,
  iii) $C_{1-6}$ alkoxy optionally substituted with 1-3 groups independently selected from —OH, halogen, $C_{1-3}$ alkyl, and $C_{3-7}$ monocyclic cycloalkyl,
  iv) $C_{1-6}$ alkyl optionally substituted with 1-3 groups independently selected from —OH, halogen, $C_{1-3}$ alkoxy, and $C_{3-7}$ monocyclic cycloalkyl,
  v) $C_{3-7}$ monocyclic cycloalkyl optionally substituted with 1-3 groups independently selected from —OH, halogen, $C_{1-3}$ alkyl, and $C_{1-3}$ alkoxy, or
  vi) —C(O)N($R^{19}$)$_2$,
  wherein one or more of $R^{9a}$, $R^{9b}$, $R^{9c}$, $R^{9d}$, and $R^{9e}$ is —C(O)N($R^{19}$)$_2$;

each $R^{19}$ is independently
  i) H,
  ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
  iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —CN, —OH, halogen, and $C_{1-3}$ alkoxy.

In some embodiments, the compound of Formula I, II, IIa, IIb or III is of Formula IIIa:

Formula IIIa or a pharmaceutically acceptable salt thereof,
wherein:
  one of $R^1$ and $R^2$ is —OH, halogen or $C_{1-3}$ alkyl, and the other of $R^1$ and $R^2$ is halogen or $C_{1-3}$ alkyl, or
  $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;

$R^1$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$$C_{1-3}$ alkyl,
  iii) —S(O)$_2$$C_{3-5}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)$R^{21}$;

$R^{21}$ is
  i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) $C_{1-6}$ alkoxy optionally substituted with 1-3 groups independently selected from —OH, halogen, $C_{1-3}$ alkyl, and $C_{3-7}$ monocyclic cycloalkyl, or
  iv) $C_{1-6}$ alkyl optionally substituted with 1-3 groups independently selected from
    a) —CN,
    b) —OH,
    c) halogen, and
    d) $C_{1-3}$ alkoxy, $R^3$ and $R^{13}$ are each H, or
$R^3$ and $R^{13}$ together form =O;
$R^{12}$ is $C_{1-3}$ alkyl;
X is —NR$^{15}$R$^{16}$, wherein $R^{15}$ and $R^{16}$ are independently
  i) H,
  ii) $C_{3-7}$ monocyclic cycloalkyl optionally substituted with 1-3 groups independently selected from —OH, halogen, $C_{1-3}$ alkyl, and $C_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
  iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
  v) $C_{1-6}$ alkyl optionally substituted with 1-6 groups independently selected from
    a) —OH,
    b) halogen, and
    c) $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;
each $R^{18}$ is independently
i) a halogen,
ii) —OH, or
iii) $C_{1-6}$ alkyl optionally substituted with 1-3 groups independently selected from —OH, halogen, $C_{1-3}$ alkoxy, and $C_{3-7}$ monocyclic cycloalkyl;

$X^1$ is N or CH;
$R^7$ is
i) $C_{1-6}$ alkyl optionally substituted with 1-3 groups independently selected from —OH, halogen, $C_{1-3}$ alkoxy, and $C_{3-7}$ monocyclic cycloalkyl, or
ii) $C_{3-7}$ monocyclic cycloalkyl optionally substituted with 1-3 groups independently selected from —OH, halogen, $C_{1-3}$ alkyl, and $C_{1-3}$ alkoxy;

Z is —O— or NH;
$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) $C_{1-6}$ alkyl optionally substituted with 1-3 groups independently selected from —OH, halogen, $C_{1-3}$ alkoxy, and $C_{3-7}$ monocyclic cycloalkyl,
v) $C_{3-7}$ monocyclic cycloalkyl optionally substituted with 1-3 groups independently selected from —OH, halogen, $C_{1-3}$ alkyl, and $C_{1-3}$ alkoxy, or
vi) —C(O)N($R^{19}$)$_2$,
wherein one or more of $R^{9a}$, $R^{9b}$, $R^{9c}$, $R^{9d}$, and $R^{9e}$ is —C(O)N($R^{19}$)$_2$;

each $R^{19}$ is independently
i) H,
ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_1$-3 alkyl is optionally substituted with 1-3 groups independently selected from —CN, —OH, halogen, and $C_1$-3 alkoxy.

In some embodiments of the compound of Formula I, II, IIa, IIb, III, or IIIa, or a pharmaceutically acceptable salt thereof, $R^3$ and $R^{13}$ together form =O. In some embodiments of the compound of Formula I, II, IIa, IIb, or IIIa, or a pharmaceutically acceptable salt thereof, $R^3$ and $R^{13}$ are each H.

In some embodiments of the compound of Formula I, II, IIa, IIb, III, or IIIa, or a pharmaceutically acceptable salt thereof, $X^1$ is $CR^7$.

In some embodiments of the compound of Formula I, II, IIa, IIb, III, or IIIa, or a pharmaceutically acceptable salt thereof, $R^{17}$ is H. In some embodiments of the compound of Formula I, II, IIa, IIb, III, or IIIa, or a pharmaceutically acceptable salt thereof, $R^{17}$ is halogen. In some embodiments of the compound of Formula I, II, IIa, IIb, III, or IIIa, or a pharmaceutically acceptable salt thereof, $R^{17}$ is $C_1$-3 alkyl. In some embodiments of the compound of Formula I, II, IIa, IIb, III, or IIIa, or a pharmaceutically acceptable salt thereof, $R^{17}$ is $C_{1-3}$ alkoxy.

In some embodiments of the compound of Formula I, II, IIa, IIb, III or IIIa, or a pharmaceutically acceptable salt thereof, $X^1$ is CH. In some embodiments of the compound of Formula I, II, IIa, IIb, III or IIIa, or a pharmaceutically acceptable salt thereof, $X^1$ is N.

In some embodiments of the compound of Formula I, II, IIa, IIb, III, or IIIa, or a pharmaceutically acceptable salt thereof, Z is —$NR^8$—. In some embodiments of the compound of Formula I, II, IIa, IIb, III, or IIIa, or a pharmaceutically acceptable salt thereof, Z is —C($R^8$)$_2$—.

In some embodiments of the compound of Formula I, II, IIa, IIb, III or IIIa, or a pharmaceutically acceptable salt thereof, $R^8$ is H. In some embodiments of the compound of Formula I, II, IIa, IIb, III or IIIa, or a pharmaceutically acceptable salt thereof, $R^8$ is $C_{1-3}$ alkyl.

In some embodiments of the compound of Formula I, II, IIa, IIb, III or IIIa, or a pharmaceutically acceptable salt thereof, Z is —NH—. In some embodiments of the compound of Formula I, II, IIa, IIb, III, or IIIa, or a pharmaceutically acceptable salt thereof, Z is —$CH_2$—. In some embodiments of the compound of Formula I, II, IIa, IIb, III, or IIIa, or a pharmaceutically acceptable salt thereof, Z is —O—.

In some embodiments of the compound of Formula I, II, IIa, IIb, III, or IIIa, or a pharmaceutically acceptable salt thereof, $R^4$, $R^5$, $R^6$, $R^{10}$, and $R^{17}$ are H. In some embodiments of the compound of Formula I, II, IIa, IIb, III or IIIa, or a pharmaceutically acceptable salt thereof, $R^4$, $R^5$, $R^6$, and $R^{10}$ are H; $X^1$ is CH; and Z is NH. In some embodiments of the compound of Formula I, II, IIa, IIb, III, or IIIa, or a pharmaceutically acceptable salt thereof, $R^4$, $R^5$, $R^6$, and $R^{10}$ are H; $X^1$ is N; and Z is NH.

In some embodiments, the compound of Formula I, II, IIa, or III, is of Formula IV,

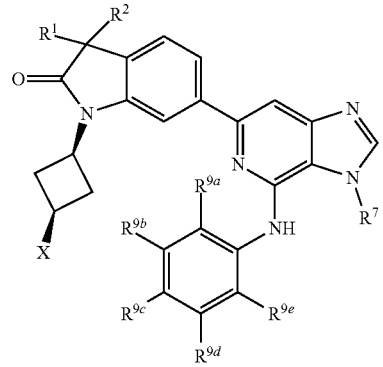

Formula IV or a pharmaceutically acceptable salt thereof, wherein the variables are as defined as in Formula I.

In some embodiments, the compound of Formula I, II, IIa, or III, is of Formula IV,

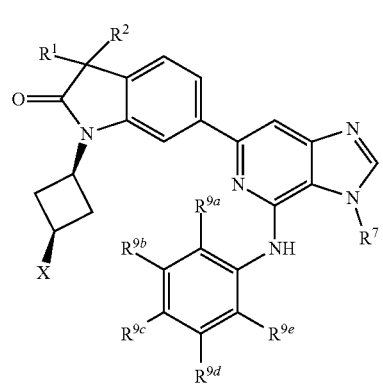

Formula IV or a pharmaceutically acceptable salt thereof,
wherein:
one of $R^1$ and $R^2$ is —OH, halogen or $C_{1-3}$ alkyl, and the other of $R^1$ and $R^2$ is halogen or $C_{1-3}$ alkyl, or R¹ and R² together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;

$R^{11}$ is
i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
ii) —S(O)₂$C_{1-3}$ alkyl,
iii) —S(O)₂$C_{3-4}$ monocyclic cycloalkyl,
iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
v) —C(O)$R^{21}$;

$R^{21}$ is
i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iii) $C_{1-6}$ alkoxy optionally substituted with 1-3 groups independently selected from —OH, halogen, $C_{1-3}$ alkyl, and $C_{3-7}$ monocyclic cycloalkyl, or
iv) $C_{1-6}$ alkyl optionally substituted with 1-3 groups independently selected from
   a) —CN,
   b) —OH,
   c) halogen, and
   d) $C_{1-3}$ alkoxy, X is —NR¹⁵R¹⁶, wherein R¹⁵ and R¹⁶ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
   a) —OH,
   b) halogen, and
   c) $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
i) a halogen,
ii) —OH, or
iii) $C_{1-6}$ alkyl optionally substituted with 1-3 groups independently selected from —OH, halogen, $C_{1-3}$ alkoxy, and $C_{3-7}$ monocyclic cycloalkyl;

$R^7$ is
i) $C_{1-6}$ alkyl optionally substituted with 1-3 groups independently selected from —OH, halogen, $C_{1-3}$ alkoxy, and $C_{3-7}$ monocyclic cycloalkyl, or
ii) $C_{3-7}$ monocyclic cycloalkyl optionally substituted with 1-3 groups independently selected from —OH, halogen, $C_{1-3}$ alkyl, and $C_{1-3}$ alkoxy;

$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) $C_{1-6}$ alkyl optionally substituted with 1-3 groups independently selected from —OH, halogen, $C_{1-3}$ alkoxy, and $C_{3-7}$ monocyclic cycloalkyl,
v) $C_{3-7}$ monocyclic cycloalkyl optionally substituted with 1-3 groups independently selected from —OH, halogen, $C_{1-3}$ alkyl, and $C_{1-3}$ alkoxy, or
vi) —C(O)N($R^{19}$)₂,
wherein one or more of $R^{9a}$, $R^{9b}$, $R^{9c}$, $R^{9d}$, and $R^{9e}$ is —C(O)N($R^{19}$)₂;

each $R^{19}$ is independently
i) H,
ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —CN, —OH, halogen, and $C_{1-3}$ alkoxy.

In some embodiments, the compound of Formula I, II, IIa, or III, is of Formula IVa:

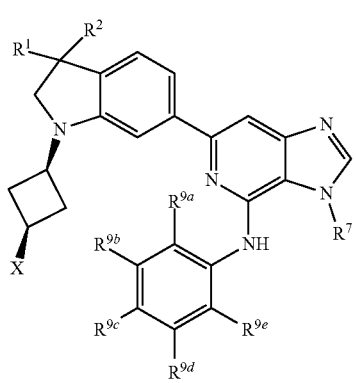

Formula IVa or a pharmaceutically acceptable salt thereof, wherein the variables are as defined as in Formula I.

In some embodiments, the compound of Formula I, II, IIa, or III, is of Formula IVa:

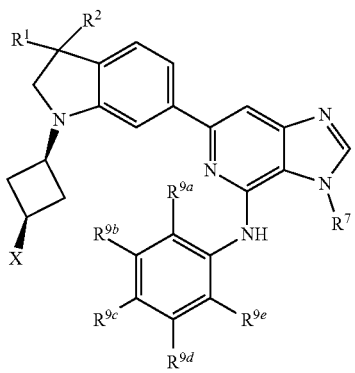

Formula IVa or a pharmaceutically acceptable salt thereof,
wherein:
one of $R^1$ and $R^2$ is —OH, halogen or $C_{1-3}$ alkyl, and the other of $R^1$ and $R^2$ is halogen or $C_{1-3}$ alkyl, or
$R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;
$R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$C$_{1-3}$ alkyl,
  iii) —S(O)$_2$C$_{3-4}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)R$^{21}$;
$R^{21}$ is
  i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) $C_{1-6}$ alkoxy optionally substituted with 1-3 groups independently selected from —OH, halogen, $C_{1-3}$ alkyl, and $C_{3-7}$ monocyclic cycloalkyl, or
  iv) $C_{1-6}$ alkyl optionally substituted with 1-3 groups independently selected from
    a) —CN,
    b) —OH,
    c) halogen, and
    d) $C_{1-3}$ alkoxy,
X is —NR$^{15}$R$^{16}$, wherein R$^{15}$ and R$^{16}$ are independently
  i) H,
  ii) $C_{3-7}$ monocyclic cycloalkyl optionally substituted with 1-3 groups independently selected from —OH, halogen, $C_{1-3}$ alkyl, and $C_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
  iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
  v) $C_{1-6}$ alkyl optionally substituted with 1-6 groups independently selected from
    a) —OH,
    b) halogen, and
    c) $C_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
  i) a halogen,
  ii) —OH, or
  iii) $C_{1-6}$ alkyl optionally substituted with 1-3 groups independently selected from —OH, halogen, $C_{1-3}$ alkoxy, and $C_{3-7}$ monocyclic cycloalkyl;
R$^7$ is
  i) $C_{1-6}$ alkyl optionally substituted with 1-3 groups independently selected from —OH, halogen, $C_{1-3}$ alkoxy, and $C_{3-7}$ monocyclic cycloalkyl, or
  ii) $C_{3-7}$ monocyclic cycloalkyl optionally substituted with 1-3 groups independently selected from —OH, halogen, $C_{1-3}$ alkyl, and $C_{1-3}$ alkoxy;
R$^{9a}$, R$^{9b}$, R$^{9c}$, R$^{9d}$, and R$^{9e}$ are independently
  i) H,
  ii) halogen,
  iii) $C_{1-6}$ alkoxy optionally substituted with 1-3 groups independently selected from —OH, halogen, $C_{1-3}$ alkyl, and $C_{3-7}$ monocyclic cycloalkyl,
  iv) $C_{1-6}$ alkyl optionally substituted with 1-3 groups independently selected from —OH, halogen, $C_{1-3}$ alkoxy, and $C_{3-7}$ monocyclic cycloalkyl,
  v) $C_{3-7}$ monocyclic cycloalkyl optionally substituted with 1-3 groups independently selected from —OH, halogen, $C_{1-3}$ alkyl, and $C_{1-3}$ alkoxy, or
  vi) —C(O)N(R$^{19}$)$_2$,
  wherein one or more of R$^{9a}$, R$^{9b}$, R$^{9c}$, R$^{9d}$, and R$^{9e}$ is —C(O)N(R$^{19}$)$_2$;
each R$^{19}$ is independently
  i) H,
  ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
  iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —CN, —OH, halogen, and $C_{1-3}$ alkoxy.

In some embodiments, the compound of Formula I, II, IIa, IIb, III, or IIIa, is of Formula IVb or IVc:

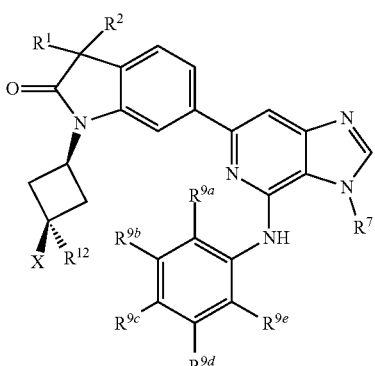

Formula IVb

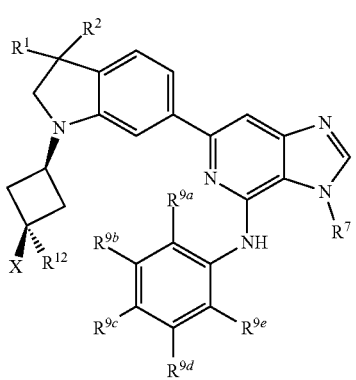

Formula IVc or a pharmaceutically acceptable salt thereof, wherein the variables are as defined as in Formula I.

In some embodiments, the compound of Formula I, II, IIa, IIb, III, or IIIa, is of Formula IVb or IVc:

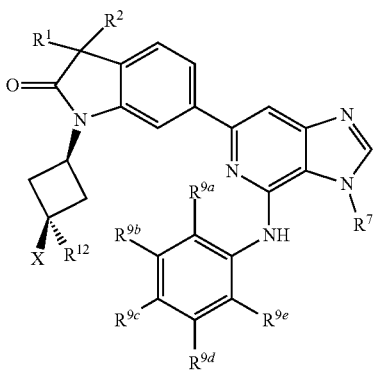

Formula IVb

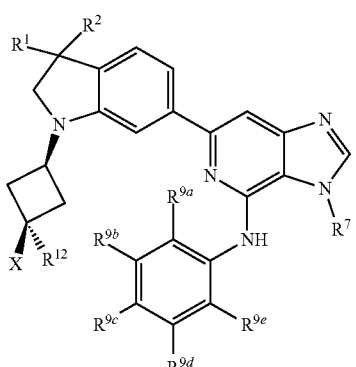

Formula IVc or a pharmaceutically acceptable salt thereof, wherein:
one of $R^1$ and $R^2$ is —OH, halogen or $C_{1-3}$ alkyl, and the other of $R^1$ and $R^2$ is halogen or $C_{1-3}$ alkyl, or $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;

$R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$C$_{1-3}$ alkyl,
  iii) —S(O)$_2$C$_{3-4}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)R$^{21}$;

$R^{21}$ is
  i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) $C_{1-6}$ alkoxy optionally substituted with 1-3 groups independently selected from —OH, halogen, $C_{1-3}$ alkyl, and $C_{3-7}$ monocyclic cycloalkyl, or
  iv) $C_{1-6}$ alkyl optionally substituted with 1-3 groups independently selected from
    a) —CN,
    b) —OH,
    c) halogen, and
    d) $C_{1-3}$ alkoxy, $R^{12}$ is $C_{1-3}$ alkyl;

X is —NR$^{15}$R$^{16}$, wherein R$^{15}$ and R$^{16}$ are independently
  i) H,
  ii) $C_{3-7}$ monocyclic cycloalkyl optionally substituted with 1-3 groups independently selected from —OH, halogen, $C_{1-3}$ alkyl, and $C_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
  iv) —C(O)C$_{1-6}$ alkyl, wherein the $C_{1-6}$ alkyl is optionally substituted with 1-3 groups independently selected from —CN, —OH, halogen, and $C_{1-3}$ alkoxy, or
  v) $C_{1-6}$ alkyl optionally substituted with 1-6 groups independently selected from
    a) —OH,
    b) halogen, and
    c) $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
  i) a halogen,
  ii) —OH, or
  iii) $C_{1-6}$ alkyl optionally substituted with 1-3 groups independently selected from —OH, halogen, $C_{1-3}$ alkoxy, and $C_{3-7}$ monocyclic cycloalkyl;

$R^7$ is
  i) $C_{1-6}$ alkyl optionally substituted with 1-3 groups independently selected from —OH, halogen, $C_{1-3}$ alkoxy, and $C_{3-7}$ monocyclic cycloalkyl, or
  ii) $C_{3-7}$ monocyclic cycloalkyl optionally substituted with 1-3 groups independently selected from —OH, halogen, $C_{1-3}$ alkyl, and $C_{1-3}$ alkoxy;

$R^{9a}$, $R^{9b}$, $R^{9c}$, $R^{9d}$, and $R^{9e}$ are independently
  i) H,
  ii) halogen,
  iii) $C_{1-6}$ alkoxy optionally substituted with 1-3 groups independently selected from —OH, halogen, $C_{1-3}$ alkyl, and $C_{3-7}$ monocyclic cycloalkyl,
  iv) $C_{1-6}$ alkyl optionally substituted with 1-3 groups independently selected from —OH, halogen, $C_{1-3}$ alkoxy, and $C_{3-7}$ monocyclic cycloalkyl,
  v) $C_{3-7}$ monocyclic cycloalkyl optionally substituted with 1-3 groups independently selected from —OH, halogen, $C_{1-3}$ alkyl, and $C_{1-3}$ alkoxy, or
  vi) —C(O)N($R^{19}$)$_2$,
wherein one or more of $R^{9a}$, $R^{9b}$, $R^{9c}$, $R^{9d}$, and $R^{9e}$ is —C(O)N($R^{19}$)$_2$;

each $R^{19}$ is independently
  i) H,
  ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
  iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —CN, —OH, halogen, and $C_{1-3}$ alkoxy.

In some embodiments of the compound of Formula I, II, IIa, IIb, III, IIIa, IV, IVa, IVb, or IVc, or a pharmaceutically acceptable salt thereof,
one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or
$R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or
$R^1$ and $R^2$ together form =O.

In some embodiments of the compound of Formula I, II, IIa, IIb, III, IIIa, IV, IVa, IVb, or IVc, or a pharmaceutically acceptable salt thereof,
one of $R^1$ and $R^2$ is —OH, halogen, or $C_{1-3}$ alkyl, and the other of $R^1$ and $R^2$ is halogen or $C_{1-3}$ alkyl, or
$R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy.

In some embodiments of the compound of Formula I, II, IIa, IIb, III, IIIa, IV, IVa, IVb, or IVc, or a pharmaceutically acceptable salt thereof, $R^1$ and $R^2$ together form =O.

In some embodiments of the compound of Formula I, II, IIa, IIb, III, IIIa, IV, IVa, IVb, or IVc, or a pharmaceutically acceptable salt thereof, one of $R^1$ and $R^2$ is H, —CN, —OH, halogen, or $C_{1-6}$ alkyl, and the other of $R^1$ and $R^2$ is H, halogen, or $C_{1-6}$ alkyl, wherein the $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is H and the other of $R^1$ and $R^2$ is H, halogen, or $C_{1-6}$ alkyl, wherein the $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is —CN and the other of $R^1$ and $R^2$ is H, halogen, or $C_{1-6}$ alkyl, wherein the $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is —OH and the other of $R^1$ and $R^2$ is H, halogen, or $C_{1-6}$ alkyl, wherein the $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is halogen and the other of $R^1$ and $R^2$ is H, halogen, or $C_{1-6}$ alkyl, wherein the $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is $C_{1-6}$ alkyl and the other of $R^1$ and $R^2$ is H, halogen, or $C_{1-6}$ alkyl, wherein each $C_{1-6}$ alkyl is optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is $C_{1-3}$ alkyl and the other of $R^1$ and $R^2$ is H, halogen, or $C_{1-6}$ alkyl, wherein the $C_{1-3}$ alkyl and the $C_{1-6}$ alkyl are each optionally substituted with 1-3 groups independently selected from —OH and halogen. In some embodiments of the compound of Formula I, II, IIa, IIb, III, IIIa, IV, IVa, IVb, or IVc, or a pharmaceutically acceptable salt thereof, one of $R^1$ and $R^2$ is $C_{1-3}$ alkyl and the other of $R^1$ and $R^2$ is H, halogen, or $C_{1-6}$ alkyl, wherein the $C_{1-3}$ alkyl is substituted with 1-3 OH groups. In some embodiments of the compound of Formula I, II, IIa, IIb, III, IIIa, IV, IVa, IVb, or IVc, or a pharmaceutically acceptable salt thereof, one of $R^1$ and $R^2$ is methyl, ethyl, or propyl and the other of $R^1$ and $R^2$ is H, halogen, or $C_{1-6}$ alkyl, wherein the methyl, ethyl, or propyl are each substituted with one OH group.

In some embodiments of the compound of Formula I, II, IIa, IIb, III, IIIa, IV, IVa, IVb, or IVc, or a pharmaceutically acceptable salt thereof, one of $R^1$ and $R^2$ is —OH, halogen, or $C_{1-3}$ alkyl, and the other of $R^1$ and $R^2$ is halogen or $C_{1-3}$ alkyl. In some embodiments of the compound of Formula I, II, IIa, IIb, III, IIIa, IV, IVa, IVb, or IVc, or a pharmaceutically acceptable salt thereof, one of $R^1$ and $R^2$ is —OH and the other of $R^1$ and $R^2$ is halogen or $C_{1-3}$ alkyl. In some embodiments of the compound of Formula I, II, IIa, IIb, III, IIIa, IV, IVa, IVb, or IVc, or a pharmaceutically acceptable salt thereof, one of $R^1$ and $R^2$ is halogen and the other of $R^1$ and $R^2$ is halogen or $C_{1-3}$ alkyl. In some embodiments of the compound of Formula I, II, IIa, IIb, III, IIIa, IV, IVa, IVb, or IVc, or a pharmaceutically acceptable salt thereof, one of $R^1$ and $R^2$ is $C_{1-3}$ alkyl and the other of $R^1$ and $R^2$ is halogen or $C_{1-3}$ alkyl.

In some embodiments of the compound of Formula I, II, IIa, IIb, III, IIIa, IV, IVa, IVb, or IVc, or a pharmaceutically acceptable salt thereof, one of $R^1$ and $R^2$ is —OH, fluoro, methyl, or ethyl and the other of $R^1$ and $R^2$ is fluoro, methyl, or ethyl. In some embodiments of the compound of Formula I, II, IIa, IIb, III, IIIa, IV, IVa, IVb, or IVc, or a pharmaceutically acceptable salt thereof, one of $R^1$ and $R^2$ is —OH and the other of $R^1$ and $R^2$ is fluoro, methyl, or ethyl. In some embodiments of the compound of Formula I, II, IIa, IIb, III, IIIa, IV, IVa, IVb, or IVc, or a pharmaceutically acceptable salt thereof, one of $R^1$ and $R^2$ is fluoro and the other of $R^1$ and $R^2$ is fluoro, methyl, or ethyl. In some embodiments of the compound of Formula I, II, IIa, IIb, III, IIIa, IV, IVa, IVb, or IVc, or a pharmaceutically acceptable salt thereof, one of $R^1$ and $R^2$ is methyl and the other of $R^1$ and $R^2$ is fluoro, methyl, or ethyl. In some embodiments of the compound of Formula I, II, IIa, IIb, III, IIIa, IV, IVa, IVb, or IVc, or a pharmaceutically acceptable salt thereof, one of $R^1$ and $R^2$ is ethyl and the other of $R^1$ and $R^2$ is fluoro, methyl, or ethyl.

In some embodiments of the compound of Formula I, II, IIa, IIb, III, IIIa, IV, IVa, IVb, or IVc, or a pharmaceutically acceptable salt thereof, $R^1$ and $R^2$ are both fluoro, methyl, or ethyl. In some embodiments of the compound of Formula I, II, IIa, IIb, III, IIIa, IV, IVa, IVb, or IVc, or a pharmaceutically acceptable salt thereof, $R^1$ and $R^2$ are both fluoro. In some embodiments of the compound of Formula I, II, IIa, IIb, III, IIIa, IV, IVa, IVb, or IVc, or a pharmaceutically acceptable salt thereof, $R^1$ and $R^2$ are both methyl. In some embodiments of the compound of Formula I, II, IIa, IIb, III, IIIa, IV, IVa, IVb, or IVc, or a pharmaceutically acceptable salt thereof, $R^1$ and $R^2$ are both ethyl. In some embodiments of the compound of Formula I, II, IIa, IIb, III, IIIa, IV, IVa, IVb, or IVc, or a pharmaceutically acceptable salt thereof, one of $R^1$ and $R^2$ is —OH and the other of $R^1$ and $R^2$ is methyl.

In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a $C_{3-7}$ monocyclic cycloalkyl optionally substituted with one $R^{11}$ and optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a $C_{3-7}$ monocyclic cycloalkyl substituted with one $R^{11}$. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a $C_3$ cycloalkyl substituted with one $R^{11}$. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a $C_3$ cycloalkyl.

In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is substituted with one $R^1$.

In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form an azetidinyl optionally substituted with one $R^{11}$ and optionally substituted with 1 or 2 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form an azetidinyl substituted with one $R^1$.

In some embodiments, the compound of Formula I, II, IIa, III, or IV is of Formula V:

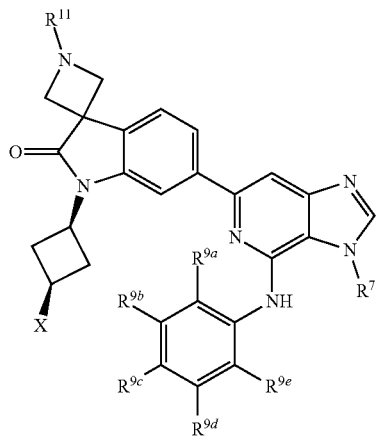

Formula V or a pharmaceutically acceptable salt thereof, wherein the variables are as defined herein.

In some embodiments, the compound of Formula I, II, IIa, IIb, III, IIIa, or IVb is of Formula Va:

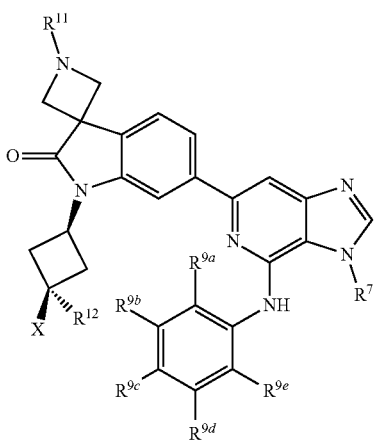

Formula Va or a pharmaceutically acceptable salt thereof, wherein the variables are as defined herein.

In some embodiments, the compound of Formula I, II, IIa, III, or IVa is of Formula Vb:

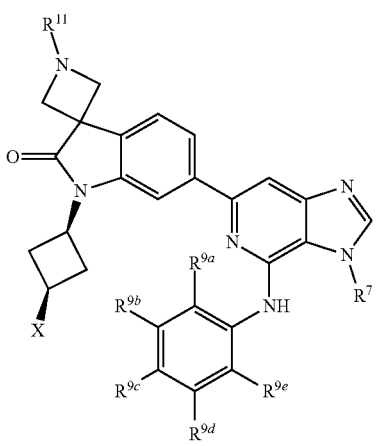

Formula Vb or a pharmaceutically acceptable salt thereof, wherein the variables are as defined herein.

In some embodiments, the compound of Formula I, II, IIa, IIb, III, IIIa, or IVc is of Formula Vc:

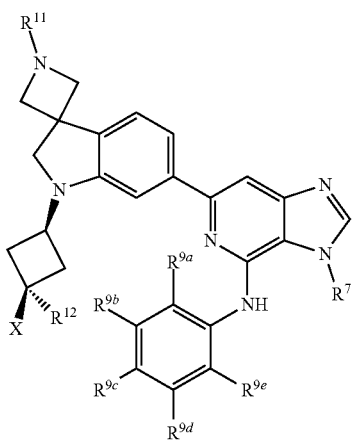

Formula Vc or a pharmaceutically acceptable salt thereof, wherein the variables are as defined herein.

In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a piperidinyl optionally substituted with one $R^{11}$ and optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a piperidinyl substituted with one $R^1$.

In some embodiments, the compound of Formula I, II, IIa, III, or IV is of Formula VI:

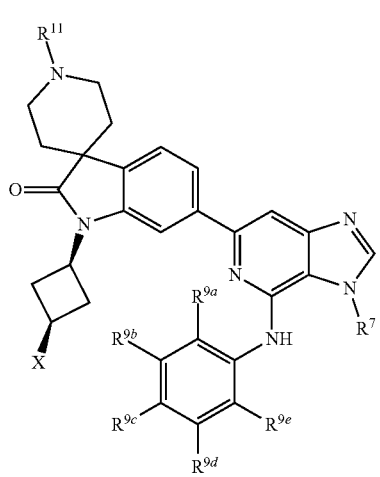

Formula VI or a pharmaceutically acceptable salt thereof, wherein the variables are as defined herein.

In some embodiments, the compound of Formula I, II, IIa, IIb, III, IIIa, or IVb is of Formula VIa:

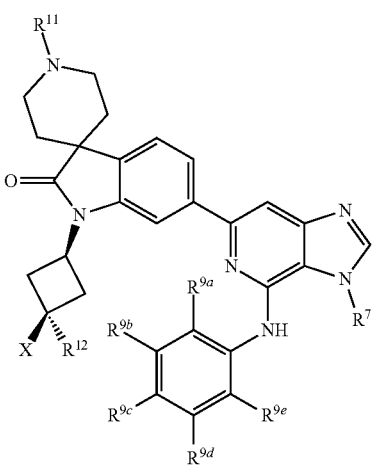

Formula VIa or a pharmaceutically acceptable salt thereof, wherein the variables are as defined herein.

In some embodiments, the compound of Formula I, II, IIa, III, or IVa is of Formula VIb:

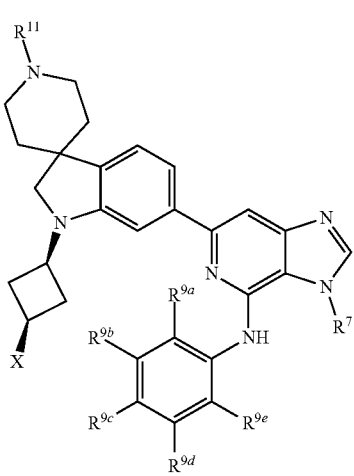

Formula VIb or a pharmaceutically acceptable salt thereof, wherein the variables are as defined herein.

In some embodiments, the compound of Formula I, II, IIa, IIb, III, IIIa, or IVc is of Formula VIc:

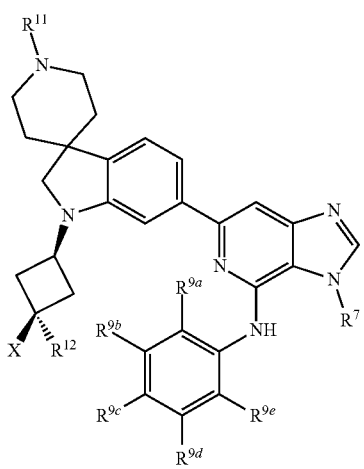

Formula VIc or a pharmaceutically acceptable salt thereof, wherein the variables are as defined herein.

In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a tetrahydropyranyl optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, or IVc, or a pharmaceutically acceptable salt thereof, $R^1$ and $R^2$ together with the carbon to which they are attached form a tetrahydropyranyl.

In some embodiments, the compound of Formula I, II, IIa, III, or IV is of Formula VII:

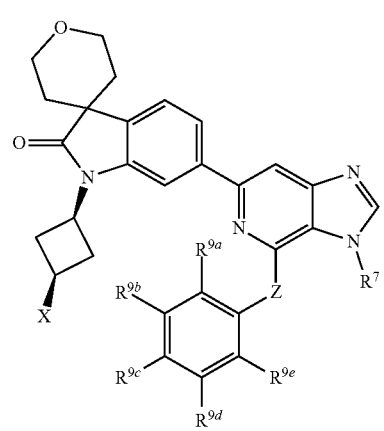

Formula VII or a pharmaceutically acceptable salt thereof, wherein the variables are as defined herein.

In some embodiments, the compound of Formula I, II, IIa, IIb, III, IIIa, or IVb is of Formula VIIa:

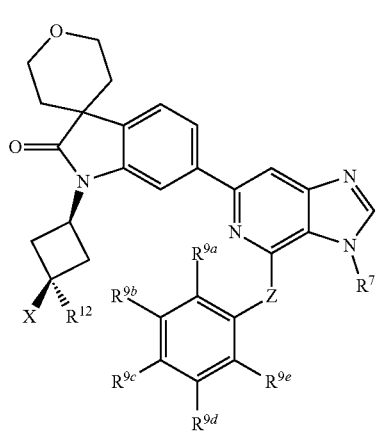

Formula VIIa or a pharmaceutically acceptable salt thereof, wherein the variables are as defined herein.

In some embodiments, the compound of Formula I, II, IIa, III, or IVa is of Formula VIIb:

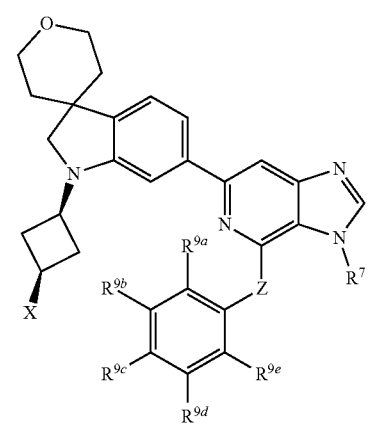

Formula VIIb or a pharmaceutically acceptable salt thereof, wherein the variables are as defined herein.

In some embodiments, the compound of Formula I, II, IIa, IIb, III, IIIa, or IVc is of Formula VIIc:

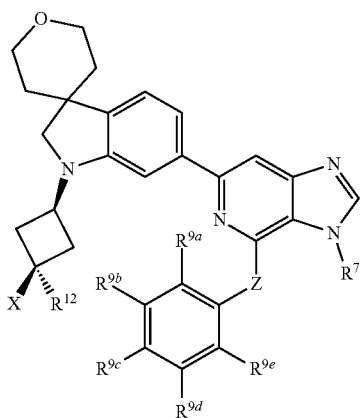

Formula VIIc or a pharmaceutically acceptable salt thereof, wherein the variables are as defined herein.

In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^{11}$ is i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy; ii) —S(O)$_2$C$_{1-6}$ alkyl; iii) —S(O)$_2$C$_{3-7}$ monocyclic cycloalkyl; iv) C$_{1-6}$ alkyl optionally substituted with 1-3 groups independently selected from —CN, —OH, halogen, $C_{1-3}$ alkoxy, and $C_{3-7}$ monocyclic cycloalkyl; or v) —C(O)R$^{21}$.

In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^{11}$ is i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy; ii) —S(O)$_2$C$_{1-3}$ alkyl; iii) —S(O)$_2$C$_{3-5}$ monocyclic cycloalkyl; iv) C$_{1-6}$ alkyl optionally substituted with 1-3 groups independently selected from —CN, —OH, halogen, $C_{1-3}$ alkoxy, and $C_{3-7}$ monocyclic cycloalkyl; or v) —C(O)R$^{21}$.

In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^1$ is i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy; ii) —S(O)$_2$C$_{1-3}$ alkyl; iii) —S(O)$_2$C$_{3-4}$ monocyclic cycloalkyl; iv) C$_{1-6}$ alkyl optionally substituted with 1-3 groups independently selected from —CN, —OH, halogen, $C_{1-3}$ alkoxy, and $C_{3-7}$ monocyclic cycloalkyl; or v) —C(O)R$^{21}$.

In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^1$ is a 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^{11}$ is a 4 membered monocyclic heterocyclyl having 1 or 2 heteroatoms independently selected from N, O, and S, wherein the 4 membered monocyclic heterocyclyl is optionally substituted with 1-3 groups independently selected from —CN, —OH, halogen, oxo, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^{11}$ is oxetanyl optionally substituted with 1-3 groups independently selected from —CN, —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VIa, VIb, or VIc, or a pharmaceutically acceptable salt thereof, $R^{11}$ is oxetanyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$C$_{1-6}$ alkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$C$_{1-3}$ alkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$CH$_3$.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$C$_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$C$_{3-5}$ monocyclic cycloalkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$C$_{3-4}$ monocyclic cycloalkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —S(O)$_2$(cyclopropyl). In some embodiments of the compound of Formula I, II, IIa, IIb, III, IIIa, IV, IVa, IVb, IVc, V, Va, Vb, Vc, VI, VIa, VIb, or VI, or a pharmaceutically acceptable salt thereof, $R^{11}$ is —S(O)$_2$CH$_3$ or —S(O)$_2$(cyclopropyl).

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is $C_{1-6}$ alkyl optionally substituted with 1-3 groups independently selected from —CN, —OH, halogen, $C_{1-3}$ alkoxy, and $C_{3-7}$ monocyclic cycloalkyl. In some embodiments of the compound of Formula I, II, IIa, IIb, III, IIIc, IV, IVa, IVb, IVc, V, Va, Vb, Vc, VI, VIa, VIb, or VIc, or a pharmaceutically acceptable salt thereof, $R^{11}$ is $C_{1-6}$ alkyl optionally substituted with 1-3 groups independently selected from —CN, —OH, halogen, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is an ethyl optionally substituted with 1-3 halogens. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{11}$ is —CH$_2$CHF$_2$.

In some embodiments of the compound of Formula I, II, IIa, IIb, III, IIIa, IV, IVa, IVb, or IVc, or a pharmaceutically acceptable salt thereof, $R^{11}$ is —C(O)R$^{21}$.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is i) H; ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy; iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy; iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy; v) —NH$_2$; vi) —NH($C_{1-6}$ alkyl), wherein the $C_{1-6}$ alkyl is optionally substituted with 1-3 groups independently selected from —CN, —OH, halogen, and $C_{1-3}$ alkoxy; vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy; viii) $C_{1-6}$ alkoxy optionally substituted with 1-3 groups independently selected from —OH, halogen, $C_{1-3}$ alkyl, and $C_{3-7}$ monocyclic cycloalkyl; or ix) $C_{1-6}$ alkyl optionally substituted with 1-3 groups independently selected from
a) —CN,
b) —OH,
c) halogen,
d) $C_{1-3}$ alkoxy,
e) $C_{3-7}$ monocyclic cycloalkyl optionally substituted with 1-3 groups independently selected from —CN, —OH, halogen, $C_{1-3}$ alkyl, and $C_{1-3}$ alkoxy,
f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
g) —OC(O)$C_{1-6}$ alkyl optionally substituted with one —OH.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy; ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy; iii) $C_{1-6}$ alkoxy optionally substituted with 1-3 groups independently selected from —OH, halogen, $C_{1-3}$ alkyl, and $C_{3-7}$ monocyclic cycloalkyl; or iv) $C_{1-6}$ alkyl optionally substituted with 1-3 groups independently selected from —CN, —OH, halogen, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is cyclopropyl, cyclobutyl, cyclopentyl, or $C_5$ bridged bicyclic cycloalkyl, each of which is optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH and halogen. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is cyclopropyl, cyclobutyl, cyclopentyl, or $C_5$ bridged bicyclic cycloalkyl, each of which is optionally substituted with 1-3 groups independently selected from —CN, —OH, halogen, methyl, and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is cyclopropyl optionally substituted with one group selected from —CN, —OH, fluoro, methyl, —CH$_2$OH, and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is cyclobutyl optionally substituted with one group selected from fluoro, methyl, and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is cyclopentyl optionally substituted with one —OH. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a $C_5$ bridged bicyclic cycloalkyl optionally substituted with one group selected from —OH and fluoro. As used herein, a $C_5$ bridged bicyclic cycloalkyl includes but is not limited to:

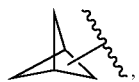

which is the same as

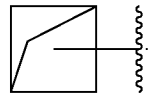

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is H. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is —NH$_2$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is —NH(C$_{1-6}$ alkyl), wherein the C$_{1-6}$ alkyl is optionally substituted with 1-3 groups independently selected from —CN, —OH, halogen, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is —N(C$_{1-6}$ alkyl)$_2$, wherein each C$_{1-6}$ alkyl can be the same or different and wherein each C$_{1-6}$ alkyl is optionally substituted with 1-3 groups independently selected from —CN, —OH, halogen, and C$_{1-3}$ alkoxy.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is oxetanyl, tetrahydrofuranyl, or tetrahydropyranyl, each of which is optionally substituted with 1-3 groups independently selected from —OH, halogen, C$_{1-3}$ alkyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is oxetanyl optionally substituted with one group selected from methyl, ethyl, and isopropyl. In some embodiments of the compound of Formula I, II, IIa, IIb III, IIIa, IV, IVa, IVb, IVc, V, Va, Vb, Vc, VI, VIa, VIb, or VIc, or a pharmaceutically acceptable salt thereof, $R^{21}$ is oxetanyl optionally substituted with one methyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is tetrahydrofuranyl optionally substituted with one methyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is tetrahydropyranyl optionally substituted with one methyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, C$_{1-3}$ alkyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a 5-membered heteroaryl having 1-4 heteroatoms independently selected from N, O, and S, wherein the 5-membered heteroaryl is optionally substituted with 1-3 groups independently selected from —OH, halogen, methyl, and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is oxazolyl, thiazolyl, isoxazolyl, oxadiazolyl, or triazolyl, each of which is optionally substituted with 1-3 groups independently selected from —OH, halogen, C$_{1-3}$ alkyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is oxazolyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is thiazolyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is isoxazolyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is oxadiazolyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is triazolyl optionally substituted with one methyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a C$_{1-6}$ alkoxy optionally substituted with 1-3 groups independently selected from —OH, halogen, C$_{1-3}$ alkyl, and C$_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a C$_{1-3}$ alkoxy optionally substituted with 1-3 groups independently selected from —OH, halogen, C$_{1-3}$ alkyl, and C$_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is a C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is —OCH$_3$.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is C$_{1-6}$ alkyl optionally substituted with 1-3 groups independently selected from: —CN; —OH; halogen; C$_{1-3}$ alkoxy; C$_{3-7}$ monocyclic cycloalkyl optionally substituted with 1-3 groups independently selected from —CN, —OH, halogen, C$_{1-3}$ alkyl, and C$_{1-3}$ alkoxy; 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy; and —OC(O)C$_{1-6}$ alkyl optionally substituted with one —OH. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is C$_{1-6}$ alkyl optionally substituted with 1-3 groups independently selected from —CN; —OH; halogen; C$_{1-3}$ alkoxy; and 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is C$_{1-6}$ alkyl optionally substituted with 1-3 groups independently selected from —CN, —OH, halogen, oxetanyl, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is C$_{1-6}$ alkyl optionally substituted with 1-3 groups independently selected from —CN, —OH, halogen, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl, ethyl, n-propyl, isopropyl, n-butyl, isobutyl, or tert-butyl, each of which is optionally substituted with 1-3 groups independently selected from —CN, —OH, halogen, oxetanyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl, ethyl, n-propyl, isopropyl, n-butyl, isobutyl, or tert-butyl, each of which is optionally substituted with 1-3 groups independently selected from —CN, —OH, halogen, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl optionally substituted with one group selected from —CN, —OH, and oxetanyl. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl optionally substituted with one group selected from —CN and —OH. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is ethyl optionally substituted with one group selected from —OH, fluoro, and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is n-propyl optionally substituted with one —OH. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is isopropyl optionally substituted with one group selected from —CN, —OH and —OCH$_3$. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is isobutyl optionally substituted with one —OH. In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is tert-butyl optionally substituted with one group selected from —OH, fluoro, and —OCH$_3$.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl optionally substituted with one group selected from —CN, —OH, and oxetanyl; ethyl optionally substituted with one group selected from —OH, fluoro, and —OCH$_3$; n-propyl optionally substituted with one —OH; isopropyl optionally substituted with one group selected from —CN, —OH and —OCH$_3$; isobutyl optionally substituted with one —OH; tert-butyl optionally substituted with one group selected from —OH, fluoro, and —OCH$_3$; —OCH$_3$; cyclopropyl optionally substituted with one group selected from —CN, —OH, fluoro, methyl, —CH$_2$OH, and —OCH$_3$; cyclobutyl optionally substituted with one group selected from fluoro, methyl, and —OCH$_3$; cyclopentyl optionally substituted with one —OH; $C_5$ bridged bicyclic cycloalkyl optionally substituted with one group selected from —OH and fluoro; oxetanyl optionally substituted with one group selected from methyl, ethyl, and isopropyl; tetrahydrofuranyl optionally substituted with one methyl; tetrahydropyranyl optionally substituted with one methyl; oxazolyl; thiazolyl; isoxazolyl; oxadiazolyl; or triazolyl optionally substituted with one methyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl optionally substituted with one group selected from —CN and —OH; ethyl optionally substituted with one group selected from —OH, fluoro, and —OCH$_3$; n-propyl optionally substituted with one —OH; isopropyl optionally substituted with one group selected from —CN, —OH and —OCH$_3$; isobutyl optionally substituted with one —OH; tert-butyl optionally substituted with one group selected from —OH, fluoro, and —OCH$_3$; —OCH$_3$; cyclopropyl optionally substituted with one group selected from —CN, —OH, fluoro, methyl, —CH$_2$OH, and —OCH$_3$; cyclobutyl optionally substituted with one group selected from fluoro, methyl, and —OCH$_3$; cyclopentyl optionally substituted with one —OH; $C_5$ bridged bicyclic cycloalkyl optionally substituted with one group selected from —OH and fluoro; or oxetanyl optionally substituted with one group selected from methyl, ethyl, and isopropyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl; methyl substituted with one oxetanyl; —CH$_2$OH; —CH$_2$(CN); ethyl; —CH(CH$_3$)OH; —CH(CH$_3$)CH$_2$OH; —CH(CH$_3$)OCH$_3$; —CH(OH)CH$_2$CH$_3$; isopropyl; —C(CH$_3$)$_2$OH; —C(CH$_3$)$_2$OCH$_3$; —C(CH$_3$)$_2$CN; tert-butyl; —C(CH$_3$)$_2$CH$_2$OH; —C(CH$_3$)$_2$CH$_2$OCH$_3$; —C(CH$_3$)$_2$CH$_2$F; —CH(OH)CH(CH$_3$)$_2$; —OCH$_3$; cyclopropyl; cyclopropyl substituted with one methyl; cyclopropyl substituted with one fluoro; cyclopropyl substituted with one —OCH$_3$; cyclopropyl substituted with one —OH; cyclopropyl substituted with one —CN; cyclopropyl substituted with one —CH$_2$OH; cyclobutyl; cyclobutyl substituted with one —OCH$_3$; cyclobutyl substituted with one methyl; cyclobutyl substituted with one fluoro; cyclopentyl substituted with one —OH; $C_5$ bridged bicyclic cycloalkyl; $C_5$ bridged bicyclic cycloalkyl substituted with one fluoro; $C_5$ bridged bicyclic cycloalkyl substituted with one —OH; oxetanyl; oxetanyl substituted with one methyl; oxetanyl substituted with one ethyl; oxetanyl substituted with one isopropyl; tetrahydrofuranyl; tetrahydrofuranyl substituted with one methyl; tetrahydropyranyl; tetrahydropyranyl substituted with one methyl; oxazolyl; thiazolyl; isoxazolyl; oxadiazolyl; or triazolyl substituted with one methyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl; —CH$_2$OH; —CH$_2$(CN); ethyl; —CH(CH$_3$)OH; —CH(CH$_3$)CH$_2$OH; —CH(CH$_3$)OCH$_3$; —CH(OH)CH$_2$CH$_3$; isopropyl; —C(CH$_3$)$_2$OH; —C(CH$_3$)$_2$OCH$_3$; —C(CH$_3$)$_2$CN; tert-butyl; —C(CH$_3$)$_2$CH$_2$OH; —C(CH$_3$)$_2$CH$_2$OCH$_3$; —C(CH$_3$)$_2$CH$_2$F; —CH(OH)CH(CH$_3$)$_2$; —OCH$_3$; cyclopropyl; cyclopropyl substituted with one methyl; cyclopropyl substituted with one fluoro; cyclopropyl substituted with one —OCH$_3$; cyclopropyl substituted with one —OH; cyclopropyl substituted with one —CN; cyclopropyl substituted with one —CH$_2$OH; cyclobutyl; cyclobutyl substituted with one methyl; cyclobutyl substituted with one fluoro; cyclopentyl substituted with one —OH; $C_5$ bridged bicyclic cycloalkyl; $C_5$ bridged bicyclic cycloalkyl substituted with one fluoro; $C_5$ bridged bicyclic cycloalkyl substituted with one —OH; oxetanyl; oxetanyl substituted with one methyl; oxetanyl substituted with one ethyl; or oxetanyl substituted with one isopropyl.

In some embodiments of the compound of Formula I, II, IIa, IIb, III, IIIa, IV, IVa, IVb, IVc, V, Va, Vb, Vc, VI, VIa, VIb, or VIc, or a pharmaceutically acceptable salt thereof, $R^{21}$ is methyl; methyl substituted with one oxetanyl; ethyl; —CH(CH₃)OH; —CH(CH₃)OCH₃; —CH(OH)CH₂CH₃; isopropyl; —C(CH₃)₂OH; —C(CH₃)₂OCH₃; —C(CH₃)₂CN; tert-butyl; —C(CH₃)₂CH₂OH; —C(CH₃)₂CH₂OCH₃; —C(CH₃)₂CH₂F; —CH(OH)CH(CH₃)₂; —OCH₃; cyclopropyl; cyclopropyl substituted with one methyl; cyclopropyl substituted with one fluoro; cyclopropyl substituted with one —OH; cyclopropyl substituted with one —OCH₃; cyclopropyl substituted with one —CN; cyclobutyl; cyclobutyl substituted with one methyl; cyclobutyl substituted with one —OCH₃; cyclobutyl substituted with one fluoro; cyclopentyl substituted with one —OH; C₅ bridged bicyclic cycloalkyl; C₅ bridged bicyclic cycloalkyl substituted with one fluoro; C₅ bridged bicyclic cycloalkyl substituted with one —OH; oxetanyl; oxetanyl substituted with one methyl; oxetanyl substituted with one ethyl; oxetanyl substituted with one isopropyl; tetrahydrofuranyl; tetrahydrofuranyl substituted with one methyl; tetrahydropyranyl; tetrahydropyranyl substituted with one methyl; oxazolyl; thiazolyl; isoxazolyl; oxadiazolyl; or triazolyl substituted with one methyl.

In some embodiments of the compound of Formula I, II, IIa, IIb, III, IIIa, IV, IVa, IVb, IVc, V, Va, Vb, Vc, VI, VIb, VIb, or VIc, or a pharmaceutically acceptable salt thereof, $R^{21}$ is methyl; ethyl; —CH(CH₃)OH; isopropyl; —C(CH₃)₂OH; tert-butyl; —OCH₃; cyclopropyl; cyclopropyl substituted with one methyl; cyclopropyl substituted with one —OH; cyclobutyl; cyclobutyl substituted with one methyl; C₅ bridged bicyclic cycloalkyl; C₅ bridged bicyclic cycloalkyl substituted with one fluoro; C₅ bridged bicyclic cycloalkyl substituted with one —OH; oxetanyl; or oxetanyl substituted with one methyl.

In some embodiments of the compound of Formula I, II, IIa, IIb, III, IIIa, IV, IVa, IVb, IVc, V, Va, Vb, Vc, VI, VIb, VIb, or VIc, or a pharmaceutically acceptable salt thereof, $R^{21}$ is methyl.

In some embodiments of the compound of Formula I, II, IIa, IIb, III, IIIa, IV, IVa, IVb, or IVc, or a pharmaceutically acceptable salt thereof, $R^{11}$ is:

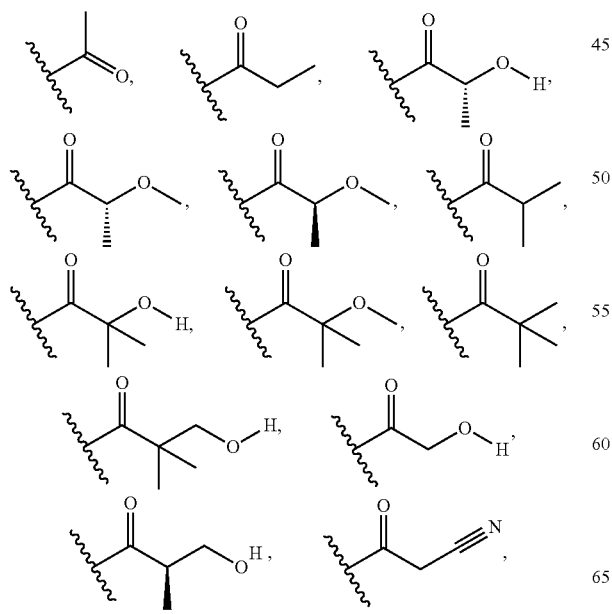

-continued

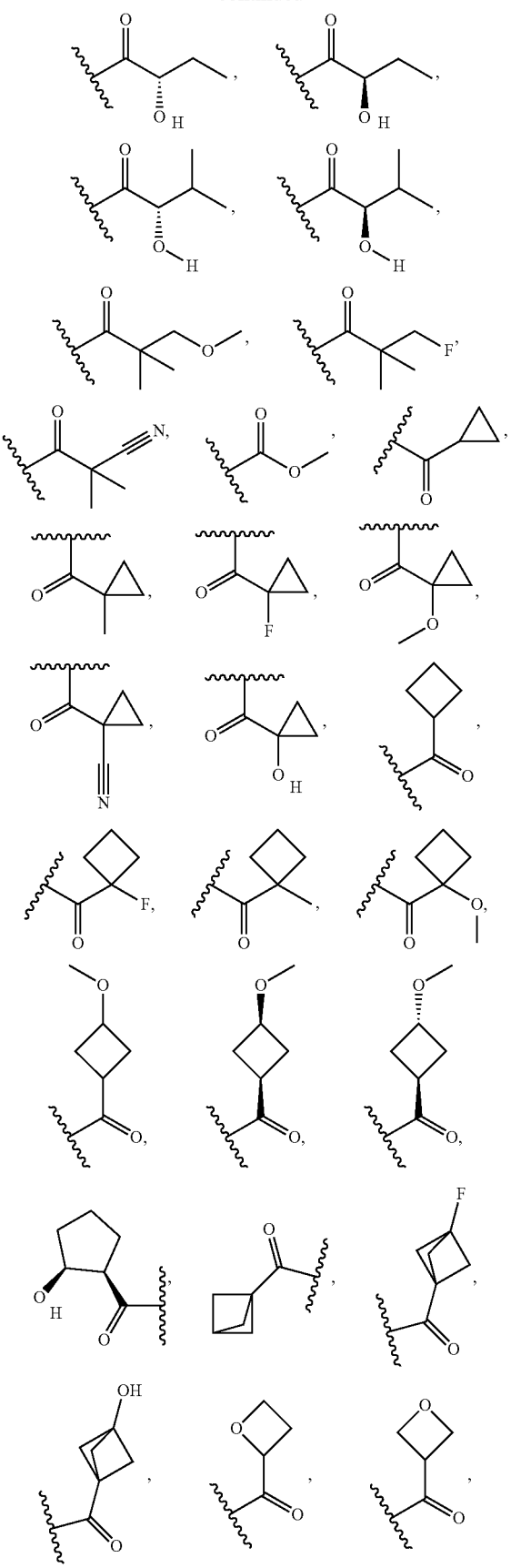

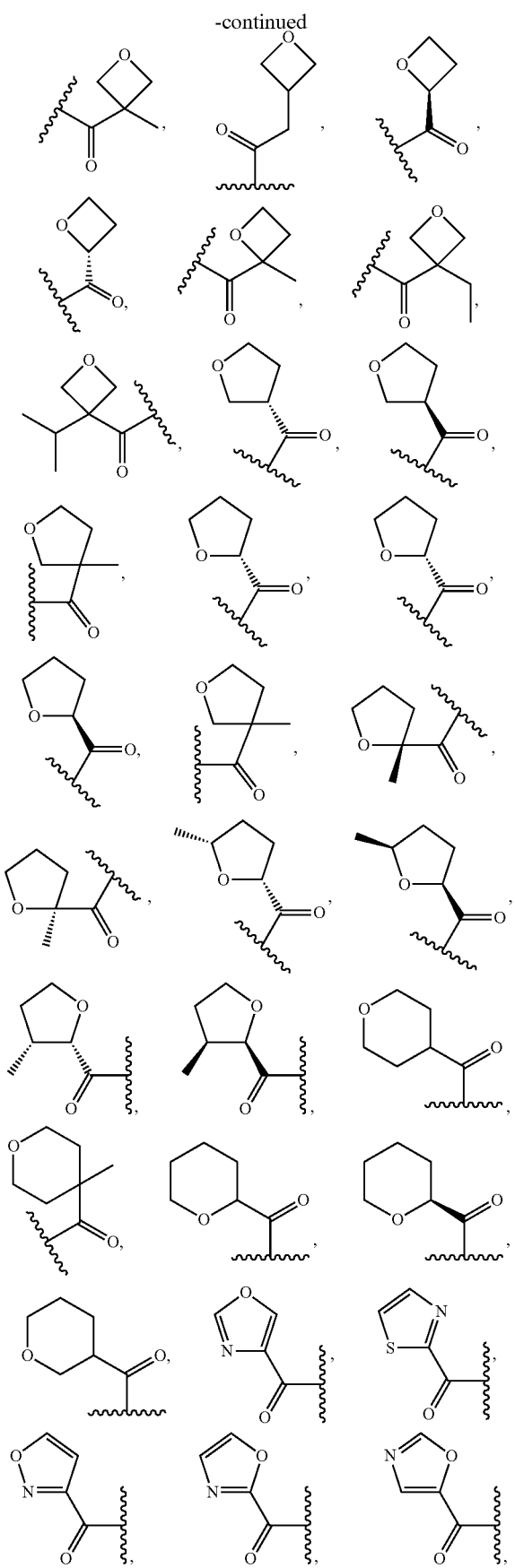
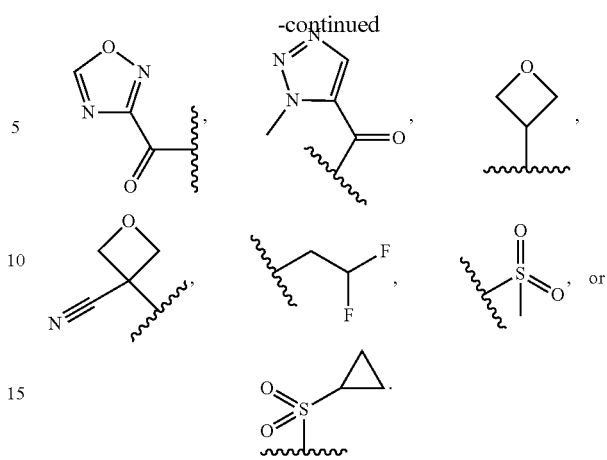

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) halogen; iii) $C_{1-6}$ alkoxy optionally substituted with 1-3 groups independently selected from —OH, halogen, $C_{1-3}$ alkyl, and $C_{3-7}$ monocyclic cycloalkyl; iv) —NH$_2$; v) —NH($C_{1-6}$ alkyl), wherein the $C_{1-6}$ alkyl is optionally substituted with 1-3 groups independently selected from —OH, halogen, and $C_{1-3}$ alkoxy; vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy; vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy; viii) —S(O)$_2$ $C_{1-6}$ alkyl; ix) —S(O)$_2$N($R^{23}$)$_2$, wherein each $R^{23}$ is independently H or $C_{1-6}$ alkyl; x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  f) —NR$^{20}$C(O)OC$_{1-3}$ alkyl, wherein $R^{20}$ is H or $C_{1-3}$ alkyl;
xi) $C_{3-7}$ monocyclic cycloalkyl optionally substituted with 1-3 groups independently selected from —OH, halogen, $C_{1-3}$ alkyl, and $C_{1-3}$ alkoxy; xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy; xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy; xiv) —COOH; xv) —C(O)N($R^{19}$)$_2$; or xvi) —C$_{1-3}$ alkylC(O)N($R^{19}$)$_2$; wherein one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) a halogen; iii) $C_{1-6}$ alkoxy optionally substituted with 1-3 groups independently selected from —OH, halogen, $C_{1-3}$ alkyl, and $C_{3-7}$ monocyclic cycloalkyl; iv) —NH$_2$; v) —NH($C_{1-3}$ alkyl), wherein the $C_{1-3}$ alkyl is optionally substituted with 1-3 groups independently selected from —OH, halogen, and $C_{1-3}$ alkoxy; vi) —N($C_{1-3}$ alkyl)$_2$, wherein each $C_{1-3}$ alkyl can be the same or different, and wherein each $C_{1-3}$ alkyl is optionally substituted with 1-3 groups independently selected from —OH, halogen, and $C_{1-3}$ alkoxy; vii) $C_{1-6}$ alkyl optionally substituted with 1-3 groups independently selected from —OH, halogen, $C_{1-3}$ alkoxy, and $C_{3-7}$ monocyclic cycloalkyl; or viii) —C(O)N ($R^{19}$)$_2$; wherein one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) a halogen; iii) $C_{1-6}$ alkoxy optionally substituted with 1-3 groups independently selected from —OH, halogen, $C_{1-3}$ alkyl, and $C_{3-7}$ monocyclic cycloalkyl; iv) $C_{1-6}$ alkyl optionally substituted with 1-3 groups independently selected from —OH, halogen, $C_{1-3}$ alkoxy, and $C_{3-7}$ monocyclic cycloalkyl; v) $C_{3-7}$ monocyclic cycloalkyl optionally substituted with 1-3 groups independently selected from —OH, halogen, $C_{1-3}$ alkyl, and $C_{1-3}$ alkoxy; or vi) —C(O)N($R^{19}$)$_2$; wherein one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) halogen; iii) —NH$_2$; iv) —NH($C_{1-3}$ alkyl); v) —N($C_{1-3}$ alkyl)$_2$, wherein each $C_{1-3}$ alkyl is the same or different; vi) $C_{1-3}$ alkyl optionally substituted with 1-3 groups independently selected from —OH and halogen; vii) —OCH$_3$ optionally substituted with 1-3 halogen groups; viii) cyclopropyl; or ix) —C(O)N($R^{19}$)$_2$; wherein one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) halogen; iii) $C_{1-3}$ alkyl optionally substituted with 1-3 groups independently selected from —OH and halogen; iv) —OCH$_3$ optionally substituted with 1-3 halogen groups; v) cyclopropyl; or vi) —C(O)N($R^{19}$)$_2$; wherein one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more $R^{9a}$, $R^{9b}$, $R^{9c}$, $R^{9d}$, and $R^{9e}$ is H and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more $R^{9a}$, $R^{9b}$, $R^{9c}$, $R^{9d}$, and $R^{9e}$ is halogen and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more $R^{9a}$, $R^{9b}$, $R^{9c}$, $R^{9d}$, and $R^{9e}$ is fluoro or chloro and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa IV, IVa, IVb, IVc, V, Va, Vb, Vc, VI, VIa, VIb, VIc, VII, VIIa, VIIb, or VIIc, or a pharmaceutically acceptable salt thereof, one or more $R^9$ is fluoro and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more $R^9$ is chloro and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is $C_{1-6}$ alkoxy optionally substituted with 1-3 groups independently selected from —OH, halogen, $C_{1-3}$ alkyl, and $C_{3-7}$ monocyclic cycloalkyl and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —OCH$_3$ optionally substituted with 1-3 fluoro groups and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —OCH$_3$ or —OCF$_3$ and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —OCH$_3$ and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —OCF$_3$ and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —NH$_2$ and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —NH($C_{1-6}$ alkyl), wherein the $C_{1-6}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —NH($C_{1-3}$ alkyl), wherein the $C_{1-3}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —NH($C_{1-3}$ alkyl) and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —N($C_{1-3}$ alkyl)$_2$, wherein each $C_{1-3}$ alkyl can be the same or different, and wherein each $C_{1-3}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —N($C_{1-3}$ alkyl)$_2$, wherein each $C_{1-3}$ alkyl is the same or different, and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —N(CH$_3$)$_2$ and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —P(O)($C_{1-3}$ alkyl)$_2$, wherein each $C_{1-3}$ alkyl can be the same or different, and wherein each $C_{1-3}$ alkyl is optionally substituted with 1-3 groups independently selected from —OH, halogen, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —P(O)($C_{1-3}$ alkyl)$_2$ and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —P(O)(CH-3)$_2$ and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —S(O)$_2$$C_{1-6}$ alkyl and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —S(O)$_2$N($R^{23}$)$_2$, wherein each $R^{23}$ is independently H or $C_{1-6}$ alkyl and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —COOH and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is $C_{3-7}$ monocyclic cycloalkyl optionally substituted with 1-3 groups independently selected from —OH, halogen, $C_{1-3}$ alkyl, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is cyclopropyl optionally substituted with 1-3 groups independently selected from —OH, halogen, $C_{1-3}$ alkyl, and $C_{1-3}$ alkoxy and one or more of $R^{9a}$, $R^{9b}$, $R^{9c}$, $R^{9d}$, and $R^{9e}$ is —C(O)N($R^{19}$)$_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is cyclopropyl and one or more of $R^{9a}$, $R^{9b}$, $R^{9c}$, $R^{9d}$, and $R^{9e}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is $C_{1-6}$ alkyl optionally substituted with 1-3 groups independently selected from a) —OH,
b) halogen,
c) $C_{1-3}$ alkoxy,
d) $C_{3-7}$ monocyclic cycloalkyl,
e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and f) —$NR^{20}C(O)OC_{1-3}$ alkyl, wherein $R^{20}$ is H or $C_{1-3}$ alkyl; and wherein one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is $C_{1-6}$ alkyl optionally substituted with 1-3 groups independently selected from —OH, halogen, $C_{1-3}$ alkoxy, and $C_{3-7}$ monocyclic cycloalkyl and one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is $C_{1-3}$ alkyl optionally substituted with 1-3 groups independently selected from —OH and halogen and one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is methyl optionally substituted with 1-3 groups independently selected from —OH and fluoro and one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is ethyl optionally substituted with one —OH and one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is methyl, ethyl, —$CF_3$, —$CHF_2$, —$CH_2OH$, or —$CH(CH_3)OH$ and one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof one or more of $R^{9a}$, $R^{9b}$, $R^{9c}$, $R^{9d}$, and $R^{9e}$ is or —$CH_2OH$ and one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —$C_{1-3}$alkylC(O)N(R^{19})_2$ and one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently i) H; ii) fluoro; iii) chloro; iv) methyl optionally substituted with 1-3 groups independently selected from —OH and fluoro; v) ethyl optionally substituted with one —OH; vi) —$OCH_3$ optionally substituted with 1-3 fluoro groups; vii) cyclopropyl; or viii) —$C(O)N(R^{19})_2$; and wherein one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently H, fluoro, chloro, methyl, ethyl, —$OCH_3$, —$CF_3$, —$CHF_2$, —$CH_2OH$, —$CH(CH_3)OH$, —$OCF_3$, cyclopropyl, —$N(CH_3)_2$, or —$C(O)N(R^{19})_2$; and wherein one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently H, fluoro, chloro, methyl, ethyl, —$OCH_3$, —$CF_3$, —$CHF_2$, —$CH_2OH$, —$CH(CH_3)OH$, —$OCF_3$, cyclopropyl, or —$C(O)N(R^{19})_2$; and wherein one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently H, fluoro, chloro, methyl, ethyl, —$CH_2OH$, —$OCH_3$, —$CF_3$, —$OCF_3$, cyclopropyl, —$N(CH_3)_2$, or —$C(O)N(R^{19})_2$; and wherein one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently H, fluoro, chloro, methyl, ethyl, —$CF_3$, —$OCF_3$, cyclopropyl, or —$C(O)N(R^{19})_2$; and wherein one or more of $R^{9a}$, $R^{9b}$, $R^{9c}$, $R^{9d}$, and $R^{9e}$ is —$C(O)N(R^{19})_2$. In some embodiments of the compound of Formula I, II, IIa, IIb, III, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, $R^{9d}$, and $R^{9e}$ are independently H, fluoro, chloro, methyl, ethyl, or —$C(O)N(R^{19})_2$; and wherein one or more of $R^{9a}$, $R^{9b}$, $R^{9c}$, $R^{9d}$, and $R^{9e}$ is —$C(O)N(R^{19})_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one of $R^{9a}$, $R^{9b}$, $R^{9c}$, and $R^{9e}$ are independently H, fluoro, chloro, methyl, or ethyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$ is H or fluoro. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9b}$ is H or methyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9b}$ is H, fluoro, or methyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9c}$ is H, fluoro, chloro, methyl, ethyl, —$CF_3$, —$OCF_3$, or cyclopropyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9c}$ is H, fluoro, and chloro. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9c}$ is methyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9e}$ is H. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9d}$ is —C(O)N($R^{19}$)$_2$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently i) H; ii) —S(O)$_2$C$_{1-6}$ alkyl; iii) C$_{1-6}$ alkyl optionally substituted with 1-6 groups independently selected from —CN, —OH, halogen, C$_{1-3}$ alkoxy, and C$_{3-7}$ monocyclic cycloalkyl; iv) C$_{3-7}$ monocyclic cycloalkyl optionally substituted with 1-6 groups independently selected from —CN, —OH, halogen, C$_{1-6}$ alkyl, and C$_{1-6}$ alkoxy, wherein the C$_{1-6}$ alkyl is optionally substituted with 1-3 groups independently selected from —CN, —OH, halogen, and C$_{1-3}$ alkoxy; or v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, C$_{1-3}$ alkyl, and C$_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently i) H; ii) C$_{1-6}$ alkyl optionally substituted with 1-6 groups independently selected from —CN, —OH, halogen, C$_{1-3}$ alkoxy, and C$_{3-7}$ monocyclic cycloalkyl; or iii) C$_{3-7}$ monocyclic cycloalkyl optionally substituted with 1-6 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —CN, —OH, halogen, and C$_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is H. In some embodiments of the compound of Formula I, II, IIa, IIb, III, IV, V, Va, Vb, Vc, VI, VIa, VIb, VIc, VII, VIIa, VIIb, or VIIc, or a pharmaceutically acceptable salt thereof, one $R^{19}$ is H. In some embodiments of the compound of Formula I, II, IIa, IIb, III, IV, IVa, IVb, IVc, V, Va, Vb, Vc, VI, VIa, VIb, VIc, VII, VIIa, VIIb, or VIIc, or a pharmaceutically acceptable salt thereof, both $R^{19}$ are H.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is C$_{1-6}$ alkyl optionally substituted with 1-6 groups independently selected from —CN, —OH, halogen, C$_{1-3}$ alkoxy, and C$_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is C$_{1-6}$ alkyl optionally substituted with 1-3 groups independently selected from —OH, halogen, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is C$_{1-4}$ alkyl optionally substituted with 1-3 groups independently selected from —OH, halogen, and C$_{1-3}$ alkoxy.

In some embodiments of the compound of Formula I, II, IIa, IIb, III, IIIa, IV, IVa, Vb, or Vc, or a pharmaceutically acceptable salt thereof, one or both $R^{19}$ is C$_{3-7}$ monocyclic cycloalkyl optionally substituted with 1-6 groups independently selected from —CN, —OH, halogen, C$_{1-6}$ alkyl, and C$_{1-6}$ alkoxy, wherein the C$_{1-3}$ alkyl is optionally substituted with 1-3 groups independently selected from —CN, —OH, halogen, and C$_{1-3}$ alkoxy. In some embodiments of the compound of Formula I, II, IIa, IIb, III, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is C$_{3-7}$ monocyclic cycloalkyl optionally substituted with 1-6 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —CN, —OH, halogen, and C$_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is C$_{3-5}$ monocyclic cycloalkyl optionally substituted with 1-3 groups independently selected from —OH, halogen, C$_{1-3}$ alkyl, and C$_{1-3}$ alkoxy, wherein the C$_{1-3}$ alkyl is optionally substituted with 1-3 groups independently selected from —CN, —OH, halogen, and C$_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is —S(O)$_2$C$_{1-6}$ alkyl. In some embodiments of the compound of Formula I, II, IIa, IIb, III, IV, IVa, IVb, IVc, V, Va, Vb, Vc, VI, VIa, VIb, VIc, VII, VIIa, VIIb, or VIIc, or a pharmaceutically acceptable salt thereof, one or both $R^{19}$ is 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, C$_{1-3}$ alkyl, and C$_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently i) H; ii) methyl; iii) ethyl optionally substituted with 1 or 2 groups independently selected from —OH, fluoro, and —OCH$_3$; iv) n-propyl optionally substituted with 1 or 2 groups independently selected from fluoro and —OCH$_3$; v) isopropyl optionally substituted with 1 or 2 fluoro groups; vi) n-butyl; vii) isobutyl optionally substituted with 1 or 2 fluoro groups; viii) sec-butyl; ix) tert-butyl; x) cyclopropyl optionally substituted with one methyl group, wherein the methyl is optionally substituted with 1-3 groups independently selected from fluoro and —OCH$_3$; or xi) cyclobutyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently i) H; ii) methyl; iii) ethyl; iv) —CH$_2$CH$_2$OH; v) —CH$_2$CH$_2$OCH$_3$; vi) —CH$_2$CHF$_2$; vii) —CH$_2$C(CH$_3$)F$_2$; vii) —CH(CH$_3$)CH$_2$F; ix) —CH(CH$_2$F)$_2$; x) n-propyl; xi) isopropyl; xii) —CH(CH$_3$)CHF$_2$; xiii) —CH$_2$CH$_2$CHF$_2$; xiv) isobutyl; xv) sec-butyl; xvi) tert-butyl; xvii) —CH$_2$CH$_2$CH$_2$OCH$_3$; xviii) cyclopropyl; xix) cyclopropyl substituted with one group selected from —CH$_2$F, —CHF$_2$ and —CH$_2$OCH$_3$; or xx) cyclobutyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently i) H; ii) methyl; iii) ethyl; iv) —CH$_2$CH$_2$OH; v) —CH$_2$CH$_2$OCH$_3$; vi) —CH$_2$CHF$_2$; vii) —CH$_2$C(CH$_3$)F$_2$; viii) n-propyl; ix)

isopropyl; x) —CH(CH₃)CH₂F; xi) —CH(CH₃)CHF₂; xii) —CH(CH₂F)₂; xiii) —CH₂CH₂CHF₂; xiv) isobutyl; xv) sec-butyl; xvi) tert-butyl; xvii) cyclopropyl; xviii) cyclopropyl substituted with one group selected from —CH₂F, —CHF₂ and —CH₂OCH₃; or xix) cyclobutyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each $R^{19}$ is independently H, methyl, isopropyl, or cyclopropyl, wherein the cyclopropyl is optionally substituted with one group selected from —CH₂F, —CHF₂ and —CH₂OCH₃.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one $R^{19}$ is H and the other $R^{19}$ is H, methyl, ethyl, or isopropyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{9a}$, $R^{9b}$, $R^{9c}$, and $R^{9e}$ are independently H, fluoro, chloro, methyl, or ethyl and $R^{9d}$ is —C(O)N($R^{19}$)₂; wherein each $R^{9d}$ is independently H or cyclopropyl, wherein the cyclopropyl is optionally substituted with a methyl, and wherein the methyl is optionally substituted with 1-3 groups independently selected from fluoro and —OCH₃. In some embodiments, $R^{9a}$, $R^{9b}$, $R^{9c}$, and $R^{9e}$ are independently H, fluoro, chloro, methyl, or ethyl and $R^{9d}$ is —C(O)N($R^{19}$)₂; wherein each $R^{19}$ is independently H or cyclopropyl, wherein the cyclopropyl is optionally substituted with a methyl, and wherein the methyl is optionally substituted with 1-3 groups fluoro groups. In some embodiments, $R^{9a}$, $R^{9b}$, $R^{9c}$, and $R^{9e}$ are independently H, fluoro, chloro, methyl, or ethyl and $R^{9d}$ is —C(O)NH($R^{19}$); wherein $R^{19}$ is cyclopropyl optionally substituted with a methyl, and wherein the methyl is optionally substituted with 1-3 groups fluoro groups. In some embodiments, $R^{9a}$, $R^{9b}$, $R^{9c}$, and $R^{9e}$ are independently H, fluoro, or chloro and $R^{9d}$ is —C(O)NH($R^{19}$); wherein $R^{19}$ is cyclopropyl optionally substituted with a methyl, and wherein the methyl is optionally substituted with 1-3 groups fluoro groups. In some embodiments, $R^{9a}$, $R^{9b}$, and $R^{9c}$ are independently fluoro or chloro, $R^{9e}$ is H, and $R^{9d}$ is —C(O)NH($R^{19}$); wherein $R^{19}$ is cyclopropyl optionally substituted with a methyl, wherein the methyl is optionally substituted with 1-3 groups fluoro groups. In some embodiments, $R^{9d}$ is

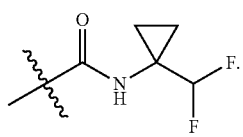 [SMILES: *C(=O)NC1(C(F)F)CC1]

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is i) H; ii) $C_{1-6}$ alkyl optionally substituted with 1-3 groups independently selected from —OH, halogen, $C_{1-3}$ alkoxy, and $C_{3-7}$ monocyclic cycloalkyl; or iii) $C_{3-7}$ monocyclic cycloalkyl optionally substituted with 1-3 groups independently selected from —OH, halogen, $C_{1-3}$ alkyl, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is H.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is $C_{1-6}$ alkyl optionally substituted with 1-3 groups independently selected from —OH, halogen, $C_{1-3}$ alkoxy, and $C_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is methyl, ethyl, isopropyl, or sec-butyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is ethyl, isopropyl, or sec-butyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is isopropyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is $C_{3-7}$ monocyclic cycloalkyl optionally substituted with 1-3 groups independently selected from —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is cyclopropyl optionally substituted with one methyl group. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is cyclopropyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is methyl, ethyl, isopropyl, sec-butyl, or cyclopropyl, wherein the cyclopropyl is optionally substituted with one methyl. In some embodiments of the compound of Formula I, II, IIa, IIb, III, IIIa, IV IVa, IVb, IVc, V, Va, Vb, Vc, VI, VIa, VIb, VIc, VII, VIIa, VIIb, or VIIc, or a pharmaceutically acceptable salt thereof, $R^7$ is ethyl, isopropyl, sec-butyl, or cyclopropyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^7$ is isopropyl or cyclopropyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is $NR^{15}R^{16}$, wherein $R^{15}$ and $R^{16}$ are independently i) H; ii) $C_{3-7}$ monocyclic cycloalkyl optionally substituted with 1-3 groups independently selected from —OH, halogen, $C_{1-3}$ alkyl, and $C_{1-3}$ alkoxy; iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy; iv) —C(O)$C_{1-6}$ alkyl, wherein the $C_{1-6}$ alkyl is optionally substituted with 1-3 groups independently selected from —CN, —OH, halogen, and $C_{1-3}$ alkoxy; or v) $C_{1-6}$ alkyl optionally substituted with 1-6 groups independently selected from a) —CN,
b) —OH,
c) halogen, d) $C_{1-3}$ alkoxy,
e) $C_{3-7}$ monocyclic cycloalkyl optionally substituted with 1-3 groups independently selected from —OH, halogen, $C_{1-3}$ alkyl, and $C_{1-3}$ alkoxy, and
f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is $NR^{15}R^{16}$, wherein $R^{15}$ and $R^{16}$ are independently i) H; ii) $C_{3-7}$ monocyclic cycloalkyl optionally substituted with 1-3 groups independently selected from —OH, halogen, $C_{1-3}$ alkyl, and $C_{1-3}$ alkoxy; iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy; iv) —C(O)$C_{1-6}$ alkyl, wherein the $C_{1-6}$ alkyl is optionally substituted with 1-3 groups independently selected from —CN, —OH, halogen, and $C_{1-3}$ alkoxy; or v) $C_{1-6}$ alkyl optionally substituted with 1-6 groups independently selected from —OH, halogen, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is $NR^{15}R^{16}$, wherein $R^{15}$ and $R^{16}$ are independently i) H; or ii) $C_{1-6}$ alkyl optionally substituted with 1-6 groups independently selected from —OH, halogen, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is H. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one of $R^5$ and $R^{16}$ is H.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is $C_{3-7}$ monocyclic cycloalkyl optionally substituted with 1-3 groups independently selected from —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is a cyclobutyl, cyclopentyl, or cyclohexyl, each of which is optionally substituted with 1-3 groups independently selected from —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is a cyclobutyl optionally substituted with 1 or 2 groups independently selected from —OH and fluoro. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^5$ and $R^{16}$ is a cyclohexyl optionally substituted with 1 or 2 fluoro groups. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is a cyclobutyl; cyclobutyl substituted with one —OH; cyclobutyl substituted with 2 fluoro groups; or cyclohexyl substituted with 2 fluoro groups.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is 5-7 membered monocyclic heterocyclyl optionally substituted with 1-3 groups independently selected from —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is tetrahydropyranyl optionally substituted with 1-3 groups independently selected from —OH, halogen, $C_{1-3}$ alkyl, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is tetrahydropyranyl optionally substituted with one group selected from fluoro and methyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is tetrahydropyranyl; tetrahydropyranyl substituted with one fluoro group; or tetrahydropyranyl substituted with one methyl group.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is a cyclobutyl, cyclopentyl, cyclohexyl, or tetrahydropyranyl, each of which is optionally substituted with 1-3 groups independently selected from —OH, halogen, $C_{1-3}$ alkyl, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is —C(O)$C_{1-6}$ alkyl, wherein the $C_{1-6}$ alkyl is optionally substituted with 1-3 groups independently selected from —CN, —OH, halogen, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is —C(O)tert-butyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is $C_{1-6}$ alkyl optionally substituted with 1-6 groups independently selected from
a) —CN,
b) —OH,
c) halogen,
d) $C_{1-3}$ alkoxy, e) $C_{3-7}$ monocyclic cycloalkyl optionally substituted with 1-3 groups independently selected from —OH, halogen, $C_{1-3}$ alkyl, and $C_{1-3}$ alkoxy, and f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is $C_{1-6}$ alkyl optionally substituted with 1-6 groups independently selected from —OH, halogen, and $C_{1-3}$ alkoxy. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is $C_{1-6}$ alkyl optionally substituted with 1-3 groups independently selected from —OH, halogen, and —OCH$_3$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is i) methyl; ii) isopropyl; iii) isobutyl optionally substituted with one group selected from —OH, fluoro, and —OCH$_3$; iv) sec-butyl; or v) $C_5$ alkyl optionally substituted with —OCH$_3$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one or both of $R^{15}$ and $R^{16}$ is i) methyl; ii) isopropyl; iii) isobutyl; iv) —CH$_2$C(CH$_3$)$_2$F; v) —CH$_2$C(CH$_3$)$_2$OCH$_3$; vi) —CH$_2$C(CH$_3$)$_2$OH; vii) sec-butyl; or viii) —CH$_2$C(CH$_3$)$_2$CH$_2$OCH$_3$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{15}$ and $R^{16}$ are independently i) H; ii) methyl; iii) isopropyl; iv) isobutyl optionally substituted with one group selected from —OH, fluoro, and —OCH$_3$; v) sec-butyl; vi) $C_5$ alkyl optionally substituted with —OCH$_3$; vii) —C(O)(tert-butyl); viii) cyclobutyl optionally substituted with 1 or 2 groups independently selected from —OH and fluoro; ix) cyclohexyl optionally substituted with 1 or 2 fluoro groups; or x) tetrahydropyranyl optionally substituted with one group selected from fluoro and methyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{15}$ and $R^{16}$ are independently i) H; ii) methyl; iii) isopropyl; iv) isobutyl; v) —CH$_2$C(CH$_3$)$_2$F; vi) —CH$_2$C(CH$_3$)$_2$OCH$_3$; vii) —CH$_2$C(CH$_3$)$_2$OH; viii) sec-butyl; ix) —CH$_2$C(CH$_3$)$_2$CH$_2$OCH$_3$; x) —C(O)(tert-butyl); xi) cyclobutyl; xii) cyclobutyl substituted with one —OH; xiii) cyclobutyl substituted with 2 fluoro groups; xiv) cyclohexyl substituted with 2 fluoro groups; xv) tetrahydropyranyl; xvi) tetrahydropyranyl substituted with one fluoro group; or xvii) tetrahydropyranyl substituted with one methyl group. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{15}$ and $R^{16}$ are independently i) H; ii) isopropyl; iii) —CH$_2$C(CH$_3$)$_2$F; iv) —CH$_2$C(CH$_3$)$_2$OH; v) —CH$_2$C(CH$_3$)$_2$OCH$_3$; vi) —C(O)(tert-butyl); vii) cyclobutyl substituted with 2 fluoro groups; viii) cyclohexyl substituted with 2 fluoro groups; or ix) tetrahydropyranyl substituted with one methyl group.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{15}$ and $R^{16}$ are independently H, methyl, or isobutyl, wherein the isobutyl is optionally substituted with one group selected from —OH, fluoro, and —OCH$_3$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one of $R^{15}$ and $R^{16}$ is H or methyl and the other of $R^{15}$ and $R^{16}$ is isobutyl optionally substituted with one group selected from —OH, fluoro, and —OCH$_3$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, $R^{15}$ and $R^{16}$ are independently H, methyl, isobutyl, —CH$_2$C(CH$_3$)$_2$OCH$_3$, CH$_2$C(CH$_3$)$_2$OH, or CH$_2$C(CH$_3$)$_2$F.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one of $R^{15}$ and $R^{16}$ is H and the other of $R^{15}$ and $R^{16}$ is i) isopropyl; iii) —CH$_2$C(CH$_3$)$_2$F; iv) —CH$_2$C(CH$_3$)$_2$OH; v) —CH$_2$C(CH$_3$)$_2$OCH$_3$; vi) —C(O)(tert-butyl); vii) cyclobutyl substituted with 2 fluoro groups; viii) cyclohexyl substituted with 2 fluoro groups; or ix) tetrahydropyranyl substituted with one methyl group.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is a 4-8 membered monocyclic, fused bicyclic, bridged bicyclic, or spirocyclic heterocyclyl having 1-3 heteroatoms independently selected from N, O, and S, wherein the 4-8 membered monocyclic, fused bicyclic, bridged bicyclic, or spirocyclic heterocyclyl is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

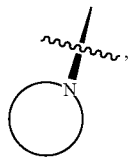

which is optionally substituted with 1-5 $R^{18}$. As used herein,

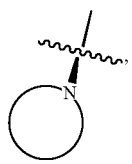

is a 4-10 membered monocyclic, fused bicyclic, bridged bicyclic, or spirocyclic heterocyclyl with at least one nitrogen ring atom, wherein the nitrogen ring atom is the point of attachment for the 4-10 membered monocyclic, fused bicyclic, bridged bicyclic, or spirocyclic heterocyclyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

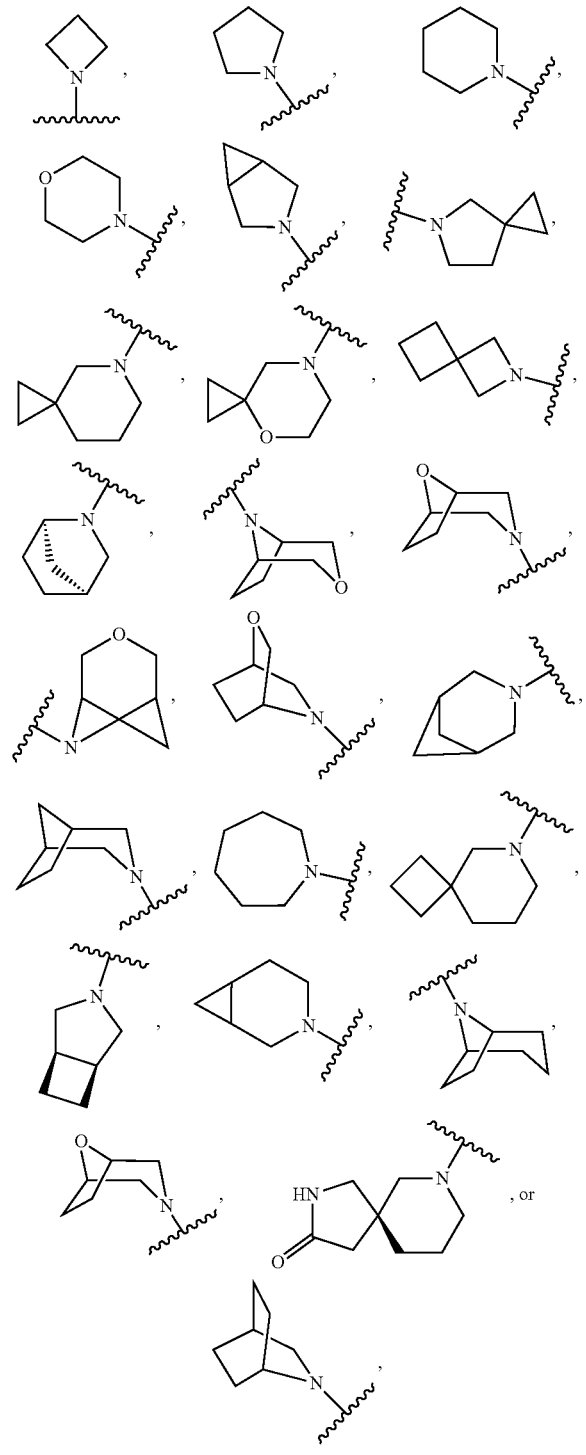

each of which is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

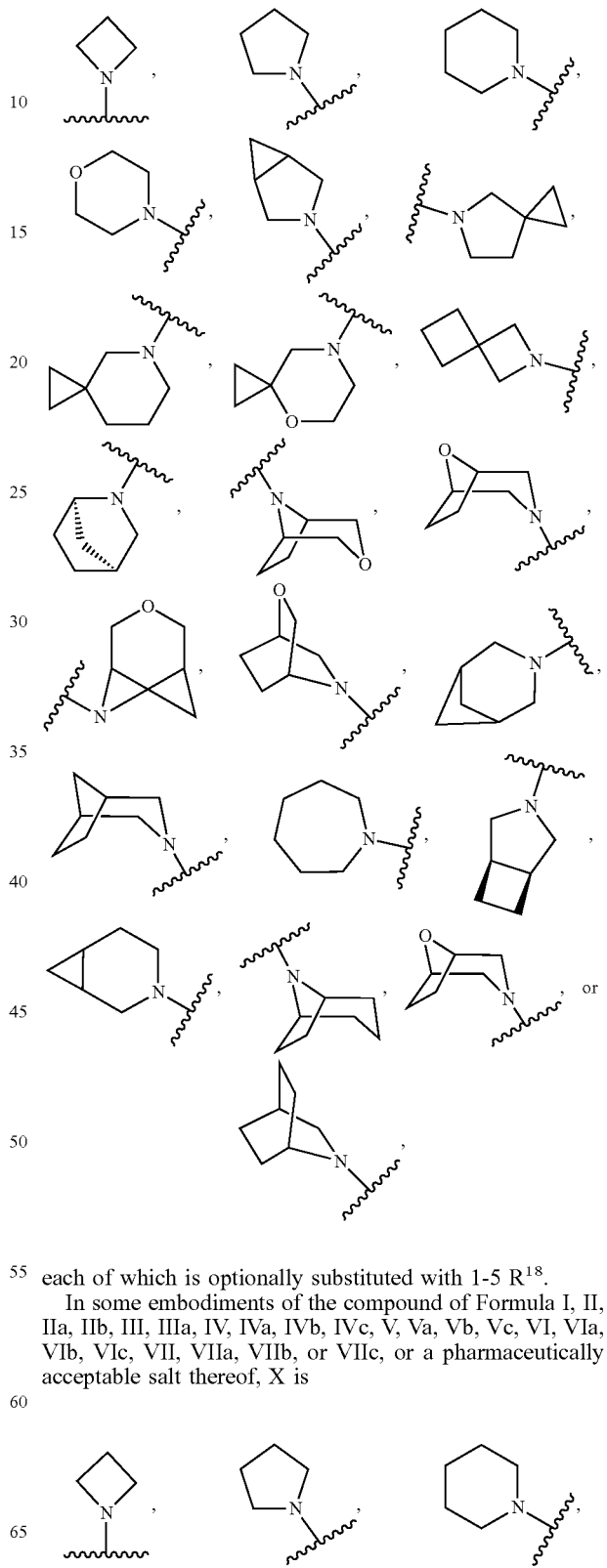

each of which is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

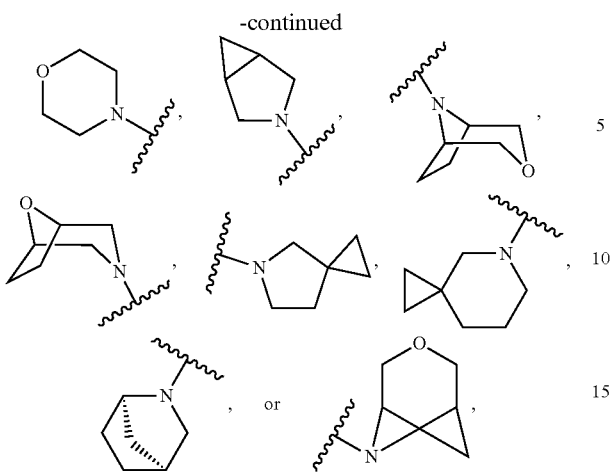

each of which is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is azetidinyl, pyrrolidinyl, piperidinyl, or morpholinyl, each of which is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is azetidinyl optionally substituted with 1-4 $R^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is azetidinyl optionally substituted with 1-3 $R^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is azetidinyl optionally substituted with 1-2 $R^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is pyrrolidinyl optionally substituted with 1-5 $R^8$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is piperidinyl optionally substituted with 1-5 $R^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is morpholinyl optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

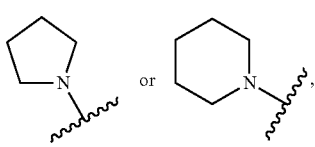 [SMILES: *N1CCCC1 ; *N1CCCCC1]

each of which is optionally substituted with 1-5 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

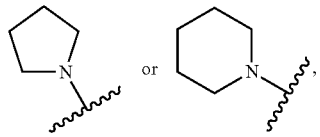 [SMILES: *N1CCCC1 ; *N1CCCCC1]

each of which is optionally substituted with 1-4 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

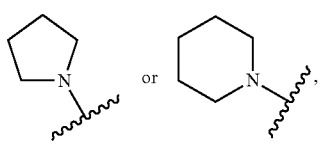 [SMILES: *N1CCCC1 ; *N1CCCCC1]

each of which is optionally substituted with 1-3 $R^{18}$. In embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

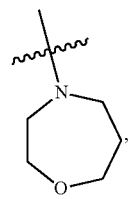

which is optionally substituted with 1-3 $R^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

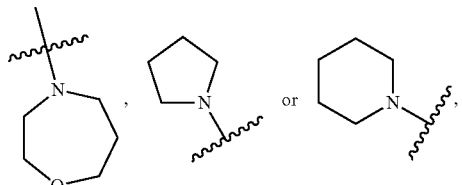

each of which is optionally substituted with 1-3 $R^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

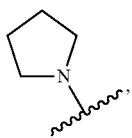 [SMILES: *N1CCCC1]

which is optionally substituted with 1-4 R$^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is which is optionally substituted with 1-3 R$^{18}$.

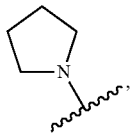 [SMILES: *N1CCCC1]

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

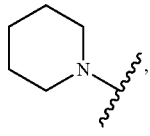

which is optionally substituted with 1-4 R$^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

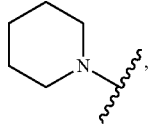

which is optionally substituted with 1-3 R$^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is unsubstituted. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with 1-5 R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with 1-4 R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with 1-3 R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with 1-2 R$^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with one R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with two R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with three R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with four R$^{18}$. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is substituted with five R$^{18}$.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, two R$^{18}$ are attached to the same carbon.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each R$^{18}$ is independently i) —CN; ii) a halogen; iii) —OH; iv) C$_{1-6}$ alkoxy optionally substituted with 1-3 groups independently selected from —OH, halogen, C$_{1-3}$ alkoxy, and C$_{3-7}$ monocyclic cycloalkyl; v) C$_{1-6}$ alkyl optionally substituted with 1-3 groups independently selected from —OH, halogen, C$_{1-3}$ alkoxy, and C$_{3-7}$ monocyclic cycloalkyl; vi) —COOH; or vii) —C(O)N(R$^{22}$)$_2$, wherein each R$^{22}$ is independently H or C$_{1-6}$ alkyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each R$^{18}$ is independently i) a halogen; ii) —OH; or iii) C$_{1-6}$ alkyl optionally substituted with 1-3 groups independently selected from —OH, halogen, C$_{1-3}$ alkoxy, and C$_{3-7}$ monocyclic cycloalkyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each R$^{18}$ is independently —OH, fluoro, or C$_{1-3}$ alkyl optionally substituted with 1-3 groups independently selected from —OH and halogen.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, each R$^{18}$ is independently —OH, fluoro, or methyl optionally substituted with 1-3 groups independently selected from —OH and fluoro.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five R$^{18}$ is —CN. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five R$^{18}$ is a halogen. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is fluoro. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is —OH. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is —COOH. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is —C(O)N($R^{22}$)$_2$, wherein each $R^{22}$ is independently H or $C_{1-6}$ alkyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is $C_{1-6}$ alkoxy optionally substituted with 1-3 groups independently selected from —OH, halogen, $C_{1-3}$ alkoxy, and $C_{3-7}$ monocyclic cycloalkyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is $C_{1-6}$ alkyl optionally substituted with 1-3 groups independently selected from —OH, halogen, $C_{1-3}$ alkoxy, and $C_{3-7}$ monocyclic cycloalkyl. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is $C_{1-3}$ alkyl optionally substituted with 1-3 groups independently selected from —OH and halogen. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is a methyl optionally substituted with 1-3 groups independently selected from —OH and fluoro. In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is a methyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, one, two, three, four, or five $R^{18}$ is fluoro or methyl.

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

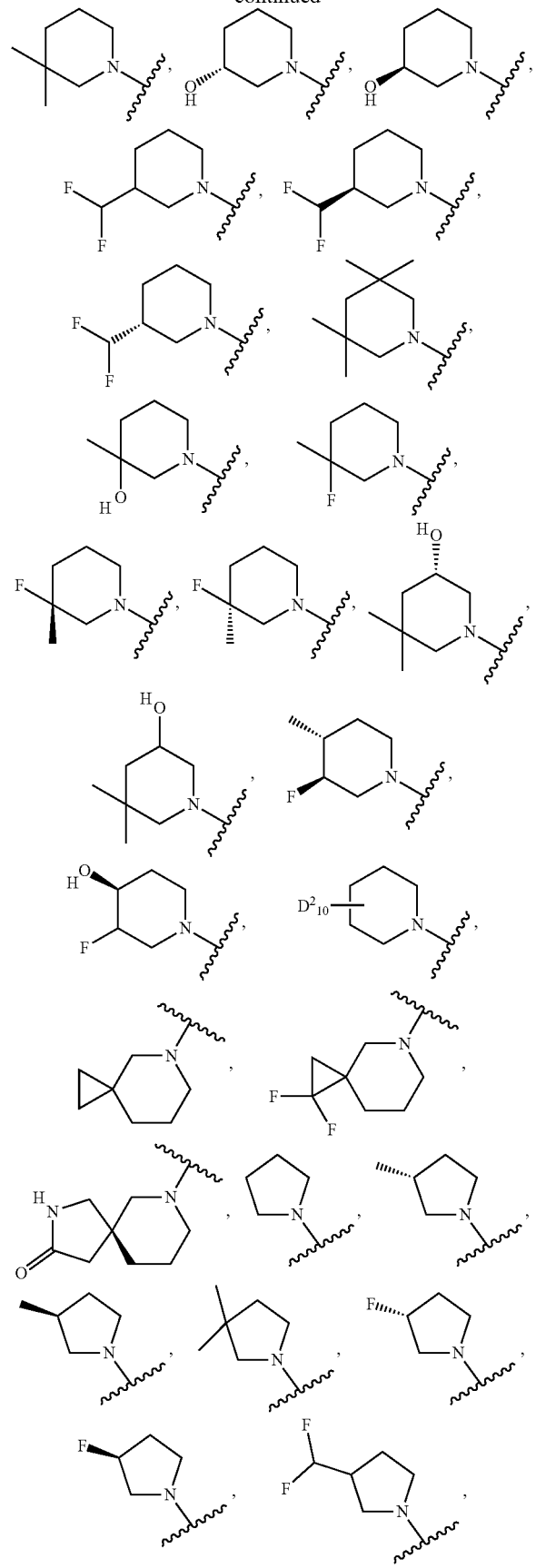

75
-continued
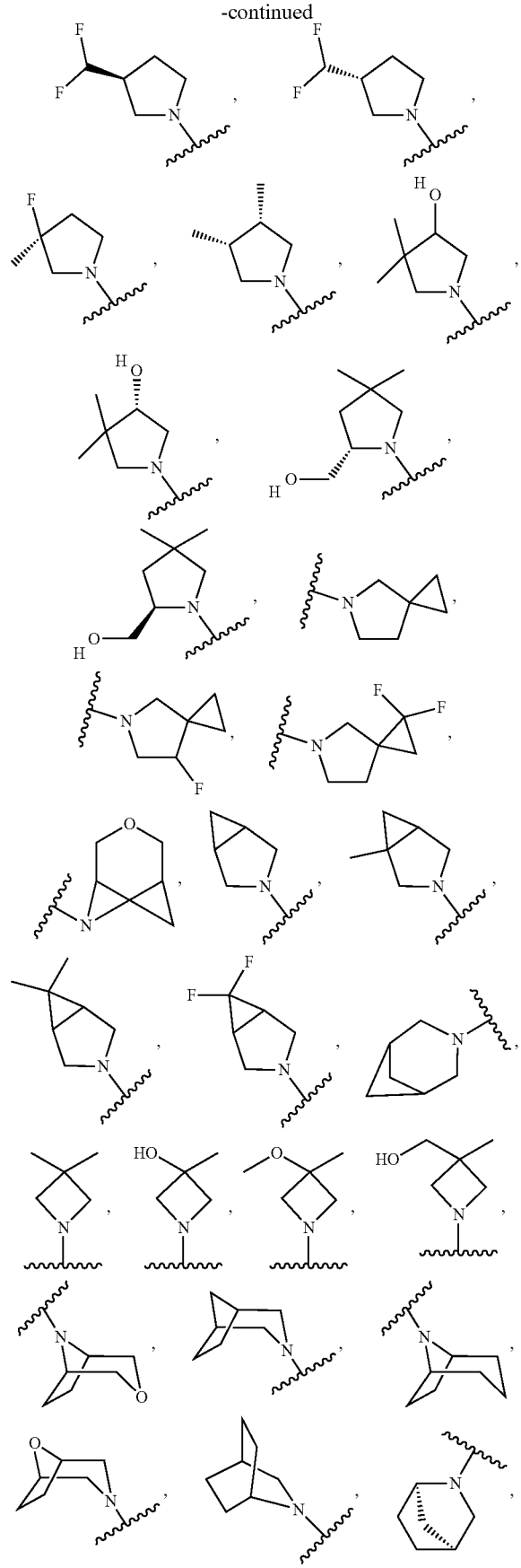
76
-continued
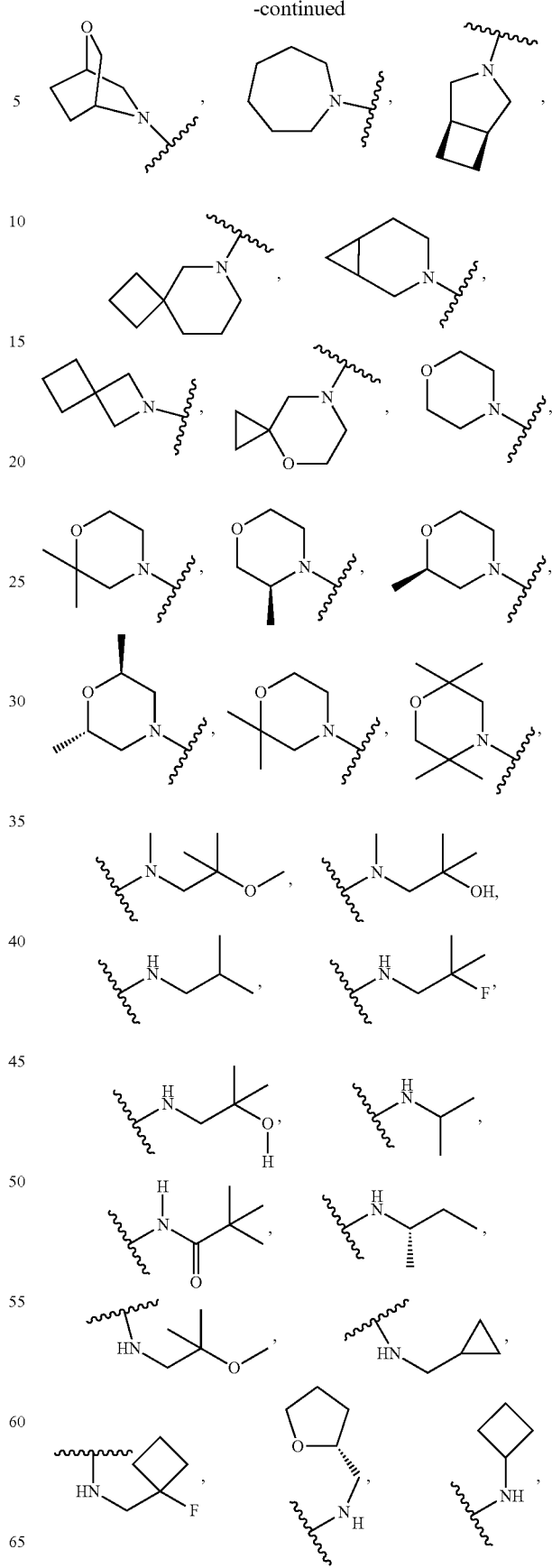

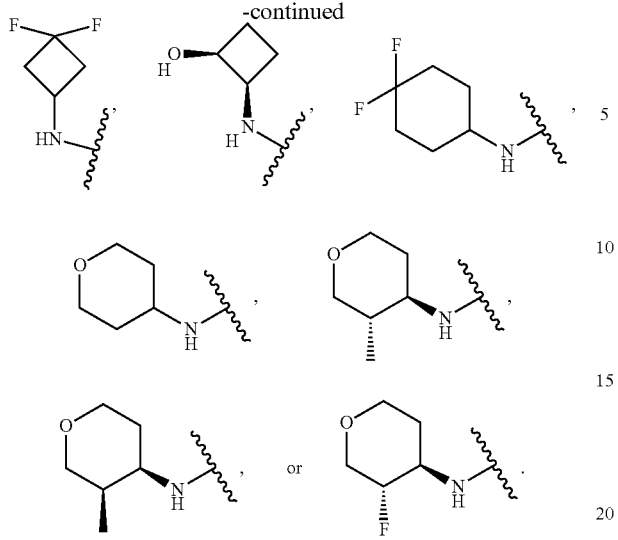

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

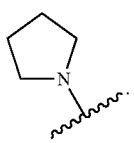

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

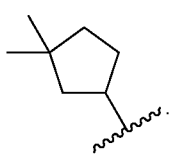 [SMILES: *C1CCC(C)(C)C1]

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

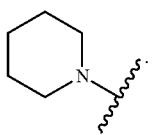

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is selected from the group consisting of:

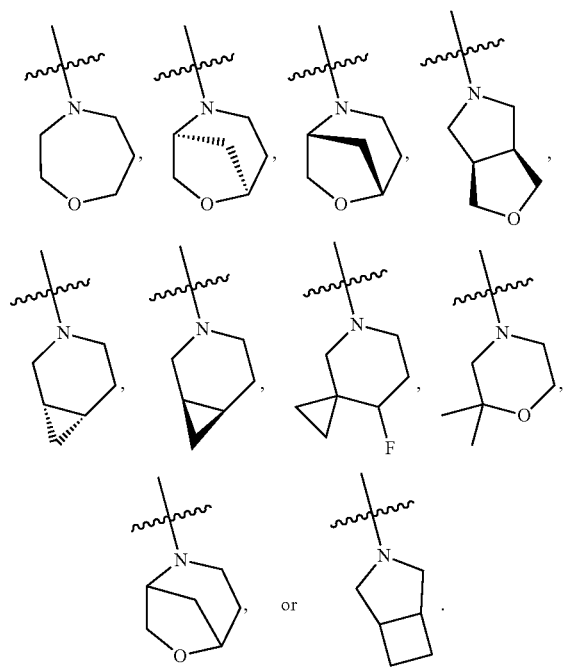

In some embodiments of the compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof, X is

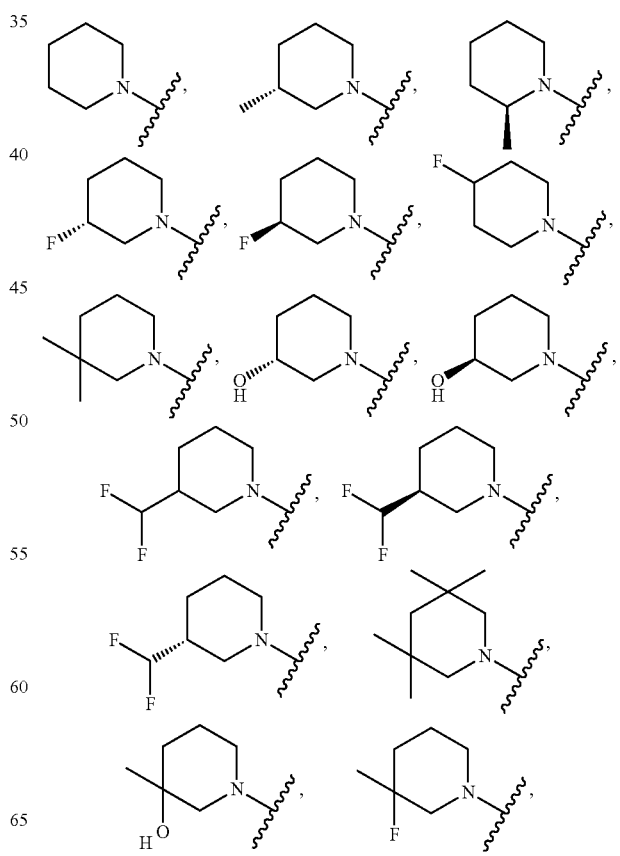

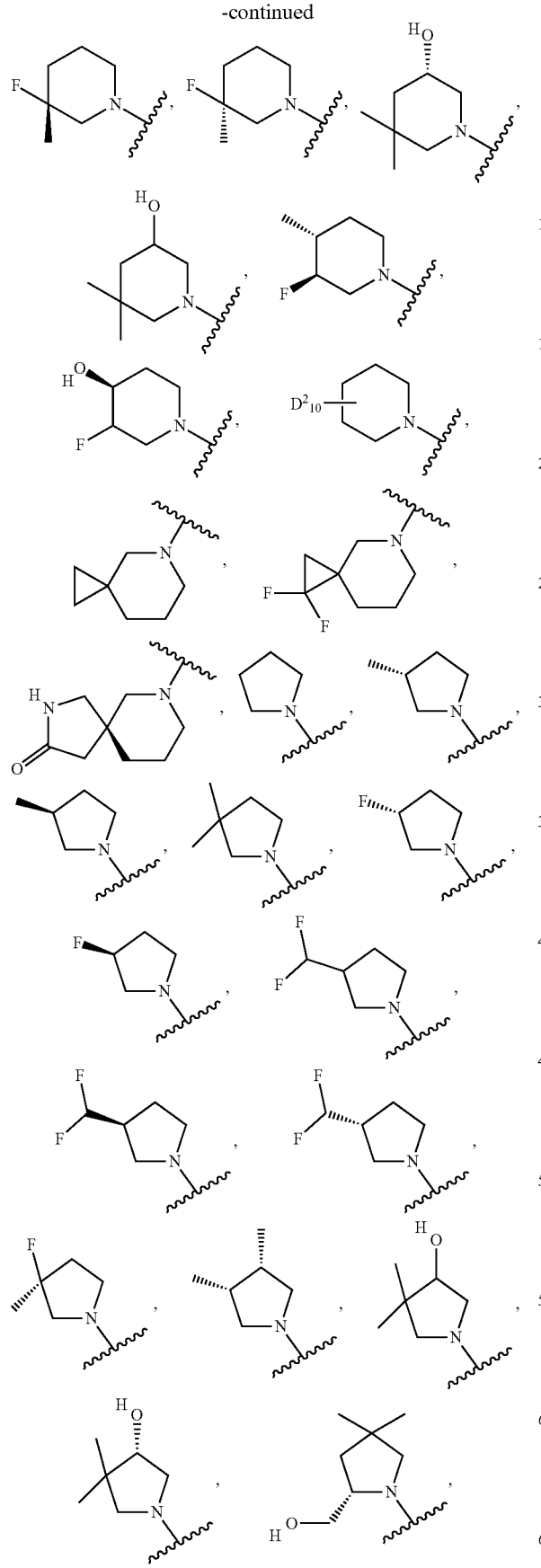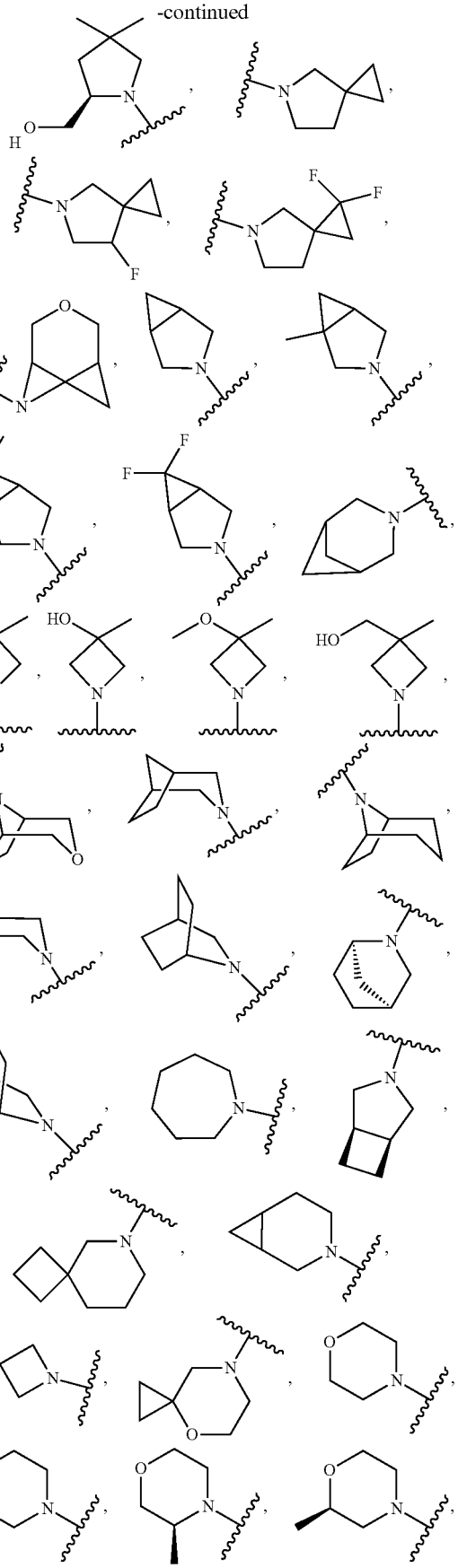

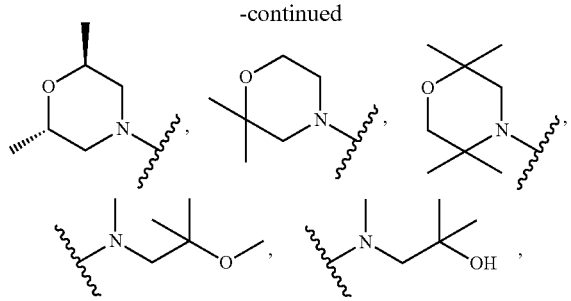
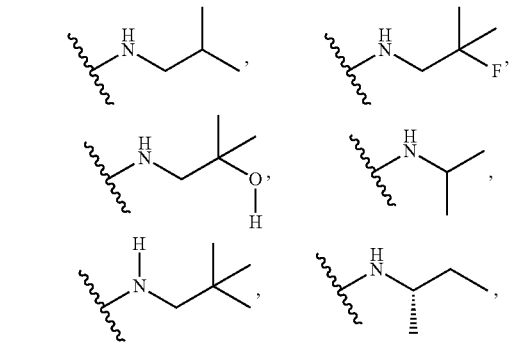
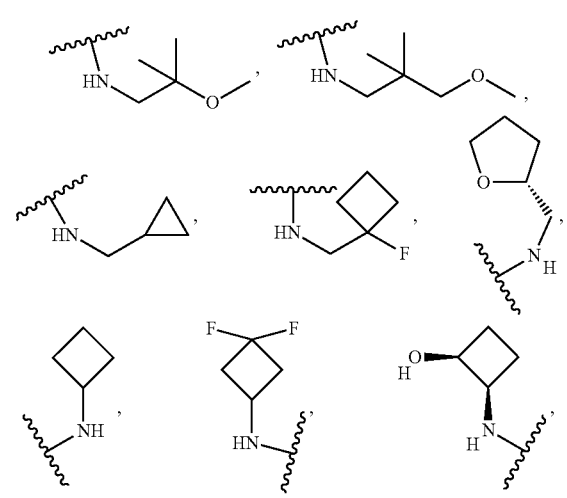
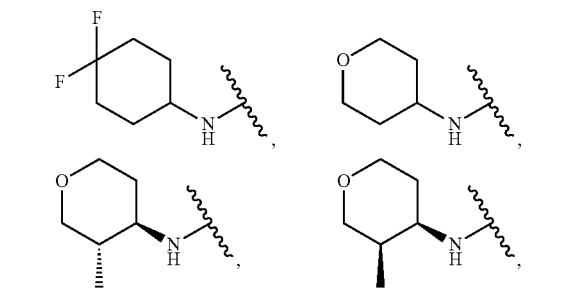
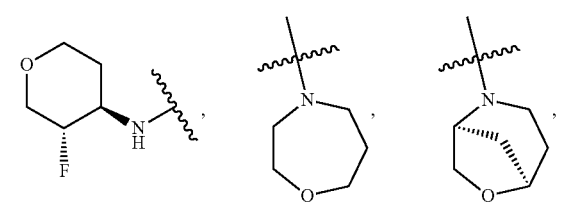
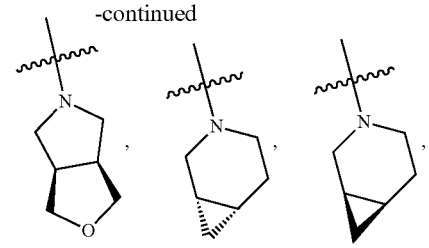
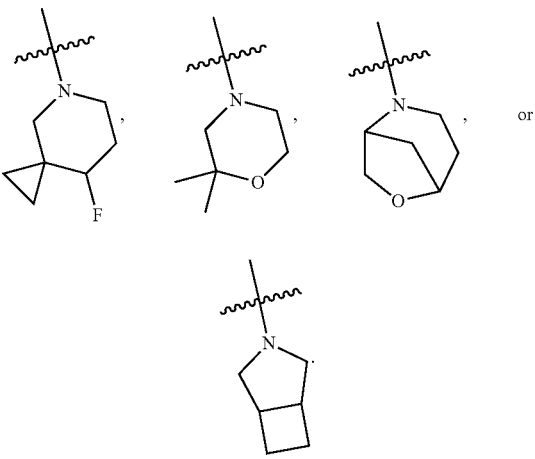
In some embodiments of the compound of Formula I, II, IIa, or III, the compound is selected from the group consisting of:
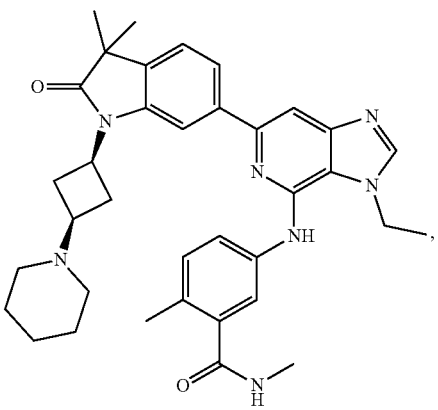
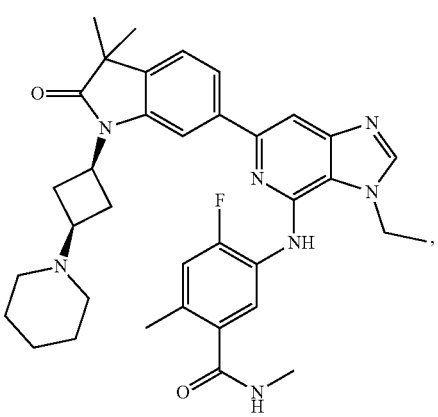

83
-continued
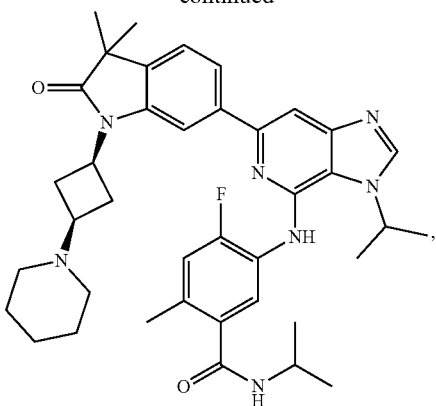
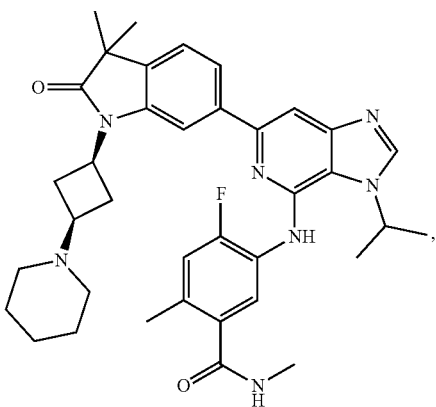
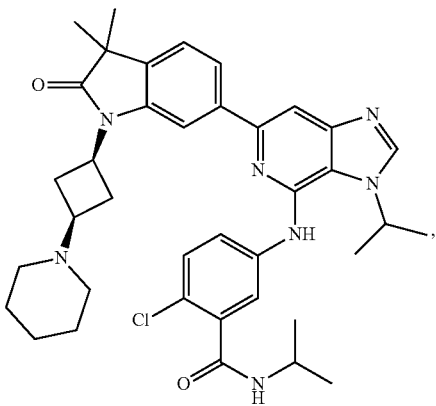
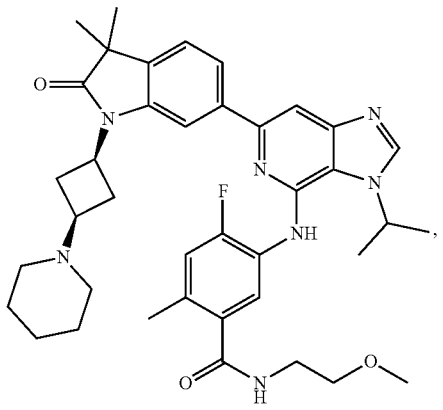
84
-continued
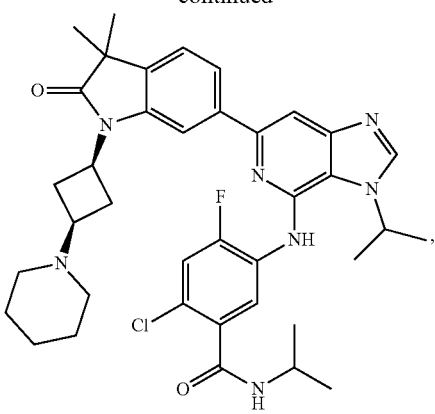
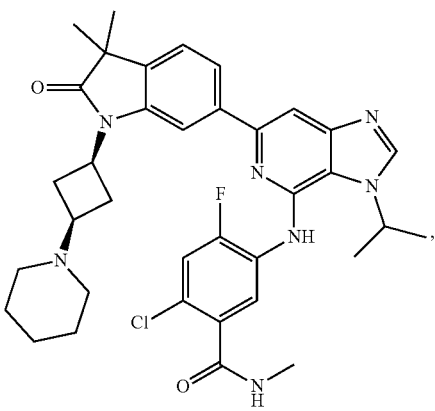
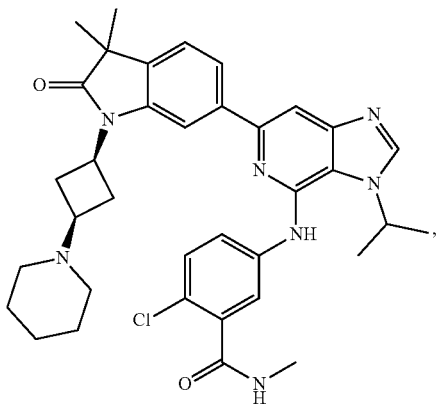
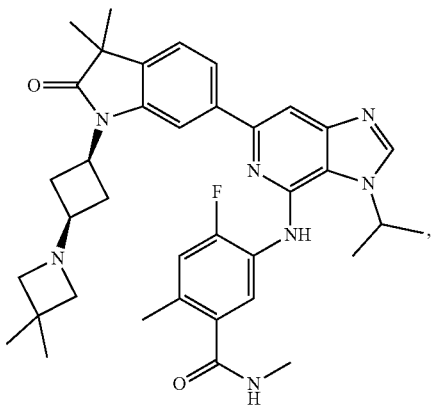

85
-continued
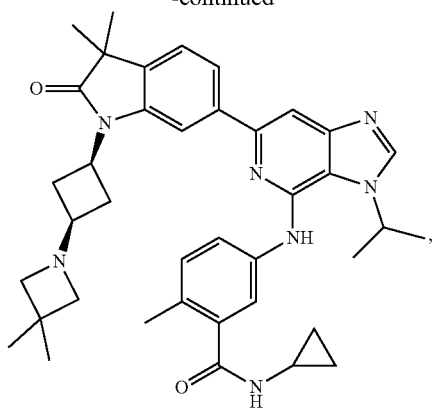
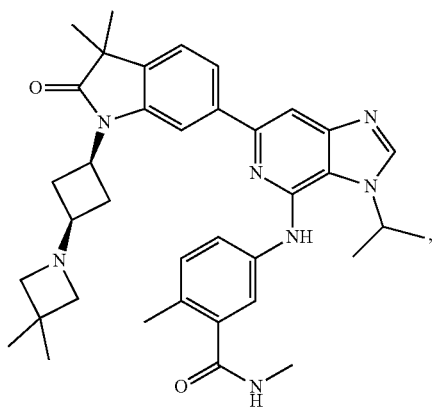
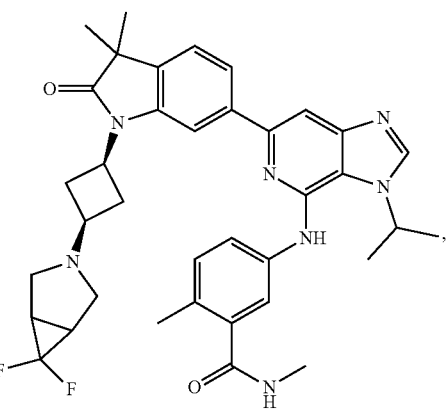
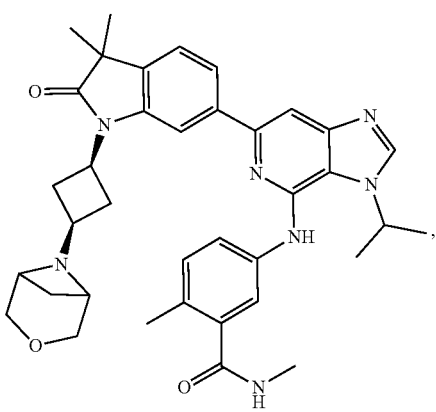
86
-continued
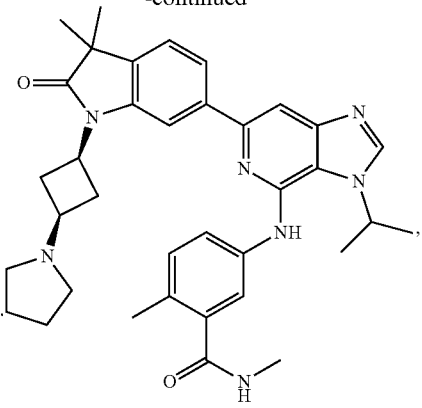
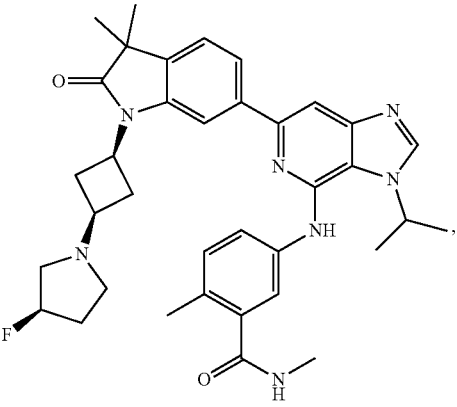
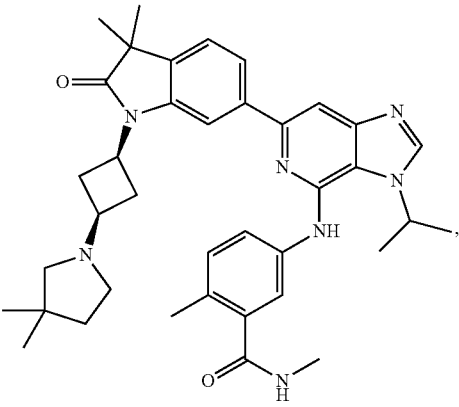
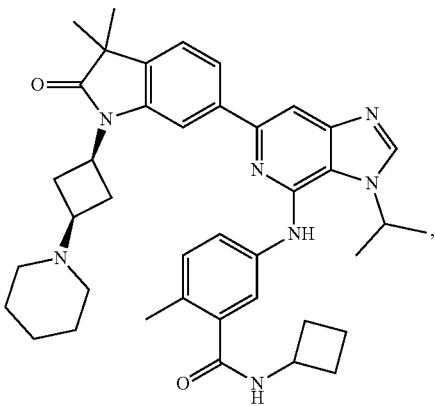

87
-continued
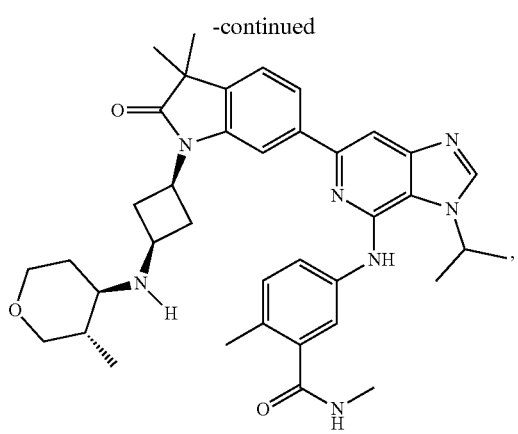
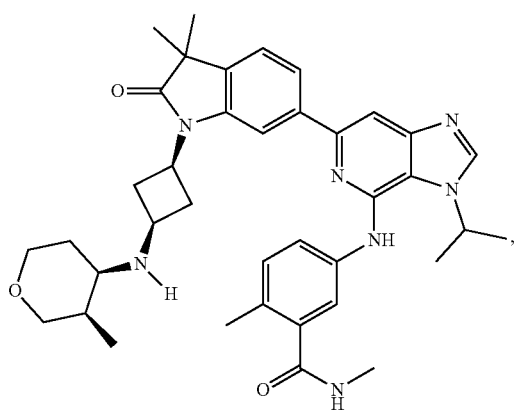
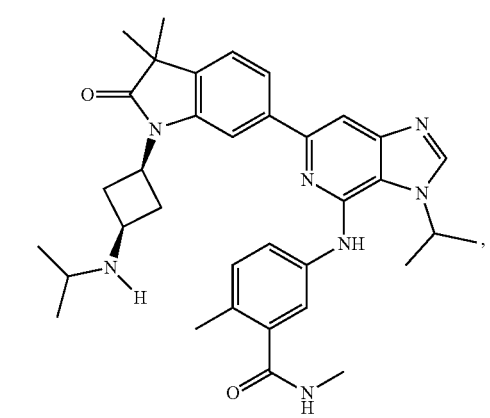
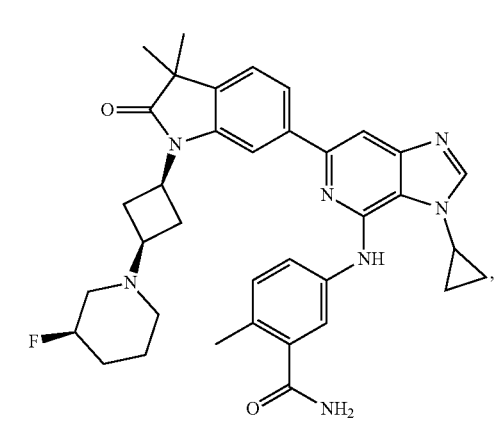
88
-continued
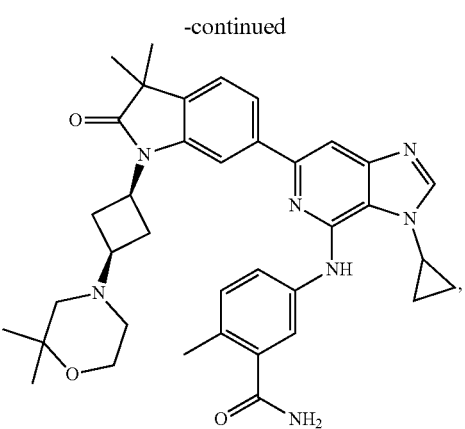
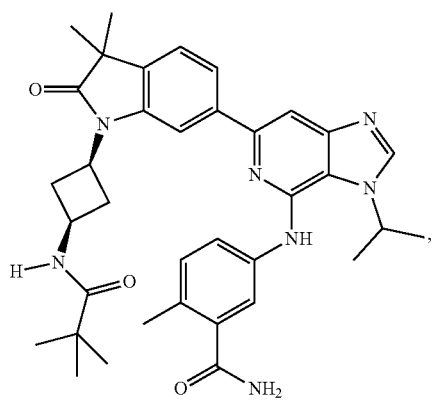
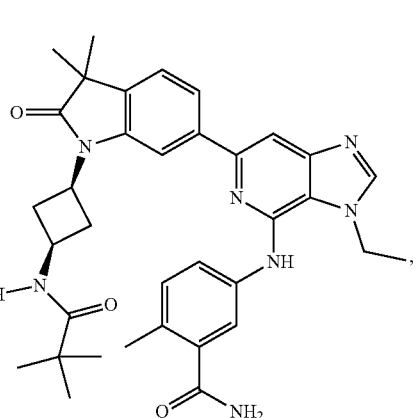
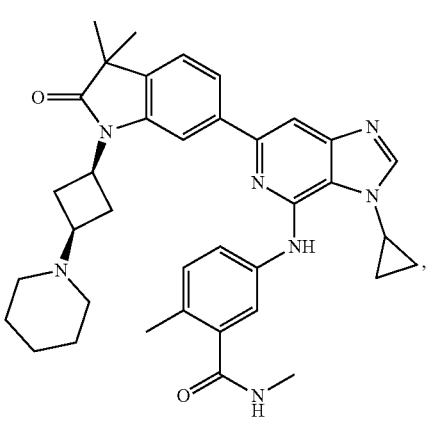

89
-continued
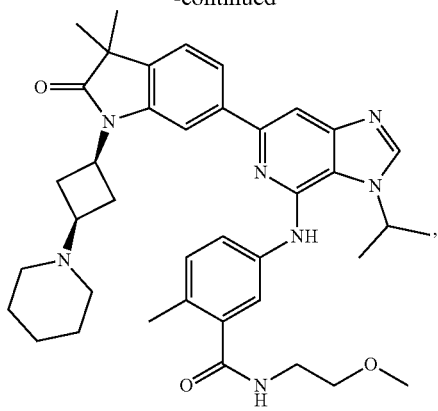
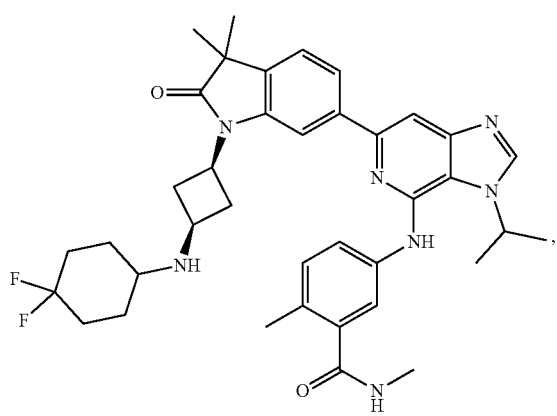
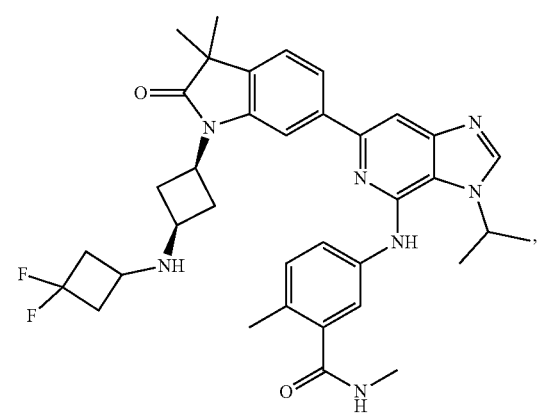
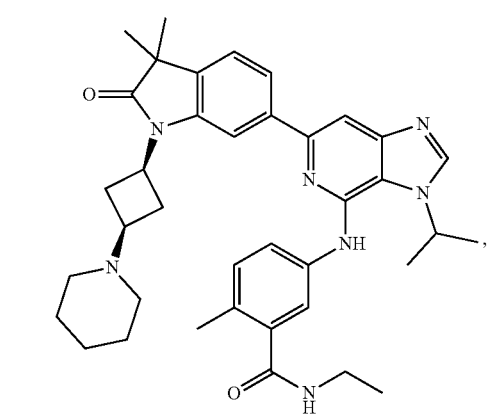
90
-continued
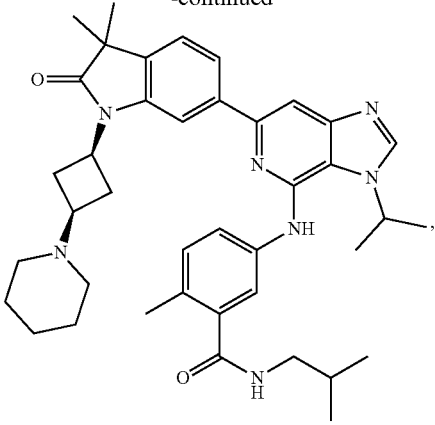
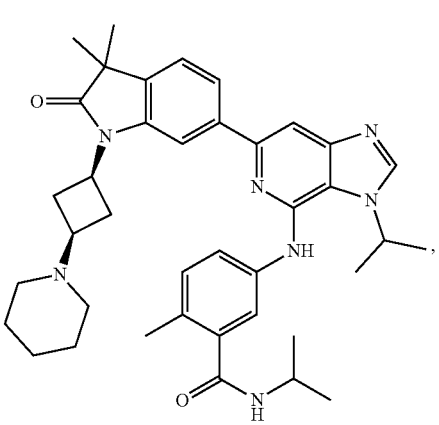
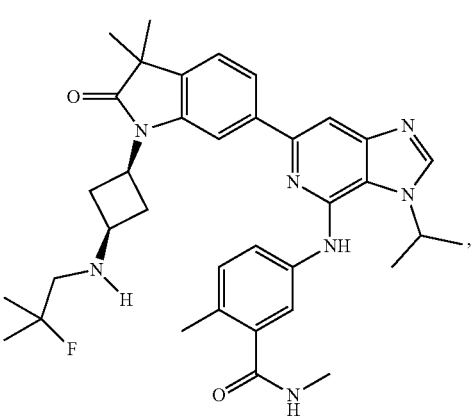
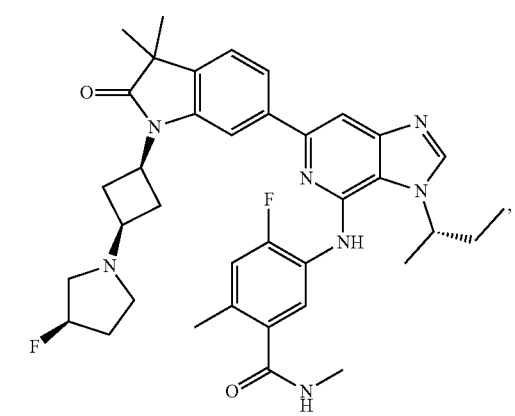

91
-continued
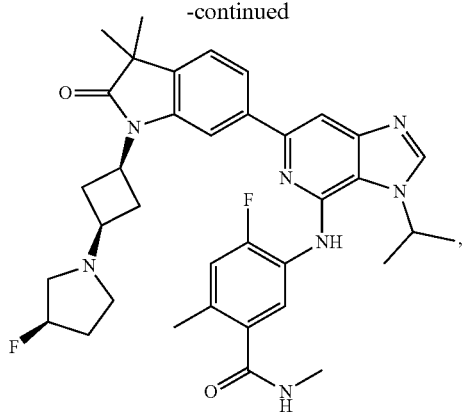
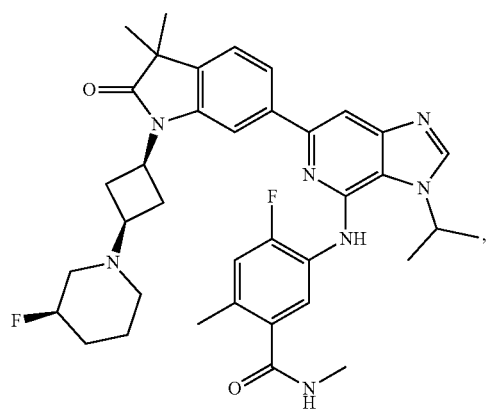
92
-continued
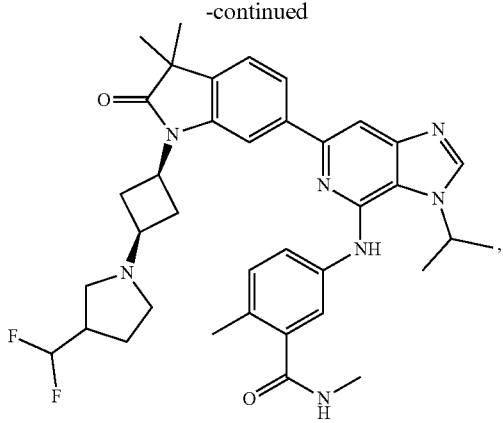
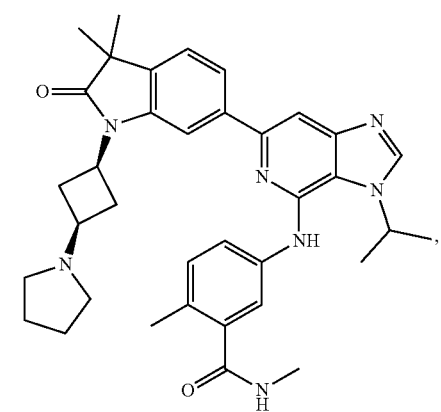
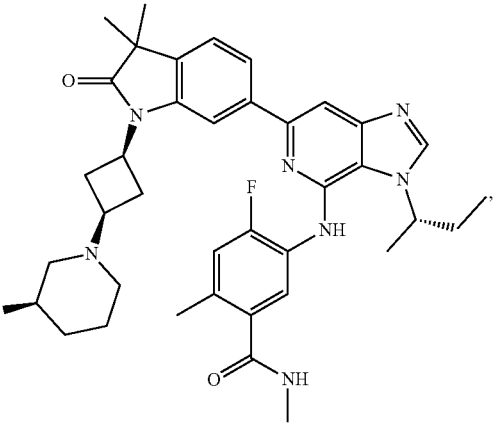
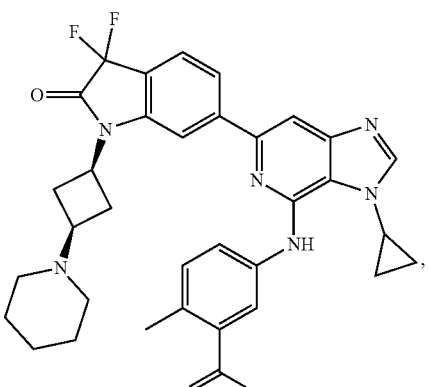

93
-continued
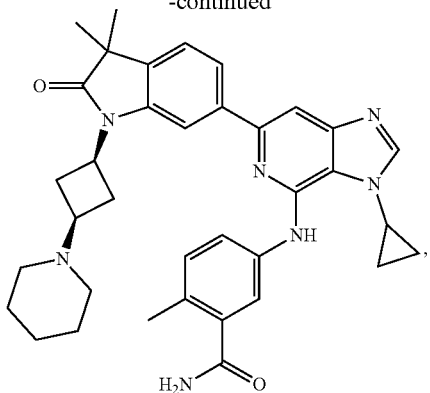
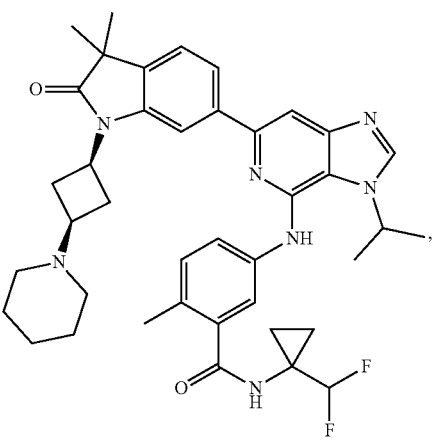
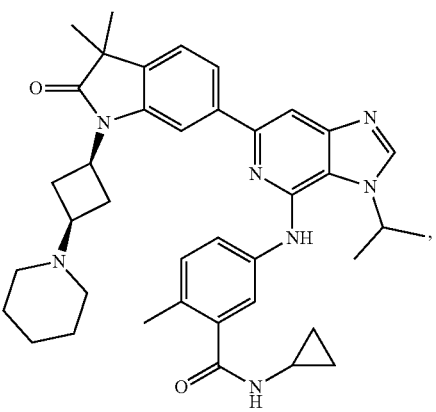
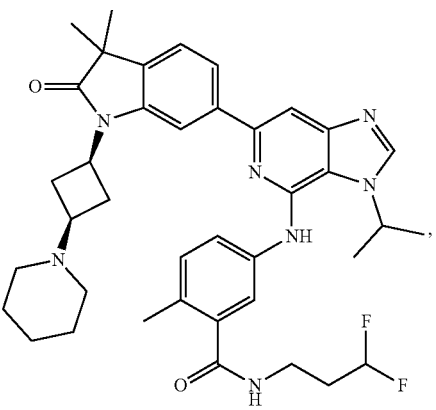
94
-continued
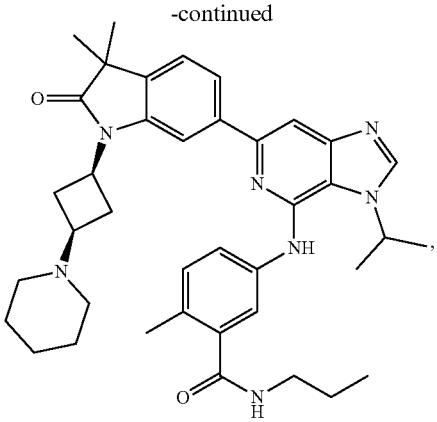
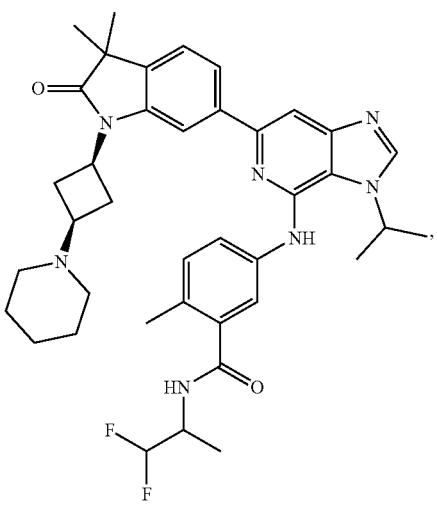
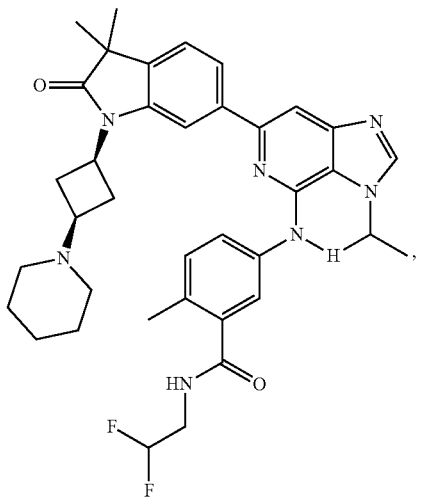

95
-continued
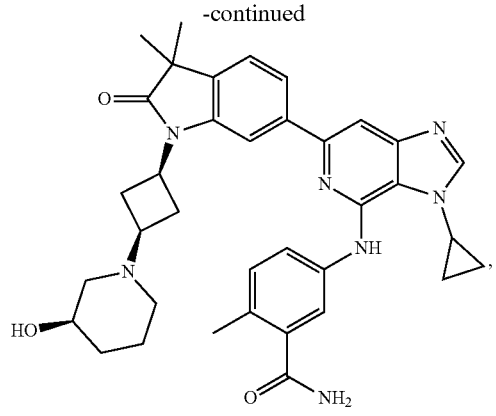
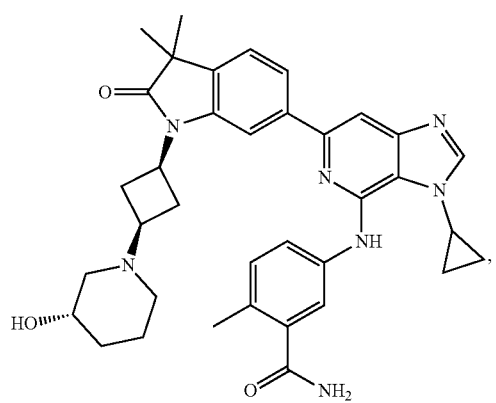
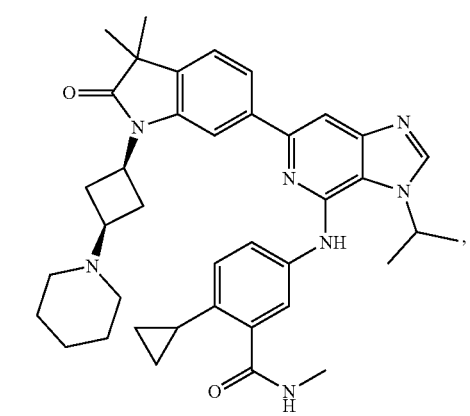
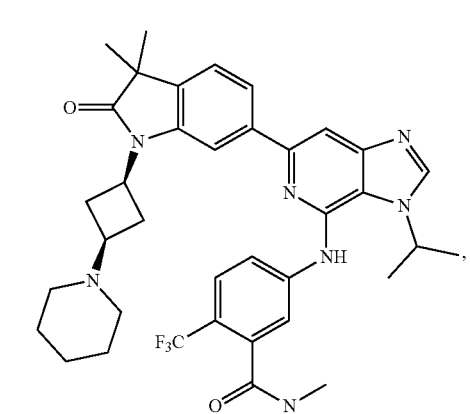
96
-continued
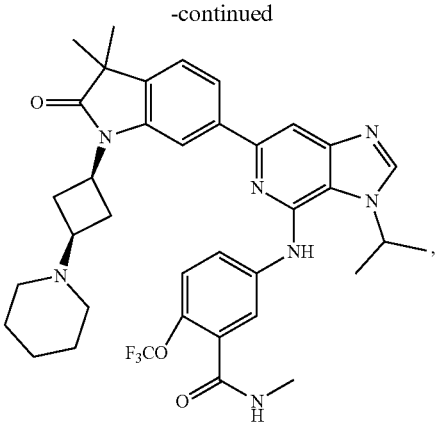
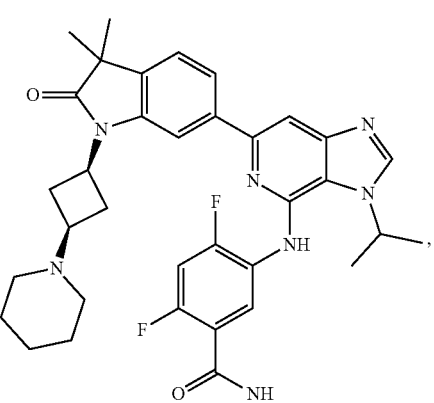
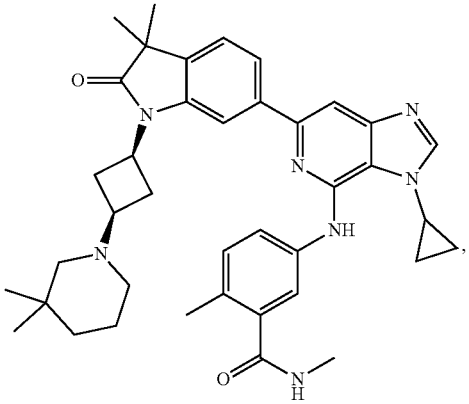
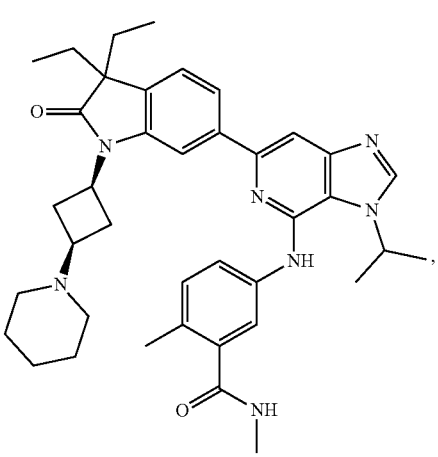

97
-continued
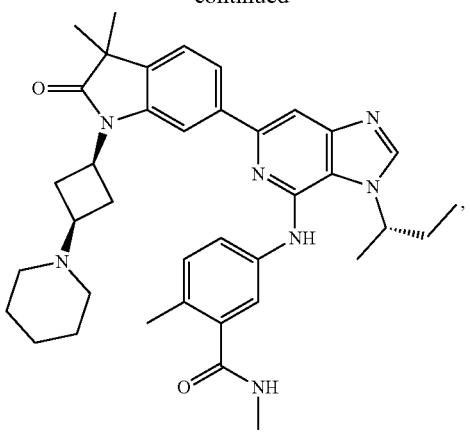
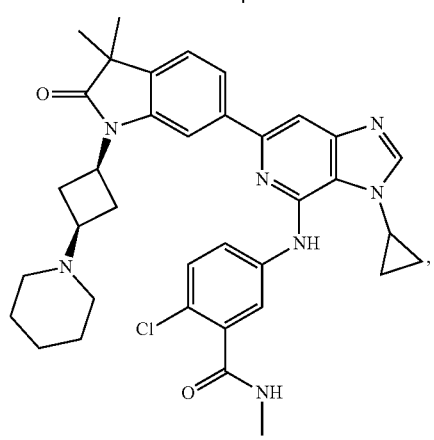
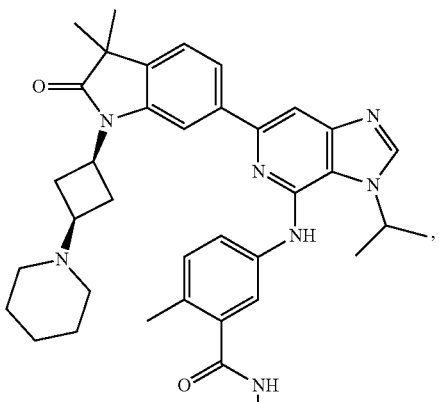
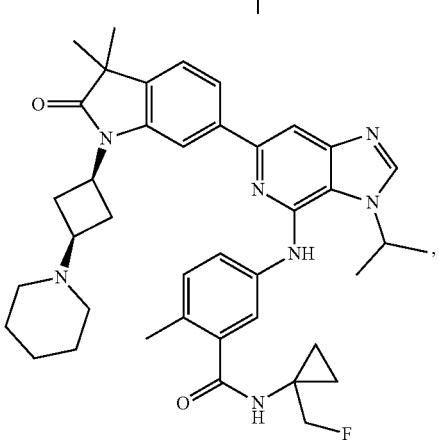
98
-continued
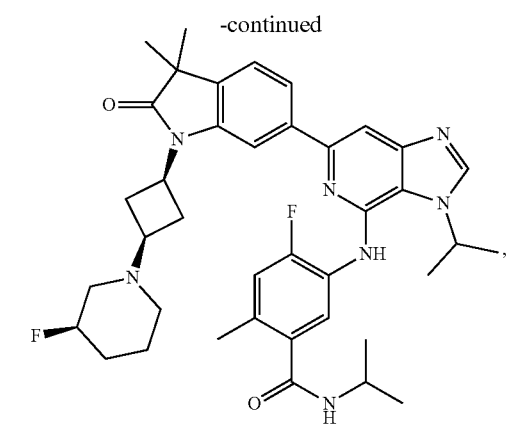
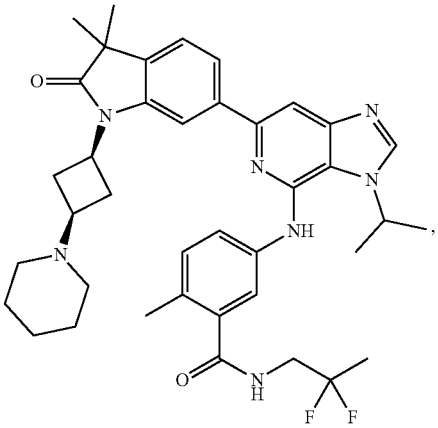
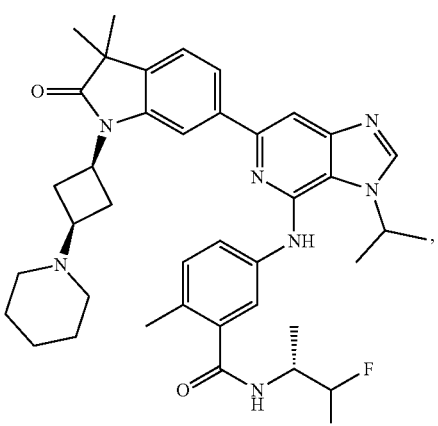
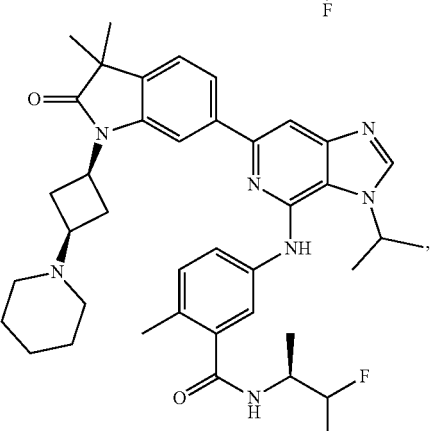

99
-continued
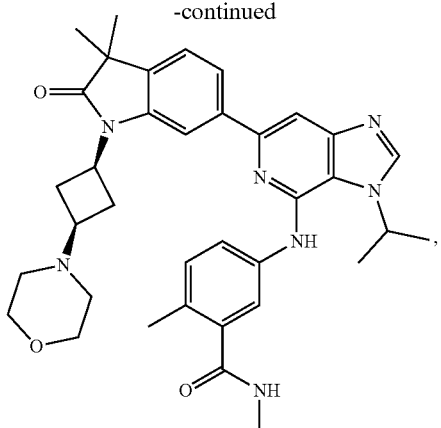
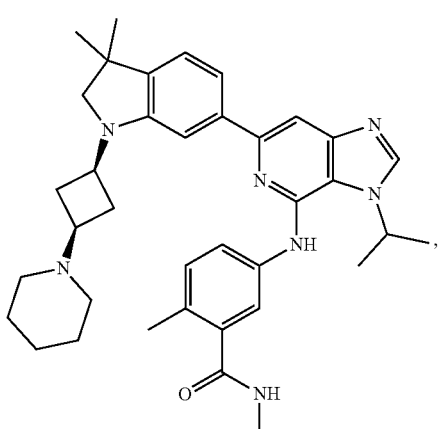
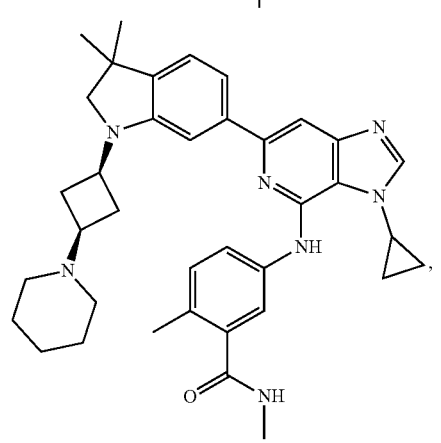
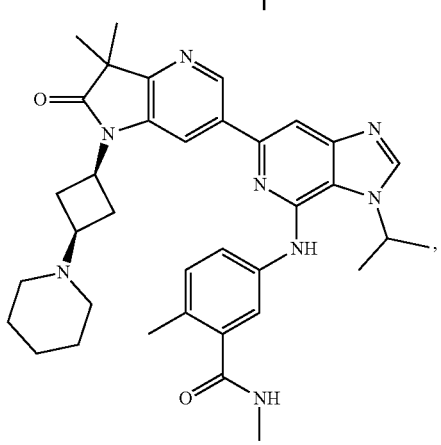
100
-continued
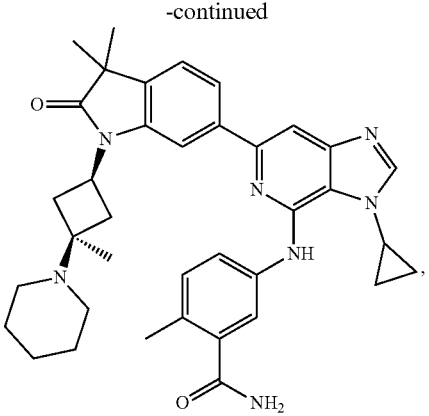
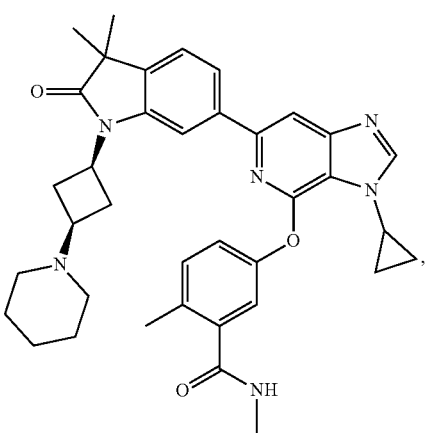
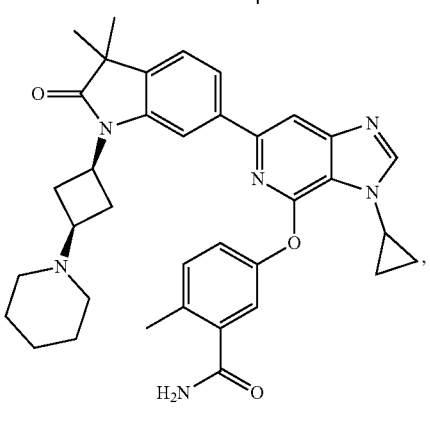
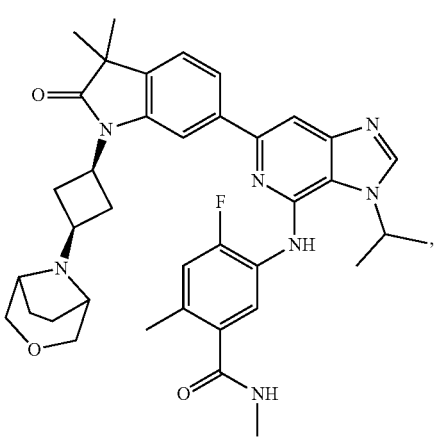

101
-continued
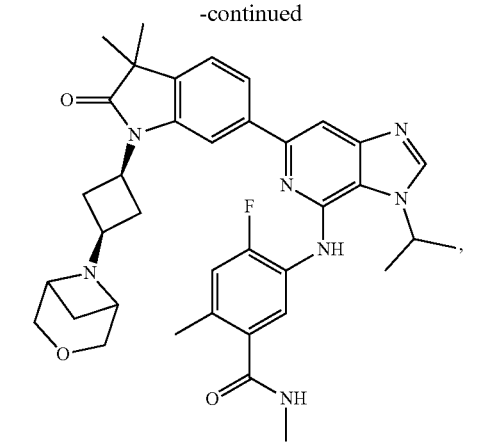
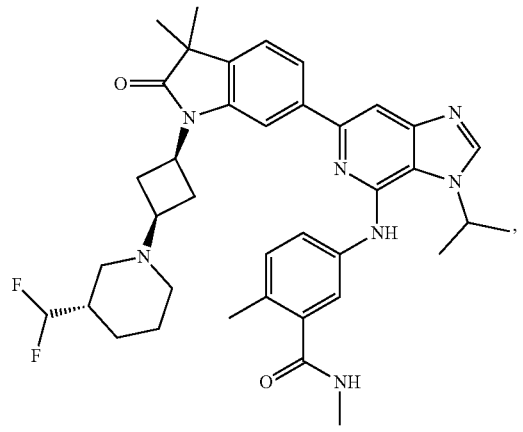
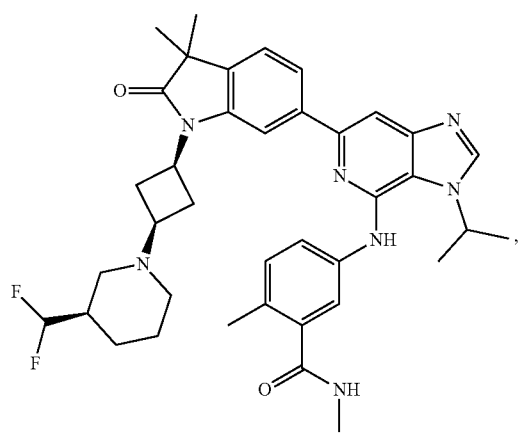
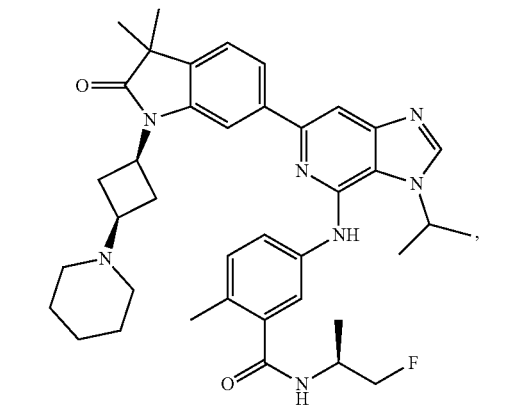
102
-continued
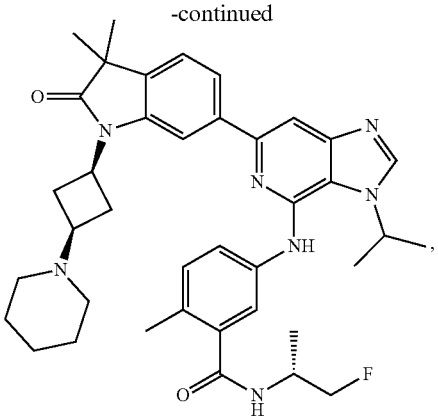
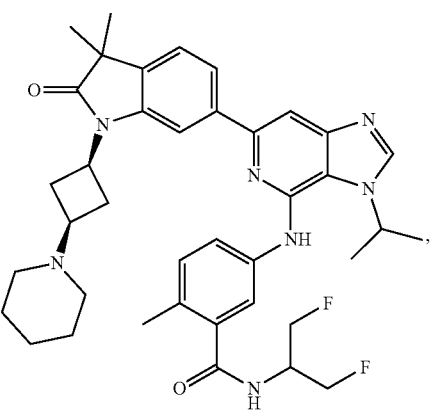
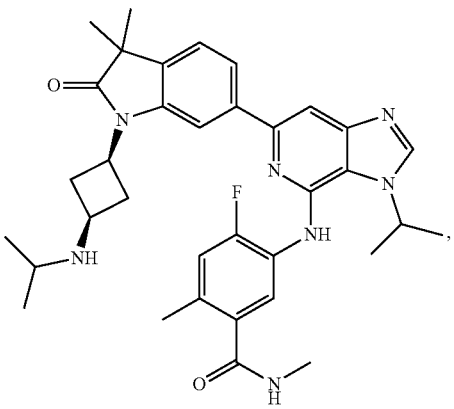
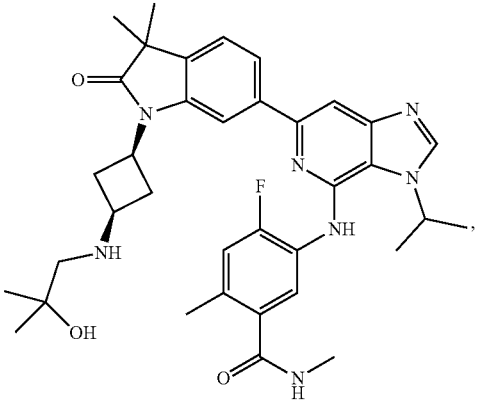

103
-continued
104
-continued
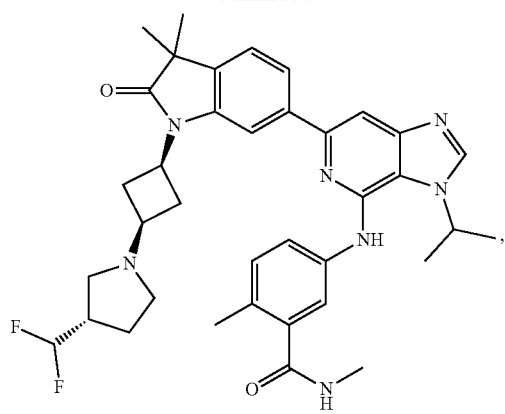
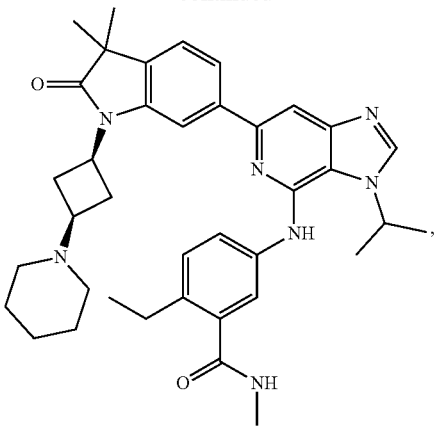

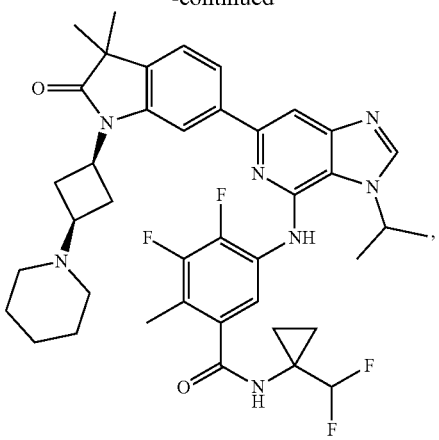
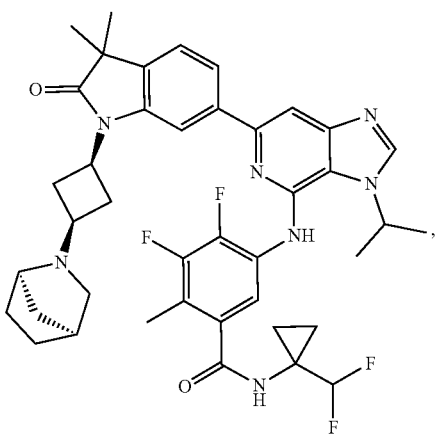
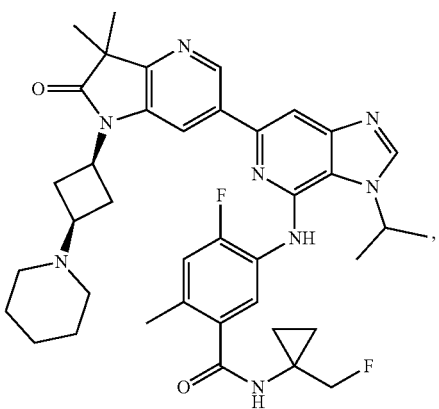
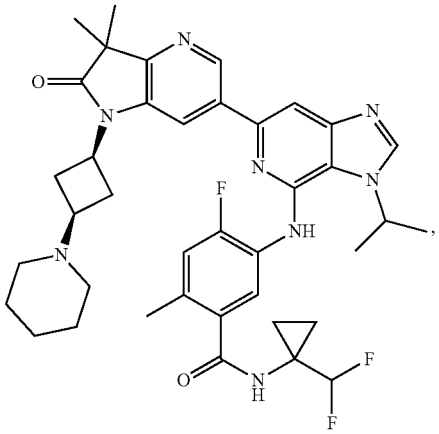
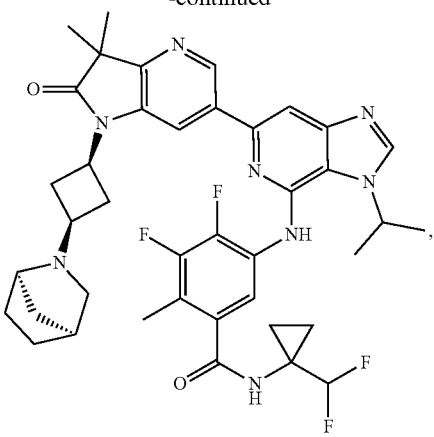
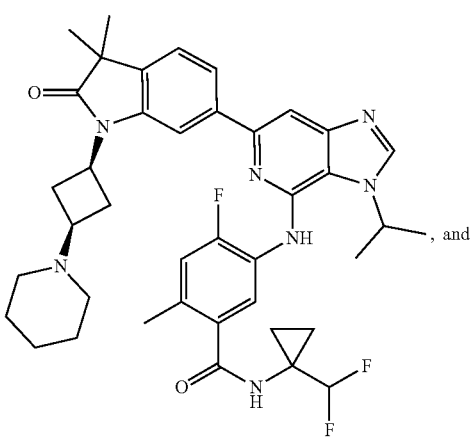
, and
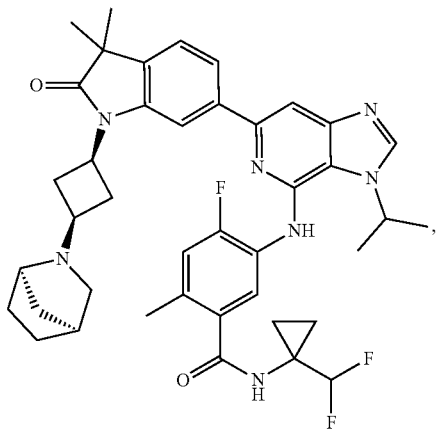
or a pharmaceutically acceptable salt thereof.
In some embodiments of the compound of Formula I, II, IIa, III, or IV, the compound is selected from the group consisting of:

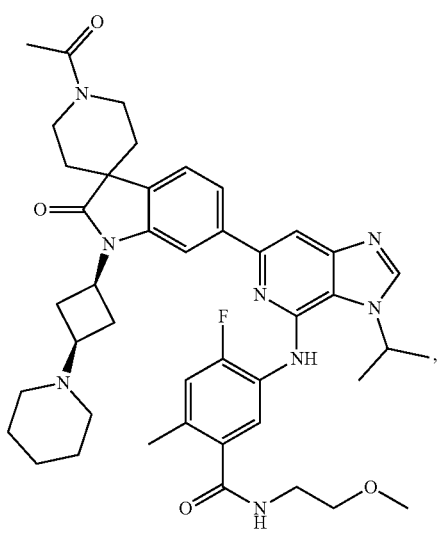
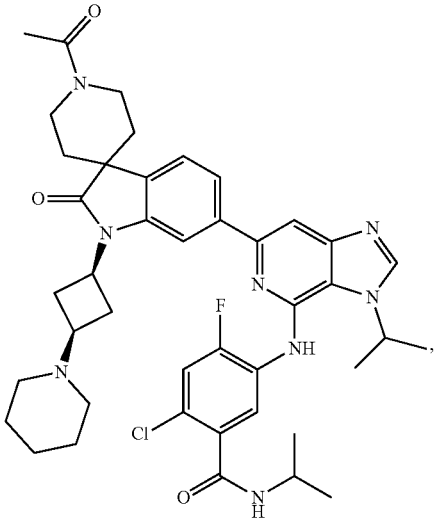
-continued
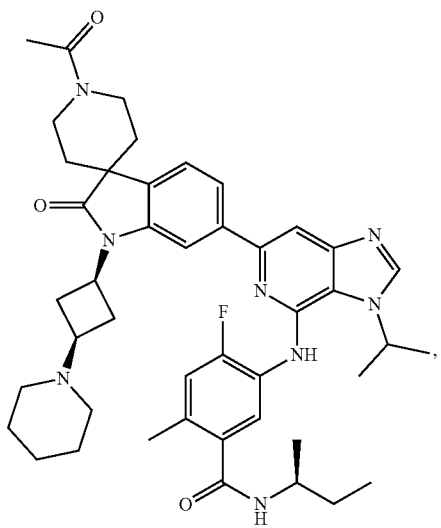
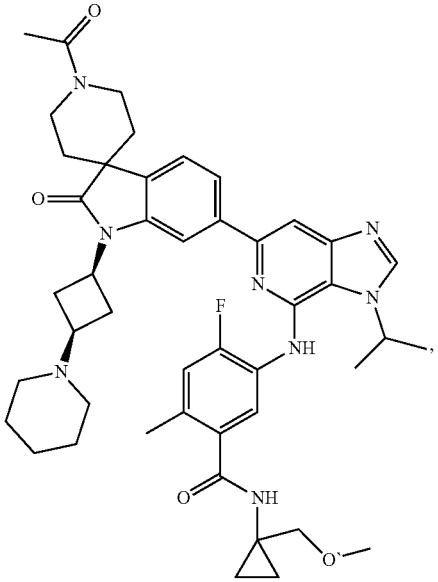

109
-continued
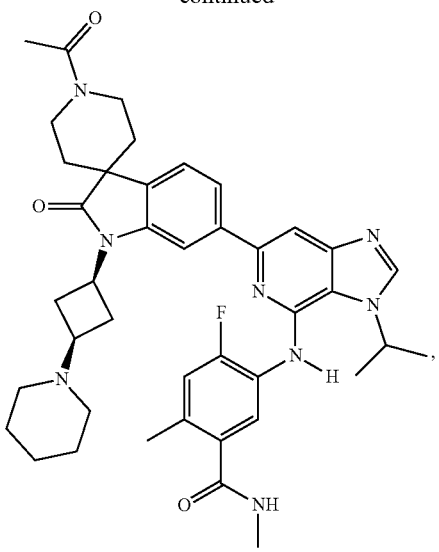
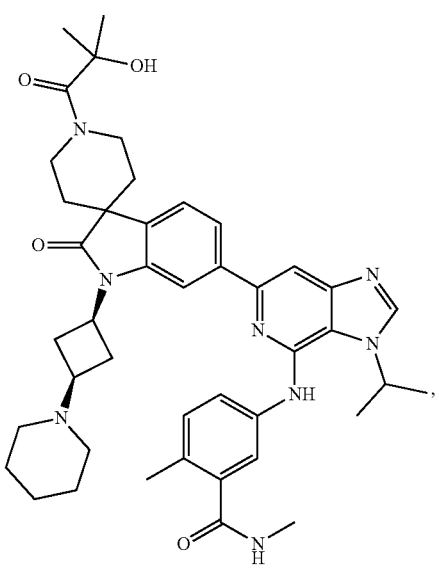
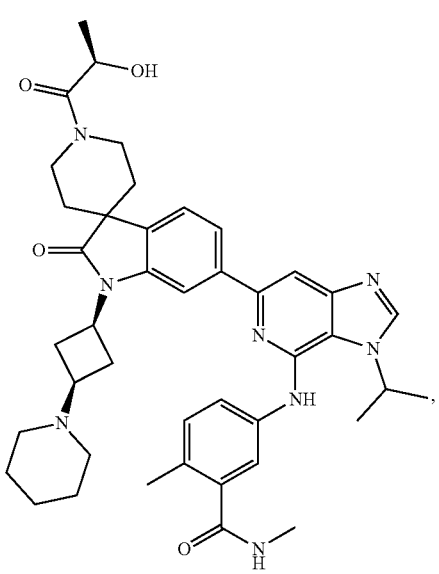
110
-continued
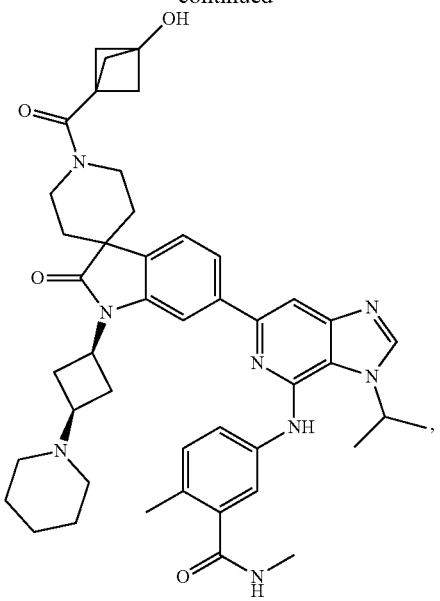
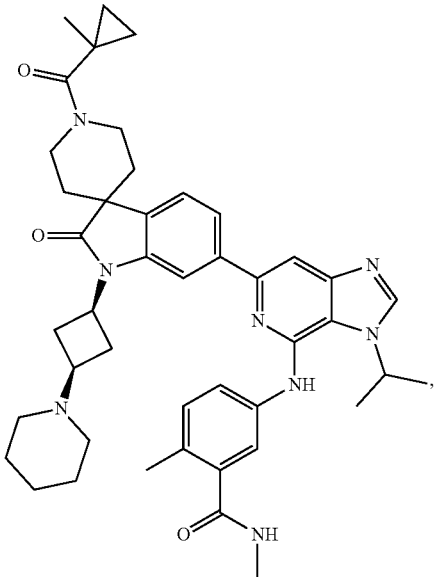

-continued
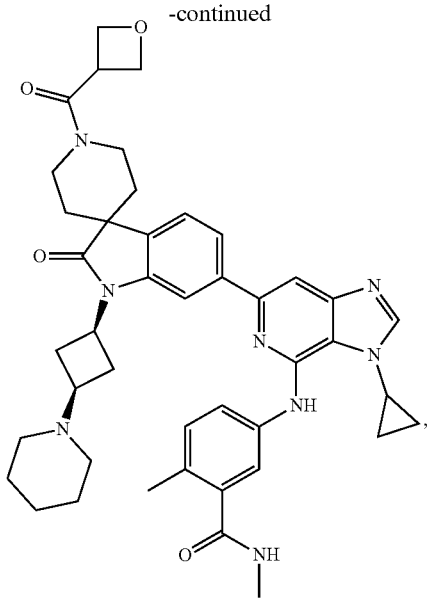
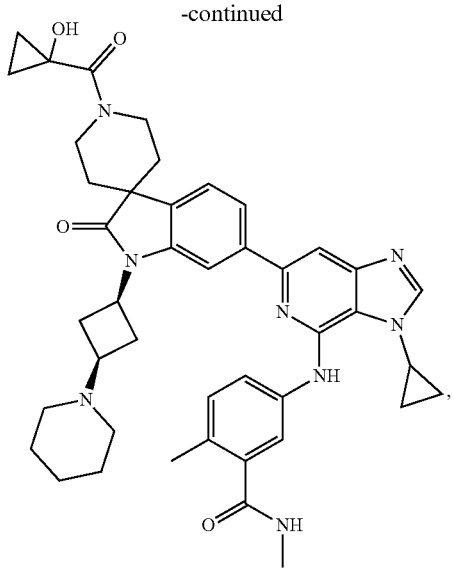
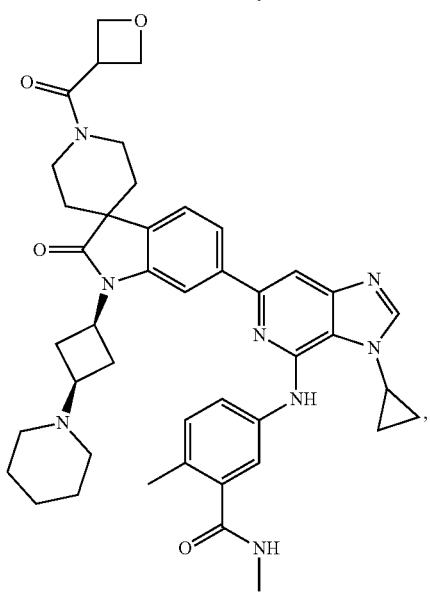
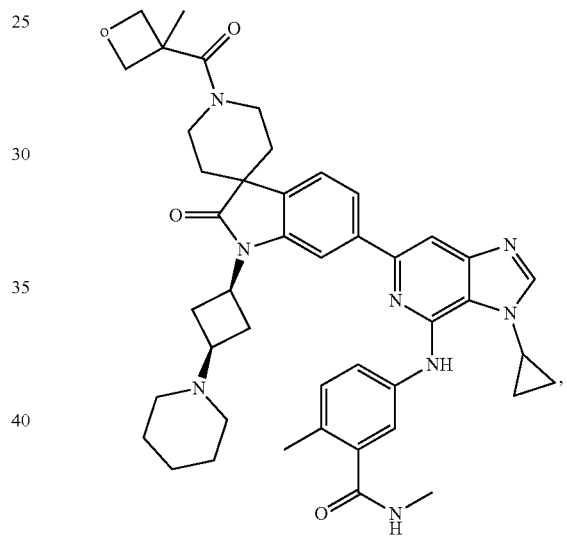
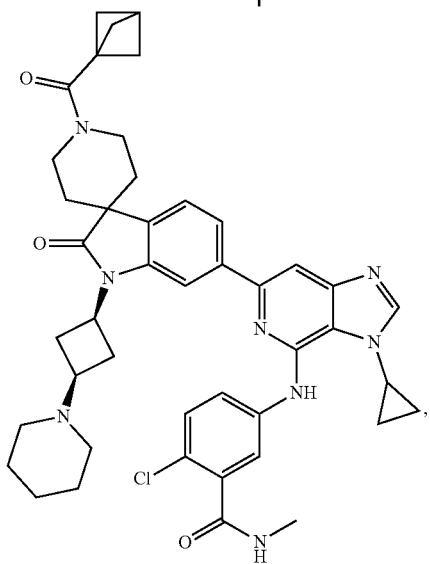
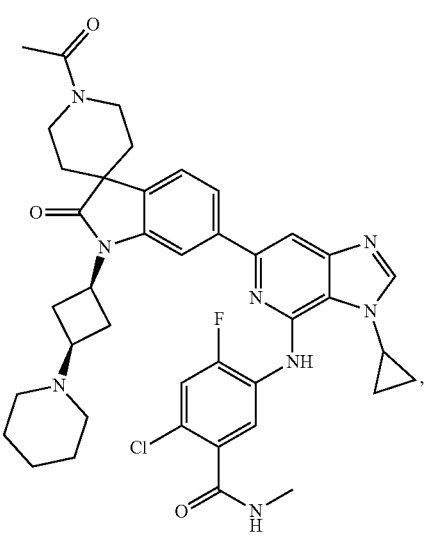

113
-continued
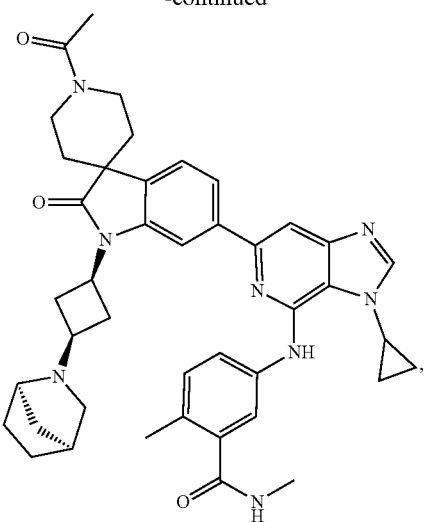
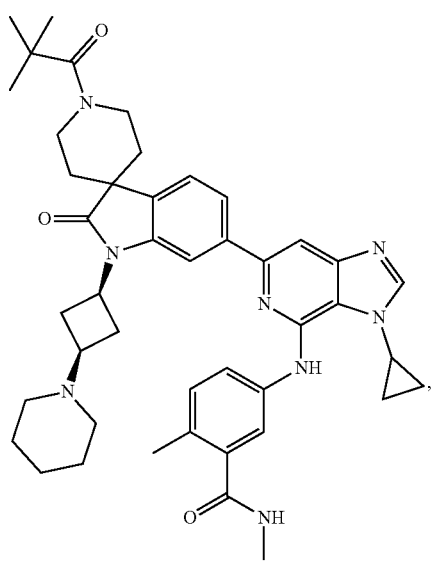
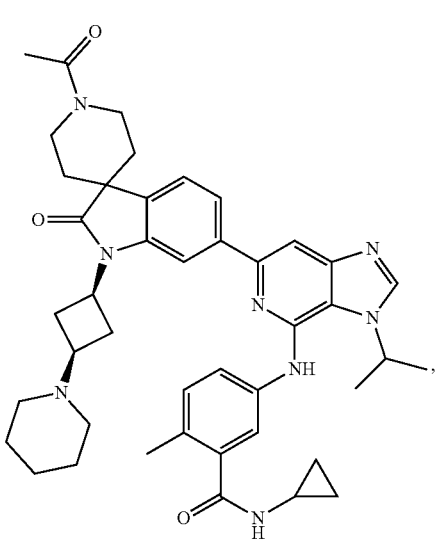
114
-continued
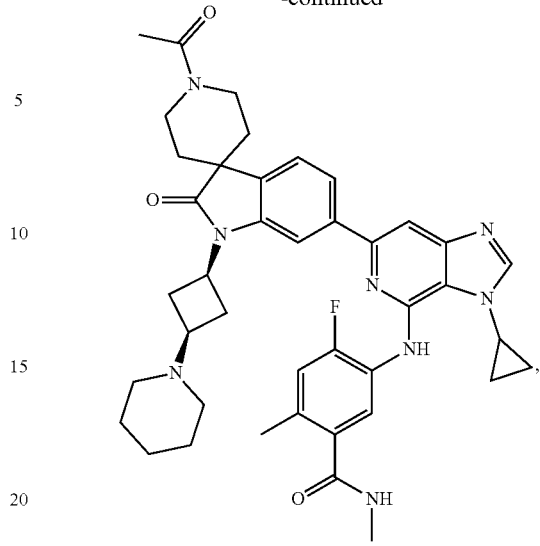
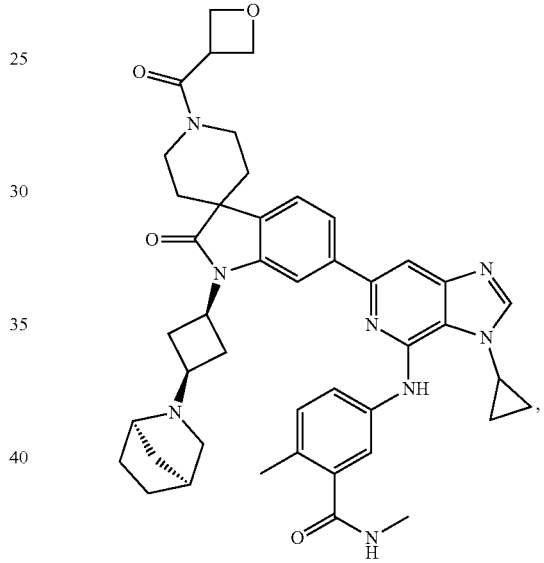
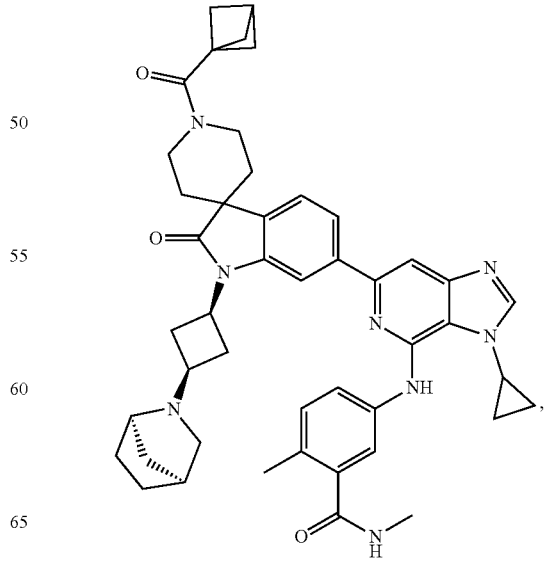

115
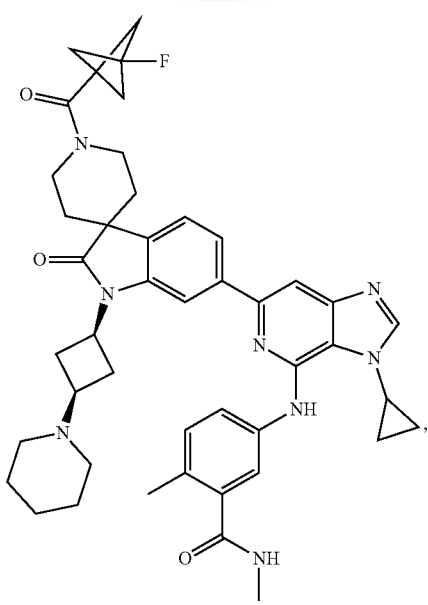
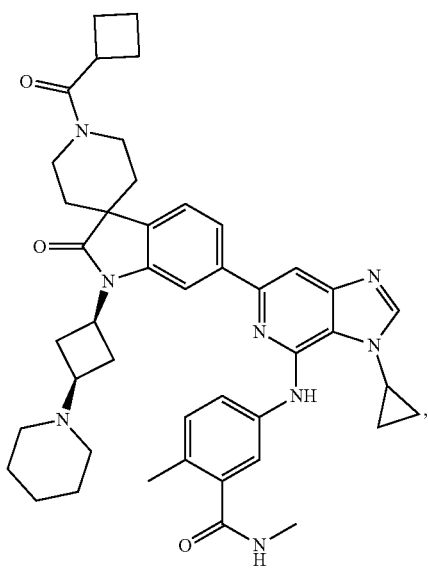
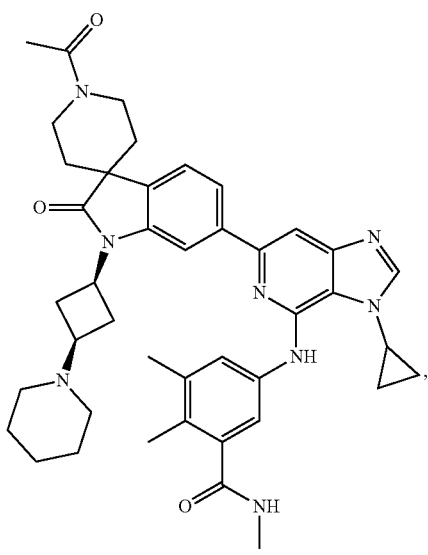
116
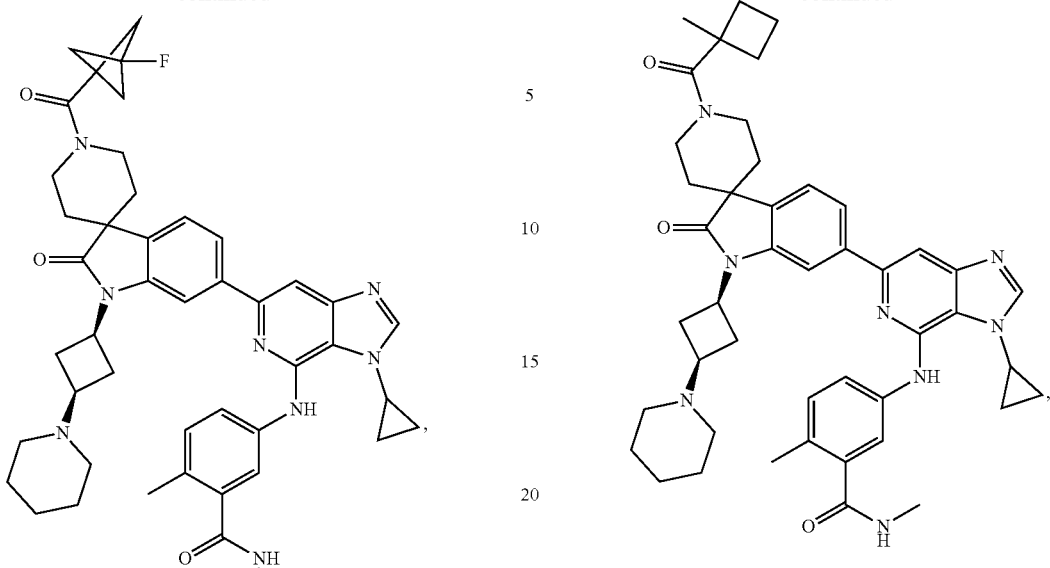
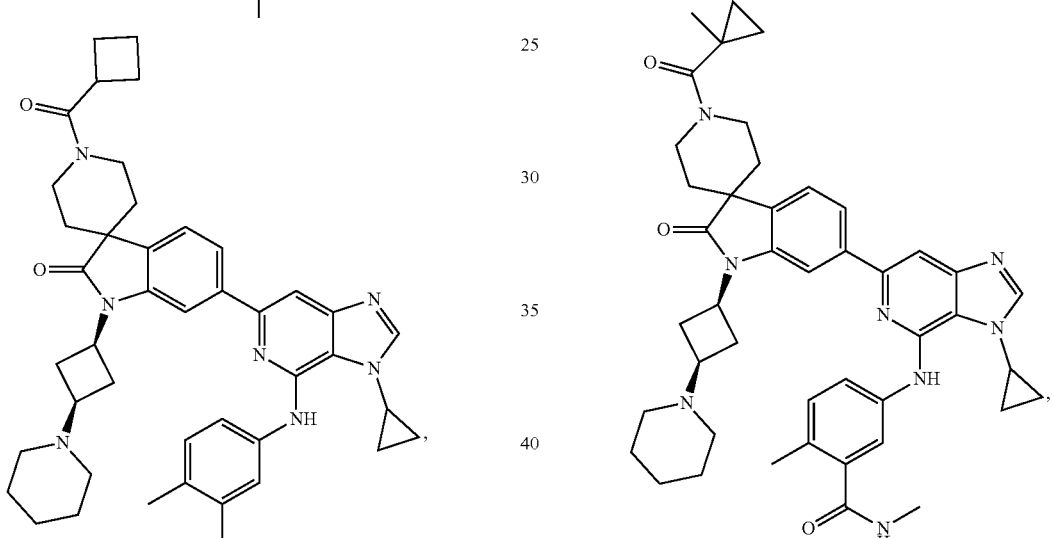
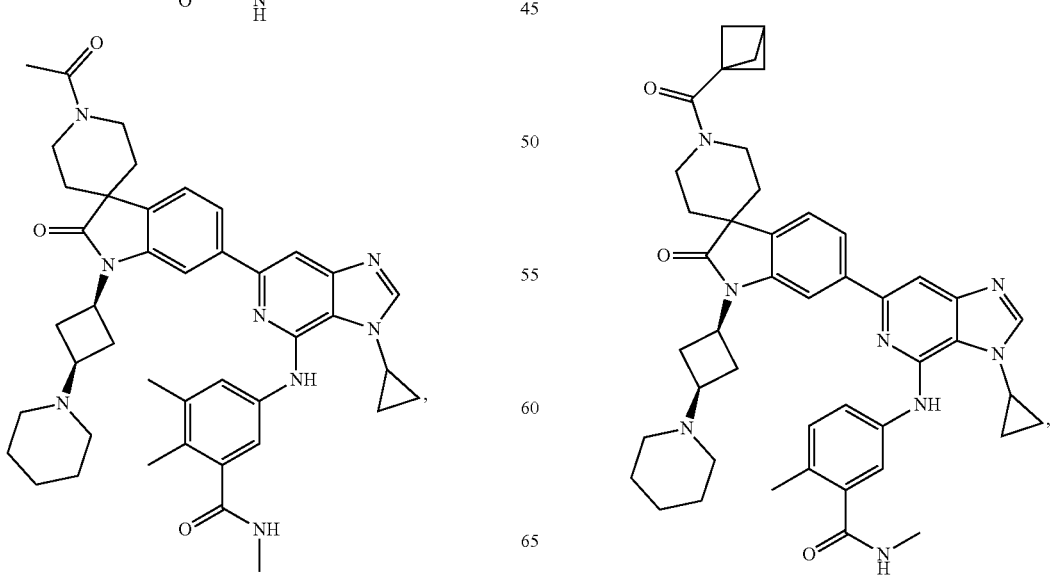

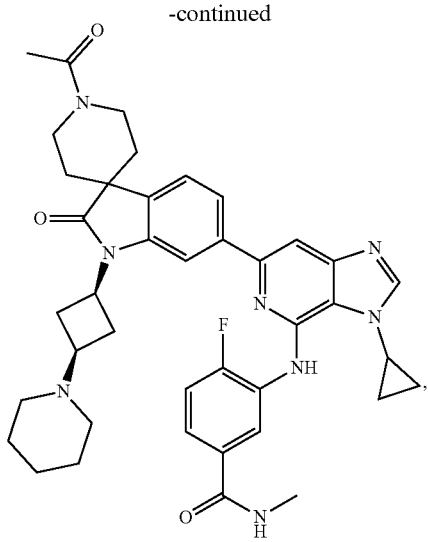
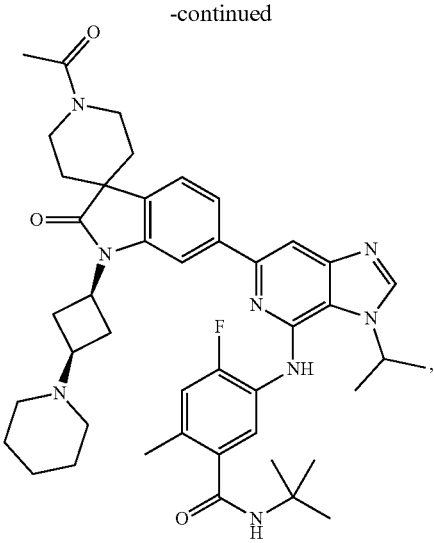
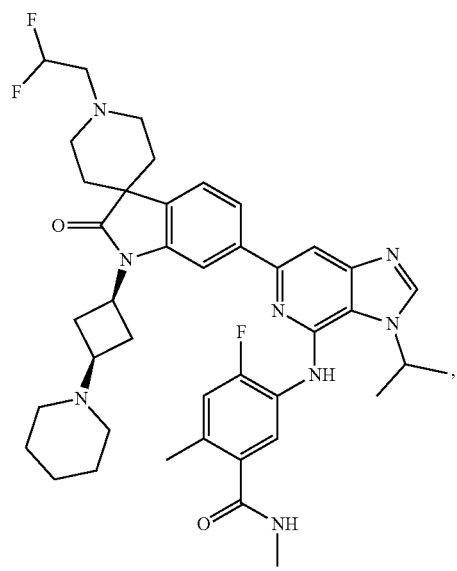
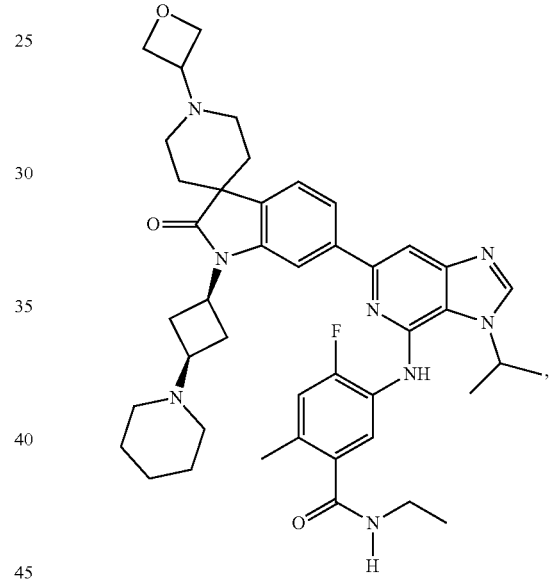
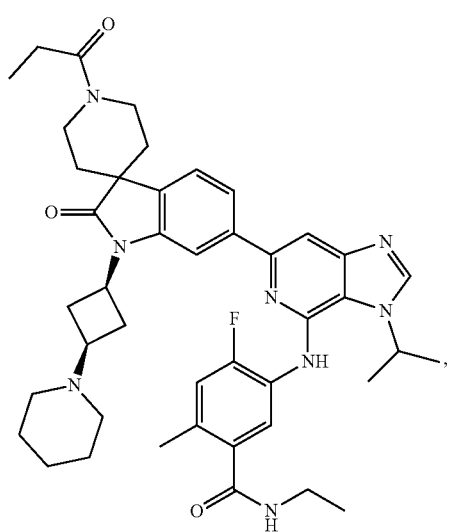
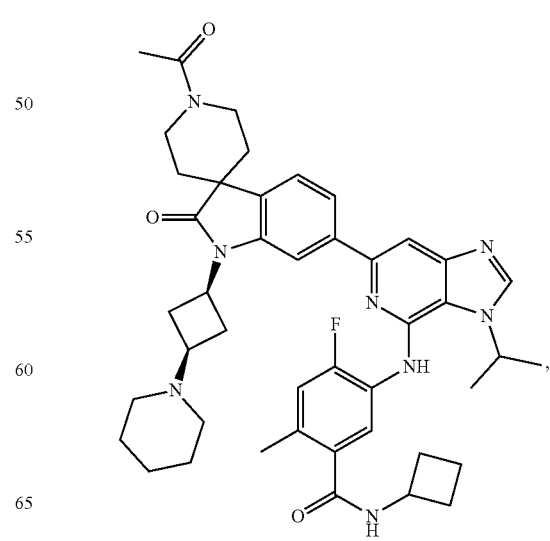

119
-continued
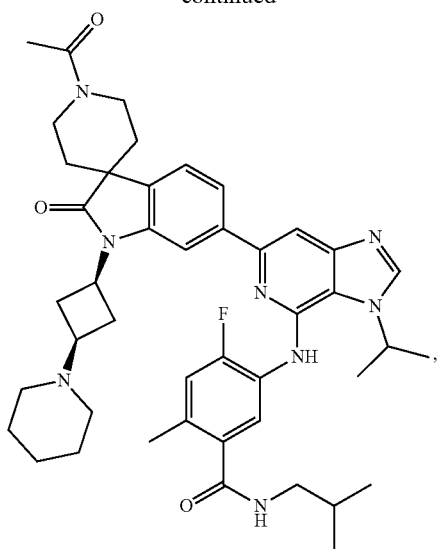
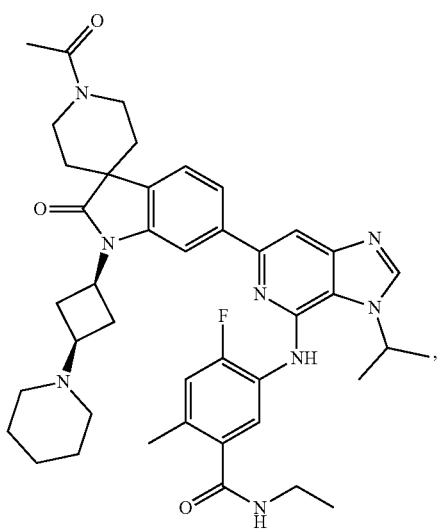
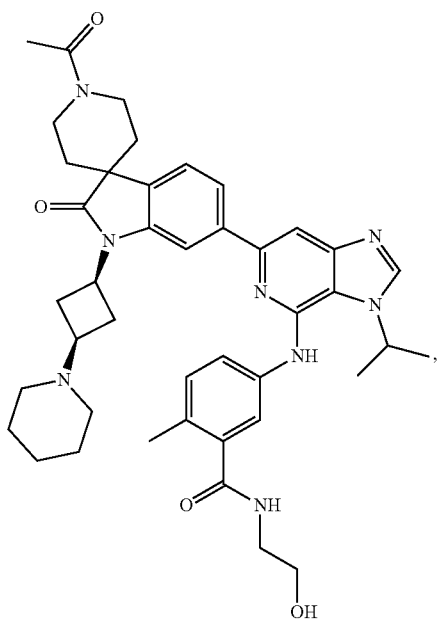
120
-continued
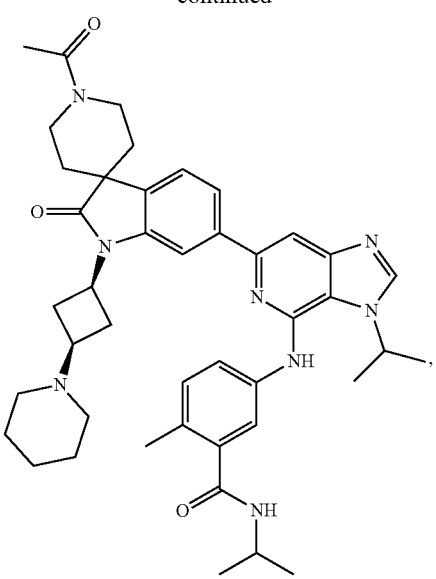
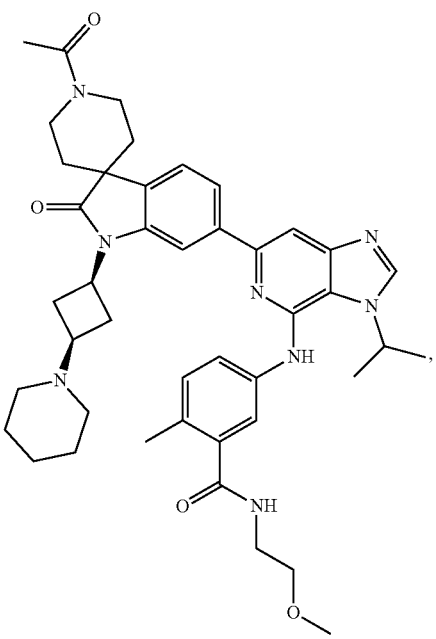

121
-continued
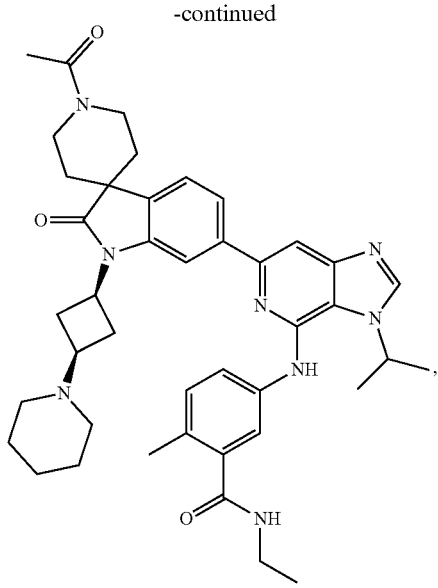
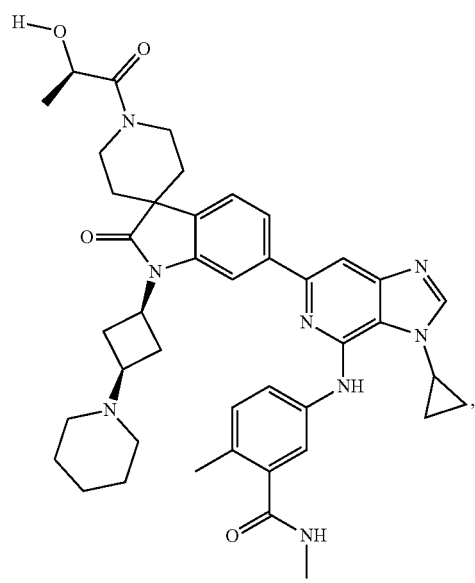
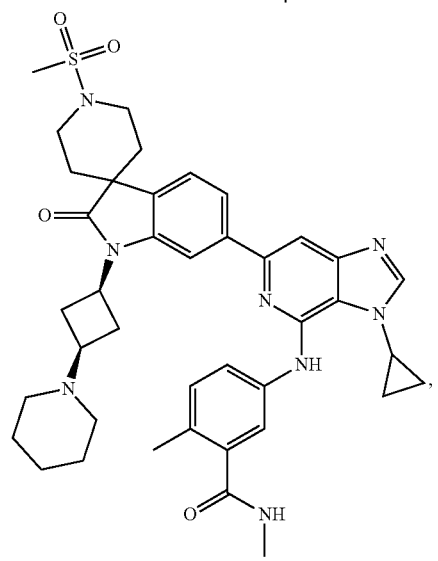
122
-continued
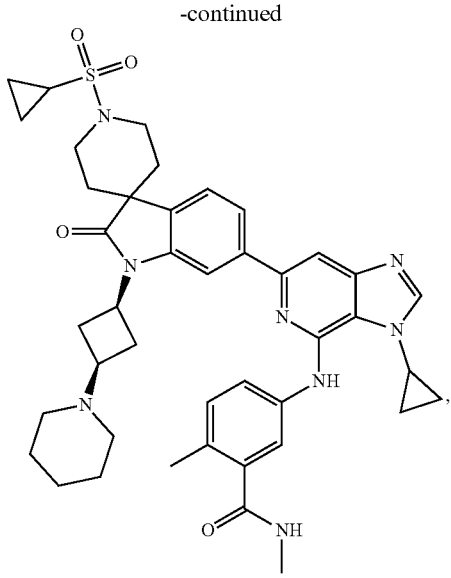
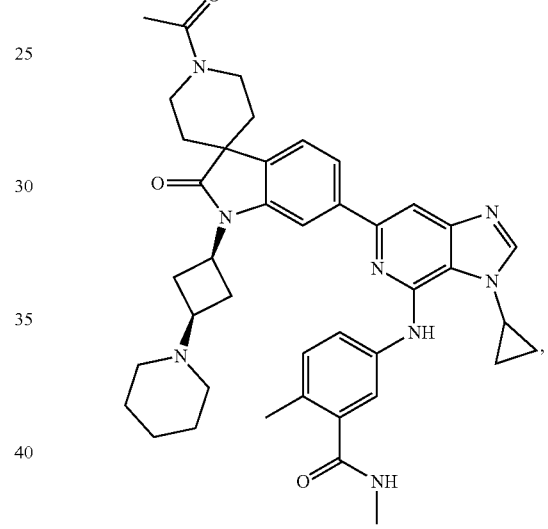
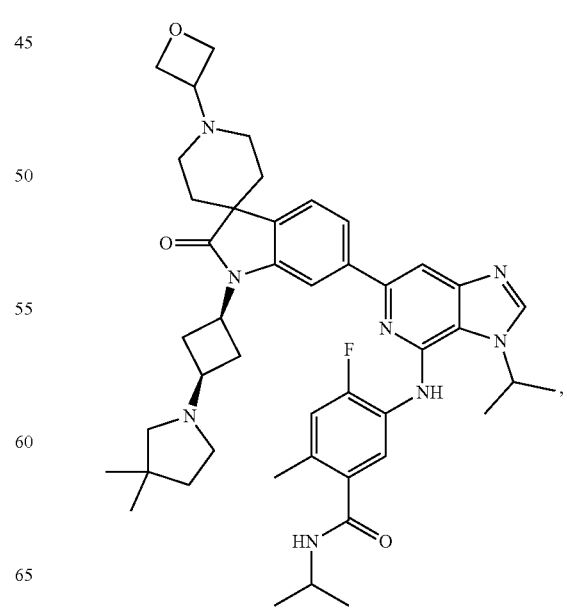

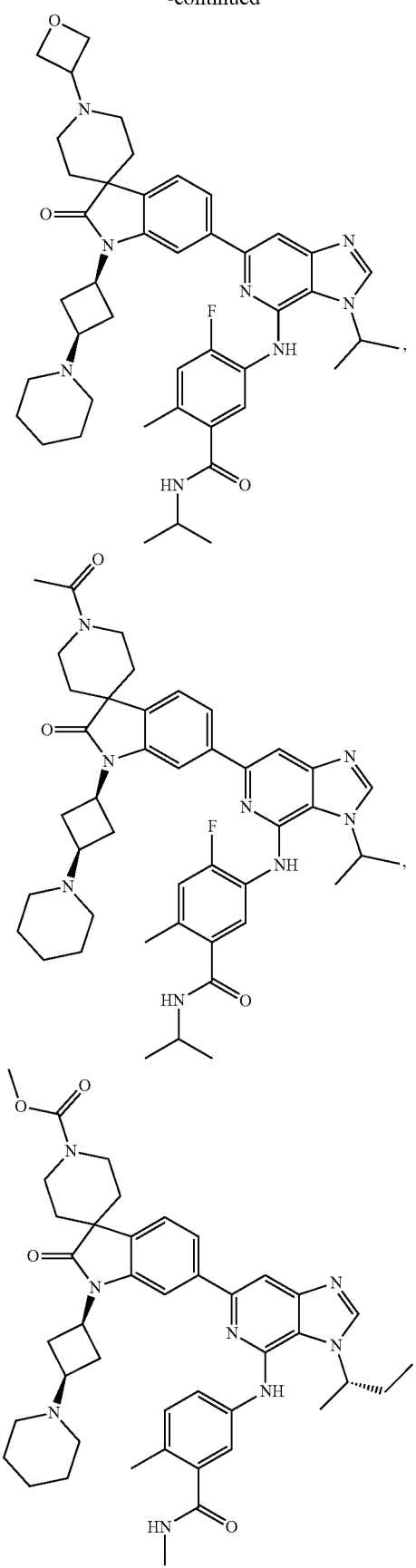
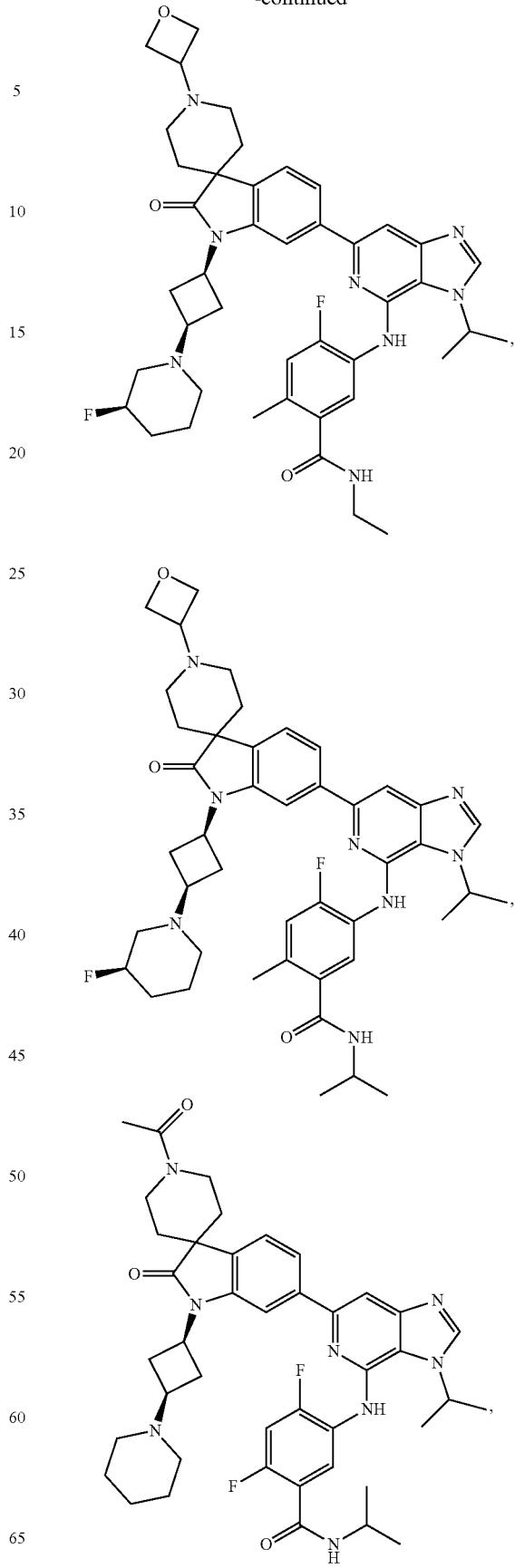

125
-continued
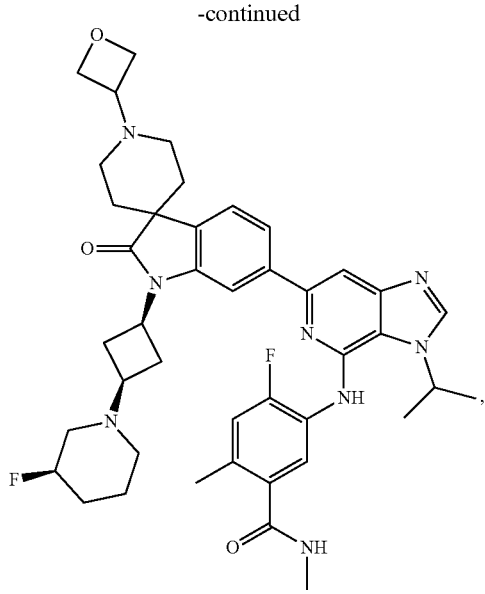
126
-continued
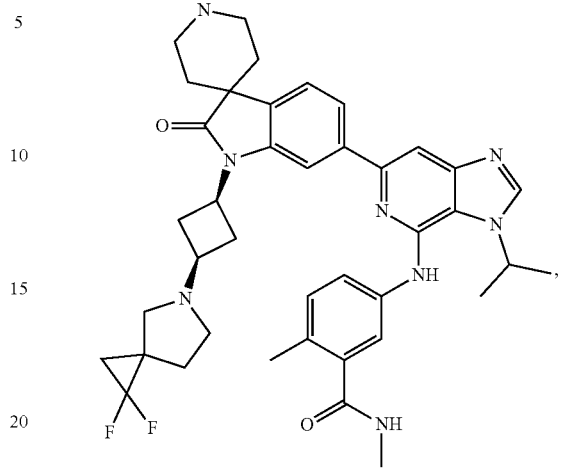
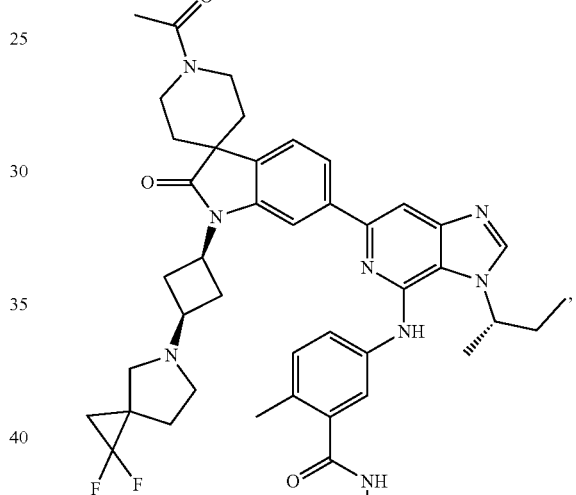
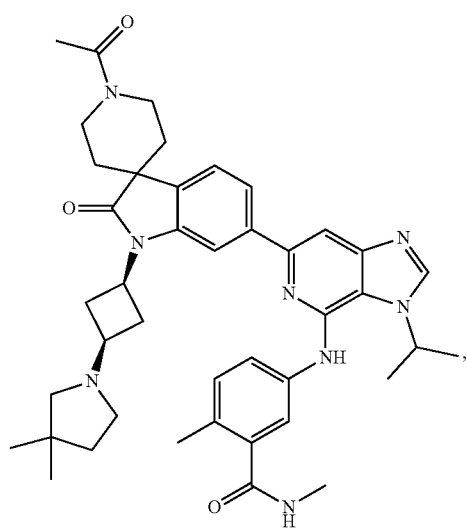
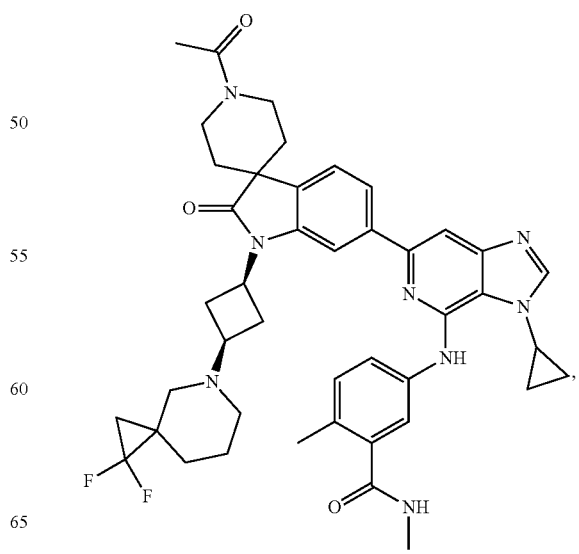

127
-continued
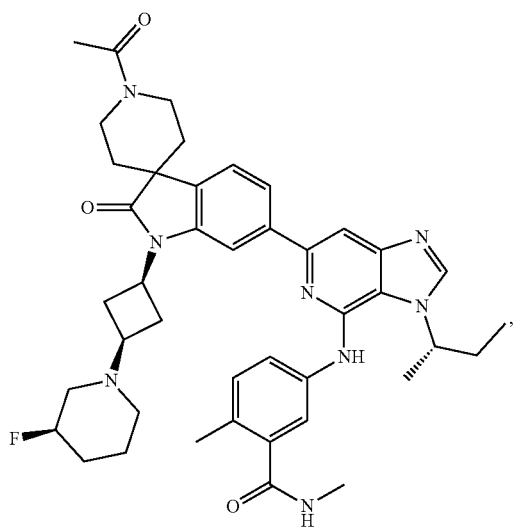
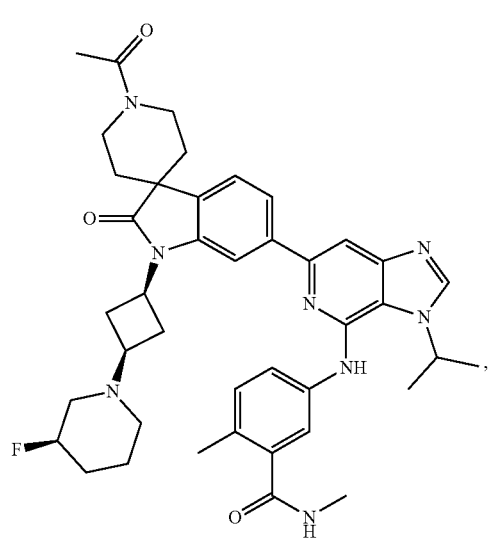
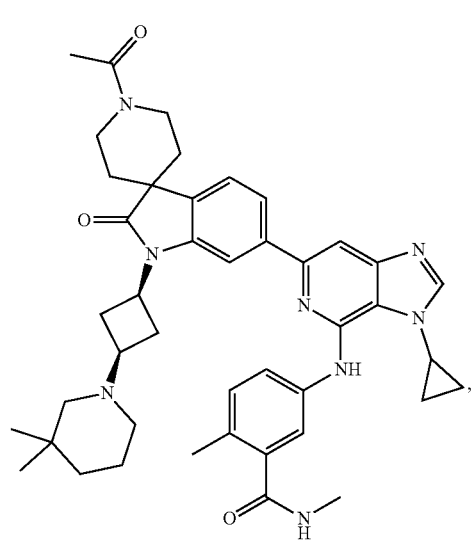
128
-continued
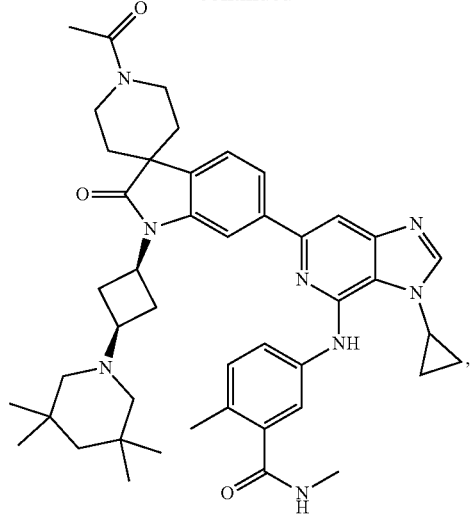
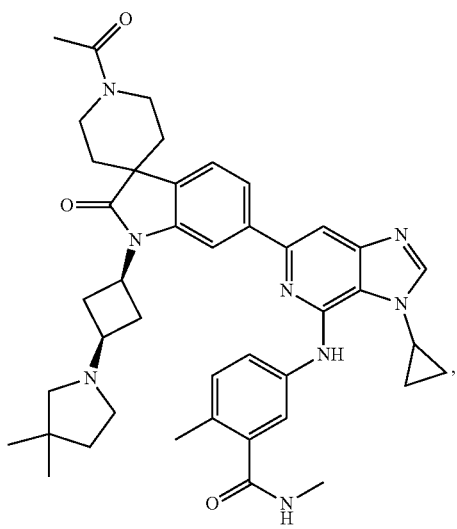
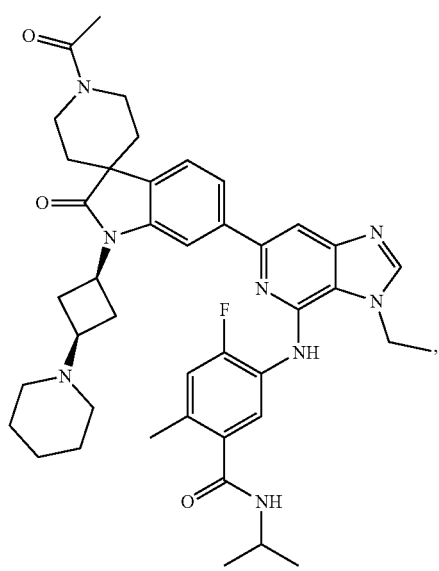

129
-continued
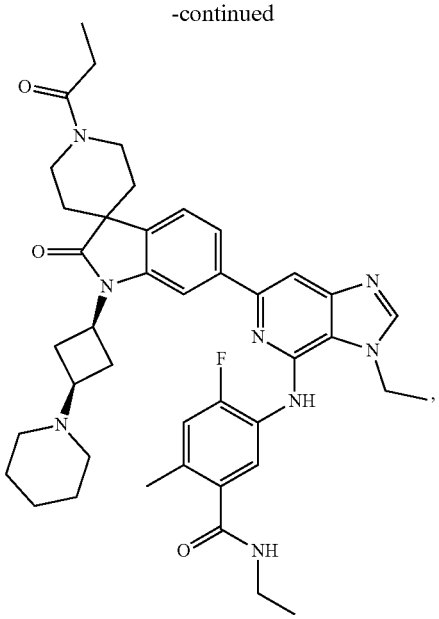
130
-continued
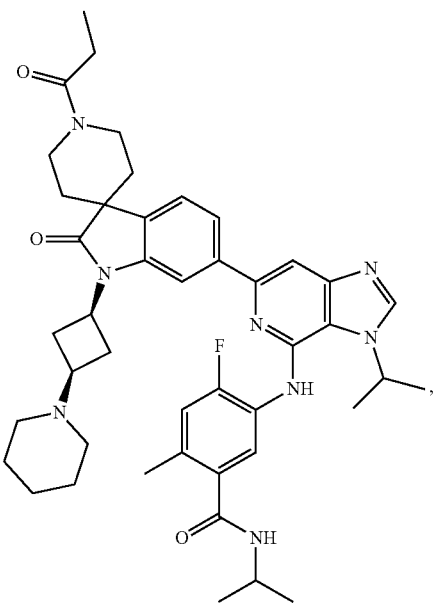
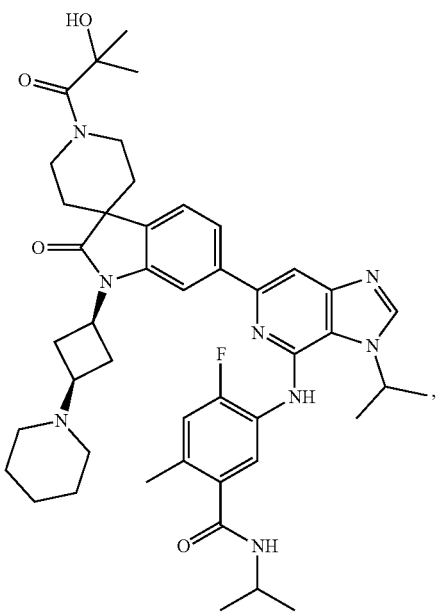

131
-continued
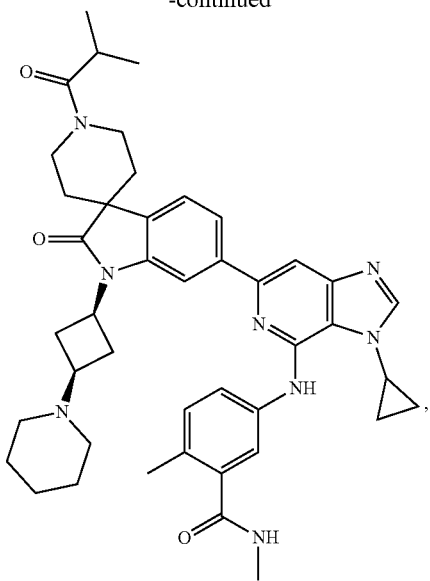
132
-continued
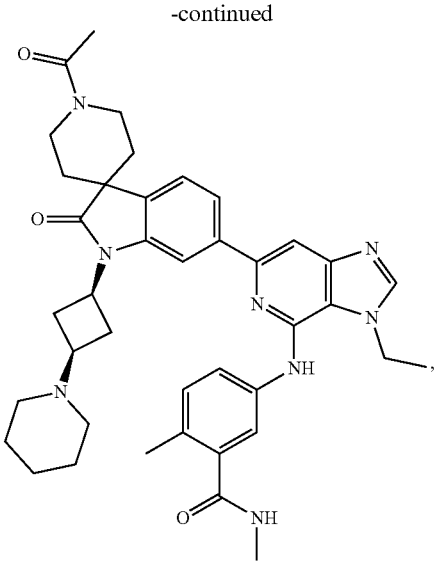
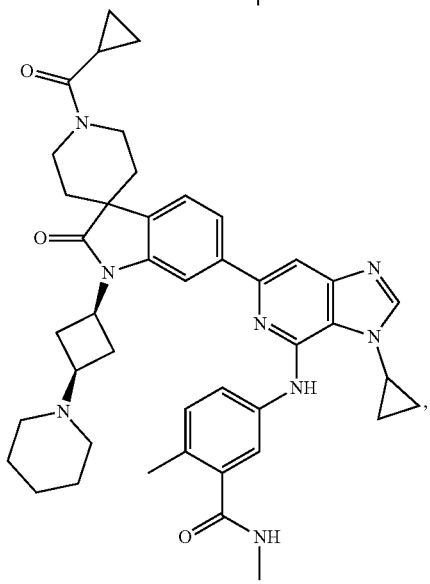
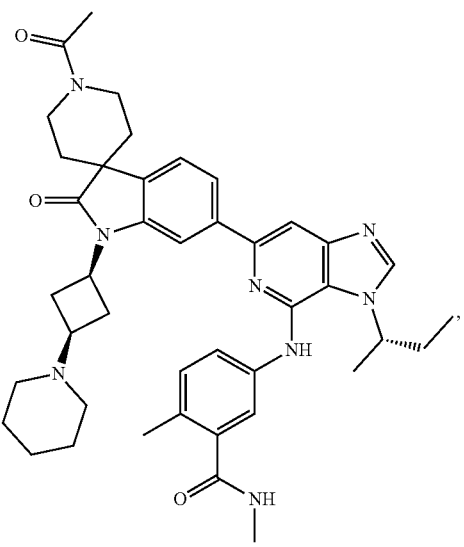
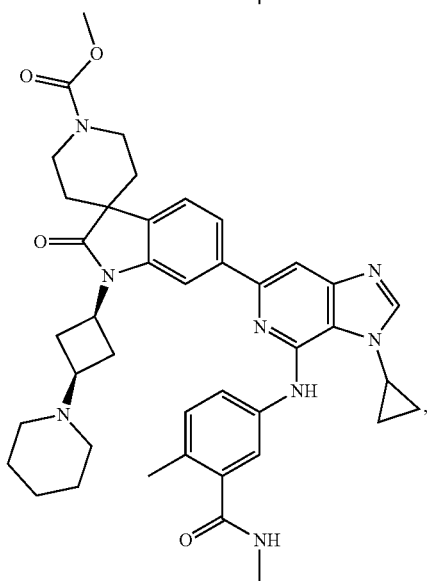
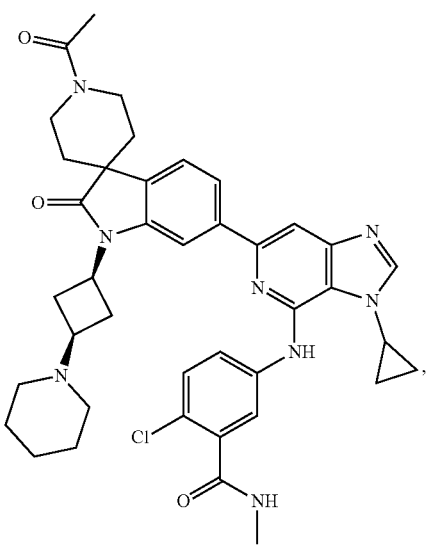

133
-continued
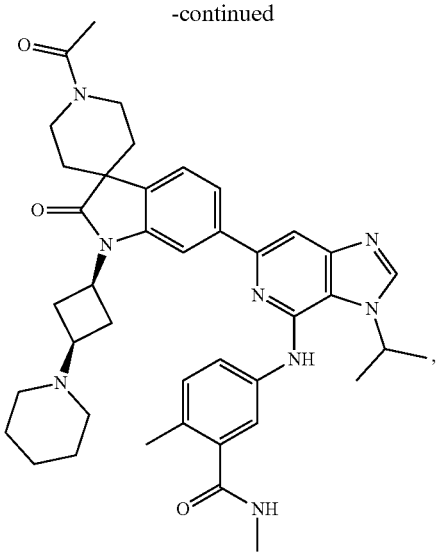
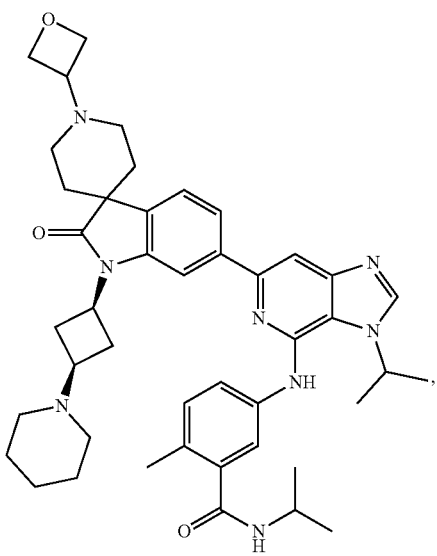
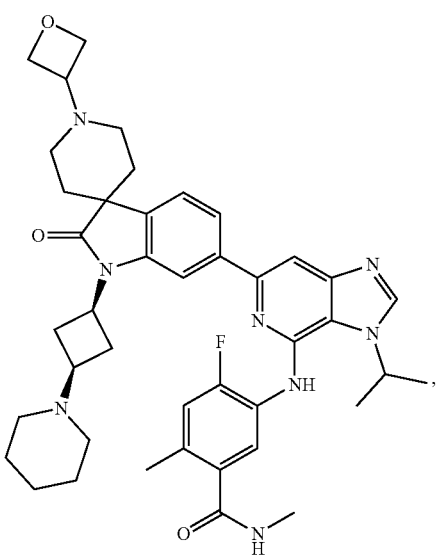
134
-continued
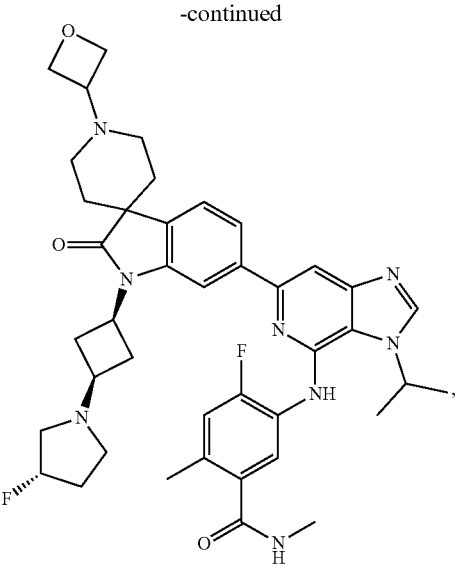
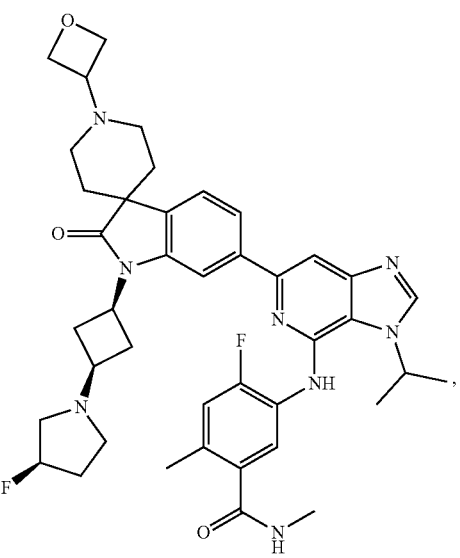
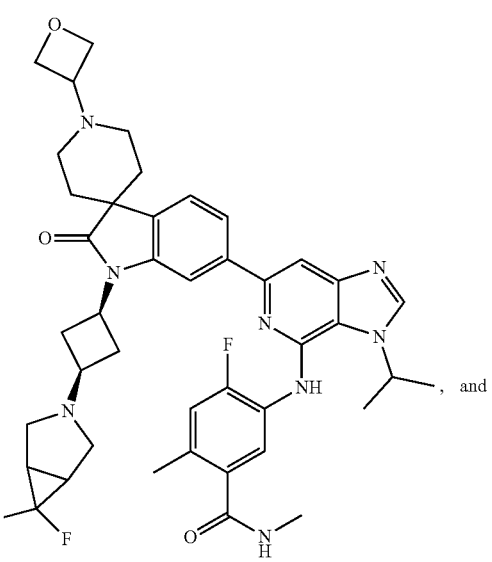
, and 135
-continued
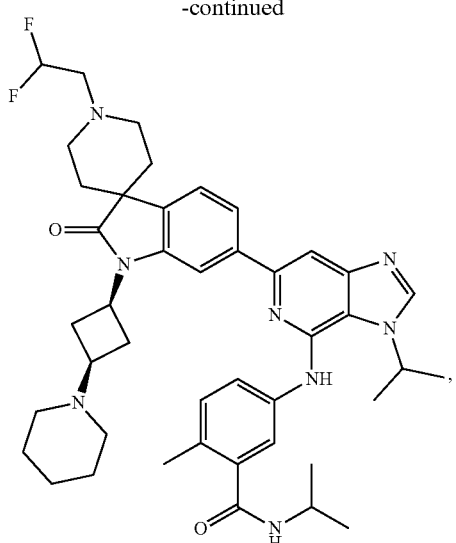
or a pharmaceutically acceptable salt thereof.
In some embodiments of the compound of Formula I, II, IIa, III, or IV, the compound is selected from the group consisting of:
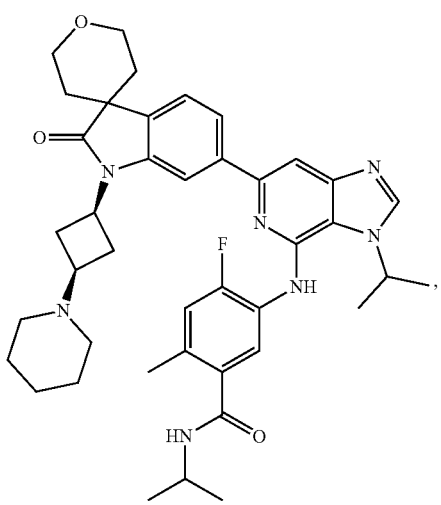
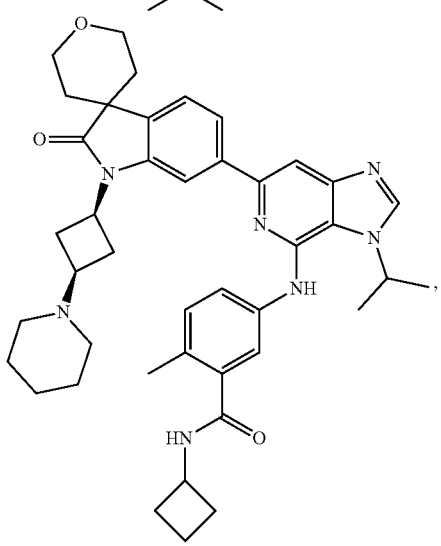
136
-continued
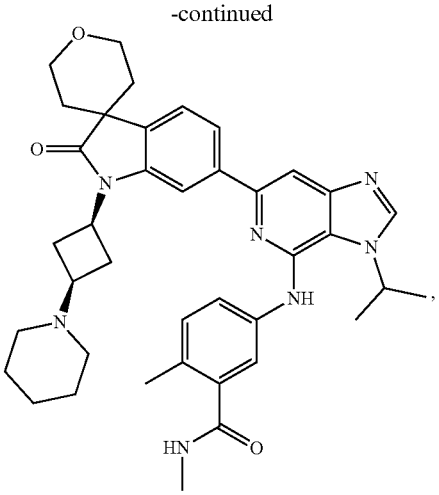
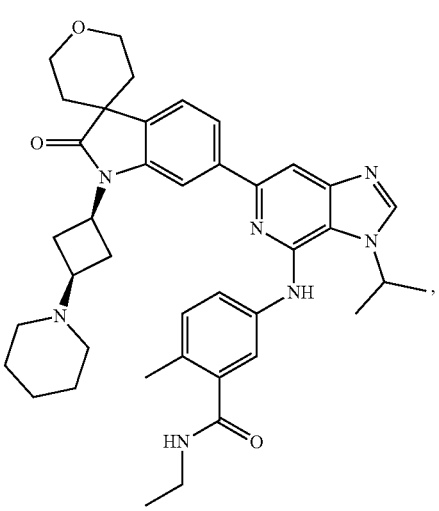
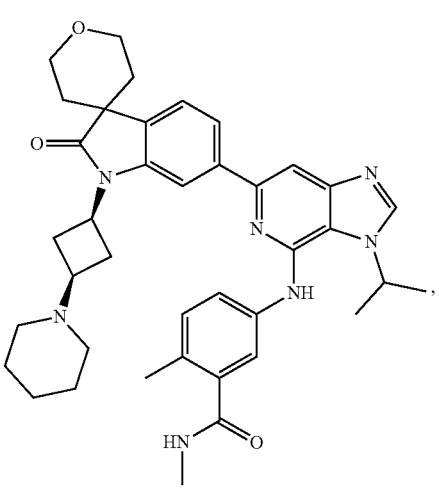

137
-continued
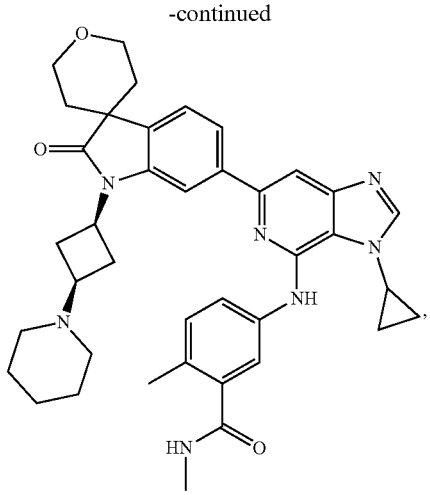
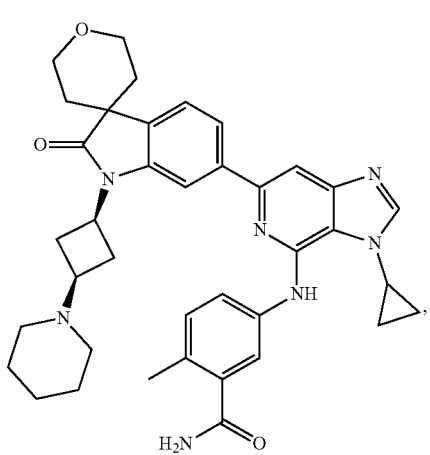
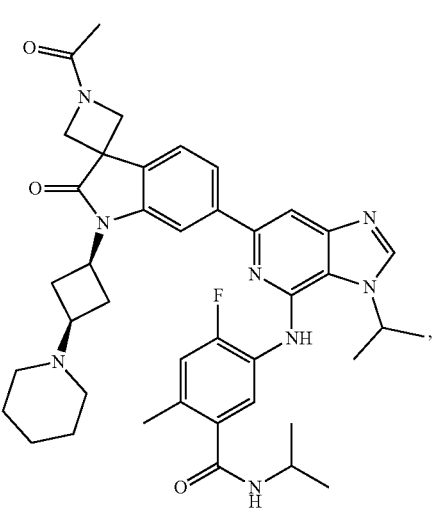
138
-continued
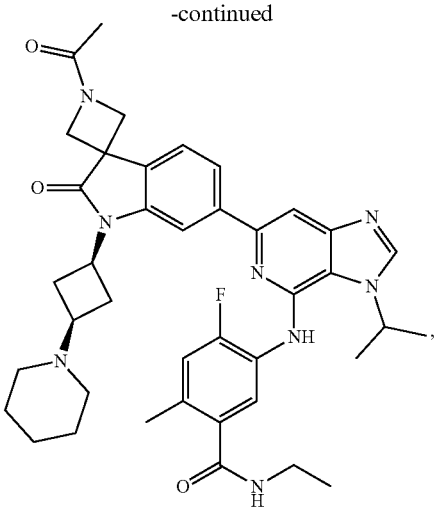
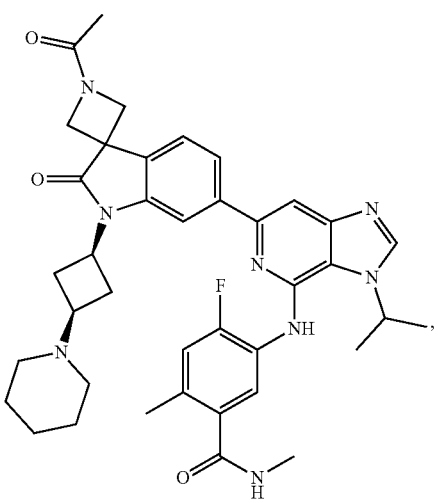
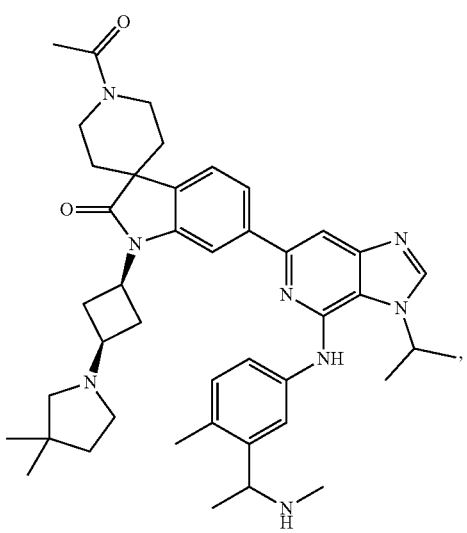

139
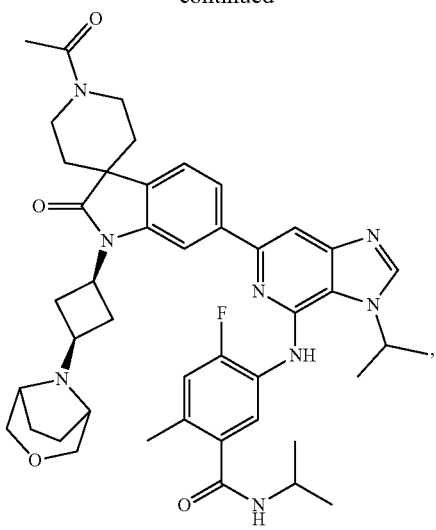
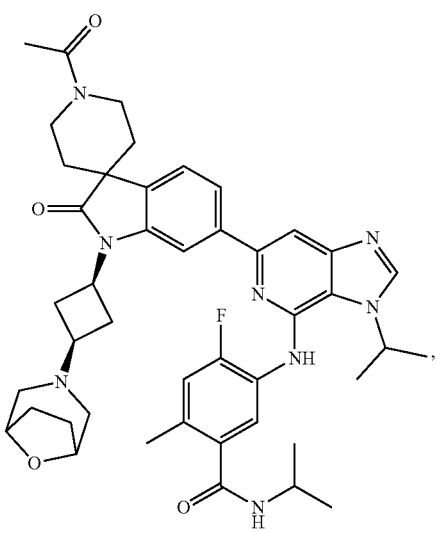
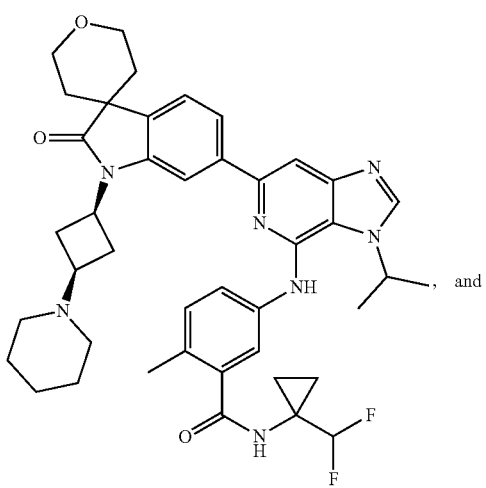
140
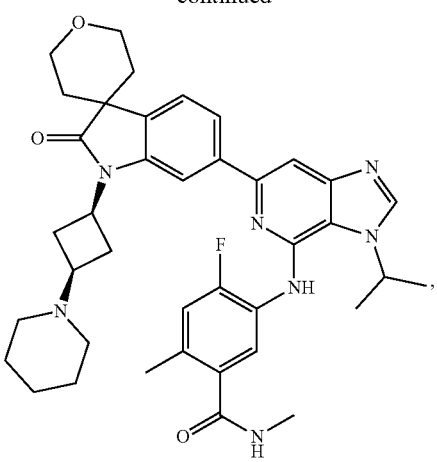
or a pharmaceutically acceptable salt thereof.
In some embodiments of the compounds of Formula I, II, IIa, IIb, III, or IIIa, the compound is:
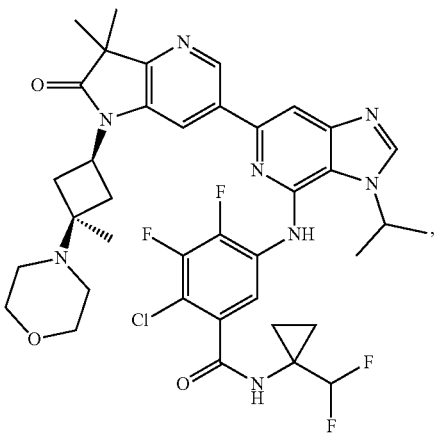
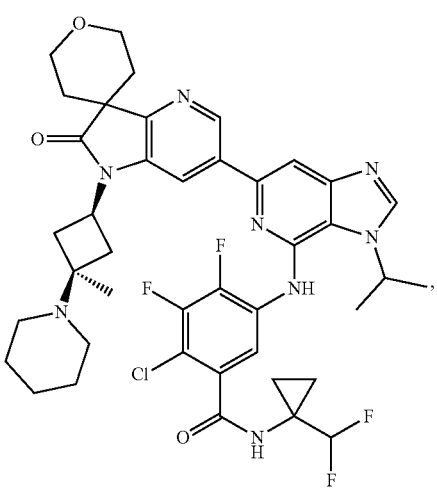

141
-continued
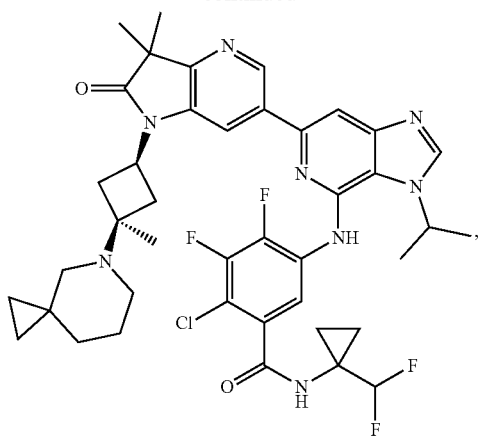
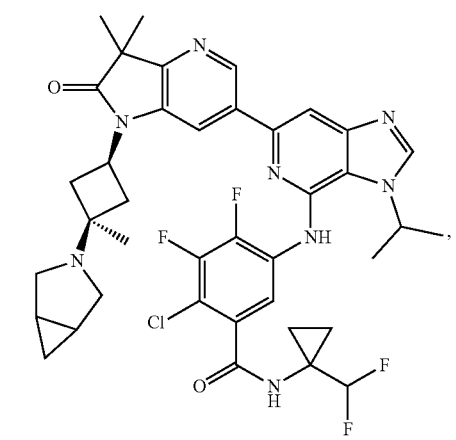
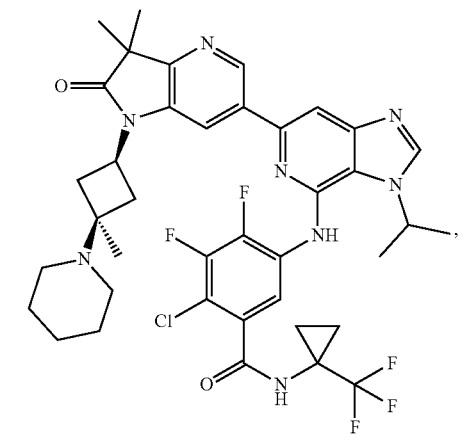
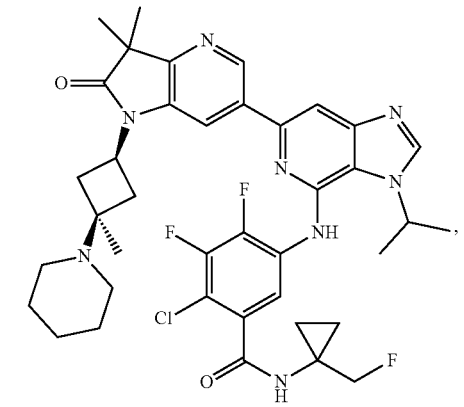
142
-continued
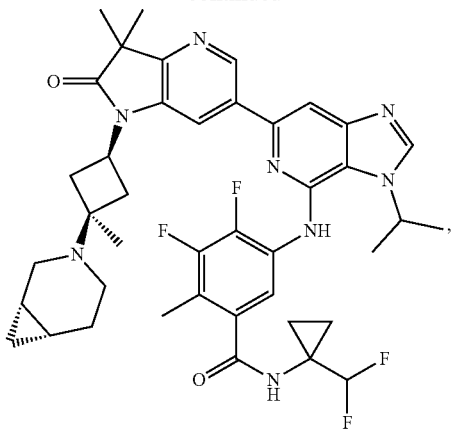
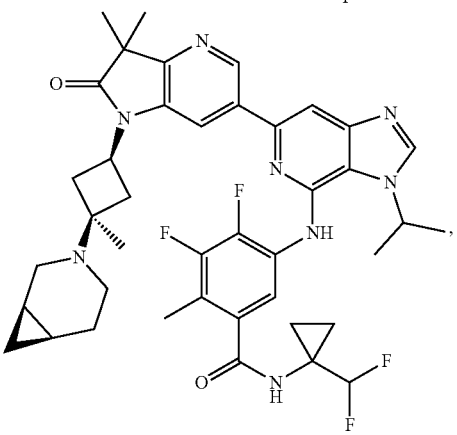
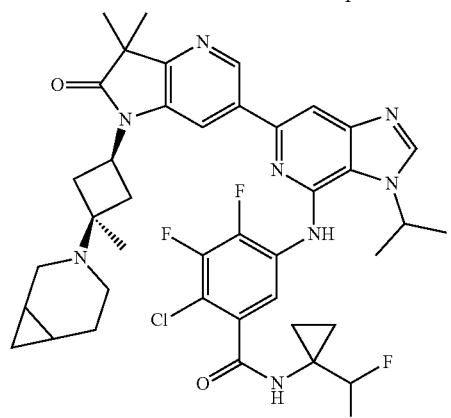
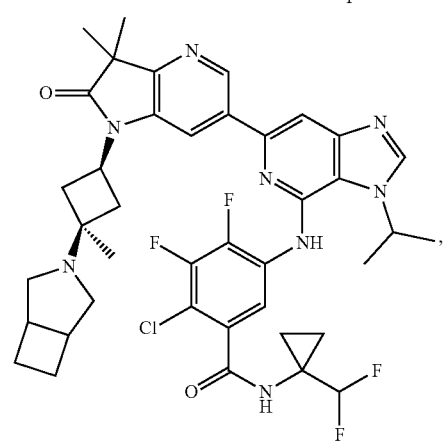

143
-continued
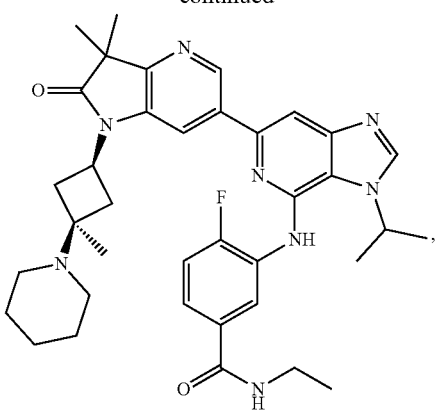
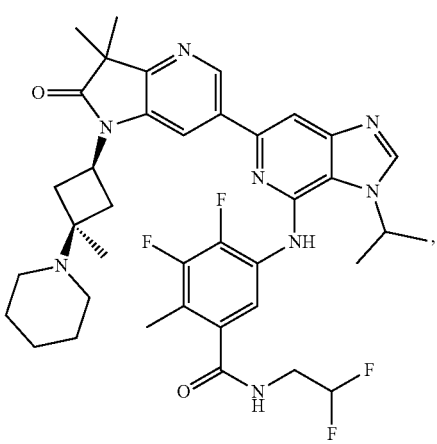
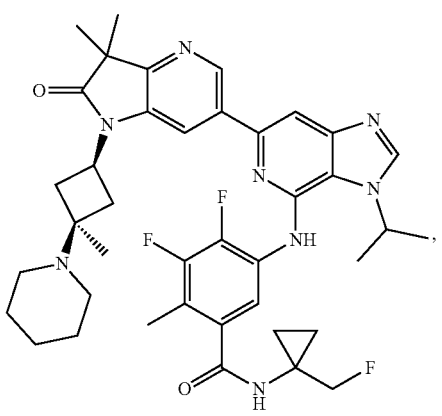
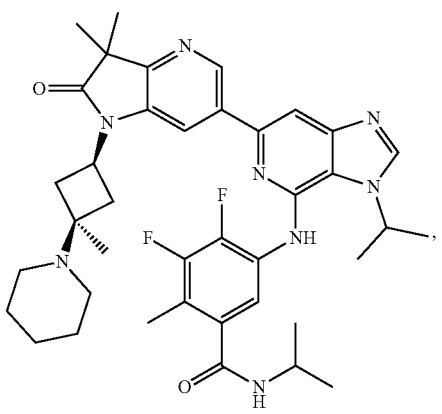
144
-continued
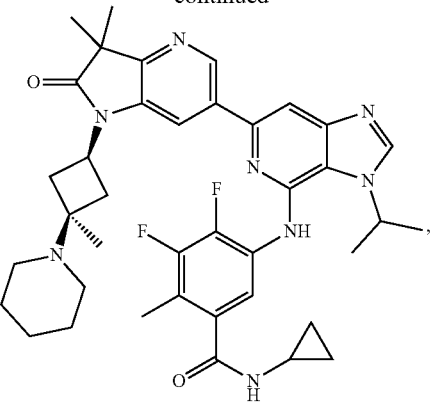
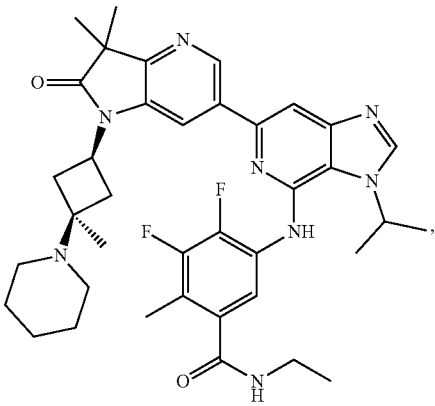
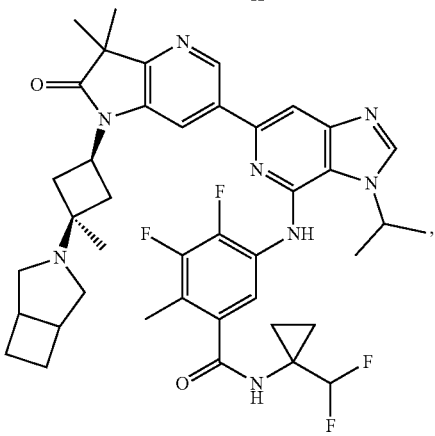
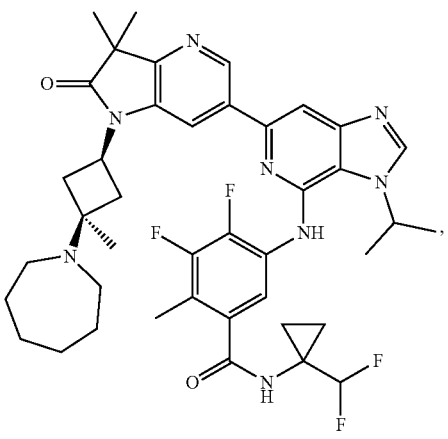

145
-continued
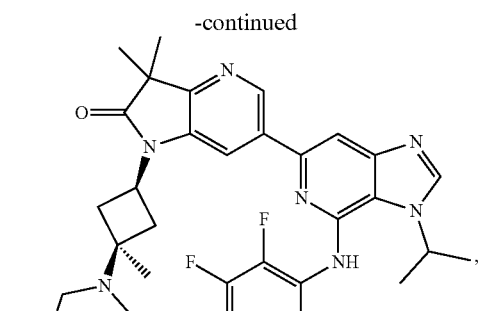
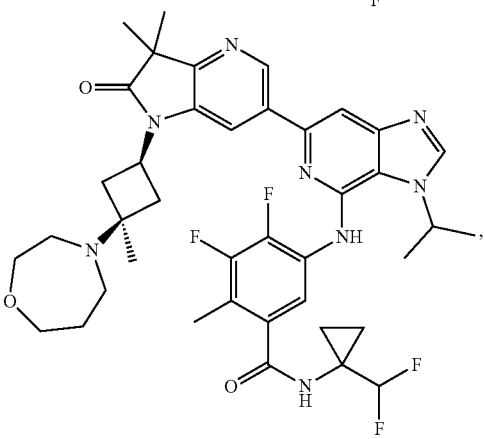
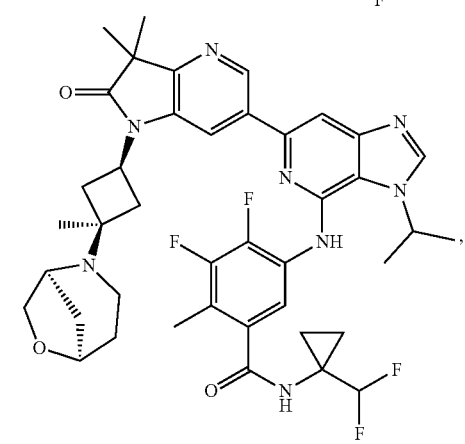
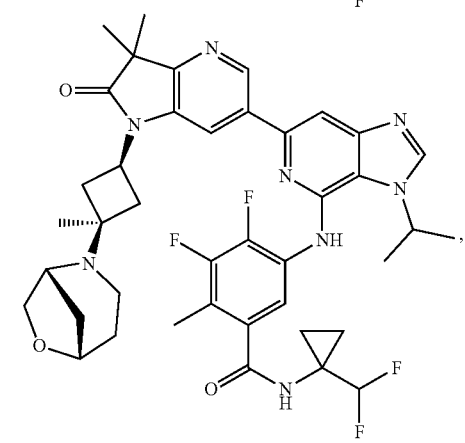
146
-continued
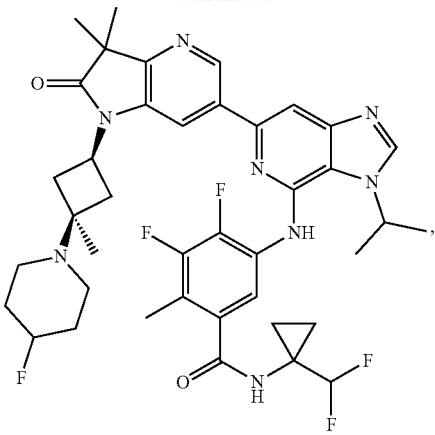
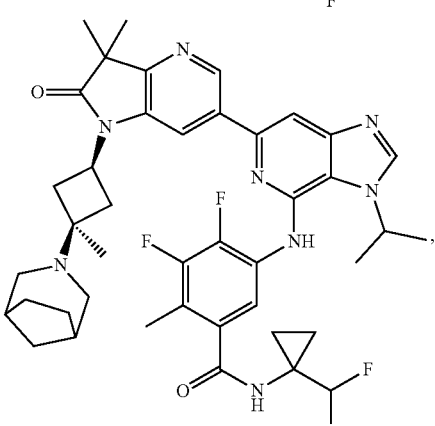
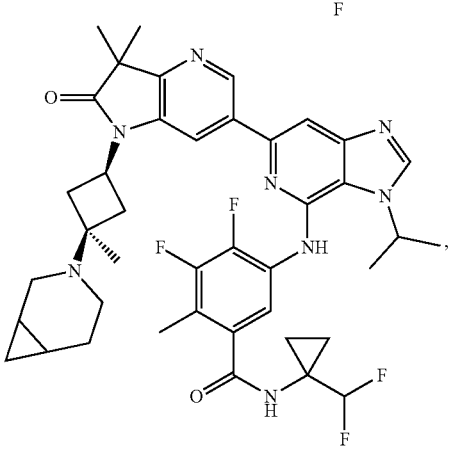
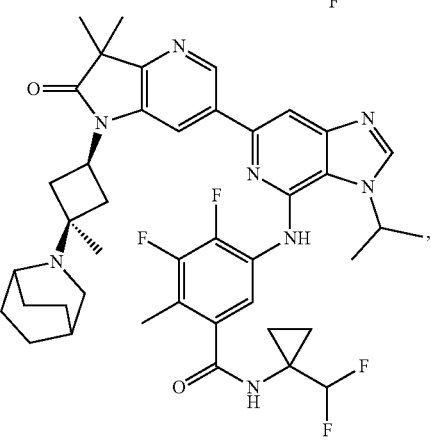

147
-continued
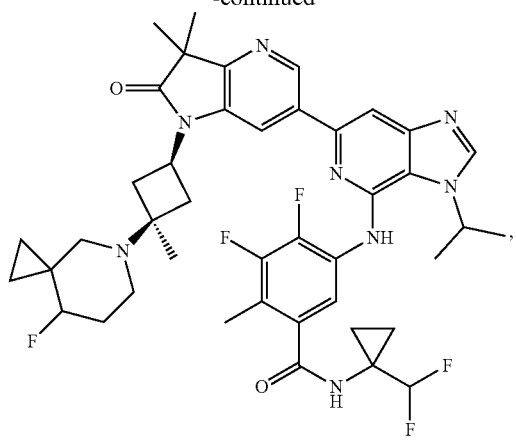
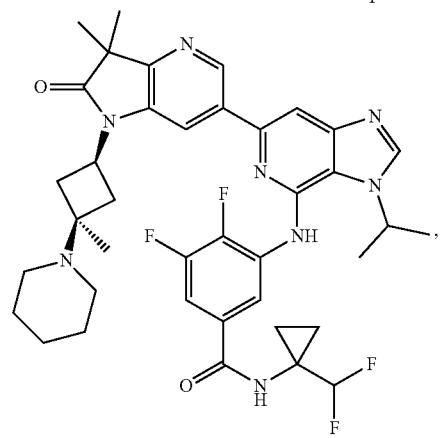
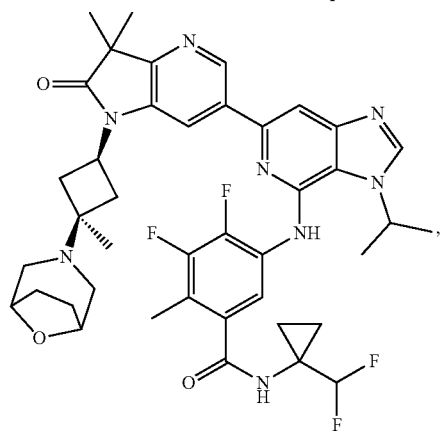
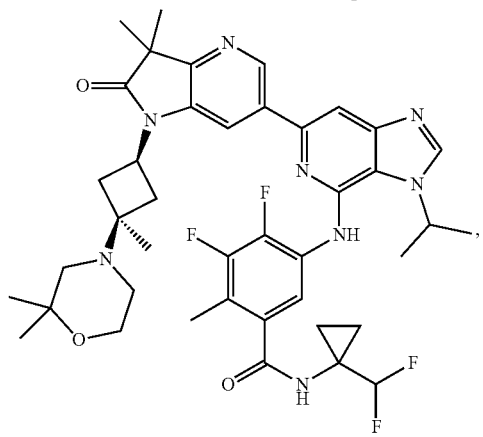
148
-continued
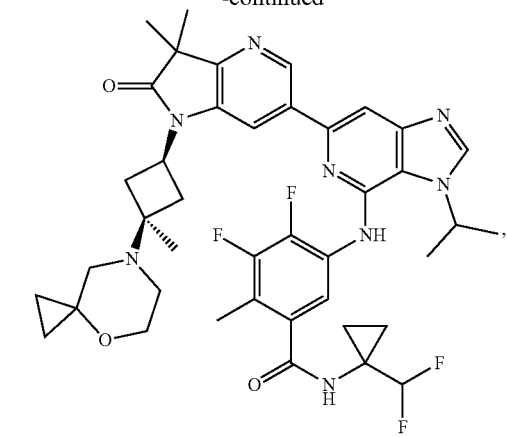
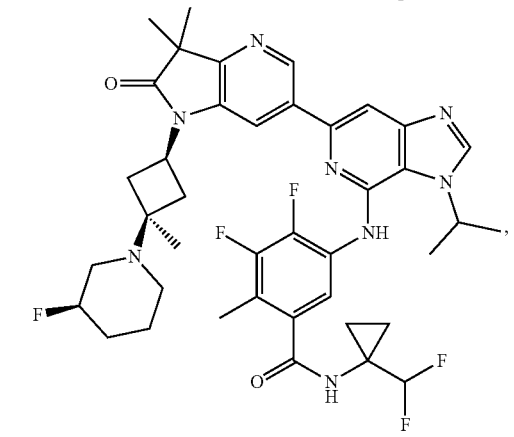
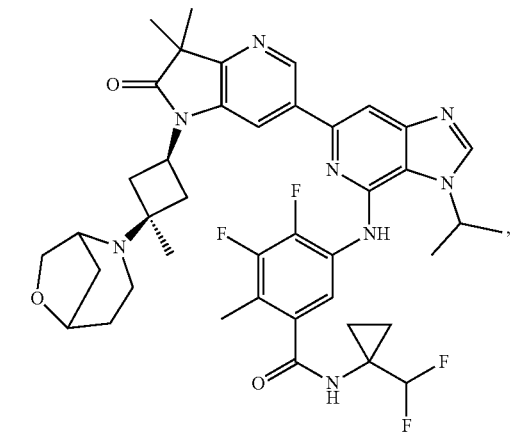
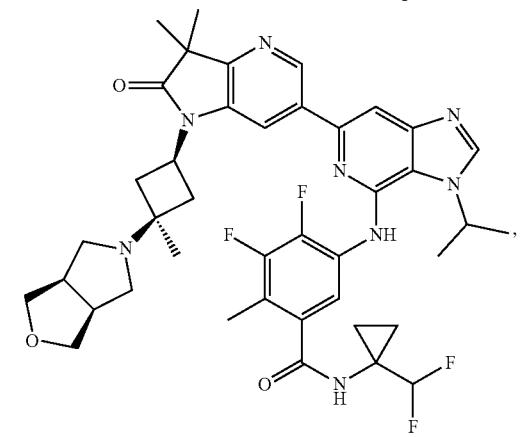

149
-continued
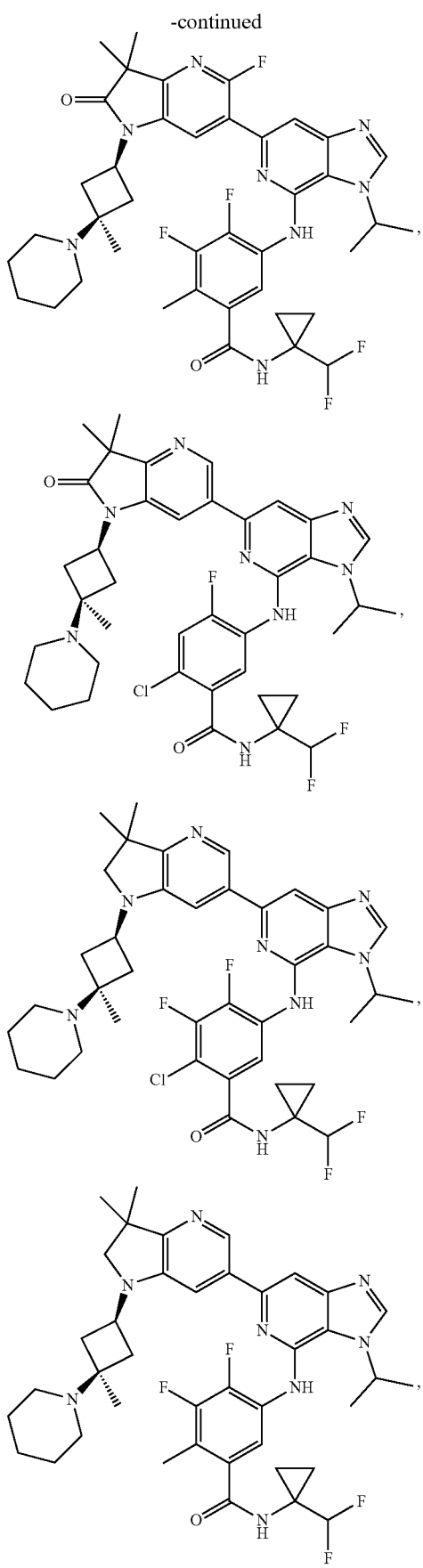
150
-continued
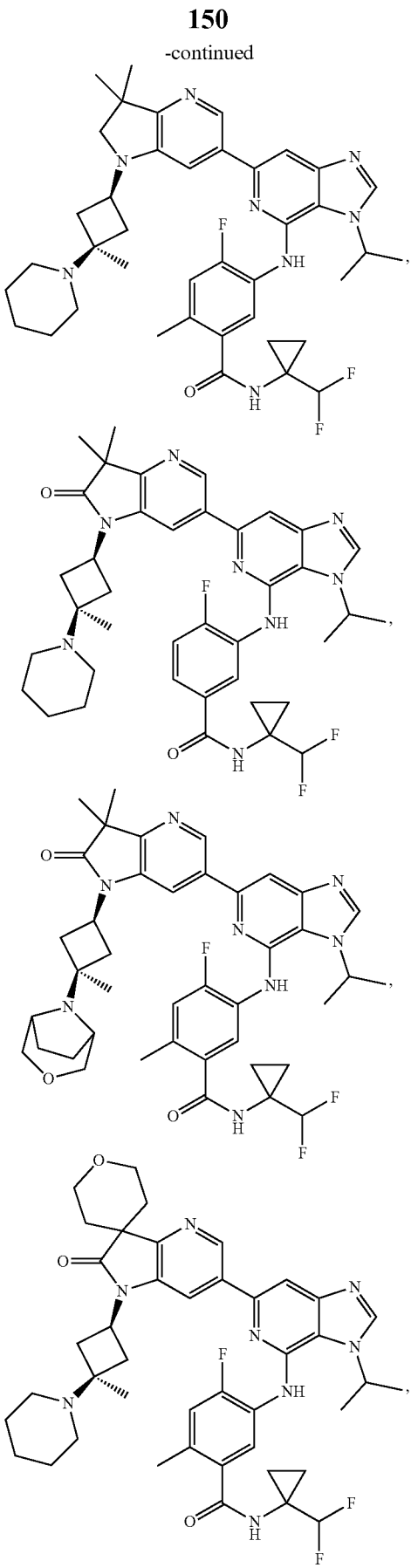

151
-continued

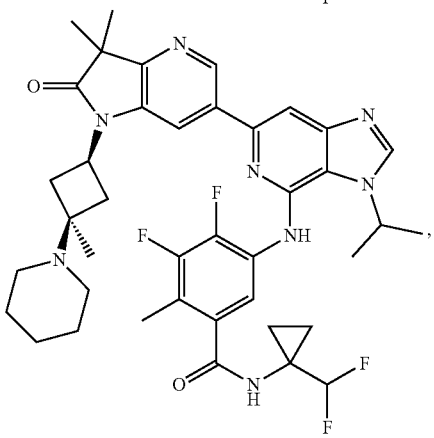
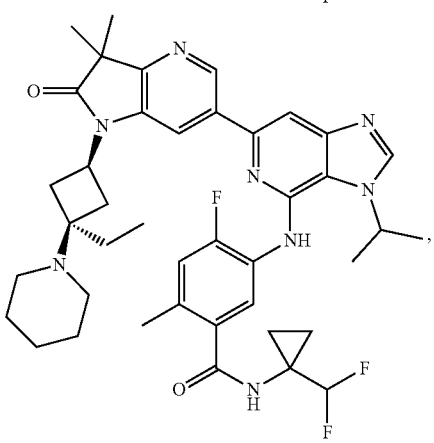
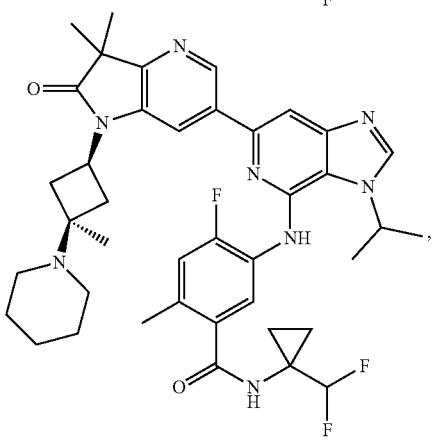
152
-continued
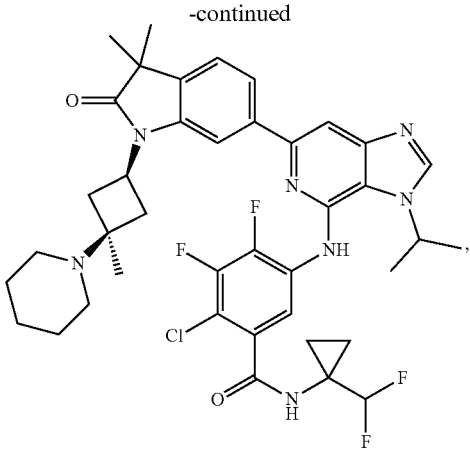
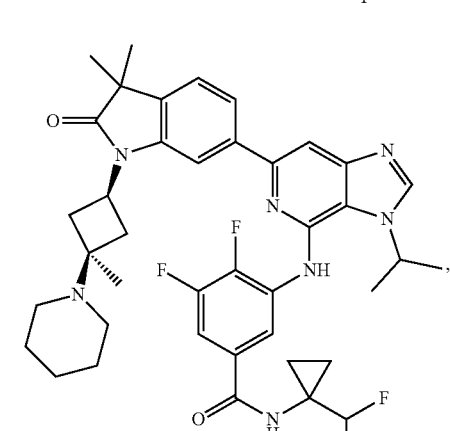
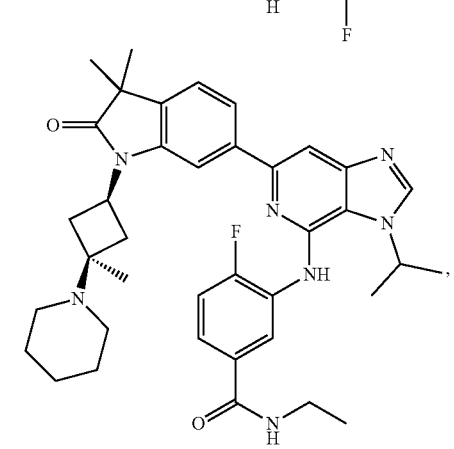
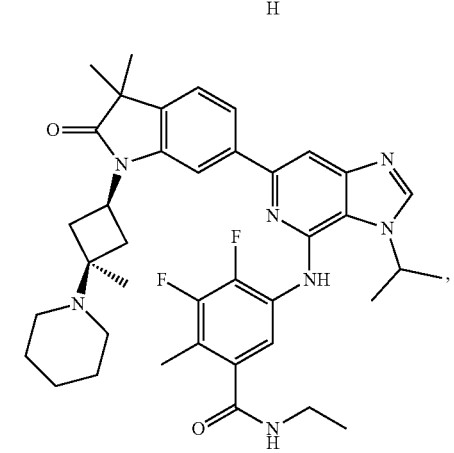

153
-continued
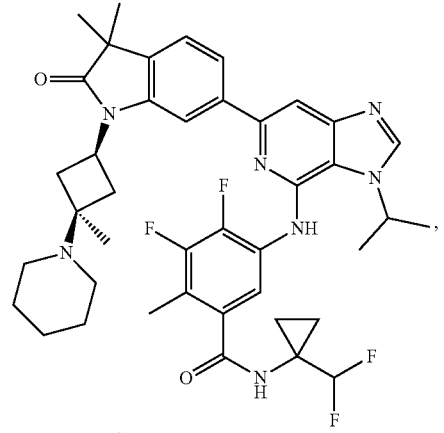
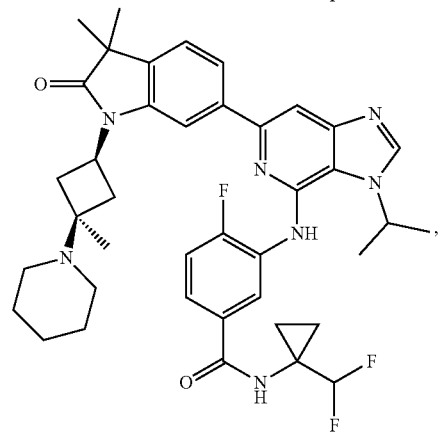
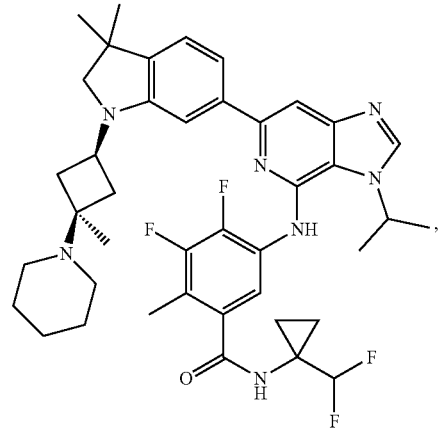
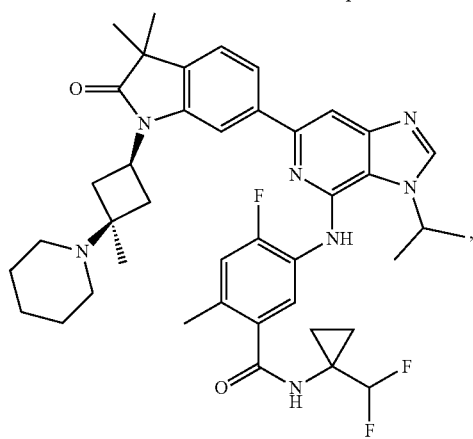
154
-continued
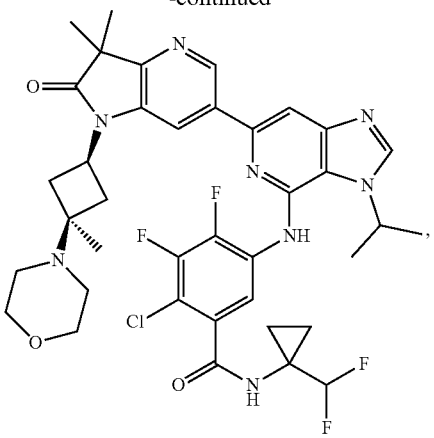
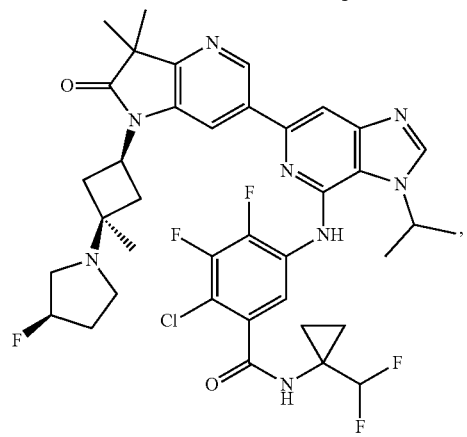
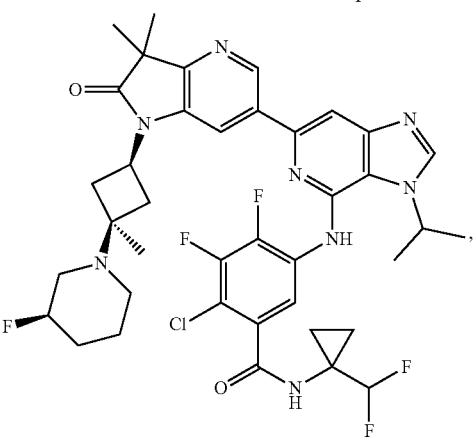
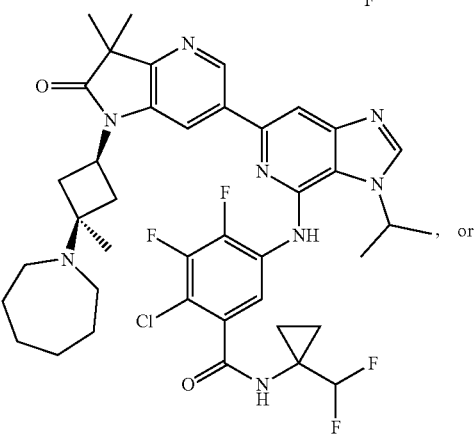, or

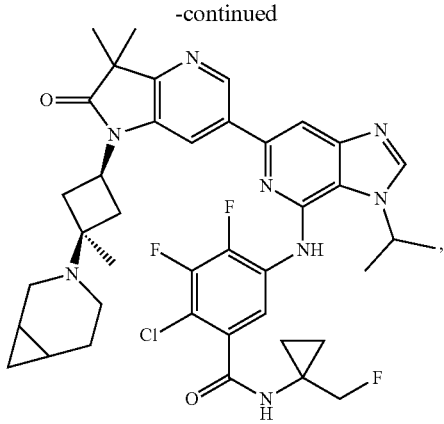
or a pharmaceutically acceptable salt thereof.
In some embodiments of the compounds of Formula I, II, IIa, IIb, III, or IIIa, the compound is:
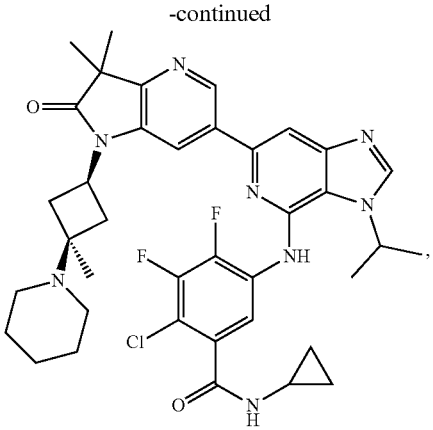
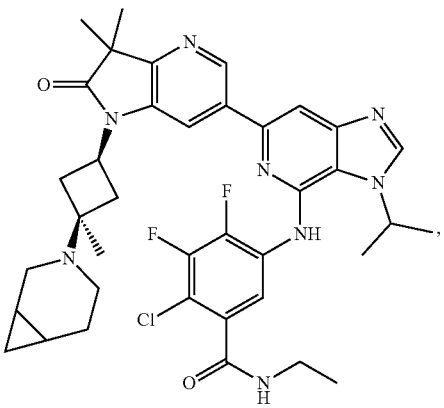
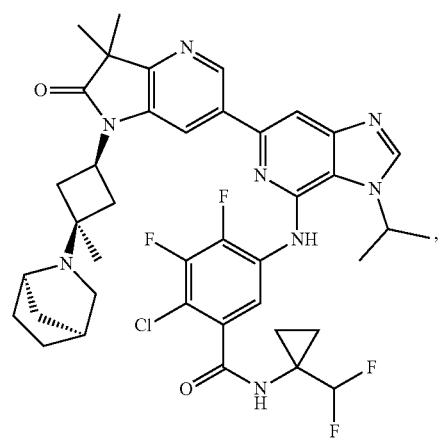
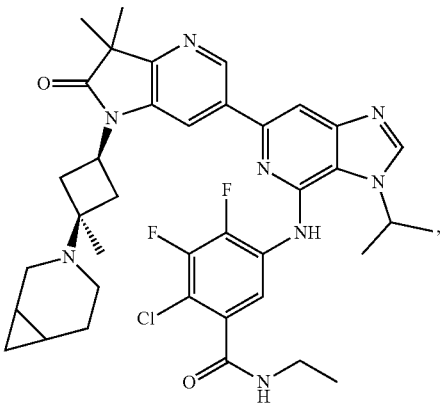
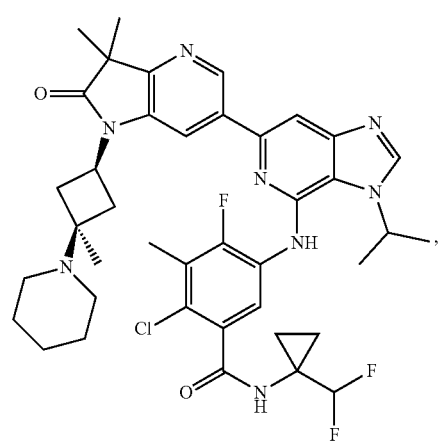
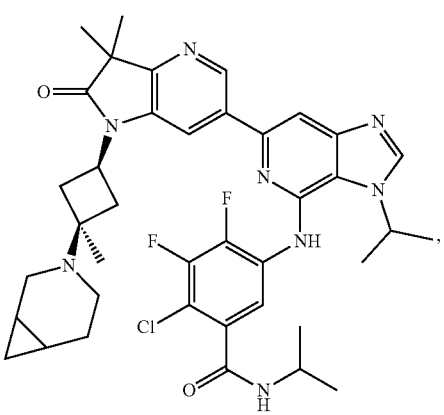

157
-continued
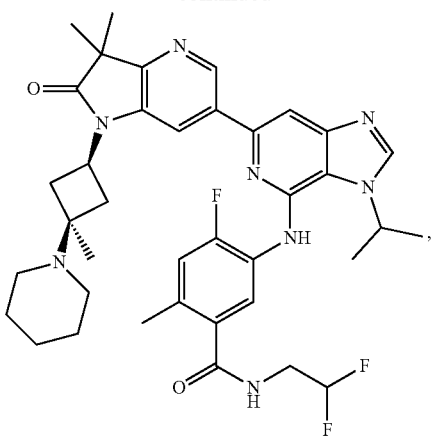
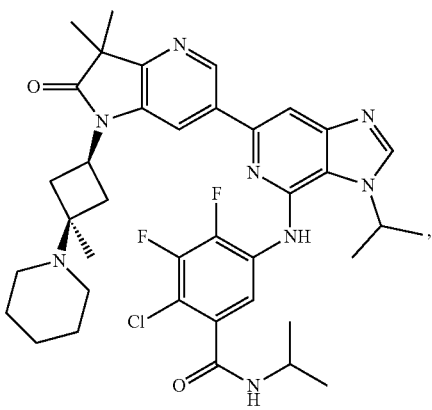
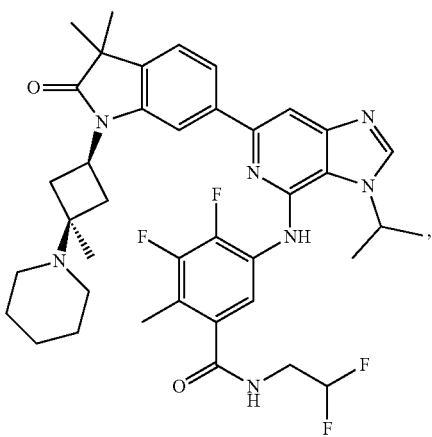
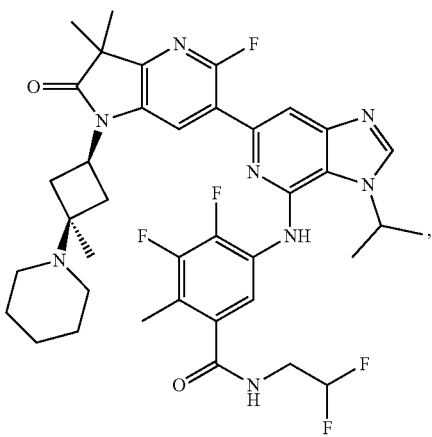
158
-continued
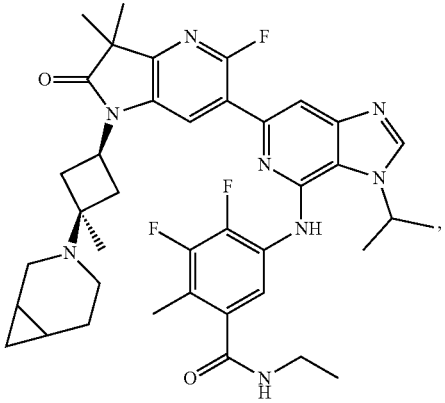
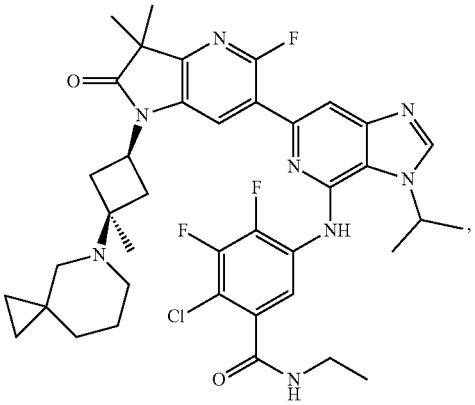
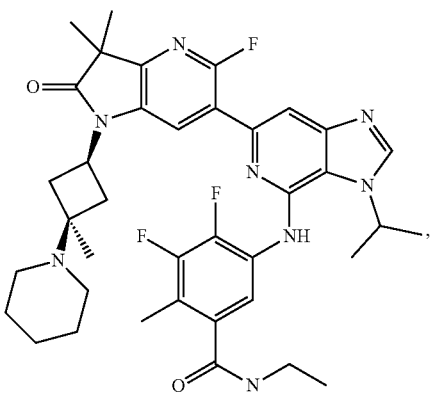
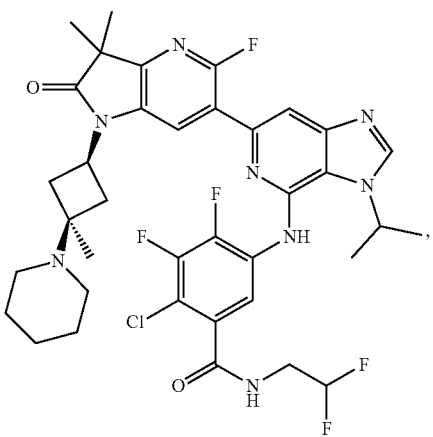

159
-continued
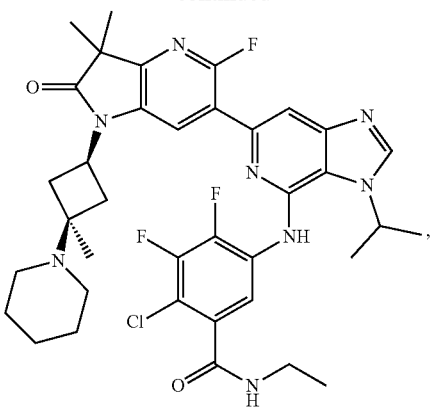
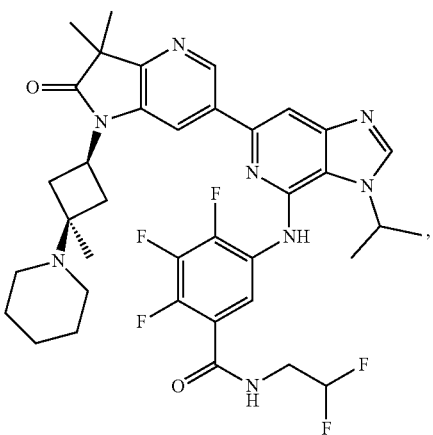
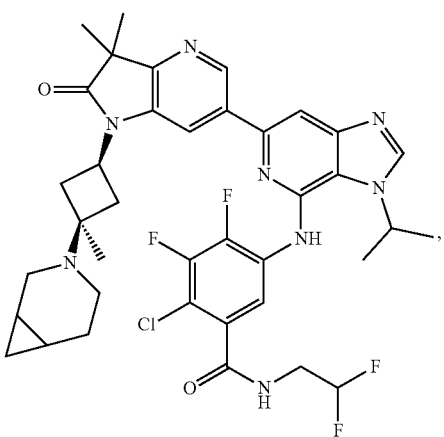
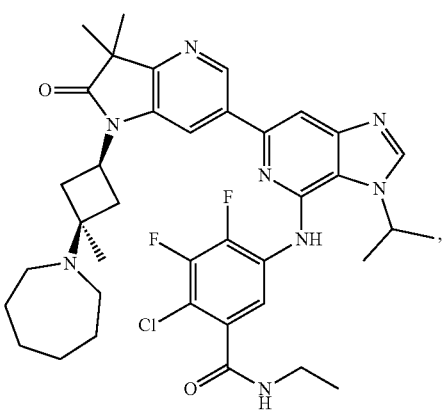
160
-continued
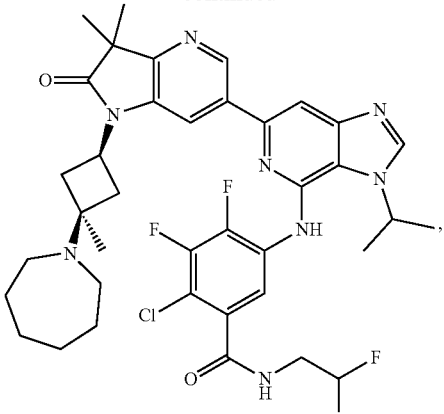
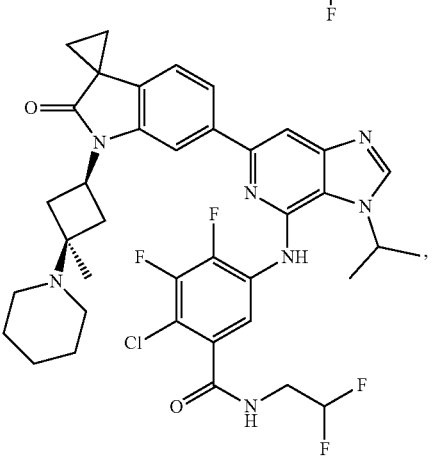
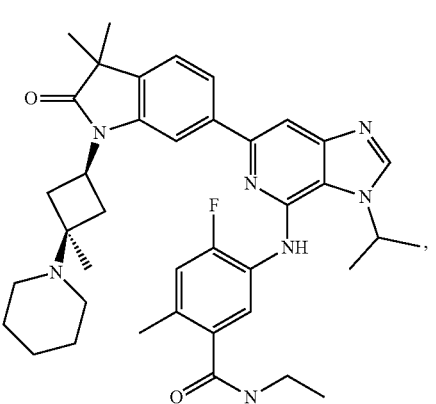
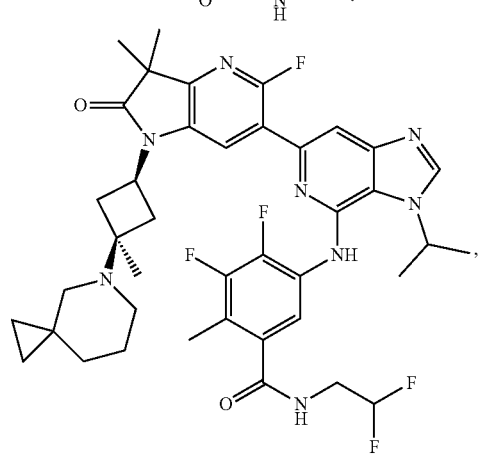

161
-continued
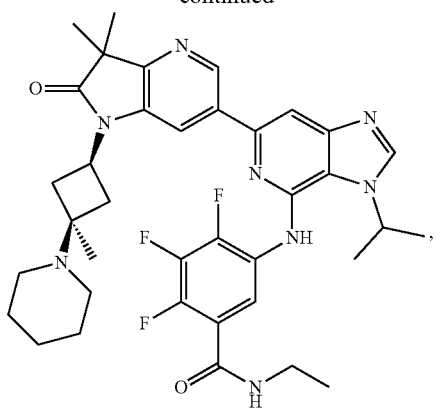
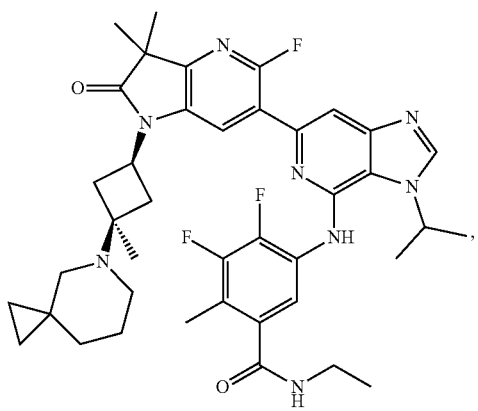
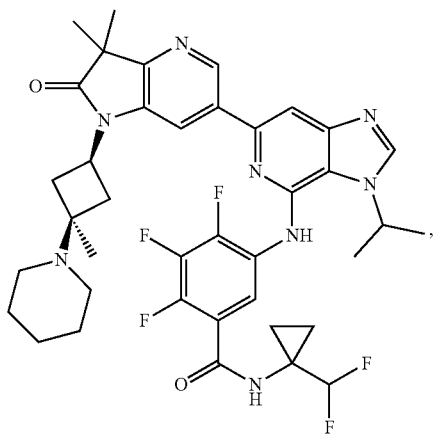
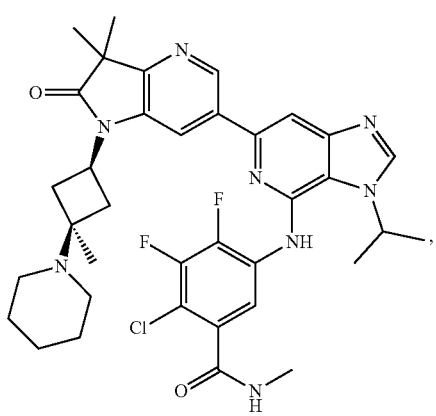
162
-continued
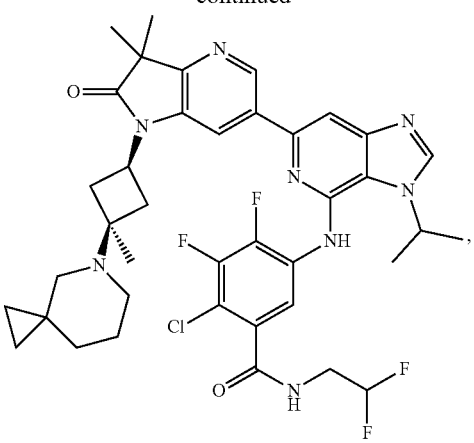
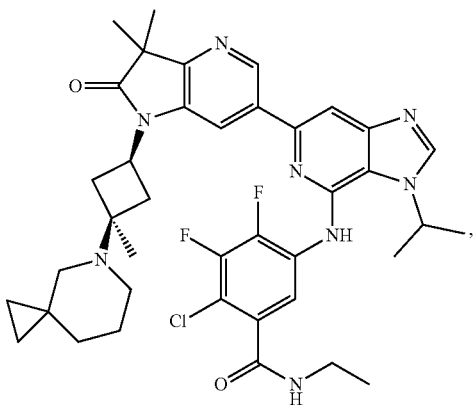
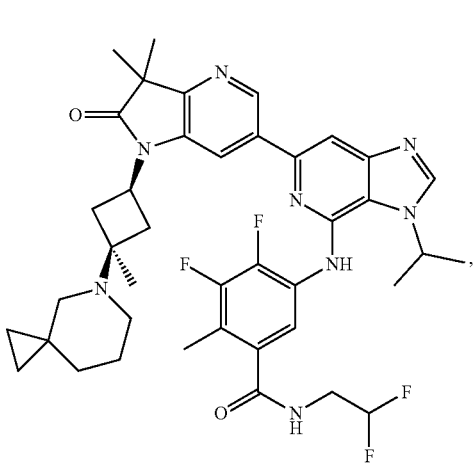
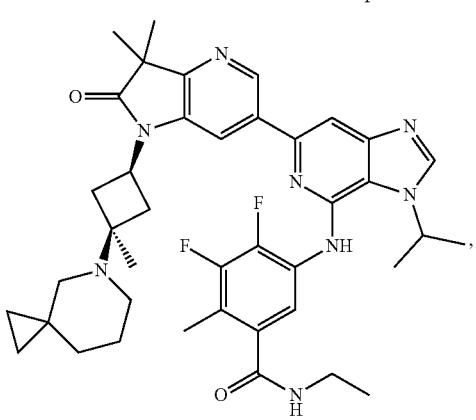

163
-continued
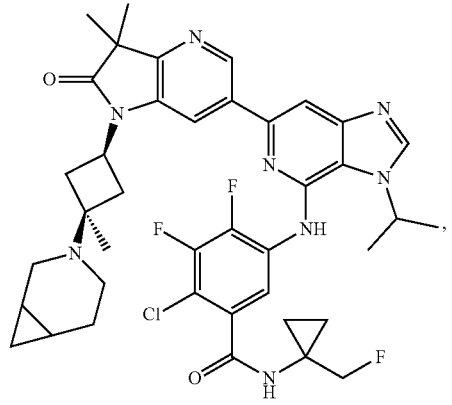
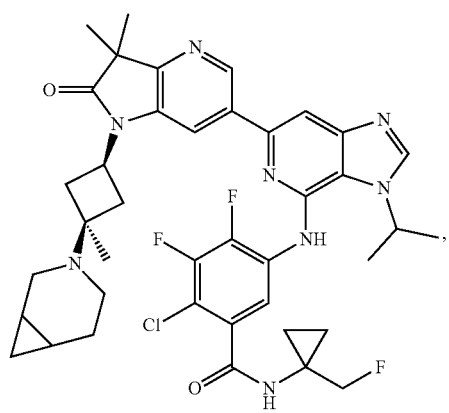
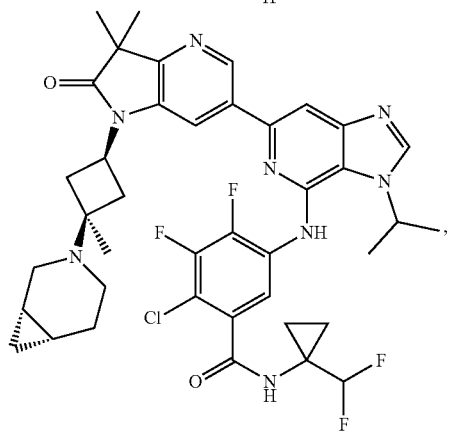
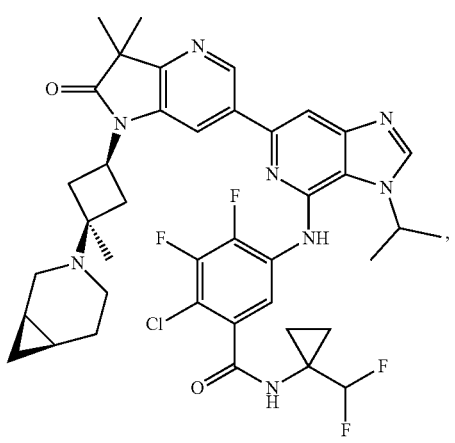
164
-continued
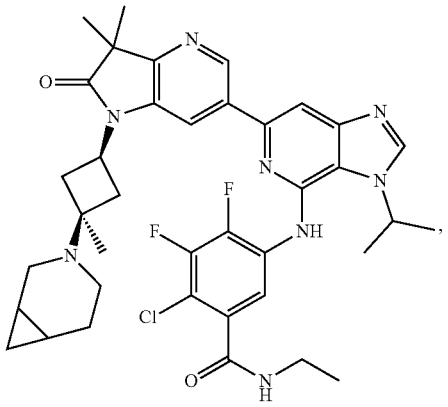
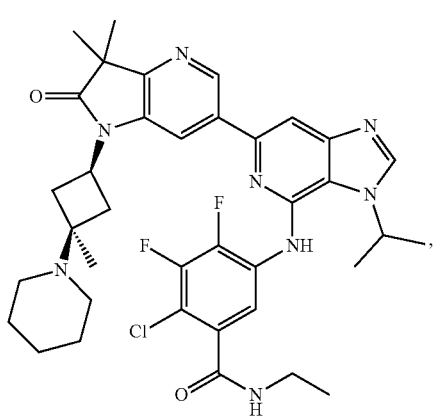
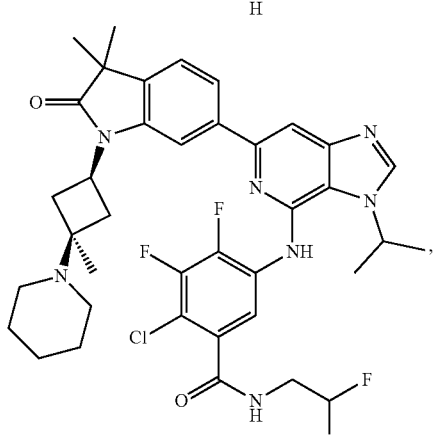
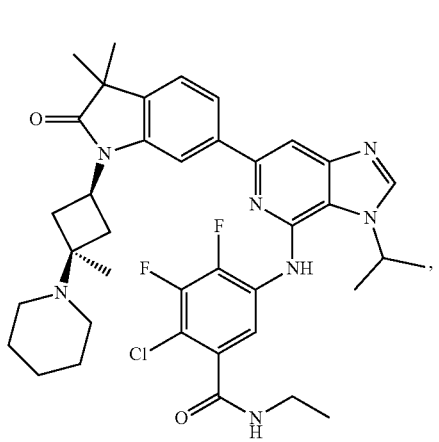

165
-continued
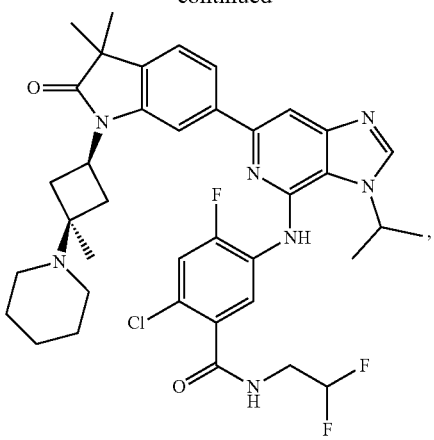
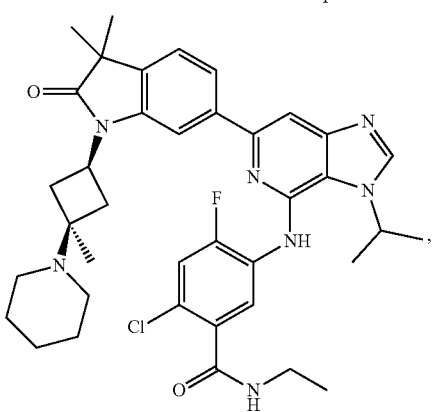
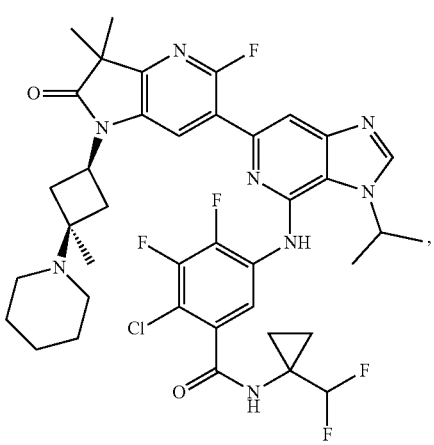
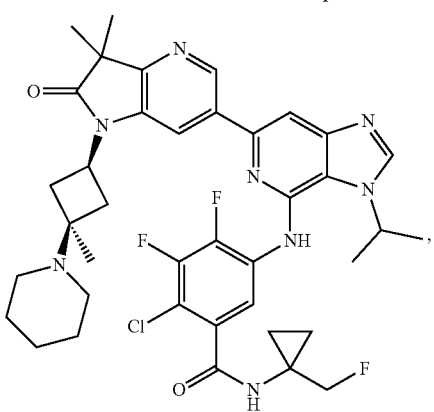
166
-continued
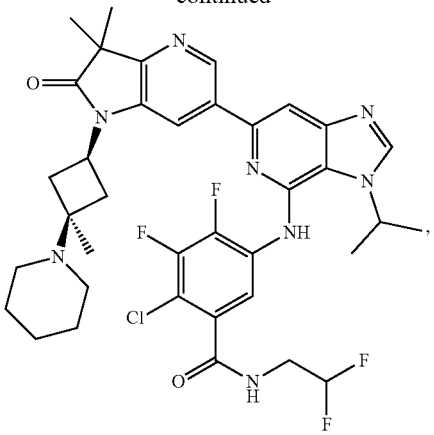
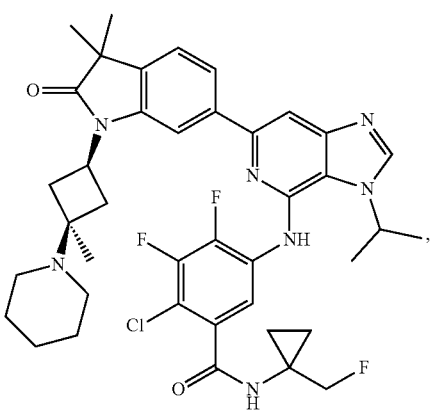
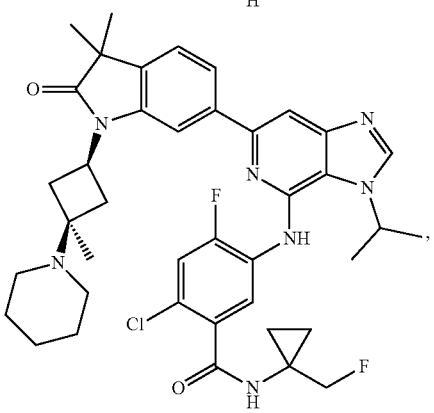
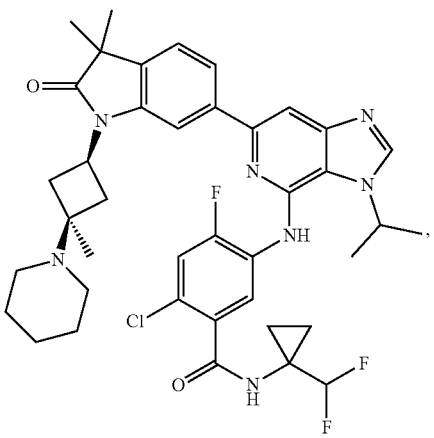

167
-continued
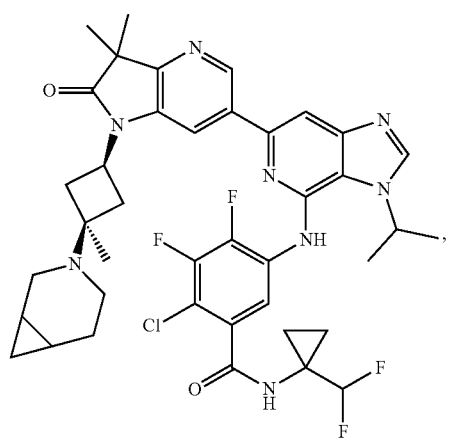
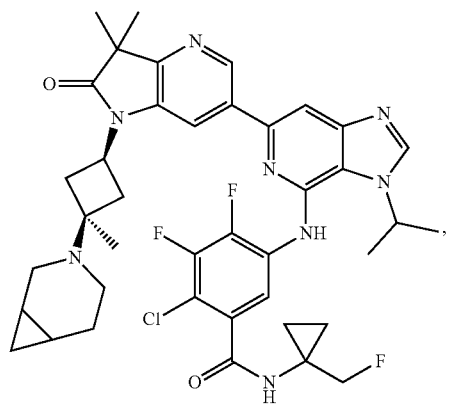
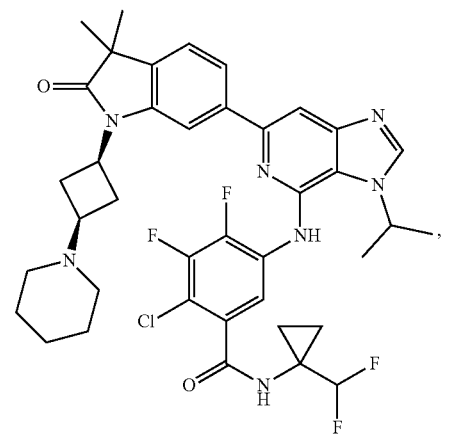
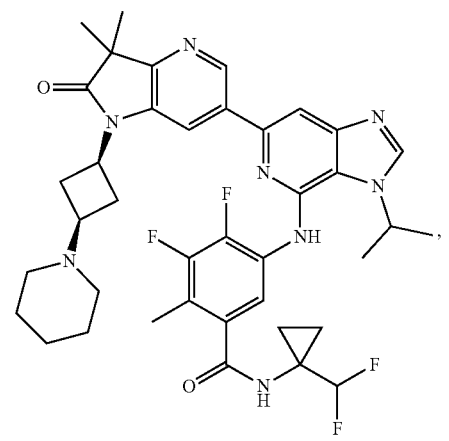
168
-continued

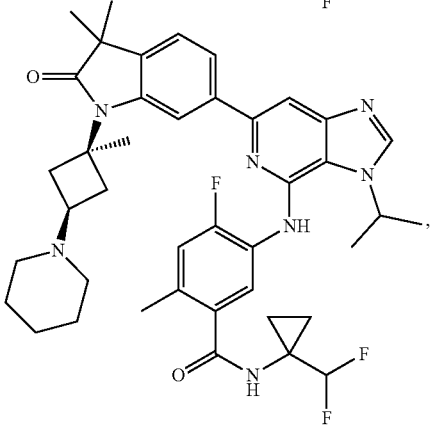
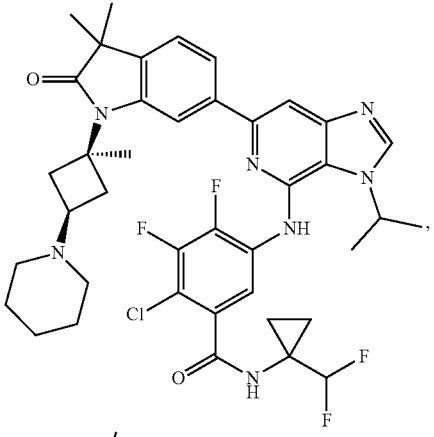
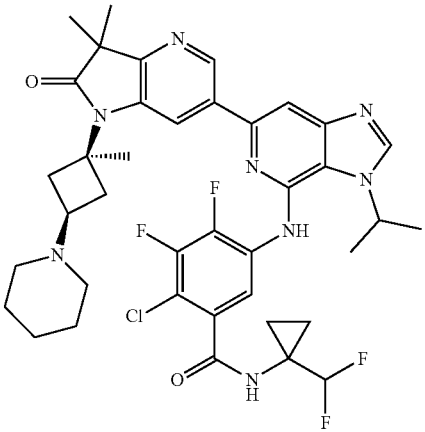
or a pharmaceutically acceptable salt thereof.

In some embodiments of the compounds of Formula I, II, IIa, IIb, III, or IIIa, the compound is:

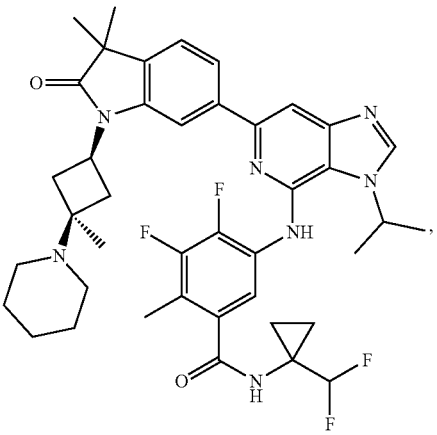 [SMILES: Cc1c(C(=O)NC2(C(F)F)CC2)cc(Nc2nc(-c3ccc4c(c3)N([C@H]3C[C@@](C)(N5CCCCC5)C3)C(=O)C4(C)C)cc3ncn(C(C)C)c23)c(F)c1F]

or a pharmaceutically acceptable salt thereof.
In some embodiments of the compounds of Formula I, II, IIa, IIb, III, or IIIa, the compound is:

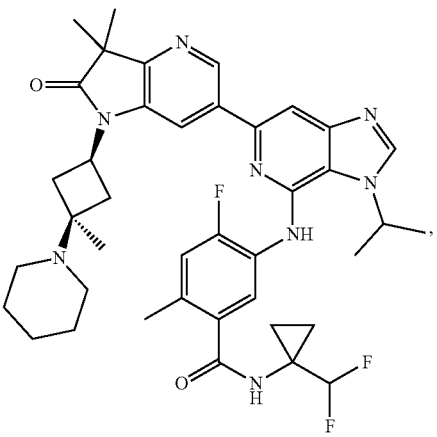 [SMILES: Cc1cc(F)c(Nc2nc(-c3cnc4c(c3)N([C@H]3C[C@@](C)(N5CCCCC5)C3)C(=O)C4(C)C)cc3ncn(C(C)C)c23)cc1C(=O)NC1(C(F)F)CC1]

or a pharmaceutically acceptable salt thereof.
In some embodiments of the compounds of Formula I, II, IIa, IIb, III, or IIIa, the compound is:

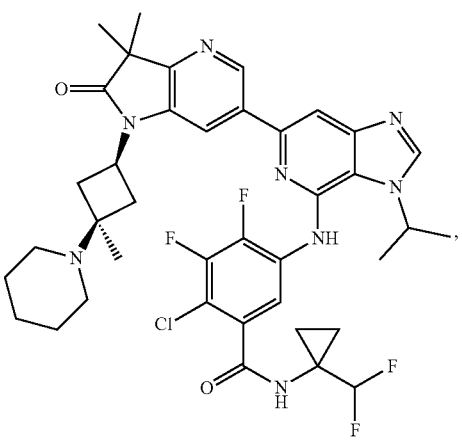 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)c(Cl)c(F)c3F)c21]

or a pharmaceutically acceptable salt thereof.
In some embodiments of the compounds of Formula I, II, IIa, IIb, III, or IIIa, the compound is:

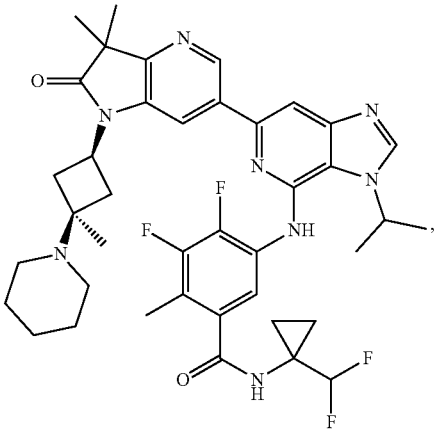 [SMILES: Cc1c(C(=O)NC2(C(F)F)CC2)cc(Nc2nc(-c3cnc4c(c3)N([C@H]3C[C@@](C)(N5CCCCC5)C3)C(=O)C4(C)C)cc3ncn(C(C)C)c23)c(F)c1F]

or a pharmaceutically acceptable salt thereof.
In some embodiments of the compound of Formula I, II, IIa, III, IV, or VI, the compound is:

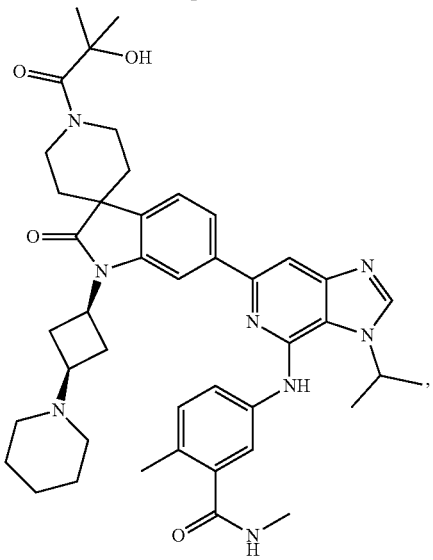 [SMILES: CNC(=O)c1cc(Nc2nc(-c3ccc4c(c3)N([C@H]3C[C@@H](N5CCCCC5)C3)C(=O)C43CCN(C(=O)C(C)(C)O)CC3)cc3ncn(C(C)C)c23)ccc1C]

or a pharmaceutically acceptable salt thereof.
In some embodiments of the compound of Formula I, II, IIa, III, IV, or VI, the compound is:

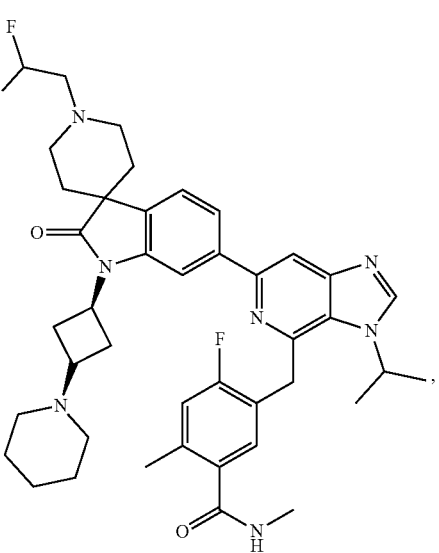

or a pharmaceutically acceptable salt thereof.

In some embodiments of the compound of Formula I, II, IIa, III, or IV, the compound is:

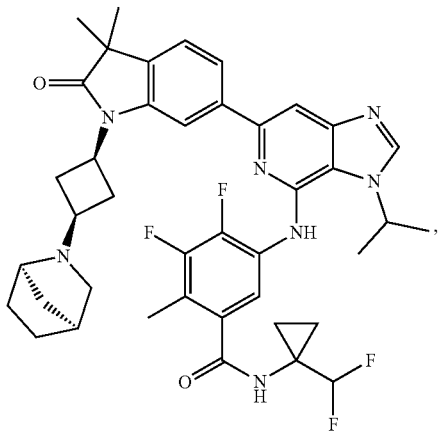

or a pharmaceutically acceptable salt thereof.

In some embodiments of the compound of Formula I, II, IIa, III, IV, or VI, the compound is:

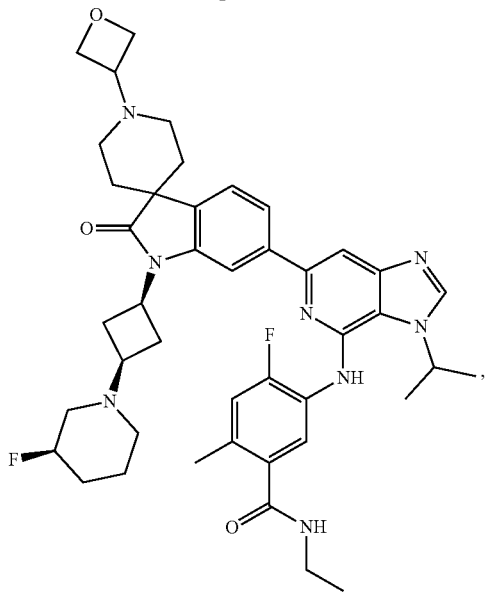 [SMILES: CCNC(=O)c1cc(Nc2nc(-c3ccc4c(c3)N([C@H]3C[C@@H](N5CCC[C@@H](F)C5)C3)C(=O)C43CCN(C4COC4)CC3)cc3ncn(C(C)C)c23)c(F)cc1C]

or a pharmaceutically acceptable salt thereof.

In some embodiments of the compound of Formula I, II, IIa, III, or IV, the compound is:

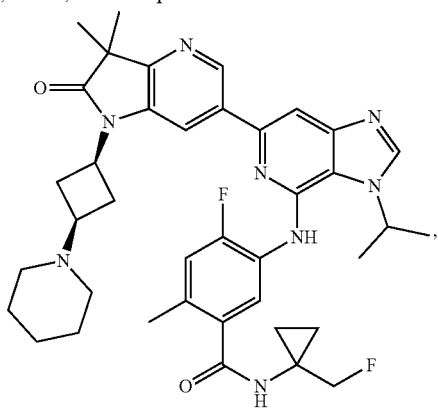

or a pharmaceutically acceptable salt thereof.

In some embodiments of the compound of Formula I, II, IIa, III, IV, or VI, the compound is:

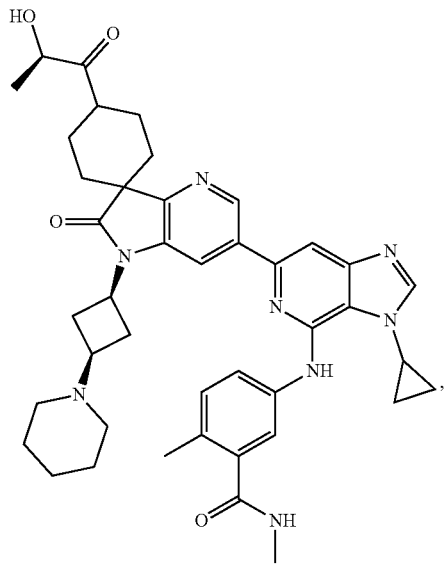 [SMILES: CNC(=O)c1cc(Nc2nc(-c3cnc4c(c3)N([C@H]3C[C@@H](N5CCCCC5)C3)C(=O)C43CCC(C(=O)[C@@H](C)O)CC3)cc3ncn(C4CC4)c23)ccc1C]

or a pharmaceutically acceptable salt thereof.

In some embodiments of the compound of Formula I, II, IIa, III, or IV, the compound is:

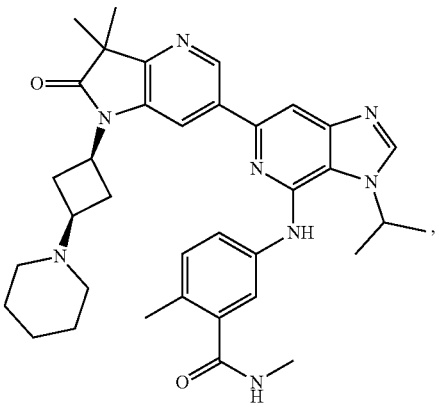 [SMILES: CNC(=O)c1cc(Nc2nc(-c3cnc4c(c3)N([C@H]3C[C@@H](N5CCCCC5)C3)C(=O)C4(C)C)cc3ncn(C(C)C)c23)ccc1C]

or a pharmaceutically acceptable salt thereof.

In some embodiments of the compound of Formula I, II, IIa, III, or IV, the compound is:

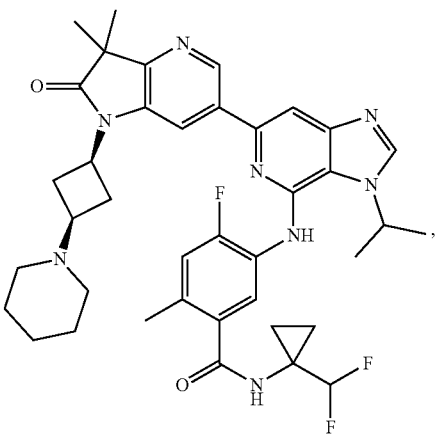 [SMILES: Cc1cc(F)c(Nc2nc(-c3cnc4c(c3)N([C@H]3C[C@@H](N5CCCCC5)C3)C(=O)C4(C)C)cc3ncn(C(C)C)c23)cc1C(=O)NC1(C(F)F)CC1]

or a pharmaceutically acceptable salt thereof.

In some embodiments of the compound of Formula I, II, IIa, III, or IV, the compound is:

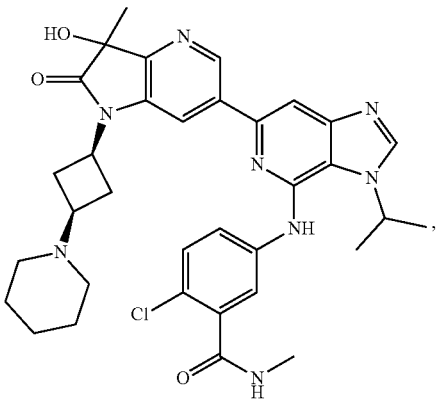 [SMILES: CNC(=O)c1cc(Nc2nc(-c3cnc4c(c3)N([C@H]3C[C@@H](N5CCCCC5)C3)C(=O)C4(C)O)cc3ncn(C(C)C)c23)ccc1Cl]

or a pharmaceutically acceptable salt thereof.

In some embodiments of the compound of Formula I, II, IIa, III, or IV, the compound is:

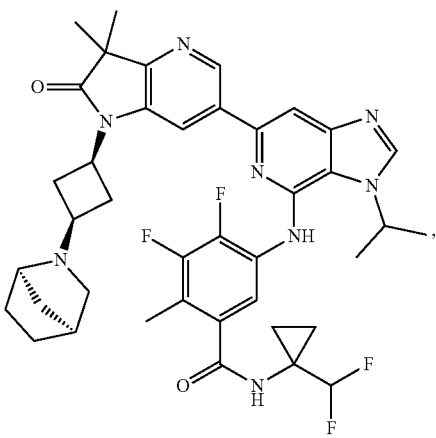 [SMILES: Cc1c(C(=O)NC2(C(F)F)CC2)cc(Nc2nc(-c3cnc4c(c3)N([C@H]3C[C@@H](N5C[C@H]6CC[C@@H]5C6)C3)C(=O)C4(C)C)cc3ncn(C(C)C)c23)c(F)c1F]

or a pharmaceutically acceptable salt thereof.

In some embodiments of the compound of Formula I, II, IIa, III, IV, or VI, the compound is:

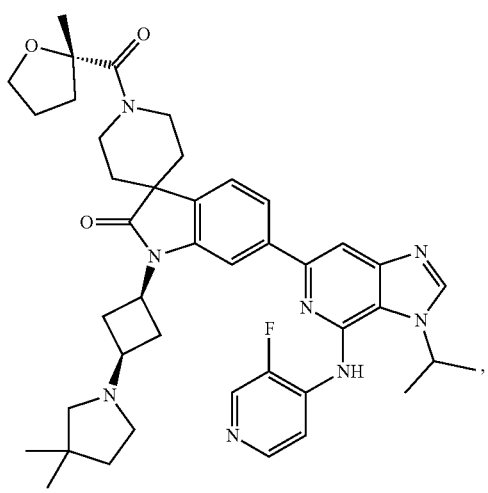 [SMILES: CC(C)n1cnc2cc(-c3ccc4c(c3)N([C@H]3C[C@@H](N5CCC(C)(C)C5)C3)C(=O)C43CCN(C(=O)[C@]4(C)CCCO4)CC3)nc(Nc3ccncc3F)c21]

or a pharmaceutically acceptable salt thereof.

In some embodiments of the compound of Formula I, II, IIa, III, or IV, the compound is:

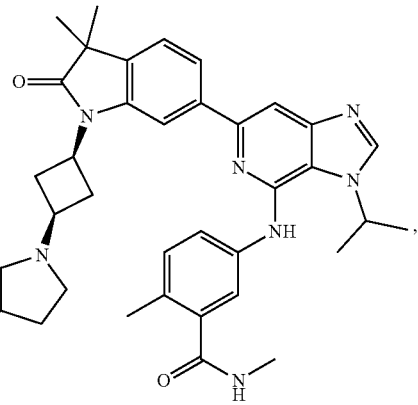

or a pharmaceutically acceptable salt thereof.

In some embodiments of the compound of Formula I, II, IIa, III, or IV, the compound is:

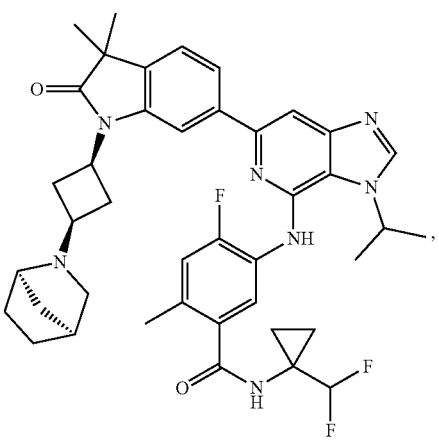 [SMILES: Cc1cc(F)c(Nc2nc(-c3ccc4c(c3)N([C@H]3C[C@@H](N5C[C@H]6CC[C@@H]5C6)C3)C(=O)C4(C)C)cc3ncn(C(C)C)c23)cc1C(=O)NC1(C(F)F)CC1]

or a pharmaceutically acceptable salt thereof.

In some embodiments of the compound of Formula I, II, IIa, III, or IV, the compound is:

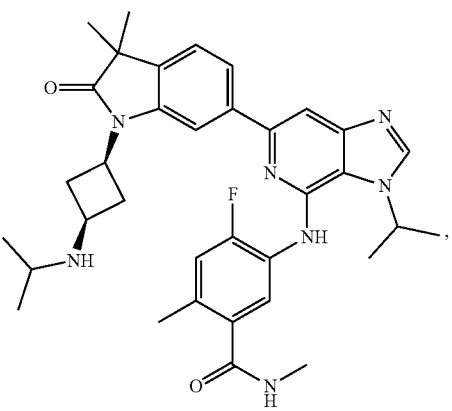 [SMILES: CNC(=O)c1cc(Nc2nc(-c3ccc4c(c3)N([C@H]3C[C@@H](NC(C)C)C3)C(=O)C4(C)C)cc3ncn(C(C)C)c23)c(F)cc1C]

or a pharmaceutically acceptable salt thereof.

In some embodiments of the compound of Formula I, II, IIa, III, or IV, the compound is:

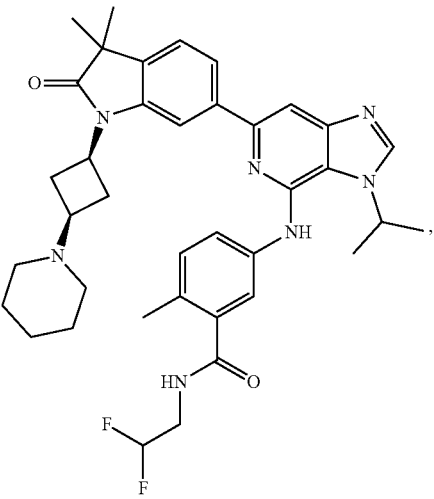 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NCC(F)F]

or a pharmaceutically acceptable salt thereof.

In some embodiments of the compound of Formula I, II, IIa, III, IV, or V, the compound is:

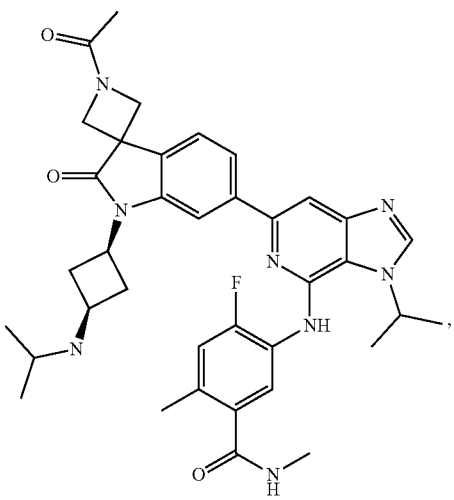 [SMILES: CNC(=O)c1cc(Nc2nc(-c3ccc4c(c3)N([C@H]3C[C@@H](NC(C)C)C3)C(=O)C43CN(C(C)=O)C3)cc3ncn(C(C)C)c23)c(F)cc1C]

or a pharmaceutically acceptable salt thereof.

III. Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

In some embodiments, the one or more additional therapeutic agents include agents that are therapeutic for a hepatitis B virus (HBV) infection, human immunodeficiency virus (HIV) infection, cancer, or a hyper-proliferative disease. In some embodiments, the one or more additional therapeutic agents include PD1 inhibitors and/or PDL1 inhibitors. In some embodiments, the one or more additional therapeutic agents that are therapeutic for HBV infection include PDL1 inhibitors and/or PDL1 inhibitors. In some embodiments, the one or more additional therapeutic agents that are therapeutic for cancer or hyper-proliferative disease include PD1 inhibitors and/or PDL1 inhibitors.

In some embodiments, the one or more additional therapeutic agents include agents that are therapeutic for HBV infection. In some embodiments, the one or more additional therapeutic agents is selected from the group consisting of: adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents include agents that are therapeutic for HIV infection. In some embodiments, the one or more additional therapeutic agents is selected from the group consisting of: 4'-ethynyl-2-fluoro-2'-deoxyadenosine, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, tenofovir alafenamide hemifumarate, emtricitabine, and lamivudine, or a pharmaceutically acceptable salt of any of the foregoing, or any combinations thereof.

In some embodiments, the one or more additional therapeutic agents include PD1 inhibitors and/or PDL1 inhibitors. In some embodiments, the one or more additional therapeutic agents is selected from the group consisting of: nivolumab, lambrolizumab, pembrolizumab, pidilizumab, PDR001, TSR-001, atezolizumab, durvalumab, or avelumab, or a pharmaceutically acceptable salt of any of the foregoing, or any combinations thereof.

In some embodiments, the one or more additional therapeutic agents include agents that are therapeutic for cancer or hyper-proliferative disease. In some embodiments, the one or more additional therapeutic agents is selected from the group consisting of: rituxan, doxorubicin, gemcitabine, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbo nitril e, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein, (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a HPK1 inhibitor for a given indication, cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one aspect, the present disclosure provides methods of inhibiting HPK1 activity in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In one aspect, the present disclosure provides methods of treating a disease or disorder associated with increased HPK1 activity in a subject in need thereof, comprising administering to the subject a therapeutically effective amount of a compound provided herein, or a pharmaceutically acceptable salt thereof, or a pharmaceutical composition provided herein.

In one aspect, the present disclosure provides methods of increasing T-cell activation in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In one aspect, the present disclosure provides methods of treating cancer in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, urothelial cancer. In some embodiments, the cancer is a solid tumor.

In one aspect, the present disclosure provides methods of inhibiting the growth or proliferation of cancer cells in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In some embodiments, the above methods further comprise administering a therapeutically effective amount of one or more additional therapeutic agents, or a pharmaceutically acceptable salt thereof.

In some embodiments, the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In some embodiments, the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino) pyrimidin-4-yl]benzamide, XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In some embodiments, the one or more additional therapeutic agents is selected from the group consisting of idelalisib, tirabrutinib, momelotinib, and entospletinib, or a pharmaceutically acceptable salt of any of the foregoing, or any combinations thereof.

In one aspect, the present disclosure provides methods of treating or preventing a hepatitis B virus (HBV) infection in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In some embodiments, the method of treating or preventing a HBV infection further comprises administering a therapeutically effective amount of one or more additional therapeutic agents, or a pharmaceutically acceptable salt thereof.

In some embodiments, the one or more additional therapeutic agents is selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In some embodiments, the one or more additional therapeutic agents is selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the one or more additional therapeutic agents is selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In some embodiments, the one or more additional therapeutic agents is selected from the group consisting of tenofovir alafenamide, tenofovir alafenamide fumarate, and tenofovir alafenamide hemifumarate, or a pharmaceutically acceptable salt of any of the foregoing, or any combinations thereof.

In one aspect, the present disclosure provides methods of treating or preventing a human immunodeficiency virus (HIV) infection in a subject in need thereof, comprising administering to the subject a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof, or a pharmaceutical composition provided herein.

In some embodiments, the method of treating or preventing a HIV infection further comprises administering a therapeutically effective amount of one or more additional therapeutic agents, or a pharmaceutically acceptable salt thereof.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir alafenamide, tenofovir alafenamide fumarate and tenofovir alafenamide hemifumarate, or a pharmaceutically acceptable salt of any of the foregoing, or any combinations thereof.

In some embodiments, the one or more additional therapeutic agents is selected from the group consisting of 4'-ethynyl-2-fluoro-2'-deoxyadenosine, bictegravir, tenofovir disoproxil, tenofovir disoproxil hemifumarate, and tenofovir disoproxil fumarate, or a pharmaceutically acceptable salt of any of the foregoing, or any combinations thereof.

In some embodiments, the one or more additional therapeutic agents is selected from the group consisting of emtricitabine and lamivudine, or a pharmaceutically acceptable salt of each thereof.

In some embodiments, the one or more additional therapeutic agents is emtricitabine or a pharmaceutically acceptable salt thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir alafenamide, and tenofovir alafenamide hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the method of treating or preventing a HIV infection further comprises administering one or more additional therapeutic agents selected from the group consisting of 4'-ethynyl-2-fluoro-2'-deoxyadenosine, bictegravir, tenofovir disoproxil, tenofovir disoproxil fumarate, and tenofovir disoproxil hemifumarate, or a pharmaceutically acceptable salt of any of the foregoing, or any combinations thereof, and further comprises administering another therapeutic agent selected from the group consisting of emtricitabine and lamivudine, or a pharmaceutically acceptable salt of each thereof.

In some embodiments, the methods described herein comprise administering a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof. In some embodiments, the methods described herein comprise administering a therapeutically effective amount of a pharmaceutical composition provided herein.

In one aspect, provided herein is a compound disclosed herein, or a pharmaceutically acceptable salt thereof, for use in therapy.

In one aspect, provided herein is a compound disclosed herein, or a pharmaceutically acceptable salt thereof, for use in a method of inhibiting hematopoietic progenitor kinase 1 (HPK1) activity in a subject in need thereof.

In one aspect, provided herein is a compound disclosed herein, or a pharmaceutically acceptable salt thereof, for use in a method of treating a disease or disorder associated with increased hematopoietic progenitor kinase 1 (HPK1) activity in a subject in need thereof.

In one aspect, provided herein is a compound disclosed herein, or a pharmaceutically acceptable salt thereof, for use in a method of increasing T-cell activation in a subject in need thereof.

In one aspect, provided herein is a compound disclosed herein, or a pharmaceutically acceptable salt thereof, for use in a method of treating cancer in a subject in need thereof.

In some embodiments, the cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer. In some embodiments, the cancer is a solid tumor.

In one aspect, provided herein is a compound disclosed herein, or a pharmaceutically acceptable salt thereof, for use in a method of inhibiting the growth or proliferation of cancer cells in a subject in need thereof.

In some embodiments, the use in a method of inhibiting the growth or proliferation of cancer cells in a subject in need thereof further comprises administering a therapeutically effective amount of one or more additional therapeutic agents, or a pharmaceutically acceptable salt thereof.

In some embodiments, the use in a method of inhibiting the growth or proliferation of cancer cells in a subject in need thereof further comprises administering one or more additional therapeutic agents selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In some embodiments, the use in a method of inhibiting the growth or proliferation of cancer cells in a subject in need thereof further comprises administering one or more additional therapeutic agents selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5-carbo nitril e, and ipilimumab, or a pharmaceutically acceptable salt of any of the foregoing, or any combinations thereof.

In some embodiments, the use in a method of inhibiting the growth or proliferation of cancer cells in a subject in need thereof further comprises administering one or more additional therapeutic agents selected from the group consisting of idelalisib, tirabrutinib, momelotinib, and entospletinib, or a pharmaceutically acceptable salt of any of the foregoing, or any combinations thereof.

In one aspect, provided herein is a compound disclosed herein, or a pharmaceutically acceptable salt thereof, for use in a method of treating or preventing a hepatitis B virus (HBV) infection in a subject in need thereof.

In some embodiments, the use in a method of treating or preventing a hepatitis B virus (HBV) infection in a subject in need thereof further comprises administering a therapeutically effective amount of one or more additional therapeutic agents, or a pharmaceutically acceptable thereof.

In some embodiments, the use in a method of treating or preventing a hepatitis B virus (HBV) infection in a subject in need thereof further comprises administering one or more additional therapeutic agents selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of tenofovir alafenamide, tenofovir alafenamide fumarate, and tenofovir alafenamide hemifumarate, or a pharmaceutically acceptable salt of any of the foregoing, or any combinations thereof.

In one aspect, provided herein is a compound disclosed herein, or a pharmaceutically acceptable salt thereof, for use in a method of treating or preventing a human immunodeficiency virus (HIV) infection in a subject in need thereof.

In some embodiments, the use in a method of treating or preventing a hepatitis B virus (HBV) infection in a subject in need thereof further comprises administering one or more additional therapeutic agents, or a pharmaceutically acceptable salt thereof.

In some embodiments, the use in a method of treating or preventing a hepatitis B virus (HBV) infection in a subject in need thereof further comprises administering one or more additional therapeutic agents selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir, tenofovir alafenamide, tenofovir alafenamide fumarate or tenofovir alafenamide hemifumarate, or a pharmaceutically acceptable salt of any of the foregoing, or any combinations thereof.

In some embodiments, the use in a method of treating or preventing a hepatitis B virus (HBV) infection in a subject in need thereof further comprises administering one or more additional therapeutic agents selected from the group consisting of 4'-ethynyl-2-fluoro-2'-deoxyadenosine, bictegravir or a pharmaceutically acceptable salt thereof, tenofovir disoproxil, tenofovir disoproxil hemifumarate or tenofovir disoproxil fumarate, or a pharmaceutically acceptable salt of any of the foregoing, or any combinations thereof.

In some embodiments, the uses described herein comprise administering a therapeutically effective amount of a compound provided herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc), or a pharmaceutically acceptable salt thereof.

V. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 μg to about 30 mg per day, or from about 30 μg to about 300 μg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, II, IIa, IIb, III, IIIa, IV, IVa, IVb, IVc, V, Va, Vb, Vc, VI, VIa, VIb, VIc, VII, VIIa, VIIb, or VIIc are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VI. Combination Therapy

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

Co-administration includes administration of unit dosages of the compounds disclosed herein before or after administration of unit dosages of one or more additional therapeutic agents. The compounds disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In some embodiments a compound of Formula I, II, IIa, IIb, III, IIIa, IV, IVa, IVb, IVc, V, Va, Vb, Vc, VI, VIa, VIb, VIc, VII, VIIa, VIIb, or VIIc, is formulated as a tablet, which may optionally contain one or more other compounds useful for treating the disease being treated. In certain embodiments, the tablet can contain another active ingredient for treating a HBV infection, HIV infection, cancer, or a hyperproliferative disease. In some embodiments, such tablets are suitable for once daily dosing Also provided herein are methods of treatment in which a compound of Formula I, II, IIa, IIb, III, IIIa, IV, IVa, IVb, IVc, V, Va, Vb, Vc, VI, VIa, VIb, VIc, VII, VIIa, VIIb, or VIIc, or a tautomer or pharmaceutically acceptable salt thereof, is given to a patient in combination with one or more additional therapeutic agents or therapy. In some embodiments, the total daily dosage of a compound of Formula I, II, IIa, III, IV, or V, or a tautomer, or a pharmaceutically acceptable salt thereof, may be about 300 mg/day administered in a single dose for a human subject.

HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In certain embodiments, a compound of Formula (J) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10,AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, AB-506, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620 (vesatolimod), GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, GS-9688 and the compounds disclosed in US20140045849 (Janssen), US20140073642 (Janssen), WO2014/056953 (Janssen), WO2014/076221 (Janssen), WO2014/128189 (Janssen), WO20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229, U.S. patent application Ser. No. 15/692,161, and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO2018104163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBVE Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Examples of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta), WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301,TAK-117, HMPL-689, tenalisib, voxtalisib, and CLR-1401.

Indoleamine-2,3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100, BGB-A333, JNJ-63723283, GLS-010 (WBP-3055), CX-072, AGEN-2034, GNS-1480 (Epidermal growth factor receptor antagonist; Programmed cell death ligand 1 inhibitor), CS-1001, M-7824 (PD-L1/TGF-β bifunctional fusion protein), Genolimzumab, BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, GS-4224, CX-072, and BMS-936559.

Examples of PD-1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO2016126460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd),WO2015044900 (Aurigene Discovery Technologies Ltd), WO2018026971 (Arising International).

Other examples of PD-1 and/or PDL-1 inhibitors include the compounds disclosed in U.S. Provisional Ser. Nos. 62/630,187, 62/640,534, 62/736,116, and 62/747,029.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), GSK-2879552, and RG-6016.

STING Agonists

Examples of STING agonists include SB-11285, AdVCA0848, STINGVAX, and the compounds disclosed in WO 2018065360 (Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Non-Nucleoside Reverse Transcriptase Inhibitors (NNRTI)

Examples of NNRTI include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

Examples of genome editing systems include a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP) or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA.

CAR-T Cell Therapy

CAR T cell therapy includes a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

TCR T cell therapy includes T cells expressing HBV-specific T cell receptors. TCR-T cells are engineered to target HBV derived peptides presented on the surface of virus-infected cells. In some embodiments, the T-cells express HBV surface antigen (HBsAg)-specific TCR. Examples of TCR-T therapy directed to treatment of HBV include LTCR-H2-1.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/

0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, or any combinations thereof.

In certain embodiments, such tablets are suitable for once daily dosing.

In some embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, or any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, or any combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812, or any combinations thereof.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC®(didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include ceniciriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide $C_{25}P$, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107; interleukin-15/Fc fusion protein; normferon; peginterferon alfa-2a; peginterferon alfa-2b; recombinant interleukin-15; RPI-MN; GS-9620; STING modulators; RIG-I modulators; NOD2 modulators; and IR-103.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira Therapeutics), US20130251673 (Novira Therapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Further examples include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07.

Additional examples of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3 S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS 1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene therapy and cell therapy include the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

CAR-T cell therapy includes a population of immune effector cells engineered to express a chimeric antigen receptor (CAR), wherein the CAR comprises an HIV antigen-binding domain. The HIV antigens include an HIV envelope protein or a portion thereof, gp120 or a portion thereof, a CD4 binding site on gp120, the CD4-induced binding site on gp120, N glycan on gp120, the V2 of gp120, and the membrane proximal region on gp41. In some embodiments, the immune effector cell is a T cell or an NK cell. In some embodiments, the T cell is a CD4+ T cell, a CD8+ T cell, or a combination thereof.

Examples of HIV CAR-T cell therapy include VC-CAR-T.

TCR-T Cell Therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

A compound as disclosed herein may be combined with one or more additional therapeutic agents in any dosage amount of the compound (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc) may be combined with the agents provided herein in any dosage amount of the compound (e.g., from 1 mg to 500 mg of compound) as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula I, II, IIa, IIb, III, IIIa, IV, IVa, IVb, IVc, V, Va, Vb, Vc, VI, VIa, VIb, VIc, VII, VIIa, VIIb, or VIIc) may be combined with the agents provided herein in any dosage amount of the compound (e.g., from 1 mg to 500 mg of compound) as if each combination of dosages were specifically and individually listed.

Cancer and/or Hyper-Proliferative Disease Combination Therapy

In one embodiment, the compound provided herein may be employed with other therapeutic methods of cancer treatment. Preferably, combination therapy with chemotherapeutic, hormonal, antibody, surgical and/or radiation treatments are contemplated.

In some embodiments, the further anti-cancer therapy is surgery and/or radiotherapy. In some embodiments, the further anti-cancer therapy is at least one additional cancer medicament.

In some embodiments, there is provided a combination comprising a compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof and at least one further cancer medicament.

In some embodiments, there is provided a combination comprising a compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof and at least one further cancer medicament, for use in therapy.

In some embodiments, there is provided the use of a combination comprising a compound of Formula I, II, IIa, IIb, III, IIIa, IV, IVa, IVb, IVc, V, Va, Vb, Vc, VI, VIa, VIb, VIc, VII, VIIa, VIIb, or VIIc, or a pharmaceutically acceptable salt thereof and at least one cancer medicament, in the manufacture of a medicament for the treatment of cancer.

Examples of further cancer medicaments include intercalating substances such as anthracycline, doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), and streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate: purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine; steroids such as gestagene, androgene, glucocorticoids, dexamethasone, prednisolone, and prednisone; anti-cancer antibodies such as monoclonal antibodies, e.g., alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, radioactively labeled antibodies and antibody-drug conjugates; anti-cancer peptides such as radioactively labeled peptides and peptide-drug conjugates; and taxane and taxane analogues such as paclitaxel and docetaxel.

In certain embodiments, a method for treating or preventing a cancer or hyper-proliferative disease in a human or animal having or at risk of having the cancer or hyper-proliferative disease is provided, comprising administering to the human or animal a therapeutically effective amount of a compound of Formula I, II, IIa, IIb, III, IIIa, IV, IVa, IVb, IVc, V, Va, Vb, Vc, VI, VIa, VIb, VIc, VII, VIIa, VIIb, or VIIc as disclosed herein, or a pharmaceutically acceptable salt thereof, in combination with a therapeutically effective amount of one or more (e.g., one, two, three, one or two, or one to three) additional therapeutic agents. In one embodiment, a method for treating a cancer or hyper-proliferative disease in a human or animal having or at risk of having the cancer or hyper-proliferative disease is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating a cancer or hyper-proliferative disease, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating cancer or hyper-proliferative disease.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, provided herein is a product comprising a compound described herein and an additional therapeutic agent as a combined preparation for simultaneous, separate, or sequential use in therapy.

The one or more additional therapeutic agents include, but are not limited to, an inhibitor, agonist, antagonist, ligand, modulator, stimulator, blocker, activator or suppressor of a gene, ligand, receptor, protein, or factor. Non-limiting examples of additional therapeutic agents include:

Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1,CHK2), chemokine (C—C motif) receptor (such as CCR2, CCR4, CCR5), chemokine (C—X—C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin Dl, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB 1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF 11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Maj or vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAPI (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1, 2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF 1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase)gene, Rosl tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Spl) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor, or any combinations thereof.

Non-limiting examples of additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

purine analogs, folate antagonists (such as pralatrexate), and related inhibitors;

antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110) and ASTX727;

antibiotics such as dactinomycin, daunorubicin, doxorubicin, idarubicin, anthracyclines, mitoxantrone, bleomycins, and plicamycin (mithramycin);

enzymes such as L-asparaginase which systemically metabolizes L-asparagine and deprives cells which do not have the capacity to synthesize their own asparagine;

antiplatelet agents;

DNAi oligonucleotides targeting Bcl-2, such as PNT2258;

agents that activate or reactivate latent human immunodeficiency virus (HIV), such as panobinostat and romidepsin;

asparaginase stimulators, such as crisantaspase (Erwinase®) and GRASPA (ERY-001, ERY-ASP), and calaspargase pegol;

pan-Trk, ROS1 and ALK inhibitors, such as entrectinib and TPX-0005;

anaplastic lymphoma kinase (ALK) inhibitors, such as alectinib and ceritinib;

antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);

antiproliferative/antimitotic antimetabolites, such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

anti-VEGFR antibodies, such as IMC-3C5, GNR-011 and tanibirumab;

anti-VEGF/DDL4 antibodies, such as ABT-165;

anti-cadherins antibodies, such as HKT-288;

anti-CD70 antibodies, such as AMG-172; anti-leucine-rich repeat containing 15 (LRRC15) antibodies, such as ABBV-085 and ARGX-110;

angiotensin receptor blockers and nitric oxide donors;

antisense oligonucleotides, such as AEG35156, IONIS-KRAS-2.5Rx, EZN-3042, RX-0201, IONIS-AR-2.5Rx, BP-100 (prexigebersen), and IONIS-STAT3-2.5Rx;

DNA interference oligonucleotides, such as PNT2258 and AZD-9150;

anti-ANG-2 antibodies, such as MEDI3617, and LY3127804;

anti-ANG-1/ANG-2 antibodies, such as AMG-780;

anti-MET/EGFR antibodies, such as LY3164530;

anti-EGFR antibodies, such as ABT-414, AMG-595, necitumumab, ABBV-221, depatuxizumab mafodotin (ABT-414), tomuzotuximab, ABT-806, vectibix, modotuximab, and RM-1929;

anti-CSF1R antibodies, such as emactuzumab, LY3022855, AMG-820, and FPA-008 (cabiralizumab);

anti-CD40 antibodies, such as RG7876, SEA-CD40, APX-005M, and ABBV-428;

anti-endoglin antibodies, such as TRC105 (carotuximab);

anti-CD45 antibodies, such as 131I-BC8 (lomab-B);

anti-HER3 antibodies, such as LJM716, and GSK2849330;

anti-HER2 antibodies, such as margetuximab, MEDI4276, and BAT-8001;

anti-HLA-DR antibodies, such as IMMU-114;

anti-IL-3 antibodies, such as JNJ-56022473;

anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, and ABBV-368;

anti-EphA3 antibodies, such as KB-004;

anti-CD20 antibodies, such as obinutuzumab, IGN-002;

anti-CD20/CD3 antibodies, such as RG7828;

anti-CD37 antibodies, such as AGS67E, and otlertuzumab (TRU-016);

anti-ENPP3 antibodies, such as AGS-16C3F;

anti-FGFR-3 antibodies, such as LY3076226, and B-701;

anti-FGFR-2 antibodies, such as GAL-F2;

anti-C5 antibodies, such as ALXN-1210;

anti-CD27 antibodies, such as varlilumab (CDX-1127);

anti-TROP-2 antibodies, such as IMMU-132 anti-NKG2a antibodies, such as monalizumab;

anti-VISTA antibodies, such as HMBD-002;

anti-PVRIG antibodies, such as COM-701;

anti-EpCAM antibodies, such as VB4-845;

anti-BCMA antibodies, such as GSK-2857916;

anti-CEA antibodies, such as RG-7813;

anti-cluster of differentiation 3 (CD3) antibodies, such as MGD015;

anti-folate receptor alpha antibodies, such as IMGN853;

MCL-1 inhibitors, such as AMG-176, S-64315, AZD-5991, 483-LM, A-1210477, UMI-77, and JKY-5-037;

epha2 inhibitors, such as MM-310;

anti LAG-3 antibodies, such as relatlimab (ONO-4482), LAG-525, MK-4280, and REGN-3767;

raf kinase/VEGFR inhibitors, such as RAF-265;

polycomb protein (EED) inhibitors, such as MAK683;

anti-fibroblast activation protein (FAP)/IL-2R antibodies, such as RG7461;

anti-fibroblast activation protein (FAP)/TRAIL-R2 antibodies, such as RG7386;

anti-fucosyl-GM1 antibodies, such as BMS-986012;

p38 MAP kinase inhibitors, such as ralimetinib;

PRMT1 inhibitors, such as MS203;

Sphingosine kinase 2 (SK2) inhibitors, such as opaganib;

FLT3-ITD inhibitors, such as BCI-332;

Nuclear erythroid 2-related factor 2 stimulators, such as omaveloxolone (RTA-408);

Tropomyosin receptor kinase (TRK) inhibitors, such as LOXO-195, and ONO-7579;

anti-ICOS antibodies, such as JTX-2011, and GSK3359609;

anti-DR5 (TRAIL2) antibodies, such as DS-8273;

anti-GD2 antibodies, such as APN-301;

anti-interleukin-17 (IL-17) antibodies, such as CJM-112;

anti-carbonic anhydrase IX antibodies, such as TX-250;

anti-CD38-attenukine, such as TAK573;

anti-Mucin 1 antibodies, such as gatipotuzumab;

Mucin 1 inhibitors, such as GO-203-2C;

MARCKS protein inhibitors, such as BIO-11006;

Folate antagonists, such as arfolitixorin;

Galectin-3 inhibitors, such as GR-MD-02;

Phosphorylated P68 inhibitors, such as RX-5902;

CD95/TNF modulators, such as ofranergene obadenovec;

PI3K/Akt/mTOR inhibitors, such as ABTL-0812;

pan-PIM kinase inhibitors, such as INCB-053914;

IL-12 gene stimulators, such as EGEN-001, and tavokinogene telseplasmid;

Heat shock protein HSP90 inhibitors, such as TAS-116, and PEN-866;

VEGF/HGF antagonists, such as MP-0250;

SYK tyrosine kinase/FLT3 tyrosine kinase inhibitors, such as TAK-659;

SYK tyrosine kinase/JAK tyrosine kinase inhibitors, such as ASN-002;

FLT3 tyrosine kinase inhibitor, such as FF-10101;

FLT3 tyrosine kinase agonist, such as CDX-301;

FLT3/MEK1 inhibitors, such as E-6201;

IL-24 antagonist, such as AD-IL24;

RIG-I agonists, such as RGT-100;

Aerolysin stimulators, such as topsalysin;
P-Glycoprotein 1 inhibitors, such as HM-30181A;
CSF-1 antagonists, such as ARRY-382, and BLZ-945;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), and TAS-4464;
Pleiotropic pathway modulators, such as avadomide (CC-122);
FoxM1 inhibitors, such as thiostrepton;
Anti-MUC1 antibodies, such as Mab-AR-20.5;
anti-CD38 antibodies, such as isatuximab, and MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, and PT-2385;
CD122 agonists such as NKTR-214;
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
EGFR/ErbB-2 inhibitors, such as varlitinib;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
Kit tyrosine kinase/PDGF receptor alpha antagonists such as DCC-2618;
KIT inhibitors, such as PLX-9486;
Exportin 1 inhibitors, such as eltanexor;
EGFR/ErbB2/Ephb4 inhibitors, such as tesevatinib;
anti-CD33 antibodies, such as IMGN-779;
anti-KMA antibodies, such as MDX-1097;
anti-TIM-3 antibodies, such as TSR-022, LY-3321367, and MBG-453;
anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-Erbb antibodies, such as CDX-3379, HLX-02, and seribantumab;
anti-APRIL antibodies, such as BION-1301;
Anti-Tigit antidbodies, such as BMS-986207, and RG-6058;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
p70s6k inhibitors, such as MSC2363318A;
methionine aminopeptidase 2 (MetAP2) inhibitors, such as M8891, and APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MEDI4736), avelumab, CK-301, (MSB0010718C), MEDI0680, CX-072, CBT-502, PDR-001 (spartalizumab), TSR-042 (dostarlimab), JTX-4014, BGB-A333, SHR-1316, CS-1001 (WBP-3155), KN-035, IBI-308, FAZ-053, and MDX1105-01;
PD-L1/VISTA antagonists such as CA-170;
anti-PD-L1/TGFβ antibodies, such as M7824;
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, and RG7741 (CHK1/2);
CXCR4 antagonists, such as BL-8040, LY2510924, burixafor (TG-0054), X4P-002, and X4P-001-IO;
EXH2 inhibitors, such as GSK2816126;
HER2 inhibitors, such as neratinib, and tucatinib (ONT-380);
KDM1 inhibitors, such as ORY-1001, IMG-7289, INCB-59872, and GSK-2879552;
CXCR2 antagonists, such as AZD-5069;
GM-CSF antibodies, such as lenzilumab;
DNA dependent protein kinase inhibitors, such as MSC2490484A (nedisertib), VX-984, and AsiDNA (DT-01);
protein kinase C (PKC) inhibitors, such as LXS-196, and sotrastaurin;
Selective estrogen receptor downregulators (SERD), such as fulvestrant (Faslodex®), RG6046, RG6047, elacestrant (RAD-1901) and AZD9496;
Selective estrogen receptor covalent antagonists (SERCAs), such as H3B-6545;
selective androgen receptor modulator (SARM), such as GTX-024, and darolutamide;
transforming growth factor-beta (TGF-beta) kinase antagonists, such as galunisertib;
anti-transforming growth factor-beta (TGF-beta) antibodies, such as LY3022859, NIS793, and XOMA 089;

bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), and MGD-009 (CD3/B7H3);

Mutant selective EGFR inhibitors, such as PF-06747775, EGF816 (nazartinib), ASP8273, ACEA-0010, and BI-1482694;

Anti-GITR (glucocorticoid-induced tumor necrosis factor receptor-related protein) antibodies, such as MEDI1873, FPA-154, INCAGN-1876, TRX-518, BMS-986156, MK-1248, and GWN-323;

anti-delta-like protein ligand 3 (DDL3) antibodies, such as rovalpituzumab tesirine;

anti-clusterin antibodies, such as AB-16B5;

anti-Ephrin-A4 (EFNA4) antibodies, such as PF-06647263;

anti-RANKL antibodies, such as denosumab;

anti-mesothelin antibodies, such as BMS-986148, and Anti-MSLN-MMAE;

anti-sodium phosphate cotransporter 2B (NaP2B) antibodies, such as lifastuzumab;

anti-c-Met antibodies, such as ABBV-399;

Adenosine A2A receptor antagonists, such as CPI-444, AZD-4635, preladenant, and PBF-509;

Alpha-ketoglutarate dehydrogenase (KGDH) inhibitors, such as CPI-613;

XPO1 inhibitors, such as selinexor (KPT-330);

Isocitrate dehydrogenase 2 (IDH2) inhibitors, such as enasidenib (AG-221);

IDH1 inhibitors such as AG-120, and AG-881 (IDH1 and IDH2), IDH-305, and BAY-1436032;

interleukin-3 receptor (IL-3R) modulators, such as SL-401;

Arginine deiminase stimulators, such as pegargiminase (ADI-PEG-20);

antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 (trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, and ABBV-085;

claudin-18 inhibitors, such as claudiximab;

β-catenin inhibitors, such as CWP-291;

anti-CD73 antibodies, such as MEDI-9447 (oleclumab), CPX-006, IPH-53, and BMS-986179;

CD73 antagonists, such as AB-680, PSB-12379, PSB-12441, and PSB-12425;

CD39/CD73 antagonists, such as PBF-1662;

chemokine receptor 2 (CCR) inhibitors, such as PF-04136309, CCX-872, and BMS-813160 (CCR2/CCR5);

thymidylate synthase inhibitors, such as ONX-0801;

ALK/ROS1 inhibitors, such as lorlatinib;

tankyrase inhibitors, such as G007-LK;

Mdm2 p53-binding protein inhibitors, such as CMG-097, and HDM-201;

c-PIM inhibitors, such as PIM447;

BRAF inhibitors, such as dabrafenib, vemurafenib, encorafenib (LGX818), and PLX8394;

sphingosine kinase-2 (SK2) inhibitors, such as Yeliva® (ABC294640);

cell cycle inhibitors, such as selumetinib (MEK1/2), and sapacitabine;

AKT inhibitors such as MK-2206, ipatasertib, afuresertib, AZD5363, ARQ-092, capivasertib, and triciribine;

anti-CTLA-4 (cytotoxic T-lymphocyte protein-4) inhibitors, such as tremelimumab, AGEN-1884, and BMS-986218;

c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361;

c-Met/VEGFR inhibitors, such as BMS-817378, and TAS-115;

c-Met/RON inhibitors, such as BMS-777607;

BRAF/EGFR inhibitors, such as BGB-283;

bcr/abl inhibitors, such as rebastinib, and asciminib;

MNK1/MNK2 inhibitors, such as eFT-508;

mTOR inhibitor/cytochrome P450 3A4 stimulators, such as TYME-88 lysine-specific demethylase-1 (LSD1) inhibitors, such as CC-90011;

Pan-RAF inhibitors, such as LY3009120, LXH254, and TAK-580;

Raf/MEK inhibitors, such as RG7304;

CSF1R/KIT and FLT3 inhibitors, such as pexidartinib (PLX3397);

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291);

topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114);

corticosteroids, such as cortisone, dexamethasone, hydrocortisone, methylprednisolone, prednisone, and prednisolone;

growth factor signal transduction kinase inhibitors;

nucleoside analogs, such as DFP-10917;

Axl inhibitors, such as BGB-324 (bemcentinib), and SLC-0211;

BET inhibitors, such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, mivebresib, BI-894999, PLX-2853, PLX-51107, CPI-0610, and GS-5829;

PARP inhibitors, such as olaparib, rucaparib, veliparib, talazoparib, ABT-767, and BGB-290;

Proteasome inhibitors, such as ixazomib, carfilzomib (Kyprolis®), and marizomi;

Glutaminase inhibitors, such as CB-839;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVac™, stapuldencel-T, eltrapuldencel-T, SL-701, BSK01™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; and GI-4000;

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, siltuximab, and AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), and BMS-906024;

anti-myostatin inhibitors, such as landogrozumab;

hyaluronidase stimulators, such as PEGPH-20;

Wnt pathway inhibitors, such as SM-04755, PRI-724, and WNT-974;

gamma-secretase inhibitors, such as PF-03084014, MK-0752, and RO-4929097;

Grb-2 (growth factor receptor bound protein-2) inhibitors, such as BP1001;

TRAIL pathway-inducing compounds, such as ONC201, and ABBV-621;

Focal adhesion kinase inhibitors, such as VS-4718, defactinib, and GSK2256098;

hedgehog inhibitors, such as saridegib, sonidegib (LDE225), glasdegib and vismodegib;

Aurora kinase inhibitors, such as alisertib (MLN-8237), and AZD-2811, AMG-900, barasertib, and ENMD-2076;

HSPB 1 modulators (heat shock protein 27, HSP27), such as brivudine, and apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), and ME-344;

mTOR/PI3K inhibitors, such as gedatolisib, GSK2141795, omipalisib, and RG6114;

Hsp90 inhibitors, such as AUY922, onalespib (AT13387), SNX-2112, and SNX5422;

Murine double minute (mdm2) oncogene inhibitors, such as DS-3032b, RG7775, AMG-232, HDM201, and idasanutlin (RG7388);

CD137 agonists, such as urelumab, and utomilumab (PF-05082566);

STING agonists, such as ADU-S100 (MIW-815), SB-11285, MK-1454, SR-8291, AdVCA0848, GSK-532, SYN-STING, MSA-1, and SR-8291;

FGFR inhibitors, such as FGF-401, INCB-054828, BAY-1163877, AZD4547, JNJ-42756493, LY2874455, and Debio-1347;

fatty acid synthase (FASN) inhibitors, such as TVB-2640;

Anti-KIR monoclonal antibodies, such as lirilumab (IPH-2102), and IPH-4102;

Antigen CD19 inhibitors, such as MOR208, MEDI-551, AFM-11, and inebilizumab;

CD44 binders, such as A6;

protein phosphateae 2A (PP2A) inhibitors, such as LB-100;

CYP17 inhibitors, such as seviteronel (VT-464), ASN-001, ODM-204, CFG920, and abiraterone acetate;

RXR agonists, such as IRX4204;

hedgehog/smoothened (hh/Smo) antagonists, such as taladegib, and patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, and GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, and OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD1775 (adavosertib);

Rho kinase (ROCK) inhibitors, such as AT13148, and KD025;

ERK inhibitors, such as GDC-0994, LY3214996, and MK-8353;

IAP inhibitors, such as ASTX660, debio-1143, birinapant, APG-1387, and LCL-161;

RNA polymerase inhibitors, such as lurbinectedin (PM-1183), and CX-5461;

Tubulin inhibitors, such as PM-184, BAL-101553 (lisavanbulin), OXI-4503, fluorapacin (AC-0001), and plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, and asunercept;

WT1 inhibitors, such as DSP-7888;

splicing factor 3B subunit1 (SF3B1) inhibitors, such as H3B-8800;

PDGFR alpha/KIT mutant-specific inhibitors such as BLU-285;

SHP-2 inhibitors, such as TNO155 (SHP-099), and RMC-4550; and retinoid Z receptor gamma (RORγ) agonists, such as LYC-55716;

In some embodiments, provided herein are methods of treating or preventing a cancer or hyper-proliferative disease in a human or animal having or at risk of having the cancer or hyper-proliferative disease is provided, comprising administering to the human or animal a therapeutically effective amount of a compound of Formula I, II, IIa, IIb, III, IIIa, IV, IVa, IVb, IVc, V, Va, Vb, Vc, VI, VIa, VIb, VIc, VII, VIIa, VIIb, or VIIc as disclosed herein, or a pharmaceutically acceptable salt thereof, in combination with a therapeutically effective amount of one or more (e.g., one, two, three, one or two, or one to three) additional therapeutic agents selected from the group consisting of apoptosis signal-regulating kinase (ASK) inhibitors; Bruton's tyrosine kinase (BTK) inhibitors; cluster of differentiation 47 (CD47) inhibitors; cyclin-dependent kinase (CDK) inhibitors; discoidin domain receptor (DDR) inhibitors; histone deacetylase (HDAC) inhibitors; indoleamine-pyrrole-2,3-dioxygenase (IDO1) inhibitors; Janus kinase (JAK) inhibitors; lysyl oxidase-like protein (LOXL) inhibitors; matrix metalloprotease (MMP) inhibitors; mitogen-activated protein kinase (MEK) inhibitors; phosphatidylinositol 3-kinase (PI3K) inhibitors; spleen tyrosine kinase (SYK) inhibitors; toll-like receptor 8 (TLR8) inhibitors; toll-like receptor 9 (TLR9) inhibitors; tyrosine-kinase inhibitors (TKIs), or a pharmaceutically acceptable salt of any of the foregoing, or any combinations thereof. Non-limiting examples include:

Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences);

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, and TAS-5315;

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621;

Cyclin-dependent Kinase (CDK) Inhibitors: CDK inhibitors include inhibitors of CDK 1, 2, 3, 4, 6, 7 and 9, such as abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02;

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations);

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat;

Indoleamine-pyrrole-2, 3-dioxygenase (IDO1) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, and LY-3381916;

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB 1518), peficitinib (ASP015K), ruxolitinib, tofacitinib (formerly tasocitinib), INCB052793, and XL019;

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics);

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics);

Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib;

Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences);

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), GS-9876, and those described in U.S. Pat. No. 8,450,321 (Gilead Connecticut) and those described in U.S. 2015/0175616;

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, VTX-1463, and VTX-763;

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042; and Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, TH-4000, and MEDI-575 (anti-PDGFR antibody).

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but are not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethyl enemelamine, triethylenephosphoramide, triethyl enethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammal1 and calicheamicin phil1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine;

polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, and ODM-204.

Examples of progesterone receptor antagonist include onapristone.

Anti-Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, and inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

Examples of immunotherapeutic agents include but are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. In some embodiments, a combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy

Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; and genetic approaches to modify cellular activity to further alter endogenous immune responsiveness against cancer.

Gene Editors

Examples of genome editing system include a CRISPR/Cas9 system, a zinc finger nuclease system, a TALEN system, a homing endonucleases system, and a meganuclease system.

CAR-T Cell Therapy and TCR-T Cell Therapy

CAR-T cell therapy includes a population of immune effector cells engineered to express a chimeric antigen receptor (CAR), wherein the CAR comprises a tumor antigen-binding domain. The immune effector cell is a T cell or an NK cell. TCR-T cell therapy includes TCR-T cells that are engineered to target tumor derived peptides present on the surface of tumor cells. Cells can be autologous or allogeneic.

In some embodiments, the CAR comprises an antigen binding domain, a transmembrane domain, and an intracellular signaling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 ld, ITGAE, CD103, ITGAL, CD 1 la, LFA-1, ITGAM, CD1 lb, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMFi, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Lyl08), SLAM (SLAMFi, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GaINAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like modulecontaining mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, and Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502,CMD-601, CMD-602, and CSG-005.

In some embodiments, the tumor targeting antigen includes: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR); Anti-CLL-1 antibodies, such as KITE-796; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T; B-lymphocyte antigen CD20, such as ATTCK-20; B-lymphocyte cell adhesion, such as UCART-22, and JCAR-018 (WO2016090190); NY-ESO-1, such as GSK-3377794, and TBI-1301; Carbonic anhydrase, such as DC-Ad-GMCAIX; Caspase 9 suicide gene, such as CaspaCIDe DLI, and BPX-501; CCR5, such as SB-728; CDw123, such as MB-102, and UCART-123; CD20m such as CBM-C20.1; CD4, such as ICG-122; CD30, such as CART30 (CBM- C30.1); CD33, such as CIK-CAR.CD33; CD38, such as T-007, and UCART-38; CD40 ligand, such as BPX-201; CEACAM protein 4 modulators, such as MG7-CART; Claudin 6, such as CSG-002; EBV targeted, such as CMD-003; EGFR, such as autologous 4H11-28z/fIL-12/EFGRt T cell; Endonuclease, such as PGN-514, and PGN-201; Epstein-Barr virus specific T-lymphocytes, such as TT-10; Erbb2, such as CST-102 and CIDeCAR; Ganglioside (GD2), such as 4SCAR-GD2; Glutamate carboxypeptidase II, such as CIK-CAR.PSMA, CART-PSMA-TGFBRDN, and P-PSMA-101; Glypican-3 (GPC3), such as TT-16 and GLY-CAR; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTRO87; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 L1CAM (CD171), such as JCAR-023; Latent membrane protein 1/Latent membrane protein 2, such as Ad5f35-LMPdl-2-transduced autologous dendritic cells; Melanoma associated antigen 10, such as MAGE-A10C796T and MAGE-A10 TCR; Melanoma associated antigen 3/Melanoma associated antigen 6 (MAGE A3/A6) such as KITE-718; Mesothelin, such as CSG-MESO and TC-210; NKG2D, such as NKR-2; Ntrkrl tyrosine kinase receptor, such as JCAR-024; T cell receptors, such as BPX-701 and IMCgp100; T-lymphocyte, such as TT-12; Tumor infiltrating lymphocytes, such as LN-144 and LN-145; and Wilms tumor protein, such as JTCR-016, WT1-CTL.

Lymphoma or Leukemia Combination Therapy

In some embodiments, the additional therapeutic agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus ($CC_{1-77}9$), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), and venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The above-mentioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and non-myeloablative allogeneic hematopoietic stem cell transplantation.

Non-Hodgkin's Lymphomas Combination Therapy

In some embodiments, the additional therapeutic agents are suitable for treating non-Hodgkin's lymphomas (NHL), especially those of B cell origin, which include monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R—CHOP, R—FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

In some embodiments, the additional therapeutic agents are suitable for treating mantle cell lymphoma (MCL), which include combination chemotherapies such as CHOP, hyperCVAD, and FCM. These regimens can also be supplemented with the monoclonal antibody rituximab to form combination therapies R-CHOP, hyperCVAD-R, and R-FCM. Any of the above-mentioned therapies may be combined with stem cell transplantation or ICE in order to treat MCL.

Other examples of therapeutic agents suitable for treating MCL include:
- immunotherapy, such as monoclonal antibodies (like rituximab) and cancer vaccines, such as GTOP-99, which are based on the genetic makeup of an individual patient's tumor;
- radioimmunotherapy, wherein a monoclonal antibody is combined with a radioisotope particle, such as iodine-131 tositumomab (BEXXAR®), yttrium-90 ibritumomab tiuxetan (ZEVALIN®), and BEXXAR® in sequential treatment with CHOP;
- autologous stem cell transplantation coupled with high-dose chemotherapy, administering proteasome inhibitors such as bortezomib (VELCADE® or PS-341), or administering antiangiogenesis agents such as thalidomide, especially in combination with rituximab;
- drugs that lead to the degradation of Bcl-2 protein and increase cancer cell sensitivity to chemotherapy, such as oblimersen, in combination with other chemotherapeutic agents;
- mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents;
- other agents such as flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17-AAG).

Waldenstrom's Macroglobulinemia Combination Therapy

In some embodiments, the additional therapeutic agents are suitable for treating Waldenstrom's Macroglobulinemia (WM), which include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combinations thereof.

Other examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

In some embodiments, the additional therapeutic agents are suitable for treating diffuse large B-cell lymphoma (DLBCL), which include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy

In some embodiments, the additional therapeutic agents are suitable for treating chronic lymphocytic leukemia (CLL), which include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

In some embodiments, the additional therapeutic agents are suitable for treating myelofibrosis, which include hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors include lestaurtinib, bosutinib, imatinib, gilteritinib, radotinib, and cabozantinib.

Hyperproliferative Disease Combination Therapy

In some embodiments, the additional therapeutic agents are suitable for treating a hyper-proliferative disease, which include gemcitabine, nab-paclitaxel, and gemcitabine/nab-paclitaxel with a JAK inhibitor and/or PI3Kδ inhibitor.

Bladder Cancer Combination Therapy

In some embodiments, the additional therapeutic agents are suitable for treating bladder cancer, which include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combinations thereof.

Breast Cancer Combination Therapy

In some embodiments, the additional therapeutic agents are suitable for treating breast cancer, which include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

In some embodiments, the additional therapeutic agents are suitable for treating triple negative breast cancer, which include cyclophosphamide, docetaxel, doxorubicin, epirubicin, fluorouracil, paclitaxel, and combinations thereof.

Colorectal Cancer Combination Therapy

In some embodiments, the additional therapeutic agents are suitable for treating colorectal cancer, which include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

In some embodiments, the additional therapeutic agents are suitable for treating castration-resistant prostate cancer, which include abiraterone, cabazitaxel, docetaxel, enzalutamide, prednisone, sipuleucel-T, and any combinations thereof.

Esophageal and Esophagogastric Junction Cancer Combination Therapy

In some embodiments, the additional therapeutic agents are suitable for treating esophageal and esophagogastric junction cancer, which include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

In some embodiments, the additional therapeutic agents are suitable for treating gastric cancer, which include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy

In some embodiments, the additional therapeutic agents are suitable for treating head & neck cancer, which include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

In some embodiments, the additional therapeutic agents are suitable for treating hepatobiliary cancer, which include capecitabine, cisplatin, fluoropyrimidine, 5-fluorourcil, gemecitabine, oxaliplatin, sorafenib, and any combinations thereof.

Hepatocellular Carcinoma Combination Therapy

In some embodiments, the additional therapeutic agents are suitable for treating hepatocellular carcinoma, which include capecitabine, doxorubicin, gemcitabine, sorafenib, and any combinations thereof.

Non-Small Cell Lung Cancer Combination Therapy

In some embodiments, the additional therapeutic agents are suitable for treating non-small cell lung cancer (NSCLC), which include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

In some embodiments, the additional therapeutic agents are suitable for treating small cell lung cancer (SCLC), which include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

In some embodiments, the additional therapeutic agents are suitable for treating melanoma, which include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

In some embodiments, the additional therapeutic agents are suitable for treating ovarian cancer, which include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

In some embodiments, the additional therapeutic agents are suitable for treating pancreatic cancer, which include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

In some embodiments, the additional therapeutic agents are suitable for treating renal cell carcinoma, which include axitinib, bevacizumab, cabozantinib, erlotinib, everolimus, levantinib, nivolumab, pazopanib, sorafenib, sunitinib, temsirolimus, and any combinations thereof.

VII. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

LIST OF ABBREVIATIONS AND ACRONYMS

Abbreviation Meaning
° C. Degree Celsius
Ac Acetyl
ACN or MeCN Acetonitrile
AcOH Acetic acid
aq. Aqueous
Ar Argon
ATP Adenosine triphosphate
Boc tert-butyloxycarbonyl
br Broad
ca circa
$CH(OCH_3)_3$ Trimethyl orthoformate
c-Pr or c-propyl cyclopropyl
Cy cyclohexyl
d Doublet or deuterated
DCE Dichloroethene
DCM or $CH_2Cl_2$ Dichloromethane
dd Doublet of doublets
DIEA or DIPEA Diisopropylethylamine
DMAc or DMA Dimethylacetamide
DMAP Dimethylaminopyridine
DMF Dimethylformamide
DMSO Dimethylsulfoxide
DME Dimethoxyethane
dt Doublet-triplet
eq Equivalents
ES/MS Electrospray mass spectrometry
Et Ethyl
EA or EtOAc Ethyl acetate
g Grams
HATU 1-[Bis(dimethylamino)methylene]-1H-1,2,3-triazolo[4,5-b]pyridinium 3-oxid hexafluorophosphate
HCOOH Formic acid
Hex Hexanes
HPLC High pressure liquid chromatography
hr or h or hrs Hours
Hz Hertz
IPA Isopropyl alcohol
i-pr or i-Pr Isopropyl
J Coupling constant (MHz)
$K_2CO_3$ Potassium carbonate
Kg or kg Kilogram
L Liter
LCMS or LC-MS Liquid chromatography-mass spectrometry
M Molar
m multiplet
M+ Mass peak
M+H+ Mass peak plus hydrogen
Me Methyl
MeOH Methanol
mg Milligram
MHz Megahertz
ml or mL Milliliter
mM Millimolar
mmol Millimole
mol Mole
MS Mass spectroscopy
Ms methanesulfonyl
N Normal
NaH Sodium hydride
n-Bu or Bu Butyl
$NH_4Cl$ Ammonium Chloride
NMR Nuclear magnetic resonance
NMP N-methylpyrrolidinone
Pd—C/Pd/C Palladium on Carbon
$Pd_2(dba)_3$ Tris(dibenzylideneacetone)dipalladium
PE Petroleum ether
Ph Phenyl
q Quartet
RP Reverse phase
RT or rt Room temperature
s Singlet
sat. or satd. Saturated
sec second(s)
sec-Bu sec-Butyl
t Triplet
T3P Propylphosphonic anhydride solution
TEA Triethylamine
t-Bu or tert-Bu or t-butyl tert-Butyl
TFA Trifluoroacetic acid
TfOH Triflic acid
THF Tetrahydrofuran
TR-FRET Time-resolved fluorescence energy transfer
wt Weight
δ Chemical shift (ppm)
μL or μl Microliter
μM Micromolar General Synthetic Schemes General Reaction Schemes I, II, III, IV, V, VI, VII, VIII, and IX are provided as further embodiments of the present disclosure and illustrate general methods which were used to prepare certain compounds of the present disclosure and which can be used to prepare additional compounds of the present disclosure. Each of the variables (e.g., $R^1$, $R^2$, $R^3$, $R^4$) of formulas (1)-(27) are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure. The compounds prepared herein can be purified using the methods known to the person of ordinary skill in the art, including those described herein. A skilled artisan will appreciate that when acids (e.g., TFA) are present in purification solvents, then the final product may be isolated as a salt (for e.g., TFA salt).

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

Reaction Scheme I

The compounds of Formula I may be prepared using the methods similar to the Reaction Scheme I shown below.

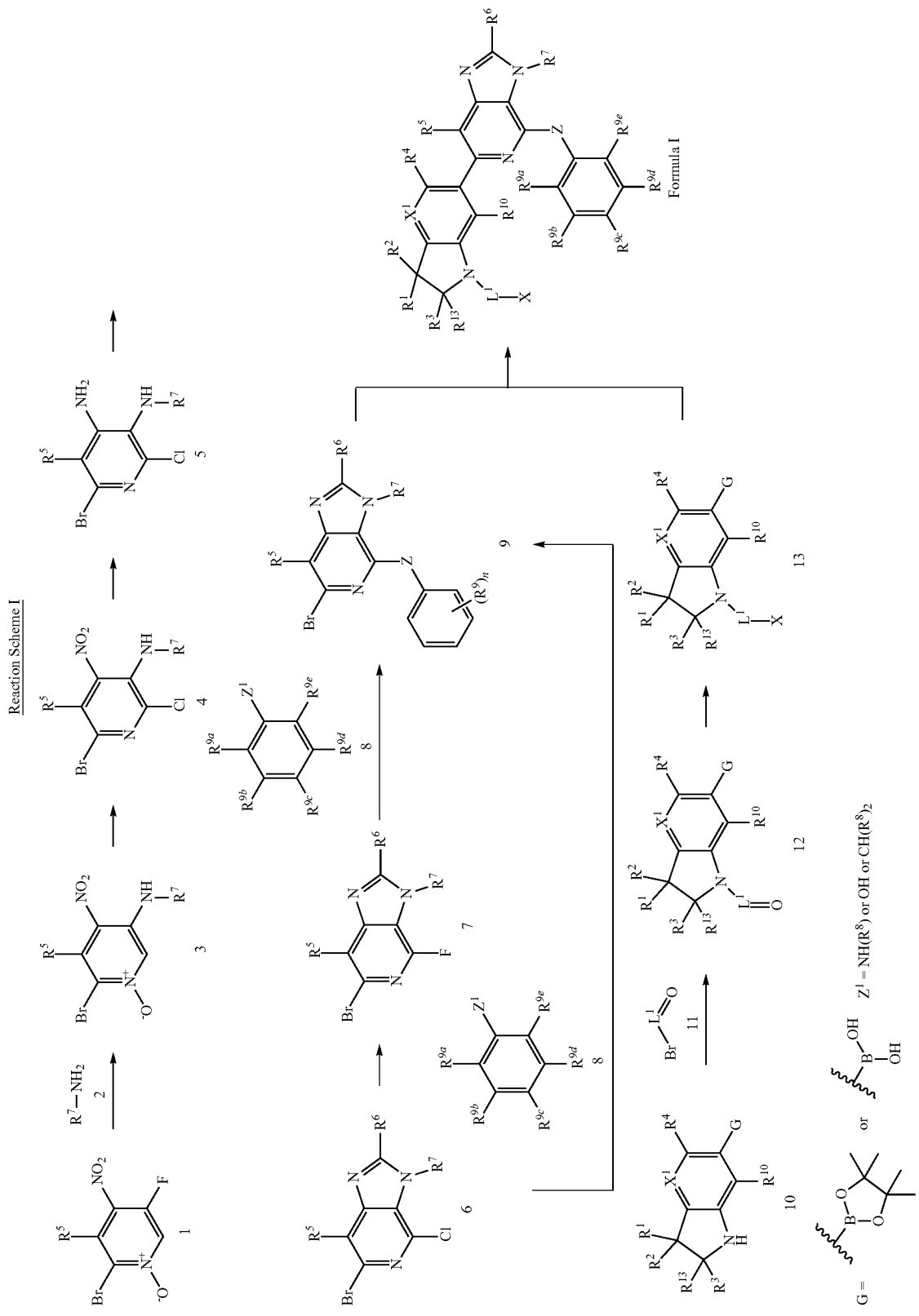
Reaction Scheme I

Step 1—Preparation of a Compound of Formula (3)

The compounds of formula (3) can be made by combining compounds (1) and (2). Compounds (1) and (2) are commercially available or can be made by methods known in the art. Compounds (1) and (2) can be mixed in a suitable solvent such as THF. After stirring at a temperature between 0° C. and 100° C. for between 10 min and 24 h or until reaction is complete, the reaction is allowed to cool to room temperature. The compound of formula (3) can be obtained by filtration or precipitation.

Step 2—Preparation of a Compound of Formula (4)

The compounds of formula (4) may be prepared by chlorination of the compounds of formula (3) by methods known in the art. A compound of formula (3) may be mixed with $POCl_3$ in a suitable solvent such as toluene. After stirring at a temperature between 0° C. and 100° C. for between 10 min and 24 h or until reaction is complete, the reaction is allowed to cool to room temperature. The solvent can then be removed under reduced pressure. To extract the compound of formula (4), an organic solvent such as ethyl acetate may be added, followed by washing with water and brine. The organic phase can be concentrated to obtain the compound of formula (4). The compound of formula (4) may be purified by any suitable methods known in the art such as chromatography on silica gel, trituration, precipitation, or crystallization.

Step 3—Preparation of a Compound of Formula (5)

The compounds of formula (5) may be prepared by reduction of the compounds of formula (4) by methods known in the art. A compound of formula (4) can be mixed with Zinc dust and ammonium chloride in suitable solvent such as THF, MeOH, or water, or a mixture of solvent consisting of THF, MeOH, and water. After stirring at a temperature between 0° C. and 100° C. for between 1 h and 24 h or until reaction is complete, the reaction is allowed to cool to room temperature and filtered through celite bed. To extract the compound of formula (5), an organic solvent such as ethyl acetate may be added, followed by washing with water and brine. The organic phase can be concentrated to obtain the compound of formula (5). The compound of formula (5) may be purified by any suitable methods known in the art such as chromatography on silica gel, trituration, precipitation, or crystallization.

Step 4—Preparation of a Compound of Formula (6)

The compounds of formula (6) may be prepared by cyclization of the compounds of formula (5) by methods known in the art. A compound of formula (5) can be mixed with trimethyl orthoformate and formic acid. After stirring at a temperature between 0° C. and 100° C. for between 1 h and 24 h or until reaction is complete, the remaining solvent is removed via distillation. To extract the compound of formula (6), an organic solvent such as dichloromethane may be added, followed by washing with water and brine. The organic phase can be concentrated to obtain the compound of formula (6). The compound of formula (6) may be purified by any suitable methods known in the art such as chromatography on silica gel, trituration, precipitation, crystallization, or washing with organic solvent such as ether including but not limited to methyl t-butyl ether.

Step 5—Preparation of a Compound of Formula (7)

The compounds of formula (7) may be prepared by fluorination of the compounds of formula (6) by methods known in the art. A compound of formula (6) can be mixed with cesium fluoride in a solvent such DMF. After stirring at a temperature between room temperature and 110° C. for between 1 h and 24 h or until reaction is complete, the reaction is cooled to between 0° C. and room temperature by adding ice water or by adding the reaction mixture to ice water. To extract the compound of formula (7), an organic solvent such as ethyl acetate may be added, followed by washing with water and brine. The organic phase can be concentrated to obtain the compound of formula (7). The compound of formula (7) may be purified by any suitable methods known in the art such as chromatography on silica gel, trituration, precipitation, or crystallization.

Step 6—Preparation of a Compound of Formula (9)

The compounds of formula (9) can be made by combining compounds of formulas (6) and (8) or combining compounds of formulas (7) and (8) by methods known in the art. Compounds of formula (8) are commercially available or can be made by methods known in the art. A compound of formula (8) can be mixed with either compounds of formula (6) or (7) in the presence of a base such as sodium hydride in a suitable solvent such as NMP or DMA. After stirring at a temperature between room temperature and 100° C. for between 1 h and 24 h or until reaction is complete, the reaction can be added to water and treated with acid such as 10% citric acid. The compound of formula (7) may be obtained by filtration or precipitation.

Step 7—Preparation of a Compound of Formula (12)

The compounds of formula (12) can be made by combining compounds of formulas (10) and (11) by methods known in the art. Compounds of formulas (10) and (11) are commercially available or can be made by methods known in the art. Compounds of formulas (10) and (11) can be mixed in the presence of a base such as potassium carbonate in a suitable solvent such as DMF. After stirring at a temperature between room temperature and 50° C. for between 1 h and 24 h or until reaction is complete, the reaction is cooled to room temperature. To extract the compound of formula (12), an organic solvent such as ethyl acetate may be added, followed by washing with water and brine. The organic phase can be concentrated to obtain the compound of formula (12). The compound of formula (12) may be purified by any suitable methods known in the art such as chromatography on silica gel, trituration, precipitation, or crystallization.

Step 8—Preparation of a Compound of Formula (13)

The compounds of formula (13) may be prepared by reductive amination of the compounds of formula (12) by methods known in the art. Compounds of formula (12) and amines, that are commercially available or synthesized by methods known in the art, can be mixed with a reducing agent such as sodium triacetoxy borohydride or sodium cyanoborohydride in the presence of acid, such as acetic acid, or Lewis acid, such as zinc chloride, in a suitable solvent such as dichloroethane or methanol. After stirring at a temperature between 0° C. and room temperature for between 1 h and 24 h or until reaction is complete, the reaction may be added to aqueous solution such as saturated aqueous sodium bicarbonate solution. To extract the compound of formula (13), an organic solvent such as methylene chloride may be added, followed by washing with water and brine. The organic phase can be concentrated to obtain the compound of formula (13). The compound of formula (13) may be purified by any suitable methods known in the art such as chromatography on silica gel, trituration, precipitation, or crystallization.

Step 9—Preparation of a Compound of Formula I

The compounds of Formula I can be made by combining the compounds of formula (9) and compounds of formula (13) by methods known in the art. Compounds of formulas (9) and (13) can be mixed in the presence of a catalyst such as tetrakis(triphenylphosphine)palladium and a base such as cesium carbonate, sodium carbonate, or potassium phosphate tribasic in a suitable solvent such as a mixture of dimethoxyethane and water, or a mixture of DMAc and water. After stirring at a temperature between 50° C. and 150° C. for between 1 and 24 hours, the reaction is allowed to cool to room temperature. Compounds of Formula I may be filtered and concentrated under reduced pressure. To extract the compound of Formula I, an organic solvent such as methylene chloride may be added, followed by washing with water and brine. The organic phase can be concentrated to obtain the compound of Formula I. The compound of Formula I may be purified by any suitable methods known in the art such as chromatography on silica gel, reverse phase chromatography, trituration, precipitation, or crystallization.

Reaction Scheme II

The compounds of Formula I may be prepared using the alternate methods similar to the Reaction Scheme II shown below.

Reaction Scheme II

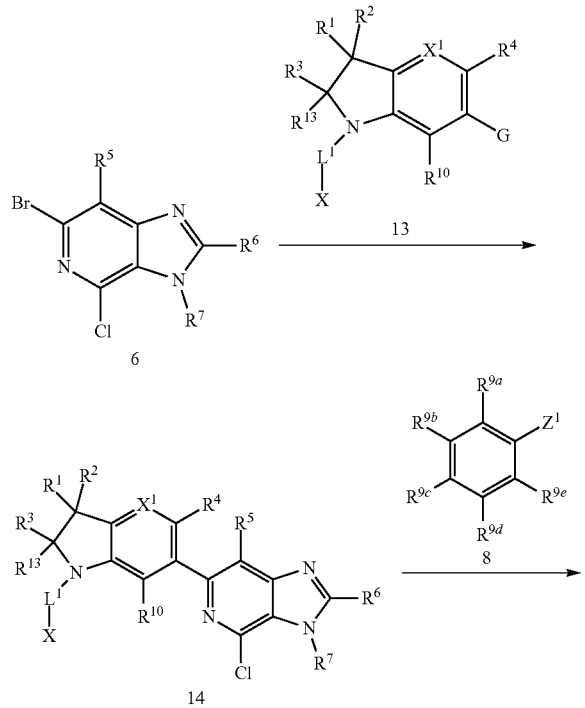

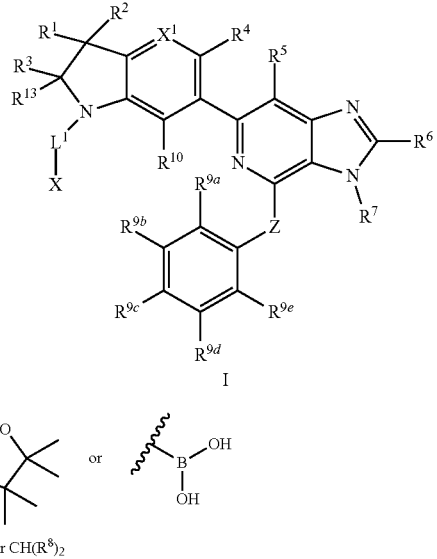

$Z^1 = NH(R^8)$ or OH or $CH(R^8)_2$

Step 1—Preparation of a Compound of Formula (14)

The compounds of formula (14) can be made by combining the compounds of formulas (6) and (13) by methods known in the art. Compounds of formulas (9) and (13) can be mixed in the presence of a catalyst such as tetrakis (triphenylphosphine)palladium and a base such as cesium carbonate, sodium carbonate, or potassium phosphate tribasic in a suitable solvent such as a mixture of dimethoxyethane and water, or a mixture of DMAc and water. After stirring at a temperature between 50° C. and 150° C. for between 1 and 24 hours, the reaction is allowed to cool to room temperature. Compounds of formula (14) may be filtered and concentrated under reduced pressure. To extract the compound of formula (14), an organic solvent such as methylene chloride may be added, followed by washing with water and brine. The organic phase can be concentrated to obtain the compound of formula (14). The compound of formula (14) may be purified by any suitable methods known in the art such as chromatography on silica gel, reverse phase chromatography, trituration, precipitation, or crystallization.

Step 2—Preparation of a Compound of Formula I

The compounds of Formula I can be made by combining the compounds of formulas (8) and (14) by methods known in the art. Compounds of formulas (8) and (14) can be mixed in the presence of a catalyst such as tris(dibenzylideneacetone)dipalladium, a ligand such as xantphos, and a base such as cesium carbonate in a suitable solvent such as dioxane. After stirring at a temperature between 50° C. and 150° C. for between 1 and 24 hours, the reaction is allowed to cool to room temperature. Compounds of Formula I may be filtered and concentrated under reduced pressure. To extract the compound of Formula I, an organic solvent such as methylene chloride may be added, followed by washing with water and brine. The organic phase can be concentrated to obtain the compound of Formula I. The compound of Formula I may be purified by any suitable methods known in the art such as chromatography on silica gel, reverse phase chromatography, trituration, precipitation, or crystallization.

Reaction Scheme III

The compounds of Formula I may be prepared using the alternate methods similar to the Reaction Scheme III shown below.

Reaction Scheme III

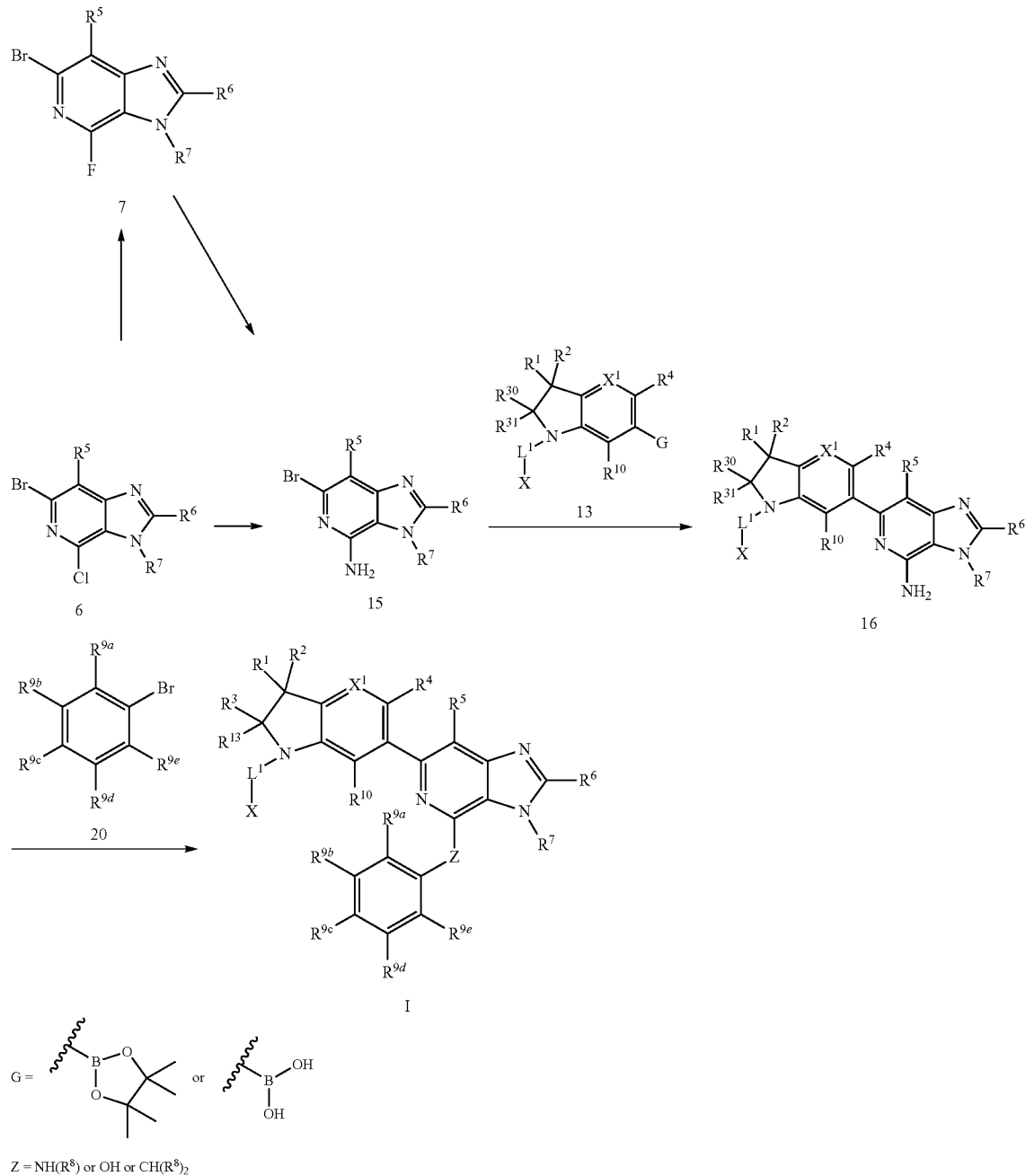

Z = NH(R$^8$) or OH or CH(R$^8$)$_2$

Step 1—Preparation of a Compound of Formula (15)

The compounds of formula (15) can be made by amination of compounds of formula (6) by methods known in the art. A compound of formula (6) can be mixed with ammonium hydroxide solution in a suitable solvent such as N-methylpyrrolidone. After stirring at a temperature between 50° C. and 150° C. for between 1 and 48 hours, the reaction is allowed to cool to room temperature. Compounds of formula (15) may be added to water and further cooled to 0° C. while stirring. The compound of formula (15) may be isolated by any suitable methods known in the art, such as filtration or precipitation.

Step 2—Preparation of a Compound of Formula (16)

The compounds of formula (16) can be made by combining the compounds of formulas (13) and (15) by methods known in the art. Compounds of formula (13) and (15) can be mixed in the presence of a catalyst such as tetrakis (triphenylphosphine)palladium and a base such as cesium carbonate, sodium carbonate, or potassium phosphate tribasic in a suitable solvent such as a mixture of dimethoxyethane and water, a mixture of dimethylacetamide and water, or a mixture of dimethylformamide, dimethoxyethane, and water. After stirring at a temperature between 50° C. and 150° C. for between 1 and 24 hours, the reaction is allowed to cool to room temperature. Compounds of formula (16) may be filtered and concentrated under reduced pressure. To extract the compound of formula (16), an organic solvent such as methylene chloride may be added, followed by washing with water and brine. The organic phase can be concentrated to obtain the compound of formula (16). The compound of formula (16) may be purified by any suitable methods known in the art such as chromatography on silica gel, reverse phase chromatography, trituration, precipitation, or crystallization.

Step 3—Preparation of a Compound of Formula I

The compounds of Formula I can be made by combining the compounds of formulas (16) and (20) by methods known in the art. Compounds of formulas (16) and (20) can be mixed in the presence of a catalyst such as tris(dibenzylideneacetone)dipalladium, a ligand such as xantphos, and a base such as cesium carbonate in a suitable solvent such as dioxane. After stirring at a temperature between 50° C. and 150° C. for between 1 and 24 hours, the reaction is allowed to cool to room temperature. Compounds of Formula I may be filtered and concentrated under reduced pressure. To extract the compound of Formula I, an organic solvent such as methylene chloride may be added, followed by washing with water and brine. The organic phase can be concentrated to obtain the compound of Formula I. The compound of Formula I may be purified by any suitable methods known in the art such as chromatography on silica gel, reverse phase chromatography, trituration, precipitation, or crystallization.

Reaction Scheme IV

The compounds of formula (I-B) may be prepared using the methods similar to the Reaction Scheme IV shown below.

Reaction Scheme IV

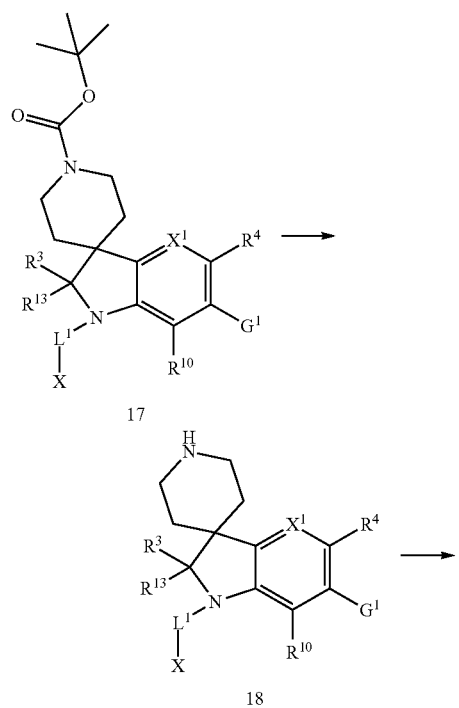

17

18

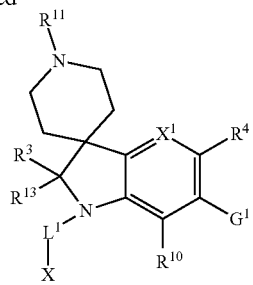

I-B

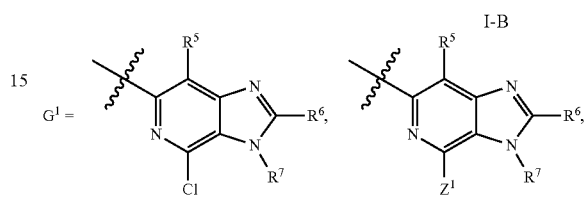

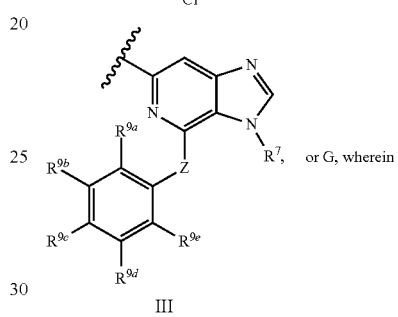

III

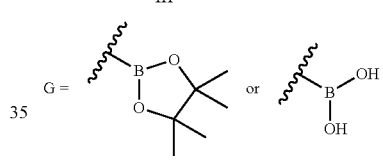

Step 1—Preparation of a Compound of Formula (18)

The compounds of formula (18) can be made by removing the tert-butyloxycarbonyl protecting group of compounds of formula (17) by methods known in the art. A compound of formula (17) can be mixed with an acidic solution such as 4M hydrochloric acid solution in a suitable solvent such as dichloromethane or dioxane. After stirring at room temperature for between 10 minutes and 24 h, the solvent is evaporated in vacuo. The compound of formula (18) may be isolated by any suitable methods known in the art, such as filtration, trituration, or precipitation.

Step 2—Preparation of a Compound of Formula (I-B)

The compounds of formula (I-B) can be made by reductive amination or amide synthesis of compounds of formula (18) by methods known in the art. Compounds of formula (18) can be mixed with amines, that are commercially available or synthesized by methods known in the art, or acid chlorides, that are commercially available or synthesized by methods known in the art, or carboxylic acids, that are commercially available or synthesized by methods known in the art, in the presence of a reducing agent such as sodium triacetoxy borohydride or sodium cyanoborohydride with an acid, such as acetic acid, or a Lewis acid, such as zinc chloride, in a suitable solvent such as dichloroethane or methanol, or in the presence of a coupling reagent such as HATU or propylphosphonic anhydride solution in a suitable solvent such as acetonitrile, dimethylformamide, and dichloroethane. After stirring at a temperature between 0° C. and 100° C. for between 1 h and 24 h, the reaction may be added to aqueous solution such as saturated aqueous sodium bicarbonate solution. To extract the compound of formula (I-B), an organic solvent such as ethyl acetate or methylene chloride may be added, followed by washing with water and brine. The organic phase can be concentrated to obtain the compound of formula (I-B). The compound of formula (I-B) may be purified by any suitable methods known in the art such as chromatography on silica gel, trituration, precipitation, or crystallization.

Reaction Scheme V

The compounds of formula (21) may be prepared using the alternate methods similar to the Reaction Scheme V shown below.

Reaction Scheme V

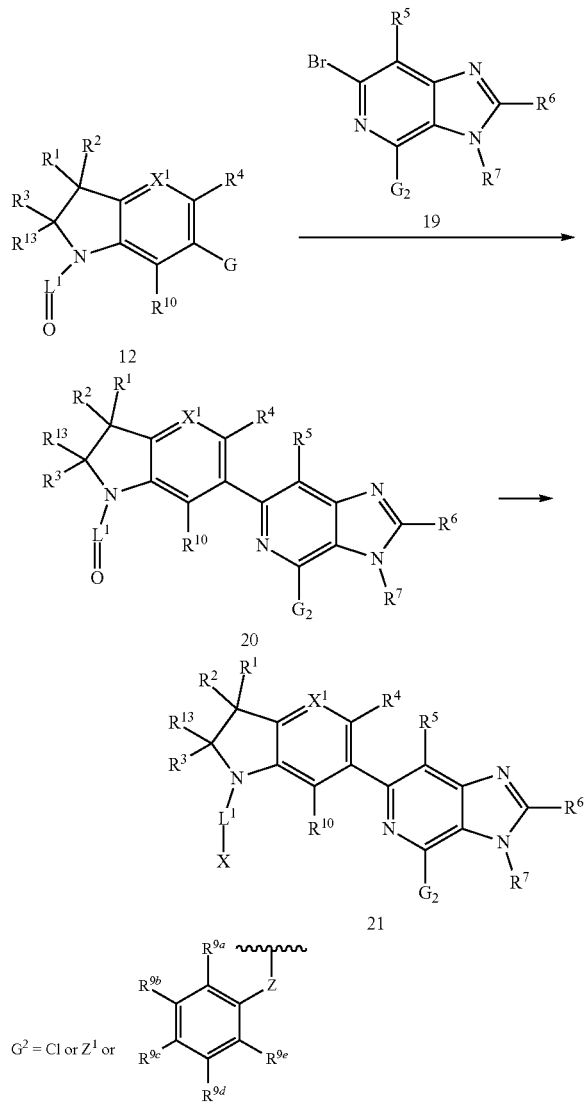

Step 1—Preparation of a Compound of Formula (20)

The compounds of formula (20) can be made by combining the compounds of formulas (19) and (12) by methods known in the art. With respect to compounds (20), $R^7$ and G are as defined herein. Compounds of formulas (19) and (12) can be mixed in the presence of a catalyst, such as tetrakis(triphenylphosphine)palladium, and a base such as cesium carbonate, sodium carbonate, or potassium phosphate tribasic, in a suitable solvent, such as a mixture of dimethoxyethane and water, a mixture of dimethylacetamide and water, or a mixture of dimethylformamide, dimethoxyethane, and water. After stirring at a temperature between 50° C. and 150° C. for between 1 and 24 hours, the reaction is allowed to cool to room temperature. Compounds of formula (20) may be filtered and concentrated under reduced pressure. To extract the compound of formula (20), an organic solvent, such as methylene chloride, may be added, followed by washing with water and brine. The organic phase can be concentrated to obtain the compound of formula (20). The compound of formula (20) may be purified by any suitable methods known in the art such as chromatography on silica gel, reverse phase chromatography, trituration, precipitation, or crystallization.

Step 2—Preparation of a Compound of Formula (21)

The compounds of formula (21) may be prepared by reductive amination of the compounds of formula (20) by methods known in the art. Compounds of formula (20) and amines, that are commercially available or synthesized by methods known in the art, can be mixed with a reducing agent such as sodium triacetoxy borohydride or sodium cyanoborohydride, in the presence of an acid, such as acetic acid, or a Lewis acid, such as zinc chloride, in a suitable solvent such as dichloroethane or methanol. After stirring at a temperature between 0° C. and room temperature for between 1 h and 24 h or until reaction is complete, the reaction may be added to an aqueous solution, such as saturated aqueous sodium bicarbonate solution. To extract the compound of formula (21), an organic solvent, such as ethyl acetate or methylene chloride, may be added, followed by washing with water and brine. The organic phase can be concentrated to obtain the compound of formula (21). The compound of formula (21) may be purified by any suitable methods known in the art, such as chromatography on silica gel, trituration, precipitation, or crystallization.

Reaction Scheme VI

The compounds of formula (22) may be prepared using the alternate methods similar to the Reaction Scheme VI shown below.

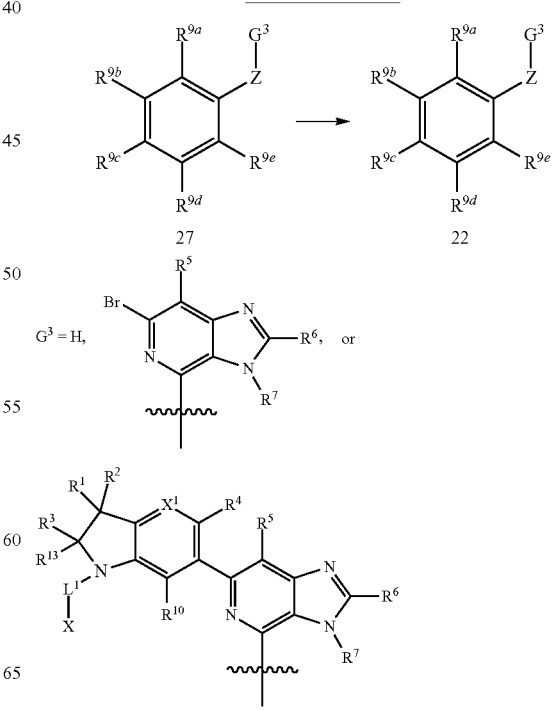

For 27: $R^{9a}$, $R^{9b}$, $R^{9c}$, $R^{9d}$, $R^{9e}$ are as defined herein and wherein one or more of $R^{9a}$, $R^{9b}$, $R^{9c}$, $R^{9d}$, $R^{9e}$ is —COOH
For 22: $R^{9a}$, $R^{9b}$, $R^{9c}$, $R^{9d}$, $R^{9e}$ are as defined herein, and wherein one or more of $R^{9a}$, $R^{9b}$, $R^{9c}$, $R^{9d}$, $R^{9e}$ is —CON$(R^{19})_2$ Step 1—Preparation of a Compound of Formula (22)

The compounds of formula (22) can be made by combining the compounds of formula (27) with the commercially available or synthetically prepared amines by methods known in the art. A compound of formula (27) can be mixed with the commercially available or synthetically prepared amines in the presence of a coupling reagent, such as HATU, and a base, such as diisopropylethylamine, in a suitable solvent, such as acetonitrile. After stirring at a temperature between room temperature and 100° C. for between 1 and 24 hours, the reaction is allowed to cool to room temperature. Compounds of formula (22) may be filtered and concentrated under reduced pressure. To extract the compound of formula (22), an organic solvent, such as methylene chloride, may be added, followed by washing with water and brine. The organic phase can be concentrated to obtain the compound of formula (22). The compound of formula (22) may be purified by any suitable methods known in the art, such as chromatography on silica gel, reverse phase chromatography, trituration, precipitation, or crystallization.

Reaction Scheme VII

The compounds of Formula I may be prepared using the alternate methods similar to the Reaction Scheme VII shown below.

Reaction Scheme VII

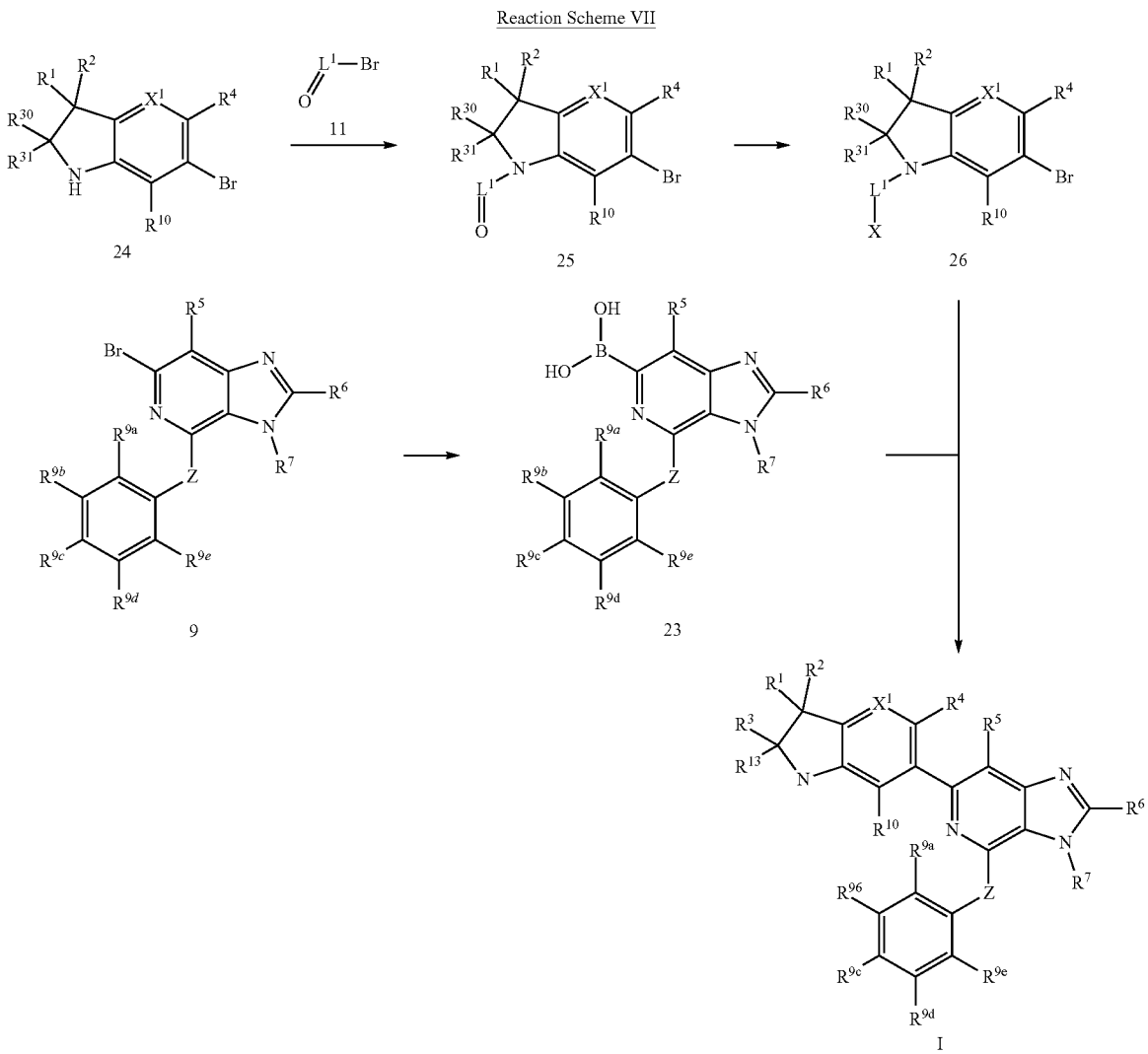

Step 1—Preparation of a Compound of Formula (23)

The compounds of formula (23) can be made by borylation of the compound of formula (9) by methods known in the art. A compound of formula (9) can be mixed with reagents, such as bis(pinacolato)diboron, in the presence of a base, such as potassium acetate, and a catalyst, such as [1,1'-Bis(diphenylphosphino)ferrocene]dichloropalladium (II) complex with dichloromethane, in a suitable solvent, such as dioxane. After stirring at a temperature between room temperature and 100° C. for between 1 h and 24 h or until reaction is complete, the compound of formula (23) may be obtained by any suitable methods known in the art such as trituration, precipitation, or crystallization.

Step 2—Preparation of a Compound of Formula (25)

The compounds of formula (25) can be made by combining compounds of formulas (24) and (11) by methods known in the art. Compounds of formulas (24) and (11) are commercially available or can be made by methods known in the art. Compounds of formulas (24) and (11) can be mixed in the presence of a base, such as potassium carbonate, in a suitable solvent, such as DMF. After stirring at a temperature between room temperature and 50° C. for between 1 h and 24 h or until reaction is complete, the reaction is cooled to room temperature. To extract the compound of formula (25), an organic solvent, such as ethyl acetate, may be added, followed by washing with water and brine. The organic phase can be concentrated to obtain the compound of formula (25). The compound of formula (25) may be purified by any suitable methods known in the art, such as chromatography on silica gel, trituration, precipitation, or crystallization.

Step 3—Preparation of a Compound of Formula (26)

The compounds of formula (26) may be prepared by reductive amination of the compounds of formula (25) by methods known in the art. Compounds of formula (25) and amines, that are commercially available or synthesized by methods known in the art, can be mixed with a reducing agent, such as sodium triacetoxy borohydride or sodium cyanoborohydride, in the presence of an acid, such as acetic acid, or a Lewis acid, such as zinc chloride, in a suitable solvent, such as dichloroethane or methanol. After stirring at a temperature between 0° C. and room temperature for between 1 h and 24 h or until reaction is complete, the reaction may be added to aqueous solution, such as saturated aqueous sodium bicarbonate solution. To extract the compound of formula (26), an organic solvent, such as ethyl acetate or methylene chloride, may be added, followed by washing with water and brine. The organic phase can be concentrated to obtain the compound of formula (26). The compound of formula (26) may be purified by any suitable methods known in the art, such as chromatography on silica gel, trituration, precipitation, or crystallization.

Step 4—Preparation of a Compound of Formula I

The compounds of Formula I can be made by combining the compounds of formulas (26) and (23) by methods known in the art. Compounds of formulas (26) and (23) can be mixed in the presence of a catalyst, such as tetrakis(triphenylphosphine)palladium, and a base, such as cesium carbonate, sodium carbonate, or potassium phosphate tribasic, in a suitable solvent, such as a mixture of dimethoxyethane and water, or a mixture of DMAc and water. After stirring at a temperature between 50° C. and 150° C. for between 1 and 24 hours, the reaction is allowed to cool to room temperature. Compounds of Formula I may be filtered and concentrated under reduced pressure. To extract the compound of Formula I, an organic solvent such as methylene chloride may be added, followed by washing with water and brine. The organic phase can be concentrated to obtain the compound of Formula I. The compound of Formula I may be purified by any suitable methods known in the art such as chromatography on silica gel, reverse phase chromatography, trituration, precipitation, or crystallization.

Reaction Scheme VIII

The compounds of Formula I may be prepared using the alternate methods similar to the Reaction Scheme VIII shown below.

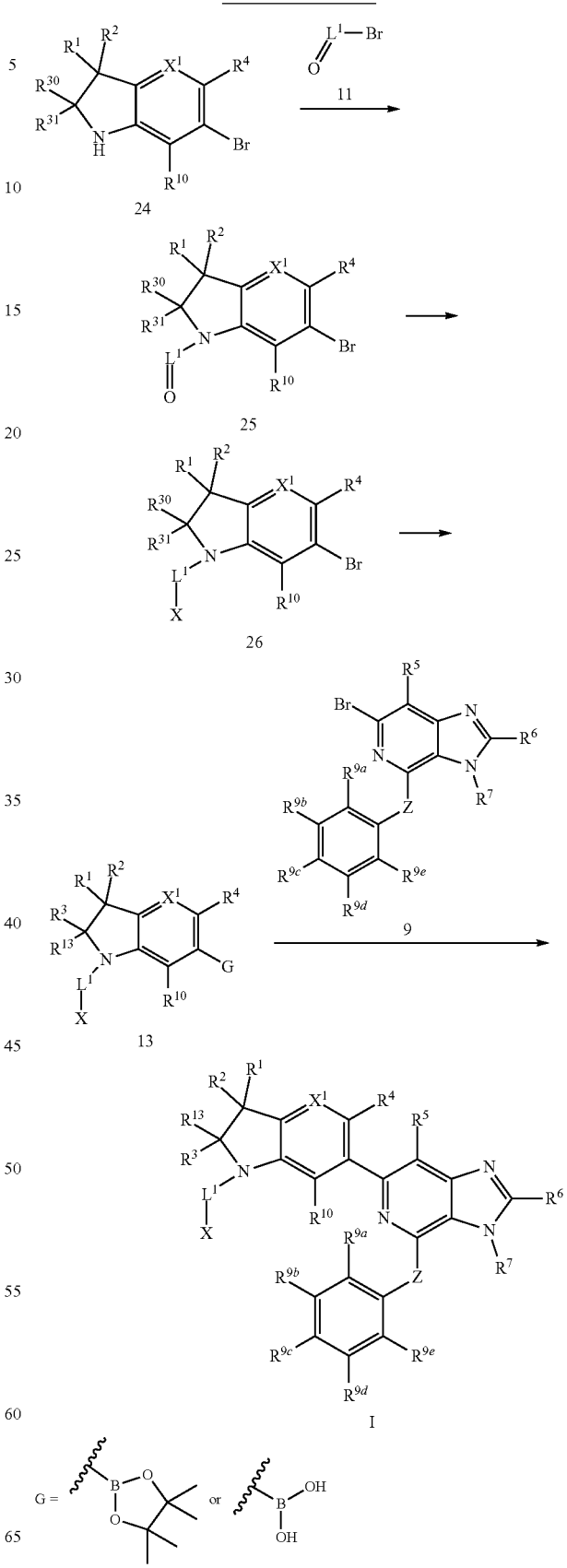

Reaction Scheme VIII

Reaction Scheme IX

The compounds of Formula I may be prepared using the alternate methods similar to the Reaction Scheme IX shown below.

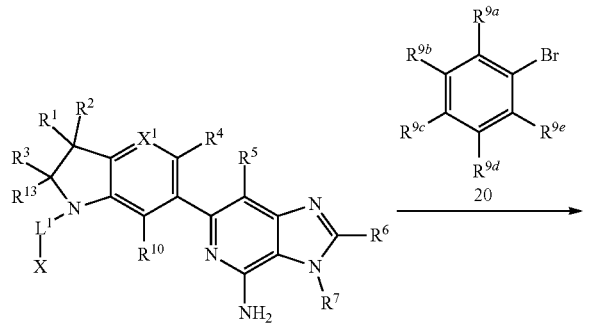

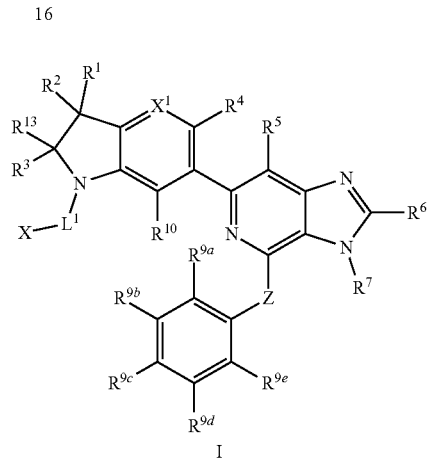

Reaction Scheme X

The compounds of Formula I may be prepared using the alternate methods similar to the Reaction Scheme X shown below.

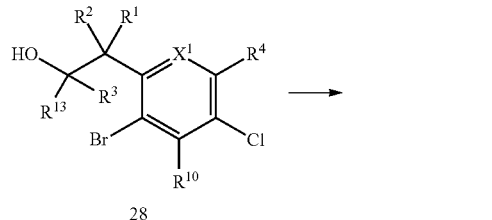

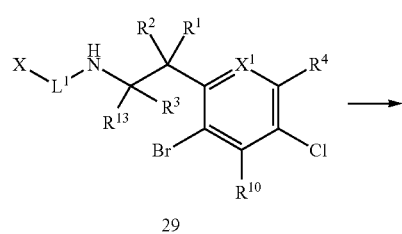

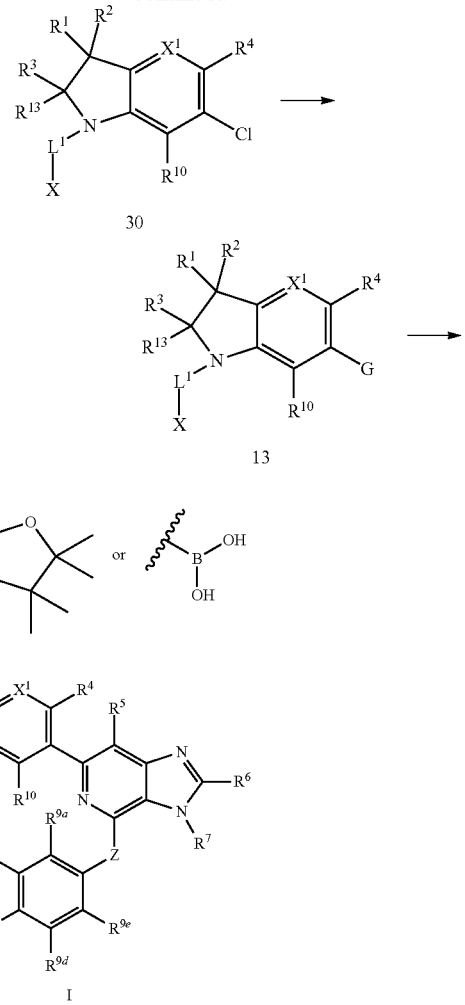

VIII. Examples

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Procedure 1: Preparation of the Compounds of Formula (6) According to Reaction Scheme I

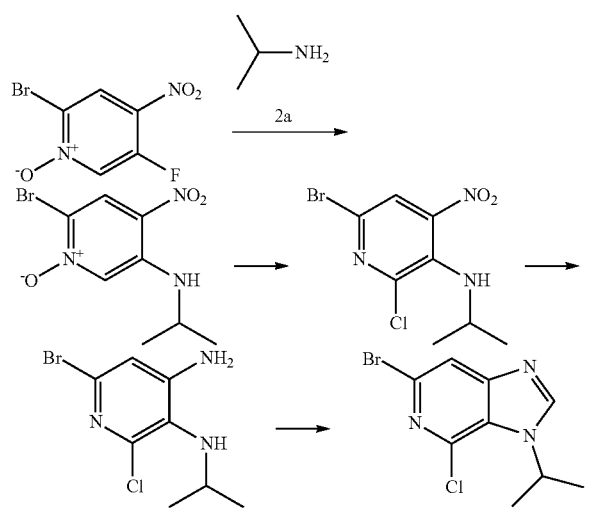

A. Preparation of 2-bromo-5-(isopropylamino)-4-nitropyridine 1-oxide

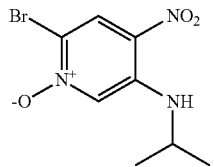

In a multi-necked, round bottomed flask was placed 2-bromo-5-fluoro-4-nitropyridine 1-oxide (1500.0 g, 6.3 mol) in THF (1.5 L) and cooled to 0° C. To this was added isopropyl amine (600.0 mL, 7.0 mol) drop wise at 0° C. over a period of 30 min. Reaction mixture was slowly warmed to room temperature and stirred for 24 h. Then, the reaction mixture was filtered, washed with THF to give 2-bromo-5-(isopropylamino)-4-nitropyridine 1-oxide which was used in the next step without further purification.

B. Preparation of 6-bromo-2-chloro-N-isopropyl-4-nitropyridin-3-amine

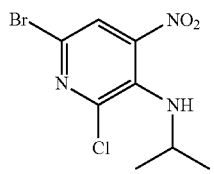

In toluene (21 L) was placed 2-bromo-5-(isopropylamino)-4-nitropyridine 1-oxide (1400.0 g, 5.1 mol). To this was added triethylamine (4.2 L) slowly dropwise at room temperature over a period of 30 min and stirred for 10 min. Then the reaction mixture was cooled to 0° C. followed by the dropwise addition of $POCl_3$ (1.4 L) over a period of 30 min. Reaction mixture was slowly warmed to room temperature and heated to 65° C. for 4 h. Then, it was cooled to room temperature, poured into ice water and extracted with ethyl acetate. The organic layer was washed with saturated $NaHCO_3$ solution, followed by brine solution, dried over sodium sulfate and concentrated under reduced pressure. The crude mixture was purified by column chromatography using 100-200 mesh silica gel and the column was gradually eluted with 10% ethyl acetate in petroleum ether to give 6-bromo-2-chloro-N-isopropyl-4-nitropyridin-3-amine.

C. Preparation of 6-bromo-2-chloro-N3-isopropylpyridine-3,4-diamine

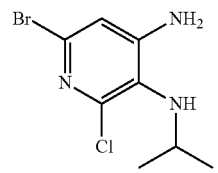

To a solution of 6-bromo-2-chloro-N-isopropyl-4-nitropyridin-3-amine (1000.0 g, 3.4 mol) in THF/MeOH (20 L/20 L) was added Zinc dust (1775.0 g, 27.2 mol) followed by the dropwise addition of a solution of $NH_4Cl$ (1816.0 g, 34.0 mol) in water (20 L) at room temperature and the resulting reaction mixture was stirred at room temperature for 1 h. Then, the reaction mixture was diluted with ethyl acetate and filtered through celite bed. The filtrate was extracted with ethyl acetate and the organic layer was dried with anhydrous sodium sulfate and concentrated under reduced pressure. The crude compound was purified by washing with methyl t-butyl ether to afford 6-bromo-2-chloro-N3-isopropylpyridine-3,4-diamine.

D. Preparation of 6-bromo-4-chloro-3-isopropyl-3H-imidazo[4,5-c]pyridine

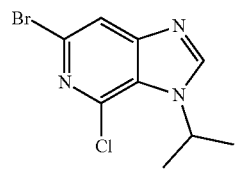

To a solution of 6-bromo-2-chloro-N3-isopropylpyridine-3,4-diamine (800.0 g, 3.0 mol) in $CH(OCH_3)_3$ (5.2 L) was added HCOOH (65 mL). After the reaction mixture was stirred at 70° C. for 3 h, the remaining solvent was removed via distillation. Then water was added and the resulting mixture was extracted with $CH_2Cl_2$. The combined organic layers were dried over anhydrous $Na_2SO_4$, concentrated, and purified by washing with methyl t-butyl ether to give 6-bromo-4-chloro-3-isopropyl-3H-imidazo[4,5-c]pyridine.

The following compounds were prepared using a similar procedure except commercially available amines including, ethylamine, cyclo-propylamine, and (S)-butylamine, were used instead of isopropylamine:

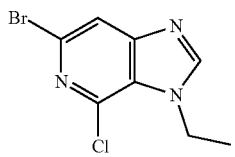

6-bromo-4-chloro-3-ethyl-3H-imidazo[4,5-c]pyridine

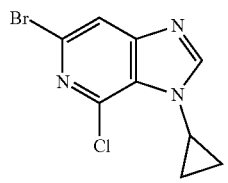 [SMILES: Clc1nc(Br)cc2ncn(C3CC3)c12]

6-bromo-4-chloro-3-cyclopropyl-3H-imidazo[4,5-c]pyridine

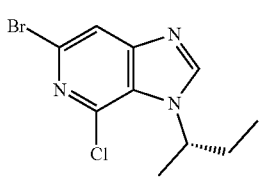

(S)-6-bromo-3-(sec-butyl)-4-chloro-3H-imidazo[4,5-c]pyridine

Procedure 2: Preparation of the Compounds of Formula (7) According to Reaction Scheme I

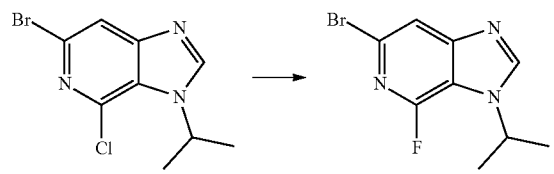

A. Preparation of 6-bromo-4-fluoro-3-isopropyl-3H-imidazo[4,5-c]pyridine

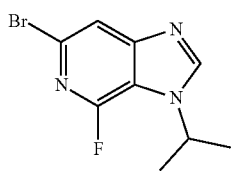

A mixture of 6-bromo-3-isopropyl-4-chloro-3H-imidazo[4,5-c]pyridine (148 g, 0.54 mol) and cesium fluoride (819 g, 5.40 mol) in DMF (1.2 L) was heated at 110° C. for 24 h. Reaction mixture was poured into ice water (1 L). The aqueous layer was extracted with ethyl acetate (3×1 L). The organic layers were dried over sodium sulfate and concentrated and the crude mixture was further purified using column chromatography (EA/Hex=2:3-1:1) to yield 6-bromo-4-fluoro-3-isopropyl-3H-imidazo[4,5-c]pyridine.

The following compounds were prepared using a similar procedure except the compounds listed under Procedure 1 were used instead of 6-bromo-3-isopropyl-4-chloro-3H-imidazo[4,5-c]pyridine:

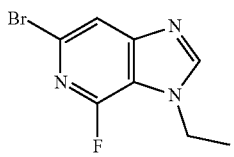

6-bromo-3-ethyl-4-fluoro-3H-imidazo[4,5-c]pyridine

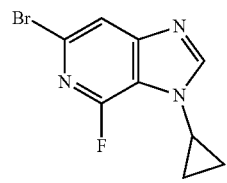

6-bromo-3-cyclopropyl-4-fluoro-3H-imidazo[4,5-c]pyridine

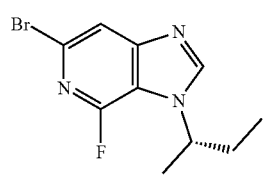

(S)-6-bromo-3-(sec-butyl)-4-fluoro-3H-imidazo[4,5-c]pyridine

Procedure 3: Preparation of the Compounds of Formula (9) According to Reaction Scheme I

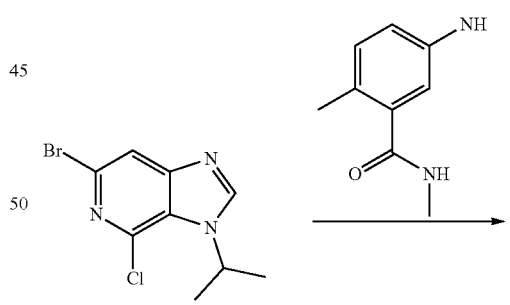

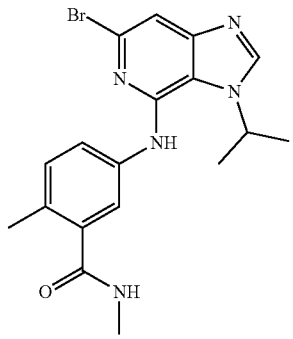 [SMILES: CNC(=O)c1cc(Nc2nc(Br)cc3ncn(C(C)C)c23)ccc1C]

A. Preparation of 5-((6-bromo-3-isopropyl-3H-imidazo[4,5-c]pyridin-4-yl)amino)-N,2-dimethylbenzamide

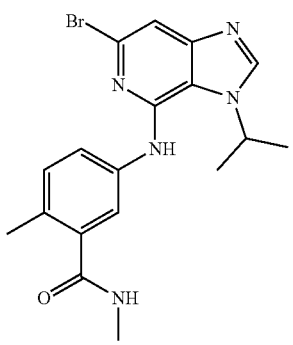

In a microwave vial were placed 6-bromo-4-fluoro-3-isopropyl-3H-imidazo[4,5-c]pyridine (200 mg, 0.77 mmol), 5-amino-N,2-dimethylbenzamide (381.74 mg, 2.32 mmol), and Pyridine.HCl (268.65 mg, 2.32 mmol) in IPA (4 ml). The mixture was placed in the microwave reactor and heated at 150° C. for 6 h. Without work-up, the reaction mixture was purified by flash chromatography (100% Hexane to 100% EtOAc followed by 100% DCM to 25% MeOH in DCM). The fractions were collected and concentrated. The resulting residue was redissolved in EtOAc and water, and extracted with EtOAc. The combined organic layers were washed with water and brine, dried (Na$_2$SO$_4$), and concentrated. To this residue was added DME and the suspension was filtered to give 5-((6-bromo-3-isopropyl-3H-imidazo[4,5-c]pyridin-4-yl)amino)-N,2-dimethylbenzamide.

The following compounds were prepared using a similar procedure with the following modification(s):
the compounds listed in Procedure 1 or 2 were used instead of 6-bromo-4-fluoro-3-isopropyl-3H-imidazo[4,5-c]pyridine; and/or
the optionally substituted amino benzamide indicated below were used instead of 5-amino-N,2-dimethylbenzamide:

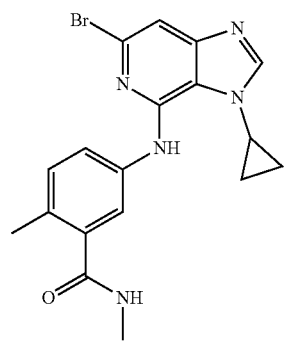 [SMILES: CNC(=O)c1cc(Nc2nc(Br)cc3ncn(C4CC4)c23)ccc1C]

5-((6-Bromo-3-cyclopropyl-3H-imidazo[4,5-c]pyridin-4-yl)amino)-N,2-dimethylbenzamide

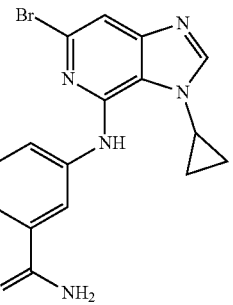

5-Amino-2-methylbenzamide was used to prepare 5-((6-Bromo-3-cyclopropyl-3H-imidazo[4,5-c]pyridin-4-yl)amino)-2-methylbenzamide

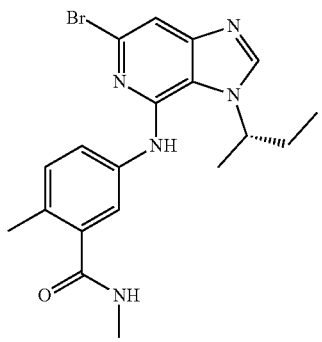 [SMILES: CC[C@H](C)n1cnc2cc(Br)nc(Nc3ccc(C)c(C(=O)NC)c3)c21]

(S)-5-((6-Bromo-3-(sec-butyl)-3H-imidazo[4,5-c]pyridin-4-yl)amino)-N,2-dimethylbenzamide

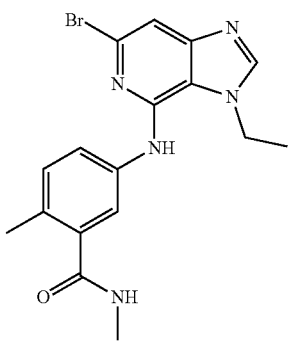 [SMILES: CCn1cnc2cc(Br)nc(Nc3ccc(C)c(C(=O)NC)c3)c21]

5-((6-Bromo-3-ethyl-3H-imidazo[4,5-c]pyridin-4-yl)amino)-N,2-dimethylbenzamide

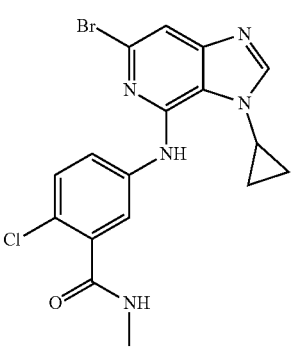 [SMILES: CNC(=O)c1cc(Nc2nc(Br)cc3ncn(C4CC4)c23)ccc1Cl]

5-Amino-2-chloro-N-methylbenzamide was used to prepare 5-((6-bromo-3-cyclopropyl-3H-imidazo[4,5-c]pyridin-4-yl)amino)-2-chloro-N-methylbenzamide

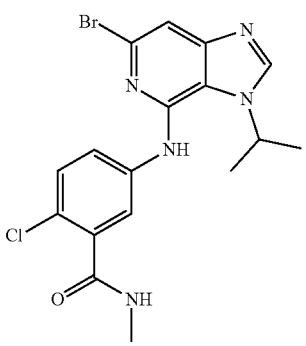 [SMILES: CNC(=O)c1cc(Nc2nc(Br)cc3ncn(C(C)C)c23)ccc1Cl]

5-Amino-2-chloro-N-methylbenzamide was used to prepare 5-((6-bromo-3-isopropyl-3H-imidazo[4,5-c]pyridin-4-yl)amino)-2-chloro-N-methylbenzamide Procedure 4: Preparation of the Compounds of Formula (9) According to Reaction Scheme I

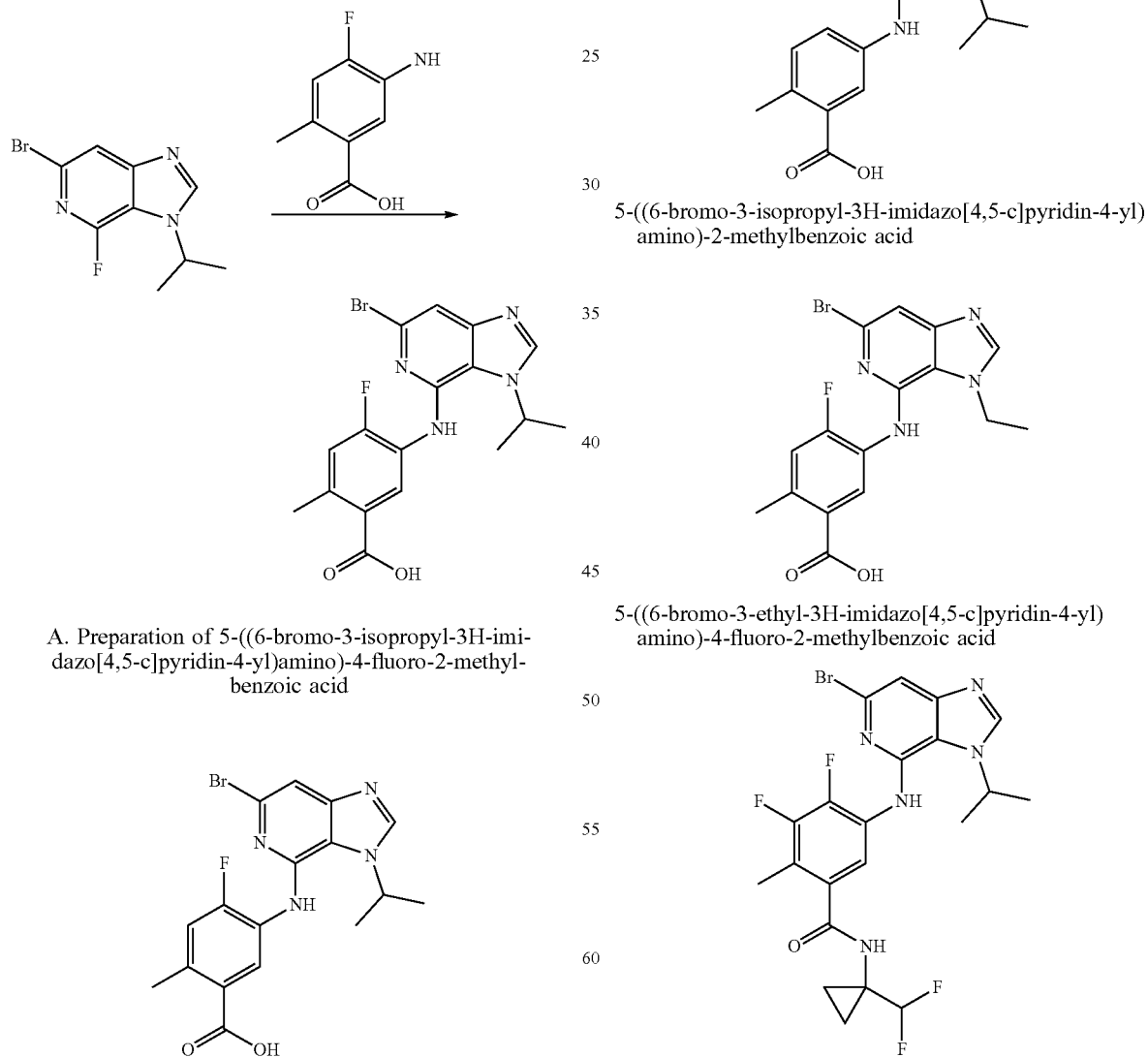

A. Preparation of 5-((6-bromo-3-isopropyl-3H-imidazo[4,5-c]pyridin-4-yl)amino)-4-fluoro-2-methylbenzoic acid

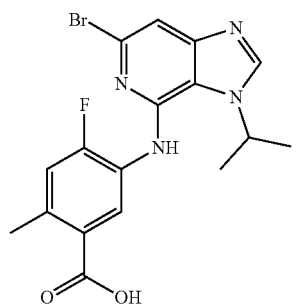 [SMILES: Cc1cc(F)c(Nc2nc(Br)cc3ncn(C(C)C)c23)cc1C(=O)O]

To a solution of 5-amino-4-fluoro-2-methylbenzoic acid (2.0 g, 18 mmol) in DMF (40 mL) was added sodium hydride (1.4 g, 36 mmol) over a period of 5 minutes. The mixture was stirred at room temperature for 15 minutes followed by the addition of 6-bromo-4-fluoro-3-isopropyl-3H-imidazo[4,5-c]pyridine (5.5 g, 21 mmol). After stirring at room temperature for 16 hours, the reaction mixture was quenched with water (200 mL). The slurry was stirred for 1 hour, filtered, and washed with water to give 6-bromo-N-(3-fluoropyridin-4-yl)-3-isopropyl-3H-imidazo[4,5-c]pyridin-4-amine.

The following compounds were prepared using a similar procedure with the following modification(s):
- 5-amino-2-methylbenzoic acid was used instead of 5-amino-4-fluoro-2-methylbenzoic acid; and/or
- 6-bromo-3-ethyl-4-fluoro-3H-imidazo[4,5-c]pyridine was used instead of 6-bromo-4-fluoro-3-isopropyl-3H-imidazo[4,5-c]pyridine; and/or
- 5-amino-N-(1-(difluoromethyl)cyclopropyl)-3,4-difluoro-2-methylbenzamide was used instead of 5-amino-4-fluoro-2-methylbenzoic acid:

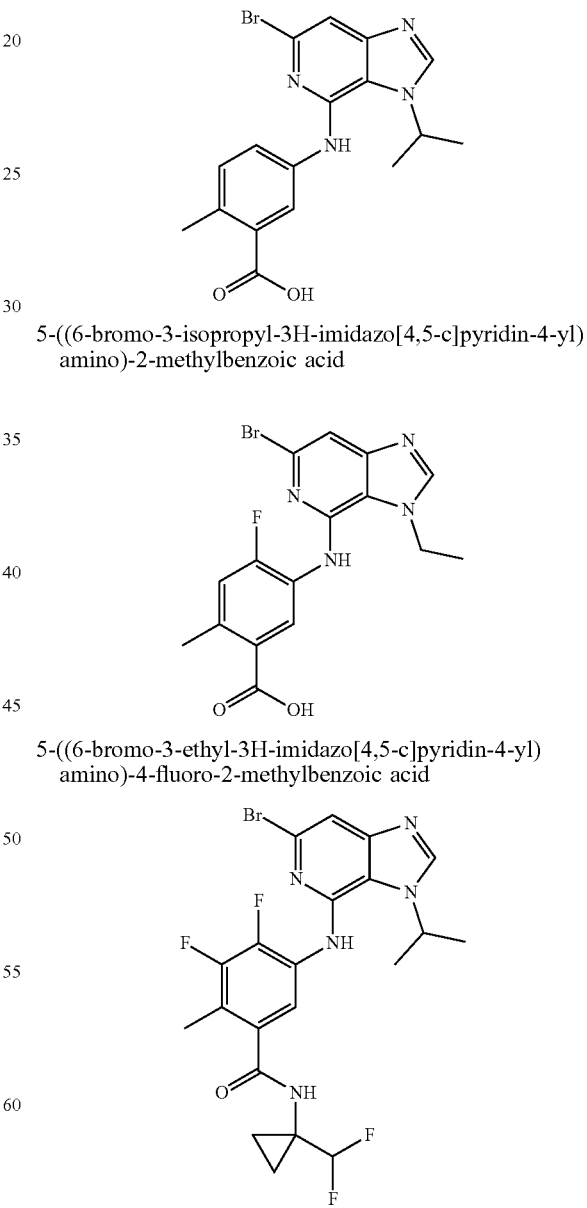

5-((6-bromo-3-isopropyl-3H-imidazo[4,5-c]pyridin-4-yl)amino)-2-methylbenzoic acid 5-((6-bromo-3-ethyl-3H-imidazo[4,5-c]pyridin-4-yl)amino)-4-fluoro-2-methylbenzoic acid 5-((6-bromo-3-isopropyl-3H-imidazo[4,5-c]pyridin-4-yl)amino)-N-(1-(difluoromethyl)cyclopropyl)-3,4-difluoro-2-methylbenzamide

Procedure 5: Preparation of the Compounds of Formula (19) According to Reaction Scheme V

A. Preparation of 5-(((6-bromo-3-isopropyl-3H-imidazo[4,5-c]pyridin-4-yl)amino)-4-fluoro-N,2-dimethylbenzamide

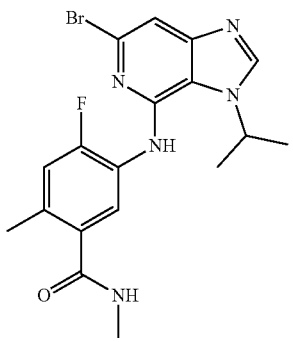 [SMILES: CNC(=O)c1cc(Nc2nc(Br)cc3ncn(C(C)C)c23)c(F)cc1C]

In a vial were placed 5-(((6-bromo-3-isopropyl-3H-imidazo[4,5-c]pyridin-4-yl)amino)-4-fluoro-2-methylbenzoic acid (1.00 g, 2.46 mmol), HATU (1.12 g, 2.95 mmol, 1.2 eq), MeCN (12 mL), DIPEA (4.28 mL, 24.6 mmol, 10.0 eq), and methylamine (4.9 mL, 9.8 mmol, 4.0 eq, 2.0 M in THF). The vial was sealed and the resulting mixture was heated at 40° C. for 2 h. Then the reaction was quenched with sat. NaHCO$_3$ and extracted with DCM. The combined organic layers were washed with 1M K$_2$CO$_3$, dried over Na$_2$SO$_4$, filtered, concentrated, and purified by flash chromatography (100% DCM to 100% MeOH) to give 5-(((6-bromo-3-isopropyl-3H-imidazo[4,5-c]pyridin-4-yl)amino)-4-fluoro-N,2-dimethylbenzamide.

The following compounds were prepared using a similar procedure with the following modification(s):
- the amines indicated below were used instead of methylamine; and/or
- the compounds listed under Procedure 4 were used instead of 5-(((6-bromo-3-isopropyl-3H-imidazo[4,5-c]pyridin-4-yl)amino)-4-fluoro-2-methylbenzoic acid:

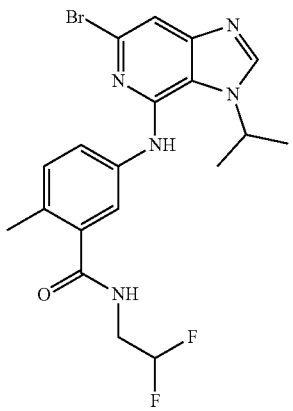 [SMILES: Cc1ccc(Nc2nc(Br)cc3ncn(C(C)C)c23)cc1C(=O)NCC(F)F]

2,2-Difluoroethan-1-amine was used instead of methylamine to prepare 5-(((6-bromo-3-isopropyl-3H-imidazo[4,5-c]pyridin-4-yl)amino)-N-(2,2-difluoroethyl)-2-methylbenzamide

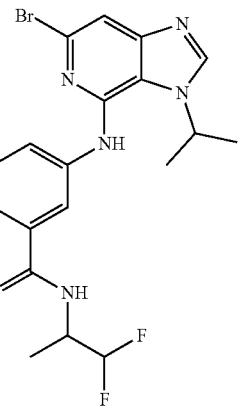

1,1-Difluoropropan-2-amine was used to prepare 5-(((6-bromo-3-isopropyl-3H-imidazo[4,5-c]pyridin-4-yl)amino)-N-(1,1-difluoropropan-2-yl)-2-methylbenzamide

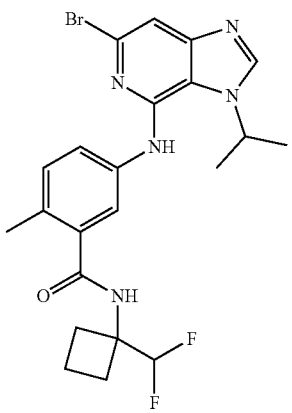 [SMILES: Cc1ccc(Nc2nc(Br)cc3ncn(C(C)C)c23)cc1C(=O)NC1(C(F)F)CCC1]

1-(Difluoromethyl)cyclobutan-1-amine was used to prepare 5-(((6-bromo-3-isopropyl-3H-imidazo[4,5-c]pyridin-4-yl)amino)-N-(1-(difluoromethyl)cyclobutyl)-2-methylbenzamide

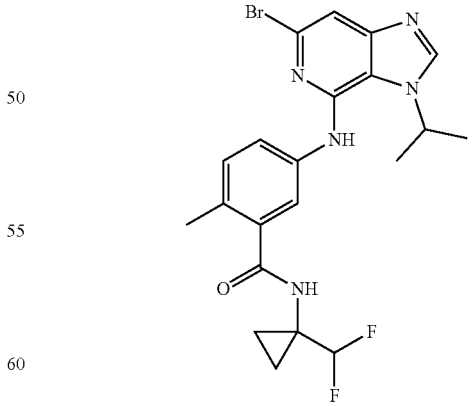

1-(Difluoromethyl)cyclopropan-1-amine was used to prepare 5-(((6-bromo-3-isopropyl-3H-imidazo[4,5-c]pyridin-4-yl)amino)-N-(1-(difluoromethyl)cyclopropyl)-2-methylbenzamide

275

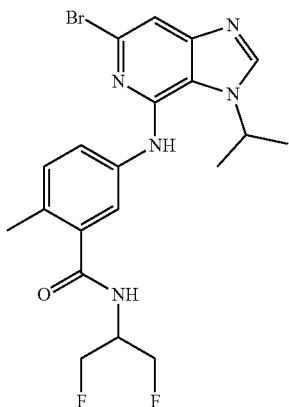 [SMILES: Cc1ccc(Nc2nc(Br)cc3ncn(C(C)C)c23)cc1C(=O)NC(CF)CF]

1,3-Difluoropropan-2-amine was used to prepare 5-((6-bromo-3-isopropyl-3H-imidazo[4,5-c]pyridin-4-yl)amino)-N-(1,3-difluoropropan-2-yl)-2-methylbenzamide

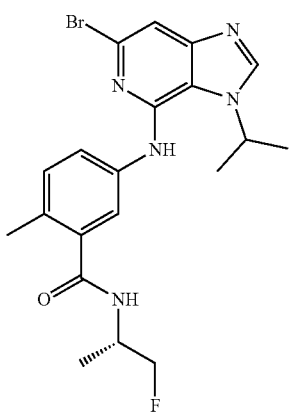 [SMILES: Cc1ccc(Nc2nc(Br)cc3ncn(C(C)C)c23)cc1C(=O)N[C@@H](C)CF]

(S)-1-Fluoropropan-2-amine was used to prepare (S)-5-((6-bromo-3-isopropyl-3H-imidazo[4,5-c]pyridin-4-yl)amino)-N-(1-fluoropropan-2-yl)-2-methylbenzamide

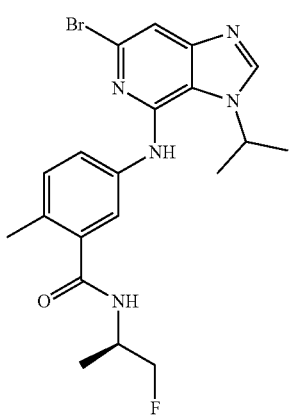 [SMILES: Cc1ccc(Nc2nc(Br)cc3ncn(C(C)C)c23)cc1C(=O)N[C@H](C)CF]

(R)-1-Fluoropropan-2-amine was used to prepare (R)-5-((6-bromo-3-isopropyl-3H-imidazo[4,5-c]pyridin-4-yl)amino)-N-(1-fluoropropan-2-yl)-2-methylbenzamide

276

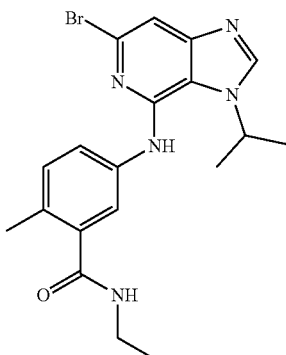

Ethylamine was used to prepare 5-((6-bromo-3-isopropyl-3H-imidazo[4,5-c]pyridin-4-yl)amino)-N-ethyl-2-methylbenzamide

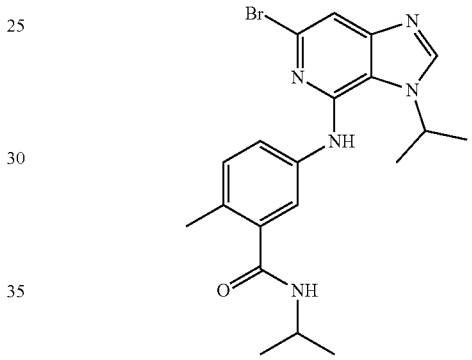

iso-Propylamine was used to prepare 5-((6-bromo-3-isopropyl-3H-imidazo[4,5-c]pyridin-4-yl)amino)-N-isopropyl-2-methylbenzamide

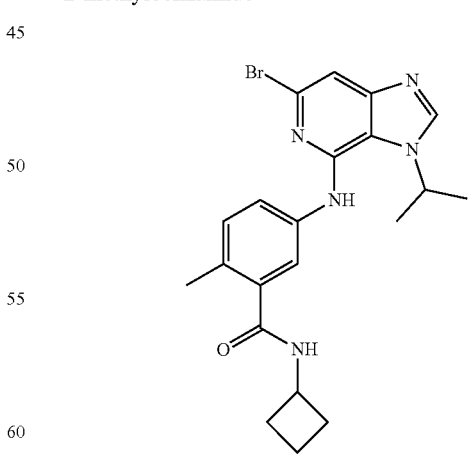

Cyclobutanamine was used to prepare 5-((6-bromo-3-isopropyl-3H-imidazo[4,5-c]pyridin-4-yl)amino)-N-cyclobutyl-2-methylbenzamide

277

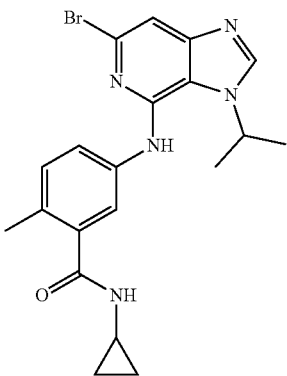 [SMILES: Cc1ccc(Nc2nc(Br)cc3ncn(C(C)C)c23)cc1C(=O)NC1CC1]

Cyclopropylamine was used to prepare 5-(((6-bromo-3-isopropyl-3H-imidazo[4,5-c]pyridin-4-yl)amino)-N-cyclopropyl-2-methylbenzamide

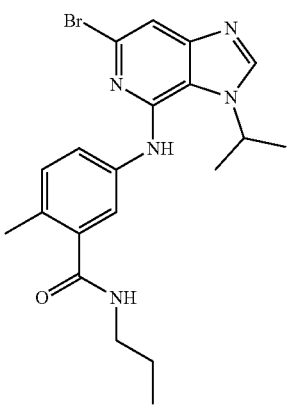 [SMILES: CCCNC(=O)c1cc(Nc2nc(Br)cc3ncn(C(C)C)c23)ccc1C]

n-Propylamine was used to prepare 5-(((6-bromo-3-isopropyl-3H-imidazo[4,5-c]pyridin-4-yl)amino)-2-methyl-N-propylbenzamide

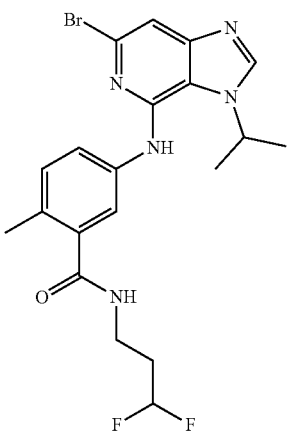 [SMILES: Cc1ccc(Nc2nc(Br)cc3ncn(C(C)C)c23)cc1C(=O)NCCC(F)F]

3,3-Difluoropropan-1-amine was used to prepare 5-(((6-bromo-3-isopropyl-3H-imidazo[4,5-c]pyridin-4-yl)amino)-N-(3,3-difluoropropyl)-2-methylbenzamide

278

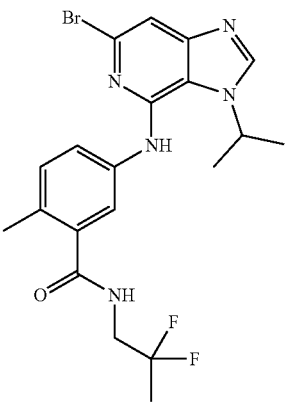 [SMILES: Cc1ccc(Nc2nc(Br)cc3ncn(C(C)C)c23)cc1C(=O)NCC(C)(F)F]

2,2-Difluoropropan-1-amine was used to prepare 5-(((6-bromo-3-isopropyl-3H-imidazo[4,5-c]pyridin-4-yl)amino)-N-(2,2-difluoropropyl)-2-methylbenzamide

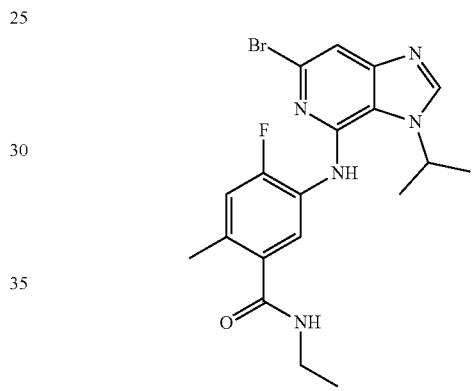

Ethylamine was used to prepare 5-(((6-bromo-3-isopropyl-3H-imidazo[4,5-c]pyridin-4-yl)amino)-N-ethyl-4-fluoro-2-methylbenzamide

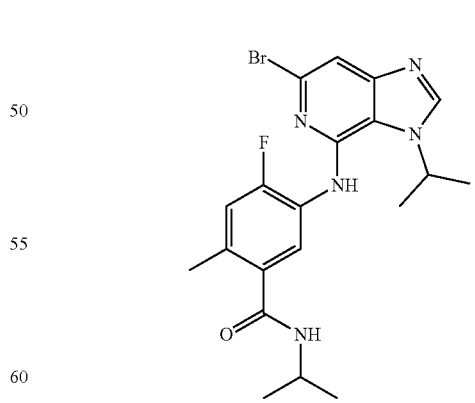

iso-Propylamine was used to prepare 5-(((6-bromo-3-isopropyl-3H-imidazo[4,5-c]pyridin-4-yl)amino)-4-fluoro-N-isopropyl-2-methylbenzamide

| 279 | 280 |
|---|---|
| 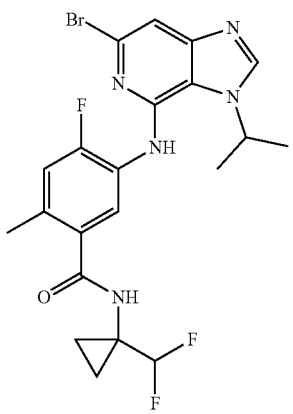 [SMILES: Cc1cc(F)c(Nc2nc(Br)cc3ncn(C(C)C)c23)cc1C(=O)NC1(C(F)F)CC1] | 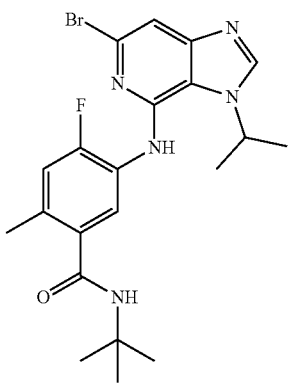 |
| 1-(Difluoromethyl)cyclopropan-1-amine was used to prepare 5-((6-bromo-3-isopropyl-3H-imidazo[4,5-c]pyridin-4-yl)amino)-N-(1-(difluoromethyl)cyclopropyl)-4-fluoro-2-methylbenzamide | tert-Butylamine was used to prepare 5-((6-bromo-3-isopropyl-3H-imidazo[4,5-c]pyridin-4-yl)amino)-N-(tert-butyl)-4-fluoro-2-methylbenzamide |
| 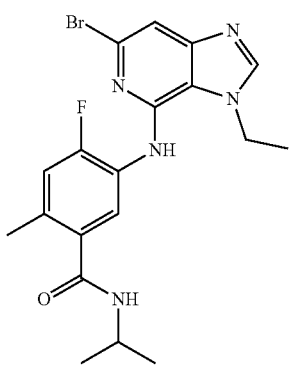 [SMILES: CCn1cnc2cc(Br)nc(Nc3cc(C(=O)NC(C)C)c(C)cc3F)c21] | 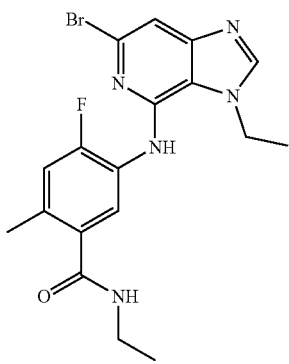 [SMILES: CCNC(=O)c1cc(Nc2nc(Br)cc3ncn(CC)c23)c(F)cc1C] |
| iso-Propylamine was used to prepare 5-((6-bromo-3-ethyl-3H-imidazo[4,5-c]pyridin-4-yl)amino)-4-fluoro-N-isopropyl-2-methylbenzamide | Cyclobutanamine was used to prepare 5-((6-bromo-3-isopropyl-3H-imidazo[4,5-c]pyridin-4-yl)amino)-N-cyclobutyl-4-fluoro-2-methylbenzamide |
| 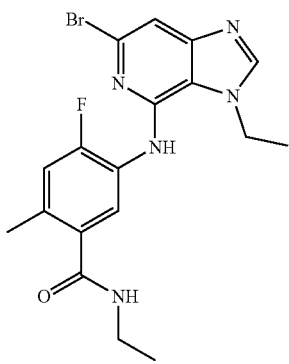 [SMILES: CCNC(=O)c1cc(Nc2nc(Br)cc3ncn(CC)c23)c(F)cc1C] | 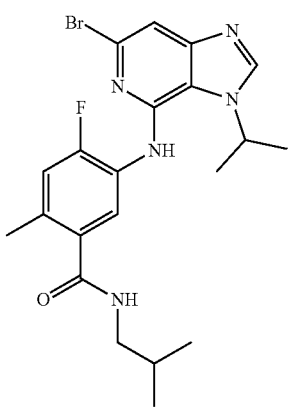 [SMILES: Cc1cc(F)c(Nc2nc(Br)cc3ncn(C(C)C)c23)cc1C(=O)NCC(C)C] |
| Ethylamine was used to prepare 5-((6-bromo-3-ethyl-3H-imidazo[4,5-c]pyridin-4-yl)amino)-4-fluoro-N-ethyl-2-methylbenzamide | 2-Methylpropan-1-amine was used to prepare 5-((6-bromo-3-isopropyl-3H-imidazo[4,5-c]pyridin-4-yl)amino)-4-fluoro-N-isobutyl-2-methylbenzamide |

Procedure 6: Preparation of the Compounds of Formula (13) According to Reaction Scheme I

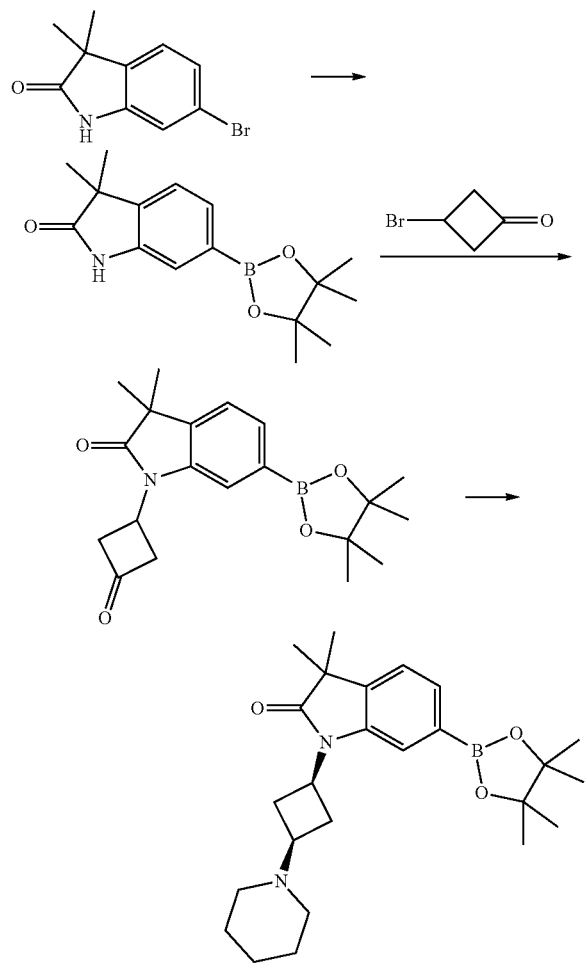

A. Preparation of 3,3-dimethyl-6-(4,4,5,5-tetramethyl-1,3,2-dioxaborolan-2-yl)indolin-2-one

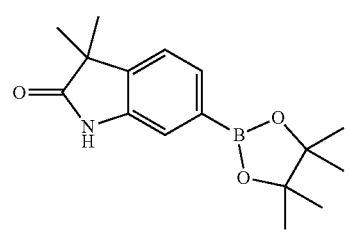 [SMILES: CC1(C)C(=O)Nc2cc(B3OC(C)(C)C(C)(C)O3)ccc21]

A mixture of 6-bromo-3,3-dimethylindolin-2-one (150 g, 625 mmol), bis(pinacolato)diboron (206 g, 812 mmol), Pd(dppf)Cl$_2$/CH$_2$Cl$_2$ (45 g, 62.5 mmol) and potassium acetate (184 g, 1875 mmol) in dimethyl sulfoxide (2000 mL) was stirred at 100° C. under Ar for 3 h. The reaction was diluted with H$_2$O (10 L) and extracted with ethyl acetate (4 L). The organic phase was washed with water followed by brine, dried over Na$_2$SO$_4$, and purified by silica gel column (PE/EA=10:1) to give 3,3-dimethyl-6-(4,4,5,5-tetramethyl-1,3,2-dioxaborolan-2-yl)indolin-2-one.

B. Preparation of 3,3-dimethyl-1-(3-oxocyclobutyl)-6-(4,4,5,5-tetramethyl-1,3,2-dioxaborolan-2-yl)indolin-2-one

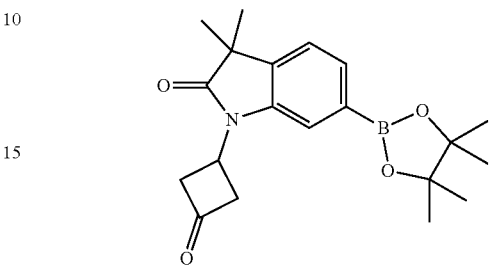

To a mixture of 3,3-dimethyl-6-(4,4,5,5-tetramethyl-1,3,2-dioxaborolan-2-yl)indolin-2-one (200 g, 696 mmol) and K$_2$CO$_3$ (240 g, 1740 mmol) in DMF (2 L) was added 3-bromocyclobutanone (160 g, 1356 mmol). After the mixture was stirred at 50° C. under Ar for 2.5 h, it was cooled to room temperature, diluted with EtOAc, and filtered to remove solids. The filtrate was diluted with additional EtOAc and water. The aqueous layer was extracted with EtOAc. The combined organic layers were washed with brine, dried over Na$_2$SO$_4$, filtered, concentrated, and purified by flash chromatography on silica gel (PE/EA=20:1) to give 3,3-dimethyl-1-(3-oxocyclobutyl)-6-(4,4,5,5-tetramethyl-1,3,2-dioxaborolan-2-yl)indolin-2-one.

The following compounds were prepared using a similar procedure except:

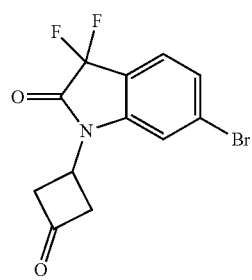 [SMILES: O=C1CC(N2C(=O)C(F)(F)c3ccc(Br)cc32)C1]

Commercially available 6-bromo-3,3-difluoroindolin-2-one was used instead of 3,3-dimethyl-6-(4,4,5,5-tetramethyl-1,3,2-dioxaborolan-2-yl)indolin-2-one to prepare 6-bromo-3,3-difluoro-1-(3-oxocyclobutyl)indolin-2-one

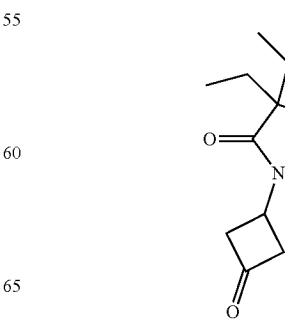

6-bromo-3,3-diethylindolin-2-one (Prepared According to the Procedure Described in Paragraph [1008] of WO2009078481) was used instead of 3,3-dimethyl-6-(4,4,5,5-tetramethyl-1,3,2-dioxaborolan-2-yl)indolin-2-one to prepare 6-bromo-3,3-diethyl-1-(3-oxocyclobutyl)indolin-2-one

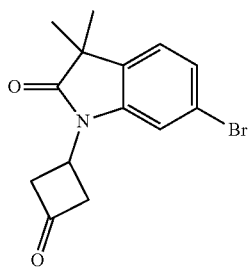 [SMILES: CC1(C)C(=O)N(C2CC(=O)C2)c2cc(Br)ccc21]

Commercially available 6-bromo-3,3-dimethylindolin-2-one was used instead of 3,3-dimethyl-6-(4,4,5,5-tetramethyl-1,3,2-dioxaborolan-2-yl)indolin-2-one to prepare 6-bromo-3,3-dimethyl-1-(3-oxocyclobutyl)indolin-2-one C. Preparation of 3,3-dimethyl-1-((1s,3s)-3-(piperidin-1-yl)cyclobutyl)-6-(4,4,5,5-tetramethyl-1,3,2-dioxaborolan-2-yl)indolin-2-one

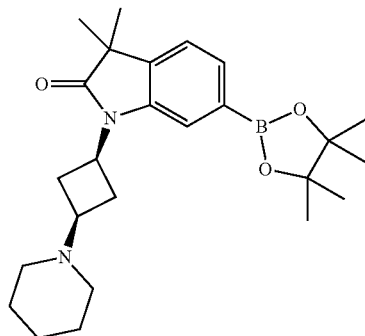 [SMILES: CC1(C)C(=O)N([C@H]2C[C@@H](N3CCCCC3)C2)c2cc(B3OC(C)(C)C(C)(C)O3)ccc21]

To a solution of 3,3-dimethyl-1-(3-oxocyclobutyl)-6-(4,4,5,5-tetramethyl-1,3,2-dioxaborolan-2-yl)indolin-2-one (7.0 g, 19.7 mmol) in dichloroethane (130 mL) was added piperidine (3.4 g, 39.4 mmol) and acetic acid (3.6 g, 59.1 mmol). The reaction was cooled to 0° C. in an ice-bath and sodium triacetoxy borohydride (6.26 g, 29.56 mmol) was added portion-wise. After completion of addition, the reaction was brought out of the ice bath and stirred at room temperature for 2 h. Then, the reaction mixture was quenched with saturated aqueous sodium bicarbonate solution and extracted with methylene chloride (3×200 mL). The combined organic layers were washed with sat. NaHCO$_3$, brine, dried over sodium sulfate, filtered, and concentrated in vacuo to give 3,3-dimethyl-1-((1s,3s)-3-(piperidin-1-yl)cyclobutyl)-6-(4,4,5,5-tetramethyl-1,3,2-dioxaborolan-2-yl)indolin-2-one, which was used in the next step without purification.

The following compounds were prepared using a similar procedure with the following modification(s):
the amines indicated below were used instead of piperidine; or
the optionally substituted oxindoles, that are commercially available or can be made by methods known in the art, such as 6-bromo-3,3-difluoro-1-(3-oxocyclobutyl)indolin-2-one and 6-bromo-3,3-diethyl-1-(3-oxocyclobutyl)indolin-2-one, were used instead of 3,3-dimethyl-1-(3-oxocyclobutyl)-6-(4,4,5,5-tetramethyl-1,3,2-dioxaborolan-2-yl)indolin-2-one:

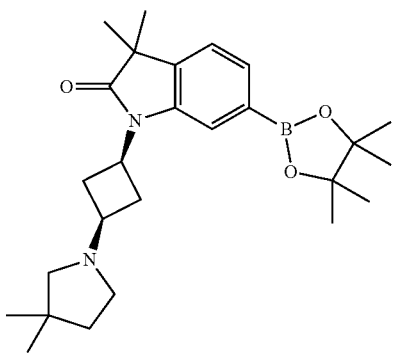

3,3-Dimethylpyrrolidine was used to prepare 1-((1s,3s)-3-(3,3-dimethylpyrrolidin-1-yl)cyclobutyl)-3,3-dimethyl-6-(4,4,5,5-tetramethyl-1,3,2-dioxaborolan-2-yl)indolin-2-one

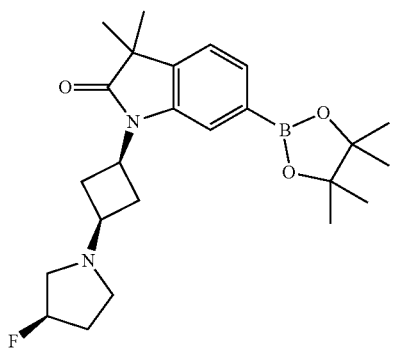 [SMILES: CC1(C)C(=O)N([C@H]2C[C@@H](N3CC[C@@H](F)C3)C2)c2cc(B3OC(C)(C)C(C)(C)O3)ccc21]

(R)-3-Fluoropyrrolidine was used to prepare 1-((1S,3s)-3-((R)-3-fluoropyrrolidin-1-yl)cyclobutyl)-3,3-dimethyl-6-(4,4,5,5-tetramethyl-1,3,2-dioxaborolan-2-yl)indolin-2-one

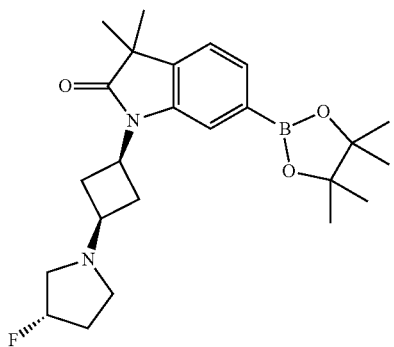 [SMILES: CC1(C)C(=O)N([C@H]2C[C@@H](N3CC[C@H](F)C3)C2)c2cc(B3OC(C)(C)C(C)(C)O3)ccc21]

(S)-3-Fluoropyrrolidine was used to prepare 1-((1R,3s)-3-((S)-3-fluoropyrrolidin-1-yl)cyclobutyl)-3,3-dimethyl-6-(4,4,5,5-tetramethyl-1,3,2-dioxaborolan-2-yl)indolin-2-one

285

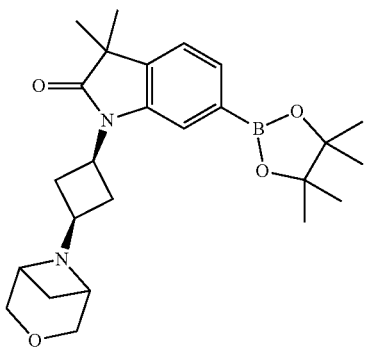 [SMILES: CC1(C)C(=O)N([C@H]2C[C@@H](N3C4COCC3C4)C2)c2cc(B3OC(C)(C)C(C)(C)O3)ccc21]

3-Oxa-6-azabicyclo[3.1.1]heptane was used to prepare 1-((1s,3s)-3-(3-oxa-6-azabicyclo[3.1.1]heptan-6-yl)cyclobutyl)-3,3-dimethyl-6-(4,4,5,5-tetramethyl-1,3,2-dioxaborolan-2-yl)indolin-2-one

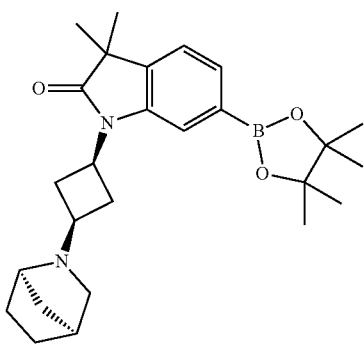 [SMILES: CC1(C)C(=O)N([C@H]2C[C@@H](N3C[C@H]4CC[C@@H]3C4)C2)c2cc(B3OC(C)(C)C(C)(C)O3)ccc21]

(1R,4S)-2-Azabicyclo[2.2.1]heptane was used to prepare 1-((1S,3s)-3-((1R,4S)-2-azabicyclo[2.2.1]heptan-2-yl)cyclobutyl)-3,3-dimethyl-6-(4,4,5,5-tetramethyl-1,3,2-dioxaborolan-2-yl)indolin-2-one

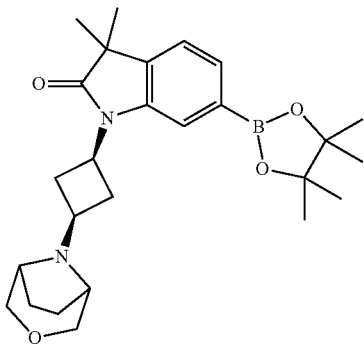 [SMILES: CC1(C)C(=O)N([C@H]2C[C@@H](N3C4CCC3COC4)C2)c2cc(B3OC(C)(C)C(C)(C)O3)ccc21]

3-Oxa-8-azabicyclo[3.2.1]octane was used to prepare 1-((1s,3s)-3-(3-oxa-8-azabicyclo[3.2.1]octan-8-yl)cyclobutyl)-3,3-dimethyl-6-(4,4,5,5-tetramethyl-1,3,2-dioxaborolan-2-yl)indolin-2-one

286

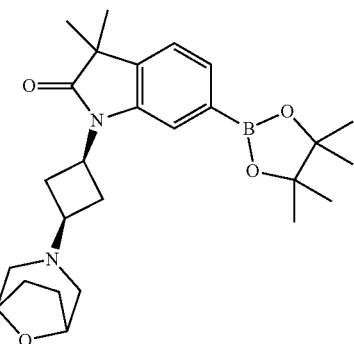

8-Oxa-3-azabicyclo[3.2.1]octane was used to prepare 1-((1s,3s)-3-(8-oxa-3-azabicyclo[30.2.1]octan-3-yl)cyclobutyl)-3,3-dimethyl-6-(4,4,5,5-tetramethyl-1,3,2-dioxaborolan-2-yl)indolin-2-one

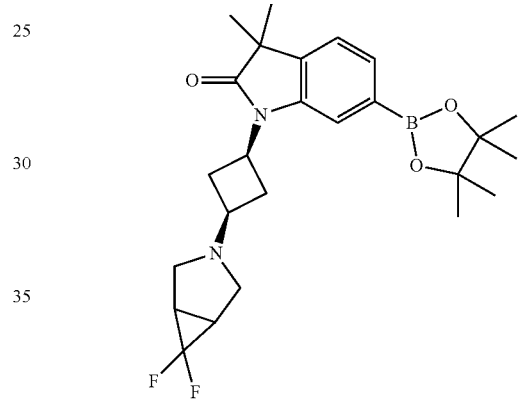

6,6-Difluoro-3-azabicyclo[3.1.0]hexane was used to prepare 1-((1s,3s)-3-(6,6-difluoro-3-azabicyclo[3.1.0]hexan-3-yl)cyclobutyl)-3,3-dimethyl-6-(4,4,5,5-tetramethyl-1,3,2-dioxaborolan-2-yl)indolin-2-one

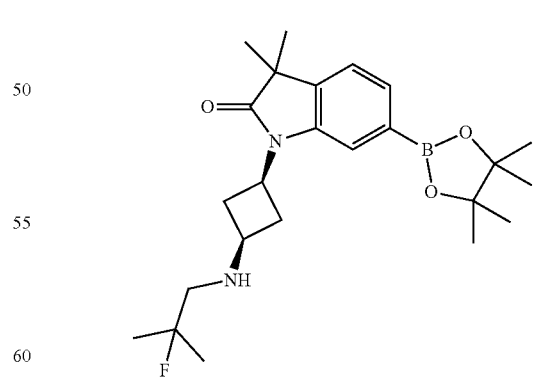

2-Fluoro-2-methylpropan-1-amine was used to prepare 1-((1s,3s)-3-((2-fluoro-2-methylpropyl)amino)cyclobutyl)-3,3-dimethyl-6-(4,4,5,5-tetramethyl-1,3,2-dioxaborolan-2-yl)indolin-2-one

| 287 | 288 |
|---|---|
| 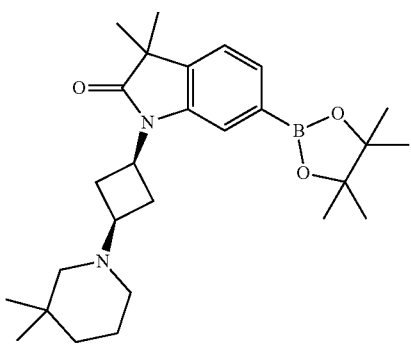 | 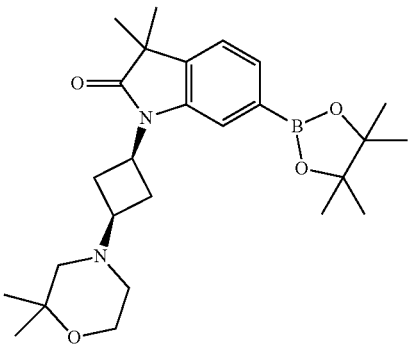 |
| 3,3-dimethylpiperidine was used to prepare 1-((1s,3s)-3-(3,3-dimethylpiperidin-1-yl)cyclobutyl)-3,3-dimethyl-6-(4,4,5,5-tetramethyl-1,3,2-dioxaborolan-2-yl)indolin-2-one | 2,2-Dimethylmorpholine was used to prepare 1-((1s,3s)-3-(2,2-dimethylmorpholino)cyclobutyl)-3,3-dimethyl-6-(4,4,5,5-tetramethyl-1,3,2-dioxaborolan-2-yl)indolin-2-one |
| 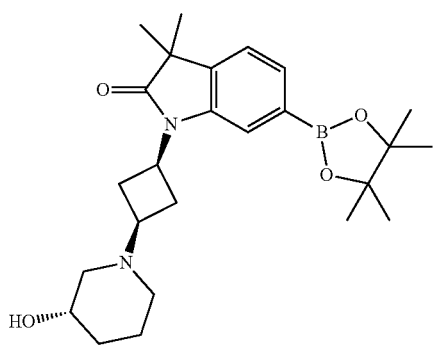 [SMILES: CC1(C)C(=O)N([C@H]2C[C@@H](N3CCC[C@H](O)C3)C2)c2cc(B3OC(C)(C)C(C)(C)O3)ccc21] | 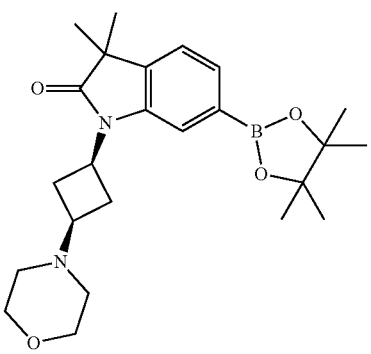 |
| (S)-Piperidin-3-ol was used to prepare 1-((1R,3s)-3-((S)-3-hydroxypiperidin-1-yl)cyclobutyl)-3,3-dimethyl-6-(4,4,5,5-tetramethyl-1,3,2-dioxaborolan-2-yl)indolin-2-one | Morpholine was used to prepare 3,3-dimethyl-1-((1s,3s)-3-morpholinocyclobutyl)-6-(4,4,5,5-tetramethyl-1,3,2-dioxaborolan-2-yl)indolin-2-one |
| 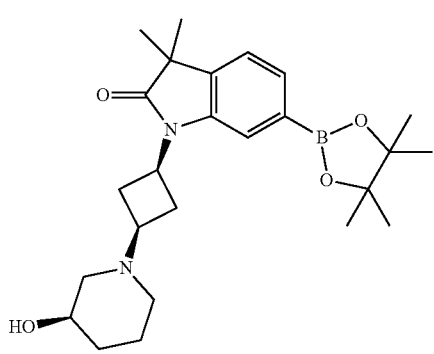 [SMILES: CC1(C)C(=O)N([C@H]2C[C@@H](N3CCC[C@@H](O)C3)C2)c2cc(B3OC(C)(C)C(C)(C)O3)ccc21] | 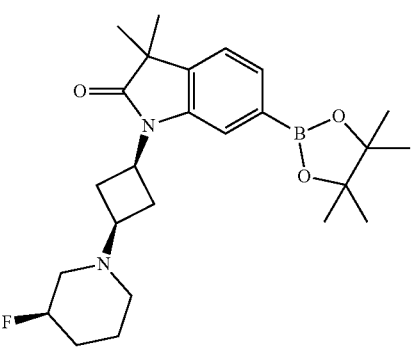 [SMILES: CC1(C)C(=O)N([C@H]2C[C@@H](N3CCC[C@@H](F)C3)C2)c2cc(B3OC(C)(C)C(C)(C)O3)ccc21] |
| (R)-Piperidin-3-ol was used to prepare 1-((1S,3s)-3-((R)-3-hydroxypiperidin-1-yl)cyclobutyl)-3,3-dimethyl-6-(4,4,5,5-tetramethyl-1,3,2-dioxaborolan-2-yl)indolin-2-one | (R)-3-Fluoropiperidine was used to prepare 1-((1S,3s)-3-((R)-3-fluoropiperidin-1-yl)cyclobutyl)-3,3-dimethyl-6-(4,4,5,5-tetramethyl-1,3,2-dioxaborolan-2-yl)indolin-2-one |

289

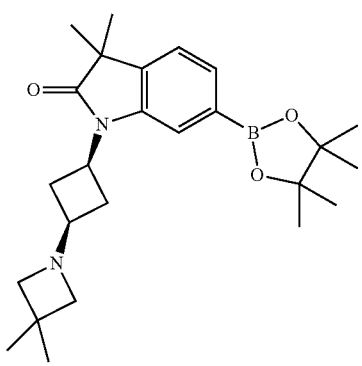

3,3-Dimethylazetidine was used to prepare 1-((1s,3s)-3-(3,3-dimethylazetidin-1-yl)cyclobutyl)-3,3-dimethyl-6-(4,4,5,5-tetramethyl-1,3,2-dioxaborolan-2-yl)indolin-2-one

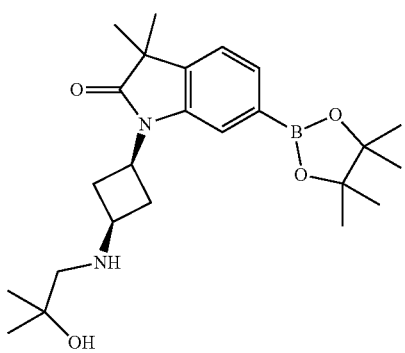 [SMILES: CC(C)(O)CN[C@H]1C[C@@H](N2C(=O)C(C)(C)c3ccc(B4OC(C)(C)C(C)(C)O4)cc32)C1]

1-Amino-2-methylpropan-2-ol was used to prepare 1-((1s,3s)-3-((2-hydroxy-2-methylpropyl)amino)cyclobutyl)-3,3-dimethyl-6-(4,4,5,5-tetramethyl-1,3,2-dioxaborolan-2-yl)indolin-2-one

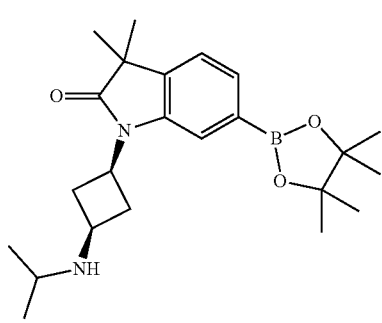 [SMILES: CC(C)N[C@H]1C[C@@H](N2C(=O)C(C)(C)c3ccc(B4OC(C)(C)C(C)(C)O4)cc32)C1]

i-Propylamine was used to prepare 1-((1s,3s)-3-(isopropylamino)cyclobutyl)-3,3-dimethyl-6-(4,4,5,5-tetramethyl-1,3,2-dioxaborolan-2-yl)indolin-2-one

290

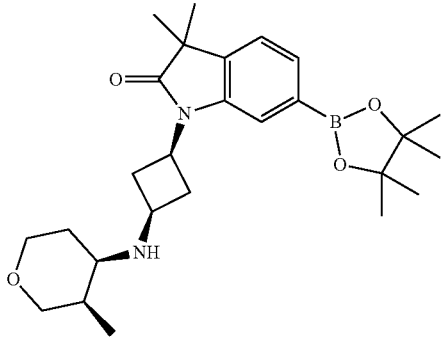 [SMILES: C[C@H]1COCC[C@H]1N[C@H]1C[C@@H](N2C(=O)C(C)(C)c3ccc(B4OC(C)(C)C(C)(C)O4)cc32)C1]

(3R,4R)-3-Methyltetrahydro-2H-pyran-4-amine was used to prepare 3,3-dimethyl-1-((1S,3s)-3-(((3R,4R)-3-methyltetrahydro-2H-pyran-4-yl)amino)cyclobutyl)-6-(4,4,5,5-tetramethyl-1,3,2-dioxaborolan-2-yl)indolin-2-one

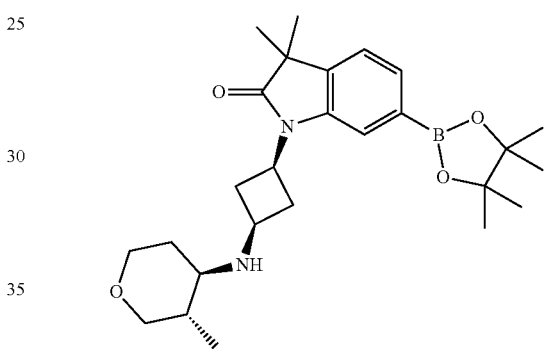

(3S,4R)-3-Methyltetrahydro-2H-pyran-4-amine was used to prepare 3,3-dimethyl-1-((1S,3s)-3-(((3S,4R)-3-methyltetrahydro-2H-pyran-4-yl)amino)cyclobutyl)-6-(4,4,5,5-tetramethyl-1,3,2-dioxaborolan-2-yl)indolin-2-one

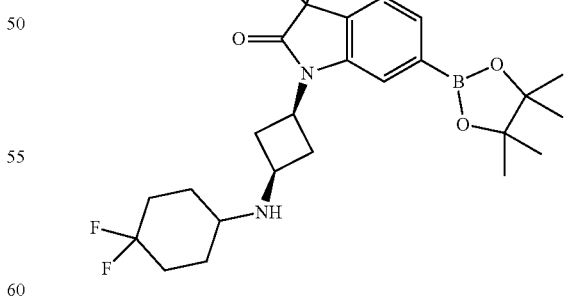

4,4-Difluorocyclohexan-1-amine was used to prepare 1-((1s,3s)-3-((4,4-difluorocyclohexyl)amino)cyclobutyl)-3,3-dimethyl-6-(4,4,5,5-tetramethyl-1,3,2-dioxaborolan-2-yl)indolin-2-one

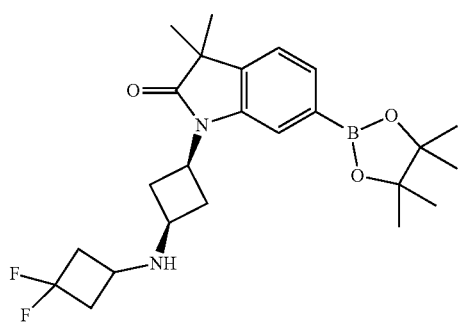 [SMILES: CC1(C)C(=O)N([C@H]2C[C@@H](NC3CC(F)(F)C3)C2)c2cc(B3OC(C)(C)C(C)(C)O3)ccc21]

3,3-Difluorocyclobutan-1-amine was used to prepare 1-((1s,3s)-3-((3,3-difluorocyclobutyl)amino)cyclobutyl)-3,3-dimethyl-6-(4,4,5,5-tetramethyl-1,3,2-dioxaborolan-2-yl)indolin-2-one

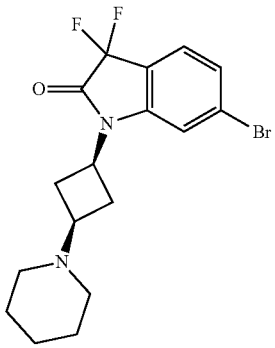 [SMILES: O=C1N([C@H]2C[C@@H](N3CCCCC3)C2)c2cc(Br)ccc2C1(F)F]

6-Bromo-3,3-difluoro-1-(3-oxocyclobutyl)indolin-2-one was used instead of 3,3-dimethyl-1-(3-oxocyclobutyl)-6-(4,4,5,5-tetramethyl-1,3,2-dioxaborolan-2-yl)indolin-2-one to prepare 6-bromo-3,3-difluoro-1-((1s,3s)-3-(piperidin-1-yl)cyclobutyl)indolin-2-one

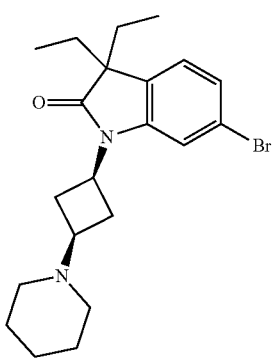 [SMILES: CCC1(CC)C(=O)N([C@H]2C[C@@H](N3CCCCC3)C2)c2cc(Br)ccc21]

6-Bromo-3,3-diethyl-1-(3-oxocyclobutyl)indolin-2-one was used instead of 3,3-dimethyl-1-(3-oxocyclobutyl)-6-(4,4,5,5-tetramethyl-1,3,2-dioxaborolan-2-yl)indolin-2-one to prepare 6-bromo-3,3-diethyl-1-((1s,3s)-3-(piperidin-1-yl)cyclobutyl)indolin-2-one Procedure 7: Preparation of the Compounds of Formula (13) According to Reaction Scheme I

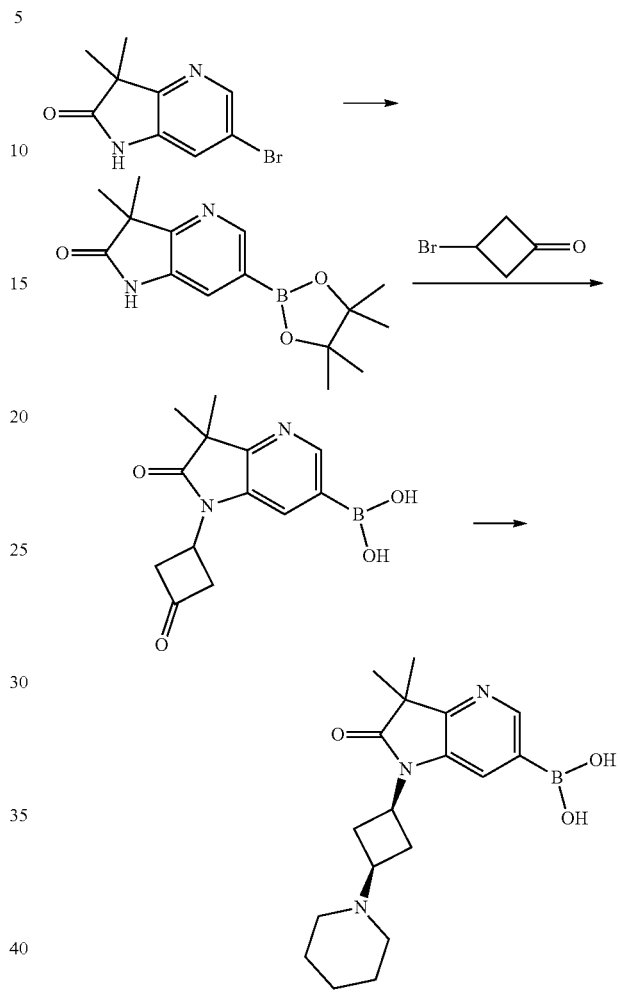

A. Preparation of 3,3-dimethyl-6-(4,4,5,5-tetramethyl-1,3,2-dioxaborolan-2-yl)-1,3-dihydro-2H-pyrrolo[3,2-b]pyridin-2-one

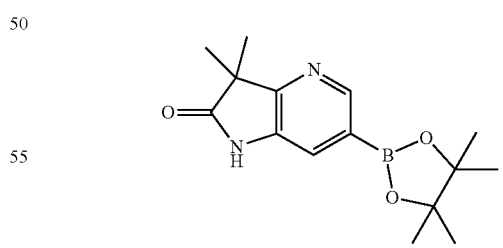

To a stirring solution of 6-bromo-3,3-dimethyl-1,3-dihydro-2H-pyrrolo[3,2-b]pyridin-2-one (4 g, 16.59 mmol) in dioxane (100 ml) were added bis(pinacolato)diboron (12.64 g, 49.77 mmol), potassium acetate (4.88 g, 49.77 mmol), and Pd(dppf)Cl₂/DCM (1354.92 mg, 1.66 mmol). The reaction mixture was degassed with N₂ for 5 min, sealed, and heated at 100° C. for 15 h. The reaction mixture was cooled to room temperature, and then filtered through a pad of celite. The filtrate was diluted with EtOAc. The organic layer was washed with brine, dried over $Na_2SO_4$, filtered, and then concentrated to give 3,3-dimethyl-6-(4,4,5,5-tetramethyl-1,3,2-dioxaborolan-2-yl)-1,3-dihydro-2H-pyrrolo[3,2-b]pyridin-2-one which was used in the next step without further purification.

The following compound was prepared using a similar procedure except 6-bromo-3,3-diethyl-1-((1s,3s)-3-(piperidin-1-yl)cyclobutyl)indolin-2-one was used instead 6-bromo-3,3-dimethyl-1,3-dihydro-2H-pyrrolo[3,2-b]pyridin-2-one:

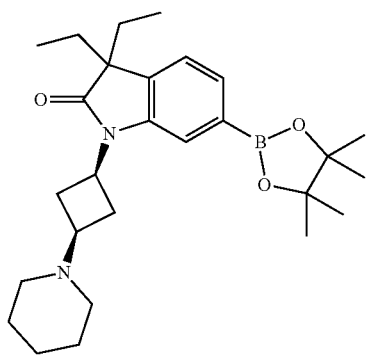 [SMILES: CCC1(CC)C(=O)N([C@H]2C[C@@H](N3CCCCC3)C2)c2cc(B3OC(C)(C)C(C)(C)O3)ccc21]

3,3-Diethyl-1-((1s,3s)-3-(piperidin-1-yl)cyclobutyl)-6-(4,4,5,5-tetramethyl-1,3,2-dioxaborolan-2-yl)indolin-2-one B. Preparation of (3,3-dimethyl-2-oxo-1-(3-oxocyclobutyl)-2,3-dihydro-1H-pyrrolo[3,2-b]pyridin-6-yl)boronic acid

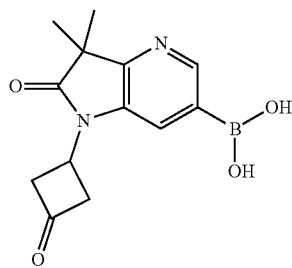 [SMILES: CC1(C)C(=O)N(C2CC(=O)C2)c2cc(B(O)O)cnc21]

To a stirring solution 3,3-dimethyl-6-(4,4,5,5-tetramethyl-1,3,2-dioxaborolan-2-yl)-1,3-dihydro-2H-pyrrolo[3,2-b]pyridin-2-one (1.1 g, 3.82 mmol) in NMP (20 ml) were added 3-bromocyclobutanone (1354.15 µl, 15.27 mmol) and $K_2CO_3$ (2.64 g, 19.09 mmol). The resulting mixture was heated at 50° C. for 15 h. The reaction mixture was cooled to room temperature and then diluted with EtOAc. The organic layer was washed with water followed by brine, dried over $Na_2SO_4$, filtered, then concentrated to give (3,3-dimethyl-2-oxo-1-(3-oxocyclobutyl)-2,3-dihydro-1H-pyrrolo[3,2-b]pyridin-6-yl)boronic acid, which was used in the next step without further purification.

C. Preparation of (3,3-dimethyl-2-oxo-1-((1s,3s)-3-(piperidin-1-yl)cyclobutyl)-2,3-dihydro-1H-pyrrolo[3,2-b]pyridin-6-yl)boronic acid

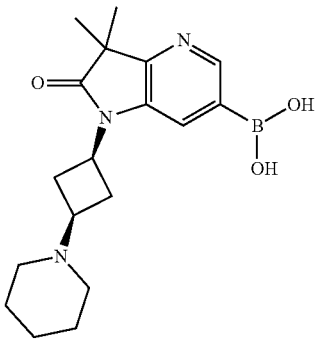 [SMILES: CC1(C)C(=O)N([C@H]2C[C@@H](N3CCCCC3)C2)c2cc(B(O)O)cnc21]

To a stirring solution of (3,3-dimethyl-2-oxo-1-(3-oxocyclobutyl)-2,3-dihydro-1H-pyrrolo[3,2-b]pyridin-6-yl)boronic acid (2 g, 5.61 mmol) in DCE (30 ml) were added piperidine (1.11 ml, 11.2 mmol), $Na(OAc)_3BH$ (1.78 g, 8.42 mmol), and AcOH (0.97 ml, 16.8 mmol) at room temperature. The resulting mixture was stirred for 2 h then quenched with satd. $NaHCO_3$. Aqueous layer was extracted with DCM and the combined organic layer was dried over $Na_2SO_4$, then concentrated to give (3,3-dimethyl-2-oxo-1-((1s,3s)-3-(piperidin-1-yl)cyclobutyl)-2,3-dihydro-1H-pyrrolo[3,2-b]pyridin-6-yl)boronic acid, which was used in the next step without further purification.

The following compound was prepared using a similar procedure except the amine indicated below was used instead of piperidine:

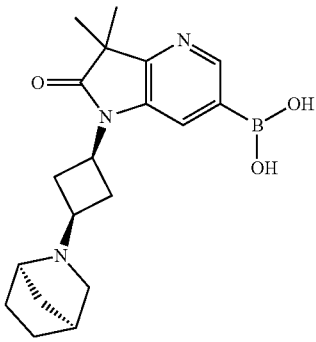 [SMILES: CC1(C)C(=O)N([C@H]2C[C@@H](N3C[C@H]4CC[C@@H]3C4)C2)c2cc(B(O)O)cnc21]

(1R,4S)-2-azabicyclo[2.2.1]heptane was used instead of piperidine to Prepare (1-((1S,3s)-3-((1R,4S)-2-azabicyclo[2.2.1]heptan-2-yl)cyclobutyl)-3,3-dimethyl-2-oxo-2,3-dihydro-1H-pyrrolo[3,2-b]pyridin-6-yl)boronic acid Procedure 8: Preparation of the Compounds of Formula (13) According to Reaction Scheme I

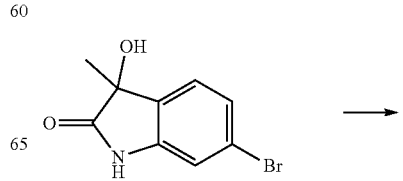

-continued

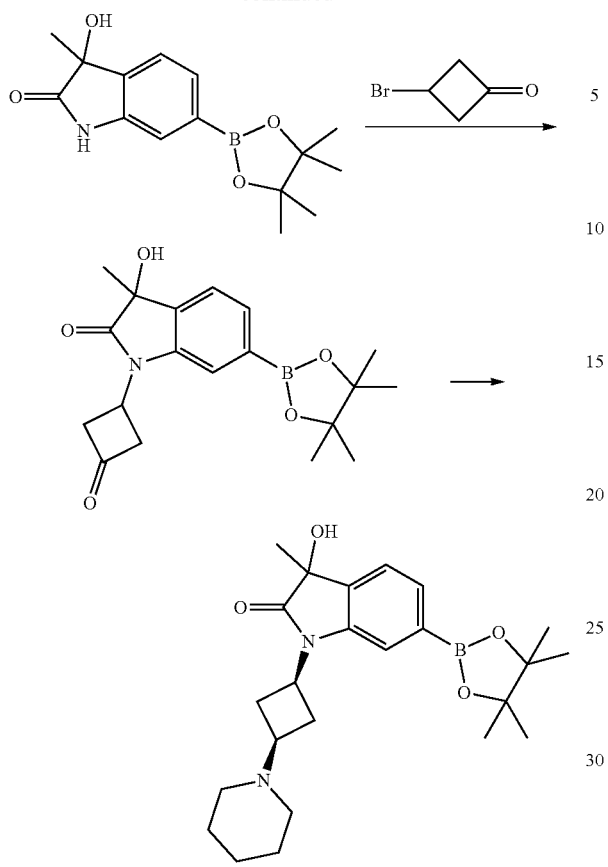

A. Preparation of 3-hydroxy-3-methyl-6-(4,4,5,5-tetramethyl-1,3,2-dioxaborolan-2-yl)-1,3-dihydro-2H-pyrrolo[3,2-b]pyridin-2-one

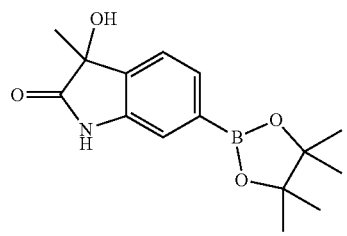 [SMILES: CC1(O)C(=O)Nc2cc(B3OC(C)(C)C(C)(C)O3)ccc21]

To a stirring solution of 6-bromo-3-hydroxy-3-methylindolin-2-one (4 g, 16.5 mmol) in dioxane (80 ml) were added bis(pinacolato)diboron (8.4 g, 33 mmol), potassium acetate (3.2 g, 33 mmol), and Pd(dppf)Cl$_2$-DCM (1.4 g, 1.65 mmol). The nitrogen gas was bubbled through the resulting suspension for 3 min then heated over night at 90° C. After cooling to room temperature, the reaction mixture was filtered and the filter cake was washed with EtOAc then concentrated in vacuo. The crude product was purified by silica gel chromatography (Hexanes/EtOAc) to afford 3-hydroxy-3-methyl-6-(4,4,5,5-tetramethyl-1,3,2-dioxaborolan-2-yl)-1,3-dihydro-2H-pyrrolo[3,2-b]pyridin-2-one.

B. Preparation of 3-hydroxy-3-methyl-1-(3-oxocyclobutyl)-6-(4,4,5,5-tetramethyl-1,3,2-dioxaborolan-2-yl)indolin-2-one

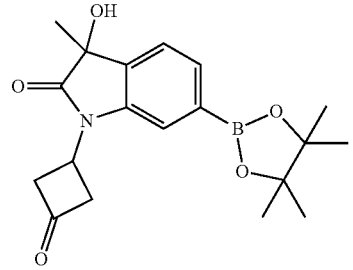 [SMILES: CC1(O)C(=O)N(C2CC(=O)C2)c2cc(B3OC(C)(C)C(C)(C)O3)ccc21]

To a stirring solution of 3-hydroxy-3-methyl-6-(4,4,5,5-tetramethyl-1,3,2-dioxaborolan-2-yl)-1,3-dihydro-2H-pyrrolo[3,2-b]pyridin-2-one in NMP (100 mL) were added 3-bromocyclobutanone (5.53 ml, 62.4 mmol) and potassium carbonate (325 mesh, 10.8 g, 78 mmol). The resulting suspension was stirred at 50° C. for overnight. After cooling to room temperature, the reaction mixture was diluted with EtOAc (100 ml) and the organic layer was washed with water (100 ml), brine (100 ml), dried over Na$_2$SO$_4$, concentrated, and purified by flash chromatography (Hexanes/EtOAc) to afford 3-hydroxy-3-methyl-1-(3-oxocyclobutyl)-6-(4,4,5,5-tetramethyl-1,3,2-dioxaborolan-2-yl)indolin-2-one.

C. Preparation of 3-hydroxy-3-methyl-1-((1s,3s)-3-(piperidin-1-yl)cyclobutyl)-6-(4,4,5,5-tetramethyl-1,3,2-dioxaborolan-2-yl)indolin-2-one

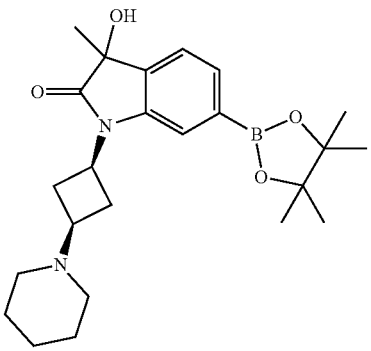 [SMILES: CC1(O)C(=O)N([C@H]2C[C@@H](N3CCCCC3)C2)c2cc(B3OC(C)(C)C(C)(C)O3)ccc21]

To a solution of 3-hydroxy-3-methyl-1-(3-oxocyclobutyl)-6-(4,4,5,5-tetramethyl-1,3,2-dioxaborolan-2-yl)indolin-2-one (3.0 g, 8.4 mmol) in dichloroethane (60 mL) was added piperidine (1.4 g, 16.8 mmol), acetic acid (1.5 mL, 25.2 mmol), and sodium triacetoxy borohydride (2.7 g, 12.6 mmol). After stirring at room temperature for 5 h, the reaction mixture was quenched with saturated aqueous sodium bicarbonate solution and extracted with methylene chloride (3×200 mL). The combined organic layers were washed with sat. NaHCO$_3$, brine, dried over sodium sulfate, filtered, and concentrated in vacuo to give 3-hydroxy-3-methyl-1-((1s,3s)-3-(piperidin-1-yl)cyclobutyl)-6-(4,4,5,5-tetramethyl-1,3,2-dioxaborolan-2-yl)indolin-2-one, which was used in the next step without purification.

Procedure 9: Preparation of the Compounds of Formula (17) Shown in Reaction Schemes I and IV

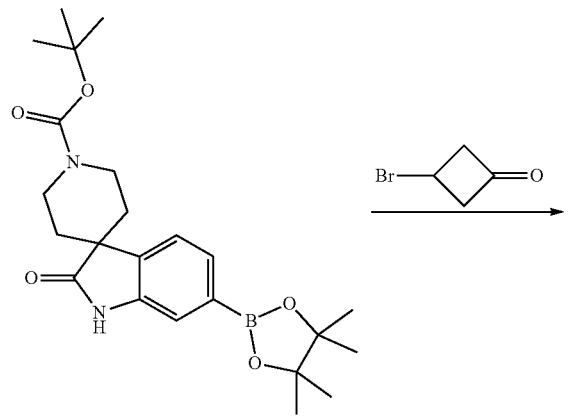
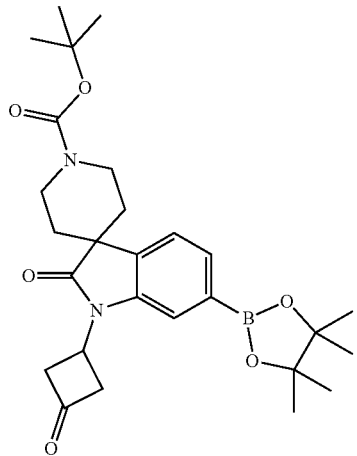 [SMILES: CC(C)(C)OC(=O)N1CCC2(CC1)C(=O)N(C1CC(=O)C1)c1cc(B3OC(C)(C)C(C)(C)O3)ccc12]
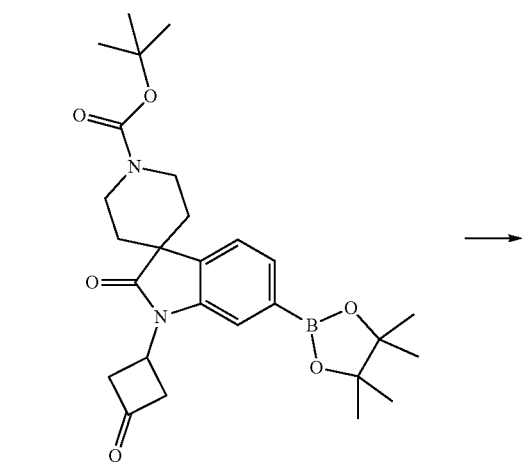
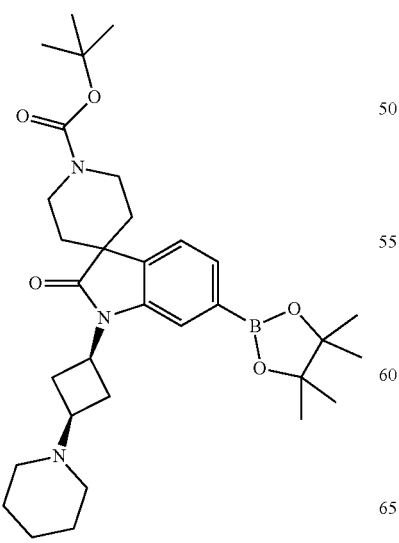
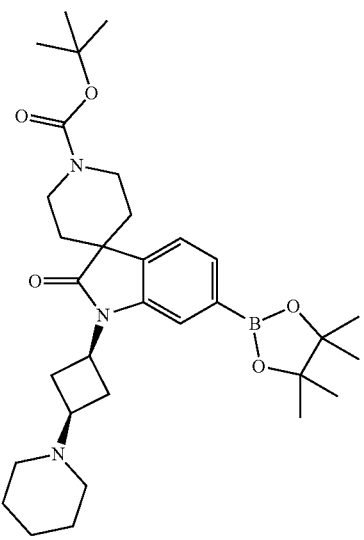 [SMILES: CC(C)(C)OC(=O)N1CCC2(CC1)C(=O)N([C@H]1C[C@@H](N3CCCCC3)C1)c1cc(B3OC(C)(C)C(C)(C)O3)ccc12]

A. Preparation of tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate To a mixture of tert-butyl 2-oxo-6-(4,4,5,5-tetramethyl-1,3,2-dioxaborolan-2-yl)spiro[indoline-3,4'-piperidine]-1'-carboxylate (0.81 g, 1.89 mmol), which can be prepared following the literature procedure (intermediate 7.33 in WO2015017610 A1, also published as), and powdered potassium carbonate (0.65 g of 325 mesh, 4.73 mmol) in DMF (7.5 mL) was added 3-bromocyclobutanone (0.21 mL, 2.53 mmol). After the mixture was heated to 50° C. for 1 h, it was cooled to room temperature and filtered to remove potassium carbonate. The filtrate was diluted with EtOAc and water, and extracted with EtOAc. The combined organic layers were washed with brine, dried (Na₂SO₄), filtered, concentrated, and purified via flash chromatography on silica gel with gradient elution (0-100% EtOAc/hexanes) to give tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate.

B. Preparation of tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate To a mixture of tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate (0.5 g, 1.0 mmol) in DCE (10 mL) was added piperidine (0.3 mL, 3.0 mmol), AcOH (0.2 mL, 3.0 mmol), and sodium triacetoxyborohydride (320 mg, 1.5 mmol). After stirring at room temperature for 16 h, the reaction mixture was diluted with sat. NaHCO$_3$ and DCM and stirred vigorously for 5 min. The organic layer was separated, dried over Na$_2$SO$_4$, and concentrated under reduced pressure to give tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate.

The following compounds were prepared using a similar procedure except the amines indicated below were used instead of piperidine:

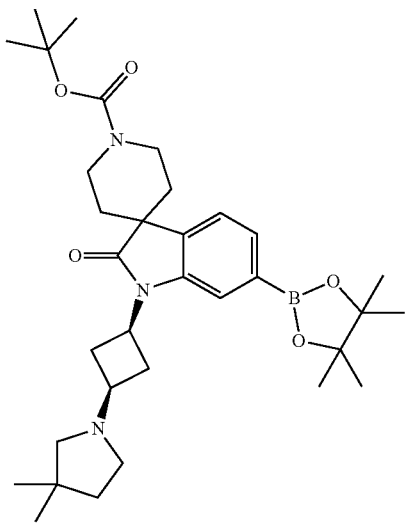 [SMILES: CC1(C)CCN([C@H]2C[C@@H](N3C(=O)C4(CCN(C(=O)OC(C)(C)C)CC4)c4ccc(B5OC(C)(C)C(C)(C)O5)cc43)C2)C1]

3,3-Dimethylpyrrolidine was used to prepare tert-butyl 1-((1s,3s)-3-(3,3-dimethylpyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate

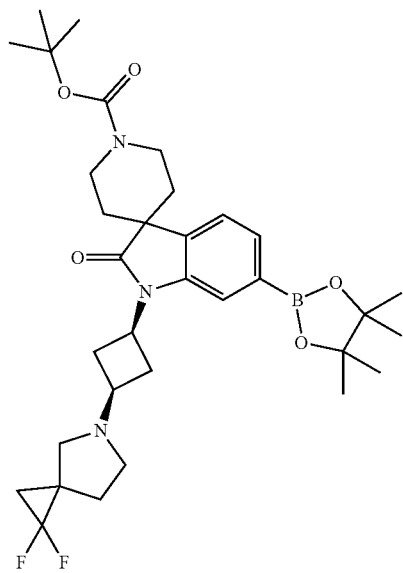 [SMILES: CC(C)(C)OC(=O)N1CCC2(CC1)C(=O)N([C@H]1C[C@@H](N3CCC4(C3)CC4(F)F)C1)c1cc(B3OC(C)(C)C(C)(C)O3)ccc12]

1,1-Difluoro-5-azaspiro[2.4]heptane was used to prepare tert-butyl 1-((1s,3s)-3-(1,1-difluoro-5-azaspiro[2.4]heptan-5-yl)cyclobutyl)-2-oxo-6-(4,4,5,5-tetramethyl-1,3,2-dioxaborolan-2-yl)spiro[indoline-3,4'-piperidine]-1'-carboxylate

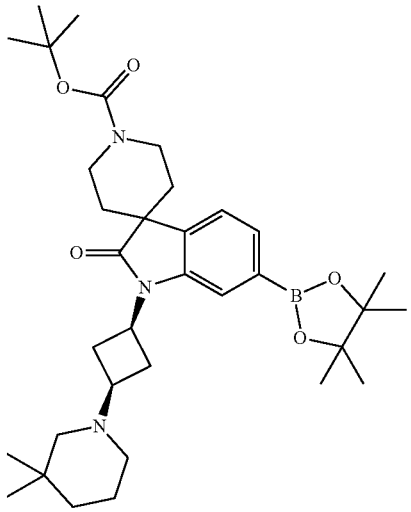

3,3-Dimethylpiperidine was used to prepare tert-butyl 1-((1s,3s)-3-(3,3-dimethylpiperidin-1-yl)cyclobutyl)-2-oxo-6-(4,4,5,5-tetramethyl-1,3,2-dioxaborolan-2-yl)spiro[indoline-3,4'-piperidine]-1'-carboxylate

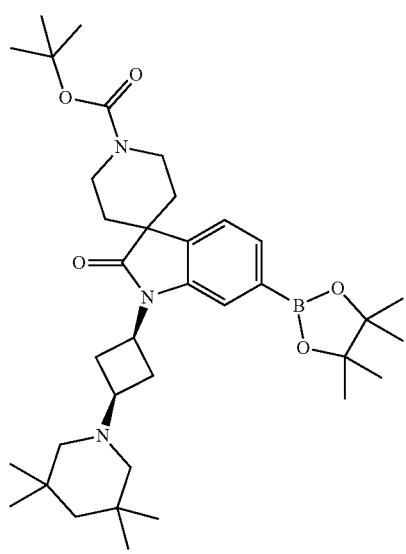

3,3,5,5-Tetramethylpiperidine was used to prepare tert-butyl 2-oxo-6-(4,4,5,5-tetramethyl-1,3,2-dioxaborolan-2-yl)-1-((1s,3s)-3-(3,3,5,5-tetramethylpiperidin-1-yl)cyclobutyl)spiro[indoline-3,4'-piperidine]-1'-carboxylate

| 301 | 302 |
|---|---|
| 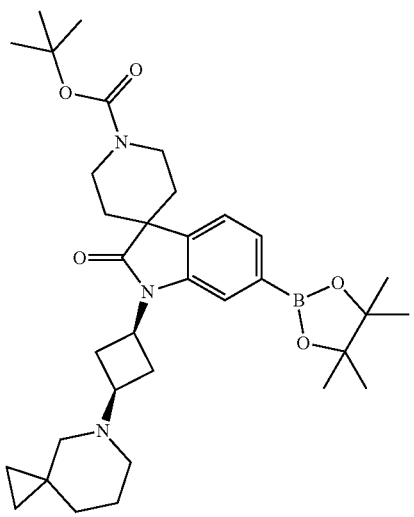 [SMILES: CC(C)(C)OC(=O)N1CCC2(CC1)C(=O)N([C@H]1C[C@@H](N3CCCC4(CC4)C3)C1)c1cc(B3OC(C)(C)C(C)(C)O3)ccc12] | 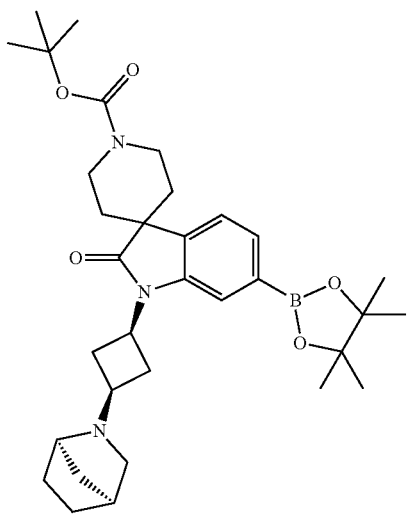 |

5-Azaspiro[2.5]octane was used to prepare tert-butyl 1-((1s,3s)-3-(5-azaspiro[2.5]octan-5-yl)cyclobutyl)-2-oxo-6-(4,4,5,5-tetramethyl-1,3,2-dioxaborolan-2-yl)spiro[indoline-3,4'-piperidine]-1'-carboxylate (1R,4S)-2-azabicyclo[2.2.1]heptane was used to prepare tert-butyl 1-((1S,3S)-3-((1R,4S)-2-azabicyclo[2.2.1]heptan-2-yl)cyclobutyl)-2-oxo-6-(4,4,5,5-tetramethyl-1,3,2-dioxaborolan-2-yl)spiro[indoline-3,4'-piperidine]-1'-carboxylate

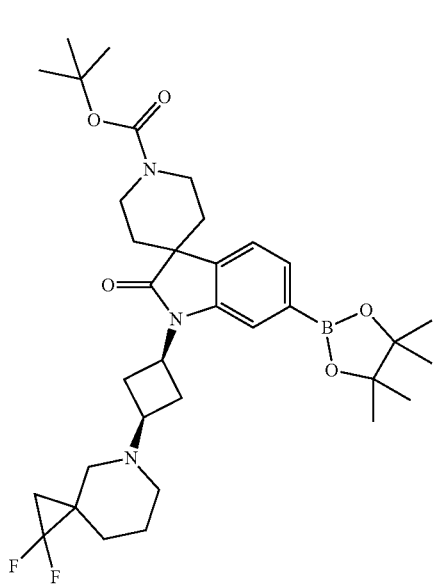 [SMILES: CC(C)(C)OC(=O)N1CCC2(CC1)C(=O)N([C@H]1C[C@@H](N3CCCC4(C3)CC4(F)F)C1)c1cc(B3OC(C)(C)C(C)(C)O3)ccc12] 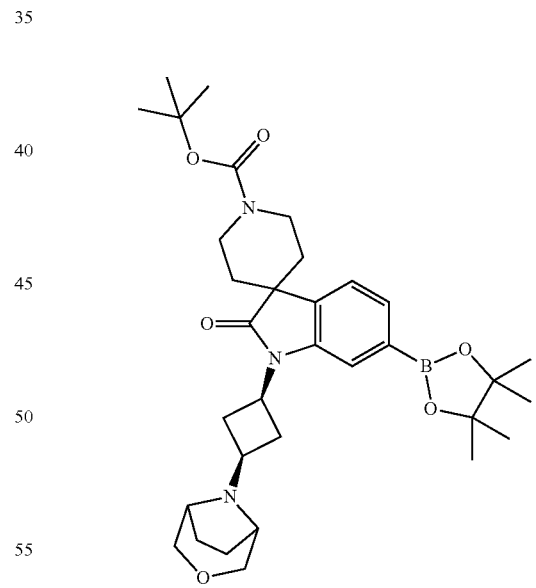

1,1-Difluoro-5-azaspiro[2.5]octane was used to prepare tert-butyl 1-((1s,3s)-3-(1,1-difluoro-5-azaspiro[2.5]octan-5-yl)cyclobutyl)-2-oxo-6-(4,4,5,5-tetramethyl-1,3,2-dioxaborolan-2-yl)spiro[indoline-3,4'-piperidine]-1'-carboxylate 3-Oxa-8-azabicyclo[3.2.1]octane was used to prepare tert-butyl 1-((1s,3s)-3-(3-oxa-8-azabicyclo[3.2.1]octan-8-yl)cyclobutyl)-2-oxo-6-(4,4,5,5-tetramethyl-1,3,2-dioxaborolan-2-yl)spiro[indoline-3,4'-piperidine]-1'-carboxylate

| 303 | 304 |
|---|---|
| 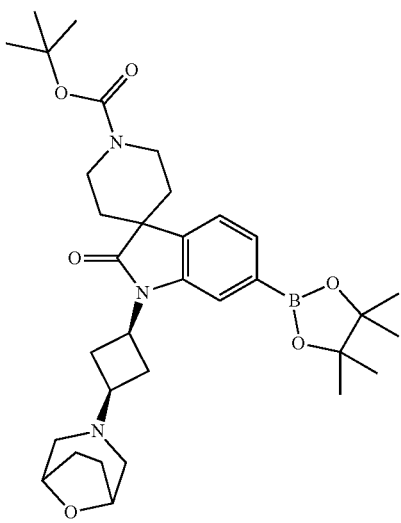 [SMILES: CC(C)(C)OC(=O)N1CCC2(CC1)C(=O)N([C@H]1C[C@@H](N3CC4CCC(C3)O4)C1)c1cc(B3OC(C)(C)C(C)(C)O3)ccc12] | 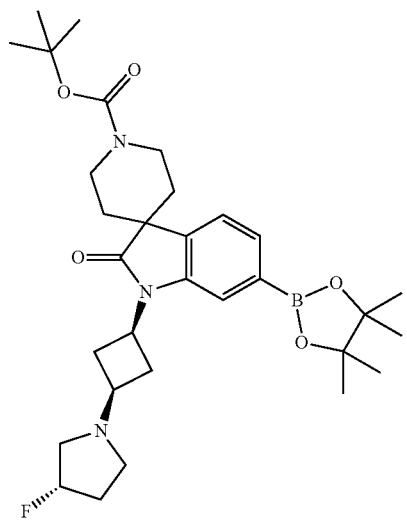 |
| 8-Oxa-3-azabicyclo[3.2.1]octane was used to prepare tert-butyl 1-((1s,3s)-3-(8-oxa-3-azabicyclo[3.2.1]octan-3-yl)cyclobutyl)-2-oxo-6-(4,4,5,5-tetramethyl-1,3,2-dioxaborolan-2-yl)spiro[indoline-3,4'-piperidine]-1'-carboxylate | (S)-3-Fluoropyrrolidine was used to prepare tert-butyl 1-((1R,3s)-3-((S)-3-fluoropyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate |
| 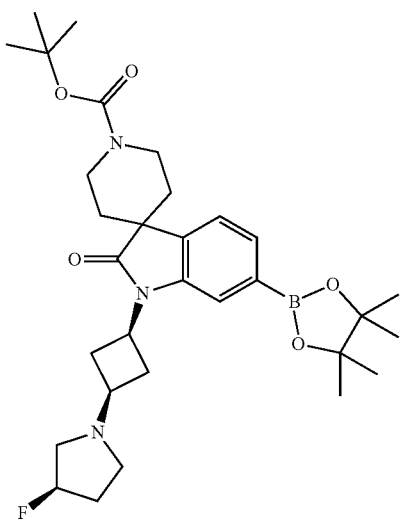 [SMILES: CC(C)(C)OC(=O)N1CCC2(CC1)C(=O)N([C@H]1C[C@@H](N3CC[C@@H](F)C3)C1)c1cc(B3OC(C)(C)C(C)(C)O3)ccc12] | 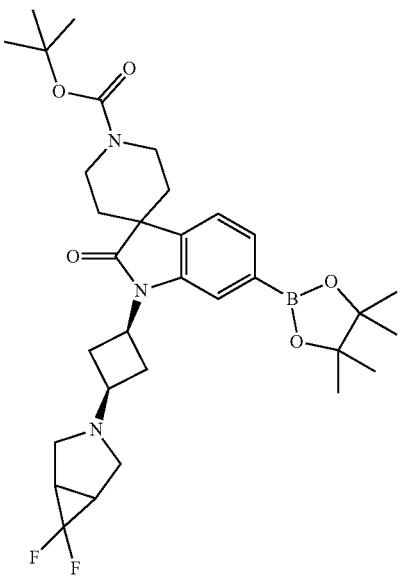 [SMILES: CC(C)(C)OC(=O)N1CCC2(CC1)C(=O)N([C@H]1C[C@@H](N3CC4C(C3)C4(F)F)C1)c1cc(B3OC(C)(C)C(C)(C)O3)ccc12] |
| (R)-3-fluoropyrrolidine was used to prepare tert-butyl 1-((1S,3s)-3-((R)-3-fluoropyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate | 6,6-Difluoro-3-azabicyclo[3.1.0]hexane was used to prepare tert-butyl 1-((1s,3s)-3-(6,6-difluoro-3-azabicyclo[3.1.0]hexan-3-yl)cyclobutyl)-2-oxo-6-(4,4,5,5-tetramethyl-1,3,2-dioxaborolan-2-yl)spiro[indoline-3,4'-piperidine]-1'-carboxylate |

C. Preparation of tert-butyl 1-((1S,3s)-3-((R)-3-fluoropiperidin-1-yl)cyclobutyl)-2-oxo-6-(4,4,5,5-tetramethyl-1,3,2-dioxaborolan-2-yl)spiro[indoline-3,4'-piperidine]-1'-carboxylate

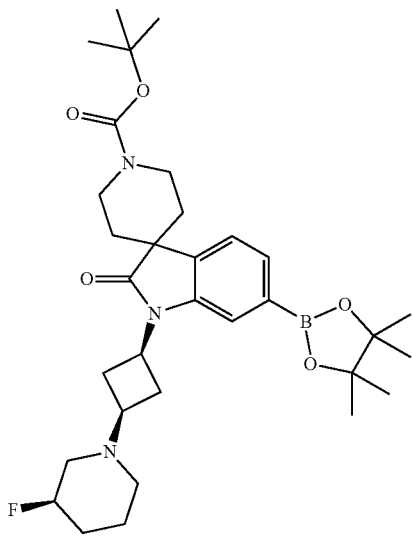 [SMILES: CC(C)(C)OC(=O)N1CCC2(CC1)C(=O)N([C@H]1C[C@@H](N3CCC[C@@H](F)C3)C1)c1cc(B3OC(C)(C)C(C)(C)O3)ccc12]

To a solution of tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate (250 mg, 0.5 mmol) in MeOH (6 mL) was added (R)-3-fluoropiperidine hydrochloride (211 mg, 1.5 mmol), zinc chloride (103 mg, 0.76 mmol), and sodium cyanoborohydride (95 mg, 1.5 mmol). After stirring overnight at room temperature, the reaction was diluted with sat. NaHCO₃ and DCM and stirred vigorously for five minutes. Then the organic layer was separated, dried (Na₂SO₄), and concentrated to give tert-butyl 1-((1S,3s)-3-((R)-3-fluoropiperidin-1-yl)cyclobutyl)-2-oxo-6-(4,4,5,5-tetramethyl-1,3,2-dioxaborolan-2-yl)spiro[indoline-3,4'-piperidine]-1'-carboxylate.

Procedure 10: Preparation of the Compounds of Formula (18) According to Reaction Scheme IV

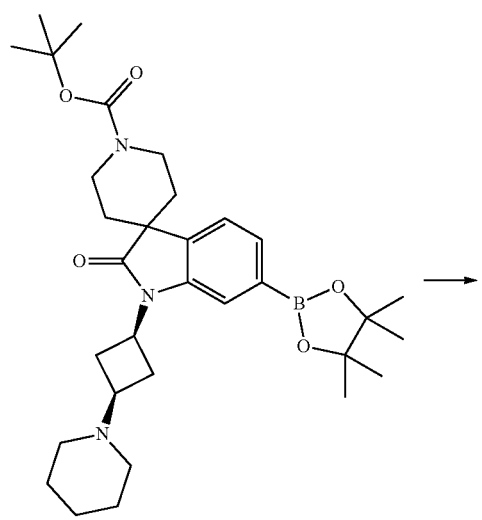

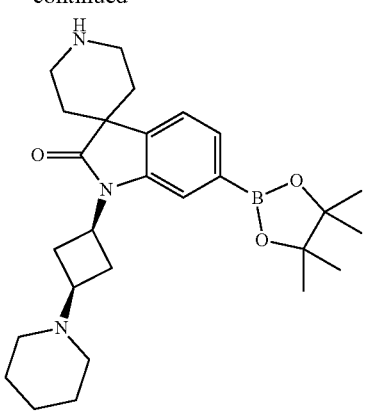

A. Preparation of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

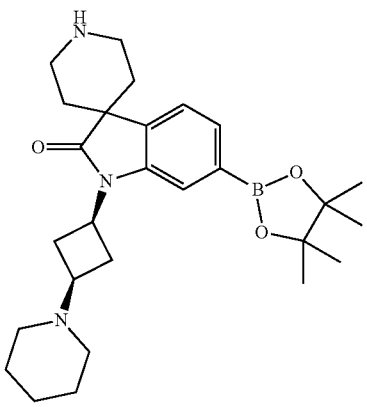 [SMILES: CC1(C)OB(c2ccc3c(c2)N([C@H]2C[C@@H](N4CCCCC4)C2)C(=O)C32CCNCC2)OC1(C)C]

To a solution of tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate (2.27 g, 4.01 mmol) in dioxane (20 mL) was added 4M hydrochloric acid solution (19.07 ml). The mixture was stirred at room temperature for 10 min, at which point LC-MS indicated complete conversion. The mixture was concentrated and the trace amounts of acid were chased off on the rotovap using methanol three times. The residue was dissolved in minimal DCM, and then crashed out with ether and hexanes. The precipitates were filtered and washed with hexanes to provide 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one.

The following compounds were prepared using a similar procedure except the compounds listed under Procedure 9 were used instead of tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate:

307

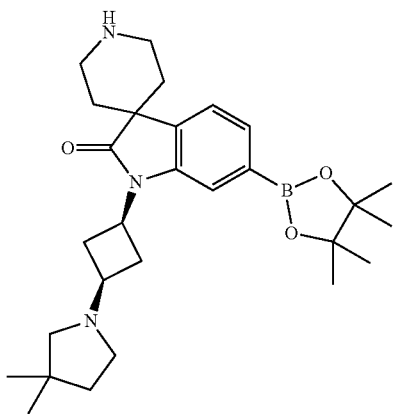

1-((1s,3s)-3-(3,3-dimethylpyrrolidin-1-yl)cyclobutyl)-6-(4,4,5,5-tetramethyl-1,3,2-dioxaborolan-2-yl)spiro[indoline-3,4'-piperidin]-2-one

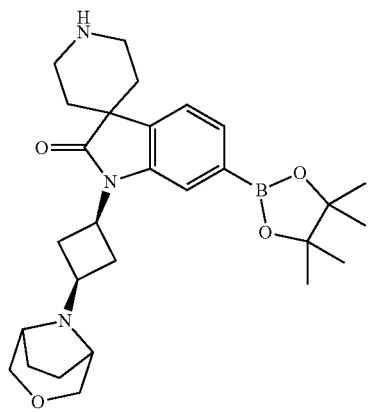 [SMILES: CC1(C)OB(c2ccc3c(c2)N([C@H]2C[C@@H](N4C5CCC4COC5)C2)C(=O)C32CCNCC2)OC1(C)C]

1-((1s,3s)-3-(3-oxa-8-azabicyclo[3.2.1]octan-8-yl)cyclobutyl)-6-(4,4,5,5-tetramethyl-1,3,2-dioxaborolan-2-yl)spiro[indoline-3,4'-piperidin]-2-one

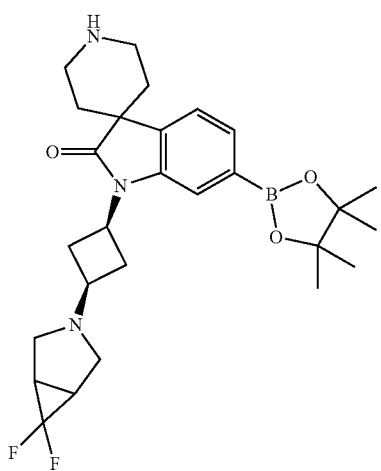 [SMILES: CC1(C)OB(c2ccc3c(c2)N([C@H]2C[C@@H](N4CC5C(C4)C5(F)F)C2)C(=O)C32CCNCC2)OC1(C)C]

1-((1s,3s)-3-(6,6-difluoro-3-azabicyclo[3.1.0]hexan-3-yl)cyclobutyl)-6-(4,4,5,5-tetramethyl-1,3,2-dioxaborolan-2-yl)spiro[indoline-3,4'-piperidin]-2-one

308

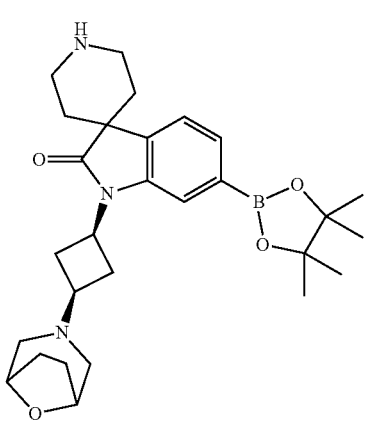 [SMILES: CC1(C)OB(c2ccc3c(c2)N([C@H]2C[C@@H](N4CC5CCC(C4)O5)C2)C(=O)C32CCNCC2)OC1(C)C]

1-((1s,3s)-3-(8-oxa-3-azabicyclo[3.2.1]octan-3-yl)cyclobutyl)-6-(4,4,5,5-tetramethyl-1,3,2-dioxaborolan-2-yl)spiro[indoline-3,4'-piperidin]-2-one

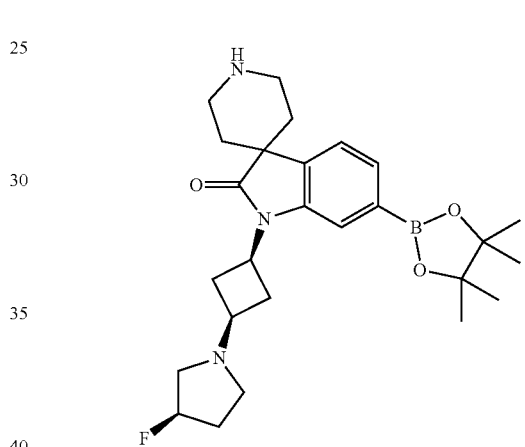

1-((1S,3s)-3-((R)-3-fluoropyrrolidin-1-yl)cyclobutyl)-6-(4,4,5,5-tetramethyl-1,3,2-dioxaborolan-2-yl)spiro[indoline-3,4'-piperidin]-2-one

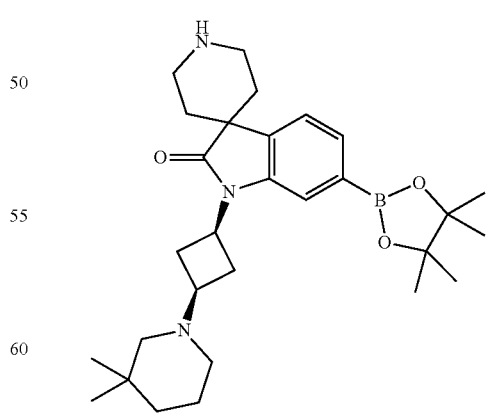

1-((1s,3s)-3-(3,3-dimethylpiperidin-1-yl)cyclobutyl)-6-(4,4,5,5-tetramethyl-1,3,2-dioxaborolan-2-yl)spiro[indoline-3,4'-piperidin]-2-one

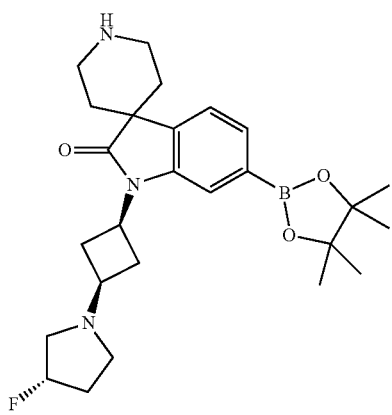 [SMILES: CC1(C)OB(c2ccc3c(c2)N([C@H]2C[C@@H](N4CC[C@H](F)C4)C2)C(=O)C32CCNCC2)OC1(C)C]

1-((1R,3s)-3-((S)-3-fluoropyrrolidin-1-yl)cyclobutyl)-6-(4,4,5,5-tetramethyl-1,3,2-dioxabrolan-2-yl)spiro[indoline-3,4'-piperidin]-2-one

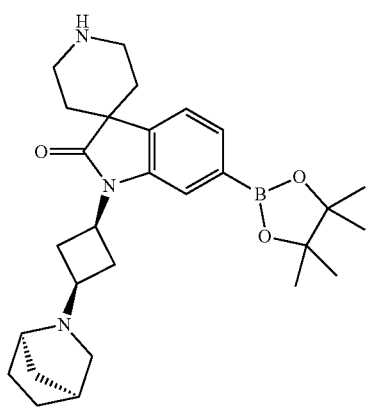 [SMILES: CC1(C)OB(c2ccc3c(c2)N([C@H]2C[C@@H](N4C[C@H]5CC[C@@H]4C5)C2)C(=O)C32CCNCC2)OC1(C)C]

1-((1S,3s)-3-((1R,4S)-2-azabicyclo[2.2.1]heptan-2-yl)cyclobutyl)-6-(4,4,5,5-tetramethyl-1,3,2-dioxaborolan-2-yl)spiro[indoline-3,4'-piperidin]-2-one Procedure 11: Preparation of the Compounds of Formula (13) According to Reaction Scheme I

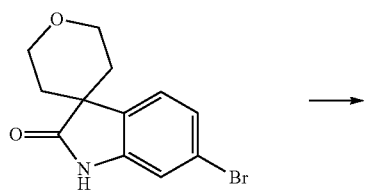

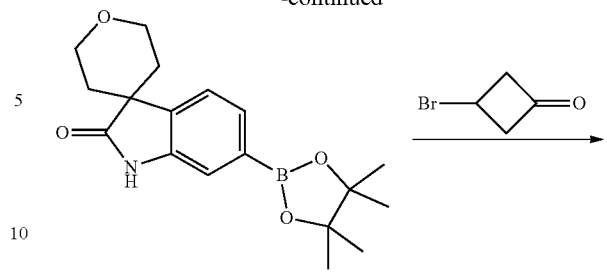

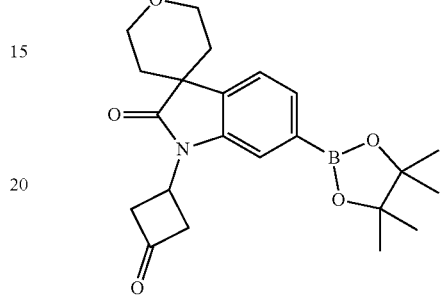

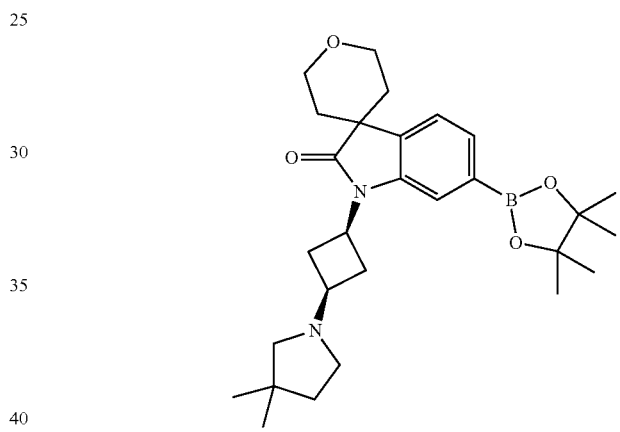

A. Preparation of 6-(4,4,5,5-tetramethyl-1,3,2-dioxaborolan-2-yl)-2',3',5',6'-tetrahydrospiro[indoline-3,4'-pyran]-2-one

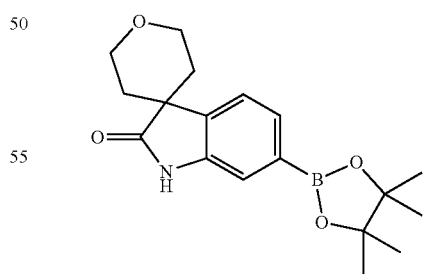

To a stirring solution of 6-bromo-2',3',5',6'-tetrahydrospiro[indoline-3,4'-pyran]-2-one (4 g, 16.5 mmol) in DMSO (1160 ml) were added bis(pinacolato)diboron (20.1 g, 24.7 mmol), potassium acetate (80.7 g, 822 mmol), and Pd(dppf)Cl₂ (20.1 g, 24.7 mmol). The nitrogen gas was bubbled through the resulting suspension for 5 min and then the suspension was heated at 90° C. for 6 h. After cooling to room temperature, the reaction mixture was diluted with EtOAc and washed with brine. The organic layer was dried ($Na_2SO_4$), filtered, concentrated, triturated with petroleum ether/EtOAc, and filtered to give 6-(4,4,5,5-tetramethyl-1,3,2-dioxaborolan-2-yl)-2',3',5',6'-tetrahydrospiro[indoline-3,4'-pyran]-2-one.

B. Preparation of 1-(3-oxocyclobutyl)-6-(4,4,5,5-tetramethyl-1,3,2-dioxaborolan-2-yl)-2',3',5',6'-tetrahydrospiro[indoline-3,4'-pyran]-2-one

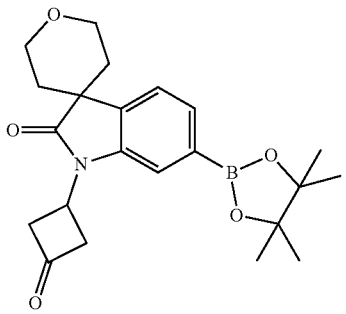 [SMILES: CC1(C)OB(c2ccc3c(c2)N(C2CC(=O)C2)C(=O)C32CCOCC2)OC1(C)C]

To a stirring solution of 6-(4,4,5,5-tetramethyl-1,3,2-dioxaborolan-2-yl)-2',3',5',6'-tetrahydrospiro[indoline-3,4'-pyran]-2-one (67.0 g, 203 mmol) in DMF (500 mL) was added potassium carbonate (70.3 g, 509 mmol). After stirring at 50° C. for 4 h, 3-bromocyclobutanone (60.6 g, 407 mmol) was added to the mixture. The resulting suspension was stirred at 50° C. for 1 h. After cooling to room temperature, the reaction mixture was filtered, concentrated, and purified by flash chromatography (Petroleum ether/EtOAc) to afford 1-(3-oxocyclobutyl)-6-(4,4,5,5-tetramethyl-1,3,2-dioxaborolan-2-yl)-2',3',5',6'-tetrahydrospiro[indoline-3,4'-pyran]-2-one.

C. Preparation of 1-((1s,3s)-3-(3,3-dimethylpyrrolidin-1-yl)cyclobutyl)-6-(4,4,5,5-tetramethyl-1,3,2-dioxaborolan-2-yl)-2',3',5',6'-tetrahydrospiro[indoline-3,4'-pyran]-2-one

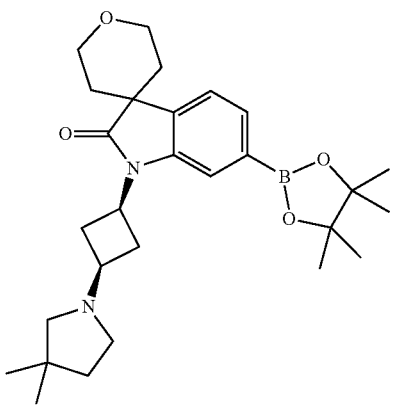

To a solution of 1-(3-oxocyclobutyl)-6-(4,4,5,5-tetramethyl-1,3,2-dioxaborolan-2-yl)-2',3',5',6'-tetrahydrospiro[indoline-3,4'-pyran]-2-one (3.0 g, 8.4 mmol) in dichloroethane (30 mL) was added 3,3-dimethylpyrrolidine (1.5 g, 15.1 mmol), acetic acid (1.4 mL, 22.7 mmol), and sodium triacetoxy borohydride (2.4 g, 11.3 mmol). After stirring at room temperature for 48 h, the reaction mixture was quenched with saturated aqueous sodium bicarbonate solution and extracted with methylene chloride. The combined organic layers were washed with sat. $NaHCO_3$, brine, dried over sodium sulfate, filtered, and concentrated in vacuo to give 1-((1s,3s)-3-(3,3-dimethylpyrrolidin-1-yl)cyclobutyl)-6-(4,4,5,5-tetramethyl-1,3,2-dioxaborolan-2-yl)-2',3',5',6'-tetrahydrospiro[indoline-3,4'-pyran]-2-one, which was used in the next step without purification.

The following compound was prepared using a similar procedure except piperidine was used instead of 3,3-dimethylpyrrolidine:

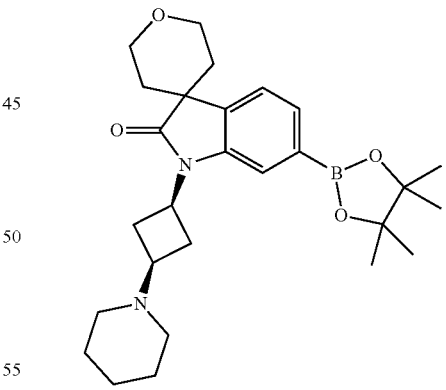

1-((1s,3s)-3-(piperidin-1-yl)cyclobutyl)-6-(4,4,5,5-tetramethyl-1,3,2-dioxaborolan-2-yl)-2',3',5',6'-tetrahydrospiro[indoline-3,4'-pyran]-2-one Procedure 12: Preparation of the Compounds of Formula (I-B) According to Reaction Scheme IV

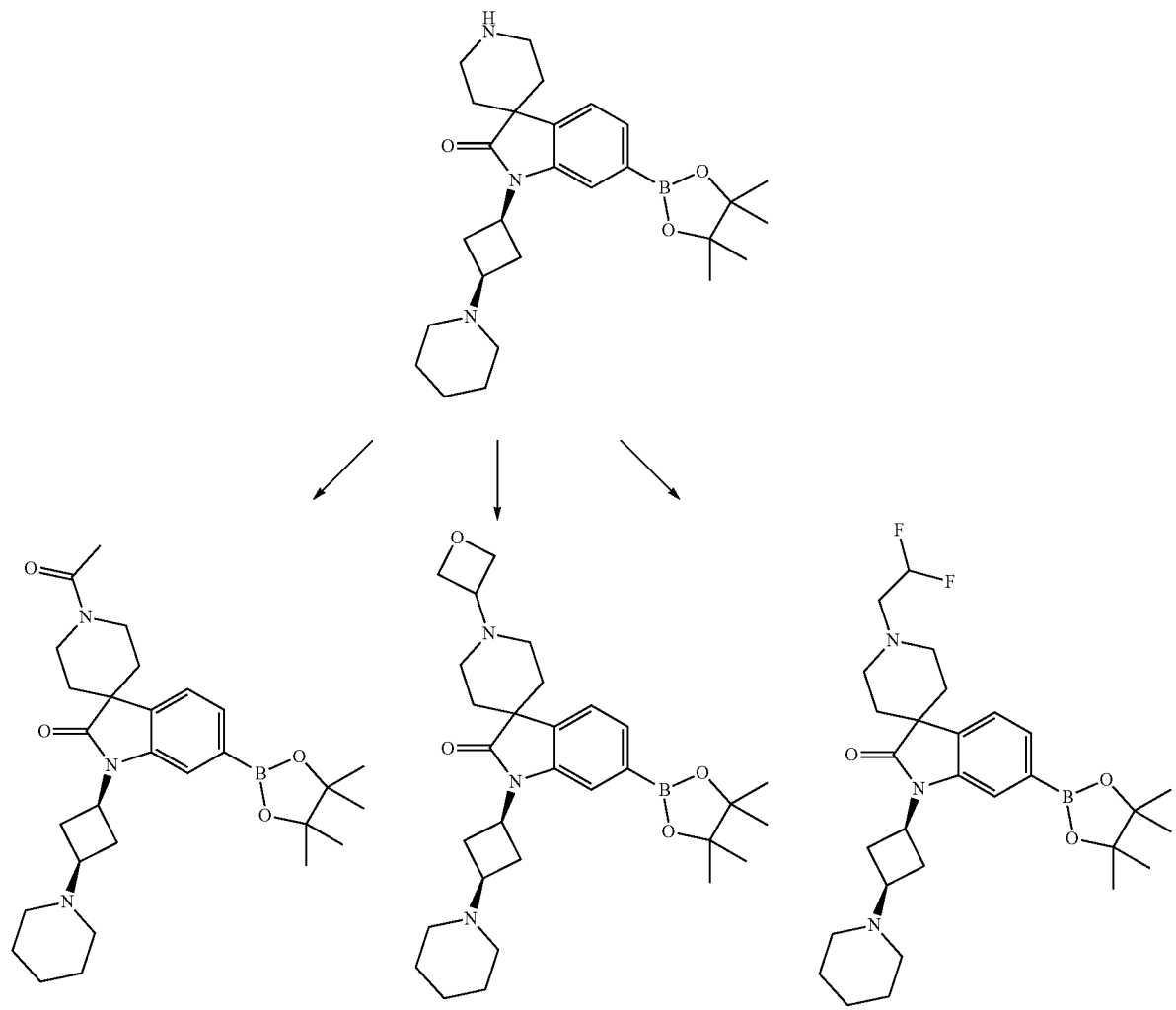

A. Preparation of 1'-acetyl-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

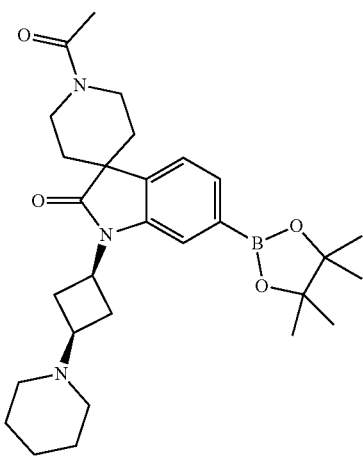 [SMILES: CC(=O)N1CCC2(CC1)C(=O)N([C@H]1C[C@@H](N3CCCCC3)C1)c1cc(B3OC(C)(C)C(C)(C)O3)ccc12]

To a suspension of 1-((1s,3s)-3-(piperidin-1-yl)cyclobutyl)-6-(4,4,5,5-tetramethyl-1,3,2-dioxaborolan-2-yl) spiro[indoline-3,4'-piperidin]-2-one (1810 mg, 3.89 mmol) and triethylamine (5.42 ml, 38.89 mmol) in dichloromethane (8 ml) was added acetic anhydride (0.55 ml, 5.83 mmol). The mixture was stirred at room temperature for 1 h, then diluted with DCM and water, and extracted with DCM. The combined organic layers were washed with brine and concentrated to provide 1'-acetyl-1-((1s,3s)-3-(piperidin-1-yl) cyclobutyl)-6-(4,4,5,5-tetramethyl-1,3,2-dioxaborolan-2-yl) spiro[indoline-3,4'-piperidin]-2-one.

The following compounds were prepared using a similar procedure except the compounds listed under Procedure 10 were used instead of 1-((1s,3s)-3-(piperidin-1-yl)cyclobutyl)-6-(4,4,5,5-tetramethyl-1,3,2-dioxaborolan-2-yl) spiro[indoline-3,4'-piperidin]-2-one.

315

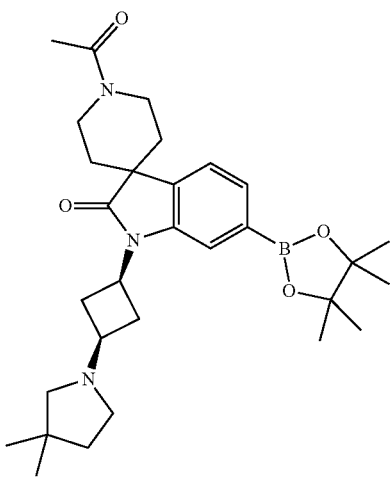

1'-Acetyl-1-((1s,3s)-3-(3,3-dimethylpyrrolidin-1-yl)cyclobutyl)-6-(4,4,5,5-tetramethyl-1,3,2-dioxaborolan-2-yl)spiro[indoline-3,4'-piperidin]-2-one

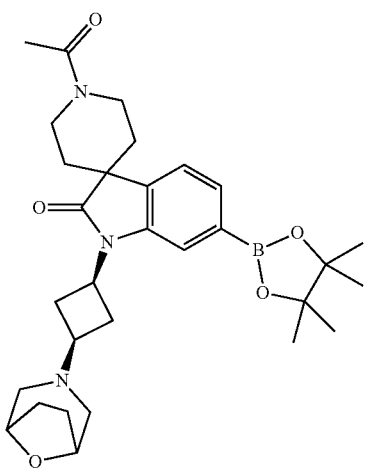 [SMILES: CC(=O)N1CCC2(CC1)C(=O)N([C@H]1C[C@@H](N3CC4CCC(C3)O4)C1)c1cc(B3OC(C)(C)C(C)(C)O3)ccc12]

1-((1s,3s)-3-(8-oxa-3-azabicyclo[3.2.1]octan-3-yl)cyclobutyl)-1'-acetyl-6-(4,4,5,5-tetramethyl-1,3,2-dioxaborolan-2-yl)spiro[indoline-3,4'-piperidin]-2-one

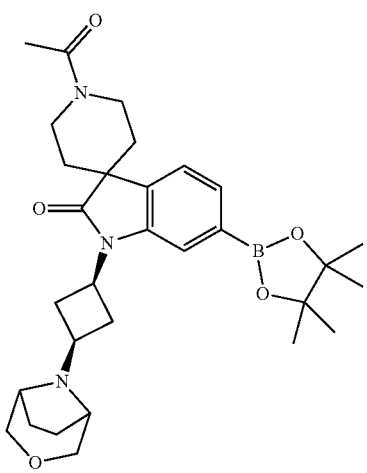 [SMILES: CC(=O)N1CCC2(CC1)C(=O)N([C@H]1C[C@@H](N3C4CCC3COC4)C1)c1cc(B3OC(C)(C)C(C)(C)O3)ccc12]

316

1-((1s,3s)-3-(3-oxa-8-azabicyclo[3.2.1]octan-8-yl)cyclobutyl)-1'-acetyl-6-(4,4,5,5-tetramethyl-1,3,2-dioxaborolan-2-yl)spiro[indoline-3,4'-piperidin]-2-one

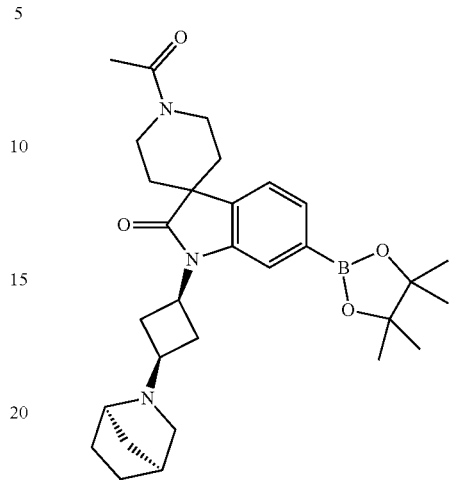

1-((1S,3s)-3-((1R,4S)-2-azabicyclo[2.2.1]heptan-2-yl)cyclobutyl)-1'-acetyl-6-(4,4,5,5-tetramethyl-1,3,2-dioxaborolan-2-yl)spiro[indoline-3,4'-piperidin]-2-one B. Preparation of 1'-(2-hydroxy-2-methylpropanoyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

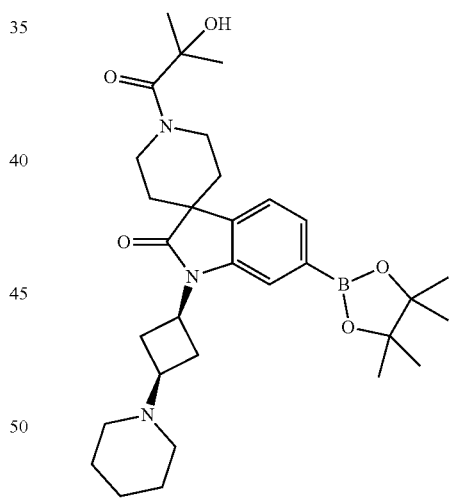

In a 20 mL vial were placed 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (200.0 mg, 0.4 mmol), 2-hydroxy-2-methylpropanoic acid (103.7 mg, 1.0 mmol), HATU (364.6 mg, 1.0 mmol), and N,N-Diisopropylethylamine (0.7 ml, 4.0 mmol) in ACN (9 ml). The mixture was stirred at room temperature for 16 h. Then the mixture was quenched with saturated NaHCO$_3$ and extracted with DCM. The combined organic layers were washed with water and brine, dried (Na$_2$SO$_4$), concentrated, and used in the next step without purification.

The following compounds were prepared using a similar procedure except the carboxylic acids indicated below were used instead of 2-hydroxy-2-methylpropanoic acid:

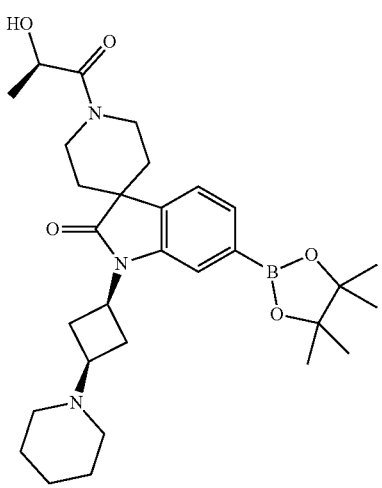 [SMILES: C[C@@H](O)C(=O)N1CCC2(CC1)C(=O)N([C@H]1C[C@@H](N3CCCCC3)C1)c1cc(B3OC(C)(C)C(C)(C)O3)ccc12]

(R)-2-Hydroxypropanoic acid was used to prepare 1'-((R)-2-hydroxypropanoyl)-1-((1s,3S)-3-(piperidin-1-yl)cyclobutyl)-6-(4,4,5,5-tetramethyl-1,3,2-dioxaborolan-2-yl)spiro[indoline-3,4'-piperidin]-2-one

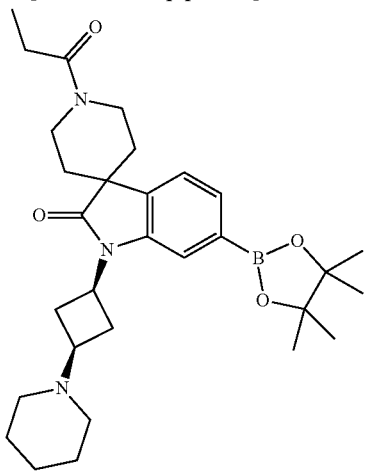

Propionic acid was used to prepare 1-((1s,3s)-3-(piperidin-1-yl)cyclobutyl)-1'-propionyl-6-(4,4,5,5-tetramethyl-1,3,2-dioxaborolan-2-yl)spiro[indoline-3,4'-piperidin]-2-one C. Preparation of 1'-(1-methylcyclopropane-1-carbonyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

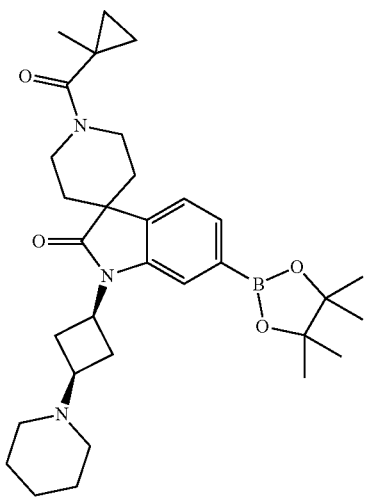 [SMILES: CC1(C(=O)N2CCC3(CC2)C(=O)N([C@H]2C[C@@H](N4CCCCC4)C2)c2cc(B4OC(C)(C)C(C)(C)O4)ccc23)CC1]

To a suspension of 1-((1s,3s)-3-(piperidin-1-yl)cyclobutyl)-6-(4,4,5,5-tetramethyl-1,3,2-dioxaborolan-2-yl) spiro[indoline-3,4'-piperidin]-2-one (0.3 g, 0.6 mmol) in DMF (3 mL) was added 1-methylcyclopropane-1-carboxylic acid (0.12 g, 1.2 mmol), DIEA (1.04 mL, 5.97 mmol) followed by a 50% solution of propylphosphonic anhydride (T3P) in EtOAc, (0.31 mL, 0.53 mmol) and the mixture was stirred at room temperature for 72 h. The mixture was then quenched with water and extracted twice with EtOAc. The combined organic layers were washed with brine, dried (Na$_2$SO$_4$), concentrated to give 1'-(1-methylcyclopropane-1-carbonyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one, which was used in the next step without purification.

The following compounds were prepared using a similar procedure with the following modification(s):
- the carboxylic acids indicated below were used instead of 1-methylcyclopropane-1-carboxylic acid; and/or
- the compounds listed under Procedure 10 were used instead of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one:

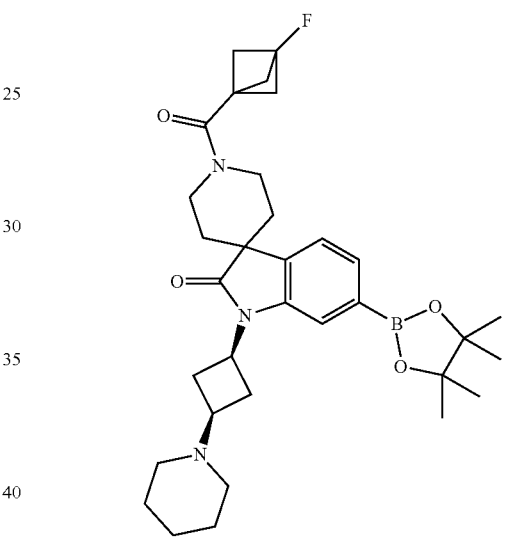

3-Fluorobicyclo[1.1.1]pentane-1-carboxylic acid was used to prepare 1'-(3-fluorobicyclo[1.1.1]pentane-1-carbonyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

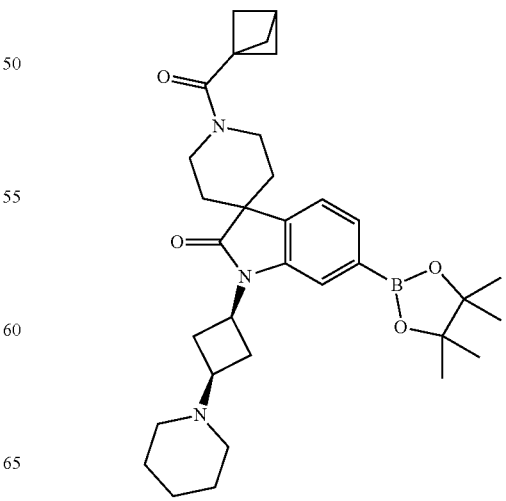

Bicyclo[1.1.1]pentane-1-carboxylic acid was used to prepare 1'-(bicyclo[1.1.1]pentane-1-carbonyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

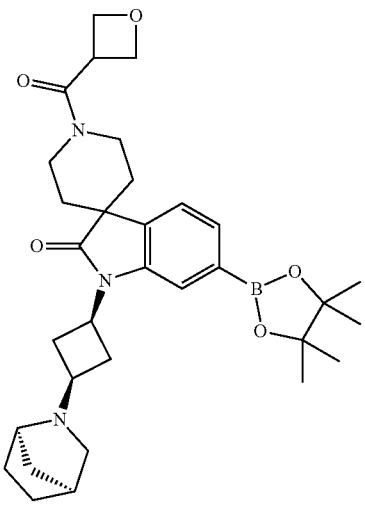 [SMILES: CC1(C)OB(c2ccc3c(c2)N([C@H]2C[C@@H](N4C[C@H]5CC[C@@H]4C5)C2)C(=O)C32CCN(C(=O)C3COC3)CC2)OC1(C)C]

Oxetane-3-carboxylic acid was used to prepare 1-((1S,3s)-3-((1R,4S)-2-azabicyclo[2.2.1]heptan-2-yl)cyclobutyl)-1'-(oxetane-3-carbonyl)-6-(4,4,5,5-tetramethyl-1,3,2-dioxaborolan-2-yl)spiro[indoline-3,4'-piperidin]-2-one

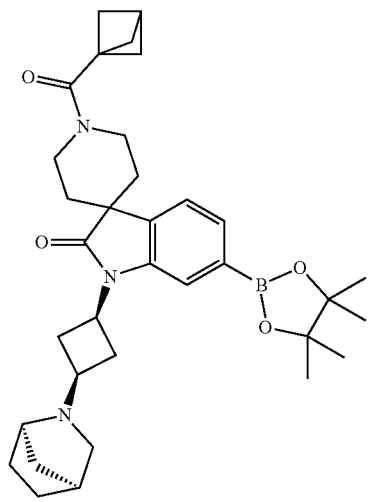 [SMILES: CC1(C)OB(c2ccc3c(c2)N([C@H]2C[C@@H](N4C[C@H]5CC[C@@H]4C5)C2)C(=O)C32CCN(C(=O)C34CC(C3)C4)CC2)OC1(C)C]

Bicyclo[1.1.1]pentane-1-carboxylic acid was used to prepare 1-((1S,3s)-3-((1R,4S)-2-azabicyclo[2.2.1]heptan-2-yl)cyclobutyl)-1'-(bicyclo[1.1.1]pentane-1-carbonyl)-6-(4,4,5,5-tetramethyl-1,3,2-dioxaborolan-2-yl)spiro[indoline-3,4'-piperidin]-2-one D. Preparation of methyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate

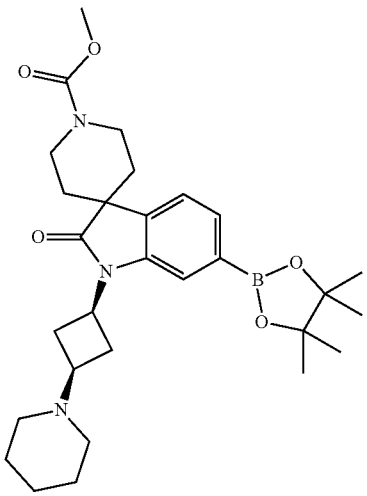 [SMILES: COC(=O)N1CCC2(CC1)C(=O)N([C@H]1C[C@@H](N3CCCCC3)C1)c1cc(B3OC(C)(C)C(C)(C)O3)ccc12]

To a suspension of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (0.3 g, 0.6 mmol) in DCM (5 mL) was added DIEA (1.0 mL, 5.6 mmol) and methyl carbonochloridate (0.1 g, 1.1 mmol). After the mixture was stirred at room temperature for 2 h, it was quenched with water and extracted with EtOAc. The combined organic layers were washed with brine, dried ($Na_2SO_4$), and concentrated to give methyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate which was used in the next step without purification.

The following compounds were prepared using a similar procedure with the following modification(s):
- the carboxylic acid chloride indicated below was used instead of methyl carbonochloridate; and/or
- the compounds listed under Procedure 10 were used instead of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one:

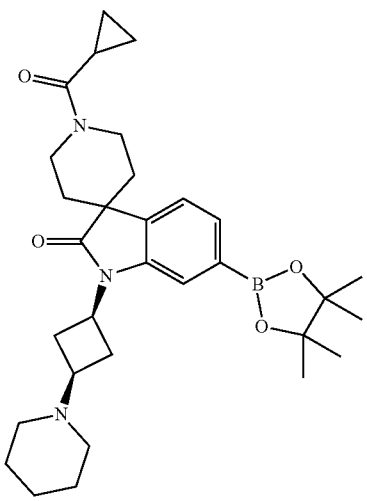 [SMILES: CC1(C)OB(c2ccc3c(c2)N([C@H]2C[C@@H](N4CCCCC4)C2)C(=O)C32CCN(C(=O)C3CC3)CC2)OC1(C)C]

321

Cyclopropanecarbonyl chloride was used to prepare 1'-(cyclopropanecarbonyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

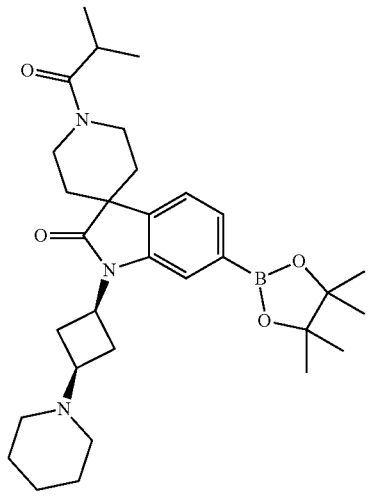 [SMILES: CC(C)C(=O)N1CCC2(CC1)C(=O)N([C@H]1C[C@@H](N3CCCCC3)C1)c1cc(B3OC(C)(C)C(C)(C)O3)ccc12]

Isobutyryl chloride was used to prepare 1'-isobutyryl-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

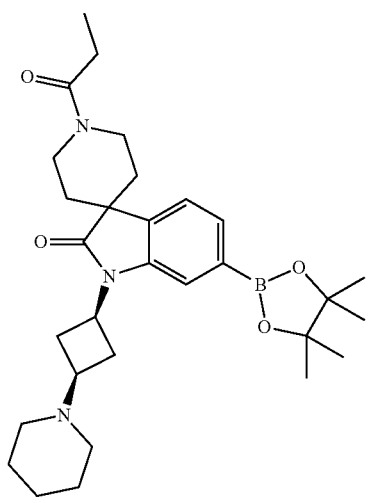 [SMILES: CCC(=O)N1CCC2(CC1)C(=O)N([C@H]1C[C@@H](N3CCCCC3)C1)c1cc(B3OC(C)(C)C(C)(C)O3)ccc12]

Propionyl chloride was used to prepare 1-((1s,3s)-3-(piperidin-1-yl)cyclobutyl)-1'-propionyl-6-(4,4,5,5-tetramethyl-1,3,2-dioxaborolan-2-yl)spiro[indoline-3,4'-piperidin]-2-one

322

E. Preparation of 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

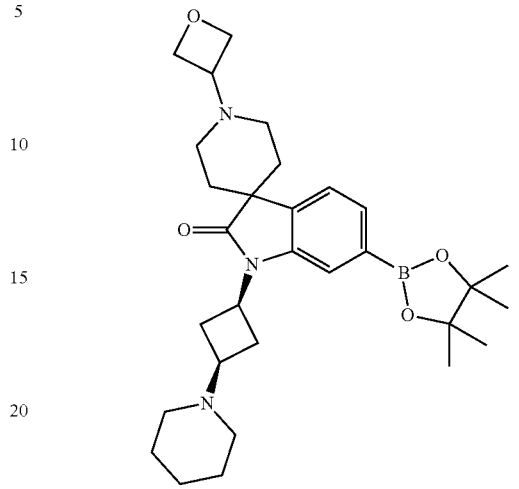

To a suspension of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (1.50 g, 2.79 mmol) and 3-oxetanone (0.49 mL, 0.60 g, 8.4 mmol) in methanol (28 mL) was added zinc chloride (570 mg, 4.18 mmol), followed by sodium cyanoborohydride (525 mg, 8.36 mmol). The mixture was sealed and heated to 40° C. with stirring for 2 h. The reaction mixture was cooled, saturated aqueous sodium bicarbonate was added, and the aqueous layer was extracted three times with ethyl acetate. The combined organic layers were dried over sodium sulfate, filtered, and concentrated under vacuum. The resulting residue was dissolved in EtOAc, washed once more with saturated aqueous sodium bicarbonate, dried over sodium sulfate, filtered, and concentrated under vacuum to afford 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one, which was used in the next step without purification.

The following compounds were prepared using a similar procedure except the compounds listed under Procedure 10 were used instead of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one.

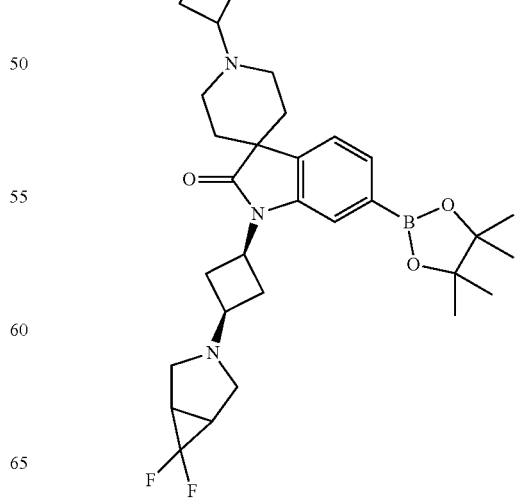

323

1-((1s,3s)-3-(6,6-difluoro-3-azabicyclo[3.1.0]hexan-3-yl)cyclobutyl)-1'-(oxetan-3-yl)-6-(4,4,5,5-tetramethyl-1,3,2-dioxaborolan-2-yl)spiro[indoline-3,4'-piperidin]-2-one

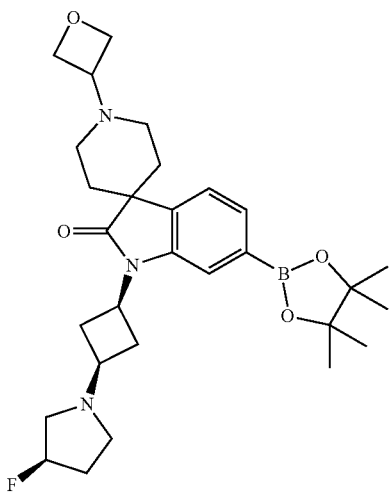 [SMILES: CC1(C)OB(c2ccc3c(c2)N([C@H]2C[C@@H](N4CC[C@@H](F)C4)C2)C(=O)C32CCN(C3COC3)CC2)OC1(C)C]

1-((1S,3s)-3-((R)-3-fluoropyrrolidin-1-yl)cyclobutyl)-1'-(oxetan-3-yl)-6-(4,4,5,5-tetramethyl-1,3,2-dioxaborolan-2-yl)spiro[indoline-3,4'-piperidin]-2-one

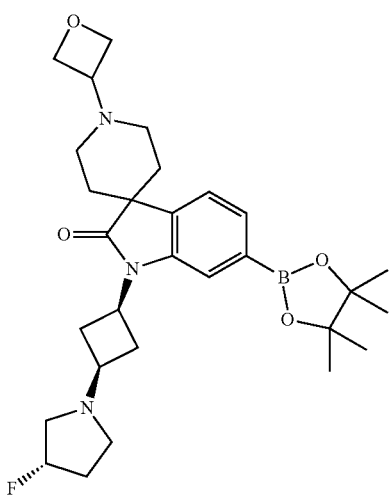 [SMILES: CC1(C)OB(c2ccc3c(c2)N([C@H]2C[C@@H](N4CC[C@H](F)C4)C2)C(=O)C32CCN(C3COC3)CC2)OC1(C)C]

1-((1R,3s)-3-((S)-3-fluoropyrrolidin-1-yl)cyclobutyl)-1'-(oxetan-3-yl)-6-(4,4,5,5-tetramethyl-1,3,2-dioxaborolan-2-yl)spiro[indoline-3,4'-piperidin]-2-one

324

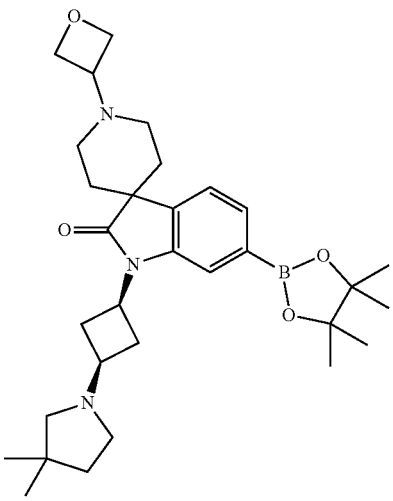

1-((1s,3s)-3-(3,3-dimethylpyrrolidin-1-yl)cyclobutyl)-1'-(oxetan-3-yl)-6-(4,4,5,5-tetramethyl-1,3,2-dioxaborolan-2-yl)spiro[indoline-3,4'-piperidin]-2-one F. Preparation of 1'-(2,2-difluoroethyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one

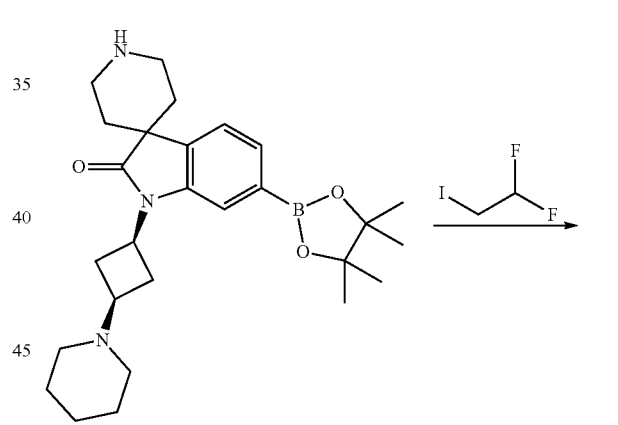

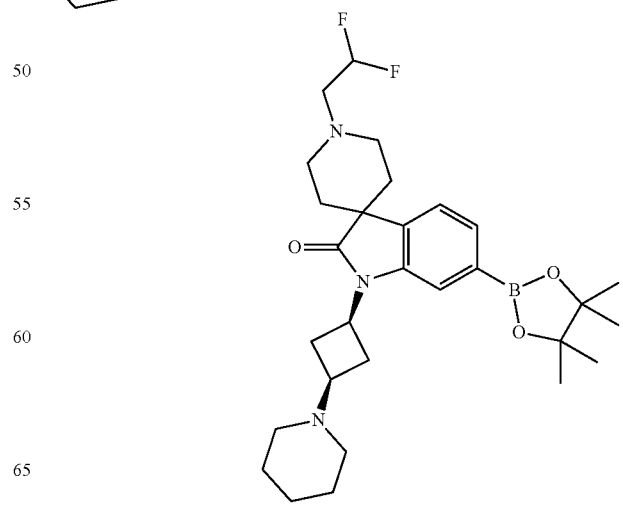

325

The mixture of 1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (1.00 g, 1.86 mmol), 1,1-difluoro-2-iodoethane (196 µL, 2.23 mmol), and potassium carbonate (1.03 g, 7.43 mmol) in DMF (1.3 mL) was placed in a sealed tube and stirred at 70° C. overnight. After stirring overnight, the reaction was quenched with saturated aqueous sodium bicarbonate and extracted with DCM. The combined organic layers were washed with water, dried over sodium sulfate, filtered, and concentrated to provide 1'-(2,2-difluoroethyl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one.

Procedure 13: Preparation of the Compounds of Formula I According to Reaction Scheme I

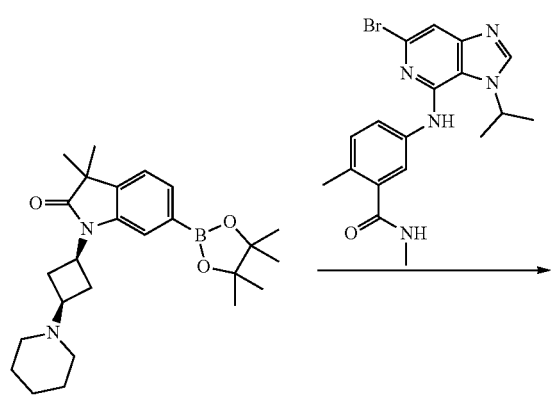

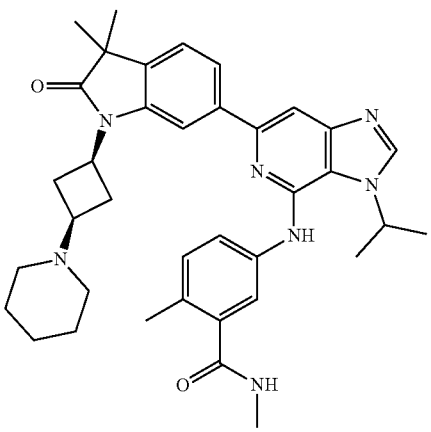 [SMILES: CNC(=O)c1cc(Nc2nc(-c3ccc4c(c3)N([C@H]3C[C@@H](N5CCCCC5)C3)C(=O)C4(C)C)cc3ncn(C(C)C)c23)ccc1C]

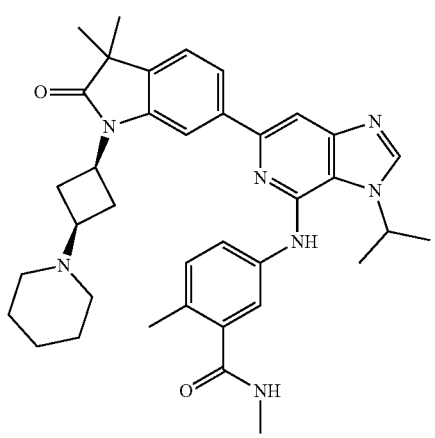

326

A. Preparation of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-N,2-dimethylbenzamide (Example 1)

In a microwave vial were placed 5-((6-bromo-3-isopropyl-3H-imidazo[4,5-c]pyridin-4-yl)amino)-N,2-dimethylbenzamide (50 mg, 0.12 mmol), 3,3-dimethyl-1-((1s,3s)-3-(piperidin-1-yl)cyclobutyl)-6-(4,4,5,5-tetramethyl-1,3,2-dioxaborolan-2-yl)indolin-2-one (52.75 mg, 0.12 mmol), Pd(PPh$_3$)$_4$ (10.05 mg, 0.01 mmol), and cesium carbonate (80.99 mg, 0.25 mmol) in DME (2 ml)/H2O (1 ml). The mixture was placed in the microwave reactor and heated at 125° C. for 25 min. Then the mixture was purified by flash chromatography (100% DCM to 50% MeOH in DCM) and reverse phase chromatography to give 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-N,2-dimethylbenzamide.

The following compounds were prepared using a similar procedure with the following modification(s):

the compounds listed under Procedure 3, 4, or 5 were used instead of 5-((6-bromo-3-isopropyl-3H-imidazo[4,5-c]pyridin-4-yl)amino)-N,2-dimethylbenzamide; and/or the compounds listed under Procedure 6, 7, 8, 9, 11, 12, 34, or 35 were used instead of 3,3-dimethyl-1-((1s,3s)-3-(piperidin-1-yl)cyclobutyl)-6-(4,4,5,5-tetramethyl-1,3,2-dioxaborolan-2-yl)indolin-2-one:

| Structure | Example # |
|---|---|
| 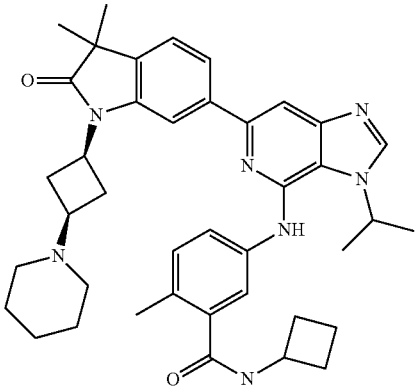 | 2 |
| 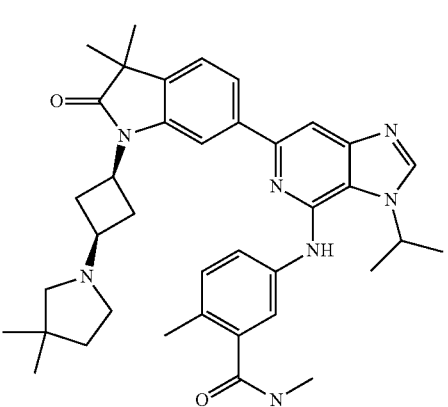 | 3 |
| 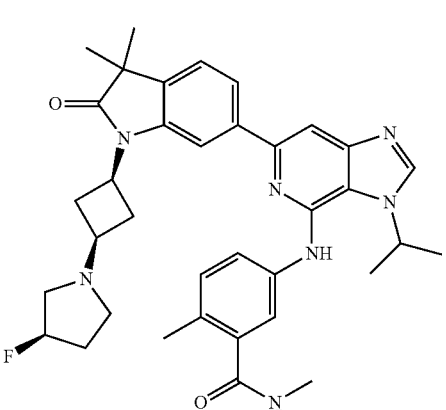 | 4 |
| 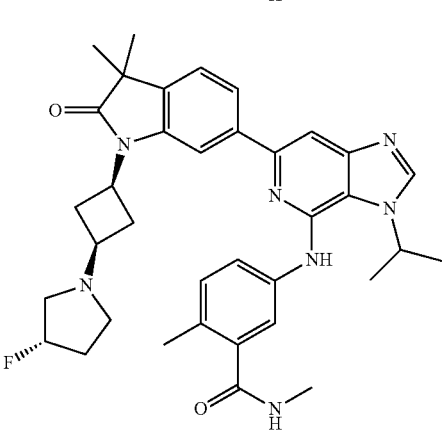 | 5 |

| Structure | Example # |
|---|---|
| 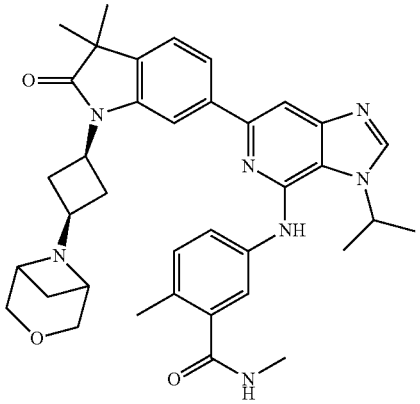 [SMILES: CNC(=O)c1cc(Nc2nc(-c3ccc4c(c3)N([C@H]3C[C@@H](N5C6COCC5C6)C3)C(=O)C4(C)C)cc3ncn(C(C)C)c23)ccc1C] | 6 |
| 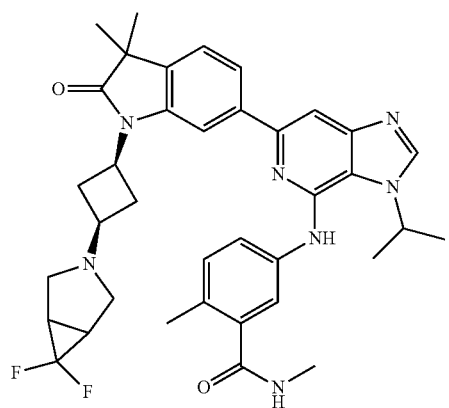 [SMILES: CNC(=O)c1cc(Nc2nc(-c3ccc4c(c3)N([C@H]3C[C@@H](N5CC6C(C5)C6(F)F)C3)C(=O)C4(C)C)cc3ncn(C(C)C)c23)ccc1C] | 7 |
| 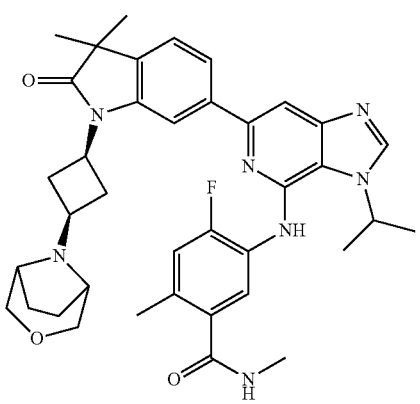 [SMILES: CNC(=O)c1cc(Nc2nc(-c3ccc4c(c3)N([C@H]3C[C@@H](N5C6CCC5COC6)C3)C(=O)C4(C)C)cc3ncn(C(C)C)c23)c(F)cc1C] | 8 |

-continued

| Structure | Example # |
|---|---|
| 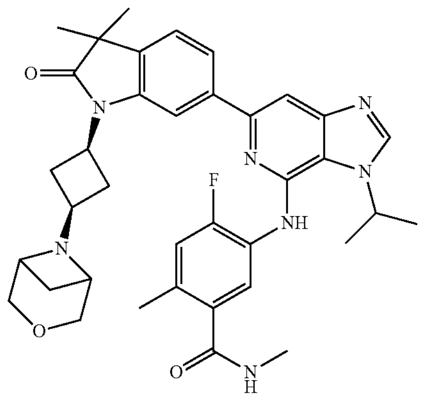 [SMILES: CNC(=O)c1cc(Nc2nc(-c3ccc4c(c3)N([C@H]3C[C@@H](N5C6COCC5C6)C3)C(=O)C4(C)C)cc3ncn(C(C)C)c23)c(F)cc1C] | 9 |
| 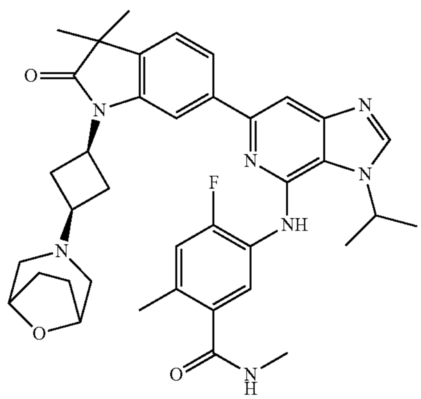 [SMILES: CNC(=O)c1cc(Nc2nc(-c3ccc4c(c3)N([C@H]3C[C@@H](N5CC6CCC(C5)O6)C3)C(=O)C4(C)C)cc3ncn(C(C)C)c23)c(F)cc1C] | 10 |
| 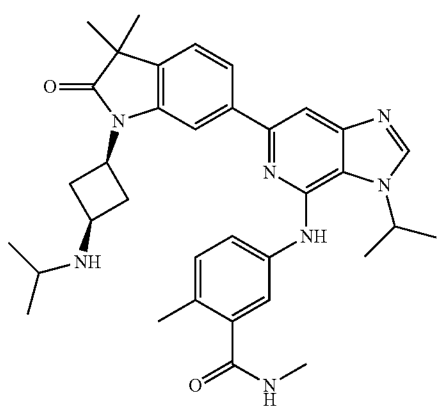 [SMILES: CNC(=O)c1cc(Nc2nc(-c3ccc4c(c3)N([C@H]3C[C@@H](NC(C)C)C3)C(=O)C4(C)C)cc3ncn(C(C)C)c23)ccc1C] | 11 |
| 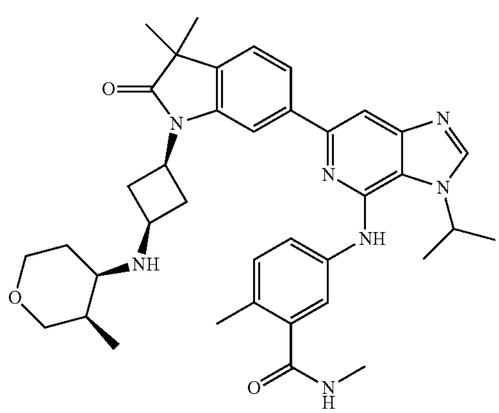 [SMILES: CNC(=O)c1cc(Nc2nc(-c3ccc4c(c3)N([C@H]3C[C@@H](N[C@@H]5CCOC[C@@H]5C)C3)C(=O)C4(C)C)cc3ncn(C(C)C)c23)ccc1C] | 12 |

| Structure | Example # |
|---|---|
| 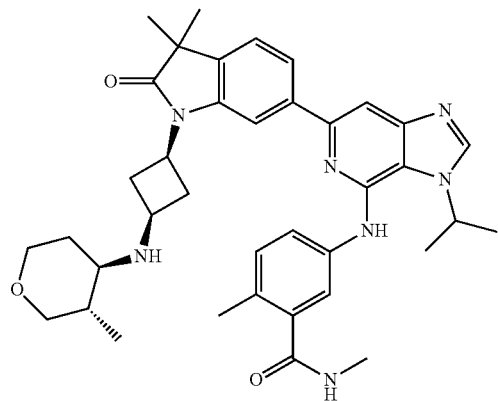 [SMILES: CNC(=O)c1cc(Nc2nc(-c3ccc4c(c3)N([C@H]3C[C@@H](N[C@@H]5CCOC[C@H]5C)C3)C(=O)C4(C)C)cc3ncn(C(C)C)c23)ccc1C] | 13 |
| 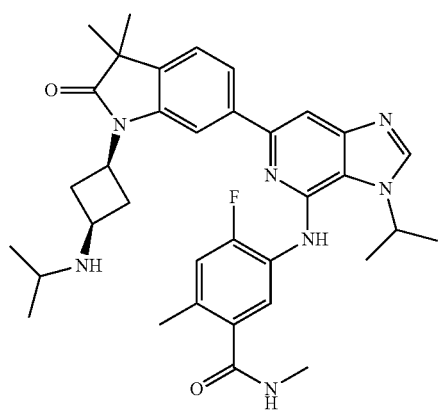 [SMILES: CNC(=O)c1cc(Nc2nc(-c3ccc4c(c3)N([C@H]3C[C@@H](NC(C)C)C3)C(=O)C4(C)C)cc3ncn(C(C)C)c23)c(F)cc1C] | 14 |
| 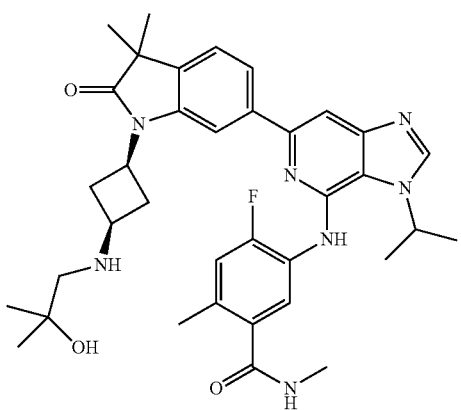 [SMILES: CNC(=O)c1cc(Nc2nc(-c3ccc4c(c3)N([C@H]3C[C@@H](NCC(C)(C)O)C3)C(=O)C4(C)C)cc3ncn(C(C)C)c23)c(F)cc1C] | 15 |

| Structure | Example # |
|---|---|
| 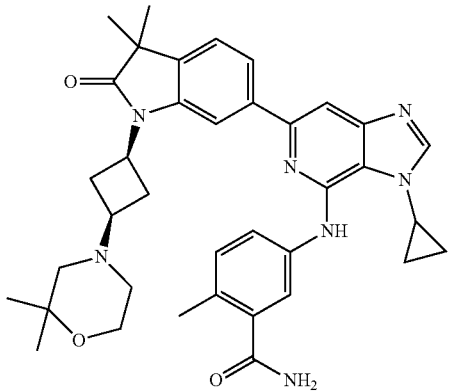 [SMILES: Cc1ccc(Nc2nc(-c3ccc4c(c3)N([C@H]3C[C@@H](N5CCOC(C)(C)C5)C3)C(=O)C4(C)C)cc3ncn(C4CC4)c23)cc1C(N)=O] | 16 |
| 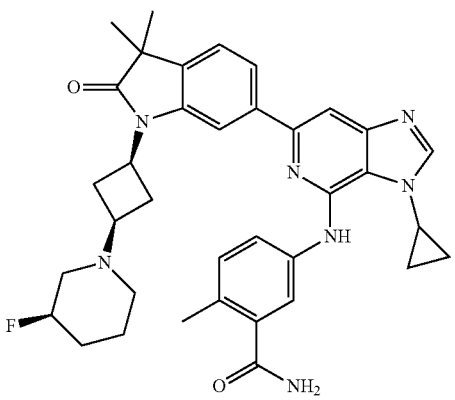 [SMILES: Cc1ccc(Nc2nc(-c3ccc4c(c3)N([C@H]3C[C@@H](N5CCC[C@@H](F)C5)C3)C(=O)C4(C)C)cc3ncn(C4CC4)c23)cc1C(N)=O] | 17 |
| 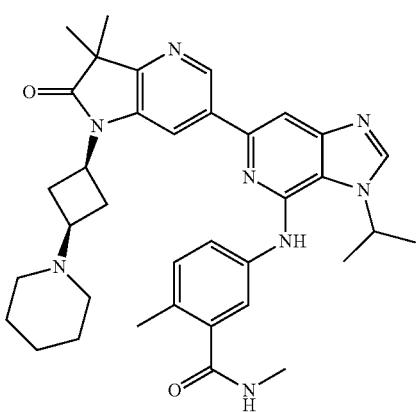 [SMILES: CNC(=O)c1cc(Nc2nc(-c3cnc4c(c3)N([C@H]3C[C@@H](N5CCCCC5)C3)C(=O)C4(C)C)cc3ncn(C(C)C)c23)ccc1C] | 18 |

| Structure | Example # |
|---|---|
| 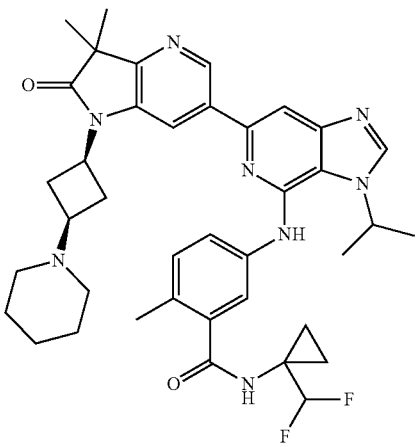 [SMILES: Cc1ccc(Nc2nc(-c3cnc4c(c3)N([C@H]3C[C@@H](N5CCCCC5)C3)C(=O)C4(C)C)cc3ncn(C(C)C)c23)cc1C(=O)NC1(C(F)F)CC1] | 19 |
| 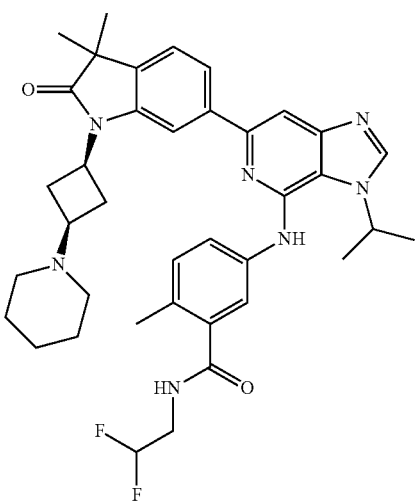 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NCC(F)F] | 20 |
| 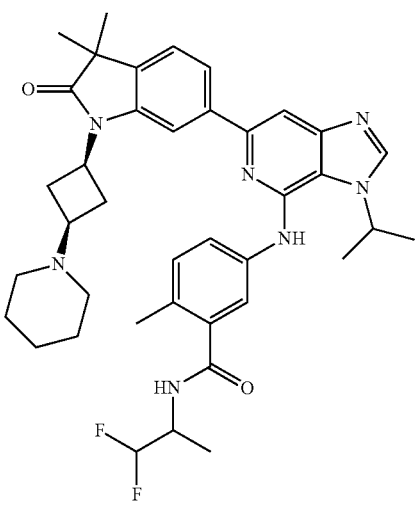 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC(C)C(F)F] | 21 |

| Structure | Example # |
|---|---|
| 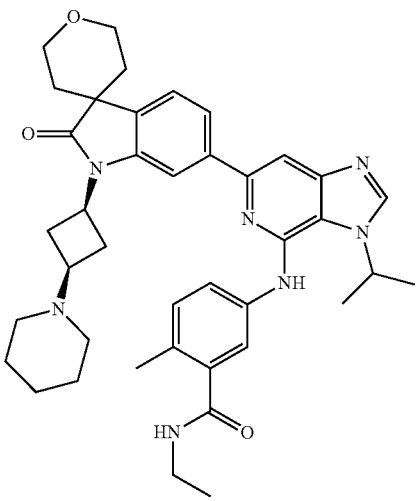 [SMILES: CCNC(=O)c1cc(Nc2nc(-c3ccc4c(c3)N([C@H]3C[C@@H](N5CCCCC5)C3)C(=O)C43CCOCC3)cc3ncn(C(C)C)c23)ccc1C] | 22 |
| 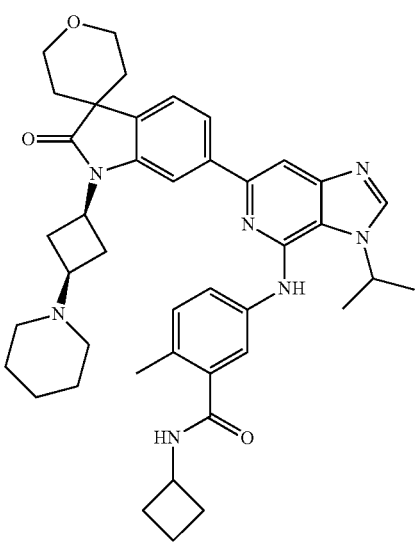 [SMILES: Cc1ccc(Nc2nc(-c3ccc4c(c3)N([C@H]3C[C@@H](N5CCCCC5)C3)C(=O)C43CCOCC3)cc3ncn(C(C)C)c23)cc1C(=O)NC1CCC1] | 23 |
| 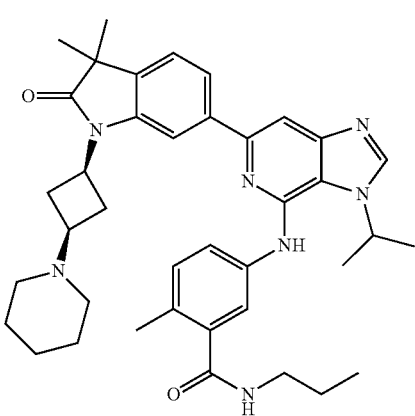 [SMILES: CCCNC(=O)c1cc(Nc2nc(-c3ccc4c(c3)N([C@H]3C[C@@H](N5CCCCC5)C3)C(=O)C4(C)C)cc3ncn(C(C)C)c23)ccc1C] | 24 |

| Structure | Example # |
|---|---|
| 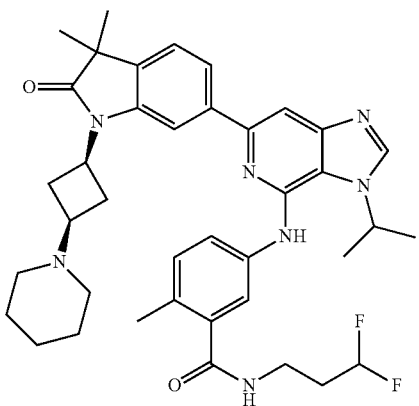 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NCCC(F)F] | 25 |
| 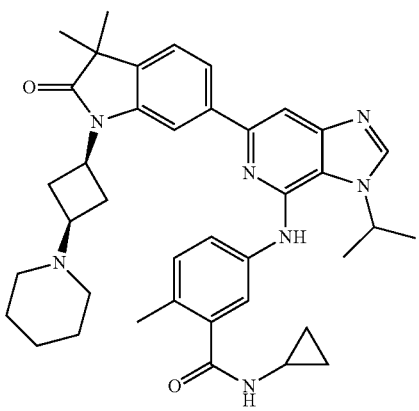 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC1CC1] | 26 |
| 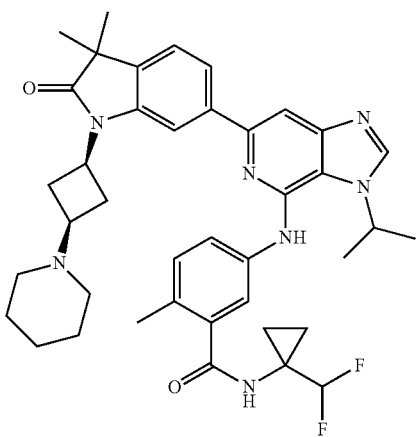 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC1(C(F)F)CC1] | 27 |

-continued
| Structure | Example # |
|---|---|
| 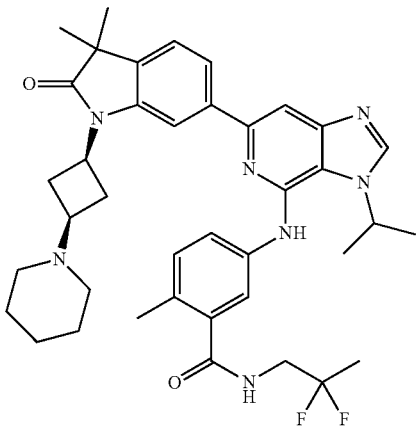 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NCC(C)(F)F] | 28 |
| 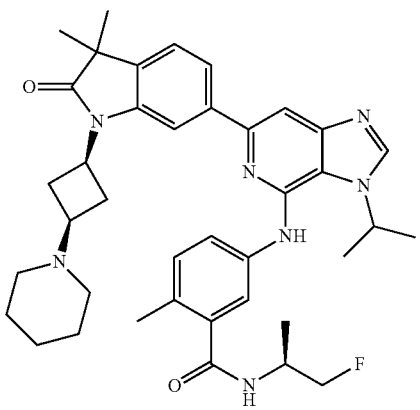 | 29 |
| 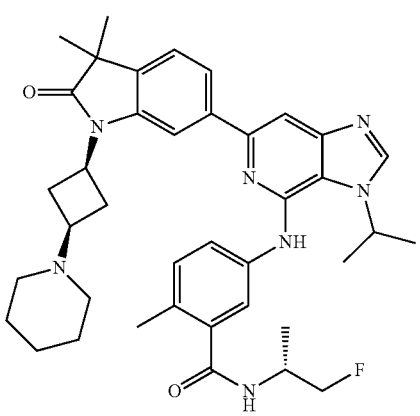 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)N[C@H](C)CF] | 30 |

-continued
| Structure | Example # |
|---|---|
| 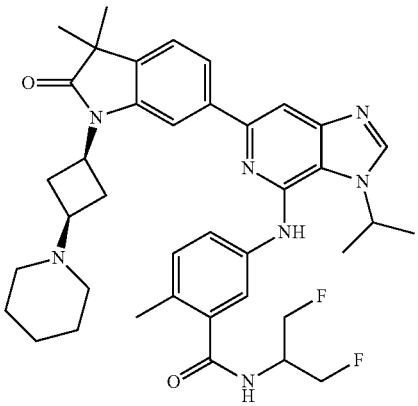 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC(CF)CF] | 31 |
| 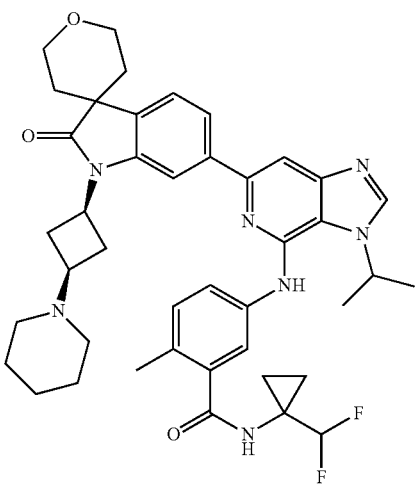 [SMILES: Cc1ccc(Nc2nc(-c3ccc4c(c3)N([C@H]3C[C@@H](N5CCCCC5)C3)C(=O)C43CCOCC3)cc3ncn(C(C)C)c23)cc1C(=O)NC1(C(F)F)CC1] | 32 |
| 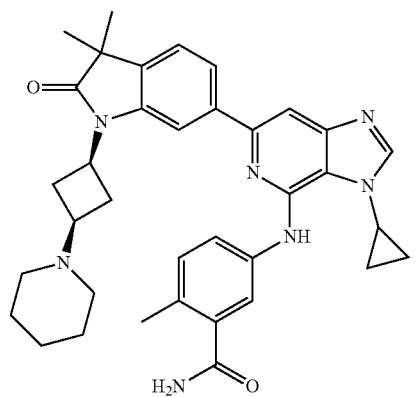 [SMILES: Cc1ccc(Nc2nc(-c3ccc4c(c3)N([C@H]3C[C@@H](N5CCCCC5)C3)C(=O)C4(C)C)cc3ncn(C4CC4)c23)cc1C(N)=O] | 33 |

| Structure | Example # |
|---|---|
| 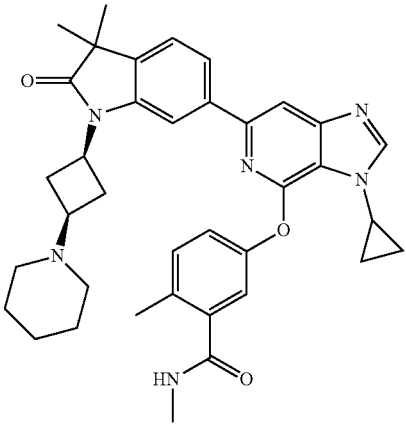 [SMILES: CNC(=O)c1cc(Oc2nc(-c3ccc4c(c3)N([C@H]3C[C@@H](N5CCCCC5)C3)C(=O)C4(C)C)cc3ncn(C4CC4)c23)ccc1C] | 34 |
| 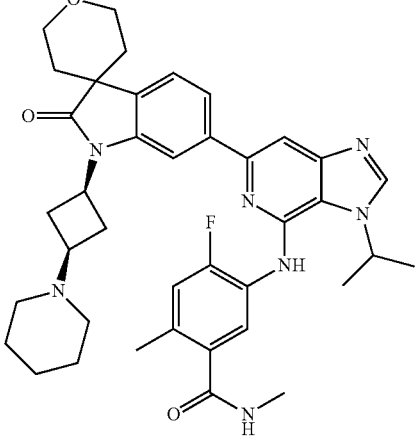 | 35 |
| 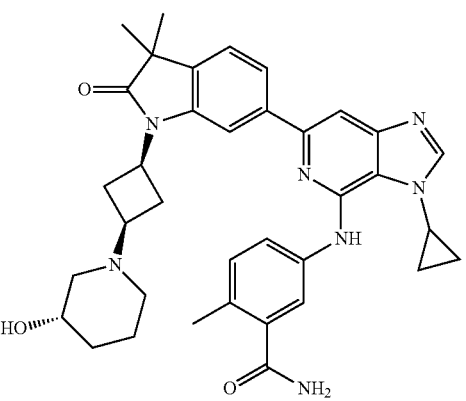 [SMILES: Cc1ccc(Nc2nc(-c3ccc4c(c3)N([C@H]3C[C@@H](N5CCC[C@H](O)C5)C3)C(=O)C4(C)C)cc3ncn(C4CC4)c23)cc1C(N)=O] | 36 |

| Structure | Example # |
|---|---|
| 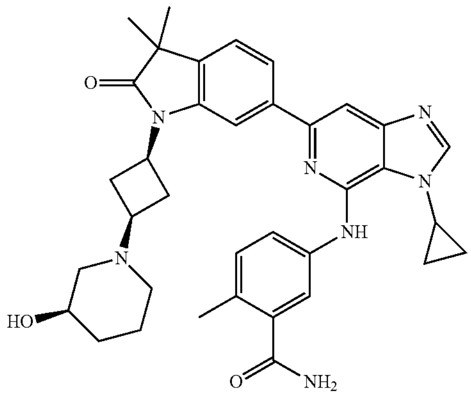 [SMILES: Cc1ccc(Nc2nc(-c3ccc4c(c3)N([C@H]3C[C@@H](N5CCC[C@@H](O)C5)C3)C(=O)C4(C)C)cc3ncn(C4CC4)c23)cc1C(N)=O] | 37 |
| 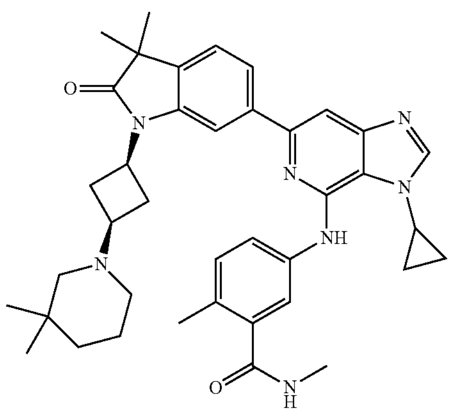 [SMILES: CNC(=O)c1cc(Nc2nc(-c3ccc4c(c3)N([C@H]3C[C@@H](N5CCCC(C)(C)C5)C3)C(=O)C4(C)C)cc3ncn(C4CC4)c23)ccc1C] | 38 |
| 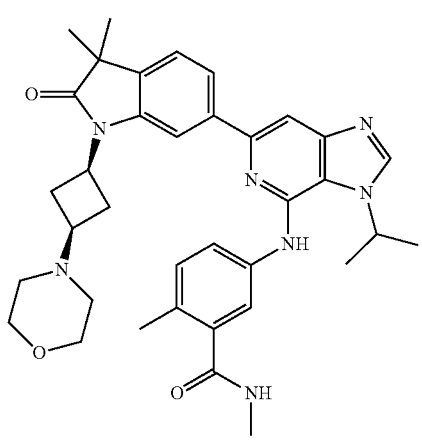 [SMILES: CNC(=O)c1cc(Nc2nc(-c3ccc4c(c3)N([C@H]3C[C@@H](N5CCOCC5)C3)C(=O)C4(C)C)cc3ncn(C(C)C)c23)ccc1C] | 39 |

| Structure | Example # |
|---|---|
| 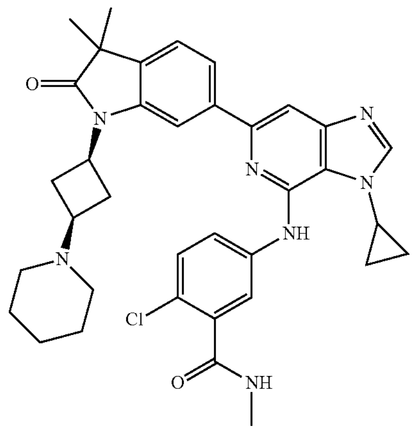 [SMILES: CNC(=O)c1cc(Nc2nc(-c3ccc4c(c3)N([C@H]3C[C@@H](N5CCCCC5)C3)C(=O)C4(C)C)cc3ncn(C4CC4)c23)ccc1Cl] | 40 |
| 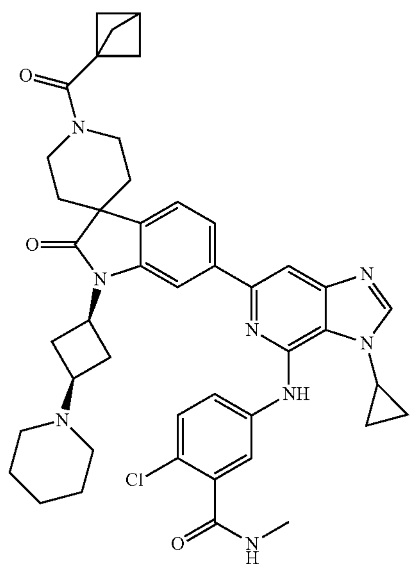 [SMILES: CNC(=O)c1cc(Nc2nc(-c3ccc4c(c3)N([C@H]3C[C@@H](N5CCCCC5)C3)C(=O)C43CCN(C(=O)C45CC(C4)C5)CC3)cc3ncn(C4CC4)c23)ccc1Cl] | 41 |
| 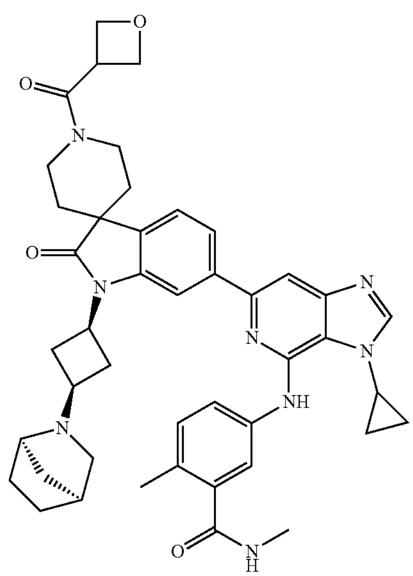 [SMILES: CNC(=O)c1cc(Nc2nc(-c3ccc4c(c3)N([C@H]3C[C@@H](N5C[C@H]6CC[C@@H]5C6)C3)C(=O)C43CCN(C(=O)C4COC4)CC3)cc3ncn(C4CC4)c23)ccc1C] | 42 |

| Structure | Example # |
|---|---|
| 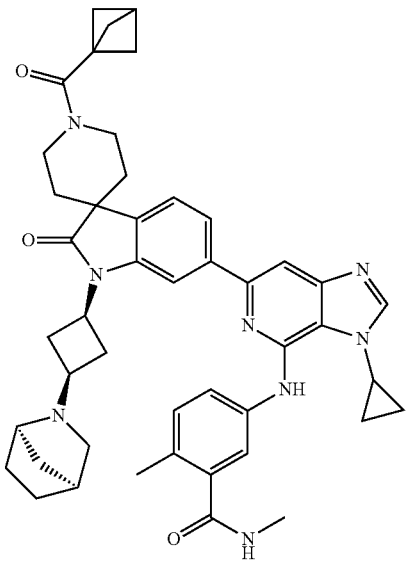 [SMILES: CNC(=O)c1cc(Nc2nc(-c3ccc4c(c3)N([C@H]3C[C@@H](N5C[C@H]6CC[C@@H]5C6)C3)C(=O)C43CCN(C(=O)C45CC(C4)C5)CC3)cc3ncn(C4CC4)c23)ccc1C] | 43 |
| 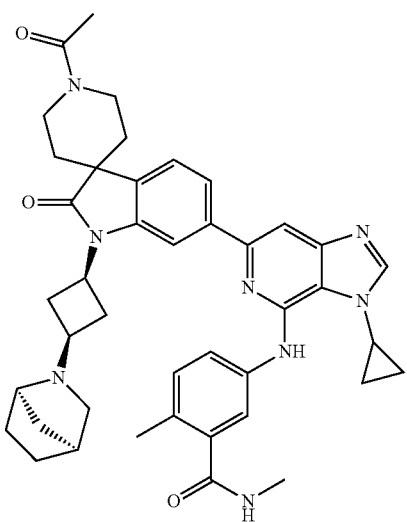 [SMILES: CNC(=O)c1cc(Nc2nc(-c3ccc4c(c3)N([C@H]3C[C@@H](N5C[C@H]6CC[C@@H]5C6)C3)C(=O)C43CCN(C(C)=O)CC3)cc3ncn(C4CC4)c23)ccc1C] | 44 |
| 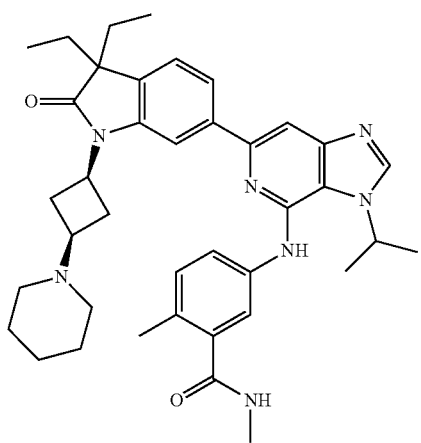 [SMILES: CCC1(CC)C(=O)N([C@H]2C[C@@H](N3CCCCC3)C2)c2cc(-c3cc4ncn(C(C)C)c4c(Nc4ccc(C)c(C(=O)NC)c4)n3)ccc21] | 45 |

| Structure | Example # |
|---|---|
| 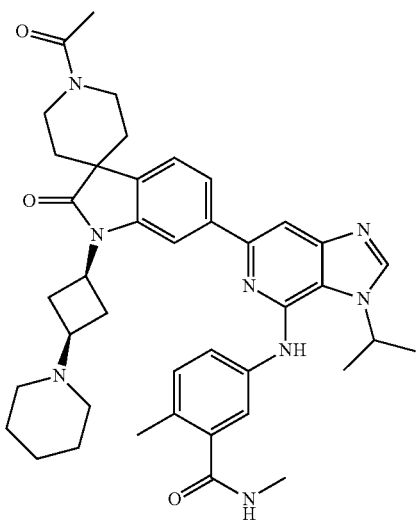 [SMILES: CNC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)ccc1C] | 46 |
| 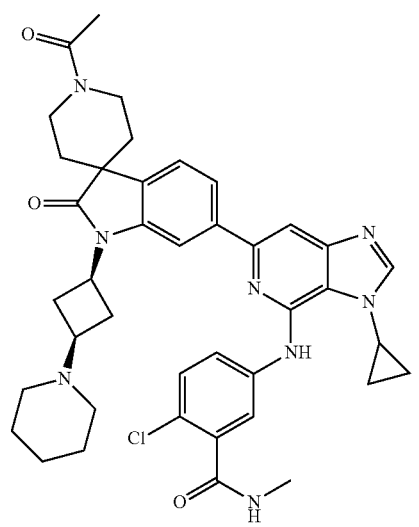 [SMILES: CNC(=O)c1cc(Nc2nc(-c3ccc4c(c3)N([C@H]3C[C@@H](N5CCCCC5)C3)C(=O)C43CCN(C(C)=O)CC3)cc3ncn(C4CC4)c23)ccc1Cl] | 47 |
| 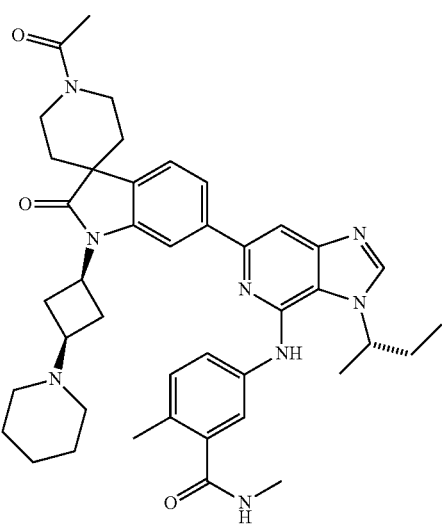 [SMILES: CC[C@H](C)n1cnc2cc(-c3ccc4c(c3)N([C@H]3C[C@@H](N5CCCCC5)C3)C(=O)C43CCN(C(C)=O)CC3)nc(Nc3ccc(C)c(C(=O)NC)c3)c21] | 48 |

| Structure | Example # |
|---|---|
| 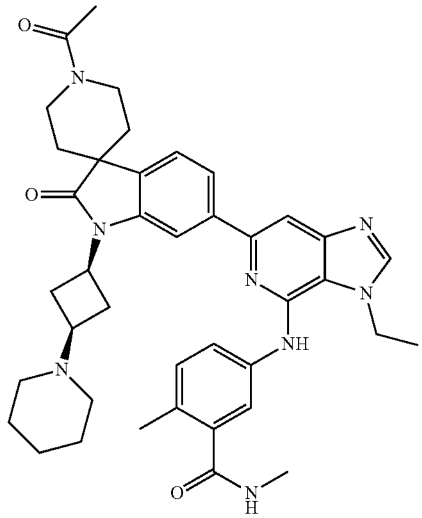 [SMILES: CCn1cnc2cc(-c3ccc4c(c3)N([C@H]3C[C@@H](N5CCCCC5)C3)C(=O)C43CCN(C(C)=O)CC3)nc(Nc3ccc(C)c(C(=O)NC)c3)c21] | 49 |
| 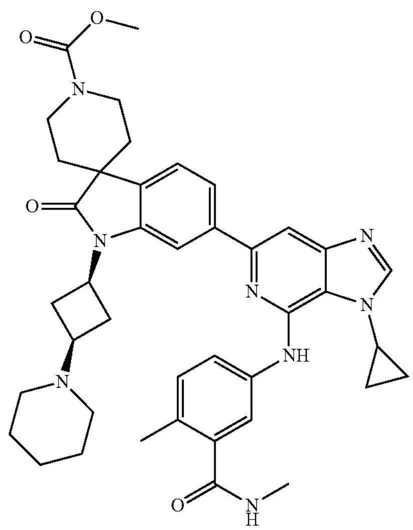 [SMILES: CNC(=O)c1cc(Nc2nc(-c3ccc4c(c3)N([C@H]3C[C@@H](N5CCCCC5)C3)C(=O)C43CCN(C(=O)OC)CC3)cc3ncn(C4CC4)c23)ccc1C] | 50 |
| 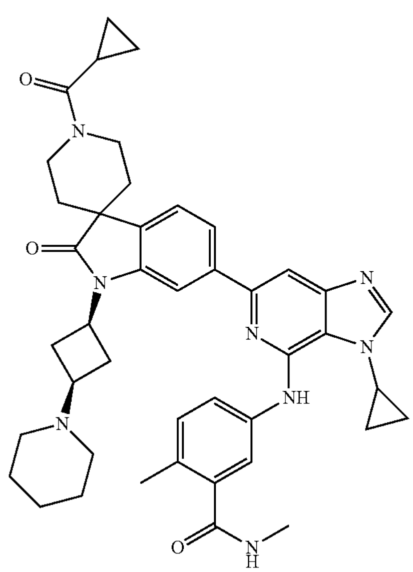 [SMILES: CNC(=O)c1cc(Nc2nc(-c3ccc4c(c3)N([C@H]3C[C@@H](N5CCCCC5)C3)C(=O)C43CCN(C(=O)C4CC4)CC3)cc3ncn(C4CC4)c23)ccc1C] | 51 |

| Structure | Example # |
|---|---|
| 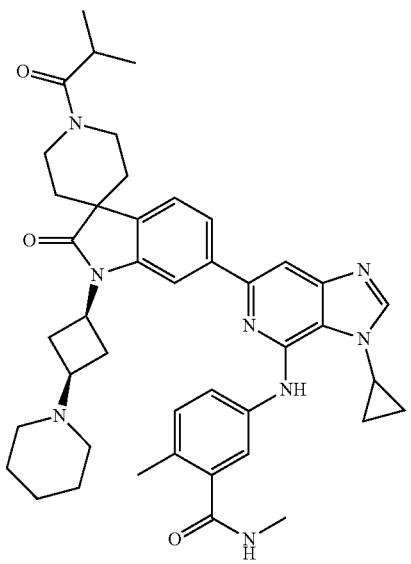 [SMILES: CNC(=O)c1cc(Nc2nc(-c3ccc4c(c3)N([C@H]3C[C@@H](N5CCCCC5)C3)C(=O)C43CCN(C(=O)C(C)C)CC3)cc3ncn(C4CC4)c23)ccc1C] | 52 |
| 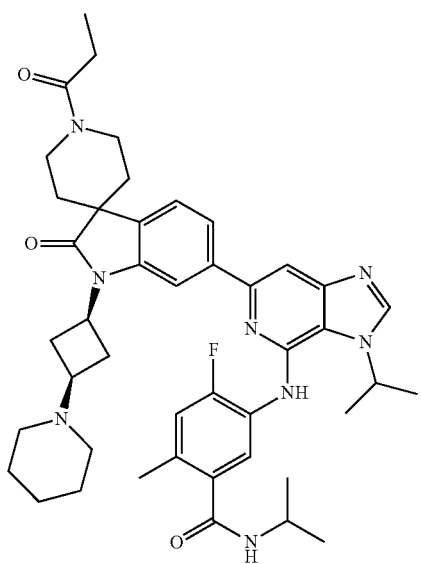 [SMILES: CCC(=O)N1CCC2(CC1)C(=O)N([C@H]1C[C@@H](N3CCCCC3)C1)c1cc(-c3cc4ncn(C(C)C)c4c(Nc4cc(C(=O)NC(C)C)c(C)cc4F)n3)ccc12] | 53 |

| Structure | Example # |
|---|---|
| 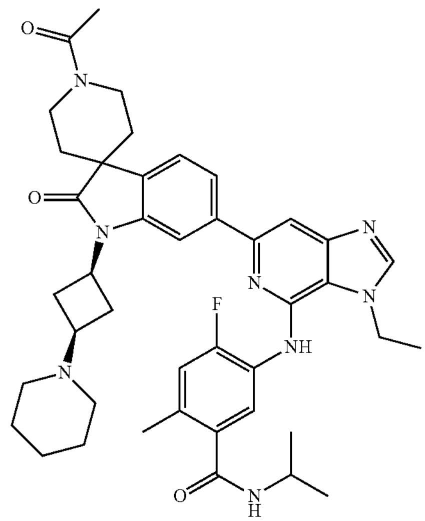 [SMILES: CCn1cnc2cc(-c3ccc4c(c3)N([C@H]3C[C@@H](N5CCCCC5)C3)C(=O)C43CCN(C(C)=O)CC3)nc(Nc3cc(C(=O)NC(C)C)c(C)cc3F)c21] | 54 |
| 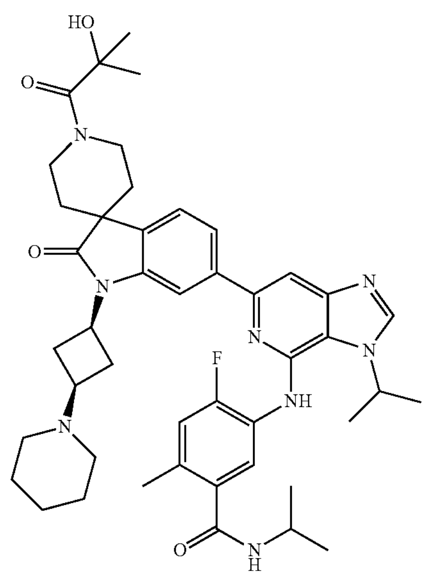 [SMILES: Cc1cc(F)c(Nc2nc(-c3ccc4c(c3)N([C@H]3C[C@@H](N5CCCCC5)C3)C(=O)C43CCN(C(=O)C(C)(C)O)CC3)cc3ncn(C(C)C)c23)cc1C(=O)NC(C)C] | 55 |
| 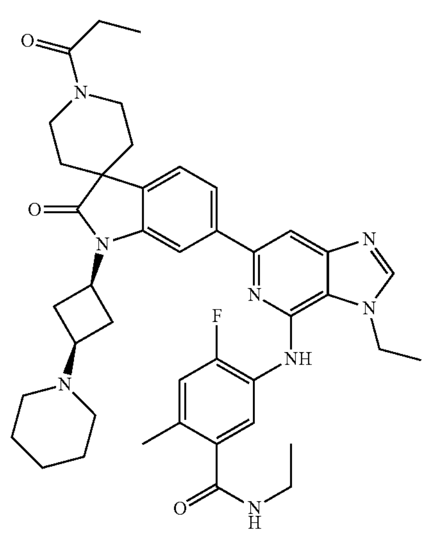 [SMILES: CCNC(=O)c1cc(Nc2nc(-c3ccc4c(c3)N([C@H]3C[C@@H](N5CCCCC5)C3)C(=O)C43CCN(C(=O)CC)CC3)cc3ncn(CC)c23)c(F)cc1C] | 56 |

| Structure | Example # |
| --- | --- |
| 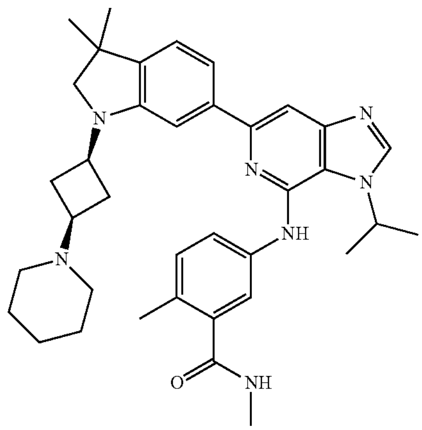 [SMILES: CNC(=O)c1cc(Nc2nc(-c3ccc4c(c3)N([C@H]3C[C@@H](N5CCCCC5)C3)CC4(C)C)cc3ncn(C(C)C)c23)ccc1C] | 57 |
| 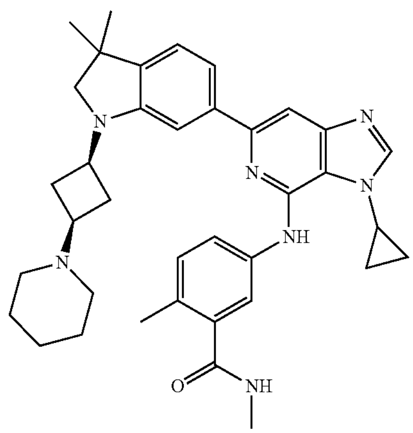 [SMILES: CNC(=O)c1cc(Nc2nc(-c3ccc4c(c3)N([C@H]3C[C@@H](N5CCCCC5)C3)CC4(C)C)cc3ncn(C4CC4)c23)ccc1C] | 58 |
| | 58a
A mixture of dioxane and water was used as a solvent instead of a mixture of DME and water to prepare this compound |

-continued

| Structure | Example # |
|---|---|
| 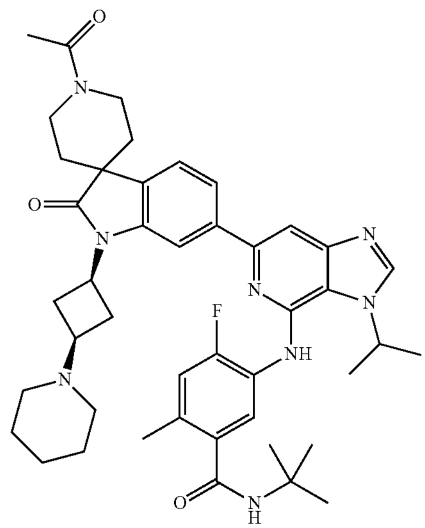 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)NC(C)(C)C)c(C)cc4F)n3)ccc12] | 59<br>Na$_2$CO$_3$ was used as a base instead of Cs$_2$CO$_3$ to prepare this compound |
| 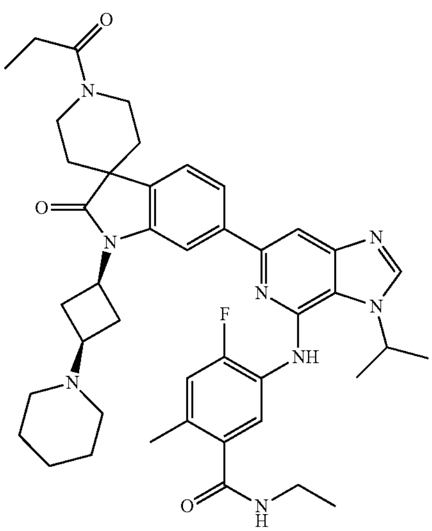 [SMILES: CCNC(=O)c1cc(Nc2nc(-c3ccc4c(c3)N([C@H]3C[C@@H](N5CCCCC5)C3)C(=O)C43CCN(C(=O)CC)CC3)cc3ncn(C(C)C)c23)c(F)cc1C] | 60<br>Na$_2$CO$_3$ was used as a base instead of Cs$_2$CO$_3$ to prepare this compound |
| 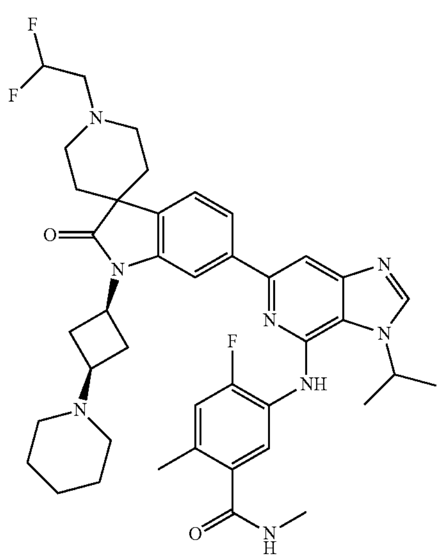 [SMILES: CNC(=O)c1cc(Nc2nc(-c3ccc4c(c3)N([C@H]3C[C@@H](N5CCCCC5)C3)C(=O)C43CCN(CC(F)F)CC3)cc3ncn(C(C)C)c23)c(F)cc1C] | 61<br>Na$_2$CO$_3$ was used as a base instead of Cs$_2$CO$_3$ to prepare this compound |

| Structure | Example # |
|---|---|
| 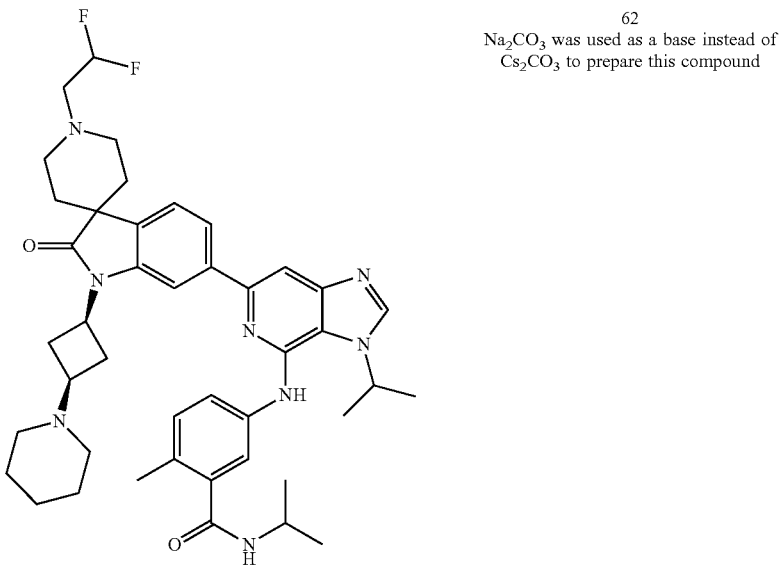 | 62<br>Na$_2$CO$_3$ was used as a base instead of Cs$_2$CO$_3$ to prepare this compound |
| 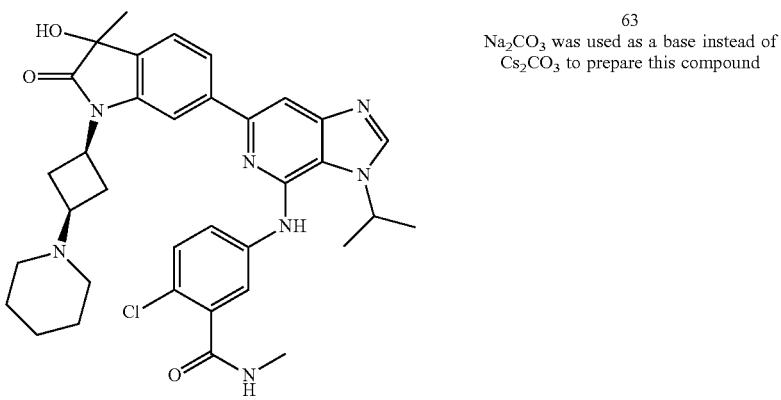 | 63<br>Na$_2$CO$_3$ was used as a base instead of Cs$_2$CO$_3$ to prepare this compound |
| 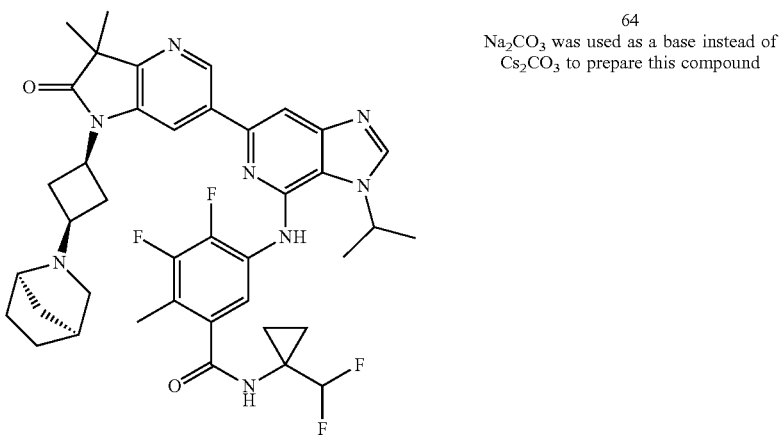 | 64<br>Na$_2$CO$_3$ was used as a base instead of Cs$_2$CO$_3$ to prepare this compound |

| Structure | Example # |
|---|---|
| 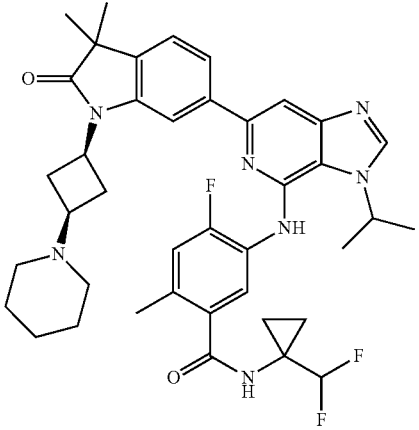 [SMILES: Cc1cc(F)c(Nc2nc(-c3ccc4c(c3)N([C@H]3C[C@@H](N5CCCCC5)C3)C(=O)C4(C)C)cc3ncn(C(C)C)c23)cc1C(=O)NC1(C(F)F)CC1] | 65 |
| 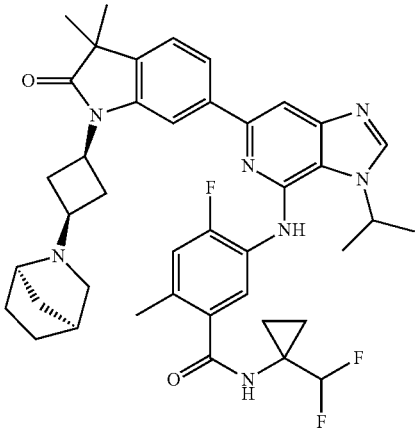 [SMILES: Cc1cc(F)c(Nc2nc(-c3ccc4c(c3)N([C@H]3C[C@@H](N5C[C@H]6CC[C@@H]5C6)C3)C(=O)C4(C)C)cc3ncn(C(C)C)c23)cc1C(=O)NC1(C(F)F)CC1] | 66 |
| 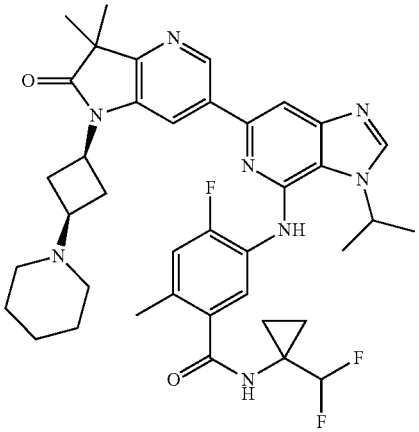 [SMILES: Cc1cc(F)c(Nc2nc(-c3cnc4c(c3)N([C@H]3C[C@@H](N5CCCCC5)C3)C(=O)C4(C)C)cc3ncn(C(C)C)c23)cc1C(=O)NC1(C(F)F)CC1] | 67 |

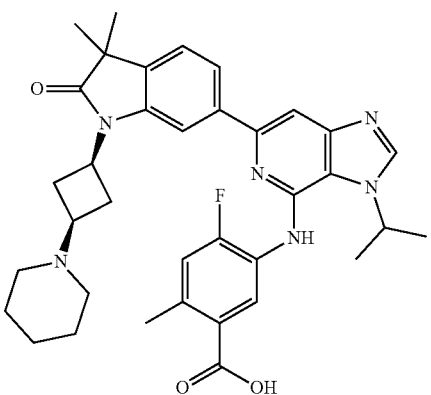 [SMILES: Cc1cc(F)c(Nc2nc(-c3ccc4c(c3)N([C@H]3C[C@@H](N5CCCCC5)C3)C(=O)C4(C)C)cc3ncn(C(C)C)c23)cc1C(=O)O]

5-((6-Bromo-3-isopropyl-3H-imidazo[4,5-c]pyridin-4-yl)amino)-4-fluoro-2-methylbenzoic acid was used instead of 5-((6-bromo-3-isopropyl-3H-imidazo[4,5-c]pyridin-4-yl)amino)-N,2-dimethylbenzamide to prepare 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-4-fluoro-2-methylbenzoic acid.

B. Preparation of 2-chloro-N-(1-(difluoromethyl)cyclopropyl)-5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-3,4-difluorobenzamide (Example 244)

2-chloro-N-(1-(difluoromethyl)cyclopropyl)-5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-3,4-difluorobenzamide was prepared using a similar procedure except that 5-((6-bromo-3-isopropyl-3H-imidazo[4,5-c]pyridin-4-yl)amino)-2-chloro-N-(1-(difluoromethyl)cyclopropyl)-3,4-difluorobenzamide was used instead of 5-((6-bromo-3-isopropyl-3H-imidazo[4,5-c]pyridin-4-yl)amino)-N,2-dimethylbenzamide.

C. Preparation of 6-(4-((3-fluoropyridin-4-yl)amino)-3-isopropyl-3H-imidazo[4,5-c]pyridin-6-yl)-1-((1s,3s)-3-(4-hydroxy-3,3-dimethylpyrrolidin-1-yl)cyclobutyl)-1'-(oxetan-3-yl)spiro[indoline-3,4'-piperidin]-2-one (Example 68)

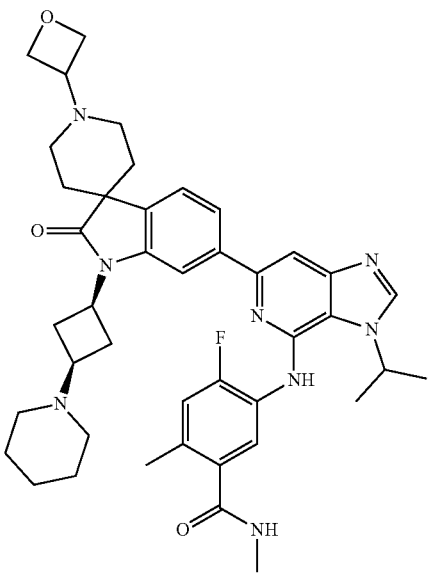 [SMILES: CNC(=O)c1cc(Nc2nc(-c3ccc4c(c3)N([C@H]3C[C@@H](N5CCCCC5)C3)C(=O)C43CCN(C4COC4)CC3)cc3ncn(C(C)C)c23)c(F)cc1C]

In a scintillation vial were placed 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (78 mg, 0.15 mmol), 5-((6-bromo-3-isopropyl-3H-imidazo[4,5-c]pyridin-4-yl)amino)-4-fluoro-N,2-dimethylbenzamide (82 mg, 0.195 mmol, 1.3 eq), Pd(PPh$_3$)$_4$ (17 mg, 0.015 mmol, 0.1 eq), in DME (0.6 mL), and Na$_2$CO$_3$ (0.3 mL, 0.6 mmol, 4.0 eq, 2.0 M in water). The mixture was flushed with nitrogen and sealed, and was stirred overnight at 100° C. Then, the mixture was allowed to cool to room temperature and quenched with 1 M K$_2$CO$_3$. The mixture was extracted with DCM/MeOH, filtered through celite, and concentrated. The crude material was purified on combiflash (12 g gold column, DCM to 15% MeOH in DCM to 50% to 100% MeOH), then reverse-phase HPLC was performed to afford 6-(4-((3-fluoropyridin-4-yl)amino)-3-isopropyl-3H-imidazo[4,5-c]pyridin-6-yl)-1-((1s,3s)-3-(4-hydroxy-3,3-dimethylpyrrolidin-1-yl)cyclobutyl)-1'-(oxetan-3-yl)spiro[indoline-3,4'-piperidin]-2-one.

The following compounds were prepared using a similar procedure with the following modification(s):

- the compounds listed under Procedure 3, 4, or 5 were used instead of 5-((6-bromo-3-isopropyl-3H-imidazo[4,5-c]pyridin-4-yl)amino)-4-fluoro-N,2-dimethylbenzamide
- the compounds listed under Procedure 6 or 12 were used instead of 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one:

| Structure | Example # |
|---|---|
| 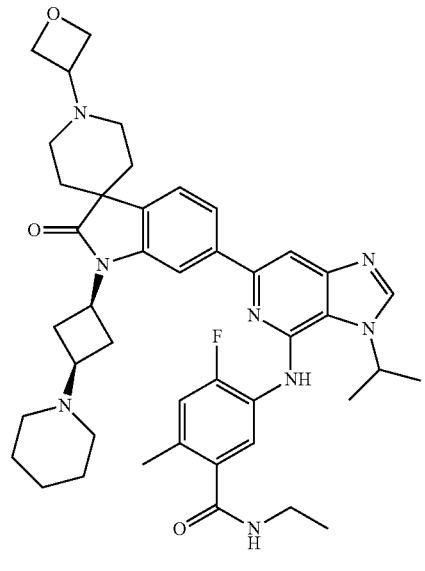 [SMILES: CCNC(=O)c1cc(Nc2nc(-c3ccc4c(c3)N([C@H]3C[C@@H](N5CCCCC5)C3)C(=O)C43CCN(C4COC4)CC3)cc3ncn(C(C)C)c23)c(F)cc1C] | 69 |
| 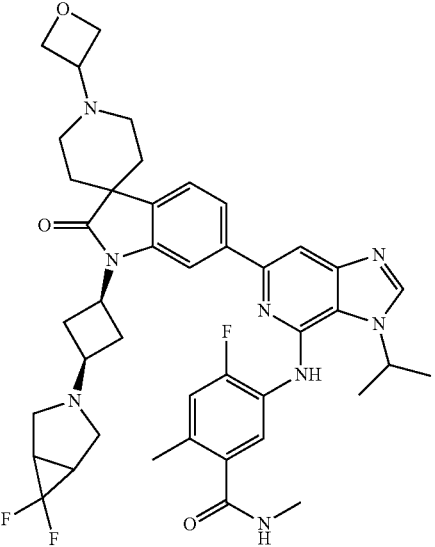 [SMILES: CNC(=O)c1cc(Nc2nc(-c3ccc4c(c3)N([C@H]3C[C@@H](N5CC6C(C5)C6(F)F)C3)C(=O)C43CCN(C4COC4)CC3)cc3ncn(C(C)C)c23)c(F)cc1C] | 70 |

| Structure | Example # |
|---|---|
| 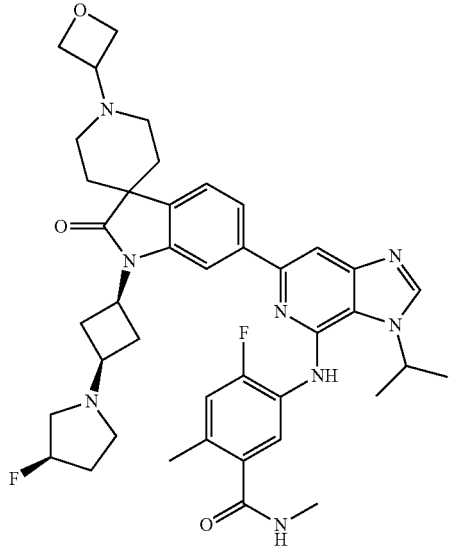 [SMILES: CNC(=O)c1cc(Nc2nc(-c3ccc4c(c3)N([C@H]3C[C@@H](N5CC[C@@H](F)C5)C3)C(=O)C43CCN(C4COC4)CC3)cc3ncn(C(C)C)c23)c(F)cc1C] | 71 |
| 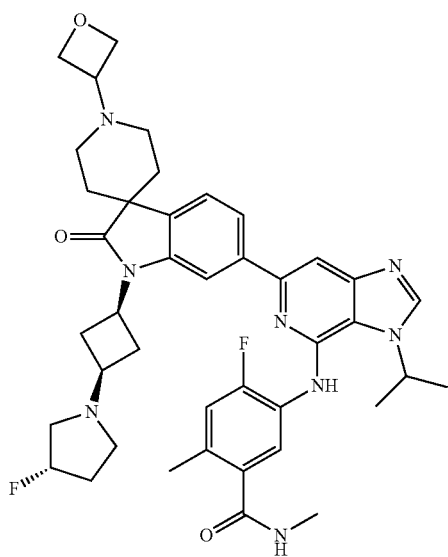 [SMILES: CNC(=O)c1cc(Nc2nc(-c3ccc4c(c3)N([C@H]3C[C@@H](N5CC[C@H](F)C5)C3)C(=O)C43CCN(C4COC4)CC3)cc3ncn(C(C)C)c23)c(F)cc1C] | 72 |

| Structure | Example # |
|---|---|
| 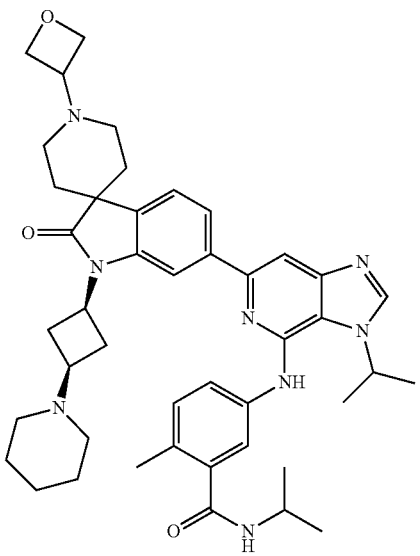 [SMILES: Cc1ccc(Nc2nc(-c3ccc4c(c3)N([C@H]3C[C@@H](N5CCCCC5)C3)C(=O)C43CCN(C4COC4)CC3)cc3ncn(C(C)C)c23)cc1C(=O)NC(C)C] | 73 |
| 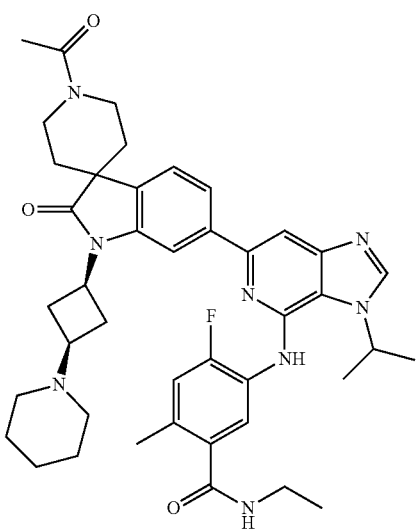 [SMILES: CCNC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)c(F)cc1C] | 74 |
| 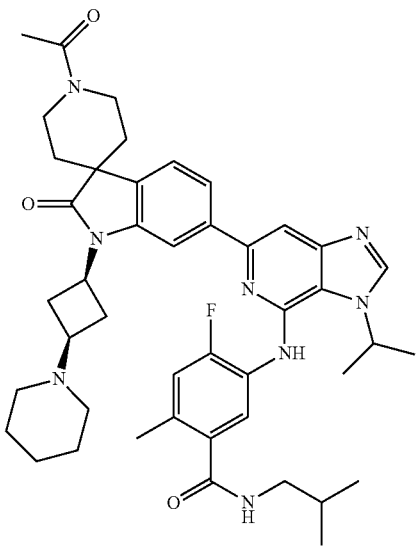 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)NCC(C)C)c(C)cc4F)n3)ccc12] | 75 |

-continued
| Structure | Example # |
|---|---|
| 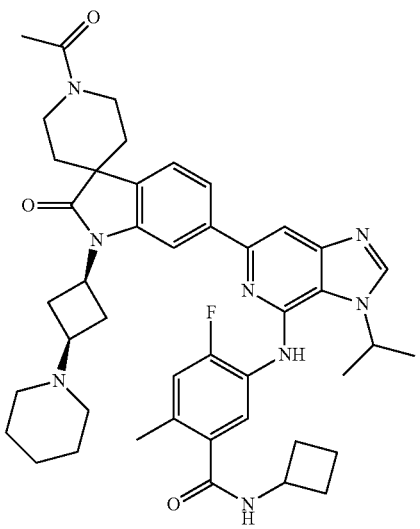 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)NC5CCC5)c(C)cc4F)n3)ccc12] | 76 |
| 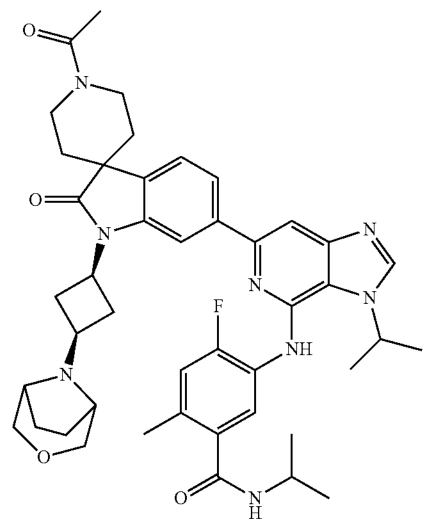 [SMILES: CC(=O)N1CCC2(CC1)C(=O)N([C@H]1C[C@@H](N3C4CCC3COC4)C1)c1cc(-c3cc4ncn(C(C)C)c4c(Nc4cc(C(=O)NC(C)C)c(C)cc4F)n3)ccc12] | 77 |
| 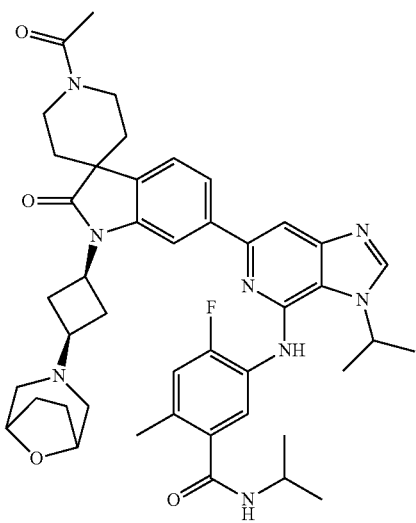 [SMILES: CC(=O)N1CCC2(CC1)C(=O)N([C@H]1C[C@@H](N3CC4CCC(C3)O4)C1)c1cc(-c3cc4ncn(C(C)C)c4c(Nc4cc(C(=O)NC(C)C)c(C)cc4F)n3)ccc12] | 78 |

| Structure | Example # |
|---|---|
| 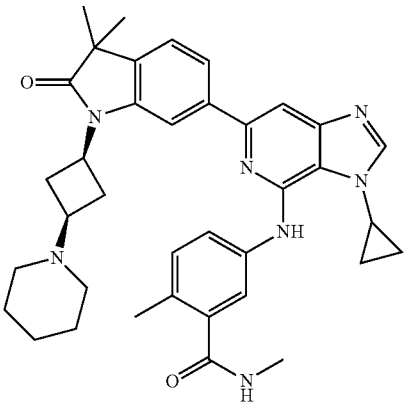 [SMILES: CNC(=O)c1cc(Nc2nc(-c3ccc4c(c3)N([C@H]3C[C@@H](N5CCCCC5)C3)C(=O)C4(C)C)cc3ncn(C4CC4)c23)ccc1C] | 79 |
| 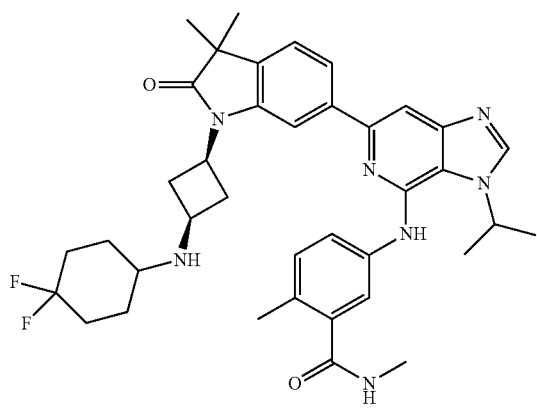 [SMILES: CNC(=O)c1cc(Nc2nc(-c3ccc4c(c3)N([C@H]3C[C@@H](NC5CCC(F)(F)CC5)C3)C(=O)C4(C)C)cc3ncn(C(C)C)c23)ccc1C] | 80<br>A mixture of DMAc and water was used as a solvent and $K_3PO_4$ as a base instead of a mixture of DME and water and $Na_2CO_3$, respectively, to prepare this compound |
| 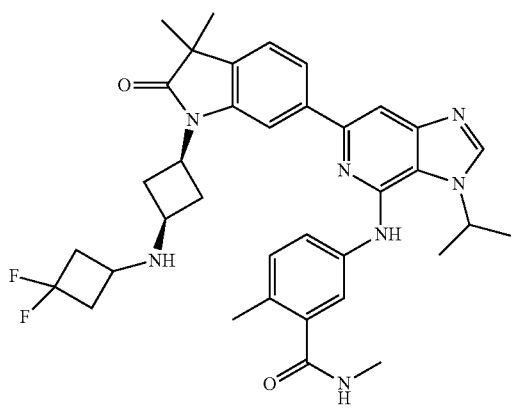 [SMILES: CNC(=O)c1cc(Nc2nc(-c3ccc4c(c3)N([C@H]3C[C@@H](NC5CC(F)(F)C5)C3)C(=O)C4(C)C)cc3ncn(C(C)C)c23)ccc1C] | 81<br>A mixture of DMAc and water was used as a solvent and $K_3PO_4$ as a base instead of a mixture of DME and water and $Na_2CO_3$, respectively, to prepare this compound |

| Structure | Example # |
|---|---|
| 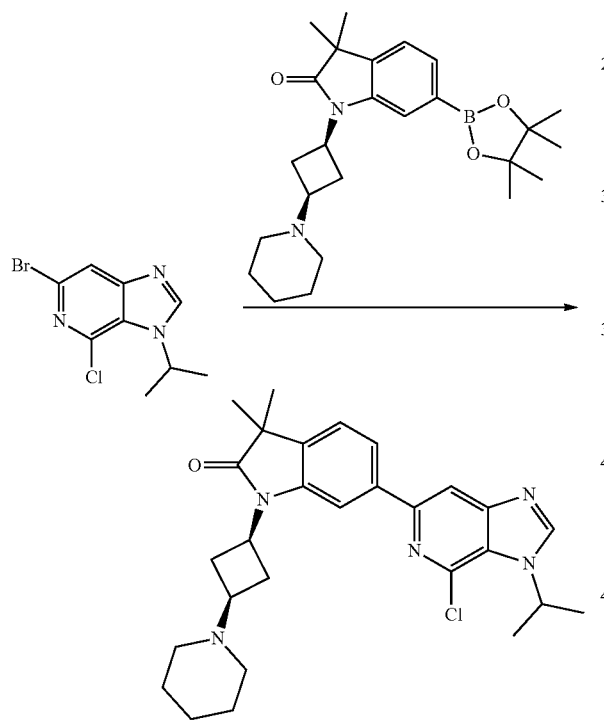 | 82<br>A mixture of DMAc and water was used as a solvent and $K_3PO_4$ as a base instead of a mixture of DME and water and $Na_2CO_3$, respectively, to prepare this compound |

Procedure 14: Preparation of the Compounds of Formula (14) According to Reaction Scheme

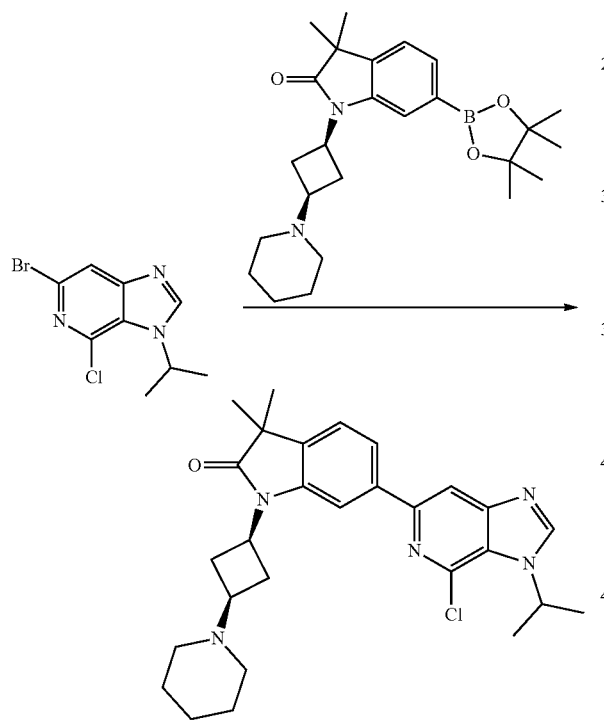

A. Preparation of 6-(4-chloro-3-isopropyl-3H-imidazo[4,5-c]pyridin-6-yl)-3,3-dimethyl-1-((1s,3s)-3-(piperidin-1-yl)cyclobutyl)indolin-2-one

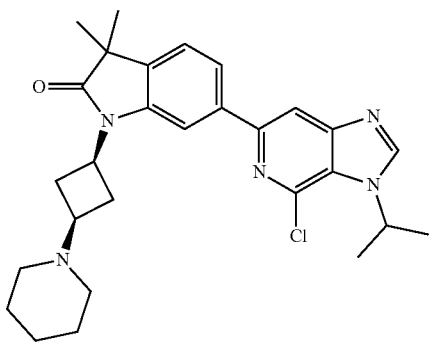 [SMILES: CC(C)n1cnc2cc(-c3ccc4c(c3)N([C@H]3C[C@@H](N5CCCCC5)C3)C(=O)C4(C)C)nc(Cl)c21]

To a solution of 3,3-dimethyl-1-((1s,3s)-3-(piperidin-1-yl)cyclobutyl)-6-(4,4,5,5-tetramethyl-1,3,2-dioxaborolan-2-yl)indolin-2-one (1.0 g, 0.305 mmol) in DME (100 ml) were added 6-bromo-4-chloro-3-isopropyl-3H-imidazo[4,5-c]pyridine (0.97 g, 3.53 mmol), $Pd(PPh_3)_4$ (55 mg, 0.047 mmol), and 2M $Na_2CO_3$ (1.77 ml, 3.53 mmol). The resulting mixture was degassed by bubbling argon gas through for 3 min and then the reaction vessel was sealed. After heating at 90° C. for 1 h, the reaction mixture was cooled then diluted with EtOAc. The organic layer was washed with water, brine, dried over $Na_2SO_4$, concentrated, and purified by flash chromatography (DCM/MeOH 50%) to afford 6-(4-chloro-3-isopropyl-3H-imidazo[4,5-c]pyridin-6-yl)-3,3-dimethyl-1-((1s,3s)-3-(piperidin-1-yl)cyclobutyl)indolin-2-one.

The following compounds were prepared using a similar procedure with the following modification(s):
- the compounds listed under Procedure 1 were used instead of 6-bromo-4-chloro-3-isopropyl-3H-imidazo[4,5-c]pyridine; and/or
- the compounds listed under Procedure 6, 7, 9, 11, or 36 were used instead of 3,3-dimethyl-1-((1s,3s)-3-(piperidin-1-yl)cyclobutyl)-6-(4,4,5,5-tetramethyl-1,3,2-dioxaborolan-2-yl)indolin-2-one; and/or
- $Cs_2CO_3$ was used as a base for the compounds indicated below:

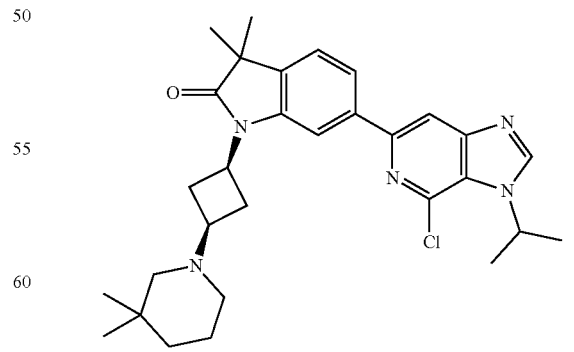

6-(4-chloro-3-isopropyl-3H-imidazo[4,5-c]pyridin-6-yl)-1-((1s,3s)-3-(3,3-dimethylpiperidin-1-yl)cyclobutyl)-3,3-dimethylindolin-2-one

| 385 | 386 |
|---|---|
| 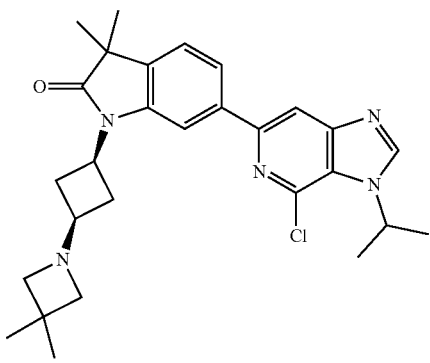 [SMILES: CC(C)n1cnc2cc(-c3ccc4c(c3)N([C@H]3C[C@@H](N5CC(C)(C)C5)C3)C(=O)C4(C)C)nc(Cl)c21] | 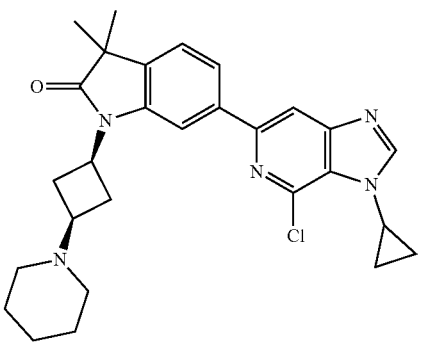 |
| 6-(4-chloro-3-isopropyl-3H-imidazo[4,5-c]pyridin-6-yl)-1-((1s,3s)-3-(3,3-dimethylazetidin-1-yl)cyclobutyl)-3,3-dimethylindolin-2-one | 2M Cs$_2$CO$_3$ was used as a base instead of 2M Na$_2$CO$_3$ to prepare 6-(4-chloro-3-cyclopropyl-3H-imidazo[4,5-c]pyridin-6-yl)-3,3-dimethyl-1-((1s,3s)-3-(piperidin-1-yl)cyclobutyl)indolin-2-one |
| 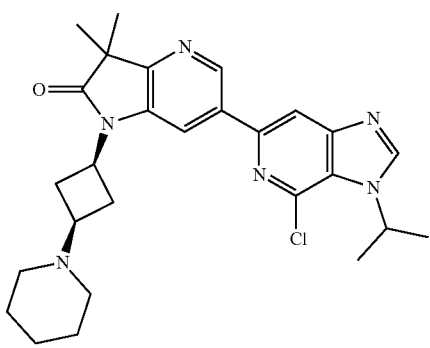 [SMILES: CC(C)n1cnc2cc(-c3cnc4c(c3)N([C@H]3C[C@@H](N5CCCCC5)C3)C(=O)C4(C)C)nc(Cl)c21] | 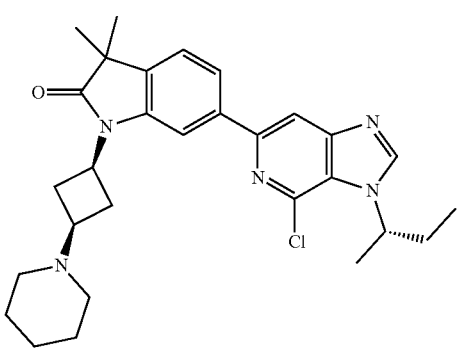 |
| 6-(4-chloro-3-isopropyl-3H-imidazo[4,5-c]pyridin-6-yl)-3,3-dimethyl-1-((1s,3s)-3-(piperidin-1-yl)cyclobutyl)-1,3-dihydro-2H-pyrrolo[3,2-b]pyridin-2-one | 2M Cs$_2$CO$_3$ was used as a base instead of 2M Na$_2$CO$_3$ to prepare 6-(3-((S)-sec-butyl)-4-chloro-3H-imidazo[4,5-c]pyridin-6-yl)-3,3-dimethyl-1-((1s,3R)-3-(piperidin-1-yl)cyclobutyl)indolin-2-one |
| 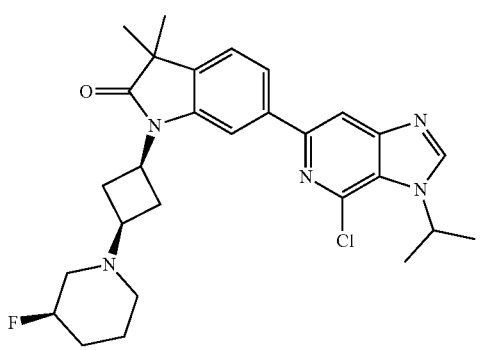 [SMILES: CC(C)n1cnc2cc(-c3ccc4c(c3)N([C@H]3C[C@@H](N5CCC[C@@H](F)C5)C3)C(=O)C4(C)C)nc(Cl)c21] | 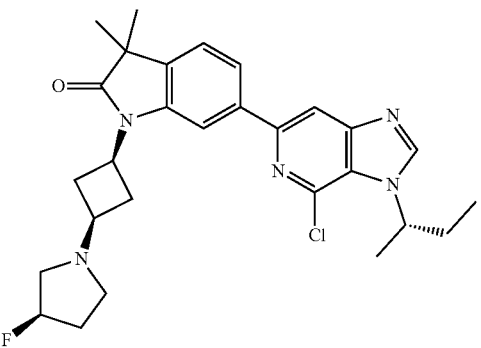 [SMILES: CC[C@H](C)n1cnc2cc(-c3ccc4c(c3)N([C@H]3C[C@@H](N5CC[C@@H](F)C5)C3)C(=O)C4(C)C)nc(Cl)c21] |
| 6-(4-Chloro-3-isopropyl-3H-imidazo[4,5-c]pyridin-6-yl)-1-((1S,3s)-3-((R)-3-fluoropiperidin-1-yl)cyclobutyl)-3,3-dimethylindolin-2-one | 6-(3-((S)-sec-butyl)-4-chloro-3H-imidazo[4,5-c]pyridin-6-yl)-1-((1S,3R)-3-((R)-3-fluoropyrrolidin-1-yl)cyclobutyl)-3,3-dimethylindolin-2-one |

387

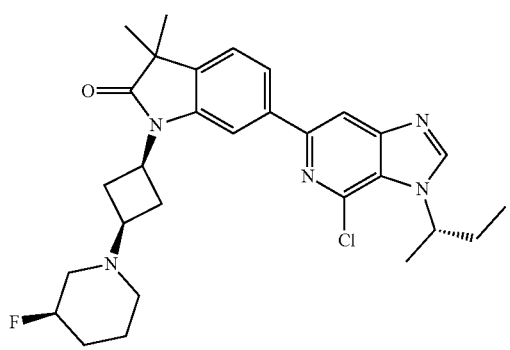 [SMILES: CC[C@H](C)n1cnc2cc(-c3ccc4c(c3)N([C@H]3C[C@@H](N5CCC[C@@H](F)C5)C3)C(=O)C4(C)C)nc(Cl)c21]

6-(3-((S)-sec-Butyl)-4-chloro-3H-imidazo[4,5-c]pyridin-6-yl)-1-((1S,3R)-3-((R)-3-fluoropiperidin-1-yl)cyclobutyl)-3,3-dimethylindolin-2-one

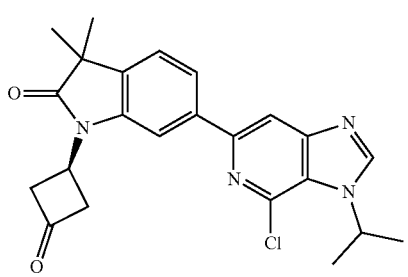

6-(4-chloro-3-isopropyl-3H-imidazo[4,5-c]pyridin-6-yl)-3,3-dimethyl-1-(3-oxocyclobutyl)indolin-2-one

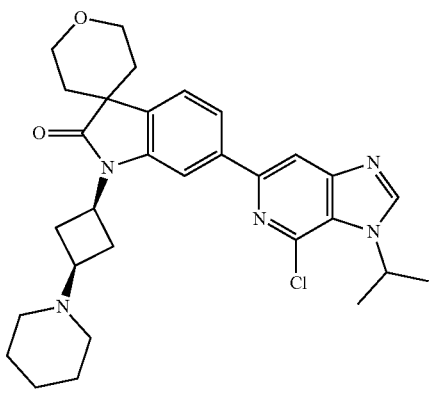 [SMILES: CC(C)n1cnc2cc(-c3ccc4c(c3)N([C@H]3C[C@@H](N5CCCCC5)C3)C(=O)C43CCOCC3)nc(Cl)c21]

6-(4-chloro-3-isopropyl-3H-imidazo[4,5-c]pyridin-6-yl)-1-((1s,3s)-3-(piperidin-1-yl)cyclobutyl)-2',3',5',6'-tetrahydrospiro[indoline-3,4'-pyran]-2-one

388

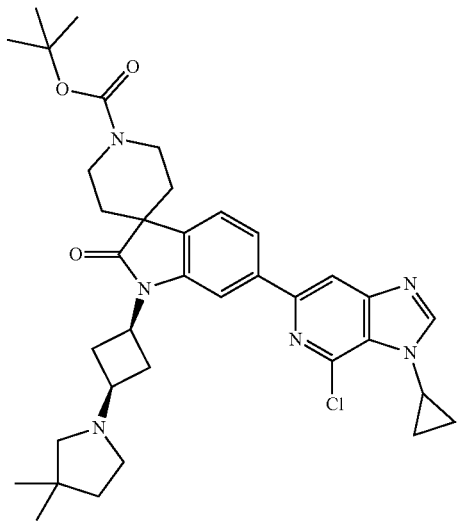 [SMILES: CC1(C)CCN([C@H]2C[C@@H](N3C(=O)C4(CCN(C(=O)OC(C)(C)C)CC4)c4ccc(-c5cc6ncn(C7CC7)c6c(Cl)n5)cc43)C2)C1]

tert-butyl 6-(4-chloro-3-cyclopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate

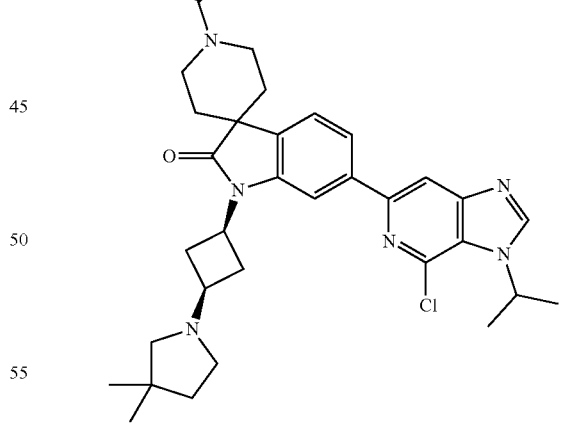

tert-butyl 6-(4-chloro-3-isopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate

389

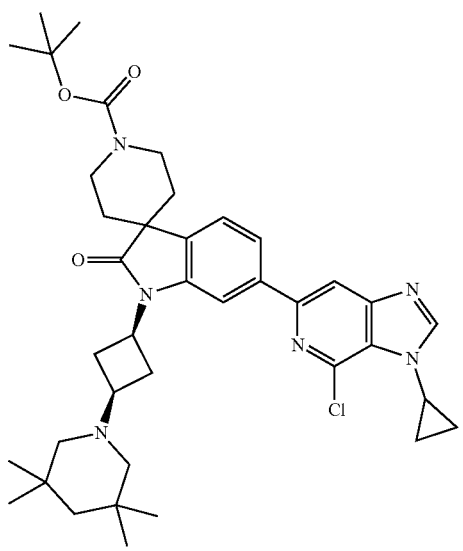 [SMILES: CC1(C)CN([C@H]2C[C@@H](N3C(=O)C4(CCN(C(=O)OC(C)(C)C)CC4)c4ccc(-c5cc6ncn(C7CC7)c6c(Cl)n5)cc43)C2)CC(C)(C)C1]

tert-butyl 6-(4-chloro-3-cyclopropyl-3H-imidazo[4,5-c]pyridin-6-yl)-2-oxo-1-((1s,3s)-3-(3,3,5,5-tetramethylpiperidin-1-yl)cyclobutyl)spiro[indoline-3,4'-piperidine]-1'-carboxylate

390

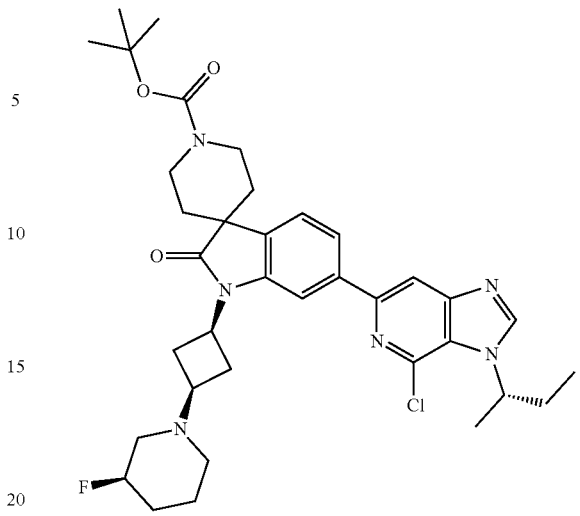

tert-butyl 6-(3-((S)-sec-butyl)-4-chloro-3H-imidazo[4,5-c]pyridin-6-yl)-1-((1S,3R)-3-((R)-3-fluoropiperidin-1-yl)cyclobutyl)-2-oxospiro[indoline-3,4'-piperidine]-1'-carboxylate

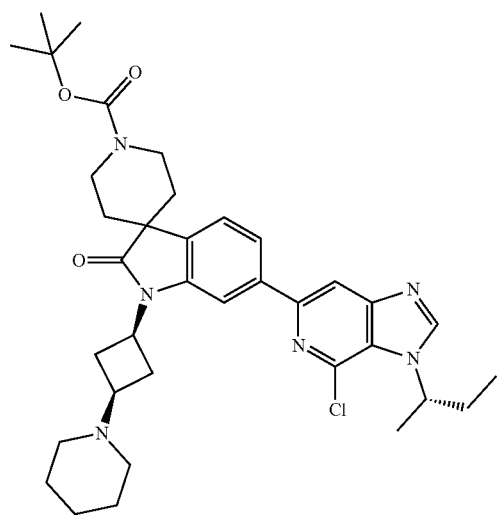 [SMILES: CC[C@H](C)n1cnc2cc(-c3ccc4c(c3)N([C@H]3C[C@@H](N5CCCCC5)C3)C(=O)C43CCN(C(=O)OC(C)(C)C)CC3)nc(Cl)c21]

tert-butyl 6-(3-((S)-sec-butyl)-4-chloro-3H-imidazo[4,5-c]pyridin-6-yl)-2-oxo-1-((1s,3R)-3-(piperidin-1-yl)cyclobutyl)spiro[indoline-3,4'-piperidine]-1'-carboxylate

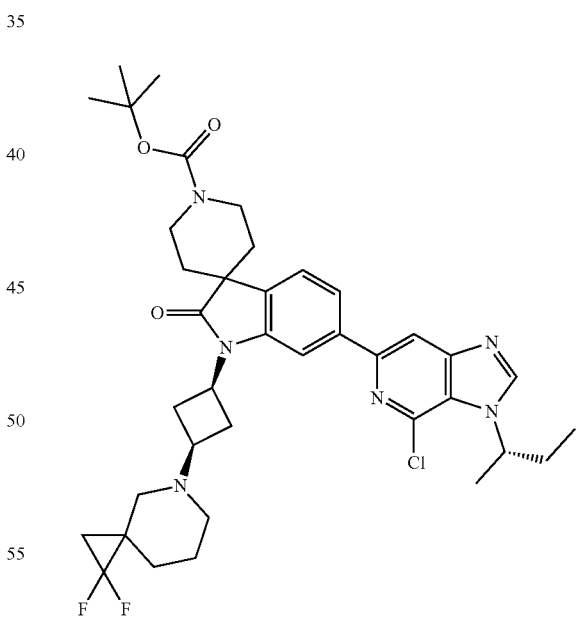

tert-butyl 6-(3-((S)-sec-butyl)-4-chloro-3H-imidazo[4,5-c]pyridin-6-yl)-1-((1s,3R)-3-(1,1-difluoro-5-azaspiro[2.4]heptan-5-yl)cyclobutyl)-2-oxospiro[indoline-3,4'-piperidine]-1'-carboxylate

391

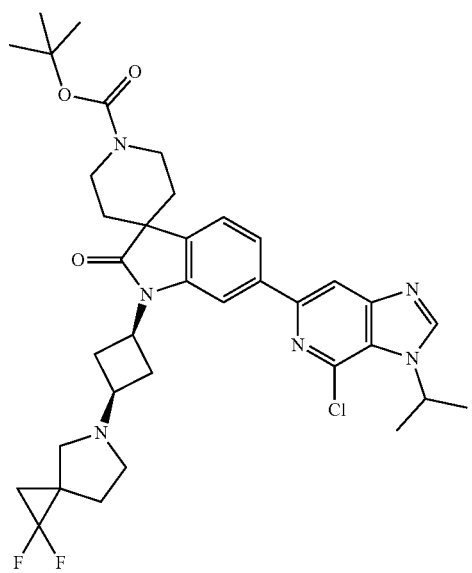 [SMILES: CC(C)n1cnc2cc(-c3ccc4c(c3)N([C@H]3C[C@@H](N5CCC6(C5)CC6(F)F)C3)C(=O)C43CCN(C(=O)OC(C)(C)C)CC3)nc(Cl)c21]

tert-butyl 6-(4-chloro-3-isopropyl-3H-imidazo[4,5-c]pyridin-6-yl)-1-((1s,3s)-3-(1,1-difluoro-5-azaspiro[2.4]heptan-5-yl)cyclobutyl)-2-oxospiro[indoline-3,4'-piperidine]-1'-carboxylate

392

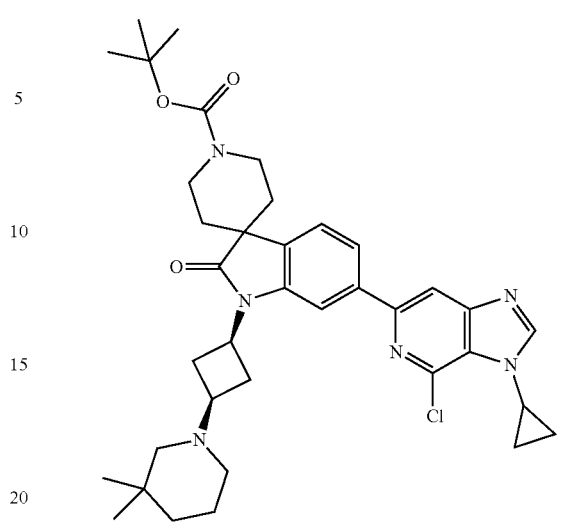

tert-butyl 6-(4-chloro-3-cyclopropyl-3H-imidazo[4,5-c]pyridin-6-yl)-1-((1s,3s)-3-(3,3-dimethylpiperidin-1-yl)cyclobutyl)-2-oxospiro[indoline-3,4'-piperidine]-1'-carboxylate

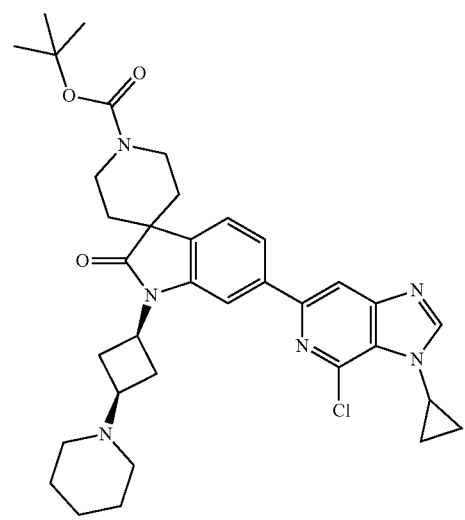 [SMILES: CC(C)(C)OC(=O)N1CCC2(CC1)C(=O)N([C@H]1C[C@@H](N3CCCCC3)C1)c1cc(-c3cc4ncn(C5CC5)c4c(Cl)n3)ccc12]

tert-butyl 6-(4-chloro-3-cyclopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate

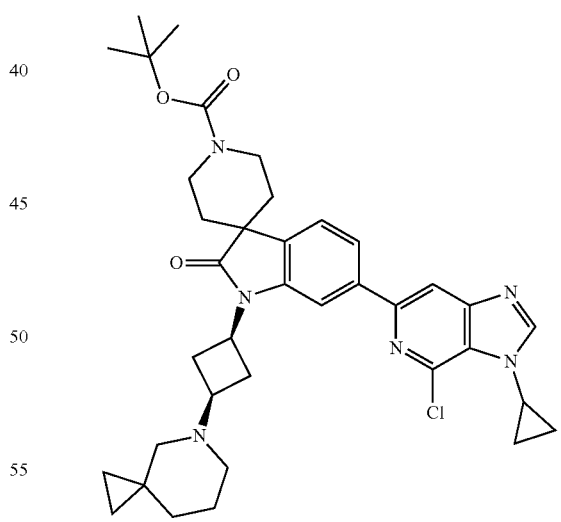

tert-butyl 1-((1s,3s)-3-(5-azaspiro[2.5]octan-5-yl)cyclobutyl)-6-(4-chloro-3-cyclopropyl-3H-imidazo[4,5-c]pyridin-6-yl)-2-oxospiro[indoline-3,4'-piperidine]-1'-carboxylate

| 393 | 394 |
|---|---|
| 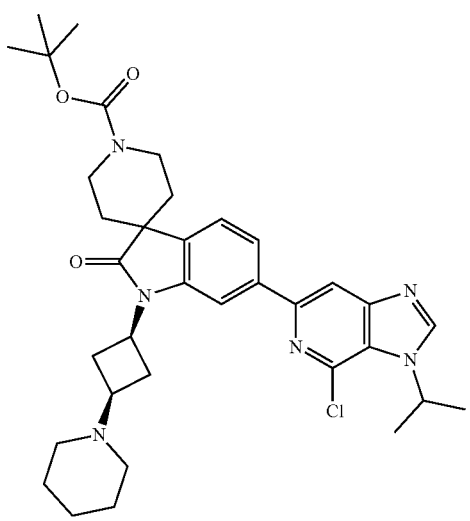 [SMILES: CC(C)n1cnc2cc(-c3ccc4c(c3)N([C@H]3C[C@@H](N5CCCCC5)C3)C(=O)C43CCN(C(=O)OC(C)(C)C)CC3)nc(Cl)c21] | 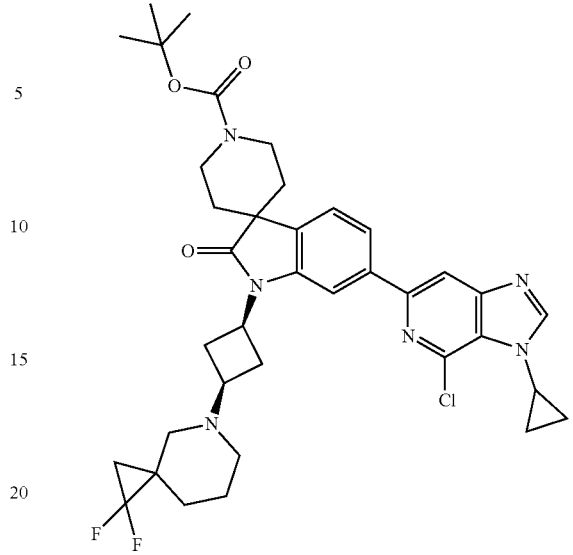 |

2M Cs$_2$CO$_3$ was used as a base instead of 2M Na$_2$CO$_3$ to prepare tert-butyl 6-(4-chloro-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate tert-butyl 6-(4-chloro-3-cyclopropyl-3H-imidazo[4,5-c]pyridin-6-yl)-1-((1s,3s)-3-(1,1-difluoro-5-azaspiro[2.5]octan-5-yl)cyclobutyl)-2-oxospiro[indoline-3,4'-piperidine]-1'-carboxylate

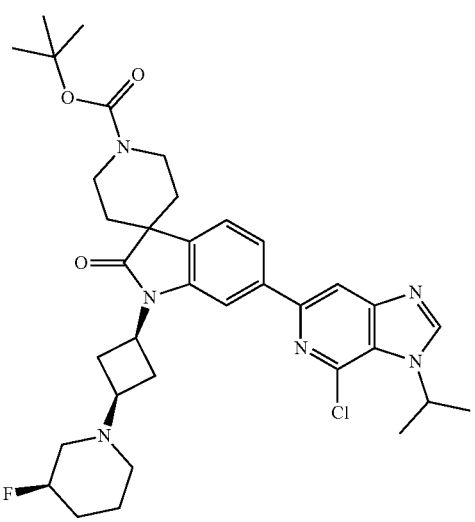 [SMILES: CC(C)n1cnc2cc(-c3ccc4c(c3)N([C@H]3C[C@@H](N5CCC[C@@H](F)C5)C3)C(=O)C43CCN(C(=O)OC(C)(C)C)CC3)nc(Cl)c21]

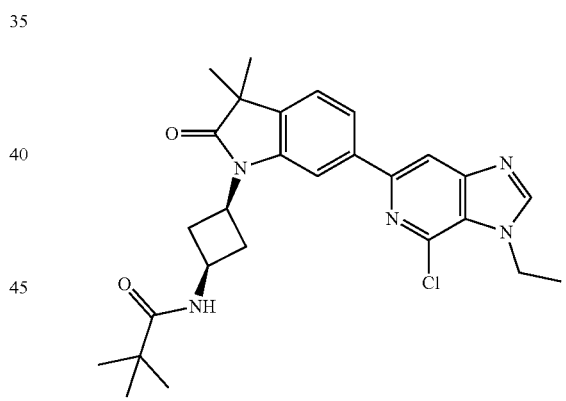

tert-butyl 6-(4-chloro-3-isopropyl-3H-imidazo[4,5-c]pyridin-6-yl)-1-((1s,3s)-3-((R)-3-difluoro-fluoropiperidin-1-yl)cyclobutyl)-2-oxospiro[indoline-3,4'-piperidine]-1'-carboxylate N-((1s,3s)-3-(3,3-dimethyl-2-oxo-6-(4,4,5,5-tetramethyl-1,3,2-dioxaborolan-2-yl)indolin-1-yl)cyclobutyl)pivalamide (synthesis described in Procedure 36) and 6-bromo-4-chloro-3-ethyl-3H-imidazo[4,5-c]pyridine were used instead of 3-dimethyl-1-((1s,3s)-3-(piperidin-1-yl)cyclobutyl)-6-(4,4,5,5-tetramethyl-1,3,2-dioxaborolan-2-yl)indolin-2-one and 6-bromo-4-chloro-3-isopropyl-3H-imidazo[4,5-c]pyridine, respectively, to prepare N-((1s,3s)-3-(6-(4-chloro-3-ethyl-3H-imidazo[4,5-c]pyridin-6-yl)-3,3-dimethyl-2-oxoindolin-1-yl)cyclobutyl)pivalamide Procedure 15: Preparation of the Compounds of Formula (14) According to Reaction Scheme II

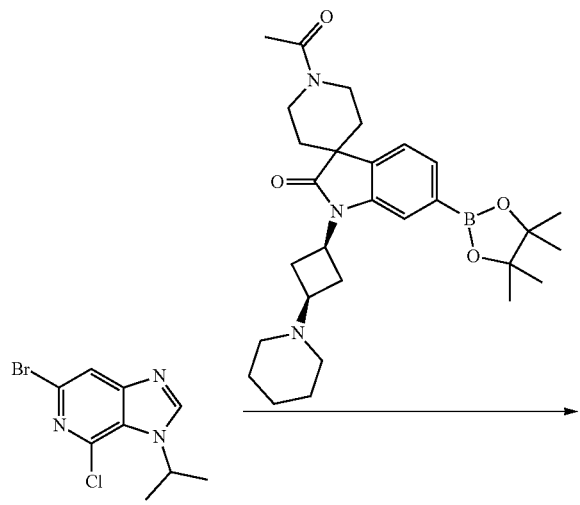

A. Preparation of 1'-acetyl-6-(4-chloro-3-isopropyl-3H-imidazo[4,5-c]pyridin-6-yl)-1-((1s,3s)-3-(piperidin-1-yl)cyclobutyl)spiro[indoline-3,4'-piperidin]-2-one In a round bottomed flask were placed 1'-acetyl-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (0.8 g, 1.6 mmol), 6-bromo-4-chloro-3-isopropyl-3H-imidazo[4,5-c]pyridine (866 mg, 3.2 mmol), Pd(PPh₃)₄ (91 mg, 0.08 mmol), and cesium carbonate (668 mg, 6.3 mmol). To this mixture were added DME (10 mL) and water (3 mL) and the resulting mixture was heated to 120° C. for 1 h under nitrogen atmosphere. Then it was diluted with EtOAc and water, and extracted with EtOAc. The combined organic layers were concentrated under reduced pressure and purified by column chromatography (0-10% DCM/MeOH) to give 1'-acetyl-6-(4-chloro-3-isopropyl-3H-imidazo[4,5-c]pyridin-6-yl)-1-((1s,3s)-3-(piperidin-1-yl)cyclobutyl)spiro[indoline-3,4'-piperidin]-2-one.

The following compounds were prepared using a similar procedure with the following modification(s):
- the compounds listed under Procedure 1 were used instead of 6-bromo-4-chloro-3-isopropyl-3H-imidazo[4,5-c]pyridine; and/or
- the compounds listed under Procedure 11, 12, or 36 were used instead of 1'-acetyl-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one:

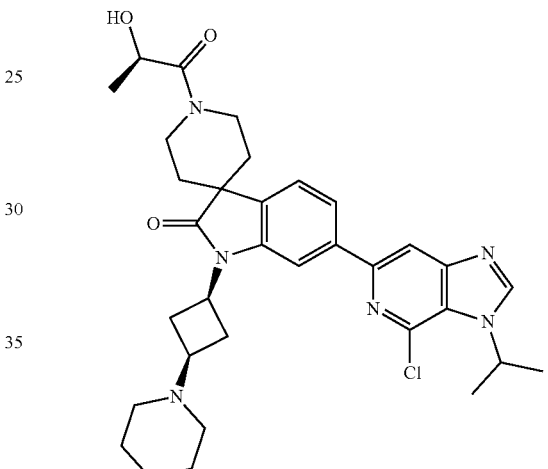

6-(4-chloro-3-isopropyl-3H-imidazo[4,5-c]pyridin-6-yl)-1'-((R)-2-hydroxypropanoyl)-1-((1s,3S)-3-(piperidin-1-yl)cyclobutyl)spiro[indoline-3,4'-piperidin]-2-one

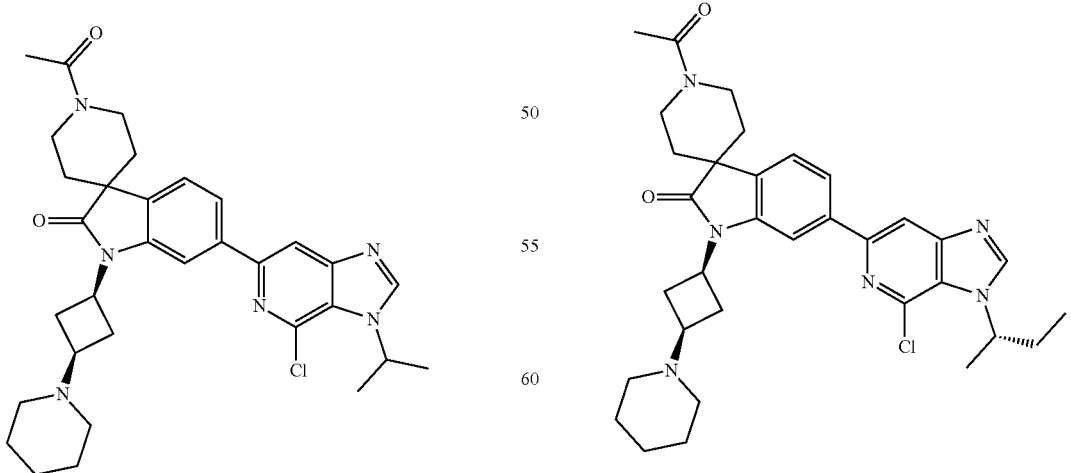

1'-acetyl-6-(3-((S)-sec-butyl)-4-chloro-3H-imidazo[4,5-c]pyridin-6-yl)-1-((1s,3)-2-hydroxypropanoyl)-3-(piperidin-((1-(piperidin-1-yl)cyclobutyl)spiro[indoline-3,4'-piperidin]-2-one

397

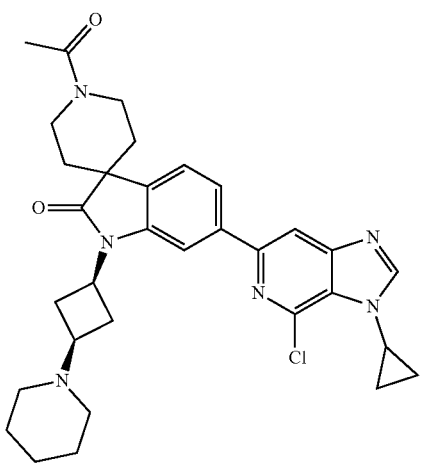 [SMILES: CC(=O)N1CCC2(CC1)C(=O)N([C@H]1C[C@@H](N3CCCCC3)C1)c1cc(-c3cc4ncn(C5CC5)c4c(Cl)n3)ccc12]

Na$_2$CO$_3$ as a base instead of Cs$_2$CO$_3$ was used to prepare 1'-acetyl-6-(4-chloro-3-cyclopropyl-3H-imidazo[4,5-c]pyridin-6-yl)-1-((1s,3s)-3-(piperidin-1-yl)cyclobutyl)spiro[indoline-3,4'-piperidin]-2-one

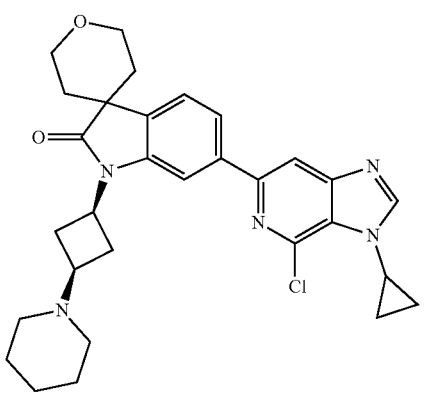 [SMILES: O=C1N([C@H]2C[C@@H](N3CCCCC3)C2)c2cc(-c3cc4ncn(C5CC5)c4c(Cl)n3)ccc2C12CCOCC2]

398

6-(4-chloro-3-cyclopropyl-3H-imidazo[4,5-c]pyridin-6-yl)-1-((1s,3s)-3-(piperidin-1-yl)cyclobutyl)-2',3',5',6'-tetrahydrospiro[indoline-3,4'-pyran]-2-one

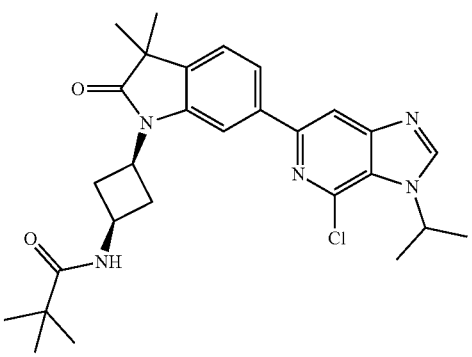 [SMILES: CC(C)n1cnc2cc(-c3ccc4c(c3)N([C@H]3C[C@@H](NC(=O)C(C)(C)C)C3)C(=O)C4(C)C)nc(Cl)c21]

N-((1s,3s)-3-(6-(4-Chloro-3-isopropyl-3H-imidazo[4,5-c]pyridin-6-yl)-3,3-dimethyl-2-oxoindolin-1-yl)cyclobutyl)pivalamide Procedure 16: Preparation of the Compounds of Formula (I-B) According to Reaction Schemes II and IV

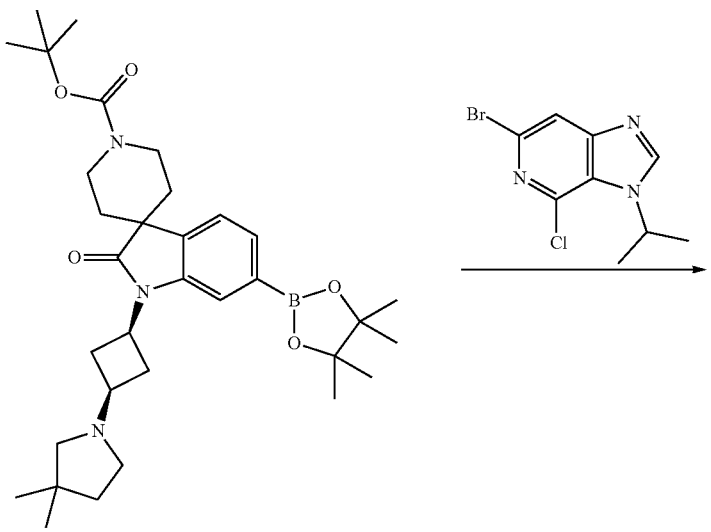

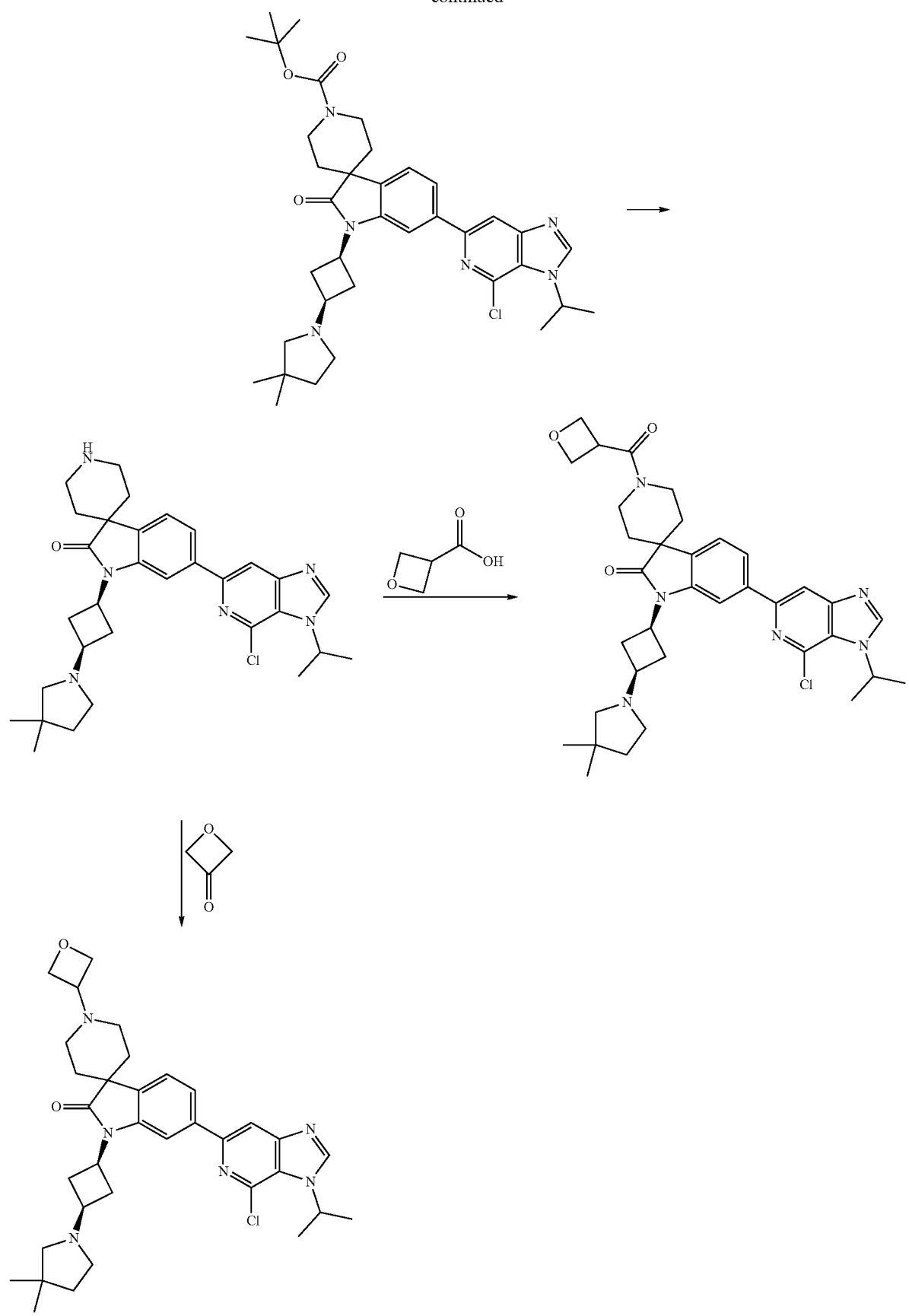

401

A. Preparation of tert-butyl 6-(4-chloro-3-isopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate

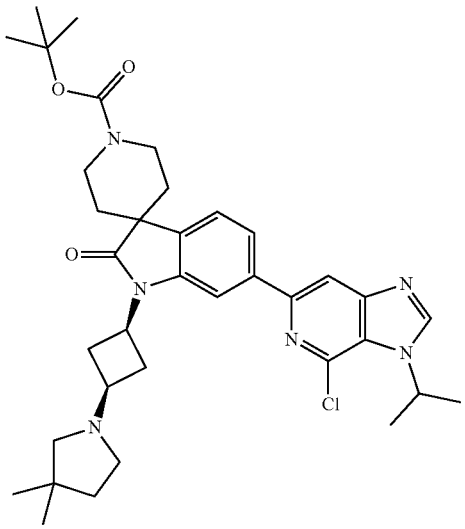 [SMILES: CC(C)n1cnc2cc(-c3ccc4c(c3)N([C@H]3C[C@@H](N5CCC(C)(C)C5)C3)C(=O)C43CCN(C(=O)OC(C)(C)C)CC3)nc(Cl)c21]

To a flask was charged tert-butyl 1-((1s,3s)-3-(3,3-dimethylpyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate (1.0 g, 1.7 mmol), 6-bromo-4-chloro-3-isopropyl-3H-imidazo[4,5-c]pyridine (0.9 g, 3.4 mmol), Pd(PPh$_3$)$_4$ (0.2 g, 0.17 mmol), and cesium carbonate (2.0 g, 6.8 mmol). DME (10 mL) and water (3 mL) were added and the reaction was heated to 120° C. for 1 h under nitrogen atmosphere. The reaction was diluted with EtOAc and water, and extracted with EtOAc. The combined organic layers were concentrated under reduced pressure and purified by column chromatography (100% DCM to 10% MeOH/DCM) to give tert-butyl 6-(4-chloro-3-isopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate.

B. Preparation of 6-(4-chloro-3-isopropyl-3H-imidazo[4,5-c]pyridin-6-yl)-1-((1s,3s)-3-(3,3-dimethylpyrrolidin-1-yl)cyclobutyl)spiro[indoline-3,4'-piperidin]-2-one

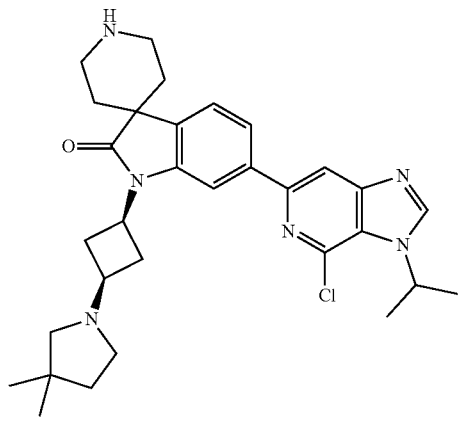 [SMILES: CC(C)n1cnc2cc(-c3ccc4c(c3)N([C@H]3C[C@@H](N5CCC(C)(C)C5)C3)C(=O)C43CCNCC3)nc(Cl)c21]

To a suspension of tert-butyl 6-(4-chloro-3-isopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate (550 mg, 0.85 mmol) in dichloromethane (5 mL) was added 4N HCl in dioxane (1 mL). After stirring at room temperature overnight, the reaction mixture was concentrated under reduced pressure to afford 6-(4-chloro-3-isopropyl-3H-imidazo[4,5-c]pyridin-6-yl)-1-((1s,3s)-3-(3,3-dimethylpyrrolidin-1-yl)cyclobutyl)spiro[indoline-3,4'-piperidin]-2-one.

The following compounds were prepared using a similar procedure except the compounds listed under the procedure 14 were used instead of tert-butyl 6-(4-chloro-3-isopropyl-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate:

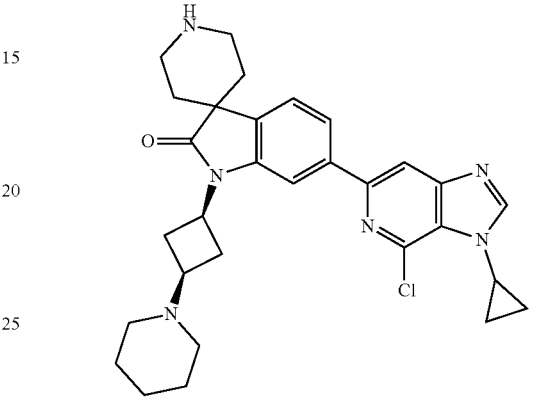

6-(4-chloro-3-cyclopropyl-3H-imidazo[4,5-c]pyridin-6-yl)-1-((1s,3s)-3-(piperidin-1-yl)cyclobutyl)spiro[indoline-3,4'-piperidin]-2-one C. Preparation of 6-(4-chloro-3-isopropyl-3H-imidazo[4,5-c]pyridin-6-yl)-1-((1s,3s)-3-(3,3-dimethylpyrrolidin-1-yl)cyclobutyl)-1'-(oxetane-3-carbonyl)spiro[indoline-3,4'-piperidin]-2-one

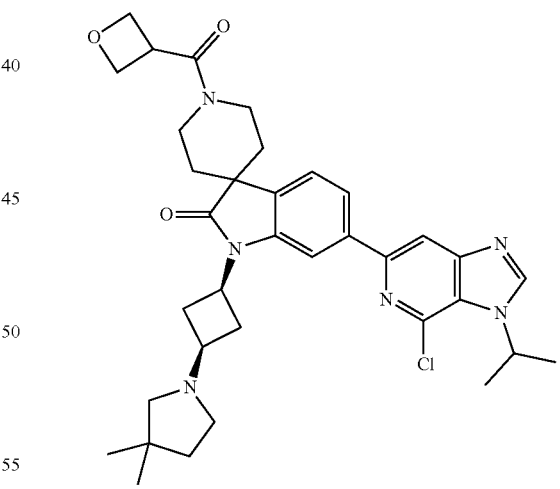

In a flask was placed 6-(4-chloro-3-isopropyl-3H-imidazo[4,5-c]pyridin-6-yl)-1-((1s,3s)-3-(3,3-dimethylpyrrolidin-1-yl)cyclobutyl)spiro[indoline-3,4'-piperidin]-2-one (82 mg, 0.14 mmol), oxetane-3-carboxylic acid (17 mg, 0.17 mmol), and DIPEA (0.70 ml, 0.12 mmol) in DMF (1 mL). To this mixture was added HATU (80 mg, 0.21 mmol). The mixture was stirred at room temperature for 1 h, then quenched with water and extracted with DCM. The combined organic layers were washed with water and brine, dried (Na$_2$SO$_4$), concentrated, and purified by reverse phase HPLC to give 6-(4-chloro-3-isopropyl-3H-imidazo[4,5-c]pyridin-6-yl)-1-((1s,3s)-3-(3,3-dimethylpyrrolidin-1-yl)cyclobutyl)-1'-(oxetane-3-carbonyl)spiro[indoline-3,4'-piperidin]-2-one.

The following compounds were prepared using a similar procedure except:

the compounds listed under Procedure 1 were used instead of 6-bromo-4-chloro-3-isopropyl-3H-imidazo[4,5-c]pyridine; and/or the compounds listed in the Procedure 10 were used instead of tert-butyl 1-((1s,3s)-3-(3,3-dimethylpyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate; and/or the carboxylic acids indicated below were used instead of oxetane-3-carboxylic acid:

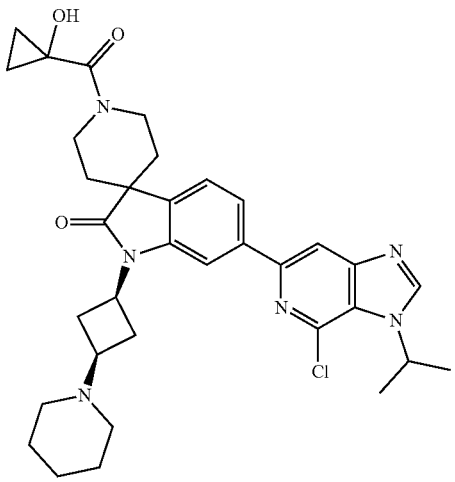 [SMILES: CC(C)n1cnc2cc(-c3ccc4c(c3)N([C@H]3C[C@@H](N5CCCCC5)C3)C(=O)C43CCN(C(=O)C4(O)CC4)CC3)nc(Cl)c21]

1-Hydroxycyclopropane-1-carboxylic acid was used to prepare 6-(4-chloro-3-isopropyl-3H-imidazo[4,5-c]pyridin-6-yl)-1'-(1-hydroxycyclopropane-1-carbonyl)-1-((1s,3s)-3-(piperidin-1-yl)cyclobutyl)spiro[indoline-3,4'-piperidin]-2-one

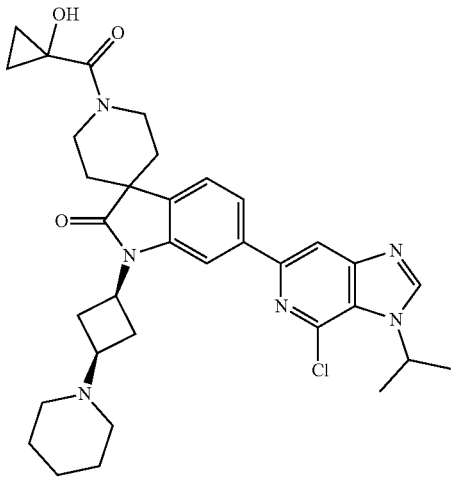 [SMILES: CC(C)n1cnc2cc(-c3ccc4c(c3)N([C@H]3C[C@@H](N5CCCCC5)C3)C(=O)C43CCN(C(=O)C4(O)CC4)CC3)nc(Cl)c21]

1-Hydroxycyclopropane-1-carboxylic acid was used to prepare 6-(4-chloro-3-cyclopropyl-3H-imidazo[4,5-c]pyridin-6-yl)-1'-(1-hydroxycyclopropane-1-carbonyl)-1-((1s,3s)-3-(piperidin-1-yl)cyclobutyl)spiro[indoline-3,4'-piperidin]-2-one

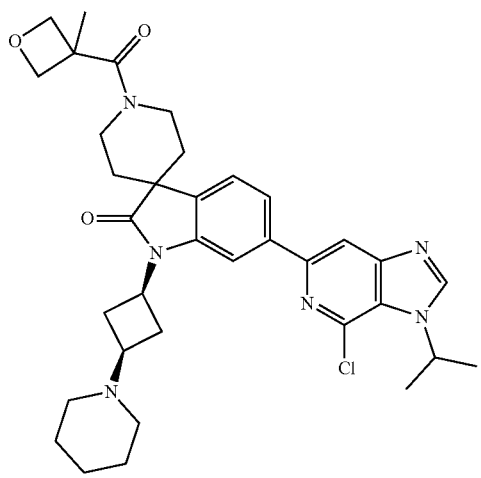 [SMILES: CC(C)n1cnc2cc(-c3ccc4c(c3)N([C@H]3C[C@@H](N5CCCCC5)C3)C(=O)C43CCN(C(=O)C4(C)COC4)CC3)nc(Cl)c21]

3-Methyloxetane-3-carboxylic acid was used to prepare 6-(4-chloro-3-isopropyl-3H-imidazo[4,5-c]pyridin-6-yl)-1'-(3-methyloxetane-3-carbonyl)-1-((1s,3s)-3-(piperidin-1-yl)cyclobutyl)spiro[indoline-3,4'-piperidin]-2-one

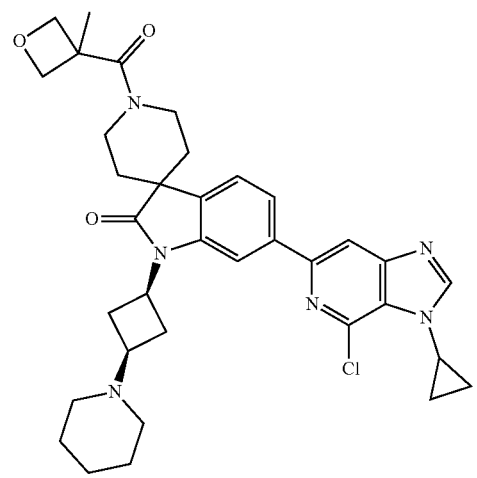 [SMILES: CC1(C(=O)N2CCC3(CC2)C(=O)N([C@H]2C[C@@H](N4CCCCC4)C2)c2cc(-c4cc5ncn(C6CC6)c5c(Cl)n4)ccc23)COC1]

3-Methyloxetane-3-carboxylic acid was used to prepare 6-(4-chloro-3-cyclopropyl-3H-imidazo[4,5-c]pyridin-6-yl)-1'-(3-methyloxetane-3-carbonyl)-1-((1s,3s)-3-(piperidin-1-yl)cyclobutyl)spiro[indoline-3,4'-piperidin]-2-one

D. Preparation of 6-(4-chloro-3-isopropyl-3H-imidazo[4,5-c]pyridin-6-yl)-1-((1s,3s)-3-(3,3-dimethylpyrrolidin-1-yl)cyclobutyl)-1'-(oxetan-3-yl)spiro[indoline-3,4'-piperidin]-2-one 6-(4-chloro-3-isopropyl-3H-imidazo[4,5-c]pyridin-6-yl)-1-((1S,3s)-3-((R)-3-fluoropiperidin-1-yl)cyclobutyl)-1'-(oxetan-3-yl)spiro[indoline-3,4'-piperidin]-2-one

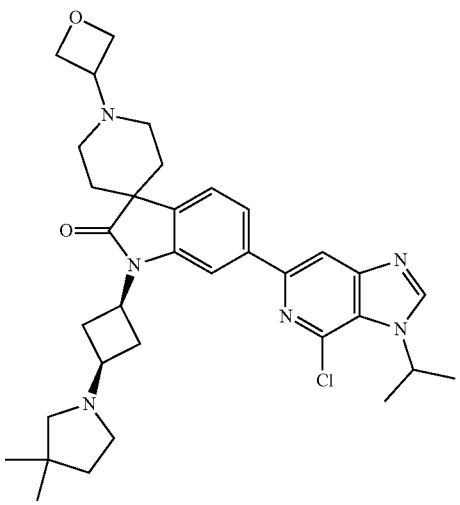 [SMILES: CC(C)n1cnc2cc(-c3ccc4c(c3)N([C@H]3C[C@@H](N5CCC(C)(C)C5)C3)C(=O)C43CCN(C4COC4)CC3)nc(Cl)c21]

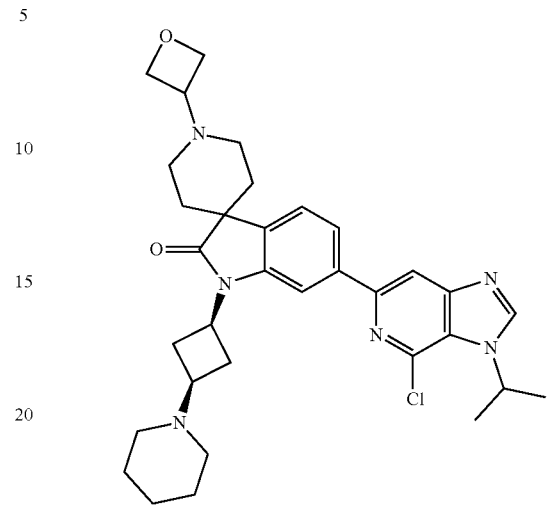

To a flask charged with 6-(4-chloro-3-isopropyl-3H-imidazo[4,5-c]pyridin-6-yl)-1-((1s,3s)-3-(3,3-dimethylpyrrolidin-1-yl)cyclobutyl)spiro[indoline-3,4'-piperidin]-2-one (460 mg, 0.84 mmol) and 3-oxetanone (182 mg, 2.5 mmol) in methanol (3 mL) was added zinc chloride (172 mg, 1.3 mmol) followed by sodium cyanoborohydride (159 mg, 2.5 mmol). The mixture was sealed and heated to 40° C., stirred for 2 h., cooled, and then quenched with saturated aqueous sodium bicarbonate. The aqueous layer was extracted three times with dichloromethane. The combined organic layers were dried over sodium sulfate, filtered, concentrated under vacuum, and purified by reverse phase HPLC to give 6-(4-chloro-3-isopropyl-3H-imidazo[4,5-c]pyridin-6-yl)-1-((1s,3s)-3-(3,3-dimethylpyrrolidin-1-yl)cyclobutyl)-1'-(oxetan-3-yl)spiro[indoline-3,4'-piperidin]-2-one.

The following compounds were prepared using a similar procedure with the following modification(s):
the compounds listed under Procedure 9 were used instead of tert-butyl 1-((1s,3s)-3-(3,3-dimethylpyrrolidin-1-yl)cyclobutyl)-2-oxo-6-(4,4,5,5-tetramethyl-1,3,2-dioxaborolan-2-yl)spiro[indoline-3,4'-piperidine]-1'-carboxylate:

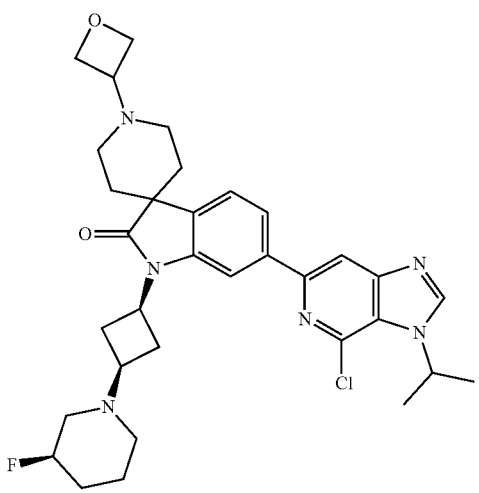 [SMILES: CC(C)n1cnc2cc(-c3ccc4c(c3)N([C@H]3C[C@@H](N5CCC[C@@H](F)C5)C3)C(=O)C43CCN(C4COC4)CC3)nc(Cl)c21]

6-(4-chloro-3-isopropyl-3H-imidazo[4,5-c]pyridin-6-yl)-1'-(oxetan-3-yl)-1-((1s,3s)-3-(piperidin-1-yl)cyclobutyl)spiro[indoline-3,4'-piperidin]-2-one Procedure 17: Preparation of the Compounds of Formula (22) According to Reaction Scheme V

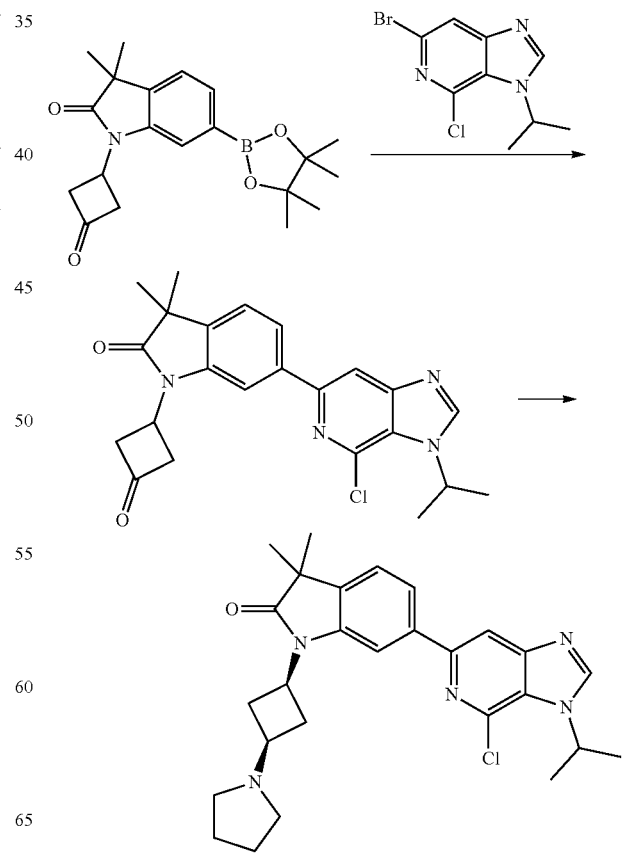

A. Preparation of 6-(4-chloro-3-isopropyl-3H-imidazo[4,5-c]pyridin-6-yl)-3,3-dimethyl-1-(3-oxocyclobutyl)indolin-2-one

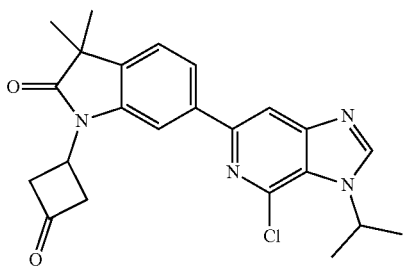 [SMILES: CC(C)n1cnc2cc(-c3ccc4c(c3)N(C3CC(=O)C3)C(=O)C4(C)C)nc(Cl)c21]

To a solution of 6-bromo-4-chloro-3-isopropyl-3H-imidazo[4,5-c]pyridine (2 g, 7.29 mmol) in DME (30 ml) were added Pd(PPh$_3$)$_4$ (589 mg, 0.51 mmol), 2M Na$_2$CO$_3$ (18.2 ml, 36 mmol), and 3,3-dimethyl-1-(3-oxocyclobutyl)-6-(4,4,5,5-tetramethyl-1,3,2-dioxaborolan-2-yl)indolin-2-one (3.1 g, 8.74 mmol). The resulting suspension was degassed by bubbling Ar gas through (2 min), sealed, then heated to 90° C. for 4 h. The reaction mixture was cooled to room temperature then diluted with EtOAc. The organic layer was washed with water, brine, dried over Na$_2$SO$_4$, concentrated, and purified by flash chromatography (Hex/EtOAc) to give 6-(4-chloro-3-isopropyl-3H-imidazo[4,5-c]pyridin-6-yl)-3,3-dimethyl-1-(3-oxocyclobutyl)indolin-2-one.

B. Preparation of 6-(4-chloro-3-isopropyl-3H-imidazo[4,5-c]pyridin-6-yl)-3,3-dimethyl-1-((1s,3s)-3-(pyrrolidin-1-yl)cyclobutyl)indolin-2-one

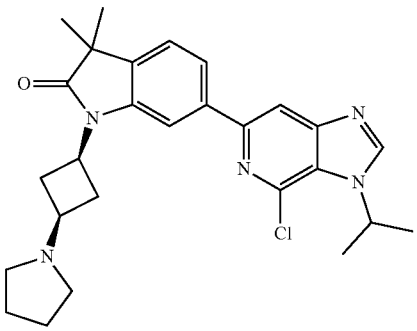 [SMILES: CC(C)n1cnc2cc(-c3ccc4c(c3)N([C@H]3C[C@@H](N5CCCC5)C3)C(=O)C4(C)C)nc(Cl)c21]

To a stirring solution of 6-(4-chloro-3-isopropyl-3H-imidazo[4,5-c]pyridin-6-yl)-3,3-dimethyl-1-(3-oxocyclobutyl)indolin-2-one (200 mg, 0.47 mmol) in DCE (5 ml) were added pyrrolidine (67 mg, 0.95 mmol), Na(OAc)$_3$BH (150 mg, 0.79 mmol), and AcOH (0.081 ml, 1.42 mmol) at room temperature. The resulting mixture was stirred for 2 h then quenched with satd. NaHCO$_3$, and extracted with DCM. The combined organic layers were dried over Na$_2$SO$_4$, then concentrated and purified by flash chromatography (Hexanes/EtOAc) to give 6-(4-chloro-3-isopropyl-3H-imidazo[4,5-c]pyridin-6-yl)-3,3-dimethyl-1-((1s,3s)-3-(pyrrolidin-1-yl)cyclobutyl)indolin-2-one.

The following compounds were prepared using a similar procedure with the following modification(s):
- the amines indicated below were used instead of pyrrolidine; and/or
- the compounds listed under Procedure 1 were used instead of 6-bromo-4-chloro-3-isopropyl-3H-imidazo[4,5-c]pyridine:

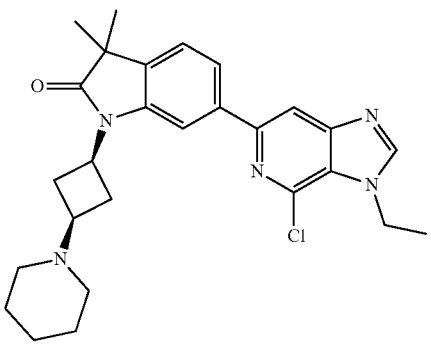 [SMILES: CCn1cnc2cc(-c3ccc4c(c3)N([C@H]3C[C@@H](N5CCCCC5)C3)C(=O)C4(C)C)nc(Cl)c21]

Piperidine was used to prepare 6-(4-chloro-3-ethyl-3H-imidazo[4,5-c]pyridin-6-yl)-3,3-dimethyl-1-((1s,3s)-3-(piperidin-1-yl)cyclobutyl)indolin-2-one

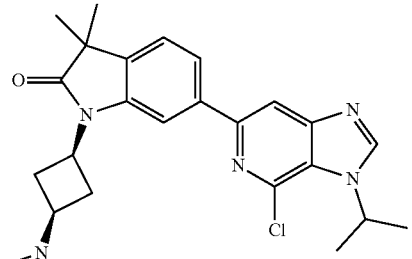

3-(Difluoromethyl)pyrrolidine was used to prepare 6-(4-chloro-3-isopropyl-3H-imidazo[4,5-c]pyridin-6-yl)-1-((1s,3s)-3-(3-(difluoromethyl)pyrrolidin-1-yl)cyclobutyl)-3,3-dimethylindolin-2-one

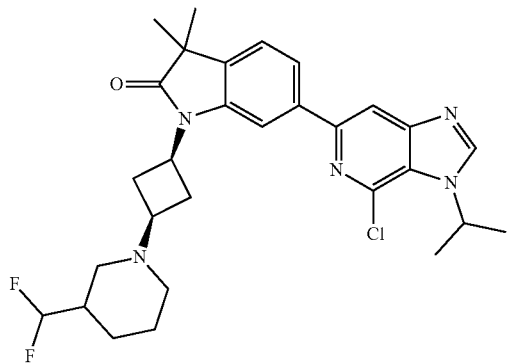 [SMILES: CC(C)n1cnc2cc(-c3ccc4c(c3)N([C@H]3C[C@@H](N5CCCC(C(F)F)C5)C3)C(=O)C4(C)C)nc(Cl)c21]

409

3-(Difluoromethyl)piperidine was used to prepare 6-(4-chloro-3-isopropyl-3H-imidazo[4,5-c]pyridin-6-yl)-1-((1s,3s)-3-(3-(difluoromethyl)piperidin-1-yl)cyclobutyl)-3,3-dimethylindolin-2-one

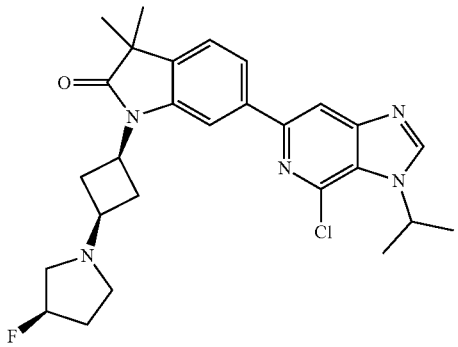 [SMILES: CC(C)n1cnc2cc(-c3ccc4c(c3)N([C@H]3C[C@@H](N5CC[C@@H](F)C5)C3)C(=O)C4(C)C)nc(Cl)c21]

(R)-3-Fluoropyrrolidine was used to prepare 6-(4-chloro-3-isopropyl-3H-imidazo[4,5-c]pyridin-6-yl)-1-((1S,3s)-3-((R)-3-fluoropyrrolidin-1-yl)cyclobutyl)-3,3-dimethylindolin-2-one

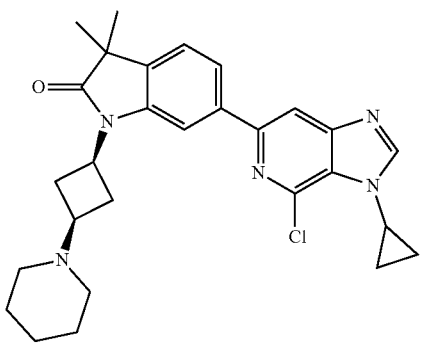 [SMILES: CC1(C)C(=O)N([C@H]2C[C@@H](N3CCCCC3)C2)c2cc(-c3cc4ncn(C5CC5)c4c(Cl)n3)ccc21]

Piperidine was used to prepare 6-(4-chloro-3-cyclopropyl-3H-imidazo[4,5-c]pyridin-6-yl)-3,3-dimethyl-1-((1s,3s)-3-(piperidin-1-yl)cyclobutyl)indolin-2-one Procedure 18: Preparation of the Compounds of Formula I According to Reaction Scheme II

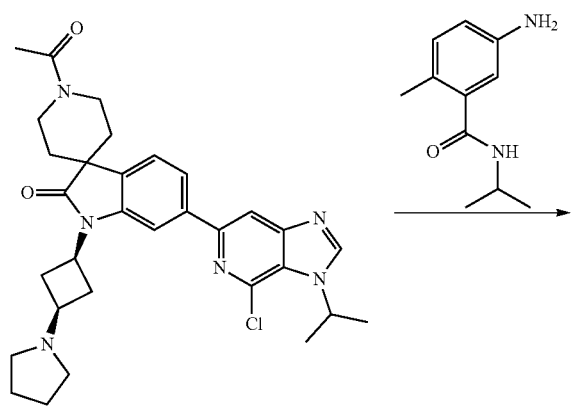

410

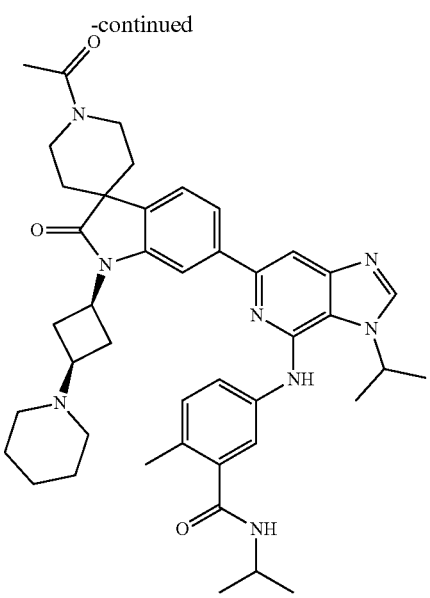

A. Preparation of 5-((6-(1'-acetyl-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-N-isopropyl-2-methylbenzamide (Example 83)

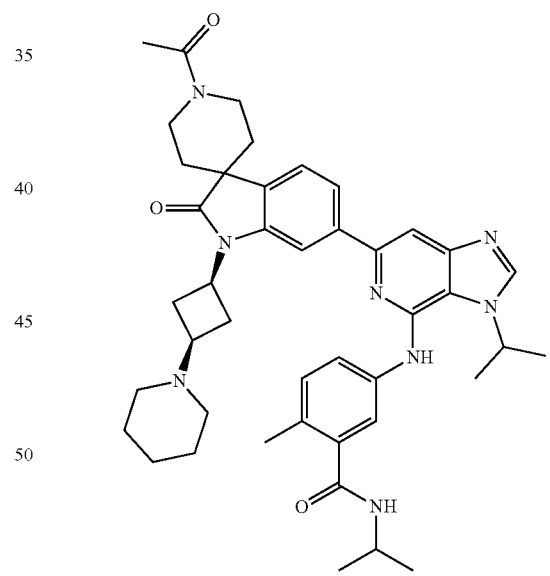

In a 40 mL microwave reaction vial were placed 1'-acetyl-6-(4-chloro-3-isopropyl-3H-imidazo[4,5-c]pyridin-6-yl)-1-((1s,3s)-3-(piperidin-1-yl)cyclobutyl)spiro[indoline-3,4'-piperidin]-2-one (880 mg, 1.53 mmol), 5-amino-N-isopropyl-2-methylbenzamide (588.33 mg, 3.06 mmol), $Pd_2(dba)_3$ (98.08 mg, 0.11 mmol), Xanthphos (110.25 mg, 0.21 mmol), and $Cs_2CO_3$ (1995.15 mg, 6.12 mmol) in Dioxane (6 ml). The mixture was sonicated and degassed for 15 sec, placed in the microwave reactor, and heated at 150° C. for 1 h. Then the mixture was purified by flash chromatography (100% DCM to 80% MeOH in DCM) followed by reverse phase chromatography to give 5-((6-(1'-acetyl-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-N-isopropyl-2-methylbenzamide.

The following compounds were prepared using a similar procedure with the following modification(s):
- the compounds listed under Procedure 14, 15, 16, 17, or 37 were used instead of 1'-acetyl-6-(4-chloro-3-isopropyl-3H-imidazo[4,5-c]pyridin-6-yl)-1-((1s,3s)-3-(piperidin-1-yl)cyclobutyl)spiro[indoline-3,4'-piperidin]-2-one; and/or
- the optionally substituted benzamides, that are commercially available, such as 5-amino-N,2-dimethylbenzamide, 5-amino-4-fluoro-N,2-dimethylbenzamide, 5-amino-2-chloro-N-methylbenzamide, and 5-amino-2-chloro-N-isopropylbenzamide, or can be made by methods known in the art, such as the compounds listed under Procedure 27 were used instead of 5-amino-N-isopropyl-2-methylbenzamide:

| Structure | Example # |
|-----------|-----------|
|           | 84 |
|           | 85 |
| 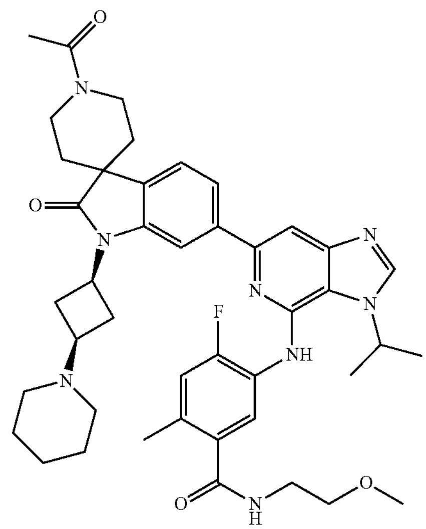 [SMILES: COCCNC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)c(F)cc1C]          | 86 |
| 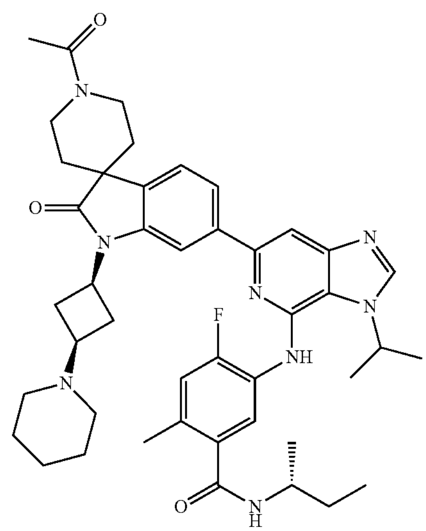 [SMILES: CC[C@@H](C)NC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)c(F)cc1C]          | 87 |
| 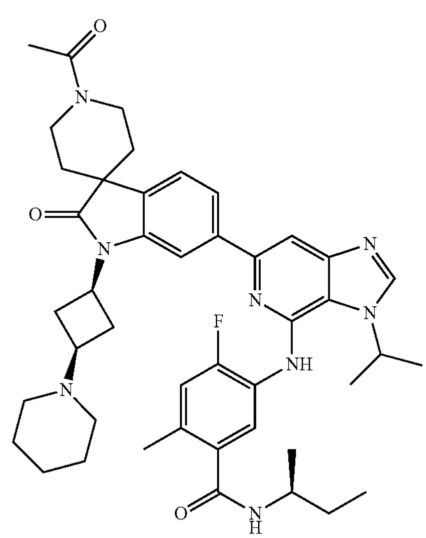 [SMILES: CC[C@H](C)NC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)c(F)cc1C]          | 88 |

| Structure | Example # |
|---|---|
| 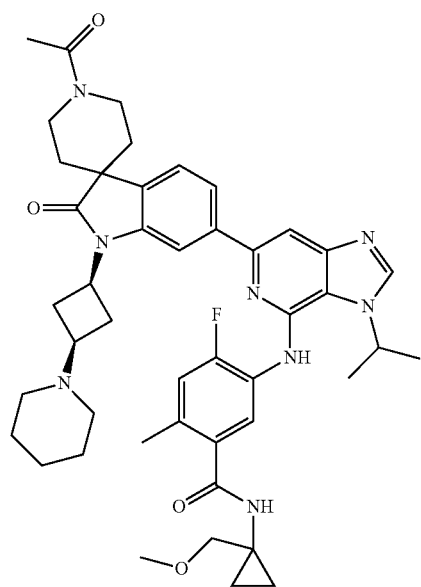 [SMILES: COCC1(NC(=O)c2cc(Nc3nc(-c4ccc5c(c4)N([C@H]4C[C@@H](N6CCCCC6)C4)C(=O)C54CCN(C(C)=O)CC4)cc4ncn(C(C)C)c34)c(F)cc2C)CC1] | 89 |
| | 90 |
| Structure | Example # |
|---|---|
| 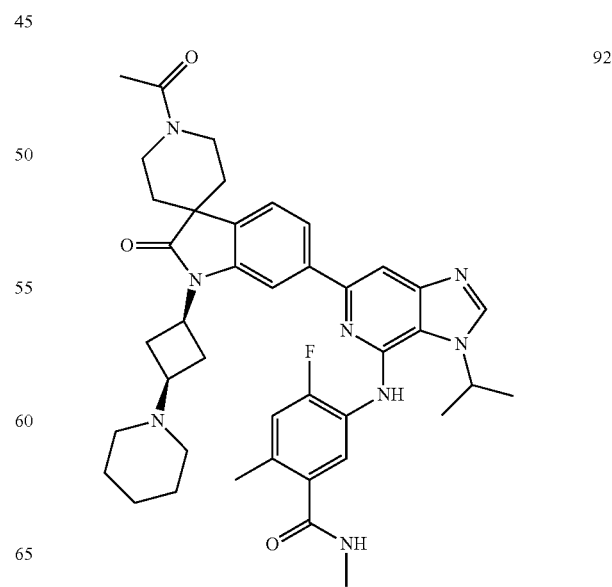 | 91 |
| | 92 |

| Structure | Example # |
|---|---|
| 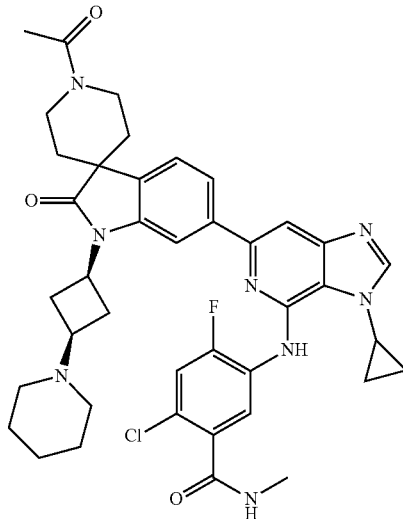 | 93 |
| 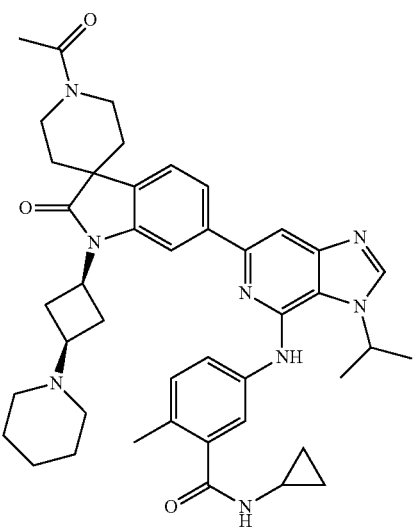 [SMILES: CC(=O)N1CCC2(CC1)C(=O)N([C@H]1C[C@@H](N3CCCCC3)C1)c1cc(-c3cc4ncn(C(C)C)c4c(Nc4ccc(C)c(C(=O)NC5CC5)c4)n3)ccc12] | 94 |
| 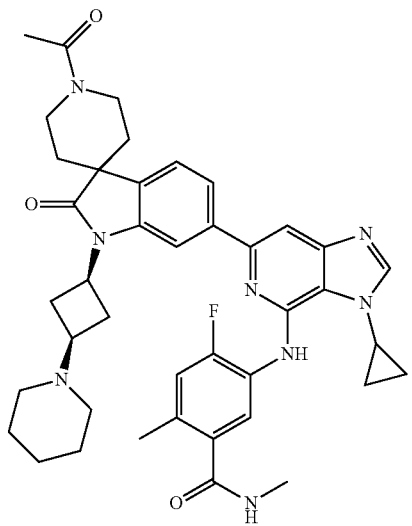 [SMILES: CNC(=O)c1cc(Nc2nc(-c3ccc4c(c3)N([C@H]3C[C@@H](N5CCCCC5)C3)C(=O)C43CCN(C(C)=O)CC3)cc3ncn(C4CC4)c23)c(F)cc1C] | 95 |
| Structure | Example # |
|---|---|
| 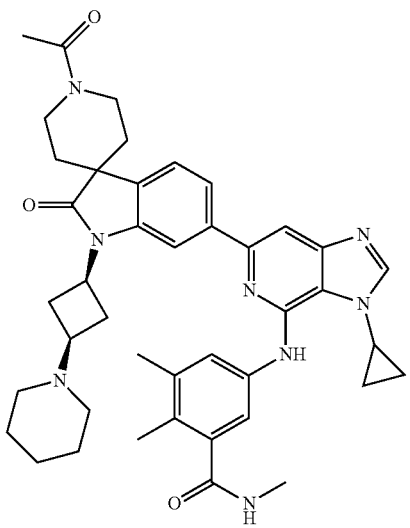 [SMILES: CNC(=O)c1cc(Nc2nc(-c3ccc4c(c3)N([C@H]3C[C@@H](N5CCCCC5)C3)C(=O)C43CCN(C(C)=O)CC3)cc3ncn(C4CC4)c23)cc(C)c1C] | 96 |
| 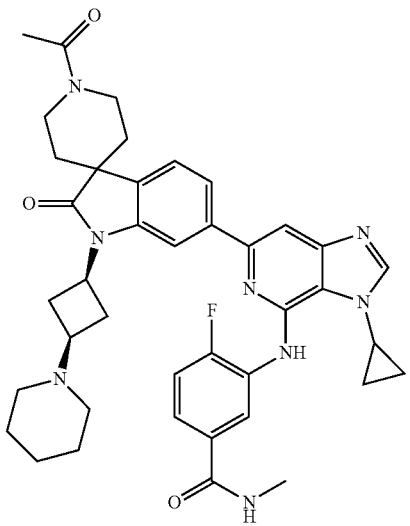 [SMILES: CNC(=O)c1ccc(F)c(Nc2nc(-c3ccc4c(c3)N([C@H]3C[C@@H](N5CCCCC5)C3)C(=O)C43CCN(C(C)=O)CC3)cc3ncn(C4CC4)c23)c1] | 97 |

| Structure | Example # |
|---|---|
| 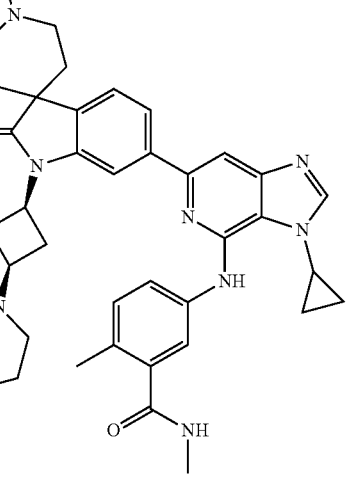 | 98 |
| 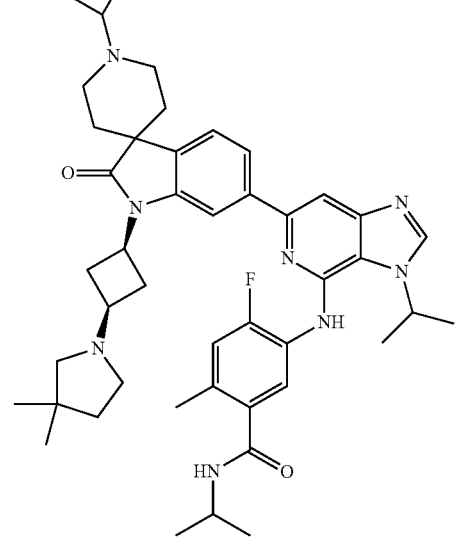 | 99 |
| Structure | Example # |
|---|---|
| 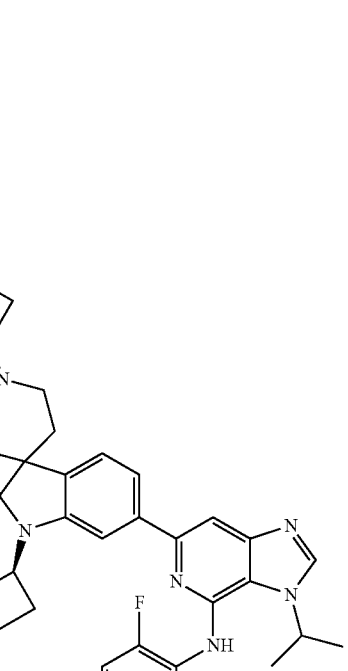 | 100 |
| | 101 |
| 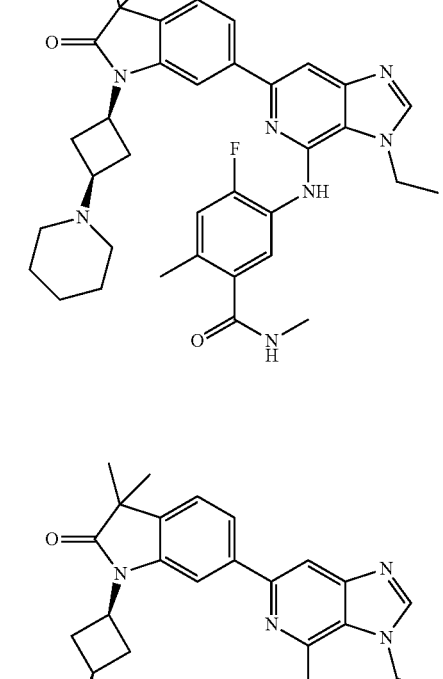 | 102 |

TABLE-continued
| Structure | Example # |
|---|---|
| 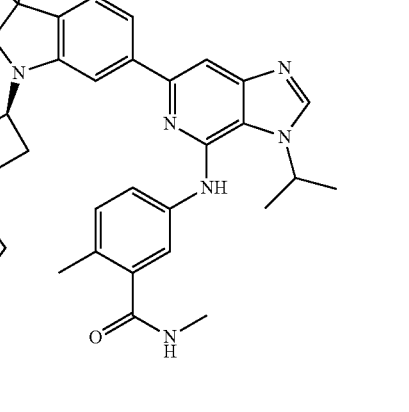 | 103 |
| 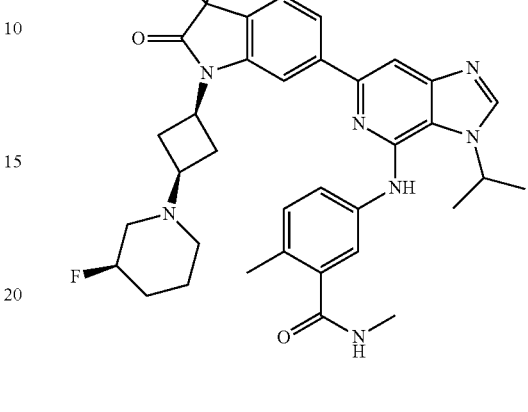 | 104 |
| 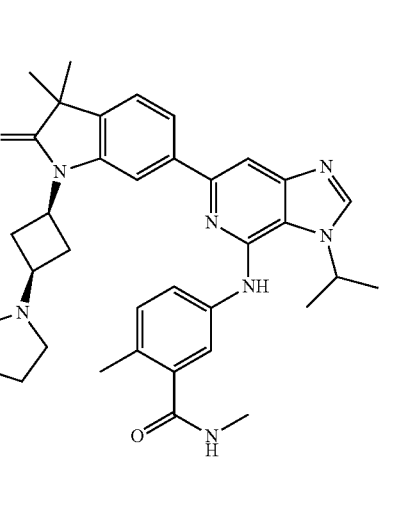 | 105 |
| 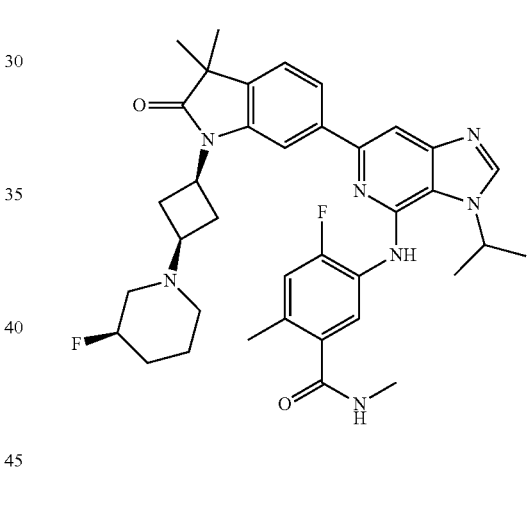 | 106 |
| 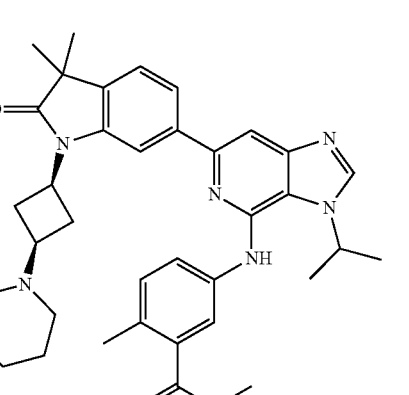 | 107 |
| 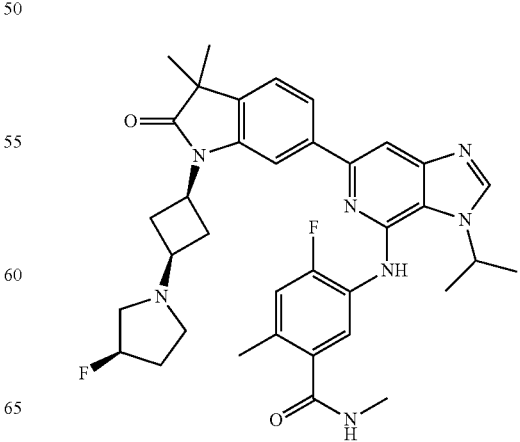 | 108 |

| Structure | Example # |
|---|---|
| 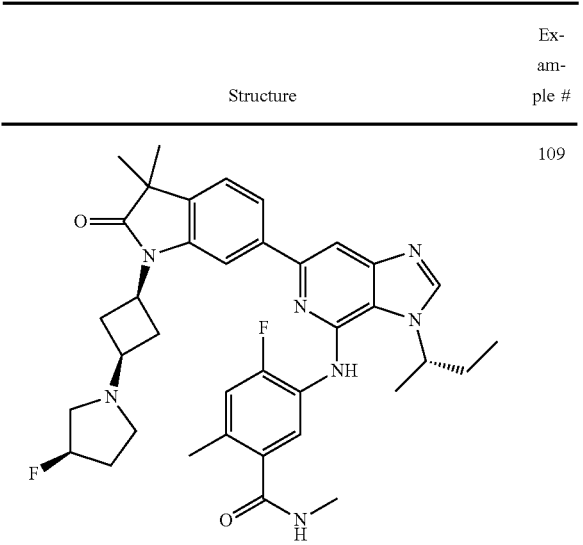 | 109 |
| | 110 |
| | 111 |
| Structure | Example # |
|---|---|
| 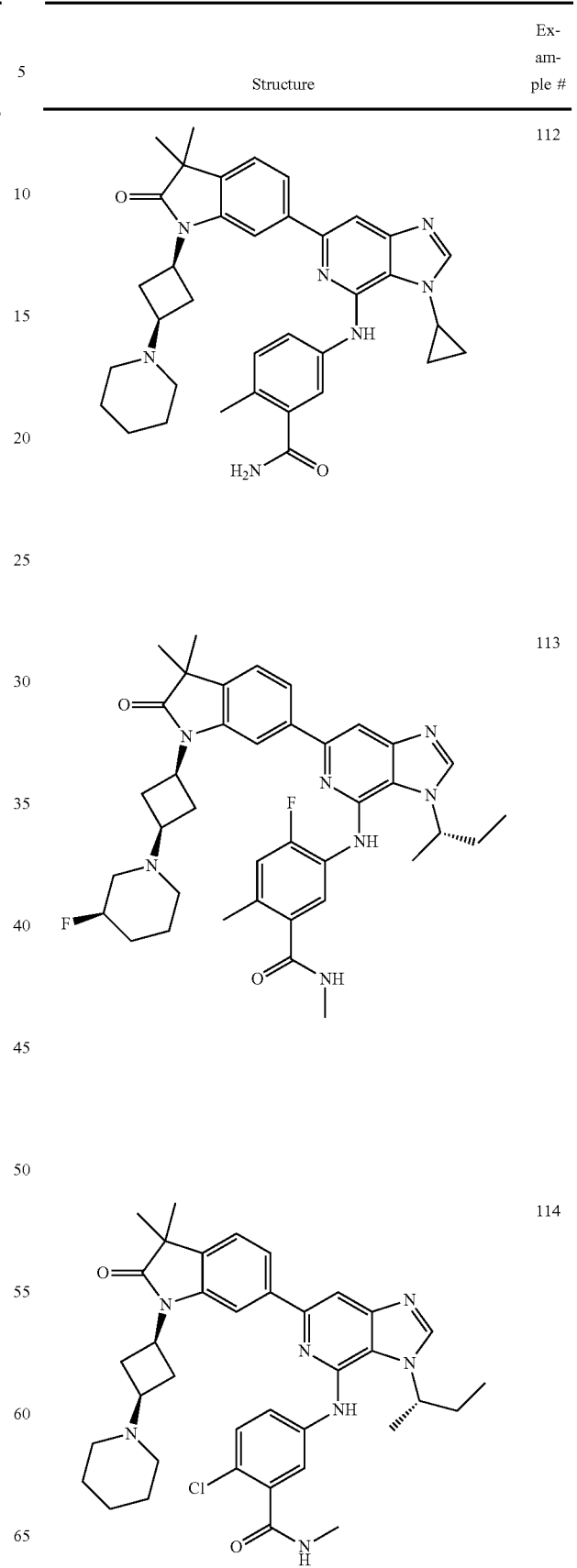 | 112 |
| | 113 |
| | 114 |

| Structure | Example # |
|-----------|-----------|
| 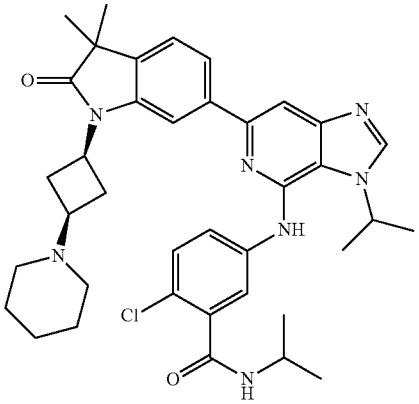 [SMILES: CC(C)NC(=O)c1cc(Nc2nc(-c3ccc4c(c3)N([C@H]3C[C@@H](N5CCCCC5)C3)C(=O)C4(C)C)cc3ncn(C(C)C)c23)ccc1Cl] | 115 |
| 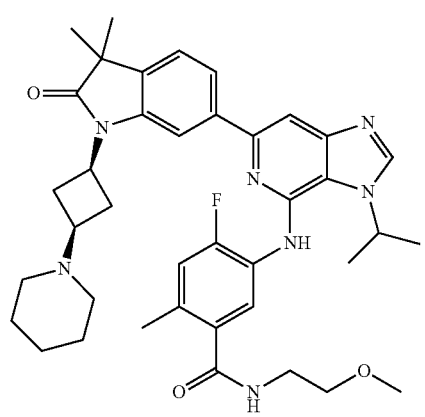 [SMILES: COCCNC(=O)c1cc(Nc2nc(-c3ccc4c(c3)N([C@H]3C[C@@H](N5CCCCC5)C3)C(=O)C4(C)C)cc3ncn(C(C)C)c23)c(F)cc1C] | 116 |
| 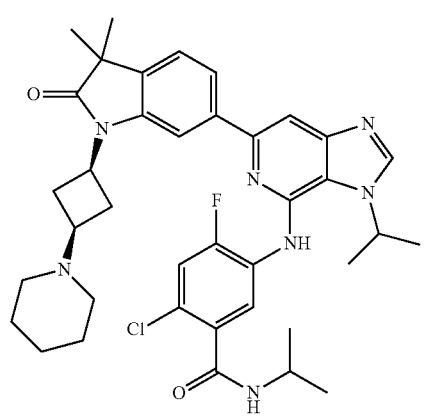 [SMILES: CC(C)NC(=O)c1cc(Nc2nc(-c3ccc4c(c3)N([C@H]3C[C@@H](N5CCCCC5)C3)C(=O)C4(C)C)cc3ncn(C(C)C)c23)c(F)cc1Cl] | 117 |
| Structure | Example # |
|-----------|-----------|
| 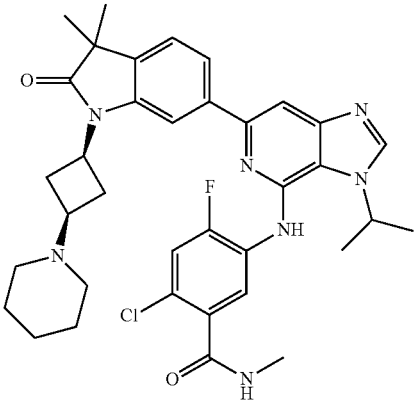 [SMILES: CNC(=O)c1cc(Nc2nc(-c3ccc4c(c3)N([C@H]3C[C@@H](N5CCCCC5)C3)C(=O)C4(C)C)cc3ncn(C(C)C)c23)c(F)cc1Cl] | 118 |
| 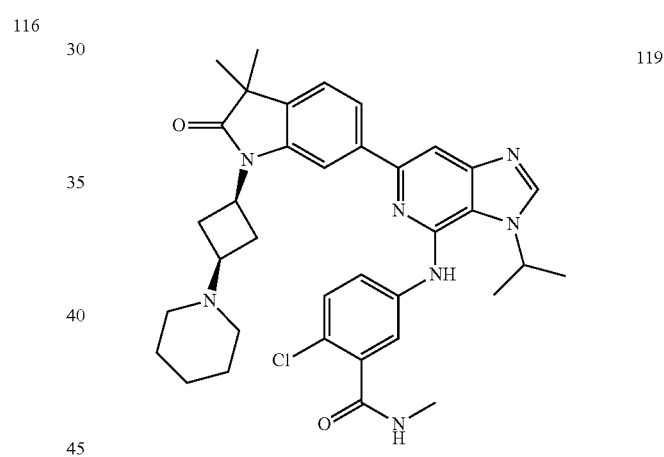 | 119 |
| 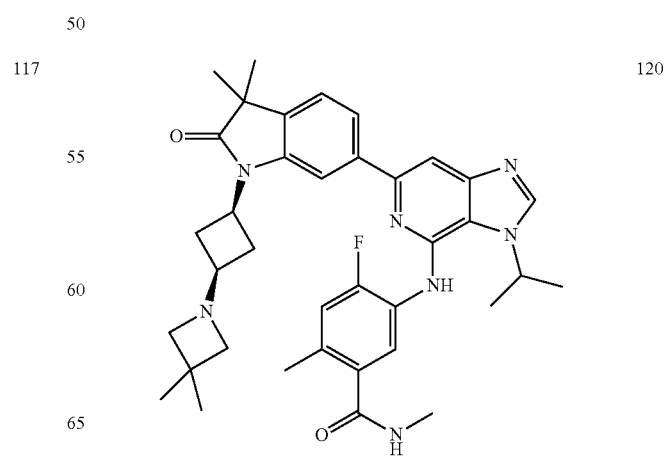 | 120 |

| Structure | Example # |
|---|---|
| 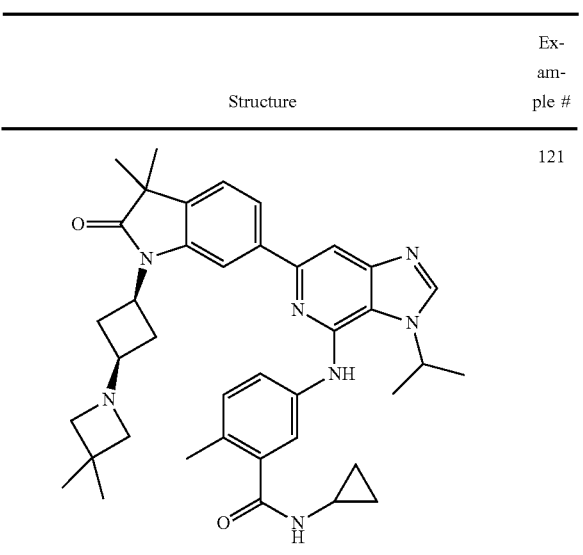 | 121 |
| 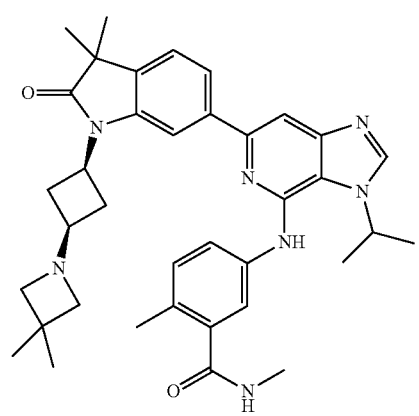 [SMILES: CNC(=O)c1cc(Nc2nc(-c3ccc4c(c3)N([C@H]3C[C@@H](N5CC(C)(C)C5)C3)C(=O)C4(C)C)cc3ncn(C(C)C)c23)ccc1C] | 122 |
| 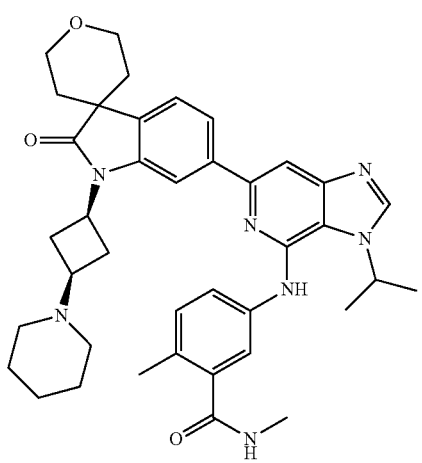 [SMILES: CNC(=O)c1cc(Nc2nc(-c3ccc4c(c3)N([C@H]3C[C@@H](N5CCCCC5)C3)C(=O)C43CCOCC3)cc3ncn(C(C)C)c23)ccc1C] | 123 |
| Structure | Example # |
|---|---|
| 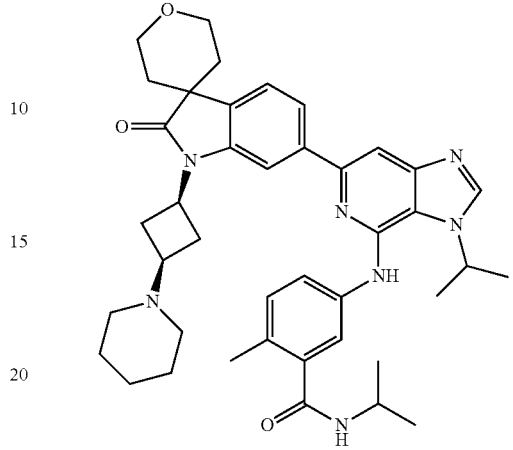 | 124 |
| 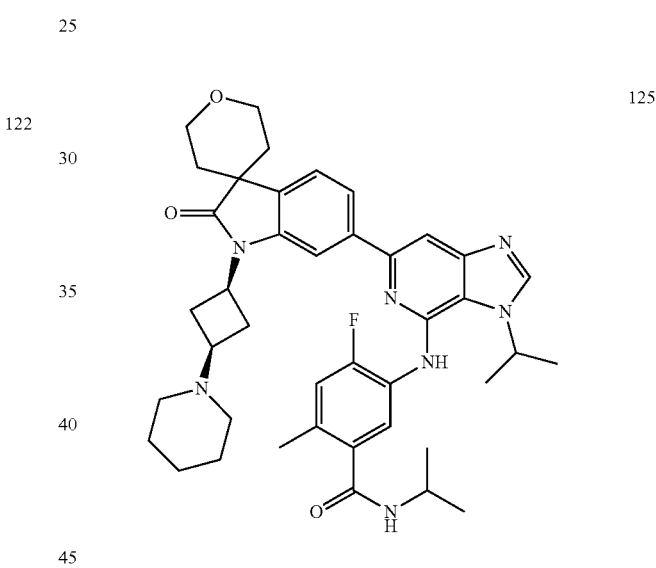 | 125 |
| 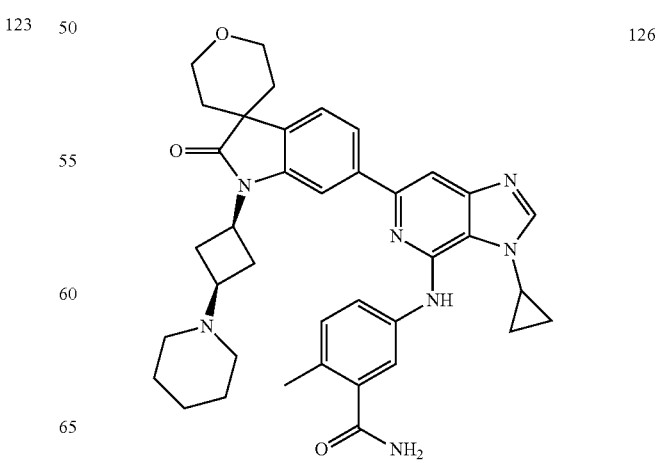 | 126 |

| Structure | Example # |
|---|---|
| 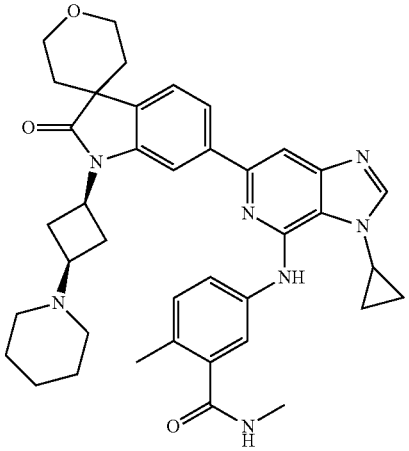 [SMILES: CNC(=O)c1cc(Nc2nc(-c3ccc4c(c3)N([C@H]3C[C@@H](N5CCCCC5)C3)C(=O)C43CCOCC3)cc3ncn(C4CC4)c23)ccc1C] | 127 |
| 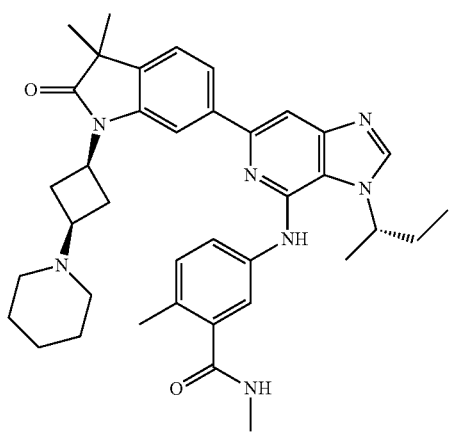 [SMILES: CC[C@H](C)n1cnc2cc(-c3ccc4c(c3)N([C@H]3C[C@@H](N5CCCCC5)C3)C(=O)C4(C)C)nc(Nc3ccc(C)c(C(=O)NC)c3)c21] | 128 |
| 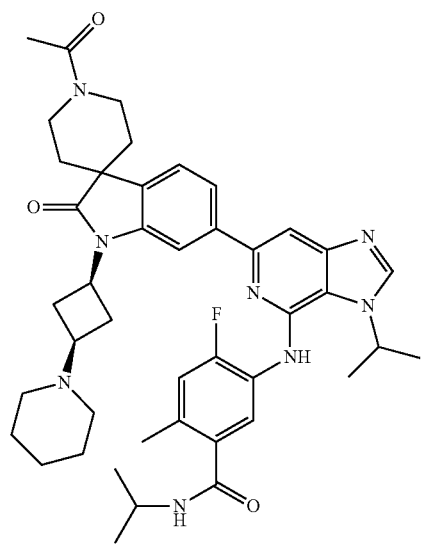 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)NC(C)C)c(C)cc4F)n3)ccc12] | 129 |
| 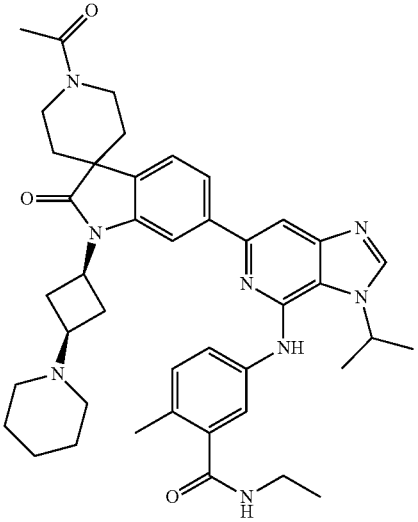 [SMILES: CCNC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)ccc1C] | 130 |
| 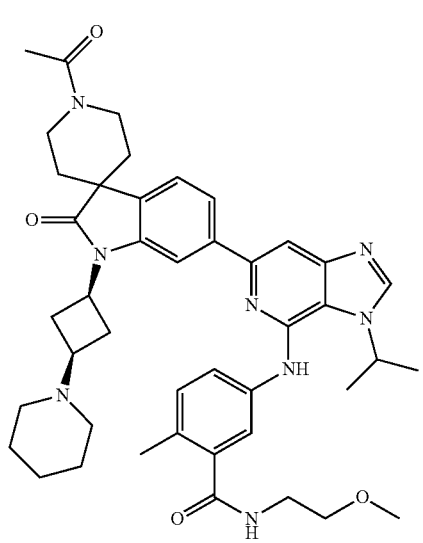 [SMILES: COCCNC(=O)c1cc(Nc2nc(-c3ccc4c(c3)N([C@H]3C[C@@H](N5CCCCC5)C3)C(=O)C43CCN(C(C)=O)CC3)cc3ncn(C(C)C)c23)ccc1C] | 131 |
| 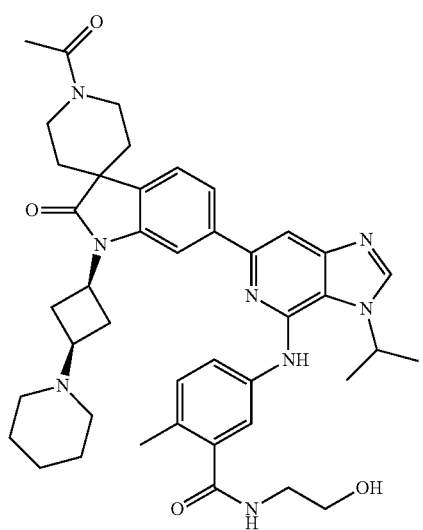 [SMILES: CC(=O)N1CCC2(CC1)C(=O)N([C@H]1C[C@@H](N3CCCCC3)C1)c1cc(-c3cc4ncn(C(C)C)c4c(Nc4ccc(C)c(C(=O)NCCO)c4)n3)ccc12] | 132 |

-continued

| Structure | Example # |
|---|---|
| (structure 133) | 133 |
| (structure 134) | 134 |

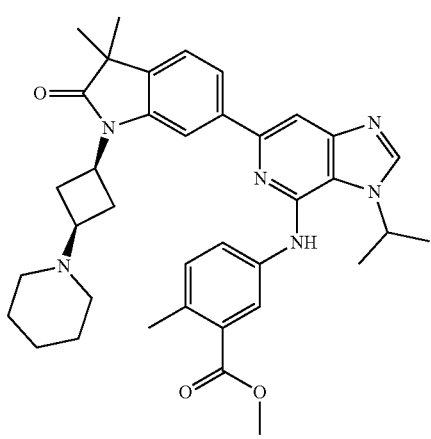 [SMILES: COC(=O)c1cc(Nc2nc(-c3ccc4c(c3)N([C@H]3C[C@@H](N5CCCCC5)C3)C(=O)C4(C)C)cc3ncn(C(C)C)c23)ccc1C]

Methyl 5-amino-2-methylbenzoate and 6-(4-chloro-3-isopropyl-3H-imidazo[4,5-c]pyridin-6-yl)-3,3-dimethyl-1-((1s,3s)-3-(piperidin-1-yl)cyclobutyl)indolin-2-one were used instead of 5-amino-N-isopropyl-2-methylbenzamide and 1'-acetyl-6-(4-chloro-3-isopropyl-3H-imidazo[4,5-c]pyridin-6-yl)-1-((1s,3s)-3-(piperidin-1-yl)cyclobutyl) spiro[indoline-3,4'-piperidin]-2-one, respectively, to prepare methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoate B. Preparation of tert-butyl 6-(3-isopropyl-4-((4-methyl-3-(methylcarbamoyl)phenyl)amino)-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate

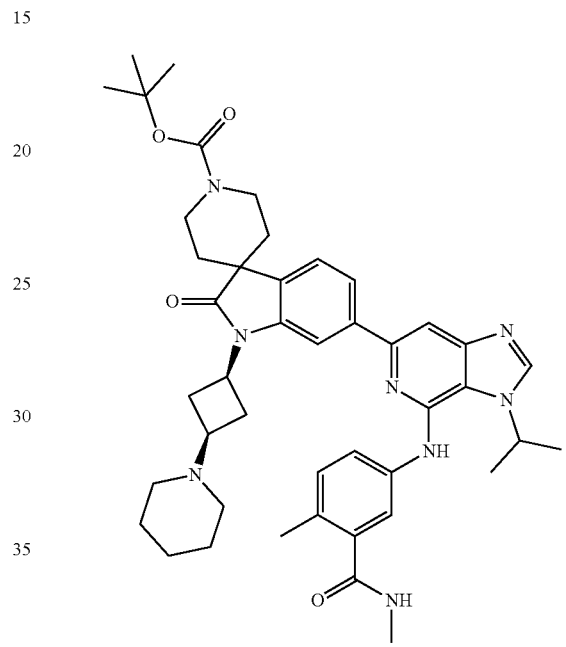

To a solution of tert-butyl 6-(4-chloro-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate (0.7 g, 1.1 mmol) in dioxane (9 ml) were added 5-amino-N,2-dimethylbenzamide (0.91 g, 5.5 mmol), $Pd_2(dba)_3$ (0.11 g, 0.11 mmol), Xanthphos (0.13 g, 0.22 mmol), and $Cs_2CO_3$ (1.8 g, 5.5 mmol). The resulting mixture was degassed by bubbling nitrogen gas through for a few minutes and then the reaction vessel was sealed. After heating for 30 minutes at 150° C. in the microwave, the reaction mixture was filtered, concentrated, and purified by silica chromatography (100% DCM to 50% MeOH in DCM) to give tert-butyl 6-(3-isopropyl-4-((4-methyl-3-(methylcarbamoyl)phenyl)amino)-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate.

The following compounds were prepared using a similar procedure except the compounds listed under Procedure 14 were used instead of tert-butyl 6-(4-chloro-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate:

| 431 | 432 |
|---|---|
| 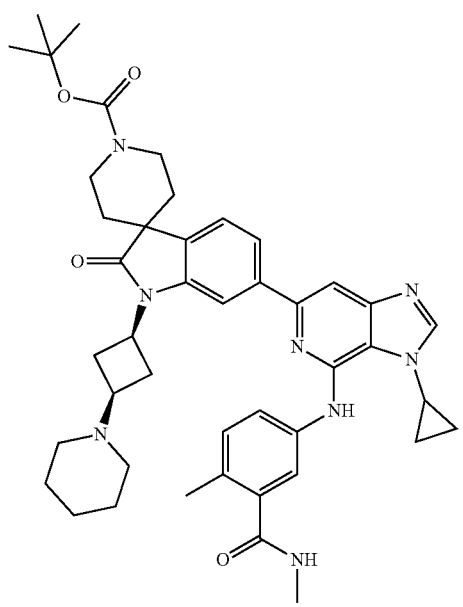 [SMILES: CNC(=O)c1cc(Nc2nc(-c3ccc4c(c3)N([C@H]3C[C@@H](N5CCCCC5)C3)C(=O)C43CCN(C(=O)OC(C)(C)C)CC3)cc3ncn(C4CC4)c23)ccc1C] | 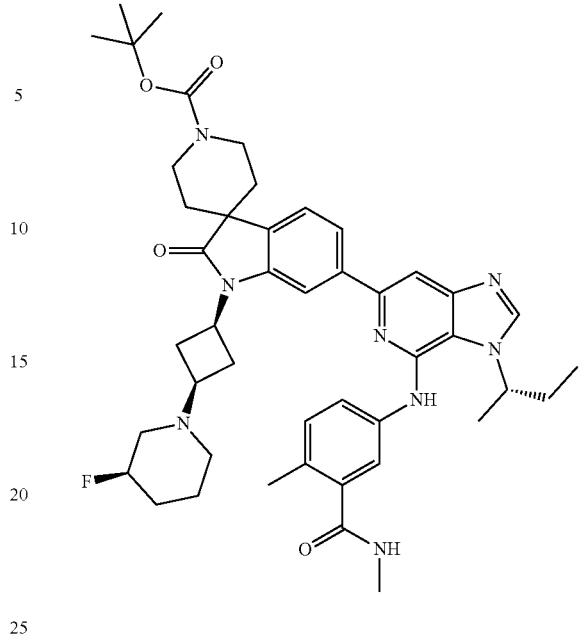 |
| tert-butyl 6-(3-cyclopropyl-4-((4-methyl-3-(methylcarbamoyl)phenyl)amino)-3H-imidazo[4,5-c]pyridin-6-yl)-2-oxo-1-((1s,3s)-3-(piperidin-1-yl)cyclobutyl)spiro[indoline-3,4'-piperidine]-1'-carboxylate | tert-butyl 6-(3-((S)-sec-butyl)-4-((4-methyl-3-(methylcarbamoyl)phenyl)amino)-3H-imidazo[4,5-c]pyridin-6-yl)-1-((1S,3R)-3-((R)-3-fluoropiperidin-1-yl)cyclobutyl)-2-oxospiro[indoline-3,4'-piperidine]-1'-carboxylate |
| 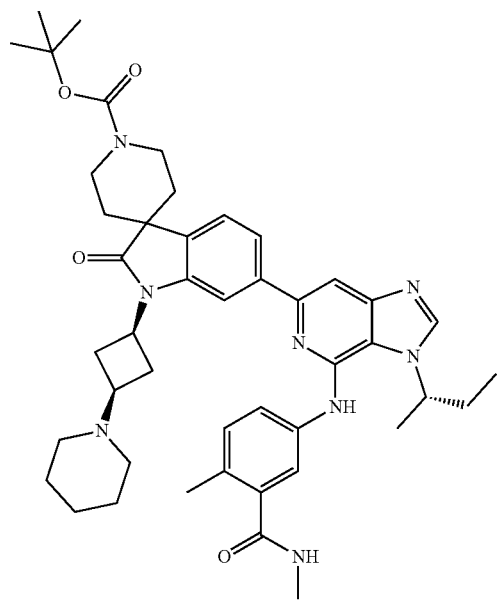 [SMILES: CC[C@H](C)n1cnc2cc(-c3ccc4c(c3)N([C@H]3C[C@@H](N5CCCCC5)C3)C(=O)C43CCN(C(=O)OC(C)(C)C)CC3)nc(Nc3ccc(C)c(C(=O)NC)c3)c21] | 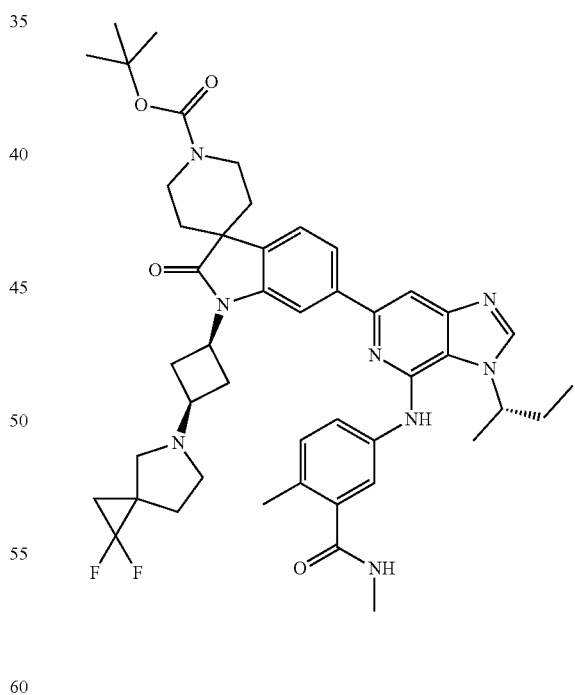 |
| tert-butyl 6-(3-((S)-sec-butyl)-4-((4-methyl-3-(methylcarbamoyl)phenyl)amino)-3H-imidazo[4,5-c]pyridin-6-yl)-2-oxo-1-((1s,3R)-3-(piperidin-1-yl)cyclobutyl)spiro[indoline-3,4'-piperidine]-1'-carboxylate | tert-butyl 6-(3-((S)-sec-butyl)-4-((4-methyl-3-(methylcarbamoyl)phenyl)amino)-3H-imidazo[4,5-c]pyridin-6-yl)-1-((1s,3R)-3-(1,1-difluoro-5-azaspiro[2.4]heptan-5-yl)cyclobutyl)-2-oxospiro[indoline-3,4'-piperidine]-1'-carboxylate |

C. Preparation of 5-((6-(3,3-dimethyl-2-oxo-1-((1s,3s)-3-pivalamidocyclobutyl)indolin-6-yl)-3-isopropyl-3H-imidazo[4,5-c]pyridin-4-yl)amino)-2-methylbenzamide (Example 135)

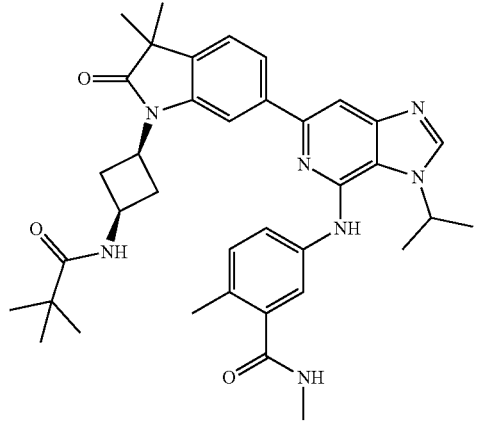 [SMILES: CNC(=O)c1cc(Nc2nc(-c3ccc4c(c3)N([C@H]3C[C@@H](NC(=O)C(C)(C)C)C3)C(=O)C4(C)C)cc3ncn(C(C)C)c23)ccc1C]

In a microwave vial were placed N-((1s,3s)-3-(6-(4-chloro-3-isopropyl-3H-imidazo[4,5-c]pyridin-6-yl)-3,3-dimethyl-2-oxoindolin-1-yl)cyclobutyl)pivalamide (83 mg, 0.5 mmol), 5-amino-N,2-dimethylbenzamide (103 mg, 0.2 mmol), RuPhos Pd G1 Methyl t-Butyl Ether Adduct (10 mg, 0.01 mmol), and Cs$_2$CO$_3$ (130 mg, 0.41 mmol) in dioxane (2 mL). The mixture was degassed with nitrogen, placed in the microwave reactor, and heated at 150° C. for 1 h. Then it was purified by flash chromatography (100% EtOAc to 60% MeOH in EtOAc) to give 5-((6-(3,3-dimethyl-2-oxo-1-((1s,3s)-3-pivalamidocyclobutyl)indolin-6-yl)-3-isopropyl-3H-imidazo[4,5-c]pyridin-4-yl)amino)-2-methylbenzamide.

Procedure 19: Preparation of the Compounds of Formula (16) According to Reaction Scheme III

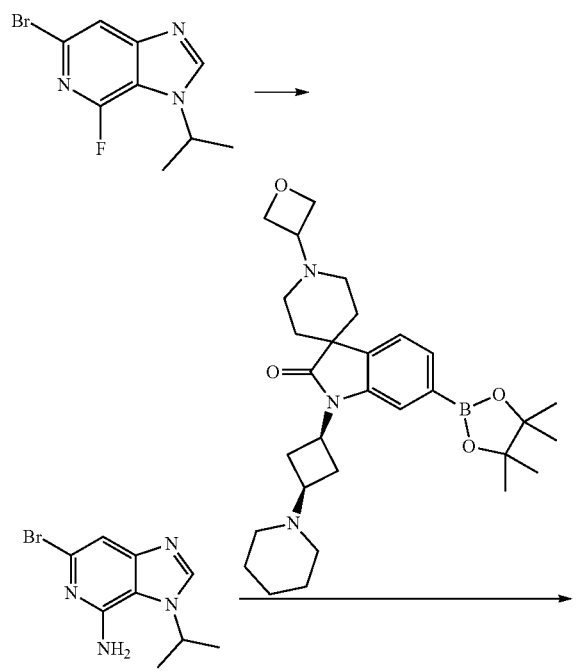

A. Preparation of 6-bromo-3-isopropyl-3H-imidazo[4,5-c]pyridin-4-amine

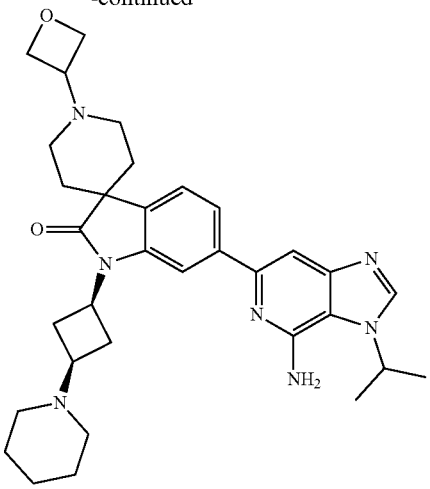

A 500 mL pressure vessel equipped with a magnetic stir bar was charged with 6-bromo-4-fluoro-3-isopropyl-3H-imidazo[4,5-c]pyridine (10.0 g, 38.8 mmol) followed by N-methylpyrrolidone (100 mL). The resulting solution was treated with ammonium hydroxide solution (28% NH$_3$, 54 mL, 390.0 mmol). The vessel was sealed, and the mixture stirred at 80° C. in a heating block for 48 h. The reaction mixture was then cooled to room temperature and carefully poured into water (900 mL). The mixture was further cooled in an ice bath with stirring, and then the mixture was filtered to afford 6-bromo-3-isopropyl-3H-imidazo[4,5-c]pyridin-4-amine.

B. Preparation of 6-(4-amino-3-isopropyl-3H-imidazo[4,5-c]pyridin-6-yl)-1'-(oxetan-3-yl)-1-((1s,3s)-3-(piperidin-1-yl)cyclobutyl)spiro[indoline-3,4'-piperidin]-2-one

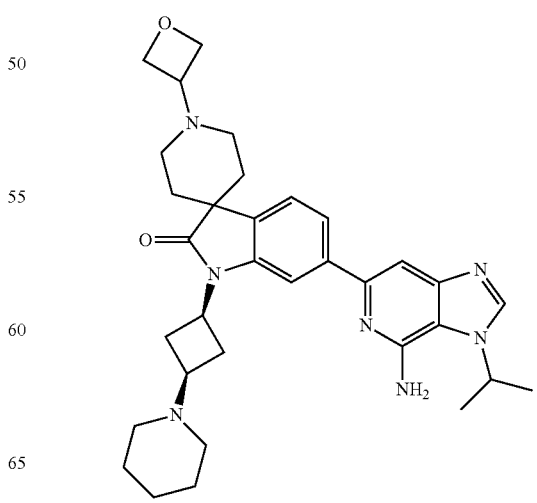

A suspension of 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one (736 mg, 1.41 mmol), 6-bromo-3-isopropyl-3H-imidazo[4,5-c]pyridin-4-amine (300 mg, 1.18 mmol), and tetrakis(triphenylphosphine)palladium (136 mg, 118 umol) in 1:1 DMF/DME (12 mL) was treated with 2 M aqueous $Na_2CO_3$ (4.1 mL, 8.2 mmol). The mixture was sparged with $N_2$ for 1 min, then sealed and stirred vigorously at 120° C. overnight. The reaction mixture was cooled to room temperature, diluted with water, and extracted three times with EtOAc. The combined organic layers were concentrated under vacuum and purified via flash chromatography on silica gel with gradient elution (0-100% EtOAc/hexanes followed by 0-100% MeOH/DCM) to afford 6-(4-amino-3-isopropyl-3H-imidazo[4,5-c]pyridin-6-yl)-1'-(oxetan-3-yl)-1-((1s,3s)-3-(piperidin-1-yl)cyclobutyl)spiro[indoline-3,4'-piperidin]-2-one.

The following compounds were prepared using a similar procedure except the compounds listed under Procedure 6, 7, 8, 9, 12, or 35 were used instead of 1'-(oxetan-3-yl)-1-((1s,3s)-3-(piperidin-1-yl)cyclobutyl)-6-(4,4,5,5-tetramethyl-1,3,2-dioxaborolan-2-yl)spiro[indoline-3,4'-piperidin]-2-one:

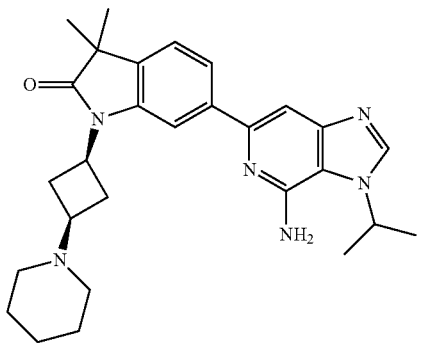 [SMILES: CC(C)n1cnc2cc(-c3ccc4c(c3)N([C@H]3C[C@@H](N5CCCCC5)C3)C(=O)C4(C)C)nc(N)c21]

6-(4-amino-3-isopropyl-3H-imidazo[4,5-c]pyridin-6-yl)-3,3-dimethyl-1-((1s,3s)-3-(piperidin-1-yl)cyclobutyl)indolin-2-one

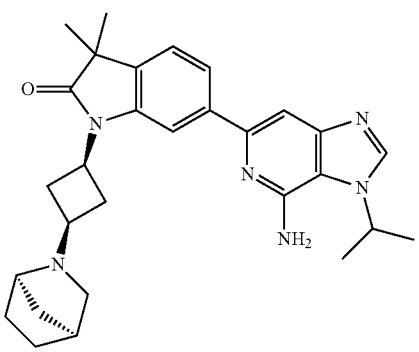 [SMILES: CC(C)n1cnc2cc(-c3ccc4c(c3)N([C@H]3C[C@@H](N5C[C@H]6CC[C@@H]5C6)C3)C(=O)C4(C)C)nc(N)c21]

1-((1S,3s)-3-((1R,4S)-2-Azabicyclo[2.2.1]heptan-2-yl)cyclobutyl)-6-(4-amino-3-isopropyl-3H-imidazo[4,5-c]pyridin-6-yl)-3,3-dimethylindolin-2-one

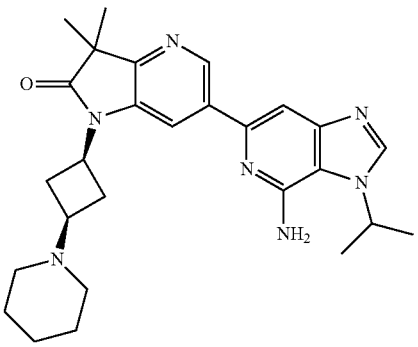 [SMILES: CC(C)n1cnc2cc(-c3cnc4c(c3)N([C@H]3C[C@@H](N5CCCCC5)C3)C(=O)C4(C)C)nc(N)c21]

6-(4-amino-3-isopropyl-3H-imidazo[4,5-c]pyridin-6-yl)-3,3-dimethyl-1-((1s,3s)-3-(piperidin-1-yl)cyclobutyl)-1,3-dihydro-2H-pyrrolo[3,2-b]pyridin-2-one

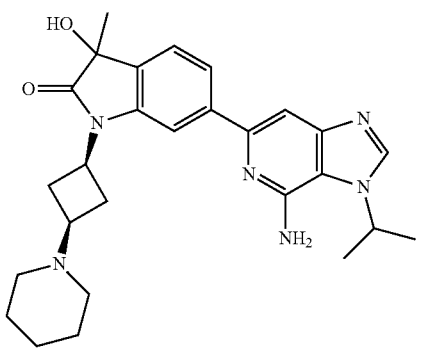 [SMILES: CC(C)n1cnc2cc(-c3ccc4c(c3)N([C@H]3C[C@@H](N5CCCCC5)C3)C(=O)C4(C)O)nc(N)c21]

6-(4-amino-3-isopropyl-3H-imidazo[4,5-c]pyridin-6-yl)-3-hydroxy-3-methyl-1-((1s,3s)-3-(piperidin-1-yl)cyclobutyl)indolin-2-one

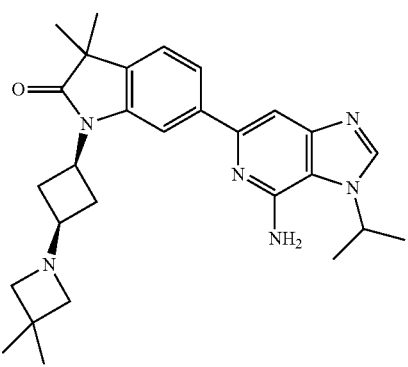 [SMILES: CC(C)n1cnc2cc(-c3ccc4c(c3)N([C@H]3C[C@@H](N5CC(C)(C)C5)C3)C(=O)C4(C)C)nc(N)c21]

6-(4-amino-3-isopropyl-3H-imidazo[4,5-c]pyridin-6-yl)-1-((1s,3s)-3-(3,3-dimethylazetidin-1-yl)cyclobutyl)-3,3-dimethylindolin-2-one

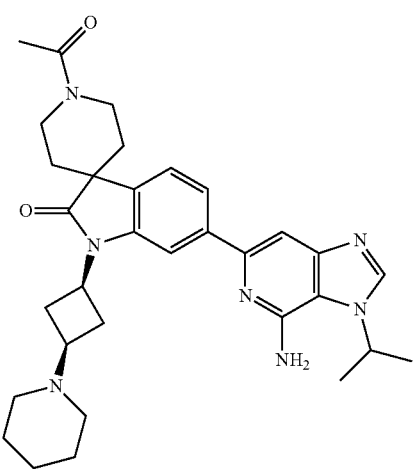 [SMILES: CC(=O)N1CCC2(CC1)C(=O)N([C@H]1C[C@@H](N3CCCCC3)C1)c1cc(-c3cc4ncn(C(C)C)c4c(N)n3)ccc12]

1'-acetyl-6-(4-amino-3-isopropyl-3H-imidazo[4,5-c]pyridin-6-yl)-1-((1s,3s)-3-(piperidin-1-yl)cyclobutyl)spiro[indoline-3,4'-piperidin]-2-one

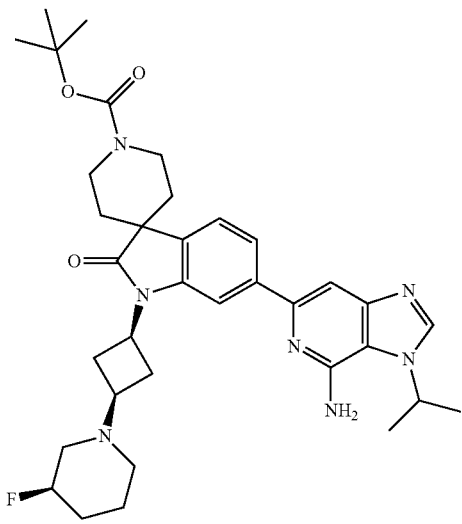 [SMILES: CC(C)n1cnc2cc(-c3ccc4c(c3)N([C@H]3C[C@@H](N5CCC[C@@H](F)C5)C3)C(=O)C43CCN(C(=O)OC(C)(C)C)CC3)nc(N)c21]

tert-butyl 6-(4-amino-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate C. Preparation of 6-(4-amino-3-isopropyl-3H-imidazo[4,5-c]pyridin-6-yl)-1'-((R)-2-hydroxypropanoyl)-1-((1s,3S)-3-(piperidin-1-yl)cyclobutyl)spiro[indoline-3,4'-piperidin]-2-one

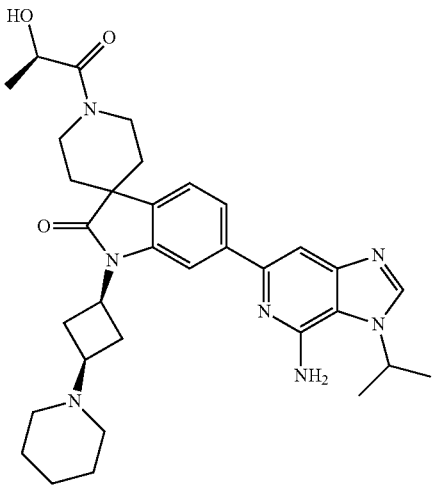 [SMILES: CC(C)n1cnc2cc(-c3ccc4c(c3)N([C@H]3C[C@@H](N5CCCCC5)C3)C(=O)C43CCN(C(=O)[C@@H](C)O)CC3)nc(N)c21]

In a microwave vial were placed 1'-((R)-2-hydroxypropanoyl)-1-((1s,3S)-3-(piperidin-1-yl)cyclobutyl)-6-(4,4,5,5-tetramethyl-1,3,2-dioxaborolan-2-yl)spiro[indoline-3,4'-piperidin]-2-one (130 mg, 0.242 mmol), 6-bromo-3-isopropyl-3H-imidazo[4,5-c]pyridin-4-amine (62 mg, 0.242 mmol), palladium tetrakis (28 mg, 0.024 mmol), and cesium carbonate (154 mg, 0.726 mmol) in DMAc (2 mL) and water (0.4 mL). The mixture was degassed with N₂, sealed, and heated to 90° C. for 2 h., partitioned between EtOAc and water, and then extracted with EtOAc. The combined organic layers were dried over MgSO₄, filtered, concentrated in vacuo, and purified by flash chromatography (DCM/MeOH/NEt₃) to give 6-(4-amino-3-isopropyl-3H-imidazo[4,5-c]pyridin-6-yl)-1'-((R)-2-hydroxypropanoyl)-1-((1s,3S)-3-(piperidin-1-yl)cyclobutyl)spiro[indoline-3,4'-piperidin]-2-one.

Procedure 20: Preparation of the Compounds of Formula I According to Reaction Scheme III

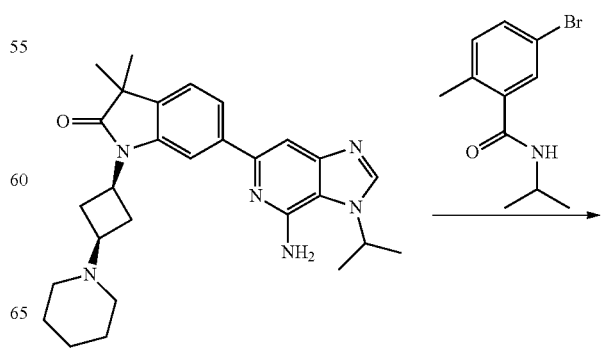

-continued

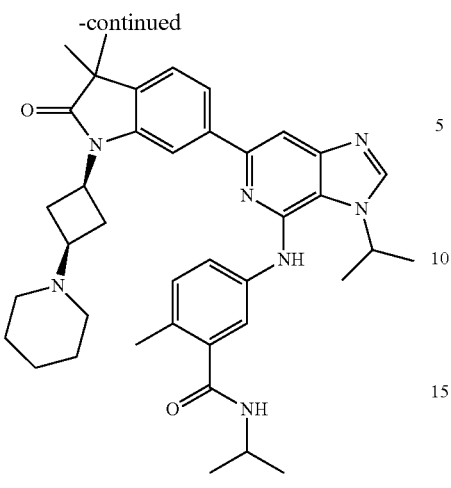

A. Preparation of 5-((6-(3,3-dimethyl-2-oxo-1-((1s, 3s)-3-(piperidin-1-yl)cyclobutyl)indolin-6-yl)-3-isopropyl-3H-imidazo[4,5-c]pyridin-4-yl)amino)-N-isopropyl-2-methylbenzamide (Example 136)

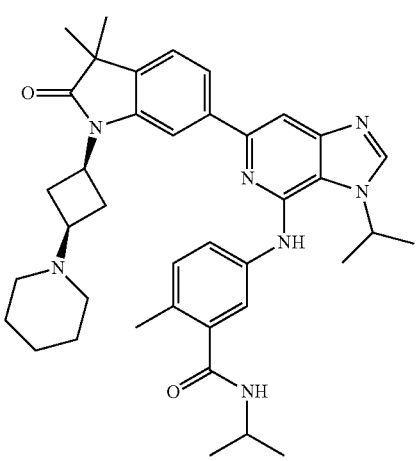 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC(C)C]

To a mixture of 5-bromo-N-isopropyl-2-methylbenzamide (44 mg, 0.171 mmol), 6-(4-amino-3-isopropyl-3H-imidazo[4,5-c]pyridin-6-yl)-3,3-dimethyl-1-((1s,3s)-3-(piperidin-1-yl)cyclobutyl)indolin-2-one (80 mg, 0.114 mmol), $Pd_2(dba)_3$ (11 mg, 0.011 mmol), Xantphos (13 mg, 0.023 mmol) and $Cs_2CO_3$ (186 mg, 0.571 mmol) was added freshly degassed dioxane. The reaction mixture was heated to 90° C. and stirred overnight. The reaction was subsequently diluted with water and extracted with EtOAc. The combined organic layers were dried over $MgSO_4$, filtered, concentrated, and purified by silica chromatography (0-80% MeOH/DCM with 0.5% $NEt_3$) and HPLC (0-75% ACN/ $H_2O$) to give 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-N-isopropyl-2-methylbenzamide.

The following compounds were prepared using a similar procedure with the following modification(s):
  the compounds listed under Procedure 19 were used instead of 6-(4-amino-3-isopropyl-3H-imidazo[4,5-c]pyridin-6-yl)-3,3-dimethyl-1-((1s,3s)-3-(piperidin-1-yl)cyclobutyl)indolin-2-one; and/or
  the benzamides listed under Procedure 28, were used instead of 5-bromo-N-isopropyl-2-methylbenzamide:

| Structure | Example # |
|---|---|
| 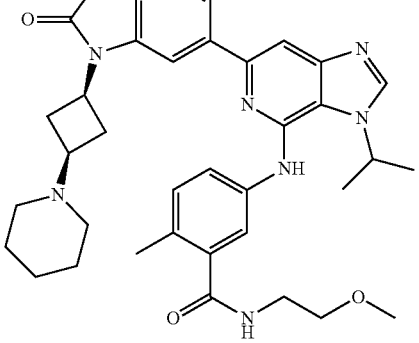 | 137 |
| 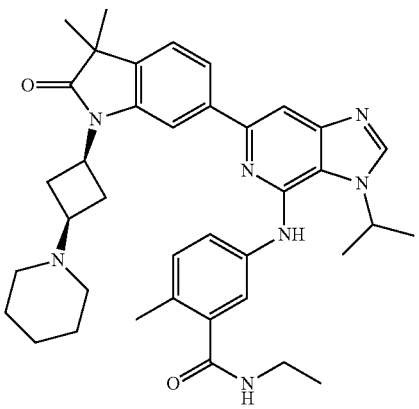 [SMILES: CCNC(=O)c1cc(Nc2nc(-c3ccc4c(c3)N([C@H]3C[C@@H](N5CCCCC5)C3)C(=O)C4(C)C)cc3ncn(C(C)C)c23)ccc1C] | 138 |
| 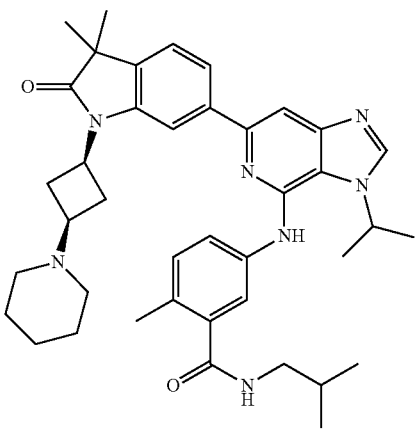 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NCC(C)C] | 139 |

| Structure | Example # |
|---|---|
| 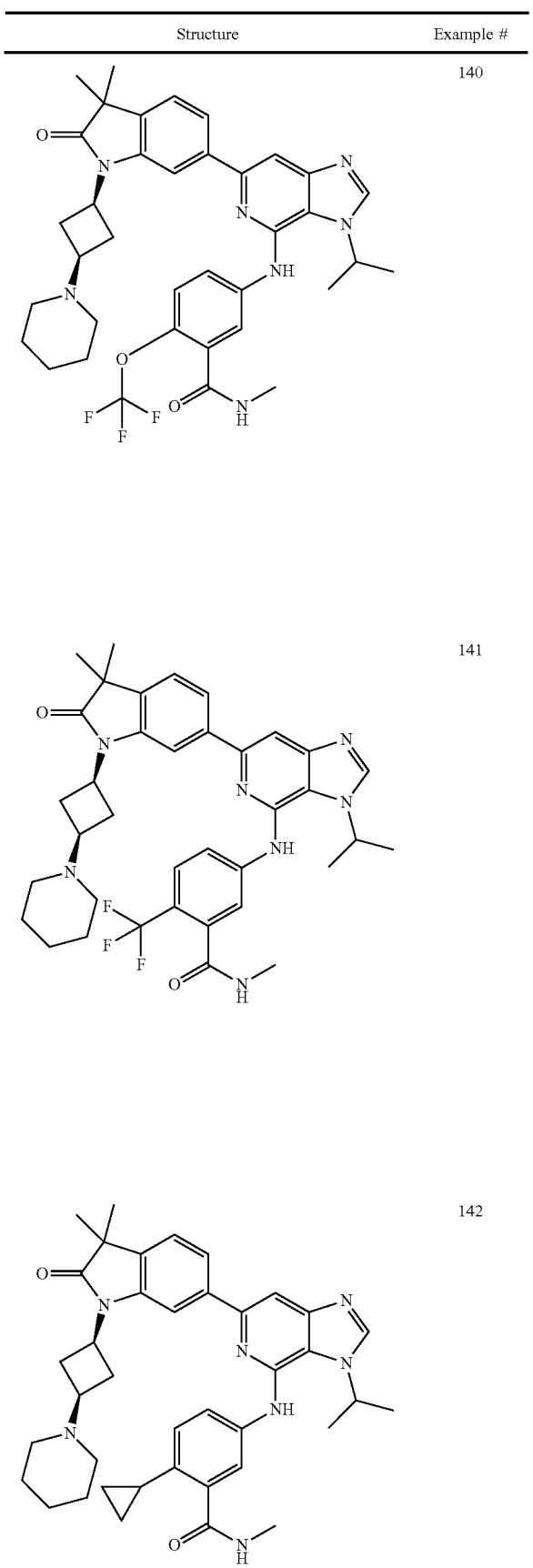 | 140 |
| 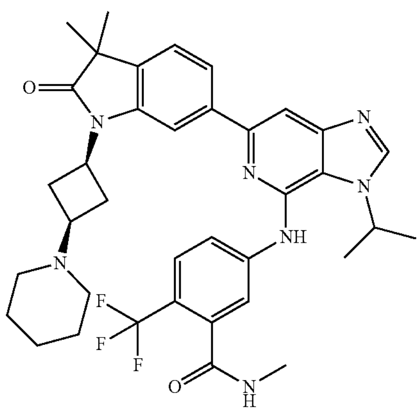 [SMILES: CNC(=O)c1cc(Nc2nc(-c3ccc4c(c3)N([C@H]3C[C@@H](N5CCCCC5)C3)C(=O)C4(C)C)cc3ncn(C(C)C)c23)ccc1C(F)(F)F] | 141 |
| 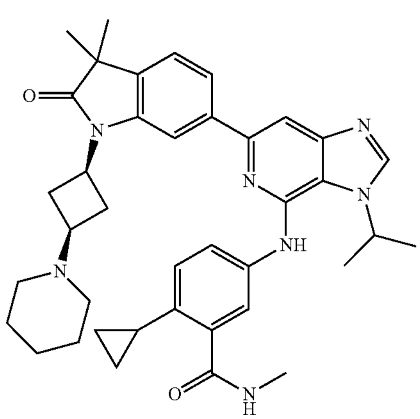 [SMILES: CNC(=O)c1cc(Nc2nc(-c3ccc4c(c3)N([C@H]3C[C@@H](N5CCCCC5)C3)C(=O)C4(C)C)cc3ncn(C(C)C)c23)ccc1C1CC1] | 142 |

| Structure | Example # |
|---|---|
| 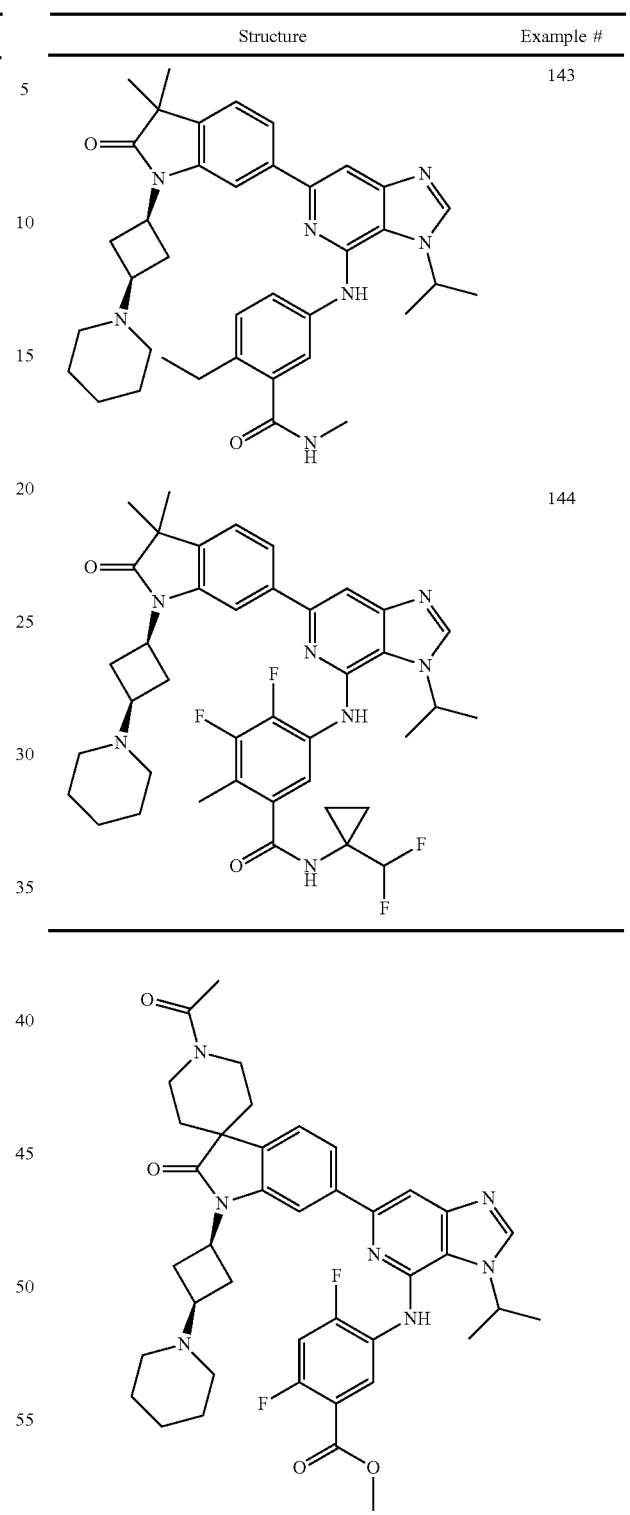 | 143 |
| 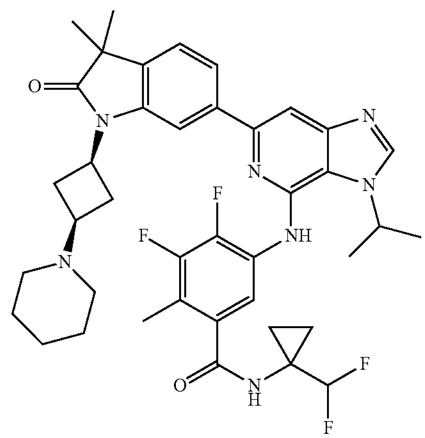 [SMILES: Cc1c(C(=O)NC2(C(F)F)CC2)cc(Nc2nc(-c3ccc4c(c3)N([C@H]3C[C@@H](N5CCCCC5)C3)C(=O)C4(C)C)cc3ncn(C(C)C)c23)c(F)c1F] | 144 |

Commercially available methyl 5-bromo-2,4-difluorobenzoate and 1'-acetyl-6-(4-amino-3-isopropyl-3H-imidazo[4,5-c]pyridin-6-yl)-1-((1s,3s)-3-(piperidin-1-yl)cyclobutyl)spiro[indoline-3,4'-piperidin]-2-one were used instead of 5-bromo-N-isopropyl-2-methylbenzamide and 6-(4-amino-3-isopropyl-3H-imidazo[4,5-c]pyridin-6-yl)-3,3-dimethyl-1-((1s,3s)-3-(piperidin-1-yl)cyclobutyl)indolin-2-one, respectively, to prepare methyl 5-((6-(1'-acetyl-2-oxo-1-((1s,3s)-3-(piperidin-1-yl)cyclobutyl)

443 spiro[indoline-3,4'-piperidin]-6-yl)-3-isopropyl-3H-imidazo[4,5-c]pyridin-4-yl)amino)-2,4-difluorobenzoate

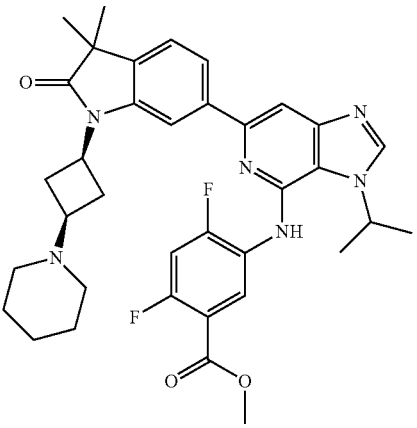 [SMILES: COC(=O)c1cc(Nc2nc(-c3ccc4c(c3)N([C@H]3C[C@@H](N5CCCCC5)C3)C(=O)C4(C)C)cc3ncn(C(C)C)c23)c(F)cc1F]

Commercially available methyl 5-bromo-2,4-difluorobenzoate was used instead of 5-bromo-N-isopropyl-2-methylbenzamide to prepare methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2,4-difluorobenzoate

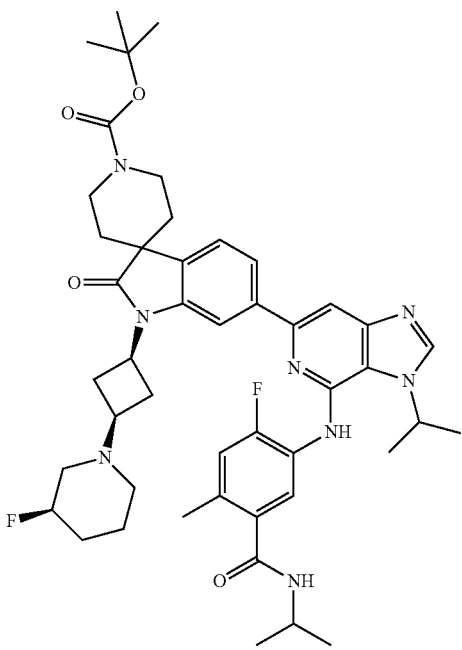 [SMILES: Cc1cc(F)c(Nc2nc(-c3ccc4c(c3)N([C@H]3C[C@@H](N5CCC[C@@H](F)C5)C3)C(=O)C43CCN(C(=O)OC(C)(C)C)CC3)cc3ncn(C(C)C)c23)cc1C(=O)NC(C)C]

5-Bromo-4-fluoro-N-isopropyl-2-methylbenzamide and tert-butyl 6-(4-amino-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate were used instead of 5-bromo-N-isopropyl-2-methylbenzamide and 6-(4-amino-3-isopropyl-3H-imidazo[4,5-c]pyridin-6-yl)-3,3-dimethyl-1-((1s,3s)-3-(piperidin-1-yl)cyclobutyl)indolin-2-one, respectively, to prepare tert-butyl 6-(4-((2-fluoro-5-(isopropylcarbamoyl)-4-methylphenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate

444

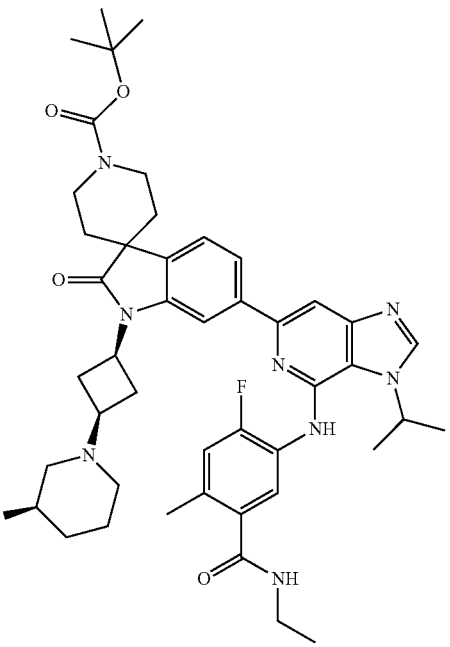

5-bromo-N-ethyl-4-fluoro-2-methylbenzamide and tert-butyl 6-(4-amino-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate were used instead of 5-bromo-N-isopropyl-2-methylbenzamide and 6-(4-amino-3-isopropyl-3H-imidazo[4,5-c]pyridin-6-yl)-3,3-dimethyl-1-((1s,3s)-3-(piperidin-1-yl)cyclobutyl)indolin-2-one, respectively, to prepare tert-butyl 6-(4-((5-(ethylcarbamoyl)-2-fluoro-4-methylphenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate B. Preparation of 5-((6-(1-((1S,3s)-3-((1R,4S)-2-azabicyclo[2.2.1]heptan-2-yl)cyclobutyl)-3,3-dimethyl-2-oxoindolin-6-yl)-3-isopropyl-3H-imidazo[4,5-c]pyridin-4-yl)amino)-N-(1-(difluoromethyl)cyclopropyl)-3,4-difluoro-2-methylbenzamide (Example 145)

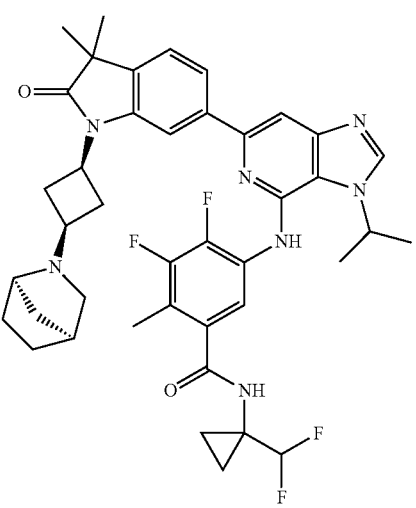 [SMILES: Cc1c(C(=O)NC2(C(F)F)CC2)cc(Nc2nc(-c3ccc4c(c3)N([C@H]3C[C@@H](N5C[C@H]6CC[C@@H]5C6)C3)C(=O)C4(C)C)cc3ncn(C(C)C)c23)c(F)c1F]

In a microwave vial were placed 1-((1S,3s)-3-((1R,4S)-2-azabicyclo[2.2.1]heptan-2-yl)cyclobutyl)-6-(4-amino-3-isopropyl-3H-imidazo[4,5-c]pyridin-6-yl)-3,3-dimethylindolin-2-one (85.21 mg, 0.18 mmol), 5-bromo-N-(1-(difluoromethyl)cyclopropyl)-3,4-difluoro-2-methylbenzamide (46 mg, 0.14 mmol), Pd$_2$(dba)$_3$×CHCl$_3$ (6.19 mg, 0.01 mmol), Xanthphos (7.83 mg, 0.01 mmol), and Cesium carbonate, 99.9% (132.2 mg, 0.41 mmol) in dioxane (1 mL). The mixture was degassed with nitrogen, placed in the microwave reactor, and heated at 150° C. for 30 min. The mixture was purified by silica chromatography (100% DCM to 100% MeOH) and reverse phase chromatography to give 5-((6-(1-((1S,3s)-3-((1R,4S)-2-azabicyclo[2.2.1]heptan-2-yl)cyclobutyl)-3,3-dimethyl-2-oxoindolin-6-yl)-3-isopropyl-3H-imidazo[4,5-c]pyridin-4-yl)amino)-N-(1-(difluoromethyl)cyclopropyl)-3,4-difluoro-2-methylbenzamide.

Procedure 21: Preparation of the Compounds of Formula I According to Reaction Scheme I

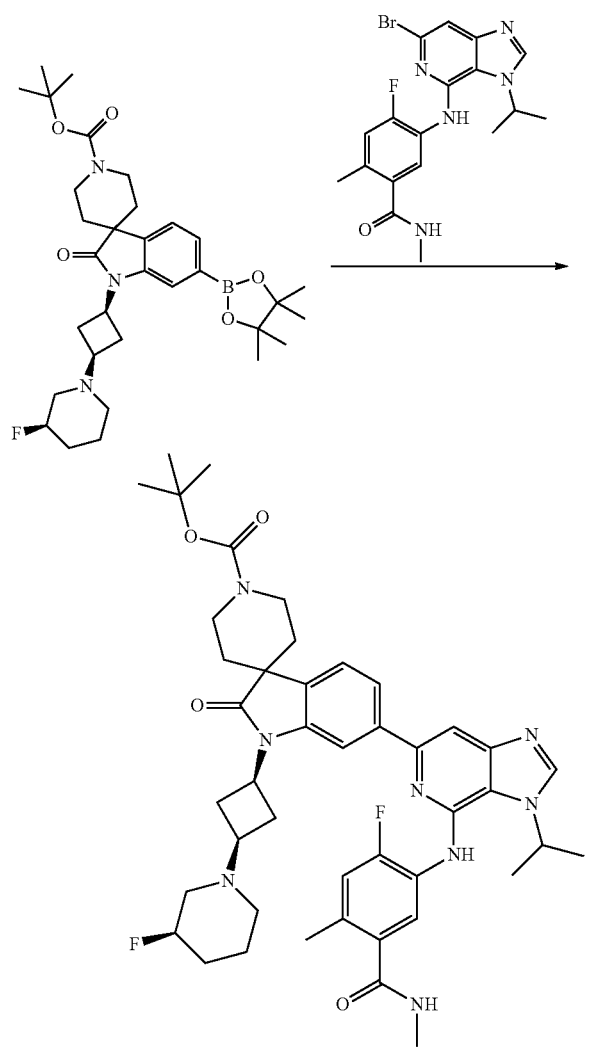 [SMILES: CC(C)(C)OC(=O)N1CCC2(CC1)C(=O)N([C@H]1C[C@@H](N3CCC[C@@H](F)C3)C1)c1cc(B3OC(C)(C)C(C)(C)O3)ccc12 ; CNC(=O)c1cc(Nc2nc(Br)cc3ncn(C(C)C)c23)c(F)cc1C ; CNC(=O)c1cc(Nc2nc(-c3ccc4c(c3)N([C@H]3C[C@@H](N5CCC[C@@H](F)C5)C3)C(=O)C43CCN(C(=O)OC(C)(C)C)CC3)cc3ncn(C(C)C)c23)c(F)cc1C]

A. Preparation of tert-butyl 6-(4-((2-fluoro-4-methyl-5-(methylcarbamoyl)phenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate

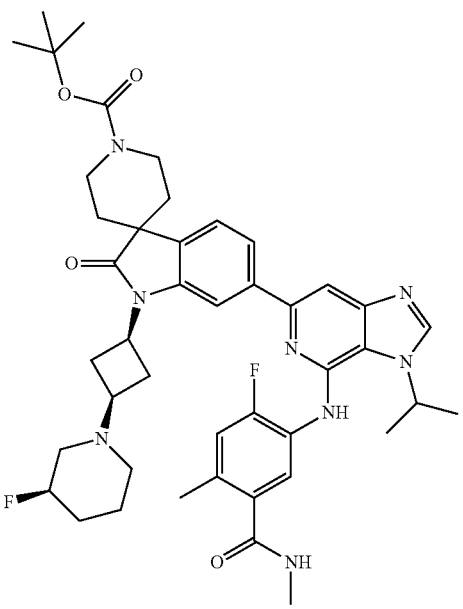

In a flask were placed tert-butyl 1-((1S,3s)-3-((R)-3-fluoropiperidin-1-yl)cyclobutyl)-2-oxo-6-(4,4,5,5-tetramethyl-1,3,2-dioxaborolan-2-yl)spiro[indoline-3,4'-piperidine]-1'-carboxylate (192 mg, 0.33 mmol), 5-((6-bromo-3-isopropyl-3H-imidazo[4,5-c]pyridin-4-yl)amino)-4-fluoro-N,2-dimethylbenzamide (115 mg, 0.27 mmol), Pd(PPh$_3$)$_4$ (22 mg, 0.02 mmol), and sodium carbonate (116 mg, 1.0 mmol) in DME (3 mL), and water (1 mL). The reaction mixture was purged with nitrogen gas, and heated at 120° C. in a microwave reactor for 25 min. The reaction was filtered through a pad of celite with MeOH, concentrated, and purified by reverse phase HPLC to give tert-butyl 6-(4-((2-fluoro-4-methyl-5-(methylcarbamoyl)phenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate.

The following compounds were prepared using a similar procedure with the following modification(s):
  the compounds listed under Procedure 3 or 34 were used instead of 5-((6-bromo-3-isopropyl-3H-imidazo[4,5-c]pyridin-4-yl)amino)-4-fluoro-N,2-dimethylbenzamide; and/or
  the compounds listed under Procedure 9 were used instead of tert-butyl 1-((1S,3s)-3-((R)-3-fluoropiperidin-1-yl)cyclobutyl)-2-oxo-6-(4,4,5,5-tetramethyl-1,3,2-dioxaborolan-2-yl)spiro[indoline-3,4'-piperidine]-1'-carboxylate:

| 447 | 448 |
|---|---|
| 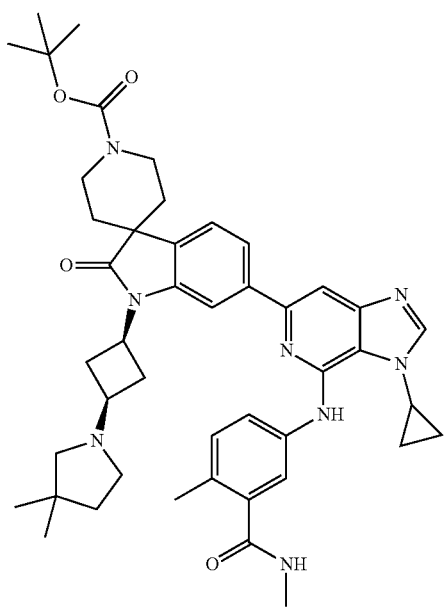 [SMILES: CNC(=O)c1cc(Nc2nc(-c3ccc4c(c3)N([C@H]3C[C@@H](N5CCC(C)(C)C5)C3)C(=O)C43CCN(C(=O)OC(C)(C)C)CC3)cc3ncn(C4CC4)c23)ccc1C] | 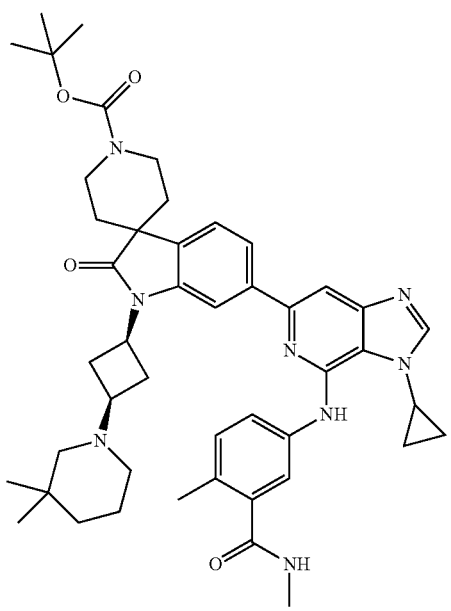 |
| tert-butyl 6-(3-cyclopropyl-4-((4-methyl-3-(methylcarbamoyl)phenyl)amino)-3H-imidazo[4,5-c]pyridin-6-yl)-1-((1s,3s)-3-(3,3-dimethylpyrrolidin-1-yl)cyclobutyl)-2-oxospiro[indoline-3,4'-piperidine]-1'-carboxylate | tert-butyl 6-(3-cyclopropyl-4-((4-methyl-3-(methylcarbamoyl)phenyl)amino)-3H-imidazo[4,5-c]pyridin-6-yl)-1-((1s,3s)-3-(3,3-dimethylpiperidin-1-yl)cyclobutyl)-2-oxospiro[indoline-3,4'-piperidine]-1'-carboxylate |
| 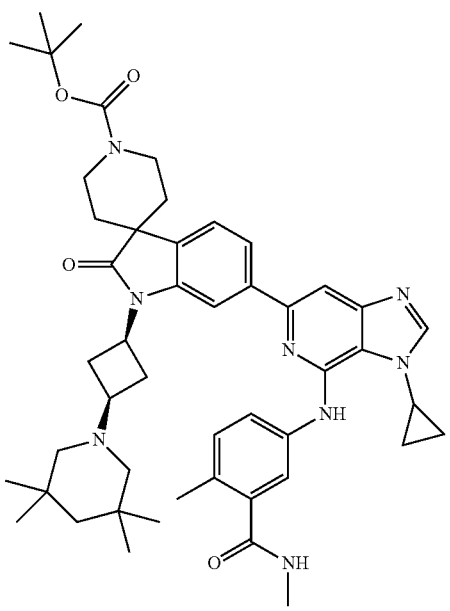 [SMILES: CNC(=O)c1cc(Nc2nc(-c3ccc4c(c3)N([C@H]3C[C@@H](N5CC(C)(C)CC(C)(C)C5)C3)C(=O)C43CCN(C(=O)OC(C)(C)C)CC3)cc3ncn(C4CC4)c23)ccc1C] | |
| tert-butyl 6-(3-cyclopropyl-4-((4-methyl-3-(methylcarbamoyl)phenyl)amino)-3H-imidazo[4,5-c]pyridin-6-yl)-2-oxo-1-((1s,3s)-3-(3,3,5,5-tetramethylpiperidin-1-yl)cyclobutyl)spiro[indoline-3,4'-piperidine]-1'-carboxylate | tert-butyl 1-((1S,3s)-3-((R)-3-fluoropiperidin-1-yl)cyclobutyl)-6-(3-isopropyl-4-((4-methyl-3-(methylcarbamoyl)phenyl)amino)-3H-imidazo[4,5-c]pyridin-6-yl)-2-oxospiro[indoline-3,4'-piperidine]-1'-carboxylate |

449

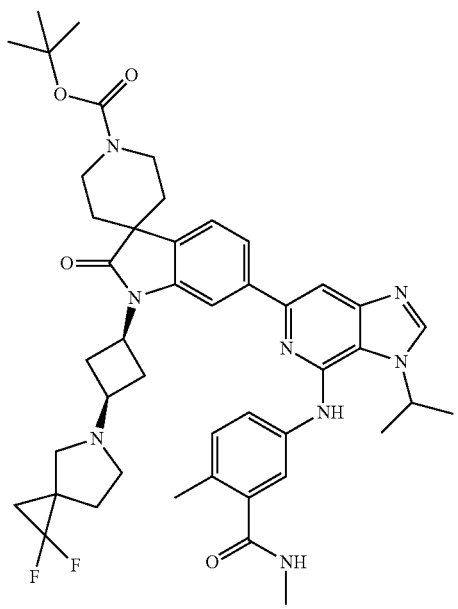 [SMILES: CNC(=O)c1cc(Nc2nc(-c3ccc4c(c3)N([C@H]3C[C@@H](N5CCC6(C5)CC6(F)F)C3)C(=O)C43CCN(C(=O)OC(C)(C)C)CC3)cc3ncn(C(C)C)c23)ccc1C]

tert-butyl 1-((1s,3s)-3-(1,1-difluoro-5-azaspiro[2.4]heptan-5-yl)cyclobutyl)-6-(3-isopropyl-4-((4-methyl-3-(methylcarbamoyl)phenyl)amino)-3H-imidazo[4,5-c]pyridin-6-yl)-2-oxospiro[indoline-3,4'-piperidine]-1'-carboxylate

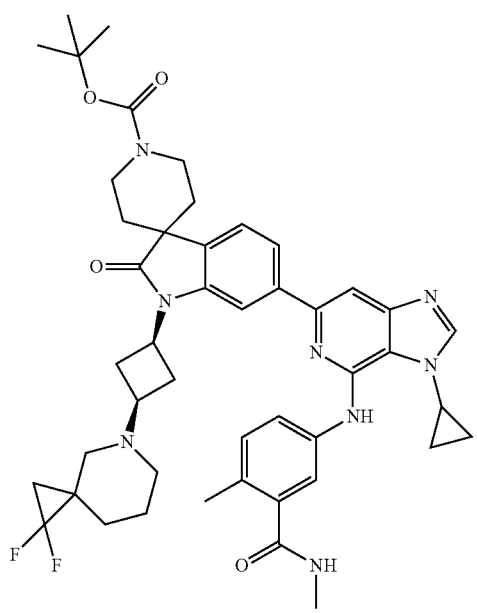 [SMILES: CNC(=O)c1cc(Nc2nc(-c3ccc4c(c3)N([C@H]3C[C@@H](N5CCCC6(C5)CC6(F)F)C3)C(=O)C43CCN(C(=O)OC(C)(C)C)CC3)cc3ncn(C4CC4)c23)ccc1C]

tert-butyl 6-(3-cyclopropyl-4-((4-methyl-3-(methylcarbamoyl)phenyl)amino)-3H-imidazo[4,5-c]pyridin-6-yl)-1-((1s,3s)-3-(1,1-difluoro-5-azaspiro[2.5]octan-5-yl)cyclobutyl)-2-oxospiro[indoline-3,4'-piperidine]-1'-carboxylate

450

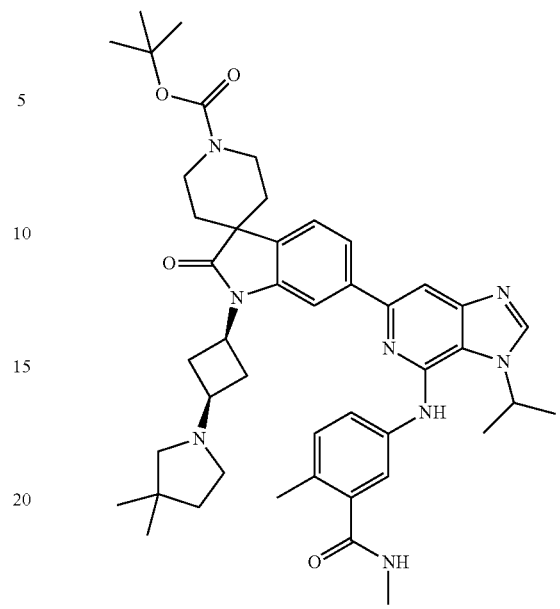

tert-butyl 1-((1s,3s)-3-(3,3-dimethylpyrrolidin-1-yl)cyclobutyl)-6-(3-isopropyl-4-((4-methyl-3-(methylcarbamoyl)phenyl)amino)-3H-imidazo[4,5-c]pyridin-6-yl)-2-oxospiro[indoline-3,4'-piperidine]-1'-carboxylate

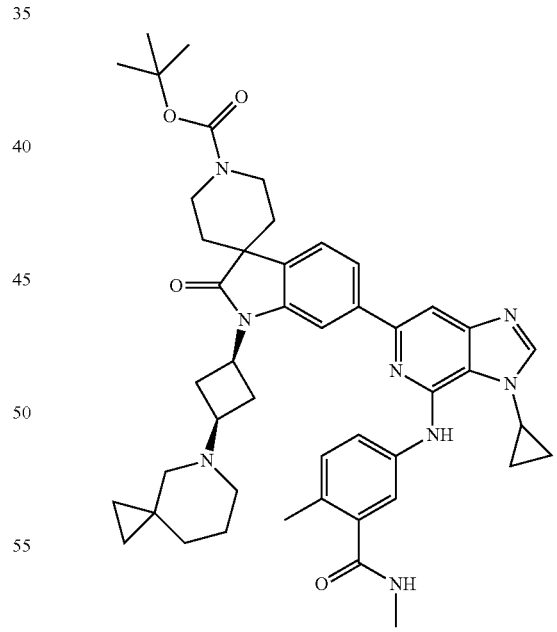

tert-butyl 1-((1s,3s)-3-(5-azaspiro[2.5]octan-5-yl)cyclobutyl)-6-(3-cyclopropyl-4-((4-methyl-3-(methylcarbamoyl)phenyl)amino)-3H-imidazo[4,5-c]pyridin-6-yl)-2-oxospiro[indoline-3,4'-piperidine]-1'-carboxylate

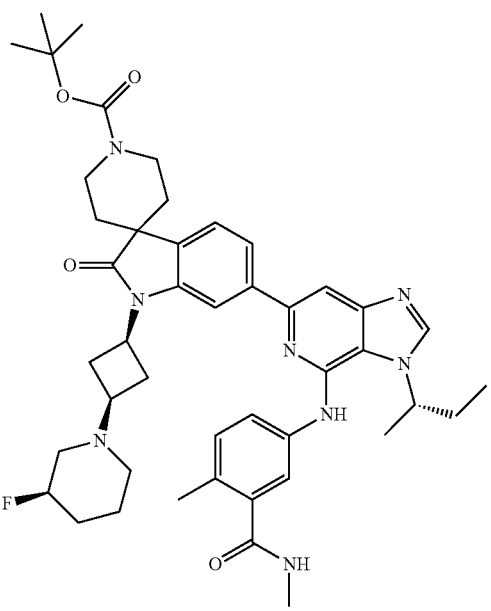 [SMILES: CC[C@H](C)n1cnc2cc(-c3ccc4c(c3)N([C@H]3C[C@@H](N5CCC[C@@H](F)C5)C3)C(=O)C43CCN(C(=O)OC(C)(C)C)CC3)nc(Nc3ccc(C)c(C(=O)NC)c3)c21]

tert-butyl 6-(3-((S)-sec-butyl)-4-((4-methyl-3-(methylcarbamoyl)phenyl)amino)-3H-imidazo[4,5-c]pyridin-6-yl)-1-((1S,3R)-3-((R)-3-fluoropiperidin-1-yl)cyclobutyl)-2-oxospiro[indoline-3,4'-piperidine]-1'-carboxylate

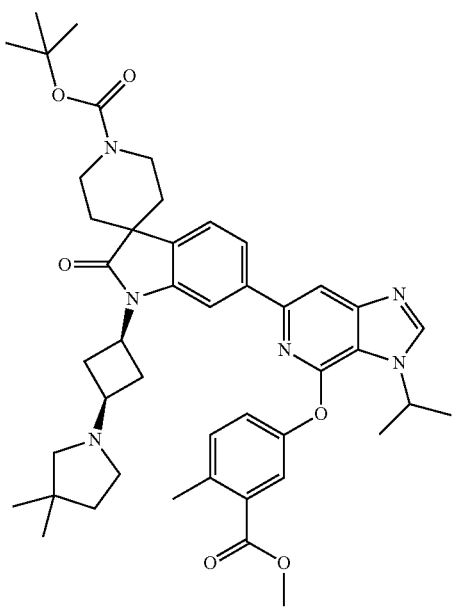 [SMILES: COC(=O)c1cc(Oc2nc(-c3ccc4c(c3)N([C@H]3C[C@@H](N5CCC(C)(C)C5)C3)C(=O)C43CCN(C(=O)OC(C)(C)C)CC3)cc3ncn(C(C)C)c23)ccc1C]

tert-butyl 1-((1s,3s)-3-(3,3-dimethylpyrrolidin-1-yl)cyclobutyl)-6-(3-isopropyl-4-(3-(methoxycarbonyl)-4-methylphenoxy)-3H-imidazo[4,5-c]pyridin-6-yl)-2-oxospiro[indoline-3,4'-piperidine]-1'-carboxylate Procedure 22: Preparation of the Compounds of Formula (18) According to Reaction Scheme IV

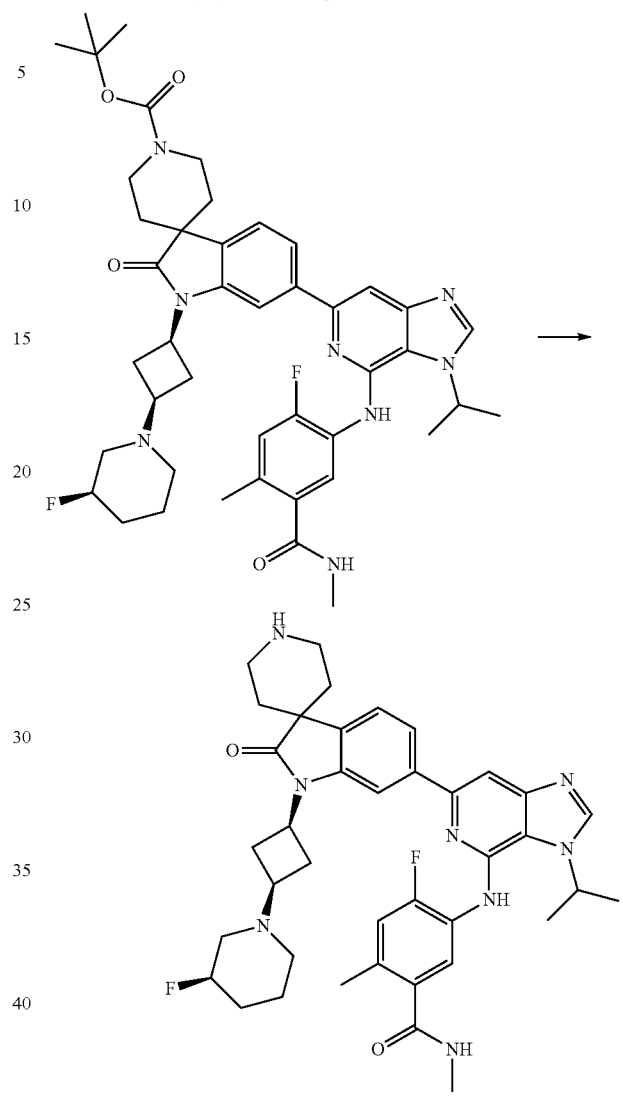

A. Preparation of 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide

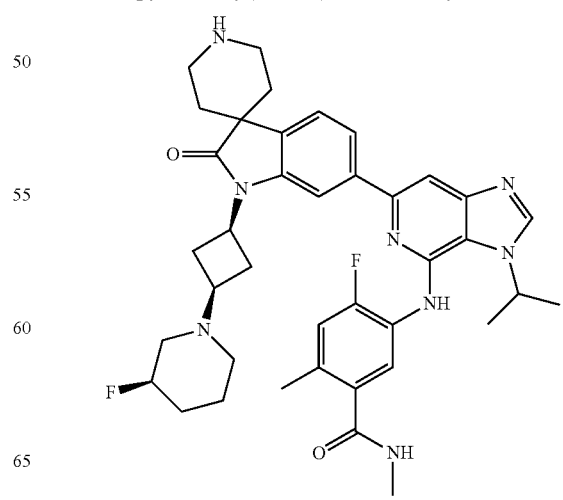

To a solution of tert-butyl 6-(4-((2-fluoro-4-methyl-5-(methylcarbamoyl)phenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate (110 mg, 0.14 mmol) in dichloromethane (1 mL) was added 4N HCl in dioxane (0.5 mL). After stirring at room temperature for 2 h, the reaction mixture was concentrated under reduced pressure to give 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide.

The following compounds were prepared using a similar procedure except the compounds listed under Procedure 18, 20, or 21 were used instead of tert-butyl 6-(4-((2-fluoro-4-methyl-5-(methylcarbamoyl)phenyl)amino)-3-isopropyl-3H-imidazo[4,5-c]pyridin-6-yl)-1-((1S,3s)-3-((R)-3-fluoropiperidin-1-yl)cyclobutyl)-2-oxospiro[indoline-3,4'-piperidine]-1'-carboxylate:

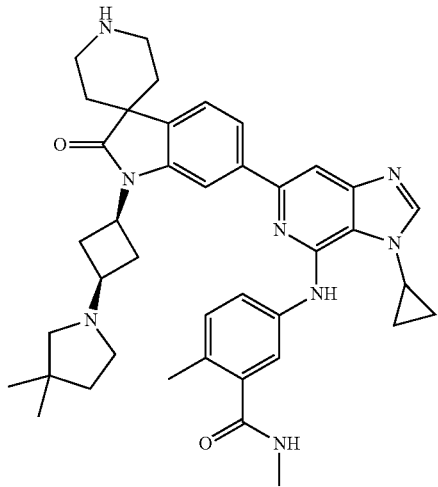 [SMILES: CNC(=O)c1cc(Nc2nc(-c3ccc4c(c3)N([C@H]3C[C@@H](N5CCC(C)(C)C5)C3)C(=O)C43CCNCC3)cc3ncn(C4CC4)c23)ccc1C]

5-((3-cyclopropyl-6-(1-((1s,3s)-3-(3,3-dimethylpyrrolidin-1-yl)cyclobutyl)-2-oxospiro[indoline-3,4'-piperidin]-6-yl)-3H-imidazo[4,5-c]pyridin-4-yl)amino)-N,2-dimethylbenzamide

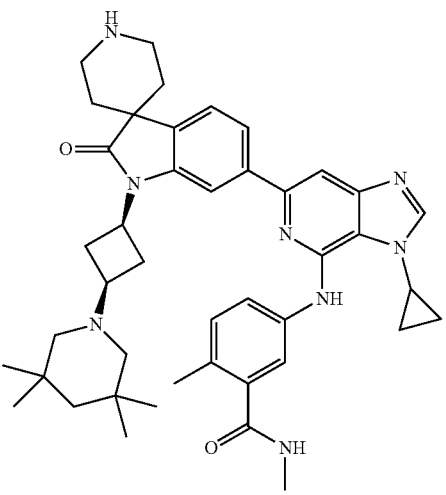 [SMILES: CNC(=O)c1cc(Nc2nc(-c3ccc4c(c3)N([C@H]3C[C@@H](N5CC(C)(C)CC(C)(C)C5)C3)C(=O)C43CCNCC3)cc3ncn(C4CC4)c23)ccc1C]

5-((3-cyclopropyl-6-(2-oxo-1-((1s,3s)-3-(3,3,5,5-tetramethylpiperidin-1-yl)cyclobutyl)spiro[indoline-3,4'-piperidin]-6-yl)-3H-imidazo[4,5-c]pyridin-4-yl)amino)-N,2-dimethylbenzamide

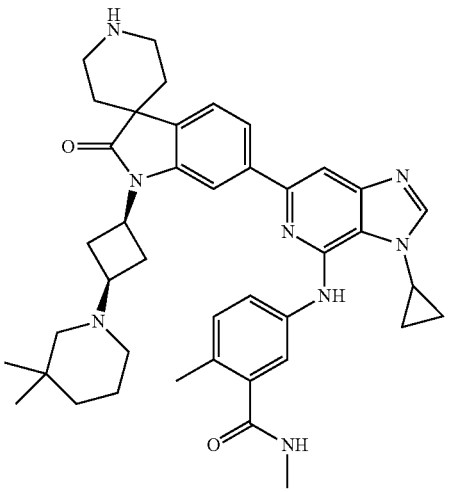

5-((3-cyclopropyl-6-(1-((1s,3s)-3-(3,3-dimethylpiperidin-1-yl)cyclobutyl)-2-oxospiro[indoline-3,4'-piperidin]-6-yl)-3H-imidazo[4,5-c]pyridin-4-yl)amino)-N,2-dimethylbenzamide

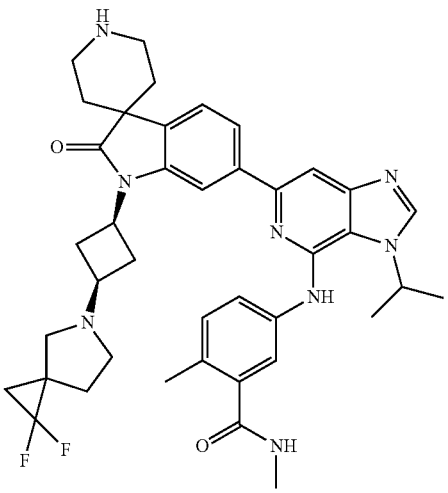 [SMILES: CNC(=O)c1cc(Nc2nc(-c3ccc4c(c3)N([C@H]3C[C@@H](N5CCC6(C5)CC6(F)F)C3)C(=O)C43CCNCC3)cc3ncn(C(C)C)c23)ccc1C]

5-((6-(1-((1s,3s)-3-(1,1-difluoro-5-azaspiro[2.4]heptan-5-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide

455

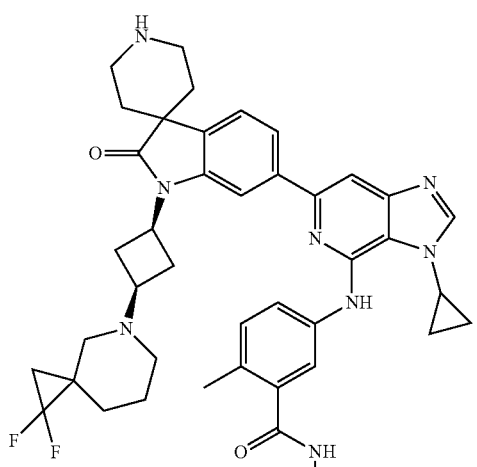

5-((3-cyclopropyl-6-(1-((1s,3s)-3-(1,1-difluoro-5-azaspiro[2.5]octan-5-yl)cyclobutyl)-2-oxospiro[indoline-3,4'-piperidin]-6-yl)-3H-imidazo[4,5-c]pyridin-4-yl)amino)-N,2-dimethylbenzamide

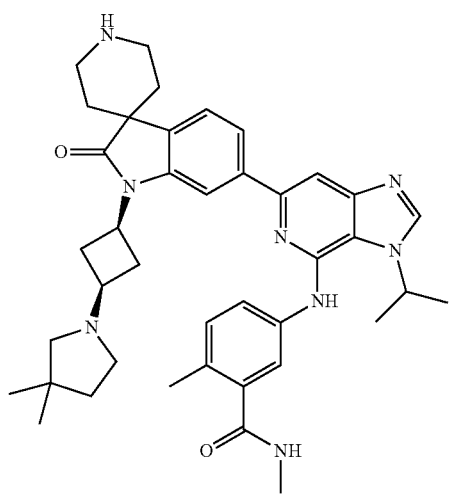 [SMILES: CNC(=O)c1cc(Nc2nc(-c3ccc4c(c3)N([C@H]3C[C@@H](N5CCC(C)(C)C5)C3)C(=O)C43CCNCC3)cc3ncn(C(C)C)c23)ccc1C]

5-((6-(1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide

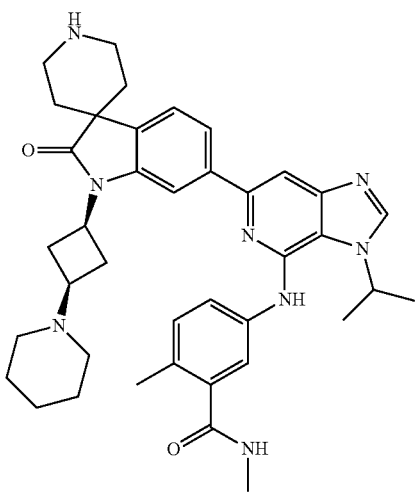 [SMILES: CNC(=O)c1cc(Nc2nc(-c3ccc4c(c3)N([C@H]3C[C@@H](N5CCCCC5)C3)C(=O)C43CCNCC3)cc3ncn(C(C)C)c23)ccc1C]

456

5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide

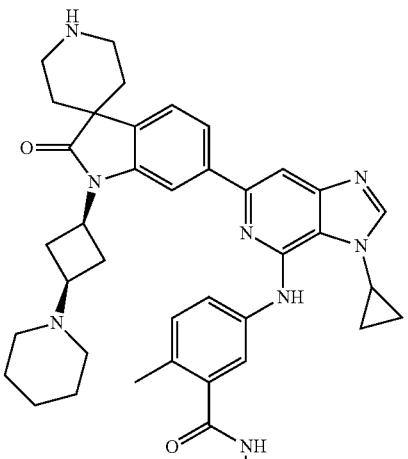

5-((3-cyclopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide

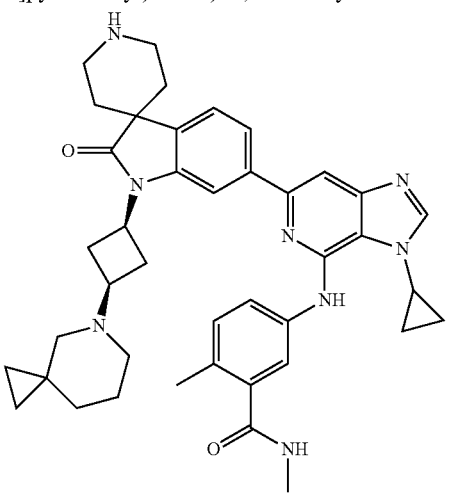

5-((6-(1-((1s,3s)-3-(5-azaspiro[2.5]octan-5-yl)cyclobutyl)-2-oxospiro[indoline-3,4'-piperidin]-6-yl)-3-cyclopropyl-3H-imidazo[4,5-c]pyridin-4-yl)amino)-N,2-dimethylbenzamide

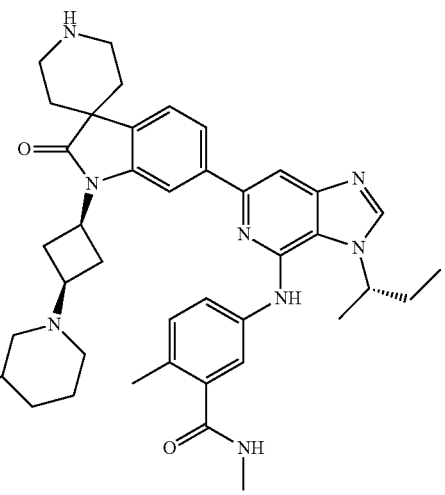

457

5-((3-((S)-sec-butyl)-6-(1-(((1S,3R)-3-((R)-3-fluoropiperi-
din-1-yl)cyclobutyl)-2-oxospiro[indoline-3,4'-piperidin]-
6-yl)-3H-imidazo[4,5-c]pyridin-4-yl)amino)-N,2-dimeth-
ylbenzamide

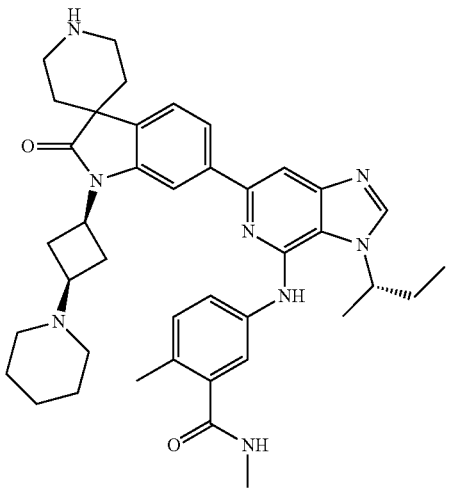 [SMILES: CC[C@H](C)n1cnc2cc(-c3ccc4c(c3)N([C@H]3C[C@@H](N5CCCCC5)C3)C(=O)C43CCNCC3)nc(Nc3ccc(C)c(C(=O)NC)c3)c21]

5-((3-((S)-sec-butyl)-6-(2-oxo-1-((1s,3R)-3-(piperidin-1-yl)
cyclobutyl)spiro[indoline-3,4'-piperidin]-6-yl)-3H-imi-
dazo[4,5-c]pyridin-4-yl)amino)-N,2-dimethylbenzamide

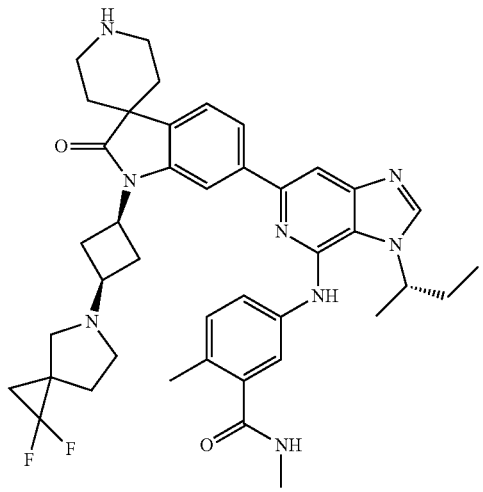 [SMILES: CC[C@H](C)n1cnc2cc(-c3ccc4c(c3)N([C@H]3C[C@@H](N5CCC6(C5)CC6(F)F)C3)C(=O)C43CCNCC3)nc(Nc3ccc(C)c(C(=O)NC)c3)c21]

5-((3-((S)-sec-butyl)-6-(1-((1s,3R)-3-(1,1-difluoro-5-
azaspiro[2.4]heptan-5-yl)cyclobutyl)-2-oxospiro[indo-
line-3,4'-piperidin]-6-yl)-3H-imidazo[4,5-c]pyridin-4-yl)
amino)-N,2-dimethylbenzamide

458

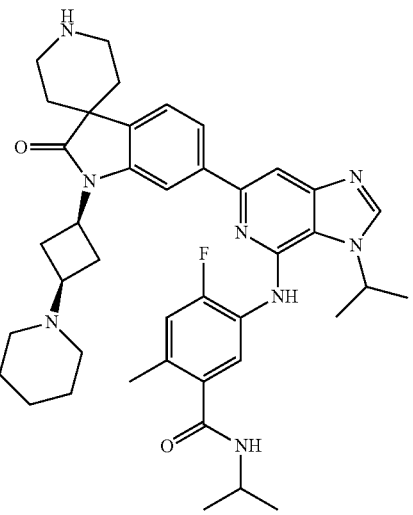

4-Fluoro-5-((6-(1-(((1S,3s)-3-((R)-3-fluoropiperidin-1-yl)
cyclobutyl)-2-oxospiro[indoline-3,4'-piperidin]-6-yl)-3-
isopropyl-3H-imidazo[4,5-c]pyridin-4-yl)amino)-N-iso-
propyl-2-methylbenzamide

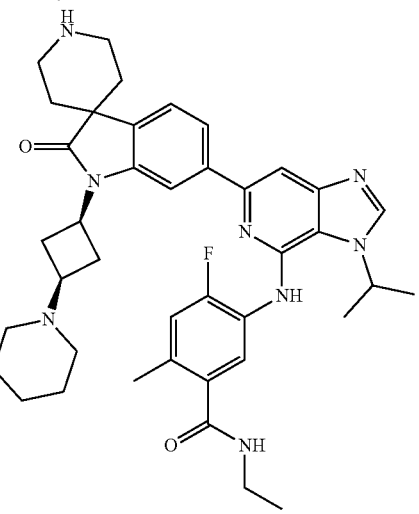

N-Ethyl-4-fluoro-5-(((6-(1-(((1S,3s)-3-((R)-3-fluoropiperi-
din-1-yl)cyclobutyl)-2-oxospiro[indoline-3,4'-piperidin]-
6-yl)-3-isopropyl-3H-imidazo[4,5-c]pyridin-4-yl)
amino)-2-methylbenzamide

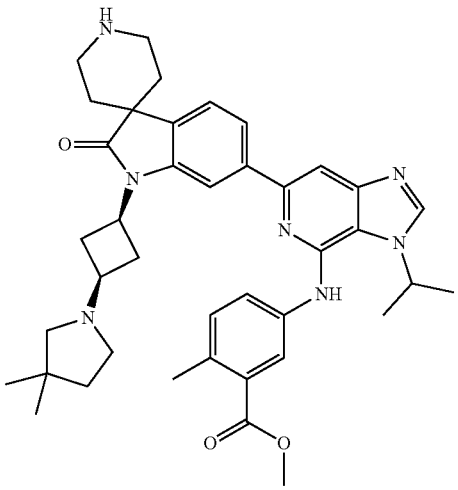 [SMILES: COC(=O)c1cc(Nc2nc(-c3ccc4c(c3)N([C@H]3C[C@@H](N5CCC(C)(C)C5)C3)C(=O)C43CCNCC3)cc3ncn(C(C)C)c23)ccc1C]

methyl 5-((6-(1-(((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)oxy)-2-methylbenzoate
Procedure 23: Preparation of the Compounds of Formula I According to Reaction Scheme IV
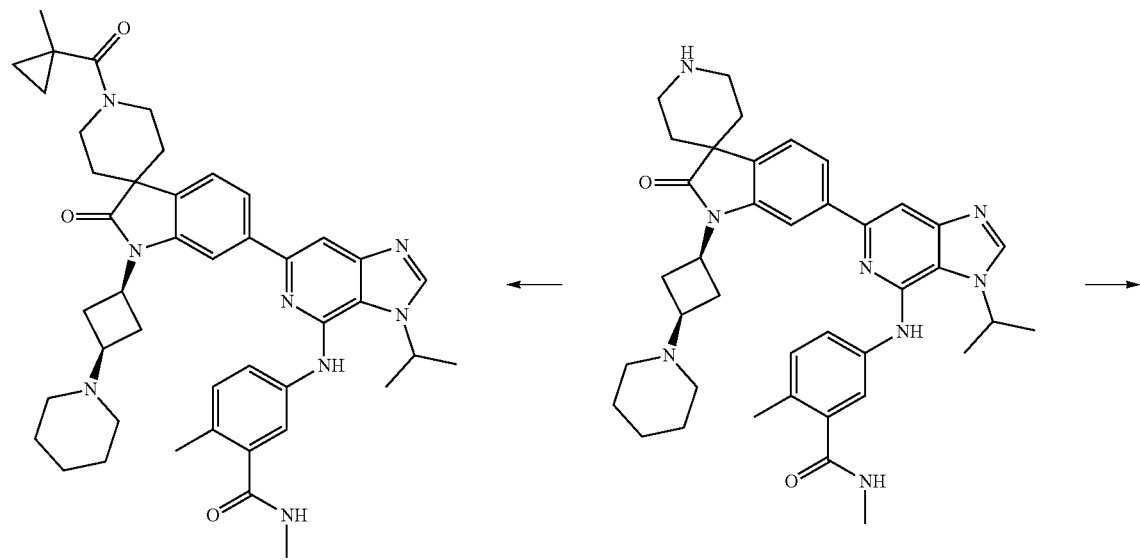
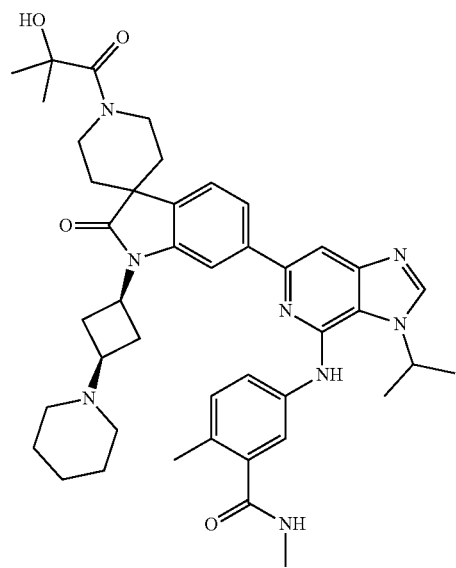 [SMILES: CNC(=O)c1cc(Nc2nc(-c3ccc4c(c3)N([C@H]3C[C@@H](N5CCCCC5)C3)C(=O)C43CCN(C(=O)C(C)(C)O)CC3)cc3ncn(C(C)C)c23)ccc1C]

A. Preparation of 5-((6-(1'-(2-hydroxy-2-methylpropanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-N,2-dimethylbenzamide (Example 146)

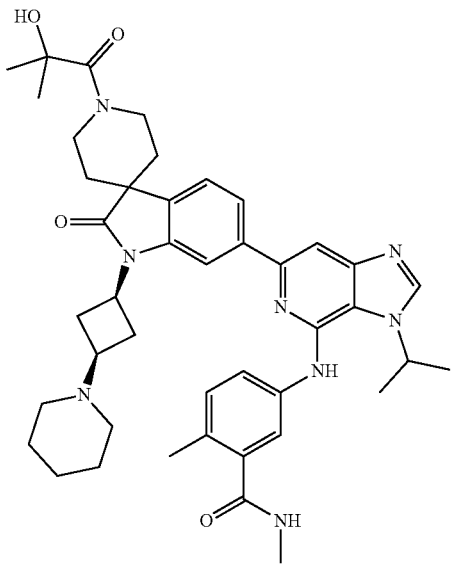

To a solution of 5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyri din-4-yl)amino)-N,2-dimethylbenzamide (0.10 g, 0.11 mmol) in DMF (1 mL) were added 2-hydroxy-2-methylpropanoic acid (0.024 g, 0.23 mmol), DIEA (0.2 mL, 1.1 mmol) and HATU (0.087 g, 0.23 mmol). The resulting mixture was stirred at room temperature for 30 minutes, and then quenched with water and extracted with EtOAc. The combined organic layers were washed with brine, dried ($Na_2SO_4$), concentrated, and purified by reverse phase chromatography (0.01% TFA in ACN/0.01% TFA in Water) to give 5-((6-(1'-(2-hydroxy-2-methylpropanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-N,2-dimethylbenzamide.

The following compounds were prepared using a similar procedure with the following modification(s):
- the compounds listed under Procedure 22 were used instead of 5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide; and/or
- the carboxylic acids, that are commercially available or can be made by methods known in the art, such as (R)-2-hydroxypropanoic acid, 3-hydroxybicyclo[1.1.1]pentane-1-carboxylic acid, 1-methylcyclobutane-1-carboxylic acid, and 1-methylcyclopropane-1-carboxylic acid were used instead of 2-hydroxy-2-methylpropanoic acid:

| Structure | Example # |
|---|---|
| 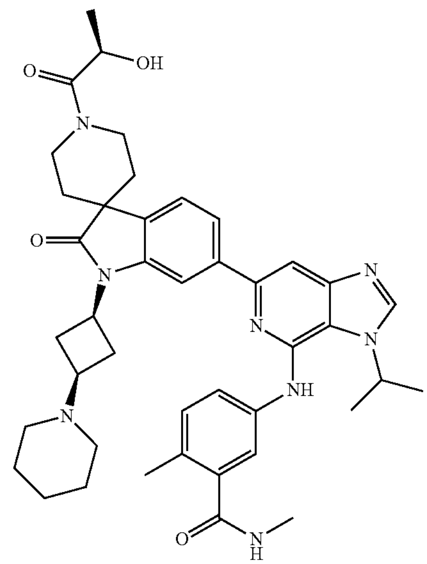 [SMILES: CNC(=O)c1cc(Nc2nc(-c3ccc4c(c3)N([C@H]3C[C@@H](N5CCCCC5)C3)C(=O)C43CCN(C(=O)[C@@H](C)O)CC3)cc3ncn(C(C)C)c23)ccc1C] | 147 |
| 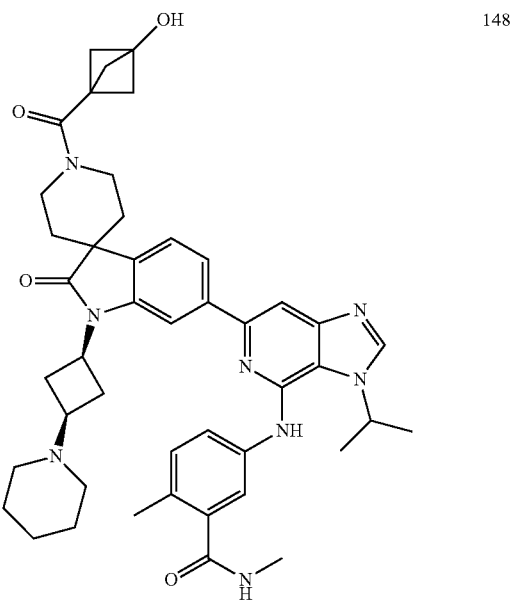 | 148 |

| Structure | Example # |
|---|---|
| 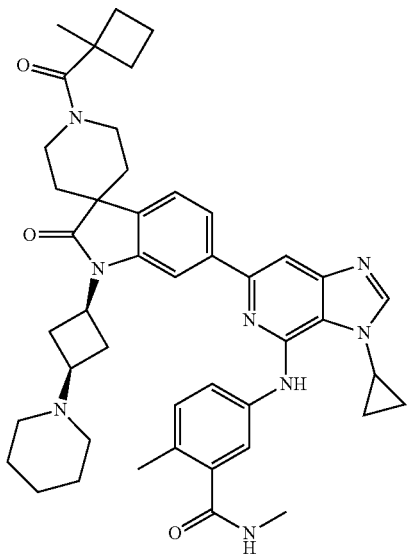 [SMILES: CNC(=O)c1cc(Nc2nc(-c3ccc4c(c3)N([C@H]3C[C@@H](N5CCCCC5)C3)C(=O)C43CCN(C(=O)C4(C)CCC4)CC3)cc3ncn(C4CC4)c23)ccc1C] | 149 |
| 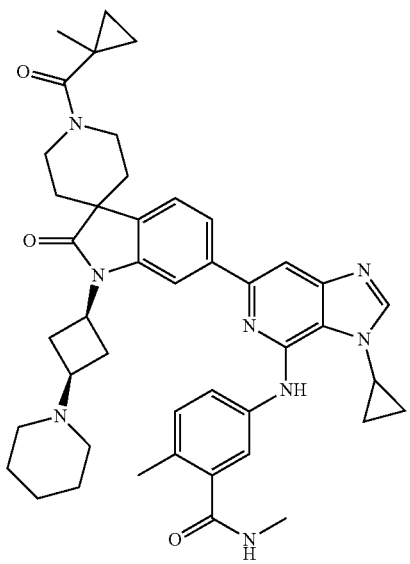 [SMILES: CNC(=O)c1cc(Nc2nc(-c3ccc4c(c3)N([C@H]3C[C@@H](N5CCCCC5)C3)C(=O)C43CCN(C(=O)C4(C)CC4)CC3)cc3ncn(C4CC4)c23)ccc1C] | 150 |
| Structure | Example # |
|---|---|
| 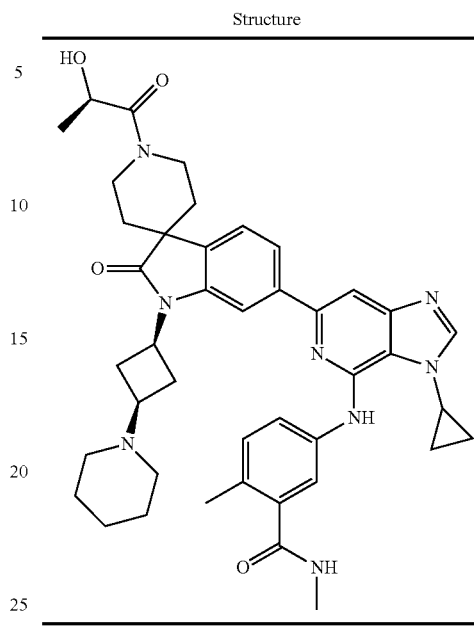 | 151 |
B. Preparation of 5-((3-isopropyl-6-(1'-(1-methylcyclopropane-1-carbonyl)-2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide (Example 152)
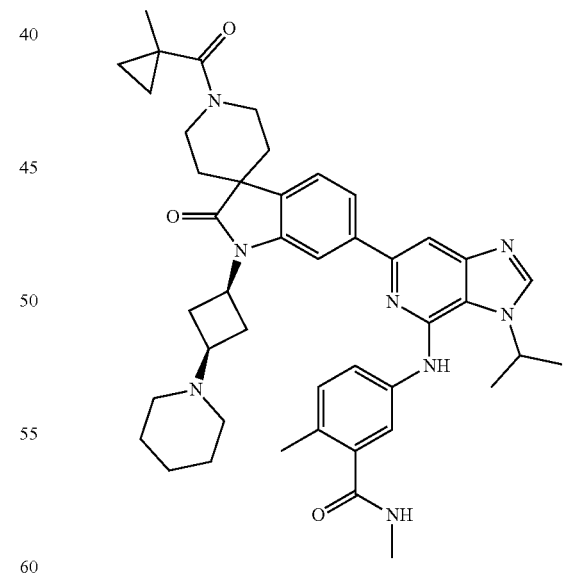
To a solution of 5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide (0.11 g, 0.11 mmol) in DMF (1 mL) were added 1-methylcyclopropane-1-carboxylic acid (0.023 g, 0.23 mmol), DIEA (0.2 mL, 1.1 mmol) and a 50% solution of propylphosphonic anhydride (T3P) in EtOAc (0.14 mL, 0.23 mmol). The resulting mixture was stirred at room temperature for 30 minutes, and then quenched with water and extracted with EtOAc. The combined organic layers were washed with brine, dried (Na$_2$SO$_4$), concentrated, and purified by silica chromatography (10% NH$_4$OH in MeOH/EtOAc/hexanes) followed by reverse phase chromatography (0.01% TFA in ACN/0.01% TFA in Water) to give 5-((3-isopropyl-6-(1'-(1-methylcyclopropane-1-carbonyl)-2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide.

The following compounds were prepared using a similar procedure with the following modification(s):

the compounds listed under Procedure 22 were used instead of 5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide; and/or the carboxylic acids, that are commercially available or can be made by methods known in the art, such as 1-methylcyclopropane-1-carboxylic acid, oxetane-3-carboxylic acid, 3-fluorobicyclo[1.1.1]pentane-1-carboxylic acid, cyclobutanecarboxylic acid, and bicyclo[1.1.1]pentane-1-carboxylic acid were used instead of 2-hydroxy-2-methylpropanoic acid:

| Structure | Example # |
|---|---|
| 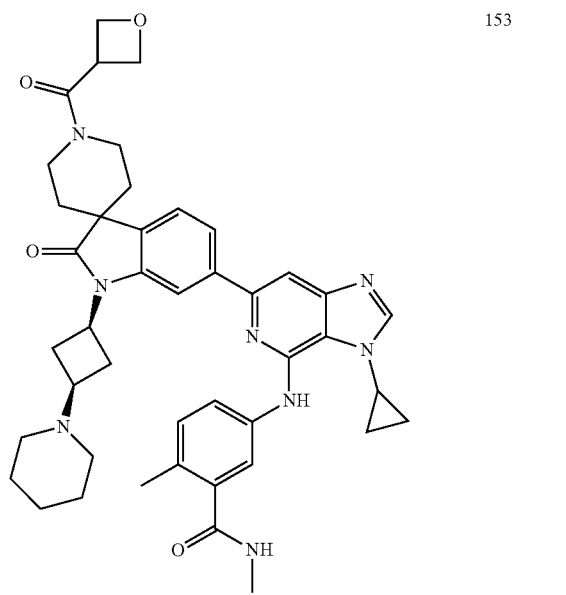 | 153 |
| 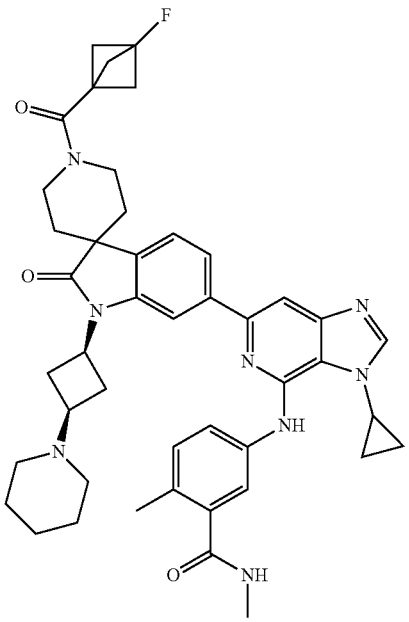 [SMILES: CNC(=O)c1cc(Nc2nc(-c3ccc4c(c3)N([C@H]3C[C@@H](N5CCCCC5)C3)C(=O)C43CCN(C(=O)C45CC(F)(C4)C5)CC3)cc3ncn(C4CC4)c23)ccc1C] | 154 |
| 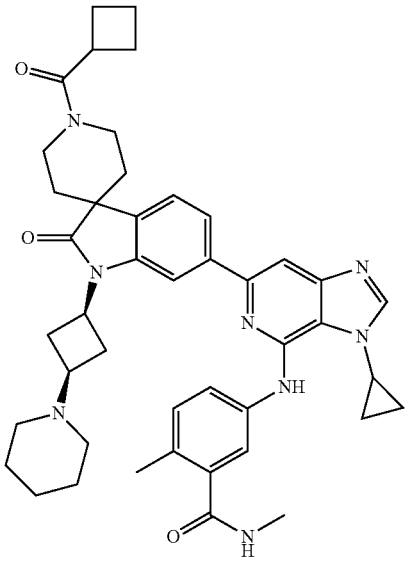 [SMILES: CNC(=O)c1cc(Nc2nc(-c3ccc4c(c3)N([C@H]3C[C@@H](N5CCCCC5)C3)C(=O)C43CCN(C(=O)C4CCC4)CC3)cc3ncn(C4CC4)c23)ccc1C] | 155 |

-continued

| Structure | Example # |
|---|---|
| 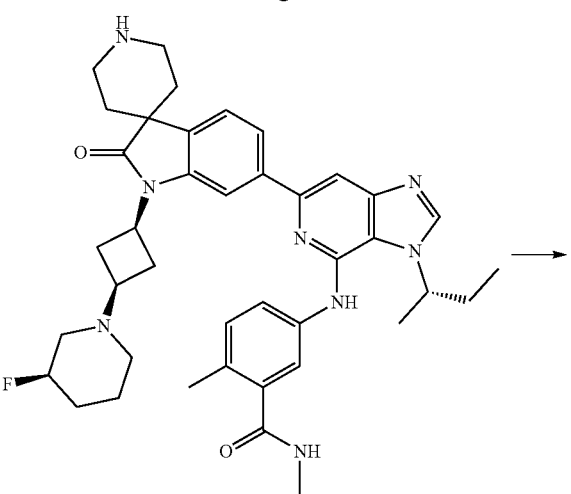 | 156 |

Procedure 24: Preparation of the Compounds of Formula I According to Reaction Scheme A. Preparation of 5-((6-(1'-acetyl-1-((1S,3R)-3-((R)-3-fluoropiperidin-1-yl)cyclobutyl)-2-oxospiro[indoline-3,4'-piperidin]-6-yl)-3-((S)-sec-butyl)-3H-imidazo[4,5-c]pyridin-4-yl)amino)-N,2-dimethylbenzamide (Example 157)

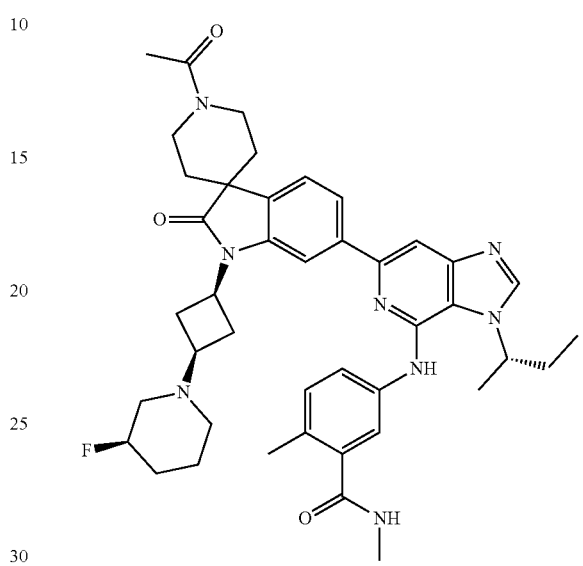

To a mixture of 5-((3-((S)-sec-butyl)-6-(1-((1S,3R)-3-((R)-3-fluoropiperidin-1-yl)cyclobutyl)-2-oxospiro[indoline-3,4'-piperidin]-6-yl)-3H-imidazo[4,5-c]pyridin-4-yl)amino)-N,2-dimethylbenzamide (45 mg, 0.07 mmol) and triethylamine (0.1 ml, 0.64 mmol) in dichloromethane (2 mL) was added acetic anhydride (0.01 ml, 0.1 mmol). After stirring at room temperature for 20 min, the reaction mixture was concentrated under reduced pressure and purified by reverse phase HPLC to afford 5-((6-(1'-acetyl-1-((1S,3R)-3-((R)-3-fluoropiperidin-1-yl)cyclobutyl)-2-oxospiro[indoline-3,4'-piperidin]-6-yl)-3-((S)-sec-butyl)-3H-imidazo[4,5-c]pyridin-4-yl)amino)-N,2-dimethylbenzamide.

The following compounds were prepared using a similar procedure with the following modification(s):

the compounds listed under Procedure 22 were used instead of 5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide; and/or Alkylsulfonyl chlorides, such as cyclopropanesulfonyl chloride and methanesulfonyl chloride, were used instead of acetic anhydride:

| Structure | Example # |
|---|---|
| 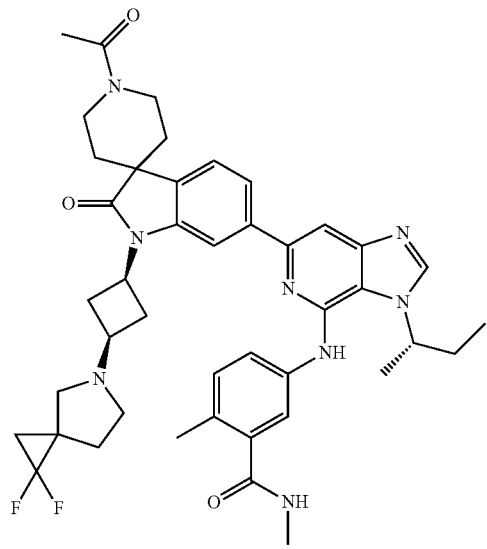 [SMILES: CC[C@H](C)n1cnc2cc(-c3ccc4c(c3)N([C@H]3C[C@@H](N5CCC6(C5)CC6(F)F)C3)C(=O)C43CCN(C(C)=O)CC3)nc(Nc3ccc(C)c(C(=O)NC)c3)c21] | 158 |
| 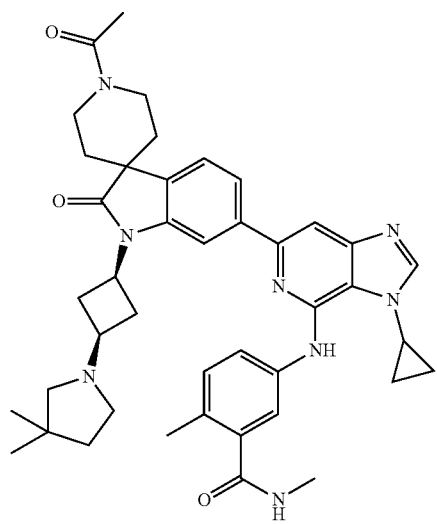 [SMILES: CNC(=O)c1cc(Nc2nc(-c3ccc4c(c3)N([C@H]3C[C@@H](N5CCC(C)(C)C5)C3)C(=O)C43CCN(C(C)=O)CC3)cc3ncn(C4CC4)c23)ccc1C] | 159 |
| 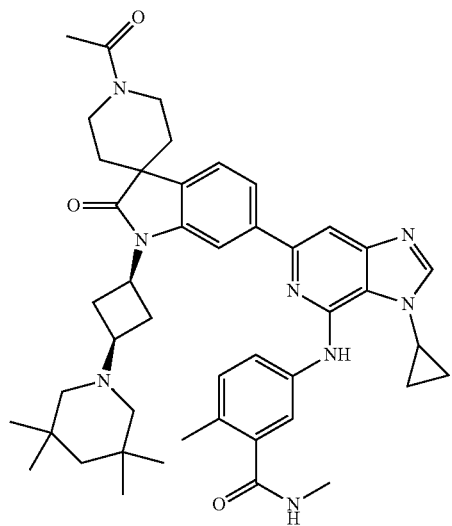 [SMILES: CNC(=O)c1cc(Nc2nc(-c3ccc4c(c3)N([C@H]3C[C@@H](N5CC(C)(C)CC(C)(C)C5)C3)C(=O)C43CCN(C(C)=O)CC3)cc3ncn(C4CC4)c23)ccc1C] | 160 |

| Structure | Example # |
|---|---|
| 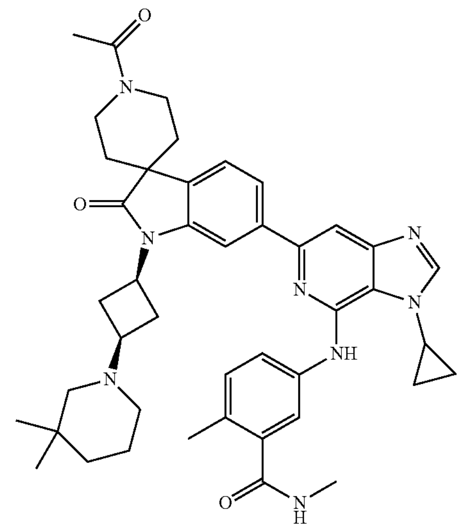 [SMILES: CNC(=O)c1cc(Nc2nc(-c3ccc4c(c3)N([C@H]3C[C@@H](N5CCCC(C)(C)C5)C3)C(=O)C43CCN(C(C)=O)CC3)cc3ncn(C4CC4)c23)ccc1C] | 161 |
| 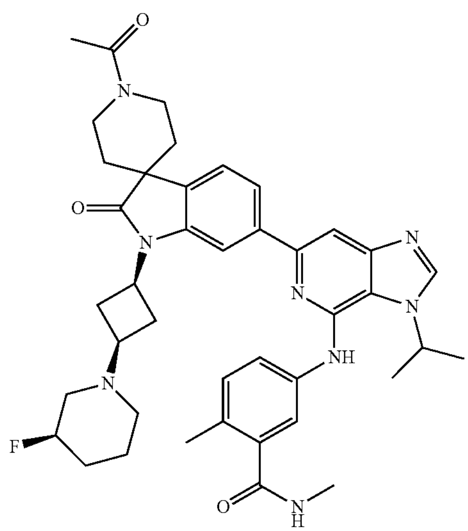 [SMILES: CNC(=O)c1cc(Nc2nc(-c3ccc4c(c3)N([C@H]3C[C@@H](N5CCC[C@@H](F)C5)C3)C(=O)C43CCN(C(C)=O)CC3)cc3ncn(C(C)C)c23)ccc1C] | 162 |
| 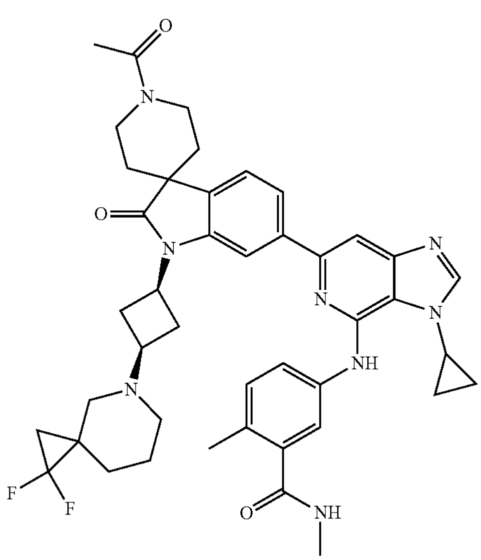 [SMILES: CNC(=O)c1cc(Nc2nc(-c3ccc4c(c3)N([C@H]3C[C@@H](N5CCCC6(C5)CC6(F)F)C3)C(=O)C43CCN(C(C)=O)CC3)cc3ncn(C4CC4)c23)ccc1C] | 163 |

| Structure | Example # |
|---|---|
| 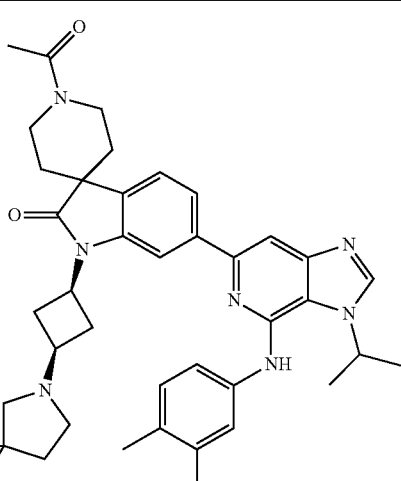 | 164 |
| 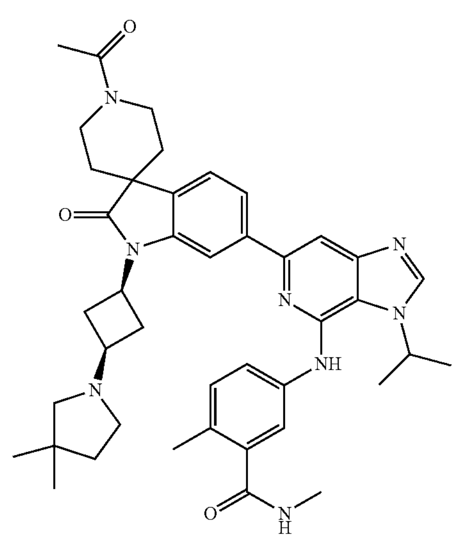 [SMILES: CNC(=O)c1cc(Nc2nc(-c3ccc4c(c3)N([C@H]3C[C@@H](N5CCC(C)(C)C5)C3)C(=O)C43CCN(C(C)=O)CC3)cc3ncn(C(C)C)c23)ccc1C] | 165 |

| Structure | Example # |
|---|---|
| 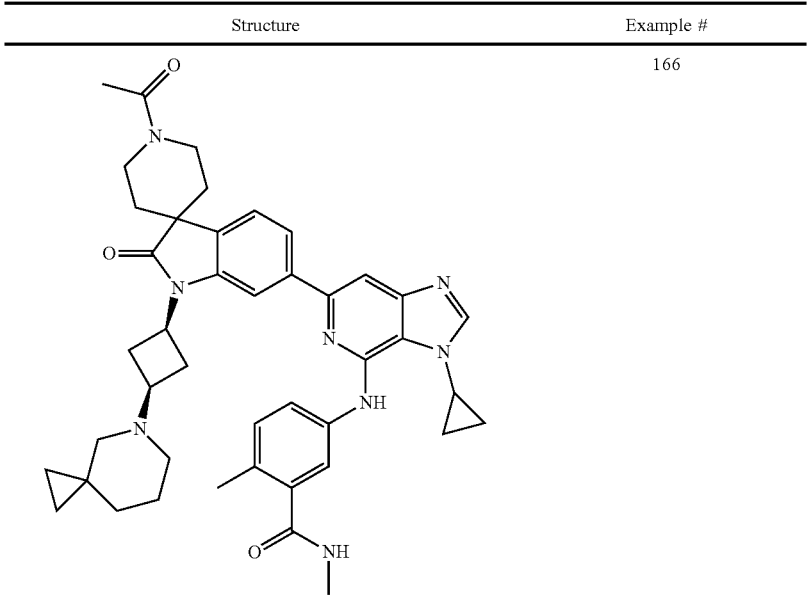 | 166 |
| 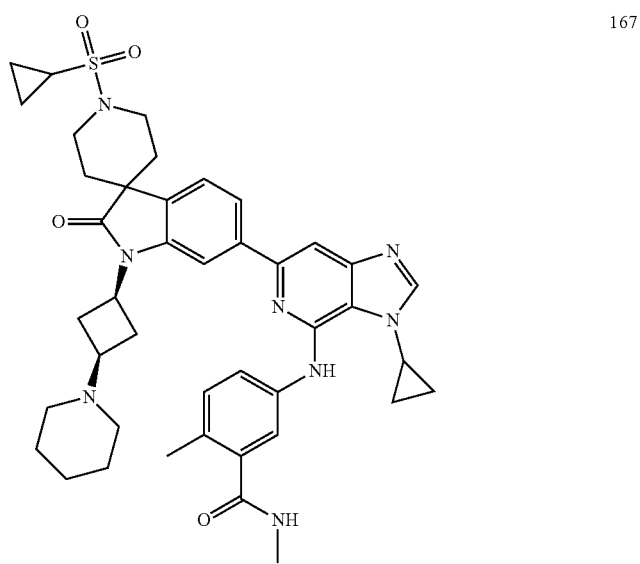 | 167 |

-continued
| Structure | Example # |
|---|---|
| 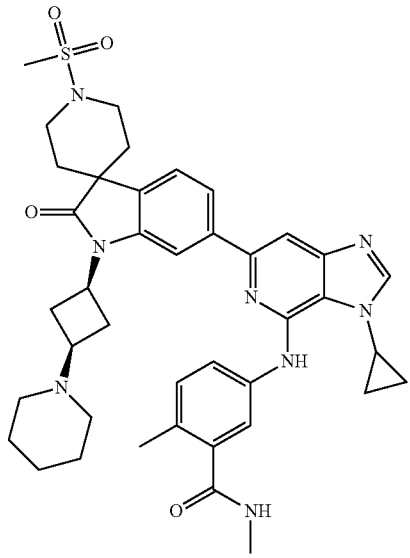 [SMILES: CNC(=O)c1cc(Nc2nc(-c3ccc4c(c3)N([C@H]3C[C@@H](N5CCCCC5)C3)C(=O)C43CCN(S(C)(=O)=O)CC3)cc3ncn(C4CC4)c23)ccc1C] | 168 |
| 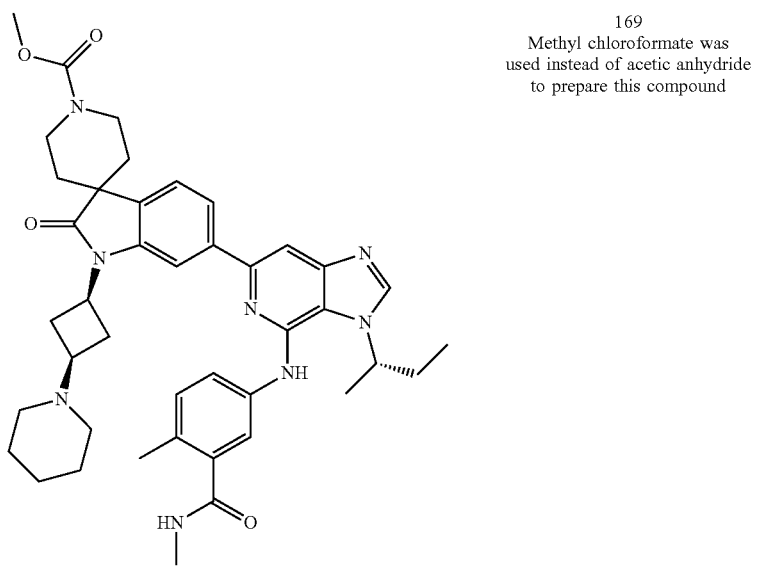 | 169<br>Methyl chloroformate was used instead of acetic anhydride to prepare this compound |

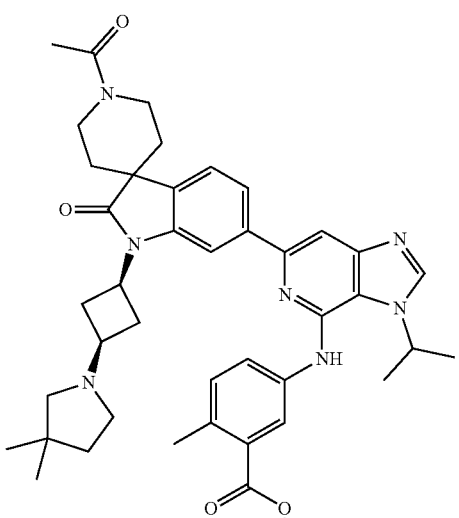

methyl 5-((6-(1'-acetyl-1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)amino)-2-methylbenzoate

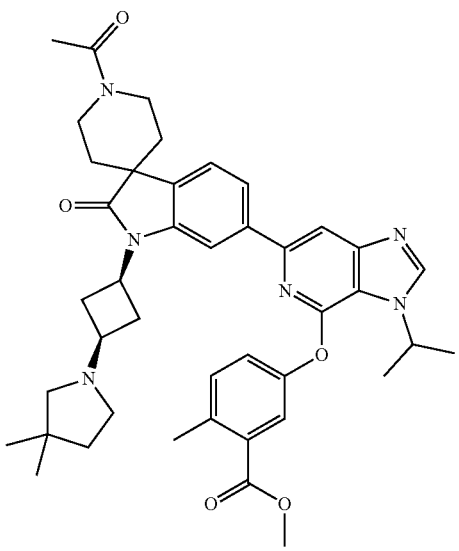 [SMILES: COC(=O)c1cc(Oc2nc(-c3ccc4c(c3)N([C@H]3C[C@@H](N5CCC(C)(C)C5)C3)C(=O)C43CCN(C(C)=O)CC3)cc3ncn(C(C)C)c23)ccc1C]

methyl 5-((6-(1'-acetyl-1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)oxy)-2-methylbenzoate Procedure 25: Preparation of the Compounds of Formula I According to Reaction Scheme IV

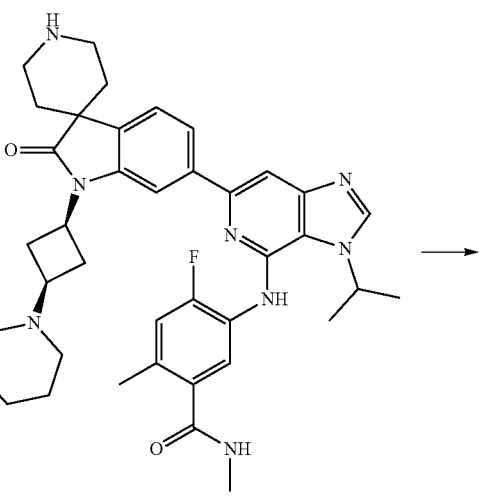

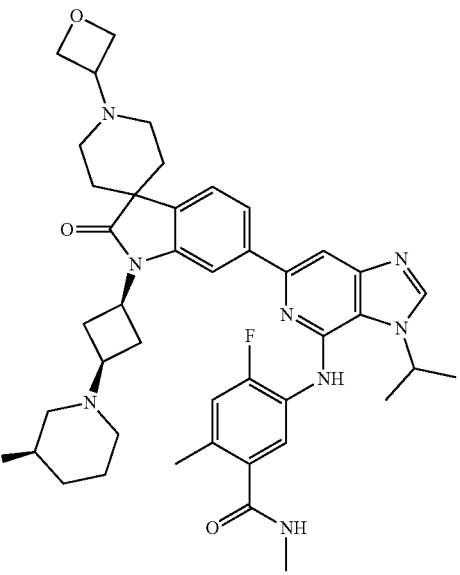

A. Preparation of 4-fluoro-5-((6-(1-((1S,3s)-3-((R)-3-fluoropiperidin-1-yl)cyclobutyl)-1'-(oxetan-3-yl)-2-oxospiro[indoline-3,4'-piperidin]-6-yl)-3-isopropyl-3H-imidazo[4,5-c]pyridin-4-yl)amino)-N,2-dimethylbenzamide (Example 170)

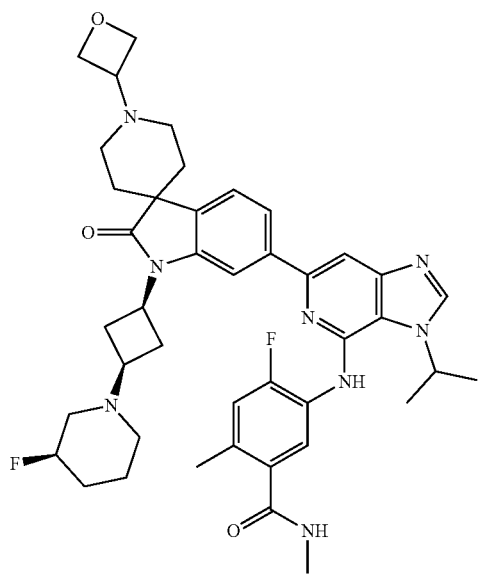 [SMILES: CNC(=O)c1cc(Nc2nc(-c3ccc4c(c3)N([C@H]3C[C@@H](N5CCC[C@@H](F)C5)C3)C(=O)C43CCN(C4COC4)CC3)cc3ncn(C(C)C)c23)c(F)cc1C]

To a mixture of 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide (70 mg, 0.10 mmol) and 3-oxetanone (21 mg, 0.30 mmol) in methanol (3 mL) was added zinc chloride (21 mg, 0.15 mmol) followed by sodium cyanoborohydride (19 mg, 0.30 mmol). The mixture was sealed and heated at 50° C. for 16 h., then cooled, quenched with saturated aqueous sodium bicarbonate, and extracted with dichloromethane. The combined organic layers were dried over sodium sulfate, filtered, concentrated, and purified on Gilson reverse phase HPLC to give 4-fluoro-5-((6-(1-((1S,3s)-3-((R)-3-fluoropiperidin-1-yl)cyclobutyl)-1'-(oxetan-3-yl)-2-oxospiro[indoline-3,4'-piperidin]-6-yl)-3-isopropyl-3H-imidazo[4,5-c]pyridin-4-yl)amino)-N,2-dimethylbenzamide.

The following compounds were prepared using a similar procedure with the following modification(s):

5-((3-cyclopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-N,2-dimethylbenzamide was used instead of 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide; and/or N-ethyl-4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-2-methylbenzamide and 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N-isopropyl-2-methylbenzamide were used instead of 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N,2-dimethylbenzamide; and/or 4-fluoro-5-((6-(1-((1S,3s)-3-((R)-3-fluoropiperidin-1-yl)cyclobutyl)-2-oxospiro[indoline-3,4'-piperidin]-6-yl)-3-isopropyl-3H-imidazo[4,5-c]pyridin-4-yl)amino)-N-isopropyl-2-methylbenzamide:

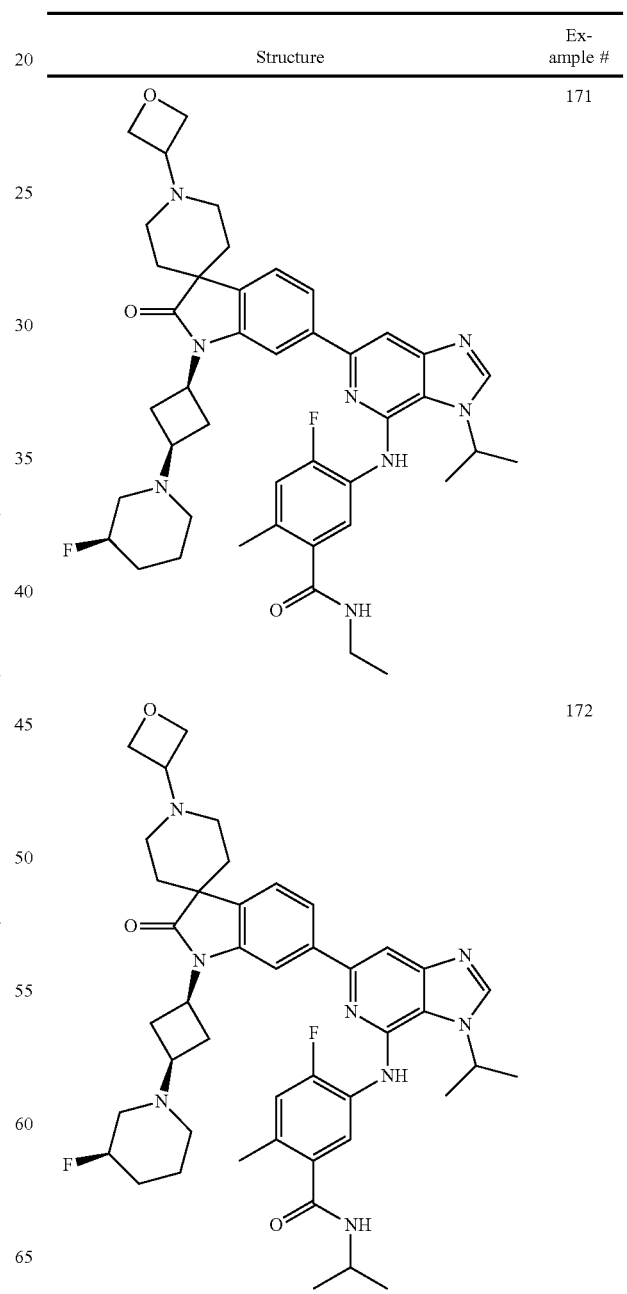

| Structure | Example # |
|---|---|
| 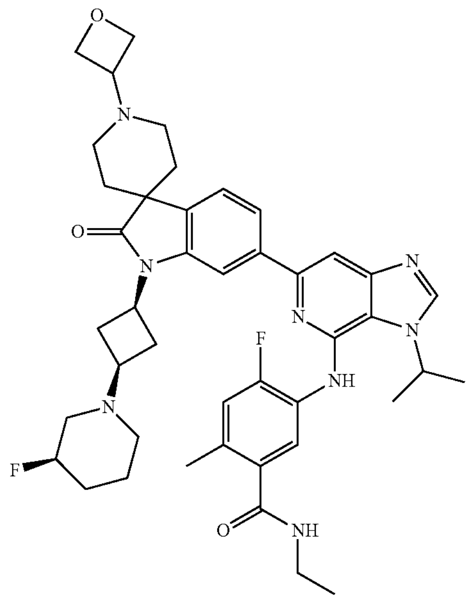 [SMILES: CCNC(=O)c1cc(Nc2nc(-c3ccc4c(c3)N([C@H]3C[C@@H](N5CCC[C@@H](F)C5)C3)C(=O)C43CCN(C4COC4)CC3)cc3ncn(C(C)C)c23)c(F)cc1C] | 171 |
| 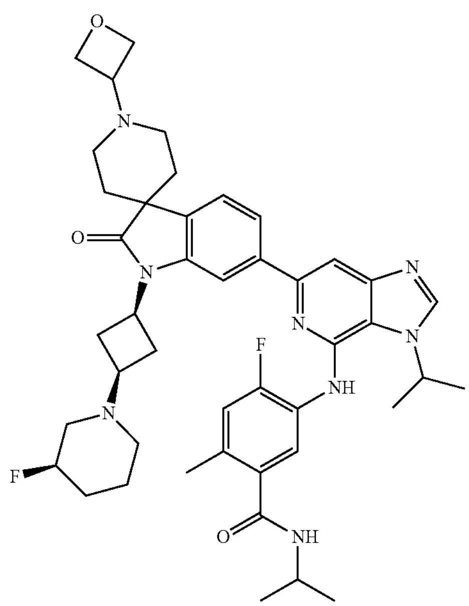 [SMILES: Cc1cc(F)c(Nc2nc(-c3ccc4c(c3)N([C@H]3C[C@@H](N5CCC[C@@H](F)C5)C3)C(=O)C43CCN(C4COC4)CC3)cc3ncn(C(C)C)c23)cc1C(=O)NC(C)C] | 172 |

483
-continued

| Structure | Example # |
|---|---|
| 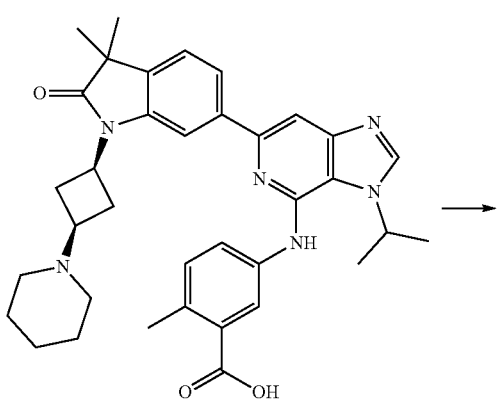 | 173 |

Procedure 26: Preparation of the Compounds of Formula I According to Reaction Scheme II

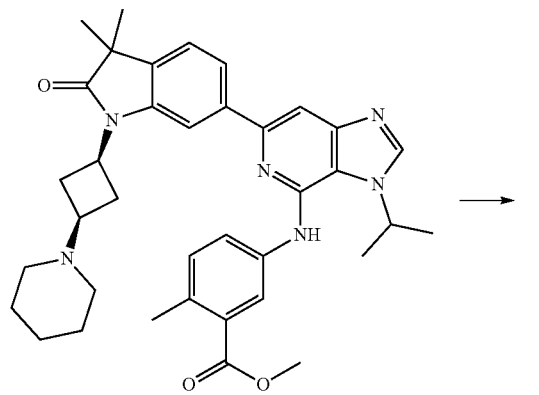

484
-continued

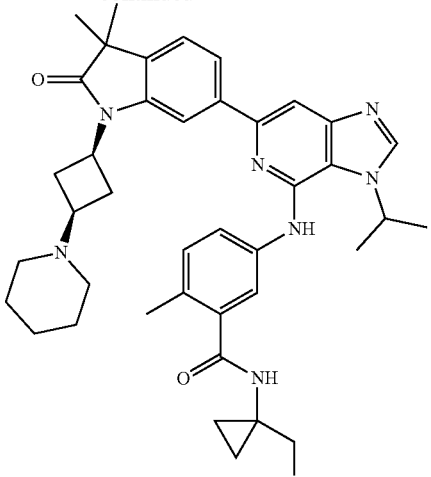

A. Preparation of 5-((6-(3,3-dimethyl-2-oxo-1-((1s, 3s)-3-(piperidin-1-yl)cyclobutyl)indolin-6-yl)-3-isopropyl-3H-imidazo[4,5-c]pyridin-4-yl)amino)-2-methylbenzoic acid

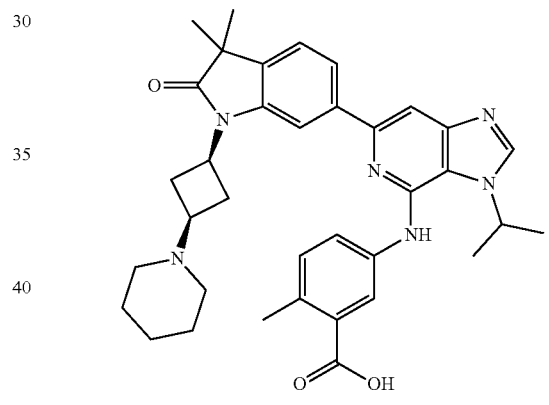

To a stirring solution of methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoate (430 mg, 0.69 mmol) in THF (20 ml) and MeOH (10 ml) was added LiOH.H$_2$O (33 mg, 1.39 mmol). The resulting mixture was warmed to 40° C. and then stirred for 2 days. After cooling to room temperature, the reaction mixture was concentrated to give 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid, which was used in the next step without further purification.

The following compounds were prepared using a similar procedure with the following modification(s):
  NaOH was used instead of LiOH; and/or
  Methyl 5-((6-(1'-acetyl-2-oxo-1-((1s,3s)-3-(piperidin-1-yl)cyclobutyl)spiro[indoline-3,4'-piperidin]-6-yl)-3-isopropyl-3H-imidazo[4,5c]pyridin-4-yl)amino)-2,4-difluorobenzoate was used instead of methyl 5-((6-(3, 3-dimethyl-2-oxo-1-((1s,3s)-3-(piperidin-1-yl) cyclobutyl)indolin-6-yl)-3-isopropyl-3H-imidazo[4,5-c]pyridin-4-yl)amino)-2-methylbenzoate; and/or Methyl 5-((6-(1'-acetyl-1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)oxy)-2-methylbenzoate was used instead of methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoate; and/or
methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2,4-difluorobenzoate was used instead of methyl 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoate:

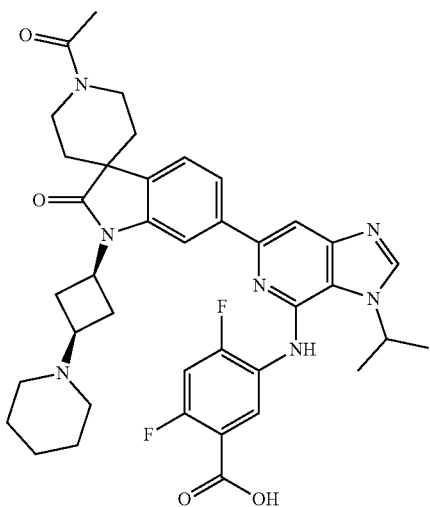 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)O)c(F)cc4F)n3)ccc12]

5-((6-(1'-Acetyl-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-2,4-difluorobenzoic acid

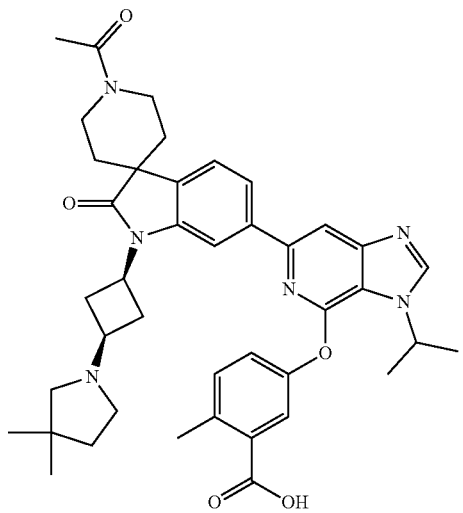 [SMILES: CC(=O)N1CCC2(CC1)C(=O)N([C@H]1C[C@@H](N3CCC(C)(C)C3)C1)c1cc(-c3cc4ncn(C(C)C)c4c(Oc4ccc(C)c(C(=O)O)c4)n3)ccc12]

5-((6-(1'-Acetyl-1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)oxy)-2-methylbenzoic acid

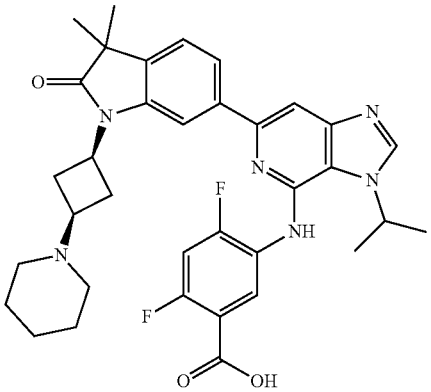 [SMILES: CC(C)n1cnc2cc(-c3ccc4c(c3)N([C@H]3C[C@@H](N5CCCCC5)C3)C(=O)C4(C)C)nc(Nc3cc(C(=O)O)c(F)cc3F)c21]

5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2,4-difluorobenzoic acid B. Preparation of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-N-(1-(fluoromethyl)cyclopropyl)-2-methylbenzamide (Example 174)

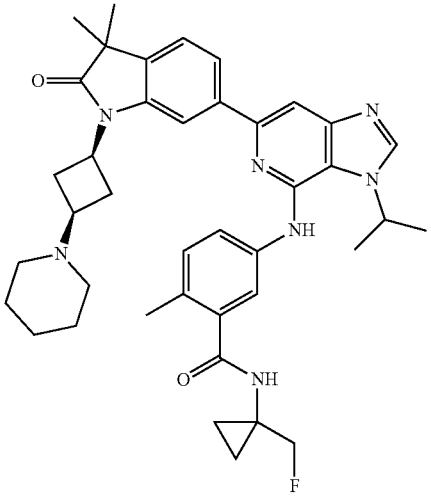 [SMILES: Cc1ccc(Nc2nc(-c3ccc4c(c3)N([C@H]3C[C@@H](N5CCCCC5)C3)C(=O)C4(C)C)cc3ncn(C(C)C)c23)cc1C(=O)NC1(CF)CC1]

To a stirring solution of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid (1.45 g, 2.4 mmol) in DMF (5 ml) were added 1-(fluoromethyl)cyclopropan-1-amine hydrochloride (300 mg, 2.4 mmol), HATU (1.8 g, 4.7 mmol), and DIEA (2.5 ml, 14.4 mmol). The resulting mixture was stirred until the starting material was sufficiently consumed. The reaction solution was quenched with water and the aqueous layer was extracted with EtOAc. The combined organic layer was washed with brine, dried over $Na_2SO_4$, concentrated, and purified by reverse phase chromatography (ACN/water) to give 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-N-(1-(fluoromethyl)cyclopropyl)-2-methylbenzamide.

The following compounds were prepared using a similar procedure with the following modification(s):

- 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-4-fluoro-2-methylbenzoic acid was used instead of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid; or
- 5-((6-(1-acetyl-2'-oxo-1'-((1s,3s)-3-(piperidin-1-yl)cyclobutyl)spiro[azetidine-3,3'-indolin]-6'-yl)-3-isopropyl-3H-imidazo[4,5-c]pyridin-4-yl)amino)-4-fluoro-2-methylbenzoic acid was used instead of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid; or
- 5-((6-(1'-acetyl-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-2,4-difluorobenzoic acid was used instead of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid; or
- 5-((6-(1'-acetyl-1-((1s,3s)-3-(3,3-dimethylpyrrolidin-1-yl)cyclobutyl)-2-oxospiro[indoline-3,4'-piperidin]-6-yl)-3-isopropyl-3H-imidazo[4,5-c]pyridin-4-yl)oxy)-2-methylbenzoic acid was used instead of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid; or
- 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2,4-difluorobenzoic acid was used instead of 5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzoic acid; and The commercially available amines, such as methylamine, ethylamine, and isopropylamine, were used instead of 1-(fluoromethyl)cyclopropan-1-aminehydrochloride:

| Structure | Example # |
|---|---|
| 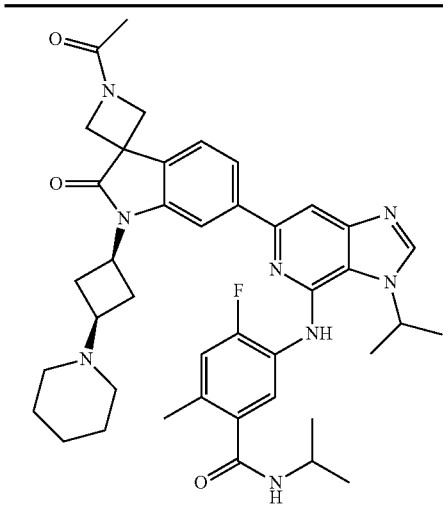 | 179 |
| 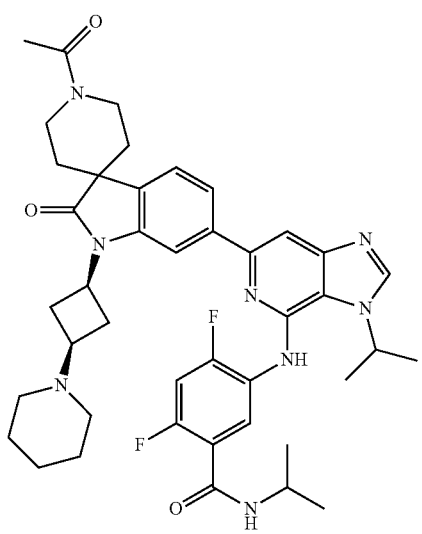 [SMILES: CC(=O)N1CCC2(CC1)C(=O)N([C@H]1C[C@@H](N3CCCCC3)C1)c1cc(-c3cc4ncn(C(C)C)c4c(Nc4cc(C(=O)NC(C)C)c(F)cc4F)n3)ccc12] | 180 |
| 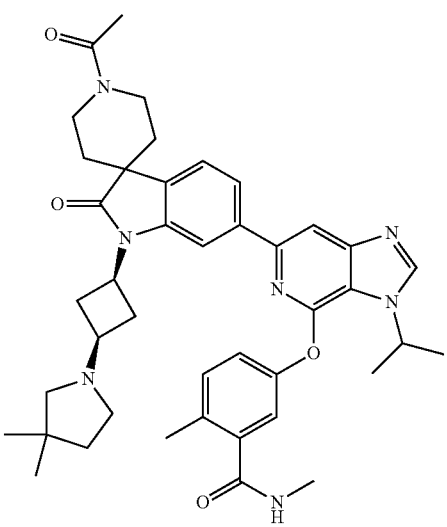 [SMILES: CNC(=O)c1cc(Oc2nc(-c3ccc4c(c3)N([C@H]3C[C@@H](N5CCC(C)(C)C5)C3)C(=O)C43CCN(C(C)=O)CC3)cc3ncn(C(C)C)c23)ccc1C] | 181 |

| Structure | Example # |
|---|---|
| 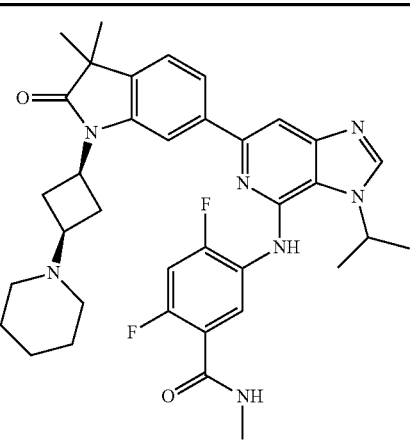 | 182 |

Procedure 27: Preparation of the Compounds of Formula (8) According to Reaction Scheme I A. Preparation of 5-amino-4-fluoro-N-(1-(methoxymethyl)cyclopropyl)-2-methylbenzamide

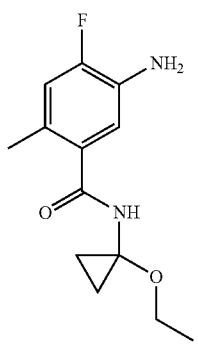 [SMILES: CCOC1(NC(=O)c2cc(N)c(F)cc2C)CC1]

To a mixture of 5-amino-4-fluoro-2-methylbenzoic acid (200.0 mg, 1.2 mmol), 1-(methoxymethyl)cyclopropan-1-amine (235.4 mg, 2.4 mmol), and DIPEA (1.0 mL, 5.9 mmol) was added T3P (1.4 mL, 2.4 mmol). After stirring at room temperature for 48 h, the reaction was quenched with water and the organic layers were extracted with EtOAc. The combined organic layers were washed with water and brine, dried (Na₂SO₄), and concentrated to give 5-amino-4-fluoro-N-(1-(methoxymethyl)cyclopropyl)-2-methylbenzamide, which was used in the next step without purification.

The following compounds were prepared using a similar procedure with the following modification(s):
  the amines indicated below were used instead of 1-(methoxymethyl)cyclopropan-1-amine; and/or
  the benzoic acids indicated below were used instead of 5-amino-4-fluoro-2-methylbenzoic acid:

491

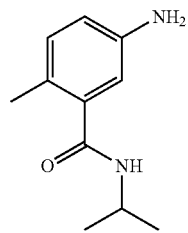

iso-Propylamine and 5-amino-2-methylbenzoic acid were used to prepare 5-amino-N-isopropyl-2-methylbenzamide

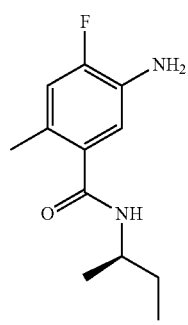 [SMILES: CC[C@@H](C)NC(=O)c1cc(N)c(F)cc1C]

(R)-Butan-2-amine was used to prepare (R)-5-amino-N-(sec-butyl)-4-fluoro-2-methylbenzamide

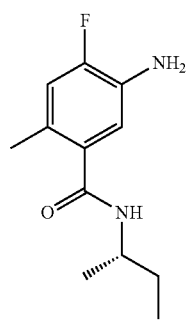 [SMILES: CC[C@H](C)NC(=O)c1cc(N)c(F)cc1C]

(S)-Butan-2-amine was used to prepare (S)-5-amino-N-(sec-butyl)-4-fluoro-2-methylbenzamide

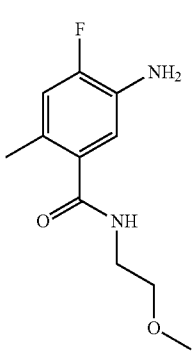

2-Methoxyethan-1-amine was used to prepare 5-amino-4-fluoro-N-(2-methoxyethyl)-2-methylbenzamide

492

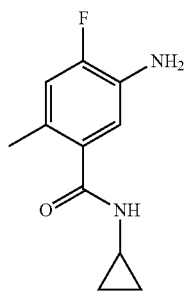

Cyclopropanamine was used to prepare 5-amino-N-cyclopropyl-4-fluoro-2-methylbenzamide

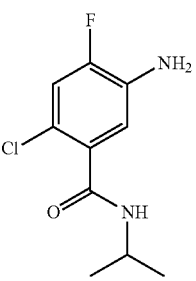

iso-Propylamine and 5-amino-2-chloro-4-fluorobenzoic acid were used to prepare 5-amino-2-chloro-4-fluoro-N-isopropylbenzamide

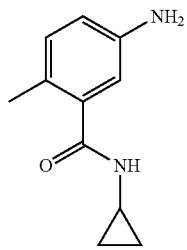

cyclo-Propylamine and 5-amino-2-methylbenzoic acid were used to prepare 5-amino-N-cyclopropyl-2-methylbenzamide

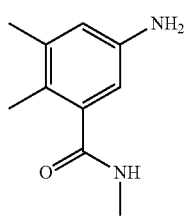

Methylamine and 5-amino-2,3-dimethylbenzoic acid were used to prepare 5-amino-N,2,3-trimethylbenzamide

493

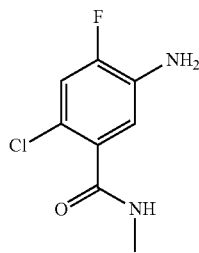

Methylamine and 5-amino-2-chloro-4-fluorobenzoic acid were used to prepare 5-amino-N,2,3-trimethylbenzamide B. Preparation of
3-amino-4-fluoro-N-methylbenzamide

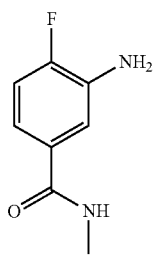

To a mixture of 3-amino-4-fluorobenzoic acid (100.0 mg, 0.7 mmol) and TEA (0.2 mL, 1.4 mmol) in DMF (2 mL) was added HATU (367.67 mg, 0 mol) followed by methylamine in 1 M THF (1.9 mL, 1.9 mmol). After stirring at room temperature overnight, the reaction was quenched with water and the organic layers were extracted with EtOAc. The combined organic layers were washed with water and brine, dried ($Na_2SO_4$), and concentrated to give 3-amino-4-fluoro-N-methylbenzamide, which was used in the next step without purification.

The following compounds were prepared using a similar procedure with the following modification(s):
- the amines indicated below were used instead of methylamine; and/or
- the benzoic acids indicated below were used instead of 3-amino-4-fluorobenzoic acid:

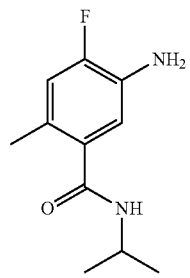

iso-Propylamine and 5-amino-4-fluoro-2-methylbenzoic acid were used to prepare 5-amino-4-fluoro-N-isopropyl-2-methylbenzamide

494

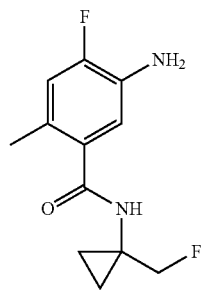 [SMILES: Cc1cc(F)c(N)cc1C(=O)NC1(CF)CC1]

1-(Fluoromethyl)cyclopropan-1-amine and 5-amino-4-fluoro-2-methylbenzoic acid were used to prepare 5-amino-4-fluoro-N-(1-(fluoromethyl)cyclopropyl)-2-methylbenzamide

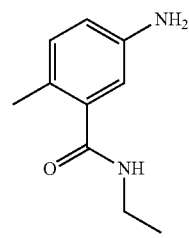

Ethylamine and 5-amino-2-methylbenzoic acid were used to prepare 5-amino-N-ethyl-2-methylbenzamide

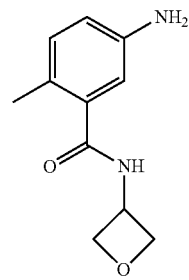

Oxetan-3-amine and 5-amino-2-methylbenzoic acid were used to prepare 5-amino-2-methyl-N-(oxetan-3-yl)benzamide

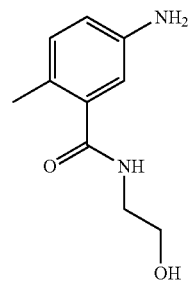

2-Aminoethan-1-ol and 5-amino-2-methylbenzoic acid were used to prepare 5-amino-N-(2-hydroxyethyl)-2-methylbenzamide

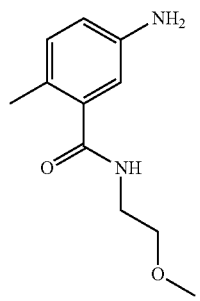

2-Methoxyethan-1-amine and 5-amino-2-methylbenzoic acid were used to prepare 5-amino-N-(2-methoxyethyl)-2-methylbenzamide Procedure 28: Preparation of the Compounds of Formula I According to Reaction Scheme III A. Preparation of 5-bromo-N-isopropyl-2-methylbenzamide

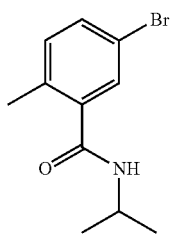

To a solution of 5-bromo-2-methylbenzoic acid (0.50 g, 2.33 mmol), HATU (1.77 g) and isopropylamine (0.499 mL, 5.81 mmol) in DMF (5 mL) was added DIPEA (1.01 mL, 5.81 mmol). The reaction was stirred at room temperature for 5 hours. Water was added to the reaction mixture and the resulting precipitate was isolated by filtration and washed with a solution of 1N HCl to give 5-bromo-N-isopropyl-2-methylbenzamide.

The following compounds were prepared using a similar procedure with the following modification(s):
  the amines indicated below were used instead of isopropylamine; and/or
  the benzoic acids indicated below were used instead of 5-bromo-2-methylbenzoic acid

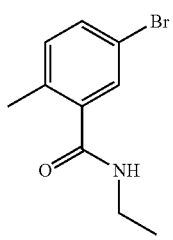

Ethylamine was used to prepare 5-bromo-N-ethyl-2-methylbenzamide

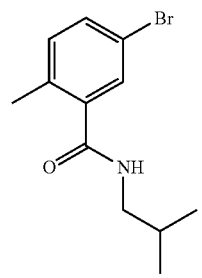

iso-Butylamine was used to prepare 5-bromo-N-isobutyl-2-methylbenzamide

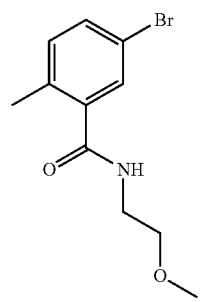

2-Methoxyethan-1-amine was used to prepare 5-bromo-N-(2-methoxyethyl)-2-methylbenzamide

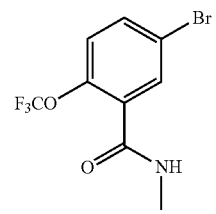

Methylamine and 5-bromo-2-(trifluoromethoxy)benzoic acid were used to prepare 5-bromo-N-methyl-2-(trifluoromethoxy)benzamide

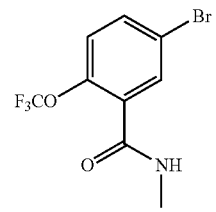

Methylamine and 5-bromo-2-(trifluoromethyl)benzoic acid were used to prepare 5-bromo-N-methyl-2-(trifluoromethyl)benzamide

497

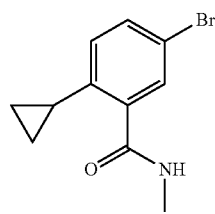

Methylamine and 5-bromo-2-cyclopropylbenzoic acid were used to prepare 5-bromo-2-cyclopropyl-N-methylbenzamide

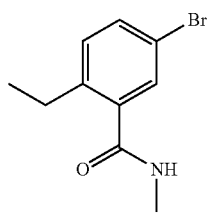

Methylamine and 5-bromo-2-ethylbenzoic acid were used to prepare 5-bromo-2-ethyl-N-methylbenzamide

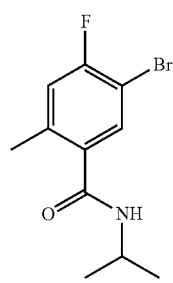

5-bromo-4-fluoro-2-methylbenzoic acid was used to prepare 5-bromo-4-fluoro-N-isopropyl-2-methylbenzamide

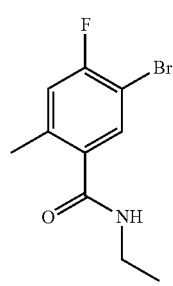

Ethylamine and 5-bromo-4-fluoro-2-methylbenzoic acid were used to prepare 5-bromo-N-ethyl-4-fluoro-2-methylbenzamide

498

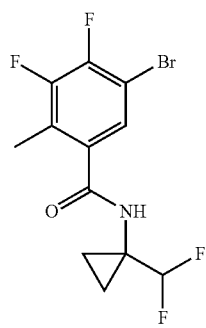 [SMILES: Cc1c(C(=O)NC2(C(F)F)CC2)cc(Br)c(F)c1F]

1-(Difluoromethyl)cyclopropan-1-amine and 5-bromo-3,4-difluoro-2-methylbenzoic acid were used to prepare 5-bromo-N-(1-(difluoromethyl)cyclopropyl)-3,4-difluoro-2-methylbenzamide Procedure 29: Preparation of the Compounds of Formula (26) According to Reaction Scheme VII

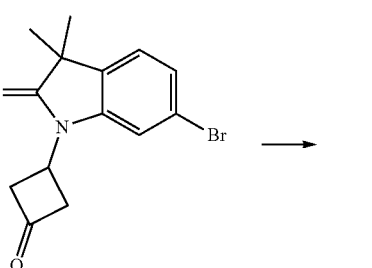

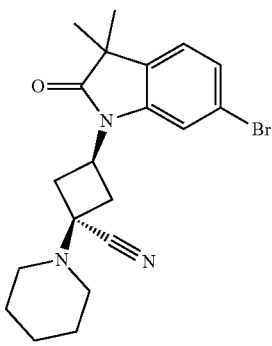 [SMILES: CC1(C)C(=O)N([C@H]2C[C@@](C#N)(N3CCCCC3)C2)c2cc(Br)ccc21]

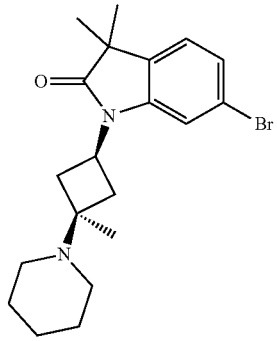 [SMILES: CC1(C)C(=O)N([C@H]2C[C@@](C)(N3CCCCC3)C2)c2cc(Br)ccc21]

499

A. Preparation of (1s,3s)-3-(6-bromo-3,3-dimethyl-2-oxoindolin-1-yl)-1-(piperidin-1-yl)cyclobutane-1-carbonitrile

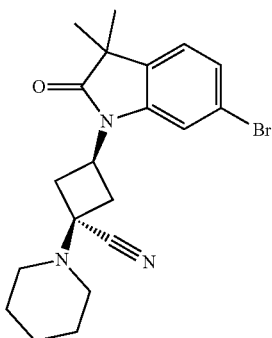

To a stirring solution of 6-bromo-3,3-dimethyl-1-(3-oxo-cyclobutyl)indolin-2-one (1.3 g, 4.16 mmol) in AcOH (7.0 ml) were added piperidine (2.1 ml, 20.8 mmol) and TMS-CN (1.0 ml, 8.3 mmol) at 0° C. The reaction mixture was warmed to room temperature and then stirred for an additional 15 h. The reaction mixture was concentrated and the residue was re-dissolved in EtOAc and the organic layer was washed with satd. NaHCO₃, water followed by brine, dried over Na₂SO₄, concentrated, and purified by flash chromatography (Hexanes/EtOAc) to afford (1s,3s)-3-(6-bromo-3,3-dimethyl-2-oxoindolin-1-yl)-1-(piperidin-1-yl)cyclobutane-1-carbonitrile.

B. Preparation of 6-bromo-3,3-dimethyl-1-((1s,3s)-3-methyl-3-(piperidin-1-yl)cyclobutyl)indolin-2-one

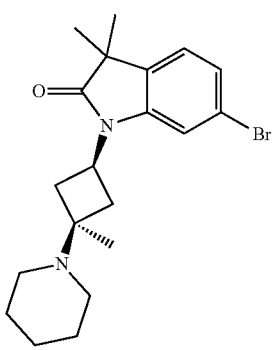

To a stirring solution of (1s,3s)-3-(6-bromo-3,3-dimethyl-2-oxoindolin-1-yl)-1-(piperidin-1-yl)cyclobutane-1-carbonitrile (300 mg, 0.75 mmol) in THF (10 ml) was added 1.0 M MeMgBr (2.2 ml, 2.24 mmol, THF) at 0° C. The resulting mixture was allowed to warm to room temperature and then stirred for an additional 15 h. The reaction mixture was quenched with satd. NH₄Cl and the aqueous layer was extracted with EtOAC. The combined organic layer was washed with brine, dried over Na₂SO₄, concentrated, and purified by flash chromatography (Hexanes/EtOAc) to afford 6-bromo-3,3-dimethyl-1-((1s,3s)-3-methyl-3-(piperidin-1-yl)cyclobutyl)indolin-2-one.

500

Procedure 30: Preparation of the Compounds of Formula (23) According to Reaction Scheme VII

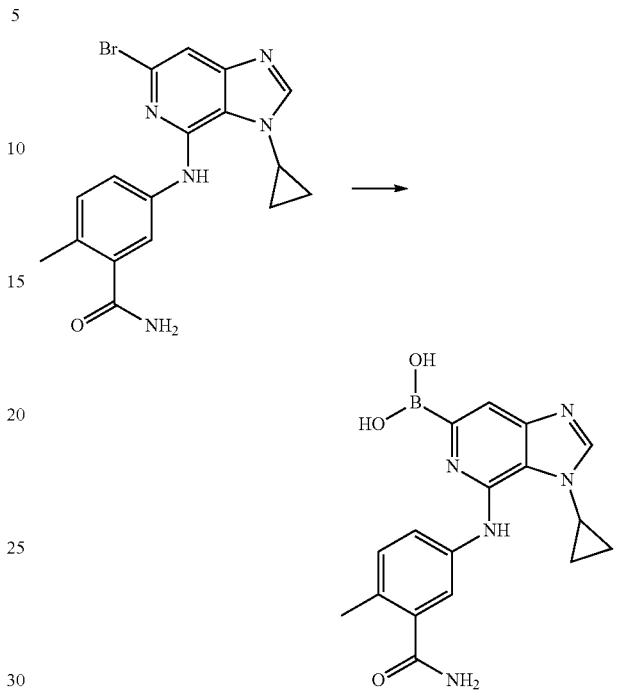

A. Preparation of (4-((3-carbamoyl-4-methylphenyl)amino)-3-cyclopropyl-3H-imidazo[4,5-c]pyridin-6-yl)boronic acid

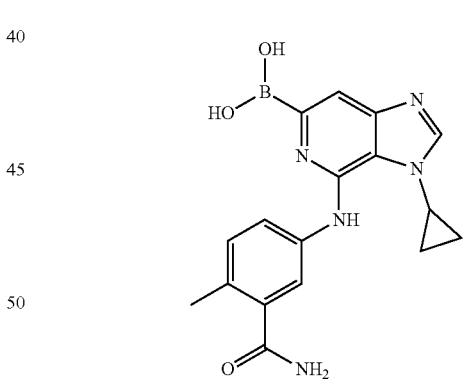

To a stirring solution of 5-((6-bromo-3-cyclopropyl-3H-imidazo[4,5-c]pyridin-4-yl)amino)-2-methylbenzamide (200 mg, 0.52 mmol) in Dioxane (20 ml) were added bis(pinacolato)diboron (263 mg, 1.0 mmol), KOAc (102 mg, 1.0 mmol), and Pd(dppf)Cl₂.DCM (42 mg, 0.052 mmol). The resulting suspension was degassed by bubbling argon gas through (2 min), sealed, and then heated at 90° C. for 15 h. The reaction mixture was cooled to room temperature, filtered, and concentrated to give (4-((3-carbamoyl-4-methylphenyl)amino)-3-cyclopropyl-3H-imidazo[4,5-c]pyridin-6-yl)boronic acid, which was used in the next step without further purification.

Procedure 31: Preparation of the Compounds of Formula I According to Reaction Scheme VII

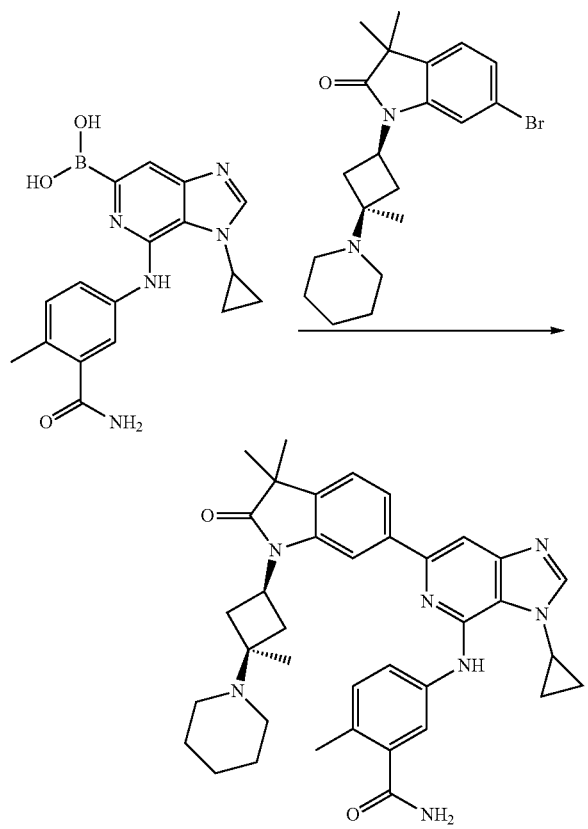

A. Preparation of 5-((3-cyclopropyl-6-(3,3-dimethyl-1-((1s,3s)-3-methyl-3-(piperidin-1-yl)cyclobutyl)-2-oxoindolin-6-yl)-3H-imidazo[4,5-c]pyridin-4-yl)amino)-2-methylbenzamide (Example 183)

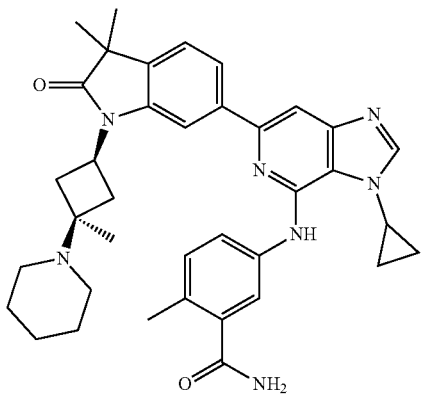 [SMILES: Cc1ccc(Nc2nc(-c3ccc4c(c3)N([C@H]3C[C@@](C)(N5CCCCC5)C3)C(=O)C4(C)C)cc3ncn(C4CC4)c23)cc1C(N)=O]

To a solution of 6-bromo-3,3-dimethyl-1-((1s,3s)-3-methyl-3-(piperidin-1-yl)cyclobutyl)indolin-2-one (40 mg, 0.026 mmol) in DME (3 ml) were added Pd(PPh$_3$)$_4$ (2.0 mg, 0.002 mmol), 2M Na$_2$CO$_3$ (0.06 ml, 0.12 mmol), and (4-((3-carbamoyl-4-methylphenyl)amino)-3-cyclopropyl-3H-imidazo[4,5-c]pyridin-6-yl)boronic acid (18 mg, 0.051 mmol). The resulting suspension was degassed by bubbling Ar gas, sealed, then heated at 120° C. for 30 min. The reaction mixture was cooled to room temperature then diluted with EtOAc. The organic layer was washed with water, brine, dried over Na$_2$SO$_4$, concentrated, and purified by flash chromatography (Hex/EtOAc) to afford 5-((3-cyclopropyl-6-(3,3-dimethyl-1-((1s,3s)-3-methyl-3-(piperidin-1-yl)cyclobutyl)-2-oxoindolin-6-yl)-3H-imidazo[4,5-c]pyridin-4-yl)amino)-2-methylbenzamide.

The following compound was prepared using a similar procedure except 6-bromo-3,3-difluoro-1-((1s,3s)-3-(piperidin-1-yl)cyclobutyl)indolin-2-one was used instead of 6-bromo-3,3-dimethyl-1-((1s,3s)-3-methyl-3-(piperidin-1-yl)cyclobutyl)indolin-2-one:

| Structure | Example # |
|---|---|
| 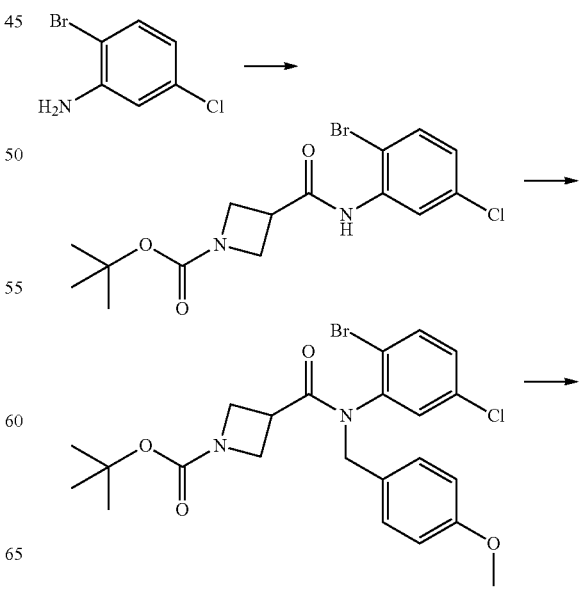 | 184 |

Procedure 32: Preparation of the Compounds of Formula (13) Shown in Reaction Scheme I 503
-continued

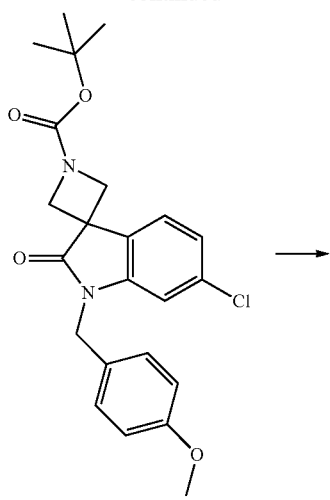

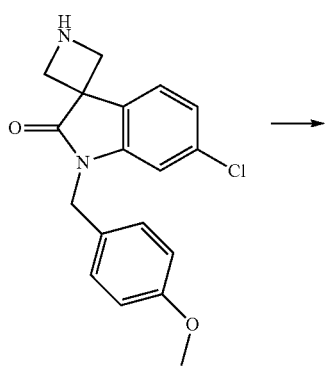

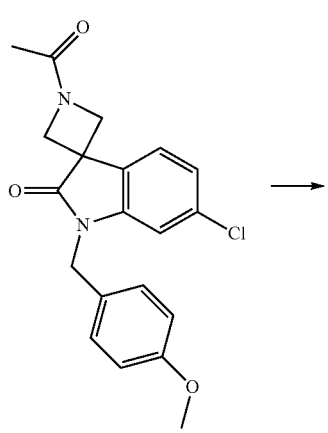

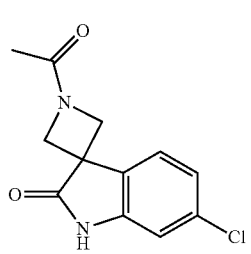

504
-continued

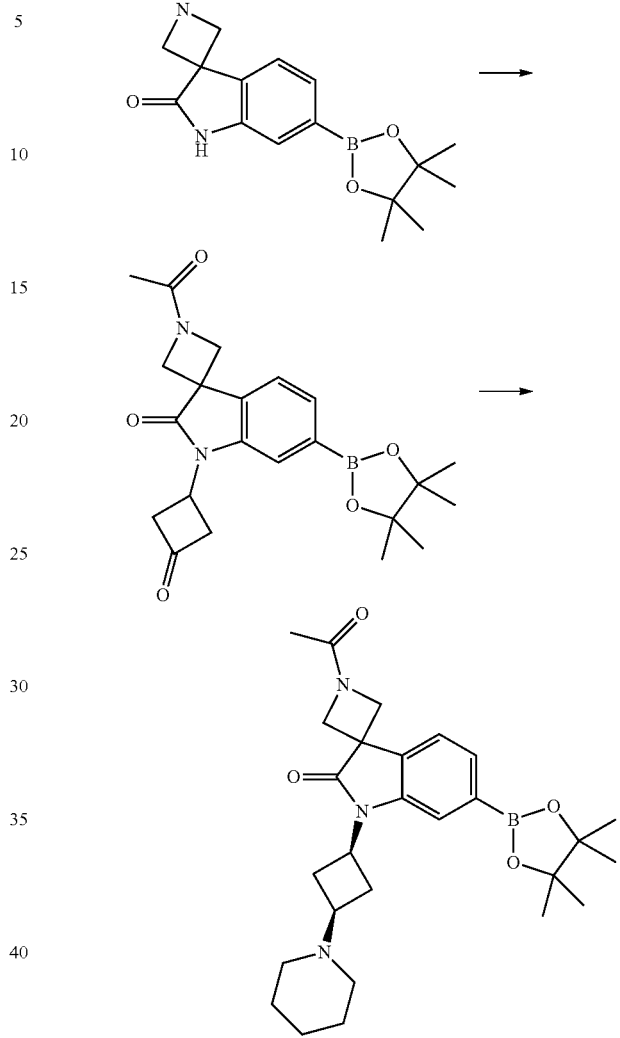

A. Preparation of tert-butyl 3-((2-bromo-5-chlorophenyl)carbamoyl)azetidine-1-carboxylate

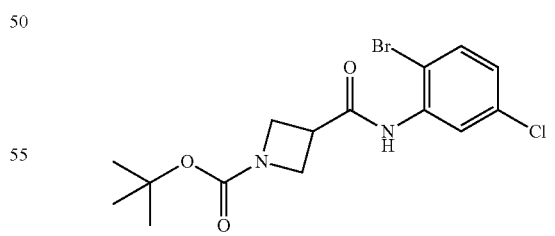

To a stirring solution of 1-(tert-butyl) 3-methyl azetidine-1,3-dicarboxylate (12.5 g, 58.1 mmol, commercially available) and 2-bromo-5-chloroaniline (10 g, 48.4 mmol) in DCM (200 ml) was added trimethylaluminum (2.0 M in toluene, 34 ml, 68 mmol) at 0° C. The resulting mixture was heated at 40° C. for overnight. After the starting material was consumed, the reaction mixture was cool to 0° C. then quenched with water. The aqueous layer was extracted with DCM and the combined organic layer was dried over Na$_2$SO$_4$, concentrated, and purified by flash chromatography (Hexane/EtOAc) to give tert-butyl 3-((2-bromo-5-chlorophenyl)carbamoyl)azetidine-1-carboxylate.

B. Preparation of tert-butyl 3-((2-bromo-5-chlorophenyl)(4-methoxybenzyl)carbamoyl)azetidine-1-carboxylate

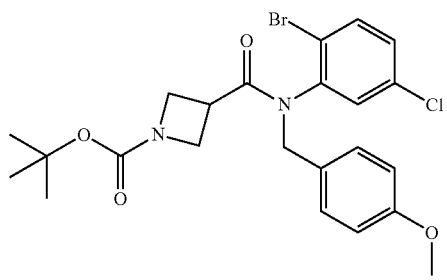 [SMILES: COc1ccc(CN(C(=O)C2CN(C(=O)OC(C)(C)C)C2)c2cc(Cl)ccc2Br)cc1]

To a stirring solution of tert-butyl 3-((2-bromo-5-chlorophenyl)carbamoyl)azetidine-1-carboxylate (10 g, 25.7 mmol) in ACN (200 ml) were added K$_2$CO$_3$ (10.6 g, 77 mmol) and PMBCl (3.83 ml, 28.2 mmol) at room temperature. The resulting mixture was warmed to 85° C. and stirred overnight. Then the resulting suspension was cooled and filtered. The filtrate was concentrated and purified by flash chromatography (Hexane/EtOAc) to afford tert-butyl 3-((2-bromo-5-chlorophenyl)(4-methoxybenzyl)carbamoyl)azetidine-1-carboxylate.

C. Preparation of tert-butyl 6'-chloro-1'-(4-methoxybenzyl)-2'-oxospiro[azetidine-3,3'-indoline]-1-carboxylate

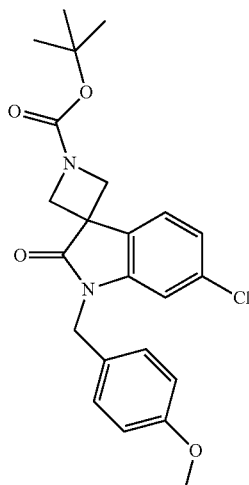

To a stirring solution of tert-butyl 3-((2-bromo-5-chlorophenyl)(4-methoxybenzyl)carbamoyl)azetidine-1-carboxylate (6 g, 11.8 mmol) in dioxane (20 mL) were added PCy$_3$ (0.165 g, 0.588 mmol), Pd(OAc)$_2$ (0.132 g, 0.588 mmol), and sodium tertbutoxide (3.39 g, 35.3 mmol) at room temperature. The resulting mixture was degassed by bubbling argon gas through for 3 minutes. The reaction vessel was sealed and heated at 80° C. for 15 min. After cooling to room temperature, the reaction mixture was quenched with saturated NH$_4$Cl solution. The aqueous layer was extracted with EtOAc. The combined organic layers were washed with brine, dried over Na$_2$SO$_3$, and concentrated to give tert-butyl 6'-chloro-1'-(4-methoxybenzyl)-2'-oxospiro[azetidine-3,3'-indoline]-1-carboxylate, which was used in the next step without further purification.

D. Preparation of 6'-chloro-1'-(4-methoxybenzyl) spiro[azetidine-3,3'-indolin]-2'-one

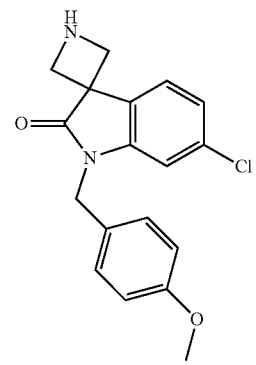 [SMILES: COc1ccc(CN2C(=O)C3(CNC3)c3ccc(Cl)cc32)cc1]

To a stirring solution of tert-butyl 6'-chloro-1'-(4-methoxybenzyl)-2'-oxospiro[azetidine-3,3'-indoline]-1-carboxylate (5.05 g, 11.8 mmol) in methanol (50 ml) was added 4 M HCl in dioxane (14.7 ml, 58.9 mmol). The reaction mixture was stirred overnight and then concentrated. The resulting residue was redissolved with the minimum amount of DCM and then added into a stirring Et$_2$O. The suspension was stirred for additional 30 minutes, filtered, washed with Et$_2$O, and dried to give 6'-chloro-1'-(4-methoxybenzyl)spiro[azetidine-3,3'-indolin]-2'-one.

E. Preparation of 1-acetyl-6'-chloro-1'-(4-methoxybenzyl)spiro[azetidine-3,3'-indolin]-2'-one

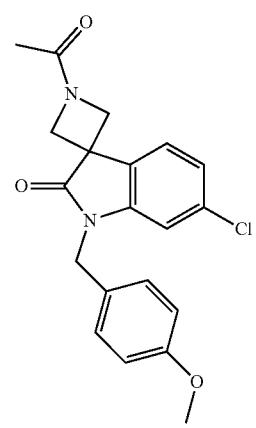 [SMILES: COc1ccc(CN2C(=O)C3(CN(C(C)=O)C3)c3ccc(Cl)cc32)cc1]

To a stirring solution of 6'-chloro-1'-(4-methoxybenzyl)spiro[azetidine-3,3'-indolin]-2'-one (2.23 g, 6.11 mmol) in DCM (20 ml) were added acetic anhydride (0.866 ml, 9.16 mmol) and triethylamine (8.51 ml, 61.1 mmol) at room temperature. After 10 min, the reaction mixture was concentrated and purified by flash chromatography to give 1-acetyl-6'-chloro-1'-(4-methoxybenzyl)spiro[azetidine-3,3'-indolin]-2'-one.

F. Preparation of 1-acetyl-6'-chlorospiro[azetidine-3,3'-indolin]-2'-one

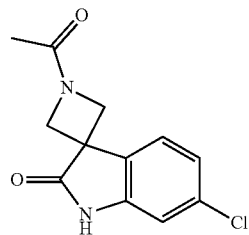 [SMILES: CC(=O)N1CC2(C1)C(=O)Nc1cc(Cl)ccc12]

To a stirring solution of 1-acetyl-6'-chloro-1'-(4-methoxybenzyl)spiro[azetidine-3,3'-indolin]-2'-one. (0.7 g, 1.89 mmol) in DCM (10 ml) were added TfOH (0.835 ml, 9.44 mmol) and TFA (7.22 ml, 94.4 mmol) at room temperature. The reaction mixture was stirred overnight and then concentrated. The residue was dissolved with EtOAc. The organic layer was washed with sat. NaHCO$_3$ and brine, dried over Na$_2$SO$_4$, concentrated, and purified by flash chromatography (DCM/MeOH) to give 1-acetyl-6'-chlorospiro[azetidine-3,3'-indolin]-2'-one.

G. Preparation of 1-acetyl-6'-(4,4,5,5-tetramethyl-1,3,2-dioxaborolan-2-yl)spiro[azetidine-3,3'-indolin]-2'-one

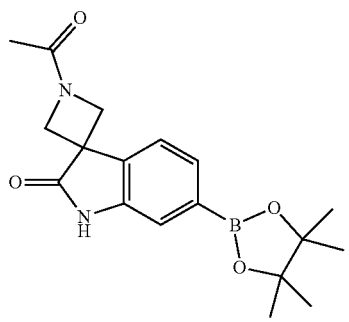 [SMILES: CC(=O)N1CC2(C1)C(=O)Nc1cc(B3OC(C)(C)C(C)(C)O3)ccc12]

To a stirring solution of 1-acetyl-6'-chlorospiro[azetidine-3,3'-indolin]-2'-one (0.35 g, 1.4 mmol) in dioxane were added bis(pinacolato)diboron (1.06 g, 4.19 mmol), potassium acetate (0.411 g, 4.19 mmol), Pd$_2$dba$_3$ (77 mg, 0.084 mmol), and Xantphos (100 mg, 0.209 mmol). The resulting suspension was degassed by bubbling argon gas through for 5 minutes. The reaction vessel was sealed and then heated at 100° C. for overnight. After cooling to room temperature, the reaction mixture was concentrated to give 1-acetyl-6'-(4,4,5,5-tetramethyl-1,3,2-dioxaborolan-2-yl)spiro[azetidine-3,3'-indolin]-2'-one, which was used in the next step without further purification.

H. Preparation of 1-acetyl-1'-(3-oxocyclobutyl)-6'-(4,4,5,5-tetramethyl-1,3,2-dioxaborolan-2-yl)spiro[azetidine-3,3'-indolin]-2'-one

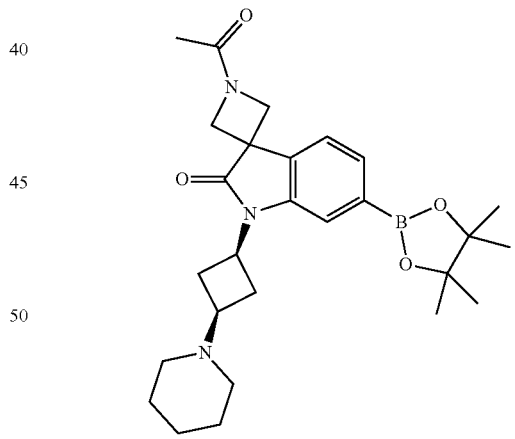

To a stirring solution of 1-acetyl-6'-(4,4,5,5-tetramethyl-1,3,2-dioxaborolan-2-yl)spiro[azetidine-3,3'-indolin]-2'-one (0.478 g, 1.4 mmol) in NMP (5 mL) were added bromocyclobutanone (0.495 ml, 5.58 mmol) and K$_2$CO$_3$ (0.964 g, 6.68 mmol) at room temperature. The resulting mixture was warmed to 50° C. and stirred overnight. After all the starting material was consumed, the reaction mixture was cooled to room temperature and then filtered. The filtrate was diluted with EtOAc. The organic layer was washed with water followed by brine, dried over Na$_2$SO$_4$, and concentrated to give 1-acetyl-1'-(3-oxocyclobutyl)-6'-(4,4,5,5-tetramethyl-1,3,2-dioxaborolan-2-yl)spiro[azetidine-3,3'-indolin]-2'-one, which was used in the next step without further purification.

I. Preparation of 1-acetyl-1'-((1s,3s)-3-(piperidin-1-yl)cyclobutyl)-6'-(4,4,5,5-tetramethyl-1,3,2-dioxaborolan-2-yl)spiro[azetidine-3,3'-indolin]-2'-one To a solution of 1-acetyl-1'-(3-oxocyclobutyl)-6'-(4,4,5,5-tetramethyl-1,3,2-dioxaborolan-2-yl)spiro[azetidine-3,3'-indoline]-2'-one (1 g, 2.44 mmol) and piperidine (0.96 ml, 9.75 mmol) in DCM (10 ml) were added acetic acid, ACS reagent (0.88 ml, 14.62 mmol) and sodium triacetoxyborohydride (1.55 g, 7.31 mmol). After the mixture was stirred for 2 h at room temperature, the mixture was quenched with sat. NaHCO$_3$ and extracted with DCM. The combined organic layers were dried over Na$_2$SO$_4$, filtered, and concentrated to give 1-acetyl-1'-((1s,3s)-3-(piperidin-1-yl)cyclobutyl)-6'-(4,4,5,5-tetramethyl-1,3,2-dioxaborolan-2-yl)spiro[azetidine-3,3'-indolin]-2'-one, which was used in the next step without further purification.

Procedure 33: Preparation of the Compounds of Formula (27) According to Reaction Scheme VI

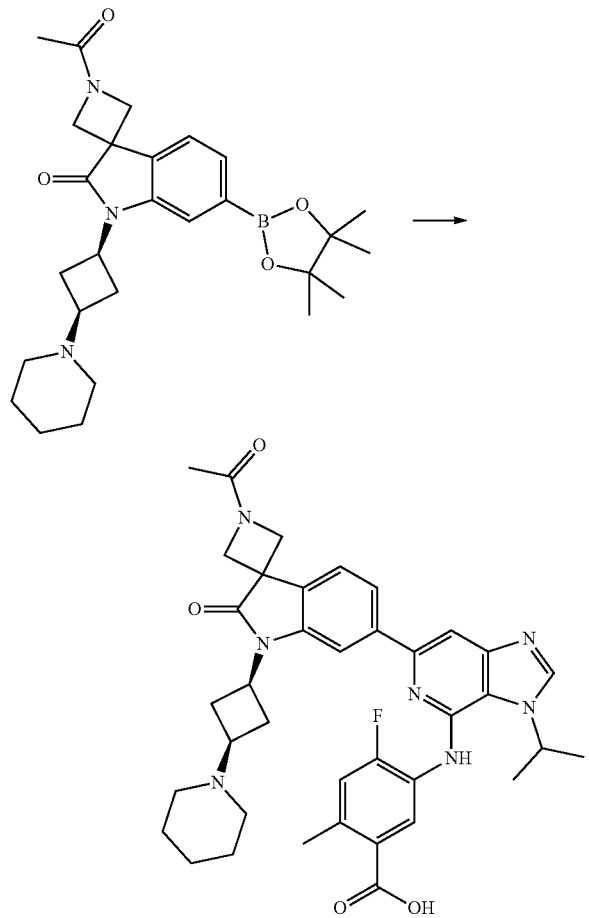

A. Preparation of 5-((6-(1-acetyl-2'-oxo-1'-((1s,3s)-3-(piperidin-1-yl)cyclobutyl)spiro[azetidine-3,3'-indolin]-6'-yl)-3-isopropyl-3H-imidazo[4,5-c]pyridin-4-yl)amino)-4-fluoro-2-methylbenzoic acid

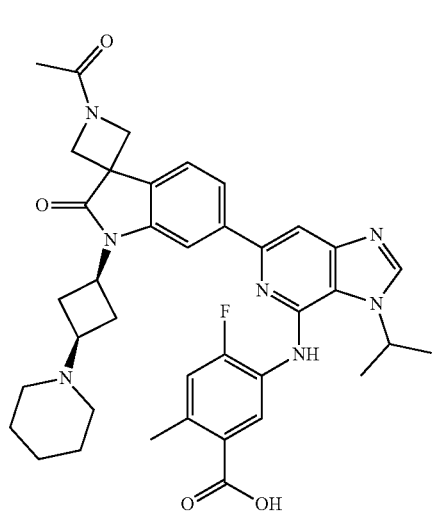 [SMILES: CC(=O)N1CC2(C1)C(=O)N([C@H]1C[C@@H](N3CCCCC3)C1)c1cc(-c3cc4ncn(C(C)C)c4c(Nc4cc(C(=O)O)c(C)cc4F)n3)ccc12]

To a mixture of 1-acetyl-1'-((1s,3s)-3-(piperidin-1-yl)cyclobutyl)-6'-(4,4,5,5-tetramethyl-1,3,2-dioxaborolan-2-yl)spiro[azetidine-3,3'-indolin]-2'-one (0.5 g, 1.04 mmol), 5-((6-bromo-3-isopropyl-3H-imidazo[4,5-c]pyridin-4-yl)amino)-4-fluoro-2-methylbenzoic acid (0.25 g, 0.63 mmol) and Pd(PPh$_3$)$_4$ (120.51 mg, 0.1 mmol) in a seal tube was added 2M Na$_2$CO$_3$ (3.65 ml) and DME (10 ml). After the mixture was heated at 90° C. for 1 h, the mixture was diluted with EtOAc and water. To the resulting mixture was added citric acid to adjust the pH to ca. 6. The organic layers were extracted with DCM, and the combined organic layers were concentrated and purified by flash chromatography (100% DCM to 100% MeOH) to afford 5-((6-(1-acetyl-2'-oxo-1'-((1s,3s)-3-(piperidin-1-yl)cyclobutyl)spiro[azetidine-3,3'-indolin]-6'-yl)-3-isopropyl-3H-imidazo[4,5-c]pyridin-4-yl)amino)-4-fluoro-2-methylbenzoic acid.

Procedure 34: Preparation of the Compounds of Formula (9) Shown in Reaction Scheme I

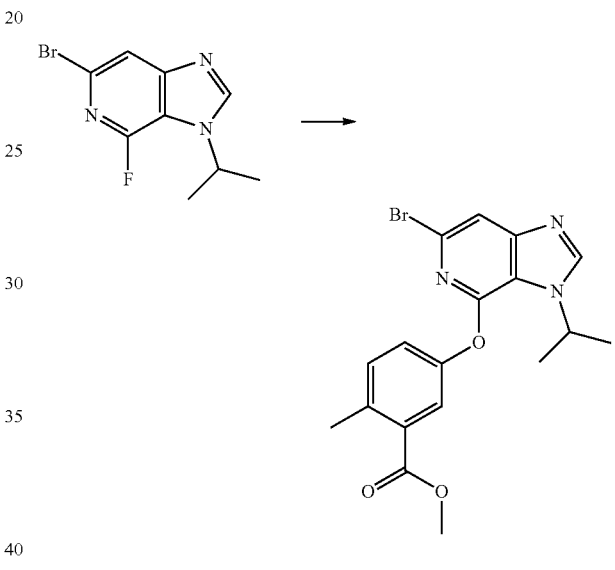

A. Preparation of methyl 5-((6-bromo-3-isopropyl-3H-imidazo[4,5-c]pyridin-4-yl)oxy)-2-methylbenzoate To a mixture of 6-bromo-4-fluoro-3-isopropyl-3H-imidazo[4,5-c]pyridine (150 mg, 0.58 mmol) and methyl 5-hydroxy-2-methylbenzoate in DMF (3 mL) was added cesium carbonate (568 mg, 1.7 mmol). After stirring for 1 h at 100° C., the reaction was filtered and concentrated under reduced pressure. The residue was purified by reverse phase HPLC give methyl 5-((6-bromo-3-isopropyl-3H-imidazo[4,5-c]pyridin-4-yl)oxy)-2-methylbenzoate.

The following compound was prepared using a similar procedure except 6-bromo-3-cyclopropyl-4-fluoro-3H-imidazo[4,5-c]pyridine and potassium carbonate were used instead of 6-bromo-4-fluoro-3-isopropyl-3H-imidazo[4,5-c]pyridine and cesium carbonate, respectively:

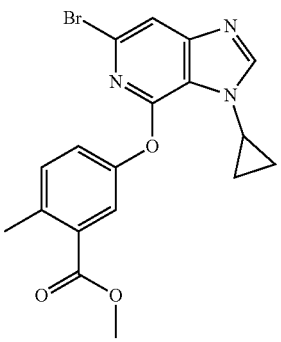 [SMILES: COC(=O)c1cc(Oc2nc(Br)cc3ncn(C4CC4)c23)ccc1C]

Methyl 5-((6-bromo-3-cyclopropyl-3H-imidazo[4,5-c]pyridin-4-yl)oxy)-2-methylbenzoate The following compound was prepared using a similar procedure except 6-bromo-3-cyclopropyl-4-fluoro-3H-imidazo[4,5-c]pyridine, 5-hydroxy-2-methylbenzamide, and potassium carbonate were used instead of 6-bromo-4-fluoro-3-isopropyl-3H-imidazo[4,5-c]pyridine, methyl 5-hydroxy-2-methylbenzoate, and cesium carbonate, respectively:

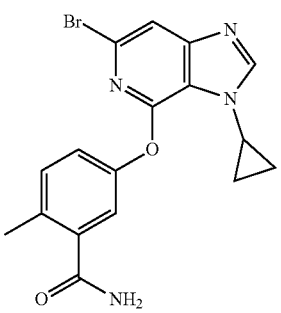 [SMILES: Cc1ccc(Oc2nc(Br)cc3ncn(C4CC4)c23)cc1C(N)=O]

5-((6-Bromo-3-cyclopropyl-3H-imidazo[4,5-c]pyridin-4-yl)oxy)-2-methylbenzamide

B. Preparation of 5-((6-bromo-3-cyclopropyl-3H-imidazo[4,5-c]pyridin-4-yl)oxy)-2-methylbenzoic acid

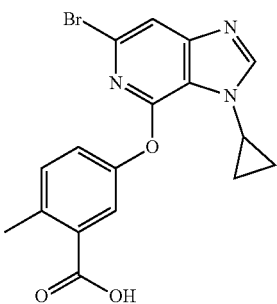 [SMILES: Cc1ccc(Oc2nc(Br)cc3ncn(C4CC4)c23)cc1C(=O)O]

In a vial were placed methyl 5-((6-bromo-3-cyclopropyl-3H-imidazo[4,5-c]pyridin-4-yl)oxy)-2-methylbenzoate (784.4 mg, 2.0 mmol) and lithium hydroxide (818 mg, 20 mmol) in THF (10 mL)/water (5 mL). The mixture was heated at 60° C. for 16 h, cooled to room temperature, concentrated, and used in the next step without purification.

C. Preparation of 5-((6-bromo-3-cyclopropyl-3H-imidazo[4,5-c]pyridin-4-yl)oxy)-N,2-dimethylbenzamide

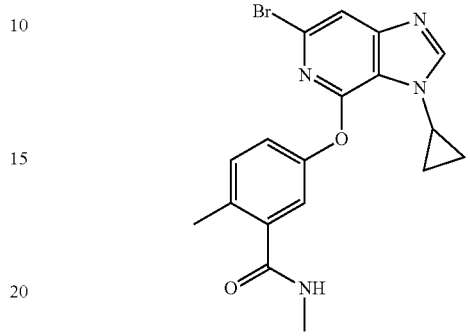

In a vial were placed 5-((6-bromo-3-cyclopropyl-3H-imidazo[4,5-c]pyridin-4-yl)oxy)-2-methylbenzoic acid (769 mg, 2.0 mmol), methylamine hydrochloride (668 mg, 9.9 mmol), diethylisopropylamine (4.2 mL, 24 mmol), and HATU (3774 mg, 9.9 mmol) in ACN (20 mL). The mixture was stirred at room temperature for 1 h. Then the mixture was quenched with water and extracted with EtOAc. The combined organic layers were washed with brine, dried, concentrated, and purified by flash chromatography (100% Hexane to 100% EtOAc then 100% DCM to 100% MeOH) to give 5-((6-bromo-3-cyclopropyl-3H-imidazo[4,5-c]pyridin-4-yl)oxy)-N,2-dimethylbenzamide.

Procedure 35: Preparation of the Compounds of Formula (13) According to Reaction Scheme I

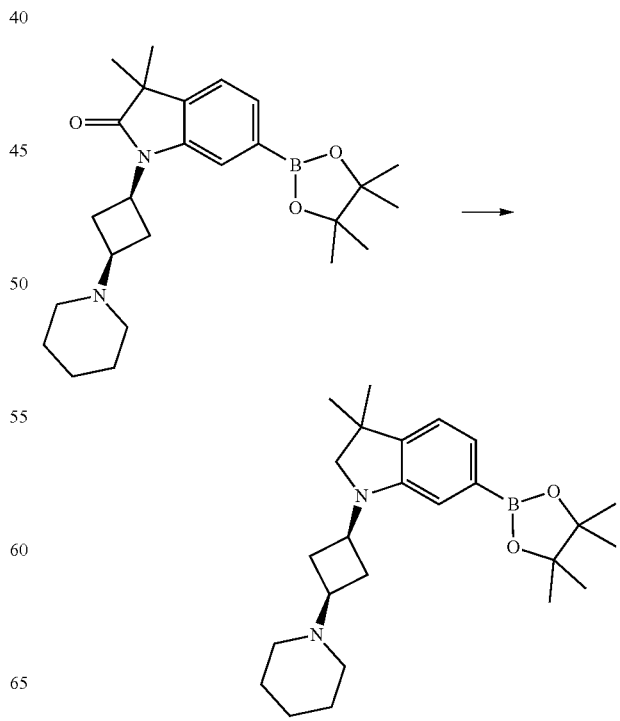

513

A. Preparation of 3,3-dimethyl-1-((1s,3s)-3-(piperidin-1-yl)cyclobutyl)-6-(4,4,5,5-tetramethyl-1,3,2-dioxaborolan-2-yl)indoline

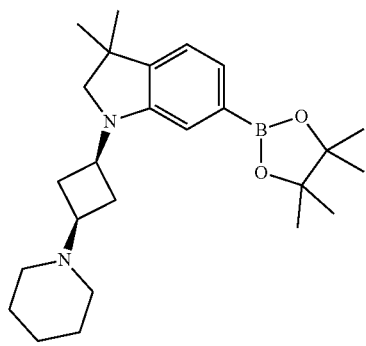 [SMILES: CC1(C)CN([C@H]2C[C@@H](N3CCCCC3)C2)c2cc(B3OC(C)(C)C(C)(C)O3)ccc21]

In a 20 mL vial was placed 3,3-dimethyl-1-((1s,3s)-3-(piperidin-1-yl)cyclobutyl)-6-(4,4,5,5-tetramethyl-1,3,2-dioxaborolan-2-yl)indolin-2-one (490 mg, 1.15 mmol) in Toluene (5 ml). To this was added Red-Al 60% wt. in Toluene (563.25 µl, 2.89 mmol). The mixture was heated at 85° C. for 2 h, and then quenched with sat. NaHCO₃. To this was added Na₂SO₄ and the mixture was stirred at room temperature for 1 h, and then filtered. The filtrate was concentrated and used in the next step without further purification.

Procedure 36: Preparation of the Compounds of Formula (13) According to Reaction Scheme I

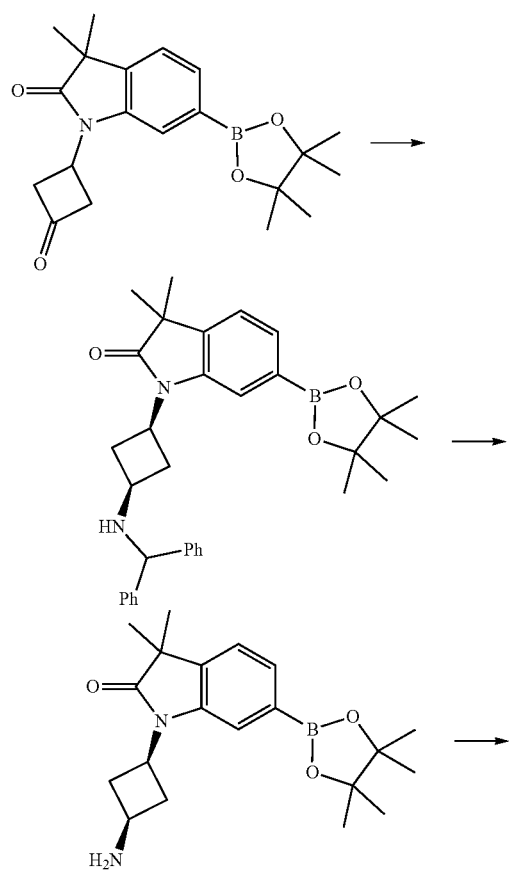

514

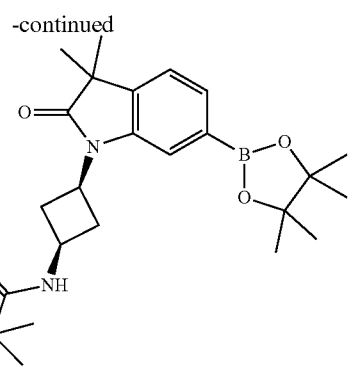

A. Preparation of 1-((1s,3s)-3-(benzhydrylamino)cyclobutyl)-3,3-dimethyl-6-(4,4,5,5-tetramethyl-1,3,2-dioxaborolan-2-yl)indolin-2-one

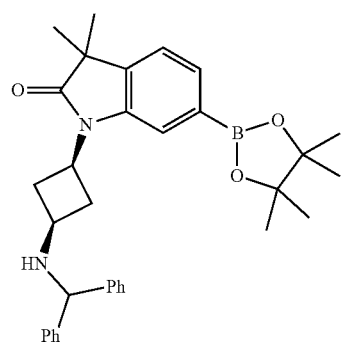 [SMILES: CC1(C)C(=O)N([C@H]2C[C@@H](NC(c3ccccc3)c3ccccc3)C2)c2cc(B3OC(C)(C)C(C)(C)O3)ccc21]

To a stirring solution of 3,3-dimethyl-1-(3-oxocyclobutyl)-6-(4,4,5,5-tetramethyl-1,3,2-dioxaborolan-2-yl)indolin-2-one (10 g, 28.1 mmol), diphenylmethanamine (9.7 ml, 56.3 mmol), and acetic acid (4.87 ml, 84.5 mmol) in DCE (100 ml) was added Na(OAc)₃ (8.9 g, 42.2 mmol). The resulting suspension was stirred overnight then quenched with satd. NaHCO₃. The mixture was filtered and then the aqueous layer was extracted with DCM. The combined organic layer was dried over Na₂SO₄, filtered, then concentrated to give 1-((1s,3s)-3-(benzhydrylamino)cyclobutyl)-3,3-dimethyl-6-(4,4,5,5-tetramethyl-1,3,2-dioxaborolan-2-yl)indolin-2-one, which was used in the next step without further purification.

B. Preparation of 1-((1s,3s)-3-aminocyclobutyl)-3,3-dimethyl-6-(4,4,5,5-tetramethyl-1,3,2-dioxaborolan-2-yl)indolin-2-one

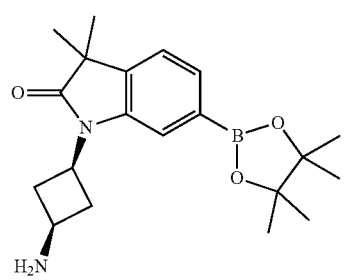 [SMILES: CC1(C)C(=O)N([C@H]2C[C@@H](N)C2)c2cc(B3OC(C)(C)C(C)(C)O3)ccc21]

To a solution of 1-((1s,3s)-3-(benzhydrylamino)cyclobutyl)-3,3-dimethyl-6-(4,4,5,5-tetramethyl-1,3,2-dioxaborolan-2-yl)indolin-2-one (23.2 g) in MeOH (30 ml) in Parr bottle was added Pd/C (10% w/w, 3.0 g, 2.8 mmol). Then the bottle was attached to Parr shaker, charged with H$_2$ (40 psi), and shaken overnight. The resulting suspension was filtered through celite then concentrated to give crude product. The residue was redissolved with Et$_2$O (200 ml) and 4 N HCl (dioxane, 28.2 ml, 112.6 mmol) was added slowly at 0° C. while stirring. After 30 min, the residue was filtered and dried to give 1-((1s,3s)-3-aminocyclobutyl)-3,3-dimethyl-6-(4,4,5,5-tetramethyl-1,3,2-dioxaborolan-2-yl)indolin-2-one.

C. Preparation of N-((1s,3s)-3-(3,3-dimethyl-2-oxo-6-(4,4,5,5-tetramethyl-1,3,2-dioxaborolan-2-yl)indolin-1-yl)cyclobutyl)pivalamide

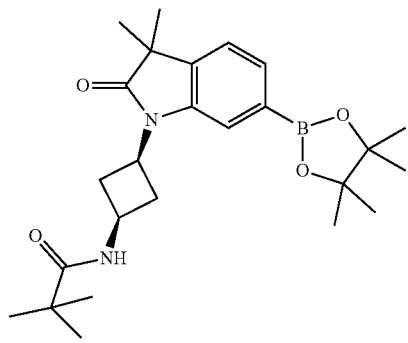 [SMILES: CC(C)(C)C(=O)N[C@H]1C[C@@H](N2C(=O)C(C)(C)c3ccc(B4OC(C)(C)C(C)(C)O4)cc32)C1]

To a solution of 1-((1s,3s)-3-aminocyclobutyl)-3,3-dimethyl-6-(4,4,5,5-tetramethyl-1,3,2-dioxaborolan-2-yl)indolin-2-one (2.9 g, 6.9 mmol) and triethylamine (4.8 mL, 34.6 mmol) in DCM (70 mL) was added pivaloyl chloride dropwise over 10 min. The reaction mixture was stirred at room temperature for 1 h. Then the reaction mixture was loaded on a silica gel column and purified (100% Hexane to 60% EtOAc in Hexane) to give N-((1s,3s)-3-(3,3-dimethyl-2-oxo-6-(4,4,5,5-tetramethyl-1,3,2-dioxaborolan-2-yl)indolin-1-yl)cyclobutyl)pivalamide.

Procedure 37: Preparation of the Compounds of Formula (14) According to Reaction Schemes II and IV

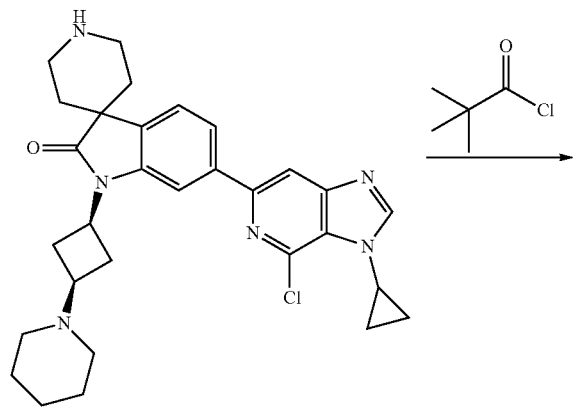

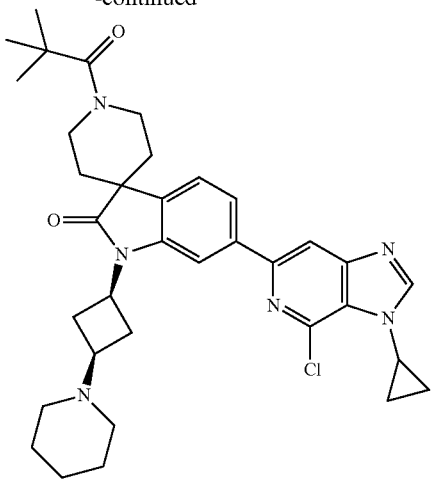

A. Preparation of 6-(4-chloro-3-cyclopropyl-3H-imidazo[4,5-c]pyridin-6-yl)-1-((1s,3s)-3-(piperidin-1-yl)cyclobutyl)-1'-pivaloylspiro[indoline-3,4'-piperidin]-2-one

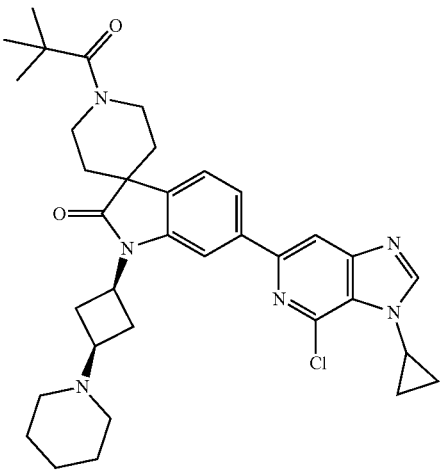 [SMILES: CC(C)(C)C(=O)N1CCC2(CC1)C(=O)N([C@H]1C[C@@H](N3CCCCC3)C1)c1cc(-c3cc4ncn(C5CC5)c4c(Cl)n3)ccc12]

To a suspension of 6-(4-chloro-3-cyclopropyl-3H-imidazo[4,5-c]pyridin-6-yl)-1-((1s,3s)-3-(piperidin-1-yl)cyclobutyl)spiro[indoline-3,4'-piperidin]-2-one (0.092 g, 0.16 mmol) in DCM (2 mL) was added triethylamine (0.23 mL, 1.6 mmol) followed by pivaloyl chloride (0.03 mL, 0.24 mmol). The resulting mixture was stirred at room temperature for 3 h and then was quenched with water and extracted with DCM. The combined organic layers were washed with brine, dried (Na$_2$SO$_4$), and concentrated to give 6-(4-chloro-3-cyclopropyl-3H-imidazo[4,5-c]pyridin-6-yl)-1-((1s,3s)-3-(piperidin-1-yl)cyclobutyl)-1'-pivaloylspiro[indoline-3,4'-piperidin]-2-one, which was used in the next step without further purification.

Procedure 38: Preparation of 5-bromo-3,4-difluoro-2-methylbenzoic acid

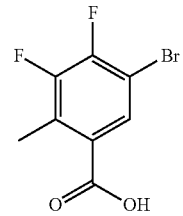

To a solution of tetramethylpiperidine (2.67 mL, 15.8 mmol) in THF (10 mL) at 0° C. was steadily dropwise added n-butyllithium (6.60 mL, 15.2 mmol). The mixture was stirred for 15 min. Then the mixture was dropwise added to a solution of 3-bromo-4,5-difluorobenzoic acid (1.50 g, 6.33 mmol) in THF (90 mL) at −78° C. The resulting reaction mixture was stirred at −78° C. for 30 min followed by the addition of iodomethane (1.97 mL, 31.7 mmol). The reaction mixture was slowly warmed to room temperature and stirred at room temperature for 16 h. The mixture was quenched with $H_2O$, acidified with 2 M HCl, and extracted with EtOAc. The combined organic layers were dried over $MgSO_4$, filtered, concentrated, and used in the next step without further purification.

Procedure 39: Preparation of 5-amino-N-(1-(difluoromethyl)cyclopropyl)-3,4-difluoro-2-methylbenzamide

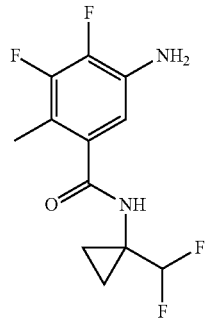 [SMILES: Cc1c(C(=O)NC2(C(F)F)CC2)cc(N)c(F)c1F]

In a vial were placed 5-bromo-N-(1-(difluoromethyl)cyclopropyl)-3,4-difluoro-2-methylbenzamide (100 mg, 0.29 mmol), $Pd_2(dba)_3$ (13 mg, 0.015 mmol), XantPhos (17 mg, 0.029 mmol), benzophenone imine (0.055 mL, 0.33 mmol), and cesium carbonate (287 mg, 0.88 mmol) in dioxane (2 mL). The mixture was degassed with argon and was heated at 90° C. for 18 h. After cooling to room temperature, the mixture was poured into water and extracted with ethyl acetate. The combined organic layers were washed with brine, dried ($MgSO_4$), filtered, and concentrated under reduced pressure. The resulting imine intermediate was dissolved in THF (3 mL) followed by the addition of 2 M HCl in water (1.1 ml). The mixture was stirred at room temperature for 3 hours and then concentrated in vacuo. To the resulting residue were added ethyl acetate and sat. $NaHCO_3$. The layers were separated and extracted with ethyl acetate. The combined organic layers were washed with brine, dried ($MgSO_4$), filtered, concentrated, and purified by flash chromatography (0.5% $NEt_3$ in DCM/MeOH) to give 5-amino-N-(1-(difluoromethyl)cyclopropyl)-3,4-difluoro-2-methylbenzamide.

Chiral Resolution

1. Separation of the Isomers of 5-((6-(1-((1s,3s)-3-(3-(difluoromethyl)pyrrolidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide

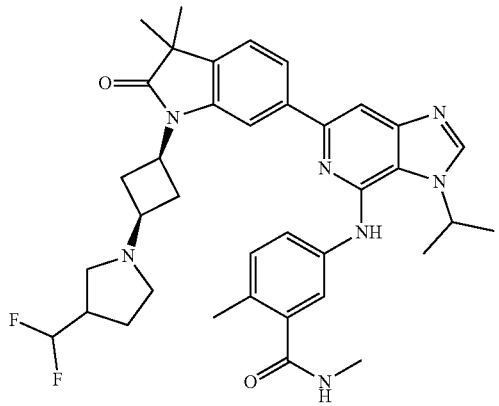 [SMILES: CNC(=O)c1cc(Nc2nc(-c3ccc4c(c3)N([C@H]3C[C@@H](N5CCC(C(F)F)C5)C3)C(=O)C4(C)C)cc3ncn(C(C)C)c23)ccc1C]

5-((6-(1-((1s,3s)-3-(3-(difluoromethyl)pyrrolidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide (Example 104) was separated on CHIRALPAK IA SFC 5 um 21×250 mm column in 35% MeOH (modified with 10 mM $NH_3$)/$CO_2$ at 60 mL/min to give the two single isomers:

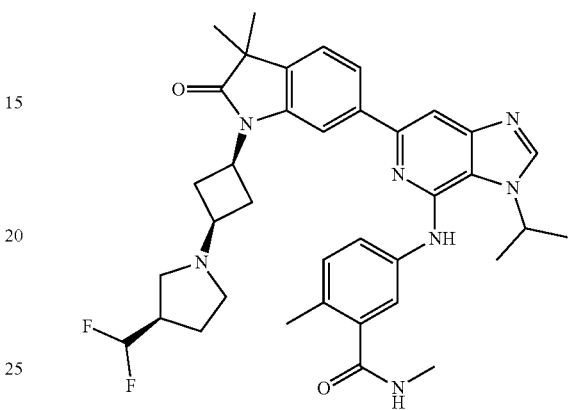

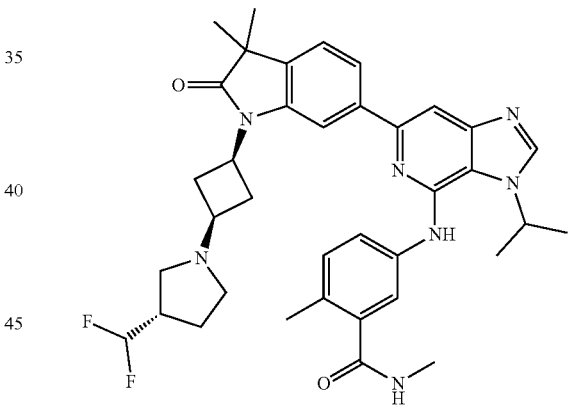

| Name | Separation method | Peak # | Example # |
|---|---|---|---|
| 5-((6-(1-((1s,3s)-3-(difluoromethyl)pyrrolidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide | CHIRALPAK IA SFC 5 um 21 × 250 mm column in 35% MeOH (modified with 10 mM $NH_3$)/$CO_2$ at 60 mL/min | 1st eluting peak | Example 104A |
| | | 2nd eluting peak | Example 104B |

2. Separation of the Isomers of 5-((6-(1-((1s,3s)-3-(3-(difluoromethyl)piperidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide

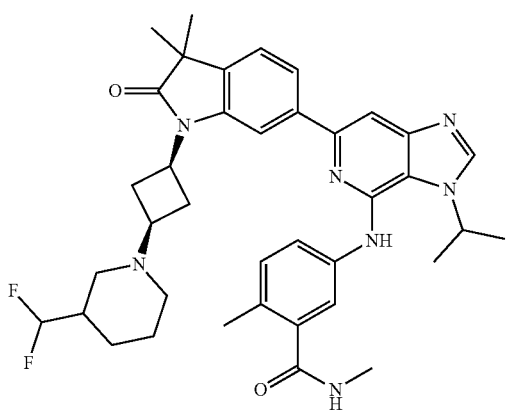 [SMILES: CNC(=O)c1cc(Nc2nc(-c3ccc4c(c3)N([C@H]3C[C@@H](N5CCCC(C(F)F)C5)C3)C(=O)C4(C)C)cc3ncn(C(C)C)c23)ccc1C]

5-((6-(1-((1s,3s)-3-(3-(difluoromethyl)piperidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide (Example 105) was separated on CHIRALPAK IA SFC 5 um 21×250 mm column in 35% MeOH (modified with 10 mM NH$_3$)/CO$_2$ at 60 mL/min to give the two single isomers:

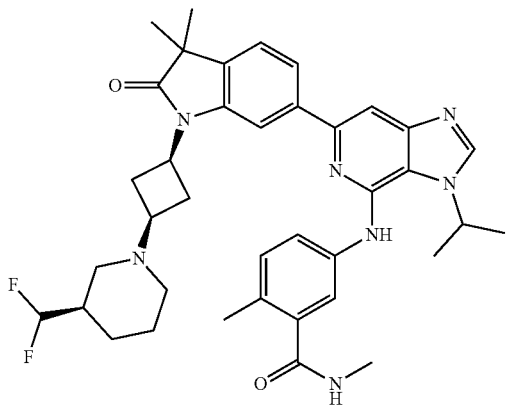

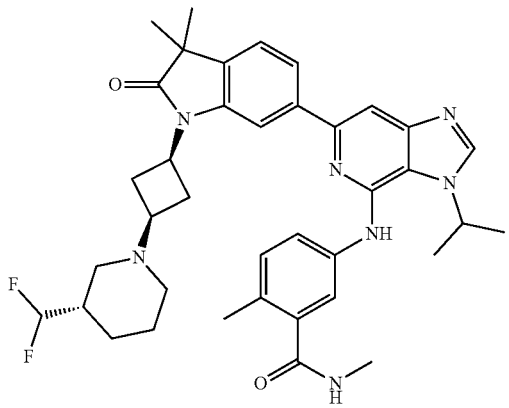

| Name | Separation method | Peak # | Example # |
|---|---|---|---|
| 5-((6-(1-((1s,3s)-3-(difluoromethyl)piperidin-1-yl)cyclobutyl)-3,3-dimethyl-2-oxoindolin-6-yl)-3-isopropyl-3H-imidazo[4,5-c]pyridin-4-yl)amino)-N,2-dimethylbenzamide | CHIRALPAK IA SFC 5 um 21 × 250 mm column in 35% MeOH (modified with 10 mM NH$_3$)/CO$_2$ at 60 mL/min | 1$^{st}$ eluting peak | Example 105A |
| | | 2$^{nd}$ eluting peak | Example 105B |

3. Separation of the Isomers of N-(1,1-difluoropropan-2-yl)-5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzamide

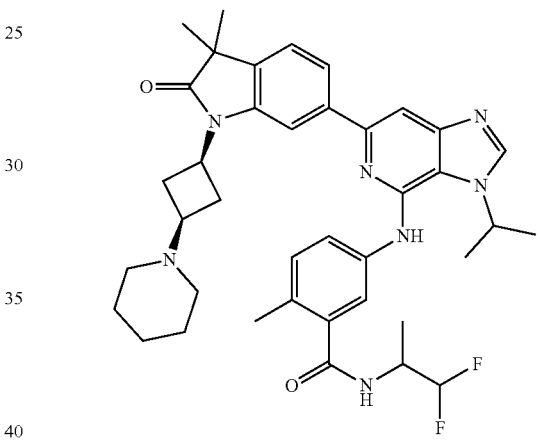

N-(1,1-difluoropropan-2-yl)-5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzamide (Example 21) was separated on CHIRALPAK IC SFC 5 um 21×250 mm column in 50% MeOH—NH$_3$ at 60 mL/min to give the two single isomers:

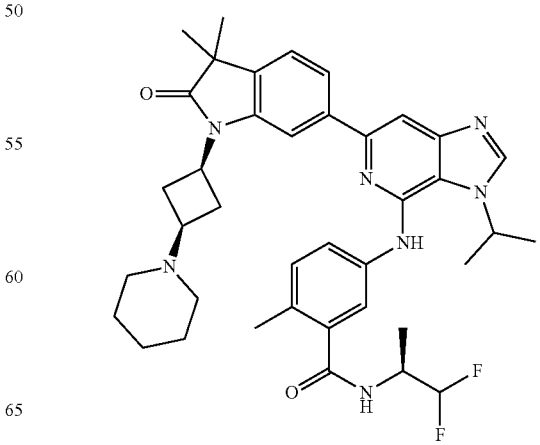

521

-continued

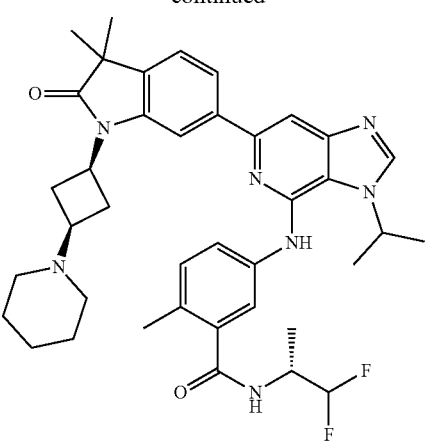

| Name | Separation method | Peak # | Example # |
|---|---|---|---|
| N-(1,1-difluoropropan-2-yl)-5-((6-(3,3-dimethyl-2-oxo-1-((1s,3s)-3-(piperidin-1-yl)cyclobutyl)indolin-6-yl)-3-isopropyl-3H-imidazo[4,5-c]pyridin-4-yl)amino)-2-methylbenzamide | CHIRALPAK IC SFC 5 um 21 × 250 mm column in 50% MeOH—NH₃ at 60 mL/min | 1ˢᵗ eluting peak 2ⁿᵈ eluting peak | Example 21A Example 21B |

Procedure 40: Preparation of the Compounds of Formula 1 According to Reaction Scheme VIII

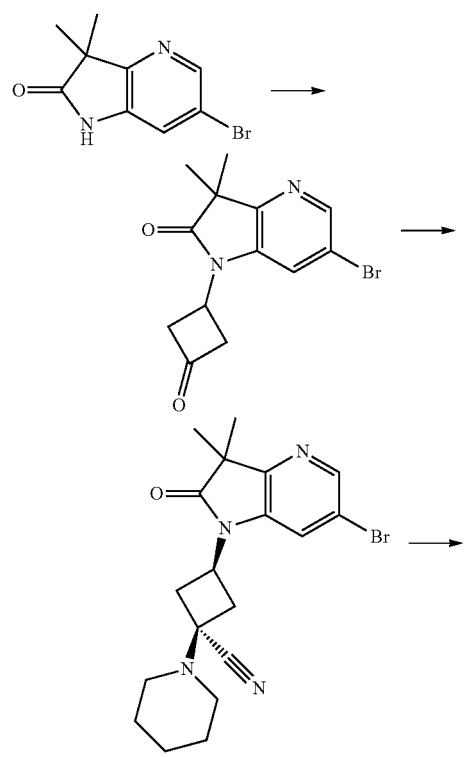

522

-continued

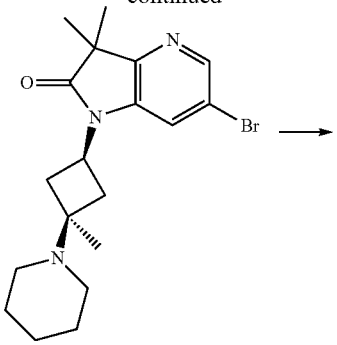

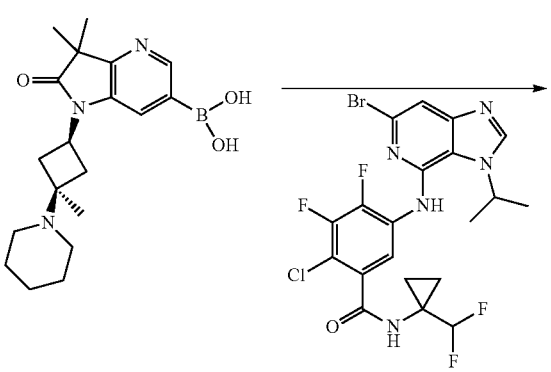

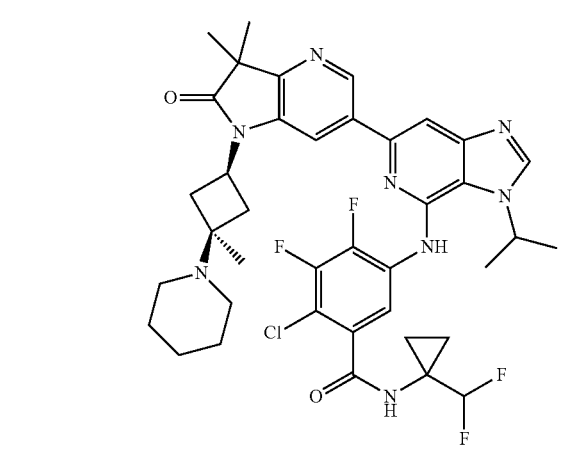 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)c(Cl)c(F)c3F)c21]

A. Preparation of 6-bromo-3,3-dimethyl-1-(3-oxo-cyclobutyl)-1,3-dihydro-2H-pyrrolo[3,2-b]pyridin-2-one In a round bottomed flask were placed commercially available 6-bromo-3,3-dimethyl-1H-pyrrolo[3,2-b]pyridin- 2-one (15 g, 62 mmol) and K$_2$CO$_3$ (13 g, 93 mmol) in acetonitrile (140 mL) under nitrogen. To this was slowly added 3-bromocyclobutanone (6.8 mL, 75 mmol). After stirring at room temperature for 1 h, the mixture was filtered, and the filtrate was concentrated. To the resulting solid was added acetonitrile. After stirring the mixture for 30 min, the precipitate was filtered to give 6-bromo-3,3-dimethyl-1-(3-oxocyclobutyl)-1,3-dihydro-2H-pyrrolo[3,2-b]pyridin-2-one.

The following compounds were prepared using a similar procedure.

3-(6-Bromo-3,3-dimethyl-2,3-dihydro-1H-pyrrolo[3,2-b]pyridin-1-yl)cyclobutan-1-one

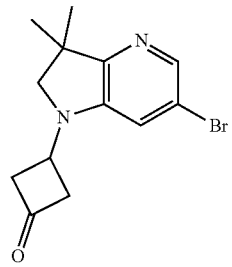 [SMILES: CC1(C)CN(C2CC(=O)C2)c2cc(Br)cnc21]

3-(6-Bromo-3,3-dimethyl-2,3-dihydro-1H-pyrrolo[3,2-b]pyridin-1-yl)cyclobutan-1-one was prepared using a similar procedure except that 6-bromo-3,3-dimethyl-2,3-dihydro-1H-pyrrolo[3,2-b]pyridine was used instead of 6-bromo-3,3-dimethyl-1H-pyrrolo[3,2-b]pyridin-2-one.

6'-Bromo-1'-(3-oxocyclobutyl)-2,3,5,6-tetrahydrospiro[pyran-4,3'-pyrrolo[3,2-b]pyridin]-2'(1'H)-one

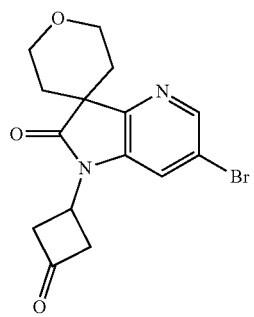 [SMILES: O=C1CC(N2C(=O)C3(CCOCC3)c3ncc(Br)cc32)C1]

6'-Bromo-1'-(3-oxocyclobutyl)-2,3,5,6-tetrahydrospiro[pyran-4,3'-pyrrolo[3,2-b]pyridin]-2'(1'H)-one was prepared using a similar procedure except that 6'-bromo-2,3,5,6-tetrahydrospiro[pyran-4,3'-pyrrolo[3,2-b]pyridin]-2'(1'H)-one was used instead of 6-bromo-3,3-dimethyl-1H-pyrrolo[3,2-b]pyridin-2-one.

6-Bromo-5-fluoro-3,3-dimethyl-1-(3-oxocyclobutyl)-1,3-dihydro-2H-pyrrolo[3,2-b]pyridin-2-one

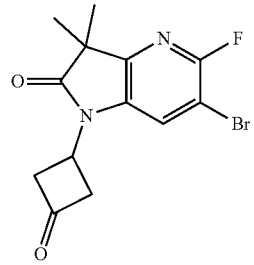 [SMILES: CC1(C)C(=O)N(C2CC(=O)C2)c2cc(Br)c(F)nc21]

6-Bromo-5-fluoro-3,3-dimethyl-1-(3-oxocyclobutyl)-1,3-dihydro-2H-pyrrolo[3,2-b]pyridin-2-one was prepared using a similar procedure except that 6-bromo-5-fluoro-3,3-dimethyl-1,3-dihydro-2H-pyrrolo[3,2-b]pyridin-2-one was used instead of 6-bromo-3,3-dimethyl-1H-pyrrolo[3,2-b]pyridin-2-one.

6-Bromo-5-fluoro-3,3-dimethyl-1-(3-oxocyclobutyl)-1,3-dihydro-2H-pyrrolo[3,2-b]pyridin-2-one

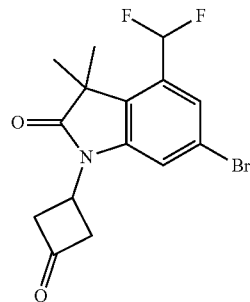 [SMILES: CC1(C)C(=O)N(C2CC(=O)C2)c2cc(Br)cc(C(F)F)c21]

6-bromo-4-(difluoromethyl)-3,3-dimethyl-1-(3-oxocyclobutyl)indolin-2-one was prepared using a similar procedure except that 6-bromo-4-(difluoromethyl)-3,3-dimethyl-indolin-2-one was used instead of 6-bromo-3,3-dimethyl-1H-pyrrolo[3,2-b]pyridin-2-one.

6'-bromo-1'-(3-oxocyclobutyl)spiro[cyclopropane-1,3'-indolin]-2'-one

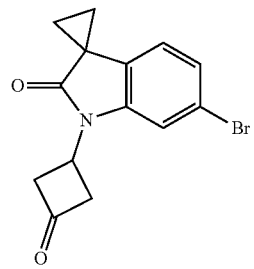 [SMILES: O=C1CC(N2C(=O)C3(CC3)c3ccc(Br)cc32)C1]

6'-bromo-1'-(3-oxocyclobutyl)spiro[cyclopropane-1,3'-indolin]-2'-one was prepared using a similar procedure except that 6'-bromospiro[cyclopropane-1,3'-indolin]-2'-one was used instead of 6-bromo-3,3-dimethyl-1H-pyrrolo[3,2-b]pyridin-2-one.

B. Preparation of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile

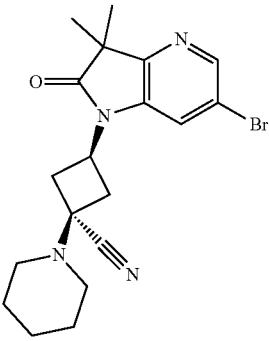 [SMILES: CC1(C)C(=O)N([C@H]2C[C@@](C#N)(N3CCCCC3)C2)c2cc(Br)cnc21]

In a round bottomed flask was placed 6-bromo-3,3-dimethyl-1-(3-oxocyclobutyl)-1,3-dihydro-2H-pyrrolo[3,2-b]pyridin-2-one (20 g, 65 mmol) in acetic acid (110 mL). To this were added piperidine (7.7 mL, 78 mmol) and TMS-CN (16 mL, 130 mmol) at 0° C. The reaction mixture was warmed to room temperature and stirred for 18 h. Then it was concentrated, diluted with EtOAc, and filtered. The solid was re-dissolved in DCM, washed with sat. NaHCO$_3$ and brine, dried (Na$_2$SO$_4$), and concentrated to give (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

The following compounds were prepared using a similar procedure.

(i) (1s,3s)-3-(6-Bromo-3,3-dimethyl-2,3-dihydro-1H-pyrrolo[3,2-b]pyridin-1-yl)-1-(piperidin-1-yl)cyclobutane-1-carbonitrile

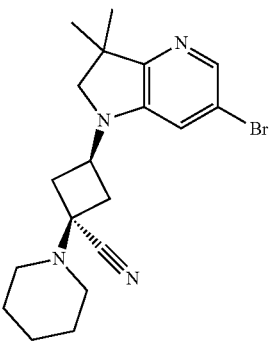 [SMILES: CC1(C)CN([C@H]2C[C@@](C#N)(N3CCCCC3)C2)c2cc(Br)cnc21]

(1s,3s)-3-(6-Bromo-3,3-dimethyl-2,3-dihydro-1H-pyrrolo[3,2-b]pyridin-1-yl)-1-(piperidin-1-yl)cyclobutane-1-carbonitrile was prepared using a similar procedure except that 3-(6-bromo-3,3-dimethyl-2,3-dihydro-1H-pyrrolo[3,2-b]pyridin-1-yl)cyclobutan-1-one was used instead of 6-bromo-3,3-dimethyl-1-(3-oxocyclobutyl)-1,3-dihydro-2H-pyrrolo[3,2-b]pyridin-2-one.

(ii) (1s,3s)-3-(6-Bromo-3,3-dimethyl-2-oxo-2,3-dihydro-1H-pyrrolo[3,2-b]pyridin-1-yl)-1-morpholinocyclobutane-1-carbonitrile

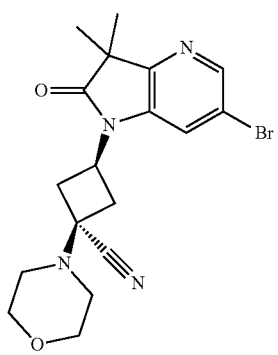 [SMILES: CC1(C)C(=O)N([C@H]2C[C@@](C#N)(N3CCOCC3)C2)c2cc(Br)cnc21]

(1s,3s)-3-(6-Bromo-3,3-dimethyl-2-oxo-2,3-dihydro-1H-pyrrolo[3,2-b]pyridin-1-yl)-1-morpholinocyclobutane-1-carbonitrile was prepared using a similar procedure except that morpholine was used instead of piperidine.

(iii) (1s,3s)-3-(6'-Bromo-2'-oxo-2,3,5,6-tetrahydrospiro[pyran-4,3'-pyrrolo[3,2-b]pyridin]-1'(2'H)-yl)-1-(piperidin-1-yl)cyclobutane-1-carbonitrile

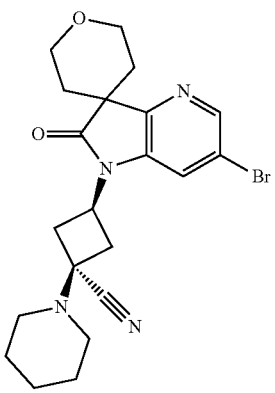 [SMILES: N#C[C@]1(N2CCCCC2)C[C@@H](N2C(=O)C3(CCOCC3)c3ncc(Br)cc32)C1]

(1s,3s)-3-(6'-Bromo-2'-oxo-2,3,5,6-tetrahydrospiro[pyran-4,3'-pyrrolo[3,2-b]pyridin]-1'(2'H)-yl)-1-(piperidin-1-yl)cyclobutane-1-carbonitrile was prepared using a similar procedure except that 6'-bromo-1'-(3-oxocyclobutyl)-2,3,5,6-tetrahydrospiro[pyran-4,3'-pyrrolo[3,2-b]pyridin]-2'(1'H)-one was used instead of 6-bromo-3,3-dimethyl-1-(3-oxocyclobutyl)-1,3-dihydro-2H-pyrrolo[3,2-b]pyridin-2-one.

(iv) (1s,3s)-3-(6-Bromo-5-fluoro-3,3-dimethyl-2-oxo-2,3-dihydro-1H-pyrrolo[3,2-b]pyridin-1-yl)-1-(piperidin-1-yl)cyclobutane-1-carbonitrile

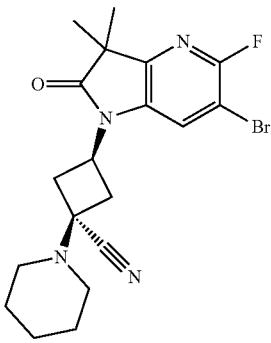 [SMILES: CC1(C)C(=O)N([C@H]2C[C@@](C#N)(N3CCCCC3)C2)c2cc(Br)c(F)nc21]

(1s,3s)-3-(6-Bromo-5-fluoro-3,3-dimethyl-2-oxo-2,3-dihydro-1H-pyrrolo[3,2-b]pyridin-1-yl)-1-(piperidin-1-yl)cyclobutane-1-carbonitrile was prepared using a similar procedure except that 6-bromo-5-fluoro-3,3-dimethyl-1-(3-oxocyclobutyl)-1,3-dihydro-2H-pyrrolo[3,2-b]pyridin-2-one was used instead of 6-bromo-3,3-dimethyl-1-(3-oxocyclobutyl)-1,3-dihydro-2H-pyrrolo[3,2-b]pyridin-2-one.

C. Preparation of (1s,3s)-3-(6-bromo-3,3-dimethyl-2-oxo-2,3-dihydro-1H-pyrrolo[3,2-b]pyridin-1-yl)-1-(1,4-oxazepan-4-yl)cyclobutane-1-carbonitrile

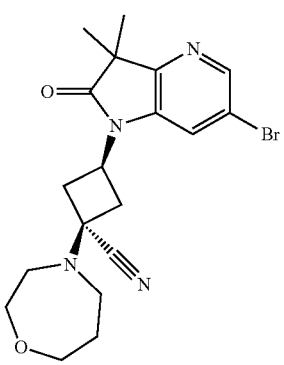 [SMILES: CC1(C)C(=O)N([C@H]2C[C@@](C#N)(N3CCCOCC3)C2)c2cc(Br)cnc21]

In a 20 mL vial were placed 6-bromo-3,3-dimethyl-1-(3-oxocyclobutyl)pyrrolo[3,2-b]pyridin-2-one (1.0 g, 3.2 mmol), 1,4-oxazepane hydrochloride (0.53 g, 3.9 mmol), Ti(OiPr)$_4$ (1.9 mL, 6.5 mmol) in AcOH (5 mL). After stirring at room temperature for 5 min, the mixture was cooled to 0° C. followed by the addition of TMS-CN (0.81 mL, 6.5 mmol). The reaction mixture was warmed to room temperature and stirred for 16 h. Then, it was concentrated, diluted with DCM and sat. NaHCO$_3$, and extracted with DCM. The combined organic layers were dried (Na$_2$SO$_4$), filtered through a pad of Celite, concentrated, and purified by flash chromatography (100% DCM to 100% EtOAc) to give (1s,3s)-3-(6-bromo-3,3-dimethyl-2-oxo-2,3-dihydro-1H-pyrrolo[3,2-b]pyridin-1-yl)-1-(1,4-oxazepan-4-yl)cyclobutane-1-carbonitrile.

The following compounds were prepared using a similar procedure.

(i) (1s,3s)-1-(6-Oxa-2-azabicyclo[3.2.1]octan-2-yl)-3-(6-bromo-3,3-dimethyl-2-oxo-2,3-dihydro-1H-pyrrolo[3,2-b]pyridin-1-yl)cyclobutane-1-carbonitrile

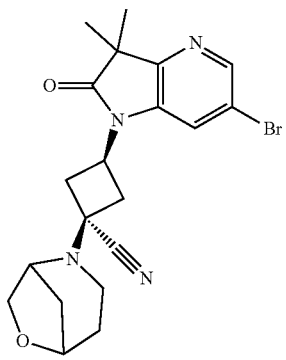 [SMILES: CC1(C)C(=O)N([C@H]2C[C@@](C#N)(N3CCC4CC3CO4)C2)c2cc(Br)cnc21]

(1s,3s)-1-(6-Oxa-2-azabicyclo[3.2.1]octan-2-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 6-oxa-2-azabicyclo[3.2.1]octane hydrochloride was used instead of 1,4-oxazepane hydrochloride.

(ii) (1s,3s)-1-(2-Oxa-5-azabicyclo[2.2.2]octan-5-yl)-3-(6-bromo-3,3-dimethyl-2-oxo-2,3-dihydro-1H-pyrrolo[3,2-b]pyridin-1-yl)cyclobutane-1-carbonitrile

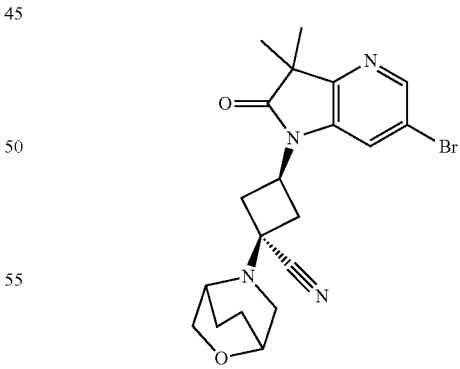

(1s,3s)-1-(2-Oxa-5-azabicyclo[2.2.2]octan-5-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 2-oxa-5-azabicyclo[2.2.2]octane hydrochloride was used instead of 1,4-oxazepane hydrochloride.

(iii) (1s,3s)-3-(6-Bromo-3,3-dimethyl-2-oxo-2,3-dihydro-1H-pyrrolo[3,2-b]pyridin-1-yl)-1-(5-azaspiro[2.5]octan-5-yl)cyclobutane-1-carbonitrile

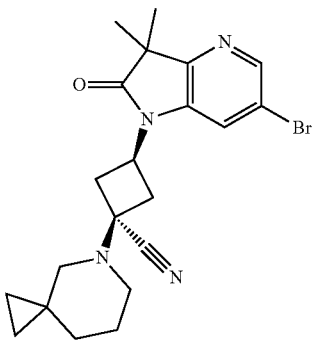 [SMILES: CC1(C)C(=O)N([C@H]2C[C@@](C#N)(N3CCCC4(CC4)C3)C2)c2cc(Br)cnc21]

(1s,3s)-3-(6-Bromo-3,3-dimethyl-2-oxo-2,3-dihydro-1H-pyrrolo[3,2-b]pyridin-1-yl)-1-(5-azaspiro[2.5]octan-5-yl)cyclobutane-1-carbonitrile was prepared using a similar procedure except 5-azaspiro[2.5]octane hydrochloride was used instead of 1,4-oxazepane hydrochloride.

(iv) (1s,3s)-1-(3-Azabicyclo[3.2.0]heptan-3-yl)-3-(6-bromo-3,3-dimethyl-2-oxo-2,3-dihydro-1H-pyrrolo[3,2-b]pyridin-1-yl)cyclobutane-1-carbonitrile

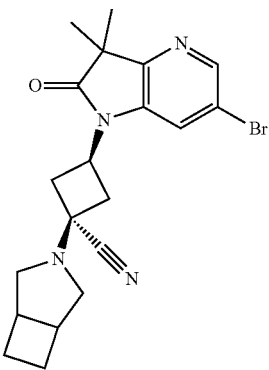 [SMILES: CC1(C)C(=O)N([C@H]2C[C@@](C#N)(N3CC4CCC4C3)C2)c2cc(Br)cnc21]

(1s,3s)-1-(3-Azabicyclo[3.2.0]heptan-3-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 3-azabicyclo[3.2.0]heptane hydrochloride was used instead of 1,4-oxazepane hydrochloride.

(v) (1s,3s)-1-(3-Azabicyclo[4.1.0]heptan-3-yl)-3-(6-bromo-3,3-dimethyl-2-oxo-2,3-dihydro-1H-pyrrolo[3,2-b]pyridin-1-yl)cyclobutane-1-carbonitrile

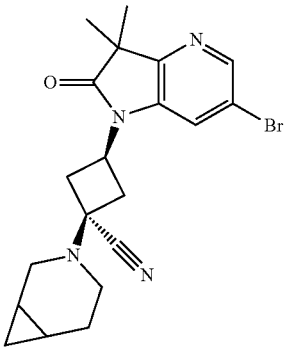 [SMILES: CC1(C)C(=O)N([C@H]2C[C@@](C#N)(N3CCC4CC4C3)C2)c2cc(Br)cnc21]

(1s,3s)-1-(3-Azabicyclo[4.1.0]heptan-3-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 3-azabicyclo[4.1.0]heptane hydrochloride was used instead of 1,4-oxazepane hydrochloride.

(vi) (1s,3s)-3-(6-Bromo-3,3-dimethyl-2-oxo-2,3-dihydro-1H-pyrrolo[3,2-b]pyridin-1-yl)-1-(2,2-dimethylmorpholino)cyclobutane-1-carbonitrile

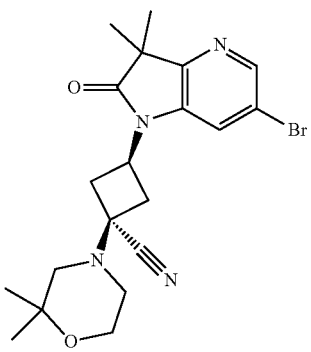 [SMILES: CC1(C)CN([C@]2(C#N)C[C@H](N3C(=O)C(C)(C)c4ncc(Br)cc43)C2)CCO1]

(1s,3s)-3-(6-Bromo-3,3-dimethyl-2-oxo-2,3-dihydro-1H-pyrrolo[3,2-b]pyridin-1-yl)-1-(2,2-dimethylmorpholino)cyclobutane-1-carbonitrile was prepared using a similar procedure except 2,2-dimethylmorpholine hydrochloride was used instead of 1,4-oxazepane hydrochloride.

(vii) (1s,3S)-3-(6-Bromo-3,3-dimethyl-2-oxo-2,3-dihydro-1H-pyrrolo[3,2-b]pyridin-1-yl)-1-((3aR,6aS)-tetrahydro-1H-furo[3,4-c]pyrrol-5(3H)-yl)cyclobutane-1-carbonitrile

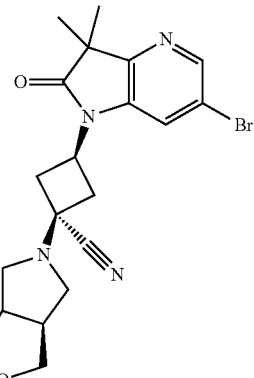

(1s,3S)-3-(6-Bromo-3,3-dimethyl-2-oxo-2,3-dihydro-1H-pyrrolo[3,2-b]pyridin-1-yl)-1-((3aR,6aS)-tetrahydro-1H-furo[3,4-c]pyrrol-5(3H)-yl)cyclobutane-1-carbonitrile was prepared using a similar procedure except hexahydro-1H-furo[3,4-c]pyrrole hydrochloride was used instead of 1,4-oxazepane hydrochloride.

(viii) (1s,3s)-1-(8-Oxa-3-azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile

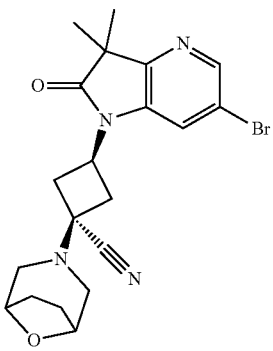 [SMILES: CC1(C)C(=O)N([C@H]2C[C@@](C#N)(N3CC4CCC(C3)O4)C2)c2cc(Br)cnc21]

(1s,3s)-1-(8-Oxa-3-azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 8-oxa-3-azabicyclo[3.2.1]octane hydrochloride was used instead of 1,4-oxazepane hydrochloride.

(ix) (1s,3s)-3-(6-Bromo-3,3-dimethyl-2-oxo-2,3-dihydro-1H-pyrrolo[3,2-b]pyridin-1-yl)-1-(4-oxa-7-azaspiro[2.5]octan-7-yl)cyclobutane-1-carbonitrile

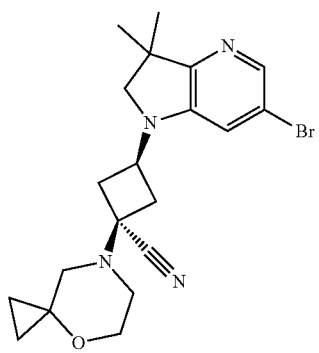 [SMILES: CC1(C)CN([C@H]2C[C@@](C#N)(N3CCOC4(CC4)C3)C2)c2cc(Br)cnc21]

(1s,3s)-3-(6-Bromo-3,3-dimethyl-2-oxo-2,3-dihydro-1H-pyrrolo[3,2-b]pyridin-1-yl)-1-(4-oxa-7-azaspiro[2.5]octan-7-yl)cyclobutane-1-carbonitrile was prepared using a similar procedure except 4-oxa-7-azaspiro[2.5]octane hydrochloride was used instead of 1,4-oxazepane hydrochloride.

(x) (1s,3s)-1-(3-Oxa-8-azabicyclo[3.2.1]octan-8-yl)-3-(6-bromo-3,3-dimethyl-2-oxo-2,3-dihydro-1H-pyrrolo[3,2-b]pyridin-1-yl)cyclobutane-1-carbonitrile

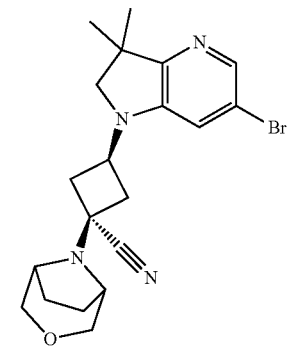 [SMILES: CC1(C)CN([C@H]2C[C@@](C#N)(N3C4CCC3COC4)C2)c2cc(Br)cnc21]

(1s,3s)-1-(3-Oxa-8-azabicyclo[3.2.1]octan-8-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 3-oxa-8-azabicyclo[3.2.1]octane hydrochloride was used instead of 1,4-oxazepane hydrochloride.

(xi) (1s,3s)-1-(3-Azabicyclo[3.1.0]hexan-3-yl)-3-(6-bromo-3,3-dimethyl-2-oxo-2,3-dihydro-1H-pyrrolo[3,2-b]pyridin-1-yl)cyclobutane-1-carbonitrile

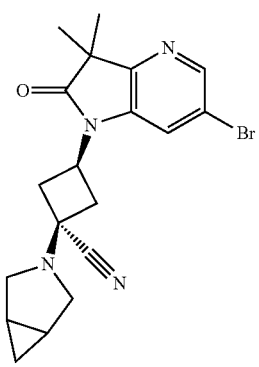 [SMILES: CC1(C)C(=O)N([C@H]2C[C@@](C#N)(N3CC4CC4C3)C2)c2cc(Br)cnc21]

(1s,3s)-1-(3-Azabicyclo[3.1.0]hexan-3-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 3-azabicyclo[3.1.0]hexane hydrochloride was used instead of 1,4-oxazepane hydrochloride.

533

(xii) (1s,3s)-1-(Azepan-1-yl)-3-(6-bromo-3,3-dimethyl-2-oxo-2,3-dihydro-1H-pyrrolo[3,2-b]pyridin-1-yl)cyclobutane-1-carbonitrile

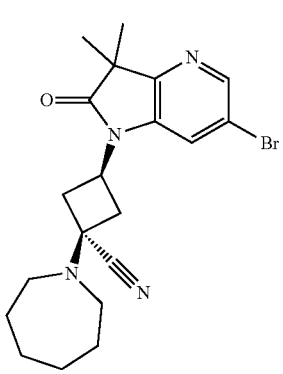 [SMILES: CC1(C)C(=O)N([C@H]2C[C@@](C#N)(N3CCCCCC3)C2)c2cc(Br)cnc21]

(1s,3s)-1-(Azepan-1-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except azepane was used instead of 1,4-oxazepane hydrochloride.

(xiii) (1s,3s)-1-(3-Azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile

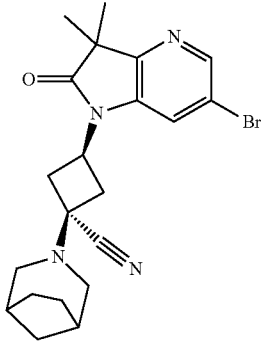 [SMILES: CC1(C)C(=O)N([C@H]2C[C@@](C#N)(N3CC4CCC(C4)C3)C2)c2cc(Br)cnc21]

(1s,3s)-1-(3-Azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile was prepared using a similar procedure except 3-azabicyclo[3.2.1]octane was used instead of 1,4-oxazepane hydrochloride.

534

(xiv) (1s,3S)-3-(6-Bromo-3,3-dimethyl-2-oxo-2,3-dihydro-1H-pyrrolo[3,2-b]pyridin-1-yl)-1-((R)-3-fluoropiperidin-1-yl)cyclobutane-1-carbonitrile

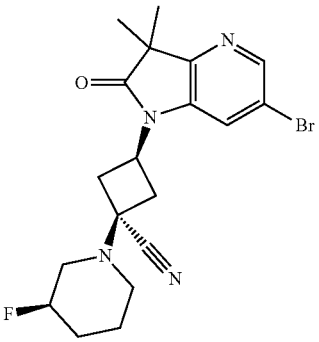 [SMILES: CC1(C)C(=O)N([C@H]2C[C@@](C#N)(N3CCC[C@@H](F)C3)C2)c2cc(Br)cnc21]

(1s,3S)-3-(6-Bromo-3,3-dimethyl-2-oxo-2,3-dihydro-1H-pyrrolo[3,2-b]pyridin-1-yl)-1-((R)-3-fluoropiperidin-1-yl)cyclobutane-1-carbonitrile was prepared using a similar procedure except that (R)-3-fluoropiperidine was used instead of 1,4-oxazepane hydrochloride.

(xv) (1s,3s)-3-(6-bromo-3,3-dimethyl-2-oxo-2,3-dihydro-1H-pyrrolo[3,2-b]pyridin-1-yl)-1-(4-fluoropiperidin-1-yl)cyclobutane-1-carbonitrile

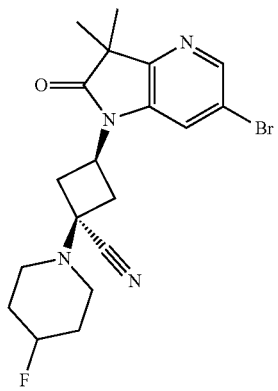 [SMILES: CC1(C)C(=O)N([C@H]2C[C@@](C#N)(N3CCC(F)CC3)C2)c2cc(Br)cnc21]

(1s,3s)-3-(6-bromo-3,3-dimethyl-2-oxo-2,3-dihydro-1H-pyrrolo[3,2-b]pyridin-1-yl)-1-(4-fluoropiperidin-1-yl)cyclobutane-1-carbonitrile was prepared using a similar procedure except that 4-fluoropiperidine was used instead of 1,4-oxazepane hydrochloride.

(xvi) (1s,3s)-3-(6-bromo-3,3-dimethyl-2-oxo-2,3-dihydro-1H-pyrrolo[3,2-b]pyridin-1-yl)-1-(4-fluoropiperidin-1-yl)cyclobutane-1-carbonitrile

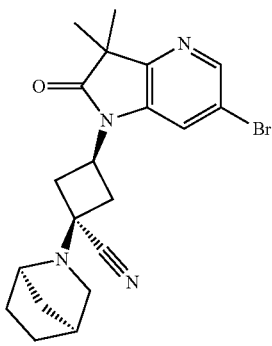 [SMILES: CC1(C)C(=O)N([C@H]2C[C@@](C#N)(N3C[C@H]4CC[C@@H]3C4)C2)c2cc(Br)cnc21]

(1s,3s)-3-(6-bromo-3,3-dimethyl-2-oxo-2,3-dihydro-1H-pyrrolo[3,2-b]pyridin-1-yl)-1-(4-fluoropiperidin-1-yl)cyclobutane-1-carbonitrile was prepared using a similar procedure except that (1R,4S)-2-azabicyclo[2.2.1]heptane hydrochloride was used instead of 1,4-oxazepane hydrochloride.

(xvii) (1s,3s)-1-(3-azabicyclo[4.1.0]heptan-3-yl)-3-(6-bromo-5-fluoro-3,3-dimethyl-2-oxo-2,3-dihydro-1H-pyrrolo[3,2-b]pyridin-1-yl)cyclobutane-1-carbonitrile

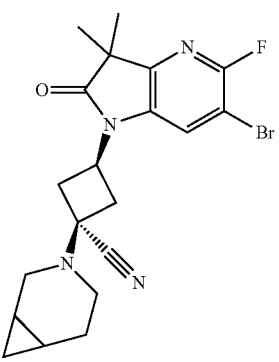 [SMILES: CC1(C)C(=O)N([C@H]2C[C@@](C#N)(N3CCC4CC4C3)C2)c2cc(Br)c(F)nc21]

(1s,3s)-1-(3-azabicyclo[4.1.0]heptan-3-yl)-3-(6-bromo-5-fluoro-3,3-dimethyl-2-oxo-2,3-dihydro-1H-pyrrolo[3,2-b]pyridin-1-yl)cyclobutane-1-carbonitrile was prepared using a similar procedure except that 3-azabicyclo[4.1.0]heptane hydrochloride and 6-bromo-5-fluoro-3,3-dimethyl-1-(3-oxocyclobutyl)-1,3-dihydro-2H-pyrrolo[3,2-b]pyridin-2-one were used instead of 1,4-oxazepane hydrochloride and 6-bromo-3,3-dimethyl-1-(3-oxocyclobutyl)-1,3-dihydro-2H-pyrrolo[3,2-b]pyridin-2-one, respectively.

(xviii) (1s,3s)-3-(6-bromo-5-fluoro-3,3-dimethyl-2-oxo-2,3-dihydro-1H-pyrrolo[3,2-b]pyridin-1-yl)-1-(5-azaspiro[2.5]octan-5-yl)cyclobutane-1-carbonitrile

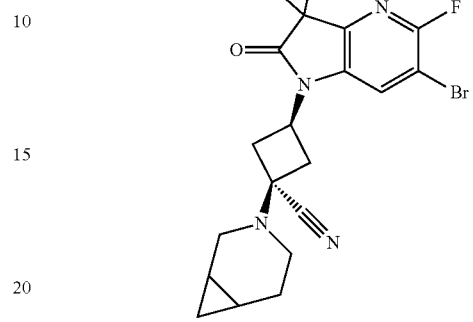

(1s,3s)-3-(6-bromo-5-fluoro-3,3-dimethyl-2-oxo-2,3-dihydro-H-pyrrolo[3,2-b]pyridin-1-yl)-1-(5-azaspiro[2.5]octan-5-yl)cyclobutane-1-carbonitrile was prepared using a similar procedure except that 5-azaspiro[2.5]octane hydrochloride and 6-bromo-5-fluoro-3,3-dimethyl-1-(3-oxocyclobutyl)-1,3-dihydro-2H-pyrrolo[3,2-b]pyridin-2-one were used instead of 1,4-oxazepane hydrochloride and 6-bromo-3,3-dimethyl-1-(3-oxocyclobutyl)-1,3-dihydro-2H-pyrrolo[3,2-b]pyridin-2-one, respectively.

(xix) (1s,3s)-3-(6-bromo-4-(difluoromethyl)-3,3-dimethyl-2-oxoindolin-1-yl)-1-(piperidin-1-yl)cyclobutane-1-carbonitrile

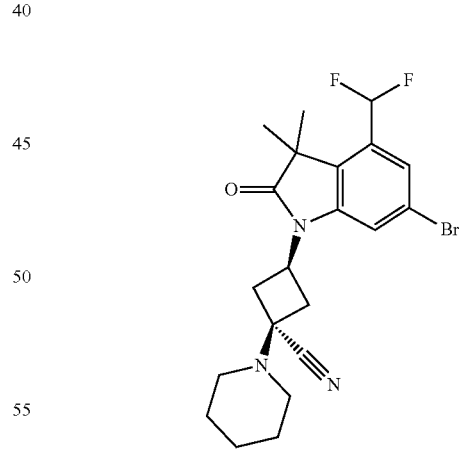

(1s,3s)-3-(6-bromo-4-(difluoromethyl)-3,3-dimethyl-2-oxoindolin-1-yl)-1-(piperidin-1-yl)cyclobutane-1-carbonitrile was prepared using a similar procedure except that 6-bromo-4-(difluoromethyl)-3,3-dimethyl-1-(3-oxocyclobutyl)indolin-2-one was used instead of 6-bromo-3,3-dimethyl-1-(3-oxocyclobutyl)-1,3-dihydro-2H-pyrrolo[3,2-b]pyridin-2-one.

537

(xx) (1s,3s)-3-(6'-bromo-2'-oxospiro[cyclopropane-1,3'-indolin]-1'-yl)-1-(piperidin-1-yl)cyclobutane-1-carbonitrile

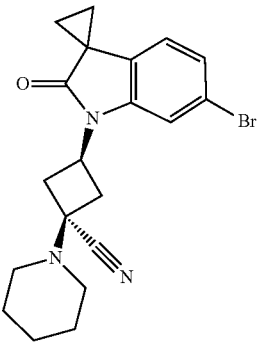 [SMILES: N#C[C@]1(N2CCCCC2)C[C@@H](N2C(=O)C3(CC3)c3ccc(Br)cc32)C1]

(1s,3s)-3-(6'-bromo-2'-oxospiro[cyclopropane-1,3'-indolin]-1'-yl)-1-(piperidin-1-yl)cyclobutane-1-carbonitrile was prepared using a similar procedure except that 6'-bromo-1'-(3-oxocyclobutyl)spiro[cyclopropane-1,3'-indolin]-2'-one was used instead of 6-bromo-3,3-dimethyl-1-(3-oxocyclobutyl)-1,3-dihydro-2H-pyrrolo[3,2-b]pyridin-2-one.

(xxi) (1s,3s)-3-(6-Bromo-3,3-dimethyl-2-oxo-2,3-dihydro-1H-pyrrolo[3,2-b]pyridin-1-yl)-1-(8-hydroxy-5-azaspiro[2.5]octan-5-yl)cyclobutane-1-carbonitrile

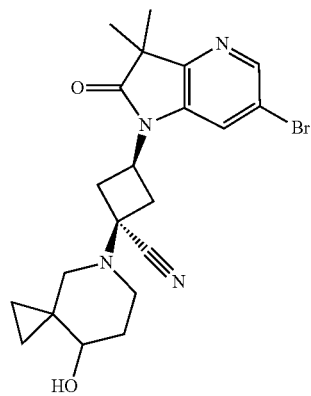 [SMILES: CC1(C)C(=O)N([C@H]2C[C@@](C#N)(N3CCC(O)C4(CC4)C3)C2)c2cc(Br)cnc21]

(1s,3s)-3-(6-Bromo-3,3-dimethyl-2-oxo-2,3-dihydro-1H-pyrrolo[3,2-b]pyridin-1-yl)-1-(8-hydroxy-5-azaspiro[2.5]octan-5-yl)cyclobutane-1-carbonitrile was prepared using a similar procedure except that the reaction was carried out with 5-azaspiro[2.5]octan-8-ol hydrochloride at 40° C. instead of 1,4-oxazepane hydrochloride at room temperature.

538

D. Preparation of (1s,3s)-3-(6-bromo-3,3-dimethyl-2-oxo-2,3-dihydro-1H-pyrrolo[3,2-b]pyridin-1-yl)-1-(8-fluoro-5-azaspiro[2.5]octan-5-yl)cyclobutane-1-carbonitrile

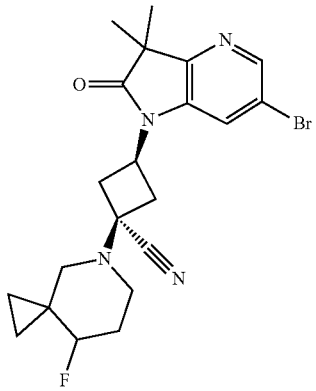 [SMILES: CC1(C)C(=O)N([C@H]2C[C@@](C#N)(N3CCC(F)C4(CC4)C3)C2)c2cc(Br)cnc21]

In a 25 mL flask was placed 3-(6-bromo-3,3-dimethyl-2-oxo-pyrrolo[3,2-b]pyridin-1-yl)-1-(8-hydroxy-5-azaspiro[2.5]octan-5-yl)cyclobutanecarbonitrile (0.16 g, 0.36 mmol) in DCM (2 mL). To this mixture was added (diethylamino)sulfur trifluoride (0.090 ml, 0.72 mmol) at 0° C. After the mixture warmed to room temperature and stirred for 1 h, it was quenched with sat. $K_2CO_3$ and extracted with DCM. The combined organic layers were dried ($Na_2SO_4$), concentrated, and purified by flash chromatography (100% DCM to 100% EtOAc) to give (1s,3s)-3-(6-bromo-3,3-dimethyl-2-oxo-2,3-dihydro-1H-pyrrolo[3,2-b]pyridin-1-yl)-1-(8-fluoro-5-azaspiro[2.5]octan-5-yl)cyclobutane-1-carbonitrile.

E. Preparation of 6'-bromo-2,3,5,6-tetrahydrospiro[pyran-4,3'-pyrrolo[3,2-b]pyridin]-2'(1'H)-one

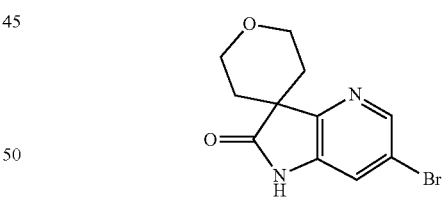

In a 250 mL, single neck, round bottomed flask were placed commercially available 6-bromo-1,3-dihydropyrrolo[3,2-b]pyridin-2-one (1.0 g, 4.7 mmol) and N,N,N',N'-tetramethylethylenediamine (1.4 mL, 9.0 mmol) in THF (20 mL). The mixture was cooled to −78° C., and to this was dropwise added a solution of n-BuLi (4.7 mL, 12 mmol, 2.5 M). The resulting reaction mixture was warmed to room temperature and stirred for 18 h. Then, it was quenched with sat. $NH_4Cl$ and extracted with DCM. The combined organic layers were dried ($Na_2SO_4$), concentrated, and purified by flash chromatography (100% Hexane to 100% EtOAc) to give 6'-bromo-2,3,5,6-tetrahydrospiro[pyran-4,3'-pyrrolo[3,2-b]pyridin]-2'(1'H)-one.

F. Preparation of 6-bromo-3,3-dimethyl-1-((1s,3s)-3-methyl-3-(piperidin-1-yl)cyclobutyl)-1,3-dihydro-2H-pyrrolo[3,2-b]pyridin-2-one

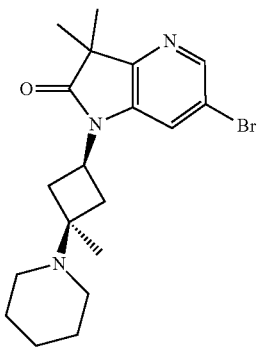 [SMILES: CC1(C)C(=O)N([C@H]2C[C@@](C)(N3CCCCC3)C2)c2cc(Br)cnc21]

In a round bottomed, single neck, 500 mL flask were placed (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile (5.0 g, 12 mmol) and AgOTf (5.1 g, 20 mmol) in THF (100 ml) under nitrogen. The mixture was stirred at room temperature for 10 min and then it was cooled to −78° C. To this was dropwise added MeMgBr (12 mL, 3.0 M in ether). Then it was immediately warmed to −10° C. After stirring at −10° C. for 15 min, the reaction mixture was quenched with sat. NH₄Cl and sat. NaHCO₃ and extracted with DCM. The combined organic layers were dried (Na₂SO₄), filtered, concentrated, and purified by flash chromatography (100% DCM to 100% EtOAc) to afford 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

The following compounds were prepared using a similar procedure.

(i) 6-Bromo-3,3-dimethyl-1-((1s,3s)-3-methyl-3-(piperidin-1-yl)cyclobutyl)-2,3-dihydro-1H-pyrrolo[3,2-b]pyridine

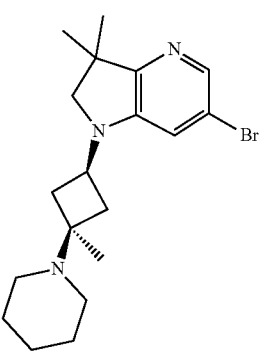 [SMILES: CC1(C)CN([C@H]2C[C@@](C)(N3CCCCC3)C2)c2cc(Br)cnc21]

6-Bromo-3,3-dimethyl-1-((1s,3s)-3-methyl-3-(piperidin-1-yl)cyclobutyl)-2,3-dihydro-1H-pyrrolo[3,2-b]pyridine was prepared using a similar procedure except that (1s,3s)-3-(6-bromo-3,3-dimethyl-2,3-dihydro-1H-pyrrolo[3,2-b]pyridin-1-yl)-1-(piperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(ii) 6-Bromo-1-((1r,3s)-3-ethyl-3-(piperidin-1-yl)cyclobutyl)-3,3-dimethyl-1,3-dihydro-2H-pyrrolo[3,2-b]pyridin-2-one

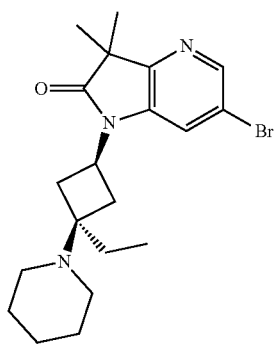 [SMILES: CC[C@]1(N2CCCCC2)C[C@@H](N2C(=O)C(C)(C)c3ncc(Br)cc32)C1]

6-Bromo-1-((1r,3s)-3-ethyl-3-(piperidin-1-yl)cyclobutyl)-3,3-dimethyl-1,3-dihydro-2H-pyrrolo[3,2-b]pyridin-2-one was prepared using a similar procedure except that EtMgBr was used instead of MeMgBr.

(iii) 6-Bromo-3,3-dimethyl-1-((1s,3s)-3-methyl-3-(1,4-oxazepan-4-yl)cyclobutyl)-1,3-dihydro-2H-pyrrolo[3,2-b]pyridin-2-one

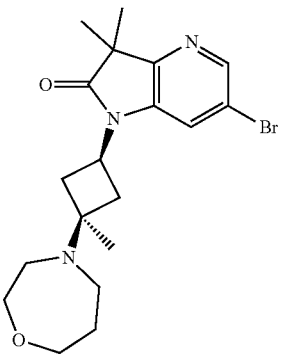

6-Bromo-3,3-dimethyl-1-((1s,3s)-3-methyl-3-(1,4-oxazepan-4-yl)cyclobutyl)-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(1,4-oxazepan-4-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

541

(iv) 6'-Bromo-1'-((1s,3s)-3-methyl-3-(piperidin-1-yl) cyclobutyl)-2,3,5,6-tetrahydrospiro[pyran-4,3'-pyrrolo[3,2-b]pyridin]-2'(1'H)-one

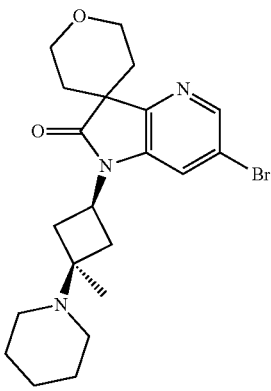 [SMILES: C[C@]1(N2CCCCC2)C[C@@H](N2C(=O)C3(CCOCC3)c3ncc(Br)cc32)C1]

6'-Bromo-1'-((1s,3s)-3-methyl-3-(piperidin-1-yl)cyclobutyl)-2,3,5,6-tetrahydrospiro[pyran-4,3'-pyrrolo[3,2-b]pyridin]-2'(1'H)-one was prepared using a similar procedure except that (1s,3s)-3-(6'-bromo-2'-oxo-2,3,5,6-tetrahydrospiro[pyran-4,3'-pyrrolo[3,2-b]pyridin]-1'(2'H)-yl)-1-(piperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(v) 1-((1s,3s)-3-(2-Oxa-5-azabicyclo[2.2.2]octan-5-yl)-3-methylcyclobutyl)-6-bromo-3,3-dimethyl-1,3-dihydro-2H-pyrrolo[3,2-b]pyridin-2-one

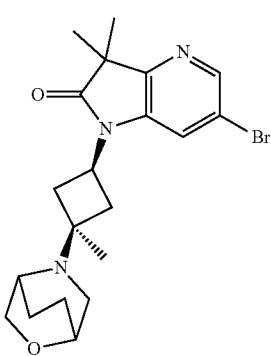 [SMILES: CC1(C)C(=O)N([C@H]2C[C@@](C)(N3CC4CCC3CO4)C2)c2cc(Br)cnc21]

1-((1s,3s)-3-(2-oxa-5-azabicyclo[2.2.2]octan-5-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(2-oxa-5-azabicyclo[2.2.2]octan-5-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

542

(vi) 6-Bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one

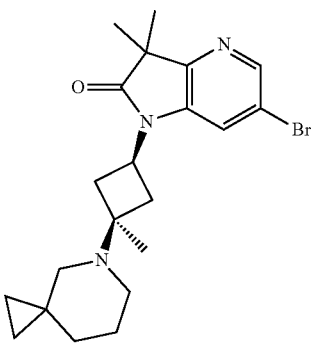 [SMILES: CC1(C)C(=O)N([C@H]2C[C@@](C)(N3CCCC4(CC4)C3)C2)c2cc(Br)cnc21]

6-Bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(5-azaspiro[2.5]octan-5-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(vii) 6-Bromo-1-((1s,3s)-3-(8-fluoro-5-azaspiro[2.5]octan-5-yl)-3-methylcyclobutyl)-3,3-dimethyl-1,3-dihydro-2H-pyrrolo[3,2-b]pyridin-2-one

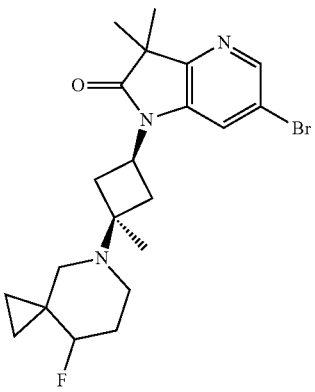 [SMILES: CC1(C)C(=O)N([C@H]2C[C@@](C)(N3CCC(F)C4(CC4)C3)C2)c2cc(Br)cnc21]

6-Bromo-1-((1s,3s)-3-(8-fluoro-5-azaspiro[2.5]octan-5-yl)-3-methylcyclobutyl)-3,3-dimethyl-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(8-fluoro-5-azaspiro[2.5]octan-5-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

543

(viii) 1-((1s,3s)-3-(3-Azabicyclo[3.2.0]heptan-3-yl)-3-methylcyclobutyl)-6-bromo-3,3-dimethyl-1,3-dihydro-2H-pyrrolo[3,2-b]pyridin-2-one

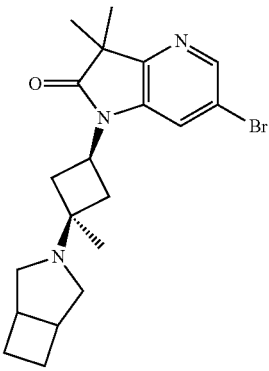 [SMILES: CC1(C)C(=O)N([C@H]2C[C@@](C)(N3CC4CCC4C3)C2)c2cc(Br)cnc21]

1-((1s,3s)-3-(3-Azabicyclo[3.2.0]heptan-3-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(3-azabicyclo[3.2.0]heptan-3-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(ix) 1-((1s,3s)-3-(3-Azabicyclo[4.1.0]heptan-3-yl)-3-methylcyclobutyl)-6-bromo-3,3-dimethyl-1,3-dihydro-2H-pyrrolo[3,2-b]pyridin-2-one

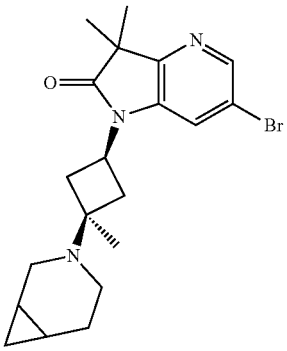 [SMILES: CC1(C)C(=O)N([C@H]2C[C@@](C)(N3CCC4CC4C3)C2)c2cc(Br)cnc21]

1-((1s,3s)-3-(3-Azabicyclo[4.1.0]heptan-3-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(3-azabicyclo[4.1.0]heptan-3-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

544

(x) 6-Bromo-1-((1s,3s)-3-(2,2-dimethylmorpholino)-3-methylcyclobutyl)-3,3-dimethyl-1,3-dihydro-2H-pyrrolo[3,2-b]pyridin-2-one

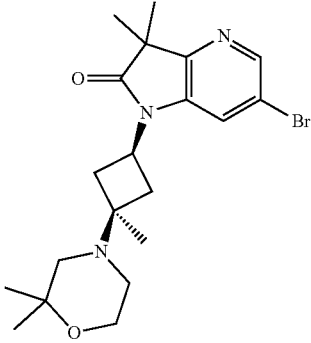 [SMILES: CC1(C)CN([C@]2(C)C[C@H](N3C(=O)C(C)(C)c4ncc(Br)cc43)C2)CCO1]

6-Bromo-1-((1s,3s)-3-(2,2-dimethylmorpholino)-3-methylcyclobutyl)-3,3-dimethyl-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(2,2-dimethylmorpholino)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xi) 6-Bromo-3,3-dimethyl-1-((1S,3s)-3-methyl-3-((3aR,6aS)-tetrahydro-1H-furo[3,4-c]pyrrol-5(3H)-yl)cyclobutyl)-1,3-dihydro-2H-pyrrolo[3,2-b]pyridin-2-one

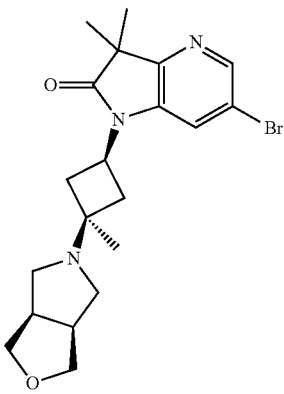 [SMILES: CC1(C)C(=O)N([C@H]2C[C@@](C)(N3C[C@H]4COC[C@H]4C3)C2)c2cc(Br)cnc21]

6-Bromo-3,3-dimethyl-1-((1S,3s)-3-methyl-3-((3aR,6aS)-tetrahydro-1H-furo[3,4-c]pyrrol-5(3H)-yl)cyclobutyl)-1,3-dihydro-2H-pyrrolo[3,2-b]pyridin-2-one was prepared using a similar procedure except that (1s,3S)-3-(6-bromo-3,3-dimethyl-2-oxo-2,3-dihydro-1H-pyrrolo[3,2-b]pyridin-1-yl)-1-((3aR,6aS)-tetrahydro-1H-furo[3,4-c]pyrrol-5(3H)-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

545

(xii) 1-((1s,3s)-3-(8-Oxa-3-azabicyclo[3.2.1]octan-3-yl)-3-methylcyclobutyl)-6-bromo-3,3-dimethyl-1,3-dihydro-2H-pyrrolo[3,2-b]pyridin-2-one

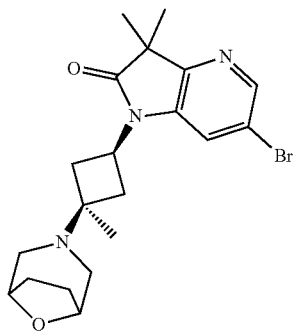 [SMILES: CC1(C)C(=O)N([C@H]2C[C@@](C)(N3CC4CCC(C3)O4)C2)c2cc(Br)cnc21]

1-((1s,3s)-3-(8-Oxa-3-azabicyclo[3.2.1]octan-3-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(8-oxa-3-azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xiii) 6-Bromo-3,3-dimethyl-1-((1s,3s)-3-methyl-3-morpholinocyclobutyl)-1,3-dihydro-2H-pyrrolo[3,2-b]pyridin-2-one

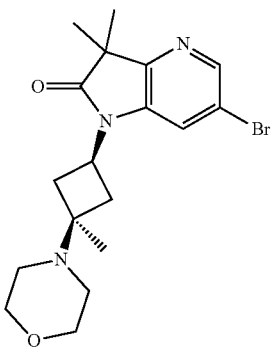 [SMILES: CC1(C)C(=O)N([C@H]2C[C@@](C)(N3CCOCC3)C2)c2cc(Br)cnc21]

6-Bromo-3,3-dimethyl-1-((1s,3s)-3-methyl-3-morpholinocyclobutyl)-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-morpholinocyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

546

(xiv) 6-Bromo-1-((1S,3s)-3-((R)-3-fluoropiperidin-1-yl)-3-methylcyclobutyl)-3,3-dimethyl-1,3-dihydro-2H-pyrrolo[3,2-b]pyridin-2-one

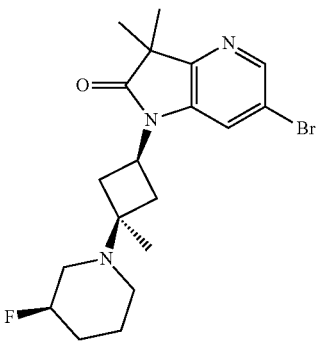 [SMILES: CC1(C)C(=O)N([C@H]2C[C@@](C)(N3CCC[C@@H](F)C3)C2)c2cc(Br)cnc21]

6-Bromo-1-((1S,3s)-3-((R)-3-fluoropiperidin-1-yl)-3-methylcyclobutyl)-3,3-dimethyl-1,3-dihydro-2H-pyrrolo[3,2-b]pyridin-2-one was prepared using a similar procedure except that (1s,3S)-3-(6-bromo-3,3-dimethyl-2-oxo-2,3-dihydro-1H-pyrrolo[3,2-b]pyridin-1-yl)-1-((R)-3-fluoropiperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xv) 6-Bromo-1-((1s,3s)-3-(4-fluoropiperidin-1-yl)-3-methylcyclobutyl)-3,3-dimethyl-1,3-dihydro-2H-pyrrolo[3,2-b]pyridin-2-one

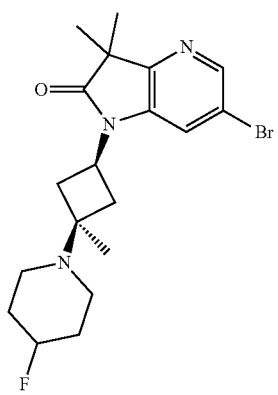 [SMILES: CC1(C)C(=O)N([C@H]2C[C@@](C)(N3CCC(F)CC3)C2)c2cc(Br)cnc21]

6-Bromo-1-((1s,3s)-3-(4-fluoropiperidin-1-yl)-3-methylcyclobutyl)-3,3-dimethyl-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(4-fluoropiperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

547

(xvi) 1-((1s,3s)-3-(3-Azabicyclo[3.1.0]hexan-3-yl)-3-methylcyclobutyl)-6-bromo-3,3-dimethyl-1,3-dihydro-2H-pyrrolo[3,2-b]pyridin-2-one

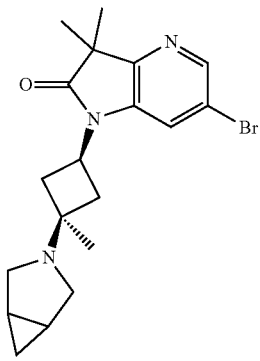 [SMILES: CC1(C)C(=O)N([C@H]2C[C@@](C)(N3CC4CC4C3)C2)c2cc(Br)cnc21]

1-((1s,3s)-3-(3-Azabicyclo[3.1.0]hexan-3-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(3-azabicyclo[3.1.0]hexan-3-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xvii) 1-((1s,3s)-3-(3-Oxa-8-azabicyclo[3.2.1]octan-8-yl)-3-methylcyclobutyl)-6-bromo-3,3-dimethyl-1,3-dihydro-2H-pyrrolo[3,2-b]pyridin-2-one

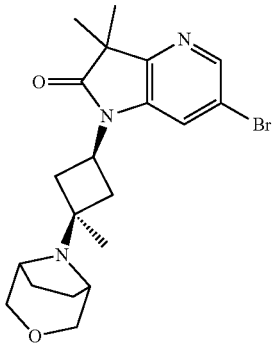 [SMILES: CC1(C)C(=O)N([C@H]2C[C@@](C)(N3C4CCC3COC4)C2)c2cc(Br)cnc21]

1-((1s,3s)-3-(3-Oxa-8-azabicyclo[3.2.1]octan-8-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(3-oxa-8-azabicyclo[3.2.1]octan-8-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

548

(xviii) 1-((1s,3s)-3-(6-Oxa-2-azabicyclo[3.2.1]octan-2-yl)-3-methylcyclobutyl)-6-bromo-3,3-dimethyl-1,3-dihydro-2H-pyrrolo[3,2-b]pyridin-2-one

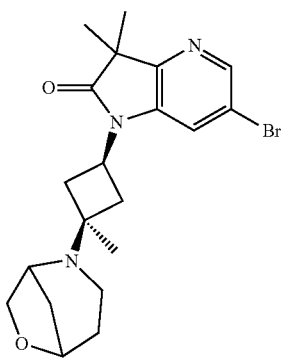 [SMILES: CC1(C)C(=O)N([C@H]2C[C@@](C)(N3CCC4CC3CO4)C2)c2cc(Br)cnc21]

1-((1s,3s)-3-(6-Oxa-2-azabicyclo[3.2.1]octan-2-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(6-oxa-2-azabicyclo[3.2.1]octan-2-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xix) 6-Bromo-3,3-dimethyl-1-((1s,3s)-3-methyl-3-(4-oxa-7-azaspiro[2.5]octan-7-yl)cyclobutyl)-1,3-dihydro-2H-pyrrolo[3,2-b]pyridin-2-one

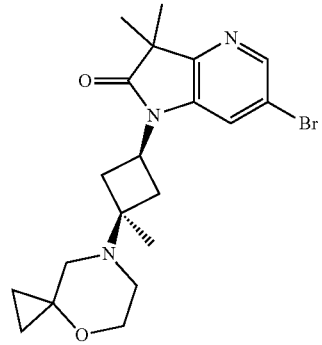 [SMILES: CC1(C)C(=O)N([C@H]2C[C@@](C)(N3CCOC4(CC4)C3)C2)c2cc(Br)cnc21]

6-Bromo-3,3-dimethyl-1-((1s,3s)-3-methyl-3-(4-oxa-7-azaspiro[2.5]octan-7-yl)cyclobutyl)-1,3-dihydro-2H-pyrrolo[3,2-b]pyridin-2-one was prepared using a similar procedure except that (1s,3s)-3-(6-bromo-3,3-dimethyl-2-oxo-2,3-dihydro-1H-pyrrolo[3,2-b]pyridin-1-yl)-1-(4-oxa-7-azaspiro[2.5]octan-7-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

549

(xx) 1-((1s,3s)-3-(Azepan-1-yl)-3-methylcyclobutyl)-6-bromo-3,3-dimethyl-1,3-dihydro-2H-pyrrolo[3,2-b]pyridin-2-one

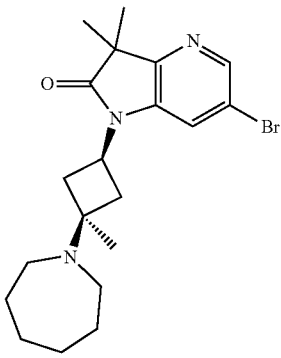 [SMILES: CC1(C)C(=O)N([C@H]2C[C@@](C)(N3CCCCCC3)C2)c2cc(Br)cnc21]

1-((1s,3s)-3-(Azepan-1-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(azepan-1-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxi) 1-((1s,3s)-3-(3-Azabicyclo[3.2.1]octan-3-yl)-3-methylcyclobutyl)-6-bromo-3,3-dimethyl-1,3-dihydro-2H-pyrrolo[3,2-b]pyridin-2-one

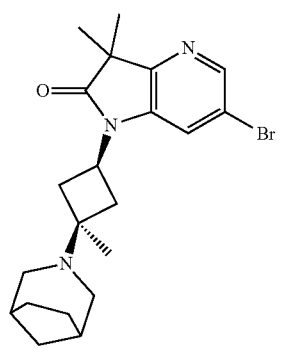 [SMILES: CC1(C)C(=O)N([C@H]2C[C@@](C)(N3CC4CCC(C4)C3)C2)c2cc(Br)cnc21]

1-((1s,3s)-3-(3-Azabicyclo[3.2.1]octan-3-yl)-3-methylcyclobutyl)-6-bromo-3,3-dimethyl-1,3-dihydro-2H-pyrrolo[3,2-b]pyridin-2-one was prepared using a similar procedure except that (1s,3s)-1-(3-azabicyclo[3.2.1]octan-3-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

550

(xxii) 1-((1S,3s)-3-((1R,4S)-2-azabicyclo[2.2.1]heptan-2-yl)-3-methylcyclobutyl)-6-bromo-3,3-dimethyl-1,3-dihydro-2H-pyrrolo[3,2-b]pyridin-2-one

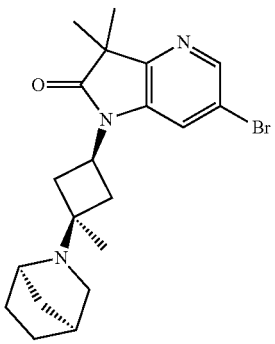 [SMILES: CC1(C)C(=O)N([C@H]2C[C@@](C)(N3C[C@H]4CC[C@@H]3C4)C2)c2cc(Br)cnc21]

1-((1S,3s)-3-((1R,4S)-2-azabicyclo[2.2.1]heptan-2-yl)-3-methylcyclobutyl)-6-bromo-3,3-dimethyl-1,3-dihydro-2H-pyrrolo[3,2-b]pyridin-2-one was prepared using a similar procedure except that (1s,3S)-1-((1R,4S)-2-azabicyclo[2.2.1]heptan-2-yl)-3-(6-bromo-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxiii) 1-((1s,3s)-3-(3-azabicyclo[4.1.0]heptan-3-yl)-3-methylcyclobutyl)-6-bromo-5-fluoro-3,3-dimethyl-1,3-dihydro-2H-pyrrolo[3,2-b]pyridin-2-one

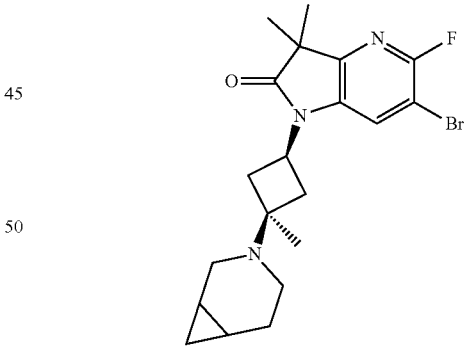

1-((1s,3s)-3-(3-azabicyclo[4.1.0]heptan-3-yl)-3-methylcyclobutyl)-6-bromo-5-fluoro-3,3-dimethyl-1,3-dihydro-2H-pyrrolo[3,2-b]pyridin-2-one was prepared using a similar procedure except that (1s,3s)-1-(3-azabicyclo[4.1.0]heptan-3-yl)-3-(6-bromo-5-fluoro-3,3-dimethyl-2-oxo-2,3-dihydro-1H-pyrrolo[3,2-b]pyridin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxiv) 6-bromo-5-fluoro-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one

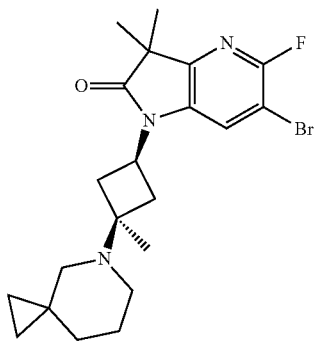 [SMILES: CC1(C)C(=O)N([C@H]2C[C@@](C)(N3CCCC4(CC4)C3)C2)c2cc(Br)c(F)nc21]

6-bromo-5-fluoro-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one was prepared using a similar procedure except that (1s,3s)-3-(6-bromo-5-fluoro-3,3-dimethyl-2-oxo-2,3-dihydro-1H-pyrrolo[3,2-b]pyridin-1-yl)-1-(5-azaspiro[2.5]octan-5-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxv) 6-Bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one

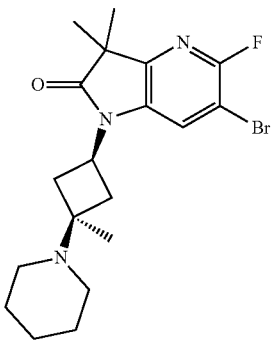 [SMILES: CC1(C)C(=O)N([C@H]2C[C@@](C)(N3CCCCC3)C2)c2cc(Br)c(F)nc21]

6-Bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one was prepared using a similar procedure except that (1s,3s)-3-(6-bromo-5-fluoro-3,3-dimethyl-2-oxo-2,3-dihydro-1H-pyrrolo[3,2-b]pyridin-1-yl)-1-(piperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxvi) 6-bromo-4-(difluoromethyl)-3,3-dimethyl-1-((1s,3s)-3-methyl-3-(piperidin-1-yl)cyclobutyl)indolin-2-one

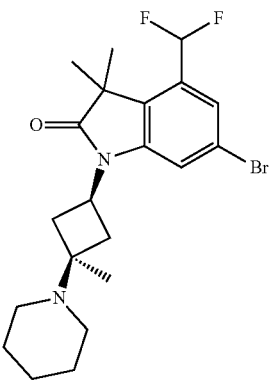 [SMILES: CC1(C)C(=O)N([C@H]2C[C@@](C)(N3CCCCC3)C2)c2cc(Br)cc(C(F)F)c21]

6-bromo-4-(difluoromethyl)-3,3-dimethyl-1-((1s,3s)-3-methyl-3-(piperidin-1-yl)cyclobutyl)indolin-2-one was prepared using a similar procedure except that (1ls,3s)-3-(6-bromo-4-(difluoromethyl)-3,3-dimethyl-2-oxoindolin-1-yl)-1-(piperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

(xxvii) 6'-bromo-1'-((1s,3s)-3-methyl-3-(piperidin-1-yl)cyclobutyl)spiro[cyclopropane-1,3'-indolin]-2'-one

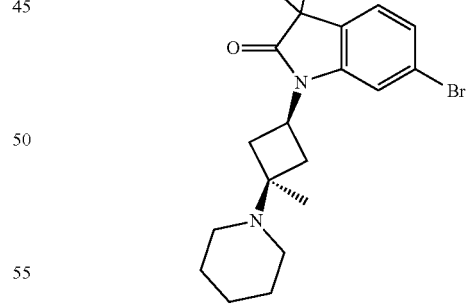

6'-bromo-1'-((1s,3s)-3-methyl-3-(piperidin-1-yl)cyclobutyl)spiro[cyclopropane-1,3'-indolin]-2'-one was prepared using a similar procedure except that (1s,3s)-3-(6'-bromo-2'-oxospiro[cyclopropane-1,3'-indolin]-1'-yl)-1-(piperidin-1-yl)cyclobutane-1-carbonitrile was used instead of (1s,3s)-3-(6-bromo-3,3-dimethyl-2-oxo-2,3-dihydro-1H-pyrrolo[3,2-b]pyridin-1-yl)-1-(piperidin-1-yl)cyclobutane-1-carbonitrile.

G. Preparation of 6-bromo-4-(hydroxymethyl)-3,3-dimethylindolin-2-one

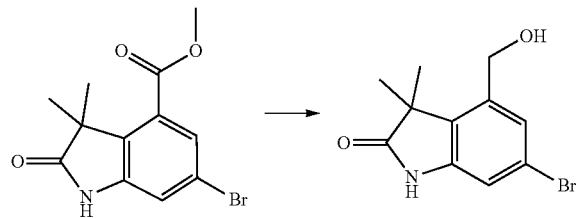 [SMILES: COC(=O)c1cc(Br)cc2c1C(C)(C)C(=O)N2 ; CC1(C)C(=O)Nc2cc(Br)cc(CO)c21]

In a round bottomed, single neck, 100 mL flask was placed methyl 6-bromo-3,3-dimethyl-2-oxo-indoline-4-carboxylate (2.6 g, 8.7 mmol) in MeOH (17 mL). To this was added NaBH$_4$ (3.4 g, 88 mmol) and the resulting mixture was heated at 50° C. for 18 h. Then it was cooled to RT, concentrated, and diluted with DCM and water. The organic layer was washed with brine, dried (Na$_2$SO$_4$), filtered, concentrated, and used in the next step without purification.

H. Preparation of 6-bromo-3,3-dimethyl-2-oxoindoline-4-carbaldehyde

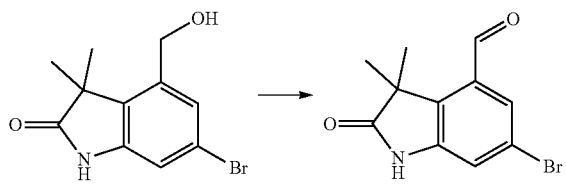

In a round bottomed, single neck, 100 mL flask was placed 6-bromo-4-(hydroxymethyl)-3,3-dimethyl-indolin-2-one (1.8 g, 6.6 mmol) in DCM (26 mL). To this was added Dess Martin periodinane (4.2 g, 10 mmol) and the resulting mixture was stirred at RT for 18 h. Then it was extracted with DCM and the combined organic layers were washed with brine, dried (Na$_2$SO$_4$), filtered, concentrated, and used in the next step without purification.

I. Preparation of 6-bromo-4-(difluoromethyl)-3,3-dimethylindolin-2-one

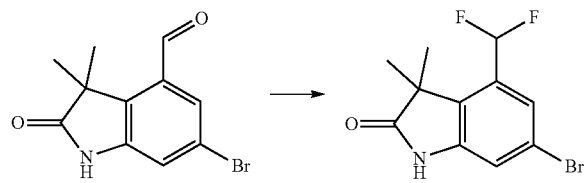 [SMILES: CC1(C)C(=O)Nc2cc(Br)cc(C=O)c21 ; CC1(C)C(=O)Nc2cc(Br)cc(C(F)F)c21]

In a round bottomed, single neck, 100 mL flask was placed 6-bromo-3,3-dimethyl-2-oxo-indoline-4-carbaldehyde (0.8 g, 3.0 mmol) in DCM (15 mL). To this was added Deoxo-Fluor" solution (1.0 g, 4.4 mmol) and the resulting mixture was stirred at RT for 18 h. Then it was extracted with DCM and the combined organic layers were washed with brine, dried (Na$_2$SO$_4$), filtered, concentrated, and purified using flash chromatography (100% Hexane to 100% EtOAc then 100% DCM to 100% MeOH) to give 6-bromo-4-(difluoromethyl)-3,3-dimethylindolin-2-one.

J. Preparation of tert-butyl 5-bromo-2-chloro-3,4-difluorobenzoate

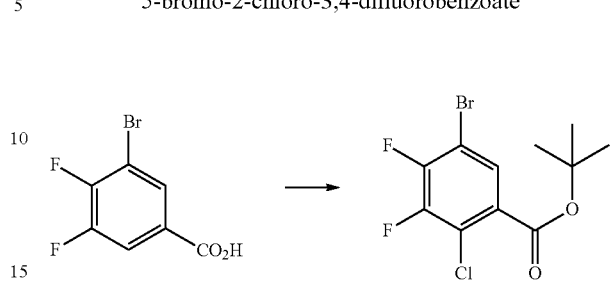

In a 1000 mL, round bottomed, single neck flask was placed 2,2,6,6-tetramethylpiperidine (10.7 mL, 63.3 mmol) in THF (300 mL). The solution was cooled to −78° C., and to this was dropwise added n-BuLi (25 mL, 63 mmol, 2.5 M in hexanes). The resulting reaction mixture was stirred at −78° C. for 15 min. To this was dropwise added a solution of 3-bromo-4,5-difluorobenzoic acid (6.00 g, 25.3 mmol) in THF (50 mL) at −78 C. The mixture was stirred at −78 C for 30 min, after which hexachloroethane (30.0 g, 126 mmol) in 50 mL THF was added dropwise. The mixture was warmed to room temperature and stirred for 18 h. It was quenched with H$_2$O, concentrated, re-dissolved in H$_2$O, and washed with hexanes. The aqueous layer was acidified with conc. HCl. The solids were collected by filtration, dissolved in EtOAc, dried (Na$_2$SO$_4$), concentrated, and re-dissolved in THF (100 mL). To this were added Boc$_2$O (12.2 g, 55.7 mmol) and DMAP (620 mg, 5.1 mmol) at room temperature. The reaction mixture was stirred at room temperature for 18 h. Then, it was concentrated and purified by flash column chromatography (10% EtOAc in Hexane to 25% EtOAc in Hexane) to give tert-butyl 5-bromo-2-chloro-3,4-difluorobenzoate.

K. Preparation of 5-amino-2-chloro-3,4-difluorobenzoic acid hydrochloride

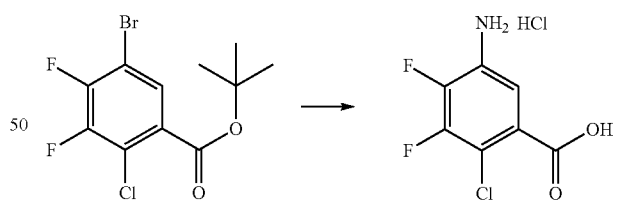

In a 500 mL, single neck, round bottomed flask were placed tert-butyl 5-bromo-2-chloro-3,4-difluorobenzoate (4.75 g, 14.5 mmol), Pd$_2$(dba)$_3$ (664 mg, 0.725 mmol), Xantphos (839 mg, 1.45 mmol), Cs$_2$CO$_3$ (7.09 g, 21.8 mmol), and BocNH$_2$ (2.04 g, 17.4 mmol) in dioxane (50 mL). The reaction mixture was purged with nitrogen and stirred at 100° C. for 18 h. Then it was cooled to room temperature, filtered through a pad of Celite, washed with DCM, and concentrated. The residue was washed through a silica column (10% EtOAc in Hexane to 100% EtOAc), concentrated, and dissolved in dioxane (15 mL). To this was added HCl (73.0 mL, 289 mmol, 4.0 M in dioxane), and the resulting mixture was stirred at 55° C. for 5 h. Then, it was cooled to 0° C. and the resulting precipitate was collected by filtration to give 5-amino-2-chloro-3,4-difluorobenzoic acid hydrochloride. This compound was used without any further purification.

L. Preparation of 5-((6-bromo-3-isopropyl-3H-imidazo[4,5-c]pyridin-4-yl)amino)-2-chloro-3,4-difluorobenzoic acid

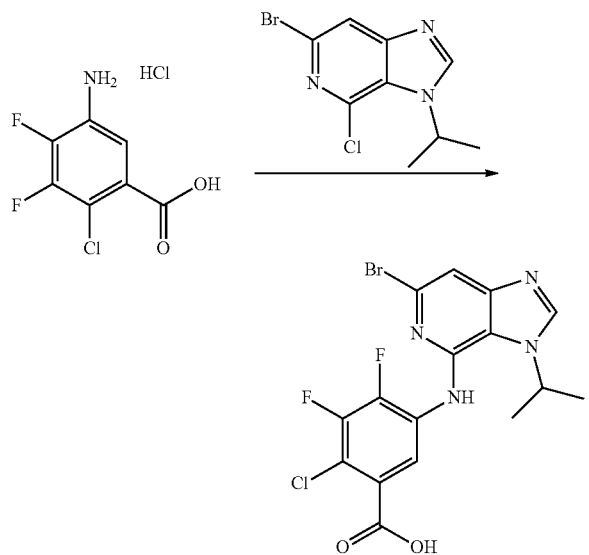

In a 250 mL, single neck, round bottomed flask equipped with a reflux condenser was placed 5-amino-2-chloro-3,4-difluorobenzoic acid hydrochloride (4.10 g, 16.8 mmol) in DMF (17 mL). The mixture was cooled to 0° C., and to this was added NaH (2.67 g, 67.2 mmol, 60% dispersion in mineral oil). The resulting mixture was stirred at 0° C. for 5 min followed by the addition of 6-bromo-4-chloro-3-isopropyl-3H-imidazo[4,5-c]pyridine (5.07 g, 18.5 mmol). After the reaction mixture was stirred at 60° C. for 30 min, it was cooled to room temperature and was quenched with an aqueous solution of citric acid. The precipitates were collected by filtration, washed with $H_2O$, and dried under vacuum to give 5-((6-bromo-3-isopropyl-3H-imidazo[4,5-c]pyridin-4-yl)amino)-2-chloro-3,4-difluorobenzoic acid. This compound was used without any further purification.

The following compounds were prepared using a similar procedure.

(i) 5-((6-Bromo-3-isopropyl-3H-imidazo[4,5-c]pyridin-4-yl)amino)-2-chloro-4-fluorobenzoic acid

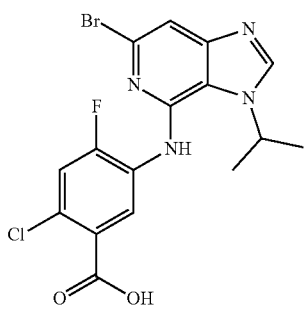 [SMILES: CC(C)n1cnc2cc(Br)nc(Nc3cc(C(=O)O)c(Cl)cc3F)c21]

5-((6-Bromo-3-isopropyl-3H-imidazo[4,5-c]pyridin-4-yl)amino)-2-chloro-4-fluorobenzoic acid was prepared using a similar procedure except that commercially available 5-amino-2-chloro-4-fluorobenzoic acid was used instead of 5-amino-2-chloro-3,4-difluorobenzoic acid hydrochloride.

(ii) 3-((6-Bromo-3-isopropyl-3H-imidazo[4,5-c]pyridin-4-yl)amino)-4-fluorobenzoic acid

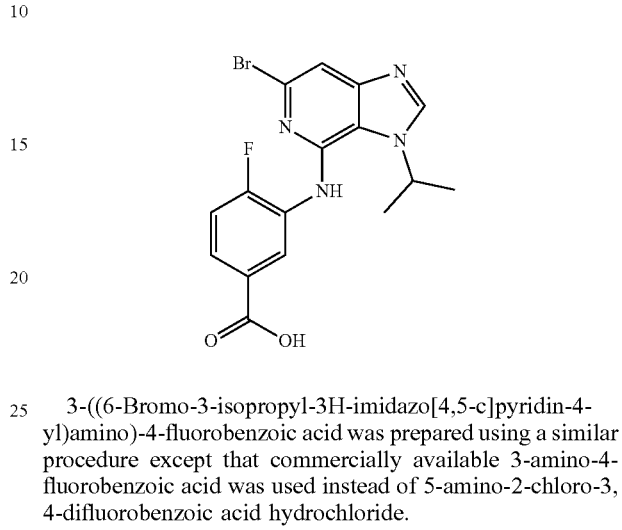

3-((6-Bromo-3-isopropyl-3H-imidazo[4,5-c]pyridin-4-yl)amino)-4-fluorobenzoic acid was prepared using a similar procedure except that commercially available 3-amino-4-fluorobenzoic acid was used instead of 5-amino-2-chloro-3,4-difluorobenzoic acid hydrochloride.

M. Preparation of 5-((6-bromo-3-isopropyl-3H-imidazo[4,5-c]pyridin-4-yl)amino)-2-chloro-N-(1-(difluoromethyl)cyclopropyl)-3,4-difluorobenzamide

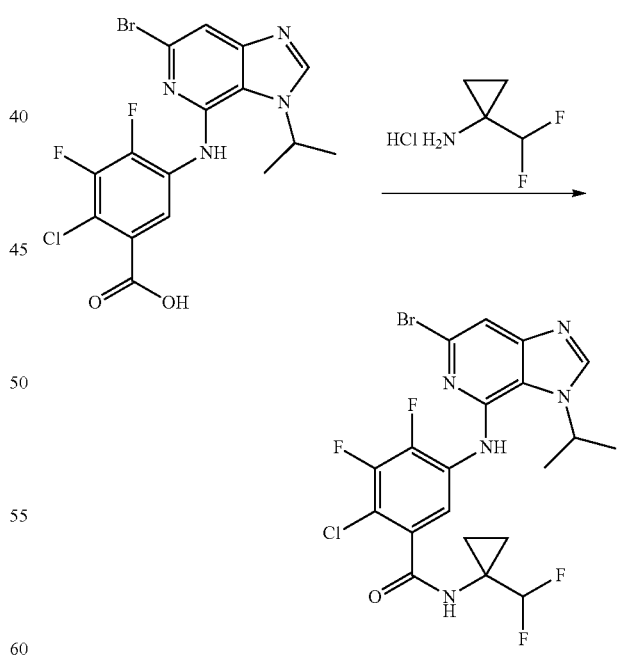

In a 250 mL, single neck, round bottomed flask were placed 5-((6-bromo-3-isopropyl-3H-imidazo[4,5-c]pyridin-4-yl)amino)-2-chloro-3,4-difluorobenzoic acid (1.50 g, 3.37 mmol), 1-(difluoromethyl)cyclopropan-1-amine hydrochloride (0.725 g, 5.05 mmol), and HATU (2.30 g, 6.06 mmol) in DMF (15 mL). To this was added $N(iPr)_2Et$ (2.93 mL, 16.8 mmol) at room temperature, and the resulting mixture was stirred at 60° C. for 1 h. The mixture was cooled to room temperature and quenched with H₂O. The precipitates were collected by filtration, washed with H₂O and then Et₂O, and dried under vacuum to give 5-((6-bromo-3-isopropyl-3H-imidazo[4,5-c]pyridin-4-yl)amino)-2-chloro-N-(1-(difluoromethyl)cyclopropyl)-3,4-difluorobenzamide. This compound was used without any further purification.

The following compounds were prepared using a similar procedure.

(i) 5-((6-Bromo-3-isopropyl-3H-imidazo[4,5-c]pyridin-4-yl)amino)-2-chloro-N-(1-(difluoromethyl)cyclopropyl)-4-fluorobenzamide

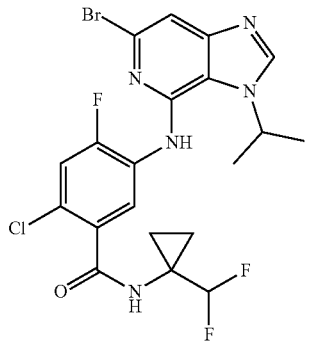 [SMILES: CC(C)n1cnc2cc(Br)nc(Nc3cc(C(=O)NC4(C(F)F)CC4)c(Cl)cc3F)c21]

5-((6-Bromo-3-isopropyl-3H-imidazo[4,5-c]pyridin-4-yl)amino)-2-chloro-N-(1-(difluoromethyl)cyclopropyl)-4-fluorobenzamide was prepared using a similar procedure except that 5-((6-bromo-3-isopropyl-3H-imidazo[4,5-c]pyridin-4-yl)amino)-2-chloro-4-fluorobenzoic acid was used instead of 5-((6-bromo-3-isopropyl-3H-imidazo[4,5-c]pyridin-4-yl)amino)-2-chloro-3,4-difluorobenzoic acid.

(ii) 5-((6-Bromo-3-isopropyl-3H-imidazo[4,5-c]pyridin-4-yl)amino)-N-(1-(difluoromethyl)cyclopropyl)-3,4-difluoro-2-methylbenzamide

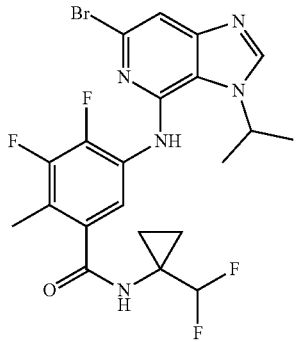 [SMILES: Cc1c(C(=O)NC2(C(F)F)CC2)cc(Nc2nc(Br)cc3ncn(C(C)C)c23)c(F)c1F]

5-((6-bromo-3-isopropyl-3H-imidazo[4,5-c]pyridin-4-yl)amino)-N-(1-(difluoromethyl)cyclopropyl)-3,4-difluoro-2-methylbenzamide was prepared using a similar procedure except that 5-((6-bromo-3-isopropyl-3H-imidazo[4,5-c]pyridin-4-yl)amino)-3,4-difluoro-2-methylbenzoic acid was used instead of 5-((6-bromo-3-isopropyl-3H-imidazo[4,5-c]pyridin-4-yl)amino)-2-chloro-3,4-difluorobenzoic acid.

(iii) 5-((6-Bromo-3-isopropyl-3H-imidazo[4,5-c]pyridin-4-yl)amino)-3,4-difluoro-N-(1-(fluoromethyl)cyclopropyl)-2-methylbenzamide

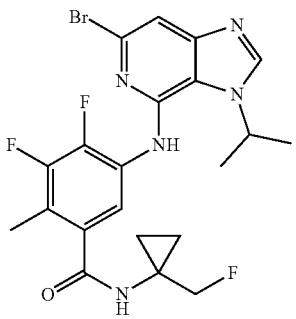 [SMILES: Cc1c(C(=O)NC2(CF)CC2)cc(Nc2nc(Br)cc3ncn(C(C)C)c23)c(F)c1F]

5-((6-Bromo-3-isopropyl-3H-imidazo[4,5-c]pyridin-4-yl)amino)-3,4-difluoro-N-(1-(fluoromethyl)cyclopropyl)-2-methylbenzamide was prepared using a similar procedure except that 5-((6-bromo-3-isopropyl-3H-imidazo[4,5-c]pyridin-4-yl)amino)-3,4-difluoro-2-methylbenzoic acid and 1-(fluoromethyl)cyclopropan-1-amine hydrochloride were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(iv) 5-((6-Bromo-3-isopropyl-3H-imidazo[4,5-c]pyridin-4-yl)amino)-N-(2,2-difluoroethyl)-3,4-difluoro-2-methylbenzamide

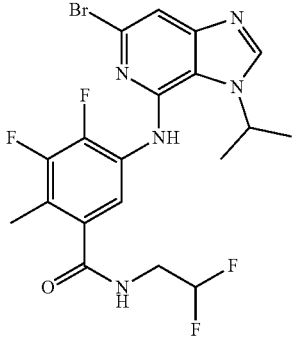

5-((6-Bromo-3-isopropyl-3H-imidazo[4,5-c]pyridin-4-yl)amino)-N-(2,2-difluoroethyl)-3,4-difluoro-2-methylbenzamide was prepared using a similar procedure except that 5-((6-bromo-3-isopropyl-3H-imidazo[4,5-c]pyridin-4-yl)amino)-3,4-difluoro-2-methylbenzoic acid and 2,2-difluoroethan-1-amine were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(v) 5-((6-Bromo-3-isopropyl-3H-imidazo[4,5-c]
pyridin-4-yl)amino)-3,4-difluoro-N-isopropyl-2-
methylbenzamide

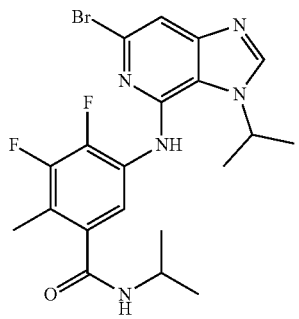 [SMILES: Cc1c(C(=O)NC(C)C)cc(Nc2nc(Br)cc3ncn(C(C)C)c23)c(F)c1F]

5-((6-Bromo-3-isopropyl-3H-imidazo[4,5-c]pyridin-4-yl)amino)-3,4-difluoro-N-isopropyl-2-methylbenzamide was prepared using a similar procedure except that 5-((6-bromo-3-isopropyl-3H-imidazo[4,5-c]pyridin-4-yl)amino)-3,4-difluoro-2-methylbenzoic acid and propan-2-amine were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(vi) 5-((6-Bromo-3-isopropyl-3H-imidazo[4,5-c]
pyridin-4-yl)amino)-N-cyclopropyl-3,4-difluoro-2-
methylbenzamide

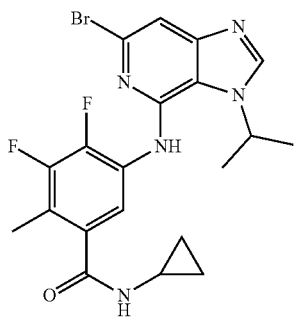 [SMILES: Cc1c(C(=O)NC2CC2)cc(Nc2nc(Br)cc3ncn(C(C)C)c23)c(F)c1F]

5-((6-Bromo-3-isopropyl-3H-imidazo[4,5-c]pyridin-4-yl)amino)-N-cyclopropyl-3,4-difluoro-2-methylbenzamide was prepared using a similar procedure except that 5-((6-bromo-3-isopropyl-3H-imidazo[4,5-c]pyridin-4-yl)amino)-3,4-difluoro-2-methylbenzoic acid and cyclopropanamine were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(vii) 5-((6-Bromo-3-isopropyl-3H-imidazo[4,5-c]
pyridin-4-yl)amino)-N-ethyl-3,4-difluoro-2-methyl-
benzamide

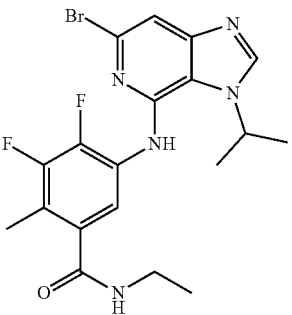

5-((6-Bromo-3-isopropyl-3H-imidazo[4,5-c]pyridin-4-yl)amino)-N-ethyl-3,4-difluoro-2-methylbenzamide was prepared using a similar procedure except that 5-((6-bromo-3-isopropyl-3H-imidazo[4,5-c]pyridin-4-yl)amino)-3,4-difluoro-2-methylbenzoic acid and ethylamine were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(viii) 5-((6-Bromo-3-isopropyl-3H-imidazo[4,5-c]
pyridin-4-yl)amino)-2-chloro-3,4-difluoro-N-(1-
(trifluoromethyl)cyclopropyl)benzamide

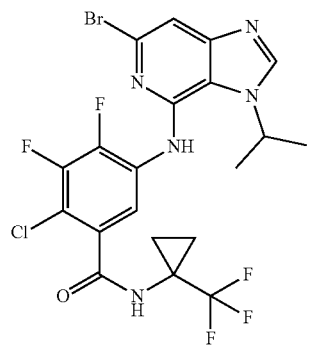 [SMILES: CC(C)n1cnc2cc(Br)nc(Nc3cc(C(=O)NC4(C(F)(F)F)CC4)c(Cl)c(F)c3F)c21]

5-((6-Bromo-3-isopropyl-3H-imidazo[4,5-c]pyridin-4-yl)amino)-2-chloro-3,4-difluoro-N-(1-(trifluoromethyl)cyclopropyl)benzamide was prepared using a similar procedure except that commercially available 1-(trifluoromethyl)cyclopropan-1-amine hydrochloride was used instead of 1-(difluoromethyl)cyclopropan-1-amine hydrochloride.

(ix) 5-((6-Bromo-3-isopropyl-3H-imidazo[4,5-c]pyridin-4-yl)amino)-2-chloro-3,4-difluoro-N-(1-(fluoromethyl)cyclopropyl)benzamide

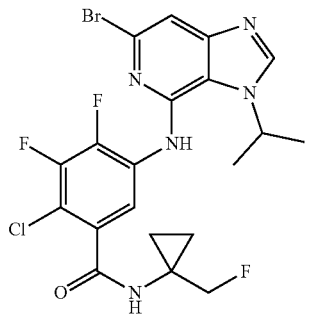 [SMILES: CC(C)n1cnc2cc(Br)nc(Nc3cc(C(=O)NC4(CF)CC4)c(Cl)c(F)c3F)c21]

5-((6-Bromo-3-isopropyl-3H-imidazo[4,5-c]pyridin-4-yl)amino)-2-chloro-3,4-difluoro-N-(1-(fluoromethyl)cyclopropyl)benzamide was prepared using a similar procedure except that 1-(fluoromethyl)cyclopropan-1-amine hydrochloride was used instead of 1-(difluoromethyl)cyclopropan-1-amine hydrochloride.

(x) 5-((6-bromo-3-isopropyl-3H-imidazo[4,5-c]pyridin-4-yl)amino)-2-chloro-N-(2,2-difluoroethyl)-3,4-difluorobenzamide

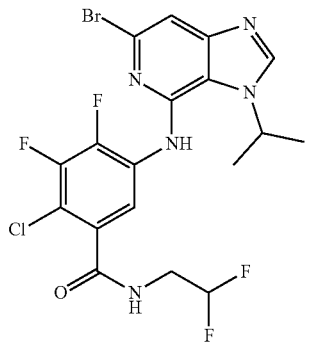 [SMILES: CC(C)n1cnc2cc(Br)nc(Nc3cc(C(=O)NCC(F)F)c(Cl)c(F)c3F)c21]

5-((6-bromo-3-isopropyl-3H-imidazo[4,5-c]pyridin-4-yl)amino)-2-chloro-N-(2,2-difluoroethyl)-3,4-difluorobenzamide was prepared using a similar procedure except that 2,2-difluoroethan-1-amine hydrochloride was used instead of 1-(difluoromethyl)cyclopropan-1-amine hydrochloride.

(xi) 5-((6-bromo-3-isopropyl-3H-imidazo[4,5-c]pyridin-4-yl)amino)-2-chloro-N-cyclopropyl-3,4-difluorobenzamide

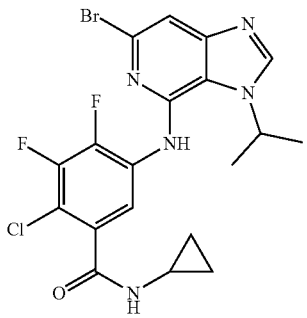 [SMILES: CC(C)n1cnc2cc(Br)nc(Nc3cc(C(=O)NC4CC4)c(Cl)c(F)c3F)c21]

5-((6-bromo-3-isopropyl-3H-imidazo[4,5-c]pyridin-4-yl)amino)-2-chloro-N-cyclopropyl-3,4-difluorobenzamide was prepared using a similar procedure except that cyclopropanamine hydrochloride was used instead of instead of 1-(difluoromethyl)cyclopropan-1-amine hydrochloride.

(xii) 5-((6-bromo-3-isopropyl-3H-imidazo[4,5-c]pyridin-4-yl)amino)-2-chloro-N-ethyl-3,4-difluorobenzamide

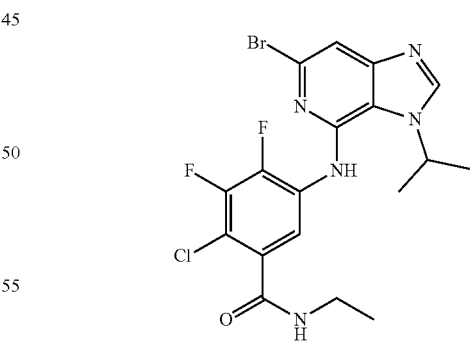

5-((6-bromo-3-isopropyl-3H-imidazo[4,5-c]pyridin-4-yl)amino)-2-chloro-N-ethyl-3,4-difluorobenzamide was prepared using a similar procedure except that ethylamine hydrochloride was used instead of instead of 1-(difluoromethyl)cyclopropan-1-amine hydrochloride.

(xiii) 5-((6-bromo-3-isopropyl-3H-imidazo[4,5-c]pyridin-4-yl)amino)-2-chloro-3,4-difluoro-N-methylbenzamide

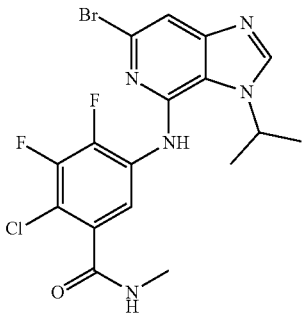 [SMILES: CNC(=O)c1cc(Nc2nc(Br)cc3ncn(C(C)C)c23)c(F)c(F)c1Cl]

5-((6-bromo-3-isopropyl-3H-imidazo[4,5-c]pyridin-4-yl)amino)-2-chloro-3,4-difluoro-N-methylbenzamide was prepared using a similar procedure except that methylamine hydrochloride was used instead of instead of 1-(difluoromethyl)cyclopropan-1-amine hydrochloride.

(xiv) 5-((6-bromo-3-isopropyl-3H-imidazo[4,5-c]pyridin-4-yl)amino)-2-chloro-3,4-difluoro-N-isopropylbenzamide

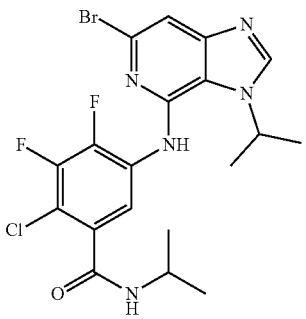 [SMILES: CC(C)NC(=O)c1cc(Nc2nc(Br)cc3ncn(C(C)C)c23)c(F)c(F)c1Cl]

5-((6-bromo-3-isopropyl-3H-imidazo[4,5-c]pyridin-4-yl)amino)-2-chloro-3,4-difluoro-N-isopropylbenzamide was prepared using a similar procedure except that isopropylamine hydrochloride was used instead of instead of 1-(difluoromethyl)cyclopropan-1-amine hydrochloride.

(xv) 5-((6-bromo-3-isopropyl-3H-imidazo[4,5-c]pyridin-4-yl)amino)-N-(2,2-difluoroethyl)-4-fluoro-2-methylbenzamide

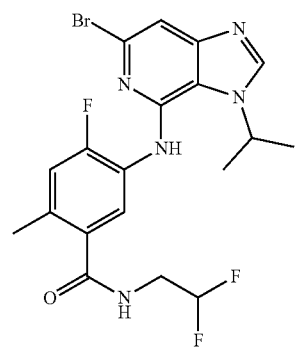 [SMILES: Cc1cc(F)c(Nc2nc(Br)cc3ncn(C(C)C)c23)cc1C(=O)NCC(F)F]

5-((6-bromo-3-isopropyl-3H-imidazo[4,5-c]pyridin-4-yl)amino)-N-(2,2-difluoroethyl)-4-fluoro-2-methylbenzamide was prepared using a similar procedure except that 2,2-difluoroethan-1-amine hydrochloride and 5-((6-bromo-3-isopropyl-3H-imidazo[4,5-c]pyridin-4-yl)amino)-4-fluoro-2-methylbenzoic acid were used instead of 1-(difluoromethyl)cyclopropan-1-amine hydrochloride and 5-((6-bromo-3-isopropyl-3H-imidazo[4,5-c]pyridin-4-yl)amino)-2-chloro-3,4-difluorobenzoic acid, respectively.

(xvi) 5-((6-bromo-3-isopropyl-3H-imidazo[4,5-c]pyridin-4-yl)amino)-N-ethyl-4-fluoro-2-methylbenzamide

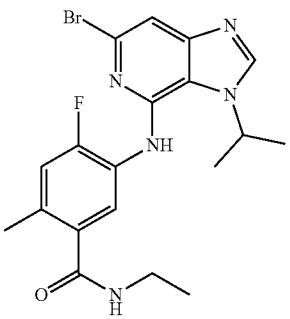 [SMILES: CCNC(=O)c1cc(Nc2nc(Br)cc3ncn(C(C)C)c23)c(F)cc1C]

5-((6-bromo-3-isopropyl-3H-imidazo[4,5-c]pyridin-4-yl)amino)-N-ethyl-4-fluoro-2-methylbenzamide was prepared using a similar procedure except that ethylamine hydrochloride and 5-((6-bromo-3-isopropyl-3H-imidazo[4,5-c]pyridin-4-yl)amino)-4-fluoro-2-methylbenzoic acid were used instead of 1-(difluoromethyl)cyclopropan-1-amine hydrochloride and 5-((6-bromo-3-isopropyl-3H-imidazo[4,5-c]pyridin-4-yl)amino)-2-chloro-3,4-difluorobenzoic acid, respectively.

(xvii) 5-((6-bromo-3-isopropyl-3H-imidazo[4,5-c]pyridin-4-yl)amino)-2-chloro-N-(2,2-difluoroethyl)-4-fluorobenzamide

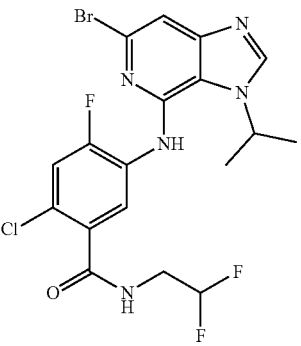 [SMILES: CC(C)n1cnc2cc(Br)nc(Nc3cc(C(=O)NCC(F)F)c(Cl)cc3F)c21]

5-((6-bromo-3-isopropyl-3H-imidazo[4,5-c]pyridin-4-yl)amino)-2-chloro-N-(2,2-difluoroethyl)-4-fluorobenzamide was prepared using a similar procedure except that 2,2-difluoroethan-1-amine hydrochloride and 5-((6-bromo-3-isopropyl-3H-imidazo[4,5-c]pyridin-4-yl)amino)-2-chloro-4-fluorobenzoic acid were used instead of 1-(difluoromethyl)cyclopropan-1-amine hydrochloride and 5-((6-bromo-3-isopropyl-3H-imidazo[4,5-c]pyridin-4-yl)amino)-2-chloro-3,4-difluorobenzoic acid, respectively.

(xviii) 5-((6-bromo-3-isopropyl-3H-imidazo[4,5-c]
pyridin-4-yl)amino)-2-chloro-N-ethyl-4-fluorobenz-
amide

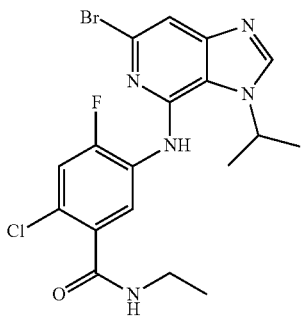 [SMILES: CCNC(=O)c1cc(Nc2nc(Br)cc3ncn(C(C)C)c23)c(F)cc1Cl]

5-((6-bromo-3-isopropyl-3H-imidazo[4,5-c]pyridin-4-yl)
amino)-2-chloro-N-ethyl-4-fluorobenzamide was prepared
using a similar procedure except that ethylamine hydrochloride and 5-((6-bromo-3-isopropyl-3H-imidazo[4,5-c]pyridin-4-yl)amino)-2-chloro-4-fluorobenzoic acid were used instead of 1-(difluoromethyl)cyclopropan-1-amine hydrochloride and 5-((6-bromo-3-isopropyl-3H-imidazo[4,5-c]pyridin-4-yl)amino)-2-chloro-3,4-difluorobenzoic acid, respectively.

(xix) 5-((6-bromo-3-isopropyl-3H-imidazo[4,5-c]
pyridin-4-yl)amino)-2-chloro-4-fluoro-N-(1-(fluo-
romethyl)cyclopropyl)benzamide

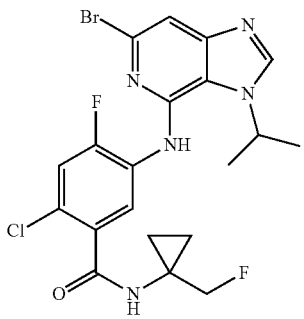 [SMILES: CC(C)n1cnc2cc(Br)nc(Nc3cc(C(=O)NC4(CF)CC4)c(Cl)cc3F)c21]

5-((6-bromo-3-isopropyl-3H-imidazo[4,5-c]pyridin-4-yl)
amino)-2-chloro-4-fluoro-N-(1-(fluoromethyl)cyclopropyl)
benzamide was prepared using a similar procedure except
that 1-(fluoromethyl)cyclopropan-1-amine hydrochloride
and 5-((6-bromo-3-isopropyl-3H-imidazo[4,5-c]pyridin-4-yl)amino)-2-chloro-4-fluorobenzoic acid were used instead
of 1-(difluoromethyl)cyclopropan-1-amine hydrochloride
and 5-((6-bromo-3-isopropyl-3H-imidazo[4,5-c]pyridin-4-yl)amino)-2-chloro-3,4-difluorobenzoic acid, respectively.

(xx) 5-((6-bromo-3-isopropyl-3H-imidazo[4,5-c]
pyridin-4-yl)amino)-2-chloro-N-(1-(difluoromethyl)
cyclopropyl)-4-fluoro-3-methylbenzamide

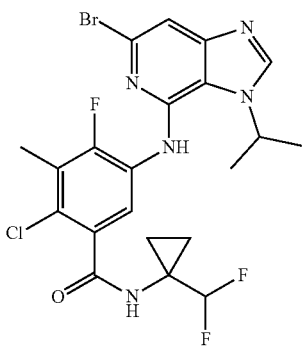 [SMILES: Cc1c(F)c(Nc2nc(Br)cc3ncn(C(C)C)c23)cc(C(=O)NC2(C(F)F)CC2)c1Cl]

5-((6-bromo-3-isopropyl-3H-imidazo[4,5-c]pyridin-4-yl)
amino)-2-chloro-N-(1-(difluoromethyl)cyclopropyl)-4-
fluoro-3-methylbenzamide was prepared using a similar
procedure except that 5-((6-bromo-3-isopropyl-3H-imidazo
[4,5-c]pyridin-4-yl)amino)-2-chloro-4-fluoro-3-methylbenzoic acid was used instead of 5-((6-bromo-3-isopropyl-3H-imidazo[4,5-c]pyridin-4-yl)amino)-2-chloro-3,4-
difluorobenzoic acid.

(xxi) 5-((6-bromo-3-isopropyl-3H-imidazo[4,5-c]
pyridin-4-yl)amino)-N-(1-(difluoromethyl)cyclopro-
pyl)-2,3,4-trifluorobenzamide

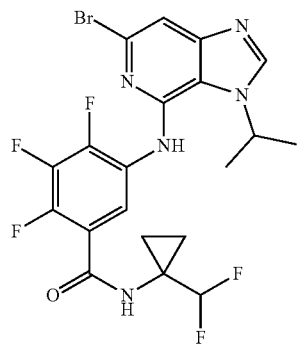

5-((6-bromo-3-isopropyl-3H-imidazo[4,5-c]pyridin-4-yl)
amino)-N-(1-(difluoromethyl)cyclopropyl)-2,3,4-trifluorobenzamide was prepared using a similar procedure except
that 5-((6-bromo-3-isopropyl-3H-imidazo[4,5-c]pyridin-4-yl)amino)-2,3,4-trifluorobenzoic acid was used instead of
5-((6-bromo-3-isopropyl-3H-imidazo[4,5-c]pyridin-4-yl)
amino)-2-chloro-3,4-difluorobenzoic acid.

(xxii) 5-((6-bromo-3-isopropyl-3H-imidazo[4,5-c] pyridin-4-yl)amino)-N-ethyl-2,3,4-trifluorobenz-amide

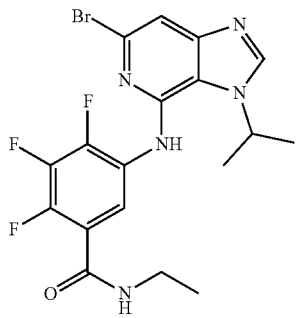 [SMILES: CCNC(=O)c1cc(Nc2nc(Br)cc3ncn(C(C)C)c23)c(F)c(F)c1F]

5-((6-bromo-3-isopropyl-3H-imidazo[4,5-c]pyridin-4-yl) amino)-N-ethyl-2,3,4-trifluorobenzamide was prepared using a similar procedure except that 5-((6-bromo-3-isopropyl-3H-imidazo[4,5-c]pyridin-4-yl)amino)-2,3,4-trifluorobenzoic acid and ethylamine hydrochloride was used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride, respectively.

(xxiii) 5-((6-bromo-3-isopropyl-3H-imidazo[4,5-c] pyridin-4-yl)amino)-N-(2,2-difluoroethyl)-2,3,4-trifluorobenzamide

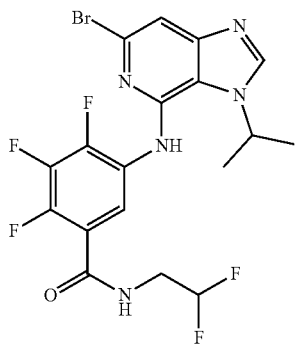

5-((6-bromo-3-isopropyl-3H-imidazo[4,5-c]pyridin-4-yl) amino)-N-(2,2-difluoroethyl)-2,3,4-trifluorobenzamide was prepared using a similar procedure except that 5-((6-bromo-3-isopropyl-3H-imidazo[4,5-c]pyridin-4-yl)amino)-2,3,4-trifluorobenzoic acid and 2,2-difluoroethan-1-amine hydrochloride was used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride, respectively.

(xxiv) 3-((6-Bromo-3-isopropyl-3H-imidazo[4,5-c] pyridin-4-yl)amino)-N-(1-(difluoromethyl)cyclopropyl)-4-fluorobenzamide

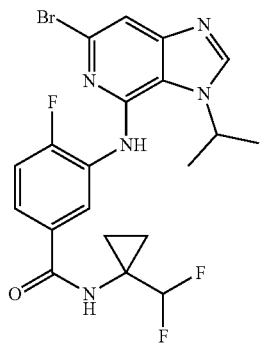 [SMILES: CC(C)n1cnc2cc(Br)nc(Nc3cc(C(=O)NC4(C(F)F)CC4)ccc3F)c21]

3-((6-Bromo-3-isopropyl-3H-imidazo[4,5-c]pyridin-4-yl)amino)-N-(1 (difluoromethyl)cyclopropyl)-4-fluorobenzamide was prepared using a similar procedure except that 3-((6-bromo-3-isopropyl-3H-imidazo[4,5-c]pyridin-4-yl) amino)-4-fluorobenzoic acid was used instead of 5-((6-bromo-3-isopropyl-3H-imidazo[4,5-c]pyridin-4-yl)amino)-2-chloro-3,4-difluorobenzoic acid.

(xxv) 3-((6-Bromo-3-isopropyl-3H-imidazo[4,5-c] pyridin-4-yl)amino)-N-ethyl-4-fluorobenzamide

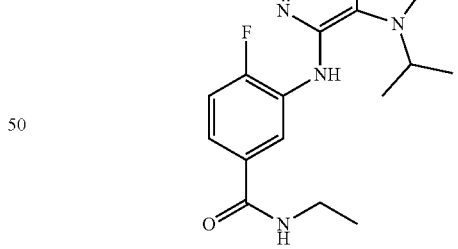

3-((6-Bromo-3-isopropyl-3H-imidazo[4,5-c]pyridin-4-yl)amino)-N-ethyl-4-fluorobenzamide was prepared using a similar procedure except that 3-((6-bromo-3-isopropyl-3H-imidazo[4,5-c]pyridin-4-yl)amino)-4-fluorobenzoic acid and ethylamine were used instead of 5-((6-bromo-3-isopropyl-3H-imidazo[4,5-c]pyridin-4-yl)amino)-2-chloro-3,4-difluorobenzoic acid and 1-(difluoromethyl)cyclopropan-1-amine hydrochloride.

(xxvi) 3-Bromo-N-(1-(difluoromethyl)cyclopropyl)-4,5-difluorobenzamide

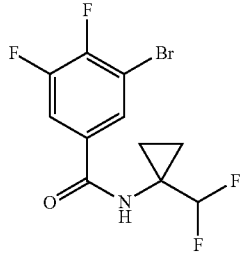 [SMILES: O=C(NC1(C(F)F)CC1)c1cc(F)c(F)c(Br)c1]

3-Bromo-N-(1-(difluoromethyl)cyclopropyl)-4,5-difluorobenzamide was prepared using a similar procedure except that 3-bromo-4,5-difluorobenzoic acid was used instead of 5-((6-bromo-3-isopropyl-3H-imidazo[4,5-c]pyridin-4-yl)amino)-2-chloro-3,4-difluorobenzoic acid.

N. Preparation of 5-bromo-3,4-difluoro-2-methylbenzoic acid

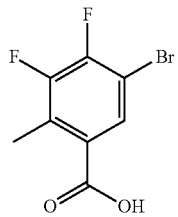

In a 1 L, round bottomed, single neck flask was placed 2,2,6,6-tetramethylpiperidine (10.7 mL, 63.3 mmol) in THF (30 mL). The solution was cooled to 0° C. under a nitrogen atmosphere, and to this was dropwise added n-BuLi (24.3 mL, 60.8 mmol, 2.5 M in hexane). After stirring at 0° C. for 15 min, it was dropwise added to a stirring solution of 3-bromo-4,5-difluorobenzoic acid (6.00 g, 25.3 mmol) in THF (300 mL) at –78° C. under a nitrogen atmosphere. The mixture was stirred at –78° C. for 30 min. To this solution was dropwise added iodomethane (7.89 mL, 127 mmol) at –78° C. The resulting reaction mixture was slowly warmed to room temperature and stirred for 18 h. It was quenched with H$_2$O, acidified with 2 M HCl, and extracted with EtOAc. The combined organic layers were washed with water, dried (Na$_2$SO$_4$), and concentrated under vacuum to afford 5-bromo-3,4-difluoro-2-methylbenzoic acid, which was carried on to the subsequent reaction without further purification.

O. Preparation of tert-butyl 5-bromo-3,4-difluoro-2-methylbenzoate

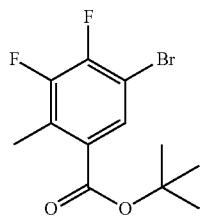

In a 250 mL, single neck, round bottomed flask were placed 5-bromo-3,4-difluoro-2-methylbenzoic acid (5.00 g, 19.9 mmol) and 4-(dimethylamino)pyridine (730 mg, 5.98 mmol) in DCM (40 mL) and t-BuOH (40 mL). To this was added di-tert-butyl dicarbonate (8.69 g, 39.8 mmol). After the reaction mixture was stirred at room temperature for 18 h, it was concentrated under vacuum. The resulting crude product was dissolved in EtOAc, washed with 10% aqueous citric acid and brine, dried (Na$_2$SO$_4$), concentrated, and purified by flash chromatography (100% Hexane to 5% EtOAc in Hexane) to afford tert-butyl 5-bromo-3,4-difluoro-2-methylbenzoate.

P. Preparation of tert-butyl 5-((tert-butoxycarbonyl)amino)-3,4-difluoro-2-methylbenzoate

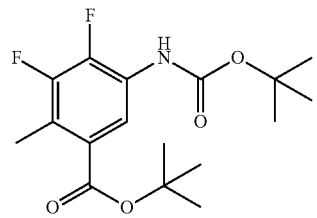 [SMILES: Cc1c(C(=O)OC(C)(C)C)cc(NC(=O)OC(C)(C)C)c(F)c1F]

In a sealed tube were placed tert-butyl 5-bromo-3,4-difluoro-2-methylbenzoate (4.86 g, 15.8 mmol), tert-butyl carbamate (7.42 g, 63.3 mmol), Pd$_2$(dba)$_3$*CHCl$_3$ (724 mg, 791 umol), Xantphos (916 mg, 1.58 mmol), and Cs$_2$CO$_3$ (7.73 g, 23.7 mmol) in dioxane (67 mL). The reaction mixture was purged with nitrogen and stirred at 100° C. for 3 h. Then, it was cooled to room temperature, diluted with EtOAc, and filtered through a pad of Celite. The filtrate was concentrated and purified by flash chromatography (100% Hexane to 30% EtOAc in Hexane) to afford tert-butyl 5-((tert-butoxycarbonyl)amino)-3,4-difluoro-2-methylbenzoate.

Q. Preparation of 5-amino-3,4-difluoro-2-methylbenzoic acid

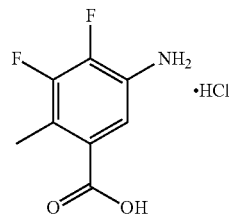

In a 100 mL, single neck, round bottomed flask was placed tert-butyl 5-((tert-butoxycarbonyl)amino)-3,4-difluoro-2-methylbenzoate (3.29 g, 9.58 mmol) in dioxane (20 mL). To this was added HCl (24.0 mL, 96.0 mmol, 4 M in dioxane), and the resulting reaction mixture was stirred at room temperature for 18 h. Then, it was cooled to 0° C., and the precipitates were collected by filtration and washed with cold dioxane to afford 5-amino-3,4-difluoro-2-methylbenzoic acid hydrochloride. This compound was used without any further purification.

R. Preparation of 2-chloro-4-fluoro-3-methyl-5-nitrobenzoic acid

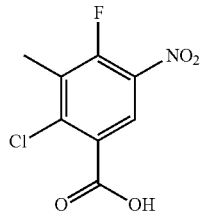

In a 100 mL, single neck, round bottomed flask was placed 2-chloro-4-fluoro-3-methylbenzoic acid (2.0 g, 11 mmol) in conc. sulfuric acid (20 mL). To this was drop-wise added 69% HNO₃ (0.69 mL) at 0° C. The resulting mixture was warmed to RT and stirred for 3 h. Then, it was poured into the flask containing 300 mL of ice water. The resulting precipitates were collected by filtration, washed with water, and dried to give 2-chloro-4-fluoro-3-methyl-5-nitrobenzoic acid.

S. Preparation of 5-amino-2-chloro-4-fluoro-3-methylbenzoic acid

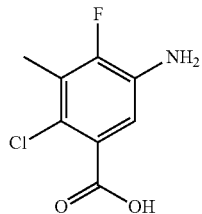

In a 100 mL, single neck, round bottomed flask were placed 2-chloro-4-fluoro-3-methyl-5-nitrobenzoic acid (1.0 g, 4.3 mmol) and 10 wt % Pd/C (0.22 g, 0.21 mmol) in THF (10 mL). The mixture was purged with N₂ for 10 min, purged with H₂, and then charged with a balloon filled with H₂. To this was added HCl in dioxane (2.2 mL, 4 M). The mixture was stirred at RT for 16 h, solubilized with MeOH, filtered through a pad of Celite, concentrated, re-suspended in dioxane. The resulting solids were collected by filtration to give 5-amino-2-chloro-4-fluoro-3-methylbenzoic acid.

T. Preparation of 5-((6-bromo-3-isopropyl-3H-imidazo[4,5-c]pyridin-4-yl)amino)-3,4-difluoro-2-methylbenzoic acid

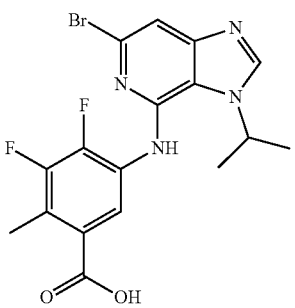 [SMILES: Cc1c(C(=O)O)cc(Nc2nc(Br)cc3ncn(C(C)C)c23)c(F)c1F]

In a 100 mL, single neck, round bottomed flask equipped with a reflux condenser was placed 5-amino-3,4-difluoro-2-methylbenzoic acid hydrochloride (1.17 g, 5.23 mmol) in NMP (12 mL). The mixture was cooled to 0° C., and to this was added NaH (0.837 g, 20.9 mmol, 60% dispersion in mineral oil). The resulting mixture was stirred at room temperature for 15 min followed by the addition of 6-bromo-4-fluoro-3-isopropyl-3H-imidazo[4,5-c]pyridine (1.62 g, 6.28 mmol). After the reaction mixture was stirred at 60° C. for 18 h, it was cooled to room temperature and was quenched with an aqueous solution of citric acid. The precipitates were collected by filtration, washed with H₂O, and dried under vacuum to give 5-((6-bromo-3-isopropyl-3H-imidazo[4,5-c]pyridin-4-yl)amino)-3,4-difluoro-2-methylbenzoic acid. This compound was used without any further purification.

The following compounds were prepared using a similar procedure.

(i) 5-((6-bromo-3-isopropyl-3H-imidazo[4,5-c]pyridin-4-yl)amino)-2-chloro-4-fluoro-3-methylbenzoic acid

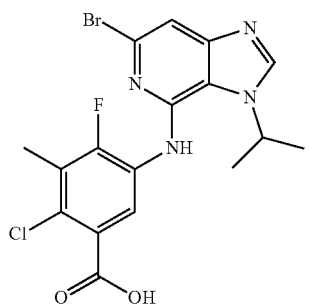 [SMILES: Cc1c(F)c(Nc2nc(Br)cc3ncn(C(C)C)c23)cc(C(=O)O)c1Cl]

5-((6-bromo-3-isopropyl-3H-imidazo[4,5-c]pyridin-4-yl)amino)-2-chloro-4-fluoro-3-methylbenzoic acid was prepared using a similar procedure except that 5-amino-2-chloro-4-fluoro-3-methylbenzoic acid was used instead of 5-amino-3,4-difluoro-2-methylbenzoic acid.

(ii) 5-((6-bromo-3-isopropyl-3H-imidazo[4,5-c]pyridin-4-yl)amino)-2,3,4-trifluorobenzoic acid

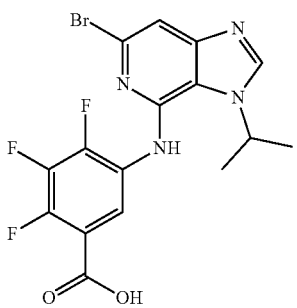

5-((6-bromo-3-isopropyl-3H-imidazo[4,5-c]pyridin-4-yl)amino)-2,3,4-trifluorobenzoic acid was prepared using a similar procedure except that 5-amino-2,3,4-trifluorobenzoic acid was used instead of 5-amino-3,4-difluoro-2-methylbenzoic acid.

U. Preparation of N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 185)

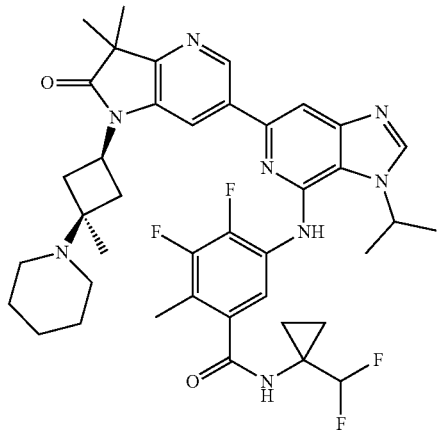 [SMILES: Cc1c(C(=O)NC2(C(F)F)CC2)cc(Nc2nc(-c3cnc4c(c3)N([C@H]3C[C@@](C)(N5CCCCC5)C3)C(=O)C4(C)C)cc3ncn(C(C)C)c23)c(F)c1F]

In a microwave vial were placed 6-bromo-3,3-dimethyl-1-((1s,3s)-3-methyl-3-(piperidin-1-yl)cyclobutyl)-1,3-dihydro-2H-pyrrolo[3,2-b]pyridin-2-one (120 mg, 0.31 mmol), bis(pinacolato)diboron (93.2 mg, 0.37 mmol), Pd(PPh$_3$)$_4$ (35.3 mg, 0.03 mmol), and KOAc (90.1 mg, 0.92 mmol). The mixture was sonicated and degassed with N$_2$, placed in the microwave reactor, heated at 150° C. for 45 min, and cooled to RT. To this mixture were added 5-((6-bromo-3-isopropyl-3H-imidazo[4,5-c]pyridin-4-yl)amino)-N-(1-(difluoromethyl)cyclopropyl)-3,4-difluoro-2-methylbenzamide (157 mg, 0.31 mmol) and 2M Na$_2$CO$_3$ (0.31 mL). The mixture was placed in the microwave reactor, heated at 125° C. for 25 min, and cooled to RT. Then it was purified by flash chromatography (100% DCM to 100% MeOH) followed by reverse phase chromatography (0.1% TFA in Water/0.1% TFA in ACN) to give N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide.

The following compounds were prepared using a similar procedure.

(i) 5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(fluoromethyl)cyclopropyl)-2-methylbenzamide (Example 186)

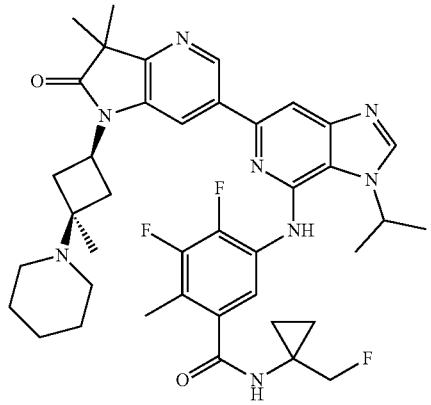 [SMILES: Cc1c(C(=O)NC2(CF)CC2)cc(Nc2nc(-c3cnc4c(c3)N([C@H]3C[C@@](C)(N5CCCCC5)C3)C(=O)C4(C)C)cc3ncn(C(C)C)c23)c(F)c1F]

5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(fluoromethyl)cyclopropyl)-2-methylbenzamide was prepared using a similar procedure except that 5-((6-bromo-3-isopropyl-3H-imidazo[4,5-c]pyridin-4-yl)amino)-3,4-difluoro-N-(1-(fluoromethyl)cyclopropyl)-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(ii) N-(1-(Difluoromethyl)cyclopropyl)-3,4-difluoro-5-((6-(1-((1s,3s)-3-(8-fluoro-5-azaspiro[2.5]octan-5-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 187)

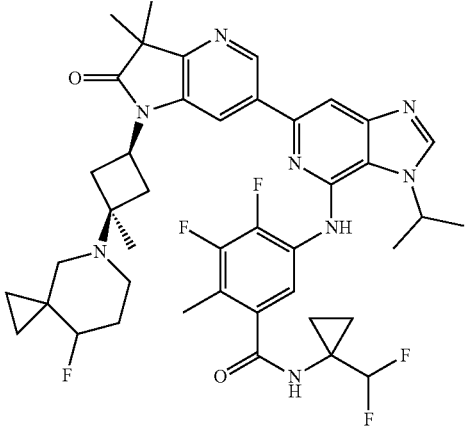 [SMILES: Cc1c(C(=O)NC2(C(F)F)CC2)cc(Nc2nc(-c3cnc4c(c3)N([C@H]3C[C@@](C)(N5CCC(F)C6(CC6)C5)C3)C(=O)C4(C)C)cc3ncn(C(C)C)c23)c(F)c1F]

N-(1-(Difluoromethyl)cyclopropyl)-3,4-difluoro-5-((6-(1-((1s,3s)-3-(8-fluoro-5-azaspiro[2.5]octan-5-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-1-((1s,3s)-3-(8-fluoro-5-azaspiro[2.5]octan-5-yl)-3-methylcyclobutyl)-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(iii) N-(1-(Difluoromethyl)cyclopropyl)-5-((6-(1-((1s,3s)-3-(2,2-dimethylmorpholino)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 188)

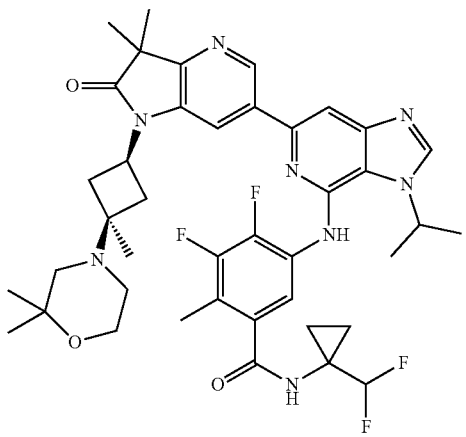 [SMILES: Cc1c(C(=O)NC2(C(F)F)CC2)cc(Nc2nc(-c3cnc4c(c3)N([C@H]3C[C@@](C)(N5CCOC(C)(C)C5)C3)C(=O)C4(C)C)cc3ncn(C(C)C)c23)c(F)c1F]

N-(1-(Difluoromethyl)cyclopropyl)-5-((6-(1-((1s,3s)-3-(2,2-dimethylmorpholino)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-1-((1s,3s)-3-(2,2-dimethylmorpholino)-3-methylcyclobutyl)-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(iv) N-(1-(Difluoromethyl)cyclopropyl)-5-((6-(3,3-dimethyl-1-((1S,3s)-3-methyl-3-((3 aR,6aS)-tetrahydro-1H-furo[3,4-c]pyrrol-5(3H)-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 189)

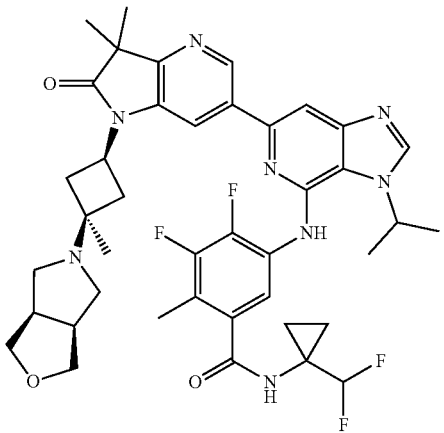 [SMILES: Cc1c(C(=O)NC2(C(F)F)CC2)cc(Nc2nc(-c3cnc4c(c3)N([C@H]3C[C@@](C)(N5C[C@H]6COC[C@H]6C5)C3)C(=O)C4(C)C)cc3ncn(C(C)C)c23)c(F)c1F]

N-(1-(Difluoromethyl)cyclopropyl)-5-((6-(3,3-dimethyl-1-((1S,3s)-3-methyl-3-((3 aR,6aS)-tetrahydro-1H-furo[3,4-c]pyrrol-5(3H)-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1S,3s)-3-methyl-3-((3aR,6aS)-tetrahydro-1H-furo[3,4-c]pyrrol-5(3H)-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(v) 5-((6-(1-((1s,3s)-3-(6-Oxa-2-azabicyclo[3.2.1]octan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 190)

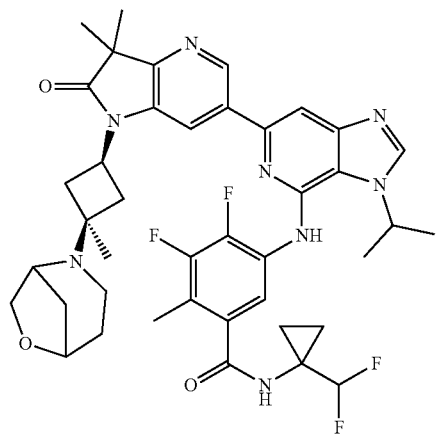 [SMILES: Cc1c(C(=O)NC2(C(F)F)CC2)cc(Nc2nc(-c3cnc4c(c3)N([C@H]3C[C@@](C)(N5CCC6CC5CO6)C3)C(=O)C4(C)C)cc3ncn(C(C)C)c23)c(F)c1F]

5-((6-(1-((1s,3s)-3-(6-Oxa-2-azabicyclo[3.2.1]octan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide was prepared using a similar procedure except that 1-((1s,3s)-3-(6-oxa-2-azabicyclo[3.2.1]octan-2-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

Chiral Resolution: Separation of the isomers of 5-((6-(1-((1s,3s)-3-(6-oxa-2-azabicyclo[3.2.1]octan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide.

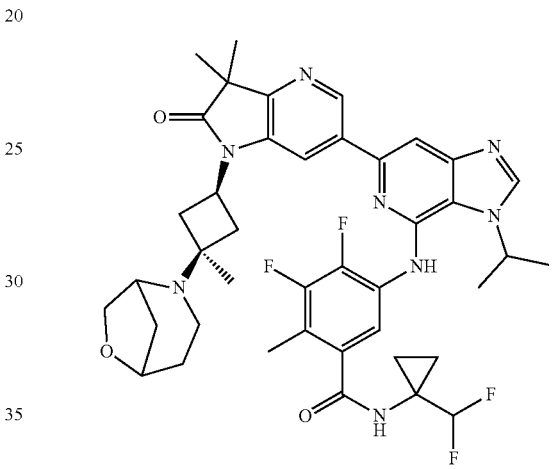

5-((6-(1-((1s,3s)-3-(6-oxa-2-azabicyclo[3.2.1]octan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide was separated on CHIRALPAK IA SFC 5 um 21×250 mm column in 35% MeOH (modified with 10 mM $NH_3$)/$CO_2$ at 60 mL/min to give the two single isomers which were further purified by reverse phase chromatography (0.1% TFA in Water/0.1% TFA in ACN):

| Name | Separation method | Peak # | Example # |
|---|---|---|---|
| 5-((6-(1-((1s,3s)-3-(6-oxa-2-azabicyclo[3.2.1]octan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide | CHIRALPAK IA SFC 5 um 21 × 250 mm column in 35% MeOH (modified with 10 mM $NH_3$)/$CO_2$ at 60 mL/min | $1^{st}$ eluting peak | Example 191 |
| | | $2^{nd}$ eluting peak | Example 192 |

(vi) N-(1-(Difluoromethyl)cyclopropyl)-5-((6-(3,3-dimethyl-1-((1s,3s)-3-methyl-3-(4-oxa-7-azaspiro[2.5]octan-7-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 193)

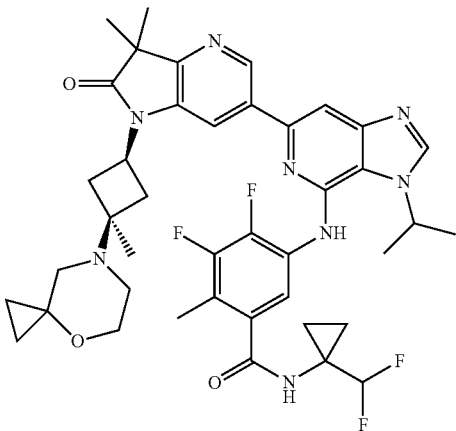 [SMILES: Cc1c(C(=O)NC2(C(F)F)CC2)cc(Nc2nc(-c3cnc4c(c3)N([C@H]3C[C@@](C)(N5CCOC6(CC6)C5)C3)C(=O)C4(C)C)cc3ncn(C(C)C)c23)c(F)c1F]

N-(1-(Difluoromethyl)cyclopropyl)-5-((6-(3,3-dimethyl-1-((1s,3s)-3-methyl-3-(4-oxa-7-azaspiro[2.5]octan-7-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(4-oxa-7-azaspiro[2.5]octan-7-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(vii) N-(1-(Difluoromethyl)cyclopropyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 194)

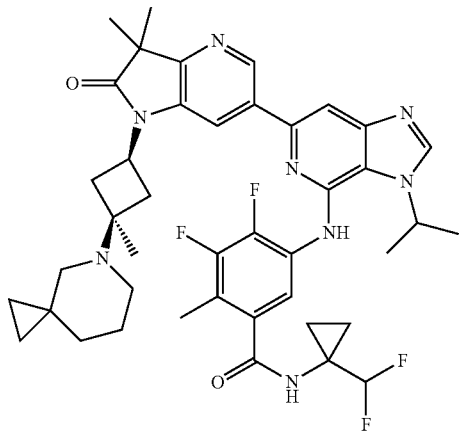 [SMILES: Cc1c(C(=O)NC2(C(F)F)CC2)cc(Nc2nc(-c3cnc4c(c3)N([C@H]3C[C@@](C)(N5CCCC6(CC6)C5)C3)C(=O)C4(C)C)cc3ncn(C(C)C)c23)c(F)c1F]

N-(1-(Difluoromethyl)cyclopropyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(viii) N-(1-(Difluoromethyl)cyclopropyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 195)

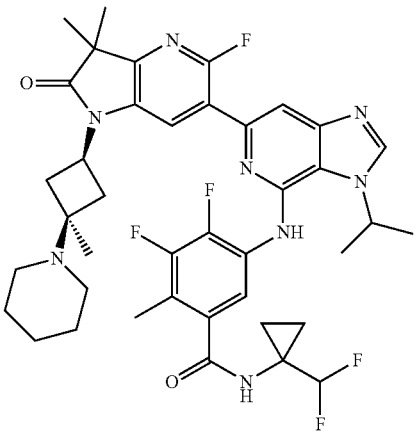 [SMILES: Cc1c(C(=O)NC2(C(F)F)CC2)cc(Nc2nc(-c3cc4c(nc3F)C(C)(C)C(=O)N4[C@H]3C[C@@](C)(N4CCCCC4)C3)cc3ncn(C(C)C)c23)c(F)c1F]

N-(1-(Difluoromethyl)cyclopropyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(ix) N-(1-(Difluoromethyl)cyclopropyl)-3,4-difluoro-5-((6-(1-((1S,3s)-3-((R)-3-fluoropiperidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 196)

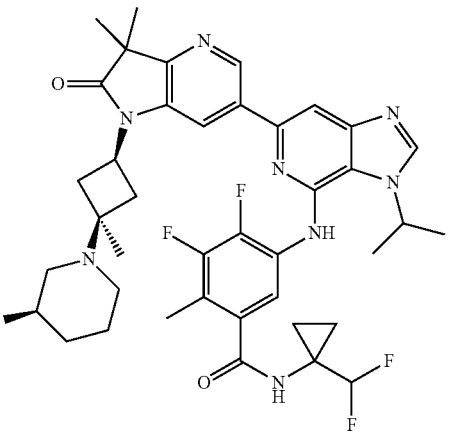

N-(1-(difluoromethyl)cyclopropyl)-3,4-difluoro-5-((6-(1-((1S,3s)-3-((R)-3-fluoropiperidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)

amino)-2-methylbenzamide was prepared using a similar procedure except that 6-bromo-1-((1S,3s)-3-((R)-3-fluoropiperidin-1-yl)-3-methylcyclobutyl)-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(x) N-(1-(Difluoromethyl)cyclopropyl)-3,4-difluoro-5-((6-(1-((1s,3s)-3-(4-fluoropiperidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 197)

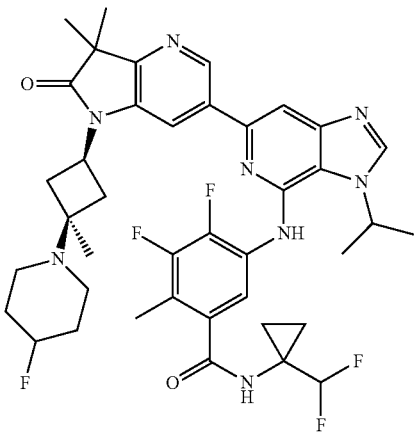 [SMILES: Cc1c(C(=O)NC2(C(F)F)CC2)cc(Nc2nc(-c3cnc4c(c3)N([C@H]3C[C@@](C)(N5CCC(F)CC5)C3)C(=O)C4(C)C)cc3ncn(C(C)C)c23)c(F)c1F]

N-(1-(Difluoromethyl)cyclopropyl)-3,4-difluoro-5-((6-(1-((1s,3s)-3-(4-fluoropiperidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-1-((s,3s)-3-(4-fluoropiperidin-1-yl)-3-methylcyclobutyl)-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(xi) 2-Chloro-N-(1-(difluoromethyl)cyclopropyl)-5-((6-(3,3-dimethyl-1-((1s,3s)-3-methyl-3-(1,4-oxazepan-4-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide (Example 198)

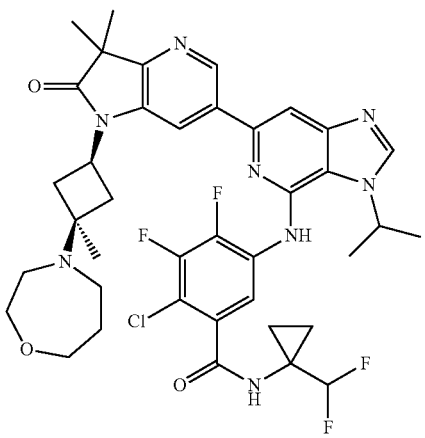 [SMILES: CC(C)n1cnc2cc(-c3cnc4c(c3)N([C@H]3C[C@@](C)(N5CCCOCC5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-5-((6-(3,3-dimethyl-1-((1s,3s)-3-methyl-3-(1,4-oxazepan-4-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-(1,4-oxazepan-4-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xii) 2-Chloro-N-(1-(difluoromethyl)cyclopropyl)-5-((6-(3,3-dimethyl-1-((1s,3s)-3-methyl-3-morpholinocyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide (Example 199)

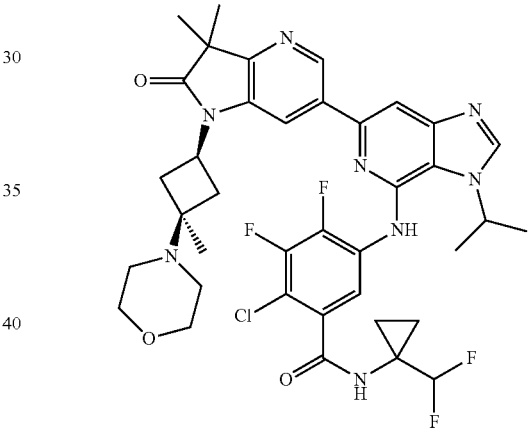

2-Chloro-N-(1-(difluoromethyl)cyclopropyl)-5-((6-(3,3-dimethyl-1-((1s,3s)-3-methyl-3-morpholinocyclobutyl)-2-oxo-2,3-dihydro-H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-morpholinocyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xiii) 2-Chloro-N-(1-(difluoromethyl)cyclopropyl)-3,4-difluoro-5-((6-(1-((1S,3s)-3-((R)-3-fluoropyrrolidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)benzamide (Example 200)

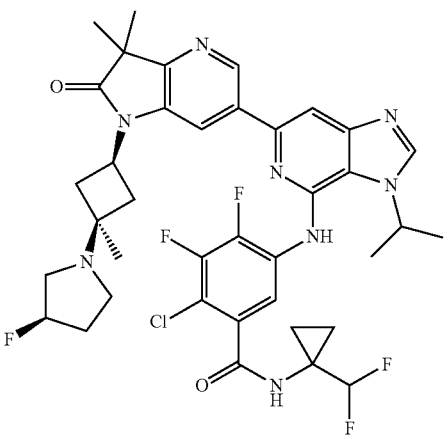 [SMILES: CC(C)n1cnc2cc(-c3cnc4c(c3)N([C@H]3C[C@@](C)(N5CC[C@@H](F)C5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-3,4-difluoro-5-((6-(1-((1S,3s)-3-((R)-3-fluoropyrrolidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)benzamide was prepared using a similar procedure except that 6-bromo-1-((1S,3s)-3-((R)-3-fluoropyrrolidin-1-yl)-3-methylcyclobutyl)-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xiv) 2-Chloro-N-(1-(difluoromethyl)cyclopropyl)-3,4-difluoro-5-((6-(1-((1S,3s)-3-((R)-3-fluoropiperidin-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)benzamide (Example 201)

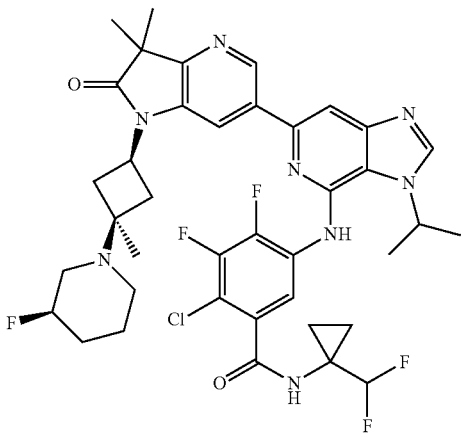 [SMILES: CC(C)n1cnc2cc(-c3cnc4c(c3)N([C@H]3C[C@@](C)(N5CCC[C@@H](F)C5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-3,4-difluoro-5-((6-(1-((1S,3s)-3-((R)-3-fluoropiperidin-1-yl)-3-methyl cyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)benzamide was prepared using a similar procedure (Example 185) except that 6-bromo-1-((1S,3s)-3-((R)-3-fluoropiperidin-1-yl)-3-methylcyclobutyl)-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xv) 2-Chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluorobenzamide (Example 202)

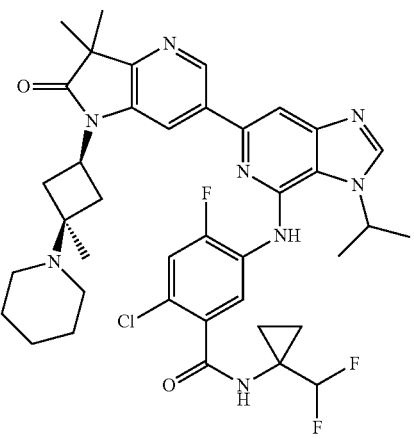 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)c(Cl)cc3F)c21]

2-Chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluorobenzamide was prepared using a similar procedure except that 5-((6-bromo-3-isopropyl-3H-imidazo[4,5-c]pyridin-4-yl)amino)-2-chloro-N-(1-(difluoromethyl)cyclopropyl)-4-fluorobenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xvi) 2-Chloro-N-(1-(difluoromethyl)cyclopropyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide (Example 203)

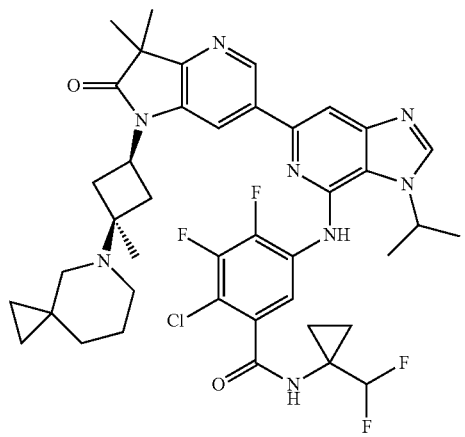 [SMILES: CC(C)n1cnc2cc(-c3cnc4c(c3)N([C@H]3C[C@@](C)(N5CCCC6(CC6)C5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xvii) 2-Chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(trifluoromethyl)cyclopropyl)benzamide (Example 204)

2-Chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(trifluoromethyl)cyclopropyl)benzamide was prepared using a similar procedure except that 5-((6-bromo-3-isopropyl-3H-imidazo[4,5-c]pyridin-4-yl)amino)-2-chloro-3,4-difluoro-N-(1-(trifluoromethyl)cyclopropyl)benzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xviii) 5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 205)

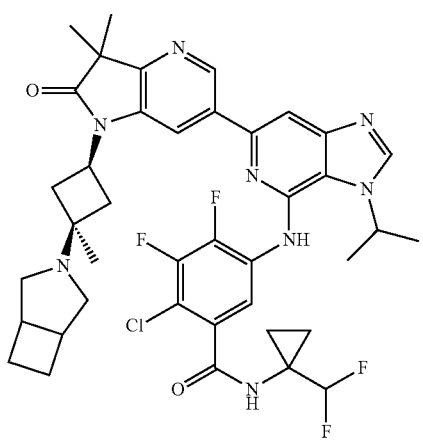 [SMILES: CC(C)n1cnc2cc(-c3cnc4c(c3)N([C@H]3C[C@@](C)(N5CC6CCC6C5)C3)C(=O)C4(C)C)nc(Nc3cc(C(=O)NC4(C(F)F)CC4)c(Cl)c(F)c3F)c21]

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(3-azabicyclo[3.2.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xix) N-(1-(Difluoromethyl)cyclopropyl)-4-fluoro-5-((3-isopropyl-6-(1'-((1s,3s)-3-methyl-3-(piperidin-1-yl)cyclobutyl)-2'-oxo-1',2,2',3,5,6-hexahydrospiro[pyran-4,3'-pyrrolo[3,2-b]pyridin]-6'-yl)-3H-imidazo[4,5-c]pyridin-4-yl)amino)-2-methylbenzamide (Example 206)

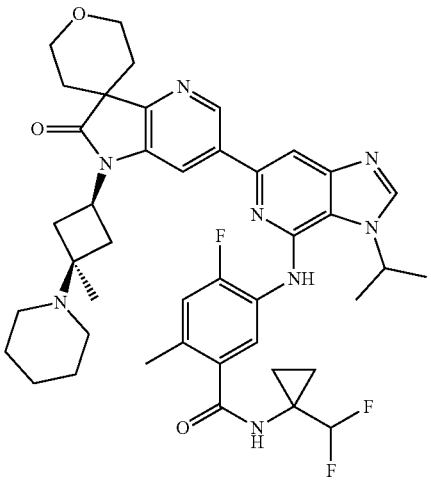 [SMILES: Cc1cc(F)c(Nc2nc(-c3cnc4c(c3)N([C@H]3C[C@@](C)(N5CCCCC5)C3)C(=O)C43CCOCC3)cc3ncn(C(C)C)c23)cc1C(=O)NC1(C(F)F)CC1]

N-(1-(Difluoromethyl)cyclopropyl)-4-fluoro-5-((3-isopropyl-6-(1'-((1s,3s)-3-methyl-3-(piperidin-1-yl)cyclobutyl)-2'-oxo-1',2,2',3,5,6-hexahydrospiro[pyran-4,3'-pyrrolo[3,2-b]pyridin]-6'-yl)-3H-imidazo[4,5-c]pyridin-4-yl)amino)-2-methylbenzamide was prepared using a similar procedure except that 6'-bromo-1'-((s,3s)-3-methyl-3-(piperidin-1-yl)cyclobutyl)-2,3,5,6-tetrahydrospiro[pyran-4,3'-pyrrolo[3,2-b]pyridin]-2'(1'H)-one and 5-((6-bromo-3-isopropyl-3H-imidazo[4,5-c]pyridin-4-yl)amino)-N-(1-(difluoromethyl)cyclopropyl)-4-fluoro-2-methylbenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xx) 2-Chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6- yl)-3-isopropyl-3H-imidazo[4,5-c]pyridin-4-yl)amino)-3,4-difluorobenzamide (Example 207)

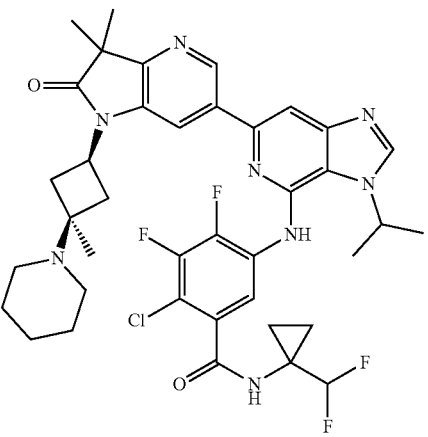 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrol[32-b]pyridin-6-yl)-3-isopropyl-3H-imidazo[4,5-c]pyridin-4-yl)amino)-3,4-difluorobenzamide was prepared using a similar procedure (Example 185) except that 5-((6-bromo-3-isopropyl-3H-imidazo[4,5-c]pyridin-4-yl)amino)-2-chloro-N-(1-(difluoromethyl)cyclopropyl)-3,4-difluorobenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxi) N-(1-(Difluoromethyl)cyclopropyl)-5-((6-(3,3-dimethyl-1-((1s,3s)-3-methyl-3-(1,4-oxazepan-4-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 208)

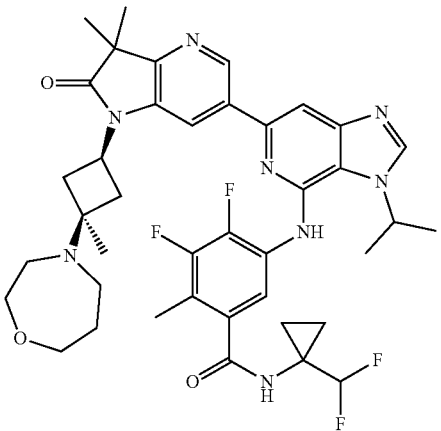

N-(1-(Difluoromethyl)cyclopropyl)-5-((6-(3,3-dimethyl-1-((1s,3s)-3-methyl-3-(1,4-oxazepan-4-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(1,4-oxazepan-4-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(xxii) 5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 209)

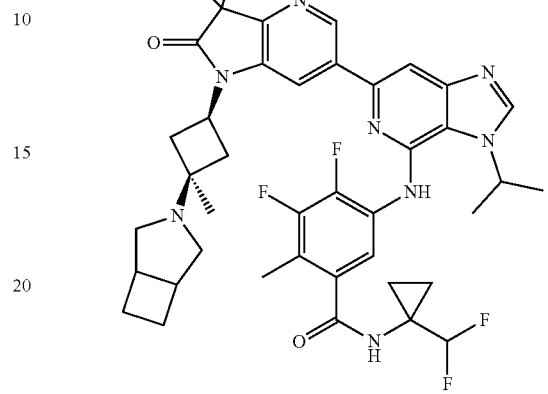

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide was prepared using a similar procedure except that 1-((1s,3s)-3-(3-azabicyclo[3.2.0]heptan-3-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(xxiii) 2-Chloro-N-(1-(difluoromethyl)cyclopropyl)-3,4-difluoro-5-((3-isopropyl-6-(1'-((1s,3s)-3-methyl-3-(piperidin-1-yl)cyclobutyl)-2'-oxo-1',2,2',3,5,6-hexahydrospiro[pyran-4,3'-pyrrolo[3,2-b]pyridin]-6'-yl)-3H-imidazo[4,5-c]pyridin-4-yl)amino)benzamide (Example 210)

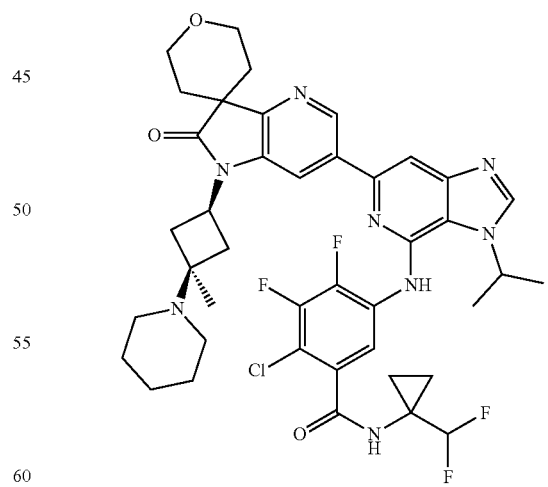

2-Chloro-N-(1-(difluoromethyl)cyclopropyl)-3,4-difluoro-5-((3-isopropyl-6-(1'-((1s,3s)-3-methyl-3-(piperidin-1-yl)cyclobutyl)-2'-oxo-1',2,2',3,5,6-hexahydrospiro[pyran-4,3'-pyrrolo[3,2-b]pyridin]-6'-yl)-3H-imidazo[4,5-c]pyridin-4-yl)amino)benzamide was prepared using a similar procedure except that 6'-bromo-1'-((1s,3s)-3-methyl-3-(piperidin-1-yl)cyclobutyl)-2,3,5,6-tetrahydrospiro[pyran-4,3'-pyrrolo[3,2-b]pyridin]-2'(1'H)-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxiv) 2-Chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(fluoromethyl)cyclopropyl)benzamide (Example 211)

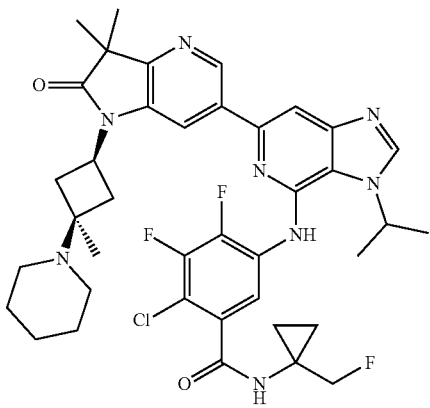 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(CF)CC4)c(Cl)c(F)c3F)c21]

2-Chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-(1-(fluoromethyl)cyclopropyl)benzamide was prepared using a similar procedure except that 5-((6-bromo-3-isopropyl-3H-imidazo[4,5-c]pyridin-4-yl)amino)-2-chloro-3,4-difluoro-N-(1-(fluoromethyl)cyclopropyl)benzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxv) 5-((6-(1-((1s,3s)-3-(3-Oxa-8-azabicyclo[3.2.1]octan-8-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-4-fluoro-2-methylbenzamide (Example 212)

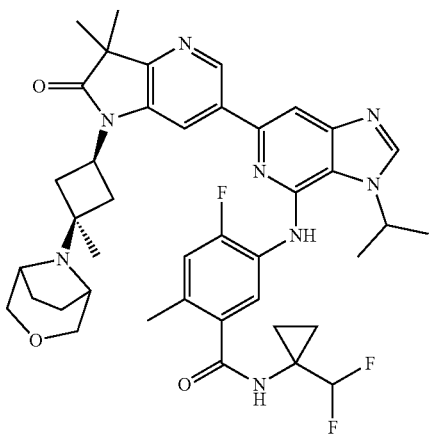 [SMILES: Cc1cc(F)c(Nc2nc(-c3cnc4c(c3)N([C@H]3C[C@@](C)(N5C6CCC5COC6)C3)C(=O)C4(C)C)cc3ncn(C(C)C)c23)cc1C(=O)NC1(C(F)F)CC1]

5-((6-(1-((1s,3s)-3-(3-Oxa-8-azabicyclo[3.2.1]octan-8-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-4-fluoro-2-methylbenzamide was prepared using a similar procedure except that 1-((1s,3s)-3-(3-oxa-8-azabicyclo[3.2.1]octan-8-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxvi) N-(1-(Difluoromethyl)cyclopropyl)-5-((6-(1-((1r,3s)-3-ethyl-3-(piperidin-1-yl)cyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-4-fluoro-2-methylbenzamide (Example 213)

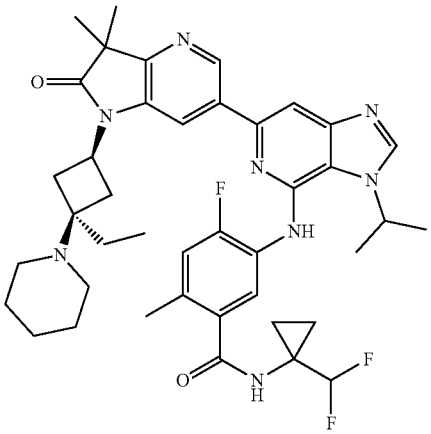 [SMILES: CC[C@]1(N2CCCCC2)C[C@@H](N2C(=O)C(C)(C)c3ncc(-c4cc5ncn(C(C)C)c5c(Nc5cc(C(=O)NC6(C(F)F)CC6)c(C)cc5F)n4)cc32)C1]

N-(1-(Difluoromethyl)cyclopropyl)-5-((6-(1-((1r,3s)-3-ethyl-3-(piperidin-1-yl)cyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-4-fluoro-2-methylbenzamide was prepared using a similar procedure except that 6-bromo-1-((1r,3s)-3-ethyl-3-(piperidin-1-yl)cyclobutyl)-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxvii) N-(1-(Difluoromethyl)cyclopropyl)-5-((6-(3, 3-dimethyl-1-((1s,3s)-3-methyl-3-(piperidin-1-yl) cyclobutyl)-2,3-dihydro-1H-pyrrolo[3,2-b]pyridin-6-yl)-3-isopropyl-3H-imidazo[4,5-c]pyridin-4-yl) amino)-3,4-difluoro-2-methylbenzamide (Example 214)

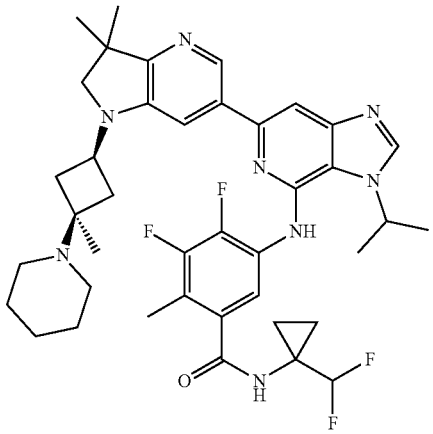 [SMILES: Cc1c(C(=O)NC2(C(F)F)CC2)cc(Nc2nc(-c3cnc4c(c3)N([C@H]3C[C@@](C)(N5CCCCC5)C3)CC4(C)C)cc3ncn(C(C)C)c23)c(F)c1F]

N-(1-(difluoromethyl)cyclopropyl)-5-((6-(3,3-dimethyl-1-((1s,3s)-3-methyl-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(piperidin-1-yl)cyclobutyl)-2,3-dihydro-1H-pyrrolo[3,2-b]pyridine was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(xxviii) N-(1-(Difluoromethyl)cyclopropyl)-5-((6-(3, 3-dimethyl-1-((1s,3s)-3-methyl-3-morpholinocyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluoro-2-methylbenzamide (Example 215)

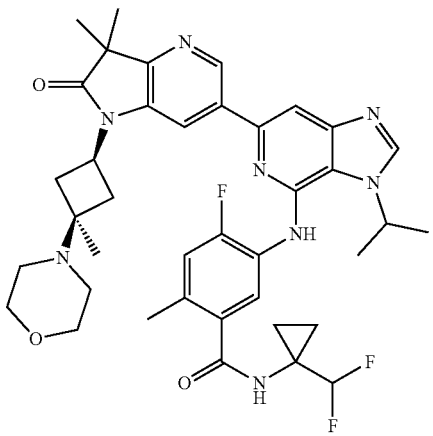 [SMILES: Cc1cc(F)c(Nc2nc(-c3cnc4c(c3)N([C@H]3C[C@@](C)(N5CCOCC5)C3)C(=O)C4(C)C)cc3ncn(C(C)C)c23)cc1C(=O)NC1(C(F)F)CC1]

N-(1-(Difluoromethyl)cyclopropyl)-5-((6-(1-((1r,3s)-3-ethyl-3-(piperidin-1-yl)cyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-4-fluoro-2-methylbenzamide was prepared using a similar procedure except that 6-bromo-3,3-dimethyl-1-((1s,3s)-3-methyl-3-morpholinocyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxix) N-(1-(Difluoromethyl)cyclopropyl)-5-((6-(3, 3-dimethyl-1-((1s,3s)-3-methyl-3-(piperidin-1-yl) cyclobutyl)-2-oxo-2,3-dihydro-1H-pyrrolo[3,2-b] pyridin-6-yl)-3-isopropyl-3H-imidazo[4,5-c]pyridin-4-yl)amino)-4-fluoro-2-methylbenzamide (Example 216)

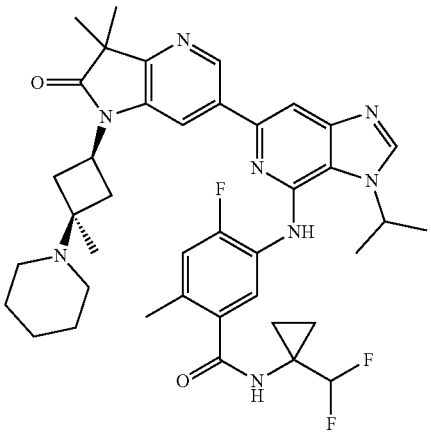 [SMILES: Cc1cc(F)c(Nc2nc(-c3cnc4c(c3)N([C@H]3C[C@@](C)(N5CCCCC5)C3)C(=O)C4(C)C)cc3ncn(C(C)C)c23)cc1C(=O)NC1(C(F)F)CC1]

N-(1-(Difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluoro-2-methylbenzamide was prepared using a similar procedure except that 5-((6-bromo-3-isopropyl-3H-imidazo[4,5-c]pyridin-4-yl)amino)-N-(1-(difluoromethyl)cyclopropyl)-4-fluoro-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxx) N-(2,2-Difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3, 4-difluoro-2-methylbenzamide (Example 217)

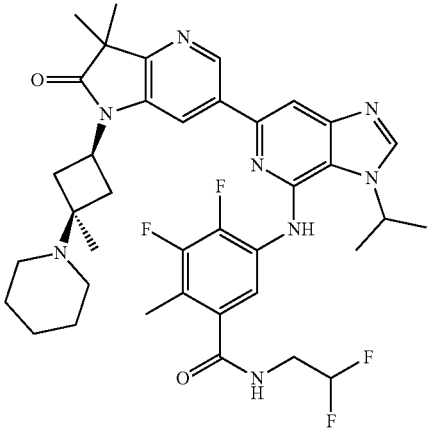 [SMILES: Cc1c(C(=O)NCC(F)F)cc(Nc2nc(-c3cnc4c(c3)N([C@H]3C[C@@](C)(N5CCCCC5)C3)C(=O)C4(C)C)cc3ncn(C(C)C)c23)c(F)c1F]

N-(2,2-Difluoroethyl)-5-((6-(3,3-dimethyl-1-((1s,3s)-3-methyl-3-(piperidin-1-yl)cyclobutyl)-2-oxo-2,3-dihydro- 1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 5-((6-bromo-3-isopropyl-3H-imidazo[4,5-c]pyridin-4-yl)amino)-N-(2,2-difluoroethyl)-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxi) N-(1-(difluoromethyl)cyclopropyl)-3-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluorobenzamide (Example 218)

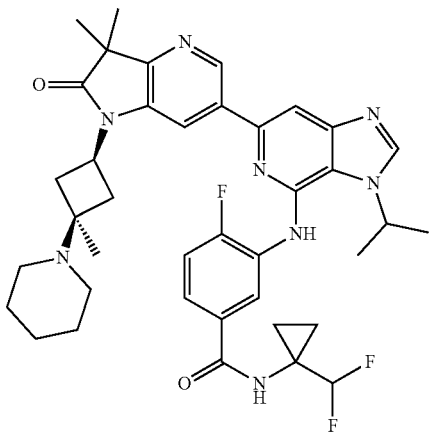 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)ccc3F)c21]

N-(2,2-Difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 3-((6-bromo-3-isopropyl-3H-imidazo[4,5-c]pyridin-4-yl)amino)-N-(1-(difluoromethyl)cyclopropyl)-4-fluorobenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxii) N-(1-(Difluoromethyl)cyclopropyl)-5-((6-(3,3-dimethyl-1-((1s,3s)-3-methyl-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-4-fluoro-2-methylbenzamide (Example 219)

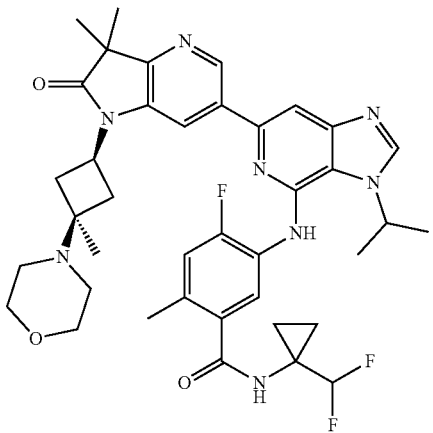

N-(1-(Difluoromethyl)cyclopropyl)-5-((6-(3,3-dimethyl-1-((1s,3s)-3-methyl-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-4-fluoro-2-methylbenzamide was prepared using a similar procedure except that 6-bromo-3,3-dimethyl-1-((1s,3s)-3-methyl-3-(piperidin-1-yl)cyclobutyl)-2,3-dihydro-1H-pyrrolo[3,2-b]pyridine and 5-((6-bromo-3-isopropyl-3H-imidazo[4,5-c]pyridin-4-yl)amino)-N-(1-(difluoromethyl)cyclopropyl)-4-fluoro-2-methylbenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxiii) 5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-isopropyl-2-methylbenzamide (Example 220)

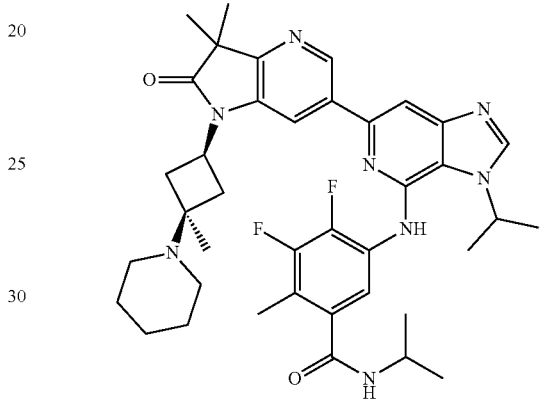

5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-isopropyl-2-methylbenzamide was prepared using a similar procedure except that 5-((6-bromo-3-isopropyl-3H-imidazo[4,5-c]pyridin-4-yl)amino)-3,4-difluoro-N-isopropyl-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxiv) N-Cyclopropyl-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 221)

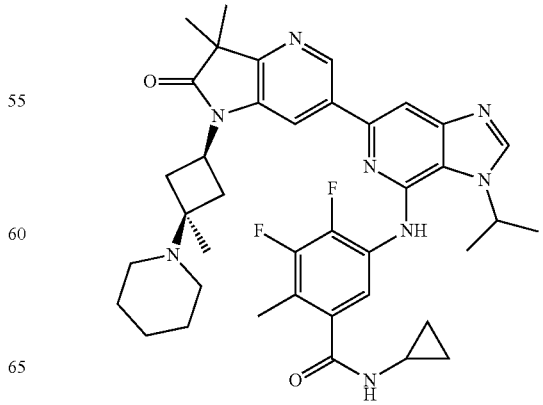

N-Cyclopropyl-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 5-((6-bromo-3-isopropyl-3H-imidazo[4,5-c]pyridin-4-yl)amino)-N-cyclopropyl-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxv) 5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide (Example 222)

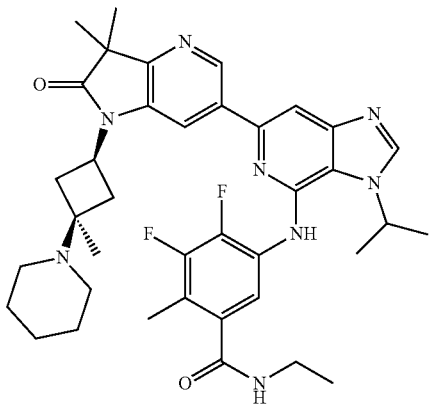

5-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide was prepared using a similar procedure except that 5-((6-bromo-3-isopropyl-3H-imidazo[4,5-c]pyridin-4-yl)amino)-N-ethyl-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxvi) 3-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-4-fluorobenzamide (Example 223)

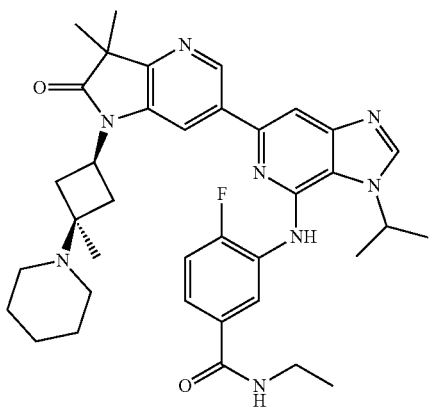

3-((6-(3,3-Dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-4-fluorobenzamide was prepared using a similar procedure except that 3-((6-bromo-3-isopropyl-3H-imidazo[4,5-c]pyridin-4-yl)amino)-N-ethyl-4-fluorobenzamide was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(xxxvii) 2-chloro-N-(1-(difluoromethyl)cyclopropyl)-5-((6-(3,3-dimethyl-2-oxo-1-((1s,3s)-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-3,4-difluorobenzamide (Example 245)

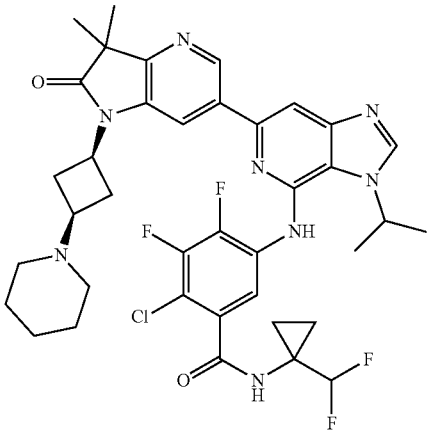 [SMILES: CC(C)n1cnc2cc(-c3cnc4c(c3)N([C@H]3C[C@@H](N5CCCCC5)C3)C(=O)C4(C)C)nc(Nc3cc(C(=O)NC4(C(F)F)CC4)c(Cl)c(F)c3F)c21]

2-chloro-N-(1-(difluoromethyl)cyclopropyl)-5-((6-(3,3-dimethyl-2-oxo-1-((1s,3s)-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xxxviii) N-(1-(difluoromethyl)cyclopropyl)-5-((6-(3,3-dimethyl-2-oxo-1-((1s,3s)-3-(piperidin-1-yl)cyclobutyl)-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide (Example 246)

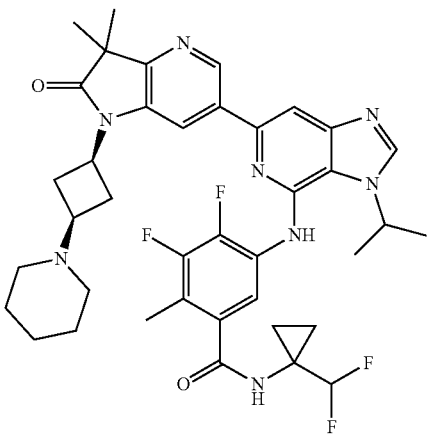 [SMILES: Cc1c(C(=O)NC2(C(F)F)CC2)cc(Nc2nc(-c3cnc4c(c3)N([C@H]3C[C@@H](N5CCCCC5)C3)C(=O)C4(C)C)cc3ncn(C(C)C)c23)c(F)c1F]

N-(1-(difluoromethyl)cyclopropyl)-5-((6-(3,3-dimethyl-2-oxo-1-((1s,3s)-3-(piperidin-1-yl)cyclobutyl)-2,3-dihydro- 1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-(piperidin-1-yl)cyclobutyl)-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(xxxix) 6-(4-Amino-3-isopropyl-3H-imidazo[4,5-c]pyridin-6-yl)-3,3-dimethyl-1-((1s,3s)-3-methyl-3-(piperidin-1-yl)cyclobutyl)-1,3-dihydro-2H-pyrrolo[3,2-b]pyridin-2-one

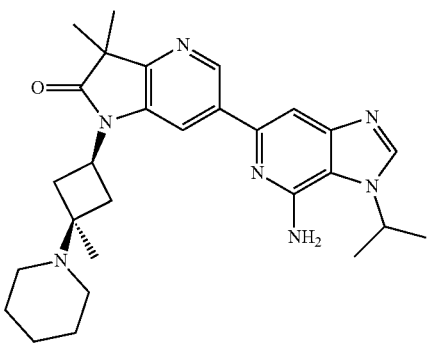 [SMILES: CC(C)n1cnc2cc(-c3cnc4c(c3)N([C@H]3C[C@@](C)(N5CCCCC5)C3)C(=O)C4(C)C)nc(N)c21]

6-(4-amino-3-isopropyl-3H-imidazo[4,5-c]pyridin-6-yl)-3,3-dimethyl-1-((1s,3s)-3-methyl-3-(piperidin-1-yl)cyclobutyl)-1,3-dihydro-2H-pyrrolo[3,2-b]pyridin-2-one was prepared using a similar procedure except that 6-bromo-3-isopropyl-3H-imidazo[4,5-c]pyridin-4-amine was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

V. Preparation of 5-((6-(1-((1s,3s)-3-(2-oxa-5-azabicyclo[2.2.2]octan-5-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 224)

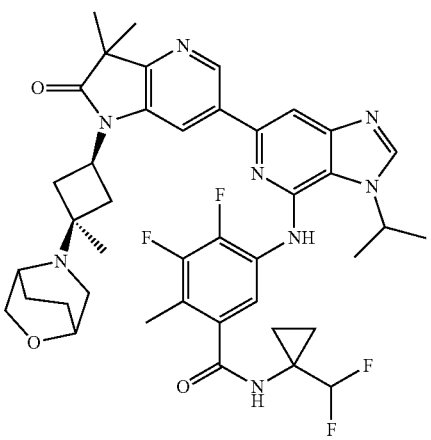 [SMILES: Cc1c(C(=O)NC2(C(F)F)CC2)cc(Nc2nc(-c3cnc4c(c3)N([C@H]3C[C@@](C)(N5CC6CCC5CO6)C3)C(=O)C4(C)C)cc3ncn(C(C)C)c23)c(F)c1F]

In a sealed tube were placed 6-bromo-3,3-dimethyl-1-[3-methyl-3-(2-oxa-5-azabicyclo[2.2.2]octan-5-yl)cyclobutyl]pyrrolo[3,2-b]pyridin-2-one (150 mg, 0.36 mmol), bis(pinacolato)diboron (109 mg, 0.43 mmol), Pd(PPh₃)₄ (80.0 mg, 0.07 mmol), and KOAc (105 mg, 1.07 mmol) in dioxane (1 ml) under nitrogen. After stirring at 140° C. for 1 h, the mixture was to room temperature. To this were added 5-[(6-bromo-3-isopropyl-imidazo[4,5-c]pyridin-4-yl)amino]-N-[1-(difluoromethyl)cyclopropyl]-3,4-difluoro-2-methyl-benzamide (184 mg, 0.36 mmol) and 2M Na₂CO₃ (0.89 mL, 1.78 mmol). The resulting mixture was heated at 90° C. for 1 h, and then it was quenched with water. The mixture was extracted with EtOAc, concentrated, and purified by flash chromatography (100% DCM to 100% MeOH in DCM) and reverse phase chromatography (0.1% TFA in Water/0.1% TFA in ACN) to give 5-((6-(1-((1s,3s)-3-(2-oxa-5-azabicyclo[2.2.2]octan-5-yl)-3-methylcyclobutyl)-3,3-dimethyl-2-oxo-2,3-dihydro-H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide.

The following compounds were prepared using a similar procedure.

(i) 5-((6-(1-((1s,3s)-3-(3-Azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 225)

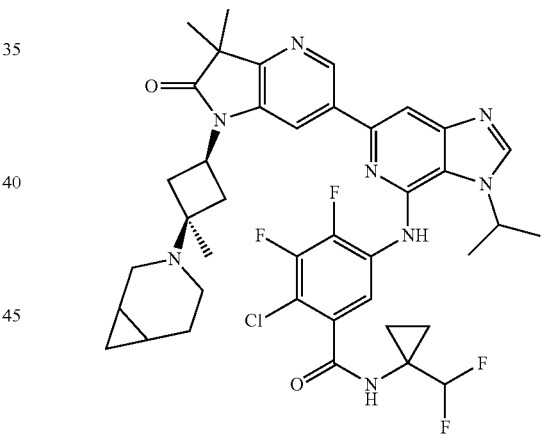

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(3-azabicyclo[3.2.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(ii) 5-((6-(1-((1s,3s)-3-(Azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 226)

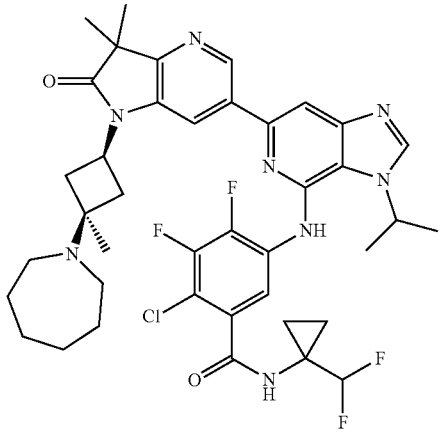 [SMILES: CC(C)n1cnc2cc(-c3cnc4c(c3)N([C@H]3C[C@@](C)(N5CCCCCC5)C3)C(=O)C4(C)C)nc(Nc3cc(C(=O)NC4(C(F)F)CC4)c(Cl)c(F)c3F)c21]

5-((6-(1-((1s,3s)-3-(Azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(azepan-1-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(iii) 5-((6-(1-((1s,3s)-3-(3-Azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide (Example 227)

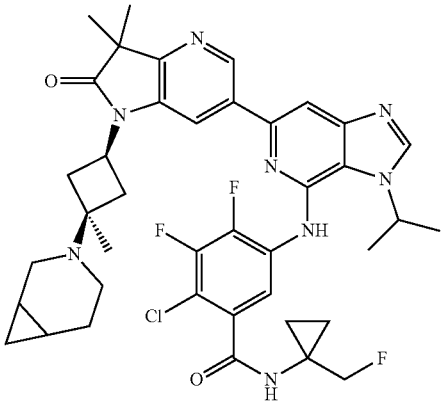 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NC4(CF)CC4)c(Cl)c(F)c3F)c21]

5-((6-(1-((1s,3s)-3-(3-Azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide was prepared using a similar procedure except that 1-((1s,3s)-3-(3-azabicyclo[3.2.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-(1-(fluoromethyl)cyclopropyl)benzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

(iv) 5-((6-(1-((1s,3s)-3-(8-Oxa-3-azabicyclo[3.2.1]octan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 228)

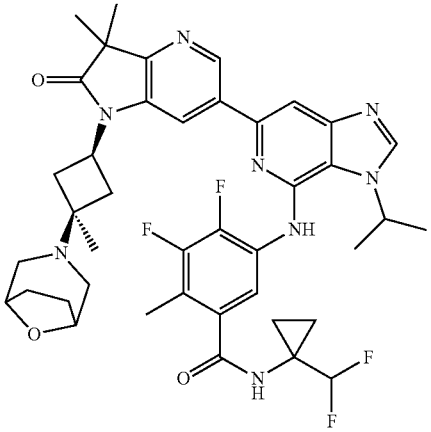

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(8-oxa-3-azabicyclo[3.2.1]octan-3-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(v) 5-((6-(1-((1s,3s)-3-(Azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 229)

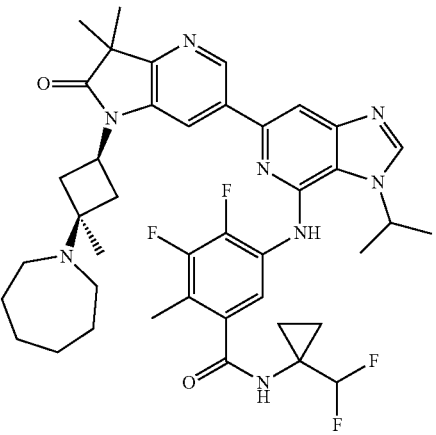

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(azepan-1-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(vi) 5-((6-(1-((1s,3s)-3-(3-Azabicyclo[3.2.1]octan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 230)

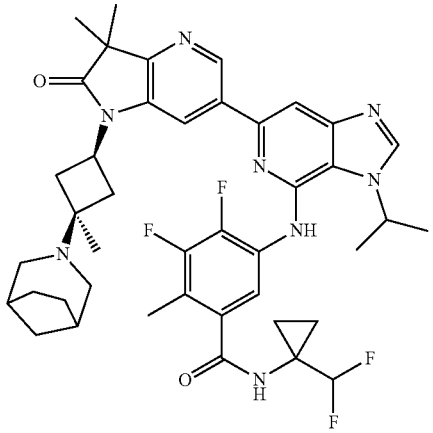 [SMILES: Cc1c(C(=O)NC2(C(F)F)CC2)cc(Nc2nc(-c3cnc4c(c3)N([C@H]3C[C@@](C)(N5CC6CCC(C5)O6)C3)C(=O)C4(C)C)cc3ncn(C(C)C)c23)c(F)c1F]

5-((6-(1-((1s,3s)-3-(3-Azabicyclo[3.2.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(3-azabicyclo[3.2.1]octan-3-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

(vii) 5-((6-(1-((1s,3s)-3-(3-Azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 231)

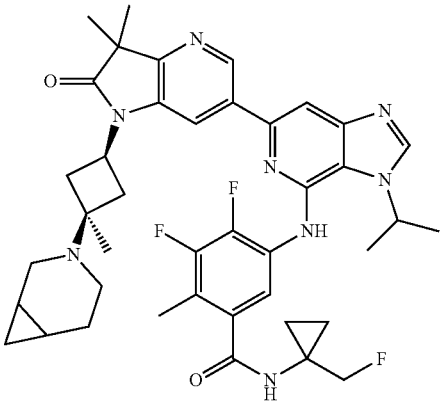

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide was prepared using a similar procedure except that 1-((1s,3s)-3-(3-azabicyclo[3.2.0]heptan-3-yl)-3-methylcyclobutyl)-6-bromo-3,3-dimethyl-1,3-dihydro-2H-pyrrolo[3,2-b]pyridin-2-one was used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one.

Chiral Separation: Separation of the isomers of 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide (Example 231)

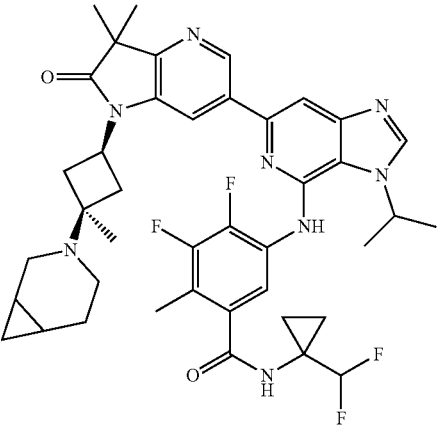 [SMILES: Cc1c(C(=O)NC2(C(F)F)CC2)cc(Nc2nc(-c3cnc4c(c3)N([C@H]3C[C@@](C)(N5CCC6CC6C5)C3)C(=O)C4(C)C)cc3ncn(C(C)C)c23)c(F)c1F]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide was separated on CHIRALPAK IA SFC 5 um 21×250 mm column in 35% MeOH (modified with 10 mM NH$_3$)/CO$_2$ at 60 mL/min to give the two single isomers which were further purified by reverse chromatography (0.1% TFA in Water/0.1% TFA in ACN):

| Name | Separation method | Peak # | Example # |
|---|---|---|---|
| 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-(1-(difluoromethyl)cyclopropyl)-3,4-difluoro-2-methylbenzamide | CHIRALPAK IA SFC 5 um 21 × 250 mm column in 35% MeOH (modified with 10 mM NH$_3$)/CO$_2$ at 60 mL/min | 1$^{st}$ eluting peak 2$^{nd}$ eluting peak | Example 232 Example 233 |

(viii) 5-((6-(1-((1s,3s)-3-(3-Azabicyclo[3.1.0]hexan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 234)

(ix) 5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide (Example 247)

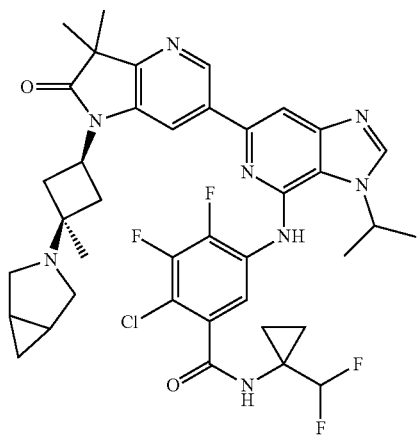 [SMILES: CC(C)n1cnc2cc(-c3cnc4c(c3)N([C@H]3C[C@@](C)(N5CC6CC6C5)C3)C(=O)C4(C)C)nc(Nc3cc(C(=O)NC4(C(F)F)CC4)c(Cl)c(F)c3F)c21]

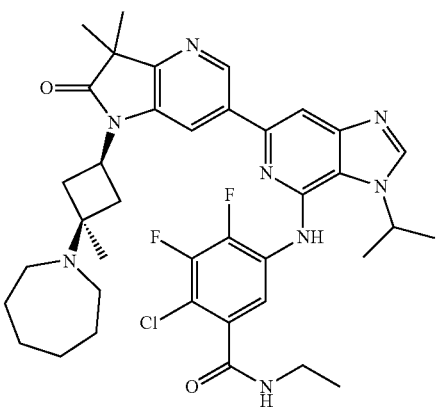 [SMILES: CCNC(=O)c1cc(Nc2nc(-c3cnc4c(c3)N([C@H]3C[C@@](C)(N5CCCCCC5)C3)C(=O)C4(C)C)cc3ncn(C(C)C)c23)c(F)c(F)c1Cl]

5-((6-(1-((1s,3s)-3-(3-Azabicyclo[3.1.0]hexan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(3-azabicyclo[3.1.0]hexan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide.

5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide was prepared using a similar procedure except that 1-((1s,3s)-3-(azepan-1-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(x) 5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(2,2-difluoroethyl)-3,4-difluorobenzamide (Example 248)

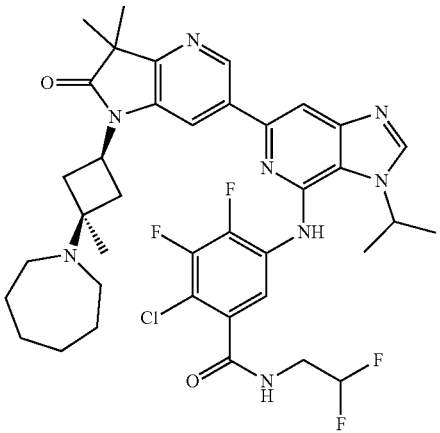 [SMILES: CC(C)n1cnc2cc(-c3cnc4c(c3)N([C@H]3C[C@@](C)(N5CCCCCC5)C3)C(=O)C4(C)C)nc(Nc3cc(C(=O)NCC(F)F)c(Cl)c(F)c3F)c21]

5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(2,2-difluoroethyl)-3,4-difluorobenzamide was prepared using a similar procedure except that 1-((1s,3s)-3-(azepan-1-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xi) 5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide (Example 249)

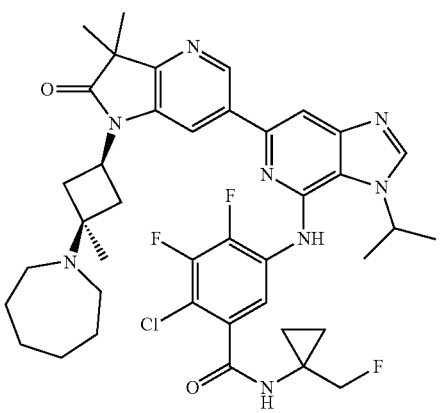 [SMILES: CC(C)n1cnc2cc(-c3cnc4c(c3)N([C@H]3C[C@@](C)(N5CCCCCC5)C3)C(=O)C4(C)C)nc(Nc3cc(C(=O)NC4(CF)CC4)c(Cl)c(F)c3F)c21]

5-((6-(1-((1s,3s)-3-(azepan-1-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide was prepared using a similar procedure except that 1-((1s,3s)-3-(azepan-1-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-(1-(fluoromethyl)cyclopropyl)benzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xii) 2-chloro-N-(2,2-difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide (Example 250)

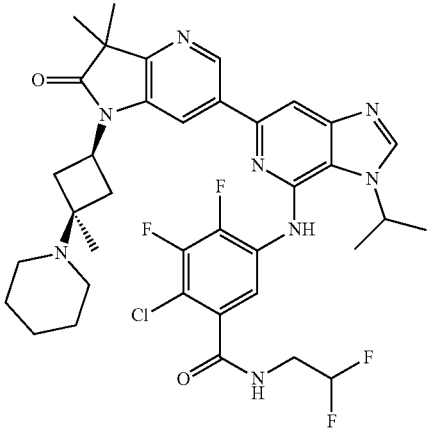 [SMILES: CC(C)n1cnc2cc(-c3cnc4c(c3)N([C@H]3C[C@@](C)(N5CCCCC5)C3)C(=O)C4(C)C)nc(Nc3cc(C(=O)NCC(F)F)c(Cl)c(F)c3F)c21]

2-chloro-N-(2,2-difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xiii) 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide (Example 251)

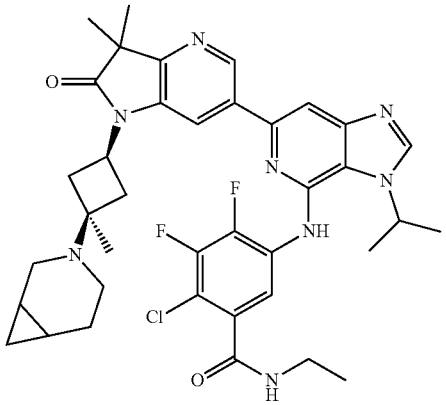 [SMILES: CCNC(=O)c1cc(Nc2nc(-c3cnc4c(c3)N([C@H]3C[C@@](C)(N5CCC6CC6C5)C3)C(=O)C4(C)C)cc3ncn(C(C)C)c23)c(F)c(F)c1Cl]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide was prepared using a similar procedure except that 1-((1s,3s)-3-(3-azabicyclo[4.1.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

Chiral Separation: Separation of the isomers of 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide (Example 251)

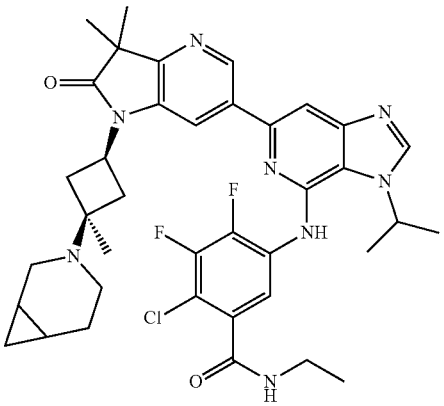 [SMILES: CCNC(=O)c1cc(Nc2nc(-c3cnc4c(c3)N([C@H]3C[C@@](C)(N5CCC6CC6C5)C3)C(=O)C4(C)C)cc3ncn(C(C)C)c23)c(F)c(F)c1Cl]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide was separated on CHIRALPAK IA SFC 5 um 21×250 mm column in 35% MeOH (modified with 10 mM NH$_3$)/CO$_2$ at 60 mL/min to give the two single isomers which were further purified by reverse chromatography (0.1% TFA in Water/0.1% TFA in ACN):

| Name | Separation method | Peak # | Example # |
|---|---|---|---|
| 5-((6-(1-((1s,3s)-3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-ethyl-3,4-difluorobenzamide | CHIRALPAK IA SFC 5 um 21 × 250 mm column in 35% MeOH (modified with 10 mM NH$_3$)/CO$_2$ at 60 mL/min | $1^{st}$ eluting peak | 252 |
| | | $2^{nd}$ eluting peak | 253 |

(xiv) 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-isopropylbenzamide (Example 254)

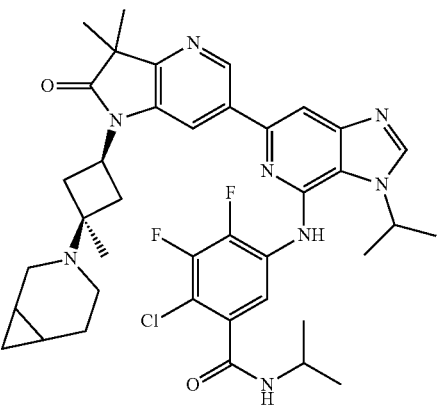 [SMILES: CC(C)NC(=O)c1cc(Nc2nc(-c3cnc4c(c3)N([C@H]3C[C@@](C)(N5CCC6CC6C5)C3)C(=O)C4(C)C)cc3ncn(C(C)C)c23)c(F)c(F)c1Cl]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N- isopropylbenzamide was prepared using a similar procedure except that 1-((1s,3s)-3-(3-azabicyclo[4.1.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-isopropylbenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xv) 5-((6-(1-((1s,3s)-3-(3-azabicyclo[4.1.0]heptan-3-yl)-3-methylcyclobutyl)-5-fluoro-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide (Example 255)

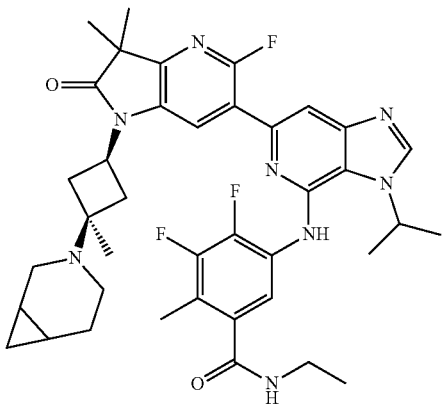 [SMILES: CCNC(=O)c1cc(Nc2nc(-c3cc4c(nc3F)C(C)(C)C(=O)N4[C@H]3C[C@@](C)(N4CCC5CC5C4)C3)cc3ncn(C(C)C)c23)c(F)c(F)c1C]

5-((6-(1-((1s,3s)-3-(3-azabicyclo[4.1.0]heptan-3-yl)-3-methylcyclobutyl)-5-fluoro-3,3-dimethyl-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide was prepared using a similar procedure except that 1-((1s,3s)-3-(3-azabicyclo[4.1.0]heptan-3-yl)-3-methylcyclobutyl)-6-bromo-5-fluoro-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-N-ethyl-3,4-difluoro-2-methylbenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xvi) 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(2,2-difluoroethyl)-3,4-difluorobenzamide (Example 256)

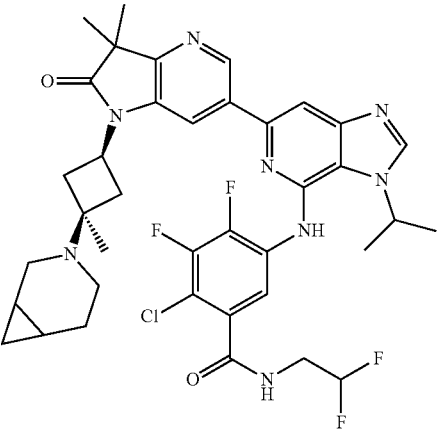 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NCC(F)F)c(Cl)c(F)c3F)c21]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(2,2-difluoroethyl)-3,4-difluorobenzamide was prepared using a similar procedure except that 1-((1s,3s)-3-(3-azabicyclo[4.1.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

(xvii) 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide (Example 257)

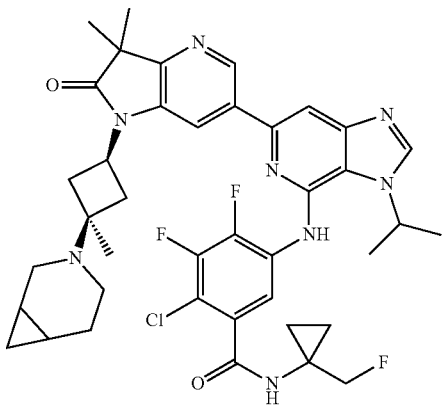 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NC4(CF)CC4)c(Cl)c(F)c3F)c21]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide was prepared using a similar procedure except that 1-((1s,3s)-3-(3-azabicyclo[4.1.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-(1-(fluoromethyl)cyclopropyl)benzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

Chiral Separation: Separation of the isomers of 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide (Example 257)

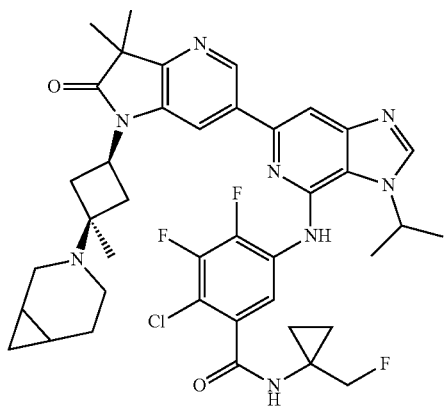 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NC4(CF)CC4)c(Cl)c(F)c3F)c21]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide was separated on CHIRALPAK IA SFC 5 um 21×250 mm column in 35% MeOH (modified with 10 mM $NH_3$)/$CO_2$ at 60 mL/min to give the two single isomers which were further purified by reverse chromatography (0.1% TFA in Water/0.1% TFA in ACN):

(xviii) 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 260)

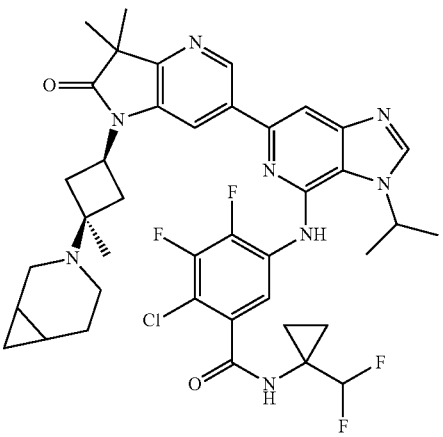 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NC4(C(F)F)CC4)c(Cl)c(F)c3F)c21]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1s,3s)-3-(3-azabicyclo[4.1.0]heptan-3-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluorobenzamide were used instead of 6-bromo-3,3-dimethyl-1-[3-methyl-3-(2-oxa-5-azabicyclo[2.2.2]octan-5-yl)cyclobutyl]pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-3,4-difluoro-2-methylbenzamide, respectively.

Chiral Separation: Separation of the isomers of 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 260)

| Name | Separation method | Peak # | Example # |
| --- | --- | --- | --- |
| 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-3,4-difluoro-N-(1-(fluoromethyl)cyclopropyl)benzamide | CHIRALPAK IA SFC 5 um 21 × 250 mm column in 35% MeOH (modified with 10 mM $NH_3$)/$CO_2$ at 60 mL/min | $1^{st}$ eluting peak | 258 |
| | | $2^{nd}$ eluting peak | 259 |

611

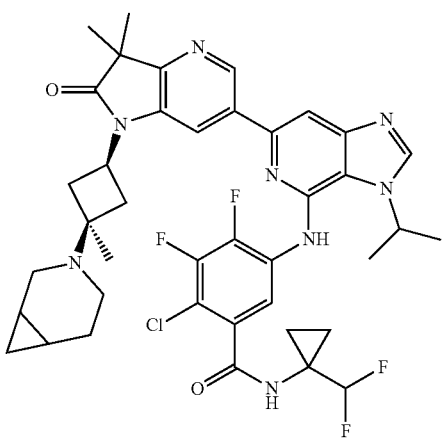 [SMILES: CC(C)n1cnc2cc(-c3cnc4c(c3)N([C@H]3C[C@@](C)(N5CCC6CC6C5)C3)C(=O)C4(C)C)nc(Nc3cc(C(=O)NC4(C(F)F)CC4)c(Cl)c(F)c3F)c21]

5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was separated on CHIRALPAK IA SFC 5 um 21×250 mm column in 35% MeOH (modified with 10 mM NH$_3$)/CO$_2$ at 60 mL/min to give the two single isomers which were further purified by reverse chromatography (0.1% TFA in Water/0.1% TFA in ACN):

| Name | Separation method | Peak # | Example # |
|---|---|---|---|
| 5-((6-(1-((1s,3s)-3-(3-azabicyclo[4.1.0]heptan-3-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide | CHIRALPAK IA SFC 5 um 21 × 250 mm column in 35% MeOH (modified with 10 mM NH$_3$)/CO$_2$ at 60 mL/min | 1$^{st}$ eluting peak | 261 |
| | | 2$^{nd}$ eluting peak | 262 |

(ix) 6-(4-Amino-3-isopropyl-3H-imidazo[4,5-c]pyridin-6-yl)-3,3-dimethyl-1-((1s,3s)-3-methyl-3-(piperidin-1-yl)cyclobutyl)indolin-2-one

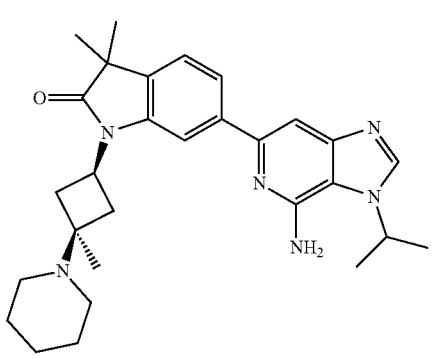 [SMILES: CC(C)n1cnc2cc(-c3ccc4c(c3)N([C@H]3C[C@@](C)(N5CCCCC5)C3)C(=O)C4(C)C)nc(N)c21]

6-(4-Amino-3-isopropyl-3H-imidazo[4,5-c]pyridin-6-yl)-3,3-dimethyl-1-((1s,3s)-3-methyl-3-(piperidin-1-yl)cyclobutyl)indolin-2-one was prepared using a similar procedure except that 6-bromo-3-isopropyl-3H-imidazo[4,5-c]pyridin-4-amine was used instead of 5-((6-bromo-3-isopropyl-3H-imidazo[4,5-c]pyridin-4-yl)amino)-N-(1-(difluoromethyl)cyclopropyl)-3,4-difluoro-2-methylbenzamide.

W. Preparation of 6-bromo-3,3-dimethyl-1-(3-oxo-cyclobutyl)indolin-2-one

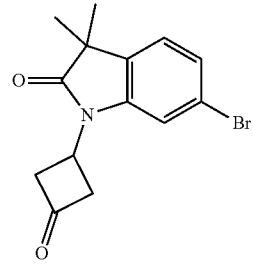

In a 500 mL, single neck, round bottomed flask were placed 6-bromo-3,3-dimethylindolin-2-one (5.0 g, 20.8 mmol) and Cs$_2$CO$_3$ (20.4 g, 62.5 mmol) in NMP (80 mL). To this was dropwise added 3-bromocyclobutan-1-one (4.7 g, 31.2 mmol) under nitrogen. After the mixture was stirred at room temperature for 1.5 h, it was quenched with water and extracted with EtOAc. The combined organic layers were washed with water, brine, dried (Na$_2$SO$_4$), concentrated, and purified by flash chromatography to give 6-bromo-3,3-dimethyl-1-(3-oxocyclobutyl)indolin-2-one.

X. Preparation of (1s,3s)-3-(6-bromo-3,3-dimethyl-2-oxoindolin-1-yl)-1-(piperidin-1-yl)cyclobutane-1-carbonitrile

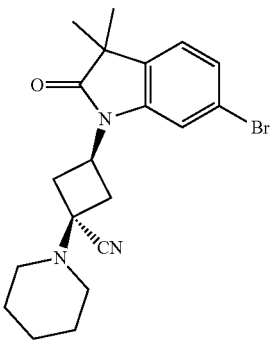 [SMILES: CC1(C)C(=O)N([C@H]2C[C@@](C#N)(N3CCCCC3)C2)c2cc(Br)ccc21]

In 250 mL, single neck, round bottomed flask was placed 6-bromo-3,3-dimethyl-1-(3-oxocyclobutyl)indolin-2-one (4.0 g, 12.9 mmol) in AcOH (22 mL), and the mixture was cooled to 0° C. To this was dropwise added piperidine (2.2. g, 25.9 mmol) followed by the portion-wise addition of TMS-CN (2.9 g, 29.8 mmol). The reaction mixture was warmed to room temperature and stirred for 18 h. Then, it was concentrated, quenched with sat. NaHCO$_3$, and extracted with DCM. The combined organic layers were washed with water and brine, dried (Na₂SO₄), and concentrated. The residue was re-suspended in EtOAc and stirred at room temperature for 10 minutes. The solid was collected by filtration, washed with EtOAc, and dried to give (1s,3s)-3-(6-bromo-3,3-dimethyl-2-oxoindolin-1-yl)-1-(piperidin-1-yl)cyclobutane-1-carbonitrile. This compound was used without any further purification.

Y. Preparation of 6-bromo-3,3-dimethyl-1-((1s,3s)-3-methyl-3-(piperidin-1-yl)cyclobutyl)indolin-2-one

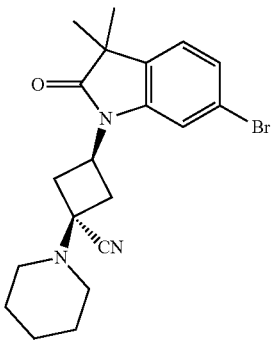 [SMILES: CC1(C)C(=O)N([C@H]2C[C@@](C#N)(N3CCCCC3)C2)c2cc(Br)ccc21]

In a 250 mL, single neck, round bottomed flask were placed silver triflate (352.5 mg, 1.4 mmol) and (1s,3s)-3-(6-bromo-3,3-dimethyl-2-oxoindolin-1-yl)-1-(piperidin-1-yl)cyclobutane-1-carbonitrile (345.0 mg, 0.9 mmol) in THF (9 mL). The mixture was stirred at room temperature for 5 minutes, and cooled to −78° C. To this was drop wise added MeMgBr (1.0 mL, 3.4 mmol, 3.0 M in ether). The resulting mixture was stirred at −78° C. for 45 minutes, quenched with water, and extracted with EtOAc. Combined organic layers were washed with water, brine, dried (Na₂SO₄), concentrated, and purified by flash chromatography (100% Hexane to 100% EtOAc) to give 6-bromo-3,3-dimethyl-1-((1s,3s)-3-methyl-3-(piperidin-1-yl)cyclobutyl)indolin-2-one.

Z. Preparation of N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide (Example 235)

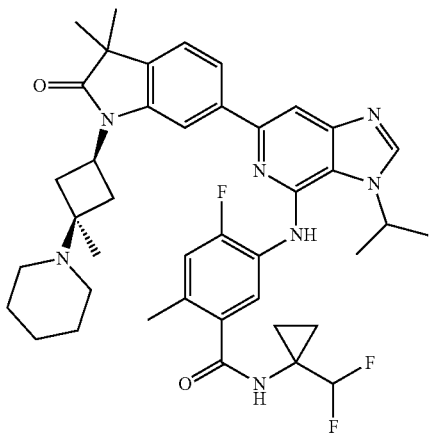 [SMILES: Cc1cc(F)c(Nc2nc(-c3ccc4c(c3)N([C@H]3C[C@@](C)(N5CCCCC5)C3)C(=O)C4(C)C)cc3ncn(C(C)C)c23)cc1C(=O)NC1(C(F)F)CC1]

In a 100 mL, single neck, round bottomed flask were placed 6-bromo-3,3-dimethyl-1-((1s,3s)-3-methyl-3-(piperidin-1-yl)cyclobutyl)indolin-2-one (145.0 mg, 0.4 mmol), bispinacolato diboron (112.9 mg, 0.4 mmol), potassium acetate (109.1 mg, 1.1 mmol) and Pd(dppf)Cl₂-DCM adduct (42.8 mg, 0.04 mmol) in dioxane (3 mL) under nitrogen. The mixture was stirred at 90° C. for 18 h. Then it was cooled to room temperature, diluted with EtOAc, and filtered through a pad of Celite. The filtrate was washed with water, brine, dried (Na₂SO₄) and concentrated. To this residue were added 5-((6-bromo-3-isopropyl-3H-imidazo[4,5-c]pyridin-4-yl)amino)-N-(1-(difluoromethyl)cyclopropyl)-4-fluoro-2-methylbenzamide (91.0 mg, 0.2 mmol), Pd(PPh₃)₄ (21.1 mg, 0.02 mmol), and 2M Cs₂CO₃ (0.46 mL, 0.9 mmol) in DME (2 mL) under nitrogen. After stirring at 100° C. for 2 h, the mixture was cooled to room temperature and filtered through a pad of Celite. The filtrate was concentrated and purified by flash chromatography (10% NH₄OH/MeOH/EtOAc/Hexane) followed by reverse phase chromatography (0.1% TFA in Water/0.1% in ACN) to give N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide.

The following compounds were prepared using a similar procedure.

(i) N-(1-(Difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluoro-2-methylbenzamide (Example 236)

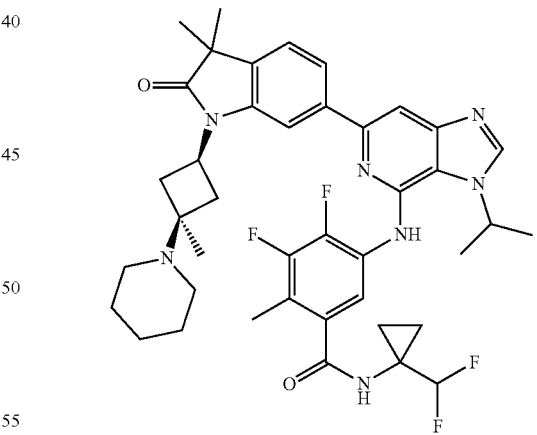

N-(1-(Difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl) amino)-3,4-difluoro-2-methylbenzamide was prepared using a similar procedure except that 5-((6-bromo-3-isopropyl-3H-imidazo[4,5-c]pyridin-4-yl)amino)-N-(1-(difluoromethyl)cyclopropyl)-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(ii) N-(1-(Difluoromethyl)cyclopropyl)-5-((6-(3,3-dimethyl-1-((1s,3s)-3-methyl-3-(piperidin-1-yl)cyclobutyl)indolin-6-yl)-3-isopropyl-3H-imidazo[4,5-c]pyridin-4-yl)amino)-3,4-difluoro-2-methylbenzamide (Example 237)

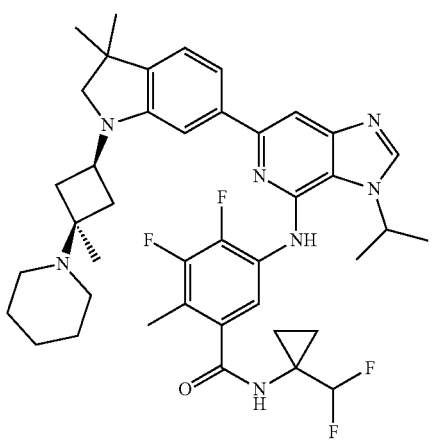 [SMILES: Cc1c(C(=O)NC2(C(F)F)CC2)cc(Nc2nc(-c3ccc4c(c3)N([C@H]3C[C@@](C)(N5CCCCC5)C3)CC4(C)C)cc3ncn(C(C)C)c23)c(F)c1F]

N-(1-(Difluoromethyl)cyclopropyl)-5-((6-(3,3-dimethyl-1-((1s,3s)-3-methyl-3-(piperidin-1-yl)cyclobutyl)indolin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(piperidin-1-yl)cyclobutyl)indoline and 5-((6-bromo-3-isopropyl-3H-imidazo[4,5-c]pyridin-4-yl)amino)-N-(1-(difluoromethyl)cyclopropyl)-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide.

(iii) N-(1-(Difluoromethyl)cyclopropyl)-3-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluorobenzamide (Example 238)

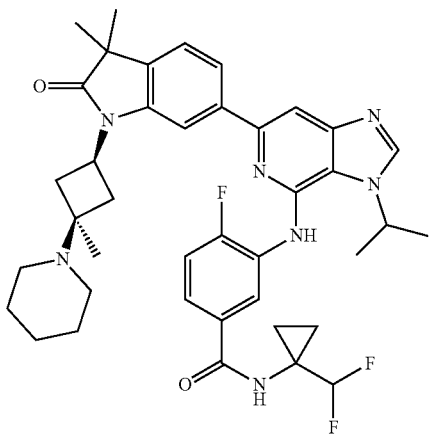 [SMILES: CC(C)n1cnc2cc(-c3ccc4c(c3)N([C@H]3C[C@@](C)(N5CCCCC5)C3)C(=O)C4(C)C)nc(Nc3cc(C(=O)NC4(C(F)F)CC4)ccc3F)c21]

N-(1-(Difluoromethyl)cyclopropyl)-3-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluorobenzamide was prepared using a similar procedure except that 3-((6-bromo-3-isopropyl-3H-imidazo[4,5-c]pyridin-4-yl)amino)-N-(1-(difluoromethyl)cyclopropyl)-4-fluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(iv) 5-((6-(3,3-Dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-3,4-difluoro-2-methylbenzamide (Example 239)

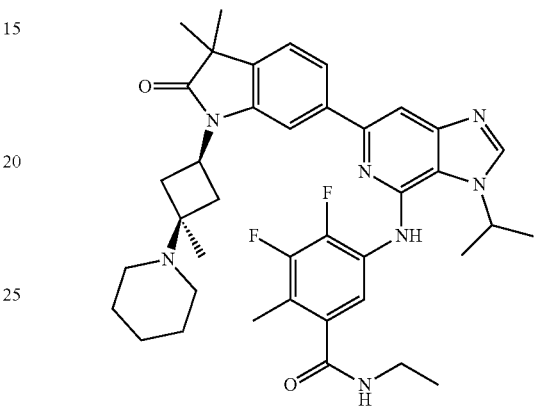

5-((6-(3,3-Dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-3,4-difluoro-2-methylbenzamide was prepared using a similar procedure except that 5-((6-bromo-3-isopropyl-3H-imidazo[4,5-c]pyridin-4-yl)amino)-N-ethyl-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(v) 3-((6-(3,3-Dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluorobenzamide (Example 240)

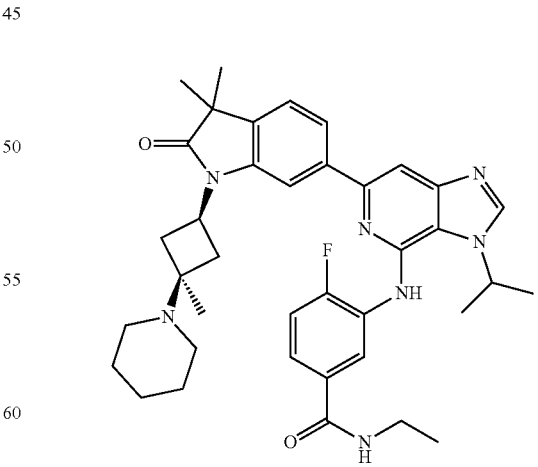

3-((6-(3,3-Dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluorobenzamide was prepared using a similar procedure except that 3-((6-bromo- 3-isopropyl-3H-imidazo[4,5-c]pyridin-4-yl)amino)-N-ethyl-4-fluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(vi) 2-Chloro-N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluorobenzamide (Example 241)

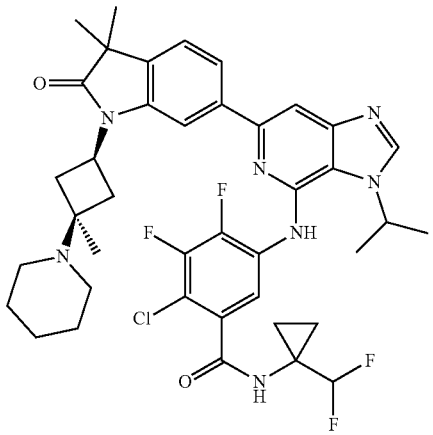

2-Chloro-N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluorobenzamide was prepared using a similar procedure except that 5-((6-bromo-3-isopropyl-3H-imidazo[4,5-c]pyridin-4-yl)amino)-2-chloro-N-(1-(difluoromethyl)cyclopropyl)-3,4-difluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(vii) 5-((6-(1-((1S,3s)-3-((1R,4S)-2-azabicyclo[2.2.1]heptan-2-yl)-3-methylcyclobutyl)-3,3-dimethyl-2-oxo-2,3-dihydro-1H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide (Example 263)

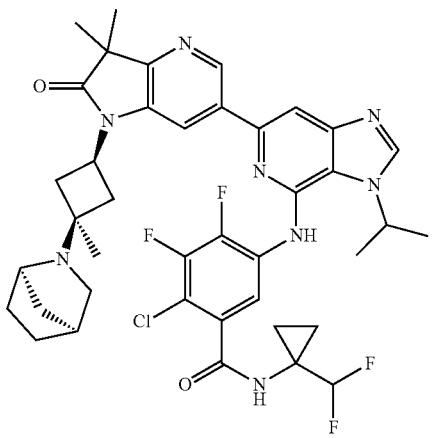 [SMILES: CC(C)n1cnc2cc(-c3cnc4c(c3)N([C@H]3C[C@@](C)(N5C[C@H]6CC[C@@H]5C6)C3)C(=O)C4(C)C)nc(Nc3cc(C(=O)NC4(C(F)F)CC4)c(Cl)c(F)c3F)c21]

5-((6-(1-((1S,3s)-3-((1R,4S)-2-azabicyclo[2.2.1]heptan-2-yl)-3-methylcyclobutyl)-3,3-dimethyl-2-oxo-2,3-dihydro-H-pyrrolo[3,2-b]pyridin-6-yl)-3-isopropyl-3H-imidazo[4,5-c]pyridin-4-yl)amino)-2-chloro-N-(1-(difluoromethyl)cyclopropyl)-3,4-difluorobenzamide was prepared using a similar procedure except that 1-((1S,3s)-3-((1R,4S)-2-azabicyclo[2.2.1]heptan-2-yl)-3-methylcyclobutyl)-6-bromo-3,3-dimethyl-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(viii) 2-chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4-fluoro-3-methylbenzamide (Example 264)

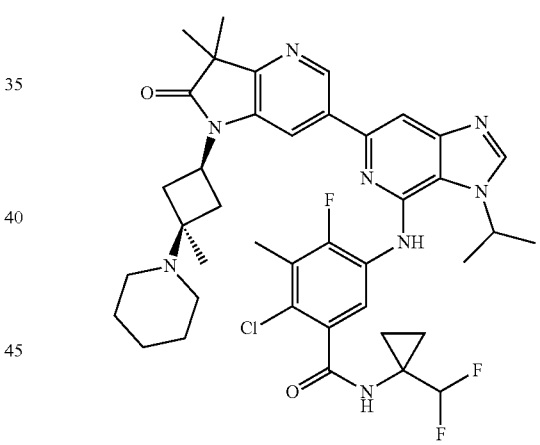

2-chloro-N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrol[3,2-b]pyridin-6-yl)-3-isopropyl-3H-imidazo[4,5-c]pyridin-4-yl)amino)-4-fluoro-3-methylbenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-4-fluoro-3-methylbenzamide instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(ix) 2-chloro-N-cyclopropyl-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide (Example 265)

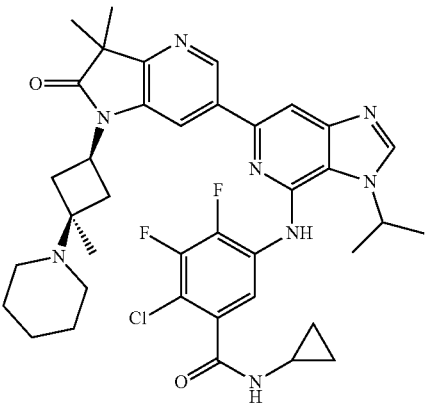 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4CC4)c(Cl)c(F)c3F)c21]

2-chloro-N-cyclopropyl-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-cyclopropyl-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(x) N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide (Example 266)

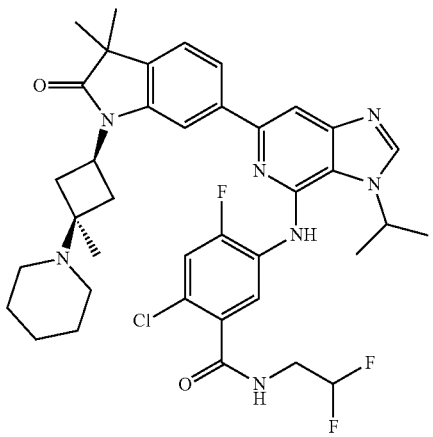 [SMILES: CC(C)n1cnc2cc(-c3ccc4c(c3)N([C@H]3C[C@@](C)(N5CCCCC5)C3)C(=O)C4(C)C)nc(Nc3cc(C(=O)NCC(F)F)c(Cl)cc3F)c21]

N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide was prepared using a similar procedure except that 5-((6-bromo-3-isopropyl-3H-imidazo[4,5-c]pyridin-4-yl)amino)-N-(2,2-difluoroethyl)-4-fluoro-2-methylbenzamide was used instead of 5-((6-bromo-3-isopropyl- 3H-imidazo[4,5-c]pyridin-4-yl)amino)-N-(1-(difluoromethyl)cyclopropyl)-4-fluoro-2-methylbenzamide.

(xi) 2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-isopropylbenzamide (Example 267)

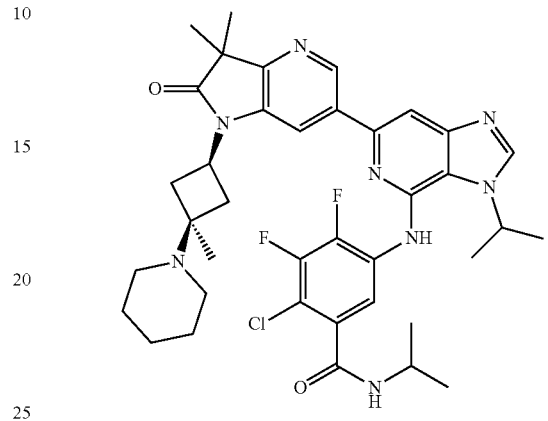

2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-isopropylbenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-isopropylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xii) N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluoro-2-methylbenzamide (Example 268)

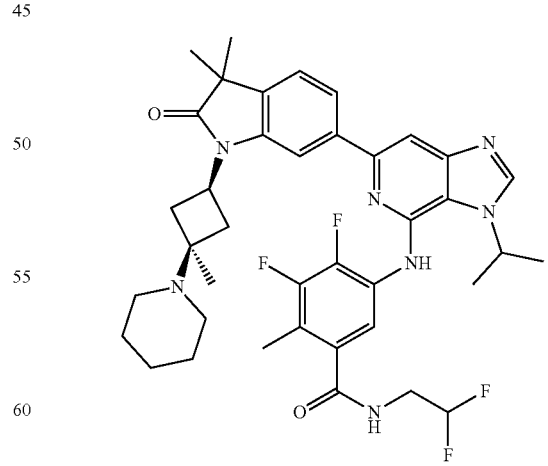

N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluoro-2-methylbenzamide was prepared using a similar procedure except that 5-((6-bromo-3-isopropyl-3H-imidazo

[4,5-c]pyridin-4-yl)amino)-N-(2,2-difluoroethyl)-3,4-difluoro-2-methylbenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xiii) N-(2,2-difluoroethyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 269)

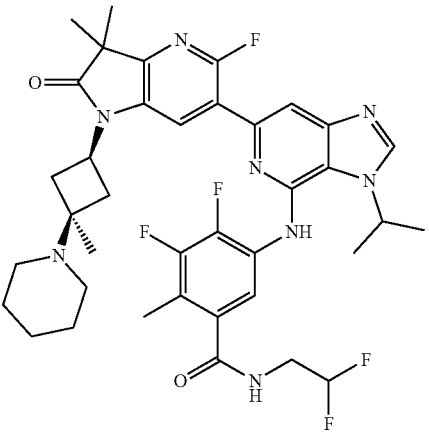 [SMILES: Cc1c(C(=O)NCC(F)F)cc(Nc2nc(-c3cc4c(nc3F)C(C)(C)C(=O)N4[C@H]3C[C@@](C)(N4CCCCC4)C3)cc3ncn(C(C)C)c23)c(F)c1F]

N-(2,2-difluoroethyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrol[3,2-b]pyridin-6-yl)-3-isopropyl-3H-imidazo[4,5-c]pyridin-4-yl)amino)-2-methylbenzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(2,2-difluoroethyl)-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xiv) 2-chloro-N-ethyl-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide (Example 270)

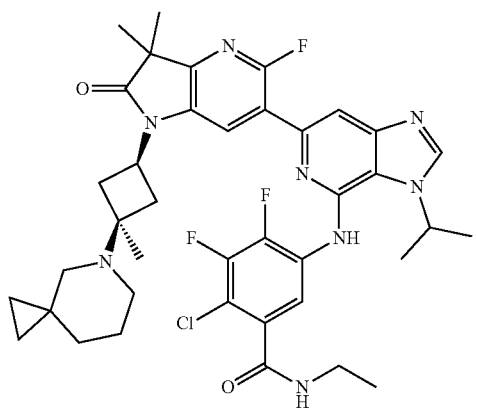 [SMILES: CCNC(=O)c1cc(Nc2nc(-c3cc4c(nc3F)C(C)(C)C(=O)N4[C@H]3C[C@@](C)(N4CCCC5(CC5)C4)C3)cc3ncn(C(C)C)c23)c(F)c(F)c1Cl]

2-chloro-N-ethyl-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide was prepared using a similar procedure except that 6-bromo-5-fluoro-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xv) N-ethyl-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 271)

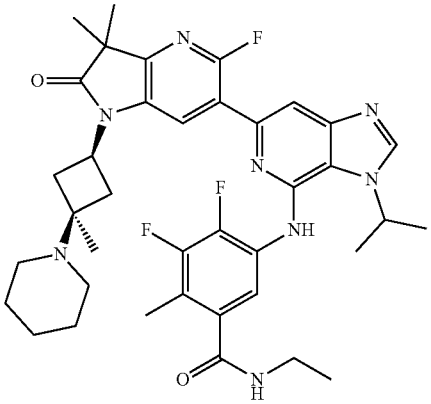 [SMILES: CCNC(=O)c1cc(Nc2nc(-c3cc4c(nc3F)C(C)(C)C(=O)N4[C@H]3C[C@@](C)(N4CCCCC4)C3)cc3ncn(C(C)C)c23)c(F)c(F)c1C]

N-ethyl-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-ethyl-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xvi) 2-chloro-N-(2,2-difluoroethyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide (Example 272)

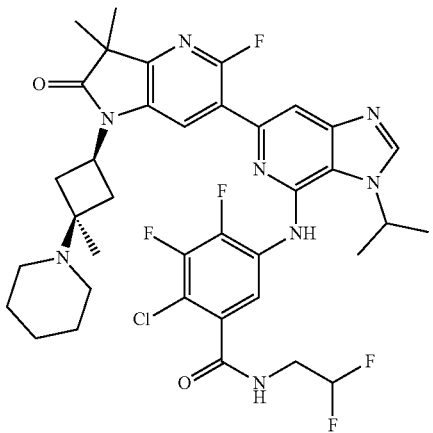 [SMILES: CC(C)n1cnc2cc(-c3cc4c(nc3F)C(C)(C)C(=O)N4[C@H]3C[C@@](C)(N4CCCCC4)C3)nc(Nc3cc(C(=O)NCC(F)F)c(Cl)c(F)c3F)c21]

2-chloro-N-(2,2-difluoroethyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xvii) 2-chloro-N-ethyl-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide (Example 273)

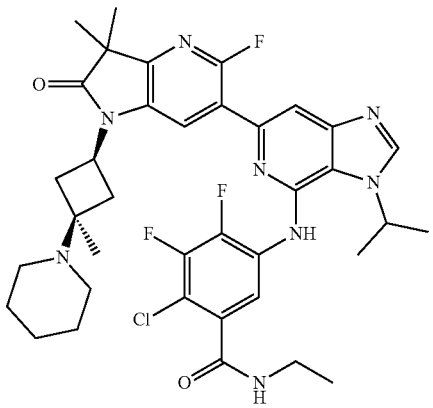 [SMILES: CCNC(=O)c1cc(Nc2nc(-c3cc4c(nc3F)C(C)(C)C(=O)N4[C@H]3C[C@@](C)(N4CCCCC4)C3)cc3ncn(C(C)C)c23)c(F)c(F)c1Cl]

2-chloro-N-ethyl-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrol[3,2-b]pyridin-6-yl)-3-isopropyl-3H-imidazo[4,5-c]pyridin-4-yl)amino)benzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xviii) N-(2,2-difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2,3,4-trifluorobenzamide (Example 274)

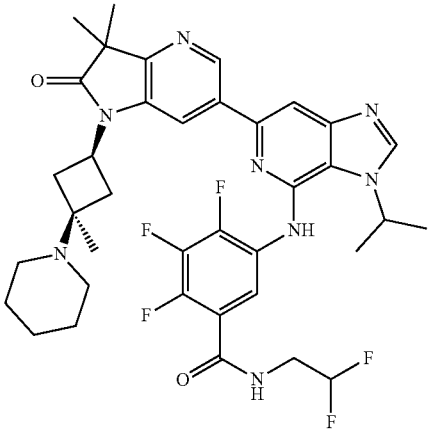 [SMILES: CC(C)n1cnc2cc(-c3cnc4c(c3)N([C@H]3C[C@@](C)(N5CCCCC5)C3)C(=O)C4(C)C)nc(Nc3cc(C(=O)NCC(F)F)c(F)c(F)c3F)c21]

N-(2,2-difluoroethyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2,3,4-trifluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(2,2-difluoroethyl)-2,3,4-trifluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

625

(xix) 2-chloro-N-(2,2-difluoroethyl)-3,4-difluoro-5-((3-isopropyl-6-(1'-((1s,3s)-3-methyl-3-(piperidin-1-yl)cyclobutyl)-2'-oxospiro[cyclopropane-1,3'-indolin]-6'-yl)-3H-imidazo[4,5-c]pyridin-4-yl)amino)benzamide (Example 275)

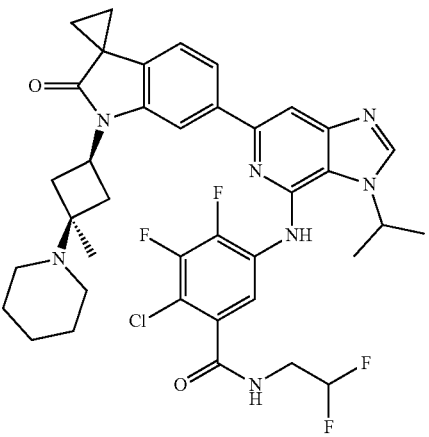 [SMILES: CC(C)n1cnc2cc(-c3ccc4c(c3)N([C@H]3C[C@@](C)(N5CCCCC5)C3)C(=O)C43CC3)nc(Nc3cc(C(=O)NCC(F)F)c(Cl)c(F)c3F)c21]

2-chloro-N-(2,2-difluoroethyl)-3,4-difluoro-5-((3-isopropyl-6-(1'-((1s,3s)-3-methyl-3-(piperidin-1-yl)cyclobutyl)-2'-oxospiro[cyclopropane-1,3'-indolin]-6'-yl)-3H-imidazo[4,5-c]pyridin-4-yl)amino)benzamide was prepared using a similar procedure except that 6'-bromo-1'-((1s,3s)-3-methyl-3-(piperidin-1-yl)cyclobutyl)spiro[cyclopropane-1,3'-indolin]-2'-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xx) 5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluoro-2-methylbenzamide (Example 276)

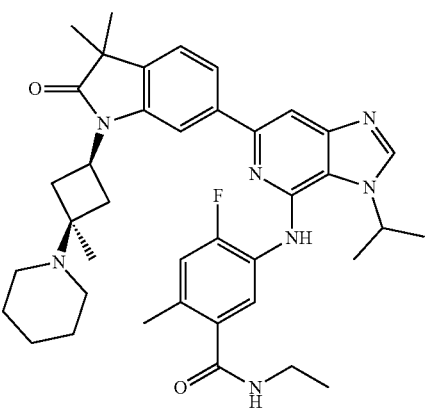 [SMILES: CCNC(=O)c1cc(Nc2nc(-c3ccc4c(c3)N([C@H]3C[C@@](C)(N5CCCCC5)C3)C(=O)C4(C)C)cc3ncn(C(C)C)c23)c(F)cc1C]

5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluoro-2-methylbenzamide was prepared using a similar procedure except that 5-((6-bromo-3-isopropyl-3H-imidazo[4,5-c]pyridin-4-yl)amino)-N-ethyl-4-fluoro-2-methylbenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxi) N-(2,2-difluoroethyl)-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 277)

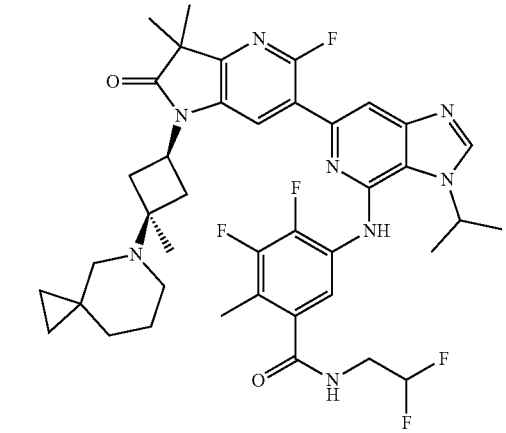 [SMILES: Cc1c(C(=O)NCC(F)F)cc(Nc2nc(-c3cc4c(nc3F)C(C)(C)C(=O)N4[C@H]3C[C@@](C)(N4CCCC5(CC5)C4)C3)cc3ncn(C(C)C)c23)c(F)c1F]

N-(2,2-difluoroethyl)-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-5-fluoro-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(2,2-difluoroethyl)-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxii) 5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-2,3,4-trifluorobenzamide (Example 278)

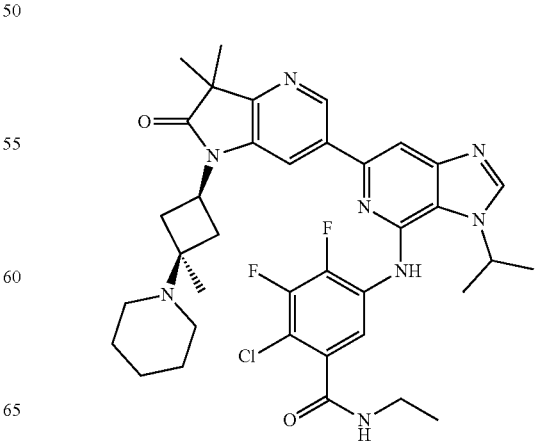

5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-2,3,4-trifluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-ethyl-2,3,4-trifluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxiii) N-ethyl-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide (Example 279)

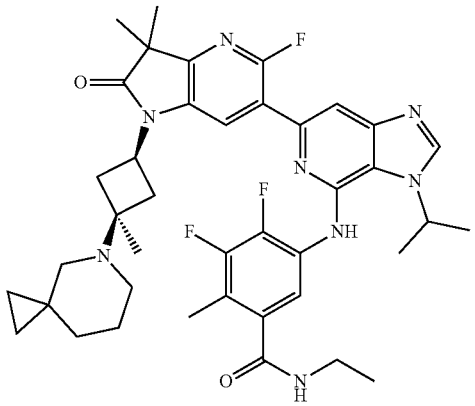 [SMILES: CCNC(=O)c1cc(Nc2nc(-c3cc4c(nc3F)C(C)(C)C(=O)N4[C@H]3C[C@@](C)(N4CCCC5(CC5)C4)C3)cc3ncn(C(C)C)c23)c(F)c(F)c1C]

N-ethyl-3,4-difluoro-5-((6-(5-fluoro-3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2-methylbenzamide was prepared using a similar procedure except that 6-bromo-5-fluoro-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-ethyl-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxiv) N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2,3,4-trifluorobenzamide (Example 280)

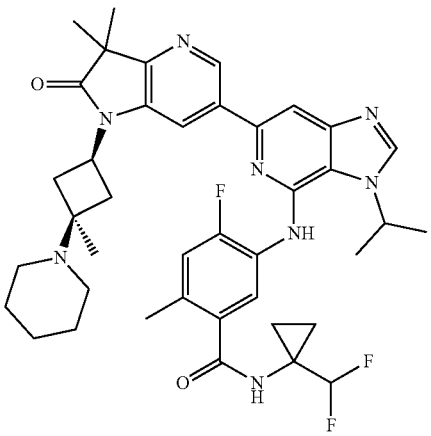 [SMILES: Cc1cc(F)c(Nc2nc(-c3cnc4c(c3)N([C@H]3C[C@@](C)(N5CCCCC5)C3)C(=O)C4(C)C)cc3ncn(C(C)C)c23)cc1C(=O)NC1(C(F)F)CC1]

N-(1-(difluoromethyl)cyclopropyl)-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-2,3,4-trifluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(1-(difluoromethyl)cyclopropyl)-2,3,4-trifluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxv) 2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-methylbenzamide (Example 281)

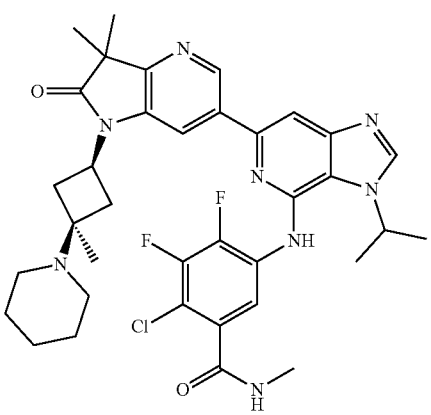 [SMILES: CNC(=O)c1cc(Nc2nc(-c3cnc4c(c3)N([C@H]3C[C@@](C)(N5CCCCC5)C3)C(=O)C4(C)C)cc3ncn(C(C)C)c23)c(F)c(F)c1Cl]

2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-N-methylbenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-3,4-difluoro-N-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxvi) 2-chloro-N-(2,2-difluoroethyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluorobenzamide
(Example 282)

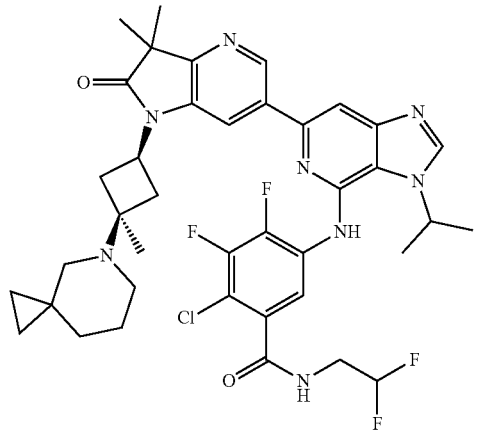 [SMILES: Cc1c(C(=O)NCC(F)F)cc(Nc2nc(-c3cnc4c(c3)N([C@H]3C[C@@](C)(N5CCCC6(CC6)C5)C3)C(=O)C4(C)C)cc3ncn(C(C)C)c23)c(F)c1F]

2-chloro-N-(2,2-difluoroethyl)-5-((6-(3,3-dimethyl-1-((1s,3s)-3-methyl-3-(5-azaspiro[2.5]octan-5-yl)cyclobutyl)-2-oxo-2,3-dihydro-H-pyrrolo[3,2-b]pyridin-6-yl)-3-isopropyl-3H-imidazo[4,5-c]pyridin-4-yl)amino)-3,4-difluorobenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(2,2-difluoroethyl)-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxvii) 2-chloro-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluorobenzamide (Example 283)

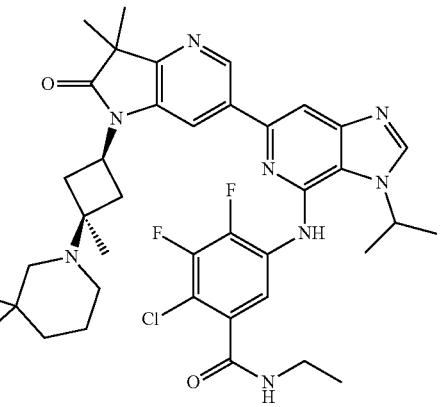

2-chloro-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluorobenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxviii) N-(2,2-difluoroethyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide
(Example 284)

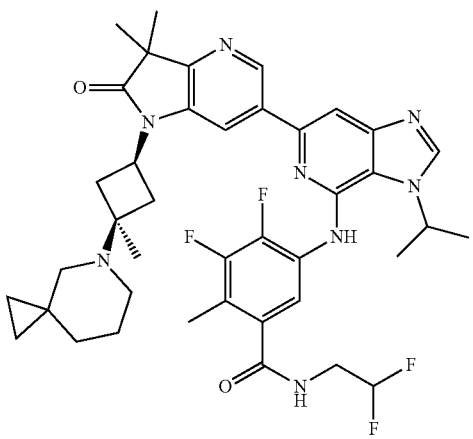

N-(2,2-difluoroethyl)-5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-3,4-difluoro-2-methylbenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-(2,2-difluoroethyl)-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxix) 5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide (Example 285)

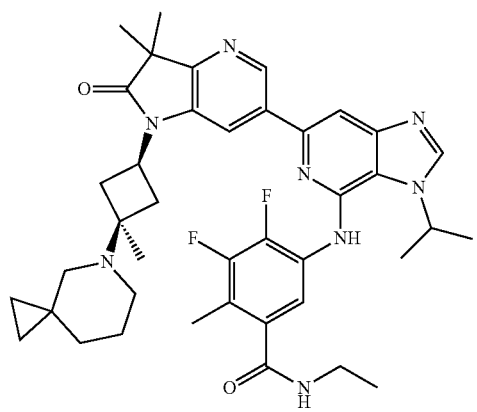 [SMILES: CCNC(=O)c1cc(Nc2nc(-c3cnc4c(c3)N([C@H]3C[C@@](C)(N5CCCC6(CC6)C5)C3)C(=O)C4(C)C)cc3ncn(C(C)C)c23)c(F)c(F)c1C]

5-((6-(3,3-dimethyl-1-((1s,3s)-3-methyl-3-(5-azaspiro[2.5]octan-5-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluoro-2-methylbenzamide was prepared using a similar procedure except that 6-bromo-3,3-dimethyl-1-((1s,3s)-3-methyl-3-(5-azaspiro[2.5]octan-5-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-N-ethyl-3,4-difluoro-2-methylbenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxx) 2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluorobenzamide (Example 286)

2-chloro-5-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-N-ethyl-3,4-difluorobenzamide was prepared using a similar procedure except that 6-bromo-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-ethyl-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxxi) 2-chloro-N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluorobenzamide (Example 287)

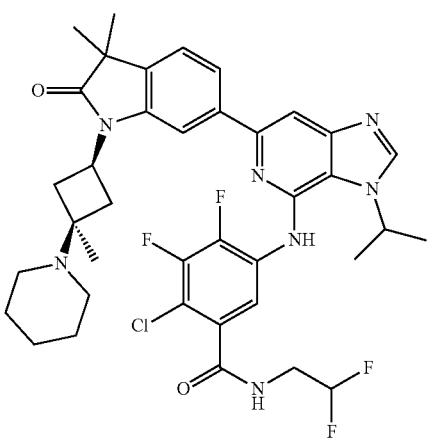

2-chloro-N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)

amino)-3,4-difluorobenzamide was prepared using a similar procedure except that 5-((6-bromo-3-isopropyl-3H-imidazo[4,5-c]pyridin-4-yl)amino)-2-chloro-N-(2,2-difluoroethyl)-3,4-difluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxii) 2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-3,4-difluorobenzamide (Example 288)

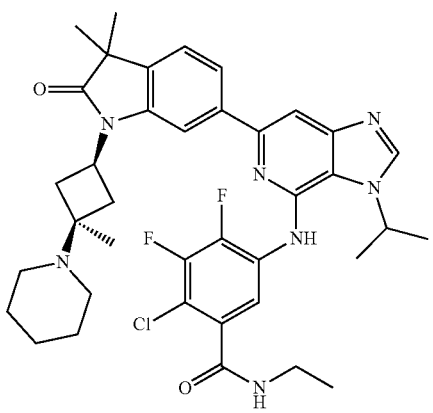 [SMILES: CCNC(=O)c1cc(Nc2nc(-c3ccc4c(c3)N([C@H]3C[C@@](C)(N5CCCCC5)C3)C(=O)C4(C)C)cc3ncn(C(C)C)c23)c(F)c(F)c1Cl]

2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-3,4-difluorobenzamide was prepared using a similar procedure except that 5-((6-bromo-3-isopropyl-3H-imidazo[4,5-c]pyridin-4-yl)amino)-2-chloro-N-ethyl-3,4-difluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxiii) 2-chloro-N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluorobenzamide (Example 289)

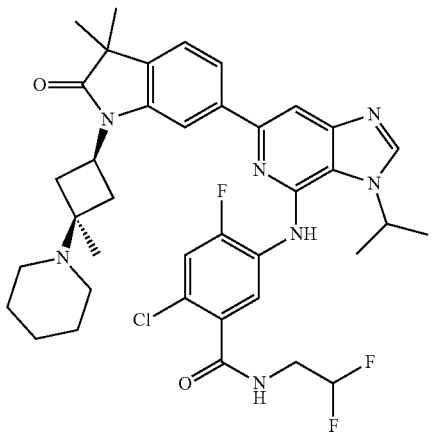 [SMILES: CC(C)n1cnc2cc(-c3ccc4c(c3)N([C@H]3C[C@@](C)(N5CCCCC5)C3)C(=O)C4(C)C)nc(Nc3cc(C(=O)NCC(F)F)c(Cl)cc3F)c21]

2-chloro-N-(2,2-difluoroethyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)

amino)-4-fluorobenzamide was prepared using a similar procedure except that 5-((6-bromo-3-isopropyl-3H-imidazo[4,5-c]pyridin-4-yl)amino)-2-chloro-N-(2,2-difluoroethyl)-4-fluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxiv) 2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluorobenzamide (Example 290)

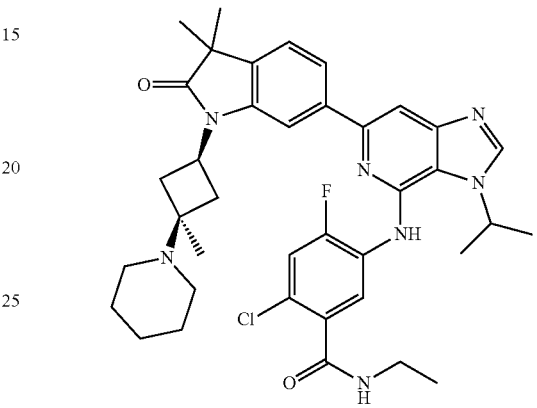

2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-N-ethyl-4-fluorobenzamide was prepared using a similar procedure except that 5-((6-bromo-3-isopropyl-3H-imidazo[4,5-c]pyridin-4-yl)amino)-2-chloro-N-ethyl-4-fluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxv) 2-chloro-N-(1-(difluoromethyl)cyclopropyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)benzamide (Example 291)

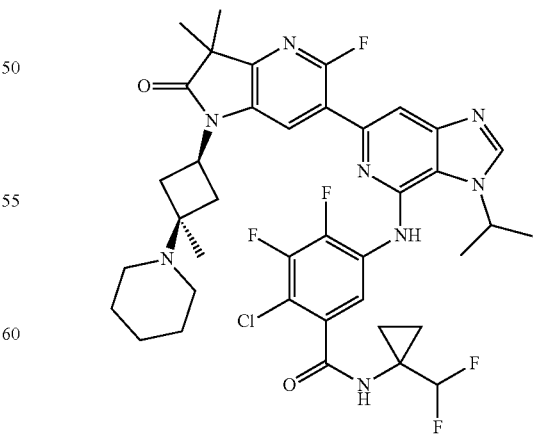

2-chloro-N-(1-(difluoromethyl)cyclopropyl)-3,4-difluoro-5-((6-(5-fluoro-3,3-dimethyl-1-((1s,3s)-3-methyl-3-(piperidin-1-yl)cyclobutyl)-2-oxo-2,3-dihydro-1H-pyrrolo

[3,2-b]pyridin-6-yl)-3-isopropyl-3H-imidazo[4,5-c]pyridin-4-yl)amino)benzamide was prepared using a similar procedure except that 6-bromo-5-fluoro-3,3-dimethyl-1-((1s,3s)-3-methyl-3-(piperidin-1-yl)cyclobutyl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 6-bromo-3,3-dimethyl-1-((1s,3s)-3-methyl-3-(piperidin-1-yl)cyclobutyl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

(xxxvi) 2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluoro-N-(1-(fluoromethyl)cyclopropyl)benzamide (Example 292)

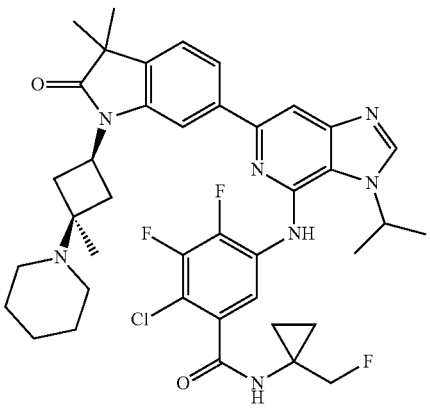 [SMILES: CC(C)n1cnc2cc(-c3ccc4c(c3)N([C@H]3C[C@@](C)(N5CCCCC5)C3)C(=O)C4(C)C)nc(Nc3cc(C(=O)NC4(CF)CC4)c(Cl)c(F)c3F)c21]

2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-3,4-difluoro-N-(1-(fluoromethyl)cyclopropyl)benzamide was prepared using a similar procedure except that 5-((6-bromo-3-isopropyl-3H-imidazo[4,5-c]pyridin-4-yl)amino)-2-chloro-3,4-difluoro-N-(1-(fluoromethyl)cyclopropyl)benzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxvii) 2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-N-(1-(fluoromethyl)cyclopropyl)benzamide (Example 293)

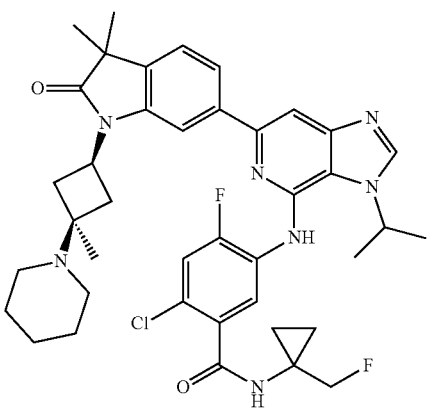 [SMILES: CC(C)n1cnc2cc(-c3ccc4c(c3)N([C@H]3C[C@@](C)(N5CCCCC5)C3)C(=O)C4(C)C)nc(Nc3cc(C(=O)NC4(CF)CC4)c(Cl)cc3F)c21]

2-chloro-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluoro-N-(1-(fluoromethyl)cyclopropyl)benzamide was prepared using a similar procedure except that 5-((6-bromo-3-isopropyl-3H-imidazo[4,5-c]pyridin-4-yl)amino)-2-chloro-4-fluoro-N-(1-(fluoromethyl)cyclopropyl)benzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

(xxxviii) 2-chloro-N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluorobenzamide (Example 294)

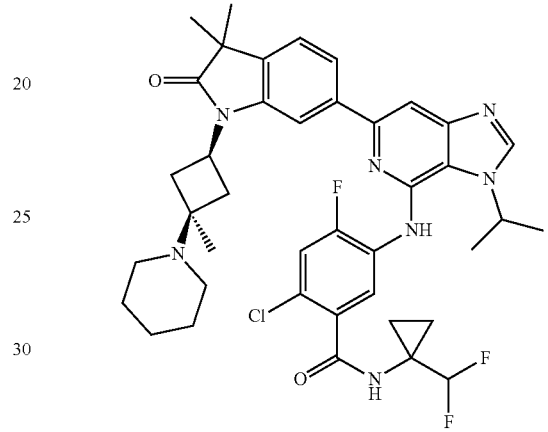

2-chloro-N-(1-(difluoromethyl)cyclopropyl)-5-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4-fluorobenzamide was prepared using a similar procedure except that 5-((6-bromo-3-isopropyl-3H-imidazo[4,5-c]pyridin-4-yl)amino)-2-chloro-N-(1-(difluoromethyl)cyclopropyl)-4-fluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

AA. Preparation of 6-bromo-5-fluoro-3,3-dimethyl-1,3-dihydro-2H-pyrrolo[3,2-b]pyridin-2-one

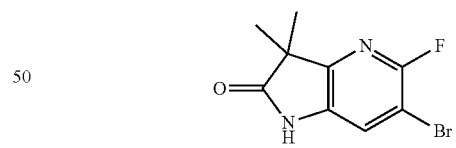

In a 100 mL, single neck, round bottomed flask were placed 6-bromo-3,3-dimethyl-1,3-dihydro-2H-pyrrolo[3,2-b]pyridin-2-one (250 mg, 1.04 mmol), DMAP (13.0 mg, 0.10 mmol), and Boc$_2$O (294 mg, 1.35 mmol) in THF (5 mL). After stirring at room temperature for 18 hrs, the mixture was concentrated and purified by flash column chromatography (100% Hexane to 100% EtOAc) to give tert-butyl 6-bromo-3,3-dimethyl-2-oxo-2,3-dihydro-1H-pyrrolo[3,2-b]pyridine-1-carboxylate which was dissolved in MeCN (dried over sieves, 10 mL). To this was added AgF$_2$ (438 mg, 3.0 mmol), and the resulting reaction mixture was stirred at 40° C. for 18 h. Then, the reaction mixture was cooled to room temperature and filtered through a pad of Celite. The filtrate was concentrated and purified by flash column chromatography (100% Hexane to 100% EtOAc) to give tert-butyl 6-bromo-5-fluoro-3,3-dimethyl-2-oxo-2,3-dihydro-1H-pyrrolo[3,2-b]pyridine-1-carboxylate which was dissolved in DCM (3 mL). To this was added TFA (0.45 mL, 5.93 mmol). After stirring at room temperature for 30 min, the reaction mixture was quenched with sat. NaHCO$_3$ and extract with DCM. The combined organic layers were dried (Na$_2$SO$_4$), concentrated, and purified by flash column chromatography (100% Hexanes to 100% EtOAc) to give 6-bromo-5-fluoro-3,3-dimethyl-1,3-dihydro-2H-pyrrolo[3,2-b]pyridin-2-one.

Procedure 41: Preparation of the Compounds of Formula I According to Reaction Scheme IX

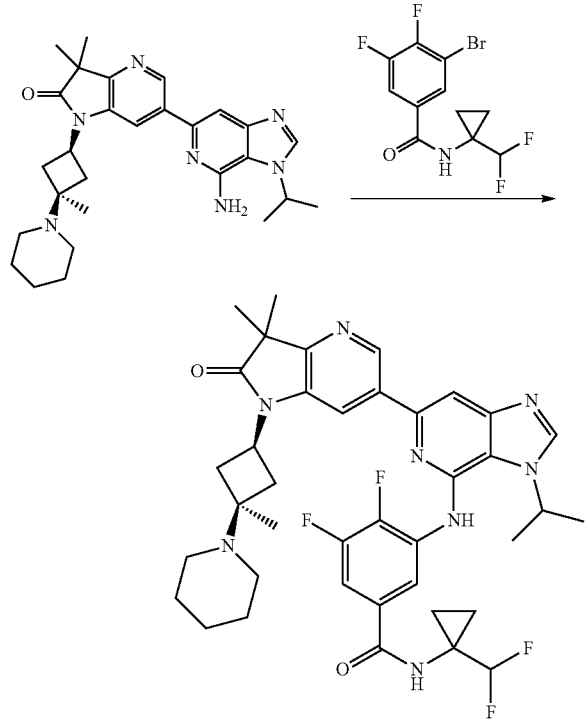

A. Preparation of N-(1-(difluoromethyl)cyclopropyl)-3-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4,5-difluorobenzamide (Example 242)

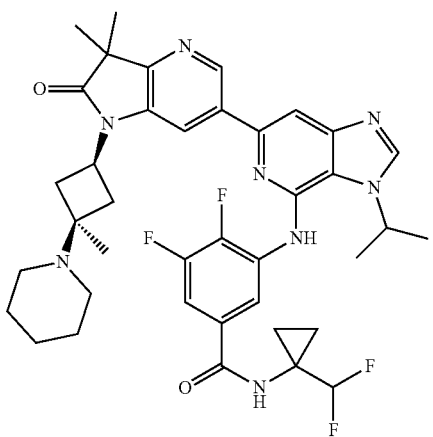 [SMILES: CC(C)n1cnc2cc(-c3cnc4c(c3)N([C@H]3C[C@@](C)(N5CCCCC5)C3)C(=O)C4(C)C)nc(Nc3cc(C(=O)NC4(C(F)F)CC4)cc(F)c3F)c21]

In a microwave vial were placed 6-(4-amino-3-isopropyl-3H-imidazo[4,5-c]pyridin-6-yl)-3,3-dimethyl-1-((1s,3s)-3-methyl-3-(piperidin-1-yl)cyclobutyl)-1,3-dihydro-2H-pyrrolo[3,2-b]pyridin-2-one (95.0 mg, 0.19 mmol), 3-bromo-N-(1-(difluoromethyl)cyclopropyl)-4,5-difluorobenzamide (127 mg, 0.39 mmol), Pd$_2$(dba)$_3$ (17.8 mg, 0.02 mmol), Xanthphos (20 mg, 0.04 mmol), and Cs$_2$CO$_3$ (254 mg, 0.78 mmol) in Dioxane (3 mL) under nitrogen. The mixture was placed in the microwave reactor and heated at 150° C. for 45 min. Then it was purified by flash chromatography (100% DCM to 100% MeOH) followed by reverse phase chromatography (0.1% TFA in Water/0.1% TFA in ACN) to give N-(1-(difluoromethyl)cyclopropyl)-3-((6-(3,3-dimethyl-1-((1s,3s)-3-methyl-3-(piperidin-1-yl)cyclobutyl)-2-oxo-2,3-dihydro-1H-pyrrolo[3,2-b]pyridin-6-yl)-3-isopropyl-3H-imidazo[4,5-c]pyridin-4-yl)amino)-4,5-difluorobenzamide.

B. Preparation of N-(1-(difluoromethyl)cyclopropyl)-3-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4,5-difluorobenzamide (Example 243)

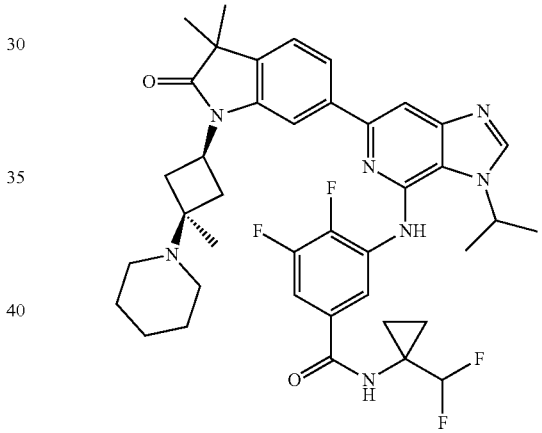

In a 100 mL, single neck, round bottomed flask were placed 6-(4-amino-3-isopropyl-imidazo[4,5-c]pyridin-6-yl)-3,3-dimethyl-1-[3-methyl-3-(1-piperidyl)cyclo butyl]indolin-2-one (127 mg, 0.26 mmol), 3-bromo-N-[1-(difluoromethyl)cyclopropyl]-4,5-difluoro-benzamide (170 mg, 0.52 mmol), XantPhos Pd G4 (50.2 mg, 0.05 mmol), and Cesium carbonate (48.6 mg, 0.78 mmol) in dioxane (10 mL) under nitrogen. After stirring at 150° C. for 18 h, the reaction mixture was transferred to a microwave vial, placed in the microwave reactor, and heated at 150° C. for 1 h. Then it was filtered through a pad of Celite, washed with MeOH, concentrated, and purified by flash chromatography (DCM/5% NEt3 in MeOH) and reverse phase chromatography (0.1% TFA in Water/0.1% TFA in ACN) to give N-(1-(difluoromethyl)cyclopropyl)-3-((6-(3,3-dimethyl-1-((1s,3s)-3-methyl-3-(piperidin-1-yl)cyclobutyl)-2-oxoindolin-6-yl)-3-isopropyl-3H-imidazo[4,5-c]pyridin-4-yl)amino)-4,5-difluorobenzamide.

Procedure 42: Preparation of the Compounds of Formula I According to Reaction Scheme X

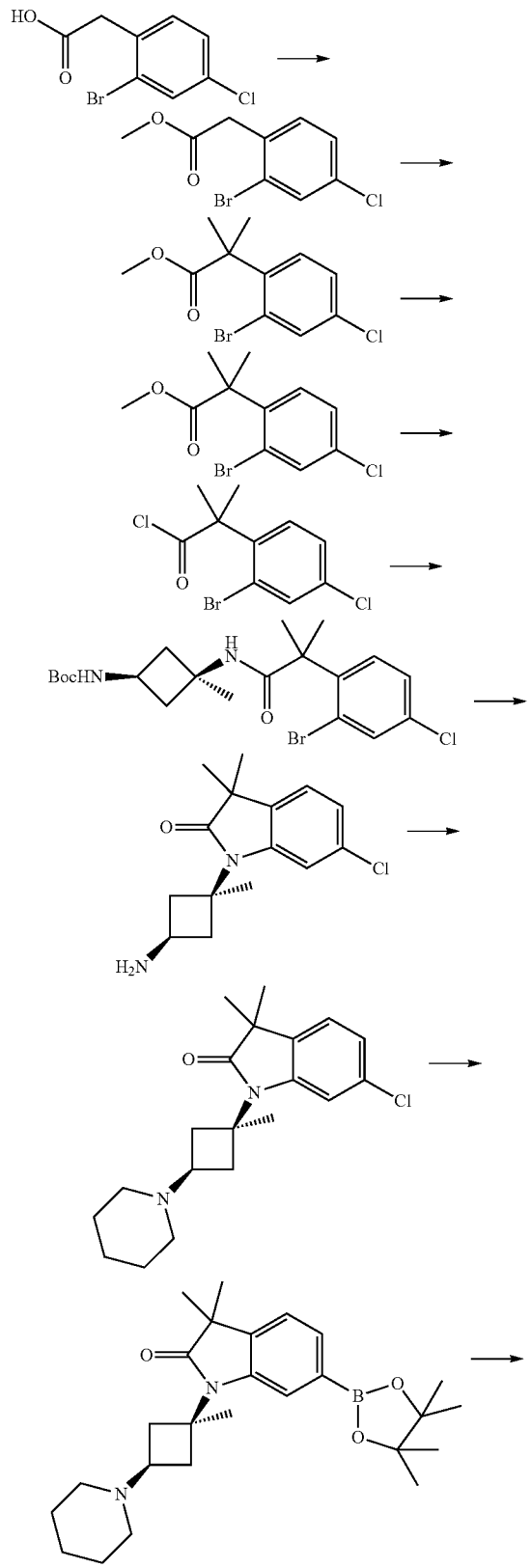

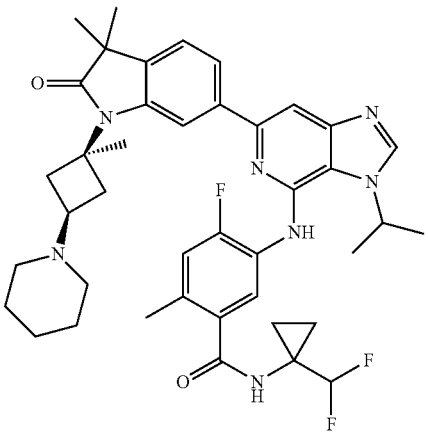

A. Preparation of methyl 2-(2-bromo-4-chlorophenyl)acetate

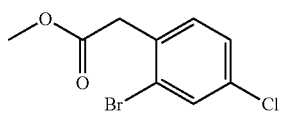

In a 100 mL, single neck, round bottomed flask was placed commercially available 2-(2-bromo-4-chloro-phenyl)acetic acid (5 g, 20.0 mmol) in methanol (30 mL). To this was added $H_2SO_4$ (0.3 mL) and the resulting mixture was stirred at RT for 16 h. Then, it was concentrated, re-dissolved in DCM and sat. $NaHCO_3$, and extracted with DCM. The combined organic layers were washed with water and brine, dried ($Na_2SO_4$), purified by flash chromatography (100% Hexane to 100% EtOAc) to afford methyl 2-(2-bromo-4-chlorophenyl)acetate.

B. Preparation of methyl 2-(2-bromo-4-chlorophenyl)-2-methylpropanoate

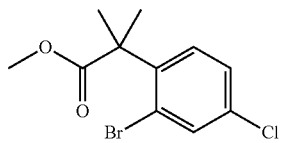

In a 100 mL, single neck, round bottomed flask was placed methyl 2-(2-bromo-4-chlorophenyl)acetate (5.0 g, 19 mmol) in THF (30 mL). To this was added NaH (2.3 g, 57 mmol) at 0° C. and the resulting mixture was stirred for 20 min followed by the addition of MeI (8.1 g, 57 mmol). After the mixture was warmed to RT and stirred for 5 hr, it was quenched with sat. $NH_4Cl$ and extracted with DCM. The combined organic layers were washed with water and brine, dried ($Na_2SO_4$), and purified by flash chromatography (100% Hexane to 100% EtOAc) to give methyl 2-(2-bromo-4-chlorophenyl)-2-methylpropanoate.

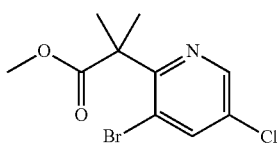

Methyl 2-(3-bromo-5-chloropyridin-2-yl)-2-methylpropanoate was prepared using a similar procedure except that commercially available methyl 2-(3-bromo-5-chloropyridin-2-yl)acetate was used instead of methyl 2-(2-bromo-4-chlorophenyl)acetate.

C. Preparation of 2-(2-bromo-4-chlorophenyl)-2-methylpropanoic acid

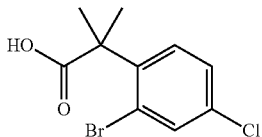

In a 100 mL, single neck, round bottomed flask equipped with a reflux condenser was placed methyl 2-(2-bromo-4-chlorophenyl)-2-methylpropanoate (2.2 g, 7.5 mol) in methanol (10 mL) and water (10 mL). To this was added NaOH (2 g, 50 mmol) and the resulting mixture was stirred at 110° C. for 16 h. Then it was cooled to RT, concentrated under reduced pressure, re-dissolved in water. To this was added citric acid to lower pH to 6. The precipitates were collected by filtration, washed with water, and dried to give 2-(2-bromo-4-chlorophenyl)-2-methylpropanoic acid which was used in the next step without further purification.

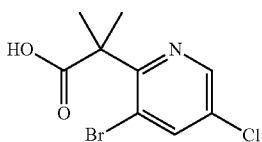

2-(3-Bromo-5-chloropyridin-2-yl)-2-methylpropanoic acid was prepared using a similar procedure except that methyl 2-(3-bromo-5-chloropyridin-2-yl)-2-methylpropanoate was used instead of methyl 2-(2-bromo-4-chlorophenyl)-2-methylpropanoate.

D. Preparation of 2-(2-bromo-4-chlorophenyl)-2-methylpropanoyl chloride

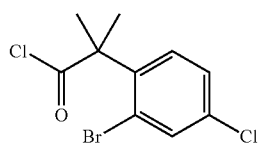

In a 100 mL, single neck, round bottomed flask equipped with a reflux condenser was placed 2-(2-bromo-4-chlorophenyl)-2-methyl-propanoic acid (800 mg, 2.9 mmol). To this was added thionyl chloride (6.3 mL, 86 mmol) and DMF (0.5 mL). The resulting mixture was stirred at 80° C. for 3 h. Then it was cooled to RT and concentrated to give 2-(2-bromo-4-chlorophenyl)-2-methylpropanoyl chloride which was used in the next step without further purification.

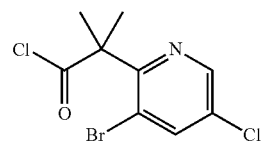

2-(3-Bromo-5-chloropyridin-2-yl)-2-methylpropanoyl chloride was prepared using a similar procedure except that 2-(3-bromo-5-chloropyridin-2-yl)-2-methylpropanoic acid was used instead of 2-(2-bromo-4-chlorophenyl)-2-methylpropanoic acid.

E. Preparation of tert-butyl ((1s,3s)-3-(2-(2-bromo-4-chlorophenyl)-2-methylpropanamido)-3-methylcyclobutyl)carbamate

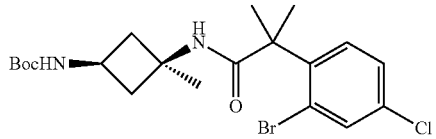 [SMILES: CC(C)(C)OC(=O)N[C@H]1C[C@@](C)(NC(=O)C(C)(C)c2ccc(Cl)cc2Br)C1]

In a 100 mL, single neck, round bottomed flask was placed 2-(2-bromo-4-chlorophenyl)-2-methylpropanoyl chloride (820 mg, 2.8 mmol) in dichloromethane (10 mL). To this were added to tert-butyl ((1s,3s)-3-amino-3-methylcyclobutyl)carbamate (560 mg, 2.8 mmol) and DIPEA (5 mL, 29 mmol). The resulting mixture was stirred at RT for 16 h. Then, it was quenched with water and extracted with DCM. The combined organic layers were washed with water and brine, dried (Na$_2$SO$_4$), and concentrated to give tert-butyl ((1s,3s)-3-(2-(2-bromo-4-chlorophenyl)-2-methylpropanamido)-3-methylcyclobutyl)carbamate which was used in the next step without purification.

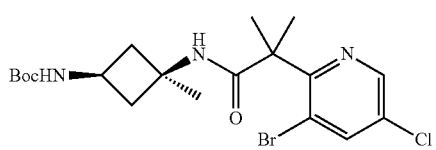 [SMILES: CC(C)(C)OC(=O)N[C@H]1C[C@@](C)(NC(=O)C(C)(C)c2ncc(Cl)cc2Br)C1]

tert-Butyl ((1s,3s)-3-(2-(3-bromo-5-chloropyridin-2-yl)-2-methylpropanamido)-3-methylcyclobutyl)carbamate was prepared using a similar procedure except that 2-(3-bromo-5-chloropyridin-2-yl)-2-methylpropanoyl chloride was used instead of 2-(2-bromo-4-chlorophenyl)-2-methylpropanoyl chloride.

F. Preparation of 1-((1s,3s)-3-amino-1-methylcyclobutyl)-6-chloro-3,3-dimethylindolin-2-one

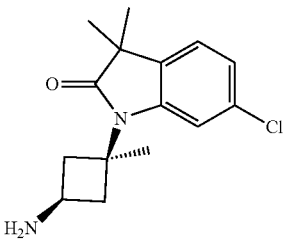 [SMILES: CC1(C)C(=O)N([C@]2(C)C[C@H](N)C2)c2cc(Cl)ccc21]

In a 100 mL, single neck, round bottomed flask were placed tert-butyl ((1s,3s)-3-(2-(2-bromo-4-chlorophenyl)-2-methylpropanamido)-3-methylcyclobutyl)carbamate (600 mg, 1.3 mmol) and KOH (600 mg, 11 mmol) in DMSO (6 mL). After the mixture was stirred at 120° C. for 16 h, it was cooled to RT, diluted with water, neutralized with 2 N HCl, and extracted with DCM:IPA (3:1). The combined organic layers were concentrated and purified by flash chromatography (100% DCM to 100% MeOH) to give 1-((1s,3s)-3-amino-1-methylcyclobutyl)-6-chloro-3,3-dimethylindolin-2-one.

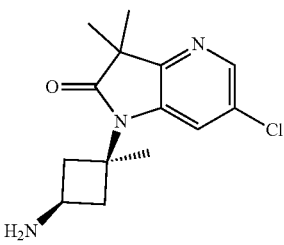 [SMILES: CC1(C)C(=O)N([C@]2(C)C[C@H](N)C2)c2cc(Cl)cnc21]

1-((1s,3s)-3-Amino-1-methylcyclobutyl)-6-chloro-3,3-dimethyl-1,3-dihydro-2H-pyrrolo[3,2-b]pyridin-2-one was prepared using a similar procedure except that tert-butyl ((1s,3s)-3-(2-(3-bromo-5-chloropyridin-2-yl)-2-methylpropanamido)-3-methylcyclobutyl)carbamate was used instead of tert-butyl ((1s,3s)-3-(2-(2-bromo-4-chlorophenyl)-2-methylpropanamido)-3-methylcyclobutyl)carbamate.

G. Preparation of 6-chloro-3,3-dimethyl-1-((1s,3s)-1-methyl-3-(piperidin-1-yl)cyclobutyl)indolin-2-one

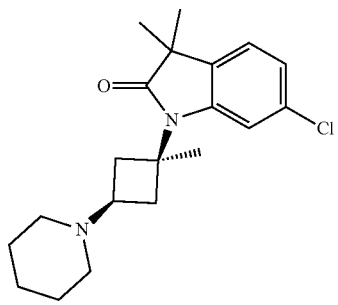 [SMILES: CC1(C)C(=O)N([C@]2(C)C[C@H](N3CCCCC3)C2)c2cc(Cl)ccc21]

In a 200 mL, single neck, round bottomed flask was placed 1-((1s,3s)-3-amino-1-methylcyclobutyl)-6-chloro-3,3-dimethylindolin-2-one (40 mg 0.14 mmol) in dichloromethane (20 mL). To this was added glutaraldehyde (120 mg, 0.86 mmol) in dichloromethane (40 mL) followed by the addition of sodium triacetoxyborohydride (91 mg, 0.43 mmol) and acetic acid (26 mg, 0.43 mmol). After the mixture was stirred at RT for 3 h, it was quenched with sat. NaHCO₃ and extracted with DCM. The combined organic layers were washed with sat. NaHCO₃ and brine, concentrated, and purified by flash chromatography (100% DCM to 100% MeOH) to give 6-chloro-3,3-dimethyl-1-((1s,3s)-1-methyl-3-(piperidin-1-yl)cyclobutyl)indolin-2-one.

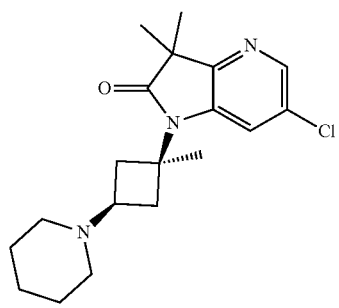 [SMILES: CC1(C)C(=O)N([C@]2(C)C[C@H](N3CCCCC3)C2)c2cc(Cl)cnc21]

6-Chloro-3,3-dimethyl-1-((1s,3s)-1-methyl-3-(piperidin-1-yl)cyclobutyl)-1,3-dihydro-2H-pyrrolo[3,2-b]pyridin-2-one was prepared using a similar procedure except that 1-((1s,3s)-3-amino-1-methylcyclobutyl)-6-chloro-3,3-dimethyl-1,3-dihydro-2H-pyrrolo[3,2-b]pyridin-2-one was used instead of 1-((1s,3s)-3-amino-1-methylcyclobutyl)-6-chloro-3,3-dimethylindolin-2-one.

H. Preparation of 3,3-dimethyl-1-((1s,3s)-1-methyl-3-(piperidin-1-yl)cyclobutyl)-6-(4,4,5,5-tetramethyl-1,3,2-dioxaborolan-2-yl)indolin-2-one

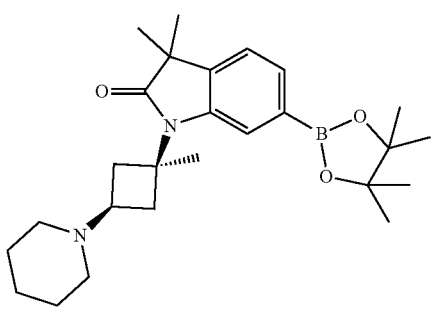 [SMILES: CC1(C)C(=O)N([C@]2(C)C[C@H](N3CCCCC3)C2)c2cc(B3OC(C)(C)C(C)(C)O3)ccc21]

In a sealed tube were placed 6-chloro-3,3-dimethyl-1-((1s,3s)-1-methyl-3-(piperidin-1-yl)cyclobutyl)indolin-2-one (40 mg, 0.12 mmol), bis(pinacolato)diboron (88 mg, 0.35 mmol), potassium acetate (45 mg, 0.46 mmol), Pd₂dba₃ (5.3 mg, 0.0058 mmol) and XPhos (8.3 mg, 0.017 mol) in dioxane (2 mL). The mixture was sparged with nitrogen for 5 min and stirred at 100° C. for 72 h. Then, it was cooled to RT, diluted with EtOAc, and filtered through a pad of Celite. The filtrate was concentrated to give 3,3-dimethyl-1-((1s,3s)-1-methyl-3-(piperidin-1-yl)cyclobutyl)-6-(4,4,5,5-tetramethyl-1,3,2-dioxaborolan-2-yl)indolin-2-one which was used in the next step without purification.

645

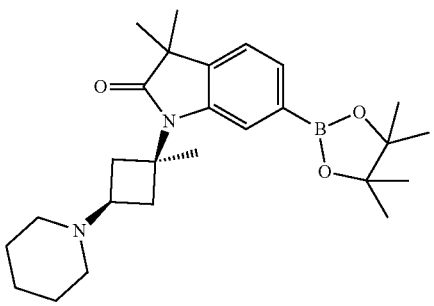 [SMILES: CC1(C)C(=O)N([C@]2(C)C[C@H](N3CCCCC3)C2)c2cc(B3OC(C)(C)C(C)(C)O3)ccc21]

3,3-Dimethyl-1-((1s,3s)-1-methyl-3-(piperidin-1-yl)cyclobutyl)-6-(4,4,5,5-tetramethyl-1,3,2-dioxaborolan-2-yl)-1,3-dihydro-2H-pyrrolo[3,2-b]pyridin-2-one was prepared using a similar procedure except that 6-chloro-3,3-dimethyl-1-((1s,3s)-1-methyl-3-(piperidin-1-yl)cyclobutyl)-1,3-dihydro-2H-pyrrolo[3,2-b]pyridin-2-one was used instead of 6-chloro-3,3-dimethyl-1-((1s,3s)-1-methyl-3-(piperidin-1-yl)cyclobutyl)indolin-2-one.

I. Preparation of N-(1-(difluoromethyl)cyclopropyl)-5-((6-(3,3-dimethyl-1-((1s,3s)-1-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide (Example 295)

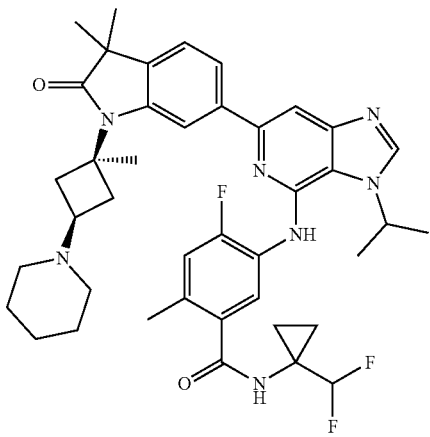 [SMILES: Cc1cc(F)c(Nc2nc(-c3ccc4c(c3)N([C@]3(C)C[C@H](N5CCCCC5)C3)C(=O)C4(C)C)cc3ncn(C(C)C)c23)cc1C(=O)NC1(C(F)F)CC1]

In a sealed tube were placed 3,3-dimethyl-1-((1s,3s)-1-methyl-3-(piperidin-1-yl)cyclobutyl)-6-(4,4,5,5-tetramethyl-1,3,2-dioxaborolan-2-yl)indolin-2-one (40 mg, 0.046 mmol), 5-((6-bromo-3-isopropyl-3H-imidazo[4,5-c]pyridin-4-yl)amino)-N-(1-(difluoromethyl)cyclopropyl)-4-fluoro-2-methylbenzamide (110 mg, 0.23 mmol), Pd(PPh₃)₄ (2.6 mg, 0.0023 mmol), 2 M Na₂CO₃ (0.068 mL) in dioxane (4 mL). The mixture was degassed with N₂ and stirred at 90° C. for 2 h. Then, it was cooed to RT, diluted with EtOAc (4 mL), and filtered through a pad of Celite. The filtrate was concentrated and purified by flash chromatography (100% DCM to 100% MeOH) and reverse phase chromatography (0.1% TFA in ACN/0.1% TFA in water) to give N-(1-(difluoromethyl)cyclopropyl)-5-((6-(3,3-dimethyl-1-((1s,3s)-1-methyl-3-(piperidin-1-yl)cyclobutyl)-2-oxoindolin-6-yl)-3-isopropyl-3H-imidazo[4,5-c]pyridin-4-yl)amino)-4-fluoro-2-methylbenzamide.

646

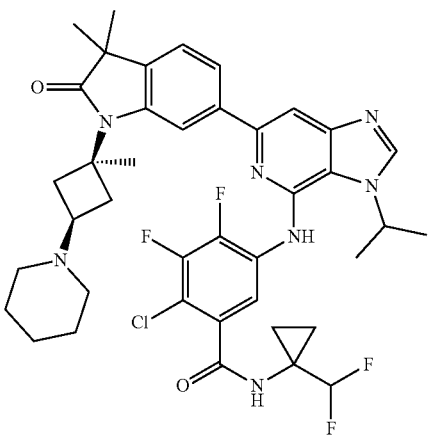 [SMILES: CC(C)n1cnc2cc(-c3ccc4c(c3)N([C@]3(C)C[C@H](N5CCCCC5)C3)C(=O)C4(C)C)nc(Nc3cc(C(=O)NC4(C(F)F)CC4)c(Cl)c(F)c3F)c21]

2-Chloro-N-(1-(difluoromethyl)cyclopropyl)-5-((6-(3,3-dimethyl-1-((1s,3s)-1-methyl-3-(piperidin-1-yl)cyclobutyl)-2-oxoindolin-6-yl)-3-isopropyl-3H-imidazo[4,5-c]pyridin-4-yl)amino)-3,4-difluorobenzamide (Example 296) was prepared using a similar procedure except that 5-((6-bromo-3-isopropyl-3H-imidazo[4,5-c]pyridin-4-yl)amino)-2-chloro-N-(1-(difluoromethyl)cyclopropyl)-3,4-difluorobenzamide was used instead of 5-((6-bromo-3-isopropyl-3H-imidazo[4,5-c]pyridin-4-yl)amino)-N-(1-(difluoromethyl)cyclopropyl)-4-fluoro-2-methylbenzamide.

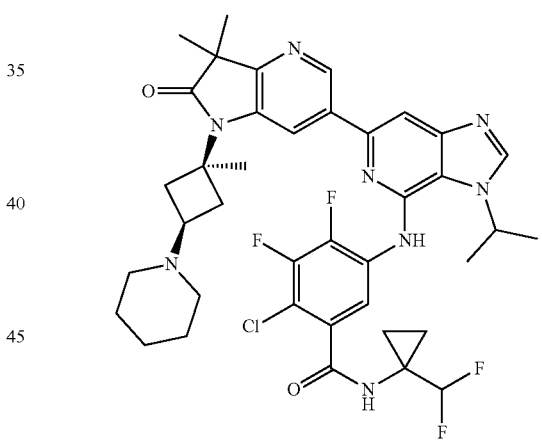

2-Chloro-N-(1-(difluoromethyl)cyclopropyl)-5-((6-(3,3-dimethyl-1-((1s,3s)-1-methyl-3-(piperidin-1-yl)cyclobutyl)-2-oxo-2,3-dihydro-1H-pyrrol[3,2-b]pyridin-6-yl)-3-isopropyl-3H-imidazo[4,5-c]pyridin-4-yl)amino)-3,4-difluorobenzamide (Example 297) was prepared using a similar procedure except that 3,3-dimethyl-1-((1s,3s)-1-methyl-3-(piperidin-1-yl)cyclobutyl)-6-(4,4,5,5-tetramethyl-1,3,2-dioxaborolan-2-yl)-1,3-dihydro-2H-pyrrolo[3,2-b]pyridin-2-one and 5-((6-bromo-3-isopropyl-3H-imidazo[4,5-c]pyridin-4-yl)amino)-2-chloro-N-(1-(difluoromethyl)cyclopropyl)-3,4-difluorobenzamide were used instead of 3,3-dimethyl-1-((1s,3s)-1-methyl-3-(piperidin-1-yl)cyclobutyl)-6-(4,4,5,5-tetramethyl-1,3,2-dioxaborolan-2-yl)indolin-2-one and 5-((6-bromo-3-isopropyl-3H-imidazo[4,5-c]pyridin-4-yl)amino)-N-(1-(difluoromethyl)cyclopropyl)-4-fluoro-2-methylbenzamide, respectively.

Analytical Data for Examples 1-297 are set forth in Table 1.

HPK1 IC$_{50}$ Assay

The enzymatic activity of human HPK1 (MAP4K1) was monitored in a biochemical assay in the presence or absence of compounds and using a synthetic peptide substrate. An increase in phosphorylation of the peptide by HPK1 was indicative of its kinase activity.

Recombinant HPK1 kinase domain produced via baculovirus infection of insect cells was obtained from Proteros (Proteros Biostructures #PR-0322) and was pre-activated in the presence of 2 mM ATP (Sigma-Aldrich, cat #GE27-2056-01) and 2 mM magnesium chloride for 16 hours at 4° C. The protein reaction mixture was then loaded to a desalting column (Thermo Fisher Scientific, Cat #89889) to remove excess ATP. HPK1 was eluted with buffer containing 20 mM Tris (2-Amino-2-(hydroxymethyl)propane-1,3-diol) pH 8.0, 150 mM NaCl, 2 mM dithiothreitol and 5% glycerol, and was frozen at −80° C. for later use. HPK1 dual phosphorylation was confirmed by mass spectrometry.

Ten nanoliters of test compounds dissolved in DMSO at various concentrations were dispensed into a 384-well ProxiPlate (PerkinElmer #6008289). Five microliters of a solution of recombinant HPK1 diluted in HPK1 kinase assay buffer (50 mM BES [N,N-Bis(2-hydroxyethyl)-2-aminoethanesulfonic acid], pH 7.0; 10 mM magnesium chloride; 0.01% Triton X-100; 1 mM dithiothreitol; 0.01% bovine serum albumin; 0.1 mM sodium orthovanadate) was added to the compound-containing plate and was incubated for 15 minutes at 25° C. Five microliters of a mixture of ATP (Sigma-Aldrich #A6559) and peptide substrate STK S1 (Cisbio #61ST1BLC) diluted in HPK1 kinase assay buffer was then added to start the reaction. Final concentrations were 0.15 nM for HPK1, 10 μM for ATP, and 1 μM for the STK S1 peptide substrate. The reaction mixture was incubated at 25° C. for 3 hours and was stopped with the addition of 10 μl of an EDTA (Ethylenediaminetetraacetic acid)-containing detection buffer (Cisbio #62SDBRDF) supplemented with Europium cryptate-labeled anti-phospho-serine/threonine antibodies (Cisbio #62ST1PEJ) and XL665-labeled streptavidin (Cisbio #610SAXLG). The mixture was incubated for 16 hours at room temperature and peptide phosphorylation was measured by time-resolved fluorescence energy transfer (665 nm/620 nm) on an Envision plate reader (PerkinElmer).

Data in Table 1 were normalized based on positive (staurosporine) and negative (DMSO) controls. Least squares curve fittings were performed using a four-parameter variable slope nonlinear regression model. IC$_{50}$ is defined as the concentration of compound required to inhibit 50% of maximum phosphorylation. IC$_{50}$ values from multiple experiments were averaged by geometric mean and the standard deviation was calculated.

TABLE 1

| Example # | ES/MS m/z | $^1$H-NMR | HPK1 IC$_{50}$ (nM) |
|---|---|---|---|
| 1 | 620.4 | $^1$H NMR (400 MHz, DMSO-d6) delta 9.42 (d, J = 9.5 Hz, 1H), 8.77 (s, 1H), 8.49 (s, 1H), 8.15 (q, J = 4.5 Hz, 1H), 7.86 (s, 1H), 7.75 (dd, J = 7.8, 1.5 Hz, 1H), 7.60-7.46 (m, 3H), 7.38 (d, J = 7.8 Hz, 1H), 7.23-7.06 (m, 1H), 5.30 (p, J = 6.5 Hz, 1H), 4.34-4.08 (m, 1H), 3.43 (dd, J = 51.1, 10.0 Hz, 3H), 2.97-2.65 (m, 8H), 2.30 (s, 3H), 1.82 (d, J = 14.0 Hz, 2H), 1.55 (d, J = 6.5 Hz, 9H), 1.28 (s, 8H). | 0.08 |
| 2 | 660.4 | $^1$H NMR (400 MHz, DMSO-d6) delta 9.35-9.25 (m, 1H), 8.66 (s, 1H), 8.54-8.38 (m, 2H), 7.89 (s, 1H), 7.78 (dd, J = 7.8, 1.4 Hz, 1H), 7.61 (d, J = 1.4 Hz, 1H), 7.59 (d, J = 2.4 Hz, 1H), 7.50 (dd, J = 8.2, 2.4 Hz, 1H), 7.38 (d, J = 7.9 Hz, 1H), 7.19 (d, J = 8.4 Hz, 1H), 5.30 (p, J = 6.6 Hz, 1H), 4.37 (hex, J = 8.2 Hz, 1H), 4.26 (p, J = 7.8 Hz, 1H), 3.49 (q, J = 8.5 Hz, 1H), 3.42-3.35 (m, 2H), 2.99-2.87 (m, 2H), 26.87-2.72 (m, 4H), 2.30 (s, 3H), 2.21-2.12 (m, 2H), 2.00-1.88 (m, 2H), 1.87-1.79 (m, 2H), 1.75-1.67 (m, 1H), 1.67-1.53 (m, 10H), 1.47-1.35 (m, 1H), 1.29 (s, 6H). | 0.1 |
| 3 | 634.4 | $^1$H NMR (400 MHz, DMSO-d6) delta 10.40-10.05 (m, 2H), 8.81 (s, 1H), 8.74 (s, 1H), 8.40-8.25 (m, 2H), 7.79 (d, J = 7.9 Hz, 1H), 7.67 (s, 1H), 7.65-7.52 (m, 2H), 5.19-5.07 (m, 1H), 4.50 (q, J = 6.5 Hz, 1H), 4.44-4.30 (m, 1H), 4.04-3.46 (m, 6H), 3.28-3.09 (m, 1H), 3.09-2.90 (m, 2H), 2.85-2.75 (m, 2H), 2.48-2.05 (m, 3H), 1.90-1.64 (m, 5H), 1.58-1.34 (m, 9H), 1.24 (t, J = 6.5 Hz, 3H), 0.91 (t, J = 7.4 Hz, 3H). | 0.1 |
| 4 | 624.4 | $^1$H NMR (400 MHz, DMSO-d6) delta 10.70-10.46 (m, 1H), 8.62 (s, 1H), 8.44 (s, 1H), 8.16 (q, J = 4.6 Hz, 1H), 7.88 (s, 1H), 7.77 (dd, J = 7.8, 1.4 Hz, 1H), 7.60 (d, J = 8.1 Hz, 1H), 7.55 (d, J = 2.4 Hz, 1H), 7.52-7.46 (m, 1H), 7.39 (d, J = 7.8 Hz, 1H), 7.19 (d, J = 8.3 Hz, 1H), 5.62-5.40 (m, 1H), 5.29 (p, J = 6.6 Hz, 1H), 4.35 (q, J = 8.4 Hz, 1H), 3.95-3.50 (m, 6H), 3.03-2.92 (m, 2H), 2.86-2.72 (m, 6H), 2.31 (s, 3H), 1.55 (d, J = 6.4 Hz, 6H), 1.30 (s, 6H). | 0.1 |
| 5 | 624.4 | $^1$H NMR (400 MHz, DMSO-d6) delta 10.71-10.52 (m, 1H), 8.75 (s, 1H), 8.49 (s, 1H), 8.17 (q, J = 4.6 Hz, 1H), 7.87 (s, 1H), 7.77 (dd, J = 7.8, 1.5 Hz, 1H), 7.59 (d, J = 7.3 Hz, 1H), 7.55 (d, J = 2.4 Hz, 1H), 7.52-7.46 (m, 1H), 7.39 (d, J = 7.8 Hz, 1H), 7.20 (d, | 0.2 |

TABLE 1-continued

| Example # | ES/MS m/z | ¹H-NMR | HPK1 IC$_{50}$ (nM) |
|---|---|---|---|
| | | J = 8.2 Hz, 1H), 5.52 (d, J = 51.4 Hz, 1H), 5.31 (p, J = 6.6 Hz, 1H), 4.33 (p, J = 8.1 Hz, 1H), 3.96-3.49 (m, 3H), 3.42-3.20 (m, 1H), 2.98 (q, J = 10.2 Hz, 2H), 2.86-2.72 (m, 5H), 2.60-2.05 (m, 3H, overlapped with solvent), 2.32 (s, 3H), 1.57 (d, J = 6.4 Hz, 6H), 1.30 (s, 6H). | |
| 6 | 634.4 | ¹H NMR (400 MHz, DMSO-d6) delta 9.29-9.10 (m, 1H), 8.62 (s, 1H), 8.44 (s, 1H), 8.17 (q, J = 4.5 Hz, 1H), 7.87 (s, 1H), 7.78 (dt, J = 7.8, 2.0 Hz, 1H), 7.63-7.54 (m, 2H), 7.49-7.44 (m, 1H), 7.42-7.34 (m, 1H), 7.20 (d, J = 8.4 Hz, 1H), 5.28 (p, J = 6.5 Hz, 1H), 4.56-4.41 (m, 1H), 4.38-4.16 (m, 5H), 4.14-4.02 (m, 1H), 3.19-3.11 (m, 1H), 2.99-2.69 (m, 7H), 2.33 (s, 3H), 2.20-1.99 (m, 1H), 1.55 (d, J = 6.6 Hz, 6H), 1.30 (s, 6H). | 0.1 |
| 7 | 654.3 | ¹H NMR (400 MHz, DMSO-d6) delta 11.25-10.15 (m, 1H), 8.73 (s, 1H), 8.49 (s, 1H), 8.21-8.15 (m, 1H), 7.87 (s, 1H), 7.77 (d, J = 7.5 Hz, 1H), 7.57 (s, 1H), 7.55 (d, J = 2.4 Hz, 1H), 7.52-7.44 (m, 1H), 7.39 (d, J = 7.8 Hz, 1H), 7.20 (d, J = 8.3 Hz, 1H), 5.37-5.21 (m, 1H), 4.29 (p, J = 8.2 Hz, 1H), 3.85 (s, 2H), 3.69 (s, 2H), 3.14 (s, 1H), 3.04-2.85 (m, 4H), 2.81-2.70 (m, 5H), 2.32 (s, 3H), 1.56 (d, J = 6.5 Hz, 6H), 1.30 (s, 6H). | 0.4 |
| 8 | 666.4 | ¹H NMR (400 MHz, DMSO-d6) delta 9.92 (s, 1H), 8.66 (s, 1H), 8.34 (s, 1H), 8.19 (d, J = 4.7 Hz, 1H), 7.83 (s, 1H), 7.68 (d, J = 7.9 Hz, 2H), 7.43-7.34 (m, 2H), 7.20 (d, J = 12.0 Hz, 1H), 5.32-5.22 (m, 1H), 4.08 (p, J = 8.6 Hz, 1H), 3.95 (s, 2H), 3.87 (d, J = 12.4 Hz, 2H), 3.72 (d, J = 12.2 Hz, 2H), 3.54 (q, J = 8.2 Hz, 1H), 2.96 (q, J = 9.8, 9.2 Hz, 2H), 2.91-2.82 (m, 2H), 2.73 (d, J = 4.5 Hz, 3H), 2.36 (s, 3H), 2.22-2.13 (m, 2H), 2.13-2.05 (m, 2H), 1.59 (d, J = 6.5 Hz, 6H), 1.30 (s, 6H). | 0.08 |
| 9 | 652.3 | ¹H NMR (400 MHz, DMSO-d6) delta 10.42-9.15 (m, 1H), 8.71 (s, 1H), 8.40-8.33 (m, 1H), 8.23-8.17 (m, 1H), 7.84 (s, 1H), 7.73-7.60 (m, 2H), 7.43 (s, 1H), 7.37 (d, J = 7.8 Hz, 1H), 7.23 (dd, J = 12.1, 2.9 Hz, 1H), 5.29 (p, J = 6.8 Hz, 1H), 4.53-3.99 (m, 8H), 3.22-2.76 (m, 5H), 2.74 (d, J = 4.5 Hz, 3H), 2.41-2.37 (m, 3H), 2.16-2.04 (m, 1H), 1.59 (d, J = 6.6 Hz, 6H), 1.29 (d, J = 1.8 Hz, 6H). | 0.1 |
| 10 | 666.3 | ¹H NMR (400 MHz, DMSO-d6) delta 9.35 (s, 1H), 8.65 (s, 1H), 8.35 (s, 1H), 8.21-8.16 (m, 1H), 7.85 (s, 1H), 7.68 (dd, J = 7.9, 1.4 Hz, 1H), 7.63 (d, J = 8.2 Hz, 1H), 7.43 (s, 1H), 7.36 (d, J = 7.8 Hz, 1H), 7.20 (d, J = 12.1 Hz, 1H), 5.27 (p, J = 6.6 Hz, 1H), 4.52 (s, 2H), 4.13 (p, J = 8.5 Hz, 1H), 3.70-3.58 (m, 1H), 3.41-3.33 (m, 2H), 3.06 (t, J = 10.9 Hz, 2H), 3.00-2.88 (m, 2H), 2.79-2.69 (m, 5H), 2.38 (s, 3H), 2.04-1.92 (m, 4H), 1.59 (d, J = 6.5 Hz, 6H), 1.29 (s, 6H). | 0.1 |
| 11 | 594.3 | ¹H NMR (400 MHz, Methanol-d4) delta 9.06 (s, 1H), 7.79-7.71 (m, 2H), 7.65 (d, J = 2.4 Hz, 1H), 7.60 (d, J = 1.4 Hz, 1H), 7.40-7.33 (m, 2H), 7.27 (d, J = 8.3 Hz, 1H), 5.33 (p, J = 6.6 Hz, 1H), 4.37 (p, J = 8.2 Hz, 1H), 3.81 (p, J = 8.1 Hz, 1H), 3.39 (p, J = 6.4 Hz, 1H), 2.91 (t, J = 8.0 Hz, 4H), 2.85 (s, 3H), 2.40 (s, 3H), 1.68 (d, J = 6.6 Hz, 6H), 1.38-1.28 (m, 12H). | 0.1 |
| 12 | 650.3 | ¹H NMR (400 MHz, Methanol-d4) delta 9.08 (s, 1H), 7.78-7.71 (m, 2H), 7.69 (d, J = 2.3 Hz, 1H), 7.61 (d, J = 1.4 Hz, 1H), 7.41-7.32 (m, 2H), 7.26 (d, J = 8.3 Hz, 1H), 5.33 (p, J = 6.6 Hz, 1H), 4.36 (p, J = 8.2 Hz, 1H), 4.01 (dd, J = 11.8, 4.8 Hz, 1H), 3.88 (p, J = 7.8 Hz, 1H), 3.76 (d, J = 11.7 Hz, 1H), 3.57 (d, J = 12.0 Hz, 1H), 3.54-3.38 (m, 2H), 2.96 (d, J = 4.0 Hz, 4H), 2.85 (s, 3H), 2.40 (s, 3H), 2.10 (s, 1H), 1.94-1.82 (m, 1H), 1.77 (d, J = 12.7 Hz, 1H), 1.68 (d, J = 6.6 Hz, 6H), 1.35 (s, 6H), 1.15 (d, J = 7.1 Hz, 3H). | 0.09 |
| 13 | 650.3 | ¹H NMR (400 MHz, Methanol-d4) delta 9.09 (s, 1H), 7.80 (d, J = 8.9 Hz, 2H), 7.74 (d, J = 2.3 Hz, 1H), 7.66 (d, J = 1.3 Hz, 1H), 7.44-7.37 (m, 2H), 7.31 (d, J = 8.3 Hz, 1H), 5.37 (q, J = 6.6 Hz, 1H), 4.46 (q, J = 7.7 Hz, 1H), 4.06 (d, J = 12.3 Hz, 1H), 4.03-3.88 (m, 2H), 3.54-3.42 (m, 1H), 3.15 (t, J = 11.3 Hz, 2H), 3.10-2.97 (m, 3H), 2.90 (s, 4H), 2.45 (s, 3H), | 0.1 |

TABLE 1-continued

| Example # | ES/MS m/z | ¹H-NMR | HPK1 IC$_{50}$ (nM) |
|---|---|---|---|
| | | 2.06 (d, J = 12.4 Hz, 1H), 1.94-1.81 (m, 1H), 1.73 (dd, J = 6.5, 5.2 Hz, 7H), 1.41 (s, 6H), 1.11 (d, J = 6.6 Hz, 3H). | |
| 14 | 612.3 | ¹H NMR (400 MHz, Methanol-d4) delta 8.98 (s, 1H), 7.88 (d, J = 8.0 Hz, 1H), 7.77 (s, 1H), 7.72 (dd, J = 7.8, 1.5 Hz, 1H), 7.54 (d, J = 1.3 Hz, 1H), 7.35 (d, J = 7.8 Hz, 1H), 7.17 (d, J = 11.7 Hz, 1H), 5.33 (p, J = 6.5 Hz, 1H), 4.32 (q, J = 8.1 Hz, 1H), 3.85 (t, J = 7.8 Hz, 1H), 3.43 (p, J = 6.5 Hz, 1H), 2.92 (t, J = 8.0 Hz, 4H), 2.87 (s, 3H), 2.45 (s, 3H), 1.73 (d, J = 6.5 Hz, 6H), 1.43-1.33 (m, 12H). | 0.3 |
| 15 | 642.3 | ¹H NMR (400 MHz, Methanol-d4) delta 9.08 (s, 1H), 7.90 (s, 1H), 7.80 (s, 1H), 7.76 (dd, J = 7.8, 1.5 Hz, 1H), 7.57 (d, J = 1.6 Hz, 1H), 7.42-7.36 (m, 1H), 7.26-7.18 (m, 1H), 5.37 (p, J = 6.8 Hz, 1H), 4.41 (p, J = 8.1 Hz, 1H), 3.81 (q, J = 7.4 Hz, 1H), 3.05-2.93 (m, 6H), 2.91 (s, 3H), 2.50 (d, J = 1.8 Hz, 3H), 1.77 (dd, J = 6.7, 1.9 Hz, 6H), 1.41 (d, J = 1.9 Hz, 6H), 1.38 (d, J = 1.9 Hz, 6H). | 0.1 |
| 16 | 634.4 | ¹H NMR (400 MHz, Chloroform-d) delta 8.24 (s, 1H), 8.18 (s, 1H), 8.02 (s, 0H), 7.93 (d, J = 2.4 Hz, 0H), 7.66 (d, J = 0.5 Hz, 1H), 7.55-7.47 (m, 1H), 7.43 (dd, J = 7.8, 1.4 Hz, 1H), 7.36-7.29 (m, 1H), 7.23-7.16 (m, 2H), 6.09 (s, 1H), 4.90 (t, J = 8.9 Hz, 1H), 4.38 (s, 1H), 4.01 (s, 1H), 3.67 (d, J = 53.6 Hz, 2H), 3.43 (s, 3H), 2.90 (s, 1H), 2.71-2.54 (m, 4H), 2.44 (s, 1H), 1.23 (d, J = 16.2 Hz, 8H), 1.07 (s, 3H), 0.97-0.81 (m, 2H). | 0.1 |
| 17 | 622.4 | ¹H NMR (400 MHz, Chloroform-d) delta 8.14 (s, 1H), 7.87 (s, 1H), 7.66 (s, 1H), 7.51 (d, J = 7.1 Hz, 1H), 7.29 (d, J = 7.6 Hz, 1H), 7.20 (d, J = 8.1 Hz, 1H), 7.00 (s, 1H), 5.17-4.72 (m, 1H), 3.51 (d, J = 10.2 Hz, 2H), 2.80-2.60 (m, 2H), 2.05 (d, J = 35.4 Hz, 0H), 1.25 (s, 8H), 0.85 (d, J = 18.2 Hz, 1H), 0.07 (d, J = 4.3 Hz, 4H). | 0.04 |
| 18 | 621.4 | ¹H NMR (400 MHz, DMSO-d6) delta 9.34 (s, 1H), 8.85 (d, J = 1.7 Hz, 1H), 8.66 (s, 1H), 8.48 (s, 1H), 8.19-8.13 (m, 1H), 7.98 (s, 1H), 7.85 (d, J = 1.8 Hz, 1H), 7.57-7.48 (m, 2H), 7.20 (d, J = 8.2 Hz, 1H), 5.35-5.24 (m, 1H), 4.33-4.22 (m, 1H), 3.60-3.49 (m, 1H), 3.39 (d, J = 11.8 Hz, 2H), 2.98-2.75 (m, 5H), 2.74 (d, J = 4.6 Hz, 3H), 2.31 (s, 3H), 1.84 (d, J = 14.2 Hz, 2H), 1.76-1.59 (m, 3H), 1.56 (d, J = 6.5 Hz, 6H), 1.43 (t, J = 14.4 Hz, 1H), 1.31 (s, 6H). | 0.4 |
| 19 | 697.5 | ¹H NMR (400 MHz, DMSO-d6) delta 9.47 (d, J = 7.7 Hz, 1H), 8.83 (t, J = 1.8 Hz, 3H), 8.59 (s, 1H), 7.98 (s, 1H), 7.86 (d, J = 1.7 Hz, 1H), 7.59 (d, J = 2.3 Hz, 1H), 7.52 (dd, J = 8.3, 2.4 Hz, 1H), 7.21 (d, J = 8.3 Hz, 1H), 6.11 (t, J = 57.3 Hz, 1H), 5.41-5.29 (m, 1H), 4.32 (h, J = 8.5, 7.8 Hz, 1H), 3.58-3.45 (m, 1H), 3.39 (d, J = 11.8 Hz, 2H), 2.99-2.74 (m, 5H), 2.31 (s, 3H), 1.84 (d, J = 14.1 Hz, 2H), 1.76-1.62 (m, 3H), 1.58 (d, J = 6.5 Hz, 6H), 1.46-1.37 (m, 1H), 1.31 (s, 6H), 1.11-1.03 (m, 2H), 0.96-0.88 (m, 2H). | 0.3 |
| 20 | 670.4 | ¹H NMR (400 MHz, DMSO-d6) delta 9.33 (s, 1H), 8.63 (t, J = 6.1 Hz, 1H), 8.53 (s, 1H), 7.87 (s, 1H), 7.74 (dd, J = 7.8, 1.4 Hz, 1H), 7.57 (s, 1H), 7.55-7.50 (m, 2H), 7.37 (d, J = 7.7 Hz, 1H), 7.20 (d, J = 8.7 Hz, 1H), 6.23-5.92 (m, 1H), 5.34-5.23 (m, 1H), 4.25 (q, J = 8.3 Hz, 1H), 3.69-3.55 (m, 2H), 3.47 (q, J = 7.9 Hz, 1H), 3.37 (d, J = 11.9 Hz, 2H), 2.98-2.69 (m, 7H), 2.31 (s, 3H), 1.82 (d, J = 14.1 Hz, 2H), 1.54 (d, J = 6.5 Hz, 8H), 1.27 (s, 6H). | 0.05 |
| 21 | 684.4 | ¹H NMR (400 MHz, DMSO-d6) delta 9.48 (s, 1H), 8.90 (d, J = 12.5 Hz, 1H), 8.62 (d, J = 6.2 Hz, 1H), 8.52 (d, J = 8.4 Hz, 1H), 7.87 (d, J = 0.9 Hz, 1H), 7.74 (dd, J = 7.8, 1.4 Hz, 1H), 7.57-7.49 (m, 3H), 7.38 (d, J = 7.8 Hz, 1H), 7.21 (d, J = 8.4 Hz, 1H), 5.97 (td, J = 56.2, 3.4 Hz, 1H), 5.35 (s, 1H), 4.43-4.18 (m, 2H), 3.54-3.31 (m, 3H), 2.84 (dp, J = 41.0, 11.3, 10.6 Hz, 7H), 2.31 (s, 3H), 1.82 (d, J = 14.1 Hz, 2H), 1.75-1.46 (m, 9H), 1.41 (t, J = 12.5 Hz, 1H), 1.27 (s, 6H), 1.14 (d, J = 7.0 Hz, 3H). | 0.05 |

TABLE 1-continued

| Example # | ES/MS m/z | ¹H-NMR | HPK1 IC$_{50}$ (nM) |
|---|---|---|---|
| 21A (1$^{st}$ eluting peak) | 684.4 | ¹H NMR (400 MHz, DMSO-d6) delta 9.48 (s, 1H), 8.90 (d, J = 12.5 Hz, 1H), 8.62 (d, J = 6.2 Hz, 1H), 8.52 (d, J = 8.4 Hz, 1H), 7.87 (d, J = 0.9 Hz, 1H), 7.74 (dd, J = 7.8, 1.4 Hz, 1H), 7.57-7.49 (m, 3H), 7.38 (d, J = 7.8 Hz, 1H), 7.21 (d, J = 8.4 Hz, 1H), 5.97 (td, J = 56.2, 3.4 Hz, 1H), 5.35 (s, 1H), 4.43-4.18 (m, 2H), 3.54-3.31 (m, 3H), 2.84 (dp, J = 41.0, 11.3, 10.6 Hz, 7H), 2.31 (s, 3H), 1.82 (d, J = 14.1 Hz, 2H), 1.75-1.46 (m, 9H), 1.41 (t, J = 12.5 Hz, 1H), 1.27 (s, 6H), 1.14 (d, J = 7.0 Hz, 3H). | 0.07 |
| 21B (2$^{nd}$ eluting peak) | 684.4 | ¹H NMR (400 MHz, DMSO-d6) delta 9.48 (s, 1H), 8.90 (d, J = 12.5 Hz, 1H), 8.62 (d, J = 6.2 Hz, 1H), 8.52 (d, J = 8.4 Hz, 1H), 7.87 (d, J = 0.9 Hz, 1H), 7.74 (dd, J = 7.8, 1.4 Hz, 1H), 7.57-7.49 (m, 3H), 7.38 (d, J = 7.8 Hz, 1H), 7.21 (d, J = 8.4 Hz, 1H), 5.97 (td, J = 56.2, 3.4 Hz, 1H), 5.35 (s, 1H), 4.43-4.18 (m, 2H), 3.54-3.31 (m, 3H), 2.84 (dp, J = 41.0, 11.3, 10.6 Hz, 7H), 2.31 (s, 3H), 1.82 (d, J = 14.1 Hz, 2H), 1.75-1.46 (m, 9H), 1.41 (t, J = 12.5 Hz, 1H), 1.27 (s, 6H), 1.14 (d, J = 7.0 Hz, 3H). | 0.07 |
| 22 | 676.4 | ¹H NMR (400 MHz, DMSO-d6) delta 9.36 (s, 1H), 8.68 (s, 1H), 8.47 (s, 1H), 8.23 (t, J = 5.6 Hz, 1H), 7.88 (s, 1H), 7.77 (dd, J = 7.8, 1.4 Hz, 1H), 7.62-7.55 (m, 2H), 7.54-7.46 (m, 2H), 7.17 (d, J = 8.3 Hz, 1H), 5.30 (q, J = 6.7 Hz, 1H), 4.26 (t, J = 8.2 Hz, 1H), 4.03 (q, J = 5.7 Hz, 1H), 3.87-3.77 (m, 1H), 3.42 (dd, J = 39.1, 9.9 Hz, 3H), 3.27-3.16 (m, 2H), 2.92 (q, J = 9.8 Hz, 2H), 2.78 (d, J = 11.8 Hz, 4H), 2.30 (s, 3H), 1.87-1.47 (m, 15H), 1.39 (d, J = 13.0 Hz, 1H), 1.05 (t, J = 7.2 Hz, 3H). | 0.07 |
| 23 | 702.4 | ¹H NMR (400 MHz, DMSO-d6) delta 9.44 (s, 1H), 8.86 (s, 1H), 8.58-8.52 (m, 1H), 8.50 (d, J = 7.7 Hz, 1H), 7.89 (s, 1H), 7.76 (dd, J = 7.8, 1.5 Hz, 1H), 7.58 (d, J = 8.0 Hz, 2H), 7.56-7.47 (m, 2H), 7.19 (d, J = 8.3 Hz, 1H), 5.34 (p, J = 6.5 Hz, 1H), 4.30 (dq, J = 43.8, 8.2 Hz, 2H), 4.04 (p, J = 5.7 Hz, 2H), 3.83 (dt, J = 10.8, 5.0 Hz, 2H), 3.52-3.30 (m, 3H), 3.00-2.84 (m, 2H), 2.78 (td, J = 13.9, 12.7, 8.7 Hz, 5H), 2.29 (s, 3H), 2.16 (td, J = 8.3, 4.1 Hz, 2H), 1.93 (dq, J = 11.8, 9.4 Hz, 2H), 1.87-1.48 (m, 15H), 1.41 (t, J = 12.3 Hz, 1H). | 0.2 |
| 24 | 648.4 | ¹H NMR (400 MHz, DMSO-d6) delta 9.52 (s, 1H), 8.89 (s, 1H), 8.57 (s, 1H), 8.23 (t, J = 5.7 Hz, 1H), 7.87 (s, 1H), 7.75 (dd, J = 7.8, 1.4 Hz, 1H), 7.57 (t, J = 1.8 Hz, 2H), 7.49 (dd, J = 8.2, 2.4 Hz, 1H), 7.37 (d, J = 7.8 Hz, 1H), 7.19 (d, J = 8.3 Hz, 1H), 5.34 (p, J = 6.6 Hz, 1H), 4.23 (p, J = 8.3 Hz, 1H), 3.48 (h, J = 8.4 Hz, 1H), 3.36 (d, J = 11.7 Hz, 2H), 3.15 (q, J = 6.6 Hz, 2H), 2.95-2.70 (m, 7H), 2.31 (s, 3H), 1.81 (d, J = 14.1 Hz, 2H), 1.56 (d, J = 6.5 Hz, 8H), 1.50-1.34 (m, 3H), 1.27 (s, 6H), 0.81 (t, J = 7.4 Hz, 3H). | 0.08 |
| 25 | 684.4 | ¹H NMR (400 MHz, DMSO-d6) delta 9.52 (s, 1H), 9.00 (s, 1H), 8.62 (s, 1H), 8.39 (t, J = 5.7 Hz, 1H), 7.88 (s, 1H), 7.75 (dd, J = 7.8, 1.4 Hz, 1H), 7.56 (d, J = 2.4 Hz, 2H), 7.51 (dd, J = 8.2, 2.4 Hz, 1H), 7.38 (d, J = 7.8 Hz, 1H), 7.21 (d, J = 8.3 Hz, 1H), 6.08 (tt, J = 56.5, 4.5 Hz, 1H), 5.36 (p, J = 6.5 Hz, 1H), 4.29-4.16 (m, 1H), 3.48 (h, J = 8.1 Hz, 1H), 3.42-3.29 (m, 4H), 2.95-2.70 (m, 6H), 2.32 (s, 3H), 2.04 (ttd, J = 18.0, 7.0, 4.5 Hz, 2H), 1.82 (d, J = 14.1 Hz, 2H), 1.57 (d, J = 6.5 Hz, 8H), 1.41 (dd, J = 14.7, 10.5 Hz, 1H), 1.27 (s, 6H). | 0.07 |
| 26 | 646.4 | ¹H NMR (400 MHz, DMSO-d6) delta 9.46 (s, 1H), 8.83 (s, 1H), 8.53 (s, 1H), 8.29 (d, J = 4.5 Hz, 1H), 7.88 (s, 1H), 7.77 (dd, J = 7.8, 1.5 Hz, 1H), 7.57 (dd, J = 8.1, 1.9 Hz, 2H), 7.50 (dd, J = 8.2, 2.4 Hz, 1H), 7.40 (d, J = 7.8 Hz, 1H), 7.20 (d, J = 8.3 Hz, 1H), 5.34 (p, J = 6.6 Hz, 1H), 4.35-4.22 (m, 1H), 3.52 (h, J = 8.3 Hz, 1H), 3.39 (d, J = 11.7 Hz, 2H), 2.99-2.75 (m, 7H), 2.31 (s, 3H), 1.84 (d, J = 14.0 Hz, 2H), 1.57 (d, J = 6.5 Hz, 9H), 1.43 (t, J = 12.5 Hz, 1H), 1.30 (s, 6H), 0.65 (td, J = 7.0, 4.7 Hz, 2H), 0.51-0.42 (m, 2H). | 0.1 |
| 27 | 696.4 | ¹H NMR (400 MHz, DMSO-d6) delta 9.51 (s, 1H), 8.90 (d, J = 2.9 Hz, 1H), 8.82 (s, 1H), 8.60 (s, 1H), 7.89 (s, 1H), 7.75 (dd, J = 7.7, 1.4 Hz, 1H), 7.62-7.49 (m, 3H), 7.39 (d, J = 7.8 Hz, 1H), 7.21 (d, J = | 0.07 |

TABLE 1-continued

| Example # | ES/MS m/z | ¹H-NMR | HPK1 IC$_{50}$ (nM) |
|---|---|---|---|
| | | 8.1 Hz, 1H), 6.09 (t, J = 57.3 Hz, 1H), 5.36 (p, J = 6.6 Hz, 1H), 4.35-4.22 (m, 1H), 3.58-3.32 (m, 4H), 3.02-2.74 (m, 6H), 2.31 (s, 3H), 1.84 (d, J = 14.0 Hz, 2H), 1.77-1.52 (m, 7H), 1.49-1.35 (m, 1H), 1.30 (s, 7H), 1.11-1.04 (m, 2H), 0.88 (hept, J = 2.5 Hz, 2H). | |
| 28 | 684.4 | ¹H NMR (400 MHz, DMSO-d6) delta 9.40 (d, J = 10.0 Hz, 1H), 8.76 (s, 1H), 8.67 (t, J = 6.4 Hz, 1H), 8.55 (s, 1H), 7.89 (s, 1H), 7.76 (dd, J = 7.8, 1.5 Hz, 1H), 7.61-7.48 (m, 3H), 7.38 (d, J = 7.8 Hz, 1H), 7.22 (d, J = 8.2 Hz, 1H), 5.32 (p, J = 6.5 Hz, 1H), 4.25 (p, J = 8.3 Hz, 1H), 3.67 (td, J = 13.9, 6.3 Hz, 2H), 3.56-3.32 (m, 3H), 3.00-2.72 (m, 6H), 2.33 (s, 3H), 1.84 (d, J = 14.2 Hz, 2H), 1.76-1.49 (m, 12H), 1.41 (q, J = 12.7, 11.4 Hz, 1H), 1.29 (s, 6H). | 0.1 |
| 29 | 666.4 | ¹H NMR (400 MHz, DMSO-d6) delta 9.47 (s, 1H), 8.85 (d, J = 15.6 Hz, 1H), 8.58 (d, J = 6.8 Hz, 1H), 8.31 (d, J = 7.8 Hz, 1H), 7.88 (s, 1H), 7.76 (d, J = 7.8 Hz, 1H), 7.55 (dd, J = 20.7, 9.2 Hz, 3H), 7.39 (d, J = 7.7 Hz, 1H), 7.21 (d, J = 8.2 Hz, 1H), 5.44-5.28 (m, 1H), 4.41 (d, J = 5.7 Hz, 1H), 4.27 (dt, J = 12.9, 5.8 Hz, 3H), 3.58-3.31 (m, 3H), 2.99-2.71 (m, 7H), 2.32 (s, 3H), 1.84 (d, J = 14.0 Hz, 2H), 1.77-1.53 (m, 8H), 1.48-1.34 (m, 1H), 1.29 (s, 6H), 1.11 (d, J = 6.6 Hz, 3H). | 0.1 |
| 30 | 666.4 | ¹H NMR (400 MHz, DMSO-d6) delta 9.55 (s, 1H), 9.01-8.92 (m, 1H), 8.66-8.61 (m, 1H), 8.32 (d, J = 7.8 Hz, 1H), 7.89 (s, 1H), 7.76 (d, J = 7.7 Hz, 1H), 7.55 (ddd, J = 17.7, 7.1, 1.8 Hz, 3H), 7.40 (d, J = 7.7 Hz, 1H), 7.22 (d, J = 8.2 Hz, 1H), 5.38 (p, J = 6.3, 5.9 Hz, 1H), 4.41 (dd, J = 5.6, 1.9 Hz, 1H), 4.35-4.22 (m, 3H), 3.58-3.32 (m, 3H), 3.01-2.71 (m, 6H), 2.33 (s, 3H), 1.84 (d, J = 14.1 Hz, 2H), 1.59 (d, J = 6.6 Hz, 8H), 1.42 (ddt, J = 16.1, 12.5, 6.3 Hz, 1H), 1.29 (s, 6H), 1.11 (d, J = 6.7 Hz, 3H). | 0.1 |
| 31 | 684.4 | ¹H NMR (400 MHz, DMSO-d6) delta 9.49 (s, 1H), 8.87 (d, J = 13.8 Hz, 1H), 8.61 (d, J = 7.0 Hz, 2H), 7.89 (d, J = 1.0 Hz, 1H), 7.76 (dd, J = 7.8, 1.4 Hz, 1H), 7.56 (t, J = 9.4 Hz, 3H), 7.39 (d, J = 7.7 Hz, 1H), 7.23 (d, J = 8.1 Hz, 1H), 5.35 (s, 1H), 4.60 (d, J = 4.5 Hz, 2H), 4.48 (d, J = 4.1 Hz, 2H), 4.26 (p, J = 8.3 Hz, 1H), 3.49 (q, J = 8.1 Hz, 1H), 3.39 (d, J = 11.8 Hz, 2H), 2.98-2.73 (m, 6H), 2.33 (s, 3H), 1.84 (d, J = 14.1 Hz, 2H), 1.77-1.49 (m, 8H), 1.49-1.36 (m, 1H), 1.29 (s, 6H). | 0.08 |
| 32 | 738.4 | ¹H NMR (400 MHz, DMSO-d6) delta 9.48 (s, 1H), 8.84 (d, J = 12.2 Hz, 2H), 8.58 (s, 1H), 7.90 (s, 1H), 7.76 (dd, J = 7.9, 1.4 Hz, 1H), 7.64-7.48 (m, 4H), 7.21 (d, J = 8.2 Hz, 1H), 6.09 (t, J = 57.3 Hz, 1H), 5.35 (p, J = 6.7 Hz, 1H), 4.35-4.21 (m, 1H), 4.12-4.02 (m, 2H), 3.85 (dt, J = 10.9, 5.0 Hz, 2H), 3.56-3.34 (m, 3H), 2.96 (qd, J = 9.2, 2.6 Hz, 2H), 2.87-2.73 (m, 4H), 2.31 (s, 3H), 1.89-1.52 (m, 15H), 1.41 (d, J = 12.2 Hz, 1H), 1.10-1.04 (m, 2H), 0.89 (hept, J = 3.5, 2.7 Hz, 2H). | 0.08 |
| 33 | 605.3 | ¹H NMR (400 MHz, Methanol-d4) delta 8.77 (d, J = 0.6 Hz, 1H), 7.89 (s, 1H), 7.67 (dd, J = 7.8, 1.5 Hz, 1H), 7.58 (dt, J = 2.5, 0.4 Hz, 1H), 7.46 (d, J = 1.4 Hz, 1H), 7.41 (dt, J = 8.4, 0.6 Hz, 1H), 7.37-7.30 (m, 2H), 4.31-4.20 (m, 1H), 4.00-3.91 (m, 1H), 3.72-3.63 (m, 1H), 3.53 (d, J = 12.2 Hz, 2H), 3.02 (qd, J = 9.0, 2.7 Hz, 2H), 2.88 (tdd, J = 12.4, 6.5, 3.3 Hz, 3H), 2.56-2.52 (m, 3H), 2.01 (d, J = 14.5 Hz, 2H), 1.88 (d, J = 13.3 Hz, 1H), 1.83-1.66 (m, 1H), 1.56 (qt, J = 12.8, 3.8 Hz, 1H), 1.38-1.23 (m, 11H). | 0.2 |
| 34 | 619.4 | ¹H NMR (400 MHz, Methanol-d4) delta 8.75-8.72 (m, 1H), 7.90 (d, J = 0.5 Hz, 1H), 7.67 (dd, J = 7.8, 1.5 Hz, 1H), 7.46 (d, J = 1.4 Hz, 1H), 7.44-7.39 (m, 2H), 7.36-7.31 (m, 2H), 4.32-4.20 (m, 1H), 3.92 (dq, J = 10.8, 3.6 Hz, 1H), 3.68 (p, J = 8.0 Hz, 1H), 3.54 (d, J = 12.4 Hz, 2H), 3.03 (qd, J = 9.0, 2.7 Hz, 2H), 2.94-2.84 (m, 7H), 2.49 (s, 3H), 2.01 (d, J = 14.6 Hz, 2H), 1.88 (d, J = 13.5 Hz, 1H), 1.75 (q, J = 13.8, 13.3 Hz, 2H), 1.56 (qt, J = 13.4, 4.1Hz, 1H), 1.37-1.23 (m, 11H). | 0.6 |

TABLE 1-continued

| Example # | ES/MS m/z | ¹H-NMR | HPK1 IC$_{50}$ (nM) |
|---|---|---|---|
| 35 | 680.4 | ¹H NMR (400 MHz, DMSO-d6) delta 9.51 (s, 1H), 8.90 (d, J = 4.0 Hz, 1H), 8.47 (s, 1H), 8.21 (q, J = 4.6 Hz, 1H), 7.87 (s, 1H), 7.68 (dd, J = 7.8, 1.4 Hz, 1H), 7.59 (dd, J = 14.3, 8.0 Hz, 2H), 7.46 (d, J = 1.5 Hz, 1H), 7.22 (d, J = 12.0 Hz, 1H), 5.33 (p, J = 6.6 Hz, 1H), 4.16 (p, J = 8.3 Hz, 1H), 4.05 (dt, J = 11.5, 5.7 Hz, 2H), 3.84 (dt, J = 10.9, 5.1 Hz, 2H), 3.52 (h, J = 8.4 Hz, 1H), 3.39 (d, J = 11.7 Hz, 2H), 2.93 (qd, J = 9.3, 2.7 Hz, 2H), 2.87-2.70 (m, 6H), 2.39 (s, 3H), 1.90-1.54 (m, 15H), 1.43 (ddt, J = 12.2, 7.4, 3.9 Hz, 1H). | 0.1 |
| 36 | 620.4 | ¹H NMR (400 MHz, Methanol-d4) delta 8.84 (s, 1H), 8.41 (d, J = 2.9 Hz, 1H), 7.83-7.76 (m, 1H), 7.73 (d, J = 1.4 Hz, 1H), 7.68 (d, J = 1.1 Hz, 1H), 7.53 (d, J = 8.3 Hz, 1H), 7.43 (d, J = 7.8 Hz, 1H), 7.32 (d, J = 8.3 Hz, 1H), 4.47 (q, J = 8.0 Hz, 1H), 4.19 (d, J = 27.5 Hz, 2H), 3.83 (s, 0H), 3.71 (t, J = 8.0 Hz, 1H), 3.51 (d, J = 11.7 Hz, 1H), 3.42 (d, J = 12.6 Hz, 1H), 3.02 (ddt, J = 52.7, 41.1, 10.9 Hz, 6H), 2.49 (s, 3H), 2.01-1.67 (m, 3H), 1.53-1.36 (m, 10H). | 0.1 |
| 37 | 620.4 | ¹H NMR (400 MHz, Methanol-d4) delta 8.60 (d, J = 4.3 Hz, 1H), 8.46 (d, J = 2.4 Hz, 1H), 7.81 (d, J = 7.8 Hz, 1H), 7.75 (d, J = 1.4 Hz, 1H), 7.67 (s, 1H), 7.53 (dd, J = 8.3, 2.5 Hz, 1H), 7.43 (d, J = 7.8 Hz, 1H), 7.31 (d, J = 8.3 Hz, 1H), 4.47 (t, J = 8.1 Hz, 1H), 4.22 (s, 1H), 4.10 (s, 1H), 3.72 (t, J = 7.8 Hz, 1H), 3.59-3.38 (m, 1H), 3.14 (d, J = 8.5 Hz, 1H), 3.06 (d, J = 13.1 Hz, 4H), 2.91 (d, J = 11.4 Hz, 0H), 2.49 (s, 3H), 2.01-1.65 (m, 3H), 1.42 (s, 12H). | 0.1 |
| 38 | 646 | ¹H NMR (400 MHz, Methanol-d4) delta 8.31 (s, 1H), 8.19 (s, 1H), 7.84-7.55 (m, 4H), 7.37 (d, J = 7.8 Hz, 1H), 7.24 (d, J = 8.4 Hz, 1H), 4.47-4.36 (m, 1H), 4.04-3.95 (m, 1H), 3.65-335 (m, 3H), 3.20-2.50 (m, 13H), 2.39 (s, 3H), 1.92-176 (s, 2H), 1.53-1.30 (m, 10H), 1.07 (s, 6H). | 0.07 |
| 39 | 622.3 | ¹H NMR (400 MHz, DMSO-d6) delta 10.12-9.97 (m), 8.70, 8.46, 8.15 (d, J = 4.6 Hz), 7.88, 7.78 (dd, J = 7.8, 1.4 Hz), 7.63-7.47 (m), 7.39 (d, J = 7.7 Hz), 7.20 (d, J = 8.3 Hz), 5.30 (p, J = 6.5 Hz), 4.42-4.21 (m), 4.02 (d, J = 13.3 Hz), 3.75-3.53 (m), 3.40 (d, J = 12.2 Hz), 3.17-2.62 (m), 2.32, 1.56 (d, J = 6.5 Hz), 1.30 (s, 6H). | 0.1 |
| 40 | 638.5 | ¹H NMR (400 MHz, DMSO-d6) delta 9.35 (d, J = 9.4 Hz, 1H), 8.54-8.30 (m, 3H), 8.02 (d, J = 2.7 Hz, 1H), 7.95-7.72 (m, 3H), 7.59 (d, J = 1.5 Hz, 1H), 7.43 (dd, J = 21.6, 8.3 Hz, 2H), 4.40-4.23 (m, 1H), 4.12 (p, J = 6.4 Hz, 1H), 3.56-3.26 (m, 3H), 3.07-2.58 (m, 8H), 1.99-1.50 (m, 6H), 1.45-1.15 (m, 11H). | 0.1 |
| 41 | 773.7 | ¹H NMR (400 MHz, DMSO-d6) delta 9.37 (s, 1H), 8.44 (s, 1H), 8.39 (q, J = 3.6, 3.0 Hz, 2H), 7.97 (d, J = 2.6 Hz, 1H), 7.91 (dd, J = 8.8, 2.7 Hz, 1H), 7.86 (s, 1H), 7.80 (dd, J = 7.9, 1.5 Hz, 1H), 7.64 (d, J = 1.5 Hz, 1H), 7.60 (d, J = 7.8 Hz, 1H), 7.47 (d, J = 8.8 Hz, 1H), 4.40-4.28 (m, 1H), 4.13 (s, 1H), 4.04-3.81 (m, 2H), 3.41 (d, J = 11.8 Hz, 3H), 3.06-2.79 (m, 5H), 2.77 (d, J = 4.6 Hz, 3H), 2.13 (d, J = 6.9 Hz, 6H), 1.90-1.53 (m, 12H), 1.41 (d, J = 13.1 Hz, 1H), 1.24 (d, J = 7.5 Hz, 5H). | 0.07 |
| 42 | 755.5 | ¹H NMR (400 MHz, Chloroform-d) delta 7.95 (s, 1H), 7.93 (d, J = 1.4 Hz, 1H), 7.83 (d, J = 12.6 Hz, 2H), 7.77 (d, J = 7.8 Hz, 1H), 7.68 (d, J = 1.4 Hz, 1H), 7.56 (s, 1H), 7.22 (d, J = 8.3 Hz, 2H), 5.87 (d, J = 5.0 Hz, 1H), 5.00 (dt, J = 17.5, 6.4 Hz, 2H), 4.85 (dt, J = 9.5, 4.9 Hz, 2H), 4.39 (t, J = 8.7 Hz, 1H), 4.26 (d, J = 14.0 Hz, 1H), 4.18-4.01 (m, 1H), 3.86 (dd, J = 13.5, 8.9 Hz, 2H), 3.74 (s, 1H), 3.28 (d, J = 28.3 Hz, 2H), 3.00 (dd, J = 5.0, 1.5 Hz, 3H), 2.67 (dd, J = 17.8, 9.7 Hz, 5H), 2.45 (d, J = 1.3 Hz, 3H), 2.41-2.29 (m, 2H), 1.84 (d, J = 11.3 Hz, 3H), 1.65 (d, J = 9.9 Hz, 2H), 1.42 (d, J = 7.6 Hz, 5H), 1.31-1.23 (m, 4H). | 0.06 |
| 43 | 765.6 | ¹H NMR (400 MHz, DMSO-d6) delta 9.82 (s, 0H), 9.35 (s, 1H), 8.37 (s, 1H), 8.21 (s, 1H), 8.18 (d, J = 4.6 Hz, 1H), 7.89 (s, 0H), 7.85 (d, J = 2.4 Hz, 1H), 7.83-7.77 (m, 2H), 7.76 (s, 1H), 7.64-7.55 (m, 2H), 7.21 (d, J = 8.3 Hz, 1H), 4.25 (t, J = 8.5 Hz, 1H), 4.19- | 0.08 |

TABLE 1-continued

| Example # | ES/MS m/z | ¹H-NMR | HPK1 IC$_{50}$ (nM) |
|---|---|---|---|
| | | 4.06 (m, 1H), 4.02-3.70 (m, 6H), 3.68-3.55 (m, 1H), 3.23 (s, 1H), 2.98-2.78 (m, 5H), 2.74 (dd, J = 4.7, 0.6 Hz, 3H), 2.69-2.64 (m, 0H), 2.36-2.25 (m, 3H), 2.11 (d, J = 10.9 Hz, 7H), 1.93 (d, J = 11.4 Hz, 1H), 1.82-1.56 (m, 8H), 1.36 (s, 1H), 1.25 (d, J = 8.0 Hz, 4H). | |
| 44 | 713.5 | ¹H NMR (400 MHz, DMSO-d6) delta 8.30 (d, J = 0.4 Hz, 1H), 8.23-8.15 (m, 2H), 8.12 (d, J = 1.5 Hz, 1H), 7.94 (dd, J = 8.3, 2.4 Hz, 1H), 7.87-7.81 (m, 2H), 7.77 (s, 1H), 7.51 (d, J = 7.9 Hz, 1H), 7.21 (d, J = 8.5 Hz, 1H), 4.60-4.47 (m, 1H), 4.17-4.09 (m, 1H), 3.97-3.81 (m, 2H), 3.73 (q, J = 6.3 Hz, 2H), 3.06-2.93 (m, 1H), 2.77 (d, J = 4.6 Hz, 3H), 2.72-2.57 (m, 4H), 2.31 (s, 4H), 2.24 (d, J = 8.8 Hz, 1H), 2.09 (d, J = 0.8 Hz, 3H), 1.88-1.72 (m, 2H), 1.73-1.55 (m, 5H), 1.55-1.29 (m, 3H), 1.30-1.23 (m, 4H), 1.22-1.17 (m, 2H). | 0.2 |
| 45 | 648.5 | ¹H NMR (400 MHz, DMSO-d6) delta 9.39 (d, J = 9.6 Hz, 1H), 8.68 (s, 1H), 8.47 (s, 1H), 8.14 (q, J = 4.5 Hz, 1H), 7.99-7.75 (m, 2H), 7.67-7.42 (m, 3H), 7.23 (dd, J = 37.4, 8.1 Hz, 2H), 5.28 (p, J = 6.5 Hz, 1H), 4.24 (t, J = 8.2 Hz, 1H), 3.56-3.25 (m, 3H), 3.04-2.62 (m, 9H), 2.30 (s, 3H), 1.95-1.20 (m, 16H), 0.50 (t, J = 7.3 Hz, 6H). | 0.1 |
| 46 | 703.5 | ¹H NMR (400 MHz, DMSO-d6) delta 9.38 (d, J = 9.8 Hz, 1H), 8.71 (s, 1H), 8.47 (s, 1H), 8.14 (q, J = 4.6 Hz, 1H), 7.88 (s, 1H), 7.76 (dd, J = 7.9, 1.5 Hz, 1H), 7.62-7.43 (m, 4H), 7.17 (d, J = 9.0 Hz, 1H), 5.28 (p, J = 6.5 Hz, 1H), 4.63-3.23 (m, 7H), 3.08-2.62 (m, 10H), 2.30 (s, 3H), 2.07 (s, 3H), 1.91-1.28 (m, 16H). | 0.1 |
| 47 | 721.6 | ¹H NMR (400 MHz, DMSO-d6) delta 9.44 (s, 1H), 8.56-8.24 (m, 3H), 8.05-7.71 (m, 4H), 7.66-7.33 (m, 3H), 4.70-3.24 (m, 12H), 3.10-2.59 (m, 6H), 2.07 (s, 3H), 1.94-1.12 (m, 14H). | 0.2 |
| 48 | 717.6 | ¹H NMR (400 MHz, DMSO-d6) delta 9.35 (s, 1H), 8.67 (s, 1H), 8.43 (s, 1H), 8.14 (d, J = 4.7 Hz, 1H), 7.89 (s, 1H), 7.75 (dd, J = 8.2, 1.4 Hz, 1H), 7.65-7.33 (m, 4H), 7.16 (d, J = 8.1 Hz, 1H), 5.08 (q, J = 6.6 Hz, 1H), 4.55-3.27 (m, 7H), 3.12-2.63 (m, 10H), 2.29 (s, 3H), 2.07 (s, 3H), 1.96-1.50 (m, 14H), 1.41 (t, J = 12.9 Hz, 1H), 0.76 (t, J = 7.3 Hz, 3H). | 0.1 |
| 49 | 689.5 | ¹H NMR (400 MHz, DMSO-d6) delta 9.34 (s, 1H), 8.44 (d, J = 29.5 Hz, 2H), 8.14 (q, J = 4.5 Hz, 1H), 7.92-7.73 (m, 2H), 7.69-7.42 (m, 4H), 7.18 (d, J = 8.3 Hz, 1H), 4.62 (q, J = 7.1 Hz, 2H), 4.26 (p, J = 8.2 Hz, 1H), 4.12-3.25 (m, 8H), 3.07-2.63 (m, 8H), 2.30 (s, 3H), 2.07 (s, 3H), 1.93-1.50 (m, 10H), 1.38 (t, J = 7.2 Hz, 3H). | 0.1 |
| 50 | 717.6 | ¹H NMR (400 MHz, DMSO-d6) delta 9.44 (d, J = 10.1 Hz, 1H), 8.51 (s, 1H), 8.29-8.11 (m, 2H), 7.95-7.73 (m, 4H), 7.67-7.45 (m, 2H), 7.21 (d, J = 8.4 Hz, 1H), 5.05-4.00 (m, 6H), 3.91-3.27 (m, 11H), 3.04-2.66 (m, 7H), 2.30 (s, 3H), 2.03-1.09 (m, 11H). | 0.1 |
| 51 | 727.6 | ¹H NMR (400 MHz, DMSO-d6) delta 9.38 (d, J = 9.8 Hz, 1H), 8.44 (s, 1H), 8.32-8.04 (m, 2H), 7.98-7.73 (m, 4H), 7.74-7.51 (m, 2H), 7.21 (d, J = 8.4 Hz, 1H), 4.47-3.25 (m, 8H), 3.07-2.65 (m, 9H), 2.30 (s, 3H), 2.12-1.14 (m, 16H), 0.87-0.58 (m, 4H). | 0.1 |
| 52 | 729.6 | ¹H NMR (400 MHz, DMSO-d6) delta 9.32 (s, 1H), 8.33 (s, 1H), 8.22-8.13 (m, 2H), 7.95-7.76 (m, 4H), 7.71-7.48 (m, 2H), 7.20 (d, J = 8.3 Hz, 1H), 4.32 (t, J = 8.1 Hz, 1H), 4.12 (d, J = 4.4 Hz, 1H), 3.84 (d, J = 33.9 Hz, 3H), 3.41 (s, 3H), 3.00-2.65 (m, 9H), 2.29 (s, 3H), 1.91-1.53 (m, 9H), 1.43-1.14 (m, 5H), 1.04 (dd, J = 11.3, 6.6 Hz, 7H). | 0.09 |
| 53 | 763.5 | ¹H NMR (400 MHz, DMSO-d6) delta 9.38 (d, J = 9.6 Hz, 1H), 8.67 (s, 1H), 8.49-8.34 (m, 1H), 8.14 (d, J = 7.9 Hz, 1H), 7.86 (s, 1H), 7.66-7.42 (m, 4H), 7.17 (d, J = 12.1 Hz, 1H), 5.38-5.14 (m, 1H), 4.33-3.93 (m, 2H), 3.89-3.60 (m, 2H), 3.57-3.21 (m, 3H), 3.03-2.65 (m, 7H), 2.41-2.18 (m, 5H), 1.90-1.47 (m, 16H), 1.38 (d, J = 13.2 Hz, 1H), 1.14-0.90 (m, 9H). | 0.08 |

TABLE 1-continued

| Example # | ES/MS m/z | ¹H-NMR | HPK1 IC$_{50}$ (nM) |
|---|---|---|---|
| 54 | 735.5 | ¹H NMR (400 MHz, DMSO-d6) delta 9.42 (d, J = 9.6 Hz, 1H), 8.58 (s, 1H), 8.39 (s, 1H), 8.15 (d, J = 7.9 Hz, 1H), 7.84 (s, 1H), 7.76-7.62 (m, 2H), 7.49 (d, J = 7.5 Hz, 2H), 7.18 (d, J = 12.1 Hz, 1H), 4.63 (q, J = 7.1 Hz, 2H), 4.29-3.28 (m, 9H), 3.07-2.62 (m, 5H), 2.35 (s, 3H), 2.06 (s, 3H), 1.95-1.23 (m, 14H), 1.07 (d, J = 6.5 Hz, 6H). | 0.4 |
| 55 | 793.5 | ¹H NMR (400 MHz, DMSO-d6) delta 9.35 (s, 1H), 8.66 (s, 1H), 8.40 (s, 1H), 8.14 (d, J = 7.8 Hz, 1H), 7.86 (s, 1H), 7.73-7.42 (m, 4H), 7.17 (d, J = 12.1 Hz, 1H), 5.27 (q, J = 6.7 Hz, 1H), 4.45-3.68 (m, 8H), 3.55-3.22 (m, 3H), 3.05-2.59 (m, 7H), 2.34 (s, 3H), 1.91-1.44 (m, 15H), 1.35 (s, 5H), 1.07 (d, J = 6.6 Hz, 6H). | 0.2 |
| 56 | 735.5 | ¹H NMR (400 MHz, DMSO-d6) delta 9.40 (d, J = 9.8 Hz, 1H), 8.53 (s, 1H), 8.36 (s, 1H), 8.26 (t, J = 5.6 Hz, 1H), 7.84 (s, 1H), 7.75-7.60 (m, 2H), 7.54-7.41 (m, 2H), 7.18 (d, J = 12.0 Hz, 1H), 4.62 (q, J = 7.1 Hz, 2H), 4.18 (p, J = 8.3 Hz, 1H), 3.96-3.61 (m, 4H), 3.55-3.08 (m, 5H), 3.04-2.65 (m, 6H), 2.43-2.31 (m, 5H), 1.89-1.23 (m, 13H), 1.03 (dt, J = 9.5, 7.3 Hz, 6H). | 0.3 |
| 57 | 606.4 | ¹H NMR (400 MHz, DMSO-d6) delta 9.67 (d, J = 9.5 Hz, 1H), 9.01 (s, 1H), 8.62-8.40 (m, 1H), 8.15 (q, J = 4.5 Hz, 1H), 7.71 (s, 1H), 7.59-7.47 (m, 2H), 7.31 (dd, J = 7.7, 1.5 Hz, 1H), 7.18 (dt, J = 8.0, 0.7 Hz, 1H), 7.09-6.94 (m, 2H), 5.59-5.15 (m, 1H), 3.88 (p, J = 8.2 Hz, 1H), 3.51-3.29 (m, 3H), 3.12 (s, 2H), 2.84-2.68 (m, 5H), 2.57-2.44 (m, 3H), 2.40-2.25 (m, 5H), 1.83 (d, J = 14.2 Hz, 2H), 1.56 (d, J = 6.5 Hz, 8H), 1.46-1.34 (m, 1H), 1.24 (m, 6H). | 0.2 |
| 58a | 701.61 | ¹H NMR (400 MHz, DMSO-d6) delta 9.40 (s, 1H), 8.51 (s, 1H), 8.25 (s, 1H), 8.17 (q, J = 4.6 Hz, 1H), 7.91 (d, J = 2.4 Hz, 1H), 7.85-7.77 (m, 2H), 7.64 (d, J = 1.5 Hz, 1H), 7.56 (d, J = 7.9 Hz, 1H), 7.22 (d, J = 8.4 Hz, 1H), 4.32 (p, J = 8.3 Hz, 1H), 4.20-4.12 (m, 1H), 3.89 (dd, J = 31.5, 7.9 Hz, 2H), 3.73 (dd, J = 11.9, 5.5 Hz, 2H), 3.52 (q, J = 7.9 Hz, 1H), 3.40 (d, J = 11.8 Hz, 2H), 3.07-2.72 (m, 8H), 2.32 (s, 3H), 2.12-2.06 (m, 4H), 1.89-1.54 (m, 8H), 1.32-1.23 (m, 3H). | 0.1 |
| 58 | 604.3 | ¹H NMR (400 MHz, DMSO-d6) delta 9.68 (d, J = 9.6 Hz, 1H), 8.62 (s, 1H), 8.31-7.98 (m, 2H), 7.94 (d, J = 2.4 Hz, 1H), 7.81 (dd, J = 8.3, 2.4 Hz, 1H), 7.61 (s, 1H), 7.37 (dd, J = 7.7, 1.5 Hz, 1H), 7.29-6.97 (m, 3H), 4.17 (p, J = 5.3 Hz, 1H), 3.93 (p, J = 8.2 Hz, 1H), 3.58-3.27 (m, 3H), 3.13 (s, 2H), 2.75 (d, J = 4.6 Hz, 5H), 2.61-2.51 (m, 2H), 2.41-2.21 (m, 4H), 1.93-1.00 (m, 17H). | 0.6 |
| 59 | 763.4 | ¹H NMR (400 MHz, DMSO-d6) delta 9.36 (d, J = 9.6 Hz, 1H), 8.70 (s, 1H), 8.41 (s, 1H), 7.89 (s, 1H), 7.87 (s, 1H), 7.72-7.62 (m, 1H), 7.57-7.44 (m, 3H), 7.17 (d, J = 12.1 Hz, 1H), 5.36-5.20 (m, 1H), 4.20 (p, J = 8.5 Hz, 1H), 3.91-3.80 (m, 2H), 3.79-3.63 (m, 2H), 3.52 (q, J = 8.1 Hz, 1H), 3.40 (d, J = 11.8 Hz, 2H), 3.02-2.84 (m, 2H), 2.85-2.72 (m, 4H), 2.35 (s, 3H), 2.08 (s, 3H), 1.90-1.62 (m, 8H), 1.62-1.54 (m, 7H), 1.47-1.35 (m, 1H), 1.33 (s, 9H). | 0.3 |
| 60 | 749.4 | ¹H NMR (400 MHz, DMSO-d6) delta 9.31 (s, 1H), 8.62 (s, 1H), 8.38 (s, 1H), 8.27 (t, J = 5.6 Hz, 1H), 7.88 (s, 1H), 7.67 (d, J = 8.1 Hz, 1H), 7.61 (d, J = 8.2 Hz, 1H), 7.53-7.49 (m, 2H), 7.19 (d, J = 12.0 Hz, 1H), 5.33-5.21 (m, 1H), 4.19 (p, J = 8.1 Hz, 1H), 3.93-3.65 (m, 4H), 3.51 (q, J = 8.0 Hz, 1H), 3.39 (d, J = 12.0 Hz, 2H), 3.22 (p, J = 7.1 Hz, 2H), 3.04-2.71 (m, 5H), 2.44-2.34 (m, 6H), 1.84 (d, J = 14.1 Hz, 2H), 1.80-1.53 (m, 13H), 1.48-1.34 (m, 1H), 1.08-1.01 (m, 6H). | 0.2 |
| 61 | 743.4 | ¹H NMR (400 MHz, DMSO-d6) delta 9.50 (s, 1H), 8.65 (s, 1H), 8.38 (s, 1H), 8.20 (q, J = 4.4 Hz, 1H), 7.91 (s, 1H), 7.72 (d, J = 7.6 Hz, 1H), 7.61 (s, 1H), 7.51 (s, 1H), 7.19 (d, J = 12.1 Hz, 1H), 6.73-6.40 (m, 1H), 5.28 (p, J = 6.3 Hz, 1H), 4.20 (p, J = 8.4 Hz, 1H), 3.95-3.25 (m, 8H), 2.97-2.87 (m, 2H), 2.87-2.71 (m, 8H), 2.38 (s, 3H), 2.02 (s, 3H), 1.84 (d, J = 14.2 Hz, 2H), 1.76-1.55 (m, 10H), 1.48-1.36 (m, 1H). | 0.2 |

TABLE 1-continued

| Example # | ES/MS m/z | ¹H-NMR | HPK1 IC$_{50}$ (nM) |
|---|---|---|---|
| 62 | 753.4 | ¹H NMR (400 MHz, DMSO-d6) delta 9.66-9.53 (m, 1H), 8.71 (s, 1H), 8.51 (s, 1H), 8.12 (d, J = 7.8 Hz, 1H), 7.93 (s, 1H), 7.82 (dd, J = 7.8, 1.5 Hz, 1H), 7.64 (s, 1H), 7.58-7.44 (m, 2H), 7.18 (d, J = 8.4 Hz, 1H), 6.59 (t, J = 53.7 Hz, 2H), 5.32 (p, J = 6.5 Hz, 1H), 4.28 (p, J = 8.4 Hz, 1H), 4.11-3.98 (m, 1H), 3.80 (s, 2H), 3.64 (s, 2H), 3.54-3.30 (m, 5H), 2.98-2.88 (m, 2H), 2.88-2.73 (m, 4H), 2.31 (s, 3H), 2.26-1.89 (m, 4H), 1.84 (d, J = 14.1 Hz, 2H), 1.76-1.59 (m, 3H), 1.57 (d, J = 6.5 Hz, 6H), 1.48-1.35 (m, 1H), 1.10 (d, J = 6.6 Hz, 6H). | 0.1 |
| 63 | 642.4 | ¹H NMR (400 MHz, DMSO-d6) delta 9.34 (s, 1H), 8.68-8.54 (m, 1H), 8.40-8.30 (m, 1H), 8.00-7.88 (m, 1H), 7.81-7.74 (m, 1H), 7.62-7.50 (m, 3H), 7.48-7.31 (m, 2H), 6.16-5.69 (m, 1H), 5.27-5.22 (m, 1H), 4.23 (s, 2H), 2.99-2.63 (m, 6H), 2.47-2.30 (m, 4H), 1.98-1.14 (m, 16H). | 0.1 |
| 64 | 745.4 | ¹H NMR (400 MHz, DMSO-d6) δ 9.86 (s, 1H), 9.39 (s, 1H), 8.98 (s, 1H), 8.74-8.61 (m, 3H), 8.00 (s, 1H), 7.76-7.66 (m, 1H), 7.50-7.30 (m, 1H), 6.06 (t, J = 56.9 Hz, 1H), 5.34-5.22 (m, 1H), 4.30-4.10 (m, 1H), 3.97 (s, 1H), 3.66-3.55 (m, 1H), 3.40-3.35 (m, 1H), 3.30-3.21 (m, 1H), 2.95 (d, J = 8.1 Hz, 1H), 2.90-2.81 (m, 1H), 2.65 (d, J = 19.5 Hz, 1H), 2.29 (d, J = 2.2 Hz, 3H), 2.01-1.88 (m, 1H), 1.74 (t, J = 12.2 Hz, 4H), 1.67-1.55 (m, 7H), 1.53 (d, J = 6.5 Hz, 1H), 1.39 (t, J = 8.1 Hz, 1H), 1.30 (s, 6H), 1.16-1.04 (m, 2H), 0.95-0.90 (m, 2H). | 0.1 |
| 65 | 714.4 | ¹H NMR (400 MHz, DMSO-d6) δ 9.42 (s, 1H), 8.84 (s, 1H), 8.75 (s, 1H), 8.45 (s, 1H), 7.85 (s, 1H), 7.68-7.60 (m, 2H), 7.46 (d, J = 1.5 Hz, 1H), 7.36 (d, J = 7.7 Hz, 1H), 7.21 (d, J = 12.1 Hz, 1H), 6.07 (t, J = 57.2 Hz, 1H), 5.30 (p, J = 6.6 Hz, 1H), 4.20 (p, J = 8.4 Hz, 1H), 3.51 (p, J = 8.2 Hz, 1H), 3.40 (d, J = 11.9 Hz, 2H), 3.00-2.70 (m, 7H), 2.36 (s, 3H), 1.91-1.33 (m, 11H), 1.28 (s, 6H), 1.10-1.03 (m, 2H), 0.88 (s, 2H). | 0.1 |
| 66 | 726.4 | ¹H NMR (400 MHz, DMSO-d6) δ 9.37 (s, 1H), 8.85 (d, J = 2.9 Hz, 1H), 8.69 (d, J = 3.6 Hz, 1H), 8.42 (s, 1H), 7.83 (s, 1H), 7.68-7.54 (m, 2H), 7.47-7.31 (m, 2H), 7.22 (d, J = 11.9 Hz, 1H), 6.07 (t, J = 57.1 Hz, 1H), 5.29 (p, J = 6.5 Hz, 1H), 4.22-4.04 (m, 1H), 3.96 (s, 1H), 3.78-3.55 (m, 1H), 3.44-3.19 (m, 1H), 3.02-2.60 (m, 6H), 2.36 (s, 3H), 1.98 (t, J = 13.8 Hz, 1H), 1.84-1.50 (m, 11H), 1.28 (s, 6H), 1.07 (q, J = 5.0, 4.6 Hz, 2H), 0.89 (s, 3H). | 0.09 |
| 67 | 715.4 | ¹H NMR (400 MHz, DMSO-d6) δ 9.37 (d, J = 9.6 Hz, 1H), 8.86 (s, 1H), 8.74-8.65 (m, 2H), 8.45 (s, 1H), 7.96 (s, 1H), 7.77 (d, J = 1.6 Hz, 1H), 7.63 (d, J = 8.1 Hz, 1H), 7.22 (d, J = 12.0 Hz, 1H), 6.09 (t, J = 57.2 Hz, 1H), 5.35-5.24 (m, 1H), 4.32-4.19 (m, 1H), 3.58-3.45 (m, 1H), 3.40 (d, J = 11.9 Hz, 2H), 2.97-2.75 (m, 6H), 2.36 (s, 3H), 1.85 (d, J = 14.2 Hz, 2H), 1.76-1.61 (m, 3H), 1.59 (d, J = 6.5 Hz, 6H), 1.42 (t, J = 12.6 Hz, 1H), 1.29 (s, 6H), 1.06 (t, J = 3.6 Hz, 2H), 0.92 (d, J = 6.0 Hz, 2H). | 0.3 |
| 68 | 735.4 | ¹H NMR (400 MHz, DMSO-d6) delta 11.20-10.66 (m, 1H), 9.82-9.48 (m, 1H), 8.68 (s, 1H), 8.39 (s, 1H), 8.20 (d, J = 4.7 Hz, 1H), 8.02-7.12 (m, 6H), 5.29 (p, J = 6.5 Hz, 1H), 4.97-4.42 (m, 5H), 4.25-4.08 (m, 1H), 3.64-3.13 (m, 7H), 3.00-2.86 (m, 2H), 2.86-2.71 (m, 7H), 2.45-1.77 (m, 9H), 1.78-1.51 (m, 9H), 1.51-1.34 (m, 1H). | 0.2 |
| 69 | 749.4 | ¹H NMR (400 MHz, DMSO-d6) delta 10.90-10.64 (m, 1H), 9.60-9.40 (m, 1H), 8.60 (s, 1H), 8.42-8.35 (m, 1H), 8.28 (t, J = 5.6 Hz, 1H), 7.99-7.11 (m, 5H), 5.27 (p, J = 6.4 Hz, 1H), 4.95-4.65 (m, 5H), 4.55-4.13 (m, 3H), 3.61-3.33 (m, 4H), 3.22 (p, J = 7.0 Hz, 3H), 2.98-2.87 (m, 2H), 2.86-2.74 (m, 4H), 2.40-1.96 (m, 7H), 1.88-1.76 (m, 3H), 1.76-1.53 (m, 9H), 1.48-1.35 (m, 1H), 1.07 (t, J = 7.2 Hz, 3H). | 0.1 |
| 70 | 769.4 | ¹H NMR (400 MHz, DMSO-d6) delta 8.68 (s, 1H), 8.39 (s, 1H), 8.21 (d, J = 4.6 Hz, 1H), 8.01-7.36 (m, 5H), 7.20 (d, J = 11.9 Hz, 2H), 5.29 (p, J = 6.4 Hz, 1H), 4.96-4.69 (m, 5H), 4.18 (p, J = 8.6, 8.1 Hz, | 0.7 |

TABLE 1-continued

| Example # | ES/MS m/z | ¹H-NMR | HPK1 IC$_{50}$ (nM) |
|---|---|---|---|
| | | 1H), 3.94-3.03 (m, 9H), 3.03-2.82 (m, 3H), 2.80-2.65 (m, 4H), 2.60-2.44 (m, 1H, overlapped with solvent), 2.38 (s, 3H), 2.43-1.69 (m, 5H), 1.59 (d, J = 6.6 Hz, 6H). | |
| 71 | 739.4 | ¹H NMR (400 MHz, DMSO-d6) delta 11.18-10.61 (m, 2H), 8.66 (s, 1H), 8.38 (s, 1H), 8.21 (d, J = 4.6 Hz, 1H), 8.02-7.10 (m, 6H), 5.64-5.39 (m, 1H), 5.28 (p, J = 6.7 Hz, 1H), 4.95-4.44 (m, 5H), 4.23 (s, 1H), 3.99-3.14 (m, 9H), 3.03-2.85 (m, 2H), 2.83-2.71 (m, 5H), 2.45-1.72 (m, 9H), 1.59 (d, J = 6.5 Hz, 6H). | 0.1 |
| 72 | 739.4 | ¹H NMR (400 MHz, DMSO-d6) delta 11.21-10.64 (m, 2H), 8.65 (s, 1H), 8.37 (s, 1H), 8.21 (d, J = 4.6 Hz, 1H), 8.01-7.07 (m, 6H), 5.51 (d, J = 53.0, 1H), 5.29 (p, J = 6.4 Hz, 1H), 4.86-4.46 (m, 5H), 4.31-4.16 (m, 1H), 3.97-3.15 (m, 9H), 2.95 (p, J = 9.6 Hz, 1H), 2.86-2.69 (m, 4H), 2.43-1.72 (m, 9H), 1.59 (d, J = 6.5 Hz, 6H). | 0.2 |
| 73 | 745.5 | ¹H NMR (400 MHz, DMSO-d6) delta 11.23-10.72 (m, 1H), 9.83-9.53 (m, 1H), 8.71 (s, 1H), 8.51 (s, 1H), 8.12 (d, J = 7.9 Hz), 8.03-7.21 (m, 6H), 7.18 (d, J = 8.4 Hz, 1H), 5.32 (p, J = 6.6 Hz, 1H), 4.95-4.40 (m, 5H), 4.28 (p, J = 8.4 Hz, 1H), 4.05 (hex, J = 6.8 Hz, 1H), 3.70-3.13 (m, 7H), 2.93 (q, J = 9.3 Hz, 2H), 2.87-2.74 (m, 4H), 2.40-1.50 (m, 19H), 1.50-1.32 (m, 1H), 1.10 (d, J = 6.6 Hz, 6H). | 0.1 |
| 74 | 735.4 | ¹H NMR (400 MHz, DMSO-d6) delta 9.37 (s, 1H), 8.76-8.70 (m, 1H), 8.43 (s, 1H), 8.27 (t, J = 5.6 Hz, 1H), 7.87 (s, 1H), 7.67 (d, J = 8.0 Hz, 1H), 7.61 (d, J = 8.2 Hz, 1H), 7.56-7.46 (m, 2H), 7.20 (d, J = 12.0 Hz, 1H), 5.36-5.20 (m, 1H), 4.17 (p, J = 8.3 Hz, 1H), 3.93-3.79 (m, 2H), 3.77-3.66 (m, 2H), 3.51 (q, J = 8.1 Hz, 1H), 3.39 (d, J = 11.7 Hz, 2H), 3.22 (p, J = 7.1 Hz, 2H), 3.03-2.71 (m, 6H), 2.38 (s, 3H), 2.08 (s, 3H), 1.89-1.62 (m, 8H), 1.62-1.54 (m, 7H), 1.48-1.34 (m, 1H), 1.06 (t, J = 7.2, 3H). | 0.2 |
| 75 | 763.4 | ¹H NMR (400 MHz, DMSO-d6) delta 9.34 (s, 1H), 8.69 (s, 1H), 8.40 (s, 1H), 8.27 (t, J = 5.9 Hz, 1H), 7.86 (s, 1H), 7.65 (d, J = 7.9 Hz, 1H), 7.59 (d, J = 8.2 Hz, 1H), 7.51-7.47 (m, 2H), 7.18 (d, J = 12.1 Hz, 1H), 5.34-5.21 (m, 1H), 4.16 (p, J = 8.2 Hz, 1H), 3.93-3.76 (m, 2H), 3.76-3.63 (m, 2H), 3.49 (q, J = 8.0 Hz, 1H), 3.38 (d, J = 11.7 Hz, 2H), 3.00 (t, J = 6.4 Hz, 2H), 2.97-2.81 (m, 2H), 2.81-2.71 (m, 3H), 2.35 (s, 3H), 2.06 (s, 3H), 1.86-1.51 (m, 17H), 1.45-1.32 (m, 1H), 0.82 (d, J = 6.7 Hz, 6H). | 0.2 |
| 76 | 761.4 | ¹H NMR (400 MHz, DMSO-d6) delta 9.37 (s, 1H), 8.73 (s, 1H), 8.53 (d, J = 7.7 Hz, 1H), 8.44 (s, 1H), 7.88 (s, 1H), 7.71-7.64 (m, 1H), 7.62 (d, J = 8.2 Hz, 1H), 7.54-7.47 (m, 2H), 7.20 (d, J = 12.1 Hz, 1H), 5.30 (p, J = 6.5 Hz, 1H), 4.37 (hex, J = 8.1 Hz, 1H), 4.18 (p, J = 8.6 Hz, 1H), 3.93-3.78 (m, 2H), 3.77-3.66 (m, 2H), 3.51 (q, J = 8.1 Hz, 1H), 3.39 (d, J = 11.8 Hz, 2H), 3.02-2.72 (m, 6H), 2.36 (s, 3H), 2.23-2.12 (m, 2H), 2.08 (s, 3H), 1.94 (p, J = 9.6 Hz, 2H), 1.88-1.53 (m, 16H), 1.47-1.34 (m, 1H). | 0.2 |
| 77 | 777.4 | ¹H NMR (400 MHz, DMSO-d6) delta 9.92 (d, J = 8.9 Hz, 1H), 8.62 (s, 1H), 8.36 (s, 1H), 8.14 (d, J = 7.9 Hz, 1H), 7.85 (s, 1H), 7.71-7.61 (m, 2H), 7.52 (d, J = 7.8 Hz, 1H), 7.44 (s, 1H), 7.18 (d, J = 12.2 Hz, 1H), 5.28 (p, J = 6.4 Hz, 1H), 4.17-3.98 (m, 2H), 3.96 (s, 2H), 3.93-3.80 (m, 4H), 3.79-3.66 (m, 4H), 3.59-3.46 (m, 1H), 3.07-2.81 (m, 4H), 2.34 (s, 3H), 2.21-2.05 (m, 7H), 1.87-1.73 (m, 2H), 1.69 (t, J = 5.9 Hz, 2H), 1.58 (d, J = 6.5 Hz, 6H), 1.09 (d, J = 6.5 Hz, 6H). | 0.06 |
| 78 | 777.4 | ¹H NMR (400 MHz, DMSO-d6) delta 9.38 (s, 1H), 8.65 (s, 1H), 8.40 (s, 1H), 8.14 (d, J = 7.9 Hz, 1H), 7.86 (s, 1H), 7.71-7.64 (m, 1H), 7.58 (d, J = 8.2 Hz, 1H), 7.51 (d, J = 7.8 Hz, 1H), 7.47 (s, 1H), 7.19 (d, J = 12.1 Hz, 1H), 5.29 (p, J = 6.7 Hz, 1H), 4.52 (s, 2H), 4.14 (p, J = 8.4 Hz, 1H), 4.04 (hex, J = 6.7 Hz, 1H), 3.93-3.79 (m, 2H), 3.79-3.57 (m, 3H), 3.38 (d, J = 11.9 Hz, 2H), 3.15-2.86 (m, 4H), 2.81-2.70 (m, 2H), 2.37 (s, 3H), 2.08 (s, 3H), 2.05-1.92 (m, 4H), 1.87-1.72 (m, 2H), 1.68 (t, J = 5.9 Hz, 2H), 1.59 (d, J = 6.5 Hz, 6H), 1.10 (d, J = 6.5 Hz, 6H). | 0.2 |

TABLE 1-continued

| Example # | ES/MS m/z | $^1$H-NMR | HPK1 IC$_{50}$ (nM) |
|---|---|---|---|
| 79 | 618.51 | $^1$H NMR (400 MHz, DMSO-d6) delta 9.36 (s, 1H), 8.42 (s, 1H), 8.23 (s, 1H), 8.19 (q, J = 4.6 Hz, 1H), 7.95 (d, J = 2.3 Hz, 1H), 7.85-7.78 (m, 2H), 7.78 (s, 1H), 7.63 (s, 1H), 7.41 (d, J = 7.8 Hz, 1H), 7.22 (d, J = 8.3 Hz, 1H), 4.32 (p, J = 8.3 Hz, 1H), 4.15 (s, 1H), 3.53 (q, J = 8.2 Hz, 2H), 3.40 (d, J = 11.8 Hz, 2H), 3.04-2.70 (m, 8H), 2.31 (s, 3H), 1.83 (d, J = 14.0 Hz, 2H), 1.65 (dt, J = 40.1, 13.0 Hz, 4H), 1.29 (d, J = 19.6 Hz, 10H). | 0.2 |
| 80 | 670.3 | $^1$H NMR (400 MHz, Methanol-d4) delta 9.25 (s, 1H), 7.79 (d, J = 2.3 Hz, 1H), 7.75 (dd, J = 7.8, 1.6 Hz, 1H), 7.69 (d, J = 2.5 Hz, 1H), 7.61 (s, 1H), 7.44-7.35 (m, 2H), 7.30 (d, J = 8.3 Hz, 1H), 5.39 (q, J = 6.5 Hz, 1H), 4.39 (p, J = 8.2 Hz, 1H), 3.88 (p, J = 7.7 Hz, 1H), 3.35 (d, J = 13.4 Hz, 1H), 2.95 (t, J = 7.9 Hz, 4H), 2.91-2.85 (m, 3H), 2.43 (s, 3H), 2.18 (d, J = 12.3 Hz, 4H), 2.07-1.84 (m, 2H), 1.80-1.66 (m, 8H), 1.37 (s, 6H). | 0.1 |
| 81 | 642.3 | $^1$H NMR (400 MHz, Methanol-d4) delta 9.20 (s, 1H), 7.79 (s, 1H), 7.76 (dd, J = 7.8, 1.5 Hz, 1H), 7.67 (d, J = 2.3 Hz, 1H), 7.62 (d, J = 1.4 Hz, 1H), 7.44-7.36 (m, 2H), 7.30 (d, J = 8.3 Hz, 1H), 5.38 (p, J = 6.6 Hz, 1H), 4.41 (p, J = 8.3 Hz, 1H), 3.83 (dt, J = 11.2, 5.6 Hz, 1H), 3.75 (q, J = 8.0 Hz, 1H), 3.17-2.95 (m, 4H), 2.95-2.83 (m, 7H), 2.44 (s, 3H), 1.72 (d, J = 6.6 Hz, 6H), 1.38 (s, 6H). | 0.3 |
| 82 | 626.3 | $^1$H NMR (400 MHz, Methanol-d4) delta 9.07 (s, 1H), 7.80-7.74 (m, 2H), 7.66 (d, J = 2.4 Hz, 1H), 7.63 (d, J = 1.4 Hz, 1H), 7.43-7.36 (m, 2H), 7.30 (d, J = 8.3 Hz, 1H), 5.35 (p, J = 6.4 Hz, 1H), 4.46 (p, J = 8.0 Hz, 1H), 3.81 (p, J = 7.6 Hz, 1H), 3.26 (s, 1H), 3.09-2.91 (m, 4H), 2.89 (s, 3H), 2.43 (s, 3H), 1.71 (d, J = 6.6 Hz, 6H), 1.57 (s, 3H), 1.52 (s, 3H), 1.39 (s, 6H). | 0.08 |
| 83 | 731.5 | $^1$H NMR (400 MHz, DMSO-d6) delta 9.40 (d, J = 9.1 Hz, 1H), 8.70 (s, 1H), 8.51 (s, 1H), 8.12 (d, J = 7.9 Hz, 1H), 7.90 (s, 1H), 7.78 (dd, J = 7.8, 1.5 Hz, 1H), 7.63 (d, J = 1.5 Hz, 1H), 7.56-7.45 (m, 3H), 7.18 (d, J = 8.2 Hz, 1H), 5.31 (p, J = 6.6 Hz, 1H), 4.27 (q, J = 8.3 Hz, 1H), 4.05 (dq, J = 13.8, 6.9 Hz, 1H), 3.39 (d, J = 12.2 Hz, 3H), 3.02-2.73 (m, 5H), 2.31 (s, 3H), 2.08 (d, J = 3.7 Hz, 4H), 1.83 (t, J = 10.5 Hz, 4H), 1.69 (t, J = 5.8 Hz, 2H), 1.59-1.54 (m, 7H), 1.31 (d, J = 6.6 Hz, 1H), 1.10 (d, J = 6.6 Hz, 6H). | 0.1 |
| 84 | 743.6 | $^1$H NMR (400 MHz, DMSO-d6) delta 9.33 (s, 1H), 8.36 (s, 1H), 8.29-8.13 (m, 2H), 7.90 (d, J = 2.4 Hz, 1H), 7.88-7.79 (m, 3H), 7.66 (s, 1H), 7.60 (d, J = 7.9 Hz, 1H), 7.22 (d, J = 8.3 Hz, 1H), 4.34 (t, J = 8.1 Hz, 1H), 4.13 (s, 1H), 3.95 (s, 1H), 3.80 (d, J = 10.1 Hz, 1H), 3.06-2.71 (m, 5H), 2.32 (d, J = 5.5 Hz, 4H), 1.84 (d, J = 13.8 Hz, 9H), 1.76-1.54 (m, 7H), 1.45 (d, J = 19.3 Hz, 1H), 1.27 (d, J = 10.3 Hz, 5H), 1.06 (t, J = 7.2 Hz, 4H). | 0.2 |
| 85 | 757.4 | $^1$H NMR (400 MHz, DMSO-d6) delta 9.42 (d, J = 10.0 Hz, 1H), 8.45 (s, 1H), 8.25 (s, 1H), 8.19 (q, J = 4.5 Hz, 1H), 7.88 (d, J = 2.4 Hz, 1H), 7.86-7.79 (m, 3H), 7.66-7.61 (m, 2H), 4.88 (dd, J = 22.8, 5.8 Hz, 2H), 7.22 (d, J = 8.4 Hz, 1H), 4.32 (q, J = 7.2, 6.0 Hz, 3H), 4.20-4.13 (m, 1H), 3.78 (d, J = 9.0 Hz, 1H), 3.61-3.47 (m, 2H), 3.40 (d, J = 11.7 Hz, 2H), 3.18 (d, J = 13.6 Hz, 1H), 3.08-2.78 (m, 4H), 2.76 (d, J = 4.6 Hz, 3H), 2.32 (s, 3H), 1.90-1.56 (m, 13H), 1.41 (d, J = 12.5 Hz, 1H), 1.27 (dq, J = 4.8, 2.4 Hz, 4H). | 0.1 |
| 86 | 765.5 | $^1$H NMR (400 MHz, DMSO-d6) delta 9.39 (s, 1H), 8.69 (s, 1H), 8.42 (s, 1H), 8.30 (t, J = 5.4 Hz, 1H), 7.86 (s, 1H), 7.65 (dd, J = 7.8, 1.4 Hz, 1H), 7.57 (d, J = 8.2 Hz, 1H), 7.52-7.46 (m, 2H), 7.18 (d, J = 12.1 Hz, 1H), 5.36-5.19 (m, 1H), 4.16 (t, J = 8.1 Hz, 1H), 3.94-3.76 (m, 1H), 3.71 (t, J = 6.8 Hz, 1H), 3.49 (q, J = 8.1 Hz, 1H), 3.37 (tt, J = 10.1, 4.9 Hz, 7H), 3.18 (s, 3H), 3.05-2.68 (m, 9H), 2.36 (s, 3H), 2.06 (s, 3H), 1.92-1.50 (m, 12H), 1.41 (t, J = 12.7 Hz, 1H). | 0.2 |
| 87 | 763.5 | $^1$H NMR (400 MHz, DMSO-d6) delta 9.49 (d, J = 9.7 Hz, 1H), 8.77 (s, 1H), 8.47 (s, 1H), 8.09 (d, J = 8.4 Hz, 1H), 7.88 (s, 1H), 7.64 (dd, J = 22.0, 8.0 Hz, 2H), 7.51 (d, J = 8.5 Hz, 2H), 7.20 (d, J = 12.1 Hz, 1H), 5.32 (p, J = 6.6 Hz, 1H), 4.19 (p, J = 8.2 Hz, 1H), 3.86 (dq, J = 13.7, 7.2 Hz, 3H), 3.73 (dt, J = 17.1, 7.9 | 0.3 |

TABLE 1-continued

| Example # | ES/MS m/z | ¹H-NMR | HPK1 IC$_{50}$ (nM) |
|---|---|---|---|
|  |  | Hz, 2H), 3.53 (q, J = 8.1 Hz, 1H), 3.40 (d, J = 11.8 Hz, 2H), 3.02-2.73 (m, 6H), 2.37 (s, 3H), 2.08 (s, 3H), 1.89-1.55 (m, 15H), 1.43 (p, J = 7.5 Hz, 3H), 1.07 (d, J = 6.5 Hz, 3H), 0.83 (t, J = 7.4 Hz, 3H). |  |
| 88 | 763.5 | ¹H NMR (400 MHz, DMSO-d6) delta 9.36 (s, 1H), 8.68 (s, 1H), 8.42 (s, 1H), 8.08 (d, J = 8.3 Hz, 1H), 7.88 (s, 1H), 7.64 (dd, J = 20.4, 8.3 Hz, 2H), 7.51 (dd, J = 4.6, 3.3 Hz, 2H), 7.19 (d, J = 12.1 Hz, 1H), 5.30 (q, J = 6.6 Hz, 1H), 4.20 (t, J = 8.1 Hz, 1H), 3.86 (p, J = 7.6 Hz, 3H), 3.79-3.64 (m, 1H), 3.52 (q, J = 8.2 Hz, 1H), 3.40 (d, J = 11.6 Hz, 2H), 3.03-2.74 (m, 7H), 2.37 (s, 3H), 2.08 (s, 3H), 1.91-1.53 (m, 15H), 1.43 (p, J = 7.1 Hz, 3H), 1.07 (t, J = 5.8 Hz, 3H), 0.82 (t, J = 7.4 Hz, 3H). | 0.2 |
| 89 | 769.4 | ¹H NMR (400 MHz, DMSO-d6) delta 9.46 (s, 1H), 8.77 (s, 1H), 8.69 (s, 1H), 8.39 (d, J = 7.8 Hz, 1H), 7.94 (s, 1H), 7.69 (dd, J = 7.8, 1.4 Hz, 1H), 7.63 (dd, J = 10.6, 9.6 Hz, 2H), 7.53 (d, J = 7.9 Hz, 1H), 7.48 (d, J = 1.4 Hz, 1H), 5.29 (p, J = 6.6 Hz, 1H), 4.20 (t, J = 8.2 Hz, 1H), 4.02 (dt, J = 7.5, 6.4 Hz, 1H), 3.94-3.81 (m, 1H), 3.73 (dq, J = 12.8, 6.2 Hz, 2H), 3.54 (q, J = 8.2 Hz, 1H), 3.41 (d, J = 11.8 Hz, 2H), 2.95 (dq, J = 28.2, 9.8 Hz, 2H), 2.78 (dd, J = 13.2, 7.9 Hz, 4H), 2.08 (s, 3H), 1.92-1.52 (m, 14H), 1.41 (d, J = 12.5 Hz, 1H), 1.11 (d, J = 6.6 Hz, 6H). | 0.2 |
| 90 | 791.5 | ¹H NMR (400 MHz, DMSO-d6) delta 9.44 (d, J = 9.8 Hz, 1H), 8.79 (s, 1H), 8.51 (s, 1H), 8.45 (s, 1H), 7.88 (s, 1H), 7.66 (dd, J = 7.9, 1.5 Hz, 1H), 7.57-7.48 (m, 3H), 7.18 (d, J = 12.1 Hz, 1H), 5.39-5.24 (m, 1H), 4.19 (t, J = 8.0 Hz, 1H), 3.95-3.80 (m, 1H), 3.80-3.64 (m, 2H), 3.51 (t, J = 8.1 Hz, 2H), 3.46 (s, 2H), 3.39 (d, J = 11.7 Hz, 3H), 3.21 (s, 3H), 2.93 (dd, J = 25.6, 10.2 Hz, 1H), 2.79 (dd, J = 12.0, 7.1 Hz, 5H), 2.35 (d, J = 0.6 Hz, 3H), 2.08 (s, 3H), 1.92-1.64 (m, 5H), 1.62-1.53 (m, 7H), 1.48-1.26 (m, 1H), 0.76-0.66 (m, 4H). | 0.3 |
| 91 | 747.4 | ¹H NMR (400 MHz, DMSO-d6) delta 9.47 (d, J = 9.1 Hz, 1H), 8.81 (s, 1H), 8.46 (s, 1H), 8.34 (d, J = 4.4 Hz, 1H), 7.88 (s, 1H), 7.67 (dd, J = 7.9, 1.5 Hz, 1H), 7.59 (d, J = 8.2 Hz, 1H), 7.52 (d, J = 7.9 Hz, 1H), 7.48 (d, J = 1.5 Hz, 1H), 7.20 (d, J = 12.1 Hz, 1H), 5.37-5.26 (m, 1H), 4.24-4.14 (m, 1H), 3.95-3.79 (m, 2H), 3.74 (q, J = 6.4 Hz, 2H), 3.53 (dt, J = 17.1, 7.6 Hz, 1H), 3.40 (d, J = 11.9 Hz, 2H), 3.00-2.86 (m, 2H), 2.86-2.73 (m, 3H), 2.37 (s, 3H), 2.08 (s, 3H), 1.89-1.62 (m, 8H), 1.60 (dd, J = 6.6, 1.3 Hz, 7H), 1.48-1.29 (m, 1H), 0.66 (td, J = 7.1, 4.8 Hz, 2H), 0.50-0.42 (m, 2H). | 0.1 |
| 92 | 721.4 | 1H NMR (400 MHz, DMSO-d6) delta 9.42 (d, J = 9.3 Hz, 1H), 8.72 (s, 1H), 8.45-8.37 (m, 1H), 8.20 (q, J = 4.5 Hz, 1H), 7.88 (s, 1H), 7.67 (dd, J = 7.9, 1.5 Hz, 1H), 7.61 (d, J = 8.2 Hz, 1H), 7.55-7.45 (m, 2H), 7.20 (d, J = 12.2 Hz, 1H), 5.29 (p, J = 6.5 Hz, 1H), 4.23-4.11 (m, 2H), 3.95-3.79 (m, 1H), 3.77-3.66 (m, 2H), 3.51 (q, J = 8.0 Hz, 1H), 3.39 (d, J = 11.9 Hz, 2H), 2.91 (dt, J = 26.9, 10.2 Hz, 2H), 2.84-2.75 (m, 6H), 2.73 (d, J = 4.6 Hz, 3H), 2.42-2.35 (m, 3H), 2.08 (s, 3H), 1.90-1.63 (m, 8H), 1.59 (d, J = 6.5 Hz, 6H). | 0.08 |
| 93 | 739.6 | 1H NMR (400 MHz, DMSO-d6) delta 9.31 (s, 1H), 8.70 (d, J = 8.7 Hz, 1H), 8.45 (d, J = 4.7 Hz, 1H), 8.39 (s, 1H), 8.34 (d, J = 2.9 Hz, 1H), 7.88 (s, 1H), 7.79 (dd, J = 7.9, 1.5 Hz, 1H), 7.65 (d, J = 11.1 Hz, 1H), 7.58 (d, J = 1.5 Hz, 1H), 7.53 (d, J = 7.8 Hz, 1H), 4.32 (t, J = 8.1 Hz, 1H), 4.15-4.03 (m, 1H), 4.02-3.79 (m, 1H), 3.79-3.65 (m, 3H), 3.52 (s, 3H), 2.98 (dd, J = 26.5, 10.2 Hz, 2H), 2.83 (dd, J = 18.6, 9.4 Hz, 4H), 2.77 (d, J = 4.7 Hz, 3H), 2.09 (s, 3H), 1.91-1.77 (m, 3H), 1.76-1.55 (m, 5H), 1.40 (d, J = 12.8 Hz, 1H), 1.32 (d, J = 3.7 Hz, 2H), 1.24 (d, J = 5.8 Hz, 3H). | 0.2 |
| 94 | 729.5 | 1H NMR (400 MHz, DMSO-d6) delta 9.31 (s, 1H), 8.54 (s, 1H), 8.42 (s, 1H), 8.29 (d, J = 4.5 Hz, 1H), 7.91 (s, 1H), 7.78 (d, J = 8.3 Hz, 1H), 7.63 (d, J = 1.5 Hz, 1H), 7.58-7.50 (m, 2H), 7.48 (dd, J = 8.1, 2.3 Hz, 1H), 7.17 (d, J = 8.4 Hz, 1H), 5.34-5.20 (m, 0H), 4.30 (t, J = 8.0 Hz, 1H), 3.99-3.61 (m, 4H), | 0.06 |

TABLE 1-continued

| Example # | ES/MS m/z | 1H-NMR | HPK1 IC$_{50}$ (nM) |
|---|---|---|---|
| | | 3.50 (d, J = 7.9 Hz, 2H), 3.06-2.76 (m, 9H), 2.34-2.27 (m, 3H), 2.09 (s, 3H), 1.92-1.59 (m, 10H), 1.60-1.51 (m, 6H), 0.65 (td, J = 7.1, 4.8 Hz, 2H), 0.52-0.40 (m, 2H). | |
| 95 | 719.5 | 1H NMR (400 MHz, DMSO-d6) delta 9.35 (d, J = 9.8 Hz, 1H), 8.64 (d, J = 8.5 Hz, 1H), 8.42 (s, 1H), 8.23 (q, J = 4.5 Hz, 1H), 8.20 (d, J = 2.9 Hz, 1H), 7.83 (d, J = 3.1 Hz, 1H), 7.80 (d, J = 1.5 Hz, 1H), 7.59 (d, J = 1.5 Hz, 1H), 7.52 (d, J = 7.9 Hz, 1H), 7.25 (d, J = 12.4 Hz, 1H), 4.36-4.24 (m, 1H), 4.09 (dt, J = 7.1, 3.3 Hz, 1H), 3.97-3.63 (m, 5H), 3.52 (d, J = 8.1 Hz, 1H), 3.40 (d, J = 11.8 Hz, 2H), 3.06-2.78 (m, 4H), 2.76 (d, J = 4.6 Hz, 3H), 2.35 (s, 3H), 2.09 (s, 3H), 1.94-1.53 (m, 10H), 1.40 (d, J = 12.2 Hz, 1H), 1.36-1.21 (m, 4H). | 0.3 |
| 96 | 715.6 | 1H NMR (400 MHz, DMSO-d6) delta 9.30 (s, 1H), 8.36 (s, 1H), 8.19-8.13 (m, 2H), 7.88-7.83 (m, 2H), 7.80 (s, 1H), 7.66 (dd, J = 4.4, 1.8 Hz, 2H), 7.56 (d, J = 7.9 Hz, 1H), 4.35 (t, J = 8.2 Hz, 1H), 4.19-4.07 (m, 1H), 3.99-3.79 (m, 3H), 3.62 (s, 2H), 3.40 (d, J = 12.5 Hz, 2H), 2.95-2.79 (m, 4H), 2.75 (d, J = 4.6 Hz, 3H), 2.30 (s, 3H), 2.18 (s, 3H), 2.09 (s, 3H), 1.94-1.77 (m, 3H), 1.66 (d, J = 47.7 Hz, 6H), 1.40 (d, J = 12.6 Hz, 1H), 1.32-1.21 (m, 4H). | 0.2 |
| 97 | 705.3 | 1H NMR (400 MHz, DMSO-d6) delta 9.35 (s, 1H), 8.98 (dd, J = 8.1, 2.2 Hz, 1H), 8.50 (d, J = 4.7 Hz, 1H), 8.42 (d, J = 3.2 Hz, 1H), 8.31 (d, J = 2.8 Hz, 1H), 7.88-7.78 (m, 2H), 7.64 (d, J = 1.5 Hz, 1H), 7.59 (ddd, J = 8.5, 4.6, 2.2 Hz, 1H), 7.54 (d, J = 7.9 Hz, 1H), 7.44 (dd, J = 11.0, 8.5 Hz, 1H), 4.36 (t, J = 8.2 Hz, 1H), 4.12-4.05 (m, 1H), 3.98-3.68 (m, 2H), 3.37 (d, J = 12.4 Hz, 4H), 2.94 (dd, J = 30.4, 10.0 Hz, 2H), 2.82 (d, J = 4.5 Hz, 4H), 2.09 (s, 4H), 1.92-1.53 (m, 11H), 1.48-1.21 (m, 5H). | 0.4 |
| 98 | 743.1 | 1H NMR (400 MHz, DMSO-d6) delta 9.41 (d, J = 9.6 Hz, 1H), 8.41 (s, 1H), 8.24 (s, 1H), 8.19 (q, J = 4.6 Hz, 1H), 7.89-7.81 (m, 3H), 7.80 (s, 1H), 7.65 (d, J = 1.5 Hz, 1H), 7.60 (d, J = 7.9 Hz, 1H), 7.22 (d, J = 8.3 Hz, 1H), 4.33 (t, J = 8.2 Hz, 1H), 4.14 (dt, J = 6.6, 4.1 Hz, 1H), 3.92 (s, 5H), 3.52 (q, J = 8.1 Hz, 1H), 3.40 (d, J = 11.7 Hz, 2H), 3.04-2.94 (m, 2H), 2.92-2.79 (m, 2H), 2.76 (d, J = 4.6 Hz, 3H), 2.32 (s, 3H), 1.91-1.53 (m, 10H), 1.42 (t, J = 12.5 Hz, 1H), 1.26 (s, 13H). | 0.09 |
| 99 | 763.4 | 1H NMR (400 MHz, DMSO-d6) delta 9.78 (s, 1H), 8.71 (s, 1H), 8.46 (s, 1H), 8.16 (d, J = 7.8 Hz, 1H), 7.89 (s, 1H), 7.60 (d, J = 85.2 Hz, 3H), 7.17 (d, J = 12.1 Hz, 1H), 5.37-5.23 (m, 1H), 4.78 (dt, J = 23.7, 7.5 Hz, 4H), 4.24-3.93 (m, 2H), 3.43 (dd, J = 57.4, 9.9 Hz, 6H), 2.84 (dd, J = 47.9, 10.0 Hz, 6H), 2.35 (s, 3H), 2.32-1.92 (m, 3H), 1.86-1.51 (m, 10H), 1.40 (t, J = 12.4 Hz, 1H), 1.09 (d, J = 6.5 Hz, 5H). | 0.2 |
| 100 | 777.4 | 1H NMR (400 MHz, DMSO-d6) delta 10.96 (d, J = 129.8 Hz, 2H), 8.89 (s, 1H), 8.55 (s, 1H), 8.19 (d, J = 7.8 Hz, 1H), 7.97-7.38 (m, 5H), 7.19 (d, J = 12.0 Hz, 1H), 5.39-5.27 (m, 1H), 4.78 (dt, J = 28.8, 7.4 Hz, 4H), 4.22-3.93 (m, 2H), 3.80-3.13 (m, 7H), 2.97-2.62 (m, 3H), 2.37 (s, 3H), 2.05-1.69 (m, 2H), 1.59 (d, J = 6.5 Hz, 5H), 1.16 (s, 3H), 1.13-0.99 (m, 8H). | 0.3 |
| 101 | 624.4 | 1H NMR (400 MHz, DMSO-d6) delta 9.36 (s, 1H), 8.52 (s, 1H), 8.33 (s, 1H), 8.21 (q, J = 4.5 Hz, 1H), 7.83 (d, 1H), 7.73 (d, J = 8.2 Hz, 1H), 7.67 (d, J = 7.7 Hz, 1H), 7.46 (s, 1H), 7.35 (d, J = 7.7 Hz, 1H), 7.20 (d, J = 12.0 Hz, 1H), 4.62 (q, J = 7.2 Hz, 2H), 4.17 (q, J = 8.2 Hz, 1H), 3.51 (q, J = 8.2 Hz, 1H), 3.38 (d, J = 11.7 Hz, 2H), 2.91 (d, J = 10.0 Hz, 2H), 2.80 (m, 4H), 2.72 (d, J = 4.5 Hz, 3), 2.37 (s, 3H), 1.83 (d, J = 14.0 Hz, 2H), 1.63 (m, 2H), 1.43 (t, J = 7.2 Hz, 3H), 1.27 (s, 6H). | 0.2 |
| 102 | 605.4 | 1H NMR (400 MHz, DMSO-d6) delta 9.33 (s, 1H), 8.43 (m, 2H), 8.17 (d, J = 4.8 Hz, 1H), 7.86 (s, 1H), 7.82-7.72 (m, 1H)), 7.69-7.50 (m, 3H), 7.39 (d, J = 7.8 Hz, 1H), 7.19 (d, J = 8.3 Hz, 1H), 4.63 (q, J = 7.1 Hz, 2H), 4.27 (t, J = 8.1 Hz, 1H), 3.51 (q, J = 8.0 Hz, | 0.09 |

TABLE 1-continued

| Example # | ES/MS m/z | $^1$H-NMR | HPK1 IC$_{50}$ (nM) |
|---|---|---|---|
| | | 1H), 3.45-3.33 (m, 2H), 3.00-2.88 (m, 1H), 2.88-2.76 (m, 3H), 2.74 (d, J = 4.5 Hz, 2H), 2.31 (s, 3H), 1.84 (d, J = 14.1 Hz, 2H), 1.66 (dd, J = 41.6, 13.1 Hz, 2H), 1.40 (t, J = 7.2 Hz, 3H), 1.30 (s, 6H). | |
| 103 | 606.4 | 1H NMR (400 MHz, DMSO-d6) delta 10.13 (s, 1H), 8.80 (s, 1H), 8.51 (s, 1H), 8.21-8.12 (m, 1H), 7.87 (s, 1H), 7.76 (dd, J = 7.8, 1.4 Hz, 1H), 7.65-7.47 (m, 4H), 7.39 (d, J = 7.8 Hz, 1H), 7.21 (d, J = 8.3 Hz, 1H), 5.38-5.27 (m, 1H), 4.38-4.25 (m, 1H), 3.73-3.60 (m, 1H), 3.54-3.46 (m, 1H), 3.07-2.88 (m, 2H), 2.85-2.71 (m, 6H), 2.32 (s, 3H), 2.07-2.02 (m, 2H), 1.94-1.86 (m, 2H), 1.57 (d, J = 6.5 Hz, 6H), 1.30 (s, 6H). | 0.1 |
| 104 | 656.5 | 1H NMR (400 MHz, DMSO-d6) delta 10.41 (d, J = 45.7 Hz, 1H), 8.72 (s, 1H), 8.48 (s, 1H), 8.16 (q, J = 4.6 Hz, 1H), 7.87 (s, 1H), 7.77 (dd, J = 7.8, 1.4 Hz, 1H), 7.57 (dd, J = 14.2, 1.9 Hz, 2H), 7.50 (dd, J = 8.2, 2.4 Hz, 1H), 7.39 (d, J = 7.8 Hz, 1H), 7.19 (d, J = 8.3 Hz, 1H), 5.30 (p, J = 6.5 Hz, 1H), 4.38-4.29 (m, 1H), 3.77-3.72 (m, 2H), 3.63-3.58 (m, 2H), 3.20-2.93 (m, 4H), 2.83-2.71 (m, 6H), 2.32 (s, 3H), 2.14-2.07 (m, 1H), 1.90-1.85 (m, 1H), 1.56 (d, J = 6.5 Hz, 6H), 1.30 (s, 6H). | 0.2 |
| 104A (1$^{st}$ eluting peak) | 656.3 | 1H NMR (400 MHz, DMSO-d6) delta 10.50 (d, J = 48.1 Hz, 1H), 8.91 (s, 1H), 8.55 (s, 1H), 8.21-8.12 (m, 1H), 7.87 (d, J = 1.2 Hz, 1H), 7.77 (d, J = 7.7 Hz, 1H), 7.60-7.55 (m, 2H), 7.51 (dd, J = 8.8, 2.1 Hz, 1H), 7.40 (d, J = 7.7 Hz, 1H), 7.21 (d, J = 8.2 Hz, 1H), 6.43-5.97 (m, 1H), 5.41-5.29 (m, 1H), 4.38-4.29 (m, 1H), 3.75 (s, 2H), 3.36-3.31 (m, 1H), 3.19-2.89 (m, 4H), 2.83-2.77 (m, 3H), 2.77-2.71 (m, 3H), 2.33 (s, 3H), 2.17-2.05 (m, 1H), 1.91-1.86 (m, 1H), 1.58 (d, J = 6.4 Hz, 6H), 1.30 (s, 6H). | 0.2 |
| 104B (2$^{nd}$ eluting peak) | 656.3 | 1H NMR (400 MHz, DMSO-d6) delta 10.50 (d, J = 47.4 Hz, 1H), 8.90 (s, 1H), 8.54 (s, 1H), 8.16 (q, J = 4.5 Hz, 1H), 7.87 (s, 1H), 7.76 (d, J = 7.7 Hz, 1H), 7.60-7.47 (m, 3H), 7.40 (d, J = 7.7 Hz, 1H), 7.21 (d, J = 8.2 Hz, 1H), 6.44-5.97 (m, 1H), 5.35 (p, J = 6.5 Hz, 1H), 4.38-4.29 (m, 1H), 3.75 (s, 2H), 3.61 (s, 2H), 3.20-2.89 (m, 4H), 2.83-2.77 (m, 2H), 2.75 (d, J = 4.4 Hz, 3H), 2.33 (s, 3H), 2.14-2.07 (m, 1H), 1.91-1.86 (m, 1H), 1.58 (d, J = 6.4 Hz, 6H), 1.30 (s, 6H). | 0.2 |
| 105 | 670.5 | 1H NMR (400 MHz, DMSO-d6) delta 9.80 (s, 1H), 8.78 (s, 1H), 8.51 (s, 1H), 8.19 (d, J = 4.7 Hz, 1H), 7.91 (s, 1H), 7.81 (dd, J = 7.8, 1.4 Hz, 1H), 7.62 (d, J = 1.4 Hz, 1H), 7.60-7.50 (m, 2H), 7.42 (d, J = 7.8 Hz, 1H), 7.22 (d, J = 8.3 Hz, 1H), 6.28-5.96 (m, 1H), 5.40-5.28 (m, 1H), 4.38-4.24 (m, 1H), 3.64-3.57 (m, 1H), 3.52-3.44 (m, 2H), 3.08-2.94 (m, 2H), 2.93-2.85 (m, 4H), 2.77 (d, J = 4.5 Hz, 3H), 2.35 (s, 3H), 2.03-1.95 (m, 1H), 1.93-1.85 (m, 1H), 1.74-1.66 (m, 1H), 1.60 (dd, J = 6.6, 1.5 Hz, 6H), 1.50-1.36 (m, 1H), 1.32 (s, 6H). | 0.2 |
| 105A (1$^{st}$ eluting peak) | 670.4 | 1H NMR (400 MHz, DMSO-d6) delta 9.91 (s, 1H), 8.96 (s, 1H), 8.57 (s, 1H), 8.16 (q, J = 4.5 Hz, 1H), 7.88 (s, 1H), 7.77 (dd, J = 7.7, 1.4 Hz, 1H), 7.59-7.48 (m, 3H), 7.40 (d, J = 7.8 Hz, 1H), 7.20 (d, J = 8.2 Hz, 1H), 6.09 (td, J = 55.6, 3.2 Hz, 1H), 5.42-5.30 (m, 1H), 4.33-4.20 (m, 1H), 3.60-3.55 (m, 0H), 3.44 (d, J = 11.4 Hz, 2H), 3.04-2.88 (m, 2H), 2.90-2.78 (m, 5H), 2.74 (d, J = 4.5 Hz, 3H), 2.41-2.36 (m, 1H), 2.33 (s, 3H), 1.96 (d, J = 14.3 Hz, 1H), 1.86 (d, J = 12.8 Hz, 1H), 1.75-1.63 (m, 1H), 1.58 (d, J = 6.8 Hz, 6H), 1.48-1.30 (m, 1H), 1.29 (s, 6H). | 0.2 |
| 105B (2$^{nd}$ eluting peak) | 670.4 | 1H NMR (400 MHz, DMSO-d6) delta 9.70 (s, 1H), 8.72 (s, 1H), 8.47 (s, 1H), 8.15 (q, J = 4.6 Hz, 1H), 7.88 (s, 1H), 7.78 (dd, J = 7.7, 1.3 Hz, 1H), 7.59 (s, 1H), 7.57-7.47 (m, 2H), 7.39 (d, J = 7.8 Hz, 1H), 7.19 (d, J = 8.3 Hz, 1H), 6.25-5.91 (m, 1H), 5.36-5.24 (m, 1H), 4.33-4.22 (m, 1H), 3.61-3.54 (m, 1H), 3.49-3.41 (m, 2H), 3.05-2.89 (m, 2H), 2.89-2.78 (m, 5H), 2.74 (d, J = 4.6 Hz, 3H), 2.32 (s, 3H), 1.96 (d, J = 14.3 Hz, 1H), 1.86 (d, J = 12.7 Hz, 1H), 1.75-1.63 (m, 1H), 1.56 (d, J = 6.4 Hz, 6H), 1.47-1.33 (m, 1H), 1.30 (s, 6H). | 0.09 |

TABLE 1-continued

| Example # | ES/MS m/z | 1H-NMR | HPK1 IC$_{50}$ (nM) |
|---|---|---|---|
| 106 | 638.5 | 1H NMR (400 MHz, DMSO-d6) delta 9.86 (s, 1H), 8.85 (s, 1H), 8.53 (s, 1H), 8.16 (q, J = 4.5 Hz, 1H), 7.87 (s, 1H), 7.76 (dd, J = 7.7, 1.4 Hz, 1H), 7.58-7.48 (m, 3H), 7.39 (d, J = 7.8 Hz, 1H), 7.19 (d, J = 8.2 Hz, 1H), 5.39-5.27 (m, 1H), 5.15 (d, J = 45.4 Hz, 1H), 4.30-4.21 (m, 1H), 3.70-3.47 (m, 1H), 3.41-3.10 (m, 2H), 3.04-2.90 (m, 2H), 2.83 (d, J = 15.9 Hz, 3H), 2.73 (d, J = 4.5 Hz, 3H), 2.32 (s, 3H), 2.03-1.94 (m, 1H), 1.91-1.76 (m, 2H), 1.74-1.66 (m, 1H), 1.57 (dd, J = 6.5, 1.8 Hz, 6H), 1.29 (s, 6H). | 0.07 |
| 107 | 656.4 | 1H NMR (400 MHz, DMSO-d6) delta 9.84 (s, 1H), 8.76 (s, 1H), 8.41 (s, 1H), 8.20 (q, J = 4.6 Hz, 1H), 7.85 (s, 1H), 7.71-7.60 (m, 2H), 7.44 (s, 1H), 7.36 (d, J = 7.8 Hz, 1H), 7.20 (d, J = 12.0 Hz, 1H), 5.30 (p, J = 6.5 Hz, 1H), 5.17 (d, J = 45.0 Hz, 1H), 4.22-4.13 (m, 1H), 3.68-3.54 (m, 2H), 3.43-3.13 (m, 2H), 3.03-2.90 (m, 3H), 2.85-2.70 (m, 6H), 2.38 (s, 3H), 2.04-1.95 (m, 1H), 1.93-1.76 (m, 2H), 1.60 (dd, J = 6.5, 2.0 Hz, 6H), 1.28 (s, 6H). | 0.1 |
| 108 | 642.4 | 1H NMR (400 MHz, DMSO-d6) delta 10.70-10.44 (m, 2H), 8.60 (s, 1H), 8.34 (s, 1H), 8.20 (d, J = 5.6 Hz, 1H), 7.85 (s, 1H), 7.66 (dd, J = 12.9, 8.1 Hz, 2H), 7.47 (d, J = 7.9 Hz, 1H), 7.36 (d, J = 7.8 Hz, 1H), 7.25-7.16 (m, 1H), 5.64-5.41 (m, 2H), 5.30-5.22 (m, 1H), 4.28-4.23 (m, 1H), 3.91-3.53 (m, 4H), 3.30-3.25 (m, 1H), 2.98-2.93 (m, 3H), 2.76-2.70 (m, 3H), 2.37 (s, 3H), 1.58 (d, J = 6.5 Hz, 6H), 1.28 (s, 6H). | 0.1 |
| 109 | 656.5 | 1H NMR (400 MHz, DMSO-d6) delta 10.68 (s, 1H), 8.71 (s, 1H), 8.36 (s, 1H), 8.21 (d, J = 4.9 Hz, 1H), 7.85 (s, 1H), 7.64 (dd, J = 20.7, 8.0 Hz, 2H), 7.45 (s, 1H), 7.36 (d, J = 7.8 Hz, 1H), 7.21 (d, J = 12.4 Hz, 1H), 5.61-5.56 (m, 1H), 5.48-5.43 (m, 1H), 5.13-5.06 (m, 1H), 4.27-4.20 (m, 1H), 3.94-3.54 (m, 4H), 3.41-3.15 (m, 2H), 3.01-2.88 (m, 2H), 2.73 (d, J = 4.5 Hz, 3H), 2.38 (s, 3H), 2.30-2.05 (m, 1H), 2.00-1.84 (m, 2H), 1.60 (d, J = 6.6 Hz, 3H), 1.28 (s, 6H), 0.82 (t, J = 7.3 Hz, 3H). | 0.3 |
| 110 | 684.5 | 1H NMR (400 MHz, DMSO-d6) delta 9.83 (s, 1H), 8.74 (s, 1H), 8.42 (s, 1H), 8.14 (d, J = 7.8 Hz, 1H), 7.85 (s, 1H), 7.64 (dd, J = 13.7, 7.9 Hz, 2H), 7.46 (s, 1H), 7.36 (d, J = 7.7 Hz, 1H), 7.19 (d, J = 12.0 Hz, 1H), 5.31 (p, J = 6.7 Hz, 1H), 5.25-5.08 (m, 1H), 4.22-4.15 (m, 1H), 4.10-3.97 (m, 1H), 3.68-3.54 (m, 1H), 3.39 (d, J = 12.0 Hz, 1H), 3.34-3.26 (m, 1H), 3.24-3.13 (m, 1H), 2.98 (q, J = 10.1 Hz, 3H), 2.80 (d, J = 16.7 Hz, 3H), 2.37 (s, 3H), 2.04-1.96 (m, 1H), 1.85-1.80 (m, 1H), 1.71-1.66 (m, 1H), 1.60 (d, J = 6.5 Hz, 6H), 1.28 (s, 6H), 1.10 (d, J = 6.5 Hz, 6H). | 0.2 |
| 111 | 639.5 | 1H NMR (400 MHz, DMSO-d6) delta 9.46 (d, J = 9.1 Hz, 1H), 8.77 (s, 1H), 8.73 (s, 1H), 8.46 (s, 1H), 8.24-8.16 (m, 1H), 7.96 (s, 1H), 7.73 (s, 1H), 7.58 (d, J = 8.1 Hz, 1H), 7.22 (d, J = 11.9 Hz, 1H), 5.37-5.26 (m, 1H), 4.29-4.17 (m, 1H), 3.59-3.48 (m, 1H), 3.39 (d, J = 11.9 Hz, 2H), 2.96-2.78 (m, 7H), 2.74 (d, J = 4.5 Hz, 3H), 2.39 (s, 3H), 1.85 (d, J = 14.2 Hz, 2H), 1.76-1.61 (m, 2H), 1.60 (d, J = 6.5 Hz, 6H), 1.48-1.38 (m, 1H), 1.29 (s, 6H). | 0.3 |
| 112 | 604.3 | 1H NMR (400 MHz, DMSO-d6) delta 9.29 (s, 1H), 8.37 (s, 1H), 8.22 (s, 1H), 8.08 (d, J = 2.4 Hz, 1H), 7.86-7.68 (m, 4H), 7.63 (d, J = 1.5 Hz, 1H), 7.45-7.38 (m, 2H), 7.22 (d, J = 8.4 Hz, 1H), 4.32 (t, J = 8.1 Hz, 1H), 4.19-4.11 (m, 1H), 3.40 (d, J = 11.7 Hz, 2H), 3.01-2.74 (m, 7H), 2.36 (s, 3H), 1.83 (d, J = 14.2 Hz, 2H), 1.71 (d, J = 12.9 Hz, 1H), 1.60 (d, J = 13.5 Hz, 2H), 1.31 (s, 6H), 1.30-1.22 (m, 4H). | 0.09 |
| 113 | 670.4 | 1H NMR (400 MHz, DMSO-d6) delta 9.86 (s, 1H), 8.86 (s, 1H), 8.44 (s, 1H), 8.22 (q, J = 4.5 Hz, 1H), 7.86 (s, 1H), 7.67 (dd, J = 7.8, 1.4 Hz, 1H), 7.62 (d, J = 8.2 Hz, 1H), 7.43 (s, 1H), 7.37 (d, J = 7.7 Hz, 1H), 7.21 (d, J = 12.0 Hz, 1H), 5.24-5.08 (m, 2H), 4.22-4.13 (m, 1H), 3.71-3.54 (m, 2H), 3.42-3.13 (m, 3H), 3.03-2.88 (m, 3H), 2.88-2.76 (m, 1H), 2.74 (d, J = 4.6 Hz, 3H), 2.41-2.36 (m, 3H), 2.09-1.80 (m, 4H), 1.71 (d, J = 14.4 Hz, 1H), 1.62 (d, J = 6.6 Hz, 3H), 1.28 (s, 6H), 0.83 (t, J = 7.4 Hz, 3H). | 0.1 |

TABLE 1-continued

| Example # | ES/MS m/z | ¹H-NMR | HPK1 IC$_{50}$ (nM) |
|---|---|---|---|
| 114 | 654.4 | 1H NMR (400 MHz, DMSO-d6) delta 9.37 (d, J = 9.2 Hz, 1H), 8.68 (d, J = 6.1 Hz, 2H), 8.36 (q, J = 4.6 Hz, 1H), 7.95 (s, 1H), 7.77 (dd, J = 7.8, 1.4 Hz, 1H), 7.57 (ddd, J = 8.4, 4.6, 2.1 Hz, 3H), 7.46-7.36 (m, 2H), 5.08 (d, J = 6.7 Hz, 1H), 4.36-4.21 (m, 1H), 3.51 (q, J = 8.0 Hz, 1H), 3.42 (d, J = 11.3 Hz, 2H), 3.37 (s, 1H), 3.03-2.88 (m, 2H), 2.88-2.78 (m, 2H), 2.75 (d, J = 4.6 Hz, 3H), 1.86 (ddd, J = 14.4, 10.6, 4.5 Hz, 5H), 1.77-1.52 (m, 6H), 1.50-1.35 (m, 1H), 1.30 (s, 6H), 0.77 (t, J = 7.4 Hz, 3H). | 0.05 |
| 115 | 668.3 | 1H NMR (400 MHz, DMSO-d6) delta 9.33 (s, 1H), 8.68 (d, J = 19.1 Hz, 2H), 8.32 (d, J = 7.8 Hz, 1H), 7.93 (s, 1H), 7.77 (dd, J = 7.8, 1.5 Hz, 1H), 7.61-7.57 (m, 2H), 7.55 (d, J = 2.7 Hz, 1H), 7.40 (dd, J = 14.7, 8.1 Hz, 2H), 5.36-5.22 (m, 1H), 4.28 (t, J = 8.1 Hz, 1H), 4.09-3.93 (m, 1H), 3.45 (dd, J = 38.2, 10.0 Hz, 3H), 3.02-2.86 (m, 2H), 2.88-2.72 (m, 4H), 1.84 (d, J = 14.1 Hz, 2H), 1.78-1.47 (m, 8H), 1.40 (d, J = 12.2 Hz, 1H), 1.29 (s, 6H), 1.10 (d, J = 6.6 Hz, 6H). | 0.1 |
| 116 | 682.5 | 1H NMR (400 MHz, DMSO-d6) delta 9.50 (s, 1H), 8.77 (s, 1H), 8.45 (s, 1H), 8.31 (t, J = 5.4 Hz, 1H), 7.84 (s, 1H), 7.65 (dd, J = 7.8, 1.3 Hz, 1H), 7.58 (d, J = 8.2 Hz, 1H), 7.44 (d, J = 1.5 Hz, 1H), 7.34 (d, J = 7.8 Hz, 1H), 7.19 (d, J = 12.0 Hz, 1H), 5.38-5.23 (m, 1H), 4.15 (t, J = 8.2 Hz, 1H), 3.50 (q, J = 8.1 Hz, 1H), 3.44-3.30 (m, 6H), 3.18 (s, 3H), 2.97-2.69 (m, 6H), 2.36 (s, 3H), 1.89-1.52 (m, 11H), 1.39 (d, J = 12.6 Hz, 1H), 1.26 (s, 6H). | 0.2 |
| 117 | 686.4 | 1H NMR (400 MHz, DMSO-d6) delta 9.35 (s, 1H), 8.64 (d, J = 18.0 Hz, 2H), 8.36 (d, J = 7.8 Hz, 1H), 7.90 (d, J = 0.8 Hz, 1H), 7.66 (dd, J = 8.1, 5.9 Hz, 2H), 7.59 (d, J = 10.8 Hz, 1H), 7.45 (s, 1H), 7.36 (d, J = 7.7 Hz, 1H), 5.34-5.16 (m, 1H), 4.18 (t, J = 8.2 Hz, 1H), 4.00 (q, J = 6.8 Hz, 1H), 3.60-3.47 (m, 1H), 3.39 (d, J = 11.9 Hz, 2H), 2.92 (q, J = 9.8, 9.2 Hz, 2H), 2.78 (d, J = 10.8 Hz, 3H), 1.83 (d, J = 14.1 Hz, 2H), 1.57 (d, J = 6.6 Hz, 10H), 1.39 (d, J = 12.8 Hz, 1H), 1.26 (s, 6H), 1.09 (d, J = 6.6 Hz, 6H). | 0.2 |
| 118 | 658.4 | 1H NMR (400 MHz, DMSO-d6) delta 9.31 (s, 1H), 8.60 (d, J = 12.1 Hz, 2H), 8.40 (d, J = 4.7 Hz, 1H), 7.91 (s, 1H), 7.72-7.64 (m, 2H), 7.60 (d, J = 10.8 Hz, 1H), 7.44 (s, 1H), 7.36 (d, J = 7.8 Hz, 1H), 5.30-5.14 (m, 1H), 4.18 (t, J = 8.2 Hz, 1H), 3.53 (t, J = 8.1 Hz, 1H), 3.39 (d, J = 11.8 Hz, 2H), 2.92 (q, J = 9.8 Hz, 2H), 2.84-2.70 (m, 7H), 1.83 (d, J = 14.0 Hz, 2H), 1.56 (d, J = 6.6 Hz, 8H), 1.40 (d, J = 12.5 Hz, 1H), 1.27 (s, 5H). | 0.09 |
| 119 | 640.3 | 1H NMR (400 MHz, DMSO-d6) delta 9.39 (d, J = 9.2 Hz, 1H), 8.71 (d, J = 13.0 Hz, 2H), 8.38 (q, J = 4.5 Hz, 1H), 7.95 (s, 1H), 7.78 (dd, J = 7.9, 1.4 Hz, 1H), 7.60 (d, J = 7.8 Hz, 3H), 7.43 (dd, J = 17.8, 8.1 Hz, 3H), 5.34-5.21 (m, 1H), 4.29 (t, J = 7.9 Hz, 1H), 3.52 (q, J = 8.2 Hz, 1H), 3.40 (d, J = 11.8 Hz, 2H), 2.93 (dt, J = 11.5, 8.9 Hz, 2H), 2.88-2.77 (m, 4H), 2.75 (d, J = 4.6 Hz, 3H), 1.85 (d, J = 14.1 Hz, 2H), 1.62 (d, J = 13.9 Hz, 2H), 1.56 (d, J = 6.5 Hz, 6H), 1.43 (t, J = 12.1 Hz, 1H), 1.30 (s, 6H). | 0.07 |
| 120 | 638.4 | 1H NMR (400 MHz, DMSO-d6) delta 10.33 (d, J = 7.4 Hz, 1H), 8.74 (s, 1H), 8.41 (s, 1H), 8.22 (d, J = 4.7 Hz, 1H), 7.85 (s, 1H), 7.70-7.61 (m, 2H), 7.47 (d, J = 1.4 Hz, 1H), 7.36 (d, J = 7.8 Hz, 1H), 7.23 (d, J = 12.0 Hz, 1H), 5.36-5.22 (m, 1H), 4.34-4.19 (m, 1H), 3.86 (dt, J = 10.3, 5.3 Hz, 5H), 2.95-2.80 (m, 2H), 2.74 (d, J = 4.6 Hz, 3H), 2.67 (t, J = 8.7 Hz, 2H), 2.39 (s, 3H), 1.60 (d, J = 6.5 Hz, 6H), 1.43-1.23 (m, 12H). | 0.2 |
| 121 | 646.5 | 1H NMR (400 MHz, DMSO-d6) delta 10.41 (d, J = 7.4 Hz, 1H), 8.74 (s, 1H), 8.51 (s, 1H), 8.32 (d, J = 4.4 Hz, 1H), 7.88 (s, 1H), 7.76 (dd, J = 7.8, 1.4 Hz, 1H), 7.60 (dd, J = 16.0, 1.9 Hz, 2H), 7.46 (dd, J = 8.3, 2.4 Hz, 1H), 7.39 (d, J = 7.8 Hz, 1H), 7.20 (d, J = 8.3 Hz, 1H), 5.41-5.25 (m, 1H), 4.40 (t, J = 8.3 Hz, 1H), 3.95-3.68 (m, 7H), 2.99-2.80 (m, 3H), 2.77-2.65 (m, 3H), 2.32 (s, 3H), 1.57 (d, J = 6.5 Hz, 6H), 1.44-1.20 (m, 18H), 0.66 (td, J = 7.0, 4.7 Hz, 2H), 0.52-0.42 (m, 2H). | 0.1 |

TABLE 1-continued

| Example # | ES/MS m/z | 1H-NMR | HPK1 IC$_{50}$ (nM) |
|---|---|---|---|
| 122 | 620.5 | 1H NMR (400 MHz, DMSO-d6) delta 10.43 (d, J = 6.6 Hz, 1H), 8.78 (s, 1H), 8.52 (s, 1H), 8.18 (q, J = 4.6 Hz, 1H), 7.88 (s, 1H), 7.76 (dd, J = 7.7, 1.4 Hz, 1H), 7.61 (d, J = 1.4 Hz, 1H), 7.56 (d, J = 2.4 Hz, 1H), 7.49 (dd, J = 8.2, 2.4 Hz, 1H), 7.39 (d, J = 7.8 Hz, 1H), 7.21 (d, J = 8.3 Hz, 1H), 5.41-5.26 (m, 1H), 4.37 (t, J = 8.2 Hz, 1H), 3.85 (t, J = 6.0 Hz, 5H), 2.97-2.83 (m, 2H), 2.79-2.61 (m, 5H), 2.33 (s, 3H), 1.57 (d, J = 6.5 Hz, 6H), 1.40-1.21 (m, 12H). | 0.1 |
| 123 | 662.4 | 1H NMR (400 MHz, DMSO-d6) delta 9.45 (s, 1H), 8.51 (s, 1H), 8.16 (d, J = 4.7 Hz, 1H), 7.88 (d, J = 0.8 Hz, 1H), 7.76 (dd, J = 7.9, 1.5 Hz, 1H), 7.59 (d, J = 7.7 Hz, 2H), 7.51 (q, J = 2.1 Hz, 2H), 7.21-7.17 (m, 1H), 5.31 (d, J = 9.3 Hz, 1H), 4.24 (p, J = 8.4 Hz, 1H), 4.04 (dt, J = 11.3, 5.7 Hz, 2H), 3.83 (dt, J = 10.8, 5.0 Hz, 2H), 3.47 (p, J = 8.4 Hz, 1H), 3.36 (d, J = 11.7 Hz, 2H), 2.92 (q, J = 9.8 Hz, 2H), 2.85-2.69 (m, 6H), 2.31 (s, 3H), 1.86-1.49 (m, 16H), 1.41 (t, J = 12.3 Hz, 1H). | 0.1 |
| 124 | 717.4 | 1H NMR (400 MHz, DMSO-d6) delta 9.44 (s, 1H), 8.82 (s, 1H), 8.54 (s, 1H), 8.12 (d, J = 7.8 Hz, 1H), 7.88 (d, J = 0.7 Hz, 1H), 7.76 (dd, J = 7.8, 1.5 Hz, 1H), 7.61-7.55 (m, 2H), 7.53-7.46 (m, 2H), 7.18 (d, J = 8.2 Hz, 1H), 5.33 (s, 1H), 4.26 (p, J = 8.3 Hz, 1H), 4.02 (tt, J = 9.2, 6.3 Hz, 3H), 3.83 (dt, J = 10.9, 5.1 Hz, 2H), 3.52-3.31 (m, 3H), 2.92 (q, J = 10.0, 9.6 Hz, 2H), 2.78 (q, J = 10.6, 8.8 Hz, 4H), 2.30 (s, 3H), 1.90-1.47 (m, 15H), 1.41 (t, J = 12.6 Hz, 1H), 1.08 (d, J = 6.6 Hz, 6H). | 0.2 |
| 125 | 708.4 | 1H NMR (400 MHz, DMSO-d6) delta 9.50 (s, 1H), 8.87 (s, 1H), 8.50 (s, 1H), 8.15 (d, J = 7.9 Hz, 1H), 7.85 (s, 1H), 7.65 (dd, J = 7.9, 1.4 Hz, 1H), 7.56 (dd, J = 8.0, 5.2 Hz, 2H), 7.46 (d, J = 1.4 Hz, 1H), 7.19 (d, J = 12.1 Hz, 1H), 5.32 (p, J = 6.7 Hz, 1H), 4.16 (p, J = 8.3 Hz, 1H), 4.03 (ddd, J = 13.5, 6.4, 4.6 Hz, 3H), 3.81 (dt, J = 10.9, 5.1 Hz, 2H), 3.50 (h, J = 8.5 Hz, 1H), 3.38 (d, J = 11.7 Hz, 2H), 2.98-2.85 (m, 2H), 2.85-2.70 (m, 4H), 2.36 (s, 3H), 1.89-1.52 (m, 15H), 1.39 (q, J = 13.0, 12.6 Hz, 1H), 1.08 (d, J = 6.6 Hz, 6H). | 0.2 |
| 126 | 646.4 | 1H NMR (400 MHz, CDCl3) delta 8.16 (d, 1H), 7.87 (d, 1H), 7.73 (m, 1H), 7.63 (m, 3H), 7.51 (d, 1H), 7.41 (m, 1H), 7.16 (m, 1H), 6.49 (s, 1H), 6.24 (s, 1H), 4.40 (p, 1H), 4.21 (m, 2H), 3.92 (m, 3H), 3.76 (m, 1H), 3.04 (d, 2H), 2.72 (m, 6H), 2.47 (m, 3H), 1.84 (m, 10H), 1.52 (m, 3H), 1.32 (m, 5H). | 0.07 |
| 127 | 660.5 | 1H NMR (400 MHz, DMSO) delta 9.41 (s, 1H), 8.43 (s, 1H), 8.23 (s, 1H), 8.19 (q, 1H), 7.91 (d, 1H), 7.80 (m, 4H), 7.61 (m, 2H), 7.21 (d, 1H), 4.31 (p, 1H), 4.08 (m, 3H), 3.84 (m, 3H), 3.44 (m, 4H), 2.96 (m, 2H), 2.83 (m, 4H), 2.75 (d, 3H), 2.30 (s, 3H), 1.71 (m, 12H), 1.40 (t, 1H), 1.26 (m, 5H). | 0.1 |
| 128 | 634.5 | 1H NMR (400 MHz, DMSO-d6) delta 9.40 (d, J = 10.0 Hz, 1H), 8.73 (s, 1H), 8.46 (s, 1H), 8.14 (q, J = 4.5 Hz, 1H), 7.87 (s, 1H), 7.75 (dd, J = 7.8, 1.4 Hz, 1H), 7.60-7.27 (m, 4H), 7.17 (d, J = 8.3 Hz, 1H), 5.10 (q, J = 6.6 Hz, 1H), 4.24 (p, J = 8.3 Hz, 1H), 3.42 (dt, J = 47.2, 9.5 Hz, 4H), 3.03-2.63 (m, 10H), 2.30 (s, 3H), 2.04-1.11 (m, 15H), 0.77 (t, J = 7.4 Hz, 3H). | 0.1 |
| 129 | 749.4 | 1H NMR (400 MHz, DMSO-d6) delta 9.47 (s, 1H), 8.85 (s, 1H), 8.49 (s, 1H), 8.15 (d, J = 7.8 Hz, 1H), 7.86 (d, J = 0.9 Hz, 1H), 7.64 (dd, J = 7.9, 1.5 Hz, 1H), 7.56 (d, J = 8.2 Hz, 1H), 7.53-7.45 (m, 2H), 7.18 (d, J = 12.0 Hz, 1H), 5.38-5.25 (m, 1H), 4.16 (t, J = 8.1 Hz, 1H), 4.02 (dq, J = 13.6, 6.7 Hz, 1H), 3.93-3.76 (m, 1H), 3.70 (p, J = 7.7, 7.1 Hz, 2H), 3.49 (p, J = 8.3 Hz, 1H), 3.38 (d, J = 11.7 Hz, 2H), 3.00-2.71 (m, 7H), 2.35 (d, J = 0.8 Hz, 3H), 2.06 (s, 3H), 1.86-1.53 (m, 13H), 1.40 (t, J = 12.5 Hz, 1H), 1.08 (d, J = 6.6 Hz, 6H). | 0.2 |
| 130 | 717.62 | 1H NMR (400 MHz, DMSO-d6) delta 9.53 (d, J = 12.8 Hz, 1H), 8.88 (d, J = 9.8 Hz, 1H), 8.58 (d, J = 4.7 Hz, 1H), 8.25 (t, J = 5.7 Hz, 1H), 7.90 (s, 1H), 7.77 (d, J = 7.8 Hz, 1H), 7.60 (s, 1H), 7.58-7.47 (m, 3H), 7.20 (d, J = 8.1 Hz, 1H), 5.34 (dq, J = 13.0, 6.8, 5.3 Hz, 1H), 4.26 (p, J = 8.3 Hz, 1H), 3.49 (q, J = 8.1 | 0.1 |

TABLE 1-continued

| Example # | ES/MS m/z | 1H-NMR | HPK1 IC$_{50}$ (nM) |
|---|---|---|---|
| | | Hz, 1H), 3.38 (d, J = 11.6 Hz, 2H), 3.23 (p, J = 7.0 Hz, 2H), 3.02-2.72 (m, 7H), 2.32 (s, 3H), 2.08 (s, 3H), 1.90-1.76 (m, 4H), 1.76-1.63 (m, 3H), 1.57 (d, J = 6.4 Hz, 6H), 1.50-1.35 (m, 1H), 1.06 (t, J = 7.2 Hz, 3H). | |
| 131 | 747.54 | 1H NMR (400 MHz, DMSO-d6) delta 9.39 (d, J = 9.8 Hz, 1H), 8.75 (s, 1H), 8.53 (s, 1H), 8.27 (t, J = 5.4 Hz, 1H), 7.90 (s, 1H), 7.77 (dd, J = 7.9, 1.5 Hz, 1H), 7.62 (d, J = 1.5 Hz, 1H), 7.57-7.46 (m, 3H), 7.19 (d, J = 8.3 Hz, 1H), 5.37-5.26 (m, 1H), 4.27 (t, J = 8.2 Hz, 1H), 3.39 (dt, J = 14.1, 5.3 Hz, 6H), 3.19 (s, 3H), 2.93 (dd, J = 25.7, 10.2 Hz, 1H), 2.81 (t, J = 9.7 Hz, 5H), 2.32 (s, 3H), 2.09 (s, 4H), 1.88-1.76 (m, 3H), 1.75-1.61 (m, 3H), 1.57 (dd, J = 6.5, 1.5 Hz, 7H). | 0.2 |
| 132 | 733.52 | 1H NMR (400 MHz, DMSO-d6) delta 9.43 (d, J = 10.1 Hz, 1H), 8.78 (d, J = 2.1 Hz, 1H), 8.53 (s, 1H), 8.18 (t, J = 5.7 Hz, 1H), 7.90 (s, 1H), 7.77 (dd, J = 7.9, 1.4 Hz, 1H), 7.60 (d, J = 1.5 Hz, 1H), 7.57-7.45 (m, 3H), 7.20 (d, J = 8.2 Hz, 1H), 5.32 (p, J = 6.5 Hz, 1H), 4.32-4.21 (m, 1H), 3.47 (t, J = 6.4 Hz, 2H), 3.38 (d, J = 11.7 Hz, 2H), 3.29 (q, J = 6.2 Hz, 2H), 2.93 (dd, J = 25.1, 10.3 Hz, 2H), 2.81 (td, J = 10.4, 9.4, 5.5 Hz, 4H), 2.54 (s, 0H), 2.33 (s, 3H), 2.08 (d, J = 3.7 Hz, 4H), 1.82 (tt, J = 9.9, 4.8 Hz, 4H), 1.70 (q, J = 8.2, 6.2 Hz, 3H), 1.57 (d, J = 6.5 Hz, 8H), 1.43 (dd, J = 14.7, 10.4 Hz, 1H). | 0.1 |
| 133 | 608.2 | 1H NMR (400 MHz, DMSO-d6) delta 8.78 (s, 1H), 8.49 (s, 1H), 7.84 (s, 1H), 7.77-7.67 (m, 3H), 7.64 (dd, J = 8.0, 2.1 Hz, 2H), 7.59 (d, J = 2.4 Hz, 1H), 7.41-7.35 (m, 2H), 7.19 (d, J = 8.3 Hz, 1H), 4.69 (q, J = 7.2 Hz, 2H), 4.13 (dt, J = 22.5, 7.9 Hz, 2H), 2.77-2.61 (m, 3H), 2.35 (s, 3H), 1.45 (t, J = 7.2 Hz, 3H), 1.28 (s, 6H), 1.15 (d, J = 0.6 Hz, 1H), 1.10 (d, J = 0.6 Hz, 9H).; 1H NMR (400 MHz, DMSO-d6) delta 9.09 (s, 1H), 8.96 (s, 1H), 7.70 (dd, J = 7.3, 2.3 Hz, 1H), 7.66 (dt, J = 8.5, 2.5 Hz, 2H), 7.57-7.48 (m, 2H), 7.45 (d, J = 2.3 Hz, 1H), 7.37-7.27 (m, 2H), 7.11 (d, J = 2.4 Hz, 1H), 7.07 (dd, J = 8.4, 2.3 Hz, 1H), 4.33-4.21 (m, 1H), 4.13-3.96 (m, 3H), 2.72 (dt, J = 9.6, 4.8 Hz, 4H), 2.27 (d, J = 2.4 Hz, 3H), 1.35 (d, J = 2.4 Hz, 6H), 1.10 (t, J = 2.3 Hz, 1H), 1.03 (d, J = 2.5 Hz, 8H), 0.97 (td, J = 7.2, 2.3 Hz, 3H). | 0.9 |
| 134 | 697.3 | 1H NMR (400 MHz, DMSO-d6) δ 9.42 (d, J = 9.2 Hz, 1H), 8.75-8.66 (m, 3H), 8.46 (s, 1H), 7.96 (s, 1H), 7.76 (s, 1H), 7.59 (d, J = 8.1 Hz, 1H), 7.21 (d, J = 12.0 Hz, 1H), 5.37-5.25 (m, 1H), 4.54 (s, 1H), 4.42 (s, 1H), 4.31-4.18 (m, 1H), 3.58-3.45 (m, 1H), 3.40 (d, J = 11.9 Hz, 2H), 2.97-2.74 (m, 6H), 2.36 (s, 3H), 1.85 (d, J = 14.2 Hz, 2H), 1.76-1.62 (m, 2H), 1.60 (d, J = 6.4 Hz, 6H), 1.48-1.37 (m, 1H), 1.29 (s, 6H), 0.92-0.78 (m, 4H). | 0.3 |
| 135 | 622.4 | 1H NMR (400 MHz, DMSO-d6) delta 9.04 (s, 1H), 8.56 (s, 1H), 7.82 (s, 1H), 7.74-7.65 (m, 3H), 7.62 (d, J = 1.5 Hz, 1H), 7.58 (dd, J = 8.2, 2.4 Hz, 1H), 7.52 (d, J = 2.3 Hz, 1H), 7.40-7.32 (m, 2H), 7.18 (d, J = 8.3 Hz, 1H), 5.37 (p, J = 6.5 Hz, 1H), 4.18-4.02 (m, 2H), 2.75-2.56 (m, 2H), 2.33 (s, 3H), 1.58 (d, J = 6.5 Hz, 6H), 1.26 (s, 6H), 1.08 (s, 9H). | 0.6 |
| 136 | 648.4 | 1H NMR (400 MHz, Methanol-d4) delta 9.26 (s, 1H), 7.79 (s, 1H), 7.76 (dd, J = 7.8, 1.5 Hz, 1H), 7.74 (d, J = 2.4 Hz, 1H), 7.65 (d, J = 1.5 Hz, 1H), 7.44 (dd, J = 8.2, 2.4 Hz, 1H), 7.40 (d, J = 7.8 Hz, 1H), 7.29 (d, J = 8.3 Hz, 1H), 5.40 (p, J = 6.6 Hz, 1H), 4.43-4.31 (m, 1H), 4.16 (p, J = 6.6 Hz, 1H), 3.63 (p, J = 8.1 Hz, 1H), 3.52 (d, J = 12.3 Hz, 2H), 3.05 (dt, J = 11.6, 8.9 Hz, 2H), 2.98-2.80 (m, 4H), 2.43 (s, 3H), 2.00 (d, J = 14.5 Hz, 2H), 1.88 (d, J = 13.6 Hz, 1H), 1.73 (d, J = 6.5 Hz, 8H), 1.57 (t, J = 12.9 Hz, 1H), 1.38 (s, 6H), 1.18 (d, J = 6.6 Hz, 6H). | 0.1 |
| 137 | 664.4 | 1H NMR (400 MHz, Methanol-d4) delta 9.18 (d, J = 2.4 Hz, 1H), 7.79 (d, J = 2.9 Hz, 1H), 7.75 (dd, J = 7.9, 1.5 Hz, 1H), 7.71 (d, J = 2.5 Hz, 1H), 7.63 (d, J = 1.6 Hz, 1H), 7.44-7.35 (m, 2H), 7.29 (d, J = 8.4 Hz, 1H), 5.37 (p, J = 7.0 Hz, 1H), 4.36 (p, J = 8.0 Hz, 1H), 3.64 (p, J = 8.2 Hz, 1H), 3.51 (p, J = 3.9, 3.2 Hz, 6H), 3.25 (s, 3H), 3.03 (dt, J = 11.8, 9.2 Hz, 2H), 2.97-2.79 (m, 4H), 2.44 (d, J = 2.9 Hz, 3H), 2.00 (d, | 0.1 |

TABLE 1-continued

| Example # | ES/MS m/z | $^1$H-NMR | HPK1 IC$_{50}$ (nM) |
|---|---|---|---|
| | | J = 14.5 Hz, 2H), 1.87 (d, J = 13.0 Hz, 1H), 1.71 (dd, J = 7.0, 2.5 Hz, 8H), 1.57 (t, J = 13.0 Hz, 1H), 1.37 (s, 6H). | |
| 138 | 634.4 | 1H NMR (400 MHz, Methanol-d4) delta 9.25 (s, 1H), 7.79 (s, 1H), 7.76 (dd, J = 7.8, 1.5 Hz, 1H), 7.71 (d, J = 2.4 Hz, 1H), 7.64 (d, J = 1.5 Hz, 1H), 7.44 (dd, J = 8.2, 2.4 Hz, 1H), 7.40 (d, J = 7.8 Hz, 1H), 7.30 (d, J = 8.3 Hz, 1H), 5.39 (p, J = 6.6 Hz, 1H), 4.43-4.29 (m, 1H), 3.68-3.56 (m, 1H), 3.52 (d, J = 12.2 Hz, 2H), 3.37 (q, J = 7.3 Hz, 2H), 3.05 (qd, J = 9.1, 2.8 Hz, 2H), 2.97-2.79 (m, 4H), 2.44 (s, 3H), 2.00 (d, J = 14.2 Hz, 2H), 1.90 (s, 2H), 1.76 (m, 1H), 1.73 (d, J = 6.6 Hz, 6H), 1.56 (q, J = 12.7 Hz, 1H), 1.38 (s, 6H), 1.16 (t, J = 7.2 Hz, 3H). | 0.1 |
| 139 | 662.4 | 1H NMR (400 MHz, Methanol-d4) delta 9.30 (s, 1H), 7.81-7.78 (m, 2H), 7.76 (dd, J = 7.8, 1.5 Hz, 1H), 7.65 (d, J = 1.4 Hz, 1H), 7.43 (dd, J = 8.2, 2.4 Hz, 1H), 7.39 (d, J = 7.8 Hz, 1H), 7.30 (d, J = 8.3 Hz, 1H), 5.42 (p, J = 6.6 Hz, 1H), 4.34 (p, J = 8.1 Hz, 1H), 3.62 (p, J = 8.1 Hz, 1H), 3.52 (d, J = 12.3 Hz, 2H), 3.16 (dd, J = 6.7, 4.8 Hz, 2H), 3.03 (qd, J = 9.2, 2.7 Hz, 2H), 2.97-2.79 (m, 4H), 2.44 (s, 3H), 2.04-1.67 (m, 12H), 1.57 (t, J = 12.7 Hz, 1H), 1.38 (s, 6H), 0.88 (d, J = 6.7 Hz, 6H). | 0.06 |
| 140 | 690.3 | 1H NMR (400 MHz, Methanol-d4) delta 8.83 (s, 1H), 7.88 (d, J = 2.8 Hz, 1H), 7.84 (s, 1H), 7.76 (dd, J = 7.8, 1.5 Hz, 1H), 7.64 (s, 1H), 7.53 (dd, J = 8.9, 2.8 Hz, 1H), 7.40-7.34 (m, 2H), 5.38-5.25 (m, 1H), 4.46-4.34 (m, 1H), 3.67-3.48 (m, 3H), 3.15-3.02 (m, 2H), 2.98-2.71 (m, 7H), 2.05-1.70 (m, 5H), 1.67 (d, J = 6.6 Hz, 6H), 1.60-1.51 (m, 1H), 1.37 (s, 6H). | 0.3 |
| 141 | 674 | 1H NMR (400 MHz, Methanol-d4) delta 8.51 (s, 1H), 7.90 (s, 1H), 7.83-7.69 (m, 2H), 7.64 (s, 2H), 7.51 (s, 1H), 7.37-7.32 (m, 1H), 5.28-5.12 (m, 1H), 4.31-4.22 (m, 1H), 3.74-3.48 (m, 1H), 2.86 (s, 3H), 2.75-2.55 (m, 4H), 2.50-2.30 (m, 4H), 1.71-1.42 (m, 12H), 1.35 (s, 6H). | 0.07 |
| 142 | 646 | 1H NMR (400 MHz, Methanol-d4) delta 8.44 (s, 1H), 7.81-7.72 (m, 3H), 7.48-7.41 (m, 2H), 7.37-7.28 (m, 1H), 7.00 (d, J = 8.5 Hz, 1H), 5.25-5.11 (m, 1H), 4.38-4.24 (m, 1H), 3.05-2.84 (m, 4H), 2.82-2.43 (m, 8H), 2.27-2.10 (m, 1H), 1.71-1.49 (m, 12H), 1.35 (s, 6H), 0.99-0.85 (m, 2H), 0.78-0.61 (m, 2H). | 0.2 |
| 143 | 634 | 1H NMR (400 MHz, Methanol-d4) delta 9.15 (s, 1H), 7.82-7.75 (m, 2H), 7.68 (d, J = 2.3 Hz, 1H), 7.64 (d, J = 1.5 Hz, 1H), 7.48-7.39 (m, 2H), 7.34 (d, J = 8.3 Hz, 1H), 5.42-5.33 (m, 1H), 4.44-4.34 (m, 1H), 3.73-3.62 (m, 1H), 3.58-3.48 (m, 2H), 3.18-3.02 (m, 2H), 3.00-2.78 (m, 9H), 2.06-1.52 (m, 12H), 1.40 (s, 6H), 1.27 (t, J = 7.6 Hz, 3H). | 0.06 |
| 144 | 732.4 | 1H NMR (400 MHz, Methanol-d4) δ 8.98 (d, J = 3.1 Hz, 2H), 7.82 (s, 1H), 7.71 (td, J = 7.6, 1.6 Hz, 2H), 7.55 (d, J = 1.4 Hz, 1H), 7.40 (d, J = 7.8 Hz, 1H), 5.93 (t, J = 57.1 Hz, 1H), 5.36 (p, J = 6.6 Hz, 1H), 4.37 (p, J = 8.4 Hz, 1H), 3.67 (p, J = 8.2 Hz, 1H), 3.57 (d, J = 12.4 Hz, 2H), 3.18-3.06 (m, 2H), 3.00-2.82 (m, 4H), 2.40 (d, J = 2.3 Hz, 3H), 2.03 (d, J = 17.2 Hz, 2H), 1.91 (d, J = 13.1 Hz, 1H), 1.84-1.67 (m, 8H), 1.59 (t, J = 12.9 Hz, 1H), 1.40 (s, 6H), 1.21-1.12 (m, 2H), 1.00-0.89 (m, 2H). | 0.07 |
| 145 | 744.4 | 1H NMR (400 MHz, DMSO-d6) δ 9.91-9.31 (m, 1H), 8.96 (s, 1H), 8.70-8.56 (m, 2H), 7.88 (s, 1H), 7.67-7.60 (m, 1H), 7.45-7.32 (m, 3H), 6.04 (t, J = 56.9 Hz, 1H), 5.27 (p, J = 6.6 Hz, 1H), 4.24-4.07 (m, 2H), 3.97 (s, 1H), 3.75-3.52 (m, 1H), 3.42-3.20 (m, 1H), 3.07-2.72 (m, 5H), 2.71-2.60 (m, 1H), 2.29 (s, 3H), 2.02-1.87 (m, 1H), 1.84-1.48 (m, 10H), 1.46-1.34 (m, 1H), 1.28 (s, 6H), 1.15-1.01 (m, 2H), 0.93-0.85 (s, 2H). | 0.07 |
| 146 | 747.4 | 1H NMR (400 MHz, DMSO-d6) delta 9.36 (d, J = 9.2 Hz, 1H), 8.69 (s, 1H), 8.47 (s, 1H), 8.16 (q, J = 4.5 Hz, 1H), 7.90 (s, 1H), 7.79 (dd, J = 7.9, 1.5 Hz, 1H), 7.62 (d, J = 1.5 Hz, 1H), 7.56-7.48 (m, 3H), 7.23-7.15 (m, 1H), 5.36-5.20 (m, 1H), 4.28 (t, J = 8.3 Hz, 1H), 3.57-3.45 (m, 1H), 3.39 (d, J = 11.8 | 0.1 |

TABLE 1-continued

| Example # | ES/MS m/z | ¹H-NMR | HPK1 IC$_{50}$ (nM) |
|---|---|---|---|
| | | Hz, 2H), 2.94 (d, J = 10.3 Hz, 2H), 2.82 (t, J = 9.8 Hz, 3H), 2.73 (d, J = 4.6 Hz, 3H), 2.32 (s, 3H), 1.89-1.67 (m, 9H), 1.62 (d, J = 13.3 Hz, 2H), 1.56 (d, J = 6.5 Hz, 6H), 1.47 (s, 1H), 1.42 (s, 1H), 1.37 (s, 6H), 1.30 (s, 1H). | |
| 147 | 733.4 | 1H NMR (400 MHz, DMSO-d6) delta 9.38 (s, 1H), 8.70 (s, 1H), 8.48 (s, 1H), 8.16 (q, J = 4.5 Hz, 1H), 7.90 (d, J = 2.6 Hz, 1H), 7.78 (dd, J = 7.9, 1.4 Hz, 1H), 7.65-7.56 (m, 2H), 7.52 (d, J = 5.0 Hz, 2H), 7.19 (d, J = 8.4 Hz, 1H), 5.29 (q, J = 6.5 Hz, 1H), 4.50 (q, J = 6.5 Hz, 1H), 4.28 (t, J = 8.2 Hz, 1H), 3.88 (s, 5H), 3.58-3.44 (m, 1H), 3.39 (d, J = 12.0 Hz, 3H), 2.94 (dd, J = 20.1, 10.0 Hz, 2H), 2.81 (t, J = 9.7 Hz, 3H), 2.74 (d, J = 4.6 Hz, 3H), 2.32 (s, 3H), 1.91-1.67 (m, 8H), 1.62 (d, J = 7.0 Hz, 0H), 1.56 (d, J = 6.5 Hz, 6H), 1.49-1.35 (m, 1H), 1.31 (s, 1H), 1.24 (t, J = 7.1 Hz, 3H). | 0.2 |
| 148 | 771.4 | 1H NMR (400 MHz, DMSO-d6) delta 9.46 (d, J = 9.6 Hz, 1H), 8.80 (s, 1H), 8.52 (s, 1H), 8.17 (q, J = 4.5 Hz, 1H), 7.90 (s, 1H), 7.77 (dd, J = 7.9, 1.5 Hz, 1H), 7.63-7.56 (m, 2H), 7.55-7.49 (m, 2H), 7.20 (d, J = 8.2 Hz, 1H), 5.41-5.26 (m, 1H), 4.27 (t, J = 8.2 Hz, 1H), 3.99-3.69 (m, 4H), 3.50 (q, J = 8.1 Hz, 1H), 3.38 (d, J = 11.7 Hz, 2H), 3.03-2.77 (m, 7H), 2.74 (d, J = 4.6 Hz, 3H), 2.32 (s, 3H), 2.13 (s, 6H), 1.84 (d, J = 13.9 Hz, 2H), 1.70 (dd, J = 15.1, 9.6 Hz, 6H), 1.57 (d, J = 6.5 Hz, 6H), 1.42 (d, J = 12.7 Hz, 1H). | 0.2 |
| 149 | 755.1 | 1H NMR (400 MHz, DMSO-d6) delta 9.40 (d, J = 9.4 Hz, 1H), 8.43 (s, 1H), 8.24 (s, 1H), 8.19 (q, J = 4.5 Hz, 1H), 7.88 (d, J = 2.4 Hz, 1H), 7.83 (td, J = 8.3, 1.9 Hz, 2H), 7.80 (s, 1H), 7.65 (d, J = 1.5 Hz, 1H), 7.61 (d, J = 7.9 Hz, 1H), 7.22 (d, J = 8.3 Hz, 1H), 4.33 (t, J = 8.2 Hz, 1H), 4.20-4.10 (m, 1H), 3.59-3.46 (m, 2H), 3.40 (d, J = 12.0 Hz, 4H), 2.84 (dd, J = 25.7, 10.5 Hz, 4H), 2.76 (d, J = 4.6 Hz, 3H), 2.32 (s, 3H), 2.02-1.90 (m, 1H), 1.89-1.53 (m, 13H), 1.41 (s, 5H), 1.27 (dq, J = 7.1, 2.2 Hz, 5H). | 0.1 |
| 150 | 741.4 | 1H NMR (400 MHz, DMSO-d6) delta 9.56 (d, J = 9.8 Hz, 1H), 8.66 (s, 1H), 8.31 (s, 1H), 8.20 (q, J = 4.6 Hz, 1H), 7.91-7.78 (m, 4H), 7.68-7.58 (m, 2H), 7.24 (d, J = 8.2 Hz, 1H), 4.32 (p, J = 8.3 Hz, 1H), 4.24-4.16 (m, 1H), 3.93 (s, 4H), 3.58-3.48 (m, 1H), 3.39 (d, J = 11.8 Hz, 2H), 3.06-2.92 (m, 2H), 2.93-2.79 (m, 2H), 2.76 (d, J = 4.6 Hz, 3H), 2.32 (s, 3H), 1.71 (dq, J = 60.8, 13.8 Hz, 11H), 1.43 (t, J = 12.5 Hz, 1H), 1.29 (d, J = 3.9 Hz, 6H), 0.88 (d, J = 4.9 Hz, 2H), 0.62-0.51 (m, 2H). | 0.1 |
| 151 | 731.55 | 1H NMR (400 MHz, DMSO-d6) delta 8.43 (d, J = 2.6 Hz, 1H), 8.24 (s, 1H), 8.19 (q, J = 4.6 Hz, 1H), 7.91 (dd, J = 10.9, 2.3 Hz, 1H), 7.82 (dd, J = 13.7, 5.0 Hz, 3H), 7.65 (s, 1H), 7.57 (d, J = 35.0 Hz, 1H), 7.23 (d, J = 8.4 Hz, 1H), 4.51 (q, J = 6.5 Hz, 1H), 4.33 (p, J = 8.2 Hz, 1H), 4.14 (td, J = 6.6, 3.2 Hz, 1H), 3.89 (d, J = 21.1 Hz, 2H), 3.04-2.78 (m, 5H), 2.76 (d, J = 4.5 Hz, 3H), 2.32 (s, 3H), 1.84 (d, J = 14.5 Hz, 3H), 1.78-1.67 (m, 2H), 1.62 (d, J = 13.4 Hz, 2H), 1.48-1.35 (m, 1H), 1.30-1.21 (m, 8H). | 0.05 |
| 152 | 743.5 | 1H NMR (400 MHz, DMSO-d6) delta 9.45 (d, J = 9.4 Hz, 1H), 8.85 (s, 1H), 8.54 (s, 1H), 8.17 (d, J = 4.7 Hz, 1H), 7.91 (s, 1H), 7.77 (dd, J = 7.9, 1.5 Hz, 1H), 7.60 (d, J = 7.7 Hz, 2H), 7.56-7.50 (m, 2H), 7.20 (d, J = 8.3 Hz, 1H), 5.41-5.27 (m, 1H), 4.27 (t, J = 8.2 Hz, 1H), 3.92 (s, 4H), 3.51 (q, J = 8.1 Hz, 1H), 3.38 (d, J = 11.8 Hz, 2H), 2.94 (q, J = 9.7 Hz, 2H), 2.80 (d, J = 11.1 Hz, 4H), 2.74 (d, J = 4.6 Hz, 3H), 2.32 (s, 3H), 1.88-1.61 (m, 9H), 1.58 (d, J = 6.5 Hz, 6H), 1.42 (d, J = 12.4 Hz, 1H), 1.28 (s, 3H), 0.93-0.83 (m, 2H), 0.61-0.54 (m, 2H). | 0.2 |
| 153 | 743.4 | 1H NMR (400 MHz, DMSO-d6) delta 9.50 (d, J = 9.5 Hz, 1H), 8.47 (s, 1H), 8.26 (s, 1H), 8.20 (q, J = 4.5 Hz, 1H), 7.90 (d, J = 2.4 Hz, 1H), 7.87-7.78 (m, 3H), 7.64 (d, J = 1.5 Hz, 1H), 7.58 (d, J = 7.8 Hz, 1H), 7.23 (d, J = 8.4 Hz, 1H), 4.84-4.68 (m, 4H), 4.32 (t, J = 8.1 Hz, 1H), 4.25-4.12 (m, 2H), 4.07-3.92 (m, 1H), 3.86-3.71 (m, 1H), 3.71-3.59 (m, 1H), 3.52 (q, J = 8.1 Hz, 1H), 3.40 (d, J = 11.9 Hz, | 0.1 |

TABLE 1-continued

| Example # | ES/MS m/z | 1H-NMR | HPK1 IC$_{50}$ (nM) |
|---|---|---|---|
| | | 4H), 3.07-2.79 (m, 2H), 2.76 (d, J = 4.6 Hz, 4H), 2.32 (s, 3H), 1.90-1.53 (m, 11H), 1.41 (d, J = 12.7 Hz, 1H), 1.27 (tt, J = 4.1, 2.1 Hz, 4H). | |
| 154 | 771 | 1H NMR (400 MHz, DMSO-d6) delta 9.36 (d, J = 9.7 Hz, 1H), 8.41 (s, 1H), 8.23 (s, 1H), 8.19 (q, J = 4.5 Hz, 1H), 7.89 (d, J = 2.4 Hz, 1H), 7.83 (ddd, J = 7.6, 5.6, 2.0 Hz, 2H), 7.80 (s, 1H), 7.66 (d, J = 1.5 Hz, 1H), 7.59 (d, J = 7.9 Hz, 1H), 7.22 (d, J = 8.4 Hz, 1H), 4.32 (d, J = 8.1 Hz, 1H), 4.19-4.09 (m, 1H), 3.97-3.74 (m, 5H), 3.52 (q, J = 8.1 Hz, 1H), 3.40 (d, J = 11.8 Hz, 2H), 2.86 (dt, J = 26.8, 12.9 Hz, 5H), 2.76 (d, J = 4.6 Hz, 3H), 2.45 (d, J = 2.5 Hz, 6H), 2.32 (s, 3H), 1.89-1.55 (m, 9H), 1.41 (d, J = 12.7 Hz, 1H), 1.27 (d, J = 8.6 Hz, 4H). | 0.06 |
| 155 | 741.2 | 1H NMR (400 MHz, DMSO-d6) delta 9.34 (s, 1H), 8.40 (s, 1H), 8.23 (s, 1H), 8.18 (t, J = 4.7 Hz, 1H), 7.90 (d, J = 2.4 Hz, 1H), 7.85-7.80 (m, 2H), 7.80 (s, 1H), 7.65 (d, J = 1.5 Hz, 1H), 7.57 (d, J = 7.9 Hz, 1H), 7.24-7.20 (m, 1H), 4.33 (t, J = 8.2 Hz, 1H), 4.19-4.08 (m, 1H), 3.83 (d, J = 44.5 Hz, 5H), 3.66-3.46 (m, 2H), 3.42 (dd, J = 17.4, 9.2 Hz, 3H), 3.09-2.79 (m, 5H), 2.76 (d, J = 4.6 Hz, 3H), 2.31 (s, 3H), 2.29-2.05 (m, 3H), 1.99-1.54 (m, 10H), 1.41 (d, J = 12.6 Hz, 1H), 1.27 (d, J = 8.9 Hz, 5H). | 0.06 |
| 156 | 753.6 | 1H NMR (400 MHz, DMSO-d6) delta 9.34 (s, 1H), 8.39 (s, 1H), 8.23 (s, 1H), 8.18 (q, J = 4.5 Hz, 1H), 7.89 (d, J = 2.3 Hz, 1H), 7.86-7.80 (m, 2H), 7.80 (s, 1H), 7.66 (d, J = 1.5 Hz, 1H), 7.59 (d, J = 7.9 Hz, 1H), 7.22 (d, J = 8.4 Hz, 1H), 4.32 (q, J = 8.3 Hz, 1H), 4.17-4.10 (m, 1H), 4.05-3.71 (m, 6H), 3.52 (q, J = 8.1 Hz, 1H), 3.40 (d, J = 11.8 Hz, 2H), 3.08-2.79 (m, 5H), 2.76 (d, J = 4.6 Hz, 3H), 2.32 (s, 3H), 2.14 (s, 6H), 1.90-1.55 (m, 9H), 1.41 (d, J = 12.8 Hz, 1H), 1.27 (d, J = 8.9 Hz, 4H). | 0.06 |
| 157 | 735 | 1H NMR (400 MHz, Methanol-d4) delta 8.98 (s, 1H), 7.80 (s, 1H), 7.77 (dd, J = 7.9, 1.5 Hz, 1H), 7.64 (s, 1H), 7.60 (d, J = 2.3 Hz, 1H), 7.51 (d, J = 7.9 Hz, 1H), 7.36 (dd, J = 8.3, 2.4 Hz, 1H), 7.26 (d, J = 8.3 Hz, 1H), 5.17-5.09 (m, 2H), 4.44-4.36 (m, 1H), 4.12-3.99 (m, 3H), 3.91-3.52 (m, 4H), 3.18-2.93 (m, 6H), 2.87 (s, 3H), 2.41 (s, 3H), 2.19 (s, 3H), 2.09-1.83 (m, 10H), 1.71-1.67 (m, 3H), 0.97-0.92 (m, 3H). | 0.2 |
| 158 | 765 | 1H NMR (400 MHz, Methanol-d4) delta 8.45 (s, 1H), 7.83-7.68 (m, 3H), 7.50-7.34 (m, 3H), 7.20 (d, J = 8.0 Hz, 1H), 5.03-4.93 (m, 1H), 4.38-4.26 (m, 1H), 4.09-3.77 (m, 4H), 3.09-2.95 (m, 1H), 2.93-2.54 (m, 11H), 2.38 (s, 3H), 2.24-2.11 (m, 4H), 2.04-1.76 (m, 7H), 1.62 (d, J = 6.7 Hz, 3H), 1.44-1.26 (m, 2H), 0.85 (t, J = 7.4 Hz, 3H). | 0.2 |
| 159 | 715 | 1H NMR (400 MHz, Methanol-d4) delta 8.61 (s, 1H), 8.16 (d, J = 2.4 Hz, 1H), 7.79 (d, J = 7.9 Hz, 1H), 7.69 (s, 1H), 7.65 (s, 1H), 7.58 (dd, J = 8.2, 2.4 Hz, 1H), 7.52 (d, J = 7.9 Hz, 1H), 7.27 (d, J = 8.4 Hz, 1H), 4.45-4.43 (m, 1H), 4.13-4.02 (m, 3H), 3.94-3.81 (m, 3H), 3.75-3.67 (m, 1H), 3.50-3.35 (m, 2H), 3.17-3.08 (m, 2H), 3.00-2.92 (m, 3H), 2.89 (s, 3H), 2.41 (s, 3H), 2.20 (s, 3H), 1.98-1.83 (m, 6H), 1.45-1.35 (m, 4H), 1.30-1.18 (m, 6H). | 0.1 |
| 160 | 757 | 1H NMR (400 MHz, Methanol-d4) delta 8.72 (s, 1H), 8.14 (d, J = 2.4 Hz, 1H), 7.83 (d, J = 8.4 Hz, 1H), 7.73 (d, J = 1.4 Hz, 1H), 7.66 (s, 1H), 7.59-7.50 (m, 2H), 7.28 (d, J = 8.3 Hz, 1H), 4.67-4.59 (m, 1H), 4.22-4.14 (m, 1H), 4.12-4.06 (m, 1H), 4.02-3.96 (m, 1H), 3.94-3.68 (m, 4H), 3.38-3.34 (m, 1H), 3.24-3.17 (m, 2H), 3.08-3.00 (m, 2H), 2.89 (s, 3H), 2.65 (d, J = 12.4 Hz, 2H), 2.41 (s, 3H), 2.20 (s, 3H), 2.06-1.87 (m, 5H), 1.65-1.58 (m, 1H), 1.47-1.39 (m, 4H), 1.32 (d, J = 3.1 Hz, 6H), 1.07 (s, 6H). | 0.08 |
| 161 | 729 | 1H NMR (400 MHz, Methanol-d4) delta 8.24 (s, 1H), 7.99 (s, 1H), 7.85-7.73 (m, 3H), 7.59 (s, 1H), 7.49 (d, J = 7.8 Hz, 1H), 7.23 (d, J = 8.4 Hz, 1H), 4.47-4.37 (m, 2H), 4.21-3.70 (m, 7H), 2.95-2.65 (m, 9H), 2.39 (s, 3H), 2.19 (s, 3H), 1.95-1.84 (m, 2H), 1.86-1.79 (m, 2H), 1.70-1.60 (m, 2H), 1.42-1.25 (m, 6H), 1.00-0.85 (s, 6H). | 0.06 |

TABLE 1-continued

| Example # | ES/MS m/z | 1H-NMR | HPK1 IC$_{50}$ (nM) |
|---|---|---|---|
| 162 | 721 | 1H NMR (400 MHz, Methanol-d4) delta 8.47 (s, 1H), 7.84-7.74 (m, 2H), 7.69 (s, 1H), 7.60 (s, 1H), 7.49 (d, J = 7.9 Hz, 1H), 7.36 (dd, J = 8.2, 2.3 Hz, 1H), 7.22 (d, J = 8.4 Hz, 1H), 5.25-5.13 (m, 2H), 4.43-4.34 (m, 1H), 4.11-3.52 (m, 8H), 3.08-2.78 (m, 7H), 2.39 (s, 3H), 2.19 (s, 3H), 2.10-1.78 (m, 8H), 1.63 (d, J = 6.6 Hz, 6H). | 0.1 |
| 163 | 764 | 1H NMR (400 MHz, Methanol-d4) delta 8.22 (s, 1H), 7.93-7.81 (m, 3H), 7.76 (dd, J = 7.9, 1.5 Hz, 1H), 7.60 (s, 1H), 7.46 (d, J = 7.9 Hz, 1H), 7.23 (d, J = 8.4 Hz, 1H), 4.42-4.29 (m, 1H) 4.09-3.78 (m, 5H), 2.89 (s, 3H), 2.82-2.57 (m, 5H), 2.55-2.41 (m, 3H), 2.39 (s, 3H), 2.36-2.29 (m, 1H), 2.18 (s, 3H), 1.93-1.86 (m, 2H), 1.85-1.78 (m, 2H), 1.74-1.46 (m, 4H), 1.40-1.26 (m, 4H), 1.17-1.04 (m, 2H). | 0.1 |
| 164 | 751 | 1H NMR (400 MHz, Methanol-d4) delta 8.82 (s, 1H), 7.80-7.73 (m, 2H), 7.69-7.60 (m, 2H), 7.52-7.47 (m, 1H), 7.39-7.34 (m, 1H), 7.29-7.21 (m, 1H), 5.33-5.26 (m, 1H), 4.48-4.40 (m, 1H), 4.14-3.98 (m, 3H), 3.95-3.82 (m, 3H), 3.76-3.44 (ms, 3H), 3.25-3.10 (m, 3H), 2.95-2.85 (m, 5H), 2.41 (s, 34H), 2.19 (s, 3H), 1.96-1.88 (m, 2H), 1.87-1.80 (m, 2H), 1.76-1.63 (m, 8H). | 0.2 |
| 165 | 716 | 1H NMR (400 MHz, Methanol-d4) delta 9.23 (s, 1H), 7.83-7.72 (m, 2H), 7.64 (dd, J = 11.5, 1.9 Hz, 2H), 7.50 (d, J = 7.9 Hz, 1H), 7.43 (dd, J = 8.2, 2.4 Hz, 1H), 7.29 (d, J = 8.3 Hz, 1H), 5.43-5.31 (m, 1H), 4.43-4.31 (m, 1H), 4.15-3.96 (m, 2H), 3.90-3.65 (m, 4H), 3.46-3.32 (m, 3H), 3.17-3.02 (m, 2H), 3.00-2.80 (m, 5H), 2.43 (s, 3H), 2.19 (s, 3H), 2.09-1.77 (m, 6H), 1.71 (d, J = 6.6 Hz, 6H), 1.24 (d, J = 20.9 Hz, 6H). | 0.1 |
| 166 | 727 | 1H NMR (400 MHz, Methanol-d4) delta 8.25 (s, 1H), 8.11 (s, 1H), 7.78 (dd, J = 7.8, 1.5 Hz, 1H), 7.74-7.59 (m, 3H), 7.49 (d, J = 7.8 Hz, 1H), 7.24 (d, J = 8.4 Hz, 1H), 4.45-4.35 (m, 1H), 4.11-3.79 (m, 6H), 3.10-2.70 (m, 11H), 2.39 (s, 3H), 2.19 (s, 3H), 1.94-1.80 (m, 6H), 1.39-1.30 (m, 4H), 0.60-0.48 (m, 4H). | 0.1 |
| 167 | 763.57 | 1H NMR (400 MHz, DMSO-d6) delta 9.45 (s, 1H), 8.50 (s, 1H), 8.26 (s, 1H), 8.20 (q, J = 4.5 Hz, 1H), 7.93 (d, J = 2.4 Hz, 1H), 7.86-7.78 (m, 3H), 7.65 (s, 1H), 7.54 (d, J = 7.8 Hz, 1H), 7.23 (d, J = 8.4 Hz, 1H), 4.33 (d, 0H), 4.16 (q, J = 5.4 Hz, 1H), 3.40 (d, J = 12.6 Hz, 5H), 2.98 (q, J = 9.9, 9.4 Hz, 2H), 2.92-2.79 (m, 2H), 2.77 (d, J = 4.5 Hz, 3H), 4.82-0.48 (m, 1H), 2.32 (s, 3H), 2.00-1.80 (m, 8H), 1.75-1.54 (m, 5H), 1.49-1.33 (m, 2H), 1.31-1.25 (m, 4H), 1.09-0.96 (m, 4H). | 0.1 |
| 168 | 737.54 | 1H NMR (400 MHz, DMSO-d6) delta 9.41 (d, J = 9.4 Hz, 1H), 8.43 (s, 1H), 8.24 (s, 1H), 8.20 (q, J = 4.6 Hz, 1H), 7.91 (d, J = 2.3 Hz, 1H), 7.86-7.83 (m, 1H), 7.83-7.81 (m, 1H), 7.81 (s, 1H), 7.66 (d, J = 1.5 Hz, 1H), 7.58 (d, J = 7.8 Hz, 1H), 7.23 (d, J = 8.4 Hz, 1H), 4.33 (t, J = 8.0 Hz, 1H), 4.19-4.10 (m, 1H), 3.60-3.34 (m, 6H), 3.00 (s, 3H), 2.92-2.78 (m, 2H), 2.77 (d, J = 4.6 Hz, 3H), 2.32 (s, 3H), 2.00-1.79 (m, 5H), 1.67 (dd, J = 36.8, 13.3 Hz, 3H), 1.41 (d, J = 12.8 Hz, 1H), 1.27 (dq, J = 5.6, 2.4 Hz, 5H). | 0.1 |
| 169 | 733.4 | 1H NMR (400 MHz, Methanol-d4) delta 9.37 (d, J = 31.6 Hz, 1H), 7.83 (d, J = 3.1 Hz, 1H), 7.75 (d, J = 8.2 Hz, 1H), 7.64-7.60 (m, 3H), 7.51 (dd, J = 8.0, 3.9 Hz, 1H), 7.42 (s, 2H), 7.30 (d, J = 8.2 Hz, 1H), 5.23 (s, 1H), 4.34 (t, J = 8.4 Hz, 1H), 3.87 (s, 5H), 3.75 (d, J = 2.3 Hz, 3H), 3.68-3.45 (m, 4H), 3.07 (dq, J = 18.1, 9.8, 9.3 Hz, 2H), 2.87 (t, J = 5.9 Hz, 8H), 2.45-2.41 (m, 4H), 2.15-1.64 (m, 17H), 1.55 (q, J = 13.2 Hz, 2H), 0.98 (d, J = 9.2 Hz, 3H). | 0.1 |
| 170 | 753 | 1H NMR (400 MHz, Methanol-d4) delta 8.44 (s, 1H), 7.88 (d, J = 8.1 Hz, 1H), 7.75 (s, 1H), 7.72-7.65 (m, 2H), 7.46 (d, J = 7.7 Hz, 1H), 7.11 (d, J = 11.8 Hz, 1H), 5.26-5.18 (m, 1H), 4.79-4.64 (m, 5H), 4.60-4.50 (m, 1H), 4.28-4.18 (m, 1H), 3.76-3.68 (m, 2H), 2.88-2.56 (m, 12H), 2.52-2.36 (m, 5H), 1.97-1.77 (m, 6H), 1.72-1.50 (m, 8H). | 0.8 |

TABLE 1-continued

| Example # | ES/MS m/z | $^1$H-NMR | HPK1 IC$_{50}$ (nM) |
|---|---|---|---|
| 171 | 767 | 1H NMR (400 MHz, Methanol-d4) delta 9.16 (s, 1H), 8.01-7.71 (m, 3H), 7.58 (s, 1H), 7.51-7.34 (m, 1H), 7.16 (d, J = 11.5 Hz, 1H), 5.43-5.33 (m, 1H), 5.10 (d, J = 44.5 Hz, 1H), 5.00-4.88 (m, 4H), 4.66-4.52 m, 1H), 4.38-4.25 (m, 1H), 3.81-3.33 (m, 10H), 3.19-2.85 (m, 5H), 2.46 (s, 3H), 2.41-1.85 (m, 8H), 1.81-1.66 (m, 6H), 1.15 (t, J = 7.1 Hz, 3H). | 0.2 |
| 172 | 781 | 1H NMR (400 MHz, Methanol-d4) delta 8.90 (s, 1H), 7.95 (d, J = 8.1 Hz, 1H), 7.82-7.76 (m, 2H), 7.62 (s, 1H), 7.44 (s, 1H), 7.14 (d, J = 12.0 Hz, 1H), 5.31 (p, J = 6.3 Hz, 1H), 5.10 (d, J = 44.8 Hz, 1H), 4.99-4.86 (m, 4H), 4.66-4.52 (m, 1H), 4.40-4.30 (m, 1H), 4.13 (p, J = 6.5 Hz, 1H), 3.82-3.66 (m, 4H), 3.58-3.42 (m, 3H), 3.18-3.05 (m, 3H), 3.00-2.86 (m, 3H), 2.44 (s, 3H), 2.39-1.84 (m, 8H), 1.72 (d, J = 6.7, 6H), 1.16 (d, J = 6.7, 6H). | 0.3 |
| 173 | 715.5 | 1H NMR (400 MHz, DMSO-d6) delta 10.74 (s, 1H), 9.50 (s, 1H), 8.36 (s, 1H), 8.26-7.46 (m, 7H), 7.20 (d, J = 8.4 Hz, 1H), 4.78 (q, J = 7.6, 6.3 Hz, 4H), 4.59-3.99 (m, 3H), 3.43 (d, J = 9.1 Hz, 7H), 3.04-2.63 (m, 9H), 2.40-1.07 (m, 17H). | 0.08 |
| 174 | 678.5 | 1H NMR (400 MHz, DMSO-d6) delta 9.42 (d, J = 9.1 Hz, 1H), 8.83 (s, 1H), 8.64 (s, 1H), 8.54 (s, 1H), 7.88 (s, 1H), 7.76 (d, J = 7.8 Hz, 1H), 7.59 (s, 1H), 7.52 (d, J = 7.2 Hz, 2H), 7.39 (d, J = 7.7 Hz, 1H), 7.19 (d, J = 8.4 Hz, 1H), 5.40-5.28 (m, 1H), 4.55 (s, 1H), 4.43 (s, 1H), 4.33-4.24 (m, 1H), 3.55-3.42 (m, 1H), 3.39 (d, J = 12.0 Hz, 2H), 2.99-2.73 (m, 6H), 2.30 (s, 3H), 1.84 (d, J = 14.0 Hz, 2H), 1.76-1.61 (m, 2H), 1.57 (d, J = 6.4 Hz, 6H), 1.48-1.33 (m, 2H), 1.30 (s, 6H), 0.90-0.84 (m, 2H), 0.83-0.77 (m, 2H). | 0.09 |
| 175 | 638.4 | 1H NMR (400 MHz, DMSO-d6) delta 9.36 (d, J = 9.7 Hz, 1H), 8.77 (s, 1H), 8.41 (s, 1H), 8.19 (q, J = 4.5 Hz, 1H), 7.84 (s, 1H), 7.65 (dd, J = 7.8, 1.4 Hz, 1H), 7.61 (d, J = 8.3 Hz, 1H), 7.43 (d, J = 1.5 Hz, 1H), 7.35 (d, J = 7.8 Hz, 1H), 7.25-7.14 (m, 1H), 5.28 (p, J = 6.6 Hz, 1H), 4.15 (p, J = 8.3 Hz, 1H), 3.49 (p, J = 8.3 Hz, 1H), 3.37 (d, J = 11.8 Hz, 2H), 2.90 (dt, J = 11.7, 8.9 Hz, 2H), 2.84-2.73 (m, 3H), 2.71 (d, J = 4.6 Hz, 3H), 2.36 (d, J = 0.6 Hz, 3H), 1.82 (d, J = 14.1 Hz, 2H), 1.76-1.60 (m, 2H), 1.58 (d, J = 6.6 Hz, 6H), 1.47-1.33 (m, 1H), 1.26 (s, 6H). | 0.1 |
| 176 | 666.4 | 1H NMR (400 MHz, DMSO-d6) delta 9.38 (d, J = 9.5 Hz, 1H), 8.74 (s, 1H), 8.43 (s, 1H), 8.14 (d, J = 7.8 Hz, 1H), 7.83 (s, 1H), 7.65 (dd, J = 7.8, 1.5 Hz, 1H), 7.60 (d, J = 8.2 Hz, 1H), 7.45 (d, J = 1.4 Hz, 1H), 7.34 (d, J = 7.8 Hz, 1H), 7.18 (d, J = 12.1 Hz, 1H), 5.29 (p, J = 6.6 Hz, 1H), 4.17 (p, J = 8.3 Hz, 1H), 4.08-3.92 (m, 1H), 3.51 (h, J = 8.3 Hz, 1H), 3.38 (d, J = 11.9 Hz, 2H), 2.99-2.85 (m, 2H), 2.85-2.70 (m, 5H), 2.35 (d, J = 0.6 Hz, 3H), 1.82 (d, J = 14.1 Hz, 2H), 1.58 (d, J = 6.6 Hz, 9H), 1.38 (q, J = 12.3 Hz, 1H), 1.26 (s, 6H), 1.07 (d, J = 6.6 Hz, 6H). | 0.2 |
| 177 | 693.3 | 1H NMR (400 MHz, DMSO-d6) delta 9.38 (d, J = 9.7 Hz, 1H), 8.75 (s, 1H), 8.43 (s, 1H), 8.20 (q, J = 4.5 Hz, 1H), 7.89 (s, 1H), 7.75 (dd, J = 7.9, 1.4 Hz, 1H), 7.65 (d, J = 7.8 Hz, 1H), 7.58 (d, J = 8.2 Hz, 1H), 7.45 (d, J = 1.4 Hz, 1H), 7.19 (d, J = 12.1 Hz, 1H), 5.27 (q, J = 6.5 Hz, 1H), 4.36-4.26 (m, 2H), 4.14 (q, J = 8.1 Hz, 2H), 4.08-3.95 (m, 2H), 3.50 (q, J = 8.1 Hz, 1H), 3.37 (d, J = 11.6 Hz, 2H), 3.05-2.85 (m, 2H), 2.83-2.69 (m, 6H), 2.39-2.31 (m, 3H), 1.84 (m, 5H), 1.70 (d, J = 13.0 Hz, 1H), 1.58 (m, 7H), 1.40 (d, J = 13.0 Hz, 1H). | 0.4 |
| 178 | 707.4 | 1H NMR (400 MHz, DMSO-d6) delta 9.33 (s, 1H), 8.69 (s, 1H), 8.42 (s, 1H), 8.27 (t, J = 5.6 Hz, 1H), 7.89 (s, 1H), 7.74 (dd, J = 7.9, 1.4 Hz, 1H), 7.64 (d, J = 7.8 Hz, 1H), 7.57 (d, J = 8.2 Hz, 1H), 7.47 (d, J = 1.4 Hz, 1H), 7.18 (d, J = 12.1 Hz, 1H), 5.28 (p, J = 6.6 Hz, 1H), 4.30 (d, J = 9.2 Hz, 2H), 4.16 (p, J = 8.3 Hz, 1H), 4.07-3.96 (m, 2H), 3.50 (q, J = 8.1 Hz, 1H), 3.37 (d, J = 11.8 Hz, 2H), 3.27-3.14 (m, 2H), 2.94 (dt, J = 27.9, 10.3 Hz, 2H), 2.85-2.68 (m, 4H), 2.36 (d, J = 0.6 Hz, 3H), 1.85 (s, 5H), 1.57 (m, 8H), 1.41 (t, J = 12.6 Hz, 1H), 1.05 (t, J = 7.2 Hz, 3H). | 0.3 |

TABLE 1-continued

| Example # | ES/MS m/z | $^1$H-NMR | HPK1 IC$_{50}$ (nM) |
|---|---|---|---|
| 179 | 721.4 | 1H NMR (400 MHz, DMSO-d6) delta 9.32 (s, 1H), 8.67 (s, 1H), 8.42 (s, 1H), 8.15 (d, J = 7.8 Hz, 1H), 7.88 (s, 1H), 7.74 (dd, J = 7.8, 1.4 Hz, 1H), 7.64 (d, J = 7.8 Hz, 1H), 7.55 (d, J = 8.2 Hz, 1H), 7.48 (d, J = 1.4 Hz, 1H), 7.17 (d, J = 12.4 Hz, 1H), 5.39-5.12 (m, 1H), 4.31 (s, 2H), 4.17 (q, J = 8.2 Hz, 1H), 4.09-3.95 (m, 3H), 3.50 (q, J = 8.0 Hz, 1H), 3.38 (d, J = 11.5 Hz, 2H), 3.06-2.86 (m, 2H), 2.78 (dd, J = 13.9, 8.4 Hz, 3H), 2.39-2.33 (m, 3H), 1.85 (s, 5H), 1.57 (d, J = 6.5 Hz, 8H), 1.39 (d, J = 12.6 Hz, 1H), 1.08 (d, J = 6.6 Hz, 6H). | 1.1 |
| 180 | 753 | 1H NMR (400 MHz, Methanol-d4) delta 8.46 (s, 1H), 8.08 (t, J = 8.2 Hz, 1H), 7.77 (s, 1H), 7.72-7.66 (m, 1H), 7.63 (s, 1H), 7.43 (d, J = 7.8 Hz, 1H), 7.21 (t, J = 10.4 Hz, 1H), 5.26-5.20 (m, 1H), 4.21-4.13 (m, 2H), 4.07-3.97 (m, 2H), 3.97-3.88 (m, 1H), 3.84-3.76 (m, 1H), 2.79-2.36 (m, 9H), 2.18 (s, 3H), 1.92-1.41 (m, 15H), 1.23 (d, J = 6.8, 6H). | 0.2 |
| 181 | 718 | 1H NMR (400 MHz, Methanol-d4) delta 9.18 (s, 1H), 7.97 (s, 1H), 7.68 (dd, J = 7.9, 1.5 Hz, 1H), 7.50-7.40 (m, 4H), 7.34 (dd, J = 8.3, 2.5 Hz, 1H), 5.42-5.30 (m, 1H), 4.33-4.217 (m, 1H), 4.10-3.97 (m, 2H), 3.94-3.79 (m, 3H), 3.76-3.69 (m, 1H), 3.46-3.36 (m, 2H), 3.14-2.96 (m, 3H), 2.93-2.80 (m, 5H), 2.50 (s, 3H), 2.18 (s, 3H), 2.05-1.75 (m, 12H), 1.25 (d, J = 24.0 Hz, 6H). | 0.2 |
| 182 | 642 | 1H NMR (400 MHz, Methanol-d4) delta 8.52 (s, 1H), 8.23 (d, J = 6.7 Hz, 1H), 7.95 (s, 1H), 7.62 (d, J = 7.5 Hz, 1H), 7.38 (dd, J = 7.5, 1.4 Hz, 1H), 7.18 (s, 1H), 6.12 (d, J = 12.3 Hz, 1H), 5.73-5.63 (m, 1H), 4.64-4.46 (m, 1H), 2.93 (s, 3H), 2.48 (m, 2H), 2.12 (m, 2H), 1.79 (t, J = 7.1 Hz, 6H), 1.47 (d, J = 20.6 Hz, 6H), 1.35-1.11 (m, 8H), 0.92-0.83 (m, 2H).; 1H NMR (400 MHz, DMSO-d6) delta 8.50 (s, 1H), 8.40 (s, 1H), 8.16 (s, 1H), 7.93-7.76 (m, 3H), 7.60 (d, J = 7.9 Hz, 1H), 7.46-7.37 (m, 1H), 7.28 (d, J = 7.8 Hz, 1H), 5.27-5.17 (m, 1H), 4.37-7.27 (m, 1H), 3.28-3.25 (m, 1H) 2.77 (d, J = 3.6 Hz, 3H), 2.56-2.50 (m, 2H), 2.43-2.36 (m, 2H), 2.32-2.19 (m, 4H), 1.60-1.50 (m, 10H), 1.45-1.36 (m, 2H), 1.22 (s, 6H). | 0.2 |
| 183 | 618.4 | 1H NMR (400 MHz, DMSO-d6) delta 9.06 (s, 1H), 8.32 (s, 1H), 8.20 (s, 1H), 7.96 (d, J = 2.4 Hz, 1H), 7.89-7.82 (m, 2H), 7.80 (s, 1H), 7.71 (s, 1H), 7.61 (s, 1H), 7.42 (d, J = 7.8 Hz, 1H), 7.22 (d, J = 8.3 Hz, 1H), 4.46-4.37 (m, 1H), 3.29-3.17 (m, 2H), 3.02-2.94 (m, 2H), 2.94-2.86 (m, 2H), 2.77-2.70 (m, 3H), 2.34 (s, 3H), 1.87-1.79 (m, 3H), 1.74-1.63 (m, 2H), 1.52 (s, 3H), 1.32 (s, 7H), 1.30-1.22 (m, 5H). | 0.05 |
| 184 | 612.3 | 1H NMR (400 MHz, DMSO-d6) delta 9.29 (d, J = 10.4 Hz, 1H), 8.39 (s, 1H), 8.27 (s, 1H), 8.10 (d, J = 2.3 Hz, 1H), 8.07-8.00 (m, 1H), 7.94 (s, 1H), 7.77 (q, J = 2.8, 2.3 Hz, 3H), 7.68 (dd, J = 8.2, 2.4 Hz, 1H), 7.43 (s, 1H), 7.23 (d, J = 8.6 Hz, 1H), 4.43-4.30 (m, 1H), 4.21-4.11 (m, 1H), 3.40 (d, J = 11.9 Hz, 2H), 2.92 (t, J = 8.1 Hz, 4H), 2.87-2.73 (m, 2H), 2.36 (s, 3H), 1.88-1.51 (m, 6H), 1.41 (t, J = 12.6 Hz, 1H), 1.31-1.23 (m, 4H). | 0.9 |
| 185 | 747.3 | $^1$H NMR (400 MHz, DMSO-d6) δ 9.13 (bs, 1H), 8.97 (s, 1H), 8.76-8.58 (m, 3H), 8.04 (s, 1H), 7.72 (s, 1H), 7.40 (d, J = 7.0 Hz, 1H), 6.07 (t, J = 57.0 Hz, 1H), 5.38-5.15 (m, 1H), 4.32 (m, 1H), 3.23 (m, 2H), 2.93 (m, 4H), 2.70 (m, 2H), 2.28 (s, 3H), 1.85 (m, 2H), 1.76-1.38 (m, 13H), 1.31 (s, 6H), 1.15-1.05 (m, 2H), 0.93 (m, 2H). | 0.1 |
| 186 | 729.4 | $^1$H NMR (400 MHz, DMSO-d6) δ 9.09 (m, 1H), 8.80 (s, 1H), 8.73-8.60 (m, 3H), 8.03 (s, 1H), 7.72 (s, 1H), 7.37 (d, J = 6.9 Hz, 1H), 5.32-5.17 (m, 1H), 4.49 (d, J = 52 Hz, 2H), 4.32 (m, 1H), 3.23 (m, 2H), 2.94 (m, 4H), 2.76-2.59 (m, 2H), 2.28 (s, 3H), 1.85 (m, 2H), 1.69 (m, 13H), 1.31 (m, 6H), 0.86 (m, 4H). | .07 |
| 187 | 791.4 | $^1$H NMR (400 MHz, DMSO-d6) δ 9.54 (bs, 1H), 8.97 (s, 2H), 8.70 (s, 1H), 8.66 (s, 1H), 8.03 (s, 1H), 7.73 (s, 1H), 7.42 (d, J = 6.9 Hz, 1H), 6.06 (t, J = 57.0 Hz, 1H), 5.28 (m, 1H), 4.32 (m, 2H), 4.14 (m, 1H), 3.47 (m, 1H), 3.30 (m, 1H), 3.15 (m, 2H), 2.90 (m, 1H), 2.72-2.05 (m, 8H), 1.62-1.52 (m, 9H), 1.30 (s, 6H), 1.08 (m, 2H), 0.92-0.60 (m, 7H). | 0.2 |

TABLE 1-continued

| Example # | ES/MS m/z | ¹H-NMR | HPK1 IC$_{50}$ (nM) |
|---|---|---|---|
| 188 | 777.4 | ¹H NMR (400 MHz, DMSO-d6) δ 9.19 (s, 1H), 8.98 (s, 1H), 8.71 (d, J = 8.0 Hz, 2H), 8.03 (s, 1H), 7.78 (s, 1H), 7.42 (d, J = 6.9 Hz, 1H), 6.07 (t, J = 57.1 Hz, 1H), 5.38-5.20 (m, 1H), 4.41 (m, 1H), 3.87 (m, 2H), 3.28 (m, 3H), 3.04 (m, 2H), 2.86 (m, 1H), 2.63 (m, 3H), 2.29 (s, 3H), 1.60 (m, 8H), 1.45-1.19 (m, 12H), 1.07 (m, 2H), 0.93 (m, 2H). | 0.4 |
| 189 | 775.4 | ¹H NMR (400 MHz, DMSO-d6) δ 10.09 (m, 1H), 8.98 (s, 1H), 8.71 (s, 2H), 8.68 (s, 1H), 8.04 (s, 1H), 7.93 (d, J = 10.2 Hz, 1H), 7.43 (d, J = 6.9 Hz, 1H), 6.07 (t, J = 57.0 Hz, 1H), 5.30 (m, 1H), 4.51 (m, 1H), 3.85-3.67 (m, 4H), 3.58-3.43 (m, 3H), 3.33-3.10 (m, 3H), 3.02 (m, 2H), 2.82 (m, 2H), 2.29 (s, 3H), 1.70-1.61 (m, 4H), 1.60 (m, 6H), 1.31 (s, 6H), 1.08 (m, 2H), 0.93 (m, 2H). | 0.2 |
| 190 | 775.4 | ¹H NMR (400 MHz, DMSO-d6) δ 9.54 (bs, 1H), 8.98 (s, 1H), 8.69 (s, 2H), 8.67 (s, 1H), 8.03 (s, 1H), 7.74 (s, 1H), 7.41 (d, J = 7.0 Hz, 1H), 6.07 (t, J = 57.0 Hz, 1H), 5.28 (m, 1H), 4.47-4.28 (m, 4H), 3.85 (m, 1H), 3.36 (m, 1H), 3.31 (m, 1H), 3.10 (m, 1H), 3.01 (m, 1H), 2.79-2.59 (m, 2H), 2.34-2.23 (m, 4H), 2.03 (m, 1H), 1.89-1.68 (m, 3H), 1.62 (m, 9H), 1.31 (s, 6H), 1.08 (m, 2H), 0.93 (m, 2H). | 0.07 |
| 191 | 775.4 | ¹H NMR (400 MHz, DMSO-d6) δ 9.54 (bs, 1H), 8.98 (s, 1H), 8.69 (s, 2H), 8.67 (s, 1H), 8.03 (s, 1H), 7.74 (s, 1H), 7.41 (d, J = 7.0 Hz, 1H), 6.07 (t, J = 57.0 Hz, 1H), 5.28 (m, 1H), 4.47-4.28 (m, 4H), 3.85 (m, 1H), 3.36 (m, 1H), 3.31 (m, 1H), 3.10 (m, 1H), 3.01 (m, 1H), 2.79-2.59 (m, 2H), 2.34-2.23 (m, 4H), 2.03 (m, 1H), 1.89-1.68 (m, 3H), 1.62 (m, 9H), 1.31 (s, 6H), 1.08 (m, 2H), 0.93 (m, 2H). | 0.09 |
| 192 | 775.4 | ¹H NMR (400 MHz, DMSO-d6) δ 9.54 (bs, 1H), 8.98 (s, 1H), 8.69 (s, 2H), 8.67 (s, 1H), 8.03 (s, 1H), 7.74 (s, 1H), 7.41 (d, J = 7.0 Hz, 1H), 6.07 (t, J = 57.0 Hz, 1H), 5.28 (m, 1H), 4.47-4.28 (m, 4H), 3.85 (m, 1H), 3.36 (m, 1H), 3.31 (m, 1H), 3.10 (m, 1H), 3.01 (m, 1H), 2.79-2.59 (m, 2H), 2.34-2.23 (m, 4H), 2.03 (m, 1H), 1.89-1.68 (m, 3H), 1.62 (m, 9H), 1.31 (s, 6H), 1.08 (m, 2H), 0.93 (m, 2H). | 0.1 |
| 193 | 775.4 | ¹H NMR (400 MHz, DMSO-d6) δ 9.78 (m, 1H), 8.96 (s, 1H), 8.69 (d, J = 8.8 Hz, 2H), 8.64 (s, 1H), 8.03 (s, 1H), 7.74 (s, 1H), 7.42 (d, J = 6.9 Hz, 1H), 6.06 (t, J = 57.0 Hz, 1H), 5.27 (m, 1H), 4.36 (m, 1H), 4.00 (m, 1H), 3.80 (m, 1H), 3.60 (m, 1H), 3.34 (m, 1H), 3.27-3.12 (m, 2H), 3.01-2.89 (m, 2H), 2.65 (m, 2H), 2.28 (s, 3H), 1.65-1.50 (m, 9H), 1.31 (s, 6H), 1.11-1.04 (m, 2H), 0.96-0.86 (m, 3H), 0.84-0.70 (m, 3H). | 0.2 |
| 194 | 773.5 | ¹H NMR (400 MHz, DMSO-d6) δ 9.03 (s, 1H), 8.97 (s, 1H), 8.69 (d, J = 10.3 Hz, 2H), 8.64 (s, 1H), 8.02 (s, 1H), 7.70 (s, 1H), 7.41 (d, J = 6.9 Hz, 1H), 6.06 (t, J = 56.8 Hz, 1H), 5.27 (m, 1H), 4.30 (m, 1H), 3.33 (m, 2H), 3.13 (m, 1H), 2.98 (m, 1H), 2.81 (m, 1H), 2.67 (s, 3H), 2.31 (m, 2H), 2.08 (m, 1H), 1.90 (m, 3H), 1.65-1.47 (m, 7H), 1.31 (m, 7H), 1.08 (m, 2H), 0.95 (m, 3H), 0.63 (m, 1H), 0.55-0.40 (m, 3H). | 0.06 |
| 195 | 765.4 | ¹H NMR (400 MHz, DMSO-d6) δ 9.14 (s, 1H), 8.92 (s, 1H), 8.75 (s, 1H), 8.68 (s, 1H), 7.77 (s, 1H), 7.63 (d, J = 8.1 Hz, 1H), 7.37 (d, J = 7.0 Hz, 1H), 6.02 (t, J = 56.9 Hz, 1H), 5.29 (m, 1H), 4.24 (m, 1H), 3.19 (m, 2H), 2.91 (s, 4H), 2.59 (m, 2H), 2.26 (s, 3H), 1.83-1.36 (m, 15H), 1.31 (s, 6H), 1.07 (m, 2H), 0.89 (m, 2H). | 0.07 |
| 196 | 765.4 | ¹H NMR (400 MHz, DMSO-d6) δ 9.46 (m, 1H), 8.97 (s, 1H), 8.70 (d, J = 5.8 Hz, 2H), 8.65 (s, 1H), 8.03 (s, 1H), 7.71 (s, 1H), 7.41 (d, J = 7.0 Hz, 1H), 6.07 (t, J = 57.0 Hz, 1H), 5.34-5.26 (m, 1H), 5.19 (m, 1H), 4.33 (m, 1H), 3.59-3.43 (m, 1H), 3.43-3.18 (m, 2H), 3.15-2.86 (m, 3H), 2.76-2.60 (m, 2H), 2.29 (s, 3H), 2.05 (m, 14H), 1.31 (s, 6H), 1.12-1.02 (m, 2H), 0.93 (m, 2H). | 0.1 |
| 197 | 765 | ¹H NMR (400 MHz, DMSO-d6) δ 9.54 (m, 1H), 8.97 (s, 1H), 8.81-8.49 (m, 3H), 8.04 (s, 1H), 7.75 (s, 1H), 7.41 (m, 1H), 6.07 (t, J = 57.0 Hz, 1H), 5.39-5.14 (m, 1H), 5.02 (m, 1H), 4.33 (m, 1H), 3.40-2.98 (m, 7H), 2.71 (m, 2H), 2.38-1.84 (m, 7H), 1.65-1.43 (m, 9H), 1.30 (s, 6H), 1.00 (m, 4H). | 0.1 |

TABLE 1-continued

| Example # | ES/MS m/z | ¹H-NMR | HPK1 IC$_{50}$ (nM) |
|---|---|---|---|
| 198 | 783.3 | ¹H NMR (400 MHz, DMSO-d6) δ 9.61 (bs, 1H), 9.17 (s, 1H), 8.94 (s, 1H), 8.80-8.62 (m, 2H), 8.10 (s, 1H), 7.70 (d, J = 1.9 Hz, 1H), 7.50 (dd, J = 7.5, 2.2 Hz, 1H), 6.04 (t, J = 56.7 Hz, 1H), 5.26 (m, 1H), 4.29 (m, 1H), 3.93-3.76 (m, 3H), 3.39-3.19 (m, 4H), 2.99 (m, 2H), 2.72 (m, 2H), 2.05 (m, 2H), 1.71-1.49 (m, 10H), 1.31 (s, 6H), 1.21-1.03 (m, 2H), 1.03-0.88 (m, 2H). | 0.01 |
| 199 | 769.3 | ¹H NMR (400 MHz, DMSO-d6) δ 9.93 (bs, 1H), 9.17 (s, 1H), 8.95 (s, 1H), 8.72 (d, J = 1.7 Hz, 1H), 8.69 (s, 1H), 8.11 (s, 1H), 7.76 (d, J = 1.8 Hz, 1H), 7.51 (m, 1H), 6.05 (t, J = 57.0 Hz, 1H), 5.26 (m, 1H), 4.38 (m, 1H), 4.03 (m, 2H), 3.70 (m, 2H), 3.27 (m, 2H), 3.18-3.00 (m, 4H), 2.64 (m, 2H), 1.62-1.54 (m, 9H), 1.31 (s, 6H), 1.12-1.08 (m, 2H), 0.96-0.91 (m, 2H). | 0.1 |
| 200 | 771.3 | ¹H NMR (400 MHz, DMSO-d6) δ 9.18 (s, 1H), 8.94 (s, 1H), 8.71 (s, 1H), 8.69 (m, 2H), 8.11 (s, 1H), 7.97 (m, 1H), 7.54 (dd, J = 7.5, 2.1 Hz, 1H), 6.05 (t, J = 56.7 Hz, 1H), 5.52 (m, 1H), 5.27 (m, 1H), 4.58 (m, 1H), 3.97-3.68 (m, 2H), 3.67-3.38 (m, 2H), 3.28-3.15 (m, 2H), 2.47-2.34 (m, 3H), 2.34-1.95 (m, 1H), 1.66 (m, 3H), 1.59 (s, 6H), 1.31 (s, 6H), 1.12-1.07 (m, 2H), 0.96-0.90 (m, 2H). | 0.1 |
| 201 | 785.3 | ¹H NMR (400 MHz, DMSO-d6) δ 9.49 (m, 1H), 9.18 (s, 1H), 8.96 (s, 1H), 8.73 (d, J = 1.7 Hz, 1H), 8.70 (s, 1H), 8.10 (s, 1H), 7.70 (d, J = 1.8 Hz, 1H), 7.50 (dd, J = 7.5, 2.0 Hz, 1H), 6.05 (t, J = 56.8 Hz, 1H), 5.32-5.11 (m, 2H), 4.33 (m, 1H), 3.57-3.17 (m, 3H), 3.15-2.94 (m, 3H), 2.74-2.57 (m, 2H), 2.05-1.64 (m, 4H), 1.59 (d, J = 6.5 Hz, 6H), 1.54 (s, 3H), 1.32 (s, 6H), 1.12-1.08 (m, 2H), 0.96-0.91 (m, 2H). | 0.2 |
| 202 | 749.3 | ¹H NMR (400 MHz, DMSO-d6) δ 9.05 (m, 2H), 8.75 (s, 1H), 8.63 (d, J = 13.0 Hz, 2H), 8.07 (s, 1H), 7.74 (s, 1H), 7.68 (d, J = 8.2 Hz, 1H), 7.57 (d, J = 10.8 Hz, 1H), 6.07 (t, J = 57.0 Hz, 1H), 5.36-5.16 (m, 1H), 4.44-4.17 (m, 1H), 3.23 (m, 2H), 2.94 (m, 4H), 2.67 (m, 2H), 1.86 (m, 2H), 1.67-1.24 (m, 19H), 1.08 (m, 2H), 0.92 (m, 2H). | 0.1 |
| 203 | 793.3 | ¹H NMR (400 MHz, DMSO-d6) δ 9.14 (m, 2H), 8.95 (s, 1H), 8.76-8.62 (m, 2H), 8.09 (s, 1H), 7.69 (d, J = 1.9 Hz, 1H), 7.51 (m, 1H), 6.04 (t, J = 56.7 Hz, 1H), 5.26 (m, 1H), 4.30 (m, 1H), 3.41-3.23 (m, 2H), 3.14 (t, J = 10.4 Hz, 1H), 3.00 (m, 1H), 2.84 (t, J = 10.4 Hz, 1H), 2.64 (m, 2H), 2.00-1.77 (m, 3H), 1.59-1.52 (m, 10H), 1.31 (s, 6H), 1.17-1.03 (m, 2H), 0.95 (m, 3H), 0.65-0.57 (m, 1H), 0.49 (m, 3H). | 0.07 |
| 204 | 785.3 | ¹H NMR (400 MHz, DMSO-d6) δ 9.40 (s, 1H), 9.20 (d, J = 10.3 Hz, 1H), 8.96 (s, 1H), 8.78-8.44 (m, 2H), 8.11 (s, 1H), 7.71 (d, J = 1.8 Hz, 1H), 7.49 (m, 1H), 5.26 (m, 1H), 4.32 (m, 1H), 3.23 (m, 2H), 3.01-2.74 (m, 4H), 2.67 (m, 2H), 1.97-1.20 (m, 23H), 1.14 (m, 2H). | 0.2 |
| 205 | 779.3 | ¹H NMR (400 MHz, DMSO-d6) δ 10.15 (m, 1H), 9.17 (s, 1H), 8.92 (s, 1H), 8.70 (s, 1H), 8.66 (s, 1H), 8.11 (d, J = 2.7 Hz, 1H), 7.97 (s, 1H), 7.59-7.49 (m, 1H), 6.05 (t, J = 56.3 Hz, 1H), 5.26 (m, 1H), 4.63-4.52 (m, 1H), 3.72 (m, 2H), 3.33 (m, 4H), 3.07 (m, 2H), 2.22 (m, 2H), 1.88-1.24 (m, 18H), 1.10 (m, 2H), 0.94 (m, 2H). | 0.1 |
| 206 | 771.4 | ¹H NMR (400 MHz, DMSO-d6) δ 9.17 (bs, 1H), 8.86 (s, 1H), 8.76 (s, 1H), 8.65 (s, 1H), 8.45 (s, 1H), 8.03 (s, 1H), 7.77 (s, 1H), 7.58 (s, 1H), 7.19 (d, J = 12.0 Hz, 1H), 6.09 (t, J = 57.2 Hz, 1H), 5.29 (m, 1H), 4.33 (m, 1H), 4.11 (m, 1H), 3.98-3.88 (m, 1H), 3.22 (m, 2H), 3.02-2.84 (m, 4H), 2.70-2.61 (m, 2H), 2.35 (m, 3H), 1.85-1.35 (m, 21H), 1.07 (m, 2H), 0.92 (m, 2H). | 0.07 |
| 207 | 767.3 | ¹H NMR (400 MHz, DMSO-d6) δ 9.14 (m, 2H), 8.89 (s, 1H), 8.63 (m, 2H), 8.04 (s, 1H), 7.64 (s, 1H), 7.43 (m, 1H), 5.98 (t, J = 56.8 Hz, 1H), 5.20 (m, 1H), 4.25 (m, 1H), 3.16 (m, 2H), 2.96-2.77 (m, 4H), 2.62 (m, 2H), 1.78-1.45 (m, 15H), 1.24 (s, 6H), 1.04 (m, 2H), 0.87 (m, 2H). | 0.08 |
| 208 | 763.4 | ¹H NMR (400 MHz, DMSO-d6) δ 9.61 (bs, 1H), 8.97 (s, 1H), 8.69-8.63 (m, 3H), 8.03 (d, J = 2.1 Hz, 1H), 7.71 (s, 1H), 7.41 (d, J = 7.0 Hz, 1H), 6.07 (t, J = 56.4 Hz, 1H), 5.35-5.21 (m, 1H), 4.40-4.22 (m, 1H), | 0.09 |

TABLE 1-continued

| Example # | ES/MS m/z | ¹H-NMR | HPK1 IC$_{50}$ (nM) |
|---|---|---|---|
| | | 3.30 (m, 8H), 2.99 (m, 2H), 2.74 (m, 5H), 2.31 (m, 3H), 2.16-1.94 (m, 2H), 1.66-1.50 (m, 8H), 1.31 (m, 4H), 1.08 (m, 2H), 0.93 (m, 2H). | |
| 209 | 759.4 | ¹H NMR (400 MHz, DMSO-d6) δ 10.25 (bs, 1H), 8.98 (s, 1H), 8.74-8.64 (m, 3H), 8.05 (s, 1H), 7.97 (s, 1H), 7.44 (d, J = 6.8 Hz, 1H), 6.07 (t, J = 57.1 Hz, 1H), 5.29 (m, 1H), 4.57 (m, 1H), 3.77-3.49 (m, 2H), 3.32 (m, 4H), 3.21-2.93 (m, 2H), 2.43 (m, 2H), 2.29 (m, 5H), 1.95 (m, 11H), 1.30 (s, 6H), 1.08 (m, 2H), 0.93 (m, 2H). | 0.08 |
| 210 | 809.3 | ¹H NMR (400 MHz, DMSO-d6) δ 9.14 (m, 2H), 8.94 (s, 1H), 8.77 (d, J = 1.7 Hz, 1H), 8.65 (s, 1H), 8.13 (s, 1H), 7.73 (d, J = 1.8 Hz, 1H), 7.51 (dd, J = 7.5, 2.1 Hz, 1H), 6.04 (t, J = 56.8 Hz, 1H), 5.25 (m, 1H), 4.32 (m, 1H), 4.11 (m, 2H), 3.94 (m, 2H), 3.22 (m, 2H), 3.08-2.84 (m, 4H), 2.71-2.59 (m, 2H), 1.84-1.43 (m, 20H), 1.18-1.03 (m, 2H), 0.93 (m, 2H). | 0.08 |
| 211 | 749 | ¹H NMR (400 MHz, DMSO-d6) δ 9.15 (bs, 1H), 9.01 (s, 1H), 8.92 (s, 1H), 8.73 (d, J = 1.7 Hz, 1H), 8.67 (s, 1H), 8.10 (s, 1H), 7.71 (d, J = 1.8 Hz, 1H), 7.47 (m, 1H), 5.26 (m, 1H), 4.47 (d, J = 49.0 Hz, 2H), 4.32 (m, 1H), 3.23 (m, 2H), 2.95 (m, 4H), 2.67 (m, 2H), 1.85 (m, 2H), 1.81-1.38 (m, 13H), 1.31 (s, 6H), 0.95-0.75 (m, 4H). | 0.1 |
| 212 | 757.4 | ¹H NMR (400 MHz, DMSO-d6) δ 9.79 (bs, 1H), 8.87 (s, 1H), 8.77 (s, 1H), 8.69 (s, 1H), 8.48 (s, 1H), 8.07 (s, 1H), 8.00 (s, 1H), 7.66 (d, J = 8.0 Hz, 1H), 7.21 (d, J = 12.0 Hz, 1H), 6.10 (t, J = 57.3 Hz, 1H), 5.38-5.26 (m, 1H), 4.70-4.57 (m, 1H), 4.49-4.43 (m, 2H), 3.96 (m, 2H), 3.82 (m, 2H), 3.52-3.37 (m, 1H), 2.46-2.33 (m, 5H), 2.15 (m, 2H), 2.10-1.99 (m, 2H), 1.69 (s, 3H), 1.61 (d, J = 6.4 Hz, 6H), 1.31 (s, 6H), 1.09-1.04 (m, 2H), 0.95-0.90 (m, 2H). | 0.3 |
| 213 | 743.4 | ¹H NMR (400 MHz, DMSO-d6) δ 8.98 (m, 1H), 8.86 (s, 1H), 8.73 (s, 1H), 8.67 (s, 1H), 8.45 (s, 1H), 8.01 (s, 1H), 7.71 (s, 1H), 7.61 (d, J = 8.1 Hz, 1H), 7.18 (d, J = 12.1 Hz, 1H), 6.10 (t, J = 57.3 Hz, 1H), 5.29 (m, 1H), 4.21 (m, 1H), 3.28 (m, 2H), 2.96 (m, 3H), 2.87 (m, 3H), 2.35 (s, 3H), 1.91-1.80 (m, 4H), 1.69 (m, 3H), 1.59 (d, J = 6.4 Hz, 6H), 1.50-1.39 (m, 1H), 1.31 (s, 6H), 1.16 (m, 3H), 1.07 (m, 2H), 0.92 (m, 2H). | 0.3 |
| 214 | 733.4 | ¹H NMR (400 MHz, DMSO-d6) δ 9.23 (bs, 1H), 8.97 (s, 1H), 8.67 (s, 1H), 8.65 (s, 1H), 8.24 (s, 1H), 7.94 (s, 1H), 7.42 (s, 1H), 7.38 (d, J = 7.2 Hz, 1H), 6.08 (t, J = 57.0 Hz, 1H), 5.27 (m, 1H), 4.06 (m, 1H), 3.34-3.13 (m, 4H), 2.92 (m, 2H), 2.37-2.27 (m, 5H), 1.88 (m, 2H), 1.80-1.65 (m, 3H), 1.58-1.50 (m, 9H), 1.48-1.39 (m, 2H), 1.31 (s, 6H), 1.28 (m, 1H), 1.07 (m, 2H), 0.92 (m, 2H). | 0.1 |
| 215 | 731.4 | ¹H NMR (400 MHz, DMSO-d6) δ 10.12 (bs, 1H), 8.87 (s, 1H), 8.82 (s, 1H), 8.72 (s, 1H), 8.52 (s, 1H), 8.00 (d, J = 1.4 Hz, 1H), 7.78 (s, 1H), 7.62 (d, J = 8.0 Hz, 1H), 7.20 (d, J = 11.9 Hz, 1H), 6.10 (t, J = 57.4 Hz, 1H), 5.39-5.27 (m, 1H), 4.44-4.31 (m, 1H), 4.02 (m, 2H), 3.71 (m, 2H), 3.28-3.23 (m, 1H), 3.16-3.00 (m, 5H), 2.69-2.59 (m, 2H), 2.36 (s, 3H), 1.64-1.54 (m, 9H), 1.30 (s, 6H), 1.10-1.05 (m, 2H), 0.95-0.90 (m, 2H). | 0.1 |
| 216 | 729.4 | ¹H NMR (400 MHz, DMSO-d6) δ 9.12 (bs, 1H), 8.85 (s, 1H), 8.73 (s, 1H), 8.67 (d, J = 2.3 Hz, 1H), 8.45 (s, 1H), 8.00 (d, J = 2.4 Hz, 1H), 7.74 (s, 1H), 7.65-7.58 (m, 1H), 7.19 (d, J = 11.6 Hz, 1H), 6.09 (t, J = 57.8 Hz, 1H), 5.34-5.25 (m, 1H), 4.36-4.27 (m, 1H), 3.23 (m, 2H), 3.00-2.87 (m, 4H), 2.73-2.62 (m, 2H), 2.35 (s, 3H), 1.85 (m, 2H), 1.75-1.63 (m, 3H), 1.62-1.04 (m, 16H), 1.09-1.04 (m, 2H), 0.94-0.89 (m, 2H). | 0.1 |
| 217 | 721.3 | ¹H NMR (400 MHz, DMSO-d6) δ 9.13 (m, 1H), 8.80 (d, J = 6.7 Hz, 1H), 8.76-8.64 (m, 3H), 8.03 (d, J = 2.3 Hz, 1H), 7.70 (s, 1H), 7.40 (d, J = 7.0 Hz, 1H), 6.39-5.29 (m, 2H), 4.31 (m, 1H), 3.23 (m, 2H), 2.93 (m, 4H), 2.69 (m, 2H), 2.31 (s, 3H), 1.84 (m, 2H), 1.69 (m, 3H), 1.59 (m, 6H), 1.51 (s, 3H), 1.44 (m, 1H), 1.30 (m, 5H). | 0.06 |

TABLE 1-continued

| Example # | ES/MS m/z | ¹H-NMR | HPK1 IC$_{50}$ (nM) |
|---|---|---|---|
| 218 | 715.4 | ¹H NMR (400 MHz, DMSO-d6) δ 9.16-9.11 (m, 1H), 9.02 (s, 1H), 8.74 (s, 2H), 8.63 (s, 1H), 8.11-8.01 (m, 2H), 7.77-7.63 (m, 3H), 7.49 (m, 1H), 7.44-7.34 (m, 1H), 6.10 (t, J = 57.5 Hz, 1H), 5.37-5.26 (m, 1H), 4.32-4.21 (m, 1H), 3.18 (m, 2H), 2.96-2.84 (m, 4H), 2.58 (m, 2H), 1.85 (m, 2H), 1.73-1.62 (m, 3H), 1.60 (m, 6H), 1.50 (s, 3H), 1.45-1.37 (m, 1H), 1.29 (s, 6H), 1.12-1.07 (m, 2H), 0.95-0.90 (m, 2H). | 0.06 |
| 219 | 715.4 | ¹H NMR (400 MHz, DMSO-d6) δ 9.22 (bs, 1H), 8.85 (s, 1H), 8.64 (s, 1H), 8.41 (s, 1H), 8.26 (s, 1H), 7.91 (s, 1H), 7.67-7.53 (m, 2H), 7.46 (s, 1H), 7.17 (d, J = 12.1 Hz, 1H), 6.11 (t, J = 57.3 Hz, 1H), 5.32-5.22 (m, 1H), 4.10-4.03 (m, 1H), 3.34-3.14 (m, 4H), 2.92 (m, 2H), 2.37-2.27 (m, 5H), 1.88 (m, 2H), 1.80-1.65 (m, 3H), 1.58 (d, J = 6.5 Hz, 6H), 1.50 (s, 3H), 1.48-1.39 (m, 2H), 1.31 (s, 6H), 1.28 (m, 1H), 1.07 (m, 2H), 0.92 (m, 2H). | 0.2 |
| 220 | 699.4 | ¹H NMR (400 MHz, DMSO-d6) δ 9.16-9.03 (m, 1H), 8.76-8.56 (m, 3H), 8.27 (d, J = 7.5 Hz, 1H), 8.03 (s, 1H), 7.72 (s, 1H), 7.35 (d, J = 6.9 Hz, 1H), 5.27 (m, 1H), 4.31 (m, 1H), 4.03 (m, 1H), 3.24 (m, 2H), 2.93 (m, 5H), 2.83-2.65 (m, 2H), 2.29 (s, 3H), 1.85 (d, J = 13.6 Hz, 2H), 1.69 (m, 3H), 1.64-1.30 (m, 15H), 1.12 (m, 6H). | 0.09 |
| 221 | 697.4 | ¹H NMR (400 MHz, DMSO-d6) δ 9.12 (s, 1H), 8.75-8.59 (m, 2H), 8.44 (d, J = 4.1 Hz, 1H), 8.03 (s, 1H), 7.71 (s, 1H), 7.34 (d, J = 6.9 Hz, 1H), 5.39-5.15 (m, 1H), 4.46-4.20 (m, 1H), 3.23 (m, 2H), 2.93 (m, 4H), 2.82 (m, 1H), 2.69 (m, 2H), 2.29 (m, 2H), 1.85 (m, 2H), 1.69 (m, 3H), 1.62-1.40 (m, 9H), 1.31 (m, 5H), 0.67 (m, 2H), 0.58-0.43 (m, 2H). | 0.07 |
| 222 | 685.4 | ¹H NMR (400 MHz, DMSO-d6) δ 9.21 (s, 1H), 8.71 (d, J = 3.5 Hz, 3H), 8.40 (d, J = 6.3 Hz, 1H), 8.03 (d, J = 2.5 Hz, 1H), 7.70 (s, 1H), 7.36 (d, J = 7.0 Hz, 1H), 5.30 (m, 1H), 3.31-3.10 (m, 4H), 2.93 (m, 4H), 2.69 (m, 2H), 2.30 (s, 3H), 1.84 (m, 2H), 1.70 (m, 3H), 1.64-1.58 (m, 5H), 1.52 (m, 2H), 1.42 (m, 1H), 1.30 (m, 5H), 1.08 (m, 3H). | 0.06 |
| 223 | 653.4 | ¹H NMR (400 MHz, DMSO-d6) δ 9.30 (m, 1H), 8.78 (dd, J = 12.6, 2.4 Hz, 2H), 8.65 (s, 1H), 8.52 (d, J = 6.5 Hz, 1H), 8.11-8.01 (m, 2H), 7.70-7.64 (m, 2H), 7.44-7.34 (m, 1H), 5.40-5.28 (m, 1H), 4.32-4.19 (m, 1H), 3.35-3.22 (m, 1H), 3.16 (m, 2H), 2.96-2.83 (m, 4H), 2.60-2.51 (m, 2H), 1.84 (m, 2H), 1.71-1.42 (m, 14H), 1.29 (s, 6H), 1.11 (m, 3H). | 0.2 |
| 224 | 775.4 | ¹H NMR (400 MHz, DMSO-d6) δ 10.23 (bs, 1H), 9.93 (s, 1H), 8.98 (s, 1H), 8.67 (m, 3H), 8.04 (d, J = 12.1 Hz, 2H), 7.44 (d, J = 6.9 Hz, 1H), 6.07 (t, J = 57.0 Hz, 1H), 5.29 (m, 1H), 4.67 (m, 1H), 4.39-4.26 (m, 1H), 4.04 (m, 4H), 3.80 (m, 1H), 3.72 (m, 1H), 3.58 (m, 1H), 3.54-3.40 (m, 1H), 3.26 (m, 1H), 2.53 (m, 2H), 2.45 (m, 1H), 2.17-1.24 (m, 18H), 1.08 (m, 2H), 0.93 (m, 2H). | 0.06 |
| 225 | 779.3 | ¹H NMR (400 MHz, DMSO-d6) δ 9.17-9.11 (m, 2H), 8.93 (s, 1H), 8.73 (s, 1H), 8.66 (d, J = 2.7 Hz, 1H), 8.10 (d, J = 2.7 Hz, 1H), 7.69 (s, 1H), 7.50 (d, J = 7.2 Hz, 1H), 6.04 (t, J = 56.6 Hz, 1H), 5.25 (m, 1H), 4.30 (m, 1H), 3.64 (m, 1H), 3.02 (m, 2H), 2.88 (m, 2H), 2.65 (m, 3H), 2.25 (s, 1H), 1.98 (m, 1H), 1.64-1.51 (m, 6H), 1.44-1.10 (m, 11H), 0.93 (m, 2H), 0.78 (m, 1H), 0.62 (m, 1H). | 0.08 |
| 226 | 781.3 | ¹H NMR (400 MHz, DMSO-d6) δ 8.98 (s, 1H), 8.78-8.59 (m, 3H), 8.50 (s, 1H), 8.03 (d, J = 2.2 Hz, 1H), 7.82 (s, 1H), 7.42 (d, J = 7.0 Hz, 1H), 6.07 (t, J = 57.0 Hz, 1H), 5.28 (m, 1H), 4.42 (m, 1H), 3.23 (m, 4H), 3.10 (m, 2H), 2.43 (m, 2H), 2.29 (s, 3H), 1.79-1.55 (m, 14H), 1.52-1.40 (m, 1H), 1.32 (s, 6H), 1.08 (m, 2H), 0.93 (m, 2H). | 0.1 |
| 227 | 761.3 | ¹H NMR (400 MHz, DMSO-d6) δ 9.13 (s, 1H), 9.01 (s, 1H), 8.92 (s, 1H), 8.73 (d, J = 1.8 Hz, 1H), 8.68 (s, 1H), 8.09 (s, 1H), 7.68 (d, J = 1.8 Hz, 1H), 7.47 (dd, J = 7.5, 2.0 Hz, 1H), 5.26 (m, 1H), 4.48 (d, J = 52 Hz, 2H), 4.30 (m, 1H), 3.63 (m, 1H), 3.10-2.95 (m, | 0.1 |

TABLE 1-continued

| Example # | ES/MS m/z | ¹H-NMR | HPK1 IC$_{50}$ (nM) |
|---|---|---|---|
| | | 2H), 2.95-2.79 (m, 2H), 2.73-2.57 (m, 2H), 2.35-2.16 (m, 1H), 2.04-1.90 (m, 1H), 1.66-1.50 (m, 6H), 1.44 (s, 3H), 1.34-1.29 (m, 6H), 1.22 (m, 1H), 1.15-1.04 (m, 1H), 0.91 (m, 2H), 0.88-0.70 (m, 3H), 0.63 (m, 1H). | |
| 228 | 775.4 | ¹H NMR (400 MHz, DMSO-d6) δ 9.09 (s, 1H), 8.97 (s, 1H), 8.69 (d, J = 10.5 Hz, 2H), 8.63 (s, 1H), 8.03 (s, 1H), 7.85 (s, 1H), 7.42 (d, J = 7.0 Hz, 1H), 6.07 (t, J = 56.9 Hz, 1H), 5.38-5.15 (m, 1H), 4.57 (s, 2H), 4.49 (m, 1H), 3.32 (m, 2H), 3.27-3.10 (m, 4H), 2.29 (s, 3H), 2.02 (m, 4H), 1.62 (m, 11H), 1.32 (s, 6H), 1.07 (m, 2H), 0.93 (m, 2H). | 0.3 |
| 229 | 761.4 | ¹H NMR (400 MHz, DMSO-d6) δ 9.11 (s, 1H), 8.97 (s, 1H), 8.71 (s, 1H), 8.68 (s, 1H), 8.63 (d, J = 2.4 Hz, 1H), 8.03 (d, J = 2.4 Hz, 1H), 7.71 (s, 1H), 7.40 (d, J = 7.0 Hz, 1H), 6.07 (t, J = 57.0 Hz, 1H), 5.36-5.13 (m, 1H), 4.28 (m, 1H), 3.23 (m, 2H), 3.11 (m, 2H), 2.95 (m, 2H), 2.81-2.70 (m, 2H), 2.28 (m, 2H), 1.89 (m, 2H), 1.77 (m, 2H), 1.64 (m, 4H), 1.61-1.55 (m, 6H), 1.53 (m, 2H), 1.31 (s, 6H), 1.08 (m, 2H), 0.92 (m, 2H). | 0.08 |
| 230 | 773.4 | ¹H NMR (400 MHz, DMSO-d6) δ 8.98 (s, 1H), 8.78-8.59 (m, 3H), 8.50 (s, 1H), 8.03 (d, J = 2.2 Hz, 1H), 7.82 (s, 1H), 7.42 (d, J = 7.0 Hz, 1H), 6.07 (t, J = 57.0 Hz, 1H), 5.28 (m, 1H), 4.42 (m, 1H), 3.23 (m, 4H), 3.10 (m, 2H), 2.43 (s, 3H), 2.29 (s, 3H), 1.79 (s, 4H), 1.70 (m, 1H), 1.65-1.55 (m, 9H), 1.52-1.40 (m, 1H), 1.32 (s, 6H), 1.08 (m, 2H), 0.93 (m, 2H). | 0.1 |
| 231 | 759.4 | ¹H NMR (400 MHz, DMSO-d6) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07 (t, J = 57.0 Hz, 1H), 5.36-5.22 (m, 1H), 4.37-4.18 (m, 1H), 3.63 (m, 1H), 3.01 (m, 2H), 2.88 (m, 2H), 2.67 (m, 3H), 2.29 (s, 4H), 1.97 (m, 1H), 1.59 (d, J = 6.3 Hz, 6H), 1.44 (s, 3H), 1.31-1.24 (m, 7H), 1.09 (m, 3H), 0.93 (m, 3H), 0.78 (m, 1H), 0.61 (m, 1H). | 0.1 |
| 232 | 759.4 | ¹H NMR (400 MHz, DMSO-d6) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07 (t, J = 57.0 Hz, 1H), 5.36-5.22 (m, 1H), 4.37-4.18 (m, 1H), 3.63 (m, 1H), 3.01 (m, 2H), 2.88 (m, 2H), 2.67 (m, 3H), 2.29 (m, 4H), 1.97 (m, 1H), 1.59 (d, J = 6.3 Hz, 6H), 1.44 (s, 3H), 1.31-1.24 (m, 7H), 1.09 (m, 3H), 0.93 (m, 2H), 0.78 (m, 1H), 0.61 (m, 1H). | 0.09 |
| 233 | 759.4 | ¹H NMR (400 MHz, DMSO-d6) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07 (t, J = 57.0 Hz, 1H), 5.36-5.22 (m, 1H), 4.37-4.18 (m, 1H), 3.63 (m, 1H), 3.01 (m, 2H), 2.88 (m, 2H), 2.67 (m, 3H), 2.29 (m, 4H), 1.97 (m, 1H), 1.59 (d, J = 6.3 Hz, 6H), 1.44 (s, 3H), 1.31-1.24 (m, 7H), 1.09 (m, 3H), 0.93 (m, 2H), 0.78 (m, 1H), 0.61 (m, 1H). | 0.08 |
| 234 | 765.3 | ¹H NMR (400 MHz, DMSO-d6) δ 9.58 (s, 1H), 9.17 (s, 1H), 8.91 (s, 1H), 8.69 (d, J = 1.7 Hz, 1H), 8.65 (s, 1H), 8.11 (s, 1H), 7.98 (d, J = 1.8 Hz, 1H), 7.54 (dd, J = 7.5, 2.1 Hz, 1H), 6.05 (t, J = 56.8 Hz, 1H), 5.26 (m, 1H), 4.56 (m, 1H), 3.57 (m, 4H), 3.25 (m, 2H), 2.43-2.35 (m, 2H), 1.84 (m, 2H), 1.65 (s, 3H), 1.59 (m, 7H), 1.31 (s, 6H), 1.13-1.05 (m, 2H), 0.97-0.87 (m, 2H), 0.76 (m, 1H), 0.65 (m, 1H). | 0.3 |
| 235 | 728.4 | ¹H NMR (400 MHz, DMSO-d6) δ 9.17 (m, 1H), 8.84 (d, J = 2.1 Hz, 1H), 8.75 (s, 1H), 8.44 (s, 1H), 7.90 (d, J = 2.2 Hz, 1H), 7.71-7.60 (m, 2H), 7.45 (s, 1H), 7.36 (dd, J = 7.9, 2.3 Hz, 1H), 7.16 (dd, J = 12.1, 2.3 Hz, 1H), 6.07 (t, J = 57.0 Hz, 1H), 5.30 (m, 1H), 4.38-4.19 (m, 1H), 3.22 (m, 2H), 2.94 (m, 4H), 2.64 (m, 2H), 2.34 (d, J = 2.2 Hz, 3H), 1.84 (m, 2H), 1.78-1.64 (m, 3H), 1.59 (m, 6H), 1.51 (s, 3H), 1.29 (s, 6H), 1.07 (m, 2H), 0.87 (m, 2H). | 0.1 |
| 236 | 746.4 | ¹H NMR (400 MHz, DMSO-d6) δ 9.13 (s, 1H), 8.95 (d, J = 2.6 Hz, 1H), 8.67 (s, 2H), 7.93 (d, J = 2.6 Hz, 1H), 7.60 (m, 2H), 7.46-7.34 (m, 4H), 6.07 (t, J = 57.0 Hz, 1H), 5.28 (m, 1H), 4.30 (m, 1H), 3.22 (d, J = 11.8 Hz, 3H), 2.93 (m, 5H), 2.68 (d, J = 8.6 Hz, 3H), 2.27 (s, 3H), 1.84 (d, J = 13.3 Hz, 3H), 1.78-1.36 (m, 14H), 1.29 (m, 7H), 1.07 (m, 3H), 0.89 (m, 3H). | 0.07 |

TABLE 1-continued

| Example # | ES/MS m/z | ¹H-NMR | HPK1 IC$_{50}$ (nM) |
|---|---|---|---|
| 237 | 732.4 | ¹H NMR (400 MHz, DMSO-d6) δ 9.15 (s, 1H), 8.95 (s, 1H), 8.66 (d, J = 26.4 Hz, 2H), 7.76 (s, 1H), 7.39 (d, J = 6.9 Hz, 1H), 7.21 (d, J = 7.7 Hz, 1H), 7.02 (d, J = 4.1 Hz, 2H), 6.06 (t, J = 57.0 Hz, 1H), 5.37-5.19 (m, 1H), 3.90 (m, 1H), 3.23-3.06 (m, 4H), 3.00-2.79 (m, 3H), 2.27 (d, J = 9.2 Hz, 6H), 1.94-1.35 (m, 17H), 1.26 (s, 6H), 1.08 (m, 2H), 0.89 (m, 3H). | 0.3 |
| 238 | 714.4 | ¹H NMR (400 MHz, DMSO-d6) δ 9.04 (bs, 1H), 8.99 (s, 1H), 8.64 (d, J = 2.6 Hz, 1H), 8.54 (s, 1H), 8.08 (d, J = 7.8 Hz, 1H), 7.94 (d, J = 2.5 Hz, 1H), 7.68 (d, J = 7.9 Hz, 1H), 7.62 (m, 1H), 7.43 (s, 1H), 7.35 (m, 2H), 6.08 (t, J = 57.3 Hz, 1H), 5.28 (m, 1H), 4.21 (m, 1H), 3.17 (m, 3H), 2.89 (m, 5H), 1.85 (m, 3H), 1.80-1.63 (m, 2H), 1.63-1.55 (m, 6H), 1.47 (m, 4H), 1.28 (s, 6H), 1.10 (m, 2H), 0.91 (m, 2H). | 0.02 |
| 239 | 684.4 | ¹H NMR (400 MHz, DMSO-d6) δ 9.06 (m, 1H), 8.61 (s, 2H), 8.37 (m, 1H), 7.92 (d, J = 2.6 Hz, 1H), 7.65 (d, J = 8.0 Hz, 1H), 7.48-7.33 (m, 3H), 5.26 (m, 1H), 4.30 (m, 1H), 3.30-3.15 (m, 4H), 3.05-2.84 (m, 4H), 2.68 (m, 2H), 2.29 (s, 3H), 1.84 (m, 2H), 1.69-1.42 (m, 13H), 1.29 (s, 6H), 1.06 (m, 3H). | 0.04 |
| 240 | 652.4 | ¹H NMR (400 MHz, DMSO-d6) δ 9.12 (bs, 1H), 8.71 (s, 1H), 8.55 (s, 1H), 8.49 (d, J = 5.5 Hz, 1H), 8.09 (d, J = 7.8 Hz, 1H), 7.93 (d, J = 2.7 Hz, 1H), 7.70 (d, J = 7.9 Hz, 1H), 7.61 (m, 1H), 7.42 (s, 1H), 7.36 (m, 3H), 5.31 (m, 1H), 4.21 (m, 1H), 3.28 (m, 3H), 3.15 (m, 2H), 2.97-2.80 (m, 5H), 1.84 (m, 2H), 1.78-1.63 (m, 2H), 1.62-1.54 (m, 5H), 1.47 (m, 4H), 1.28 (s, 6H), 1.10 (m, 4H). | 0.09 |
| 241 | 766.3 | ¹H NMR (400 MHz, DMSO-d6) δ 9.12 (m, 2H), 8.69 (s, 1H), 8.00 (s, 1H), 7.66 (d, J = 7.8 Hz, 1H), 7.50 (d, J = 7.5, 2.0 Hz, 1H), 7.43-7.38 (m, 3), 6.02 (t, J = 56.8 Hz, 1H), 5.25 (m, 1H), 4.30 (m, 1H), 3.23 (m, 2H), 2.98 (m, 4H), 2.63 (m, 2H), 1.85 (m, 2H), 1.69-1.51 (m, 13H), 1.30 (s,6H), 1.10 (m, J = 6.3 Hz, 2H), 0.90 (m, 2H). | 0.1 |
| 242 | 733.3 | ¹H NMR (400 MHz, DMSO-d6) δ 9.20 (m, 1H), 9.08 (s, 1H), 8.91 (s, 1H), 8.73 (d, J = 5.8 Hz, 2H), 8.09 (d, J = 2.0 Hz, 1H), 7.90 (d, J = 6.3 Hz, 1H), 7.67 (d, J = 8.3 Hz, 2H), 6.08 (t, J = 57.1 Hz, 1H), 5.31 (m, 2H), 4.28 (m, 1H), 3.19 (m, 2H), 2.93 (m, 4H), 2.62 (m, 2H), 2.53-2.44 (m, 2H), 1.85-1.19 (m, 18H), 1.11 (m, 2H), 0.94 (m, 2H). | 0.07 |
| 243 | 732.4 | ¹H NMR (400 MHz, Methanol-d4) δ 9.22-9.06 (m, 2H), 8.06 (d, J = 6.2 Hz, 1H), 7.93 (s, 1H), 7.77-7.46 (m, 3H), 7.40 (dd, J = 7.8, 2.4 Hz, 1H), 5.96 (t, J = 57.3 Hz, 1H), 5.41 (m, 1H), 4.49-4.35 (m, 1H), 3.38 (m, 3H), 3.04 (m, 5H), 2.74 (m, 2H), 2.06 (m, 3H), 1.94-1.69 (m, 10H), 1.66-1.49 (m, 4H), 1.49-1.35 (m, 9H), 1.18 (m, 2H), 0.98 (m, 3H). | 0.05 |
| 244 | 752.3 | ¹H NMR (400 MHz, DMSO-d6) δ 9.46-9.26 (m, 1H), 9.15 (s, 1H), 8.95-8.86 (m, 1H), 8.73-8.61 (m, 1H), 7.97 (s, 1H), 7.65 (m, 1H), 7.52 (m, 1H), 7.46 (s, 1H), 7.38 (d, J = 7.8 Hz, 1H), 6.02 (t, J = 56.7 Hz, 1H), 5.25 (m, 1H), 4.20 (m, 1H), 3.54-3.34 (m, 3H), 3.04-2.92 (m, 2H), 2.89-2.72 (m, 4H), 1.85 (m, 2H), 1.78-1.53 (m, 9H), 1.49-1.36 (m, 1H), 1.29 (s, 6H), 1.13-1.06 (m, 2H), 0.95-0.86 (m, 2H). | 0.05 |
| 245 | 753.3 | ¹H NMR (400 MHz, DMSO-d6) δ 9.37 (s, 1H), 9.17 (s, 1H), 8.93 (s, 1H), 8.72 (d, J = 1.7 Hz, 1H), 8.67 (d, J = 1.2 Hz, 1H), 8.08 (s, 1H), 7.76 (d, J = 1.8 Hz, 1H), 7.54 (m, 1H), 6.04 (t, J = 56.7 Hz, 1H), 5.26 (m, 1H), 4.32-4.15 (m, 1H), 3.49 (m, 1H), 3.41 (m, 2H), 3.00-2.89 (m, 2H), 2.89-2.76 (m, 4H), 1.85 (m, 2H), 1.76-1.54 (m, 9H), 1.50-1.36 (m, 1H), 1.30 (s, 6H), 1.14-1.06 (m, 2H), 0.97-0.87 (m, 2H). | 0.1 |
| 246 | 733.3 | ¹H NMR (400 MHz, DMSO-d6) δ 9.43 (d, J = 9.2 Hz, 1H), 8.98 (s, 1H), 8.70 (m, 3H), 8.01 (d, J = 1.6 Hz, 1H), 7.76 (s, 1H), 7.43 (d, J = 7.0 Hz, 1H), 6.07 (t, J = 57.0 Hz, 1H), 5.30 (m, 1H), 4.40-4.05 (m, 1H), 3.45 (m, 3H), 2.88 (m, 6H), 2.30 (m, 3H), 2.00-1.52 (m, 12H), 1.30 (m, 7H), 1.12-0.85 (m, 4H). | 0.04 |
| 247 | 719.3 | ¹H NMR (400 MHz, DMSO-d6) δ 8.87 (s, 1H), 8.61 (m, 2H), 8.56 (m, 1H), 8.15 (d, J = 1.8 Hz, 1H), 7.94 (s, 1H), 7.53-7.42 (m, 1H), 5.26 (m, 1H), 4.65 (m, | 0.05 |

TABLE 1-continued

| Example # | ES/MS m/z | ¹H-NMR | HPK1 IC$_{50}$ (nM) |
|---|---|---|---|
| | | 1H), 3.24 (m, 2H), 2.62 (m, 2H), 2.45 (m, 4H), 2.20 (m, 2H), 1.58 (m, 14H), 1.28 (s, 6H), 1.18 (s, 3H), 1.09 (t, J = 7.2 Hz, 3H). | |
| 248 | 755.3 | ¹H NMR (400 MHz, DMSO-d6) δ 9.01 (m, 1H), 8.92 (s, 1H), 8.66-8.55 (m, 2H), 8.14 (d, J = 1.8 Hz, 1H), 7.95 (s, 1H), 7.53 (m, 1H), 6.13 (tt, J = 55.6, 3.8 Hz, 1H), 5.25 (m, 1H), 4.65 (m, 1H), 3.67 (m, 2H), 2.62 (m, 2H), 2.45 (m, 3H), 2.20 (m, 2H), 2.07 (s, 1H), 1.58 (m, 14H), 1.28 (s, 6H), 1.18 (s, 3H). | 0.05 |
| 249 | 763.3 | ¹H NMR (400 MHz, DMSO-d6) δ 9.08 (s, 1H), 9.01 (s, 1H), 8.90 (s, 1H), 8.73 (d, J = 1.7 Hz, 1H), 8.65 (s, 1H), 8.10 (s, 1H), 7.70 (d, J = 1.8 Hz, 1H), 7.47 (m, 1H), 5.25 (m, 1H), 4.47 (d, J = 49.0 Hz, 2H), 4.28 (m, 1H), 3.21 (m, 2H), 3.11 (m, 2H), 2.96 (m, 2H), 2.77-2.68 (m, 2H), 1.88 (m, 2H), 1.76 (m, 2H), 1.64 (m, 4H), 1.58 (d, J = 6.6 Hz, 6H), 1.54 (s, 3H), 1.31 (s, 6H), 0.91 (m, 2H), 0.85 (m, 2H). | 0.04 |
| 250 | 741.3 | ¹H NMR (400 MHz, DMSO-d6) delta 9.19 (s, 1H), 9.02 (m, 2H), 8.85-8.58 (m, 2H), 8.11 (s, 1H), 7.70 (d, J = 1.8 Hz, 1H), 7.49 (m, 1H), 6.39-5.91 (m, 1H), 5.27 (m, 1H), 4.31 (m, 1H), 3.67 (m, 2H), 3.23 (m, 2H), 3.03-2.80 (m, 4H), 2.67 (m, 2H), 1.78 (m, 4H), 1.65-1.49 (m, 8H), 1.49-1.36 (m, 3H), 1.31 (m, 5H). | 0.1 |
| 251 | 717.3 | ¹H NMR (400 MHz, DMSO-d6) δ 8.87 (s, 1H), 8.63 (d, J = 1.6 Hz, 1H), 8.61 (s, 1H), 8.56 (m, 1H), 8.16 (d, J = 1.8 Hz, 1H), 7.99 (s, 1H), 7.50 (m, 1H), 5.25 (m, 1H), 4.65 (m, 1H), 3.29-3.17 (m, 2H), 2.75 (m, 1H), 2.60 (m, 1H), 2.17 (m, 2H), 2.12-2.01 (m, 2H), 1.89 (m, 1H), 1.67 (m, 1H), 1.58 (m, 6H), 1.27 (s, 6H), 1.16-0.93 (m, 8H), 0.45 (m, 1H), 0.26 (m, 1H). | 0.04 |
| 252 | 717.3 | ¹H NMR (400 MHz, DMSO-d6) δ 8.87 (s, 1H), 8.63 (d, J = 1.6 Hz, 1H), 8.61 (s, 1H), 8.56 (m, 1H), 8.16 (d, J = 1.8 Hz, 1H), 7.99 (s, 1H), 7.50 (m, 1H), 5.25 (m, 1H), 4.65 (m, 1H), 3.29-3.17 (m, 2H), 2.75 (m, 1H), 2.60 (m, 1H), 2.17 (m, 2H), 2.12-2.01 (m, 2H), 1.89 (m, 1H), 1.67 (m, 1H), 1.58 (m, 6H), 1.27 (s, 6H), 1.16-0.93 (m, 8H), 0.45 (m, 1H), 0.26 (m, 1H). | 0.05 |
| 253 | 717.3 | ¹H NMR (400 MHz, DMSO-d6) δ 8.87 (s, 1H), 8.63 (d, J = 1.6 Hz, 1H), 8.61 (s, 1H), 8.56 (m, 1H), 8.16 (d, J = 1.8 Hz, 1H), 7.99 (s, 1H), 7.50 (m, 1H), 5.25 (m, 1H), 4.65 (m, 1H), 3.29-3.17 (m, 2H), 2.75 (m, 1H), 2.60 (m, 1H), 2.17 (m, 2H), 2.12-2.01 (m, 2H), 1.89 (m, 1H), 1.67 (m, 1H), 1.58 (m, 6H), 1.27 (s, 6H), 1.16-0.93 (m, 8H), 0.45 (m, 1H), 0.26 (m, 1H). | 0.05 |
| 254 | 731.3 | ¹H NMR (400 MHz, DMSO-d6) δ 8.87 (s, 1H), 8.63 (d, J = 1.7 Hz, 1H), 8.60 (s, 1H), 8.45 (d, J = 7.8 Hz, 1H), 8.16 (d, J = 1.8 Hz, 1H), 7.98 (s, 1H), 7.50 (m, 1H), 5.26 (m, 1H), 4.65 (m, 1H), 4.10-3.93 (m, 1H), 2.75 (m, 1H), 2.60 (m, 1H), 2.50 (m, 1H), 2.22-2.12 (m, 2H), 2.07 (m, 3H), 1.89 (m, 1H), 1.66 (m, 1H), 1.58 (m, 6H), 1.33-1.19 (m, 6H), 1.17-0.93 (m, 11H), 0.44 (m, 1H), 0.26 (m, 1H). | 0.05 |
| 255 | 715.4 | ¹H NMR (400 MHz, DMSO-d6) delta 9.17 (s, 1H), 8.74 (s, 1H), 8.70 (s, 1H), 8.35 (m, 1H), 7.77 (s, 1H), 7.60 (d, J = 8.1 Hz, 1H), 7.34 (d, J = 6.9 Hz, 1H), 5.30 (m, 1H), 4.22 (m, 1H), 3.60 (m, 1H), 3.22 (m, 2H), 3.04-2.82 (m, 4H), 2.79 (m, 2H), 2.72-2.49 (m, 3H), 2.27 (m, 3H), 2.25-2.18 (m, 1H), 1.96 (m, 1H), 1.59 (d, J = 6.5 Hz, 6H), 1.40 (s, 3H), 1.31 (s, 6H), 1.25-1.18 (m, 1H), 1.06 (t, J = 7.2 Hz, 3H), 0.81-0.73 (m, 1H), 0.66-0.54 (m, 1H). | 0.1 |
| 256 | 753.3 | ¹H NMR (400 MHz, DMSO-d6) delta 8.98 (s, 1H), 8.78-8.59 (m, 3H), 8.50 (s, 1H), 8.03 (d, J = 2.2 Hz, 1H), 7.82 (s, 1H), 7.42 (d, J = 7.0 Hz, 1H), 6.07 (t, J = 57.0 Hz, 1H), 5.28 (p, J = 6.9 Hz, 1H), 4.42 (q, J = 8.1 Hz, 1H), 3.23 (t, J = 11.5 Hz, 4H), 3.10 (t, J = 11.0 Hz, 2H), 2.43 (s, 3H), 2.29 (s, 3H), 1.79 (s, 4H), 1.70 (d, J = 11.5 Hz, 1H), 1.65-1.55 (m, 9H), 1.52-1.40 (m, 1H), 1.32 (s, 6H), 1.08 (s, 2H), 0.93 (s, 2H). | 0.05 |
| 257 | 761.3 | ¹H NMR (400 MHz, DMSO-J$_6$) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07-5.22 (m, 2H), 4.37-4.18 (m, 1H), 3.63 (m, 1H), 3.01 (m, 2H), 2.88 (m, 2H), 2.67 (m, 3H), 2.29 (m, 4H), | 0.1 |

TABLE 1-continued

| Example # | ES/MS m/z | $^1$H-NMR | HPK1 IC$_{50}$ (nM) |
|---|---|---|---|
| | | 1.97 (m, 1H), 1.59 (m, 7H), 1.44 (m, 3H), 1.31 (s, 6H), 1.24 (m, 2H), 1.09 (m, 3H), 0.93-0.78 (m, 4H), 0.61 (m, 1H). | |
| 258 | 761.3 | $^1$H NMR (400 MHz, DMSO-d$_6$) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07-5.22 (m, 2H), 4.37-4.18 (m, 1H), 3.63 (m, 1H), 3.01 (m, 2H), 2.88 (m, 2H), 2.67 (m, 3H), 2.29 (m, 4H), 1.97 (m, 1H), 1.59 (m, 7H), 1.44 (m, 3H), 1.31 (s, 6H), 1.24 (m, 2H), 1.09 (m, 3H), 0.93-0.78 (m, 4H), 0.61 (m, 1H). | 0.09 |
| 259 | 761.3 | $^1$H NMR (400 MHz, DMSO-d$_6$) δ 9.24-9.08 (m, 1H), 8.97 (s, 1H), 8.70 (m, 3H), 8.03 (d, J = 2.1 Hz, 1H), 7.70 (s, 1H), 7.41 (d, J = 6.9 Hz, 1H), 6.07-5.22 (m, 2H), 4.37-4.18 (m, 1H), 3.63 (m, 1H), 3.01 (m, 2H), 2.88 (m, 2H), 2.67 (m, 3H), 2.29 (m, 4H), 1.97 (m, 1H), 1.59 (m, 7H), 1.44 (m, 3H), 1.31 (s, 6H), 1.24 (m, 2H), 1.09 (m, 3H), 0.93-0.78 (m, 4H), 0.61 (m, 1H). | 0.09 |
| 260 | 779.3 | $^1$H NMR (400 MHz, DMSO-d6) δ 9.17 (s, 1H), 9.11 (s, 1H), 8.93 (s, 1H), 8.73 (s, 1H), 8.66 (d, J = 2.7 Hz, 1H), 8.10 (d, J = 2.7 Hz, 1H), 7.69 (s, 1H), 7.50 (d, J = 7.2 Hz, 1H), 6.04 (t, J = 56.6 Hz, 1H), 5.25 (m, 1H), 4.30 (m, 1H), 3.64 (m, 1H), 3.02 (m, 2H), 2.88 (m, 2H), 2.65 (m, 3H), 2.25 (m, 1H), 1.98 (m, 1H), 1.64-1.51 (m, 6H), 1.44 (m, 2H), 1.31 (m, 5H), 1.24 (m, 1H), 1.10 (m, 3H), 0.93 (m, 2H), 0.78 (m, 1H), 0.62 (m, 1H). | 0.08 |
| 261 | 779.3 | $^1$H NMR (400 MHz, DMSO-d6) δ 9.17 (s, 1H), 9.11 (s, 1H), 8.93 (s, 1H), 8.73 (s, 1H), 8.66 (d, J = 2.7 Hz, 1H), 8.10 (d, J = 2.7 Hz, 1H), 7.69 (s, 1H), 7.50 (d, J = 7.2 Hz, 1H), 6.04 (t, J = 56.6 Hz, 1H), 5.25 (m, 1H), 4.30 (m, 1H), 3.64 (m, 1H), 3.02 (m, 2H), 2.88 (m, 2H), 2.65 (m, 3H), 2.25 (m, 1H), 1.98 (m, 1H), 1.64-1.51 (m, 6H), 1.44 (m, 2H), 1.31 (m, 5H), 1.24 (m, 1H), 1.10 (m, 3H), 0.93 (m, 2H), 0.78 (m, 1H), 0.62 (m, 1H). | 0.09 |
| 262 | 779.3 | $^1$H NMR (400 MHz, DMSO-d6) δ 9.17 (s, 1H), 9.11 (s, 1H), 8.93 (s, 1H), 8.73 (s, 1H), 8.66 (d, J = 2.7 Hz, 1H), 8.10 (d, J = 2.7 Hz, 1H), 7.69 (s, 1H), 7.50 (d, J = 7.2 Hz, 1H), 6.04 (t, J = 56.6 Hz, 1H), 5.25 (m, 1H), 4.30 (m, 1H), 3.64 (m, 1H), 3.02 (m, 2H), 2.88 (m, 2H), 2.65 (m, 3H), 2.25 (m, 1H), 1.98 (m, 1H), 1.64-1.51 (m, 6H), 1.44 (m, 2H), 1.31 (m, 5H), 1.24 (m, 1H), 1.10 (m, 3H), 0.93 (m, 2H), 0.78 (m, 1H), 0.62 (m, 1H). | 0.1 |
| 263 | 779.3 | $^1$H NMR (400 MHz, DMSO-d6) δ 10.07 (bs, 1H), 9.18 (m, 2H), 8.93 (s, 1H), 8.75-8.62 (m, 2H), 8.15-8.04 (m, 2H), 7.89 (d, J = 1.8 Hz, 1H), 7.53 (dd, J = 7.5, 2.1 Hz, 1H), 6.05 (t, J = 56.9 Hz, 1H), 5.26 (m, 1H), 4.50 (m, 1H), 3.32 (m, 1H), 3.27-3.07 (m, 4H), 2.72 (m, 1H), 1.92-1.68 (m, 5H), 1.69-1.53 (m, 9H), 1.43 (m, 1H), 1.32 (d, J = 5.8 Hz, 6H), 1.10 (m, 2H), 0.94 (m, 3H). | 0.05 |
| 264 | 763.3 | $^1$H NMR (400 MHz, DMSO-d6) δ 9.21 (m, 1H), 9.05 (s, 1H), 8.74 (d, J = 1.7 Hz, 1H), 8.71 (s, 1H), 8.61 (s, 1H), 8.07 (s, 1H), 7.73 (d, J = 1.8 Hz, 1H), 7.62 (d, J = 8.2 Hz, 1H), 6.08 (t, J = 57.1 Hz, 1H), 5.28 (m, 1H), 4.33 (m, 1H), 3.22 (m, 2H), 2.98-2.85 (m, 4H), 2.65 (m, 2H), 2.34 (m, 3H), 1.84 (m, 2H), 1.75-1.62 (m, 3H), 1.59 (d, J = 6.6 Hz, 6H), 1.51 (s, 3H), 1.49-1.39 (m, 1H), 1.31 (s, 6H), 1.10-1.05 (m, 2H), 0.95-0.89 (m, 2H). | 0.2 |
| 265 | 717.3 | $^1$H NMR (400 MHz, DMSO-d6) δ 9.07 (s, 1H), 8.90 (s, 1H), 8.73 (d, J = 1.7 Hz, 1H), 8.63 (d, J = 7.5 Hz, 2H), 8.10 (s, 1H), 7.71 (d, J = 1.7 Hz, 1H), 7.44 (m, 1H), 5.25 (m, 1H), 4.33 (m, 1H), 3.22 (s, 1H), 3.03-2.86 (m, 4H), 2.81 (m, 1H), 2.73-2.60 (m, 1H), 1.86 (m, 2H), 1.69 (m, 3H), 1.58 (d, J = 6.5 Hz, 6H), 1.52 (s, 3H), 1.43 (m, 1H), 1.31 (s, 6H), 0.69 (m, 2H), 0.55-0.41 (m, 2H). | 0.06 |
| 266 | 702.4 | $^1$H NMR (400 MHz, DMSO-d6) δ 9.03 (s, 1H), 8.66 (m, 1H), 8.61 (s, 1H), 8.42-8.38 (m, 1H), 7.90 (s, 1H), 7.70-7.60 (m, 2H), 7.45 (d, J = 1.4 Hz, 1H), 7.36 (d, J = 7.8 Hz, 1H), 7.17 (d, J = 12.1 Hz, 1H), | 0.06 |

TABLE 1-continued

| Example # | ES/MS m/z | $^1$H-NMR | HPK1 IC$_{50}$ (nM) |
|---|---|---|---|
| | | 6.09 (m, 1H), 5.27 (m, 1H), 4.27 (m, 1H), 3.65-3.54 (m, 2H), 3.22 (m, 2H), 2.92 (m, 4H), 2.71-2.58 (m, 3H), 2.36 (s, 3H), 1.84 (m, 2H), 1.69 (m, 3H), 1.58 (d, J = 6.6 Hz, 6H), 1.51 (s, 3H), 1.29 (s, 6H). | |
| 267 | 719.3 | $^1$H NMR (400 MHz, DMSO-d6) δ 9.16 (s, 1H), 8.94 (s, 1H), 8.74 (d, J = 1.7 Hz, 1H), 8.68 (d, J = 12.0 Hz, 1H), 8.47 (d, J = 7.7 Hz, 1H), 8.10 (s, 1H), 7.71 (m, 1H), 7.44 (m, 1H), 5.27 (m, 1H), 4.32 (m, 1H), 4.11-3.88 (m, 1H), 3.23 (m, 2H), 2.94 (m, 4H), 2.67 (m, 2H), 1.85 (m, 2H), 1.70 (m, 3H), 1.59 (d, J = 6.5 Hz, 6H), 1.52 (s, 3H), 1.43 (m, 1H), 1.31 (s, 6H), 1.13 (d, J = 6.6 Hz, 6H). | 0.1 |
| 268 | 720.4 | $^1$H NMR (400 MHz, DMSO-d6) δ 9.10 (s, 1H), 8.79 (m, 1H), 8.67 (d, J = 9.0 Hz, 2H), 7.93 (s, 1H), 7.64 (m, 1H), 7.44-7.35 (m, 3H), 6.11 (m, 1H), 5.34-5.23 (m, 1H), 4.29 (m, 1H), 3.72-3.55 (m, 1H), 3.23 (m, 2H), 2.93 (m, 4H), 2.66 (m, 2H), 2.30 (m, , 3H), 1.84 (m, 2H), 1.74-1.36 (m, 13H), 1.29 (s, 6H). | 0.03 |
| 269 | 739.3 | $^1$H NMR (400 MHz, DMSO-d6) delta 9.04 (s, 1H), 8.82-8.70 (m, 2H), 8.64 (s, 1H), 7.77 (d, J = 1.9 Hz, 1H), 7.62 (d, J = 8.1 Hz, 1H), 7.36 (d, J = 7.1 Hz, 1H), 6.36-5.82 (m, 1H), 5.28 (m, 1H), 4.24 (m, 1H), 3.81-3.55 (m, 1H), 3.24-3.10 (m, 2H), 2.90 (m, 3H), 2.59 (m, 2H), 2.38-2.19 (m, 3H), 1.93-1.81 (m, 2H), 1.68 (s, 3H), 1.58 (d, J = 6.6 Hz, 6H), 1.48 (s, 3H), 1.41 (m, 1H), 1.31 (s, 6H). | 0.07 |
| 270 | 749.3 | $^1$H NMR (400 MHz, DMSO-d6) delta 9.10 (d, J = 8.3 Hz, 1H), 8.98 (s, 1H), 8.72 (s, 1H), 8.53 (m, 1H), 7.84 (d, J = 1.8 Hz, 1H), 7.61 (d, J = 8.2 Hz, 1H), 7.44 (m, 1H), 5.33-5.22 (m, 1H), 4.31-4.18 (m, 1H), 3.40-3.17 (m, 4H), 3.11 (m, 1H), 3.04-2.90 (m, 1H), 2.78 (m, 1H), 2.58-2.51 (m, 1H), 2.49-2.44 (m, 1H), 1.99-1.78 (m, 3H), 1.62-1.54 (m, 8H), 1.50 (s, 3H), 1.31 (s, 6H), 1.16-1.02 (m, 3H), 0.95 (m, 1H), 0.65-0.58 (m, 1H), 0.55-0.40 (m, 3H). | 0.1 |
| 271 | 703.4 | $^1$H NMR (400 MHz, DMSO-d6) delta 9.06 (s, 1H), 8.71 (s, 1H), 8.66 (s, 1H), 8.35 (m, 1H), 7.76 (d, J = 2.0 Hz, 1H), 7.62 (d, J = 8.1 Hz, 1H), 7.34 (m, 1H), 5.28 (m, 1H), 4.23 (m, 1H), 3.22 (m, 4H), 2.98-2.81 (m, 4H), 2.71-2.57 (m, 2H), 2.27 (m, 3H), 1.84 (m, 2H), 1.68 (s, 3H), 1.58 (d, J = 6.6 Hz, 6H), 1.48 (s, 3H), 1.31 (s, 6H), 1.06 (t, J = 7.2 Hz, 3H). | 0.06 |
| 272 | 759.3 | $^1$H NMR (400 MHz, DMSO-d6) delta 9.07 (s, 1H), 9.04-8.91 (m, 2H), 8.68 (s, 1H), 7.84 (d, J = 1.8 Hz, 1H), 7.63 (d, J = 8.2 Hz, 1H), 7.46 (m, 1H), 6.10 (tt, J = 55.5, 3.6 Hz, 1H), 5.26 (m, 1H), 4.24 (m, 1H), 3.66 (m, 2H), 3.19 (m, 2H), 2.91 (m, 4H), 1.84 (m, 2H), 1.66 (m, 4H), 1.58 (d, J = 6.6 Hz, 6H), 1.48 (m, 4H), 1.31 (s, 6H). | 0.09 |
| 273 | 723.3 | $^1$H NMR (400 MHz, DMSO-d6) delta 9.19 (s, 1H), 8.99 (s, 1H), 8.72 (s, 1H), 8.54 (m, 1H), 7.84 (d, J = 1.8 Hz, 1H), 7.63 (d, J = 8.2 Hz, 1H), 7.43 (m, 1H), 5.27 (m, 1H), 4.26 (m, 1H), 3.32-3.10 (m, 4H), 3.10-2.83 (m, 4H), 2.63-2.56 (m, 1H), 1.84 (m, 2H), 1.70 (m, 2H), 1.58 (m, 7H), 1.49 (m, 4H), 1.31 (s, 6H), 1.08 (t, J = 7.2 Hz, 3H). | 0.07 |
| 274 | 725.3 | $^1$H NMR (400 MHz, DMSO-d6) delta 9.28 (m, 1H), 8.90 (m, 1H), 8.84 (s, 1H), 8.74 (s, 1H), 8.71 (s, 1H), 8.06 (s, 1H), 7.67 (s, 1H), 7.60 (m, 1H), 6.15 (tt, J = 55.7, 3.8 Hz, 1H), 5.29 (m, 1H), 4.30 (m, 1H), 3.71 (m, 2H), 3.21 (m, 2H), 2.99-2.83 (m, 4H), 2.64 (m, 2H), 1.84 (m, 2H), 1.75-1.65 (m, 3H), 1.60 (d, J = 6.5 Hz, 6H), 1.50 (s, 3H), 1.45-1.36 (m, 1H), 1.30 (s, 6H). | 0.04 |
| 275 | 738.3 | $^1$H NMR (400 MHz, DMSO-d6) δ 9.05-8.92 (m, 3H), 8.66 (s, 1H), 8.01 (s, 1H), 7.65 (m, 1H), 7.53-7.44 (m, 2H), 7.07 (d, J = 7.9 Hz, 1H), 6.11 (tt, J = 55.6, 3.7 Hz, 1H), 5.25 (m, 1H), 4.38 (m, 1H), 3.21 (m, 2H), 3.05-2.82 (m, 5H), 2.75-2.61 (m, 2H), 1.84 (m, 3H), 1.77-1.35 (m, 14H). | 0.06 |
| 276 | 666.4 | $^1$H NMR (400 MHz, DMSO-d6) delta 9.03 (s, 1H), 8.60 (s, 1H), 8.34 (s, 1H), 8.24 (m, 1H), 7.89 (s, 1H), 7.71-7.63 (m, 2H), 7.47 (d, J = 1.4 Hz, 1H), 7.36 (d, J = 7.8 Hz, 1H), 7.14 (d, J = 12.2 Hz, 1H), 5.27 (m, 1H), 4.29 (m, 1H), 3.22 (m, 2H), 2.92 (m, 4H), 2.70-2.59 (m, 4H), 2.35 (m, 3H), 1.84 (m, 2H), 1.69 (t, J = | 0.06 |

TABLE 1-continued

| Example # | ES/MS m/z | ¹H-NMR | HPK1 IC$_{50}$ (nM) |
|---|---|---|---|
| | | 14.5 Hz, 3H), 1.58 (d, J = 6.6 Hz, 6H), 1.51 (s, 3H), 1.29 (s, 6H), 1.05 (t, J = 7.2 Hz, 3H). | |
| 277 | 765.3 | ¹H NMR (400 MHz, DMSO-d6) delta 9.05 (s, 1H), 8.81-8.73 (m, 2H), 8.66 (s, 1H), 7.76 (d, J = 2.0 Hz, 1H), 7.59 (d, J = 8.2 Hz, 1H), 7.37 (m, 1H), 6.10 (tt, J = 55.8, 3.7 Hz, 1H), 5.28 (m, 1H), 4.22 (m, 1H), 3.39-3.21 (m, 2H), 3.02 (m, 2H), 2.75 (m, 1H), 2.53 (m, 5H), 2.28 (m, 3H), 1.87 (m, 3H), 1.58 (m, 6H), 1.48 (s, 3H), 1.31 (d, J = 1.2 Hz, 6H), 0.95 (m, 1H), 0.61 (m, 1H), 0.54-0.36 (m, 3H). | 0.07 |
| 278 | 689.4 | ¹H NMR (400 MHz, DMSO-d6) delta 9.24 (m, 1H), 8.80 (s, 1H), 8.74 (s, 1H), 8.72 (s, 1H), 8.51 (m, 1H), 8.06 (s, 1H), 7.67 (s, 1H), 7.57 (m, 1H), 5.29 (m, 1H), 4.35-4.28 (m, 1H), 3.28 (m, 2H), 3.21 (m, 2H), 2.96 (m, 2H), 2.89 (m, 2H), 2.64 (m, 2H), 1.84 (m, 2H), 1.70 (m, 4H), 1.60 (d, J = 6.5 Hz, 6H), 1.50 (s, 3H), 1.30 (s, 6H), 1.11 (t, J = 7.2 Hz, 3H). | 0.2 |
| 279 | 729.4 | ¹H NMR (400 MHz, DMSO-d6) delta 9.08 (m, 1H), 8.72 (s, 1H), 8.35 (m, 1H), 7.76 (d, J = 1.9 Hz, 1H), 7.60 (d, J = 8.2 Hz, 1H), 7.35 (d, J = 6.9 Hz, 1H), 5.29 (m, 1H), 4.22 (m, 1H), 3.38-3.14 (m, 3H), 3.13-3.04 (m, 1H), 2.95 (m, 1H), 2.77 (m, 1H), 2.28 (m, 3H), 1.99-1.77 (m, 4H), 1.59-1.56 (m, 6H), 1.49 (s, 3H), 1.31 (s, 6H), 1.06 (t, J = 7.1 Hz, 3H), 0.65-0.58 (m, 1H), 0.52-0.38 (m, 3H). | 0.1 |
| 280 | 751.3 | ¹H NMR (400 MHz, DMSO-d6) delta 9.20 (m, 1H), 9.10 (s, 1H), 8.80 (s, 1H), 8.71 (s, 2H), 8.06 (s, 1H), 7.69 (s, 1H), 7.54 (m, 1H), 6.05 (t, J = 56.7 Hz, 1H), 5.28 (m, 1H), 4.29 (m, 1H), 3.21 (m, 2H), 2.95 (m, 4H), 2.65 (m, 2H), 1.85 (m, 2H), 1.77-1.64 (m, 4H), 1.60 (d, J = 6.7 Hz, 6H), 1.50 (s, 3H), 1.30 (s, 6H), 1.11 (m, 2H), 0.95 (m, 2H). | 0.05 |
| 281 | 691.3 | ¹H NMR (400 MHz, DMSO-d6) delta 9.04 (s, 1H), 8.89 (s, 1H), 8.74 (d, J = 1.7 Hz, 1H), 8.64 (s, 1H), 8.50 (d, J = 4.7 Hz, 1H), 8.10 (s, 1H), 7.71 (d, J = 1.8 Hz, 1H), 7.43 (d, J = 7.1 Hz, 1H), 5.25 (m, 1H), 4.40-4.22 (m, 1H), 3.23 (m, 2H), 2.95 (m, 4H), 2.75 (m, 3H), 2.72-2.59 (m, 1H), 2.41-2.28 (m, 1H), 1.94-1.76 (m, 2H), 1.69 (m, 3H), 1.59 (s, 3H), 1.52 (m, 4H), 1.31 (s, 6H). | 0.07 |
| 282 | 767.3 | ¹H NMR (400 MHz, DMSO-d6) delta 9.13 (m, 1H), 9.02 (m, 1H), 8.99 (s, 1H), 8.73 (d, J = 1.7 Hz, 1H), 8.70 (s, 1H), 8.10 (s, 1H), 7.67 (d, J = 1.8 Hz, 1H), 7.49 (m, 1H), 6.13 (tt, J = 55.6, 3.7 Hz, 1H), 5.27 (m, 1H), 4.29 (m, 1H), 3.67 (m, 2H), 3.39-3.24 (m, 2H), 3.19-3.10 (m, 1H), 3.03-2.92 (m, 1H), 2.87-2.79 (m, 1H), 2.68-2.58 (m, 2H), 2.53-2.45 (m, 1H), 1.98-1.77 (m, 3H), 1.59 (m, 6H), 1.52 (s, 3H), 1.31 (s, 6H), 0.96 (m, 1H), 0.66-0.59 (m, 1H), 0.54-0.40 (m, 3H). | 0.1 |
| 283 | 731.3 | ¹H NMR (400 MHz, DMSO-d6) delta 9.10 (m, 1H), 8.93 (s, 1H), 8.74 (d, J = 1.7 Hz, 1H), 8.70 (s, 1H), 8.57 (m, 1H), 8.09 (s, 1H), 7.68 (d, J = 1.8 Hz, 1H), 7.45 (m, 1H), 5.26 (m, 1H), 4.30 (m, 1H), 3.39-3.20 (m, 4H), 3.19-3.10 (m, 1H), 3.04-2.92 (m, 1H), 2.82 (m, 1H), 2.68-2.58 (m, 2H), 2.50 (m, 1H), 1.98-1.80 (m, 3H), 1.58 (m, 6H), 1.52 (s, 3H), 1.31 (s, 6H), 1.09 (t, J = 7.2 Hz, 3H), 0.99-0.91 (m, 1H), 0.66-0.59 (m, 1H), 0.54-0.41 (m, 3H). | 0.09 |
| 284 | 747.4 | ¹H NMR (400 MHz, DMSO-d6) delta 9.00 (s, 1H), 8.80 (m, 1H), 8.76-8.67 (m, 2H), 8.60 (s, 1H), 8.03 (s, 1H), 7.69 (d, J = 1.8 Hz, 1H), 7.40 (d, J = 7.1 Hz, 1H), 6.33-5.94 (m, 1H), 5.27 (m, 1H), 4.40-4.16 (m, 1H), 3.76-3.57 (m, 1H), 3.22-3.07 (m, 1H), 2.98 (m, 1H), 2.81 (m, 1H), 2.72-2.59 (m, 2H), 2.32 (m, 3H), 1.90 (m, 4H), 1.70-1.40 (m, 10H), 1.31 (s, 6H), 0.96 (m, 1H), 0.62 (m, 2H), 0.58-0.40 (m, 2H). | 0.1 |
| 285 | 711.4 | ¹H NMR (400 MHz, DMSO-d6) δ 9.27-9.06 (m, 1H), 8.86-8.64 (m, 3H), 8.39 (m, 1H), 8.02 (s, 1H), 7.68 (d, J = 1.8 Hz, 1H), 7.37 (m, 1H), 5.76 (m, 1H), 5.30 (m, 1H), 4.29 (m, 1H), 3.43-3.19 (m, 4H), 3.15 (m, 1H), 2.99 (m, 1H), 2.83 (m, 1H), 2.65 (m, 2H), 2.30 (m, 3H), 1.99-1.79 (m, 3H), 1.67-1.41 (m, 9H), 1.31 (s, 6H), 1.08 (t, J = 7.2 Hz, 3H), 0.96 (m, 1H), 0.62 (m, 1H), 0.54-0.33 (m, 2H). | 0.1 |

TABLE 1-continued

| Example # | ES/MS m/z | ¹H-NMR | HPK1 IC$_{50}$ (nM) |
|---|---|---|---|
| 286 | 705.3 | ¹H NMR (400 MHz, DMSO-d6) delta 9.12 (s, 1H), 8.92 (s, 1H), 8.74 (d, J = 1.7 Hz, 1H), 8.67 (s, 1H), 8.57 (m, 1H), 8.10 (d, J = 2.9 Hz, 1H), 7.71 (d, J = 1.8 Hz, 1H), 7.45 (m, 1H), 5.26 (m, 1H), 4.32 (m, 1H), 3.34-3.14 (m, 4H), 2.95 (m, 4H), 2.67 (m, 2H), 1.85 (m, 2H), 1.69 (t, J = 13.8 Hz, 2H), 1.64-1.38 (m, 9H), 1.30 (m, 5H), 1.09 (t, J = 7.2 Hz, 3H). | 0.1 |
| 287 | 740.3 | ¹H NMR (400 MHz, DMSO-d6) delta 9.13 (s, 1H), 9.00 (m, 1H), 8.94 (s, 1H), 8.66 (s, 1H), 8.00 (s, 1H), 7.66 (m, 1H), 7.48 (m, 1H), 7.43 (d, J = 1.4 Hz, 1H), 7.39 (d, J = 7.8 Hz, 1H), 6.11 (tt, J = 55.6, 3.7 Hz, 1H), 5.31-5.20 (m, 1H), 4.35-4.25 (m, 1H), 3.66 (m, 2H), 3.22 (m, 2H), 3.06-2.82 (m, 4H), 2.65 (m, 2H), 1.85 (m, 3H), 1.69 (m, 3H), 1.58 (d, J = 6.6 Hz, 6H), 1.51 (s, 3H), 1.29 (s, 6H). | 0.08 |
| 288 | 704.3 | ¹H NMR (400 MHz, DMSO-d6) delta 9.12 (s, 1H), 8.89 (s, 1H), 8.66 (s, 1H), 8.56 (m, 1H), 8.00 (s, 1H), 7.67 (m, 1H), 7.49 (m, 1H), 7.44 (d, J = 1.4 Hz, 1H), 7.39 (d, J = 7.8 Hz, 1H), 5.25 (m, 1H), 4.29 (m, 1H), 3.23 (m, 4H), 3.06-2.83 (m, 5H), 2.64 (m, 2H), 1.85 (m, 2H), 1.69 (m, 3H), 1.58 (d, J = 6.6 Hz, 6H), 1.52 (s, 3H), 1.29 (s, 6H), 1.07 (t, J = 7.2 Hz, 3H). | 0.08 |
| 289 | 722.3 | ¹H NMR (400 MHz, DMSO-d6) delta 9.13 (d, J = 10.2 Hz, 1H), 8.90 (m, 1H), 8.68 (d, J = 2.2 Hz, 2H), 7.97 (s, 1H), 7.68 (m, 2H), 7.56 (d, J = 10.9 Hz, 1H), 7.45 (d, J = 1.5 Hz, 1H), 7.38 (d, J = 7.8 Hz, 1H), 6.09 (tt, J = 55.8, 3.8 Hz, 1H), 5.26 (m, 1H), 4.30 (m, 1H), 3.65 (m, 2H), 3.22 (m, 2H), 3.03-2.83 (m, 5H), 2.62 (m, 2H), 1.85 (m, 2H), 1.69 (m, 3H), 1.58 (d, J = 6.6 Hz, 6H), 1.52 (s, 3H), 1.29 (s, 6H). | 0.07 |
| 290 | 686.3 | ¹H NMR (400 MHz, DMSO-d6) delta 9.15 (d, J = 10.7 Hz, 1H), 8.68 (s, 1H), 8.63 (d, J = 1.8 Hz, 1H), 8.46 (m, 1H), 7.97 (s, 1H), 7.73-7.67 (m, 2H), 7.53 (d, J = 10.9 Hz, 1H), 7.46 (d, J = 1.5 Hz, 1H), 7.38 (d, J = 7.8 Hz, 1H), 5.26 (m, 1H), 4.29 (m, 1H), 3.29-3.17 (m, 4H), 2.93 (m, 5H), 2.63 (m, 2H), 1.85 (m, 2H), 1.68 (m, 3H), 1.58 (d, J = 6.6 Hz, 6H), 1.53 (s, 3H), 1.29 (s, 6H), 1.07 (t, J = 7.2 Hz, 3H). | 0.07 |
| 291 | 785.3 | ¹H NMR (400 MHz, DMSO-d6) delta 9.15 (s, 1H), 9.12 (s, 1H), 8.99 (s, 1H), 8.70 (s, 1H), 7.84 (s, 1H), 7.64 (d, J = 8.1 Hz, 1H), 7.48 (d, J = 7.2 Hz, 1H), 6.00 (t, J = 56.7 Hz, 1H), 5.27 (m, 1H), 4.25 (m, 1H), 3.19 (m, 2H), 2.92 (m, 4H), 2.60-2.53 (m, 2H), 1.84 (m, 2H), 1.75-1.63 (m, 2H), 1.58 (d, J = 6.5 Hz, 6H), 1.48 (s, 3H), 1.31 (s, 6H), 1.09 (m, 2H), 0.91 (m, 2H). | 0.08 |
| 292 | 748.3 | ¹H NMR (400 MHz, DMSO-d6) delta 9.06 (s, 1H), 8.98 (s, 1H), 8.87 (s, 1H), 8.63 (s, 1H), 8.00 (s, 1H), 7.66 (m, 1H), 7.49 (m, 1H), 7.44 (d, J = 1.4 Hz, 1H), 7.39 (d, J = 7.8 Hz, 1H), 5.24 (m, 1H), 4.46 (m, 2H), 4.29 (m, 1H), 3.23 (m, J = 11.6 Hz, 2H), 2.94 (m, 5H), 2.65 (m, 2H), 1.85 (m, 2H), 1.69 (m, 3H), 1.57 (d, J = 6.6 Hz, 6H), 1.51 (s, 3H), 1.30 (s, 6H), 0.97-0.74 (m, 4H). | 0.07 |
| 293 | 730.3 | ¹H NMR (400 MHz, DMSO-d6) delta 9.11 (s, 1H), 8.88 (s, 1H), 8.70-8.59 (m, 2H), 7.96 (s, 1H), 7.69 (m, 2H), 7.52 (d, J = 10.8 Hz, 1H), 7.45 (d, J = 1.5 Hz, 1H), 7.38 (d, J = 7.7 Hz, 1H), 5.26 (m, 1H), 4.47 (d, J = 49.1 Hz, 2H), 4.30 (m, 1H), 3.22 (m, 2H), 2.93 (m, 5H), 2.63 (m, 2H), 1.85 (m, 2H), 1.69 (m, 2H), 1.58 (d, J = 6.5 Hz, 6H), 1.53 (s, 3H), 1.43 (m, 1H), 1.29 (s, 6H), 0.89 (m, 2H), 0.80 (m, 2H). | 0.05 |
| 294 | 748.3 | ¹H NMR (400 MHz, DMSO-d6) delta 9.07 (m, 2H), 8.69-8.58 (m, 2H), 7.97 (s, 1H), 7.73-7.66 (m, 2H), 7.54 (d, J = 10.9 Hz, 1H), 7.46 (d, J = 1.4 Hz, 1H), 7.38 (d, J = 7.8 Hz, 1H), 6.04 (t, J = 57.0 Hz, 1H), 5.32-5.19 (m, 1H), 4.30 (m, 1H), 3.22 (m, 3H), 2.93 (m, 5H), 2.64 (m, 2H), 1.85 (m, 2H), 1.69 (m, 2H), 1.58 (d, J = 6.6 Hz, 6H), 1.53 (s, 3H), 1.29 (s, 6H), 1.12-1.05 (m, 2H), 0.89 (m, 2H). | 0.08 |
| 295 | 728.4 | ¹H NMR (400 MHz, DMSO-d6) δ 9.02 (m, 1H), 8.85 (s, 1H), 8.77 (s, 1H), 8.50 (s, 1H), 7.82 (s, 1H), 7.67 (m, 1H), 7.45 (d, J = 8.2 Hz, 1H), 7.38 (d, J = 7.8 Hz, 1H), 7.28 (d, J = 1.4 Hz, 1H), 7.19 (d, J = 11.9 Hz, 1H), 6.09 (t, J = 57.2 Hz, 1H), 5.31 (m, 1H), 3.68 (m, 1H), 3.34 (m, 2H), 2.80-2.56 (m, 6H), 2.39 (s, 3H), | 0.1 |

TABLE 1-continued

| Example # | ES/MS m/z | ¹H-NMR | HPK1 IC$_{50}$ (nM) |
|---|---|---|---|
| | | 1.82 (m, 2H), 1.70 (m, 1H), 1.60 (m, 6H), 1.56-1.48 (m, 1H), 1.45 (s, 3H), 1.37 (m, 1H), 1.32-1.16 (m, 8H), 1.12-1.05 (m, 2H), 0.90 (m, 2H). | |
| 296 | 766.3 | ¹H NMR (400 MHz, DMSO-d6) δ 9.17 (s, 1H), 8.99 (d, J = 9.4 Hz, 1H), 8.90 (s, 1H), 8.61 (s, 1H), 7.95 (s, 1H), 7.68 (m, 1H), 7.45-7.34 (m, 2H), 7.27 (m, 1H), 6.03 (t, J = 56.7 Hz, 1H), 5.23 (m, 1H), 3.35 (m, 3H), 2.74 (m, 4H), 2.68-2.58 (m, 2H), 1.82 (m, 2H), 1.71 (m, 1H), 1.58 (m, 6H), 1.53-1.45 (m, 5H), 1.28 (s, 6H), 1.24 (m, 1H), 1.15-1.07 (m, 2H), 0.93 (m, 2H). | 0.1 |
| 297 | 767.3 | ¹H NMR (400 MHz, DMSO-d6) δ 9.19 (s, 1H), 9.10 (d, J = 9.7 Hz, 1H), 8.94 (s, 1H), 8.79 (m, 1H), 8.65 (s, 1H), 8.10 (s, 1H), 7.51 (m, 1H), 7.45-7.38 (m, 1H), 6.05 (t, J = 56.7 Hz, 1H), 5.25 (m, 1H), 3.70 (m, 1H), 3.37 (m, 2H), 2.84-2.60 (m, 7H), 1.83 (m, 2H), 1.71-1.59 (m, 7H), 1.54 (m, 1H), 1.48 (s, 3H), 1.40 (m, 1H), 1.30 (s, 6H), 1.16-1.08 (m, 2H), 0.95 (m, 2H). | 0.2 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

What is claimed is:
1. A compound of Formula I,

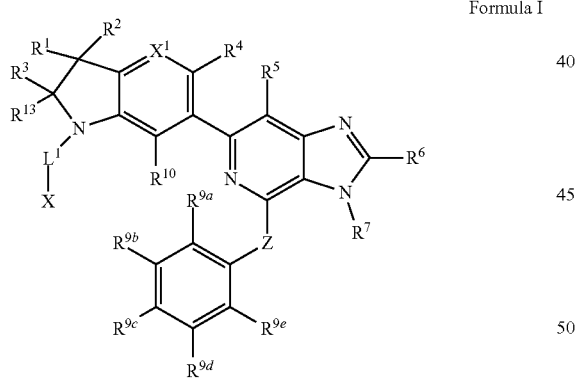

Formula I or a pharmaceutically acceptable salt thereof, wherein:
one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or
$R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or
$R^1$ and $R^2$ together form =O;
$R^{11}$ is
i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
ii) —S(O)$_2$C$_{1-6}$ alkyl,
iii) —S(O)$_2$C$_{3-7}$ monocyclic cycloalkyl,
iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
v) —C(O)R$^{21}$;
$R^{21}$ is
i) H,
ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from OH, halogen, and $C_{1-3}$ alkoxy,
iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, $C_{1-3}$ alkyl, and $C_{1-3}$ alkoxy,
v) —NH$_2$,
vi) —NH(C$_{1-6}$ alkyl), wherein the $C_{1-6}$ alkyl is optionally substituted with 1-3 groups independently selected from —CN, —OH, and $C_{1-3}$ alkoxy,
vii) —N(C$_{1-6}$ alkyl)$_2$, wherein each $C_{1-6}$ alkyl can be the same or different and wherein each $C_{1-6}$ alkyl is optionally substituted with 1-3 groups independently selected from —CN, —OH, and $C_{1-3}$ alkoxy, viii) $C_{1-6}$ alkoxy optionally substituted with 1-3 groups independently selected from —OH, halogen, $C_{1-3}$ alkyl, and $C_{3-7}$ monocyclic cycloalkyl, or
ix) $C_{1-6}$ alkyl optionally substituted with 1-3 groups independently selected from
   a) —CN,
   b) —OH,
   c) halogen,
   d) $C_{1-3}$ alkoxy,
   e) $C_{3-7}$ monocyclic cycloalkyl optionally substituted with 1-3 groups independently selected from —CN, —OH, halogen, $C_{1-3}$ alkyl, and $C_{1-3}$ alkoxy,
   f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
   g) —OC(O)$C_{1-6}$ alkyl optionally substituted with one —OH;
$R^3$ and $R^{13}$ are each H, or
$R^3$ and $R^{13}$ together form =O;
$L^1$ is a cyclobutylene optionally substituted with 1-6 groups independently selected from —OH, halogen, $C_{1-3}$ alkyl, and $C_{1-3}$ alkoxy;
X is —NR$^{15}$R$^{16}$, wherein R$^{15}$ and R$^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
   a) —CN,
   b) —OH,
   c) halogen,
   d) $C_{1-3}$ alkoxy,
   e) $C_{3-7}$ monocyclic cycloalkyl optionally substituted with 1-3 groups independently selected from —OH, halogen, $C_{1-3}$ alkyl, and $C_{1-3}$ alkoxy, and
   f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
   i) —CN,
   ii) a halogen,
   iii) —OH,
   iv) $C_{1-6}$ alkoxy optionally substituted with 1-3 groups independently selected from —OH, halogen, $C_{1-3}$ alkyl, and $C_{3-7}$ monocyclic cycloalkyl,
   v) $C_{1-6}$ alkyl optionally substituted with 1-3 groups independently selected from —OH, halogen, $C_{1-3}$ alkoxy, and $C_{3-7}$ monocyclic cycloalkyl,
   vi) —COOH, or
   vii) —C(O)N(R$^{22}$)$_2$, wherein each R$^{22}$ is independently H or $C_{1-6}$ alkyl;
$X^1$ is N or CR$^{17}$;
$R^4$, $R^5$, $R^6$, $R^{10}$ and $R^{17}$ are each independently H, halogen, $C_{1-3}$ alkyl, or $C_{1-3}$ alkoxy;
$R^7$ is
   i) H,
   ii) $C_{1-6}$ alkyl optionally substituted with 1-3 groups independently selected from —OH, halogen, $C_{1-3}$ alkoxy, and $C_{3-7}$ monocyclic cycloalkyl, or
   iii) $C_{3-7}$ monocyclic cycloalkyl optionally substituted with 1-3 groups independently selected from —OH, halogen, $C_{1-3}$ alkyl, and $C_{1-3}$ alkoxy;
Z is —O—, —C(R$^8$)$_2$—, or —NR$^8$—;
each R$^8$ is independently H or $C_{1-3}$ alkyl;
$R^{9a}$, $R^{9b}$, $R^{9c}$, $R^{9d}$, and $R^{9e}$ are independently
   i) H,
   ii) halogen,
   iii) $C_{1-6}$ alkoxy optionally substituted with 1-3 groups independently selected from —OH, halogen, $C_{1-3}$ alkyl, and $C_{3-7}$ monocyclic cycloalkyl,
   iv) —NH$_2$,
   v) —NH($C_{1-6}$ alkyl), wherein the $C_{1-6}$ alkyl is optionally substituted with 1-3 groups independently selected from —OH, halogen, and $C_{1-3}$ alkoxy,
   vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
   vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
   viii) —S(O)$_2$$C_{1-6}$ alkyl,
   ix) —S(O)$_2$N(R$^{23}$)$_2$, wherein each R$^{23}$ is independently H or $C_{1-6}$ alkyl,
   x) $C_{1-6}$ alkyl optionally substituted with 1-3 groups independently selected from
      a) —OH,
      b) halogen,
      c) $C_{1-3}$ alkoxy,
      d) $C_{3-7}$ monocyclic cycloalkyl,
      e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
      f) —NR$^{20}$C(O)OC$_{1-3}$ alkyl, wherein R$^{20}$ is H or $C_{1-3}$ alkyl,
   xi) $C_{3-7}$ monocyclic cycloalkyl optionally substituted with 1-3 groups independently selected from —OH, halogen, $C_{1-3}$ alkyl, and $C_{1-3}$ alkoxy,
   xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
   xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
   xiv) —COOH, xv) —C(O)N($R^{19}$)$_2$, or
xvi) —C$_{1-3}$alkylC(O)N($R^{19}$)$_2$,
wherein one or more of $R^{9a}$, $R^{9b}$, $R^{9c}$, $R^{9d}$, and $R^{9e}$ is —C(O)N($R^{19}$)$_2$ or —C$_{1-3}$alkylC(O)N($R^{19}$)$_2$; and
each $R^{19}$ is independently
  i) H,
  ii) —S(O)$_2$C$_{1-6}$ alkyl,
  iii) C$_{1-6}$ alkyl optionally substituted with 1-6 groups independently selected from —CN, —OH, halogen, C$_{1-3}$ alkoxy, and C$_{3-7}$ monocyclic cycloalkyl,
  iv) C$_{3-7}$ monocyclic cycloalkyl optionally substituted with 1-6 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —CN, —OH, halogen, and C$_{1-3}$ alkoxy, or
  v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, C$_{1-3}$ alkyl, and C$_{1-3}$ alkoxy.

2. The compound of claim 1, wherein the compound is of Formula II:

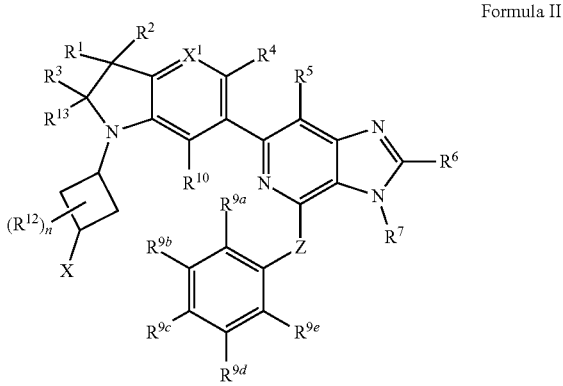

Formula II or a pharmaceutically acceptable salt thereof,
wherein
each $R^{12}$ is independently —OH, halogen, C$_{1-3}$ alkyl, or C$_{1-3}$ alkoxy; and
n is 0, 1, 2, 3, or 4.

3. The compound of claim 2, wherein the compound is of Formula IIa:

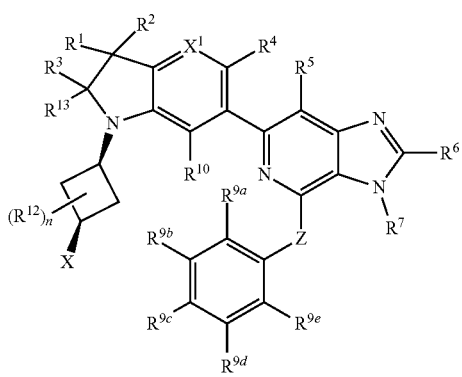

Formula IIa or a pharmaceutically acceptable salt thereof.

4. The compound of claim 3, wherein the compound has a Formula IIb:

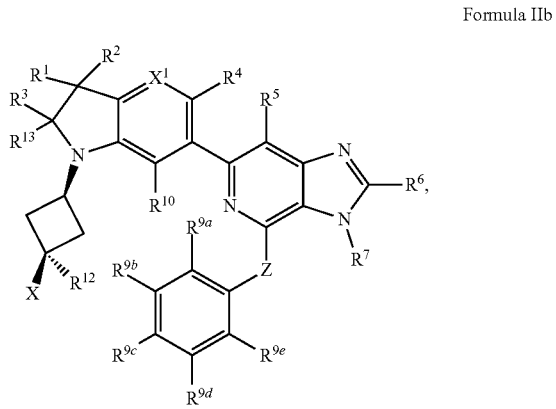

Formula IIb or the pharmaceutically acceptable salt thereof.

5. The compound of claim 1, or a pharmaceutically acceptable salt thereof, wherein $R^4$, $R^5$, $R^6$, and $R^{10}$ are H.

6. The compound of claim 2, or a pharmaceutically acceptable salt thereof, wherein n is 0, 1, or 2.

7. The compound of claim 1, wherein the compound is of Formula III:

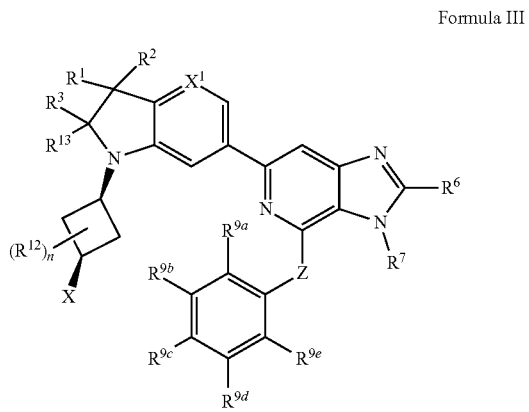

Formula III or a pharmaceutically acceptable salt thereof,
wherein:
  one of $R^1$ and $R^2$ is —OH, halogen, or C$_{1-3}$ alkyl, and the other of $R^1$ and $R^2$ is halogen or C$_{1-3}$ alkyl, or
  $R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, C$_{1-3}$ alkyl, and C$_{1-3}$ alkoxy;
  $R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy,
  ii) —S(O)$_2$C$_{1-3}$ alkyl, iii) —S(O)$_2$C$_{3-5}$ monocyclic cycloalkyl,
iv) C$_{1-6}$ alkyl optionally substituted with 1-3 groups independently selected from —CN, —OH, halogen, C$_{1-3}$ alkoxy, and C$_{3-7}$ monocyclic cycloalkyl, or
v) —C(O)R$^{21}$;
R$^{21}$ is
  i) C$_{3-7}$ monocyclic or bridged bicyclic cycloalkyl optionally substituted with 1-3 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —OH, halogen, and C$_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy,
  iii) C$_{1-6}$ alkoxy optionally substituted with 1-3 groups independently selected from —OH, halogen, C$_{1-3}$ alkyl, and C$_{3-7}$ monocyclic cycloalkyl, or
  iv) C$_{1-6}$ alkyl optionally substituted with 1-3 groups independently selected from
    a) —CN,
    b) —OH,
    c) halogen, and
    d) C$_{1-3}$ alkoxy,
R$^3$ and R$^{13}$ are each H, or
R$^3$ and R$^{13}$ together form =O;
n is 0 or 1;
R$^{12}$ is C$_{1-3}$ alkyl;
X is —NR$^{15}$R$^{16}$, wherein R$^{15}$ and R$^{16}$ are independently
  i) H,
  ii) C$_{3-7}$ monocyclic cycloalkyl optionally substituted with 1-3 groups independently selected from —OH, halogen, C$_{1-3}$ alkyl, and C$_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, C$_{1-3}$ alkyl, and C$_{1-3}$ alkoxy,
  iv) —C(O)C$_{1-6}$ alkyl, wherein the C$_{1-6}$ alkyl is optionally substituted with 1-3 groups independently selected from —CN, —OH, halogen, and C$_{1-3}$ alkoxy, or
  v) C$_{1-6}$ alkyl optionally substituted with 1-6 groups independently selected from
    a) —OH,
    b) halogen, and
    c) C$_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
  i) a halogen,
  ii) —OH, or
  iii) C$_{1-6}$ alkyl optionally substituted with 1-3 groups independently selected from —OH, halogen, C$_{1-3}$ alkoxy, and C$_{3-7}$ monocyclic cycloalkyl;
X$^1$ is N or CH;
R$^7$ is
  i) C$_{1-6}$ alkyl optionally substituted with 1-3 groups independently selected from —OH, halogen, C$_{1-3}$ alkoxy, and C$_{3-7}$ monocyclic cycloalkyl, or
  ii) C$_{3-7}$ monocyclic cycloalkyl optionally substituted with 1-3 groups independently selected from —OH, halogen, C$_{1-3}$ alkyl, and C$_{1-3}$ alkoxy;
Z is —O— or NH;
R$^{9a}$, R$^{9b}$, R$^{9c}$, R$^{9d}$, and R$^{9e}$ are independently
  i) H,
  ii) halogen,
  iii) C$_{1-6}$ alkoxy optionally substituted with 1-3 groups independently selected from —OH, halogen, C$_{1-3}$ alkyl, and C$_{3-7}$ monocyclic cycloalkyl,
  iv) C$_{1-6}$ alkyl optionally substituted with 1-3 groups independently selected from —OH, halogen, C$_{1-3}$ alkoxy, and C$_{3-7}$ monocyclic cycloalkyl,
  v) C$_{3-7}$ monocyclic cycloalkyl optionally substituted with 1-3 groups independently selected from —OH, halogen, C$_{1-3}$ alkyl, and C$_{1-3}$ alkoxy, or
  vi) —C(O)N(R$^{19}$)$_2$,
  wherein one or more of R$^{9a}$, R$^{9b}$, R$^{9c}$, R$^{9d}$, and R$^{9e}$ is —C(O)N(R$^{19}$)$_2$;
each R$^{19}$ is independently
  i) H,
  ii) C$_{1-6}$ alkyl optionally substituted with 1-6 groups independently selected from —CN, —OH, halogen, C$_{1-3}$ alkoxy, and C$_{3-7}$ monocyclic cycloalkyl, or
  iii) C$_{3-7}$ monocyclic cycloalkyl optionally substituted with 1-6 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —CN, —OH, halogen, and C$_{1-3}$ alkoxy.

8. The compound of claim 2, wherein the compound is of Formula IIIa:

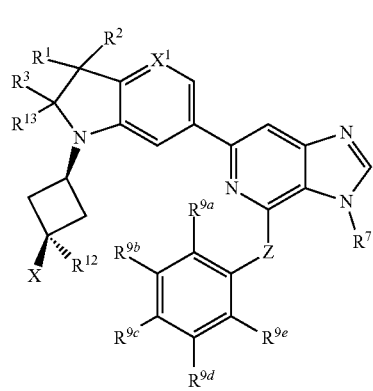

Formula IIIa or a pharmaceutically acceptable salt thereof.

9. The compound of claim 1, or a pharmaceutically acceptable salt thereof, wherein R$^3$ and R$^{13}$ together form =O.

10. The compound of claim 1, or a pharmaceutically acceptable salt thereof, wherein X$^1$ is CH.

11. The compound of claim 1, or a pharmaceutically acceptable salt thereof, wherein X$^1$ is N.

12. The compound of claim 2, or a pharmaceutically acceptable salt thereof, wherein R$^{12}$ is C$_{1-3}$ alkyl.

13. The compound of claim 1, or a pharmaceutically acceptable salt thereof, wherein Z is NH.

14. The compound of claim 1, wherein the compound is of Formula IV:

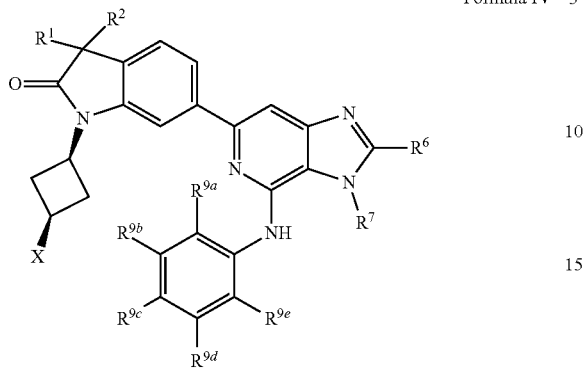

Formula IV or a pharmaceutically acceptable salt thereof,
wherein:
one of $R^1$ and $R^2$ is —OH, halogen, or $C_{1-3}$ alkyl, and the other of $R^1$ and $R^2$ is halogen or $C_{1-3}$ alkyl, or
$R^1$ and $R^2$ together with the carbon to which they are attached form a 4-6 membered monocyclic heterocyclyl having 1 or 2 heteroatoms independently selected from N, O, and S, wherein the 4-6 membered monocyclic heterocyclyl is optionally substituted with one $R^{11}$ and optionally substituted with 1-3 groups independently selected from —OH, halogen, oxo, $C_{1-3}$ alkyl, and $C_{1-3}$ alkoxy;
$R^{11}$ is
  i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  ii) —S(O)$_2$C$_{1-3}$ alkyl,
  iii) —S(O)$_2$C$_{3-4}$ monocyclic cycloalkyl,
  iv) $C_{1-6}$ alkyl optionally substituted with 1-3 groups independently selected from —CN, —OH, halogen, $C_{1-3}$ alkoxy, and $C_{3-7}$ monocyclic cycloalkyl, or
  v) —C(O)R$^{21}$;
$R^{21}$ is
  i) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) $C_{1-6}$ alkoxy optionally substituted with 1-3 groups independently selected from —OH, halogen, $C_{1-3}$ alkyl, and $C_{3-7}$ monocyclic cycloalkyl, or
  iv) $C_{1-6}$ alkyl optionally substituted with 1-3 groups independently selected from
    a) —CN,
    b) —OH,
    c) halogen, and
    d) $C_{1-3}$ alkoxy, X is —NR$^{15}$R$^{16}$, wherein R$^{15}$ and R$^{16}$ are independently
  i) H,
  ii) $C_{3-7}$ monocyclic cycloalkyl optionally substituted with 1-3 groups independently selected from —OH, halogen, $C_{1-3}$ alkyl, and $C_{1-3}$ alkoxy,
  iii) 4-7 membered monocyclic heterocyclyl having 1 or 2 heteroatoms independently selected from N, O, and S, wherein the 4-7 membered monocyclic heterocyclyl is optionally substituted with 1-3 groups independently selected from —OH, halogen, oxo, $C_{1-3}$ alkyl, and $C_{1-3}$ alkoxy,
  iv) —C(O)C$_{1-6}$ alkyl, wherein the $C_{1-6}$ alkyl is optionally substituted with 1-3 groups independently selected from —CN, —OH, halogen, and $C_{1-3}$ alkoxy, or
  v) $C_{1-6}$ alkyl optionally substituted with 1-6 groups independently selected from
    a) —OH,
    b) halogen, and
    c) $C_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
  i) a halogen,
  ii) —OH, or
  iii) $C_{1-6}$ alkyl optionally substituted with 1-3 groups independently selected from —OH, halogen, $C_{1-3}$ alkoxy, and $C_{3-7}$ monocyclic cycloalkyl;
R$^7$ is
  i) $C_{1-6}$ alkyl optionally substituted with 1-3 groups independently selected from —OH, halogen, $C_{1-3}$ alkoxy, and $C_{3-7}$ monocyclic cycloalkyl, or
  ii) $C_{3-7}$ monocyclic cycloalkyl optionally substituted with 1-3 groups independently selected from —OH, halogen, $C_{1-3}$ alkyl, and $C_{1-3}$ alkoxy;
R$^{9a}$, R$^{9b}$, R$^{9c}$, R$^{9d}$, and R$^{9e}$ are independently
  i) H,
  ii) halogen,
  iii) $C_{1-6}$ alkoxy optionally substituted with 1-3 groups independently selected from —OH, halogen, $C_{1-3}$ alkyl, and $C_{3-7}$ monocyclic cycloalkyl,
  iv) $C_{1-6}$ alkyl optionally substituted with 1-3 groups independently selected from —OH, halogen, $C_{1-3}$ alkoxy, and $C_{3-7}$ monocyclic cycloalkyl,
  v) $C_{3-7}$ monocyclic cycloalkyl optionally substituted with 1-3 groups independently selected from —OH, halogen, $C_{1-3}$ alkyl, and $C_{1-3}$ alkoxy, or
  vi) —C(O)N(R$^{19}$)$_2$,
wherein one or more of R$^{9a}$, R$^{9b}$, R$^{9c}$, R$^{9d}$, and R$^{9e}$ is —C(O)N(R$^{19}$)$_2$;
each R$^{19}$ is independently
  i) H,
  ii) $C_{1-6}$ alkyl optionally substituted with 1-6 groups independently selected from —CN, —OH, halogen, $C_{1-3}$ alkoxy, and $C_{3-7}$ monocyclic cycloalkyl, or
  iii) $C_{3-7}$ monocyclic cycloalkyl optionally substituted with 1-6 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —CN, —OH, halogen, and $C_{1-3}$ alkoxy.

15. The compound of claim 1, wherein the compound has a Formula IVa:

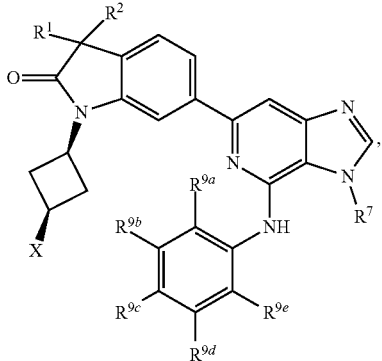

Formula IVa or the pharmaceutically acceptable salt thereof.

16. The compound of claim 2, wherein the compound has a Formula IVb:

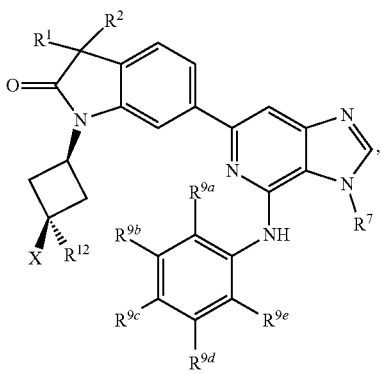

Formula IVb or the pharmaceutically acceptable salt thereof.

17. The compound of claim 2, wherein the compound has a Formula IVc:

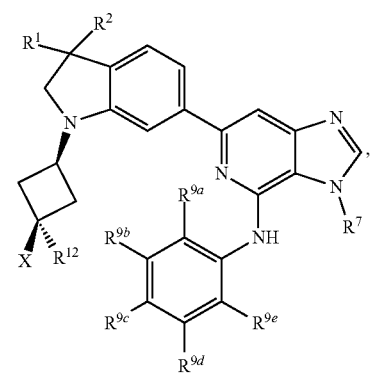

Formula IVc or the pharmaceutically acceptable salt thereof.

18. The compound of claim 1, or a pharmaceutically acceptable salt thereof, wherein one of $R^1$ and $R^2$ is —OH, fluoro, methyl, or ethyl and the other of one of $R^1$ and $R^2$ is fluoro, methyl, or ethyl.

19. The compound of claim 1, or a pharmaceutically acceptable salt thereof, wherein $R^1$ and $R^2$ are both fluoro, methyl, or ethyl.

20. The compound of claim 1, or a pharmaceutically acceptable salt thereof, wherein one or more of $R^{9a}$, $R^{9b}$, $R^{9c}$, $R^{9d}$, and $R^{9e}$ are independently:
   i) H,
   ii) halogen,
   iii) $C_{1-3}$ alkyl optionally substituted with 1-3 groups independently selected from —OH and halogen,
   iv) —$OCH_3$ optionally substituted with 1-3 halogen groups,
   v) cyclopropyl, or
   vi) —$C(O)N(R^{19})_2$,
   and wherein one or more of $R^{9a}$, $R^{9b}$, $R^{9c}$, $R^{9d}$, and $R^{9e}$ is —$C(O)N(R^{19})_2$.

21. The compound of claim 1, or a pharmaceutically acceptable salt thereof, wherein one or more of $R^{9a}$, $R^{9b}$, $R^{9c}$, $R^{9d}$, and $R^{9e}$ are independently H, fluoro, chloro, methyl, ethyl, or —$C(O)N(R^{19})_2$, and wherein one or more of $R^{9a}$, $R^{9b}$, $R^{9c}$, $R^{9d}$, and $R^{9e}$ is —$C(O)N(R^{19})_2$.

22. The compound of claim 1, or a pharmaceutically acceptable salt thereof, wherein $R^{9a}$, $R^{9b}$, $R^{9c}$, and $R^{9e}$ are independently H, fluoro, chloro, methyl, or ethyl and $R^{9d}$ is —$C(O)N(R^{19})_2$; wherein each $R^{19}$ is independently H or cyclopropyl, wherein the cyclopropyl is optionally substituted with a methyl, and wherein the methyl is optionally substituted with 1-3 groups independently selected from fluoro and —$OCH_3$.

23. The compound of claim 22, or a pharmaceutically acceptable salt thereof, wherein $R^{9a}$, $R^{9b}$, $R^{9c}$, and $R^{9e}$ are independently H, fluoro, chloro, methyl, or ethyl and $R^{9d}$ is —$C(O)N(R^{19})_2$; wherein each $R^{19}$ is independently H or cyclopropyl, wherein the cyclopropyl is optionally substituted with a methyl, and wherein the methyl is optionally substituted with 1-3 fluoro groups.

24. The compound of claim 23, or a pharmaceutically acceptable salt thereof, wherein $R^{9a}$, $R^{9b}$, $R^{9c}$, and $R^{9e}$ are independently H, fluoro, chloro, methyl, or ethyl and $R^{9d}$ is —$C(O)NH(R^{19})$; wherein $R^{19}$ is cyclopropyl optionally substituted with a methyl, and wherein the methyl is optionally substituted with 1-3 fluoro groups.

25. The compound of claim 24, or a pharmaceutically acceptable salt thereof, wherein $R^{9a}$, $R^{9b}$, $R^{9c}$, and $R^{9e}$ are independently H, fluoro, or chloro and $R^{9d}$ is —$C(O)NH(R^{19})$; wherein $R^{19}$ is cyclopropyl optionally substituted with a methyl, and wherein the methyl is optionally substituted with 1-3 fluoro groups.

26. The compound of claim 25, or a pharmaceutically acceptable salt thereof, wherein $R^{9a}$, $R^{9b}$, and $R^{9c}$ are independently fluoro or chloro, $R^{9e}$ is H, and $R^{9d}$ is —$C(O)NH(R^{19})$; wherein $R^{19}$ is cyclopropyl optionally substituted with a methyl, wherein the methyl is optionally substituted with 1-3 fluoro groups.

27. The compound of claim 26, or a pharmaceutically acceptable salt thereof, wherein $R^{9d}$ is

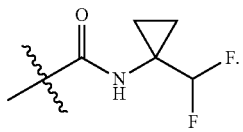 [SMILES: *C(=O)NC1(C(F)F)CC1]

28. The compound of claim 1, or a pharmaceutically acceptable salt thereof, wherein $R^{9a}$ is H or fluoro.

29. The compound of claim 28, or a pharmaceutically acceptable salt thereof, wherein $R^{9b}$ is H or methyl.

30. The compound of claim 29, or a pharmaceutically acceptable salt thereof, wherein $R^{9c}$ is H, fluoro, chloro, methyl, ethyl, —$CF_3$, —$OCF_3$, or cyclopropyl.

31. The compound of claim 30, or a pharmaceutically acceptable salt thereof, wherein $R^{9d}$ is methyl.

32. The compound of claim 31, or a pharmaceutically acceptable salt thereof, wherein $R^{9e}$ is H.

33. The compound of claim 32, or a pharmaceutically acceptable salt thereof, wherein $R^{9d}$ is —$C(O)N(R^{19})_2$.

34. The compound of claim 1, or a pharmaceutically acceptable salt thereof, wherein each $R^{19}$ is independently:
   i) H,
   ii) methyl,
   iii) ethyl optionally substituted with 1 or 2 groups independently selected from —OH, fluoro, and —$OCH_3$,
   iv) n-propyl optionally substituted with 1 or 2 groups independently selected from fluoro and —$OCH_3$,
   v) isopropyl optionally substituted with 1 or 2 fluoro groups,
   vi) n-butyl,
   vii) isobutyl optionally substituted with 1 or 2 fluoro groups,
   viii) sec-butyl,
   ix) tert-butyl,
   x) cyclopropyl optionally substituted with a methyl, wherein the methyl is optionally substituted with 1-3 groups independently selected from fluoro and —$OCH_3$, or
   xi) cyclobutyl.

35. The compound of claim 1, or a pharmaceutically acceptable salt thereof, wherein $R^7$ is methyl, ethyl, isopropyl, sec-butyl, or cyclopropyl, wherein the cyclopropyl is optionally substituted with one methyl.

36. The compound of claim 1, or a pharmaceutically acceptable salt thereof, wherein X is a 4-8 membered monocyclic, fused bicyclic, bridged bicyclic, or spirocyclic heterocyclyl having 1 or 2 heteroatoms independently selected from N and O, wherein the 4-8 membered monocyclic, fused bicyclic, bridged bicyclic, or spirocyclic heterocyclyl is optionally substituted with 1-5 $R^{18}$.

37. The compound of claim 1, or a pharmaceutically acceptable salt thereof, wherein X is azetidinyl, pyrrolidinyl, piperidinyl, or morpholinyl, each of which is optionally substituted with 1-5 $R^{18}$.

38. The compound of claim 36, or a pharmaceutically acceptable salt thereof, wherein X is:

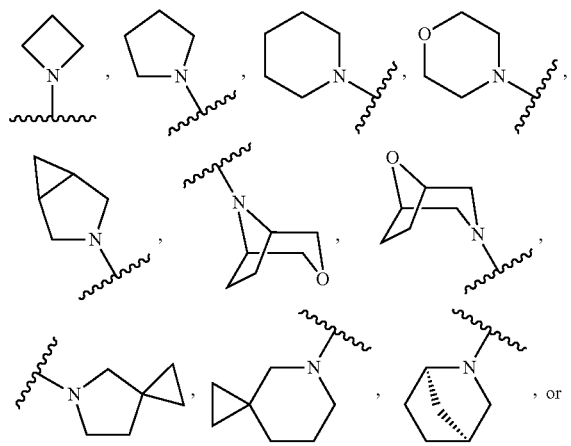

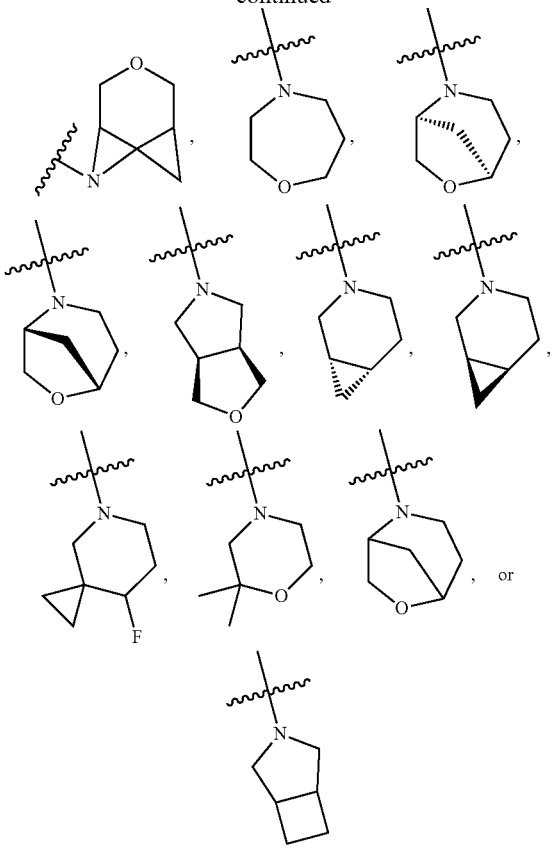

each of which is optionally substituted with 1-5 $R^{18}$.

39. The compound of claim 38, or a pharmaceutically acceptable salt thereof, wherein X is:

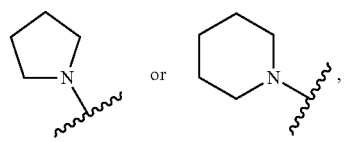 [SMILES: *N1CCCC1 ; *N1CCCCC1]

each of which is optionally substituted with 1-4 $R^{18}$.

40. The compound of claim 1, or a pharmaceutically acceptable salt thereof, wherein each $R^{18}$ is independently:
   i) —OH,
   ii) fluoro, or
   iii) $C_{1-3}$ alkyl optionally substituted with 1-3 groups independently selected from —OH and halogen.

41. A pharmaceutical composition comprising the compound of claim 1, or a pharmaceutically acceptable salt thereof, and a pharmaceutically acceptable excipient or carrier.

42. The pharmaceutical composition of claim 41, further comprising one or more additional therapeutic agents, or a pharmaceutically acceptable salt thereof.

43. A method of inhibiting hematopoietic progenitor kinase 1 (HPK1) activity in a subject in need thereof, comprising administering to the subject a therapeutically effective amount of the compound of claim 1, or a pharmaceutically acceptable salt thereof.

44. A method of increasing T-cell activation in a subject in need thereof, comprising administering to the subject a therapeutically effective amount of the compound of claim 1, or a pharmaceutically acceptable salt thereof.

45. A method of treating a cancer associated with increased HPK1 activity in a subject in need thereof, comprising administering to the subject a therapeutically effective amount of the compound of claim 1, or a pharmaceutically acceptable salt thereof.

* * * * *